(12) United States Patent
Pavco et al.

(10) Patent No.: US 7,034,009 B2
(45) Date of Patent: Apr. 25, 2006

(54) ENZYMATIC NUCLEIC ACID-MEDIATED TREATMENT OF OCULAR DISEASES OR CONDITIONS RELATED TO LEVELS OF VASCULAR ENDOTHELIAL GROWTH FACTOR RECEPTOR (VEGF-R)

(75) Inventors: Pamela Pavco, Lafayette, CO (US); James McSwiggen, Boulder, CO (US); Dan Stinchcomb, Ft. Collins, CO (US); Jaime Escobedo, Alamo, CA (US)

(73) Assignees: Sirna Therapeutics, Inc., Boulder, CO (US); Chiron Corporation, Emeryville, CA (US)

( * ) Notice: Subject to any disclaimer, the term of this patent is extended or adjusted under 35 U.S.C. 154(b) by 317 days.

(21) Appl. No.: 10/138,674

(22) Filed: May 3, 2002

(65) Prior Publication Data
US 2004/0077565 A1 Apr. 22, 2004

Related U.S. Application Data

(63) Continuation-in-part of application No. 09/870,161, filed on May 29, 2001, now abandoned, which is a continuation-in-part of application No. 09/708,690, filed on Nov. 7, 2000, now abandoned, which is a continuation-in-part of application No. 09/371,722, filed on Aug. 10, 1999, now Pat. No. 6,534,872, which is a continuation-in-part of application No. 08/584,040, filed on Jan. 11, 1996, now Pat. No. 6,346,398.
(60) Provisional application No. 60/005,974, filed on Oct. 26, 1995.

(51) Int. Cl.
*A01N 43/44* (2006.01)

(52) U.S. Cl. .............................. 514/44; 435/6; 435/325; 435/375; 536/23.1; 536/23.2; 536/24.33; 536/24.5

(58) Field of Classification Search ................. 435/325, 435/91.31; 536/24.5
See application file for complete search history.

(56) References Cited

U.S. PATENT DOCUMENTS

| 4,987,071 A | 1/1991 | Cech et al. |
| 5,334,711 A | 8/1994 | Sproat et al. |
| 5,359,051 A | 10/1994 | Cook et al. |

(Continued)

FOREIGN PATENT DOCUMENTS

| EP | 360257 | 3/1990 |
| WO | WO8902439 | 3/1989 |
| WO | WO9103162 | 3/1991 |

(Continued)

OTHER PUBLICATIONS

Parry et al. Bioactivity of anti–angiogenic ribozymes targeting Flt–1 and KDR mRNA. Nucleic Acids Research, 1999 vol. 27:2569–2577.*

Branch, A. A Good Antisense is Hard to Find. TIBS, Feb. 1998 vol. 23, pp. 45–50.*

Jen et al. Suppression of Gene Expression by Targeted Disruption of Messenger RNA: Available Options and Current Strategies. Stem Cells, 2000, vol. 18:307–319.*

(Continued)

*Primary Examiner*—Andrew Wang
*Assistant Examiner*—Terra Gibbs
(74) *Attorney, Agent, or Firm*—McDonnell Boehnen Hulbert & Berghoff LLP

(57) ABSTRACT

The present invention relates to nucleic acid molecules such as ribozymes, DNAzymes, and antisense which modulate the synthesis, expression and/or stability of an mRNA encoding one or more receptors of vascular endothelial growth factor, such as flt-1 and KDR. Nucleic acid molecules and methods for the inhibition of angiogenesis and treatment of cancer and ocular diseases are provided, optionally in conjunction with other therapeutic agents.

20 Claims, 39 Drawing Sheets

*Hammerhead Ribozyme*

U.S. PATENT DOCUMENTS

| | | |
|---|---|---|
| 5,525,468 A | 6/1996 | McSwiggen |
| 5,589,332 A | 12/1996 | Shih et al. |
| 5,631,359 A | 5/1997 | Chowrira et al. |
| 5,672,695 A | 9/1997 | Eckstein et al. |
| 5,741,679 A | 4/1998 | George et al. |
| 5,834,186 A | 11/1998 | George et al. |
| 5,871,914 A | 2/1999 | Nathan |

FOREIGN PATENT DOCUMENTS

| | | |
|---|---|---|
| WO | WO9207065 | 9/1991 |
| WO | WO9312569 | 4/1993 |
| WO | WO9315187 | 8/1993 |
| WO | WO9323057 | 11/1993 |
| WO | WO9402595 | 2/1994 |
| WO | WO9411499 | 5/1994 |
| WO | WO9421679 | 9/1994 |
| WO | WO9421791 | 9/1994 |
| WO | WO9511304 | 10/1994 |
| WO | WO9504142 | 2/1995 |
| WO | WO9504818 | 2/1995 |
| WO | WO9506731 | 3/1995 |
| WO | WO9511910 | 5/1995 |
| WO | WO9513380 | 5/1995 |
| WO | WO9521868 | 8/1995 |
| WO | WO9523225 | 8/1995 |
| WO | WO9610390 | 4/1996 |
| WO | WO9610391 | 4/1996 |
| WO | WO9610392 | 4/1996 |
| WO | WO9622689 | 8/1996 |
| WO | WO9700957 | 1/1997 |
| WO | WO9726270 | 7/1997 |
| WO | WO9813526 | 4/1998 |
| WO | WO9827104 | 6/1998 |
| WO | WO9828317 | 7/1998 |
| WO | WO9858058 | 12/1998 |
| WO | WO9904819 | 2/1999 |
| WO | WO9916871 | 4/1999 |
| WO | WO9929842 | 6/1999 |
| WO | WO9955857 | 11/1999 |
| WO | WO0024931 | 5/2000 |
| WO | WO0026226 | 5/2000 |

OTHER PUBLICATIONS

Dias et al. Potential roles of antisense oligonucleotides in cancer therapy. The example of bcl–2 antisense oligonucleotides. European Journal of Pharmaceutics and Biopharmaceutics, 2002 vol. 54:263–269.*

Ma et al. Synthetic oligonucleotides are therapeutics: the coming of age. Biotechnology Annual Review, 2000 vol. 5:155–196.*

Usman et al., "Chemical modification of hammerhead ribozymes: activity and nuclease resistance," *Nucleic Acids Syposium Series* 31:163–164 (1994).

Parry et al. 1999. "Bioactivity of anti–angiogenic ribozymes targeting *Flt*–1 and *KDR* mRNA," *Nucleic Acid Res.* 27:2569–77.

Aiello et al., "Suppression of Retinal Neovascularization in vivo by inhibition of Vascular Endothelial Growth Factor (VEGF) Using Soluble VEGF–Receptor Chimeric Proteins," *Proc. Natl. Acad. Sci. USA* 92: 10457–10461 (1995).

Aiello, et al., "Vascular Endothelial Growth Factor in Ocular Fluid of Patients with Diabetic Retinopathy and Other Retinal Disorders," 1994 *New Engl. J. Med.* 331, 1480.

Akhtar and Juliano, "Cellular Uptake and Intracellular Fate of AntiSense Oligonucleotides," *Trends Cell Biol.* 2:139–144 (1992).

Bartel and Szostak, "Isolation of New Ribozymes From a Large Pool of Random Sequences," *Science* 261:1411–1418 (1993).

Beaucage and Iyer, "The Functionalization of Oligonucleotides Via Phosphoramidite Derivatives," *Tetrahedron* 49:1925–1963 (1993).

Beigelman et al., "Chemical Modification of Hammerhead Ribozymes," *J. Biol. Chem.* 270:25702–25708 (1995).

Berkman et al., "Expression of the Vascular Permeability Factor/Vascular Endothelial Growth Factor Gene in Central Nervous System Neoplasms," 1993 *J. Clini. Invest.*91, 153.

Breaker and Joyce, "Inventing and improving ribozyme function: rational design versus iterative selection methods," *TIBTECH* 12:268–275 (1994).

Breaker et al., "A DNA enzyme with $Mg^2$–dependent RNA phosphoesterase activity," *Chemistry & Biology* 2(10):655–660 (1995).

Breaker, "Are engineered proteins getting competition from RNA?" *Current Opinion in Biotechnology* 7:442–448 (1996).

Burger et al., "Experimental Corneal Neovascularization: Biomicroscopic, Angiographic, and Morphologic Correlation," *Cornea* 4:35–41 (1985/1986).

Burgin et al., "Chemically Modified Hammerhead Ribozymes with Improved Catalytic Rates," *Biochemistry* 35:14090–14097 (1996) (volume no mistakenly listed as 6).

Carter, "Adeno–Associated Virus Vectors," *Curr. Opi. Biotech.* 3:533–539 (1992).

Caruthers et al., "Chemical Synthesis of Deoxyoligonucleotides and Deoxyoligonucleotide Analogs," *Methods in Enzymology* 211:3–19 (1992).

Cech, "Ribozymes and Their Medical Implications," *JAMA* 260:3030–3034 (1988).

Chartrand et al., "An oligodeoxyribonucleotide that supports catalytic activity in the hammerhead ribozyme domain," *Nucleic Acids Research* 23(20):4092–4096 (1995).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).

Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).

Christoffersen and Marr, "Riobozymes as Human Therapeutic Agents," *J. Med. Chem.* 38:2023–2037 (1995) (also referred to as Christofferson and Marr).

Cload and Schepartz, "Polyether Tethered Oligonucleotide Probes," *J. Am. Chem. Soc.* 113:6324–6326 (1991).

Collins and Olive, "Reaction Conditions and Kinetics of Self–Cleavage of a Ribozyme Derived From *Neurospora* VS RNA," *Biochemistry* 32:2795–2799 (1993).

Detmar et al., "Overexpression of Vascular Permeability Factor/Vascular Endothelial Growth Factor and its Receptors in Psoriasisi," 1994 *J. Exp. Med.* 180, 1141.

Dreyfus, "Restriction Ribozymes?" *Einstein Quarterly Journal of Biology and Medicine* 6:92–93 (1988).

Dropulic et al., "Functional Characterization of a U5 Ribozyme: Intracellular Suppression of Human Immunodeficiency Virus Type I Expression," *Journal of Virology* 66:1432–1441 (1992).

Durand et al., "Circular Dichroism Studies of an Oligodeoxyribonucleotide Containing a Hairpin Loop Made of a Hexaethylene Glycol Chain: Conformation and Stability," *Nucleic Acids Research* 18:6353–6359 (1990).

Duval–Valentin, "Specific inhibition of transcription by triple helix–forming oligonucleotides," *Proc. Natl. Acad. Sci. USA* 89:504–508 (1992).

Egholm et al., "PNA hybridizes to complementary oligonucleotides obeying the Watson–Crick hydrogen–bonding rules," *Nature* 365:566–568 (1993).

Elkins and Rossi, "Ch. 2—Cellular Delivery of Ribozymes," in *Delivery Strategies for Antisense Oligonucleotide Therapeutics*, edited by Akhtar, CRC Press, pp. 17–220 (1995).

Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Fava et al., "Vascular Permeability Factor/Endothelial Growth Factor (VPF/VEGF): Accumulation and Expression in Human Synovial Fluids and Rheumatoid Synovial Tissue," 1994 *J. Exp. Med.* 180, 341.

Feldstein et al., "Two sequences participating in the autolytic processing of satellite tobacco ringspot virus complementary RNA," *Gene* 82:53–61 (1989).

Ferentz and Verdine, "Disulfied Cross–Linked Oligonucleotides," *J. Am. Chem. Soc.* 113:4000–4002 (1991).

Ferrara, "Vascular Endothelial Growth Factor," 1993 *Trends Cardiovas. Med.* 3, 2244.

Folkman and Shing, "Angiogenesis," *J. Biol. Chem.* 267:10931–10934 (1992).

Folkman, "What is the Evidence that Tumors are Angiogenesis Dependent?" *Journal of the National Cancer Institute* 82:4–6 (1990).

Folkman, "Tumor Agniogenesis" 1985 *Adv. Cancer. Res.* 43, 175.

Forster and Altman, "External Guide Sequences for an RNA Enzyme," *Science* 249:783–786 (1990).

Frier et al., 1986, *Proc. Nat. Acad. Sci. USA* 83:9373–9377.

Fong et al., "Role of the Flt–1 Receptor Tyrosine Kinase in Regulating the Assembly of Vascular Endothelium," 1995 *Nature* 376, 66 Corrected from specification.

Gao and Huang, "Cytoplasmic Expression of a Reporter Gene by Co–Delivery of T7 RNA Polymerase and T7 Promoter Sequence with Cationic Liposomes," *Nucleic Acids Research* 21:2867–2872 (1993).

Gitay–Goren et al., "The Binding of Vascular Endothelial Growth Factor to Its Receptos is Dependent on Cell Surface–associated Heparin–like Molecules," 1992 *J. Biol. Chem.* 267, 6093.

Gold et al., Diversity of Oligonucleotide Functions, *Annu. Rev. Biochem.* 64:763–797 (1995).

Grant et al., "Insulin–like growth factor I acts as an angiogenic agent in rabbit cornea and retina: comparative studies with basic fibroblast growth factor," *Diabetologia* 36:282–291 (1993).

Griffin et al., "Group II intron ribozymes that cleave DNA and RNA linkages with similar efficiency, and lack contacts with substrate 2'–hydroxyl groups," *Chemistry & Biology* 2:761–770 (1995).

Guerrier–Takada et al., "The RNA Moiety of Ribonuclease P Is the Catalytic Subunit of the Enzyme," *Cell* 35:849–857 (1983).

Hampel and Tritz, "RNA Catalytic Properties of the Minimum (–)sTRSV Sequence," *Biochemistry* 28:4929–4933 (1989).

Hampel et al., "Hairpin'Catalytic RNA Model: Evidence for Helices and Sequence Requirement for Substrate RNA," *Nucleic Acids Research* 18:299–304 (1990).

Haseloff and Gerlach, "Sequences required for self–catalysed cleavage of the satellite RNA of tobacco ringspot virus," *Gene* 82:43–52 (1989).

Haseloff and Gerlach, "Simple RNA Enzymes with New and Highly Specific Endoribonuclease Activities," *Nature* 334:585–591 (1988).

Hertel et al., "Numbering System for the Hammerhead," *Nucleic Acids Research* 20:3252 (1992).

Ishiwata et al., "Physical–Chemistry Characteristics and Biodistribution of Poly(ethylene glycol)–Coated Liposomes Using Poly(oxyethylene) Cholesteryl Ether," *Chem. Pharm. Bull.* 43:1005–1011 (1995) (mistakenly referred to as Ishiwataet).

Ishizaka et al., "Isolation of Active Ribozymes from an RNA Pool of Random Sequences Using an Anchored Substrate RNA," *Biochemical and Biophysical Research Communication* 214(2):403–409 (1995).

Izant and Weintraub, "Constitutive and Conditional Suppression of Exogenous and Endogenous Genes by Anti–Sense RNA," *Science* 229:345–352 (1985).

Jaeger et al., "Improved Predictions of Secondary Structures for RNA," *Proc. Natl. Acad. Sci. USA* 86:7706–7710 (1989).

Jaschke et al., "Automated incorporation of Polyethylene Glycol into Synthetic Oligonucleotides," *Tetrahedron Letters* 34:301–304 (1993).

Jeffries and Symons, "A Catalytic 13–mer Ribozyme," *Nucleic Acids Research* 17:1371–1377 (1989) (also referred to as Jefferies).

Jellinek et al., "Inhibitions of Receptor Binding by High–Affinity RNA Ligands to Vascular Endothelial Growth Factor," *Biochemistry* 33:10450–10456 (1994).

Joyce et al., "Amplification, mutation and selection of catalytic RNA," *Gene* 82:83–87 (1989).

Joyce, "Directed Molecular Evolution," *Scientific American* 267:90–97 (1992).

Kashani–Sabet et al., "Reversal of the Malignant Phenotype by an Anti–*ras* Ribozyme," *Antisense Research & Development* 2:3–15 (1992).

Kim and Cech, "Three–dimensional model of the active site of the self–splicing rRNA precursor of *Tetrahymena*," *Proc. Natl. Acad. Sci. USA* 84:8788–8792 (1987).

Kim et al., "Inhibition of vascular endothelial growth factor–induced angiogenesis suppresses tumour growth in vivo," *Nature* 362:841–844 (1993).

Koch et al., "Vascular Endothelial Growth Factor: A Cytokine Modulating Endothelial Function in Rheumatoid Arthritis," 1994 *J. Immunol.* 152, 4149.

Kore, et al., "Sequence specificity of the hammerhead ribozyme revisistsed; the NIH rule," *Nucleic Acids Research*, 26(18):4116–4120 (1998).

Kumar and Ellington, "Artificial evolution and natural ribozymes," *FASEB J.* 9:1183–1195 (1995).

Lasic and Needham "The 'Stealth' Liposome: A Prototypical Biomaterial," *Chemical Reviews* 95:2601–2627 (1995).

Lepri et al., "Effect of Low Molecular Weight Heparan Sulphate on Angiogenesis in the Rat Cornea after Chemical Cauterization," *Journal of Ocular Pharmacology* 10:273–281 (1994).

L'Huillier et al., "Cytoplasmic Delivery of Ribozymes Leads to Efficient Reduction in α–Lactalbumin mRNA Levels in C1271 Mouse," *EMBO J.* 11:4411–4418 (1992).

Li and Altman, "Cleavage by RNase P of gene N mRNA reduces bacteriophage λ burst size," *Nucleic Acids Research* 24:835–842 (1996).

Lieber et al., "Stable High–Level Gene Expression in Mammalian Cells by T7 Phage RNA Polymerase," *Methods Enzymol.* 217:47–66 (1993).

Limbach et al., "Summary: the modified nucleosides of RNA," *Nucleic Acids Research* 22(12):2183–2196 (1994).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Liu et al., "Cationic Liposome–mediated Intravenous Gene Delivery," *J. Biol. Chem.* 270(42):24864–24870 (1995).

Long and Uhlenbeck, "Kinetic characterization of intramolecular and intermolecular hammerhead RNAs with stem II deletions," *Proc. Natl. Acad. Sci. USA* 91:6977–6981 (1994).

Ma et al., "Design and Synthesis of RNA Miniduplexes via a Synthetic Linker Approach," *Biochemistry* 32:1751–1758 (1993).

Ma et al., "Design and Synthesis of RNA Miniduplexes via a Synthetic Linker Approach. 2. Generation of Covalently Closed, Double–Stranded Cyclic HIV–1 TAR RNA Analogs with High Tat–Binding Affinity," *Nucleic Acids Research* 21:2585–2589 (1993).

Mathews et al., "A Receptor Tyrosine Kinase cDNA Isolated from a Population of Enriched Primitive Hematopoietic cells and Exhibiting Close Genetic Linkage of c–kit," 1991, *Proc. Natl. Acad. Sci.*, USA, 88, 9026.

McCurdy et al., "Deoxyoligonucleotides with Inverted Polarity: Synthesis and Use in Triple–Helix Formation" *Nucleosides & Nucleotides* 10:287–290 (1991).

McGarry and Lindquist, "Inhibition of heat shock protein synthesis by heat–inducible antisense RNA," *Proc. Natl. Acad. Sci. USA* 83:399–403 (1986).

Michels and Pyle, "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995).

Millauer et al., "Glioblastoma Growth Inhibited in vivo by a Dominant–negative Flk–1 Mutant," 1994, *Nature* 367, 576.

Millauer, "High Affintiy VEGF Binding and Developmental Expression Suggest Flk–1 as a Major Regulator of Vasculogenesis and Angiogenesis," *Cell* 72:835–846 (1993).

Miller et al., "Vascular Endothelial Growth Factor/Vascular Permeability Factor is Temporally and Spatially Correlated with Ocular Angiogenesis in a Primate Model," 1994 *Am. J. Pathol.* 145, 574.

Mitra et al., "A mammalian 2–5A system functions as an antiviral pathway in transgenic plants," *Proc. Natl. Acad. Sci. USA* 93:6780–6785 (1996).

Mukhopadhyay et al., "Antisense Regulation of Oncogenes in Human Cancer," *Critical Reviews in Oncogenesis* 7:151–190 (1996).

Nakamaye and Eckstein, "AUA–Cleaving Hammerhead Ribozymes: Attempted Selection for Improved Cleavage," *Biochemistry* 33:1271–1277 (1994.

Nathans and Smith, "Restriction Endonucleases in the Analysis and Restructuring of DNA Molecules," *Ann. Rev. Biochem.* 44:273–293 (1975).

Neufeld et al., "Vascular Endothelial Growth Factor and Its Receptors," *Progress in Growth Factor Research* 5:89–97 (1994).

Norrby, 1997, *APMIS* 105, 417–437.

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Oku et al., "Real–time analysis of liposomal trafficking in tumor–bearing mice by use of positron emission tomography," *Biochimica et Biophysica Acta* 1238:86–90 (1995).

Ono et al., "DNA Triplex Formation of Oligonucleotide Analogues Consisting of Linker Groups and Octamer Segments That Have Opposite Sugar–Phosphate Backbone Polarities," *Biochemistry* 30:9914–9921 (1991).

O'Reilly et al., "Angiostatin: A Novel Angiogenesis Inhibitor That Mediates the Suppression of Metastases by a Lewis Lung Carcinoma," *Cell* 79:315–328 (1994).

Orgel, "Selection in vitro," *Proc. R. Soc. London B.* 205:435–442 (1979).

Ormerod et al., "Effects of Altering the Eicosanoid Precursor Pool on Neovascularization and Inflammation in the Alkali–burned Rabbit Cornea," *American Journal of Pathology* 137:1243–1252 (1990).

Pandey et al., "Role ov B61, the Ligand for the Eck Receptor Tyrosine Kinase, in TNF– α–Induced Angiogenesis," *Science* 268:567–569 (1995).

Passaniti et al., "A Simple, Quantitative Method for Assessing Angiogenesis and Antiangiogenic Agents Using Reconstituted Basement Membrane, Heparin, and Fibroblast Growth Factor," *Laboratory Investigation* 67:519–528 (1992).

Perreault et al., "Mixed Deoxyribo– and Ribo–Oligonucleotides with Catalytic Activity," *Nature* 344:565–567 (1990) (often mistakenly listed as Perrault).

Perrotta and Been, "Cleavage of Oligoribonucleotides by a Ribozyme Derived from the Hepatitis Δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Pierce et al., "Vascular endothelial growth factor/vascular permeability factor expression in a mouse model of retinal neovascularization," *Proc. Natl. Acad. Sci. USA* 92:905–909 (1995).

Plouet et al., "Isolation and Characterization of a Newly Identified Endothelial Cell Mitogen Produced by AtT–20 Cells," 1989 *EMBO J.* 8, 3801.

Richardson and Schepartz, "Tethered Oligonucleotide Probes. A Strategy for the Recognition of Structured RNA," *J. Am. Chem. Soc.* 113:5109–5111 (1991).

Robinson et al., "Oligodeozynucleotides Inhibit Retinal Neovascularization in a Murine Model of Proliferation Retinopathy," *Proc. Natl. Acad. Sci. USA* 93: 4851–4856 (1996).

Rossi et al., "Ribozymes as Anti–HIV–1 Therapeutic Agents: Principles, Applications, and Problems," *Aids Research and Human Retroviruses* 8:183–189 (1992).

Santoro and Joyce, "A general purpose RNA–cleaving DNA enzyme," *Proc. Natl. Acad. Sci. USA* 94:4262–4266 (1997).

Sarver et al., "Ribozymes as Potential Anti–HIV–1 Therapeutic Agents" *Science* 247:1222–1225 (1990).

Saville and Collins, "A Site–Specific Self–Cleavage Reaction Performed by a Novel RNA in Neurospora Mitochondria," *Cell* 61:685–696 (1990).

Saville and Collins, "RNA–Mediated Ligation of Self–Cleavage Products of a *Neurospora* Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Seela and Kaiser, "Oligodeoxyribonucleotides containing 1,3–propanediol as nucleoside substitute," *Nucleic Acids Research* 15:3113–3129 (1987).

Senger et al., "Vascular permeability factor (VPF, VEGF) in tumor biology," *Cancer and Matastasis Reviews* 12:303–324 (1993).

Shalaby et al., "Failure of Blood–island Formation and Vasculogenesis in Flk–1–deficient Mice," 1995 *Nature* 376, 62.

Shweiki et al., "Patterns of Expression of Vascular Endothelial Growth Factor (VEGF) and VEGF Receptors in Mice Suggest a Role in Hormonally Regulated Angiogenesis," 1993 *Clin. Invest.* 91:2235–2243.

Stein and Cheng, "Antisense Oligonucleotides as Therapeutic Agents—Is the Bullet Really Magical?" *Science* 261:1004–1288 (1993).

Szostak, "In Vitro Genes," *TIBS* 17:89–93 (1993).

Szostak and Ellington, "Ch. 20—In Vitro Selection of Functional RNA Sequences," in *The RNA World*, edited by Gesteland and Atkins, Cold Spring Harbor Laboratory Press, pp. 511–533 (1993).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Takahashi et al., "Markedly Increased Amounts of Messenger RNAs for Vascular Endothelial Growth Factor and Placenta Growth Factor in Renal Cell Carcinoma Associated with Angiogenesis," *Cancer Research* 54:4233–4237 (1994).

Takeshita et al., "Therapeutic Angiogenesis: A Single Intraarterial Blous of Vascular Endothelial Growth Factor Augments Revascularization in a Rabbit Ischemic Hind Limb Model," 1995 *J. Clin. Invest.* 93, 662 Corrected from Specification.

Tang et al., "Examination of the catalytic fitness of the hammerhead ribozyme by in vitor selection," *RNA* 3:914–925 (1997).

Terman et al., "Identification of a New Endothelial Cell Growth Factor Receptor Tyrosine Kinase," 1991 *Oncogene* 6, 1677.

Thompson et al., "Improved accumulation and activity of ribozymes expressed from a tRNA–based RNA polymerase III promoter," *Nucleic Acids Research* 23:2259–2268 (1995).

Torrence et al., "Targeting RNA for degradation with a (2'–5') oligoadenylate–antisense chimera," *Proc. Natl. Acad. Sci. USA* 90:1300–1304 (1993).

Turner et al., "Free Energy Increments for Hydrogen Bonds in Nucleic Acid Base Pairs," *J. Am. Chem. Soc.* 109:3783–3785 (1987).

Turner et al., "Improved Parameters for Prediction of RNA Structure," *Cold Spring Harbor Symposia on Quantitative Biology* vol. Lii, pp. 123–133 (1987).

Uhlenbeck, "A Small Catalytic Oligoribonucleotide," *Nature* 328:596–600 (1987).

Usman and Cedergren, "Exploiting the chemical synthesis of RNA," *TIBS* 17:334–339 (1992) (Corrected from Specification).

Usman and McSwiggen, "Ch. 30—Catalytic RNA (Ribozymes) as Drugs," *Annual Reports in Medicinal Chemistry* 30:285–294 (1995).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman et al., "Chemical modification of hammerhead ribozymes: activity and nuclease resistance," *Nucleic Acids Syposium Series* 31:163–164 (1994).

Vaish et al., "Isolation of Hammerhead Ribozymes with Altered Core Sequences by in Vitro Selection," *Biochemistry* 36:6495–6501 (1997).

Vaisman et al., "Characterization of the Receptors for Vascular Endothelial Growth," 1990 *J. Biol. Chem.* 265, 19461.

Ventura et al., "Activation of HIV–Specific Ribozyme Activity by Self–Cleavage," *Nucleic Acids Research* 21:3249–3255 (1993).

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme," *Journal of Virology* 65:5531–5534 (1994) (Correction from Specification).

Weckbecker et al., 1992, *Angiogenesis: Key principles–Science–Technology–Medicine*, ed R. Steiner).

Wincott et al., "Synthesis, deprotection, analysis and purification of RNA and ribozymes," *Nucleic Acids Research* 23(14):2677–2684 (1995).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zaug et al., "The *Tetrahymena* Ribozyme Acts Like an RNA Restriction Endonuclease," *Nature* 324:429–433 (1986).

Zhou et al., "Synthesis of Functional mRNA in Mammalian Cells by Bacteriophage T3 RNA Polymerase," *Mol. Cell. Biol.* 10:4529–4537 (1990).

Ziche et al., "Angiogenesis Can Be Stimulated or Repressed In vivo by a Change in GM3:GD3 Ganglioside Ratio" 1992 *Lab. Invest.* 67:711–715.

Pierce, "Regulation of Vascular Endothelial Growth Factor by Oxygen in a Model of Retinopathy of Prematurity," Archives of Ophthalmology 114: 1219–1228 (1996).

Shibuya et al., "Nucleotide sequence and expression of a novel human receptor–type tyrosine kinase gene (*flt*) closely related to the *fms* family," *Oncogene* 5:519–524 (1990).

Usman et al., "Chemical modification of hammerhead ribozymes: activity and nuclease resistance," *Nucleic Acids Syposium Series* 31:163–164 (1994).

Parry et al. 1999. "Bioactivity of anti–angiogenic ribozymes targeting *Flt*–1 and *KDR* mRNA," *Nucleic Acid Res.* 27:2569–77.

U.S. Appl. No. 60/005974, filed Oct. 26, 1995, Pavco et al.

U.S. Appl. No. 60/082404, filed Apr. 20, 1998, Thompson et al.

U.S. Appl. No. 60/101171, filed Sep. 21, 1998, Hartman et al.

* cited by examiner

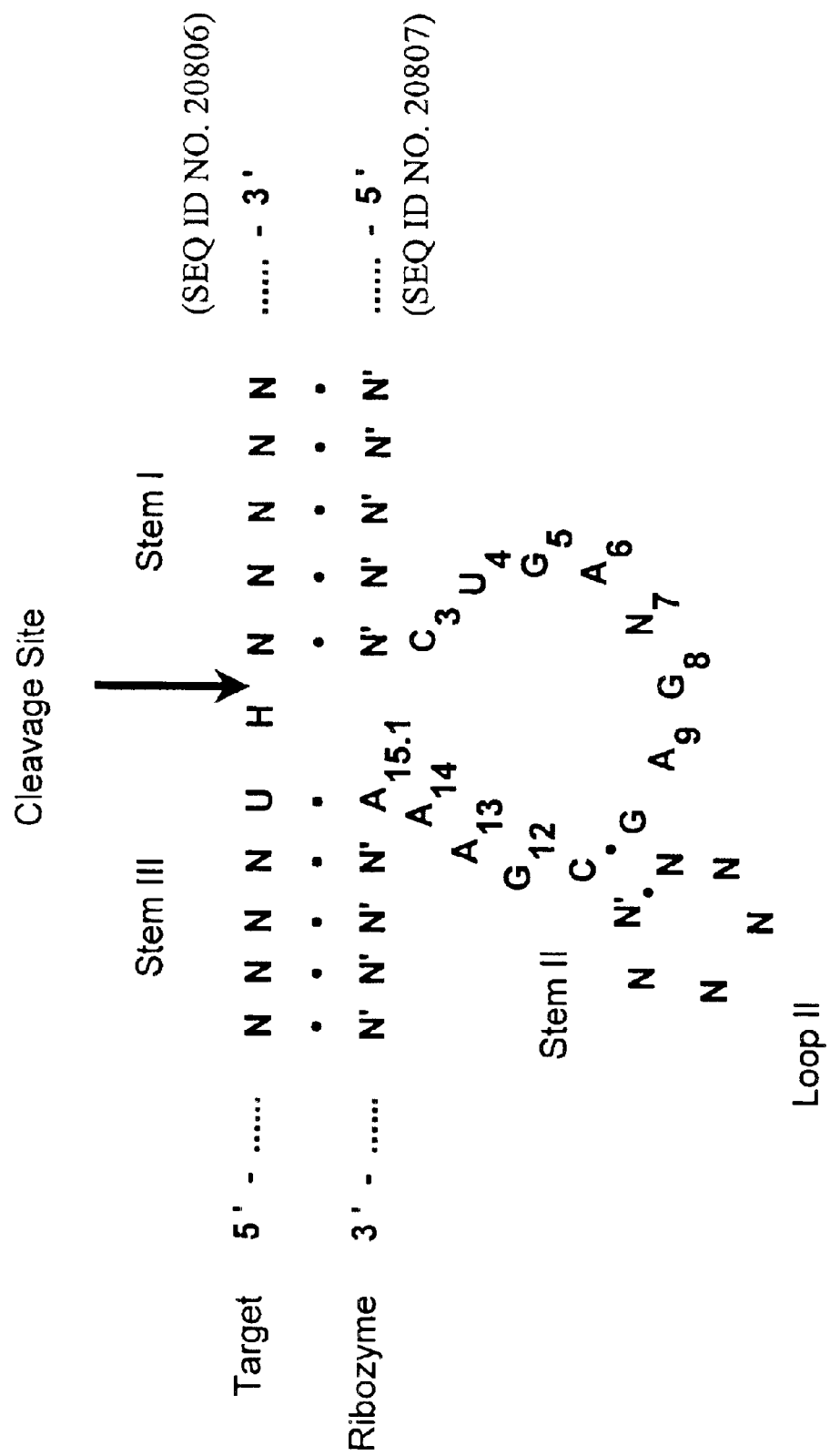
Figure 1: Hammerhead Ribozyme

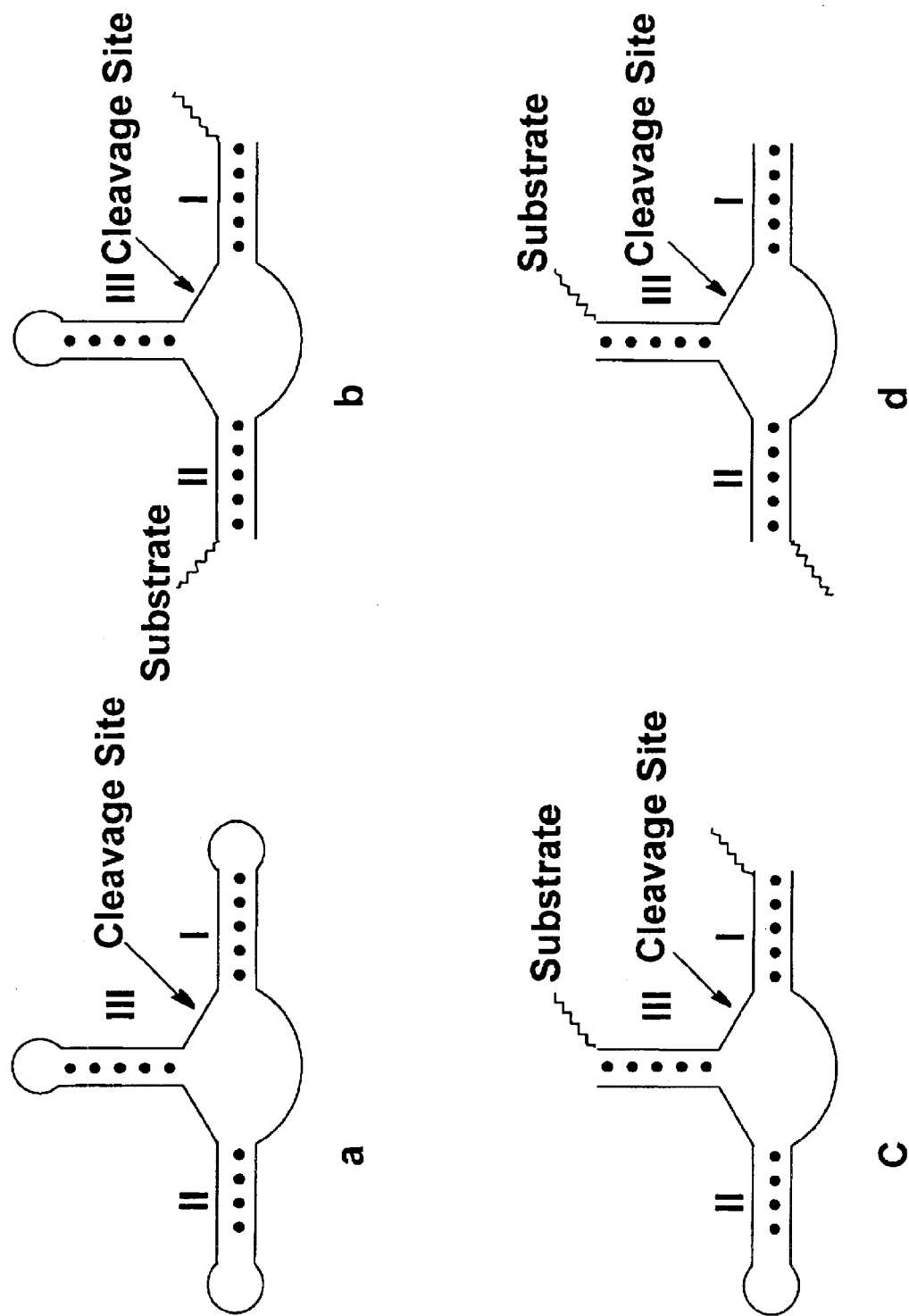
Figure 2. Hammerhead Ribozyme Substrate Motifs

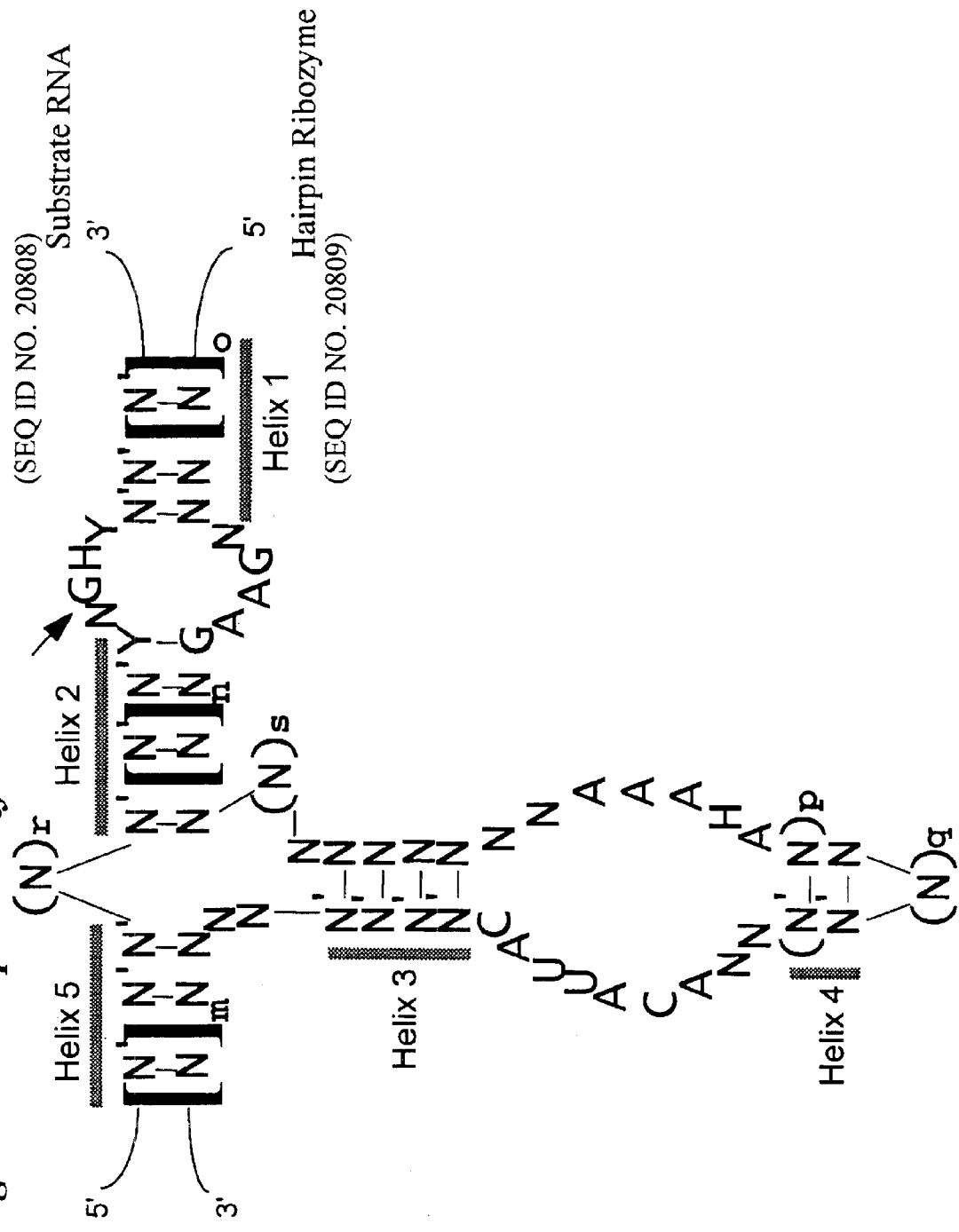
Figure 3: Hairpin Ribozyme

Figure 4: Hepatitis Delta Virus Ribozyme
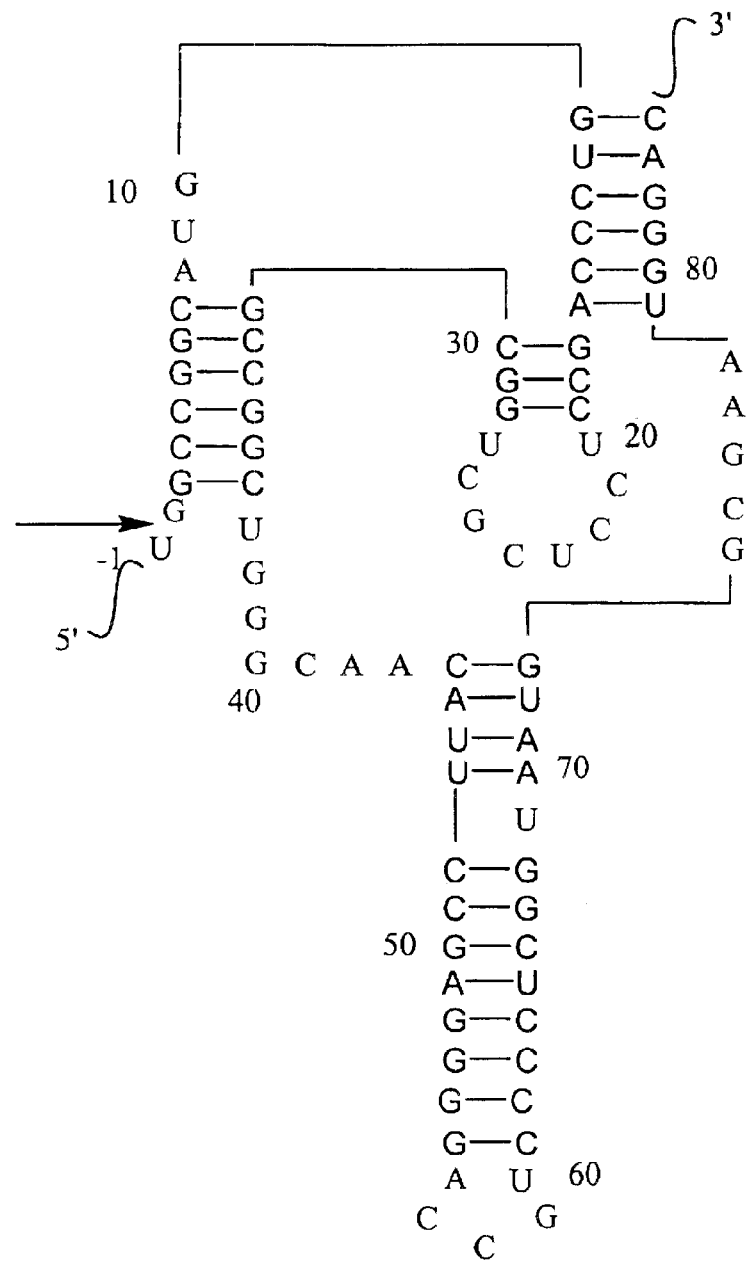
(SEQ ID NO 20810)

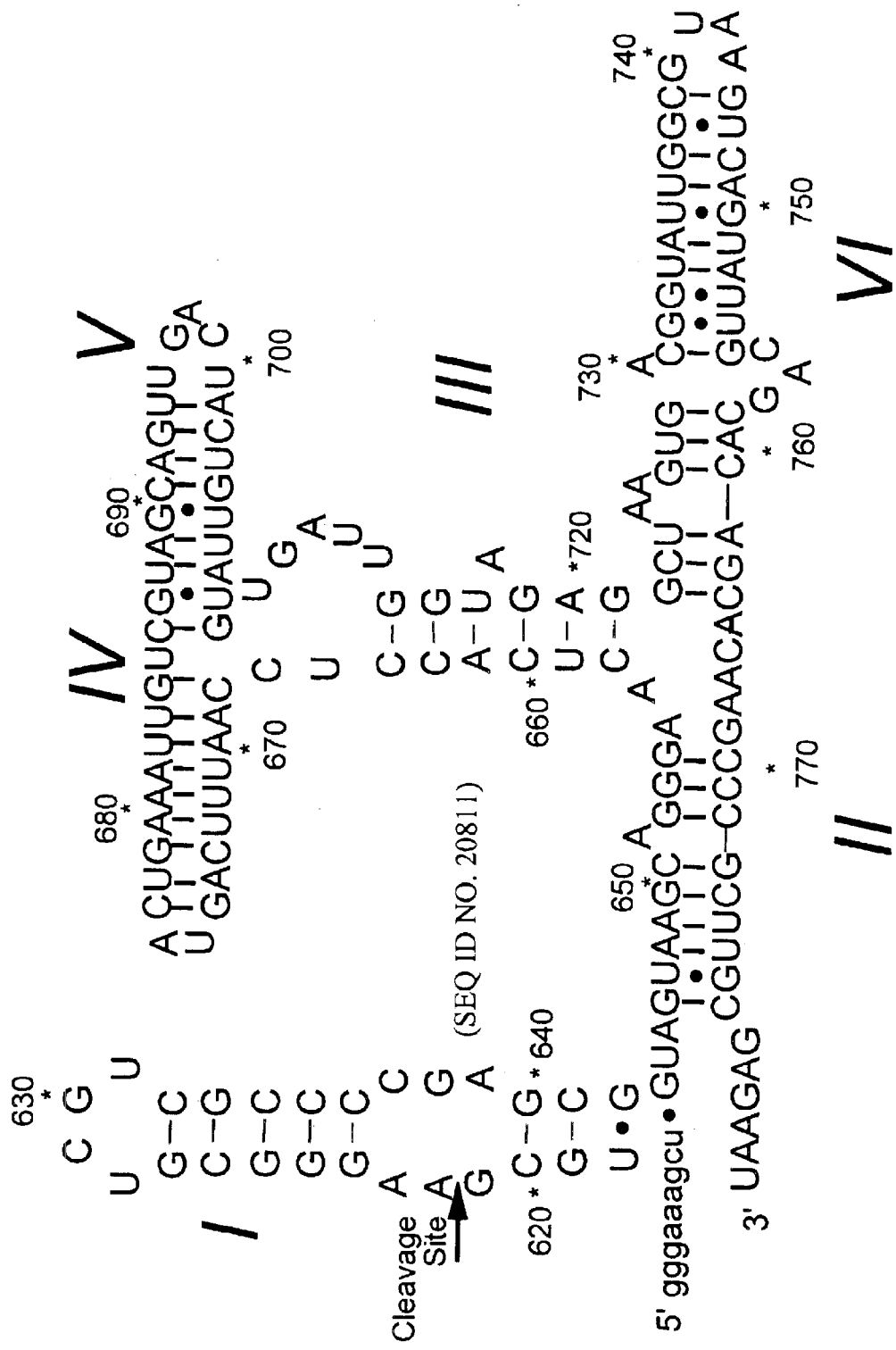
Figure 5. Neurospora vs Ribozyme

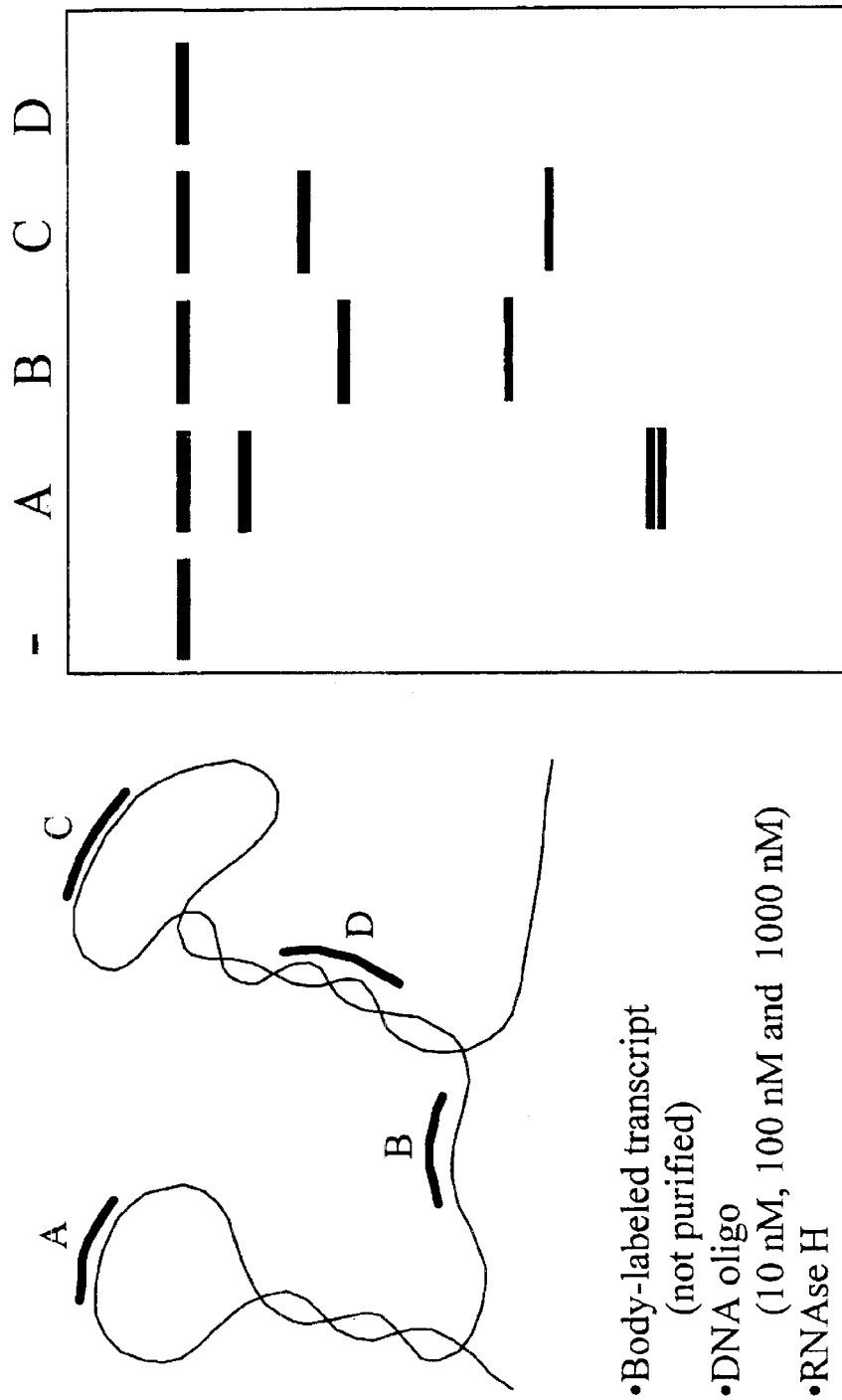
Figure 6: RNase H Assay

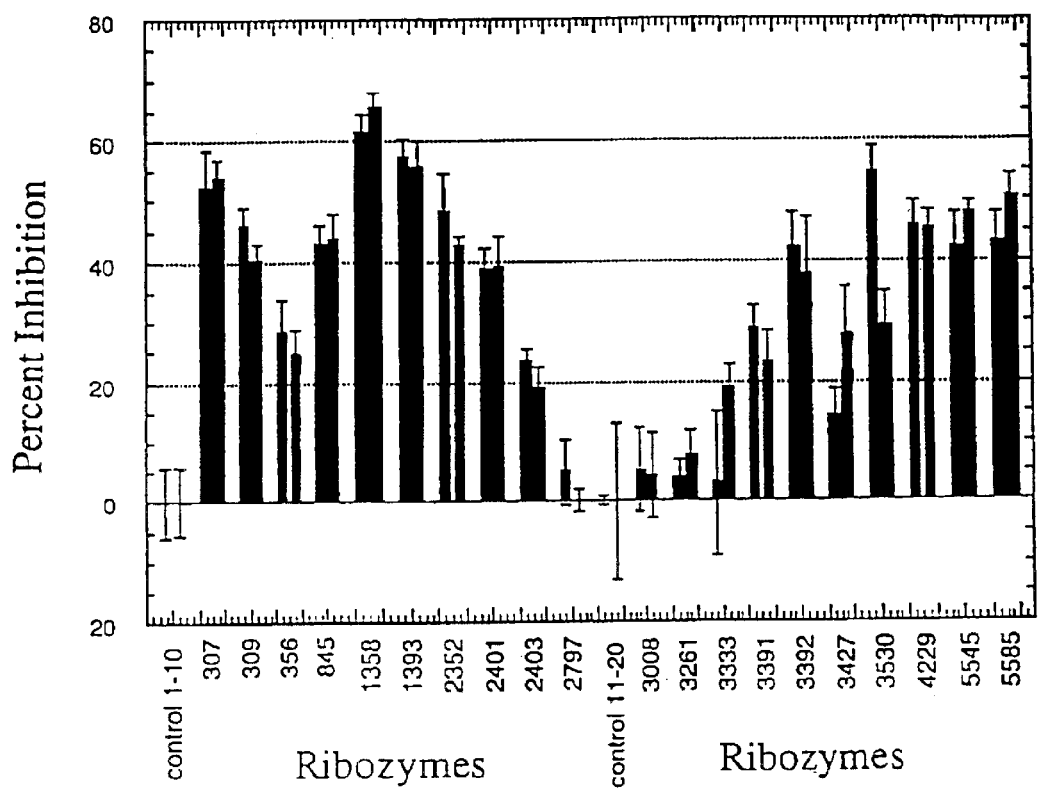
Figure 7: Anti-FLT Ribozyme-Mediated Inhibition of VEGF Binding to FLT Receptor (Human Microvascular Endothelial Cells)

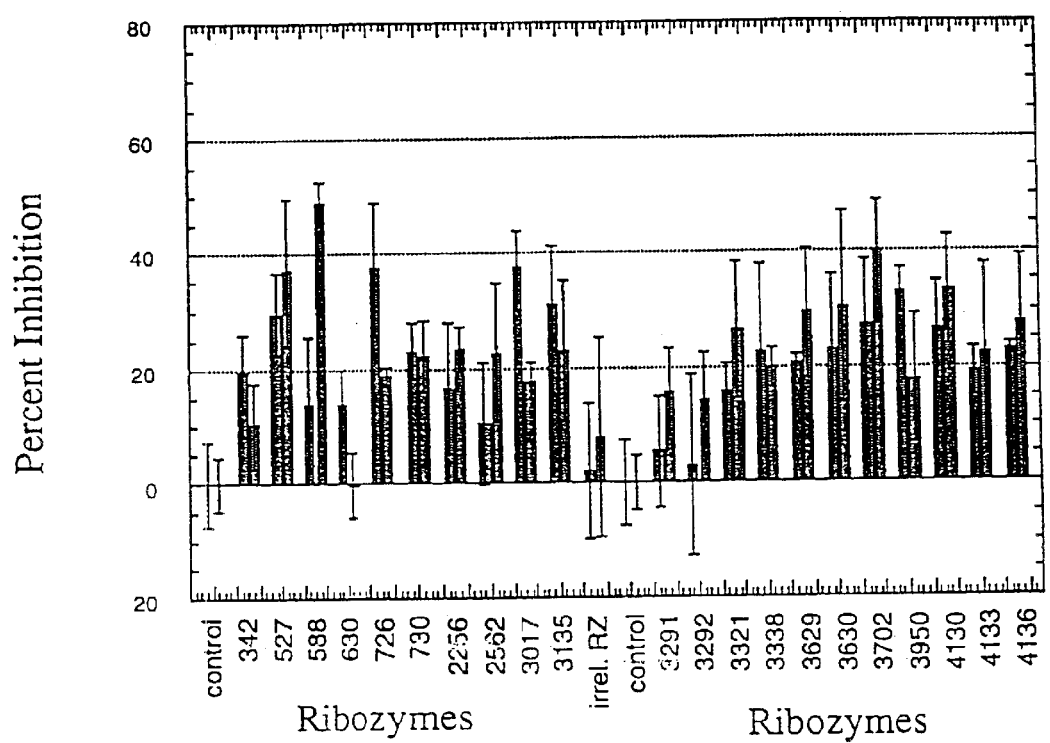
Figure 8: Anti-KDR Ribozyme-Mediated Inhibition of VEGF Binding to KDR Receptor (Human Microvascular Endothelial Cells)

Figure 9: Specificity of Anti-FLT Ribozyme-Mediated Inhibition of VEGF Binding
(Human Microvascular Endothelial Cells)
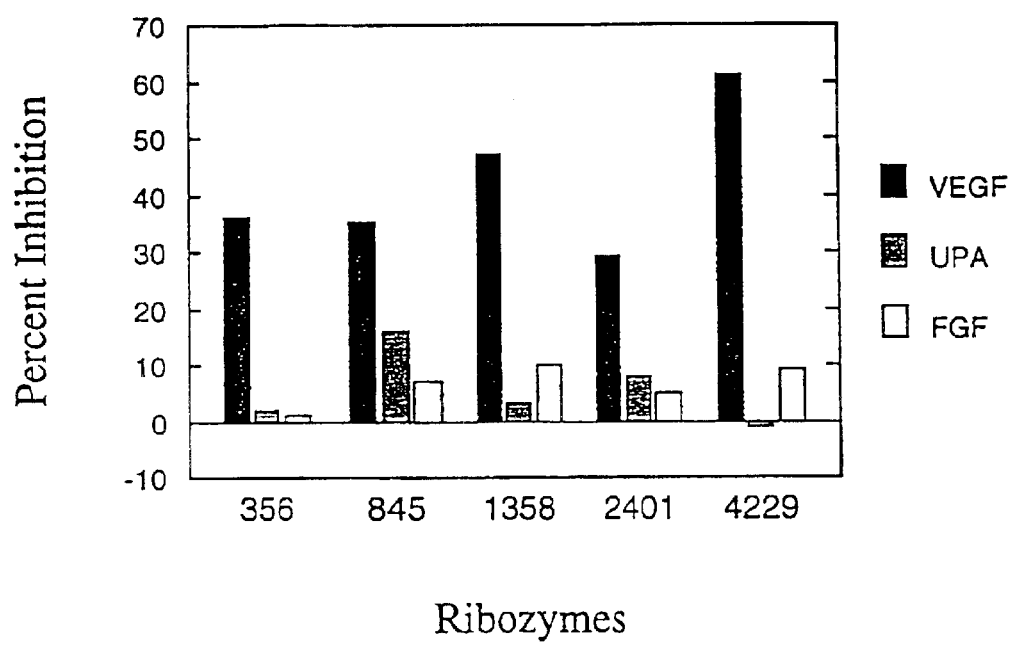

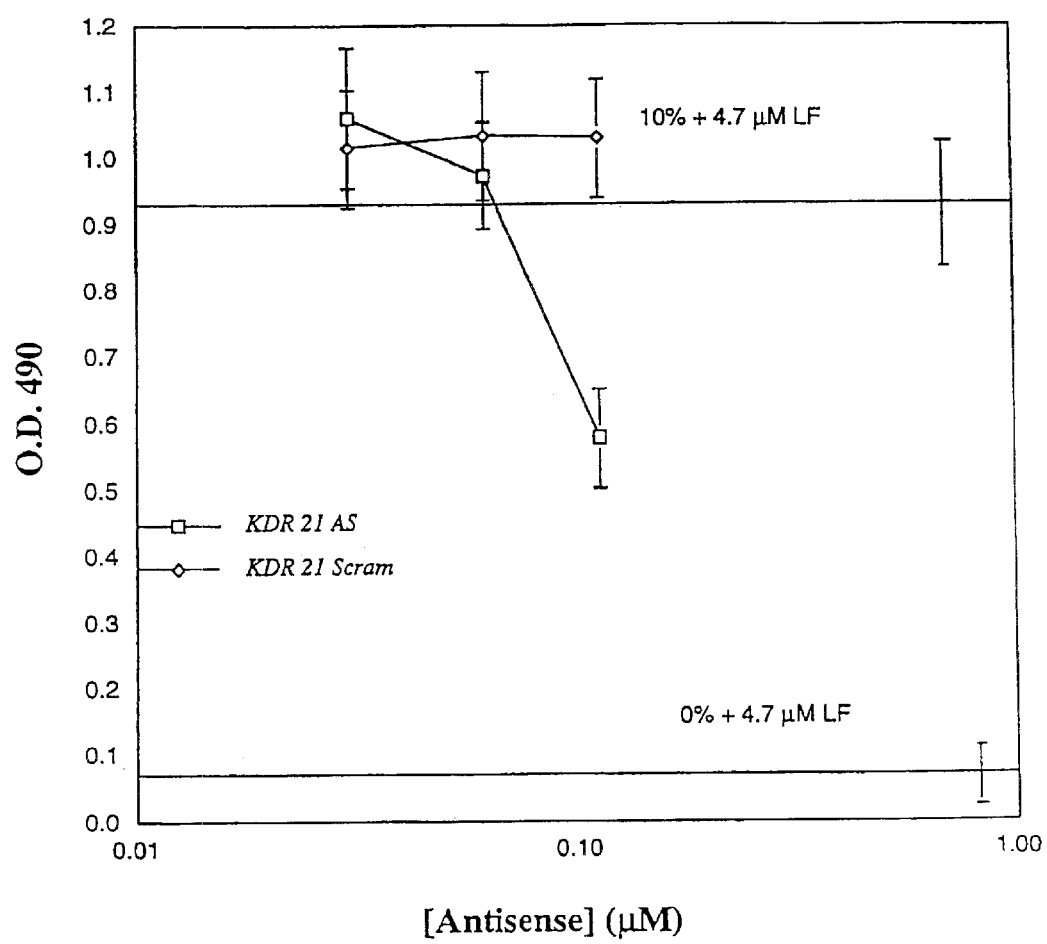
Figure 10: Anti-KDR Antisense-Mediated Inhibition of Human aortic endothelial cell (HAEC) Proliferation

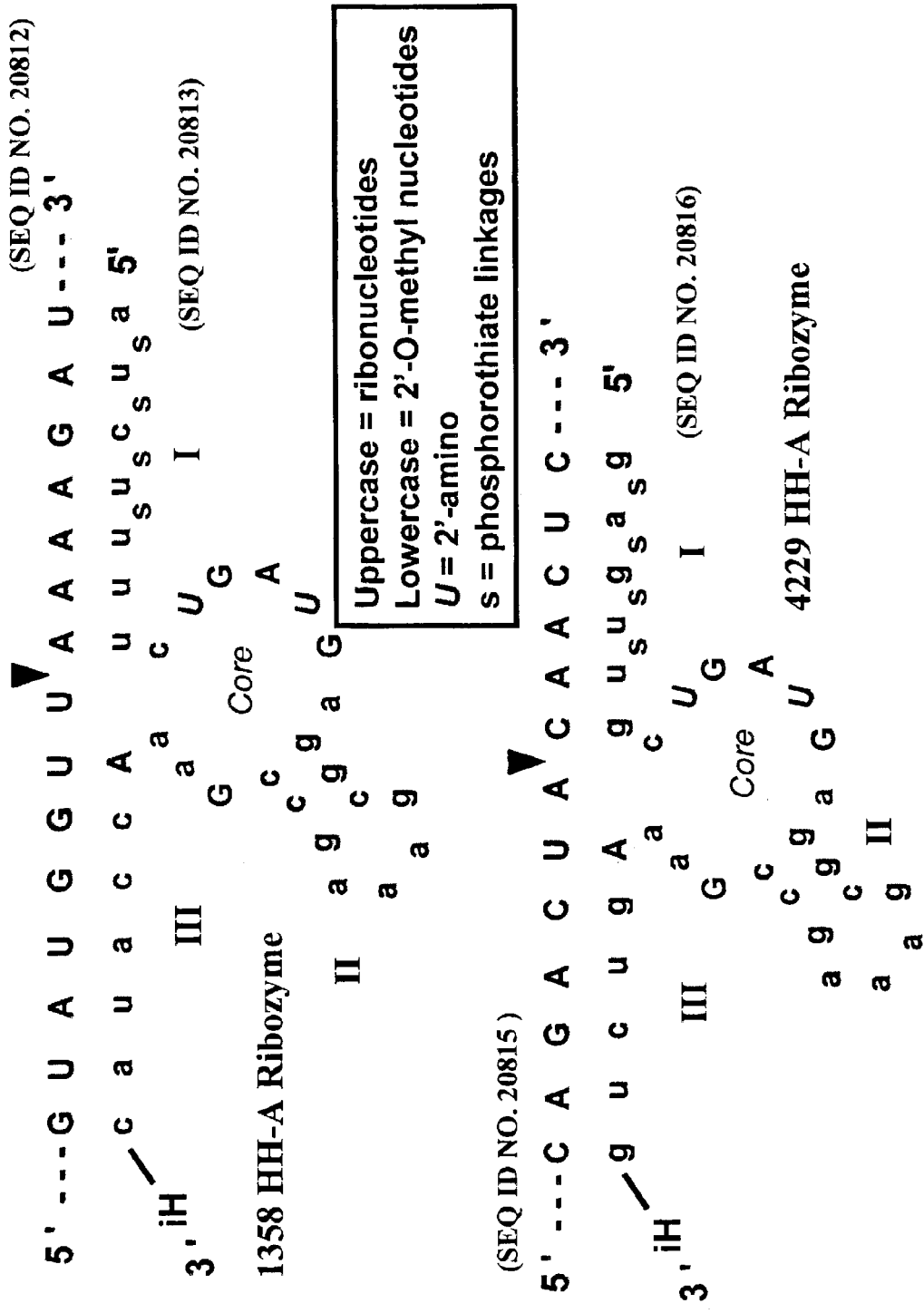
Figure 11A: Hammerhead Ribozymes Targeted Against flt-1 RNA

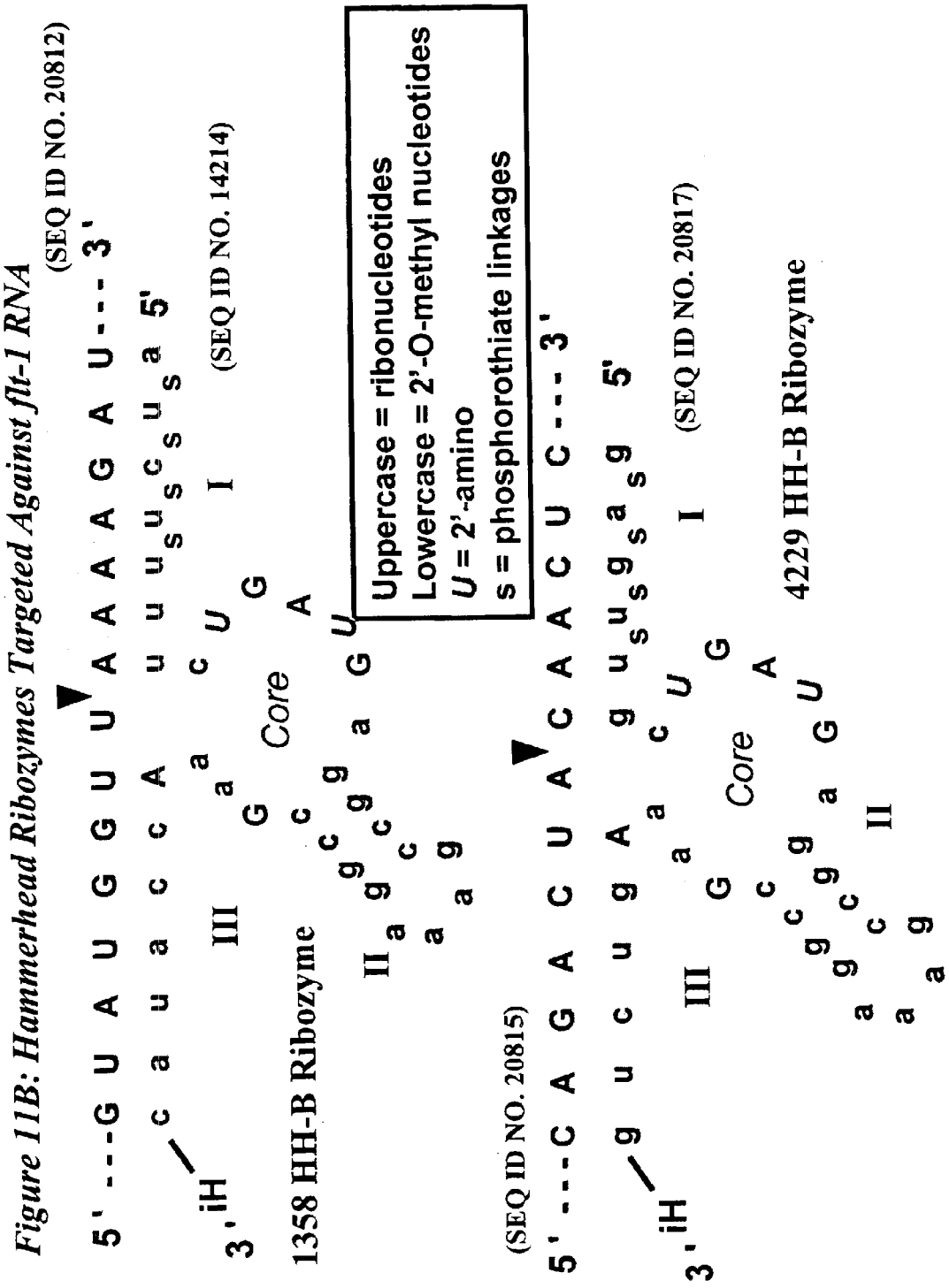
Figure 11B: Hammerhead Ribozymes Targeted Against flt-1 RNA

Figure 11C: Cleavage of flt-1 RNA by 1358 HH Ribozymes
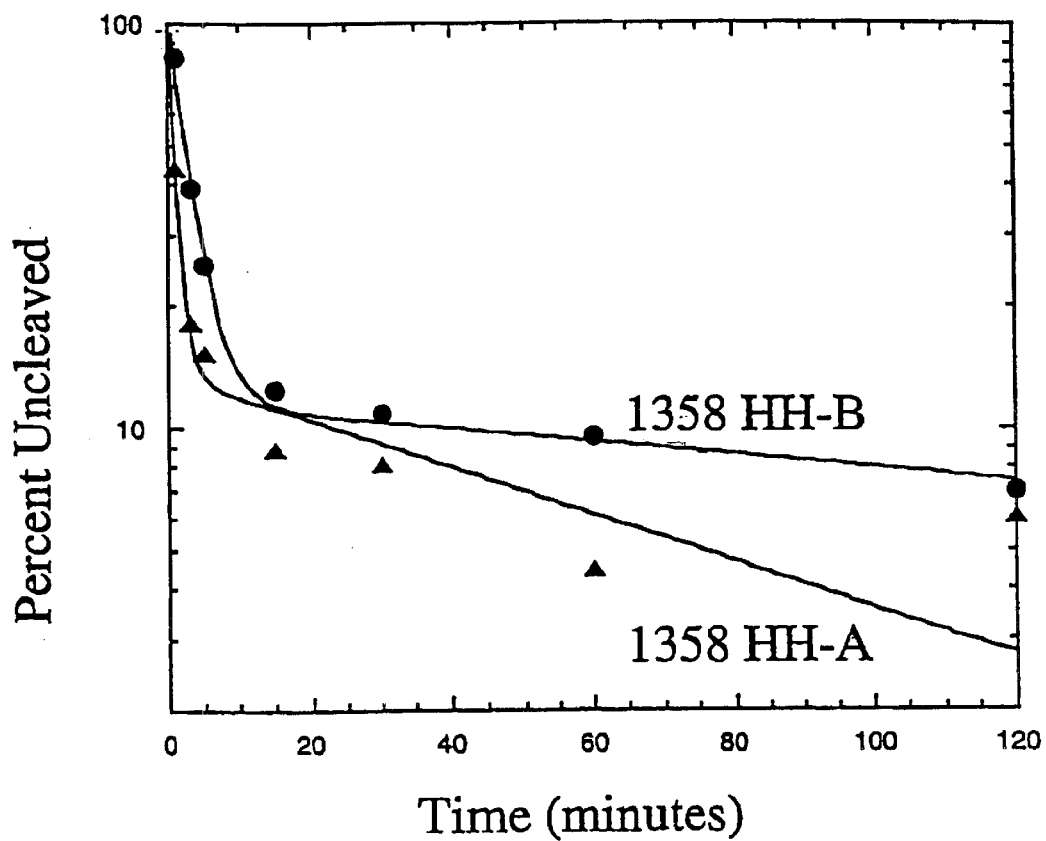
[Ribozyme] = 40 nM   [Substrate] = ~1nM Figure 11D : Cleavage of flt-1 RNA by 4229 HH Ribozymes
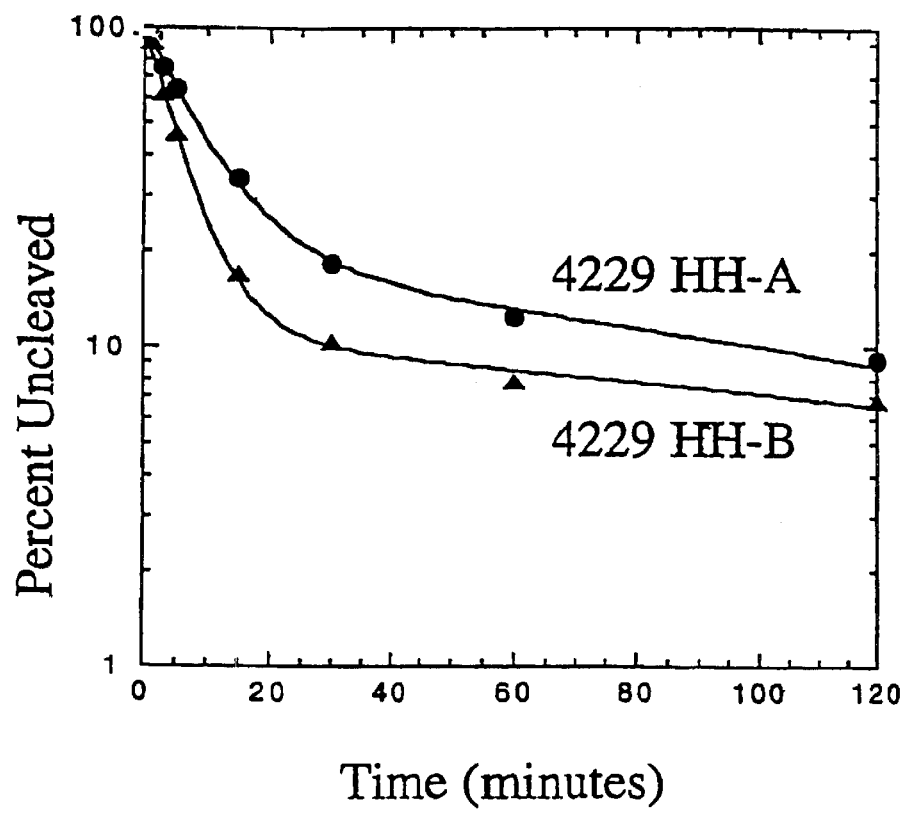
[Ribozyme] = 40 nM   [Substrate] = ~1nM

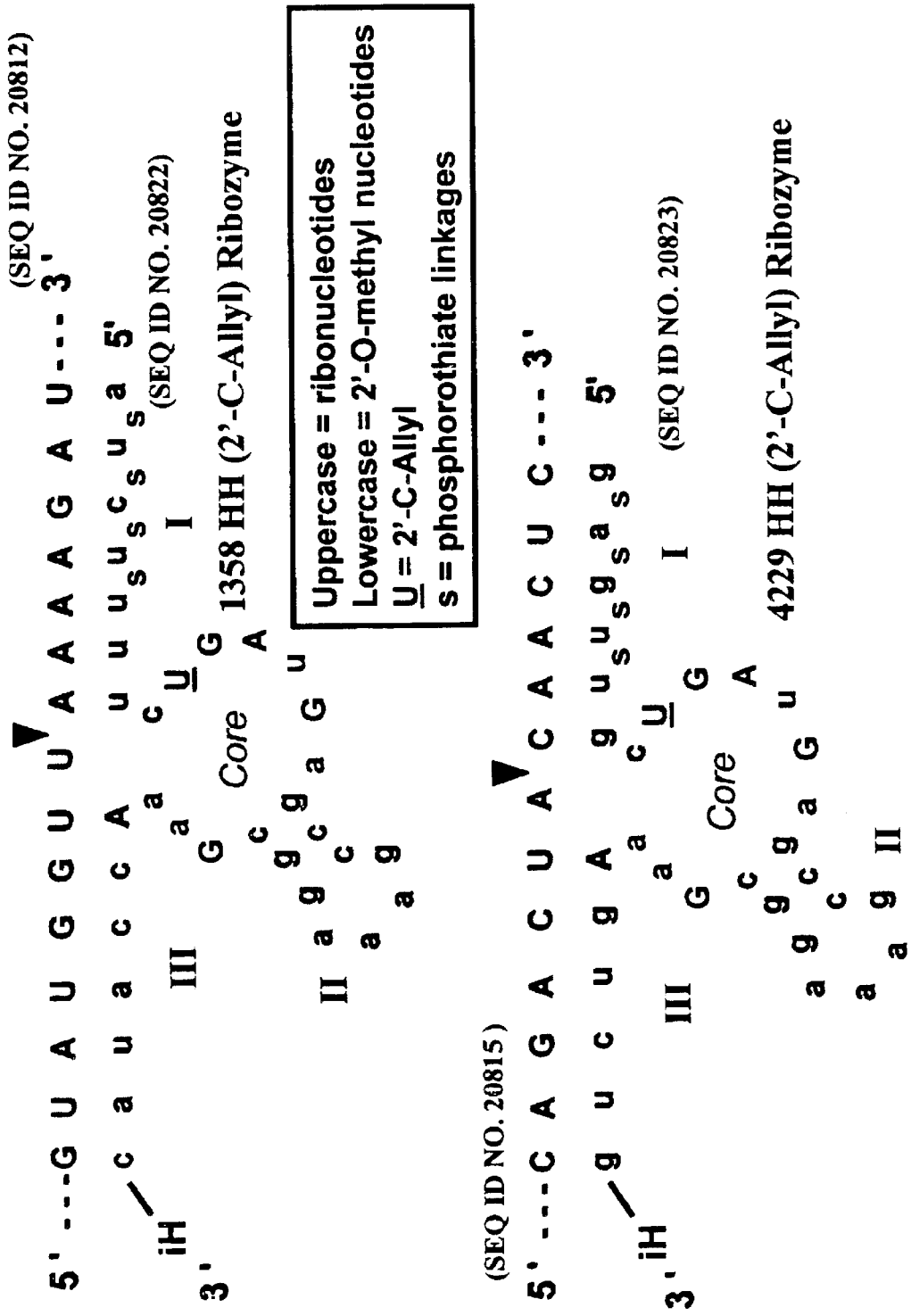
Figure 12A: Hammerhead Ribozymes Targeted Against flt-1 RNA

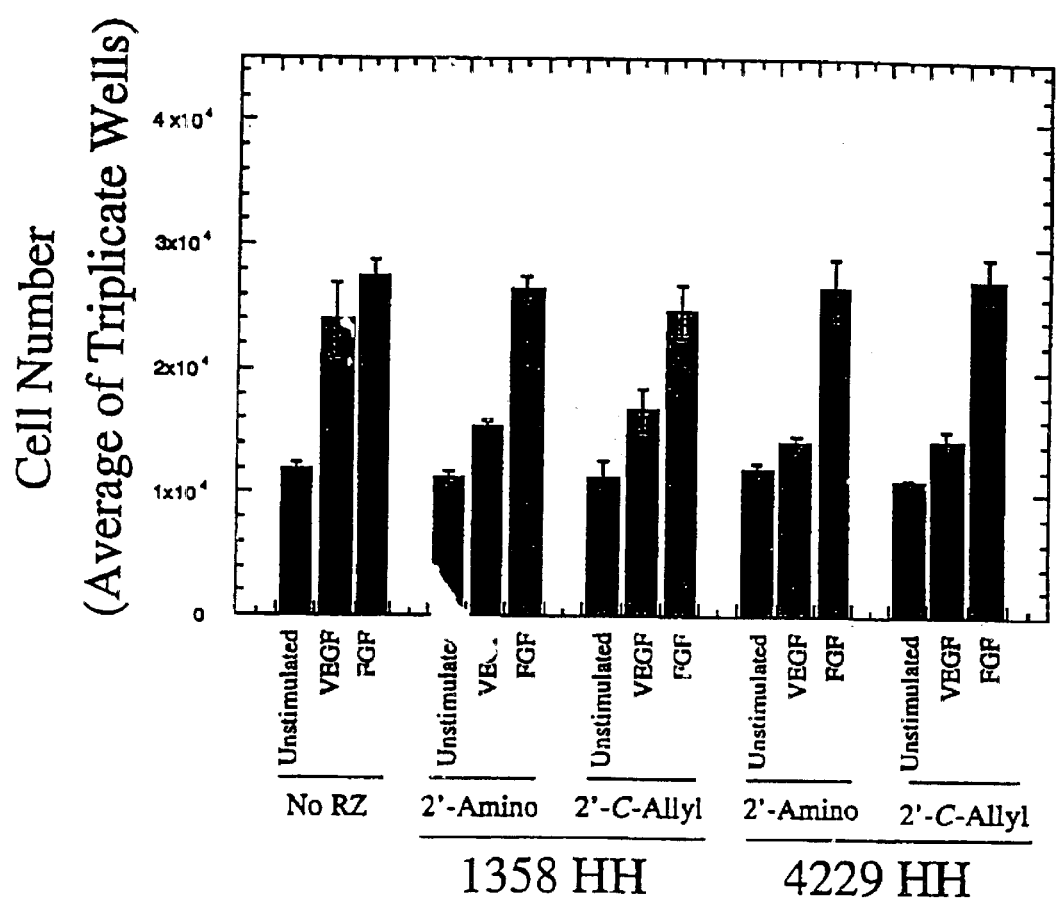
Figure 12B: Anti-flt-1 Ribozyme-Mediated Inhibition of Cell Proliferation

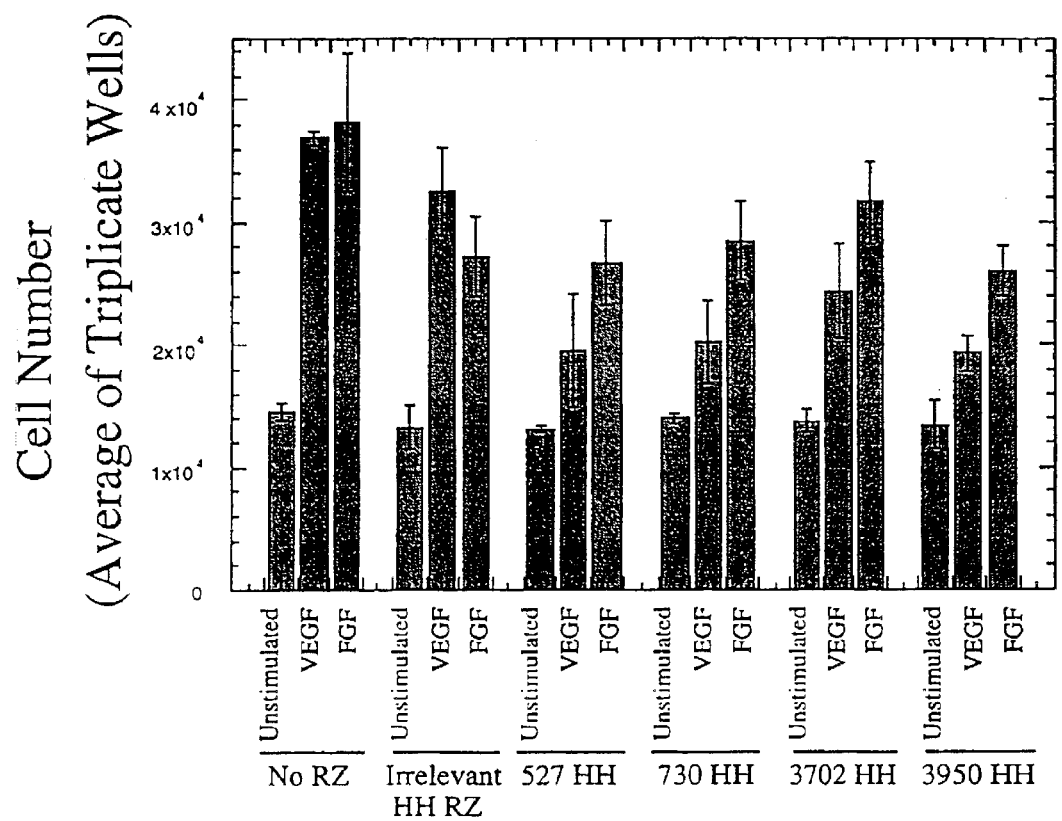
Figure 13: Anti-KDR Ribozyme-Mediated Inhibition of Cell Proliferation

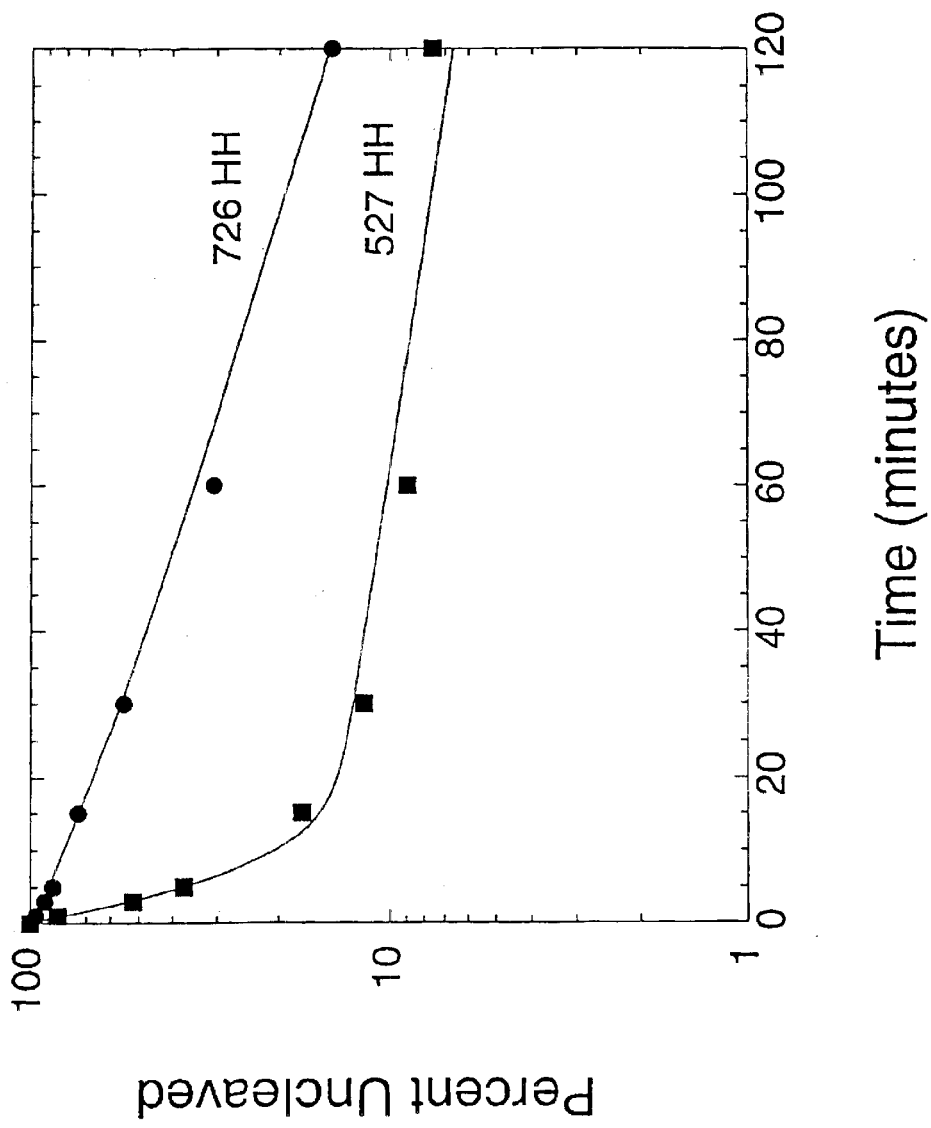
Figure 14: Cleavage of KDR RNA by Hammerhead Ribozymes

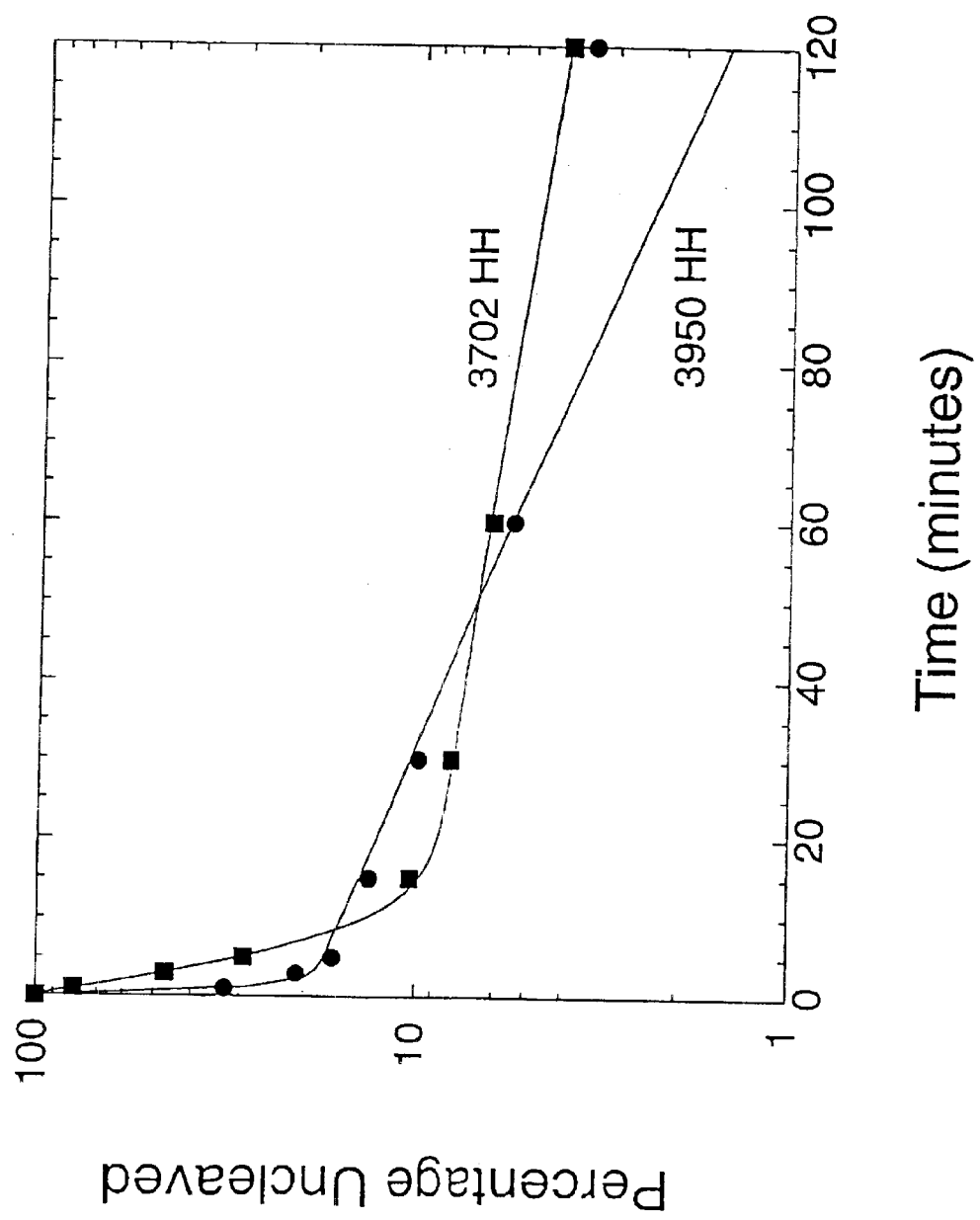
Figure 15: Cleavage of KDR RNA by Hammerhead ribozymes

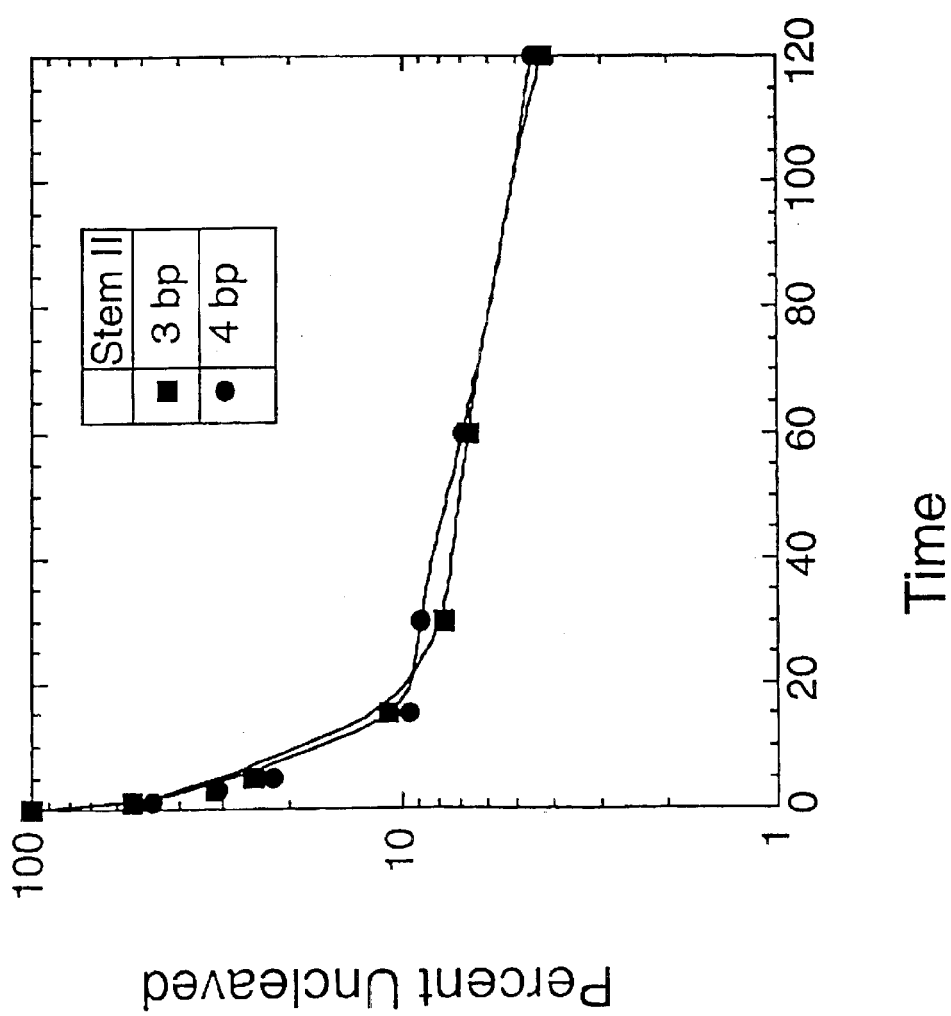
Figure 16: RNA Cleavage by FLT/KDR-I Hammerhead Ribozyme

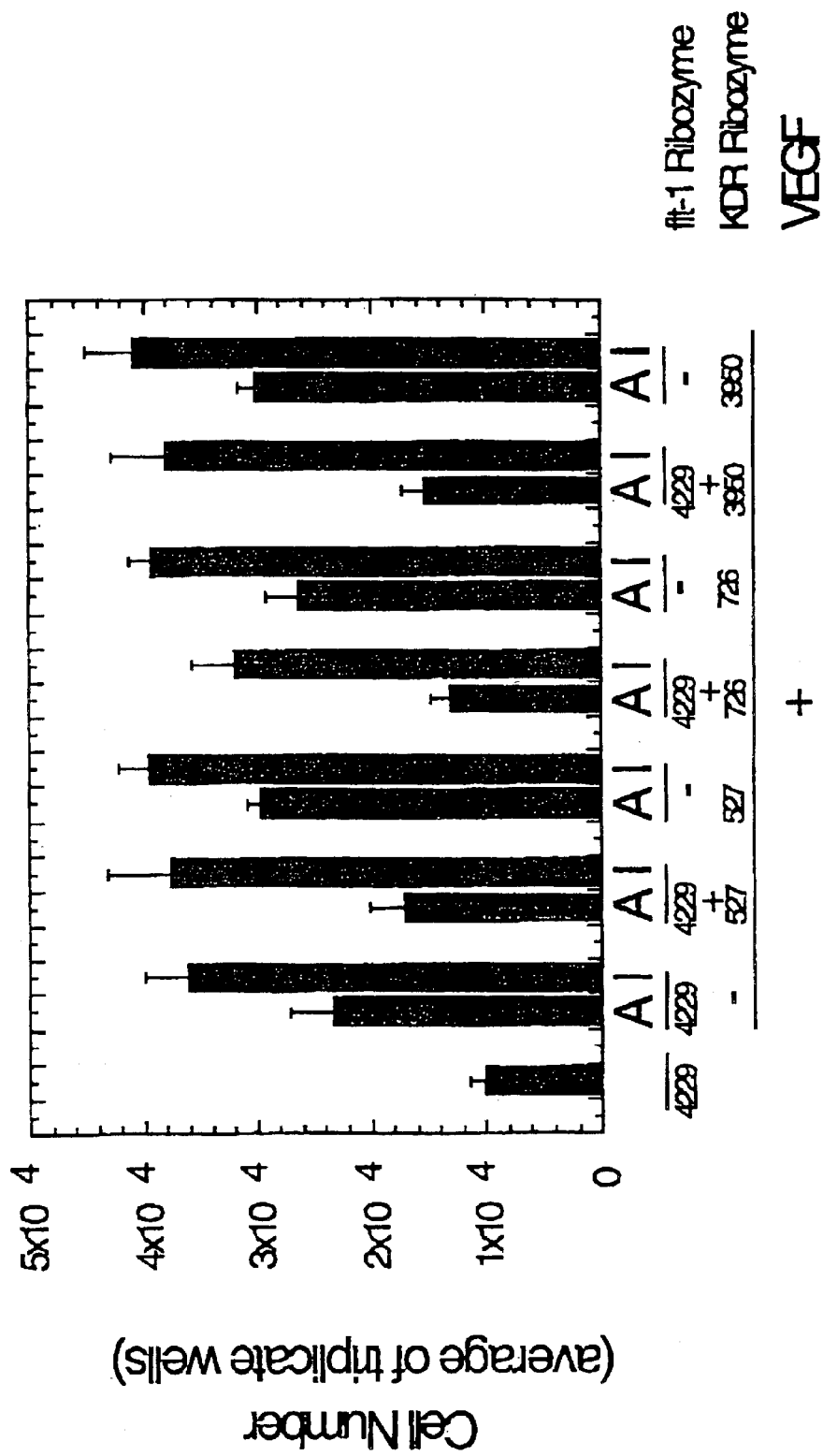

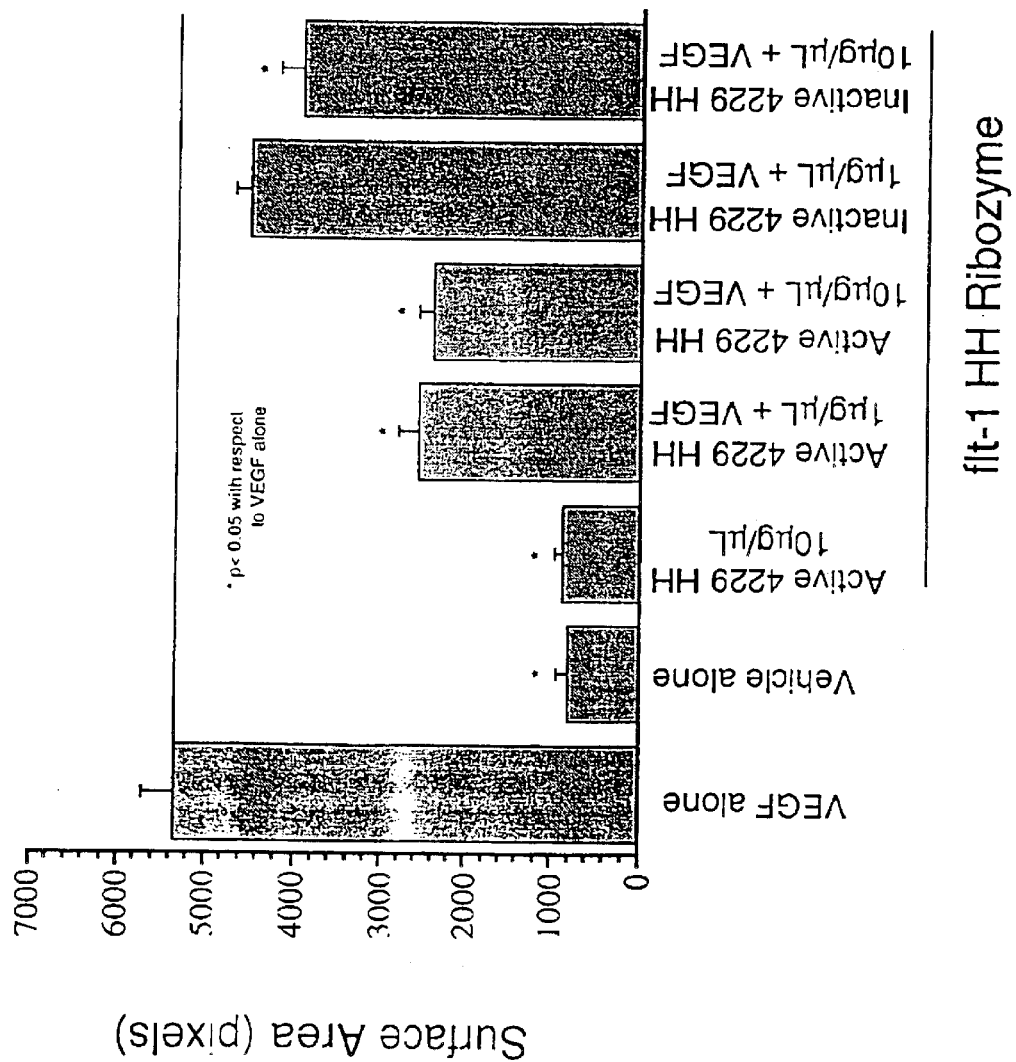
Figure 18: Inhibition of Angiogenesis by Hammerhead Ribozymes *In Vivo*

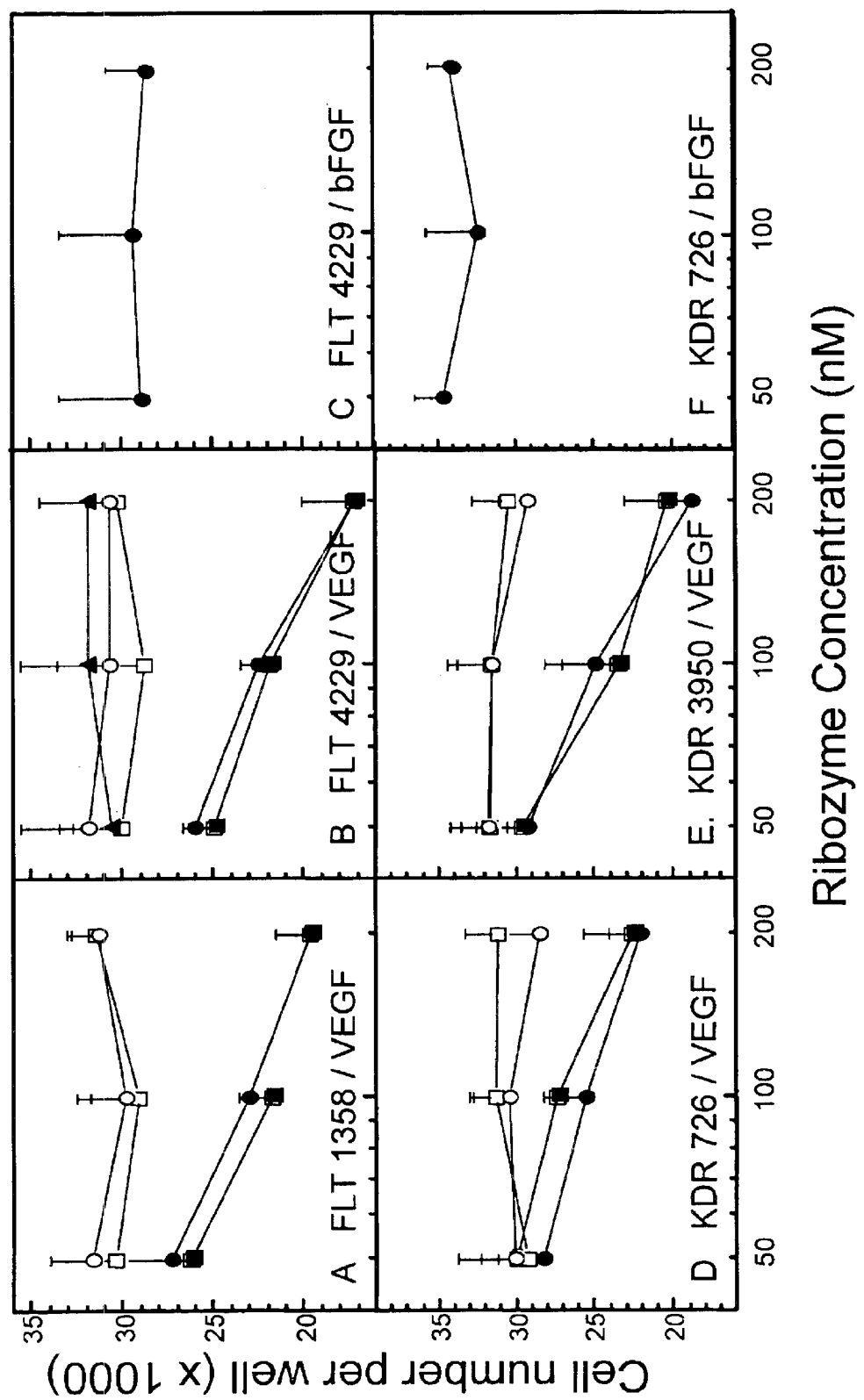
Figure 19: Ribozyme-mediated inhibition of Cell Proliferation

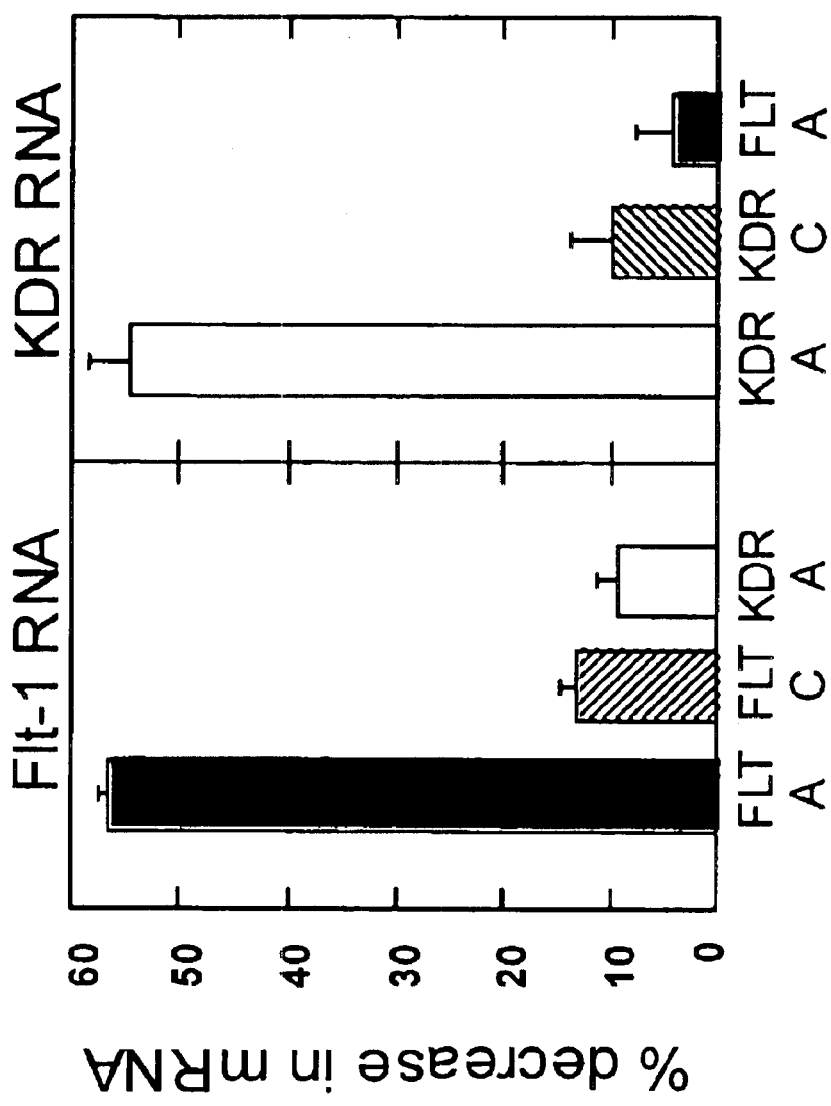
Figure 20: Target Specificity of Ribozymes

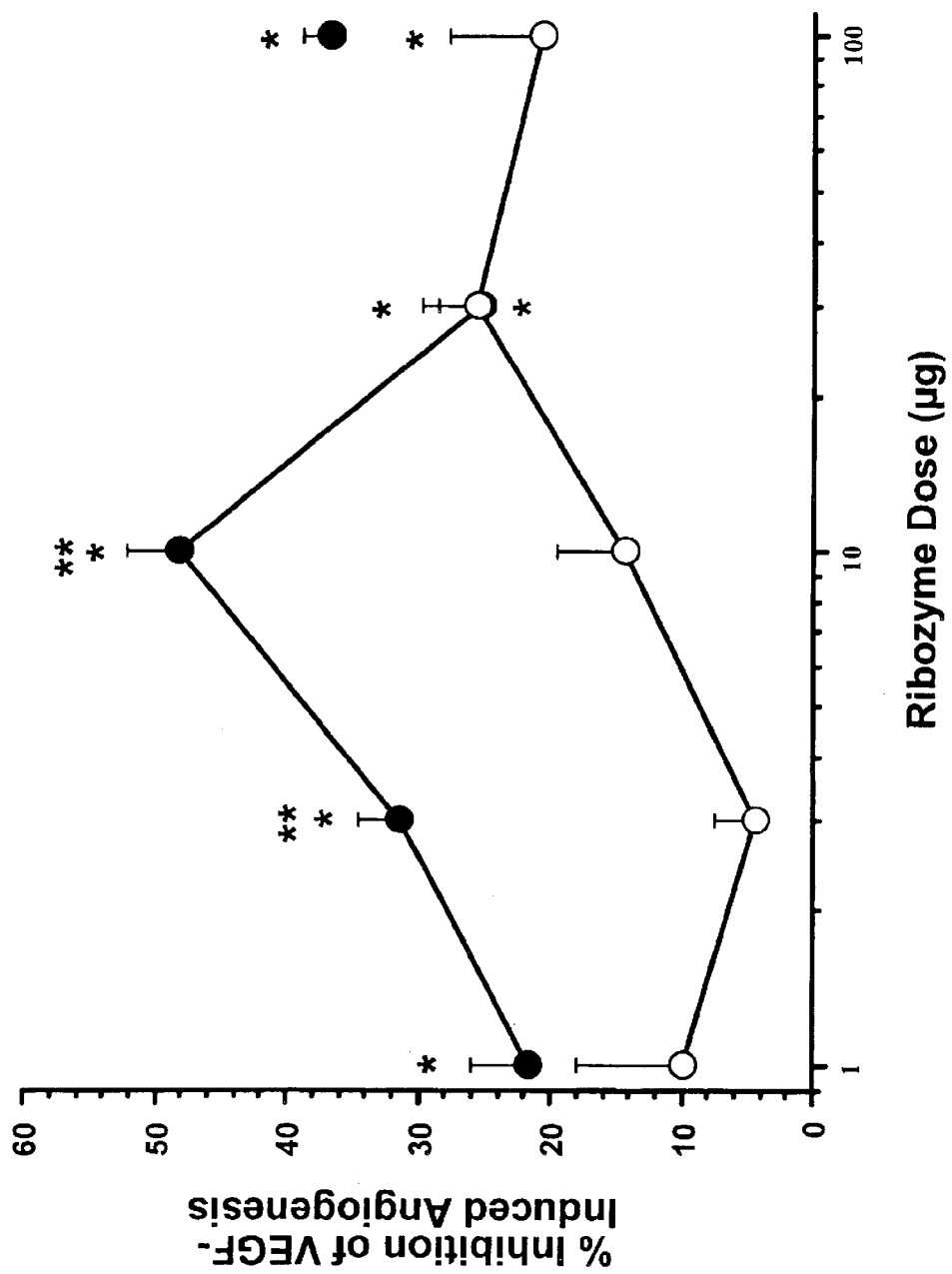
Figure 21: Anti-angiogenic activity of anti-flt ribozyme

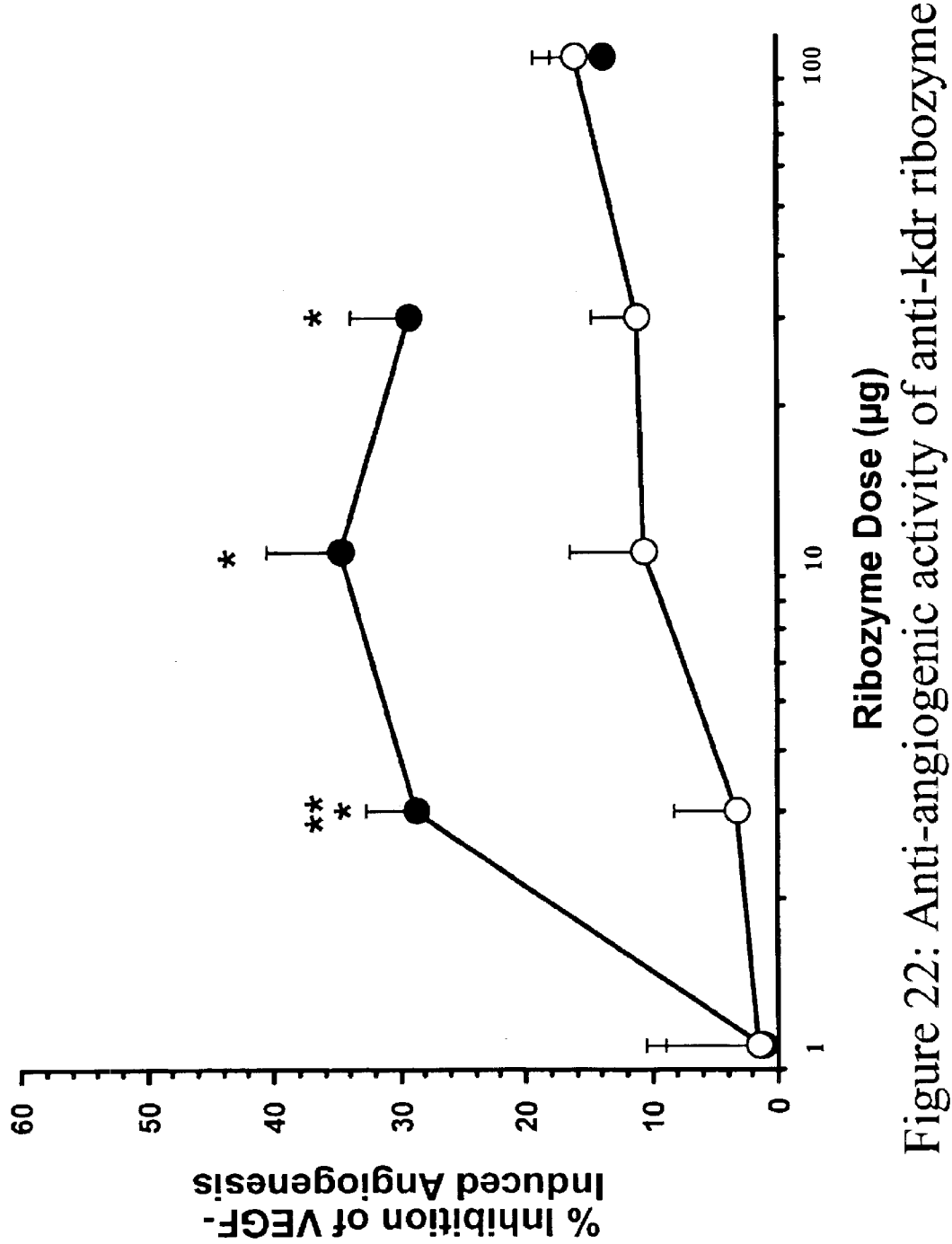
Figure 22: Anti-angiogenic activity of anti-kdr ribozyme

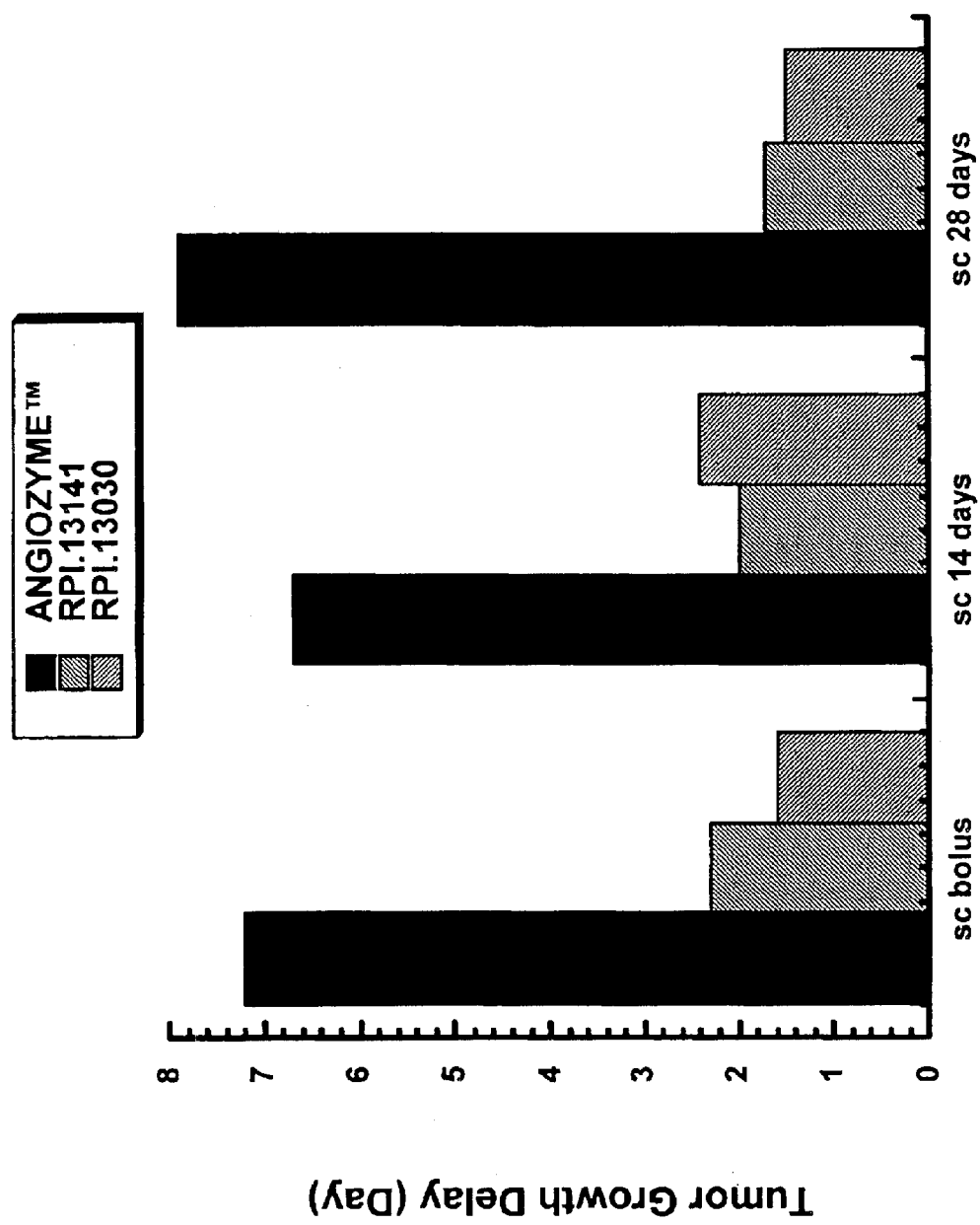
Figure 23: Ribozyme-Mediated Inhibition of Tumor Growth

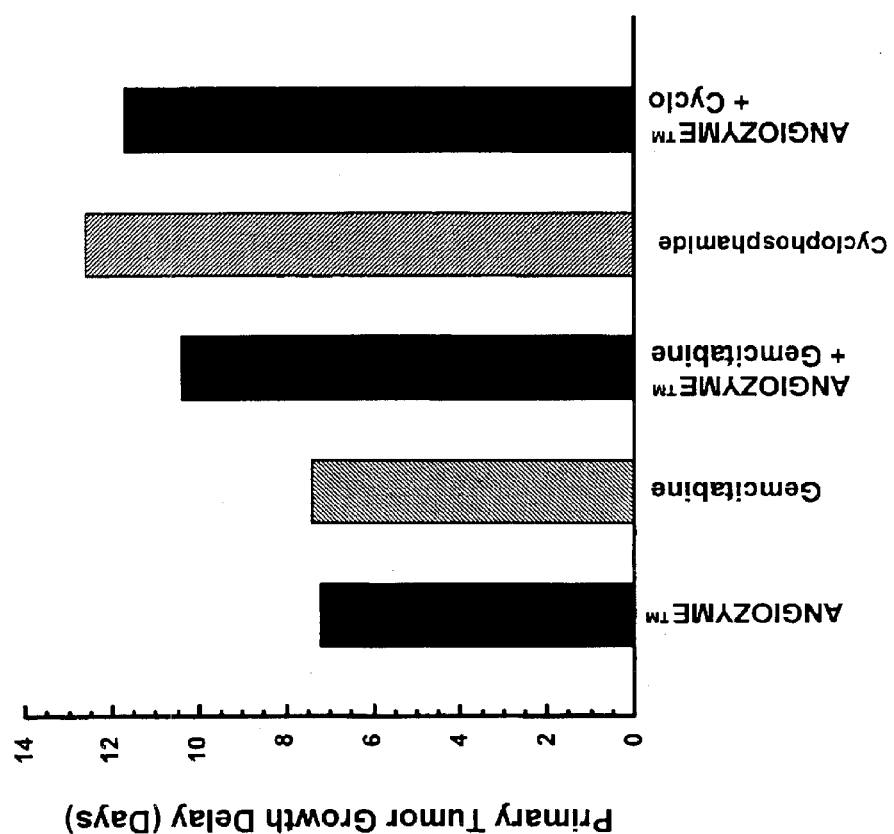
Figure 24: Effect of Ribozyme in Combination with Cytotoxic Agents on Primary Tumor Growth

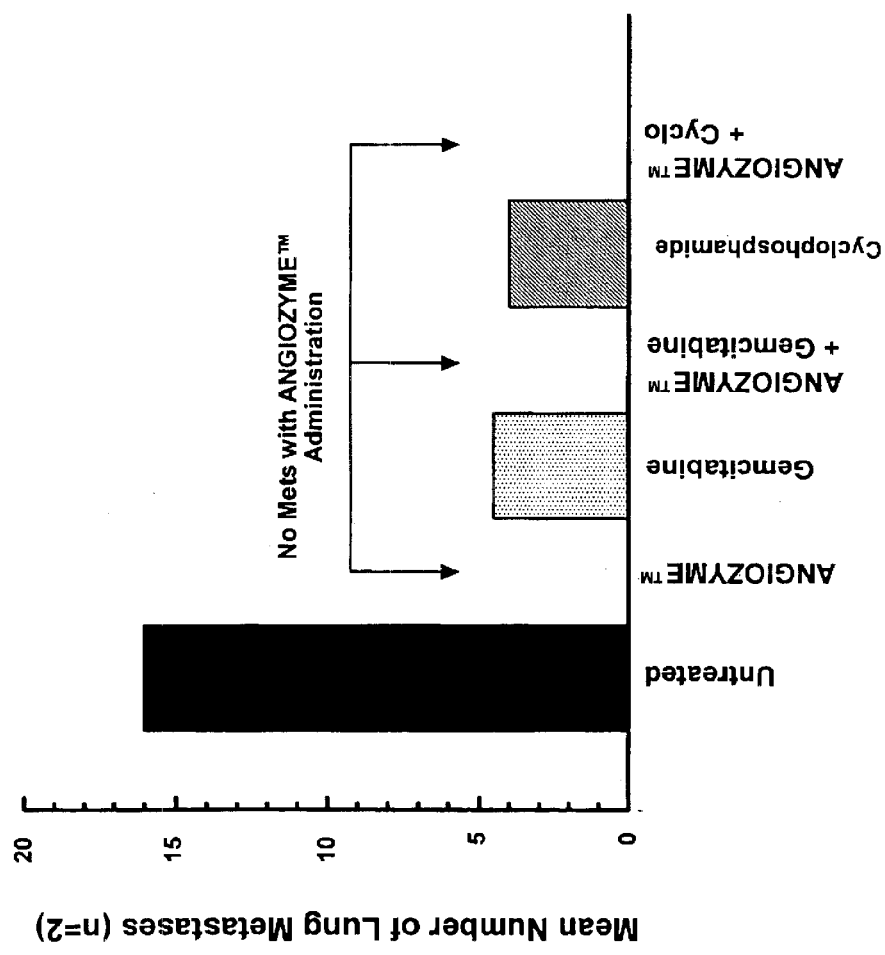
Figure 25: Effect of Ribozyme in Combination with Cytotoxic Agents on Lung Metastases

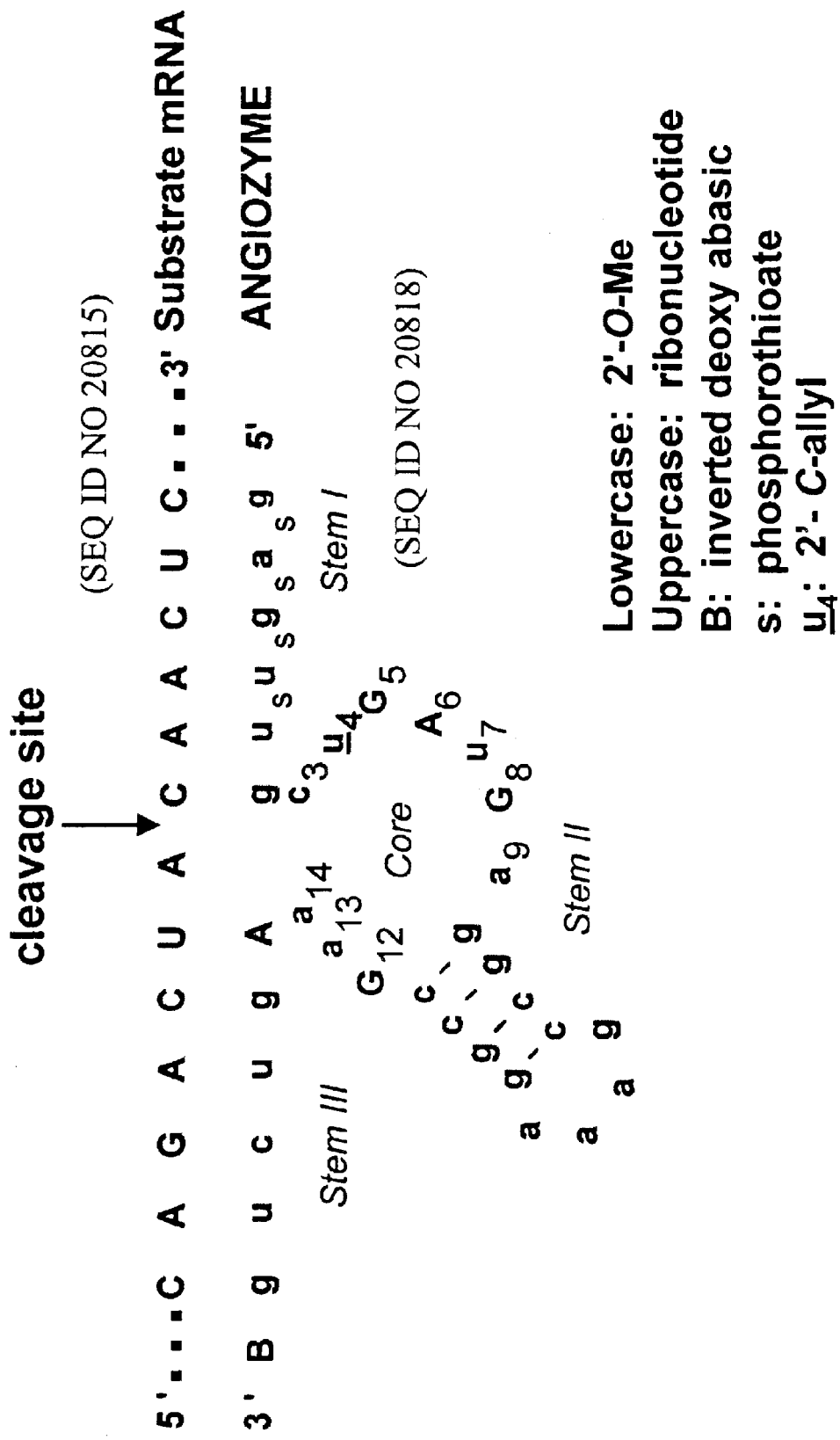
Figure 26 Anti-Flt-1 Ribozyme: ANGIOZYME

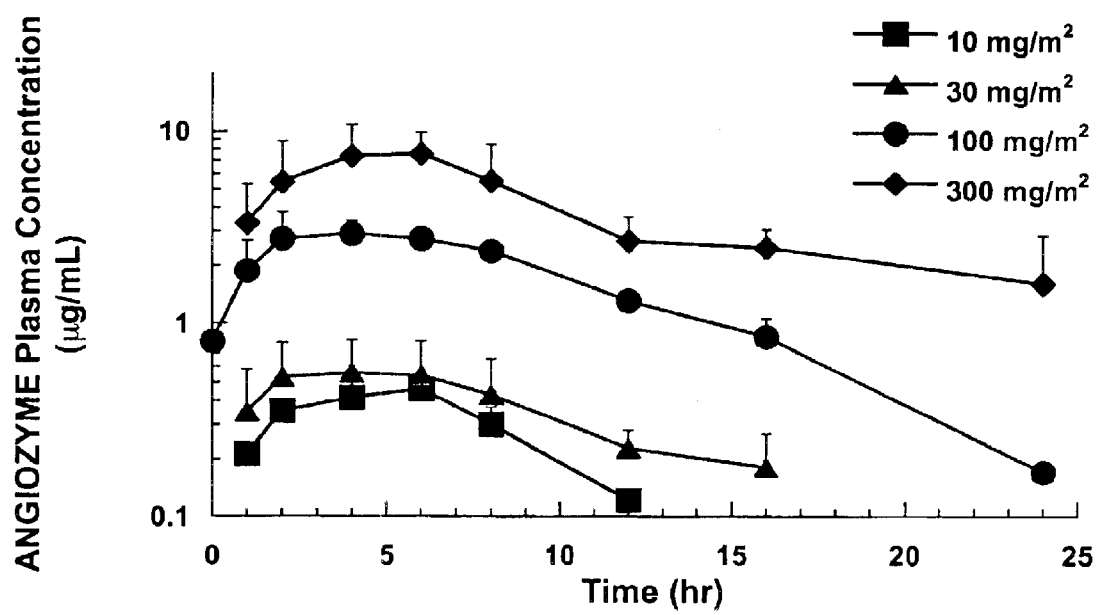
Figure 31: Plasma concentration profile of ANGIOZYME after a single subcutaneous dose of 10, 30, 100 or 300 mg/m$^2$

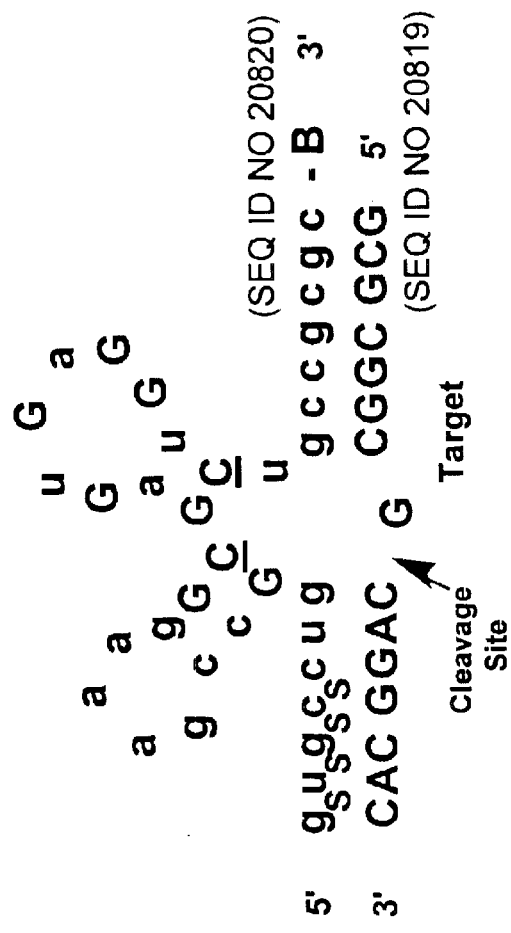
Figure 32: Stabilized Zinzyme Ribozyme Motif
Legend
Uppercase indicates natural ribo residues
C indicates 2'- d-NH$_2$-C
Lowercase indicates 2'- O-Me
Subscript s indicates phosphothioate linkage
B indicates 5'- 3' abasic moiety

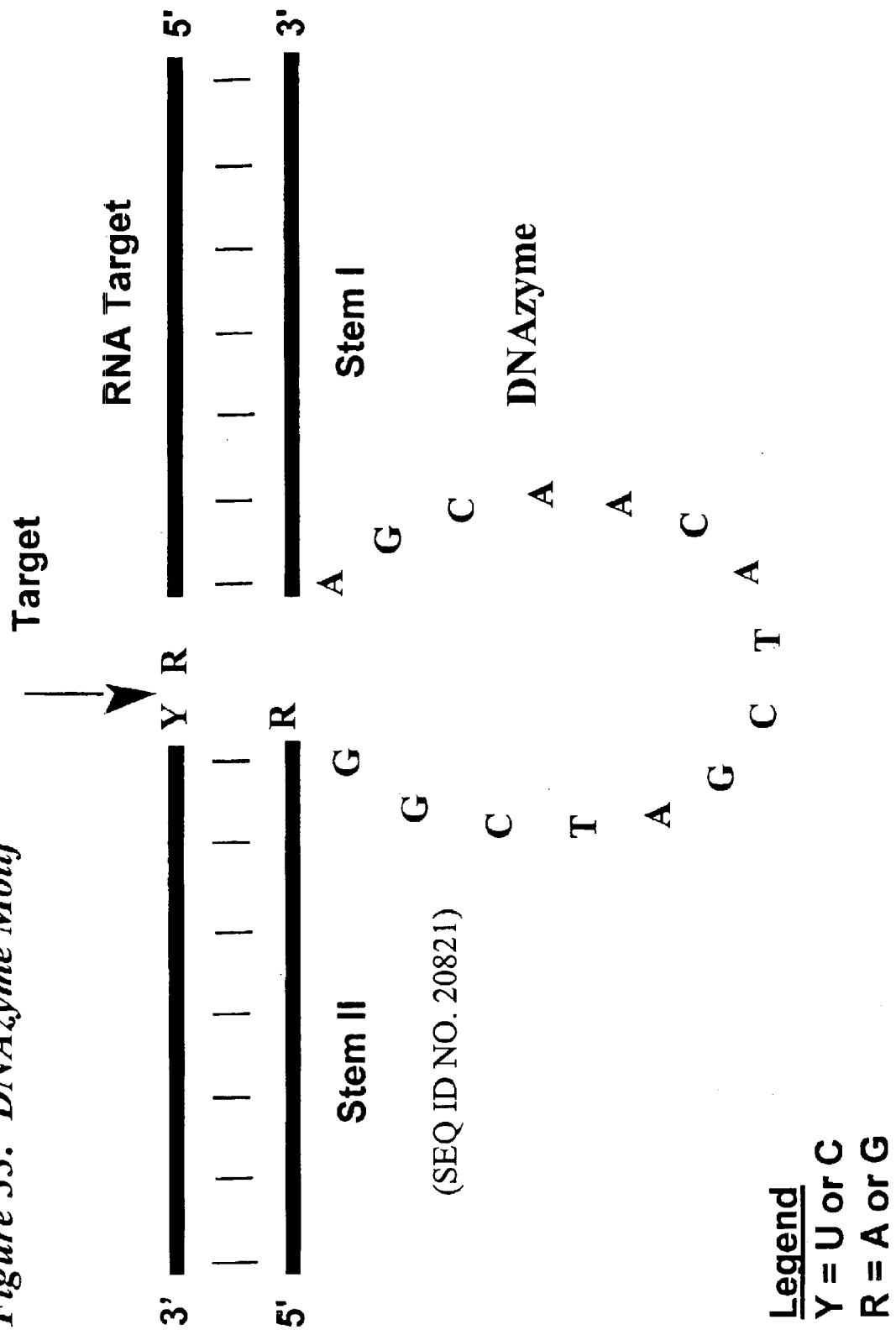
Figure 33: DNAzyme Motif

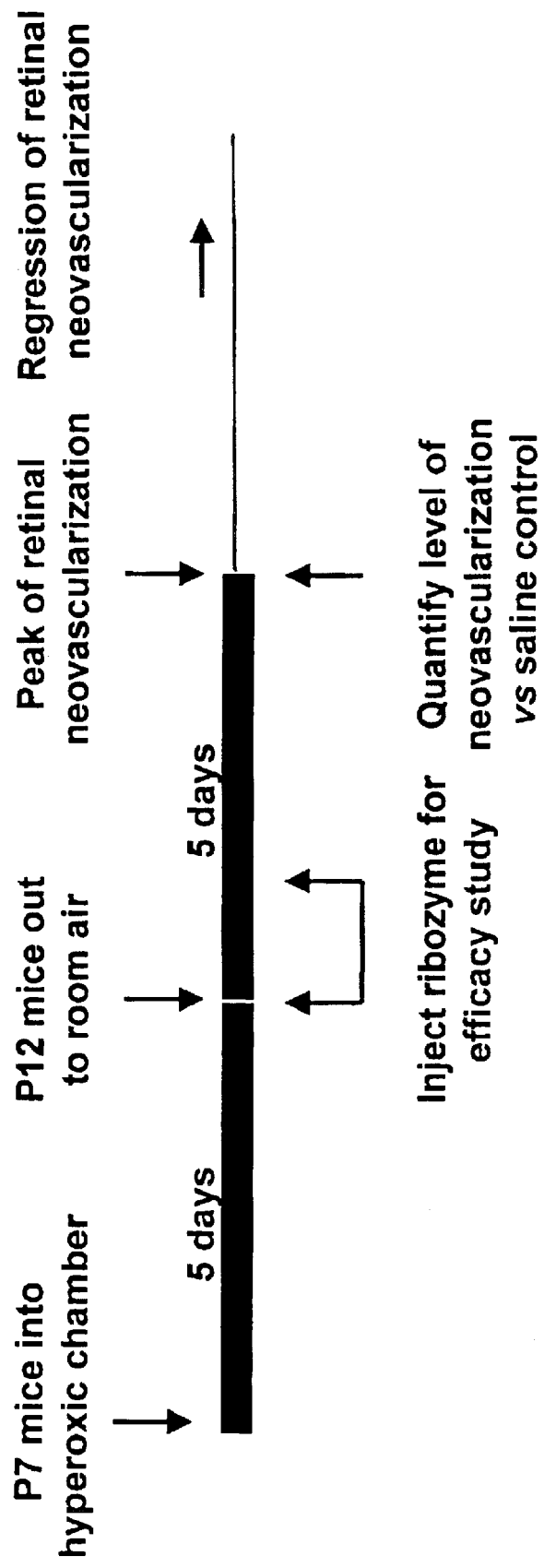
Figure 34A: Mouse Model of Proliferative Retinopathy

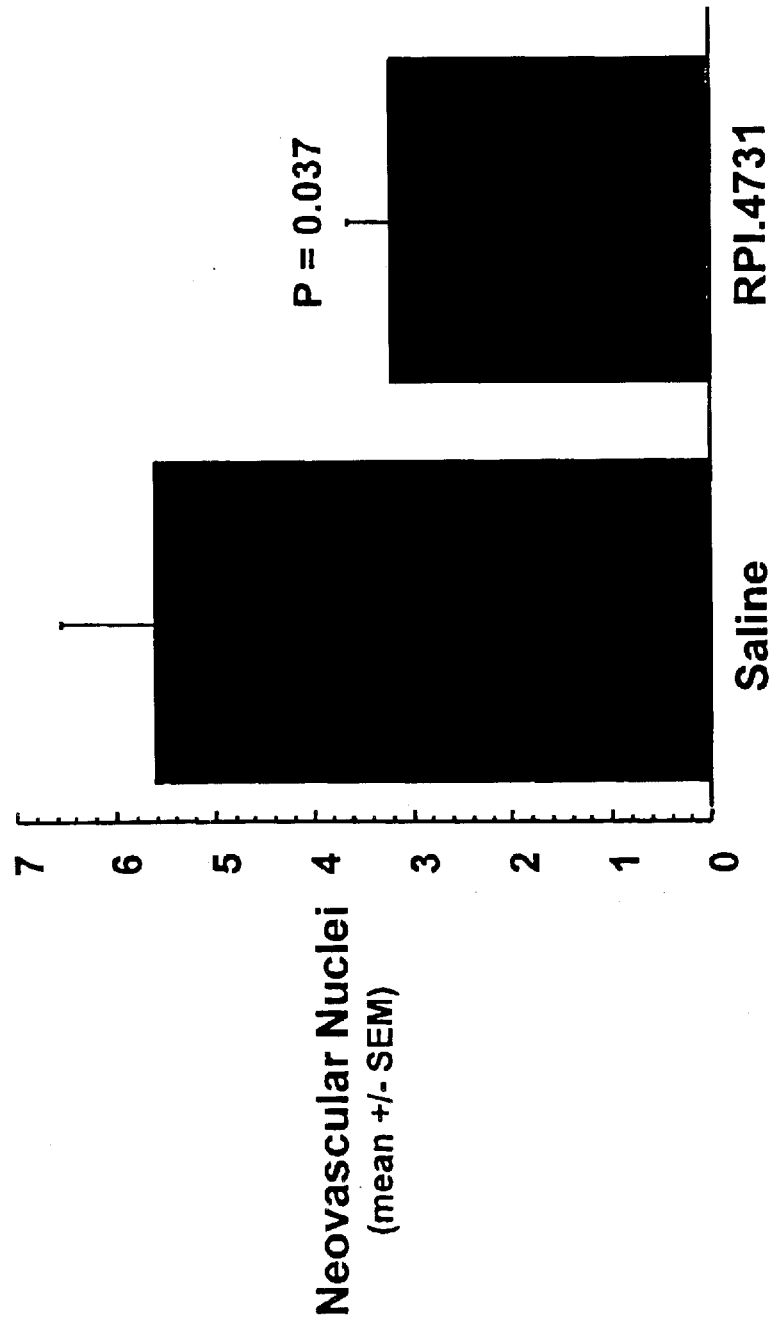

ENZYMATIC NUCLEIC ACID-MEDIATED TREATMENT OF OCULAR DISEASES OR CONDITIONS RELATED TO LEVELS OF VASCULAR ENDOTHELIAL GROWTH FACTOR RECEPTOR (VEGF-R)

This patent application is a continuation-in-part of Pavco et al., U.S. application Ser. No. 09/870,161, now abandoned, filed May 29, 2001, which is a continuation-in-part of Pavco et al., U.S. application Ser. No. 09/708,690, now abandoned, filed Nov. 7, 2000, which is a continuation-in-part of Pavco et al., U.S. application Ser. No. 09/371,722, now U.S. Pat. No. 6,534,872, filed Aug. 10, 1999, which is a continuation-in-part of Pavco et al., U.S. application Ser. No. 08/584,040, now U.S. Pat. No. 6,346,398, filed Jan. 11, 1996, which claims the benefit of Pavco et al., U.S. Application Ser. No. 60/005,974, filed Oct. 26, 1995, all of these earlier applications are entitled "Method and Reagent for Treatment of Diseases or Conditions Related to Levels of Vascular Endothelial Growth Factor Receptor". Each of these applications is hereby incorporated by reference herein in its entirety including the drawings and tables.

The sequence listing submitted on compact disc, in compliance with 37 C.F.R. § 1.52(e)(5), is incorporated by reference. Two separate compact discs are submitted, each containing the file "400.049 Sequence Listing—Revised Apr. 23, 2004, txt" (4,511,993 bytes in size), each created on CD on May 24, 2004.

BACKGROUND OF THE INVENTION

This invention relates to methods and reagents for the treatment of diseases or conditions relating to the levels of expression of vascular endothelial growth factor (VEGF) receptor(s).

The following is a discussion of relevant art, none of which is admitted to be prior art to the present invention.

VEGF, also referred to as vascular permeability factor (VPF) and vasculotropin, is a potent and highly specific mitogen of vascular endothelial cells (for a review see Ferrara, 1993 *Trends Cardiovas. Med.* 3, 244; Neufeld et al., 1994 *Prog. Growth Factor Res.* 5, 89). VEGF induced neovascularization is implicated in various pathological conditions such as tumor angiogenesis, proliferative diabetic retinopathy, hypoxia-induced angiogenesis, rheumatoid arthritis, psoriasis, wound healing and others.

VEGF, an endothelial cell-specific mitogen, is a 34–45 kDa glycoprotein with a wide range of activities that include promotion of angiogenesis, enhancement of vascular-permeability and others. VEGF belongs to the platelet-derived growth factor (PDGF) family of growth factors with approximately 18% homology with the A and B chain of PDGF at the amino acid level. Additionally, VEGF contains the eight conserved cysteine residues common to all growth factors belonging to the PDGF family (Neufeld et al., supra). VEGF protein is believed to exist predominantly as disulfide-linked homodimers; monomers of VEGF have been shown to be inactive (Plouet et al., 1989 *EMBO J.* 8, 3801).

VEGF exerts its influence on vascular endothelial cells by binding to specific high-affinity cell surface receptors. Covalent cross-linking experiments with $^{125}$I-labeled VEGF protein have led to the identification of three high molecular weight complexes of 225, 195 and 175 kDa presumed to be VEGF and VEGF receptor complexes (Vaisman et al., 1990 *J. Biol. Chem.* 265, 19461). Based on these studies VEGF-specific receptors of 180, 150 and 130 kDa molecular mass were predicted. In endothelial cells, receptors of 150 and the 130 kDa have been identified. The VEGF receptors belong to the superfamily of receptor tyrosine kinases (RTKs) characterized by a conserved cytoplasmic catalytic kinase domain and a hydrophylic kinase sequence. The extracellular domains of the VEGF receptors consist of seven immunoglobulin-like domains that are thought to be involved in VEGF binding functions.

The two most abundant and high-affinity receptors of VEGF are flt-1 (fms-like tyrosine kinase) cloned by Shibuya et al., 1990 *Oncogene* 5, 519 and KDR (kinase-insert-domain-containing receptor) cloned by Terman et al., 1991 *Oncogene* 6, 1677. The murine homolog of KDR, cloned by Mathews et al., 1991, *Proc. Natl. Acad. Sci., USA*, 88, 9026, shares 85% amino acid homology with KDR and is termed as flk-1 (fetal liver kinase-1). Recently it has been shown that the high-affinity binding of VEGF to its receptors is modulated by cell surface-associated heparin and heparin-like molecules (Gitay-Goren et al., 1992 *J. Biol. Chem.* 267, 6093).

VEGF expression has been associated with several pathological states such as tumor angiogenesis, several forms of blindness, rheumatoid arthritis, psoriasis and others. Following is a brief summary of evidence supporting the involvement of VEGF in various diseases:

1) Tumor angiogenesis: Increased levels of VEGF gene expression have been reported in vascularized and edema-associated brain tumors (Berkman et al., 1993 *J. Clini. Invest.* 91, 153). A more direct demostration of the role of VEGF in tumor angiogenesis was demonstrated by Jim Kim et al., 1993 *Nature* 362, 841 wherein, monoclonal antibodies against VEGF were successfully used to inhibit the growth of rhabdomyosarcoma, glioblastoma multiforme cells in nude mice. Similarly, expression of a dominant negative mutated form of the flt-1 VEGF receptor inhibits vascularization induced by human glioblastoma cells in nude mice (Millauer et al., 1994, *Nature* 367, 576).

2) Ocular diseases: Aiello et al., 1994 *New Engl. J. Med.* 331, 1480, showed that the ocular fluid of a majority of patients suffering from diabetic retinopathy and other retinal disorders, contains a high concentration of VEGF. Miller et al., 1994 *Am. J. Pathol.* 145, 574, reported elevated levels of VEGF mRNA in patients suffering from retinal ischemia. These observations support a direct role for VEGF in ocular diseases.

3) Psoriasis: Detmar et al., 1994 *J. Exp. Med.* 180, 1141 reported that VEGF and its receptors were over-expressed in psoriatic skin and psoriatic dermal microvessels, suggesting that VEGF plays a significant role in psoriasis.

4) Rheumatoid arthritis: Immunohistochemistry and in situ hybridization studies on tissues from the joints of patients suffering from rheumatoid arthritis show an increased level of VEGF and its receptors (Fava et al., 1994 *J. Exp. Med.* 180, 341). Additionally, Koch et al., 1994 *J. Immunol.* 152, 4149, found that VEGF-specific antibodies were able to significantly reduce the mitogenic activity of synovial tissues from patients suffering from rheumatoid arthritis. These observations support a direct role for VEGF in rheumatoid arthritis.

In addition to the above data on pathological conditions involving excessive angiogenesis, a number of studies have demonstrated that VEGF is both necessary and sufficient for neovascularization. Takashita et al., 1995 *J. Clin. Invest.* 93, 662, demonstrated that a single injection of VEGF augmented collateral vessel development in a rabbit model of ischemia. VEGF also can induce neovascularization when injected into the cornea. Expression of the VEGF gene in CHO cells is sufficient to confer tumorigenic potential to the cells. Kim et al., supra and Millauer et al., supra used monoclonal antibodies against VEGF or a dominant negative form of flk-1 receptor to inhibit tumor-induced neovascularization.

During development, VEGF and its receptors are associated with regions of new vascular growth (Millauer et al., 1993 *Cell* 72, 835; Shalaby et al., 1993 *J. Clin. Invest*. 91, 2235). Furthermore, transgenic mice lacking either of the VEGF receptors are defective in blood vessel formation, in fact these mice do not survive; flk-1 appears to be required for differentiation of endothelial cells, while flt-1 appears to be required at later stages of vessel formation (Shalaby et al., 1995 *Nature* 376, 62; Fung et al., 1995 *Nature* 376, 66). Thus, these receptors must be present to properly signal endothelial cells or their precursors to respond to vascularization-promoting stimuli.

All of the conditions listed above, involve extensive vascularization. This hyper-stimulation of endothelial cells may be alleviated by VEGF antagonists. Thus most of the therapeutic efforts for the above conditions have concentrated on finding inhibitors of the VEGF protein.

Kim et al., 1993 *Nature* 362, 841 have been successful in inhibiting VEGF-induced tumor growth and angiogenesis in nude mice by treating the mice with VEGF-specific monoclonal antibody.

Koch et al., 1994 *J. Immunol*. 152, 4149 showed that the mitogenic activity of microvascular endothelial cells found in rheumatoid arthritis (RA) synovial tissue explants and the chemotactic property of endothelial cells from RA synovial fluid can be neutralized significantly by treatment with VEGF-specific antibodies.

Ullrich et al., International PCT Publication No. WO 94/11499 and Millauer et al., 1994 *Nature* 367, 576 used a soluble form of flk-1 receptor (dominant-negative mutant) to prevent VEGF-mediated tumor angiogenesis in immunodeficient mice.

Kendall and Thomas, International PCT Publication No. WO 94/21679 describe the use of naturally occuring or recombinantly-engineered soluble forms of VEGF receptors to inhibit VEGF activity.

Robinson, International PCT Publication No. WO 95/04142 describes the use of antisense oligonucleotides targeted against VEGF RNA to inhibit VEGF expression.

Jellinek et al., 1994 *Biochemistry* 33, 10450 describe the use of VEGF-specific high-affinity RNA aptamers to inhibit the binding of VEGF to its receptors.

Rockwell and Goldstein, International PCT Publication No. WO 95/21868, describe the use of anti-VEGF receptor monoclonal antibodies to neutralize the effect of VEGF on endothelial cells.

SUMMARY OF THE INVENTION

The invention features novel nucleic acid-based compounds [e.g., enzymatic nucleic acid molecules (ribozymes such as Inozyme, G-cleaver, amberzyme, zinzyme), DNAzyme, antisense nucleic acids, 2–5A antisense chimeras, triplex forming nucleic acid, decoy nucleic acids, aptamers, allozymes, antisense nucleic acids containing RNA cleaving chemical groups (Cook et al., U.S. Pat. No. 5,359,051)] and methods for their use to down regulate or inhibit the expression of receptors of VEGF (VEGF-R).

In one embodiment, the invention features the use of one or more of the nucleic acid-based compounds to inhibit the expression of flt-1 and/or flk-1/KDR receptors.

In another embodiment, the present invention features a compound having Formula I: (SEQ ID NO: 20818).

5' $g_s a_s g_s u_s$ugc$\underline{U}$GAuGagg ccgaaa ggccGaaAgucugB 3' wherein each a is 2'-O-methyl adenosine nucleotide, each g is a 2'-O-methyl guanosine nucleotide, each c is a 2'-O-methyl cytidine nucleotide, each u is a 2'-O-methyl uridine nucleotide, each A is adenosine, each G is guanosine, each s individually represents a phosphorothioate internucleotide linkage, $\underline{U}$ is 2'-deoxy-2'-C-allyl uridine, and B is an inverted deoxyabasic moiety.

In another embodiment, the present invention features a compound having Formula II: (SEQ ID NO: 13488).

5'-$u_s a_s c_s$ $a_s$au uc$\underline{U}$ GAu Gag gcg aaa gcc Gaa Aag aca aB-3' wherein each a is 2'-O-methyl adenosine nucleotide, each g is a 2'-O-methyl guanosine nucleotide, each c is a 2'-O-methyl cytidine nucleotide, each u is a 2'-O-methyl uridine nucleotide, each A is adenosine, each G is guanosine, each s individually represents a phosphorothioate internucleotide linkage, $\underline{U}$ is 2'-deoxy-2'-C-allyl uridine, and B is an inverted deoxyabasic moiety.

In one embodiment, the invention features a composition comprising a compound of Formula I and/or II in a pharmaceutically acceptable carrier or diluent.

In another embodiment, the invention features a method of administering to a cell, for example a mammalian cell or human cell, the compound of Formula I and/or II, comprising contacting the cell with the compound under conditions suitable for administration, for example in the presence of a delivery reagent. Examples of suitable delivery reagents include a lipid, cationic lipid, phospholipid, or liposome as described herein and known in the art.

In one embodiment, the invention features a method of administering to a cell the compound of Formula I or II in conjunction with a chemotherapeutic agent comprising contacting the cell with the compound and the chemotherapeutic agent under conditions suitable for administration.

Examples of chemotherapeutic agents that can be combined with the compound of Formula I and/or II include but are not limited to 5-fluoro uridine, Leucovorin, Irinotecan (CAMPTOSAR® or CPT-11 or Camptothecin-11 or Campto), Paclitaxel, or Carboplatin or a combination thereof.

In another embodiment, the present invention also features a cell comprising the compound of Formula I and/or II, wherein the cell is a mammalian cell. For example, in one embodiment the mammalian cell is a human cell.

In one embodiment, the invention features a method of inhibiting angiogenesis, for example tumor angiogenesis, in a patient comprising the step of contacting the patient with the compound of Formula I and/or II under conditions suitable for said inhibition. In one embodiment, the patient is a mammal, for example, a human.

In another embodiment, the invention features a method of treatment of a patient having a condition associated with an increased level of VEGF receptor, for example, cancers such as breast cancer, lung cancer, colorectal cancer, renal cancer, pancreatic cancer, or melanoma, or ocular indications such as diabetic retinopathy, or age related macular degeneration, comprising contacting one or more cells of the patient with the compound of Formula I and/or II, under conditions suitable for the treatment. In one embodiment, the patient is a human.

In another embodiment, the invention features a method of treatment of a patient having an ocular condition associated with an increased level of a VEGF receptor, for example, diabetic retinopathy, or age related macular degeneration, comprising contacting one or more cells of the patient with a nucleic acid molecule, such as an enzymatic nucleic acid molecule, targeted against a VEGF receptor RNA, e.g., a molecule according to Formula I and/or II, under conditions suitable for the treatment. In one embodiment, the patient is a human.

In yet another embodiment, a method of treatment of the invention further comprises the use of one or more drug therapies under conditions suitable for the treatment.

In one embodiment, the present invention also features a method of cleaving RNA comprising a sequence of flt-1 comprising contacting the compound of Formula I with the RNA under conditions suitable for the cleavage of the RNA, for example, where the cleavage is carried out in the presence of a divalent cation such as Mg2+.

In another embodiment, the invention features a method of administering to a mammal, for example a human, the compound of Formula I and/or II comprising contacting the mammal with the compound under conditions suitable for the administration, for example, in the presence of a delivery reagent such as a lipid, cationic lipid, phospholipid, or liposome.

In yet another embodiment, the invention features a method of administering to a mammal the compound of Formula I and/or II in conjunction with a chemotherapeutic agent comprising contacting the mammal, for example a human, with the compound and the chemotherapeutic agent under conditions suitable for the administration.

In another embodiment, the invention features a composition comprising the nucleic acid molecule of the instant invention and a pharmaceutically acceptable carrier or diluent.

By "inhibit" it is meant that the activity of VEGF-R or level of VEGF-R mRNAs or equivalent RNAs encoding VEGF-R is reduced below that observed in the absence of a nucleic acid molecule of the instant invention. In one embodiment, inhibition with enzymatic nucleic acid preferably is below that level observed in the presence of an enzymatically inactive or attenuated molecule that is able to bind to the same site on the mRNA, but is unable to cleave that RNA. In another embodiment, inhibition with antisense oligonucleotides is preferably below that level observed in the presence of, for example, an oligonucleotide with scrambled sequence or with mismatches. In another embodiment, inhibition of a VEGF-R gene with the nucleic acid molecule of the instant invention is greater in the presence of the nucleic acid molecule than in its absence.

By "enzymatic nucleic acid molecule" it is meant an RNA molecule which has complementarity in a substrate binding region to a specified gene target, and also has an enzymatic activity which is active to specifically cleave target RNA. That is, the enzymatic RNA molecule is able to intermolecularly cleave RNA and thereby inactivate a target RNA molecule. The complementary region(s) allows sufficient hybridization of the enzymatic RNA molecule to the target RNA and thus permit cleavage. One hundred percent complementarity is preferred, but complementarity as low as 50–75% can also be useful in this invention. The nucleic acids can be modified at the base, sugar, and/or phosphate groups. The term enzymatic nucleic acid is used interchangeably with phrases such as ribozymes, catalytic RNA, enzymatic RNA, enzymatic DNA, catalytic DNA, catalytic oligonucleotides, nucleozyme, DNAzyme, Zinzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not meant to be limiting and those skilled in the art will recognize that all that is important in an enzymatic nucleic acid molecule of this invention is that it have a specific substrate binding site which is complementary to one or more of the target nucleic acid regions, and that it have nucleotide sequences within or surrounding that substrate binding site which impart a nucleic acid cleaving activity to the molecule (Cech et al., U.S. Pat. No. 4,987,071; Cech et al., 1988, JAMA).

By "enzymatic portion" or "catalytic domain" is meant that portion/region of the enzymatic nucleic acid essential for cleavage of a nucleic acid substrate (for example see FIG. 1).

By "substrate binding arm" or "substrate binding domain" is meant that portion/region of a enzymatic nucleic acid which is complementary to (i.e., able to base-pair with) a portion of its substrate. Generally, such complementarity is 100%, but can be less if desired. For example, as few as 10 bases out of 14 can be base-paired. Such arms are shown generally in FIG. 1. That is, these arms contain sequences within an enzymatic nucleic acid are intended to bring enzymatic nucleic acid and target RNA together through complementary base-pairing interactions. The enzymatic nucleic acid of the invention can have binding arms that are contiguous or non-contiguous and can be of varying lengths. The length of the binding arm(s) are preferably greater than or equal to four nucleotides, and are of sufficient length to stably interact with the target RNA; specifically 12–100 nucleotides; more specifically 14–24 nucleotides long. If two binding arms are chosen, the design is such that the length of the binding arms are symmetrical (i.e., each of the binding arms is of the same length; e.g., five and five nucleotides, six and six nucleotides or seven and seven nucleotides long) or asymmetrical (i.e., the binding arms are of different length; e.g., six and three nucleotides; three and six nucleotides long; four and five nucleotides long; four and six nucleotides long; four and seven nucleotides long; and the like).

By "DNAzyme" is meant an enzymatic nucleic acid molecule lacking a 2'-OH group. In particular embodiments, the enzymatic nucleic acid molecule can have an attached linker(s) or other attached or associated groups, moieties, or chains containing one or more nucleotides with 2'-OH groups.

By "zinzyme" motif or configuration is meant a class II enzymatic nucleic acid molecule comprising a motif as generally described in FIG. 32 and in Beigelman et al., International PCT publication No. WO 99/55857 and U.S. patent application Ser. No. 09/918,728, which is herein incorporated by reference in its entirety, including the drawings. Zinzymes possess endonuclease activity to cleave RNA substrates having a cleavage triplet including but not limited to, YG/Y, where Y is uridine or cytidine, and G is guanosine and/represents the cleavage site. Zinzymes can be chemically modified to increase nuclease stability through various substitutions, including substituting 2'-O-methyl guanosine nucleotides for guanosine nucleotides. In addition, differing nucleotide and/or non-nucleotide linkers can be used to substitute the 5'-gaaa-2' loop of the motif. Zinzymes represent a non-limiting example of an enzymatic nucleic acid molecule that does not require a ribonucleotide (2'-OH) group within its own nucleic acid sequence for activity.

By "sufficient length" is meant a nucleic acid molecule long enough to provide the intended function under the expected condition. For example, a nucleic acid molecule of the invention needs to be of "sufficient length" to provide stable binding to a target site under the expected binding conditions and environment. In another non-limiting example, for the binding arms of an enzymatic nucleic acid, "sufficient length" means that the binding arm sequence is long enough to provide stable binding to a target site under the expected reaction conditions and environment. The binding arms are not so long as to prevent useful turnover of the nucleic acid molecule.

By "stably interact" is meant interaction of the oligonucleotides with target, such as a target protein or target nucleic acid (e.g., by forming hydrogen bonds with complementary amino acids or nucleotides in the target under physiological conditions) that is sufficient for the intended purpose (e.g., specific binding to a protein target to disrupt the function of that protein or cleavage of target RNA/DNA by an enzyme).

By "equivalent" RNA to VEGF-R is meant to include those naturally occurring RNA molecules having homology (partial or complete) to VEGF-R, or encoding for proteins with similar function as VEGF-R in various animals, including human, rodent, primate, rabbit and pig. The equivalent RNA sequence also includes in addition to the coding region, regions such as 5'untranslated region, 3'-untranslated region, introns, intron-exon junction and the like.

By "homology" is meant the nucleotide sequence of two or more nucleic acid molecules is partially or completely identical.

By "antisense nucleic acid" it is meant a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004). Typically, antisense molecules will be complementary to a target sequence along a single contiguous sequence of the antisense molecule. However, in certain embodiments, an antisense molecule may bind to substrate such that the substrate molecule forms a loop, and/or an antisense molecule may bind such that the antisense molecule forms a loop. Thus, the antisense molecule may be complementary to two (or even more) non-contiguous substrate sequences or two (or even more) non-contiguous sequence portions of an antisense molecule may be complementary to a target sequence or both.

By "2–5A antisense chimera" it is meant, an antisense oligonucleotide containing a 5' phosphorylated 2'-5'-linked adenylate residues. These chimeras bind to target RNA in a sequence-specific manner and activate a cellular 2–5A-dependent ribonuclease which, in turn, cleaves the target RNA (Torrence et al., 1993 *Proc. Natl. Acad. Sci. USA* 90, 1300).

By "triplex DNA" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504).

By "gene" it is meant a nucleic acid that encodes an RNA, for example, nucleic acid sequences including, but not limited to, structural genes encoding a polypeptide.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., ribozyme cleavage, antisense or triple helix inhibition. Determination of binding free energies for nucleic acid molecules is well known in the art (see, e.g., Turner et al., 1987, CSH Symp. Quant. Biol. LII pp. 123–133; Frier et al., 1986, Proc. Nat. Acad. Sci. USA 83:9373–9377; Turner et al., 1987, J. Am. Chem. Soc. 109:3783–3785. A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

Seven basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA destroys its ability to direct synthesis of an encoded protein. After an enzymatic nucleic acid has bound and cleaved its RNA target, it is released from that RNA to search for another target and can repeatedly bind and cleave new targets. Thus, a single enzymatic nucleic acid molecule is able to cleave many molecules of target RNA. In addition, the enzymatic nucleic acid is a highly specific inhibitor of gene expression, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

Enzymatic nucleic acids that cleave the specified sites in VEGF-R mRNAs represent a novel therapeutic approach to treat tumor angiogenesis, and cancers including, but not limited to, tumor and cancer types shown under Diagnosis in Table XX, ocular diseases, rhuematoid arthritis, psoriasis and others. The enzymatic nucleic acid molecules of the instant invention are able to inhibit the activity of VEGF-R (specifically flt-1 and flk-1/KDR) and the catalytic activity of the enzymatic nucleic acid molecules is required for their inhibitory effect. Those of ordinary skill in the art will find it clear from the exemplary nucleic acid molecules described that other enzymatic nucleic acid molecules that cleave VEGF-R mRNAs can be readily designed and are within the scope of the invention.

In one of the embodiments of the inventions described herein, the enzymatic nucleic acid molecule is formed in a hammerhead or hairpin motif, but can also be formed in the motif of a hepatitis delta virus, group I intron, group II intron or RNase P RNA (in association with an RNA guide sequence), Neurospora VS RNA, DNAzymes, Zinzymes, NCH cleaving motifs, or G-cleavers. Examples of such hammerhead motifs are described by Dreyfus, supra, Rossi et al., 1992, *AIDS Research and Human Retroviruses* 8, 183; of hairpin motifs by Hampel et al., EP0360257, Hampel and Tritz, 1989 *Biochemistry* 28, 4929, Feldstein et al., 1989, *Gene* 82, 53, Haseloff and Gerlach, 1989, *Gene*, 82, 43, and Hampel et al., 1990 *Nucleic Acids Res*. 18, 299; Chowrira &

McSwiggen, U.S. Pat. No. 5,631,359; of the hepatitis delta virus motif is described by Perrotta and Been, 1992 *Biochemistry* 31, 16; of the RNase P motif by Guerrier-Takada et al., 1983 *Cell* 35, 849; Forster and Altman, 1990, *Science* 249, 783; Li and Altman, 1996, *Nucleic Acids Res.* 24, 835; Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799; Guo and Collins, 1995, *EMBO. J.* 14, 363); Group II introns are described by Griffin et al., 1995, *Chem. Biol.* 2, 761; Michels and Pyle, 1995, *Biochemistry* 34, 2965; Pyle et al., International PCT Publication No. WO 96/22689; of the Group I intron by Cech et al., U.S. Pat. No. 4,987,071; of Zinzymes as is generally described by Beigelman et al., International PCT publication No. WO 99/55857 (see for example FIG. 32); and of DNAzymes as is generally described by Usman et al., International PCT Publication No. WO 95/11304; Chartrand et al., 1995, *NAR* 23, 4092; Breaker et al., 1995, *Chem. Bio.* 2, 655; Santoro et al., 1997, *PNAS* 94, 4262 (see for example FIG. 33). NCH cleaving motifs are described in Ludwig & Sproat, International PCT Publication No. WO 98/58058; and G-cleavers are described in Kore et al., 1998, *Nucleic Acids Research* 26, 4116–4120 and Eckstein et al., International PCT Publication No. WO 99/16871. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule (Cech et al., U.S. Pat. No. 4,987,071).

Enzymatic nucleic acid molecules of the invention that are allosterically regulated ("allozymes") can be used to modulate VEGR receptor expression. These allosteric enzymatic nucleic acids or allozymes (see for example George et al., U.S. Pat. Nos. 5,834,186 and 5,741,679, Shih et al., U.S. Pat. No. 5,589,332, Nathan et al., U.S. Pat. No. 5,871,914, Nathan and Ellington, International PCT publication No. WO 00/24931, Breaker et al., International PCT Publication Nos. WO 00/26226 and 98/27104, and Sullenger et al., International PCT publication No. WO 99/29842) are designed to respond to a signaling agent. For example, allozymes can be designed to respond to signaling agents, such as flt-1 or kdr protein, flt-1 or kdr RNA, other proteins and/or RNAs involved in VEGF activity, and also, for example, compounds, metals, polymers, molecules and/or drugs that are targeted to VEGF or VEGF receptor, such as flt-1 or kdr expressing cells etc., which in turn modulate the activity of the enzymatic nucleic acid molecule. In response to interaction with a predetermined signaling agent, the activity of the allosteric enzymatic nucleic acid molecule is activated or inhibited such that the expression of a particular target is selectively down-regulated. The target can comprise flt-1 or kdr and/or a predetermined cellular component or receptor that modulates VEGF activity.

In a specific example, allosteric enzymatic nucleic acid molecules that are activated by interaction with a RNA encoding a flt-1 protein are used as therapeutic agents in vivo. The presence of RNA encoding the flt-1 protein activates the allosteric enzymatic nucleic acid molecule that subsequently cleaves the RNA encoding the flt-1 protein, resulting in the inhibition of flt-1 protein expression. In this manner, cells that express the flt-1 protein are selectively targeted.

In another non-limiting example, an allozyme can be activated by an flt-1 protein or peptide that caused the allozyme to inhibit the expression of flt-1 gene by, for example, cleaving RNA encoded by flt-1 gene. In this non-limiting example, the allozyme acts as a decoy to inhibit the function of flt-1 and also inhibit the expression of flt-1 once activated by the flt-1 protein.

In one embodiment, the nucleic acid molecule of the invention, e.g., antisense molecule, triplex DNA, or ribozyme, is 13 to 100 nucleotides in length, e.g., in specific embodiments 35, 36, 37, or 38 nucleotides in length (e.g., for particular ribozymes). In particular embodiments, the nucleic acid molecule is 15–100, 17–100, 20–100, 21–100, 23–100, 25–100, 27–100, 30–100, 32–100, 35–100, 40–100, 50–100, 60–100, 70–100, or 80–100 nucleotides in length. Instead of 100 nucleotides being the upper limit on the length ranges specified above, the upper limit of the length range can be, for example, 30, 40, 50, 60, 70, or 80 nucleotides. Thus, for any of the length ranges, the length range for particular embodiments has a lower limit as specified, with an upper limit as specified which is greater than the lower limit. For example, in a particular embodiment, the length range can be 35–50 nucleotides in length. All such ranges are expressly included. Also in particular embodiments, a nucleic acid molecule can have a length which is any of the lengths specified above, for example, 21 nucleotides in length.

In one embodiment, the invention provides a method for producing a class of enzymatic cleaving agents which exhibit a high degree of specificity for the RNA of a desired target. The enzymatic nucleic acid molecule is preferably targeted to a highly conserved sequence region of target mRNAs encoding VEGF-R proteins (specifically flt-1 and flk-1/KDR) such that specific treatment of a disease or condition can be provided with either one or several enzymatic nucleic acids. Such enzymatic nucleic acid molecules can be delivered exogenously to specific tissue or cellular targets as required. Alternatively, the enzymatic nucleic acid molecules can be expressed from DNA and/or RNA vectors that are delivered to specific cells.

By "highly conserved sequence region" is meant a nucleotide sequence of one or more regions in a nucleic acid molecule that does not vary significantly from one generation to the other or from one biological system to the other.

Synthesis of nucleic acids greater than 100 nucleotides in length is difficult using automated methods, and the therapeutic cost of such molecules is prohibitive. In this invention, small nucleic acid motifs (e.g., antisense oligonucleotides, hammerhead or the hairpin ribozymes) are used for exogenous delivery. The simple structure of these molecules increases the ability of the nucleic acid to invade targeted regions of the mRNA structure. However, these nucleic acid molecules can also be expressed within cells from eukaryotic promoters (e.g., Izant and Weintraub, 1985 *Science* 229, 345; McGarry and Lindquist, 1986 *Proc. Natl. Acad. Sci. USA* 83, 399; SullengerScanlon et al., 1991, *Proc. Natl. Acad. Sci. USA*, 88, 10591–5; Kashani-Sabet et al., 1992 *Antisense Res. Dev.*, 2, 3–15; Dropulic et al., 1992 *J. Virol*, 66, 1432–41; Weerasinghe et al., 1991 *J. Virol*, 65, 5531–4; Ojwang et al., 1992 *Proc. Natl. Acad. Sci. USA* 89, 10802–6; Chen et al., 1992 *Nucleic Acids Res.*, 20, 4581–9; Sarver et al., 1990 *Science* 247, 1222–1225; Thompson et al., 1995 *Nucleic Acids Res.* 23, 2259). Those skilled in the art realize that any nucleic acid can be expressed in eukaryotic cells from the appropriate DNA/RNA vector. The activity of such nucleic acids can be augmented by their release from the primary transcript by a ribozyme (Draper et al., PCT WO93/23569, and Sullivan et al., PCT WO94/02595, both hereby incorporated in their totality by reference herein; Ohkawa et al., 1992 *Nucleic Acids Symp. Ser.*, 27, 15–6; Taira et al., 1991, *Nucleic Acids Res.*, 19, 5125–30; Ventura et al., 1993 *Nucleic Acids Res.*, 21, 3249–55; Chowrira et al., 1994 *J. Biol. Chem.* 269, 25856).

The nucleic acid molecules of the invention are useful for the prevention of diseases and conditions related to the level of VEGF-R, including cancer (including but not limited to tumor and cancer types shown under Diagnosis in Table XX), diabetic retinopathy, macular degeneration, neovascular glaucoma, myopic degeneration, arthritis, psoriasis, verruca vulgaris, angiofibroma of tuberous sclerosis, pot-wine stains, Sturge Weber syndrome, Kippel-Trenaunay-Weber syndrome, Osler-Weber-Rendu syndrome and any other diseases or conditions that are related to the levels of VEGF-R (specifically flt-1 and flk-1/KDR) in a cell or tissue.

By "diseases or conditions related to the level of VEGF-R" is meant that the reduction of VEGF-R (specifically flt-1 and flk-1/KDR) RNA levels and thus reduction in the level of the respective protein will relieve, to some extent, the symptoms of the disease or condition.

Nucleic acid molecules of the invention are added directly, or can be complexed with cationic lipids, packaged within liposomes, or otherwise delivered to target cells or tissues. The nucleic acid or nucleic acid complexes can be locally administered to relevant tissues ex vivo, or in vivo through injection, infusion pump or stent, with or without their incorporation in biopolymers.

In one embodiment, the enzymatic nucleic acid molecule of the invention has one or more binding arms which are complementary to the substrate sequences in Tables II to IX, XIV–XIX, XXII, and XXIII. Examples of such enzymatic nucleic acid molecules also are shown in Tables II to IX, XIV–XIX, XXII, and XXIII. Examples of such enzymatic nucleic acid molecules consist essentially of sequences defined in these Tables.

In yet another embodiment, the invention features antisense nucleic acid molecules and 2–5A chimera including sequences complementary to the target sequences shown in Tables II to IX, XIV–XIX, XXII, and XXIII. Such nucleic acid molecules can include sequences as shown for the binding arms of the enzymatic nucleic acid molecules in Tables II to IX, XIV–XIX, XXII, and XXIII. Similarly, triplex molecules can be provided targeted to the corresponding DNA target regions, and containing the DNA equivalent of a target sequence or a sequence complementary to the specified target (substrate) sequence. Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both.

By "consists essentially of" is meant that the active nucleic acid molecule of the invention, for example, an enzymatic nucleic acid molecule, contains an enzymatic center or core equivalent to those in the examples, and binding arms able to bind RNA such that cleavage at the target site occurs. Other sequences can be present that do not interfere with such cleavage. Thus, a core region can, for example, include one or more loop, stem-loop structure, or linker that does not prevent enzymatic activity. Thus, the underlined regions in the sequences in Tables II, IV, VI, VIII, XIV and XVI can be such a loop, stem-loop, nucleotide linker, and/or non-nucleotide linker and can be represented generally as sequence "X". For example, a core sequence for a hammerhead enzymatic nucleic acid can comprise a conserved sequence, such as 5'-CUGAUGAG-3' and 5'-CGAA-3' connected by "X", where X is 5'-<u>GCCGUUAGGC</u>-3' (SEQ ID NO: 20822), or any other Stem II region known in the art, or a nucleotide and/or non-nucleotide linker. Similarly, for other nucleic acid molecules of the instant invention, such as Inozyme, G-cleaver, amberzyme, zinzyme, DNAzyme, antisense, 2–5A antisense, triplex forming nucleic acid, and decoy nucleic acids, other sequences or non-nucleotide linkers can be present that do not interfere with the function of the nucleic acid molecule.

X can be a linker of $\geq 2$ nucleotides in length, preferably 3, 4, 5, 6, 7, 8, 9, 10, 15, 20, 26, 30, where the nucleotides can preferably be internally base-paired to form a stem of preferably $\geq 2$ base pairs. Alternatively or in addition, X may be a non-nucleotide linker. In yet another embodiment, the nucleotide linker (X) can be a nucleic acid aptamer, such as an ATP aptamer, HIV Rev aptamer (RRE), HIV Tat aptamer (TAR) and others (for a review see Gold et al., 1995, *Annu. Rev. Biochem.*, 64, 763; and Szostak & Ellington, 1993, in *The RNA World*, ed. Gesteland and Atkins, pp. 511, CSH Laboratory Press).

A "nucleic acid aptamer" as used herein is meant to indicate a nucleic acid sequence capable of interacting with a ligand. The ligand can be any natural or a synthetic molecule, including but not limited to a resin, metabolites, nucleosides, nucleotides, drugs, toxins, transition state analogs, peptides, lipids, proteins, amino acids, nucleic acid molecules, hormones, carbohydrates, receptors, cells, viruses, bacteria and others.

In yet another embodiment, the non-nucleotide linker (X) is as defined herein. The term "non-nucleotide" as used herein include either abasic nucleotide, polyether, polyamine, polyamide, peptide, carbohydrate, lipid, or polyhydrocarbon compounds. Specific examples include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113:5109; Ma et al., *Nucleic Acids Res.* 1993, 21:2585 and *Biochemistry* 1993, 32:1751; Durand et al., *Nucleic Acids Res.* 1990, 18:6353; McCurdy et al., *Nucleosides & Nucleotides* 1991, 10:287; Jschke et al., *Tetrahedron Lett.* 1993, 34:301; Ono et al., *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. A "non-nucleotide" further means any group or compound which can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine. Thus, in one embodiment, the invention features an enzymatic nucleic acid molecule having one or more non-nucleotide moieties, and having enzymatic activity to cleave an RNA or DNA molecule.

In another aspect of the invention, enzymatic nucleic acid molecules that cleave target RNA molecules and inhibit VEGF-R (specifically flt-1 and flk-1/KDR) activity are expressed from transcription units inserted into DNA or RNA vectors. The recombinant vectors are preferably DNA plasmids or viral vectors. Enzymatic nucleic acid expressing viral vectors can be constructed based on, but not limited to, adeno-associated virus, retrovirus, adenovirus, or alphavirus vectors. Preferably, the recombinant vectors capable of expressing the enzymatic nucleic acid molecules are delivered as described above, and persist in target cells. Alternatively, viral vectors can be used that provide for transient expression of enzymatic nucleic acids. Such vectors can be repeatedly administered as necessary. Once expressed, the enzymatic nucleic acids cleave the target mRNA. Delivery of enzymatic nucleic acids expressing vectors can be systemic, such as by intravenous or intramuscular administration, by administration to target cells ex-planted from the patient followed by reintroduction into the patient, or by any other means that would allow for introduction into the desired target cell.

By "vectors" is meant any nucleic acid- and/or viral-based technique used to deliver a desired nucleic acid.

By "patient" is meant an organism which is a donor or recipient of explanted cells or the cells themselves. "Patient" also refers to an organism to which the nucleic acid molecules of the invention can be administered. In one embodiment, the patient is a mammal or mammalian cells. Preferably, the patient is a human or human cells.

The nucleic acid molecules of the instant invention, individually, or in combination or in conjunction with other drugs, can be used to treat diseases or conditions discussed above. For example, to treat a disease or condition associated with VEGF-R, the patient can be treated, or other appropriate cells can be treated, as is evident to those skilled in the art, individually with a nucleic acid molecule of the invention or in combination with one or more drugs under conditions suitable for the treatment.

For example, to treat a disease or condition associated with VEGF-R levels, such as cancer (e.g., colorectal cancer, breast cancer) or ocular diseases (e.g., diabetic retinopathy or age related macular degeneration) a patient may be treated, or other appropriate cells may be treated, as is evident to those skilled in the art, individually or in combination with one or more drugs under conditions suitable for the treatment.

In a further embodiment, the described molecules, such as antisense or enzymatic nucleic acid molecules can be used in combination with other known treatments to treat conditions or diseases discussed above. For example, the described molecules can be used in combination with one or more known therapeutic agents to treat cancer.

In another embodiment, the invention features nucleic acid-based techniques (e.g., enzymatic nucleic acid molecules (ribozymes such as Inozyme, G-cleaver, amberzyme, zinzyme), DNAzyme, antisense nucleic acids, 2–5A antisense chimeras, triplex forming nucleic acid, decoy nucleic acids, aptamers, allozymes, antisense nucleic acids containing RNA cleaving chemical groups (Cook et al., U.S. Pat. No. 5,359,051)] and methods for their use to down regulate or inhibit the expression of genes capable of inducing angiogenesis (e.g., flt-1 and kdr).

In another embodiment, the invention features nucleic acid-based techniques (e.g., enzymatic nucleic acid molecules (ribozymes such as Inozyme, G-cleaver, amberzyme, zinzyme), DNAzyme, antisense nucleic acids, 2–5A antisense chimeras, triplex forming nucleic acid, decoy nucleic acids, aptamers, allozymes, antisense nucleic acids containing RNA cleaving chemical groups (Cook et al., U.S. Pat. No. 5,359,051)] and methods for their use to down regulate or inhibit the expression of VEGF receptor.

Other features and advantages of the invention will be apparent from the following description of the preferred embodiments thereof, and from the claims.

BRIEF DESCRIPTION OF THE DRAWINGS

FIG. 1 is a diagrammatic representation of the hammerhead ribozyme domain known in the art. Stem II can be $\geq 2$ base-pair long.

FIGS. 2a–d show hammerhead ribozyme substrate motifs. FIG. 2a is a diagrammatic representation of the hammerhead ribozyme domain known in the art; FIG. 2b is a diagrammatic representation of the hammerhead ribozyme as divided by Uhlenbeck (1987, Nature, 327, 596–600) into a substrate and enzyme portion; FIG. 2c is a similar diagram showing the hammerhead divided by Haseloff and Gerlach (1988, Nature, 334, 585–591) into two portions; and FIG. 2d is a similar diagram showing the hammerhead divided by Jeffries and Symons (1989, Nucl. Acids. Res., 17, 1371–1371) into two portions.

FIG. 3 is a diagrammatic representation of the general structure of a hairpin ribozyme. Helix 2 (H2) is provided with at least 4 base pairs (i.e., n is 1, 2, 3 or 4) and helix 5 can be optionally provided of length 2 or more bases (preferably 3–20 bases, i.e., m is from 1–20 or more). Helix 2 and helix 5 can be covalently linked by one or more bases (i.e., r is $\geq 1$ base). Helix 1, 4 or 5 can also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides can be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more can be modified chemically (abasic, base, sugar and/or phosphate modifications) or replaced with another base without significant effect. Helix 4 can be formed from two separate molecules, i.e., without a connecting loop. The connecting loop when present can be a ribonucleotide with or without modifications to its base, sugar or phosphate. "q" is $\geq 2$ bases. The connecting loop can also be replaced with a non-nucleotide linker molecule. H refers to bases A, U, or C. Y refers to pyrimidine bases. "_____" refers to a covalent bond.

FIG. 4 is a representation of the general structure of the hepatitis delta virus ribozyme domain known in the art.

FIG. 5 is a representation of the general structure of the VS RNA ribozyme domain.

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

FIG. 7 shows the effect of hammerhead ribozymes targeted against flt-1 receptor on the binding of VEGF to the surface of human microvascular endothelial cells.

Figure 27:
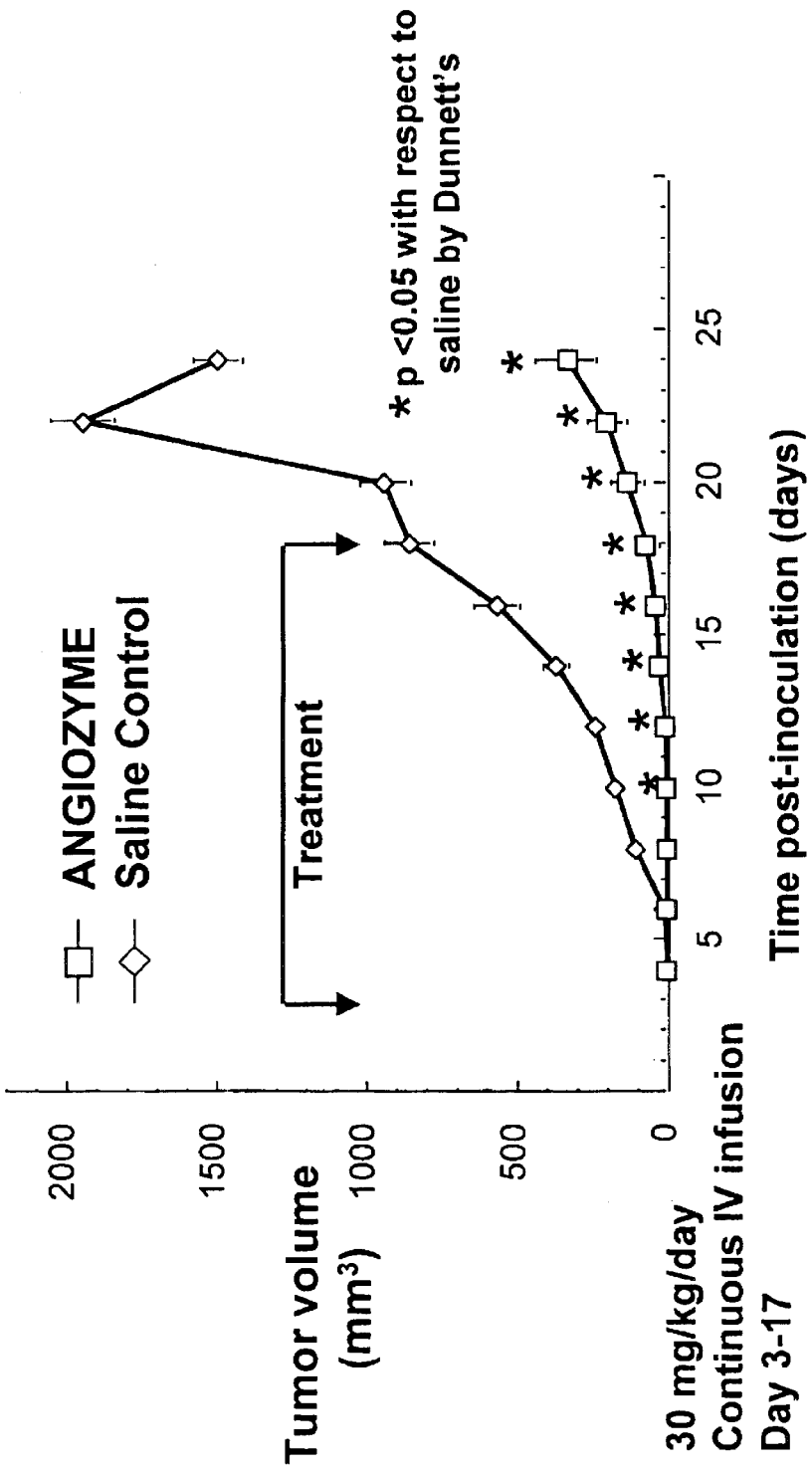

Sequences of the ribozymes used are shown in Table II; the length of stem II region is 3 bp. The hammerhead ribozymes were chemically modified such that the ribozyme consists of ribose residues at five positions (see FIG. 11); U4 and U7 positions contain 2'-NH$_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose. The results of two separate experiments are shown as separate bars for each set. Each bar represents the average of triplicate samples. The standard deviation is shown with error bars. For the flt-1 data, 500 nM ribozyme (3:1 charge ratio with LipofectAMINE®) was used. Control 1–10 is the control for ribozymes 307–2797, control 11–20 is the control for ribozymes 3008–5585. The Control 1–10 and Control 11–20 represent the treatment of cells with LipofectAMINE® alone without any ribozymes.

FIG. 8 shows the effect of hammerhead ribozymes targeted against KDR receptor on the binding of VEGF to KDR on the surface of human microvascular endothelial cells. Sequences of the ribozymes used are shown in Table IV; the length of stem II region is 3 bp. The hammerhead ribozymes were chemically modified such that the ribozyme consists of ribose residues at five positions (see FIG. 11); U4 and U7 positions contain 2'-NH$_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose. The Control 1–10 and Control 11–20 represent the treatment of cells with LipofectAMINE® alone without any ribozymes. Irrel. RZ, is a control experiment wherein the cells are treated with a non-KDR-targeted ribozyme complexed with Lipofectamine®. 200 nM ribozyme (3:1 charge ratio with LipofectAMINE®) was used. In addition to the KDR-targeted ribozymes, the effect on VEGF binding of a ribozyme targeted to an irrelevant mRNA (irrel. RZ) is also shown. Because the affinity of KDR for VEGF is about 10-fold lower than the affinity of flt-1 for VEGF, a higher concentration of VEGF was used in the binding assay.

FIG. 9 shows the specificity of hammerhead ribozymes targeted against flt-1 receptor. Inhibition of the binding of VEGF, urokinase plasminogen activator (UPA) and fibroblast growth factor (FGF) to their corresponding receptors as a function of anti-FLT ribozymes is shown. The sequence and description of the ribozymes used are as described in FIG. 7 above. The average of triplicate samples is given; percent inhibition as calculated below.

FIG. 10 shows the inhibition of the proliferation of Human aortic endothelial cells (HAEC) mediated by phosphorothioate antisense oligodeoxynucleotides targeted against human KDR receptor RNA. Cell proliferation (O.D. 490) as a function of antisense oligodeoxynucleotide concentration is shown. KDR 21AS represents a 21 nt phosphorothioate antisense oligodeoxynucleotide targeted against KDR RNA. KDR 21 Scram represents a 21 nt phosphorothioate oligodeoxynucleotide having a scrambled sequence. LF represents the lipid carrier Lipofectin.

"FIGS. 11A and B show a diagrammatic representation of hammerhead ribozymes targeted against flt-1 RNA and in vitro cleavage of flt-1 RNA by hammerhead ribozymes. The hammerhead (HH) ribozymes were chemically modified such that the ribozyme consists of ribose residues at five positions; U4 and U7 positions contain 2'-NH$_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose (designated as 3'-iH). FIG. 11A shows hammerhead ribozymes 1358 HH-A and 4229 HH-A, which contain a 3 base-paired stem II region. FIG. 11B shows hammerhead ribozymes 1358 HH-B and 4229 HH-B, which contain a 4 base-paired stem II region. FIGS. 11C and 11D show in vitro cleavage kinetics of hammerhead ribozymes targeted against sites 1358 and 4229 within the flt-1 RNA."

"FIG. 12A shows a diagrammatic representation of hammerhead (HH) ribozymes targeted against sites 1358 and 4229 within the flt-1 RNA. The hammerhead (HH) ribozymes were chemically modified such that the ribozyme consists of ribose residues at five positions; U4 position contains 2'-C-allyl modification, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose (designated as 3'-iH). FIG. 12B shows a graphical representation of the inhibition of cell proliferation mediated by 1358HH and 4229HH ribozymes."

FIG. 13 shows inhibition of human microvascular endothelial cell proliferation mediated by anti-KDR hammerhead ribozymes. The figure is a graphical representation of the inhibition of cell proliferation mediated by hammerhead ribozymes targeted against sites 527, 730, 3702 and 3950 within the KDR RNA. Irrelevant HH RZ is a hammerhead ribozyme targeted to an irrelevant target. All of these ribozymes, including the Irrelevant HH RZ, were chemically modified such that the ribozyme consists of ribose residues at five positions; U4 and U7 positions contain 2'-NH$_2$ modifications, the remaining nucleotide positions contain 2'-O-methyl substitutions; four nucleotides at the 5' termini contain phosphorothioate substitutions. Additionally, the 3' end of the ribozyme contains a 3'-3' linked inverted abasic deoxyribose (3'-iH).

FIG. 14 shows in vitro cleavage of KDR RNA by hammerhead ribozymes. The hammerhead (HH) ribozymes were chemically modified such that the ribozyme consists of ribose residues at five positions; U4 and U7 positions contain 2'-NH$_2$ modifications, the remaining nucleotide positions contain 2'-O-methyl substitutions. Additionally, the 3' end of the ribozyme contains a 3'-3' linked inverted abasic deoxyribose (designated as 3'-iH). 726 HH and 527 HH contain 4 base-paired stem II region. Percent in vitro cleavage kinetics as a function of time of HH ribozymes targeted against sites 527 and 726 within the KDR RNA is shown.

FIG. 15 shows in vitro cleavage of KDR RNA by hammerhead ribozymes. The hammerhead (HH) ribozymes were chemically modified such that the ribozyme consists of ribose residues at five positions; U4 and U7 positions contain 2'-NH$_2$ modifications, the remaining nucleotide positions contain 2'-O-methyl substitutions. Additionally, the 3' end of the ribozyme contains a 3'-3' linked inverted abasic deoxyribose (designated as 3'-iH). 3702 HH and 3950 HH contain 4 base-paired stem II region. Percent in vitro cleavage kinetics as a function of time of HH ribozymes targeted against sites 3702 and 3950 within the KDR RNA is shown.

FIG. 16 shows in vitro cleavage of RNA by hammerhead ribozymes that are targeted to sites that are conserved between flt-1 and KDR RNA. The hammerhead (HH) ribozymes were chemically modified such that the ribozyme consists of ribose residues at five positions; U4 and U7 positions contain 2'-NH$_2$ modifications, the remaining nucleotide positions contain 2'-O-methyl substitutions. Additionally, the 3' end of the ribozyme contains a 3'-3' linked inverted abasic deoxyribose (designated as 3'-iH). FLT/KDR-IHH ribozyme was synthesized with either a 4 base-paired or a 3 base-paired stem II region. FLT/KDR-IHH can cleave site 3388 within flt-1 RNA and site 3151 within KDR RNA. Percent in vitro cleavage kinetics as a function of time of HH ribozymes targeted against sites 3702 and 3950 within the KDR RNA is shown.

FIG. 17 shows inhibition of human microvascular endothelial cell proliferation mediated by anti-KDR and anti-flt-1 hammerhead ribozymes. The figure is a graphical representation of the inhibition of cell proliferation mediated by hammerhead ribozymes targeted against sites KDR sites 527, 726 or 3950 or flt-1 site 4229. The figure also shows enhanced inhibition of cell proliferation by a combination of flt-1 and KDR hammerhead ribozymes. 4229+527, indicates the treatment of cells with both the flt 4229 and the KDR 527 ribozymes. 4229+726, indicates the treatment of cells with both the flt 4229 and the KDR 726 ribozymes. 4229+3950, indicates the treatment of cells with both the flt 4229 and the KDR 3950 ribozymes. VEGF-, indicates the basal level of cell proliferation in the absence of VEGF. A, indicates catalytically active ribozyme; I, indicates catalytically inactive ribozyme. All of these ribozymes were chemically modified such that the ribozyme consists of ribose residues at five positions; U4 and U7 positions contain 2'-NH$_2$ modifications, the remaining nucleotide positions contain 2'-O-methyl substitutions; four nucleotides at the 5' termini contain phosphorothioate substitutions. Additionally, the 3' end of the ribozyme contains a 3'-3' linked inverted abasic deoxyribose (3'-iH).

FIG. 18 shows the inhibition of VEGF-induced angiogenesis in rat cornea mediated by anti-flt-1 hammerhead ribozyme. All of these ribozymes were chemically modified such that the ribozyme consists of ribose residues at five positions; U4 position contains 2'-C-allyl modifications, the remaining nucleotide positions contain 2'-O-methyl substitutions; four nucleotides at the 5' termini contain phosphorothioate substitutions. Additionally, the 3' end of the ribozyme contains a 3'-3' linked inverted abasic deoxyribose (3'-iH). A decrease in the Surface Area corresponds to a reduction in angiogenesis. VEGF alone corresponds to treatment of the cornea with VEGF and no ribozymes. Vehicle alone corresponds to the treatment of the cornea with the carrier alone and no VEGF. This control gives a basal level of Surface Area. Active 4229 HH, corresponds to the treatment of cornea with the flt-1 4229 HH ribozyme in the absence of any VEGF. This control also gives a basal level of Surface Area. Active 4229 HH+VEGF, corresponds to the co-treatment of cornea with the flt-1 4229 HH ribozyme and VEGF. Inactive 4229 HH+VEGF, corresponds to the co-treatment of cornea with a catalytically inactive version of 4229 HH ribozyme and VEGF.

FIG. 19 shows ribozyme-mediated inhibition of cell proliferation. Cultured HMVEC-d were treated with ribozyme or attenuated controls as LIPOFECTAMINE™ complexes. After treatment, cells were stimulated with VEGF$_{165}$ or bFGF and allowed to grow for 48 h prior to determining the cell number. Each ribozyme was tested in triplicate at three concentrations and data are presented as mean cell number per well +SD. The data obtained following ribozyme treatment and VEGF stimulation are presented in panels A & B for anti-Flt-1 ribozymes and panels D & E for anti-KDR ribozymes. Representative data obtained following ribozyme treatment and bFGF stimulation are shown in panel C for one anti-Flt-1 ribozyme and in panel F for one anti-KDR ribozyme. In all panels, active ribozymes are represented with filled symbols; attenuated controls with open symbols. In addition to the ribozymes and attenuated controls listed in Table XII, a second set having the same sequences but with an additional basepair in the "stem II" region of the ribozyme are also shown for VEGF-induced proliferation studies. These 4 bp stem II ribozymes and attenuated controls have one additional base pair such that the stem II/loop sequence is ggccgaaaggcc (SEQ ID NO: 20823). Therefore, ribozymes and controls with 3 or 4 basepair stem IIs are denoted with circles and squares, respectively. The data for one irrelevant ribozyme (filled triangle, panel B) are also shown. This irrelevant ribozyme contains an active core sequence but has no binding site in either Flt-1 or KDR mRNA. Its sequence is 5'-g$_s$a$_s$a$_s$g$_s$gaacUGAuGaggccgaaaggccGaaA gauggcT-3' (SEQ ID NO: 20824) with modifications as in Table XII except that T indicates a 3'-3' inverted deoxythymidine. For reference, the average number of cells in control wells after 48 h in the absence of VEGF or bFGF for each of the panels are as follows: A, B, C, 12477±617; D, E, F, 17182±1053.

FIG. 20 shows target specificity of anti-Flt-1 and KDR ribozymes. Cultured HMVEC-d were treated with LIPOFECTAMINE™ complexes containing 200 nM active ribozyme (A) or attenuated control (C) and analyzed by RNAse protection following 24 h of VEGF-stimulated growth. Data obtained for ribozymes and attenuated controls that target Flt-1 site 4229 or KDR site 726 are shown. Data were normalized to the level of an internal mRNA control (cyclophilin) and are presented as percent decrease in Flt-1 (left panel) or KDR mRNA (right panel) relative to an untreated control. Error bars indicate the range of duplicate samples.

FIG. 21 shows antiangiogenic efficacy of ribozyme in the rat corneal model of VEGF-induced angiogenesis. The percent inhibition of VEGF-induced angiogenesis for locally administered anti-Flt-1 (site 4229) ribozyme (filled circles) and their attenuated controls (open circles) are plotted over the dose range tested. Pixels associated with background structures including the iris were subtracted from all treatment groups. Data are expressed as mean percent reduction in VEGF-induced angiogenesis ±SEM. *$p<0.05$ relative to VEGF/vehicle treated controls by Dunnett's, **$p<0.05$ relative to attenuated dose-matched controls by Tukey-Kramer.

FIG. 22 shows antiangiogenic efficacy of ribozyme in the rat corneal model of VEGF-induced angiogenesis. The percent inhibition of VEGF-induced angiogenesis for locally administered anti-KDR (site 726) ribozyme (filled circles) and their attenuated controls (open circles) are plotted over the dose range tested. Pixels associated with background structures including the iris were subtracted from all treatment groups. Data are expressed as mean percent reduction in VEGF-induced angiogenesis ±SEM. *$p<0.05$ relative to VEGF/vehicle treated controls by Dunnett's, **$p<0.05$ relative to attenuated dose-matched controls by Tukey-Kramer.

FIG. 23 shows the effect of subcutaneous bolus administration of ANGIOZYME™ in a mouse Lewis Lung Carcinoma (LLC) model.

FIG. 24 shows the effect of ANGIOZYME™ in combination with gemcitabine or cyclophosphamide on primary tumor growth in the mouse LLC model.

FIG. 25 shows the effect of ANGIOZYME™ in combination with gemcitabine or cyclophosphamide on tumor metastases in the mouse LLC model.

FIG. 26 shows a secondary structure model of ANGIOZYME™ ribozyme bound to its RNA target.

FIG. 27 shows a time course of inhibition of primary tumor growth following systemic administration of ANGIOZYME™ in the LLC mouse model.

Figure 28:
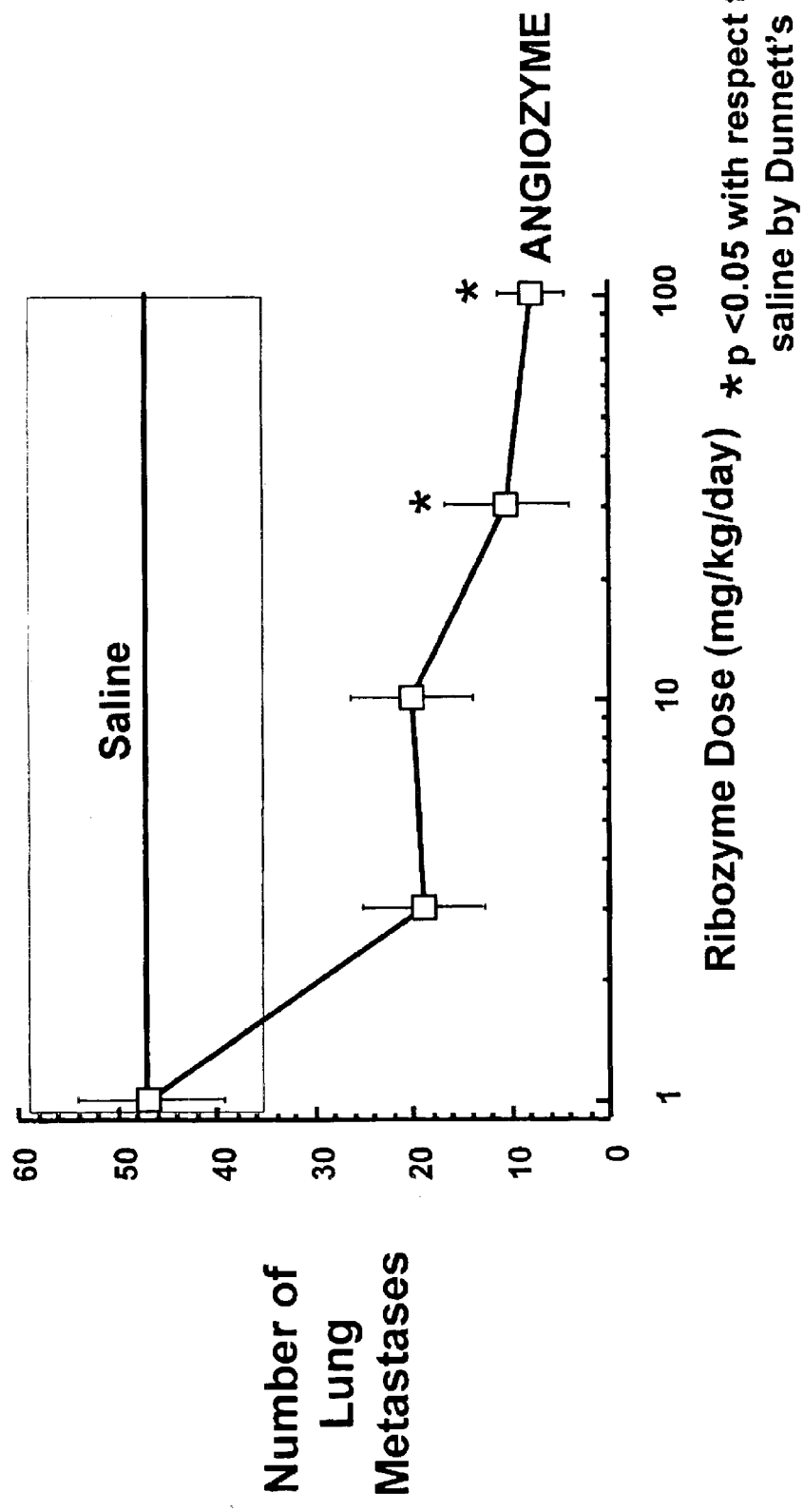

FIG. 28 shows inhibition of primary tumor growth following systemic administration of ANGIOZYME™ according to a certain dosing regimen in the LLC mouse model.

Figure 29:
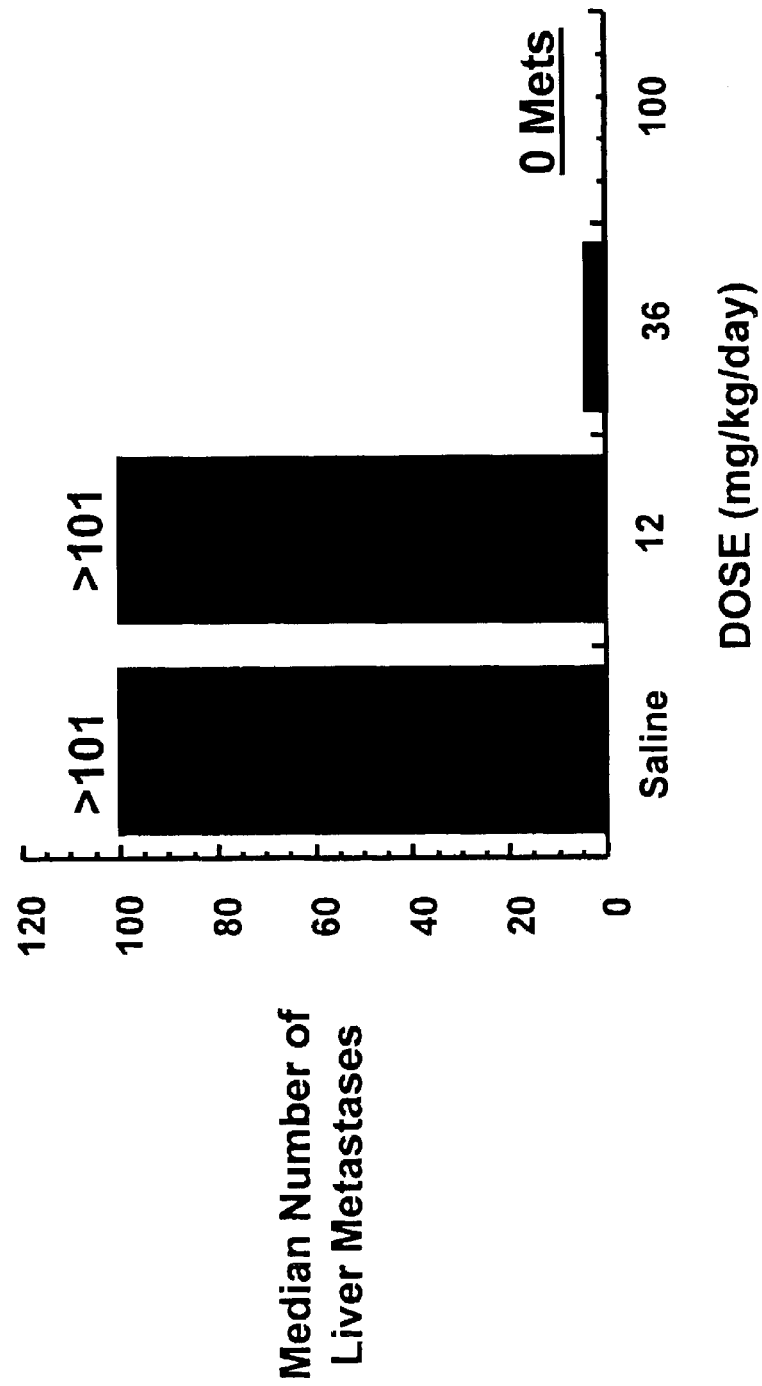

FIG. 29 shows a dose-dependent inhibition of tumor metastases following systemic administration of ANGIOZYME™ in a mouse colorectal model.

Figure 30:
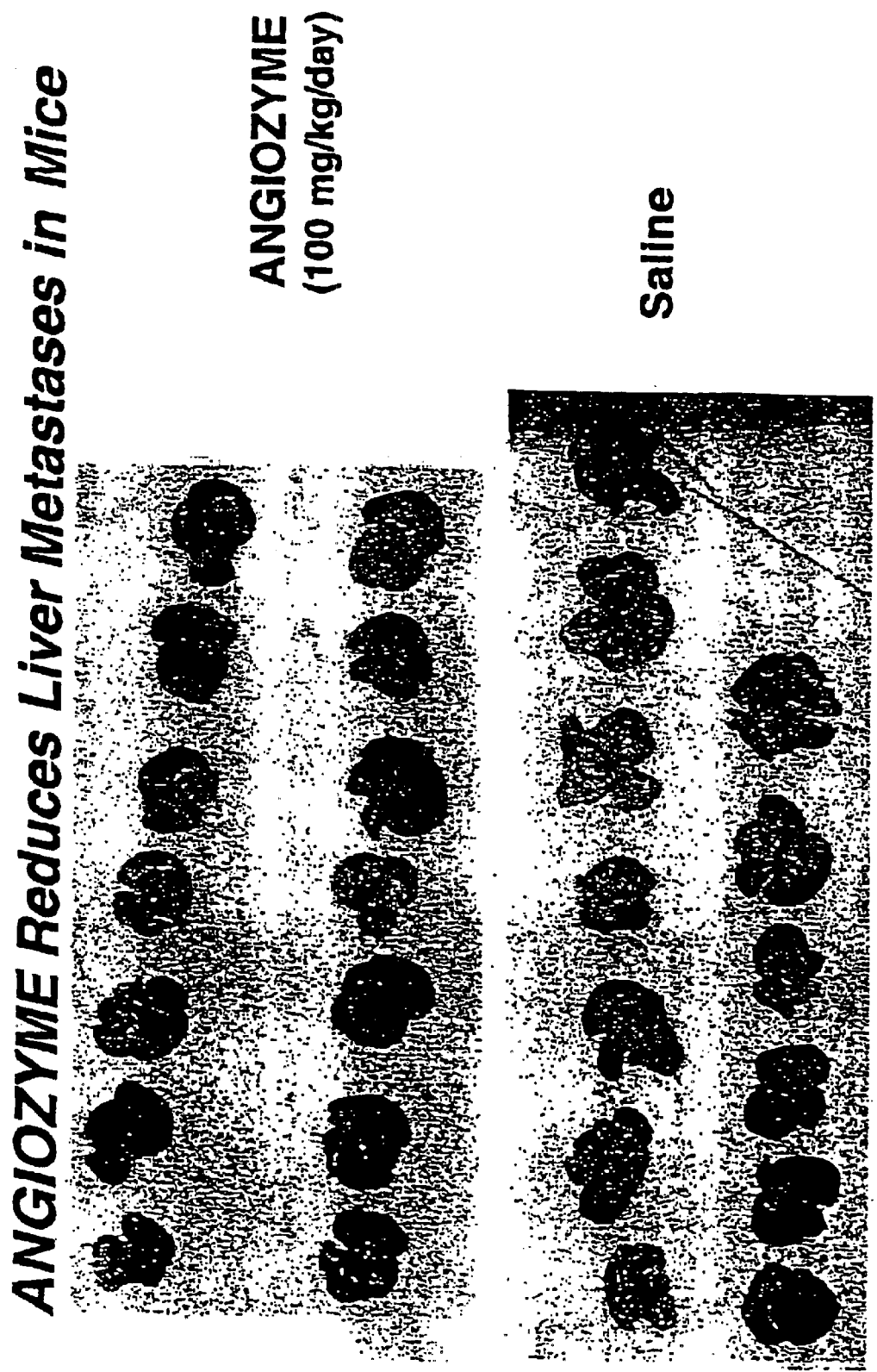

FIG. 30 shows inhibition of liver metastases following systemic administration of ANGIOZYME™ in a mouse colorectal model.

FIG. 31 is a graph showing the plasma concentration profile of ANGIOZYME™ after a single subcutaneous (SC) dose of 10, 30, 100 or 300 mg/m$^2$.

FIG. 32 shows an example of the Zinzyme enzymatic nucleic acid motif that is chemically stabilized (see for example Beigelman et al., International PCT publication No. WO 99/55857, incorporated by reference herein; also referred to as Class A or Class II Motif). The Zinzyme motif is a class of enzymatic nucleic molecules that do not require the presence of a ribonucleotide (2'-OH) group for its activity.

FIG. 33 shows an example of a DNAzyme motif described generally, for example in Santoro et al., 1997, *PNAS*, 94, 4262.

FIGS. 34A and B show a mouse model protocol and results of proliferative retinopathy. FIG. 34A shows anoutline for the mouse model of proliferative retinopathy showing the points of ribozyme administration. FIG. 34B shows a graph demonstrating the efficacy of a VEGF-receptor-targeted enzymatic nucleic acid molecule in a mouse model of proliferative retinopathy.

DETAILED DESCRIPTION OF THE INVENTION

Mechanism of Action of Nucleic Acid Molecules of the Invention

Antisense: Antisense molecules can be modified or unmodified RNA, DNA, or mixed polymer oligonucleotides and primarily function by specifically binding to matching sequences resulting in inhibition of peptide synthesis (Wu-Pong, November 1994, *BioPharm*, 20–33). The antisense oligonucleotide binds to target RNA by Watson Crick base-pairing and blocks gene expression by preventing ribosomal translation of the bound sequences either by steric blocking or by activating RNase H enzyme. Antisense molecules can also alter protein synthesis by interfering with RNA processing or transport from the nucleus into the cytoplasm (Mukhopadhyay & Roth, 1996, *Crit. Rev. in Oncogenesis* 7, 151–190).

In addition, binding of single stranded DNA to RNA can result in nuclease degradation of the heteroduplex (Wu-Pong, supra; Crooke, supra). To date, the only backbone modified DNA chemistry which acts as substrates for RNase H are phosphorothioates and phosphorodithioates. Recently it has been reported that 2'-arabino and 2'-fluoro arabino-containing oligos can also activate RNase H activity.

A number of antisense molecules have been described that utilize novel configurations of chemically modified nucleotides, secondary structure, and/or RNase H substrate domains (Woolf et al., International PCT Publication No. WO 98/13526; Thompson et al., U.S. Ser. No. 60/082,404 which was filed on Apr. 20, 1998; Hartmann et al., U.S. Ser. No. 60/101,174 which was filed on Sep. 21, 1998) all of these are incorporated by reference herein in their entirety.

Triplex Forming Oligonucleotides (TFO): Single stranded DNA can be designed to bind to genomic DNA in a sequence specific manner. TFOs are comprised of pyrimidine-rich oligonucleotides which bind DNA helices through Hoogsteen Base-pairing (Wu-Pong, supra). The resulting triple helix composed of the DNA sense, DNA antisense, and TFO disrupts RNA synthesis by RNA polymerase. The TFO mechanism can result in gene expression or cell death since binding may be irreversible (Mukhopadhyay & Roth, supra).

2–5A Antisense Chimera: The 2–5A system is an interferon mediated mechanism for RNA degradation found in higher vertebrates (Mitra et al., 1996, *Proc Nat Acad Sci USA* 93, 6780–6785). Two types of enzymes, 2–5A synthetase and RNase L, are required for RNA cleavage. The 2–5A synthetases require double stranded RNA to form 2'-5' oligoadenylates (2–5A). 2–5A then acts as an allosteric effector for utilizing RNase L which has the ability to cleave single stranded RNA. The ability to form 2–5A structures with double stranded RNA makes this system particularly useful for inhibition of viral replication.

(2'-5') oligoadenylate structures can be covalently linked to antisense molecules to form chimeric oligonucleotides capable of RNA cleavage (Torrence, supra). These molecules putatively bind and activate a 2–5A dependent RNase, the oligonucleotide/enzyme complex then binds to a target RNA molecule which can then be cleaved by the RNase enzyme.

Enzymatic Nucleic Acid: Seven basic varieties of naturally-occurring enzymatic RNAs are presently known. In addition, several in vitro selection (evolution) strategies (Orgel, 1979, *Proc. R. Soc. London*, B 205, 435) have been used to evolve new nucleic acid catalysts capable of catalyzing cleavage and ligation of phosphodiester linkages (Joyce, 1989, *Gene*, 82, 83–87; Beaudry et al., 1992, *Science* 257, 635–641; Joyce, 1992, *Scientific American* 267, 90–97; Breaker et al., 1994, *TIBTECH* 12, 268; Bartel et al., 1993, *Science* 261:1411–1418; Szostak, 1993, *TIBS* 17, 89–93; Kumar et al., 1995, *FASEB J.*, 9, 1183; Breaker, 1996, *Curr. Op. Biotech.*, 7, 442; Santoro et al., 1997, *Proc. Natl. Acad. Sci.*, 94, 4262; Tang et al., 1997, *RNA* 3, 914; Nakamaye & Eckstein, 1994, supra; Long & Uhlenbeck, 1994, supra; Ishizaka et al., 1995, supra; Vaish et al., 1997, *Biochemistry* 36, 6495; all of these are incorporated by reference herein). Each can catalyze a series of reactions including the hydrolysis of phosphodiester bonds in trans (and thus can cleave other RNA molecules) under physiological conditions.

Enzymatic nucleic acid molecules of this invention block to some extent VEGF-R (specifically flt-1 and flk-1/KDR) production and can be used to treat disease or diagnose such disease. Enzymatic nucleic acid molecules are delivered to cells in culture, to cells or tissues in animal models of angiogenesis and/or RA and to human cells or tissues ex vivo or in vivo. Enzymatic nucleic acid molecule cleavage of VEGF-R RNAs (specifically RNAs that encode flt-1 and flk-1/KDR) in these systems can alleviate disease symptoms.

The enzymatic nature of enzymatic nucleic acid molecules, such as ribozymes, has significant advantages, such as the concentration of enzymatic nucleic acid necessary to affect a therapeutic treatment is lower. This advantage reflects the ability of the enucleic acid molecule to act enzymatically. Thus, a single enzymatic nucleic acid molecule is able to cleave many molecules of target RNA. In addition, the enzymatic nucleic acid molecule is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to completely eliminate catalytic activity of an enzymatic nucleic acid molecule.

Nucleic acid molecules having an endonuclease enzymatic activity are able to repeatedly cleave other separate RNA molecules in a nucleotide base sequence-specific manner. Such enzymatic nucleic acid molecules can be targeted to virtually any RNA transcript, and achieved efficient cleavage in vitro (Zaug et al., 324, *Nature* 429 1986; Uhlenbeck, 1987 *Nature* 328, 596; Kim et al., 84 *Proc. Natl. Acad. Sci. USA* 8788, 1987; Dreyfus, 1988, *Einstein Quart. J. Bio. Med.*, 6, 92; Haseloff and Gerlach, 334 *Nature* 585, 1988; Cech, 260 *JAMA* 3030, 1988; and Jefferies et al., 17 *Nucleic Acids Research* 1371, 1989; Santoro et al., 1997 supra).

Because of their sequence specificity, enzymatic nucleic acids, such as trans-cleaving ribozymes can be used as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Enzymatic nucleic acid molecules can be designed to cleave specific RNA targets within the background of cellular RNA. Such a cleavage event renders the RNA non-functional and abrogates protein expression from that RNA. In this manner, synthesis of a protein associated with a disease state can be selectively inhibited.

Target sites

Targets for useful enzymatic nucleic acid molecules and antisense nucleic acids can be determined as disclosed in Draper et al., WO 93/23569; Sullivan et al., WO 93/23057; Thompson et al., WO 94/02595; Draper et al., WO 95/04818; McSwiggen et al., U.S. Pat. No. 5,525,468, and hereby incorporated by reference herein in totality. Other examples include the following PCT applications which concern inactivation of expression of disease-related genes: WO 95/23225, WO 95/13380, WO 94/02595, incorporated by reference herein. Rather than repeat the guidance provided in those documents here, below are provided specific examples of such methods, not limiting to those with skill in the art. Enzymatic nucleic acid molecules to such targets are designed as described in those applications and synthesized to be tested in vitro and in vivo, as also described. The sequence of human and mouse flt-1, KDR and/or flk-1 mRNAs were screened for optimal enzymatic nucleic acid target sites using a computer folding algorithm. Hammerhead, hairpin, NCH, or G-Cleaver ribozyme cleavage sites were identified. These sites are shown in Tables II to IX, XIV–XIX, XXII, and XXIII (all sequences are 5' to 3' in the tables; X can be any base-paired sequence, the actual sequence is not relevant here). The nucleotide base position is noted in the Tables as that site to be cleaved by the designated type of ribozyme. While mouse and human sequences can be screened and enzymatic nucleic acid molecules thereafter designed, the human targeted sequences are of most utility. However, as discussed in Stinchcomb et al., WO 95/23225, mouse targeted enzymatic nucleic acid can be useful to test efficacy of action of the enzymatic nucleic acid molecule prior to testing in humans. The nucleotide base position is noted in the Tables as that site to be cleaved by the designated type of enzymatic nucleic acid.

For example, hammerhead or hairpin ribozymes were designed that could bind and cleave target RNA in a sequence-specific manner. The ribozymes were individually analyzed by computer folding (Jaeger et al., 1989 *Proc. Natl. Acad. Sci. USA*, 86, 7706) to assess whether the ribozyme sequences fold into the appropriate secondary structure. Those ribozymes with unfavorable intramolecular interactions between the binding arms and the catalytic core were eliminated from consideration. Varying binding arm lengths can be chosen to optimize activity.

Referring to FIG. 6, mRNA was screened for accessible cleavage sites by the method described generally in Draper et al., PCT WO93/23569, hereby incorporated by reference herein. Briefly, DNA oligonucleotides complementary to potential hammerhead or hairpin ribozyme cleavage sites were synthesized. A polymerase chain reaction was used to generate substrates for T7 RNA polymerase transcription from human and mouse flt-1, KDR and/or flk-1 cDNA clones. Labeled RNA transcripts were synthesized in vitro from the templates. The oligonucleotides and the labeled transcripts were annealed, RNAseH was added and the mixtures were incubated for the designated times at 37° C. Reactions were stopped and RNA separated on sequencing polyacrylamide gels. The percentage of the substrate cleaved was determined by autoradiographic quantitation using a PhosphorImaging system. From these data, antisense oligonucleotides, and ribozymes, such as hammerhead or hairpin ribozyme sites are chosen as the most accessible.

Ribozymes of the hammerhead or hairpin motif were designed to anneal to various sites in the mRNA message. The binding arms are complementary to the target site sequences described above. The ribozymes were chemically synthesized. The method of synthesis used follows the procedure for normal RNA synthesis as described below and in Usman et al., 1987 *J. Am. Chem. Soc.*, 109, 7845; Scaringe et al., 1990 *Nucleic Acids Res.*, 18, 5433; and Wincott et al., 1995 *Nucleic Acids Res.* 23, 2677–2684.

Synthesis of Nucleic Acid Molecules

Synthesis of nucleic acids greater than 100 nucleotides in length is difficult using automated methods, and the therapeutic cost of such molecules is prohibitive. In this invention, small nucleic acid motifs ("small refers to nucleic acid motifs no more than 100 nucleotides in length, preferably no more than 80 nucleotides in length, and most preferably no more than 50 nucleotides in length; e.g., antisense oligonucleotides, hammerhead or the hairpin ribozymes) are preferably used for exogenous delivery. The simple structure of these molecules increases the ability of the nucleic acid to invade targeted regions of RNA structure. Exemplary molecules of the instant invention were chemically synthesized, and others can similarly be synthesized. Oligodeoxyribonucleotides were synthesized using standard protocols as described in Caruthers et al., 1992, *Methods in Enzymology* 211, 3–19, and is incorporated herein by reference.

The method of synthesis used for normal RNA including certain enzymatic nucleic acid molecules follows the procedure as described in Usman et al., 1987 *J. Am. Chem. Soc.*, 109, 7845; Scaringe et al., 1990 *Nucleic Acids Res.*, 18, 5433; and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end. In a non-limiting example, small scale syntheses were conducted on a 394 Applied Biosystems, Inc. synthesizer using a 0.2 μmol scale protocol with a 7.75 min coupling step for alkylsilyl protected nucleotides and a 2.5 min coupling step for 2'-O-methylated nucleotides. Table XI outlines the amounts and the contact times of the reagents used in the synthesis cycle. Alternatively, syntheses at the 0.2 μmol scale can be done on a 96-well plate synthesizer, such as the instrument produced by Protogene (Palo Alto, Calif.) with minimal modification to the cycle. A 15-fold excess (31 μL of 0.1 M=3.1 μmol) of phosphoramidite and a 38.7-fold excess of S-ethyl tetrazole (31 μL of 0.25 M=7.75 μmol) relative to polymer-bound 5'-hydroxyl was used in each coupling cycle. Average coupling yields on the 394 Applied Biosystems, Inc. synthesizer, determined by colorimetric quantitation of the trityl fractions, were 97.5–99%. Other oligonucleotide synthesis reagents for the 394 Applied Biosystems, Inc. synthesizer; detritylation solution was 3% TCA in methylene chloride (ABI); capping was performed with 16% N-methylimidazole in THF (ABI) and 10% acetic anhydride/10% 2,6-lutidine in THF (ABI); oxidation solution was 16.9 mM $I_2$, 49 mM pyridine, 9% water in THF (PERSEPTIVE™). Burdick & Jackson Synthesis Grade acetonitrile was used directly from the reagent bottle. S-Ethyltetrazole solution (0.25 M in acetonitrile) was made up from the solid obtained from American International Chemical, Inc.

Deprotection of the RNA was performed using either a two-pot or one-pot protocol. For the two-pot protocol, the polymer-bound trityl-on oligoribonucleotide was transferred to a 4 mL glass screw top vial and suspended in a solution of 40% aq. methylamine (1 mL) at 65° C. for 10 min. After cooling to −20° C., the supernatant was removed from the polymer support. The support was washed three times with 1.0 mL of EtOH:MeCN:H2O/3:1:1, vortexed and the supernatant was then added to the first supernatant. The combined supernatants, containing the oligoribonucleotide, were dried to a white powder. The base deprotected oligoribonucleotide was resuspended in anhydrous TEA/HF/NMP solution (300 μL of a solution of 1.5 mL N-methylpyrrolidinone, 750 μL TEA and 1 mL TEA.3HF to provide a 1.4 M HF concentration) and heated to 65° C. After 1.5 h, the oligomer was quenched with 1.5 M $NH_4HCO_3$.

Alternatively, for the one-pot protocol, the polymer-bound trityl-on oligoribonucleotide was transferred to a 4 mL glass screw top vial and suspended in a solution of 33% ethanolic methylamine/DMSO:1/1 (0.8 mL) at 65° C. for 15 min. The vial was brought to r.t. TEA.3HF (0.1 mL) was added and the vial was heated at 65° C. for 15 min. The sample was cooled at −20° C. and then quenched with 1.5 M $NH_4HCO_3$.

For purification of the trityl-on oligomers, the quenched $NH_4HCO_3$ solution was loaded onto a C-18 containing cartridge that had been prewashed with acetonitrile followed by 50 mM TEAA. After washing the loaded cartridge with water, the RNA was detritylated with 0.5% TFA for 13 min. The cartridge was then washed again with water, salt exchanged with 1 M NaCl and washed with water again. The oligonucleotide was then eluted with 30% acetonitrile.

Inactive hammerhead ribozymes or binding attenuated control (BAC) oligonucleotides) were synthesized by substituting a U for $G_5$ and a U for $A_{14}$ (numbering from Hertel, K. J., et al., 1992, *Nucleic Acids Res.*, 20, 3252).

The average stepwise coupling yields were >98% (Wincott et al., 1995 *Nucleic Acids Res.* 23, 2677–2684). Those of ordinary skill in the art will recognize that the scale of synthesis can be adapted to be larger or smaller than the example described above including but not limited to 96 well format, all that is important is the ratio of chemicals used in the reaction.

Alternatively, the nucleic acid molecules of the present invention can be synthesized separately and joined together by ligation (Moore et al., 1992, *Science* 256, 9923; Draper et al., International PCT publication No. WO 93/23569; Shabarova et al., 1991, *Nucleic Acids Research* 19, 4247).

Enzymatic nucleic acid molecules are modified extensively to enhance stability by modification with nuclease resistant groups, for example, 2'-amino, 2'-C-allyl, 2'-flouro, 2'-O-methyl, 2'-H (for a review see Usman and Cedergren, 1992 *TIBS* 17, 34; Usman et al., 1994 *Nucleic Acids Symp. Ser.* 31, 163). Enzymatic nucleic acid molecules are purified by gel electrophoresis using general methods or are purified by high pressure liquid chromatography (HPLC; See Wincott et al., Supra, the totality of which is hereby incorporated herein by reference) and are resuspended in water.

For example, the sequences of the ribozymes that are chemically synthesized, useful in this study, are shown in Tables II to IX, XIV–XIX, XXII, and XXIII. Those in the art will recognize that these sequences are representative only of many more such sequences where the enzymatic portion of the ribozyme (all but the binding arms) is altered to affect activity. Stem-loop IV sequence of hairpin ribozymes listed in, for example, Table III (5'-CACGUUGUG-3') can be altered (substitution, deletion, and/or insertion) to contain any sequence, provided a minimum of two base-paired stem structure can form. Preferably, no more than 200 bases are inserted at these locations. The sequences listed in Tables II to X, XII–XIX, XXII, and XXIII may be formed of ribonucleotides or other nucleotides or non-nucleotides. Such ribozymes with enzymatic activity are equivalent to the ribozymes described specifically in the Tables.

Optimizing Activity of the Nucleic Acid Molecule of the Invention.

Enzymatic nucleic acid activity can be optimized as described by Stinchcomb et al., supra. The details will not be repeated here, but include altering the length of the enzymatic nucleic acid binding arms (stems I and III, see FIG. 2c), or chemically synthesizing enzymatic nucleic acid with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; Rossi et al., International Publication No. WO 91/03162; Beigelman et al., 1995 *J. Biol. Chem.* in press; as well as Sproat, U.S. Pat. No. 5,334,711 which describe various chemical modifications that can be made to the sugar moieties of enzymatic RNA molecules). Modifications which enhance their efficacy in cells, and removal of stem II bases to shorten RNA synthesis times and reduce chemical requirements are desired. (All these publications are hereby incorporated by reference herein).

There are several examples in the art describing sugar, base and phosphate modifications that can be introduced into enzymatic nucleic acid molecules without significantly effecting catalysis and with significant enhancement in their nuclease stability and efficacy. For example, enzymatic nucleic acid molecules are modified to enhance stability and/or enhance catalytic activity by modification with nuclease resistant groups, for example, 2'-amino, 2'-C-allyl, 2'-fluoro, 2'-O-methyl, 2'-H, nucleotide base modifications (for a review see Usman and Cedergren, 1992 *TIBS* 17, 34; Usman et al., 1994 *Nucleic Acids Symp. Ser.* 31, 163; Burgin et al., 1996 *Biochemistry* 35, 14090). Sugar modification of enzymatic nucleic acid molecules have been extensively described in the art (see Eckstein et al., International Publication PCT No. WO 92/07065; Perrault et al. *Nature* 1990, 344, 565–568; Pieken et al. *Science* 1991, 253, 314–317; Usman and Cedergren, *Trends in Biochem. Sci.* 1992, 17, 334–339; Usman et al. International Publication PCT No. WO 93/15187; Sproat, U.S. Pat. No. 5,334,711 and Beigelman et al., 1995 *J. Biol. Chem.* 270, 25702; all of the references are hereby incorporated in their totality by reference herein). Such publications describe general methods and strategies to determine the location of incorporation of sugar, base and/or phosphate modifications and the like into enzymatic nucleic acid without inhibiting catalysis, and are incorporated by reference herein. In view of such teachings, similar modifications can be used as described herein to modify the nucleic acid catalysts of the instant invention.

Nucleic acid catalysts having chemical modifications which maintain or enhance enzymatic activity are provided. Such nucleic acid is also generally more resistant to nucleases than unmodified nucleic acid. Thus, in a cell and/or in vivo the activity may not be significantly lowered. As exemplified herein such enzymatic nucleic acid molecules are useful in a cell and/or in vivo even if activity over all is reduced 10 fold (Burgin et al., 1996, *Biochemistry*, 35, 14090). Such enzymatic nucleic acid molecules herein are said to "maintain" the enzymatic activity of an all RNA enzymatic nucleic acid molecules.

Therapeutic nucleic acid molecules (e.g., enzymatic nucleic acid molecules and antisense nucleic acid molecules) delivered exogenously must optimally be stable within cells until translation of the target RNA has been inhibited long enough to reduce the levels of the undesirable protein. This period of time varies between hours to days depending upon the disease state. Clearly, these nucleic acid molecules must be resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

By "enhanced enzymatic activity" is meant to include activity measured in cells and/or in vivo where the activity is a reflection of both catalytic activity and enzymatic nucleic acid stability. In this invention, the product of these properties is increased or not significantly (less that 10 fold) decreased in vivo compared to an all RNA enzymatic nucleic acid molecule.

In one embodiment, the nucleic acid molecules comprises a 5' and/or a 3'-cap structure.

By "cap structure" is meant chemical modifications, which have been incorporated at the terminus of the oligonucleotide (see for example Wincott et al., WO 97/26270, incorporated by reference herein). These terminal modifications protect the nucleic acid molecule from exonuclease degradation, and may help in delivery and/or localization within a cell. The cap may be present at the 5'-terminus (5'-cap) or at the 3'-terminus (3'-cap) or may be present on both terminus. In non-limiting examples: the 5'-cap is selected from the group comprising inverted abasic residue (moiety), 4',5'-methylene nucleotide; 1-(beta-D-erythrofuranosyl)nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Beigelman et al., International PCT publication No. WO 97/26270, incorporated by reference herein).

In yet another embodiment, the 3'-cap is selected from a group comprising, 4',5'-methylene nucleotide; 1-(beta-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moeity; 5'-5'-inverted abasic moeity; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moeities (for more details see Beaucage and Iyer, 1993, *Tetrahedron* 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine.

By "nucleotide" as used herein is as recognized in the art to include natural bases (standard), and modified bases well known in the art. Such bases are generally located at the 1' position of a sugar moiety. A nucleotide generally comprises a base, sugar and a phosphate group. The nucleotide may also be abasic, i.e., lacking a base. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; all hereby incorporated by reference herein). Several examples of modified nucleic acid bases are known in the art and has recently been summarized by Limbach et al., 1994, *Nucleic Acids Res.* 22, 2183. Some of the non-limiting examples of base modifications that can be introduced into enzymatic nucleic acids without significantly effecting their catalytic activity include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine) and others (Burgin et al., 1996, *Biochemistry*, 35, 14090).

By "modified bases" in this aspect is meant nucleotide bases other than adenine, guanine, cytosine and uracil at 1' position or their equivalents; such bases may be used within the catalytic core of the enzyme and/or in the substrate-binding regions.

By "abasic" is meant sugar moieties lacking a base or having other chemical groups in place of a base at the 1' position.

By "unmodified nucleoside" is meant one of the bases adenine, cytosine, guanine, uracil joined to the 1' carbon of β-D-ribo-furanose.

By "modified nucleoside" is meant any nucleotide base that contains a modification in the chemical structure of an unmodified nucleotide base, sugar and/or phosphate.

In connection with 2'-modified nucleotides as described for the present invention, by "amino" is meant 2'-$NH_2$ or 2'-O—$NH_2$, which can be modified or unmodified. Such modified groups are described, for example, in Eckstein et al., U.S. Pat. No. 5,672,695 and Matulic-Adamic et al., WO 98/28317, respectively, which are both incorporated by reference in their entireties.

Various modifications to nucleic acid (e.g., antisense and ribozyme) structure can be made to enhance the utility of these molecules. Such modifications enhance shelf-life, half-life in vitro, stability, and ease of introduction of such oligonucleotides to the target site, e.g., to enhance penetration of cellular membranes, and confer the ability to recognize and bind to targeted cells.

Use of these molecules can lead to better treatment of the disease progression by affording the possibility of combination therapies (e.g., multiple enzymatic nucleic acid molecules targeted to different genes, enzymatic nucleic acid molecules coupled with known small molecule inhibitors, or intermittent treatment with combinations of enzymatic nucleic acid molecules (including different ribozyme motifs) and/or other chemical or biological molecules). The treatment of patients with nucleic acid molecules can also include combinations of different types of nucleic acid molecules. Therapies can be devised which include a mixture of enzymatic nucleic acid molecules (including different ribozyme motifs), antisense and/or 2–5A chimera molecules to one or more targets to alleviate symptoms of a disease.

Administration of Nucleic Acid Molecules

Sullivan, et al., supra, describes the general methods for delivery of enzymatic RNA molecules. Enzymatic nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, enzymatic nucleic acid molecules can be directly delivered ex vivo to cells or tissues with or without the aforementioned vehicles. Alternatively, the nucleic acid/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of nucleic acid delivery and administration are provided in Sullivan et al., supra and Draper et al., supra which have been incorporated by reference herein.

Methods for the delivery of nucleic acid molecules is described in Akhtar et al., 1992, *Trends Cell Bio.*, 2, 139; and *Delivery Strategies for Antisense Oligonucleotide Therapeutics*, ed. Akhtar, 1995 which are both incorporated herein by reference. Sullivan et al., PCT WO 94/02595, further describes the general methods for delivery of enzymatic RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, nucleic acid molecules can be directly delivered ex vivo to cells or tissues with or without the aforementioned vehicles. Alternatively, the nucleic acid/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of nucleic acid delivery and administration are provided in Sullivan et al., supra and Draper et al., PCT WO93/23569 which have been incorporated by reference herein.

The molecules of the instant invention can be used as pharmaceutical agents. Pharmaceutical agents prevent, inhibit the occurrence, or treat (alleviate a symptom to some extent, preferably all of the symptoms) of a disease state in a patient.

The negatively charged polynucleotides of the invention can be administered (e.g., RNA, DNA or protein) and introduced into a patient by any standard means, with or without stabilizers, buffers, and the like, to form a pharmaceutical composition. When it is desired to use a liposome delivery mechanism, standard protocols for formation of liposomes can be followed. The compositions of the present invention may also be formulated and used as tablets, capsules or elixirs for oral administration; suppositories for rectal administration; sterile solutions; suspensions for injectable administration; and the like.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or patient, preferably a human. Suitable forms, in part, depend upon the use or the route of entry, for example oral, transdermal, or by injection. Such forms should not prevent the composition or formulation to reach a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

By "systemic administration" is meant in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach may provide enhanced delivery of the drug to target cells by taking advantage of the specificity of macrophage and lymphocyte immune recognition of abnormal cells, such as the cancer cells.

The invention also features the use of a composition comprising surface-modified liposomes containing poly (ethylene glycol)lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601–2627; Ishiwata et al., *Chem. Pharm. Bull.* 1995, 43, 1005–1011). Such liposomes have been shown to accumulate selectively in tumors, presumably by extravasation and capture in the neovascularized target tissues (Lasic et al., *Science* 1995, 267, 1275–1276; Oku et al., 1995, *Biochim. Biophys. Acta*, 1238, 86–90). Long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864–24870; Choi et al., International PCT Publication No. WO 96/10391; Ansell et al., International PCT Publication No. WO 96/10390; Holland et al., International PCT Publication No. WO 96/10392; all of these are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985) hereby incorporated by reference herein. For example, preservatives, stabilizers, dyes and flavoring agents may be provided. Id. at 1449. These include sodium benzoate, sorbic acid and esters of p-hydroxybenzoic acid. In addition, antioxidants and suspending agents can be used. Id.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer.

The nucleic acid molecules of the invention and formulations thereof can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a patient in combination with other therapeutic compounds to increase the overall therapeutic effect. The use of multiple compounds to treat an indication can increase the beneficial effects while reducing the presence of side effects.

Another means of accumulating high concentrations of a nucleic acid molecule of the invention (e.g., ribozyme or antisense) within cells is to incorporate the nucleic acid-encoding sequences into a DNA or RNA expression vector. Transcription of the nucleic acid sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37; Thompson et al., 1995 supra). Several investigators have demonstrated that enzymatic nucleic acid or antisese expressed from such promoters can function in mammalian cells (e.g. Izant and Weintraub, 1985 *Science* 229, 345; McGarry and Lindquist, 1986 *Proc. Natl. Acad. Sci. USA* 83, 399; Kashani-Sabet et al., 1992 *Antisense Res. Dev.*, 2, 3–15; Ojwang et al., 1992 *Proc. Natl. Acad. Sci. USA*, 89, 10802–6; Chen et al., 1992 *Nucleic Acids Res.*, 20, 4581–9; Yu et al., 1993 *Proc. Natl. Acad. Sci. USA*, 90, 6340–4; L'Huillier et al., 1992 *EMBO J.* 11, 4411–8; Lisziewicz et al., 1993 *Proc. Natl. Acad. Sci. U.S.A.*, 90, 8000–4; Thompson et al., 1995 *Nucleic Acids Res.* 23, 2259). The above nucleic acid transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

In one embodiment of the invention, a transcription unit expressing an enzymatic nucleic acid that cleaves RNAs that encode flt-1, KDR and/or flk-1 are inserted into a plasmid DNA vector or an adenovirus or adeno-associated virus DNA viral vector or a retroviral RNA vector. Viral vectors have been used to transfer genes and lead to either transient or long term gene expression (Zabner et al., 1993 *Cell* 75, 207; Carter, 1992 *Curr. Opi. Biotech.* 3, 533). The adenovirus, AAV or retroviral vector is delivered as recombinant viral particles. The DNA may be delivered alone or complexed with vehicles (as described for RNA above). The recombinant adenovirus or AAV or retroviral particles are locally administered to the site of treatment, e.g., through incubation or inhalation in vivo or by direct application to cells or tissues ex vivo. Retroviral vectors have also been used to express enzymatic nucleic acid in mammalian cells (Ojwang et al., 1992 supra; Thompson et al., 1995 supra).

Flt-1, KDR and/or flk-1 are attractive nucleic acid-based therapeutic targets by several criteria. The interaction between VEGF and VEGF-R is well-established. Efficacy can be tested in well-defined and predictive animal models. Finally, the disease conditions are serious and current therapies are inadequate. Whereas protein-based therapies would inhibit VEGF activity nucleic acid-based therapy provides a direct and elegant approach to directly modulate flt-1, KDR and/or flk-1 expression.

Because flt-1 and KDR mRNAs are highly homologous in certain regions, some enzymatic nucleic acid target sites are also homologous (see Table X). In this case, a single enzymatic nucleic acid cantarget both flt-1 and KDR mRNAs. At partially homologous sites, a single enzymatic nucleic acid can sometimes be designed to accommodate a site on both mRNAs by including G/U base pairing. For example, if there is a G present in an enzymatic nucleic acid target site in KDR mRNA at the same position there is an A in the flt-1 ribozyme target site, the enzymatic nucleic acid can be synthesized with a U at the complementary position and it will bind both to sites. The advantage of one enzymatic nucleic acid that targets both VEGF-R mRNAs is clear, especially in cases where both VEGF receptors may contribute to the progression of angiogenesis in the disease state.

"Angiogenesis" refers to formation of new blood vessels, which is an essential process in reproduction, development and wound repair. "Tumor angiogenesis" refers to the induction of the growth of blood vessels from surrounding tissue into a solid tumor. Tumor growth and tumor metastasis are dependent on angiogenesis (for a review see Folkman, 1985 supra; Folkman 1990 *J. Natl. Cancer Inst.*, 82, 4; Folkman and Shing, 1992 *J. Biol. Chem.* 267, 10931).

Angiogenesis plays an important role in other diseases such as arthritis wherein new blood vessels have been shown to invade the joints and degrade cartilage (Folkman and Shing, supra).

"Retinopathy" refers to inflammation of the retina and/or degenerative condition of the retina which may lead to occlusion of the retina and eventual blindness. In "diabetic retinopathy" angiogenesis causes the capillaries in the retina to invade the vitreous resulting in bleeding and blindness which is also seen in neonatal retinopathy (for a review see Folkman, 1985 supra; Folkman 1990 supra; Folkman and Shing, 1992 supra).

The following examples further illustrate the present invention but should not be construed to limit the present invention in any way.

EXAMPLE 1 flt-1, KDR and/or flk-1 Ribozymes

By engineering ribozyme motifs, Applicant has designed several ribozymes directed against flt-1, KDR and/or flk-1 encoded mRNA sequences. These ribozymes were synthesized with modifications that improve their nuclease resistance (Beigelman et al., 1995 *J Biol. Chem.* 270, 25702) and enhance their activity in cells. The ability of ribozymes to cleave target sequences in vitro was evaluated essentially as described in Thompson et al., PCT Publication No. WO 93/23057; Draper et al., PCT Publication No. WO 95/04818.

EXAMPLE 2

Effect of Ribozymes on the Binding of VEGF to flt-1, KDR and/or flk-1 Receptors Several common human cell lines are available that express endogenous flt-1, KDR and/or flk-1. flt-1, KDR and/or flk-1 which can be detected easily with monoclonal antibodies. Use of appropriate fluorescent reagents and fluorescence-activated cell-sorting (FACS) permit direct quantitation of surface flt-1, KDR and/or flk-1 on a cell-by-cell basis. Active ribozymes are expected to directly reduce flt-1, KDR and/or flk-1 expression and thereby reduce VEGF binding to the cells. In this example, human umbelical cord microvascular endothelial cells were used.

Cell Preparation:

Plates were coated with 1.5% gelatin and allowed to stand for one hour. Cells (e.g., microvascular endothelial cells derived from human umbilical cord vein) were plated at 20,000 cells/well (24 well plate) in 200 μl growth media and incubated overnight (~1 doubling) to yield ~40,000 cells (75–80% confluent).

Ribozyme Treatment:

Media was removed from cells and the cells were washed two times with 300 μl 1×PBS:$Ca^{2+}$:$Mg^{2+}$ mixture. A complex of 200–500 nM ribozyme and LipofectAMINE® (3:1 lipid:phosphate ratio) in 200 μl OptiMEM® (5% FBS) was added to the cells. The cells were incubated for 6 hr (equivalent to 2–3 VEGF-R turnovers).

$^{125}$I VEGF Binding Assay:

The assay was carried out on ice to inhibit internalization of VEGF during the experiment. The media containing the ribozyme was removed from the cells and the cells were washed twice with 300 μl 1×PBS:$Ca^{2+}$:$Mg^{2+}$ mixture containing 1% BSA. Appropriate $^{125}$I VEGF solution (100,000 cpm/well, +/−10× cold 1×PBS, 1% BSA) was applied to the cells. The cells were incubated on ice for 1 hour. $^{125}$I VEGF-containing solution was removed and the cells were washed three times with 300 μl 1×PBS:$Ca^{2+}$:$Mg^{2+}$ mixture containing 1% BSA. To each well 300 μl of 100 mM Tris-HCl, pH 8.0, 0.5% Triton X-100 was added and the mixture was incubated for 2 minutes. The $^{125}$I VEGF-binding was quantitated using standard scintillation counting techniques. Percent inhibition was calculated as follows:

$$\text{Percent Inhibition} = \frac{\text{cpm }^{125}I \text{ VEGF bound by the ribozyme-treated samples}}{\text{cpm }^{125}I \text{ VEGF bound by the Control sample}} \times 100$$

EXAMPLE 3

Effect of Hammerhead Ribozymes Targeted Against flt-1 Receptor on the Binding of VEGF Hammerhead ribozymes targeted to twenty sites within flt-1 RNA were synthesized as described above. The sequences of the ribozymes used are shown in Table II; the length of the stem II region is 3 bp. The hammerhead ribozymes were chemically modified such that the ribozyme consists of ribose residues at five positions; U4 and U7 positions contain 2'-$NH_2$ modifications, the remaining nucleotide positions contain 2'-O-methyl substitutions; four nucleotides at the 5' terminus contains phosphorothioate substitutions. Additionally, 3' end of the ribozyme contains a 3'-3' linked inverted abasic ribose.

Referring to FIG. 7, the effect of hammerhead ribozymes targeted against flt-1 receptor on the binding of VEGF to flt-1 on the surface of human microvascular endothelial cells is shown. The majority of the ribozymes tested were able to inhibit the expression of flt-1 and thereby were able to inhibit the binding of VEGF.

In order to determine the specificity of ribozymes targeted against flt-1 RNA, the effect of five anti-flt-1 ribozymes on the binding of VEGF, UPA (urokinase plasminogen activator) and FGF (fibroblast growth factor) to their corresponding receptors were assayed. As shown in FIG. 9, there was significant inhibition of VEGF binding to its receptors on cells treated with anti-flt-1 ribozymes. There was no specific inhibition of the binding of UPA and FGF to their corresponding receptors. These data strongly suggest that anti-flt-1 ribozymes specifically cleave flt-1 RNA and not RNAs encoding the receptors for UPA and FGF, resulting in the inhibition of flt-1 receptor expression on the surface of the cells. Thus the ribozymes are responsible for the inhibition of VEGF binding but not the binding of UPA and FGF.

EXAMPLE 4

Effect of Hammerhead Ribozymes Targeted Against KDR Receptor on the Binding of VEGF Hammerhead ribozymes targeted to twenty-one sites within KDR RNA were synthesized as described above. The sequences of the ribozymes used are shown in Table IV; the length of stem II region is 3 bp. The hammerhead ribozymes were chemically modified such that the ribozyme consists of ribose residues at five positions; U4 and U7 positions contain 2'-$NH_2$ modifications, the remaining nucleotide positions contain 2'-O-methyl substitutions; four nucleotides at the 5' terminus contains phosphorothioate substitutions. Additionally, the 3' end of the ribozyme contains a 3'-3' linked inverted abasic deoxyribose.

Referring to FIG. 8, the effect of hammerhead ribozymes targeted against KDR receptor on the binding of VEGF to KDR on the surface of human microvascular endothelial cells is shown. A majority of the ribozymes tested were able to inhibit the expression of KDR and thereby were able to inhibit the binding of VEGF. As a control, the cells were treated with a ribozyme that is not targeted towards KDR RNA (irrel. RZ); there was no specific inhibition of VEGF binding. The results from this control experiment strongly suggest that the inhibition of VEGF binding observed with anti-KDR ribozymes is a ribozyme-mediated inhibition.

EXAMPLE 5

Effect of Ribozymes Targeted Against VEGF Receptors on Cell Proliferation

Cell Preparation:

24-well plates were coated with 1.5% gelatin (porcine skin 300 bloom). After 1 hour, excess gelatin is washed off of the plate. Microvascular endothelial cells were plated at 5,000 cells/well (24 well plate) in 200 µl growth media. The cells were allowed to grow for ~18 hours (~1 doubling) to yield ~10,000 cells (25–30% confluent).

Ribozyme Treatment:

Media was removed from the cells, and the cells were washed two times with 300 µl 1×PBS:$Ca^{2+}$:$Mg^{2+}$ mixture.

For anti-flt-1HH ribozyme experiment (FIG. 12) a complex of 500 nM ribozyme; 15 µM LFA (3:1 lipid:phosphate ratio) in 200 µl OptiMEM (5% FCS) media was added to the cells. Incubation of cells was carried out for 6 hours (equivalent to 2–3 VEGF receptor turnovers).

For anti-KDR HH ribozyme experiment (FIG. 13) a complex of 200 nM ribozyme; 5.25 µM LFA (3:1 lipid:phosphate ratio) in 200 µl OptiMEM (5% FCS) media was added to the cells. Incubation of cells was carried out for 3 hours.

Proliferation:

After three or six hours, the media was removed from the cells and the cells were washed with 300 µl 1×PBS:$Ca^{2+}$:$Mg^{2+}$ mixture. Maintenance media (contains dialyzed 10% FBS) +/−VEGF or basic FGF at 10 ng/ml was added to the cells. The cells were incubated for 48 or 72 hours. The cells were trypsinized and counted (Coulter counter). Trypan blue was added on one well of each treatment as a control.

As shown in FIG. 12B, VEGF and basic FGF stimulate human microvascular endothelial cell proliferation. However, treatment of cells with 1358 HH or 4229 HH ribozymes, targeted against flt-1 mRNA, results in a significant decrease in the ability of VEGF to stimulate endothelial cell proliferation. These ribozymes do not inhibit the FGF-mediated stimulation of endothelial cell proliferation.

Human microvascular endothelial cells were also treated with hammerhead ribozymes targeted against sites 527, 730, 3702 or 3950 within the KDR mRNA. As shown in FIG. 13, all four ribozymes caused significant inhibition of VEGF-mediated induction of cell proliferation. No significant inhibition of cell proliferation was observed when the cells were treated with a hammerhead ribozyme targeted to an irrelevant RNA. Additionally, none of the ribozymes inhibited FGF-mediated stimulation of cell proliferation.

These results strongly suggest that hammerhead ribozymes targeted against either flt-1 or KDR mRNA specifically inhibit VEGF-mediated induction of endothelial cell proliferation.

EXAMPLE 6

Effect of Antisense Oligonucleotides Targeted Against VEGF Receptors on Cell Proliferation (Colorimetric Assay)

The following are some of the reagents used in the proliferation assay:

Cells: Human aortic endothelial cells (HAEC) from Clonetics®. Cells at early passage are preferably used.

Uptake Medium: EBM (from Clonetics®); 1% L-Glutamine; 20 mM Hepes; No serum; No antibiotics.

Growth Medium: EGM (from Clonetics®); FBS to 20%; 1% L-Glutamine; 20 mM Hepes.

Cell Plating: 96-well tissue culture plates were coated with 0.2% gelatin (50 µl/well). The gelatin was incubated in the wells at room temperature for 15–30 minutes. The gelatin was removed by aspiration and the wells were washed with PBS:$Ca^{2+}$:$Mg^{2+}$ mixture. PBS mixture was left in the wells until cells were ready to be added. HAEC cells were detached by trypsin treatment and resuspended at $1.25 \times 10^4$/ml in growth medium. PBS was removed from plates and 200 µl of cells (i.e. $2.5 \times 10^3$ cells/well) were added to each well. The cells were allowed to grow for 48 hours before the proliferation assay.

Assay: Growth medium was removed from the wells. The cells were washed twice with PBS:$Ca^{2+}$:$Mg^{2+}$ mixture without antibiotics. A formulation of lipid/antisense oligonucleotide (antisense oligonucleotide is used here as a non-limiting example) complex was added to each well (100 µl/well) in uptake medium. The cells were incubated for 2–3 hours at 37° C. in a $CO_2$ incubator. After uptake, 100 µl/well of growth medium was added (gives final FBS concentration of 10%). After approximately 72 hours, 40 µl MTS® stock solution (made as described by manufacturer) was added to each well and incubated at 37° C. for 1–3 hours, depending on the color development. (For this assay, 2 hours was sufficient). The intensity of color formation was determined on a plate reader at 490 nM.

Phosphorothioate-substituted antisense oligodeoxynucleotides were custom synthesized by The Midland Certified Reagent Company®, Midland, Tex. Following non-limiting antisense oligodeoxynucleotides targeted against KDR RNA were used in the proliferation assay:

KDR 21 AS:        5'-GCA GCA CCT TGC TCT    (SEQ ID NO: 20825)
                  CCA TCC-3'

SCRAMBLED CONTROL: 5'-CTG CCA ACT TCC CAT   (SEQ ID NO: 20826)
                   GCC TGC-3'

As shown in FIG. 10, proliferation of HAEC cells is specifically inhibited by increasing concentrations of the phosphorothioate anti-KDR-antisense oligodeoxynucleotide. The scrambled antisense oligonucleotide is not expected to bind the KDR RNA and therefore is not expected to inhibit KDR expression. As expected, there is no detectable inhibition of proliferation of HAEC cells treated with a phosphorothioate antisense oligonucleotide with scrambled sequence.

EXAMPLE 7

In vitro Cleavage of flt-1 RNA by Hammerhead Ribozymes

Referring to FIG. 11A, hammerhead ribozymes (HH) targeted against sites 1358 and 4229 within the flt-1 RNA were synthesized as described above.
RNA Cleavage Assay In Vitro:

Substrate RNA was 5' end-labeled using [γ-$^{32}$P] ATP and T4 polynucleotide kinase (US Biochemicals). Cleavage reactions were carried out under ribozyme "excess" conditions. Trace amount (≦1 nM) of 5' end-labeled substrate and 40 nM unlabeled ribozyme were denatured and renatured separately by heating to 90° C. for 2 minutes and snap-cooling on ice for 10-15 minutes. The ribozyme and substrate were incubated, separately, at 37° C. for 10 minutes in a buffer containing 50 mM Tris-HCl and 10 mM $MgCl_2$. The reaction was initiated by mixing the ribozyme and substrate solutions and incubating at 37° C. Aliquots of 5 μl were taken at regular intervals of time and the reaction was quenched by mixing with equal volume of 2× formamide stop mix. The samples were resolved on 20% denaturing polyacrylamide gels. The results were quantified and percentage of target RNA cleaved is plotted as a function of time.

Referring to FIGS. 11B and 11C, hammerhead ribozymes targeted against sites 1358 and 4229 within the flt-1 RNA are capable of cleaving target RNA efficiently in vitro.

EXAMPLE 8

In vitro Cleavage of KDR RNA by Hammerhead Ribozymes

In this non-limiting example, hammerhead ribozymes targeted against sites 726, 527, 3702 and 3950 within KDR RNA were synthesized as described above. RNA cleavage reactions were carried out in vitro essentially as described under Example 7.

Referring to FIGS. 14 and 15, all four ribozymes were able to cleave their cognate target RNA efficiently in a sequence-specific manner.

EXAMPLE 9

In vitro Cleavage of RNA by Hammerhead Ribozymes Targeted Against Cleavage Sites that are Homologous Between KDR and flt-1 mRNA Given that flt-1 and KDR mRNAs are highly homologous in certain regions, some ribozyme target sites are also homologous (see Table X). In this case, a single ribozyme will target both flt-1 and KDR mRNAs. Hammerhead ribozyme (FLT/KDR-1) targeted against one of the homologous sites between flt-1 and KDR (flt-1 site 3388 and KDR site 3151) was synthesized as described above. Ribozymes with either a 3 bp stem II or a 4 bp stem II were synthesized. RNA cleavage reactions were carried out in vitro essentially as described under Example 7.

Referring to FIG. 16, FLT/KDR-I ribozyme with either a 3 or a 4 bp stem II was able to cleave its target RNA efficiently in vitro.

EXAMPLE 10

Effect of Multiple Ribozymes Targeted Against Both flt-1 and KDR RNA on Cell Proliferation Since both flt-1 and KDR receptors of VEGF are involved in angiogenesis, the inhibition of the expression of both of these genes can be an effective approach to inhibit angiogenesis.

Human microvascular endothalial cells were treated with hammerhead ribozymes targeted against sites flt-1 4229 alone, KDR 527 alone, KDR 726 alone, KDR 3950 alone, flt-1 4229+KDR 527, flt-1 4229+KDR 726 or flt-1 4229+KDR 3950. As shown in FIG. 17, all the combinations of active ribozymes (A) caused significant inhibition of VEGF-mediated induction of cell proliferation. No significant inhibition of cell proliferation was observed when the cells were treated with a catalytically inactive (I) hammerhead ribozymes. Additionally, cells treated with ribozymes targeted against both flt-1 and KDR RNAs-flt-1 4229+KDR 527; flt-1 4229+KDR 726; flt-1 4229+KDR 3950, were able to cause a greater inhibition of VEGF-mediated induction of cell proliferation when compared with individual ribozymes targeted against either flt-1 or KDR RNA (see flt-1 4229 alone; KDR 527 alone; KDR 726 alone; KDR 3950 alone). This strongly suggests that treatment of cells with multiple ribozymes can be a more effective means of inhibition of gene expression.
Animal Models There are several animal models in which the anti-angiogenesis effect of nucleic acids of the present invention, such as enzymatic nucleic acids, directed against VEGF-R mRNAs can be tested. Typically a corneal model has been used to study angiogenesis in rat and rabbit since recruitment of vessels can easily be followed in this normally avascular tissue (Pandey et al., 1995 Science 268: 567–569). In these models, a small Teflon or Hydron disk pretreated with an angiogenesis factor (e.g. bFGF or VEGF) is inserted into a pocket surgically created in the cornea. Angiogenesis is monitored 3 to 5 days later. Enzymatic nucleic acids directed against VEGF-R mRNAs are delivered in the disk as well, or dropwise to the eye over the time course of the experiment. In another eye model, hypoxia has been shown to cause both increased expression of VEGF and neovascularization in the retina (Pierce et al., 1995 Proc. Natl. Acad. Sci. USA. 92: 905–909; Shweiki et al., 1992 J. Clin. Invest. 91: 2235–2243).

In human glioblastomas, it has been shown that VEGF is at least partially responsible for tumor angiogenesis (Plate et al., 1992 *Nature* 359, 845). Animal models have been developed in which glioblastoma cells are implanted subcutaneously into nude mice and the progress of tumor growth and angiogenesism is studied (Kim et al., 1993 supra; Millauer et al., 1994 supra).

Another animal model that addresses neovascularization involves Matrigel, an extract of basement membrane that becomes a solid gel when injected subcutaneously (Passaniti et al., 1992 *Lab. Invest.* 67: 519–528). When the Matrigel is supplemented with angiogenesis factors such as VEGF, vessels grow into the Matrigel over a period of 3 to 5 days and angiogenesis can be assessed. Again, nucleic acids directed against VEGF-R mRNAs are delivered in the Matrigel.

Several animal models exist for screening of anti-angiogenic agents. These include corneal vessel formation following corneal injury (Burger et al., 1985 *Cornea* 4: 35–41; Lepri, et al., 1994 *J. Ocular Pharmacol.* 10: 273–280; Ormerod et al., 1990 *Am. J. Pathol.* 137: 1243–1252) or intracorneal growth factor implant (Grant et al., 1993 *Diabetologia* 36: 282–291; Pandey et al. 1995 supra; Zieche et al., 1992 *Lab. Invest.* 67: 711–715), vessel growth into Matrigel matrix containing growth factors (Passaniti et al., 1992 supra), female reproductive organ neovascularization following hormonal manipulation (Shweiki et al., 1993 *Clin. Invest.* 91: 2235–2243), several models involving inhibition of tumor growth in highly vascularized solid tumors (O'Reilly et al., 1994 *Cell* 79: 315–328; Senger et al., 1993 *Cancer and Metas. Rev.* 12: 303–324; Takahasi et al., 1994 *Cancer Res.* 54: 4233–4237; Kim et al., 1993 supra), and transient hypoxia-induced neovascularization in the mouse retina (Pierce et al., 1995 *Proc. Natl. Acad. Sci. USA.* 92: 905–909).

The cornea model, described in Pandey et al. supra, is the most common and well characterized anti-angiogenic agent efficacy screening model. This model involves an avascular tissue into which vessels are recruited by a stimulating agent (growth factor, thermal or alkalai burn, endotoxin). The corneal model utilizes the intrastromal corneal implantation of a Teflon pellet soaked in a VEGF-Hydron solution to recruit blood vessels toward the pellet which can be quantitated using standard microscopic and image analysis techniques. To evaluate their anti-angiogenic efficacy, nucleic acids are applied topically to the eye or bound within Hydron on the Teflon pellet itself. This avascular cornea as well as the Matrigel (see below) provide for low background assays. While the corneal model has been performed extensively in the rabbit, studies in the rat have also been conducted.

The mouse model (Passaniti et al., supra) is a non-tissue model which utilizes Matrigel, an extract of basement membrane (Kleinman et al., 1986) or Millipore® filter disk, which can be impregnated with growth factors and anti-angiogenic agents in a liquid form prior to injection. Upon subcutaneous administration at body temperature, the Matrigel or Millipore® filter disk forms a solid implant. VEGF embedded in the Matrigel or Millipore® filter disk is used to recruit vessels within the matrix of the Matrigel or Millipore® filter disk which can be processed histologically for endothelial cell specific vWF (factor VIII antigen) immunohistochemistry, Trichrome-Masson stain, or hemoglobin content. Like the cornea, the Matrigel or Millipore® filter disk are avascular; however, it is not tissue. In the Matrigel or Millipore® filter disk model, nucleic acids are administered within the matrix of the Matrigel or Millipore® filter disk to test their anti-angiogenic efficacy. Thus, delivery issues in this model, as with delivery of nucleic acids by Hydron-coated Teflon pellets in the rat cornea model, may be less problematic due to the homogeneous presence of the nucleic acid within the respective matrix.

These models offer a distinct advantage over several other angiogenic models listed previously. The ability to use VEGF as a pro-angiogenic stimulus in both models is highly desirable since the instant nucleic acid molecules target only VEGFr mRNA. In other words, the involvement of other non-specific types of stimuli in the cornea and Matrigel models is not advantageous from the standpoint of understanding the pharmacologic mechanism by which the anti-VEGFr mRNA nucleic acid molecules produce their effects. In addition, the models allow for testing the specificity of the anti-VEGFr mRNA nucleic acids by using either a- or bFGF as a pro-angiogenic factor. Vessel recruitment using FGF should not be affected in either model by anti-VEGFr mRNA nucleic acid molecules. Other models of angiogenesis including vessel formation in the female reproductive system using hormonal manipulation (Shweiki et al., 1993 supra); a variety of vascular solid tumor models which involve indirect correltations with angiogenesis (O'Reilly et al., 1994 supra; Senger et al., 1993 supra; Takahasi et al., 1994 supra; Kim et al., 1993 supra); and retinal neovascularization following transient hypoxia (Pierce et al., 1995 supra) were not selected for efficacy screening due to their non-specific nature, although there is a correlation between VEGF and angiogenesis in these models.

Other model systems to study tumor angiogenesis is reviewed by Folkman, 1985 *Adv. Cancer. Res.* 43, 175.

Use of Murine Models

For a typical systemic study involving 10 mice (20 g each) per dose group, 5 doses (1, 3, 10, 30 and 100 mg/kg daily over 14 days continuous administration), approximately 400 mg of enzymatic nucleic acid, formulated in saline is used. A similar study in young adult rats (200 g) requires over 4 g. Parallel pharmacokinetic studies involve the use of similar quantities of enzymatic nucleic acid further justifying the use of murine models.

Enzymatic Nucleic Acids and Lewis Lung Carcinoma and B-16 Melanoma Murine Models Identifying a common animal model for systemic efficacy testing of enzymatic nucleic acid is an efficient way of screening enzymatic nucleic acid for systemic efficacy.

The Lewis lung carcinoma and B-16 murine melanoma models are well accepted models of primary and metastatic cancer and are used for initial screening of anti-cancer agents. These murine models are not dependent upon the use of immunodeficient mice, are relatively inexpensive, and minimize housing concerns. Both the Lewis lung and B-16 melanoma models involve subcutaneous implantation of approximately $10^6$ tumor cells from metastatically aggressive tumor cell lines (Lewis lung lines 3LL or D122, LLc-LN7; B-16-BL6 melanoma) in C57BL/6J mice. Alternatively, the Lewis lung model can be produced by the surgical implantation of tumor spheres (approximately 0.8 mm in diameter). Metastasis also can be modeled by injecting the tumor cells directly intravenously. In the Lewis lung model, microscopic metastases can be observed approximately 14 days following implantation with quantifiable macroscopic metastatic tumors developing within 21–25 days. The B-16 melanoma exhibits a similar time course with tumor neovascularization beginning 4 days following implantation. Since both primary and metastatic tumors exist in these models after 21–25 days in the same animal, multiple measurements can be taken as indices of efficacy. Primary tumor volume and growth latency as well as the number of micro- and macroscopic metastatic lung foci or number of animals exhibiting metastases can be quantitated. The percent increase in lifespan can also be measured. Thus, these models provide suitable primary efficacy assays for screening systemically administered enzymatic nucleic acids and enzymatic nucleic acid formulations.

In the Lewis lung and B-16 melanoma models, systemic pharmacotherapy with a wide variety of agents usually begins 1–7 days following tumor implantation/inoculation with either continuous or multiple administration regimens. Concurrent pharmacokinetic studies can be performed to determine whether sufficient tissue levels of ribozymes can be achieved for pharmacodynamic effect to be expected. Furthermore, primary tumors and secondary lung metastases can be removed and subjected to a variety of in vitro studies (i.e. target RNA reduction).

Flt-1, KDR and/or flk-1 protein levels can be measured clinically or experimentally by FACS analysis. Flt-1, KDR and/or flk-1 encoded mRNA levels are assessed by Northern analysis, RNase-protection, primer extension analysis and/or quantitative RT-PCR. Enzymatic nucleic acids that block flt-1, KDR and/or flk-1 protein encoding mRNAs and therefore result in decreased levels of flt-1, KDR and/or flk-1 activity by more than 20% in vitro can be identified.

Enzymatic nucleic acids and/or genes encoding them are delivered by either free delivery, liposome delivery, cationic lipid delivery, adeno-associated virus vector delivery, adenovirus vector delivery, retrovirus vector delivery or plasmid vector delivery in these animal model experiments (see above).

Patients can be treated by locally administering nucleic acids targeted against VEGF-R by direct injection. Routes of administration include, but are not limited to, intravascular, intramuscular, subcutaneous, intraarticular, aerosol inhalation, oral (tablet, capsule or pill form), topical, systemic, ocular, intraperitoneal and/or intrathecal delivery.

EXAMPLE 11

Ribozyme-mediated Inhibition of Angiogenesis In Vivo

The purpose of this study was to assess the anti-angiogenic activity of hammerhead ribozymes targeted against flt-1 4229 site in the rat cornea model of VEGF induced angiogenesis (see above). These ribozymes have either active or inactive catalytic core and either bind and cleave or just bind to VEGF-R mRNA of the flt-1 subtype. The active ribozymes, that are able to bind and cleave the target RNA, have been shown to inhibit ($^{125}$I-labeled) VEGF binding in cultured endothelial cells and produce a dose-dependent decrease in VEGF induced endothelial cell proliferation in these cells (see Examples 3–5 above). The catalytically inactive forms of these ribozymes, wherein the ribozymes can only bind to the RNA but cannot catalyze RNA cleavage, fail to show these characteristics. The ribozymes and VEGF were co-delivered using the filter disk method: Nitrocellulose filter disks (Millipore®) of 0.057 diameter were immersed in appropriate solutions and were surgically implanted in rat cornea as described by Pandey et al., supra. This delivery method has been shown to deliver rhodamine-labeled free ribozyme to scleral cells and, in all likelihood cells of the pericorneal vascular plexus. Since the active ribozymes show cell culture efficacy and can be delivered to the target site using the disk method, it is essential that these ribozymes be assessed for in vivo anti-angiogenic activity.

The stimulus for angiogenesis in this study was the treatment of the filter disk with 30 μM VEGF which is implanted within the cornea's stroma. This dose yields reproducible neovascularization stemming from the pericorneal vascular plexus growing toward the disk in a dose-response study 5 days following implant. Filter disks treated only with the vehicle for VEGF show no angiogenic response. The ribozymes were co-adminstered with VEGF on a disk in two different ribozyme concentrations. One concern with the simultaneous administration is that the ribozymes will not be able to inhibit angiogenesis since VEGF receptors can be stimulated. However, Applicant has observed that in low VEGF doses, the neovascular response reverts to normal suggesting that the VEGF stimulus is essential for maintaining the angiogenic response. Blocking the production of VEGF receptors using simultaneous administration of anti-VEGF-R mRNA ribozymes could attenuate the normal neovascularization induced by the filter disk treated with VEGF.

Materials and Methods:
1. Stock Hammerhead Ribozyme Solutions:
   a. flt-1 4229 (786 μM)—Active
   b. flt-1 4229 (736 μM)—Inactive
2. Experimental Solutions/Groups:

| Group 1 | Solution 1 | Control VEGF solution: 30 μM in 82 mM Tris base |
|---|---|---|
| Group 2 | Solution 2 | flt-1 4229 (1 μg/μL) in 30 μM VEGF/82 mM Tris base |
| Group 3 | Solution 3 | flt-1 4229 (10 μg/μL) in 30 μM VEGF/82 mM Tris base |
| Group 4 | Solution 4 | No VEGF, flt-1 4229 (10 μg/μL) in 82 mM Tris base |
| Group 5 | Solution 5 | No VEGF, No ribozyme in 82 mM Tris base |

10 eyes per group, 5 animals (Since they have similar molecular weights, the molar concentrations should be essentially similar).

Each solution (VEGF and RIBOZYMES) were prepared as a 2× solution for 1:1 mixing for final concentrations above, with the exception of solution 1 in which VEGF was 2× and diluted with ribozyme diluent (sterile water).

3. VEGF Solutions

The 2×VEGF solution (60 μM) was prepared from a stock of 0.82 μg/μL in 50 mM Tris base. 200 μL of VEGF stock was concentrated by speed vac to a final volume of 60.8 μL, for a final concentration of 2.7 μg/μL or 60 μM. Six 10 μL aliquots were prepared for daily mixing. 2× solutions for VEGF and Ribozyme was stored at 4° C. until the day of the surgery. Solutions were mixed for each day of surgery. Original 2× solutions were prepared on the day before the first day of the surgery.

4. Surgical Solutions:
Anesthesia:
   stock ketamine hydrochloride 100 mg/mL
   stock xylazine hydrochloride 20 mg/mL
   stock acepromazine 10 mg/mL
   Final anesthesia solution: 50 mg/mL ketamine, 10 mg/mL xylazine, and 0.5 mg/mL acepromazine
   5% povidone iodine for opthalmic surgical wash
   2% lidocaine (sterile) for opthalmic administration (2 drops per eye)
   sterile 0.9% NaCl for opthalmic irrigation 5. Surgical Methods:
   Standard surgical procedure was performed as described in Pandey et al., supra. Filter disks were incubated in 1 μL of each solution for approximately 30 minutes prior to implantation.

6. Experimental Protocol:
   The animal corneas were treated with the treatment groups as described above. Animals were allowed to recover for 5 days after treatment with daily observation (scoring 0–3). On the fifth day animals were euthanized and digital images of each eye was obtained for quantitaion using Image Pro Plus. Quantitated neovascular surface areas were analyzed by ANOVA followed by two post-hoc tests including Dunnets and Tukey-Kramer tests for significance at the 95% confidence level. Dunnets provide information on the significance between the differences within the means of treatments vs. controls while Tukey-Kramer provide information on the significance of differences within the means of each group.

Results are graphically represented in FIG. 18. As shown in FIG. 18, flt-1 4229 active hammerhead ribozyme at both concentrations was effective at inhibiting angiogenesis, while the inactive ribozyme did not show any significant reduction in angiogenesis. A statistically signifiant reduction in neovascular surface area was observed only with active ribozymes. This result clearly shows that the ribozymes are capable of significantly inhibiting angiogenesis in vivo. Specifically, the mechanism of inhibition appears to be by the binding and cleavage of target RNA by ribozymes.

EXAMPLE 12

Bioactivity of Anti-angiogenesis Ribozymes Targeting flt-1 and kdr RNA

Materials and Methods

Ribozymes: Hammerhead ribozymes and controls designed to have attenuated activity (attenuated controls) were synthesized and purified as previously described above. The attenuated ribozyme controls maintain the binding arm sequence of the parent ribozyme and thus are still capable of binding to the mRNA target. However, they have two nucleotide changes in the core sequence that substantially reduce their ability to carry out the cleavage reaction. Ribozymes were designed to target Flt-1 or KDR mRNA sites conserved in human, mouse, and rat. In general, ribozymes with binding arms of seven nucleotides were designed and tested. If, however, only six nucleotides surrounding the cleavage site were conserved in all three species, six nucleotide binding arms were used. A subset of ribozyme and attenuated control sequences and modifications are listed in Table XII. Data are presented herein for $2'$-$NH_2$ uridine modified ribozymes in cell proliferation studies and for $2'$-C-allyl uridine modified ribozymes in RNAse protection, in vitro cleavage and corneal studies.

In vitro ribozyme cleavage assays: In vitro RNA cleavage rates on a 15 nucleotide synthetic RNA substrate were measured as previously described above.

Cell culture: Human dermal microvascular endothelial cells (HMVEC-d, Clonetics Corp.) were maintained at 37° C. in flasks or plates coated with 1.5% porcine skin gelatin (300 bloom, Sigma) in Growth medium (Clonetics Corp.) supplemented with 10–20% fetal bovine serum (FBS, Hyclone). Cells were grown to confluency and used up to the seventh passage. Stimulation medium consisted of 50% Sigma 99 media and 50% RPMI 1640 with L-glutamine and additional supplementation with 10 µg/mL Insulin-Transferrin-Selenium (Gibco BRL) and 10% FBS. Cell growth was stimulated by incubation in Stimulation medium supplemented with 20 ng/mL of either $VEGF_{165}$ or bFGF. $VEGF_{165}$ (165 amino acids) was selected for cell culture and animal studies because it is the predominant form of the four native forms of VEGF generated by alternative mRNA splicing. Cell culture assays were carried out in triplicate.

Ribozyme and ribozyme/LIPOFECTAMINE™ formulations:

Cell culture: Ribozymes or attenuated controls (50–200 nM) were formulated for cell culture studies and used immediately. Formulations were carried out with LIPOFECTAMINE™ (Gibco BRL) at a 3:1 lipid to phosphate charge ratio in serum-free medium (OPTI-MEM™, Gibco BRL) by mixing for 20 minutes at room temperature. For example, a 3:1 lipid to phosphate charge ratio was established by complexing 200 nM ribozyme with 10.8 µg/µL LIPOFECTAMINE™ (13.5 µM DOSPA).

In vivo: For corneal studies, lyophilized ribozyme or attenuated controls were resuspended in sterile water at a final stock concentration of 170 µg/µL (highest dose). Lower doses (1.7–50 µg/µL) were prepared by serial dilution in sterile water.

Proliferation assay: HMVEC-d were seeded ($5\times10^3$ cells/well) in 48-well plates (Costar) and incubated 24–30 hours in Growth medium at 37° C. After removal of the Growth medium, cells were treated with 50–200 nM LIPOFECTAMINE™ complexes of ribozyme or attenuated controls for 2 hours in OPTI-MEM™. The ribozyme/control-containing medium was removed and the cells were washed extensively in 1×PBS. The medium was then replaced with Stimulation medium or Stimulation medium supplemented with 20 ng/mL $VEGF_{165}$ or bFGF. After 48 hours, the cell number was determined using a Coulter™ cell counter. Data are presented as cell number per well following 48 h of VEGF stimulation.

RNAse protection assay: HMVEC-d were seeded ($2\times10^5$ cells/well) in 6-well plates (Costar) and allowed to grow 32–36 hours in Growth medium at 37° C. Cells were treated with LIPOFECTAMINE™ complexes containing 200 nM ribozyme or attenuated control for 2 hours as described under "Proliferation Assay" and then incubated in Growth medium containing 20 ng/mL $VEGF_{165}$ for 24 hours. Cells were harvested and an RNAse protection assay was carried out using the Ambion Direct Protect kit and protocol with the exception that 50 mM EDTA was added to the lysis buffer to eliminate the possibility of ribozyme cleavage during sample preparation. Antisense RNA probes targeting portions of Flt-1 and KDR were prepared by transcription in the presence of $[^{32}P]$-UTP. Samples were analyzed on polyacrylamide gels and the level of protected RNA fragments was quantified using a Molecular Dynamics PhosphorImager. The levels of Flt-1 and KDR were normalized to the level of cyclophilin (human cyclophilin probe template, Ambion) in each sample. The coefficient of variation for cyclophilin levels was 11% [265940 cpm±29386 (SD)] for all conditions tested here (i.e. in the presence of either active ribozymes or attenuated controls). Thus, cyclophilin is useful as an internal standard in these studies.

Rat corneal pocket assay of VEGF-induced angiogenesis:

Animal guidelines and anesthesia. Animal housing and experimentation adhered to standards outlined in the 1996 Guide for the Care and Use of Laboratory Animals (National Research Council). Male Sprague Dawley rats (250–300 g) were anesthetized with ketamine (50 mg/kg), xylazine (10 mg/kg), and acepromazine (0.5 mg/kg) administered intramuscularly (im). The level of anesthesia was monitored every 2–3 min by applying hind limb paw pressure and examining for limb withdrawal. Atropine (0.4 mg/kg, im) was also administered to prevent potential corneal reflex-induced bradycardia.

Preparation of VEGF soaked disk. For corneal implantation, 0.57 mm diameter nitrocellulose disks, prepared from 0.45 µm pore diameter nitrocellulose filter membranes (Millipore Corporation), were soaked for 30 min in 1 µL of 30 µM $VEGF_{165}$ in 82 mM Tris HCl (pH 6.9) in covered petri dishes on ice.

Corneal surgery. The rat corneal model used in this study was a modified from Koch et al. Supra and Pandey et al., supra. Briefly, corneas were irrigated with 0.5% povidone iodine solution followed by normal saline and two drops of 2% lidocaine. Under a dissecting microscope (Leica MZ-6), a stromal pocket was created and a presoaked filter disk (see above) was inserted into the pocket such that its edge was 1 mm from the corneal limbus.

Intraconjunctival injection of test solutions. Immediately after disk insertion, the tip of a 40–50 µm OD injector (constructed in our laboratory) was inserted within the conjunctival tissue 1 mm away from the edge of the corneal limbus that was directly adjacent to the VEGF-soaked filter disk. Six hundred nanoliters of test solution (ribozyme, attenuated control or sterile water vehicle) were dispensed at a rate of 12 µL/min using a syringe pump (Kd Scientific). The injector was then removed, serially rinsed in 70% ethanol and sterile water and immersed in sterile water between each injection. Once the test solution was injected, closure of the eyelid was maintained using microaneurism clips until the animal began to recover gross motor activity. Following treatment, animals were warmed on a heating pad at 37° C.

Animal treatment groups/experimental protocol. Ribozymes targeting Flt-1 site 4229 and KDR mRNA site 726 were tested in the corneal model along with their attenuated controls. Five treatment groups were assigned to examine the effects of five doses of each test substance over a dose range of 1–100 µg on VEGF-stimulated angiogenesis. Negative (30 µM VEGF soaked filter disk and intraconjunctival injection of 600 nL sterile water) and no stimulus (Tris-soaked filter disk and intraconjunctival injection of sterile water) control groups were also included. Each group consisted of five animals (10 eyes) receiving the same treatment.

Quantitation of angiogenic response. Five days after disk implantation, animals were euthanized following im administration of 0.4 mg/kg atropine and corneas were digitally imaged. The neovascular surface area (NSA, expressed in pixels) was measured postmortem from blood-filled corneal vessels using computerized morphometry (Image Pro Plus, Media Cybernetics, v2.0). The individual mean NSA was determined in triplicate from three regions of identical size in the area of maximal neovascularization between the filter disk and the limbus. The number of pixels corresponding to the blood-filled corneal vessels in these regions was summated to produce an index of NSA. A group mean NSA was then calculated. Data from each treatment group were normalized to VEGF/ribozyme vehicle-treated control NSA and finally expressed as percent inhibition of VEGF-induced angiogenesis.

Statistics. After determining the normality of treatment group means, group mean percent inhibition of VEGF-induced angiogenesis was subjected to a one-way analysis of variance. This was followed by two post-hoc tests for significance including Dunnett's (comparison to VEGF control) and Tukey-Kramer (all other group mean comparisons) at alpha=0.05. Statistical analyses were performed using JMP v.3.1.6 (SAS Institute).

Results.

Ribozyme-mediated reduction of VEGF-induced cell proliferation: Ribozyme cleavage of Flt-1 or KDR mRNA should result in a decrease in the density of cell surface VEGF receptors. This decrease should limit VEGF binding and consequently interfere with the mitogenic signaling induced by VEGF. To determine if cell proliferation was impacted by anti-Flt-1 and/or anti-KDR ribozyme treatment, proliferation assays using cultured human microvascular cells were carried out. Ribozymes included in the proliferation assays were initially chosen by their ability to decrease the level of VEGF binding to treated cells (see FIG. 8). In these initial studies, ribozymes targeting 20 sites in the coding region of each mRNA were screened. The most effective ribozymes against two sites in each target (Table XII), Flt-1 sites 1358 and 4229 and KDR sites 726 and 3950, were included in the proliferation assays reported here (FIG. 19). In addition, attenuated analogs of each ribozyme were used as controls (Table XII). These attenuated controls are still capable of binding to the mRNA target since the binding arm sequence is maintained. However, these controls have two nucleotide changes in the core sequence that substantially reduce their ability to carry out the cleavage reaction.

The antiproliferative effect of active ribozymes targeting two lead sites on each VEGF receptor mRNA is shown in FIG. 19. The active ribozymes tested decreased the relative proliferation of HMVEC-d after VEGF stimulation, an effect that increased with ribozyme concentration. This concentration dependency was not observed following treatment with the attenuated controls designed for these sites. In fact, little or no change in cell growth was noted following treatment with the attenuated controls, even though these controls can still bind to the specific target sequences. At 200 nM, there was a distinct "window" between the anti-proliferative effects of each ribozyme and its attenuated control; a trend also observed at lower doses. This window of inhibition of proliferation (56–77% based on total cells/well) reflects the contribution of ribozyme-mediated activity. In comparison, no effect of anti-Flt-1 or anti-KDR ribozymes was noted on bFGF-stimulated cell proliferation (FIGS. 19C, 19F). Moreover, an irrelevant, but active, ribozyme whose binding sequence is not found in either Flt-1 or KDR mRNA had no effect in this assay (FIG. 19B). These data are consistent with the basic ribozyme mechanism in which binding and cleavage are necessary components. Although the relative surface distribution of Flt-1 and KDR receptors in this cell type is not known, the antiproliferative effects of these ribozymes indicate that, at least in cell culture, both receptors are functionally coupled to proliferation.

Specific reduction of Flt-1 or KDR mRNA by ribozyme treatment: To confirm that anti-Flt-1 and anti-KDR ribozymes reduce their respective mRNA targets, cellular levels of Flt-1 or KDR were quantified using an RNAse protection assay with specific Flt-1 or KDR probes. For each target, one ribozyme/attenuated control pair was chosen for continued study. Data from a representative experiment are shown in FIG. 20. Exposure of HMVEC-d to active ribozyme targeting Flt-1 site 4229 decreased Flt-1 mRNA, but not KDR mRNA. Likewise, treatment with the active ribozyme targeting KDR site 726 decreased KDR, but not Flt-1 mRNA. Both ribozymes decreased the level of their respective target RNA by greater than 50%. The degree of reduction associated with the corresponding attenuated controls was not greater than 13%.

In vitro activity of anti-Flt and anti-KDR ribozymes.

To confirm further the necessity of an active ribozyme core, in vitro cleavage activities were determined for the Flt-1 site 4229 ribozyme and the KDR site 726 ribozyme as well as their paired attenuated controls. The first order rate constants calculated from the time-course of short substrate cleavage for the anti-Flt-1 ribozyme and its attenuated control were $0.081 \pm 0.0007$ min$^{-1}$ and $0.001 \pm 6 \times 10^{-5}$ min$^{-1}$, respectively. For the anti-KDR ribozyme and its paired control, the first order rate constants were $0.434 \pm 0.024$ min$^{-1}$ and $0.002 \pm 1 \times 10^{-4}$ min$^{-1}$, respectively. Although the attenuated controls retain a very slight level of cleavage activity under these optimized conditions, the decrease in in vitro cleavage activity between each active ribozyme and its paired attenuated control is about two orders of magnitude. Thus, an active core is essential for cleavage activity in vitro and is also necessary for ribozyme activity in cell culture.

Ribozyme-mediated reduction of VEGF-induced angiogenesis in vivo. To assess whether ribozymes targeting VEGF receptor mRNA could impact the complex process of angiogenesis, prototypic anti-Flt-1 and KDR ribozymes that were identified in cell culture studies were screened in a rat corneal pocket assay of VEGF-induced angiogenesis. In this assay, corneas implanted with VEGF-containing filter disks exhibited a robust neovascular response in the corneal region between the disk and the corneal limbus (from which the new vessels emerge). Disks containing a vehicle solution elicited no angiogenic response. In separate studies, intraconjunctival injections of sterile water vehicle did not affect the magnitude of the VEGF-induced angiogenic response. In addition, ribozyme injections alone did not induce angiogenesis.

The dose-related effects of anti-Flt-1 or KDR ribozymes on the VEGF-induced angiogenic response were then examined. FIGS. 21 and 22 illustrate the quantified antiangiogenic effect of the anti-Flt-1 (site 4229) and KDR (site 726) ribozymes and their attenuated controls over a dose range from 1 to 100 µg, respectively. For both ribozymes, the maximal antiangiogenic response (48 and 36% for anti-Flt-1 and KDR ribozymes, respectively) was observed at a dose of 10 µg.

The anti-Flt-1 ribozyme produced a significantly greater antiangiogenic response than its attenuated control at 3 and 10 µg ($p<0.05$; FIG. 21). Its attenuated control exhibited a small but significant antiangiogenic response at doses above 10 µg compared to vehicle treated VEGF controls ($p<0.05$; FIG. 21). At its maximum, this response was not significantly greater than that observed with the lowest dose of active anti-Flt-1 ribozyme. The anti-KDR ribozyme significantly inhibited angiogenesis from 3 to 30 µg ($p<0.05$; FIG. 22). The anti-KDR attenuated control had no significant effect at any dose tested.

EXAMPLE 13

In Vivo Inhibition of Tumor Growth and Metastases by VEGF-R Ribozymes

A. Lewis Lung Carcinoma Mouse Model: Ribozymes were chemically synthesized as described above. The sequence of ANGIOZYME™ bound to its target RNA is shown in FIG. 26.

The tumors in this study were derived from a cell line (LLC-HM) which gives rise to reproducible numbers of spontaneous lung metastases when propagated in vivo. The LLC-HM line was obtained from Dr. Michael O'Reilly, Harvard University. Tumor neovascularization in Lewis lung carcinoma has been shown to be VEGF-dependent. Tumors from mice bearing LLC-HM (selected for the highly metastatic phenotype by serial propagation) were harvested 20 days post-inoculation. A tumor brei suspension was prepared from these tumors according to standard protocols. On day 0 of the study, $0.5 \times 10^6$ viable LLC-HM tumor cells were injected subcutaneously (sc) into the dorsum or flank of previously untreated mice (100 µL injectate). Tumors were allowed to grow for a period of 3 days prior to initiating continuous intravenous administration of saline or 30 mg/kg/d ANGIOZYME™ via Alzet mini-pumps. One set of animals was dosed from days 3 to 17, inclusive. Tumor length and width measurements and volumes were calculated according to the formula: Volume=$0.5$(length)(width)$^2$.

At post-inoculation day 25, animals were euthanized and lungs harvested. The number of lung macrometastatic nodules was counted. It should be noted that metastatic foci were quantified 8 days after the cessation of dosing. Ribozyme solutions were prepared to deliver to another set of animals 100, 10, 3, or 1 mg/kg/day of ANGIOZYME™ via Alzet mini-pumps. A total of 10 animals per dose or saline control group were surgically implanted on the left flank with osmotic mini-pumps pre-filled with the respective test solution three days following tumor inoculation. Pumps were attached to indwelling jugular vein catheters.

FIG. 27 shows the antitumor effects of ANGIOZYME™. There is a statistically significant inhibition ($p<0.05$) of primary LLC-HM tumor growth in tumors grown in the flank regions compared to saline control. ANGIOZYME™ significantly reduced ($p<0.05$) the number of lung metastatic foci in animals inoculated either in the flank regions. FIG. 28 illustrates the dose-dependent anti-metastatic effect of ANGIOZYME™ compared to saline control.

B. Mouse Colorectal Cancer Model. KM12L4a-16 is a human colorectal cancer cell line. On day 0 of the study, $0.5 \times 10^6$ KM12L4a-16 cells were implanted into the spleen of nude mice. Three days after tumor inoculation, Alzet minipumps were implanted and continuous subcutaneous delivery of either saline or 12, 36 or 100 mg/kg/day of ANGIOZYME™ was initiated. On day 5, the spleens containing the primary tumors were removed. On day 18, the Alzet minipumps were replaced with fresh pumps so that delivery of saline or ANGIOZYME™ was continuous over a 28 day period from day 3 to day 32. Animals were euthanized on day 41 and the liver tumor burden was evaluated.

Following treatment with 100 mg/kg/day of ANGIOZYME™, there was a significant reduction in the incidence and median number of liver metastasis (FIGS. 29 and 30). In saline-treated animals, the median number of metastases was 101. However, at the high dose of ANGIOZYME™ (100 mg/kg/day), the median number of metastases was zero.

EXAMPLE 14

Effect of ANGIOZYME™ Alone or in Combination with Chemotherapeutic Agents in the Mouse Lewis Lung Carcinoma Model Methods Tumor inoculations. Male C57/BL6 mice, age 6 to 8 weeks, were inoculated subcutaneously in the flank with $5 \times 10^5$ LLC-HM cells from brei preparations made from tumors grown in mice.

Ribozymes and controls. The ribozyme and controls tested in this study are given in Table XIII. RPI.4610, also known as ANGIOZYME™, is an anti-Flt-1 ribozyme that targets site 4229 in the human Flt-1 receptor mRNA (EMBL accession no. X51602). The controls tested include RPI.13141, an attenuated version of RPI.4610 in which four nucleotides in the catalytic core are changed so that the cleavage activity is dramatically decreased. RPI.13141, however, maintains the base composition and binding arms of RPI.4610 and so is still capable of binding to the target site. The second control (RPI.13030) also has changes to the catalytic core (three) to inhibit cleavage activity, but in addition the sequence of the binding arms has been scrambled so that it can no longer bind to the target sequence. One nucleotide in the arm of RPI.13030 is also changed to maintain the same base composition as RPI.4610.

Ribozyme administrations. Ribozymes and controls were resuspended in normal saline. Administration was initiated seven days following tumor inoculation. Animals either received a daily subcutaneous injection (30 mg/kg test substance) from day 7 to day 20 or were instrumented with an Alzet osmotic minipump (12 μL/day flow rate) containing a solution of ribozyme or control. Subcutaneous infusion pumps delivered the test substances (30 mg/kg/day) from day 7 to 20 (14-day pumps, 420 mg/kg total test substance) or days 7–34 (28-day pumps, 840 mg/kg total test substance). Where indicated, chemotherapeutic agents were given in combination with ribozyme treatment. Cyclophosphamide was given by ip administration on days 7, 9 and 11 (125 mg/kg). Gemcitabine was given by intraperitoneal administration on days 8, 11 and 14 (125 mg/kg). Untreated, uninstrumented animals were used as comparison. Five animals were included in each group.

Results

The antiangiogenic ribozyme, ANGIOZYME™, was tested in a model of Lewis lung carcinoma alone and in combination with two chemotherapeutic agents. Previously (see above), 30 mg/kg/day ANGIOZYME™ alone was determined to inhibit both primary tumor growth and lung metastases in a highly metastatic variant of Lewis lung (continuous 14-day intraveneous delivery via Alzet minipump).

In this study, 30 mg/kg/day ANGIOZYME™ delivered either as a daily subcutaneous bolus injection or as a continuous infusion from an Alzet minipump resulted in a delay in tumor growth (FIG. 23). On average, tumor growth to 500 mm$^3$ was delayed by approximately 7 days in animals being treated with ANGIOZYME™ compared to an untreated group. Growth of tumors in animals being treated with either of two attenuated controls was delayed by only approximately 2 days.

ANGIOZYME™ delivered by subcutaneous bolus was also tested in combination with either Gemcytabine or cyclophosphamide (FIG. 24). Tumor growth delay increased by about 3 days in the presence of combination therapy with ANGIOZYME™ and Gemcytabine over the effects of either treatment alone. The combination of ANGIOZYME™ and cyclophosphamide did not increase tumor growth delay over that of cyclophosphamide alone, however, suboptimal doses of cyclophosphamide were not included in this study. Neither of the attenuated controls increased the effect of the chemotherapeutic agents.

The effect of ANGIOZYME™ on metastases to the lung was also determined in the presence and absence of additional chemotherapeutic treatment. Macrometastases to the lungs were counted in two animals in each treatment group on day 20. Data for the daily subcutaneous administration of 30 mg/kg ANGIOZYME™ alone or with Gemcytabine or cyclophosphamide is given in FIG. 25. In the presence of ANGIOZYME™, with or without a chemotherapeutic agent, the lung metastases were reduced to zero. Treatment with either Gemcytabine or cyclophosphamide alone (mean number of metastases 4.5 and 4, respectively) were not as effective as ANGIOZYME™ alone or when used in combination with ANGIOZYME™. Neither of the attenuated controls increased the effect of the chemotherapeutic agents.

The effect on metastases to the lung was also determined following continuous treatment with ANGIOZYME™. At day 20, an average of approximately 8 macrometastases were noted in the treatment groups which had been instrumented with Alzet minipumps (either 14- or 28-day pumps). This is a decrease in metastases of approximately 50% from the untreated group. Since ANGIOZYME™ delivered by a daily subcutaneous bolus resulted in zero metastases (FIG. 4) in the two animals counted, it is possible that the additional burden of being instrumented with the minipump contributes to a slightly decreased response to ANGIOZYME™.

EXAMPLE 15

Phase I/II Study of Repetitive Dose ANGIOZYME™ Targeting the FLT-1 Receptor of VEGF A ribozyme therapeutic agent ANGIOZYME™, was assessed by daily subcutaneous administration in a phase I/II trial for 31 patients with refractory solid tumors. Demographic information relating to patients enrolled in the study are shown in Table XX. The primary study endpoint was to determine the safety and maximum tolerated dose of ANGIOZYME™. Secondary endpoints assessed ANGIOZYME™ pharmacokinetics and clinical response. Patients were treated in four cohorts of three patients at doses of 10, 30, 100, and 300 mg/m$^2$/day. Following the dose escalation phase, an additional 15 evaluable patients were entered in an expanded cohort at 100 mg/m2/day. Patients were dosed for a minimum of 29 consecutive days with 24-hour pharmacokinetic analyses on Day 1 and 29. Clinical response was assessed monthly.

Results The data from 20 patients indicated that ANGIOZYME™ was well tolerated, with no systemic adverse events. FIG. 31 shows the plasma concentration profile of ANGIOZYME™ after a single SC (subcutaneous) dose of 10, 30, 100, or 300 mg/m$^2$. The pharmacokinetic parameters of ANGIOZYME™ after SC bolus administration are outlined in Table XXI. An MTD (maximum tolerated dose) could not be established. One patient in the 300 mg/m$^2$/d group experienced a grade 3 injection site reaction. Patients in the other groups experienced intermittent grade 1 and grade 2 injection site reactions with erythema and induration. No systemic or laboratory toxicities were observed. Pharmacokinetic analyses demonstrated dose-dependent plasma concentrations with good bioavailability (70–90%), t1/2=209–384 min, and no accumulation after repeated doses. To date, 17/28 (61%) of evaluable patients have had stable disease for periods of one to six months and two patients (nasopharyngeal squamous cell carcinoma and melanoma) had minor clinical responses. The patient with nasopharyngeal carcinoma demonstrated central tumor necrosis as indicated by MRI. The longest period of treatment thus far has been 8 months for two patients at 100 mg/m$^2$/d (breast, peritoneal mesothelioma).

EXAMPLE 16

In Vivo Inhibition of Neovascularization in an Ocular Animal Model by VEGF-R Ribozymes Summary of the Mouse Model: A mouse model of proliferative retinopathy (Aiello et al., 1995, *Proc. Natl. Acad. Sci. USA* 92: 10457–10461; Robinson et al., 1996, *Proc. Natl. Acad. Sci. USA* 93: 4851–4856; Pierce et al., 1996, *Archives of Ophthalmology* 114: 1219–1228) in which neovascularization of the mouse retina is induced by exposure of 7-day old mice to 75% oxygen followed by a return to normal room air. The initial period in high oxygen causes an obliteration of developing blood vessels in the retina. Exposure to room air five days later is perceived as hypoxia by the now underperfused retina. The result is an immediate upregulation of VEGF mRNA and VEGF protein (between 6–12 hours) followed by an extensive retinal neovascularization that peaks in approximately 5 days. Although this model is more representative of retinopathy of prematurity than diabetic retinopathy, it is an accepted small animal model in which to study neovascular pathophysiology of the retina. In fact, intravitreal injection of certain antisense DNA constructs targeting VEGF mRNA have been found to be antiangiogenic in this model, as were soluble VEGF receptor chimeric proteins designed to bind VEGF in the vitreous humor (Aiello et al., 1995, *Proc. Natl. Acad. Sci. USA* 92: 10457–10461; Robinson et al., 1996, *Proc. Natl. Acad. Sci. USA* 93: 4851–4856; Pierce et al., 1996, *Archives of Ophthalmology* 114: 1219–1228).

Summary of experiment: The effect of an anti-KDR/Flk-1 ribozyme on the peak level of neovascularization was tested in the mouse model described above. As shown in FIG. 34A, P7 mice were removed from the hyperoxic chamber and the mice received two intraocular injections (P12 and P13) in the right eye of 10 μg RPI.4731, the anti-KDR/Flk-1 ribozyme. The left eye of each mouse was treated as a control and received intraocular injections of saline. Five days after being exposed to room air, neovascular nuclei in the retina of both eyes were counted. Data are presented in FIG. 34B. There was a significant decrease in retinal neovascularization (approximately 40%) compared to the control, saline-injected eyes.

RPI.4731 sequence and chemical composition:

5'-u$_s$a$_s$c$_s$ a$_s$au ucU GAu Gag gcg aaa gcc Gaa Aag aca aB-3' (SEQ ID NO: 13488)

where: uppercase G, A=ribonucleotides
lowercase=2'-OMe
U=2'-C-allyl uridine
B=inverted abasic nucleotide
S=phosphorothioate linkage Indications 1) Tumor angiogenesis: Angiogenesis has been shown to be necessary for tumors to grow into pathological size (Folkman, 1971, *PNAS* 76, 5217–5221; Wellstein & Czubayko, 1996, *Breast Cancer Res and Treatment* 38, 109–119). In addition, it allows tumor cells to travel through the circulatory system during metastasis. Increased levels of gene expression of a number of angiogenic factors such as vascular endothelial growth factor (VEGF) have been reported in vascularized and edema-associated brain tumors (Berkman et al., 1993 *J. Clini. Invest*. 91, 153). A more direct demonstration of the role of VEGF in tumor angiogenesis was demonstrated by Jim Kim et al., 1993 *Nature* 362, 841 wherein, monoclonal antibodies against VEGF were successfully used to inhibit the growth of rhabdomyosarcoma, glioblastoma multiforme cells in nude mice. Similarly, expression of a dominant negative mutated form of the flt-1 VEGF receptor inhibits vascularization induced by human glioblastoma cells in nude mice (Millauer et al., 1994, *Nature* 367, 576). Specific tumor/cancer types that can be targeted using the nucleic acid molecules of the invention include but are not limited to the tumor/cancer types described under Diagnosis in Table XX.

2) Ocular diseases: Neovascularization has been shown to cause or exacerbate ocular diseases including but not limited to, macular degeneration, neovascular glaucoma, diabetic retinopathy, myopic degeneration, and trachoma (Norrby, 1997, *APMIS* 105, 417–437). Aiello et al., 1994 *New Engl. J. Med*. 331, 1480, showed that the ocular fluid, of a majority of patients suffering from diabetic retinopathy and other retinal disorders, contains a high concentration of VEGF. Miller et al., 1994 *Am. J. Pathol*. 145, 574, reported elevated levels of VEGF mRNA in patients suffering from retinal ischemia. These observations support a direct role for VEGF in ocular diseases. Other factors, including those that stimulate VEGF synthesis, may also contribute to these indications.

3) Dermatological Disorders: Many indications have been identified which may be angiogenesis dependent including, but not limited to, psoriasis, verruca vulgaris, angiofibroma of tuberous sclerosis, pot-wine stains, Sturge Weber syndrome, Kippel-Trenaunay-Weber syndrome, and Osler-Weber-Rendu syndrome (Norrby, supra). Intradermal injection of the angiogenic factor b-FGF demonstrated angiogenesis in nude mice (Weckbecker et al., 1992, *Angiogenesis: Key principles-Science-Technology-Medicine*, ed R. Steiner) Detmar et al., 1994 *J. Exp. Med*. 180, 1141 reported that VEGF and its receptors were over-expressed in psoriatic skin and psoriatic dermal microvessels, suggesting that VEGF plays a significant role in psoriasis.

4) Rheumatoid arthritis: Immunohistochemistry and in situ hybridization studies on tissues from the joints of patients suffering from rheumatoid arthritis show an increased level of VEGF and its receptors (Fava et al., 1994 *J. Exp. Med*. 180, 341). Additionally, Koch et al., 1994 *J. Immunol*. 152, 4149, found that VEGF-specific antibodies were able to significantly reduce the mitogenic activity of synovial tissues from patients suffering from rheumatoid arthritis. These observations support a direct role for VEGF in rheumatoid arthritis. Other angiogenic factors including those of the present invention may also be involved in arthritis.

Combination Therapies

Gemcytabine and cyclophosphamide are non-limiting examples of chemotherapeutic agents that can be combined with or used in conjunction with the nucleic acid molecules (e.g. ribozymes and antisense molecules) of the instant invention. Those skilled in the art will recognize that other anti-angiogenic and/or anti-cancer compounds and therapies can be similarly be readily combined with the nucleic acid molecules of the instant invention (e.g. ribozymes and antisense molecules) and are hence within the scope of the instant invention. Such compounds and therapies are well known in the art (see for example *Cancer: Principles and Pranctice of Oncology*, Volumes 1 and 2, eds Devita, V. T., Hellman, S., and Rosenberg, S. A., J. B. Lippincott Company, Philadelphia, USA; incorporated herein by reference) and include, without limitations, folates, antifolates, pyrimidine analogs, fluoropyrimidines, purine analogs, adenosine analogs, topoisomerase I inhibitors, anthrapyrazoles, retinoids, antibiotics, anthacyclins, platinum analogs, alkylating agents, nitrosoureas, plant derived compounds such as vinca alkaloids, epipodophyllotoxins, tyrosine kinase inhibitors, taxols, radiation therapy, surgery, nutritional supplements, gene therapy, radiotherapy, for example 3D-CRT, immunotoxin therapy, for example ricin, and monoclonal antibodies. Specific examples of chemotherapeutic compounds that can be combined with or used in conjuction with the nucleic acid molecules of the invention include, but are not limited to, Paclitaxel; Docetaxel; Methotrexate; Doxorubin; Edatrexate; Vinorelbine; Tomaxifen; Leucovorin; 5-fluoro uridine (5-FU); Ionotecan; Cisplatin; Carboplatin; Amsacrine; Cytarabine; Bleomycin; Mitomycin C; Dactinomycin; Mithramycin; Hexamethylmelamine; Dacarbazine; L-asperginase; Nitrogen mustard; Melphalan, Chlorambucil; Busulfan; Ifosfamide; 4-hydroperoxycyclophosphamide, Thiotepa; Irinotecan (CAMPTOSAR®, CPT-11, Camptothecin-11, Campto) Tamoxifen, Herceptin; IMC C225; ABX-EGF: and combinations thereof.

Diagnostic Uses

The nucleic acid molecules of this invention (e.g., enzymatic nucleic acid) can be used as diagnostic tools to examine genetic drift and mutations within diseased cells or to detect the presence of flt-1, KDR and/or flk-1 RNA in a cell. The close relationship between enzymatic nucleic acid activity and the structure of the target RNA allows the detection of mutations in any region of the molecule which alters the base-pairing and three-dimensional structure of the target RNA. By using multiple enzymatic nucleic acids described in this invention, one can map nucleotide changes which are important to RNA structure and function in vitro, as well as in cells and tissues. Cleavage of target RNAs with enzymatic nucleic acid can be used to inhibit gene expression and define the role (essentially) of specified gene products in the progression of disease. In this manner, other genetic targets can be defined as important mediators of the disease. These experiments can lead to better treatment of the disease progression by affording the possibility of combinational therapies (e.g., multiple enzymatic nucleic acids targeted to different genes, enzymatic nucleic acids coupled with known small molecule inhibitors, or intermittent treatment with combinations of enzymatic nucleic acids and/or other chemical or biological molecules). Other in vitro uses of enzymatic nucleic acids of the invention are well known in the art, and include detection of the presence of mRNAs associated with flt-1, KDR and/or flk-1 related condition. Such RNA is detected by determining the presence of a cleavage product after treatment with a ribozyme using standard methodology.

In a specific example, enzymatic nucleic acids which can cleave only wild-type or mutant forms of the target RNA are used for the assay. The first enzymatic nucleic acid is used to identify wild-type RNA present in the sample and the second enzymatic nucleic acid is used to identify mutant RNA in the sample. As reaction controls, synthetic substrates of both wild-type and mutant RNA are cleaved by both enzymatic nucleic acids to demonstrate the relative enzymatic nucleic acid efficiencies in the reactions and the absence of cleavage of the "non-targeted" RNA species. The cleavage products from the synthetic substrates also serve to generate size markers for the analysis of wild-type and mutant RNAs in the sample population. Thus, each analysis requires two enzymatic nucleic acids, two substrates and one unknown sample which is combined into six reactions. The presence of cleavage products is determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., flt-1, KDR and/or flk-1) is adequate to establish risk. If probes of comparable specific activity are used for both transcripts, then a qualitative comparison of RNA levels is adequate and decreases the cost of the initial diagnosis. Higher mutant form to wild-type ratios is correlated with higher risk whether RNA levels are compared qualitatively or quantitatively. The use of enzymatic nucleic acid molecules in diagnostic applications contemplated by the instant invention is more fully described in George et al., U.S. Pat. Nos. 5,834,186 and 5,741,679, Shih et al., U.S. Pat. No. 5,589,332, Nathan et al., U.S. Pat. No. 5,871,914, Nathan and Ellington, International PCT publication No. WO 00/24931, Breaker et al., International PCT Publication Nos. WO 00/26226 and 98/27104, and Sullenger et al., International PCT publication No. WO 99/29842.

Additional Uses

Potential usefulness of sequence-specific enzymatic nucleic acid molecules of the instant invention have many of the same applications for the study of RNA that DNA restriction endonucleases have for the study of DNA (Nathans et al., 1975 Ann. Rev. Biochem. 44:273). For example, the pattern of restriction fragments can be used to establish sequence relationships between two related RNAs, and large RNAs can be specifically cleaved to fragments of a size more useful for study. The ability to engineer sequence specificity of the enzymatic nucleic acid molecule is ideal for cleavage of RNAs of unknown sequence. Applicant describes the use of nucleic acid molecules to down-regulate gene expression of target genes in bacterial, microbial, fungal, viral, and eukaryotic systems including plant, or mammalian cells.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Other embodiments are within the claims that follow.

TABLE I

Characteristics of Ribozymes

Group I Introns

Size: ~200 to >1000 nucleotides.
Requires a U in the target sequence immediately 5' of the cleavage site.
Binds 4–6 nucleotides at 5' side of cleavage site.
Over 75 known members of this class. Found in *Tetrahymena thermophila* rRNA, fungal mitochondria, chloroplasts, phage T4, blue-green algae, and others.
RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.
Hammerhead Ribozyme Size: ~13 to 40 nucleotides.
Requires the target sequence UH immediately 5' of the cleavage site.
Binds a variable number of nucleotides on both sides of the cleavage site.
14 known members of this class. Found in a number of plant pathogens (virusoids) that use RNA as the infectious agent (FIGS. 1 and 2)

TABLE I-continued

Characteristics of Ribozymes

Hairpin Ribozyme

Size: ~50 nucleotides.
Requires the target sequence GUC immediately 3' of the cleavage site.
Binds 4–6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).
Hepatitis Delta Virus (HDV) Ribozyme Size: 50–60 nucleotides (at present).
Sequence requirements not fully determined.
Binding sites and structural requirements not fully determined, although no sequences 5' of cleavage site are required.
Only 1 known member of this class. Found in human HDV (FIG. 4).
Neuraspora VS RNA Ribozyme Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (FIG. 5).

TABLE II

Human flt1 VEGF Receptor-Hammerhead Ribozyme and Substrate Sequence

| Pos | Substrate | Seq ID No | HH Ribozyme | Seq ID No |
|---|---|---|---|---|
| 10 | CGGACACUC CUCUCGGC | 1 | GCCGAGAG CUGAUGAGGCCGUUAGGCCGAA AGUGUCCG | 9420 |
| 13 | ACACUCCUC UCGGCUCC | 2 | GGAGCCGA CUGAUGAGGCCGUUAGGCCGAA AGGAGUGU | 9421 |
| 15 | ACUCCUCUC GGCUCCUC | 3 | GAGGAGCC CUGAUGAGGCCGUUAGGCCGAA AGAGGACU | 9422 |
| 20 | UCUCGGCUC CUCCCCGG | 4 | CCGGGGAG CUGAUGAGGCCGUUAGGCCGAA AGCCGAGA | 9423 |
| 23 | CGGCUCCUC CCCGGCAG | 5 | CUGCCGGG CUGAUGAGGCCGUUAGGCCGAA AGGAGCCG | 9424 |
| 43 | CGGCGGCUC GGAGCGGG | 6 | CCCGCUCC CUGAUGAGGCCGUUAGGCCGAA AGCCGCCG | 9425 |
| 54 | AGCGGGCUC CGGGGCUC | 7 | GAGCCCCG CUGAUGAGGCCGUUAGGCCGAA AGCCCGCU | 9426 |
| 62 | CCGGGGCUC GGGUGCAG | 8 | CUGCACCC CUGAUGAGGCCGUUAGGCCGAA AGCCCCGG | 9427 |
| 97 | GCGAGGAUU ACCCGGGG | 9 | CCCCGGGU CUGAUGAGGCCGUUAGGCCGAA AUCCUCGC | 9428 |
| 98 | CGAGGAUUA CCCGGGGA | 10 | UCCCCGGG CUGAUGAGGCCGUUAGGCCGAA AAUCCUCG | 9429 |
| 113 | GAAGUGGUU GUCUCCUG | 11 | CAGGAGAC CUGAUGAGGCCGUUAGGCCGAA ACCACUUC | 9430 |
| 116 | GUGGUUGUC UCCGGCU | 12 | AGCCAGGA CUGAUGAGGCCGUUAGGCCGAA ACAACCAC | 9431 |
| 118 | GGUUGUCUC CUGGCUGG | 13 | CCAGCCAG CUGAUGAGGCCGUUAGGCCGAA AGACAACC | 9432 |
| 145 | CGCGCGCUC AGGGCGCG | 14 | CGCGCCCU CUGAUGAGGCCGUUAGGCCGAA AGCGCCCG | 9433 |
| 185 | GACGGACUC UGGCGGCC | 15 | GGCCGCCA CUGAUGAGGCCGUUAGGCCGAA AGUCCGUC | 9434 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 198 | GGCCGGGUC GUUGGCCG | 16 | CGGCCAAC CUGAUGAGGCCGUUAGGCCGAA ACCCGGCC | 9435 |
| 201 | CGGGUCGUU GGCCGGGG | 17 | CCCCGGCC CUGAUGAGGCCGUUAGGCCGAA ACGACCCG | 9436 |
| 240 | GGCCGCGUC GCGCUCAC | 18 | GUGAGCGC CUGAUGAGGCCGUUAGGCCGAA ACGCGGCC | 9437 |
| 246 | GUCGCGCUC ACCAUGGU | 19 | ACCAUGGU CUGAUGAGGCCGUUAGGCCGAA AGCGCGAC | 9438 |
| 255 | ACCAUGGUC AGCUACUG | 20 | CAGUAGCU CUGAUGAGGCCGUUAGGCCGAA ACCAUGGU | 9439 |
| 260 | GGUCAGCUA CUGGGACA | 21 | UGUCCCAG CUGAUGAGGCCGUUAGGCCGAA AGCUGACC | 9440 |
| 276 | ACCGGGUC CUGCUGUG | 22 | CACAGCAG CUGAUGAGGCCGUUAGGCCGAA ACCCCGGU | 9441 |
| 294 | GCGCUGCUC AGCUGUCU | 23 | AGACAGCU CUGAUGAGGCCGUUAGGCCGAA AGCAGCGC | 9442 |
| 301 | UCAGCUGUC UGCUUCUC | 24 | GAGAAGCA CUGAUGAGGCCGUUAGGCCGAA ACAGCUGA | 9443 |
| 306 | UGUCUGCUU CUCACAGG | 25 | CCUGUGAG CUGAUGAGGCCGUUAGGCCGAA AGCAGACA | 9444 |
| 307 | GUCUGCUUC UCACAGGA | 26 | UCCUGUGA CUGAUGAGGCCGUUAGGCCGAA AAGCAGAC | 9445 |
| 309 | CUGCUUCUC ACAGGAUC | 27 | GAUCCUGU CUGAUGAGGCCGUUAGGCCGAA AGAAGCAG | 9446 |
| 317 | CACAGGAUC UAGUUCAG | 28 | CUGAACUA CUGAUGAGGCCGUUAGGCCGAA AUCCUGUG | 9447 |
| 319 | CAGGAUCUA GUUCAGGU | 29 | ACCUGAAC CUGAUGAGGCCGUUAGGCCGAA AGAUCCUG | 9448 |
| 322 | GAUCUAGUU CAGGUUCA | 30 | UGAACCUG CUGAUGAGGCCGUUAGGCCGAA ACUAGAUC | 9449 |
| 323 | AUCUAGUUC AGGUUCAA | 31 | UUGAACCU CUGAUGAGGCCGUUAGGCCGAA AACUAGAU | 9450 |
| 328 | GUUCAGGUU CAAAAUUA | 32 | UAAUUUUG CUGAUGAGGCCGUUAGGCCGAA ACCUGAAC | 9451 |
| 329 | UUCAGGUUC AAAAUUAA | 33 | UUAAUUUU CUGAUGAGGCCGUUAGGCCGAA AACCUGAA | 9452 |
| 335 | UUCAAAAUU AAAAGAUC | 34 | GAUCUUUU CUGAUGAGGCCGUUAGGCCGAA AUUUUGAA | 9453 |
| 336 | UCAAAAUUA AAAGAUCC | 35 | GGAUCUUU CUGAUGAGGCCGUUAGGCCGAA AAUUUUGA | 9454 |
| 343 | UAAAAGAUC CUGAACUG | 36 | CAGUUCAG CUGAUGAGGCCGUUAGGCCGAA AUCUUUUA | 9455 |
| 355 | AACUGAGUU UAAAAGGC | 37 | GCCUUUUA CUGAUGAGGCCGUUAGGCCGAA ACUCAGUU | 9456 |
| 356 | ACUGAGUUU AAAAGGCA | 38 | UGCCUUUU CUGAUGAGGCCGUUAGGCCGAA AACUCAGU | 9457 |
| 357 | CUGAGUUUA AAAGGCAC | 39 | GUGCCUUU CUGAUGAGGCCGUUAGGCCGAA AAACUCAG | 9458 |
| 375 | CAGCACAUC AUGCAAGC | 40 | GCUUGCAU CUGAUGAGGCCGUUAGGCCGAA AUGUGCUG | 9459 |
| 400 | CACUGCAUC UCCAAUGC | 41 | GCAUUGGA CUGAUGAGGCCGUUAGGCCGAA AUGCAGUG | 9460 |
| 402 | CUGCAUCUC CAAUGCAG | 42 | CUGCAUUG CUGAUGAGGCCGUUAGGCCGAA AGAUGCAG | 9461 |
| 427 | CAGCCCAUA AAUGGUCU | 43 | AGACCAUU CUGAUGAGGCCGUUAGGCCGAA AUGGGCUG | 9462 |
| 434 | UAAAUGGUC UUUGCCUG | 44 | CAGGCAAA CUGAUGAGGCCGUUAGGCCGAA ACCAUUUA | 9463 |
| 436 | AAUGGUCUU UGCCUGAA | 45 | UUCAGGCA CUGAUGAGGCCGUUAGGCCGAA AGACCAUU | 9464 |
| 437 | AUGGUCUUU GCCUGAAA | 46 | UUUCAGGC CUGAUGAGGCCGUUAGGCCGAA AAGACCAU | 9465 |
| 454 | UGGUGAGUA AGGAAAGC | 47 | GCUUUCCU CUGAUGAGGCCGUUAGGCCGAA ACUCACCA | 9466 |
| 477 | CUGAGCAUA ACUAAAUC | 48 | GAUUUAGU CUGAUGAGGCCGUUAGGCCGAA AUGCUCAG | 9467 |
| 481 | GCAUAACUA AAUCUGCC | 49 | GGCAGAUU CUGAUGAGGCCGUUAGGCCGAA AGUUAUGC | 9468 |
| 485 | AACUAAAUC UGCCUGUG | 50 | CACAGGCA CUGAUGAGGCCGUUAGGCCGAA AUUUAGUU | 9469 |
| 512 | CAAACAAUU CUGCAGUA | 51 | UACUGCAG CUGAUGAGGCCGUUAGGCCGAA AUUGUUUG | 9470 |
| 513 | AAACAAUUC UGCAGUAC | 52 | GUACUGCA CUGAUGAGGCCGUUAGGCCGAA AAUUGUUU | 9471 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 520 | UCUGCAGUA CUUUAACC | 53 | GGUUAAAG CUGAUGAGGCCGUUAGGCCGAA ACUGCAGA | 9472 |
| 523 | GCAGUACUU UAACCUUG | 54 | CAAGGUUA CUGAUGAGGCCGUUAGGCCGAA AGUACUGC | 9473 |
| 524 | CAGUACUUU AACCUUGA | 55 | UCAAGGUU CUGAUGAGGCCGUUAGGCCGAA AAGUACUG | 9474 |
| 525 | AGUACUUUA ACCUUGAA | 56 | UUCAAGGU CUGAUGAGGCCGUUAGGCCGAA AAAGUACU | 9475 |
| 530 | UUUAACCUU GAACACAG | 57 | CUGUGUUC CUGAUGAGGCCGUUAGGCCGAA AGGUUAAA | 9476 |
| 541 | ACACAGCUC AAGCAAAC | 58 | GUUUGCUU CUGAUGAGGCCGUUAGGCCGAA AGCUGUGU | 9477 |
| 560 | CACUGGCUU CUACAGCU | 59 | AGCUGUAG CUGAUGAGGCCGUUAGGCCGAA AGCCAGUG | 9478 |
| 561 | ACUGGCUUC UACAGCUG | 60 | CAGCUGUA CUGAUGAGGCCGUUAGGCCGAA AAGCCAGU | 9479 |
| 563 | UGGCUUCUA CAGCUGCA | 61 | UGCAGCUG CUGAUGAGGCCGUUAGGCCGAA AGAAGCCA | 9480 |
| 575 | CUGCAAAUA UCUAGCUG | 62 | CAGGUAGA CUGAUGAGGCCGUUAGGCCGAA AUUUGCAG | 9481 |
| 577 | GCAAAUAUC UAGCUGUA | 63 | UACAGCUA CUGAUGAGGCCGUUAGGCCGAA AUAUUUGC | 9482 |
| 579 | AAAUAUCUA GCUGUACC | 64 | GGUACAGC CUGAUGAGGCCGUUAGGCCGAA AGAUAUUU | 9483 |
| 585 | CUAGCUGUA CCUACUUC | 65 | GAAGUAGG CUGAUGAGGCCGUUAGGCCGAA ACAGCUAG | 9484 |
| 589 | CUGUACCUA CUUCAAAG | 66 | CUUUGAAG CUGAUGAGGCCGUUAGGCCGAA AGGUACAG | 9485 |
| 592 | UACCUACUU CAAAGAAG | 67 | CUUCUUUG CUGAUGAGGCCGUUAGGCCGAA AGUAGGUA | 9486 |
| 593 | ACCUACUUC AAAGAAGA | 68 | UCUUCUUU CUGAUGAGGCCGUUAGGCCGAA AAGUAGGU | 9487 |
| 614 | AACAGAAUC UGCAAUCU | 69 | AGAUUGCA CUGAUGAGGCCGUUAGGCCGAA AUUCUGUU | 9488 |
| 621 | UCUGCAAUC UAUAUAUU | 70 | AAUAUAUA CUGAUGAGGCCGUUAGGCCGAA AUUGCAGA | 9489 |
| 623 | UGCAAUCUA UAUAUUUA | 71 | UAAAUAUA CUGAUGAGGCCGUUAGGCCGAA AGAUUGCA | 9490 |
| 625 | CAAUCUAUA UAUUUAUU | 72 | AAUAAAUA CUGAUGAGGCCGUUAGGCCGAA AUAGAUUG | 9491 |
| 627 | AUCUAUAUA UUUAUUAG | 73 | CUAAUAAA CUGAUGAGGCCGUUAGGCCGAA AUAUAGAU | 9492 |
| 629 | CUAUAUAUU UAUUAGUG | 74 | CACUAAUA CUGAUGAGGCCGUUAGGCCGAA AUAUAUAG | 9493 |
| 630 | UAUAUAUUU AUUAGUGA | 75 | UCACUAAU CUGAUGAGGCCGUUAGGCCGAA AAUAUAUA | 9494 |
| 631 | AUAUAUUUA UUAGUGAU | 76 | AUCACUAA CUGAUGAGGCCGUUAGGCCGAA AAAUAUAU | 9495 |
| 633 | AUAUUUAUU AGUGAUAC | 77 | GUAUCACU CUGAUGAGGCCGUUAGGCCGAA AUAAAUAU | 9496 |
| 634 | UAUUUAUUA GUGAUACA | 78 | UGUAUCAC CUGAUGAGGCCGUUAGGCCGAA AAUAAAUA | 9497 |
| 640 | UUAGUGAUA CAGGUAGA | 79 | UCUACCUG CUGAUGAGGCCGUUAGGCCGAA AUCACUAA | 9498 |
| 646 | AUACAGGUA GACCUUUC | 80 | GAAAGGUC CUGAUGAGGCCGUUAGGCCGAA ACCUGUAU | 9499 |
| 652 | GUAGACCUU UCGUAGAG | 81 | CUCUACGA CUGAUGAGGCCGUUAGGCCGAA AGGUCUAC | 9500 |
| 653 | UAGACCUUU CGUAGAGA | 82 | UCUCUACG CUGAUGAGGCCGUUAGGCCGAA AAGGUCUA | 9501 |
| 654 | AGACCUUUC GUAGAGAU | 83 | AUCUCUAC CUGAUGAGGCCGUUAGGCCGAA AAAGGUCU | 9502 |
| 657 | CCUUUCGUA GAGAUGUA | 84 | UACAUCUC CUGAUGAGGCCGUUAGGCCGAA ACGAAAGG | 9503 |
| 665 | AGAGAUGUA CAGUGAAA | 85 | UUUCACUG CUGAUGAGGCCGUUAGGCCGAA ACAUCUCU | 9504 |
| 675 | AGUGAAAUC CCCGAAAU | 86 | AUUUCGGG CUGAUGAGGCCGUUAGGCCGAA AUUUCACU | 9505 |
| 684 | CCCGAAAUU AUACACAU | 87 | AUGUGUAU CUGAUGAGGCCGUUAGGCCGAA AUUUCGGG | 9506 |
| 685 | CCGAAAUUA UACACAUG | 88 | CAUGUGUA CUGAUGAGGCCGUUAGGCCGAA AAUUUCGG | 9507 |
| 687 | GAAAUUAUA CACAUGAC | 89 | GUCAUGUG CUGAUGAGGCCGUUAGGCCGAA AUAAUUUC | 9508 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 711 | AGGGAGCUC GUCAUUCC | 90 | GGAAUGAC CUGAUGAGGCCGUUAGGCCGAA AGCUCCCU | 9509 |
| 714 | GAGCUCGUC AUUCCUG | 91 | CAGGGAAU CUGAUGAGGCCGUUAGGCCGAA ACGAGCUC | 9510 |
| 717 | CUCGUCAUU CCCUGCCG | 92 | CGGCAGGG CUGAUGAGGCCGUUAGGCCGAA AUGACGAG | 9511 |
| 718 | UCGUCAUUC CCUGCCGG | 93 | CCGGCAGG CUGAUGAGGCCGUUAGGCCGAA AAUGACGA | 9512 |
| 729 | UGCCGGGUU ACGUCACC | 94 | GGUGACGU CUGAUGAGGCCGUUAGGCCGAA ACCCGGCA | 9513 |
| 730 | GCCGGGUUA CGUCACCU | 95 | AGGUGACG CUGAUGAGGCCGUUAGGCCGAA AACCCGGC | 9514 |
| 734 | GGUUACGUC ACCUAACA | 96 | UGUUAGGU CUGAUGAGGCCGUUAGGCCGAA ACGUAACC | 9515 |
| 739 | CGUCACCUA ACAUCACU | 97 | AGUGAUGU CUGAUGAGGCCGUUAGGCCGAA AGGUGACG | 9516 |
| 744 | CCUAACAUC ACUGUUAC | 98 | GUAACAGU CUGAUGAGGCCGUUAGGCCGAA AUGUUAGG | 9517 |
| 750 | AUCACUGUU ACUUUAAA | 99 | UUUAAAGU CUGAUGAGGCCGUUAGGCCGAA ACAGUGAU | 9518 |
| 751 | UCACUGUUA CUUUAAAA | 100 | UUUUAAAG CUGAUGAGGCCGUUAGGCCGAA AACAGUGA | 9519 |
| 754 | CUGUUACUU UAAAAAAG | 101 | CUUUUUUA CUGAUGAGGCCGUUAGGCCGAA AGUAACAG | 9520 |
| 755 | UGUUACUUU AAAAAGU | 102 | ACUUUUUU CUGAUGAGGCCGUUAGGCCGAA AAGUAACA | 9521 |
| 756 | GUUACUUUA AAAAGUU | 103 | AACUUUUU CUGAUGAGGCCGUUAGGCCGAA AAAGUAAC | 9522 |
| 764 | AAAAAGUU UCCACUUG | 104 | CAAGUGGA CUGAUGAGGCCGUUAGGCCGAA ACUUUUUU | 9523 |
| 765 | AAAAGUUU CCACUUGA | 105 | UCAAGUGG CUGAUGAGGCCGUUAGGCCGAA AACUUUUU | 9524 |
| 766 | AAAGUUUC CACUUGAC | 106 | GUCAAGUG CUGAUGAGGCCGUUAGGCCGAA AAACUUUU | 9525 |
| 771 | UUCCACUU GACACUUU | 107 | AAAGUGUC CUGAUGAGGCCGUUAGGCCGAA AGUGGAAA | 9526 |
| 778 | UUGACACUU UGAUCCCU | 108 | AGGGAUCA CUGAUGAGGCCGUUAGGCCGAA AGUGUCAA | 9527 |
| 779 | UGACACUUU GAUCCCUG | 109 | CAGGGAUC CUGAUGAGGCCGUUAGGCCGAA AAGUGUCA | 9528 |
| 783 | ACUUUGAUC CUGAUGG | 110 | CCAUCAGG CUGAUGAGGCCGUUAGGCCGAA AUCAAAGU | 9529 |
| 801 | AAACGCAUA AUCUGGGA | 111 | UCCCAGAU CUGAUGAGGCCGUUAGGCCGAA AUGCGUUU | 9530 |
| 804 | CGCAUAAUC UGGGACAG | 112 | CUGUCCCA CUGAUGAGGCCGUUAGGCCGAA AUUAUGCG | 9531 |
| 814 | GGGACAGUA GAAAGGGC | 113 | GCCCUUUC CUGAUGAGGCCGUUAGGCCGAA ACUGUCCC | 9532 |
| 824 | AAAGGGCUU CAUCAUAU | 114 | AUAUGAUG CUGAUGAGGCCGUUAGGCCGAA AGCCCUUU | 9533 |
| 825 | AAGGGCUUC AUCAUAUC | 115 | GAUAUGAU CUGAUGACGCCGUUAGGCCGAA AAGCCCUU | 9534 |
| 828 | GGCUUCAUC AUAUCAAA | 116 | UUUGAUAU CUGAUGAGGCCGUUAGGCCGAA AUGAAGCC | 9535 |
| 831 | UUCAUCAUA UCAAAUGC | 117 | GCAUUUGA CUGAUGAGGCCGUUAGGCCGAA AUGAUGAA | 9536 |
| 833 | CAUCAUAUC AAAUGCAA | 118 | UUGCAUUU CUGAUGAGGCCGUUAGGCCGAA AUAUGAUG | 9537 |
| 845 | UGCAACGUA CAAAGAAA | 119 | UUUCUUUG CUGAUGAGGCCGUUAGGCCGAA ACGUUGCA | 9538 |
| 855 | AAAGAAAUA GGGCUUCU | 120 | ACAAGCCC CUGAUGAGGCCGUUAGGCCGAA AUUUCUUU | 9539 |
| 861 | AUAGGGCUU CUGACCUG | 121 | CAGGUCAG CUGAUGAGGCCGUUAGGCCGAA AGCCCUAU | 9540 |
| 862 | UAGGGCUUC UGACCGUG | 122 | ACAGGUCA CUGAUGAGGCCGUUAGGCCGAA AAGCCCUA | 9541 |
| 882 | GCAACAGUC AAUGGGCA | 123 | UGCCCAUU CUGAUGAGGCCGUUAGGCCGAA ACUGUUGC | 9542 |
| 892 | AUGGGCAUU UGUAUAAG | 124 | CUUAUACA CUGAUGAGGCCGUUAGGCCGAA AUGCCCAU | 9543 |
| 893 | UGGGCAUUU GUAUAAGA | 125 | UCUUAUAC CUGAUGAGGCCGUUAGGCCGAA AAUGCCCA | 9544 |
| 896 | GCAUUUGUA UAAGACAA | 126 | UUGUCUUA CUCAUGAGGCCGUUAGGCCGAA ACAAAUGC | 9545 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 898 | AUUUGUAUA AGACAAAC | 127 | GUUUGUCU CUGAUGAGGCCGUUAGGCCGAA AUACAAAU | 9546 |
| 908 | GACAAACUA UCUCACAC | 128 | GUGUGAGA CUGAUGAGGCCGUUAGGCCGAA AGUUUGUC | 9547 |
| 910 | CAAACUAUC UCACACAU | 129 | AUGUGUGA CUGAUGAGGCCGUUAGGCCGAA AUAGUUUG | 9548 |
| 912 | AACUAUCUC ACACAUCG | 130 | CGAUGUGU CUGAUGAGGCCGUUAGGCCGAA AGAUAGUU | 9549 |
| 919 | UCACACAUC GACAAACC | 131 | GGUUUGUC CUGAUGAGGCCGUUAGGCCGAA AUGUGUGA | 9550 |
| 931 | AAACCAAUA CAAUCAUA | 132 | UAUGAUUG CUGAUGAGGCCGUUAGGCCGAA AUUGGUUU | 9551 |
| 936 | AAUACAAUC AUAGAUGU | 133 | ACAUCUAU CUGAUGAGGCCGUUAGGCCGAA AUUGUAUU | 9552 |
| 939 | ACAAUCAUA GAUGUCCA | 134 | UGGACAUC CUGAUGAGGCCGUUAGGCCGAA AUGAUUGU | 9553 |
| 945 | AUAGAUGUC CAAAUAAG | 135 | CUUAUUUG CUGAUGAGGCCGUUAGGCCGAA ACAUCUAU | 9554 |
| 951 | GUCCAAAUA AGCACACC | 136 | GGUGUGCU CUGAUGAGGCCGUUAGGCCGAA AUUUGGAC | 9555 |
| 969 | CGCCCAGUC AAAUUACU | 137 | AGUAAUUU CUGAUGAGGCCGUUAGGCCGAA ACUGGGCG | 9556 |
| 974 | AGUCAAAUU ACUUAGAG | 138 | CUCUAAGU CUGAUGAGGCCGUUAGGCCGAA AUUUGACU | 9557 |
| 975 | GUCAAAUUA CUUAGAGG | 139 | CCUCUAAG CUGAUGAGGCCGUUAGGCCGAA AAUVUGAC | 9558 |
| 978 | AAAUUACUU AGAGGCCA | 140 | UGGCCUCU CUGAUGAGGCCGUUAGGCCGAA AGUAAUUU | 9559 |
| 979 | AAUUACUUA GAGGCCAU | 141 | AUGGCCUC CUGAUGAGGCCGUUAGGCCGAA AAGUAAUU | 9560 |
| 988 | GAGGCCAUA CUCUUGUC | 142 | GACAAGAG CUGAUGAGGCCGUUAGGCCGAA AUGGCCUC | 9561 |
| 991 | GCCAUACUC UUGUCCUC | 143 | GAGGACAA CUGAUGAGGCCGUUAGGCCGAA AGUAUGGC | 9562 |
| 993 | CAUACUCUU GUCCUCAA | 144 | UUGAGGAC CUGAUGAGGCCGUUAGGCCGAA AGAGUAUG | 9563 |
| 996 | ACUCUUGUC CUCAAUUG | 145 | CAAUUGAG CUGAUGAGGCCGUUAGGCCGAA ACAAGAGU | 9564 |
| 999 | CUUGUCCUC AAUUGUAC | 146 | GUACAAUU CUGAUGAGGCCGUUAGGCCGAA AGGACAAG | 9565 |
| 1003 | UCCUCAAUU GUACUGCU | 147 | AGCAGUAC CUGAUGAGGCCGUUAGGCCGAA AUUGAGGA | 9566 |
| 1006 | UCAAUUGUA CUGCUACC | 148 | GGUAGCAG CUGAUGAGGCCGUUAGGCCGAA ACAAUUGA | 9567 |
| 1012 | GUACUGCUA CCACUCCC | 149 | GGGAGUGG CUGAUGAGGCCGUUAGGCCGAA AGCAGUAC | 9568 |
| 1018 | CUACCACUC CCUUGAAC | 150 | GUUCAAGG CUGAUGAGGCCGUUAGGCCGAA AGUGGUAG | 9569 |
| 1022 | CACUCCCUU GAACACGA | 151 | UCGUGUUC CUGAUGAGGCCGUUAGGCCGAA AGGGAGUG | 9570 |
| 1035 | ACGAGAGUU CAAAUGAC | 152 | GUCAUUUG CUGAUGAGGCCGUUAGGCCGAA ACUCUCGU | 9571 |
| 1036 | CGAGAGUUC AAAUGACC | 153 | GGUCAUUU CUGAUGAGGCCGUUAGGCCGAA AACUCUCG | 9572 |
| 1051 | CCUGGAGUU ACCCUGAU | 154 | AUCAGGGU CUGAUGAGGCCGUUAGGCCGAA ACUCCAGG | 9573 |
| 1052 | CUGGAGUUA CCCUGAUG | 155 | CAUCAGGG CUGAUGAGGCCGUUAGGCCGAA AACUCCAG | 9574 |
| 1069 | AAAAAAAUA AGAGAGCU | 156 | AGCUCUCU CUGAUGAGGCCGUUAGGCCGAA AUUUUUUU | 9575 |
| 1078 | AGAGAGCUU CCGUAAGG | 157 | CCUUACGG CUGAUGAGGCCGUUAGGCCGAA AGCUCUCU | 9576 |
| 1079 | GAGAGCUUC CGUAAGGC | 158 | GCCUUACG CUGAUGAGGCCGUUAGGCCGAA AAGCUCUC | 9577 |
| 1083 | GCUUCCGUA AGGCGACG | 159 | CGUCGCCU CUGAUGAGGCCGUUAGGCCGAA ACGGAAGC | 9578 |
| 1095 | CGACGAAUU GACCAAAG | 160 | CUUUGGUC CUGAUGAGGCCGUUAGGCCGAA AUUCGUCG | 9579 |
| 1108 | AAAGCAAUU CCCAUGCC | 161 | GGCAUGGG CUGAUGAGGCCGUUAGGCCGAA AUUGCUUU | 9580 |
| 1109 | AAGCAAUUC CCAUGCCA | 162 | UGGCAUGG CUGAUGAGGCCGUUAGGCCGAA AAUUGCUU | 9581 |
| 1122 | GCCAACAUA UUCUACAG | 163 | CUGUAGAA CUGAUGAGGCCGUUAGGCCGAA AUGUUGGC | 9582 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 1124 | CAACAUAUU CUACAGUG | 164 | CACUGUAG CUGAUGAGGCCGUUAGGCCGAA AUAUGUUG | 9583 |
| 1125 | AACAUAUUC UACAGUGU | 165 | ACACUGUA CUGAUGAGGCCGUUAGGCCGAA AAUAUGUU | 9584 |
| 1127 | CAUAUUCUA CAGUGUUC | 166 | GAACACUG CUGAUGAGGCCGUUAGGCCGAA AGAAUAUG | 9585 |
| 1134 | UACAGUGUU CUUACUAU | 167 | AUAGUAAG CUGAUGAGGCCGUUAGGCCGAA ACACUGUA | 9586 |
| 1135 | ACAGUGUUC UUACUAUU | 168 | AAUAGUAA CUGAUGAGGCCGUUAGGCCGAA AACACUGU | 9587 |
| 1137 | AGUGUUCUU ACUAUUGA | 169 | UCAAUAGU CUGAUGAGGCCGUUAGGCCGAA AGAACACU | 9588 |
| 1138 | GUGUUCUUA CUAUUGAC | 170 | GUCAAUAG CUGAUGAGGCCGUUAGGCCGAA AAGAACAC | 9589 |
| 1141 | UUCUUACUA UUGACAAA | 171 | UUUGUCAA CUGAUGAGGCCGUUAGGCCGAA AGUAAGAA | 9590 |
| 1143 | CUUACUAUU GACAAAAU | 172 | AUUUUGUC CUGAUGAGGCCGUUAGGCCGAA AUAGUAAG | 9591 |
| 1173 | AAAGGACUU UAUACUUG | 173 | CAAGUAUA CUGAUGAGGCCGUUAGGCCGAA AGUCCUUU | 9592 |
| 1174 | AAGGACUUU AUACUUGU | 174 | ACAAGUAU CUGAUGAGGCCGUUAGGCCGAA AAGUCCUU | 9593 |
| 1175 | AGGACUUUA UACUUGUC | 175 | GACAAGUA CUGAUGAGGCCGUUAGGCCGAA AAAGUCCU | 9594 |
| 1177 | GACUUUAUA CUUGUCGU | 176 | ACGACAAG CUGAUGAGGCCGUUAGGCCGAA AUAAAGUC | 9595 |
| 1180 | UUUAUACUU GUCGUGUA | 177 | UACACGAC CUGAUGAGGCCGUUAGGCCGAA AGUAUAAA | 9596 |
| 1183 | AUACUUGUC GUGUAAGG | 178 | CCUUACAC CUGAUGAGGCCGUUAGGCCGAA ACAAGUAU | 9597 |
| 1188 | UGUCGUGUA AGGAGUGG | 179 | CCACUCCU CUGAUGAGGCCGUUAGGCCGAA ACACGACA | 9598 |
| 1202 | UGGACCAUC AUUCAAAU | 180 | AUUUGAAU CUGAUGAGGCCGUUAGGCCGAA AUGGUCCA | 9599 |
| 1205 | ACCAUCAUU CAAAUCUG | 181 | CAGAUUUG CUGAUGAGGCCGUUAGGCCGAA AUGAUGGU | 9600 |
| 1206 | CCAUCAUUC AAAUCUGU | 182 | ACAGAUUU CUGAUGAGGCCGUUAGGCCGAA AAUGAUGG | 9601 |
| 1211 | AUUCAAAUC UGUUAACA | 183 | UGUUAACA CUGAUGAGGCCGUUAGGCCGAA AUUUGAAU | 9602 |
| 1215 | AAAUCUGUU AACACCUC | 184 | GAGGUGUU CUGAUGAGGCCGUUAGGCCGAA ACAGAUUU | 9603 |
| 1216 | AAUCUGUUA ACACCUCA | 185 | UGAGGUGU CUGAUGAGGCCGUUAGGCCGAA AACAGAUU | 9604 |
| 1223 | UAACACCUC AGUGCAUA | 186 | UAUGCACU CUGAUGAGGCCGUUAGGCCGAA AGGUGUUA | 9605 |
| 1231 | CAGUGCAUA UAUAUGAU | 187 | AUCAUAUA CUGAUGAGGCCGUUAGGCCGAA AUGCACUG | 9606 |
| 1233 | GUGCAUAUA UAUGAUAA | 188 | UUAUCAUA CUGAUGAGGCCGUUAGGCCGAA AUAUGCAC | 9607 |
| 1235 | GCAUAUAUA UGAUAAAG | 189 | CUUUAUCA CUGAUGAGGCCGUUAGGCCGAA AUAUAUGC | 9608 |
| 1240 | UAUAUGAUA AAGCAUUC | 190 | GAAUGCUU CUGAUGAGGCCGUUAGGCCGAA AUCAUAUA | 9609 |
| 1247 | UAAAGCAUU CAUCACUG | 191 | CAGUGAUG CUGAUGAGGCCGUUAGGCCGAA AUGCUUUA | 9610 |
| 1248 | AAAGCAUUC AUCACUGU | 192 | ACAGUGAU CUGAUGAGGCCGUUAGGCCGAA AAUGCUUU | 9611 |
| 1251 | GCAUUCAUC ACUGUGAA | 193 | UUCACAGU CUGAUGAGGCCGUUAGGCCGAA AUGAAUGC | 9612 |
| 1264 | UGAAACAUC GAAAACAG | 194 | CUGUUUUC CUGAUGAGGCCGUUAGGCCGAA AUGUUUCA | 9613 |
| 1281 | CAGGUGCUU GAAACCGU | 195 | ACGGUUUC CUGAUGAGGCCGUUAGGCCGAA AGCACCUG | 9614 |
| 1290 | GAAACCGUA GCUGGCAA | 196 | UUGCCAGC CUGAUGAGGCCGUUAGGCCGAA ACGGUUUC | 9615 |
| 1304 | CAAGCGGUC UUACCGGC | 197 | GCCGGUAA CUGAUGAGGCCGUUAGGCCGAA ACCGCUUG | 9616 |
| 1306 | AGCGGUCUU ACCGGCUC | 198 | GAGCCGGU CUGAUGAGGCCGUUAGGCCGAA AGACCGCU | 9617 |
| 1307 | GCGGUCUUA CCGGCUCU | 199 | AGAGCCGG CUGAUGAGGCCGUUAGGCCGAA AAGACCGC | 9618 |
| 1314 | UACCGGCUC UCUAUGAA | 200 | UUCAUAGA CUGAUGAGGCCGUUAGGCCGAA AGCCGGUA | 9619 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 1316 | CCGGCUCUC UAUGAAAG | 201 | CUUUCAUA CUGAUGAGGCCGUUAGGCCGAA AGAGCCGG | 9620 |
| 1318 | GCUCUCUA UGAAAGUG | 202 | CACUUUCA CUGAUGAGGCCGUUAGGCCGAA AGAGAGCC | 9621 |
| 1334 | GAAGGCAUU UCCCUCGC | 203 | GCGAGGGA CUGAUGAGGCCGUUAGGCCGAA AUGCCUUC | 9622 |
| 1335 | AAGGCAUUU CCCUCGCC | 204 | GGCGAGGG CUGAUGAGGCCGUUAGGCCGAA AAUGCCUU | 9623 |
| 1336 | AGGCAUUUC CUCGCCG | 205 | CGGCGAGG CUGAUGAGGCCGUUAGGCCGAA AAAUGCCU | 9624 |
| 1340 | AUUUCCCUC GCCGGAAG | 206 | CUUCCGGC CUGAUGAGGCCGUUAGGCCGAA AGGGAAAU | 9625 |
| 1350 | CCGGAAGUU GUAUGGUU | 207 | AACCAUAC CUGAUGAGGCCGUUAGGCCGAA ACUUCCGG | 9626 |
| 1353 | GAAGUUGUA UGGUUAAA | 208 | UUUAACCA CUGAUGAGGCCGUUAGGCCGAA ACAACUUC | 9627 |
| 1358 | UGUAUGGUU AAAGAUG | 209 | CAUCUUUU CUGAUGAGGCCGUUAGGCCGAA ACCAUACA | 9628 |
| 1359 | GUAUGGUUA AAGAUGG | 210 | CCAUCUUU CUGAUGAGGCCGUUAGGCCGAA AACCAUAC | 9629 |
| 1370 | AGAUGGGUU ACCGCGA | 211 | UCGCAGGU CUGAUGAGGCCGUUAGGCCGAA ACCCAUCU | 9630 |
| 1371 | GAUGGGUUA CCUGCGAC | 212 | GUCGCAGG CUGAUGAGGCCGUUAGGCCGAA AACCCAUC | 9631 |
| 1388 | UGAGAAAUC UGCUCGCU | 213 | AGCGAGCA CUGAUGAGGCCGUUAGGCCGAA AUUUCUCA | 9632 |
| 1393 | AAUCUGCUC GCUAUUUG | 214 | CAAAUAGC CUGAUGAGGCCGUUAGGCCGAA AGCAGAUU | 9633 |
| 1397 | UGCUCGCUA UUUGACUC | 215 | GAGUCAAA CUGAUGAGGCCGUUAGGCCGAA AGCGAGCA | 9634 |
| 1399 | CUCGCUAUU UGACUCGU | 216 | ACGAGUCA CUGAUGAGGCCGUUAGGCCGAA AUAGCGAG | 9635 |
| 1400 | UCGCUAUUU GACUCGUG | 217 | CACGAGUC CUGAUGAGGCCGUUAGGCCGAA AAUAGCGA | 9636 |
| 1405 | AUUUGACUC GUGGCUAC | 218 | GUAGCCAC CUGAUGAGGCCGUUAGGCCGAA AGUCAAAU | 9637 |
| 1412 | UCGUGGCUA CUCGUUAA | 219 | UUAACGAG CUGAUGAGGCCGUUAGGCCGAA AGCCACGA | 9638 |
| 1415 | UGGCUACUC GUUAAUUA | 220 | UAAUUAAC CUGAUGAGGCCGUUAGGCCGAA AGUAGCCA | 9639 |
| 1418 | CUACUCGUU AAUUAUCA | 221 | UGAUAAUU CUGAUGAGGCCGUUAGGCCGAA ACGAGUAG | 9640 |
| 1419 | UACUCGUUA AUUAUCAA | 222 | UUGAUAAU CUGAUGAGGCCGUUAGGCCGAA AACGAGUA | 9641 |
| 1422 | UCGUUAAUU AUCAAGGA | 223 | UCCUUGAU CUGAUGAGGCCGUUAGGCCGAA AUUAACGA | 9642 |
| 1423 | CGUUAAUUA UCAAGGAC | 224 | GUCCUUGA CUGAUGAGGCCGUUAGGCCGAA AAUUAACG | 9643 |
| 1425 | UUAAUUAUC AAGGACGU | 225 | ACGUCCUU CUGAUGAGGCCGUUAGGCCGAA AUAAUUAA | 9644 |
| 1434 | AAGGACGUA ACUGAAGA | 226 | UCUUCAGU CUGAUGAGGCCGUUAGGCCGAA ACGUCCUU | 9645 |
| 1456 | CAGGGAAUU AUACAAUC | 227 | GAUUGUAU CUGAUGAGGCCGUUAGGCCGAA AUUCCCUG | 9646 |
| 1457 | AGGGAAUUA UACAAUCU | 228 | AGAUUGUA CUGAUGAGGCCGUUAGGCCGAA AAUUCCCU | 9647 |
| 1459 | GGAAUUAUA CAAUCUUG | 229 | CAAGAUUG CUGAUGAGGCCGUUAGGCCGAA AUAAUUCC | 9648 |
| 1464 | UAUACAAUC UUGCUGAG | 230 | CUCAGCAA CUGAUGAGGCCGUUAGGCCGAA AUUGUAUA | 9649 |
| 1466 | UACAAUCUU GCUGAGCA | 231 | UGCUCAGC CUGAUGAGGCCGUUAGGCCGAA AGAUUGUA | 9650 |
| 1476 | CUGAGCAUA AACAGUC | 232 | GACUGUUU CUGAUGAGGCCGUUAGGCCGAA AUGCUCAG | 9651 |
| 1484 | AAACAGUC AAAUGUGU | 233 | ACACAUUU CUGAUGAGGCCGUUAGGCCGAA ACUGUUUU | 9652 |
| 1493 | AAAUGUGUU UAAAAACC | 234 | GGUUUUUA CUGAUGAGGCCGUUAGGCCGAA ACACAUUU | 9653 |
| 1494 | AAUGUGUUU AAAACCU | 235 | AGGUUUUU CUGAUGAGGCCGUUAGGCCGAA AACACAUU | 9654 |
| 1495 | AUGUGUUUA AAACCUC | 236 | GAGGUUUU CUGAUGAGGCCGUUAGGCCGAA AAACACAU | 9655 |
| 1503 | AAAAACCUC ACUGCCAC | 237 | GUGGCAGU CUGAUGAGGCCGUUAGGCCGAA AGGUUUUU | 9656 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 1513 | CUGCCACUC UAAUUGUC | 238 | GACAAUUA CUGAUGAGGCCGUUAGGCCGAA AGUGGCAG | 9657 |
| 1515 | GCCACUCUA AUUGUCAA | 239 | UUGACAAU CUGAUGAGGCCGUUAGGCCGAA AGAGUGGC | 9658 |
| 1518 | ACUCUAAUU GUCAAUGU | 240 | ACAUUGAC CUGAUGAGGCCGUUAGGCCGAA AUUAGAGU | 9659 |
| 1521 | CUAAUUGUC AAUGUGAA | 241 | UUCACAUU CUGAUGAGGCCGUUAGGCCGAA ACAAUUAG | 9660 |
| 1539 | CCCCAGAUU UACGAAAA | 242 | UUUUCGUA CUGAUGAGGCCGUUAGGCCGAA AUCUGGGG | 9661 |
| 1540 | CCCAGAUUU ACGAAAAG | 243 | CUUUUCGU CUGAUGAGGCCGUUAGGCCGAA AAUCUGGG | 9662 |
| 1541 | CCAGAUUUA CGAAAAGG | 244 | CCUUUUCG CUGAUGAGGCCGUUAGGCCGAA AAAUCUGG | 9663 |
| 1556 | GGCCGUGUC AUCGUUUC | 245 | GAAACGAU CUGAUGAGGCCGUUAGGCCGAA ACACGGCC | 9664 |
| 1559 | CGUGUCAUC GUUUCCAG | 246 | CUGGAAAC CUGAUGAGGCCGUUAGGCCGAA AUGACACG | 9665 |
| 1562 | GUCAUCGUU UCCAGACC | 247 | GGUCUGGA CUGAUGAGGCCGUUAGGCCGAA ACGAUGAC | 9666 |
| 1563 | UCAUCGUUU CCAGACCC | 248 | GGGUCUGG CUGAUGAGGCCGUUAGGCCGAA AACGAUGA | 9667 |
| 1564 | CAUCGUUUC CAGACCCG | 249 | CGGGUCUG CUGAUGAGGCCGUUAGGCCGAA AAACGAUG | 9668 |
| 1576 | ACCCGGCUC UCUACCCA | 250 | UGGGUAGA CUGAUGAGGCCGUUAGGCCGAA AGCCGGGU | 9669 |
| 1578 | CCGGCUCUC UACCCACU | 251 | AGUGGGUA CUGAUGAGGCCGUUAGGCCGAA AGAGCCGG | 9670 |
| 1580 | GGCUCUCUA CCCACUGG | 252 | CCAGUGGG CUGAUGAGGCCGUUAGGCCGAA AGAGAGCC | 9671 |
| 1602 | AGACAAAUC UGACUUG | 253 | CAAGUCAG CUGAUGAGGCCGUUAGGCCGAA AUUUGUCU | 9672 |
| 1609 | UCCUGACUU GUACCGCA | 254 | UGCGGUAC CUGAUGAGGCCGUUAGGCCGAA AGUCAGGA | 9673 |
| 1612 | UGACUUGUA CCGCAUAU | 255 | AUAUGCGG CUGAUGAGGCCGUUAGGCCGAA ACAAGUCA | 9674 |
| 1619 | UACCGCAUA UGGUAUCC | 256 | GGAUACCA CUGAUGAGGCCGUUAGGCCGAA AUGCGGUA | 9675 |
| 1624 | CAUAUGGUA UCCCUCAA | 257 | UUGAGGGA CUGAUGAGGCCGUUAGGCCGAA ACCAUAUG | 9676 |
| 1626 | UAUGGUAUC CCUCAACC | 258 | GGUUGAGG CUGAUGAGGCCGUUAGGCCGAA AUACCAUA | 9677 |
| 1630 | GUAUCCCUC AACCUACA | 259 | UGUAGGUU CUGAUGAGGCCGUUAGGCCGAA AGGGAUAC | 9678 |
| 1636 | CUCAACCUA CAAUCAAG | 260 | CUUGAUUG CUGAUGAGGCCGUUAGGCCGAA AGGUUGAG | 9679 |
| 1641 | CCUACAAUC AAGUGGUU | 261 | AACCACUU CUGAUGAGGCCGUUAGGCCGAA AUUGUAGG | 9680 |
| 1649 | CAAGUGGUU CUGGCACC | 262 | GGUGCCAG CUGAUGAGGCCGUUAGGCCGAA ACCACUUG | 9681 |
| 1650 | AAGUGGUUC UGGCACCC | 263 | GGGUGCCA CUGAUGAGGCCGUUAGGCCGAA AACCACUU | 9682 |
| 1663 | ACCCCUGUA ACC5AUAAU | 264 | AUUAUGGU CUGAUGAGGCCGUUAGGCCGAA ACAGGGGU | 9683 |
| 1669 | GUAACCAUA AUCAUUCC | 265 | GGAAUGAU CUGAUGAGGCCGUUAGGCCGAA AUGGUUAC | 9684 |
| 1672 | ACCAUAAUC AUUCCGAA | 266 | UUCGGAAU CUGAUGAGGCCGUUAGGCCGAA AUUAUGGU | 9685 |
| 1675 | AUAAUCAUU CCGAAGCA | 267 | UGCUUCGG CUGAUGAGGCCGUUAGGCCGAA AUGAUUAU | 9686 |
| 1676 | UAAUCAUUC CGAAGCAA | 268 | UUGCUUCG CUGAUGAGGCCGUUAGGCCGAA AAUGAUUA | 9687 |
| 1694 | GUGUGACUU UGUUCCA | 269 | UGGAACAA CUGAUGAGGCCGUUAGGCCGAA AGUCACAC | 9688 |
| 1695 | UGUGACUUU GUUCCAA | 270 | UUGGAACA CUGAUGAGGCCGUUAGGCCGAA AAGUCACA | 9689 |
| 1696 | GUGACUUUU GUUCCAAU | 271 | AUUGGAAC CUGAUGAGGCCGUUAGGCCGAA AAAGUCAC | 9690 |
| 1699 | ACUUUGUU CCAUAAU | 272 | AUUAUGG CUGAUGAGGCCGUUAGGCCGAA ACAAAGU | 9691 |
| 1700 | CUUUUGUUC CAAUAAUG | 273 | CAUUAUUG CUGAUGAGGCCGUUAGGCCGAA AACAAAAG | 9692 |
| 1705 | GUUCCAAUA AUGAAGAG | 274 | CUCUUCAU CUGAUGAGGCCGUUAGGCCGAA AUUGGAAC | 9693 |

TABLE II-continued

Human flt1 VEGF Receptor-Hammerhead Ribozyme and Substrate Sequence

| Pos | Substrate | Seq ID No | HH Ribozyme | Seq ID No |
|-----|-----------|-----------|-------------|-----------|
| 1715 | UGAAGAGUC CUUUAUCC | 275 | GGAUAAAG CUGAUGAGGCCGUUAGGCCGAA ACUCUUCA | 9694 |
| 1718 | AGAGUCCUU UAUCCUGG | 276 | CCAGGAUA CUGAUGAGGCCGUUAGGCCGAA AGGACUCU | 9695 |
| 1719 | GAGUCCUUU AUCCUGGA | 277 | UCCAGGAU CUGAUGAGGCCGUUAGGCCGAA AAGGACUC | 9696 |
| 1720 | AGUCCUUUA UCCUGGAU | 278 | AUCCAGGA CUGAUGAGGCCGUUAGGCCGAA AAAGGACU | 9697 |
| 1722 | UCCUUUAUC CUGGAUGC | 279 | GCAUCCAG CUGAUGAGGCCGUUAGGCCGAA AUAAAGGA | 9698 |
| 1755 | AACAGAAUU GAGAGCAU | 280 | AUGCUCUC CUGAUGAGGCCGUUAGGCCGAA AUUCUGUU | 9699 |
| 1764 | GAGAGCAUC ACUCAGCG | 281 | CGCUGAGU CUGAUGAGGCCGUUAGGCCGAA AUGCUCUC | 9700 |
| 1768 | GCAUCACUC AGCGCAUG | 282 | CAUGCGCU CUGAUGAGGCCGUUAGGCCGAA AGUGAUGC | 9701 |
| 1782 | AUGGCAAUA AUAGAAGG | 283 | CCUUCUAU CUGAUGAGGCCGUUAGGCCGAA AUUGCCAU | 9702 |
| 1785 | GCAAUAAUA GAAGGAAA | 284 | UUUCCUUC CUGAUGAGGCCGUUAGGCCGAA AUUAUUGC | 9703 |
| 1798 | GAAAGAAUA AGAUGGCU | 285 | AGCCAUCU CUGAUGAGGCCGUUAGGCCGAA AUUCUUUC | 9704 |
| 1807 | AGAUGGCUA GCACCUUG | 286 | CAAGGUGC CUGAUGAGGCCGUUAGGCCGAA AGCCAUCU | 9705 |
| 1814 | UAGCACCUU GGUUGUGG | 287 | CCACAACC CUGAUGAGGCCGUUAGGCCGAA AGGUGCUA | 9706 |
| 1818 | ACCUUGGUU GUGGCUGA | 288 | UCAGCCAC CUGAUGAGGCCGUUAGGCCGAA ACCAAGGU | 9707 |
| 1829 | GGCUGACUC UAGAAUUU | 289 | AAAUUCUA CUGAUGAGGCCGUUAGGCCGAA AGUCAGCC | 9708 |
| 1831 | CUGACUCUA GAAUUUCU | 290 | AGAAAUUC CUGAUGAGGCCGUUAGGCCGAA AGAGUCAG | 9709 |
| 1836 | UCUAGAAUU UCUGGAAU | 291 | AUUCCAGA CUGAUGAGGCCGUUAGGCCGAA AUUCUAGA | 9710 |
| 1837 | CUAGAAUUU CUGGAAUC | 292 | GAUUCCAG CUGAUGAGGCCGUUAGGCCGAA AAUUCUAG | 9711 |
| 1838 | UAGAAUUUC UGGAAUCU | 293 | AGAUUCCA CUGAUGAGGCCGUUAGGCCGAA AAAUUCUA | 9712 |
| 1845 | UCUGGAAUC UACAUUUG | 294 | CAAAUGUA CUGAUGAGGCCGUUAGGCCGAA AUUCCAGA | 9713 |
| 1847 | UGGAAUCUA CAUUUGCA | 295 | UGCAAAUG CUGAUGAGGCCGUUAGGCCGAA AGAUUCCA | 9714 |
| 1851 | AUCUACAUU UGCAUAGC | 296 | GCUAUGCA CUGAUGAGGCCGUUAGGCCGAA AUGUAGAU | 9715 |
| 1852 | UCUACAUUU GCAUAGCU | 297 | AGCUAUGC CUGAUGAGGCCGUUAGGCCGAA AAUGUAGA | 9716 |
| 1857 | AUUUGCAUA GCUUCCAA | 298 | UUGGAAGC CUGAUGAGGCCGUUAGGCCGAA AUGCAAAU | 9717 |
| 1861 | GCAUAGCUU CCAAUAAA | 299 | UUUAUUGG CUGAUGAGGCCGUUAGGCCGAA AGCUAUGC | 9718 |
| 1862 | CAUAGCUUC CAAUAAAG | 300 | CUUUAUUG CUGAUGAGGCCGUUAGGCCGAA AAGCUAUG | 9719 |
| 1867 | CUUCCAAUA AGUUGGG | 301 | CCCAACUU CUGAUGAGGCCGUUAGGCCGAA AUUGGAAG | 9720 |
| 1872 | AAUAAGUU GGGACUGU | 302 | ACAGUCCC CUGAUGAGGCCGUUAGGCCGAA ACUUUAUU | 9721 |
| 1893 | AGAAACAUA AGCUUUUA | 303 | UAAAAGCU CUGAUGAGGCCGUUAGGCCGAA AUGUUUCU | 9722 |
| 1898 | CAUAAGCUU UUAUAUCA | 304 | UGAUAUAA CUGAUGAGGCCGUUAGGCCGAA AGCUUAUG | 9723 |
| 1899 | AUAAGCUUU UAUAUCAC | 305 | GUGAUAUA CUGAUGAGGCCGUUAGGCCGAA AAGCUUAU | 9724 |
| 1900 | UAAGCUUUU AUAUCACA | 306 | UGUGAUAU CUGAUGAGGCCGUUAGGCCGAA AAAGCUUA | 9725 |
| 1901 | AAGCUUUUA UAUCACAG | 307 | CUGUGAUA CUGAUGAGGCCGUUAGGCCGAA AAAAGCUU | 9726 |
| 1903 | GCUUUUAUA UCACAGAU | 308 | AUCUGUGA CUGAUGAGGCCGUUAGGCCGAA AUAAAAGC | 9727 |
| 1905 | UUUUAUAUC ACAGAUGU | 309 | ACAUCUGU CUGAUGAGGCCGUUAGGCCGAA AUAUAAAA | 9728 |
| 1925 | AAAUGGGUU UCAUGUUA | 310 | UAACAUGA CUGAUGAGGCCGUUAGGCCGAA ACCCAUUU | 9729 |
| 1926 | AAUGGGUUU CAUGUUAA | 311 | UUAACAUG CUGAUGAGGCCGUUAGGCCGAA AACCCAUU | 9730 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 1927 | AUGGGUUUC AUGUUAAC | 312 | GUUAACAU CUGAUGAGGCCGUUAGGCCGAA AAACCCAU | 9731 |
| 1932 | UUUCAUGUU AACUUGGA | 313 | UCCAAGUU CUGAUGAGGCCGUUAGGCCGAA ACAUGAAA | 9732 |
| 1933 | UUCAUGUUA ACUUGGAA | 314 | UUCCAAGU CUGAUGAGGCCGUUAGGCCGAA AACAUGAA | 9733 |
| 1937 | UGUUAACUU GGAAAAAA | 315 | UUUUUUCC CUGAUGAGGCCGUUAGGCCGAA AGUUAACA | 9734 |
| 1976 | GAAACUGUC UUGCACAG | 316 | CUGUGCAA CUGAUGAGGCCGUUAGGCCGAA ACAGUUUC | 9735 |
| 1978 | AACUGUCUU GCACAGUU | 317 | AACUGUGC CUGAUGAGGCCGUUAGGCCGAA AGACAGUU | 9736 |
| 1986 | UGCACAGUU AACAAGUU | 318 | AACUUGUU CUGAUGAGGCCGUUAGGCCGAA ACUGUGCA | 9737 |
| 1987 | GCACAGUUA ACAAGUUC | 319 | GAACUUGU CUGAUGAGGCCGUUAGGCCGAA AACUGUGC | 9738 |
| 1994 | UAACAAGUU CUUAUACA | 320 | UGUAUAAG CUGAUGAGGCCGUUAGGCCGAA ACUUGUUA | 9739 |
| 1995 | AACAAGUUC UUAUACAG | 321 | CUGUAUAA CUGAUGAGGCCGUUAGGCCGAA AACUUGUU | 9740 |
| 1997 | CAAGUUCUU AUACAGAG | 322 | CUCUGUAU CUGAUGAGGCCGUUAGGCCGAA AGAACUUG | 9741 |
| 1998 | AAGUUCUUA UACAGAGA | 323 | UCUCUGUA CUGAUGAGGCCGUUAGGCCGAA AAGAACUU | 9742 |
| 2000 | GUUCUUAUA CAGAGACG | 324 | CGUCUCUG CUGAUGAGGCCGUUAGGCCGAA AUAAGAAC | 9743 |
| 2010 | AGAGACGUU ACUUGGAU | 325 | AUCCAAGU CUGAUGAGGCCGUUAGGCCGAA ACGUCUCU | 9744 |
| 2011 | GAGACGUUA CUUGGAUU | 326 | AAUCCAAG CUGAUGAGGCCGUUAGGCCGAA AACGUCUC | 9745 |
| 2014 | ACGUUACUU GGAUUUUA | 327 | UAAAAUCC CUGAUGAGGCCGUUAGGCCGAA AGUAACGU | 9746 |
| 2019 | ACUUGGAUU UUACUGCG | 328 | CGCAGUAA CUGAUGAGGCCGUUAGGCCGAA AUCCAAGU | 9747 |
| 2020 | CUUGGAUUU UACUGCGG | 329 | CCGCAGUA CUGAUGAGGCCGUUAGGCCGAA AAUCCAAG | 9748 |
| 2021 | UUGGAUUUU ACUGCGGA | 330 | UCCGCAGU CUGAUGAGGCCGUUAGGCCGAA AAAUCCAA | 9749 |
| 2022 | UGGAUUUUA CUGCGGAC | 331 | GUCCGCAG CUGAUGAGGCCGUUAGGCCGAA AAAAUCCA | 9750 |
| 2034 | CGGACAGUU AAUAACAG | 332 | CUGUUAUU CUGAUGAGGCCGUUAGGCCGAA ACUGUCCG | 9751 |
| 2035 | GGACAGUUA AUAACAGA | 333 | UCUGUUAU CUGAUGAGGCCGUUAGGCCGAA AACUGUCC | 9752 |
| 2038 | CAGUUAAUA ACAGAACA | 334 | UGUUCUGU CUGAUGAGGCCGUUAGGCCGAA AUUAACUG | 9753 |
| 2054 | AAUGCACUA CAGUAUUA | 335 | UAAUACUG CUGAUGAGGCCGUUAGGCCGAA AGUGCAUU | 9754 |
| 2059 | ACUACAGUA UUAGCAAG | 336 | CUUGCUAA CUGAUGAGGCCGUUAGGCCGAA ACUGUAGU | 9755 |
| 2061 | UACAGUAUU AGCAAGCA | 337 | UGCUUGCU CUGAUGAGGCCGUUAGGCCGAA AUACUGUA | 9756 |
| 2062 | ACAGUAUUA GCAAGCAA | 338 | UUGCUUGC CUGAUGAGGCCGUUAGGCCGAA AAUACUGU | 9757 |
| 2082 | AUGGCCAUC ACUAAGGA | 339 | UCCUUAGU CUGAUGAGGCCGUUAGGCCGAA AUGGCCAU | 9758 |
| 2086 | CCAUCACUA AGGAGCAC | 340 | GUGCUCCU CUGAUGAGGCCGUUAGGCCGAA AGUGAUGG | 9759 |
| 2096 | GGAGCACUC CAUCACUC | 341 | GAGUGAUG CUGAUGAGGCCGUUAGGCCGAA AGUGCUCC | 9760 |
| 2100 | CACUCCAUC ACUCUUAA | 342 | UUAAGAGU CUGAUGAGGCCGUUAGGCCGAA AUGGAGUG | 9761 |
| 2104 | CCAUCACUC UUAAUCUU | 343 | AAGAUUAA CUGAUGAGGCCGUUAGGCCGAA AGUGAUGG | 9762 |
| 2106 | AUCACUCUU AAUCUUAC | 344 | GUAAGAUU CUGAUGAGGCCGUUAGGCCGAA AGAGUGAU | 9763 |
| 2107 | UCACUCUUA AUCUUACC | 345 | GGUAAGAU CUGAUGAGGCCGUUAGGCCGAA AAGAGUGA | 9764 |
| 2110 | CUCUUAAUC UUACCAUC | 346 | GAUGGUAA CUGAUGAGGCCGUUAGGCCGAA AUUAAGAG | 9765 |
| 2112 | CUUAAUCUU ACCAUCAU | 347 | AUGAUGGU CUGAUGAGGCCGUUAGGCCGAA AGAUUAAG | 9766 |
| 2113 | UUAAUCUUA CCAUCAUG | 348 | CAUGAUGG CUGAUGAGGCCGUUAGGCCGAA AAGAUUAA | 9767 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 2118 | CUUACCAUC AUGAAUGU | 349 | ACAUUCAU CUGAUGAGGCCGUUAGGCCGAA AUGGUAAG | 9768 |
| 2127 | AUGAAUGUU UCCCUGCA | 350 | UGCAGGGA CUGAUGAGGCCGUUAGGCCGAA ACAUUCAU | 9769 |
| 2128 | UGAAUGUUU CCCUGCAA | 351 | UUGCAGGG CUGAUGAGGCCGUUAGGCCGAA AACAUUCA | 9770 |
| 2129 | GAAUGUUUC CCUGCAAG | 352 | CUUGCAGG CUGAUGAGGCCGUUAGGCCGAA AAACAUUC | 9771 |
| 2140 | UGCAAGAUU CAGGCACC | 353 | GGUGCCUG CUGAUGAGGCCGUUAGGCCGAA AUCUUGCA | 9772 |
| 2141 | GCAAGAUUC AGGCACCU | 354 | AGGUGCCU CUGAUGAGGCCGUUAGGCCGAA AAUCUUGC | 9773 |
| 2150 | AGGCACCUA UGCCUGCA | 355 | UGCAGGCA CUGAUGAGGCCGUUAGGCCGAA AGGUGCCU | 9774 |
| 2172 | AGGAAUGUA UACACAGG | 356 | CCUGUGUA CUGAUGAGGCCGUUAGGCCGAA ACAUUCCU | 9775 |
| 2174 | GAAUGUAUA CACAGGGG | 357 | CCCCUGUG CUGAUGAGGCCGUUAGGCCGAA AUACAUUC | 9776 |
| 2190 | GAAGAAAUC UCCAGAA | 358 | UUCUGGAG CUGAUGAGGCCGUUAGGCCGAA AUUUCUUC | 9777 |
| 2193 | GAAAUCCUC CAGAAGAA | 359 | UUCUUCUG CUGAUGAGGCCGUUAGGCCGAA AGGAUUUC | 9778 |
| 2208 | AAAGAAAUU ACAAUCAG | 360 | CUGAUUGU CUGAUGAGGCCGUUAGGCCGAA AUUUCUUU | 9779 |
| 2209 | AAGAAAUUA CAAUCAGA | 361 | UCUGAUUG CUGAUGAGGCCGUUAGGCCGAA AAUUUCUU | 9780 |
| 2214 | AUUACAAUC AGAGAUCA | 362 | UGAUCUCU CUGAUGAGGCCGUUAGGCCGAA AUUGUAAU | 9781 |
| 2221 | UCAGAGAUC AGGAAGCA | 363 | UGCUUCCU CUGAUGAGGCCGUUAGGCCGAA AUCUCUGA | 9782 |
| 2234 | AGCACCAUA CCUCCUGC | 364 | GCAGGAGG CUGAUGAGGCCGUUAGGCCGAA AUGGUGCU | 9783 |
| 2238 | CCAUACCUC UGCGAAA | 365 | UUUCGCAG CUGAUGAGGCCGUUAGGCCGAA AGGUAUGG | 9784 |
| 2250 | CGAAACCUC AGUGAUCA | 366 | UGAUCACU CUGAUGAGGCCGUUAGGCCGAA AGGUUUCG | 9785 |
| 2257 | UCAGUGAUC ACACAGUG | 367 | CACUGUGU CUGAUGAGGCCGUUAGGCCGAA AUCACUGA | 9786 |
| 2271 | GUGGCCAUC AGCAGUUC | 368 | GAACUGCU CUGAUGAGGCCGUUAGGCCGAA AUGGCCAC | 9787 |
| 2278 | UCAGCAGUU CCACCACU | 369 | AGUGGUGG CUGAUGAGGCCGUUAGGCCGAA ACUGCUGA | 9788 |
| 2279 | CAGCAGUUC CACCACUU | 370 | AAGUGGUG CUGAUGAGGCCGUUAGGCCGAA AACUGCUG | 9789 |
| 2287 | CCACCACUU UAGACUGU | 371 | ACAGUCUA CUGAUGAGGCCGUUAGGCCGAA AGUGGUGG | 9790 |
| 2288 | CACCACUUU AGACUGUC | 372 | GACAGUCU CUGAUGAGGCCGUUAGGCCGAA AAGUGGUG | 9791 |
| 2289 | ACCACUUUA GACUGUCA | 373 | UGACAGUC CUGAUGAGGCCGUUAGGCCGAA AAAGUGGU | 9792 |
| 2296 | UAGACUGUC AUGCUAAU | 374 | AUUAGCAU CUGAUGAGGCCGUUAGGCCGAA ACAGUCUA | 9793 |
| 2302 | GUCAUGCUA AUGGUGUC | 375 | GACACCAU CUGAUGAGGCCGUUAGGCCGAA AGCAUGAC | 9794 |
| 2310 | AAUGGUGUC CCCGAGCC | 376 | GGCUCGGG CUGAUGAGGCCGUUAGGCCGAA ACACCAUU | 9795 |
| 2320 | CCGAGCCUC AGAUCACU | 377 | AGUGAUCU CUGAUGAGGCCGUUAGGCCGAA AGGCUCGG | 9796 |
| 2325 | CCUCAGAUC ACUUGGUU | 378 | AACCAAGU CUGAUGAGGCCGUUAGGCCGAA AUCUGAGG | 9797 |
| 2329 | AGAUCACUU GGUUUAAA | 379 | UUUAAACC CUGAUGAGGCCGUUAGGCCGAA AGUGAUCU | 9798 |
| 2333 | CACUUGGUU UAAAACA | 380 | UGUUUUUA CUGAUGAGGCCGUUAGGCCGAA ACCAAGUG | 9799 |
| 2334 | ACUUGGUUU AAAACAA | 381 | UUGUUUUU CUGAUGAGGCCGUUAGGCCGAA AACCAAGU | 9800 |
| 2335 | CUUGGUUUA AAACAAC | 382 | GUUGUUUU CUGAUGAGGCCGUUAGGCCGAA AAACCAAG | 9801 |
| 2352 | CACAAAAUA CAACAAGA | 383 | UCUUGUUG CUGAUGAGGCCGUUAGGCCGAA AUUUUGUG | 9802 |
| 2370 | CCUGGAAUU AUUUUAGG | 384 | CCUAAAAU CUGAUGAGGCCGUUAGGCCGAA AUUCCAGG | 9803 |
| 2371 | CUGGAAUUA UUUUAGGA | 385 | UCCUAAAA CUGAUGAGGCCGUUAGGCCGAA AAUUCCAG | 9804 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 2373 | GGAAUUAUU UUAGGACC | 386 | GGUCCUAA CUGAUGAGGCCGUUAGGCCGAA AUAAUUCC | 9805 |
| 2374 | GAAUUAUUU UAGGACCA | 387 | UGGUCCUA CUGAUGAGGCCGUUAGGCCGAA AAUAAUUC | 9806 |
| 2375 | AAUUAUUUU AGGACCAG | 388 | CUGGUCCU CUGAUGAGGCCGUUAGGCCGAA AAAUAAUU | 9807 |
| 2376 | AUUAUUUUA GGACCAGG | 389 | CCUGGUCC CUGAUGAGGCCGUUAGGCCGAA AAAAUAAU | 9808 |
| 2399 | CACGCUGUU UAUUGAAA | 390 | UUUCAAUA CUGAUGAGGCCGUUAGGCCGAA ACAGCGUG | 9809 |
| 2400 | ACGCUGUUU AUUGAAAG | 391 | CUUUCAAU CUGAUGAGGCCGUUAGGCCGAA AACAGCGU | 9810 |
| 2401 | CGCUGUUUA UUGAAAGA | 392 | UCUUUCAA CUGAUGAGGCCGUUAGGCCGAA AAACAGCG | 9811 |
| 2403 | CUGUUUAUU GAAAGAGU | 393 | ACUCUUUC CUGAUGAGGCCGUUAGGCCGAA AUAAACAG | 9812 |
| 2412 | GAAAGAGUC ACAGAAGA | 394 | UCUUCUGU CUGAUGAGGCCGUUAGGCCGAA ACUCUUUC | 9813 |
| 2433 | GAAGGUGUC UAUCACUG | 395 | CAGUGAUA CUGAUGAGGCCGUUAGGCCGAA ACACCUUC | 9814 |
| 2435 | AGGUGUCUA UCACUGCA | 396 | UGCAGUGA CUGAUGAGGCCGUUAGGCCGAA AGACACCU | 9815 |
| 2437 | GUGUCUAUC ACUGCAAA | 397 | UUUGCAGU CUGAUGAGGCCGUUAGGCCGAA AUAGACAC | 9816 |
| 2465 | GAAGGGCUC UGUGGAAA | 398 | UUUCCACA CUGAUGAGGCCGUUAGGCCGAA AGCCCUUC | 9817 |
| 2476 | UGGAAAGUU CAGCAUAC | 399 | GUAUGCUG CUGAUGAGGCCGUUAGGCCGAA ACUUUCCA | 9818 |
| 2477 | GGAAAGUUC AGCAUACC | 400 | GGUAUGCU CUGAUGAGGCCGUUAGGCCGAA AACUUUCC | 9819 |
| 2483 | UUCAGCAUA CCUCACUG | 401 | CAGUGAGG CUGAUGAGGCCGUUAGGCCGAA AUGCUGAA | 9820 |
| 2487 | GCAUACCUC ACUGUUCA | 402 | UGAACAGU CUGAUGAGGCCGUUAGGCCGAA AGGUAUGC | 9821 |
| 2493 | CUCACUGUU CAAGGAAC | 403 | GUUCCUUG CUGAUGAGGCCGUUAGGCCGAA ACAGUGAG | 9822 |
| 2494 | UCACUGUUC AAGGAACC | 404 | GGUUCCUU CUGAUGAGGCCGUUAGGCCGAA AACAGUGA | 9823 |
| 2504 | AGGAACCUC GGACAAGU | 405 | ACUUGUCC CUGAUGAGGCCGUUAGGCCGAA AGGUUCCU | 9824 |
| 2513 | GGACAAGUC UAAUCUGG | 406 | CCAGAUUA CUGAUGAGGCCGUUAGGCCGAA ACUUGUCC | 9825 |
| 2515 | ACAAGUCUA AUCUGGAG | 407 | CUCCAGAU CUGAUGAGGCCGUUAGGCCGAA AGACUUGU | 9826 |
| 2518 | AGUCUAAUC UGGAGCUG | 408 | CAGCUCCA CUGAUGAGGCCGUUAGGCCGAA AUUAGACU | 9827 |
| 2529 | GAGCUGAUC ACUCUAAC | 409 | GUUAGAGU CUGAUGAGGCCGUUAGGCCGAA AUCAGCUC | 9828 |
| 2533 | UGAUCACUC UAACAUGC | 410 | GCAUGUUA CUGAUGAGGCCGUUAGGCCGAA AGUGAUCA | 9829 |
| 2535 | AUCACUCUA ACAUGCAC | 411 | GUGCAUGU CUGAUGAGGCCGUUAGGCCGAA AGAGUGAU | 9830 |
| 2560 | CUGCGACUC UCUUCUGG | 412 | CCAGAAGA CUGAUGAGGCCGUUAGGCCGAA AGUCGCAG | 9831 |
| 2562 | GCGACUCUC UUCUGGCU | 413 | AGCCAGAA CUGAUGAGGCCGUUAGGCCGAA AGAGUCGC | 9832 |
| 2564 | GACUCUCUU CUGGCUCC | 414 | GGAGCCAG CUGAUGAGGCCGUUAGGCCGAA AGAGAGUC | 9833 |
| 2565 | ACUCUCUUC UGGCUCCU | 415 | AGGAGCCA CUGAUGAGGCCGUUAGGCCGAA AAGAGAGU | 9834 |
| 2571 | UUCUGGCUC CUAUUAAC | 416 | GUUAAUAG CUGAUGAGGCCGUUAGGCCGAA AGCCAGAA | 9835 |
| 2574 | UGGCUCCUA UUAACCCU | 417 | AGGGUUAA CUGAUGAGGCCGUUAGGCCGAA AGGAGCCA | 9836 |
| 2576 | GCUCCUAUU AACCCUCC | 418 | GGAGGGUU CUGAUGAGGCCGUUAGGCCGAA AUAGGAGC | 9837 |
| 2577 | CUCCUAUUA ACCCUCCU | 419 | AGGAGGGU CUGAUGAGGCCGUUAGGCCGAA AAUAGGAG | 9838 |
| 2583 | UUAACCCUC CUAUCCG | 420 | CGGAUAAG CUGAUGAGGCCGUUAGGCCGAA AGGGUUAA | 9839 |
| 2586 | ACCCUCCUU AUCCGAAA | 421 | UUUCGGAU CUGAUGAGGCCGUUAGGCCGAA AGGAGGGU | 9840 |
| 2587 | CCCUCCUUA UCCGAAAA | 422 | UUUUCGGA CUGAUGAGGCCGUUAGGCCGAA AAGGAGGG | 9841 |

TABLE II-continued

Human flt1 VEGF Receptor-Hammerhead Ribozyme and Substrate Sequence

| Pos | Substrate | Seq ID No | HH Ribozyme | Seq ID No |
|-----|-----------|-----------|-------------|-----------|
| 2589 | CUCCUUAUC CGAAAAAU | 423 | AUUUUUCG CUGAUGAGGCCGUUAGGCCGAA AUAAGGAG | 9842 |
| 2606 | GAAAAGGUC UUCUUCUG | 424 | CAGAAGAA CUGAUGAGGCCGUUAGGCCGAA ACCUUUUC | 9843 |
| 2608 | AAAGGUCUU CUUCUGAA | 425 | UUCAGAAG CUGAUGAGGCCGUUAGGCCGAA AGACCUUU | 9844 |
| 2809 | AAGGUCUUC UUCUGAAA | 426 | UUUCAGAA CUGAUGAGGCCGUUAGGCCGAA AAGACCUU | 9845 |
| 2611 | GGUCUUCUU CUGAAAUA | 427 | UAUUUCAG CUGAUGAGGCCGUUAGGCCGAA AGAAGACC | 9846 |
| 2612 | GUCUUCUUC UGAAAUAA | 428 | UUAUUUCA CUGAUGAGGCCGUUAGGCCGAA AAGAAGAC | 9847 |
| 2619 | UCUGAAAUA AAGACUGA | 429 | UCAGUCUU CUGAUGAGGCCGUUAGGCCGAA AUUUCAGA | 9848 |
| 2630 | GACUGACUA CCUAUCAA | 430 | UUGAUAGG CUGAUGAGGCCGUUAGGCCGAA AGUCAGUC | 9849 |
| 2634 | GACUACCUA UCAAUUAU | 431 | AUAAUUGA CUGAUGAGGCCGUUAGGCCGAA AGGUAGUC | 9850 |
| 2636 | CUACCUAUC AAUUAUAA | 432 | UUAUAAUU CUGAUGAGGCCGUUAGGCCGAA AUAGGUAG | 9851 |
| 2640 | CUAUCAAUU AUAAUGGA | 433 | UCCAUUAU CUGAUGAGGCCGUUAGGCCGAA AUUGAUAG | 9852 |
| 2641 | UAUCAAUUA UAAUGGAC | 434 | GUCCAUUA CUGAUGAGGCCGUUAGGCCGAA AAUUGAUA | 9853 |
| 2643 | UCAAUUAUA AUGGACCC | 435 | GGGUCCAU CUGAUGAGGCCGUUAGGCCGAA AUAAUUGA | 9854 |
| 2661 | GAUGAAGUU CCUUUGGA | 436 | UCCAAAGG CUGAUGAGGCCGUUAGGCCGAA ACUUCAUC | 9855 |
| 2662 | AUGAAGUUC CUUUGGAU | 437 | AUCCAAAG CUGAUGAGGCCGUUAGGCCGAA AACUUCAU | 9856 |
| 2665 | AAGUUCCUU UGGAUGAG | 438 | CUCAUCCA CUGAUGAGGCCGUUAGGCCGAA AGGAACUU | 9857 |
| 2666 | AGUUCCUUU GGAUGAGC | 439 | GCUCAUCC CUGAUGAGGCCGUUAGGCCGAA AAGGAACU | 9858 |
| 2688 | GAGCGGCUC CCUUAUGA | 440 | UCAUAAGG CUGAUGAGGCCGUUAGGCCGAA AGCCGCUC | 9859 |
| 2692 | GGCUCCCUU AUGAUGCC | 441 | GGCAUCAU CUGAUGAGGCCGUUAGGCCGAA AGGGAGCC | 9860 |
| 2693 | GCUCCCUUA UGAUGCCA | 442 | UGGCAUCA CUGAUGAGGCCGUUAGGCCGAA AAGGGAGC | 9861 |
| 2714 | GUGGGAGUU UGCCCGGG | 443 | CCCGGGCA CUGAUGAGGCCGUUAGGCCGAA ACUCCCAC | 9862 |
| 2715 | UGGGAGUUU GCCCGGGA | 444 | UCCCGGGC CUGAUGAGGCCGUUAGGCCGAA AACUCCCA | 9863 |
| 2730 | GAGAGACUU AAACUGGG | 445 | CCCAGUUU CUGAUGAGGCCGUUAGGCCGAA AGUCUCUC | 9864 |
| 2731 | AGAGACUUA AACUGGGC | 446 | GCCCAGUU CUGAUGAGGCCGUUAGGCCGAA AAGUCUCU | 9865 |
| 2744 | GGGCAAAUC ACUUGGAA | 447 | UUCCAAGU CUGAUGAGGCCGUUAGGCCGAA AUUUGCCC | 9866 |
| 2748 | AAAUCACUU GGAAGAGG | 448 | CCUCUUCC CUGAUGAGGCCGUUAGGCCGAA AGUGAUUU | 9867 |
| 2761 | GAGGGGCUU UUGGAAAA | 449 | UUUUCCAA CUGAUGAGGCCGUUAGGCCGAA AGCCCCUC | 9868 |
| 2762 | AGGGGCUUU UGGAAAAG | 450 | CUUUUCCA CUGAUGAGGCCGUUAGGCCGAA AAGCCCCU | 9869 |
| 2763 | GGGGCUUUU GGAAAAGU | 451 | ACUUUUCC CUGAUGAGGCCGUUAGGCCGAA AAAGCCCC | 9870 |
| 2775 | AAAGUGGUU CAAGCAUC | 452 | GAUGCUUG CUGAUGAGGCCGUUAGGCCGAA ACCACUUU | 9871 |
| 2776 | AGUGGUUC AAGCAUCA | 453 | UGAUGCUU CUGAUGAGGCCGUUAGGCCGAA AACCACUU | 9872 |
| 2783 | UCAAGCAUC AGCAUUUG | 454 | CAAAUGCU CUGAUGAGGCCGUUAGGCCGAA AUGCUUGA | 9873 |
| 2789 | AUCAGCAUU UGGCAUUA | 455 | UAAUGCCA CUGAUGAGGCCGUUAGGCCGAA AUGCUGAU | 9874 |
| 2790 | UCAGCAUUU GGCAUUAA | 456 | UUAAUGCC CUGAUGAGGCCGUUAGGCCGAA AAUGCUGA | 9875 |
| 2796 | UUUGGCAUU AAGAAAUC | 457 | GAUUUCUU CUGAUGAGGCCGUUAGGCCGAA AUGCCAAA | 9876 |
| 2797 | UUGGCAUUA AGAAAUCA | 458 | UGAUUUCU CUGAUGAGGCCGUUAGGCCGAA AAUGCCAA | 9877 |
| 2804 | UAAGAAAUC ACCUACGU | 459 | ACGUAGGU CUGAUGAGGCCGUUAGGCCGAA AUUUCUUA | 9878 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 2809 | AAUCACCUA CGUGCCGG | 460 | CCGGCACG CUGAUGAGGCCGUUAGGCCGAA AGGUCAUU | 9879 |
| 2864 | CAGCGAGUA CAAAGCUC | 461 | GAGCUUUG CUGAUGAGGCCGUUAGGCCGAA ACUCGCUG | 9880 |
| 2872 | ACAAAGCUC UGAUGACU | 462 | AGUCAUCA CUGAUGAGGCCGUUAGGCCGAA AGCUUUGU | 9881 |
| 2886 | ACUGAGCUA AAAAUCUU | 463 | AAGAUUUU CUGAUGAGGCCGUUAGGCCGAA AGCUCAGU | 9882 |
| 2892 | CUAAAAAUC UUGACCCA | 464 | UGGGUCAA CUGAUGAGGCCGUUAGGCCGAA AUUUUUAG | 9883 |
| 2894 | AAAAAUCUU GACCCACA | 465 | UGUGGGUC CUGAUGAGGCCGUUAGGCCGAA AGAUUUUU | 9884 |
| 2904 | ACCCACAUU GGCCACCA | 466 | UGGUGGCC CUGAUGAGGCCGUUAGGCCGAA AUGUGGGU | 9885 |
| 2914 | GCCACCAUC UGAACGUG | 467 | CACGUUCA CUGAUGAGGCCGUUAGGCCGAA AUGGUGGC | 9886 |
| 2925 | AACGUGGUU AACCUGCU | 468 | AGCAGGUU CUGAUGAGGCCGUUAGGCCGAA ACCACGUU | 9887 |
| 2926 | ACGUGGUUA ACCUGCUG | 469 | CAGCAGGU CUGAUGAGGCCGUUAGGCCGAA AACCACGU | 9888 |
| 2962 | GAGGGCCUC UGAUGGUG | 470 | CACCAUCA CUGAUGAGGCCGUUAGGCCGAA AGGCCCUC | 9889 |
| 2973 | AUGGUGAUU GUUGAAUA | 471 | UAUUCAAC CUGAUGAGGCCGUUAGGCCGAA AUCACCAU | 9890 |
| 2976 | GUGAUUGUU GAAUACUG | 472 | CAGUAUUC CUGAUGAGGCCGUUAGGCCGAA ACAAUCAC | 9891 |
| 2981 | UGUUGAAUA CUGCAAAU | 473 | AUUUGCAG CUGAUGAGGCCGUUAGGCCGAA AUUCAACA | 9892 |
| 2990 | CUGCAAAUA UGGAAAUC | 474 | GAUUUCCA CUGAUGAGGCCGUUAGGCCGAA AUUUGCAG | 9893 |
| 2998 | AUGGAAAUC UCUCCAAC | 475 | GUUGGAGA CUGAUGAGGCCGUUAGGCCGAA AUUUCCAU | 9894 |
| 3000 | GGAAAUCUC UCCAACUA | 476 | UAGUUGGA CUGAUGAGGCCGUUAGGCCGAA AGAUUUCC | 9895 |
| 3002 | AAAUCUCUC CAACUACC | 477 | GGUAGUUG CUGAUGAGGCCGUUAGGCCGAA AGAGAUUU | 9896 |
| 3008 | CUCCAACUA CCUCAAGA | 478 | UCUUGAGG CUGAUGAGGCCGUUAGGCCGAA AGUUGGAG | 9897 |
| 3012 | AACUACCUC AAGAGCAA | 479 | UUGCUCUU CUGAUGAGGCCGUUAGGCCGAA AGGUAGUU | 9898 |
| 3029 | ACGUGACUU AUUUUUUC | 480 | GAAAAAAU CUGAUGAGGCCGUUAGGCCGAA AGUCACGU | 9899 |
| 3030 | CGUGACUUA UUUUUUCU | 481 | AGAAAAAA CUGAUGAGGCCGUUAGGCCGAA AAGUCACG | 9900 |
| 3032 | UGACUUAUU UUUUCUCA | 482 | UGAGAAAA CUGAUGAGGCCGUUAGGCCGAA AUAAGUCA | 9901 |
| 3033 | GACUUAUUU UUUCUCAA | 483 | UUGAGAAA CUGAUGAGGCCGUUAGGCCGAA AAUAAGUC | 9902 |
| 3034 | ACUUAUUUU UUCUCAAC | 484 | GUUGAGAA CUGAUGAGGCCGUUAGGCCGAA AAAUAAGU | 9903 |
| 3035 | CUUAUUUUU UCUCAACA | 485 | UGUUGAGA CUGAUGAGGCCGUUAGGCCGAA AAAAUAAG | 9904 |
| 3036 | UUAUUUUUU CUCAACAA | 486 | UUGUUGAG CUGAUGAGGCCGUUAGGCCGAA AAAAAUAA | 9905 |
| 3037 | UAUUUUUUC UCAACAAG | 487 | CUUGUUGA CUGAUGAGGCCGUUAGGCCGAA AAAAAAUA | 9906 |
| 3039 | UUUUUUCUC AACAAGGA | 488 | UCCUUGUU CUGAUGAGGCCGUUAGGCCGAA AGAAAAAA | 9907 |
| 3057 | GCAGCACUA CACAUGGA | 489 | UCCAUGUG CUGAUGAGGCCGUUAGGCCGAA AGUGCUGC | 9908 |
| 3070 | UGGAGCCUA AGAAAGAA | 490 | UUCUUUCU CUGAUGAGGCCGUUAGGCCGAA AGGCUCCA | 9909 |
| 3120 | CCAAGACUA GAUAGCGU | 491 | ACGCUAUC CUGAUGAGGCCGUUAGGCCGAA AGUCUUGG | 9910 |
| 3124 | GACUAGAUA GCGUCACC | 492 | GGUGACGC CUGAUGAGGCCGUUAGGCCGAA AUCUAGUC | 9911 |
| 3129 | GAUAGCGUC ACCAGCAG | 493 | CUGCUGGU CUGAUGAGGCCGUUAGGCCGAA ACGCUAUC | 9912 |
| 3146 | CGAAAGCUU UGCGAGCU | 494 | AGCUCGCA CUGAUGAGGCCGUUAGGCCGAA AGCUUUCG | 9913 |
| 3147 | GAAAGCUUU GCGAGCUC | 495 | GAGCUCGC CUGAUGAGGCCGUUAGGCCGAA AAGCUUUC | 9914 |
| 3155 | UGCGAGCUC CGGCUUUC | 496 | GAAAGCCG CUGAUGAGGCCGUUAGGCCGAA AGCUCGCA | 9915 |

TABLE II-continued

Human flt1 VEGF Receptor—Hammerhead Ribozyme and Substrate Sequence

| Pos | Substrate | Seq ID No | HH Ribozyme | Seq ID No |
|---|---|---|---|---|
| 3161 | CUCCGGCUU UCAGGAAG | 497 | CUUCCUGA CUGAUGAGGCCGUUAGGCCGAA AGCCGGAG | 9916 |
| 3162 | UCCGGCUUU CAGGAAGA | 498 | UCUUCCUG CUGAUGAGGCCGUUAGGCCGAA AAGCCGGA | 9917 |
| 3163 | CCGGCUUUC AGGAAGAU | 499 | AUCUUCCU CUGAUGAGGCCGUUAGGCCGAA AAAGCCGG | 9918 |
| 3172 | AGGAAGAUA AAAGUCUG | 500 | CAGACUUU CUGAUGAGGCCGUUAGGCCGAA AUCUUCCU | 9919 |
| 3178 | AUAAAAGUC UGAGUGAG | 501 | AUCACUCA CUGAUGAGGCCGUUAGGCCGAA ACUUUUAU | 9920 |
| 3189 | AGUGAUGUU GAGGAAGA | 502 | UCUUCCUC CUGAUGAGGCCGUUAGGCCGAA ACAUCACU | 9921 |
| 3205 | AGGAGGAUU CUGACGGU | 503 | ACCGUCAG CUGAUGAGGCCGUUAGGCCGAA AUCCUCCU | 9922 |
| 3206 | GGAGGAUUC UGACGGUU | 504 | AACCGUCA CUGAUGAGGCCGUUAGGCCGAA AAUCCUCC | 9923 |
| 3214 | CUGACGGUU UCUACAAG | 505 | CUUGUAGA CUGAUGAGGCCGUUAGGCCGAA ACCGUCAG | 9924 |
| 3215 | UGACGGUUU CUACAAGG | 506 | CCUUGUAG CUGAUGAGGCCGUUAGGCCGAA AACCGUCA | 9925 |
| 3216 | GACGGUUUC UACAAGGA | 507 | UCCUGGUA CUGAUGAGGCCGUUAGGCCGAA AAACCGUC | 9926 |
| 3218 | CGGUUUCUA CAAGGAGC | 508 | GCUCCUUG CUGAUGAGGCCGUUAGGCCGAA AGAAACCG | 9927 |
| 3231 | GAGCCCAUC ACUAUGGA | 509 | UCCAUAGU CUGAUGAGGCCGUUAGGCCGAA AUGGGCUC | 9928 |
| 3235 | CCAUCACUA UGGAAGAU | 510 | AUCUUCCA CUGAUGAGGCCGUUAGGCCGAA AGUGAUGG | 9929 |
| 3244 | UGGAAGAUC UGAUUUCU | 511 | AGAAAUCA CUGAUGAGGCCGUUAGGCCGAA AUCUUCCA | 9930 |
| 3249 | GAUCUGAUU UCUUACAG | 512 | CUGUAAGA CUGAUGAGGCCGUUAGGCCGAA AUCAGAUC | 9931 |
| 3250 | AUCUGAUUU CUUACAGU | 513 | ACUGUAAG CUGAUGAGGCCGUUAGGCCGAA AAUCAGAU | 9932 |
| 3251 | UCUGAUUUC UUACAGUU | 514 | AACUGUAA CUGAUGAGGCCGUUAGGCCGAA AAAUCAGA | 9933 |
| 3253 | UGAUUUCUU ACAGUUUU | 515 | AAAACUGU CUGAUGAGGCCGUUAGGCCGAA AGAAAUCA | 9934 |
| 3254 | GAUUUCUUA CAGUUUUC | 516 | GAAAACUG CUGAUGAGGCCGUUAGGCCGAA AAGAAAUC | 9935 |
| 3259 | CUUACAGUU UUCAAGUG | 517 | CACUUGAA CUGAUGAGGCCGUUAGGCCGAA ACUGUAAG | 9936 |
| 3260 | UUACAGUUU UCAAGUGG | 518 | CCACUUGA CUGAUGAGGCCGUUAGGCCGAA AACUGUAA | 9937 |
| 3261 | UACAGUUUU CAAGUGGC | 519 | GCCACUUG CUGAUGAGGCCGUUAGGCCGAA AAACUGUA | 9938 |
| 3262 | ACAGUUUUC AAGUGGCC | 520 | GGCCACUU CUGAUGAGGCCGUUAGGCCGAA AAAACUGU | 9939 |
| 3284 | CAUGGAGUU CCUGUCUU | 521 | AAGACAGG CUGAUGAGGCCGUUAGGCCGAA ACUCCAUG | 9940 |
| 3285 | AUGGAGUUC CUGUCUUC | 522 | GAAGACAG CUGAUGAGGCCGUUAGGCCGAA AACUCCAU | 9941 |
| 3290 | GUUCCUGUC UUCCAGAA | 523 | UUCUGGAA CUGAUGAGGCCGUUAGGCCGAA ACAGGAAC | 9942 |
| 3292 | UCCUGUCUU CCAGAAAG | 524 | CUUUCUGG CUGAUGAGGCCGUUAGGCCGAA AGACAGGA | 9943 |
| 3293 | CCUGUCUUC CAGAAAGU | 525 | ACUUUCUG CUGAUGAGGCCGUUAGGCCGAA AAGACAGG | 9944 |
| 3306 | AAGUGCAUU CAUCGGGA | 526 | UCCCGAUG CUGAUGAGGCCGUUAGGCCGAA AUGCACUU | 9945 |
| 3307 | AGUGCAUUC AUCGGGAC | 527 | GUCCCGAU CUGAUGAGGCCGUUAGGCCGAA AAUGCACU | 9946 |
| 3310 | GCAUUCAUC GGGACCUG | 528 | CAGGUCCC CUGAUGAGGCCGUUAGGCCGAA AUGAAUGC | 9947 |
| 3333 | AGAAACAUU CUUUUAUC | 529 | GAUAAAAG CUGAUGAGGCCGUUAGGCCGAA AUGUUUCU | 9948 |
| 3334 | GAAACAUUC UUUUAUCU | 530 | AGAUAAAA CUGAUGAGGCCGUUAGGCCGAA AAUGUUUC | 9949 |
| 3336 | AACAUUCUU UUAUCUGA | 531 | UCAGAUAA CUGAUGAGGCCGUUAGGCCGAA AGAAUGUU | 9950 |
| 3337 | ACAUUCUUU UAUCUGAG | 532 | CUCAGAUA CUGAUGAGGCCGUUAGGCCGAA AAGAAUGU | 9951 |
| 3338 | CAUUCUUUU AUCUGAGA | 533 | UCUCAGAU CUGAUGAGGCCGUUAGGCCGAA AAAGAAUG | 9952 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 3339 | AUUCUUUUA UCUGAGAA | 534 | UUCUCAGA CUGAUGAGGCCGUUAGGCCGAA AAAAGAAU | 9953 |
| 3341 | UCUUUUAUC UGAGAACA | 535 | UGUUCUCA CUGAUGAGGCCGUUAGGCCGAA AUAAAAGA | 9954 |
| 3363 | GUGAAGAUU UGUGAUUU | 536 | AAAUCACA CUGAUGAGGCCGUUAGGCCGAA AUCUUCAC | 9955 |
| 3364 | UGAAGAUUU GUGAUUUU | 537 | AAAAUCAC CUGAUGAGGCCGUUAGGCCGAA AAUCUUCA | 9956 |
| 3370 | UUUGUGAUU UUGGCCUU | 538 | AAGGCCAA CUGAUGAGGCCGUGAGGCCGAA AUCACAAA | 9957 |
| 3371 | UUGUGAUUU UGGCCUUG | 539 | CAAGGCCA CUGAUGAGGCCGUUAGGCCGAA AAUCACAA | 9958 |
| 3372 | UGUGAUUUU GGCCUUGC | 540 | GCAAGGCC CUGAUGAGGCCGUUAGGCCGAA AAAUCACA | 9959 |
| 3378 | UUUGGCCUU GCCCGGGA | 541 | UCCCGGGC CUGAUGAGGCCGUUAGGCCGAA AGGCCAAA | 9960 |
| 3388 | CCCGGGAUA UUUAUAAG | 542 | CUUAUAAA CUGAUGAGGCCGUUAGGCCGAA AUCCCGGG | 9961 |
| 3390 | CGGGAUAUU UAUAAGAA | 543 | UUCUUAUA CUGAUGAGGCCGUUAGGCCGAA AUAUCCCG | 9962 |
| 3391 | GGGAUAUUU AUAAGAAC | 544 | GUUCUUAU CUGAUGAGGCCGUUAGGCCGAA AAUAUCCC | 9963 |
| 3392 | GGAUAUUUA UAAGAACC | 545 | GGUUCUUA CUGAUGAGGCCGUUAGGCCGAA AAAUAUCC | 9964 |
| 3394 | AUAUUUAUA AGAACCCC | 546 | GGGGUUCU CUGAUGAGGCCGUUAGGCCGAA AUAAAUAU | 9965 |
| 3406 | ACCCCGAUU AUGUGAGA | 547 | UCUCACAU CUGAUGAGGCCGUUAGGCCGAA AUCGGGGU | 9966 |
| 3407 | CCCCGAUUA UGUGAGAA | 548 | UUCUCACA CUGAUGAGGCCGUUAGGCCGAA AAUCGGGG | 9967 |
| 3424 | AAGGAGAUA CUCGACUU | 549 | AAGUCGAG CUGAUGAGGCCGUUAGGCCGAA AUCUCCUU | 9968 |
| 3427 | GAGAUACUC GACUUCCU | 550 | AGGAAGUC CUGAUGAGGCCGUUAGGCCGAA AGUAUCUC | 9969 |
| 3432 | ACUCGACUU CCUCUGAA | 551 | UUCAGAGG CUGAUGAGGCCGUUAGGCCGAA AGUCGAGU | 9970 |
| 3433 | CUCGACUUC CUCUGAAA | 552 | UUUCAGAG CUGAUGAGGCCGUUAGGCCGAA AAGUCGAG | 9971 |
| 3436 | GACUUCCUC UGAAAUGG | 553 | CCAUUUCA CUGAUGAGGCCGUUAGGCCGAA AGGAAGUC | 9972 |
| 3451 | GGAUGGCUC CCGAAUCU | 554 | AGAUUCGG CUGAUGAGGCCGUUAGGCCGAA AGCCAUCC | 9973 |
| 3458 | UCCCGAAUC UAUCUUUG | 555 | CAAAGAUA CUGAUGAGGCCGUUAGGCCGAA AUUCGGGA | 9974 |
| 3460 | CCGAAUCUA UCUUUGAC | 556 | GUCAAAGA CUGAUGAGGCCGUUAGGCCGAA AGAUUCGG | 9975 |
| 3462 | GAAUCUAUC UUUGACAA | 557 | UUGUCAAA CUGAUGAGGCCGUUAGGCCGAA AUAGAUUC | 9976 |
| 3464 | AUCUAUCUU UGACAAAA | 558 | UUUUGUCA CUGAUGAGGCCGUUAGGCCGAA AGAUAGAU | 9977 |
| 3465 | UCUAUCUUU GACAAAAU | 559 | AUUUUGUC CUGAUGAGGCCGUUAGGCCGAA AAGAUAGA | 9978 |
| 3474 | GACAAAAUC UACAGCAC | 560 | GUGCUGUA CUGAUGAGGCCGUUAGGCCGAA AUUUUGUC | 9979 |
| 3476 | CAAAAUCUA CAGCACCA | 561 | UGGUGCUG CUGAUGAGGCCGUUAGGCCGAA AGAUUUUG | 9980 |
| 3500 | CGUGGGUC UUACGGAG | 562 | CUCCGUAA CUGAUGAGGCCGUUAGGCCGAA ACCACACG | 9981 |
| 3502 | UGUGGUCUU ACGGAGUA | 563 | UACUCCGU CUGAUGAGGCCGUUAGGCCGAA AGACCACA | 9982 |
| 3503 | GUGGUCUUA CGGAGUAU | 564 | AUACUCCG CUGAUGAGGCCGUUAGGCCGAA AAGACCAC | 9983 |
| 3510 | UACGGAGUA UUGCUGUG | 565 | CACAGCAA CUGAUGAGGCCGUUAGGCCGAA ACUCCGUA | 9984 |
| 3512 | CGGAGUAUU GCUGUGGG | 566 | CCCACAGC CUGAUGAGGCCGUUAGGCCGAA AUACUCCG | 9985 |
| 3525 | UGGGAAAUC UUCUCCUU | 567 | AAGGAGAA CUGAUGAGGCCGUUAGGCCGAA AUUUCCCA | 9986 |
| 3527 | GGAAAUCUU CUCCUUAG | 568 | CUAAGGAG CUGAUGAGGCCGUUAGGCCGAA AGAUUUCC | 9987 |
| 3528 | GAAAUCUUC UCCUUAGG | 569 | CCUAAGGA CUGAUGAGGCCGUUAGGCCGAA AAGAUUUC | 9988 |
| 3530 | AAUCUUCUC CUUAGGUG | 570 | CACCUAAG CUGAUGAGGCCGUUAGGCCGAA AGAAGAUU | 9989 |

TABLE II-continued

Human flt1 VEGF Receptor—Hammerhead Ribozyme and Substrate Sequence

| Pos | Substrate | Seq ID No | HH Ribozyme | Seq ID No |
|---|---|---|---|---|
| 3533 | CUUCUCCUU AGGUGGGU | 571 | ACCCACCU CUGAUGAGGCCGUUAGGCCGAA AGGAGAAG | 9990 |
| 3534 | UUCUCCUUA GGUGGGUC | 572 | GACCCACC CUGAUGAGGCCGUUAGGCCGAA AAGGAGAA | 9991 |
| 3542 | AGGUGGGUC UCCAUACC | 573 | GGUAUGGA CUGAUGAGGCCGUUAGGCCGAA ACCCACCU | 9992 |
| 3544 | GUGGGUCUC CAUACCCA | 574 | UGGGUAUG CUGAUGAGGCCGUUAGGCCGAA AGACCCAC | 9993 |
| 3548 | GUCUCCAUA CCCAGGAG | 575 | CUCCUGGG CUGAUGAGGCCGUUAGGCCGAA AUGGAGAC | 9994 |
| 3558 | CCAGGAGUA CAAAUGGA | 576 | UCCAUUUG CUGAUGAGGCCGUUAGGCCGAA ACUCCUGG | 9995 |
| 3575 | UGAGGACUU UUGCAGUC | 577 | GACUGCAA CUGAUGAGGCCGUUAGGCCGAA AGUCCUCA | 9996 |
| 3576 | GAGGACUUU UGCAGUCG | 578 | CGACUGCA CUGAUGAGGCCGUUAGGCCGAA AAGUCCUC | 9997 |
| 3577 | AGGACUUUU GCAGUCGC | 579 | GCGACUGC CUGAUGAGGCCGUUAGGCCGAA AAAGUCCU | 9998 |
| 3583 | UUUGCAGUC GCCUGAGG | 580 | CCUCAGGC CUGAUGAGGCCGUUAGGCCGAA ACUGCAAA | 9999 |
| 3613 | UGAGAGCUC CUGAGUAC | 581 | GUACUCAG CUGAUGAGGCCGUUAGGCCGAA AGCUCUCA | 10000 |
| 3620 | UCCUGAGUA CUCUACUC | 582 | GAGUAGAG CUGAUGAGGCCGUUAGGCCGAA ACUCAGGA | 10001 |
| 3623 | UGAGUACUC UACUCCUG | 583 | CAGGAGUA CUGAUGAGGCCGUUAGGCCGAA AGUACUCA | 10002 |
| 3625 | AGUACUCUA CUCCUGAA | 584 | UUCAGGAG CUGAUGAGGCCGUUAGGCCGAA AGAGUACU | 10003 |
| 3628 | ACUCUACUC CUGAAAUC | 585 | GAUUUCAG CUGAUGAGGCCGUUAGGCCGAA AGUAGAGU | 10004 |
| 3636 | CCUGAAAUC UAUCAGAU | 586 | AUCUGAUA CUGAUGAGGCCGUUAGGCCGAA AUUUCAGG | 10005 |
| 3638 | UGAAAUCUA UCAGAUCA | 587 | UGAUCUGA CUGAUGAGGCCGUUAGGCCGAA AGAUUUCA | 10006 |
| 3640 | AAAUCUAUC AGAUCAUG | 588 | CAUGAUCU CUGAUGAGGCCGUUAGGCCGAA AUAGAUUU | 10007 |
| 3645 | UAUCAGAUC AUGCUGGA | 589 | UCCAGCAU CUGAUGAGGCCGUUAGGCCGAA AUCUGAUA | 10008 |
| 3689 | GCCAAGAUU UGCAGAAC | 590 | GUUCUGCA CUGAUGAGGCCGUUAGGCCGAA AUCUUGGC | 10009 |
| 3690 | CCAAGAUUU GCAGAACU | 591 | AGUUCUGC CUGAUGAGGCCGUUAGGCCGAA AAUCUUGG | 10010 |
| 3699 | GCAGAACUU GUGGAAAA | 592 | UUUUCCAC CUGAUGAGGCCGUUAGGCCGAA AGUUCUGC | 10011 |
| 3711 | GAAAAACUA GGUGAUUU | 593 | AAAUCACC CUGAUGAGGCCGUUAGGCCGAA AGUUUUUC | 10012 |
| 3718 | UAGGUGAUU UGCUUCAA | 594 | UUGAAGCA CUGAUGAGGCCGUUAGGCCGAA AUCACCUA | 10013 |
| 3719 | AGGUGAUUU GCUUCAAG | 595 | CUUGAAGC CUGAUGAGGCCGUUAGGCCGAA AAUCACCU | 10014 |
| 3723 | GAUUUGCUU CAAGCAAA | 596 | UUUGCUUG CUGAUGAGGCCGUUAGGCCGAA AGCAAAUC | 10015 |
| 3724 | AUUUGCUUC AAGCAAAU | 597 | AUUUGCUU CUGAUGAGGCCGUUAGGCCGAA AAGCAAAU | 10016 |
| 3735 | GCAAAUGUA CAACAGGA | 598 | UCCUGUUG CUGAUGAGGCCGUUAGGCCGAA ACAUUUGC | 10017 |
| 3748 | AGGAUGGUA AAGACUAC | 599 | GUAGUCUU CUGAUGAGGCCGUUAGGCCGAA ACCAUCCU | 10018 |
| 3755 | UAAAGACUA CAUCCCAA | 600 | UUGGGAUG CUGAUGAGGCCGUUAGGCCGAA AGUCUUUA | 10019 |
| 3759 | GACUACAUC CCAAUCAA | 601 | UUGAUUGG CUGAUGAGGCCGUUAGGCCGAA AUGUAGUC | 10020 |
| 3765 | AUCCCAAUC AAUGCCAU | 602 | AUGGCAUU CUGAUGAGGCCGUUAGGCCGAA AUUGGGAU | 10021 |
| 3774 | AAUGCCAUA CUGACAGG | 603 | CCUGUCAG CUGAUGAGGCCGUUAGGCCGAA AUGGCAUU | 10022 |
| 3787 | CAGGAAAUA GUGGGUUU | 604 | AAACCCAC CUGAUGAGGCCGUUAGGCCGAA AUUUCCUG | 10023 |
| 3794 | UAGUGGGUU UACAUACU | 605 | AGUAUGUA CUGAUGAGGCCGUUAGGCCGAA ACCCACUA | 10024 |
| 3795 | AGUGGGUUU ACAUACUC | 606 | GAGUAUGU CUGAUGAGGCCGUUAGGCCGAA AACCCACU | 10025 |
| 3796 | GUGGGUUUA CAUACUCA | 607 | UGAGUAUG CUGAUGAGGCCGUUAGGCCGAA AAACCCAC | 10026 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 3800 | GUUUACAUA CUCAACUC | 608 | GAGUUGAG CUGAUGAGGCCGUUAGGCCGAA AUGUAAAC | 10027 |
| 3803 | UACAUACUC AACUCCUG | 609 | CAGGAGUU CUGAUGAGGCCGUUAGGCCGAA AGUAUGUA | 10028 |
| 3808 | ACUCAACUC CUGCCUUC | 610 | GAAGGCAG CUGAUGAGGCCGUUAGGCCGAA AGUUCAGU | 10029 |
| 3815 | UCCUGCCUU CUCUGAGG | 611 | CCUCAGAG CUGAUGAGGCCGUUAGGCCGAA AGGCAGGA | 10030 |
| 3816 | CCUGCCUUC UCUGAGGA | 612 | UCCUCAGA CUGAUGAGGCCGUUAGGCCGAA AAGGCAGG | 10031 |
| 3818 | UGCCUUCUC UGAGGACU | 613 | AGUCCUCA CUGAUGAGGCCGUUAGGCCGAA AGAAGGCA | 10032 |
| 3827 | UGAGGACUU CUUCAAGG | 614 | CCUUGAAG CUGAUGAGGCCGUUAGGCCGAA AGUCCUCA | 10033 |
| 3828 | GAGGACUUC UUCAAGGA | 615 | UCCUUGAA CUGAUGAGGCCGUUAGGCCGAA AAGUCCUC | 10034 |
| 3830 | GGACUUCUU CAAGGAAA | 616 | UUUCCUUG CUGAUGAGGCCGUUAGGCCGAA AGAAGUCC | 10035 |
| 3831 | GACUUCUUC AAGGAAAG | 617 | CUUUCCUU CUGAUGAGGCCGUUAGGCCGAA AAGAAGUC | 10036 |
| 3841 | AGGAAAGUA UUUCAGCU | 618 | AGCUGAAA CUGAUGAGGCCGUUAGGCCGAA ACUUUCCU | 10037 |
| 3843 | GAAAGUAUU UCAGCUCC | 619 | GGAGCUGA CUGAUGAGGCCGUUAGGCCGAA AUACUUUC | 10038 |
| 3844 | AAAGUAUUU CAGCUCCG | 620 | CGGAGCUG CUGAUGAGGCCGUUAGGCCGAA AAUACUUU | 10039 |
| 3845 | AAGUAUUUC AGCUCCGA | 621 | UCGGAGCU CUGAUGAGGCCGUUAGGCCGAA AAAUACUU | 10040 |
| 3850 | UUUCAGCUC CGAAGUUU | 622 | AAACUUCG CUGAUGAGGCCGUUAGGCCGAA AGCUGAAA | 10041 |
| 3857 | UCCGAAGUU UAAUUCAG | 623 | CUGAAUUA CUGAUGAGGCCGUUAGGCCGAA ACUUCGGA | 10042 |
| 3858 | CCGAAGUUU AAUUCAGG | 624 | CCUGAAUU CUGAUGAGGCCGUUAGGCCGAA AACUUCGG | 10043 |
| 3859 | CGAAGUUUA AUUCAGGA | 625 | UCCUGAAU CUGAUGAGGCCGUUAGGCCGAA AAACUUCG | 10044 |
| 3862 | AGUUUAAUU CAGGAAGC | 626 | GCUUCCUG CUGAUGAGGCCGUUAGGCCGAA AUUAAACU | 10045 |
| 3863 | GUUUAAUUC AGGAAGCU | 627 | AGCUUCCU CUGAUGAGGCCGUUAGGCCGAA AAUUAAAC | 10046 |
| 3872 | AGGAAGCUC UGAUGAUG | 628 | CAUCAUCA CUGAUGAGGCCGUUAGGCCGAA AGCUUCCU | 10047 |
| 3882 | GAUGAUGUC AGAUAUGU | 629 | ACAUAUCU CUGAUGAGGCCGUUAGGCCGAA ACAUCAUC | 10048 |
| 3887 | UGUCAGAUA UGUAAAUG | 630 | CAUUUACA CUGAUGAGGCCGUUAGGCCGAA AUCUGACA | 10049 |
| 3891 | AGAUAUGUA AAUGCUUU | 631 | AAAGCAUU CUGAUGAGGCCGUUAGGCCGAA ACAUAUCU | 10050 |
| 3898 | UAAAUGCUU UCAAGUUC | 632 | GAACUUGA CUGAUGAGGCCGUUAGGCCGAA AGCAUUUA | 10051 |
| 3899 | AAAUGCUUU CAAGUUCA | 633 | UGAACUUG CUGAUGAGGCCGUUAGGCCGAA AAGCAUUU | 10052 |
| 3900 | AAUGCUUUC AAGUUCAU | 634 | AUGAACUU CUGAUGAGGCCGUUAGGCCGAA AAAGCAUU | 10053 |
| 3905 | UUUCAAGUU CAUGAGCC | 635 | GGCUCAUG CUGAUGAGGCCGUUAGGCCGAA ACUUGAAA | 10054 |
| 3906 | UUCAAGUUC AUGAGCCU | 636 | AGGCUCAU CUGAUGAGGCCGUUAGGCCGAA AACUUGAA | 10055 |
| 3924 | GAAAGAAUC AAAACCUU | 637 | AAGGUUUU CUGAUGAGGCCGUUAGGCCGAA AUUCUUUC | 10056 |
| 3932 | CAAAACCUU GAAGAAC | 638 | GUUCUUCA CUGAUGAGGCCGUUAGGCCGAA AGGUUUUG | 10057 |
| 3933 | AAAACCUUU GAAGAACU | 639 | AGUUCUUC CUGAUGAGGCCGUUAGGCCGAA AAGGUUUU | 10058 |
| 3942 | GAAGAACUU UUACCGAA | 640 | UUCGGUAA CUGAUGAGGCCGUUAGGCCGAA AGUUCUUC | 10059 |
| 3943 | AAGAACUUU UACCGAAU | 641 | AUUCGGUA CUGAUGAGGCCGUUAGGCCGAA AAGUUCUU | 10060 |
| 3944 | AGAACUUUU ACCGAAUG | 642 | CAUUCGGU CUGAUGAGGCCGUUAGGCCGAA AAAGUUCU | 10061 |
| 3945 | GAACUUUUA CCGAAUGC | 643 | GCAUUCGG CUGAUGAGGCCGUUAGGCCGAA AAAAGUUC | 10062 |
| 3959 | UGCCACCUC CAUGUUUG | 644 | CAAACAUG CUGAUGAGGCCGUUAGGCCGAA AGGUGGCA | 10063 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 3965 | CUCCAUGUU UGAUGACU | 645 | AGUCAUCA CUGAUGAG<u>GCCGUUAGGC</u>CGAA ACAUGGAG | 10064 |
| 3966 | UCCAUGUUU GAUGACUA | 646 | UAGUCAUC CUGAUGAG<u>GCCGUUAGGC</u>CGAA AACAUGGA | 10065 |
| 3974 | UGAUGACUA CCAGGGCG | 647 | CGCCCUGG CUGAUGAG<u>GCCGUUAGGC</u>CGAA AGUCAUCA | 10066 |
| 3994 | GCAGCACUC UGUUGGCC | 648 | GGCCAACA CUGAUGAG<u>GCCGUUAGGC</u>CGAA AGUGCUGC | 10067 |
| 3998 | CACUCUGUU GGCCUCUC | 649 | GAGAGGCC CUGAUGAG<u>GCCGUUAGGC</u>CGAA ACAGAGUG | 10068 |
| 4004 | GUUGGCCUC UCCCAUGC | 650 | GCAUGGGA CUGAUGAG<u>GCCGUUAGGC</u>CGAA AGGCCAAC | 10069 |
| 4006 | UGGCCUCUC CCAUGCUG | 651 | CAGCAUGG CUGAUGAG<u>GCCGUUAGGC</u>CGAA AGAGGCCA | 10070 |
| 4022 | GAAGCGCUU CACCUGGA | 652 | UCCAGGUG CUGAUGAG<u>GCCGUUAGGC</u>CGAA AGCGCUUC | 10071 |
| 4023 | AAGCGCUUC ACCUGGAC | 653 | GUCCAGGU CUGAUGAG<u>GCCGUUAGGC</u>CGAA AAGCGCUU | 10072 |
| 4052 | CAAGGCCUC GCUCAAGA | 654 | UCUUGAGC CUGAUGAG<u>GCCGUUAGGC</u>CGAA AGGCCUUG | 10073 |
| 4056 | GCCUCGCUC AAGAUUGA | 655 | UCAAUCUU CUGAUGAG<u>GCCGUUAGGC</u>CGAA AGCGAGGC | 10074 |
| 4062 | CUCAAGAUU GACUUGAG | 656 | CUCAAGUC CUGAUGAG<u>GCCGUUAGGC</u>CGAA AUCUUGAG | 10075 |
| 4067 | GAUUGACUU GAGAGUAA | 657 | UUACUCUC CUGAUGAG<u>GCCGUUAGGC</u>CGAA AGUCAAUC | 10076 |
| 4074 | UUGAGAGUA ACCAGUAA | 658 | UUACUGGU CUGAUGAG<u>GCCGUUAGGC</u>CGAA ACUCUCAA | 10077 |
| 4081 | UAACCAGUA AAAGUAAG | 659 | CUUACUUU CUGAUGAG<u>GCCGUUAGGC</u>CGAA ACUGGUUA | 10078 |
| 4087 | GUAAAAGUA AGGAGUCG | 660 | CGACUCCU CUGAUGAG<u>GCCGUUAGGC</u>CGAA ACUUUUAC | 10079 |
| 4094 | UAAGGAGUC GGGGCUGU | 661 | ACAGCCCC CUGAUGAG<u>GCCGUUAGGC</u>CGAA ACUCCUUA | 10080 |
| 4103 | GGGGCUGUC UGAUGUCA | 662 | UGACAUCA CUGAUGAG<u>GCCGUUAGGC</u>CGAA ACAGCCCC | 10081 |
| 4110 | UCUGAUGUC AGCAGGCC | 663 | GGCCUGCU CUGAUGAG<u>GCCGUUAGGC</u>CGAA ACAUCAGA | 10082 |
| 4123 | GGCCCAGUU UCUGCCAU | 664 | AUGGCAGA CUGAUGAG<u>GCCGUUAGGC</u>CGAA ACUGGGCC | 10083 |
| 4124 | GCCCAGUUU CUGCCAUU | 665 | AAUGGCAG CUGAUGAG<u>GCCGUUAGGC</u>CGAA AACUGGGC | 10084 |
| 4125 | CCCAGUUUC UGCCAUUC | 666 | GAAUGGCA CUGAUGAG<u>GCCGUUAGGC</u>CGAA AAACUGGG | 10085 |
| 4132 | UCUGCCAUU CCAGCUGU | 667 | ACAGCUGG CUGAUGAG<u>GCCGUUAGGC</u>CGAA AUGGCAGA | 10086 |
| 4133 | CUGCCAUUC CAGCUGUG | 668 | CACAGCUG CUGAUGAG<u>GCCGUUAGGC</u>CGAA AAUGGCAG | 10087 |
| 4149 | GGGCACGUC AGCGAAGG | 669 | CCUUCGCU CUGAUGAG<u>GCCGUUAGGC</u>CGAA ACGUGCCC | 10088 |
| 4169 | GCGCAGGUU CACCUACG | 670 | CGUAGGUG CUGAUGAG<u>GCCGUUAGGC</u>CGAA ACCUGCGC | 10089 |
| 4170 | CGCAGGUUC ACCUACGA | 671 | UCGUAGGU CUGAUGAG<u>GCCGUUAGGC</u>CGAA AACCUGCG | 10090 |
| 4175 | GUUCACCUA CGACCACG | 672 | CGUGGUCG CUGAUGAG<u>GCCGUUAGGC</u>CGAA AGGUGAAC | 10091 |
| 4203 | AGGAAAAUC GCGUGCUG | 673 | CAGCACGC CUGAUGAG<u>GCCGUUAGGC</u>CGAA AUUUUCCU | 10092 |
| 4214 | GUGCUGCUC CCCGCCCC | 674 | GGGGCGGG CUGAUGAG<u>GCCGUUAGGC</u>CGAA AGCAGCAC | 10093 |
| 4229 | CCCAGACUA CAACUCGG | 675 | CCGAGUUG CUGAUGAG<u>GCCGUUAGGC</u>CGAA AGUCUGGG | 10094 |
| 4235 | CUACAACUC GGUGGUCC | 676 | GGACCACC CUGAUGAG<u>GCCGUUAGGC</u>CGAA AGUUGUAG | 10095 |
| 4242 | UCGGUGGUC CUGUACUC | 677 | GAGUACAG CUGAUGAG<u>GCCGUUAGGC</u>CGAA ACCACCGA | 10096 |
| 4247 | GGUCCUGUA CUCCACCC | 678 | GGGUGGAG CUGAUGAG<u>GCCGUUAGGC</u>CGAA ACAGGACC | 10097 |
| 4250 | CCUGUACUC CACCCCAC | 679 | GUGGGGUG CUGAUGAG<u>GCCGUUAGGC</u>CGAA AGUACAGG | 10098 |
| 4263 | CCACCCAUC UAGAGUUU | 680 | AAACUCUA CUGAUGAG<u>GCCGUUAGGC</u>CGAA AUGGGUGG | 10099 |
| 4265 | ACCCAUCUA GAGUUUGA | 681 | UCAAACUC CUGAUGAG<u>GCCGUUAGGC</u>CGAA AGAUGGGU | 10100 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 4270 | UCUAGAGUU UGACACGA | 682 | UCGUGUCA CUGAUGAGGCCGUUAGGCCGAA ACUCUAGA | 10101 |
| 4271 | CUAGAGUUU GACACGAA | 683 | UUCGUGUC CUGAUGAGGCCGUUAGGCCGAA AACUCUAG | 10102 |
| 4284 | CGAAGCCUU AUUUCUAG | 684 | CUAGAAAU CUGAUGAGGCCGUUAGGCCGAA AGGCUUCG | 10103 |
| 4285 | GAAGCCUUA UUUCUAGA | 685 | UCUAGAAA CUGAUGAGGCCGUUAGGCCGAA AAGGCUUC | 10104 |
| 4287 | AGCCUUAUU UCUAGAAG | 686 | CUUCUAGA CUGAUGAGGCCGUUAGGCCGAA AUAAGGCU | 10105 |
| 4288 | GCCUUAUUU CUAGAAGC | 687 | GCUUCUAG CUGAUGAGGCCGUUAGGCCGAA AAUAAGGC | 10106 |
| 4289 | CCUUAUUUC UAGAAGCA | 688 | UGCUUCUA CUGAUGAGGCCGUUAGGCCGAA AAAUAAGG | 10107 |
| 4291 | UUAUUUCUA GAAGCACA | 689 | UGUGCUUC CUGAUGAGGCCGUUAGGCCGAA AGAAAUAA | 10108 |
| 4305 | ACAUGUGUA UUUUAUACC | 690 | GGUAUAAA CUGAUGAGGCCGUUAGGCCGAA ACACAUGU | 10109 |
| 4307 | AUGUGUAUU UAUACCCC | 691 | GGGGUAUA CUGAUGAGGCCGUUAGGCCGAA AUACACAU | 10110 |
| 4308 | UGUGUAUUU AUACCCCC | 692 | GGGGGUAU CUGAUGAGGCCGUUAGGCCGAA AAUACACA | 10111 |
| 4309 | GUGUAUUUA UACCCCCA | 693 | UGGGGGUA CUGAUGAGGCCGUUAGGCCGAA AAAUACAC | 10112 |
| 4311 | GUAUUUAUA CCCCCAGG | 694 | CCUGGGGG CUGAUGAGGCCGUUAGGCCGAA AUAAAUAC | 10113 |
| 4325 | AGGAAACUA GCUUUUGC | 695 | GCAAAAGC CUGAUGAGGCCGUUAGGCCGAA AGUUUCCU | 10114 |
| 4329 | AACUAGCUU UUGCCAGU | 696 | ACUGGCAA CUGAUGAGGCCGUUAGGCCGAA AGCUAGUU | 10115 |
| 4330 | ACUAGCUUU UGCCAGUA | 697 | UACUGGCA CUGAUGAGGCCGUUAGGCCGAA AAGCUAGU | 10116 |
| 4331 | CUAGCUUUU GCCAGUAU | 698 | AUACUGGC CUGAUGAGGCCGUUAGGCCGAA AAAGCUAG | 10117 |
| 4338 | UUGCCAGUA UUAUGCAU | 699 | AUGCAUAA CUGAUGAGGCCGUUAGGCCGAA ACUGGCAA | 10118 |
| 4340 | GCCAGUAUU AUGCAUAU | 700 | AUAUGCAU CUGAUGAGGCCGUUAGGCCGAA AAUACGGC | 10119 |
| 4341 | CCAGUAUUA UGCAUAUA | 701 | UAUAUGCA CUGAUGAGGCCGUUAGGCCGAA AAUACUGG | 10120 |
| 4347 | UUAUGCAUA UAUAAGUU | 702 | AACUUAUA CUGAUGAGGCCGUUAGGCCGAA AUGCAUAA | 10121 |
| 4349 | AUGCAUAUA UAAGUUUA | 703 | UAAACUUA CUGAUGAGGCCGUUAGGCCGAA AUAUGCAU | 10122 |
| 4351 | GCAUAUAUA AGUUUACA | 704 | UGUAAACU CUGAUGAGGCCGUUAGGCCGAA AUAUAUGC | 10123 |
| 4355 | AUAUAAGUU UACACCUU | 705 | AAGGUGUA CUGAUGAGGCCGUUAGGCCGAA ACUUAUAU | 10124 |
| 4356 | UAUAAGUUU ACACCUUU | 706 | AAAGGUGU CUGAUGAGGCCGUUAGGCCGAA AACUUAUA | 10125 |
| 4357 | AUAAGUUUA CACCUUUA | 707 | UAAAGGUG CUGAUGAGGCCGUUAGGCCGAA AAACUUAU | 10126 |
| 4363 | UUACACCUU UAUCUUUC | 708 | GAAAGAUA CUGAUGAGGCCGUUAGGCCGAA AGGUGUAA | 10127 |
| 4364 | UACACCUUU AUCUUUCC | 709 | GGAAAGAU CUGAUGAGGCCGUUAGGCCGAA AAGGUGUA | 10128 |
| 4365 | ACACCUUUA UCUUUCCA | 710 | UGGAAAGA CUGAUGAGGCCGUUAGGCCGAA AAAGGUGU | 10129 |
| 4367 | ACCUUUAUC UUUCCAUG | 711 | CAUGGAAA CUGAUGAGGCCGUUAGGCCGAA AUAAAGGU | 10130 |
| 4369 | CUUUAUCUU UCCAUGGG | 712 | CCCAUGGA CUGAUGAGGCCGUUAGGCCGAA AGAUAAAG | 10131 |
| 4370 | UUUAUCUUU CCAUGGGA | 713 | UCCCAUGG CUGAUGAGGCCGUUAGGCCGAA AAGAUAAA | 10132 |
| 4371 | UUAUCUUUC CAUGGGAG | 714 | CUCCCAUG CUGAUGAGGCCGUUAGGCCGAA AAAGAUAA | 10133 |
| 4389 | CAGCUGCUU UUGUGAU | 715 | AUCACAAA CUGAUGAGGCCGUUAGGCCGAA AGCAGCUG | 10134 |
| 4390 | AGCUGCUUU UGUGAUU | 716 | AAUCACAA CUGAUGAGGCCGUUAGGCCGAA AAGCAGCU | 10135 |
| 4391 | GCUGCUUUU GUGAUUU | 717 | AAAUCACA CUGAUGAGGCCGUUAGGCCGAA AAAGCAGC | 10136 |
| 4392 | CUGCUUUUU GUGAUUUU | 718 | AAAAUCAC CUGAUGAGGCCGUUAGGCCGAA AAAAGCAG | 10137 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 4398 | UUUGUGAUU UUUUUAAU | 719 | AUUAAAAA CUGAUGAGGCCGUUAGGCCGAA AUCACAAA | 10138 |
| 4399 | UUGUGAUUU UUUUAAUA | 720 | UAUUAAAA CUGAUGAGGCCGUUAGGCCGAA AAUCACAA | 10139 |
| 4400 | UGUGAUUUU UUUAAUAG | 721 | CUAUUAAA CUGAUGAGGCCGUUAGGCCGAA AAAUCACA | 10140 |
| 4401 | GUGAUUUUU UUAAUAGU | 722 | ACUAUUAA CUGAUGAGGCCGUUAGGCCGAA AAAAUCAC | 10141 |
| 4402 | UGAUUUUUU UAAUAGUG | 723 | CACUAUUA CUGAUGAGGCCGUUAGGCCGAA AAAAAUCA | 10142 |
| 4403 | GAUUUUUUU AAUAGUGC | 724 | GCACUAUU CUGAUGAGGCCGUUAGGCCGAA AAAAAAUC | 10143 |
| 4404 | AUUUUUUUA AUAGUGCU | 725 | AGCACUAU CUGAUGAGGCCGUUAGGCCGAA AAAAAAAU | 10144 |
| 4407 | UUUUUAAUA GUGCUUUU | 726 | AAAAGCAC CUGAUGAGGCCGUUAGGCCGAA AUUAAAAA | 10145 |
| 4413 | AUAGUGCUU UUUUUUUU | 727 | AAAAAAAA CUGAUGAGGCCGUUAGGCCGAA AGCACUAU | 10146 |
| 4414 | UAGUGCUUU UUUUUUUU | 728 | AAAAAAAA CUGAUGAGGCCGUUAGGCCGAA AAGCACUA | 10147 |
| 4415 | AGUGCUUUU UUUUUUUG | 729 | CAAAAAAA CUGAUGAGGCCGUUAGGCCGAA AAAGCACU | 10148 |
| 4416 | GUGCUUUUU UUUUUUGA | 730 | UCAAAAAA CUGAUGAGGCCGUUAGGCCGAA AAAAGCAC | 10149 |
| 4417 | UGCUUUUUU UUUUUGAC | 731 | GUCAAAAA CUGAUGAGGCCGUUAGGCCGAA AAAAAGCA | 10150 |
| 4418 | GCUUUUUUU UUUUGACU | 732 | AGUCAAAA CUGAUGAGGCCGUUAGGCCGAA AAAAAAGC | 10151 |
| 4419 | CUUUUUUUU UUUGACUA | 733 | UAGUCAAA CUGAUGAGGCCGUUAGGCCGAA AAAAAAAG | 10152 |
| 4420 | UUUUUUUUU UUGACUAA | 734 | UUAGUCAA CUGAUGAGGCCGUUAGGCCGAA AAAAAAAA | 10153 |
| 4421 | UUUUUUUUU UGACUAAC | 735 | GUUAGUCA CUGAUGAGGCCGUUAGGCCGAA AAAAAAAA | 10154 |
| 4422 | UUUUUUUUU GACUAACA | 736 | UGUUAGUC CUGAUGAGGCCGUUAGGCCGAA AAAAAAAA | 10155 |
| 4427 | UUUUGACUA ACAAGAAU | 737 | AUUCUUGU CUGAUGAGGCCGUUAGGCCGAA AGUCAAAA | 10156 |
| 4438 | AAGAAUGUA ACUCCAGA | 738 | UCUGGAGU CUGAUGAGGCCGUUAGGCCGAA ACAUUCUU | 10157 |
| 4442 | AUGUAACUC CAGAUAGA | 739 | UCUAUCUG CUGAUGAGGCCGUUAGGCCGAA AGUUACAU | 10158 |
| 4448 | CUCCAGAUA GAGAAAUA | 740 | UAUUUCUC CUGAUGAGGCCGUUAGGCCGAA AUCUGGAG | 10159 |
| 4456 | AGAGAAAUA GUGACAAG | 741 | CUUGUCAC CUGAUGAGGCCGUUAGGCCGAA AUUUCUCU | 10160 |
| 4476 | AGAACACUA CUGCUAAA | 742 | UUUAGCAG CUGAUGAGGCCGUUAGGCCGAA AGUGUUCU | 10161 |
| 4482 | CUACUGCUA AAUCCUCA | 743 | UGAGGAUU CUGAUGAGGCCGUUAGGCCGAA AGCAGUAG | 10162 |
| 4486 | UGCUAAAUC CUCAUGUU | 744 | AACAUGAG CUGAUGAGGCCGUUAGGCCGAA AUUUAGCA | 10163 |
| 4489 | UAAAUCCUC AUGUUACU | 745 | AGUAACAU CUGAUGAGGCCGUUAGGCCGAA AGGAUUUA | 10164 |
| 4494 | CCUCAUGUU ACUCAGUG | 746 | CACUGAGU CUGAUGAGGCCGUUAGGCCGAA ACAUGAGG | 10165 |
| 4495 | CUCAUGUUA CUCAGUGU | 747 | ACACUGAG CUGAUGAGGCCGUUAGGCCGAA AACAUGAG | 10166 |
| 4498 | AUGUUACUC AGUGUUAG | 748 | CUAACACU CUGAUGAGGCCGUUAGGCCGAA AGUAACAU | 10167 |
| 4504 | CUCAGUGUU AGAGAAAU | 749 | AUUUCUCU CUGAUGAGGCCGUUAGGCCGAA ACACUGAG | 10168 |
| 4505 | UCAGUGUUA GAGAAAUC | 750 | GAUUUCUC CUGAUGAGGCCGUUAGGCCGAA AACACUGA | 10169 |
| 4513 | AGAGAAAUC CUUCCUAA | 751 | UUAGGAAG CUGAUGAGGCCGUUAGGCCGAA AUUUCUCU | 10170 |
| 4516 | GAAAUCCUU CCUAAACC | 752 | GGUUUAGG CUGAUGAGGCCGUUAGGCCGAA AGGAUUUC | 10171 |
| 4517 | AAAUCCUUC CUAAACCC | 753 | GGGUUUAG CUGAUGAGGCCGUUAGGCCGAA AAGGAUUU | 10172 |
| 4520 | UCCUUCCUA AACCCAAU | 754 | AUUGGGUU CUGAUGAGGCCGUUAGGCCGAA AGGAAGGA | 10173 |
| 4533 | CAAUGACUU CCCUGCUC | 755 | GAGCAGGG CUGAUGAGGCCGUUAGGCCGAA AGUCAUUG | 10174 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 4534 | AAUGACUUC CCUGCUCC | 756 | GGAGCAGG CUGAUGAGGCCGUUAGGCCGAA AAGUCAUU | 10175 |
| 4541 | UCCCUGCUC CAACCCCC | 757 | GGGGGUUG CUGAUGAGGCCGUUAGGCCGAA AGCAGGGA | 10176 |
| 4557 | CGCCACCUC AGGGCACG | 758 | CGUGCCCU CUGAUGAGGCCGUUAGGCCGAA AGGUGGCG | 10177 |
| 4576 | GGACCAGUU UGAUUGAG | 759 | CUCAAUCA CUGAUGAGGCCGUUAGGCCGAA ACUGGUCC | 10178 |
| 4577 | GACCAGUUU GAUUGAGG | 760 | CCUCAAUC CUGAUGAGGCCGUUAGGCCGAA AACUGGUC | 10179 |
| 4581 | AGUUUGAUU GAGGAGCU | 761 | AGCUCCUC CUGAUGAGGCCGUUAGGCCGAA AUCAAACU | 10180 |
| 4598 | GCACUGAUC ACCCAAUG | 762 | CAUUGGGU CUGAUGAGGCCGUUAGGCCGAA AUCAGUGC | 10181 |
| 4610 | CAAUGCAUC ACGUACCC | 763 | GGGUACGU CUGAUGAGGCCGUUAGGCCGAA AUGCAUUG | 10182 |
| 4615 | CAUCACGUA CCCCACUG | 764 | CAGUGGGG CUGAUGAGGCCGUUAGGCCGAA ACGUGAUG | 10183 |
| 4664 | AAGCCCGUU AGCCCCAG | 765 | CUGGGGCU CUGAUGAGGCCGUUAGGCCGAA ACGGGCUU | 10184 |
| 4665 | AGCCCGUUA GCCCCAGG | 766 | CCUGGGGC CUGAUGAGGCCGUUAGGCCGAA AACGGGCU | 10185 |
| 4678 | CAGGGGAUC ACUGGCUG | 767 | CAGCCAGU CUGAUGAGGCCGUUAGGCCGAA AUCCCCUG | 10186 |
| 4700 | AGCAACAUC UCGGGAGU | 768 | ACUCCCGA CUGAUGAGGCCGUUAGGCCGAA AUGUUGCU | 10187 |
| 4702 | CAACAUCUC GGGAGUCC | 769 | GGACUCCC CUGAUGAGGCCGUUAGGCCGAA AGAUGUUG | 10188 |
| 4709 | UCGGGAGUC UCUAGCA | 770 | UGCUAGAG CUGAUGAGGCCGUUAGGCCGAA ACUCCCGA | 10189 |
| 4712 | GGAGUCCUC UAGCAGGC | 771 | GCCUGCUA CUGAUGAGGCCGUUAGGCCGAA AGGACUCC | 10190 |
| 4714 | AGUCCUCUA GCAGGCCU | 772 | AGGCCUGC CUGAUGAGGCCGUUAGGCCGAA AGAGGACU | 10191 |
| 4723 | GCAGGCCUA AGACAUGU | 773 | ACAUGUCU CUGAUGAGGCCGUUAGGCCGAA AGGCCUGC | 10192 |
| 4802 | GAAAGAAUU UGAGACGC | 774 | GCGUCUCA CUGAUGAGGCCGUUAGGCCGAA AUUCUUUC | 10193 |
| 4803 | AAAGAAUUU GAGACGCA | 775 | UGCGUCUC CUGAUGAGGCCGUUAGGCCGAA AAUUCUUU | 10194 |
| 4840 | ACGGGCUC AGCAAUGC | 776 | GCAUUGCU CUGAUGAGGCCGUUAGGCCGAA AGCCCCGU | 10195 |
| 4852 | AAUGCCAUU UCAGUGGC | 777 | GCCACUGA CUGAUGAGGCCGUUAGGCCGAA AUGGCAUU | 10196 |
| 4853 | AUGCCAUUU CAGUGGCU | 778 | AGCCACUG CUGAUGAGGCCGUUAGGCCGAA AAUGGCAU | 10197 |
| 4854 | UGCCAUUUC AGUGGCUU | 779 | AAGCCACU CUGAUGAGGCCGUUAGGCCGAA AAAUGGCA | 10198 |
| 4862 | CAGUGGCUU CCCAGCUC | 780 | GAGCUGGG CUGAUGAGGCCGUUAGGCCGAA AGCCACUG | 10199 |
| 4863 | AGUGGCUUC CCAGCUCU | 781 | AGAGCUGG CUGAUGAGGCCGUUAGGCCGAA AAGCCACU | 10200 |
| 4870 | UCCCAGCUC UGACCCUU | 782 | AAGGGUCA CUGAUGAGGCCGUUAGGCCGAA AGCUGGGA | 10201 |
| 4878 | CUGACCCUU CUACAUUU | 783 | AAAUGUAG CUGAUGAGGCCGUUAGGCCGAA AGGGUCAG | 10202 |
| 4879 | UGACCCUUC UACAUUUG | 784 | CAAAUGUA CUGAUGAGGCCGUUAGGCCGAA AAGGGUCA | 10203 |
| 4881 | ACCCUUCUA CAUUUGAG | 785 | CUCAAAUG CUGAUGAGGCCGUUAGGCCGAA AGAAGGGU | 10204 |
| 4885 | UUCUACAUU UGAGGGCC | 786 | GGCCCUCA CUGAUGAGGCCGUUAGGCCGAA AUGUAGAA | 10205 |
| 4886 | UCUACAUUU GAGGGCCC | 787 | GGGCCCUC CUGAUGAGGCCGUUAGGCCGAA AAUGUAGA | 10206 |
| 4929 | GGGGACAUU UUCUGGAU | 788 | AUCCAGAA CUGAUGAGGCCGUUAGGCCGAA AUGUCCCC | 10207 |
| 4930 | GGGACAUUU UCUGGAUU | 789 | AAUCCAGA CUGAUGAGGCCGUUAGGCCGAA AAUGUCCC | 10208 |
| 4931 | GGACAUUUU CUGGAUUC | 790 | GAAUCCAG CUGAUGAGGCCGUUAGGCCGAA AAAUGUCC | 10209 |
| 4932 | GACAUUUUC UGGAUUCU | 791 | AGAAUCCA CUGAUGAGGCCGUUAGGCCGAA AAAAUGUC | 10210 |
| 4938 | UUCUGGAUU CUGGGAGG | 792 | CCUCCCAG CUGAUGAGGCCGUUAGGCCGAA AUCCAGAA | 10211 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 4939 | UCUGGAUUC UGGGAGGC | 793 | GCCUCCCA CUGAUGAGGCCGUUAGGCCGAA AAUCCAGA | 10212 |
| 4963 | GGACAAAUA UCUUUUUU | 794 | AAAAAAGA CUGAUGAGGCCGUUAGGCCGAA AUUUGUCC | 10213 |
| 4965 | ACAAAUAUC UUUUUUGG | 795 | CCAAAAAA CUGAUGAGGCCGUUAGGCCGAA AUAUUUGU | 10214 |
| 4967 | AAAUAUCUU UUUUGGAA | 796 | UUCCAAAA CUGAUGAGGCCGUUAGGCCGAA AGAUAUUU | 10215 |
| 4968 | AAUAUCUUU UUUGGAAC | 797 | GUUCCAAA CUGAUGAGGCCGUUAGGCCGAA AAGAUAUU | 10216 |
| 4969 | AUAUCUUUU UUGGAACU | 798 | AGUUCCAA CUGAUGAGGCCGUUAGGCCGAA AAAGAUAU | 10217 |
| 4970 | UAUCUUUUU UGGAACUA | 799 | UAGUUCCA CUGAUGAGGCCGUUAGGCCGAA AAAAGAUA | 10218 |
| 4971 | AUCUUUUUU GGAACUAA | 800 | UUAGUUCC CUGAUGAGGCCGUUAGGCCGAA AAAAAGAU | 10219 |
| 4978 | UUGGAACUA AAGCAAAU | 801 | AUUUGCUU CUGAUGAGGCCGUUAGGCCGAA AGUUCCAA | 10220 |
| 4987 | AAGCAAAUU UUAGACCU | 802 | AGGUCUAA CUGAUGAGGCCGUUAGGCCGAA AUUUGCUU | 10221 |
| 4988 | AGCAAAUUU UAGACCUU | 803 | AAGGUCUA CUGAUGAGGCCGUUAGGCCGAA AAUUUGCU | 10222 |
| 4989 | GCAAAUUUU AGACCUUU | 804 | AAAGGUCU CUGAUGAGGCCGUUAGGCCGAA AAAUUUGC | 10223 |
| 4990 | CAAAUUUUA GACCUUUA | 805 | UAAAGGUC CUGAUGAGGCCGUUAGGCCGAA AAAAUUUG | 10224 |
| 4996 | UUAGACCUU UACCUAUG | 806 | CAUAGGUA CUGAUGAGGCCGUUAGGCCGAA AGGUCUAA | 10225 |
| 4997 | UAGACCUUU ACCUAUGG | 807 | CCAUAGGU CUGAUGAGGCCGUUAGGCCGAA AAGGUCUA | 10226 |
| 4998 | AGACCUUUA CCUAUGGA | 808 | UCCAUAGG CUGAUGAGGCCGUUAGGCCGAA AAAGGUCU | 10227 |
| 5002 | CUUUACCUA UGGAAGUG | 809 | CACUUCCA CUGAUGAGGCCGUUAGGCCGAA AGGUAAAG | 10228 |
| 5013 | GAAGUGGUU CUAUGUCC | 810 | GGACAUAG CUGAUGAGGCCGUUAGGCCGAA ACCACUUC | 10229 |
| 5014 | AAGUGGUUC UAUGUCCA | 811 | UGGACAUA CUGAUGAGGCCGUUAGGCCGAA AACCACUU | 10230 |
| 5016 | GUGGUUCUA UGUCCAUU | 812 | AAUGGACA CUGAUGAGGCCGUUAGGCCGAA AGAACCAC | 10231 |
| 5020 | UUCUAUGUC CAUUCUCA | 813 | UGAGAAUG CUGAUGAGGCCGUUAGGCCGAA ACAUAGAA | 10232 |
| 5024 | AUGUCCAUU CUCAUUCG | 814 | CGAAUGAG CUGAUGAGGCCGUUAGGCCGAA AUGGACAU | 10233 |
| 5025 | UGUCCAUUC UCAUUCGU | 815 | ACGAAUGA CUGAUGAGGCCGUUAGGCCGAA AAUGGACA | 10234 |
| 5027 | UCCAUUCUC AUUCGUGG | 816 | CCACGAAU CUGAUGAGGCCGUUAGGCCGAA AGAAUGGA | 10235 |
| 5030 | AUUCUCAUU CGUGGCAU | 817 | AUGCCACG CUGAUGAGGCCGUUAGGCCGAA AUGAGAAU | 10236 |
| 5031 | UUCUCAUUC GUGGCAUG | 818 | CAUGCCAC CUGAUGAGGCCGUUAGGCCGAA AAUGAGAA | 10237 |
| 5041 | UGGCAUGUU UUGAUUUG | 819 | CAAAUCAA CUGAUGAGGCCGUUAGGCCGAA ACAUGCCA | 10238 |
| 5042 | GGCAUGUUU UGAUUUGU | 820 | ACAAAUCA CUGAUGAGGCCGUUAGGCCGAA AACAUGCC | 10239 |
| 5043 | GCAUGUUUU GAUUUGUA | 821 | UACAAAUC CUGAUGAGGCCGUUAGGCCGAA AAACAUGC | 10240 |
| 5047 | GUUUUGAUU UGUAGCAC | 822 | GUGCUACA CUGAUGAGGCCGUUAGGCCGAA AUCAAAAC | 10241 |
| 5048 | UUUUGAUUU GUAGCACU | 823 | AGUGCUAC CUGAUGAGGCCGUUAGGCCGAA AAUCAAAA | 10242 |
| 5051 | UGAUUUGUA GCACUGAG | 824 | CUCAGUGC CUGAUGAGGCCGUUAGGCCGAA ACAAAUCA | 10243 |
| 5069 | GUGGCACUC AACUCUGA | 825 | UCAGAGUU CUGAUGAGGCCGUUAGGCCGAA AGUGCCAC | 10244 |
| 5074 | ACUCAACUC UGAGCCCA | 826 | UGGGCUCA CUGAUGAGGCCGUUAGGCCGAA AGUUGAGU | 10245 |
| 5084 | GAGCCCAUA CUUUUGGC | 827 | GCCAAAAG CUGAUGAGGCCGUUAGGCCGAA AUGGGCUC | 10246 |
| 5087 | CCCAUACUU UUGGCUCC | 828 | GGAGCCAA CUGAUGAGGCCGUUAGGCCGAA AGUAUGGG | 10247 |
| 5088 | CCAUACUUU UGGCUCCU | 829 | AGGAGCCA CUGAUGAGGCCGUUAGGCCGAA AAGUAUGG | 10248 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 5089 | CAUACUUUU GGCUCCUC | 830 | GAGGAGCC CUGAUGAGGCCGUUAGGCCGAA AAAGUAUG | 10249 |
| 5094 | UUUUGGCUC CUCUAGUA | 831 | UACUAGAG CUGAUGAGGCCGUUAGGCCGAA AGCCAAAA | 10250 |
| 5097 | UGGCUCCUC UAGUAAGA | 832 | UCUUACUA CUGAUGAGGCCGUUAGGCCGAA AGGAGCCA | 10251 |
| 5099 | GCUCCUCUA GUAAGAUG | 833 | CAUCUUAC CUGAUGAGGCCGUUAGGCCGAA AGAGGAGC | 10252 |
| 5102 | CCUCUAGUA AGAUGCAC | 834 | GUGCAUCU CUGAUGAGGCCGUUAGGCCGAA ACUAGAGG | 10253 |
| 5119 | UGAAAACUU AGCCAGAG | 835 | CUCUGGCU CUGAUGAGGCCGUUAGGCCGAA AGUUUUCA | 10254 |
| 5120 | GAAAACUUA GCCAGAGU | 836 | ACUCUGGC CUGAUGAGGCCGUUAGGCCGAA AAGUUUUC | 10255 |
| 5129 | GCCAGAGUU AGGUUGUC | 837 | GACAACCU CUGAUGAGGCCGUUAGGCCGAA ACUCUGGC | 10256 |
| 5130 | CCAGAGUUA GGUUGUCU | 838 | AGACAACC CUGAUGAGGCCGUUAGGCCGAA AACUCUGG | 10257 |
| 5134 | AGUUAGGUU GUCUCCAG | 839 | CUGGAGAC CUGAUGAGGCCGUUAGGCCGAA ACCUAACU | 10258 |
| 5137 | UAGGUUGUC UCCAGGCC | 840 | GGCCUGGA CUGAUGAGGCCGUUAGGCCGAA ACAACCUA | 10259 |
| 5139 | GGUUGUCUC CAGGCCAU | 841 | AUGGCCUG CUGAUGAGGCCGUUAGGCCGAA AGACAACC | 10260 |
| 5156 | GAUGGCCUU ACACUGAA | 842 | UUCAGUGU CUGAUGAGGCCGUUAGGCCGAA AGGCCAUC | 10261 |
| 5157 | AUGGCCUUA CACUGAAA | 843 | UUUCAGUG CUGAUGAGGCCGUUAGGCCGAA AAGGCCAU | 10262 |
| 5170 | GAAAAUGUC ACAUUCUA | 844 | UAGAAUGU CUGAUGAGGCCGUUAGGCCGAA ACAUUUUC | 10263 |
| 5175 | UGUCACAUU CUAUUUUG | 845 | CAAAAUAG CUGAUGAGGCCGUUAGGCCGAA AUGUGACA | 10264 |
| 5176 | GUCACAUUC UAUUUUGG | 846 | CCAAAAUA CUGAUGAGGCCGUUAGGCCGAA AAUGUGAC | 10265 |
| 5178 | CACAUUCUA UUUUGGGU | 847 | ACCCAAAA CUGAUGAGGCCGUUAGGCCGAA AGAAUGUG | 10266 |
| 5180 | CAUUCUAUU UUGGGUAU | 848 | AUACCCAA CUGAUGAGGCCGUUAGGCCGAA AUAGAAUG | 10267 |
| 5181 | AUUCUAUUU UGGGUAUU | 849 | AAUACCCA CUGAUGAGGCCGUUAGGCCGAA AAUAGAAU | 10268 |
| 5182 | UUCUAUUUU GGGUAUUA | 850 | UAAUACCC CUGAUGAGGCCGUUAGGCCGAA AAAUAGAA | 10269 |
| 5187 | UUUUGGGUA UUAAUAUA | 851 | UAUAUUAA CUGAUGAGGCCGUUAGGCCGAA ACCCAAAA | 10270 |
| 5189 | UUGGGUAUU AAUAUAUA | 852 | UAUAUAUU CUGAUGAGGCCGUUAGGCCGAA AUACCCAA | 10271 |
| 5190 | UGGGUAUUA AUAUAUAG | 853 | CUAUAUAU CUGAUGAGGCCGUUAGGCCGAA AAUACCCA | 10272 |
| 5193 | GUAUUAAUA UAUAGUCC | 854 | GGACUAUA CUGAUGAGGCCGUUAGGCCGAA AUUAAUAC | 10273 |
| 5195 | AUUAAUAUA UAGUCCAG | 855 | CUGGACUA CUGAUGAGGCCGUUAGGCCGAA AUAUUAAU | 10274 |
| 5197 | UAAUAUAUA GUCCAGAC | 856 | GUCUGGAC CUGAUGAGGCCGUUAGGCCGAA AUAUAUUA | 10275 |
| 5200 | UAUAUAGUC CAGACACU | 857 | AGUCUGG CUGAUGAGGCCGUUAGGCCGAA ACUAUAUA | 10276 |
| 5209 | CAGACACUU AACUCAAU | 858 | AUUGAGUU CUGAUGAGGCCGUUAGGCCGAA AGUGUCUG | 10277 |
| 5210 | AGACACUUA ACUCAAUU | 859 | AAUUGAGU CUGAUGAGGCCGUUAGGCCGAA AAGUGUCU | 10278 |
| 5214 | ACUUAACUC AAUUUCUU | 860 | AAGAAAUU CUGAUGAGGCCGUUAGGCCGAA AGUUAAGU | 10279 |
| 5218 | AACUCAAUU UCUUGGUA | 861 | UACCAAGA CUGAUGAGGCCGUUAGGCCGAA AUUGAGUU | 10280 |
| 5219 | ACUCAAUUU CUUGGUAU | 862 | AUACCAAG CUGAUGAGGCCGUUAGGCCGAA AAUUGAGU | 10281 |
| 5220 | CUCAAUUUC UUGGUAUU | 863 | AAUACCAA CUGAUGAGGCCGUUAGGCCGAA AAAUUGAG | 10282 |
| 5222 | CAAUUUCUU GGUAUUAU | 864 | AUAAUACC CUGAUGAGGCCGUUAGGCCGAA AGAAAUUG | 10283 |
| 5226 | UUCUUGGUA UUAUUCUG | 865 | CAGAAUAA CUGAUGAGGCCGUUAGGCCGAA ACCAAGAA | 10284 |
| 5228 | CUUGGUAUU AUUCUGUU | 866 | AACAGAAU CUGAUGAGGCCGUUAGGCCGAA AUACCAAG | 10285 |

TABLE II-continued

Human flt1 VEGF Receptor—Hammerhead Ribozyme and Substrate Sequence

| Pos | Substrate | Seq ID No | HH Ribozyme | Seq ID No |
|---|---|---|---|---|
| 5229 | UUGGUAUUA UUCUGUUU | 867 | AAACAGAA CUGAUGAGGCCGUUAGGCCGAA AAUACCAA | 10286 |
| 5231 | GGUAUUAUU CUGUUUUG | 868 | CAAAACAG CUGAUGAGGCCGUUAGGCCGAA AUAAUACC | 10287 |
| 5232 | GUAUUAUUC UGUUUUGC | 869 | GCAAAACA CUGAUGAGGCCGUUAGGCCGAA AAUAAUAC | 10288 |
| 5236 | UAUUCUGUU UUGCACAG | 870 | CUGUGCAA CUGAUGAGGCCGUUAGGCCGAA ACAGAAUA | 10289 |
| 5237 | AUUCUGUUU UGCACAGU | 871 | ACUGUGCA CUGAUGAGGCCGUUAGGCCGAA AACAGAAU | 10290 |
| 5238 | UUCUGUUUU GCACAGUU | 872 | AACUGUGC CUGAUGAGGCCGUUAGGCCGAA AAACAGAA | 10291 |
| 5246 | UGCACAGUU AGUUGUGA | 873 | UCACAACU CUGAUGAGGCCGUUAGGCCGAA ACUGUGCA | 10292 |
| 5247 | GCACAGUUA GUUGUGAA | 874 | UUCACAAC CUGAUGAGGCCGUUAGGCCGAA AACUGUGC | 10293 |
| 5250 | CAGUUAGUU GUGAAAGA | 875 | UCUUUCAC CUGAUGAGGCCGUUAGGCCGAA ACUAACUG | 10294 |
| 5284 | AAUGCAGUC CUGAGGAG | 876 | CUCCUCAG CUGAUGAGGCCGUUAGGCCGAA ACUGCAUU | 10295 |
| 5296 | AGGAGAGUU UUCUCCAU | 877 | AUGGAGAA CUGAUGAGGCCGUUAGGCCGAA ACUCUCCU | 10296 |
| 5297 | GGAGAGUUU UCUCCAUA | 878 | UAUGGAGA CUGAUGAGGCCGUUAGGCCGAA AACUCUCC | 10297 |
| 5298 | GAGAGUUUU CUCCAUAU | 879 | AUAUGGAG CUGAUGAGGCCGUUAGGCCGAA AAACUCUC | 10298 |
| 5299 | AGAGUUUUC UCCAUAUC | 880 | GAUAUGGA CUGAUGAGGCCGUUAGGCCGAA AAAACUCU | 10299 |
| 5301 | AGUUUUCUC CAUAUCAA | 881 | UUGAUAUG CUGAUGAGGCCGUUAGGCCGAA AGAAAACU | 10300 |
| 5305 | UUCUCCAUA UCAAAACG | 882 | CGUUUUGA CUGAUGAGGCCGUUAGGCCGAA AUGGAGAA | 10301 |
| 5307 | CUCCAUAUC AAAACGAG | 883 | CUCGUUUU CUGAUGAGGCCGUUAGGCCGAA AUAUGGAG | 10302 |
| 5336 | AAAAAGGUC AAUAAGGU | 884 | ACCUUAUU CUGAUGAGGCCGUUAGGCCGAA ACCUUUUU | 10303 |
| 5340 | AGGUCAAUA AGGUCAAG | 885 | CUUGACCU CUGAUGAGGCCGUUAGGCCGAA AUUGACCU | 10304 |
| 5345 | AAUAAGGUC AAGGGAAG | 886 | CUUCCCUU CUGAUGAGGCCGUUAGGCCGAA ACCUUAUU | 10305 |
| 5361 | GACCCCGUC UCUAUACC | 887 | GGUAUAGA CUGAUGAGGCCGUUAGGCCGAA ACGGGGUC | 10306 |
| 5363 | CCCCGUCUC UAUACCAA | 888 | UUGGUAUA CUGAUGAGGCCGUUAGGCCGAA AGACGGGG | 10307 |
| 5365 | CCGUCUCUA UACCAACC | 889 | GGUUGGUA CUGAUGAGGCCGUUAGGCCGAA AGAGACGG | 10308 |
| 5367 | GUCUCUAUA CCAACCAA | 890 | UUGGUUGG CUGAUGAGGCCGUUAGGCCGAA AUAGAGAC | 10309 |
| 5382 | AAACCAAUU CACCAACA | 891 | UGUUGGUG CUGAUGAGGCCGUUAGGCCGAA AUUGGUUU | 10310 |
| 5383 | AACCAAUUC ACCAACAC | 892 | GUGUUGGU CUGAUGAGGCCGUUAGGCCGAA AAUUGGUU | 10311 |
| 5395 | AACACAGUU GGGACCCA | 893 | UGGGUCCC CUGAUGAGGCCGUUAGGCCGAA ACUGUGUU | 10312 |
| 5417 | CAGGAAGUC AGUCACGU | 894 | ACGUGACU CUGAUGAGGCCGUUAGGCCGAA ACUUCCUG | 10313 |
| 5421 | AAGUCAGUC ACGUUUCC | 895 | GGAAACGU CUGAUGAGGCCGUUAGGCCGAA ACUGACUU | 10314 |
| 5426 | AGUCACGUU UCCUUUUC | 896 | GAAAAGGA CUGAUGAGGCCGUUAGGCCGAA ACGUGACU | 10315 |
| 5427 | GUCACGUUU CCUUUUCA | 897 | UGAAAAGG CUGAUGAGGCCGUUAGGCCGAA AACGUGAC | 10316 |
| 5428 | UCACGUUUC CUUUUCAU | 898 | AUGAAAAG CUGAUGAGGCCGUUAGGCCGAA AAACGUGA | 10317 |
| 5431 | CGUUCCUU UUCAUUUA | 899 | UAAAUGAA CUGAUGAGGCCGUUAGGCCGAA AGGAAACG | 10318 |
| 5432 | GUUCCUUU UCAUUUAA | 900 | UUAAAUGA CUGAUGAGGCCGUUAGGCCGAA AAGGAAAC | 10319 |
| 5433 | UUCCUUUU CAUUUAAU | 901 | AUUAAAUG CUGAUGAGGCCGUUAGGCCGAA AAAGGAAA | 10320 |
| 5434 | UUCCUUUUC AUUUAAUG | 902 | CAUUAAAU CUGAUGAGGCCGUUAGGCCGAA AAAAGGAA | 10321 |
| 5437 | CUUUUCAUU UAAUGGGG | 903 | CCCCAUUA CUGAUGAGGCCGUUAGGCCGAA AUGAAAAG | 10322 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 5438 | UUUUCAUUU AAUGGGGA | 904 | UCCCCAUU CUGAUGAGGCCGUUAGGCCGAA AAUGAAAA | 10323 |
| 5439 | UUUCAUUUA AUGGGGAU | 905 | AUCCCCAU CUGAUGAGGCCGUUAGGCCGAA AAAUGAAA | 10324 |
| 5448 | AUGGGGAUU CCACUAUC | 906 | GAUAGUGG CUGAUGAGGCCGUUAGGCCGAA AUCCCCAU | 10325 |
| 5449 | UGGGGAUUC CACUAUCU | 907 | AGAUAGUG CUGAUGAGGCCGUUAGGCCGAA AAUCCCCA | 10326 |
| 5454 | AUUCCACUA UCUCACAC | 908 | GUGUGAGA CUGAUGAGGCCGUUAGGCCGAA AGUGGAAU | 10327 |
| 5456 | UCCACUAUC UCACACUA | 909 | UAGUGUGA CUGAUGAGGCCGUUAGGCCGAA AUAGUGGA | 10328 |
| 5458 | CACUAUCUC ACACUAAU | 910 | AUUAGUGU CUGAUGAGGCCGUUAGGCCGAA AGAUAGUG | 10329 |
| 5464 | CUCACACUA AUCUGAAA | 911 | UUUCAGAU CUGAUGAGGCCGUUAGGCCGAA AGUGUGAG | 10330 |
| 5467 | ACACUAAUC UGAAAGGA | 912 | UCCUUUCA CUGAUGAGGCCGUUAGGCCGAA AUUAGUGU | 10331 |
| 5489 | AAGAGCAUU AGCUGGCG | 913 | CGCCAGCU CUGAUGAGGCCGUUAGGCCGAA AUGCUCUU | 10332 |
| 5490 | AGAGCAUUA GCUGGCGC | 914 | GCGCCAGC CUGAUGAGGCCGUUAGGCCGAA AAUGCUCU | 10333 |
| 5501 | UGGCGCAUA UUAAGCAC | 915 | GUGCUUAA CUGAUGAGGCCGUUAGGCCGAA AUGCGCCA | 10334 |
| 5503 | GCGCAUAUU AAGCACUU | 916 | AAGUGCUU CUGAUGAGGCCGUUAGGCCGAA AUAUGCGC | 10335 |
| 5504 | CGCAUAUUA AGCACUUU | 917 | AAAGUGCU CUGAUGAGGCCGUUAGGCCGAA AAUAUGCG | 10336 |
| 5511 | UAAGCACUU UAAGCUCC | 918 | GGAGCUUA CUGAUGAGGCCGUUAGGCCGAA AGUGCUUA | 10337 |
| 5512 | AAGCACUUU AAGCUCCU | 919 | AGGAGCUU CUGAUGAGGCCGUUAGGCCGAA AAGUGCUU | 10338 |
| 5513 | AGCACUUUA AGCUCCUU | 920 | AAGGAGCU CUGAUGAGGCCGUUAGGCCGAA AAAGUGCU | 10339 |
| 5518 | UUUAAGCUC CUUGAGUA | 921 | UACUCAAG CUGAUGAGGCCGUUAGGCCGAA AGCUUAAA | 10340 |
| 5521 | AAGCUCCUU GAGUAAAA | 922 | UUUUACUC CUGAUGAGGCCGUUAGGCCGAA AGGAGCUU | 10341 |
| 5526 | CCUUGAGUA AAAGGUG | 923 | CACCUUUU CUGAUGAGGCCGUUAGGCCGAA ACUCAAGG | 10342 |
| 5537 | AAGGUGGUA UGUAAUUU | 924 | AAAUUACA CUGAUGAGGCCGUUAGGCCGAA ACCACCUU | 10343 |
| 5541 | UGGUAUGUA AUUUAUGC | 925 | GCAUAAAU CUGAUGAGGCCGUUAGGCCGAA ACAUACCA | 10344 |
| 5544 | UAUGUAAUU UAUGCAAG | 926 | CUUGCAUA CUGAUGAGGCCGUUAGGCCGAA AUUACAUA | 10345 |
| 5545 | AUGUAAUUU AUGCAAGG | 927 | CCUUGCAU CUGAUGAGGCCGUUAGGCCGAA AAUUACAU | 10346 |
| 5546 | UGUAAUUUA UGCAAGGU | 928 | ACCUUGCA CUGAUGAGGCCGUUAGGCCGAA AAAUUACA | 10347 |
| 5555 | UGCAAGGUA UUUCUCCA | 929 | UGGAGAAA CUGAUGAGGCCGUUAGGCCGAA ACCUUGCA | 10348 |
| 5557 | CAAGGUAUU UCUCCAGU | 930 | ACUGGAGA CUGAUGAGGCCGUUAGGCCGAA AUACCUUG | 10349 |
| 5558 | AAGGUAUUU CUCCAGUU | 931 | AACUGGAG CUGAUGAGGCCGUUAGGCCGAA AAUACCUU | 10350 |
| 5559 | AGGUAUUUC UCCAGUUG | 932 | CAACUGGA CUGAUGAGGCCGUUAGGCCGAA AAAUACCU | 10351 |
| 5561 | GUAUUUCUC CAGUUGGG | 933 | CCCAACUG CUGAUGAGGCCGUUAGGCCGAA AGAAAUAC | 10352 |
| 5566 | UCUCCAGUU GGGACUCA | 934 | UGAGUCCC CUGAUGAGGCCGUUAGGCCGAA ACUGGAGA | 10353 |
| 5573 | UUGGGACUC AGGAUAUU | 935 | AAUAUCCU CUGAUGAGGCCGUUAGGCCGAA AGUCCCAA | 10354 |
| 5579 | CUCAGGAUA UUAGUUAA | 936 | UUAACUAA CUGAUGAGGCCGUUAGGCCGAA AUCCUGAG | 10355 |
| 5581 | CAGGAUAUU AGUUAAUG | 937 | CAUUAACU CUGAUGAGGCCGUUAGGCCGAA AUAUCCUG | 10356 |
| 5582 | AGGAUAUUA GUUAAUGA | 938 | UCAUUAAC CUGAUGAGGCCGUUAGGCCGAA AAUAUCCU | 10357 |
| 5585 | AUAUUAGUU AAUGAGCC | 939 | GGCUCAUU CUGAUGAGGCCGUUAGGCCGAA ACUAAUAU | 10358 |
| 5586 | UAUUAGUUA AUGAGCCA | 940 | UGGCUCAU CUGAUGAGGCCGUUAGGCCGAA AACUAAUA | 10359 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 5596 | UGAGCCAUC ACUAGAAG | 941 | CUUCUAGU CUGAUGAGGCCGUUAGGCCGAA AUGGCUCA | 10360 |
| 5600 | CCAUCACUA GAAGAAAA | 942 | UUUUCUUC CUGAUGAGGCCGUUAGGCCGAA AGUGAUGG | 10361 |
| 5615 | AAGCCCAUU UUCAACUG | 943 | CAGUUGAA CUGAUGAGGCCGUUAGGCCGAA AUGGGCUU | 10362 |
| 5616 | AGCCCAUUU UCAACUGC | 944 | GCAGUUGA CUGAUGAGGCCGUUAGGCCGAA AAUGGGCU | 10363 |
| 5617 | GCCCAUUUU CAACUGCU | 945 | AGCACUUG CUGAUGAGGCCGUUAGGCCGAA AAAUGGGC | 10364 |
| 5618 | CCCAUUUUC AACUGCUU | 946 | AAGCAGUU CUGAUGAGGCCGUUAGGCCGAA AAAAUGGG | 10365 |
| 5626 | CAACUGCUU UGAAACUU | 947 | AAGUUUCA CUGAUGAGGCCGUUAGGCCGAA AGCAGUUG | 10366 |
| 5627 | AACUGCUUU GAAACUUG | 948 | CAAGUUUC CUGAUGAGGCCGUUAGGCCGAA AAGCAGUU | 10367 |
| 5634 | UUGAAACUU GCCUGGGG | 949 | CCCCAGGC CUGAUGAGGCCGUUAGGCCGAA AGUUUCAA | 10368 |
| 5644 | CCUGGGGUC UGAGCAUG | 950 | CAUGCUCA CUGAUGAGGCCGUUAGGCCGAA ACCCCAGG | 10369 |
| 5661 | AUGGGAAUA GGGAGACA | 951 | UGUCUCCC CUGAUGAGGCCGUUAGGCCGAA AUUCCCAU | 10370 |
| 5674 | GACAGGGUA GGAAAGGG | 952 | CCCUUUCC CUGAUGAGGCCGUUAGGCCGAA ACCCUGUC | 10371 |
| 5688 | GGGCGCCUA CUCUUCAG | 953 | CUGAAGAG CUGAUGAGGCCGUUAGGCCGAA AGGCGCCC | 10372 |
| 5691 | CGCCUACUC UUCAGGGU | 954 | ACCCUGAA CUGAUGAGGCCGUUAGGCCGAA AGUAGGCG | 10373 |
| 5693 | CCUACUCUU CAGGGUCU | 955 | AGACCCUG CUGAUGAGGCCGUUAGGCCGAA AGAGUAGG | 10374 |
| 5694 | CUACUCUUC AGGGUCUA | 956 | UAGACCCU CUGAUGAGGCCGUUAGGCCGAA AAGAGUAG | 10375 |
| 5700 | UUCAGGGUC UAAAGAUC | 957 | GAUCUUUA CUGAUGAGGCCGUUAGGCCGAA ACCCUGAA | 10376 |
| 5702 | CAGGGUCUA AAGAUCAA | 958 | UUGAUCUU CUGAUGAGGCCGUUAGGCCGAA AGACCCUG | 10377 |
| 5708 | CUAAAGAUC AAGUGGGC | 959 | GCCCACUU CUGAUGAGGCCGUUAGGCCGAA AUCUUUAG | 10378 |
| 5719 | GUGGGCCUU GGAUCGCU | 960 | AGCGAUCC CUGAUGAGGCCGUUAGGCCGAA AGGCCCAC | 10379 |
| 5724 | CCUUGGAUC GCUAAGCU | 961 | AGCUUAGC CUGAUGAGGCCGUUAGGCCGAA AUCCAAGG | 10380 |
| 5728 | GGAUCGCUA AGCUGGCU | 962 | AGCCAGCU CUGAUGAGGCCGUUAGGCCGAA AGCGAUCC | 10381 |
| 5737 | AGCUGGCUC UGUUUGAU | 963 | AUCAAACA CUGAUGAGGCCGUUAGGCCGAA AGCCAGCU | 10382 |
| 5741 | GGCUCUGUU UGAUGCUA | 964 | UAGCAUCA CUGAUGAGGCCGUUAGGCCGAA ACAGAGCC | 10383 |
| 5742 | GCUCUGUUU GAUGCUAU | 965 | AUAGCAUC CUGAUGAGGCCGUUAGGCCGAA AACAGAGC | 10384 |
| 5749 | UUGAUGCUA UUUAUGCA | 966 | UGCAUAAA CUGAUGAGGCCGUUAGGCCGAA AGCAUCAA | 10385 |
| 5751 | GAUGCUAUU UAUGCAAG | 967 | CUUGCAUA CUGAUGAGGCCGUUAGGCCGAA AUAGCAUC | 10386 |
| 5752 | AUGCUAUUU AUGCAAGU | 968 | ACUUGCAU CUGAUGAGGCCGUUAGGCCGAA AAUAGCAU | 10387 |
| 5753 | UGCUAUUUA UGCAAGUU | 969 | AACUUGCA CUGAUGAGGCCGUUAGGCCGAA AAAUAQCA | 10388 |
| 5761 | AUGCAAGUU AGGGUCUA | 970 | UAGACCCU CUGAUGAGGCCGUUAGGCCGAA ACUUGCAU | 10389 |
| 5762 | UGCAAGUUA GGGUCUAU | 971 | AUAGACCC CUGAUGAGGCCGUUAGGCCGAA AACUUGCA | 10390 |
| 5767 | GUUAGGGUC UAUGUAUU | 972 | AAUACAUA CUGAUGAGGCCGUUAGGCCGAA ACCCUAAC | 10391 |
| 5769 | UAGGGUCUA UGUAUUUA | 973 | UAAAUACA CUGAUGAGGCCGUUAGGCCGAA AGACCCUA | 10392 |
| 5773 | GUCUAUGUA UUUAGGAU | 974 | AUCCUAAA CUGAUGAGGCCGUUAGGCCGAA ACAUAGAC | 10393 |
| 5775 | CUAUGUAUU UAGGAUGC | 975 | GCAUCCUA CUGAUGAGGCCGUUAGGCCGAA AUACAUAG | 10394 |
| 5776 | UAUGUAUUU AGGAUGCG | 976 | CGCAUCCU CUGAUGAGGCCGUUAGGCCGAA AAUACAUA | 10395 |
| 5777 | AUGUAUUUA GGAUGCGC | 977 | GCGCAUCC CUGAUGAGGCCGUUAGGCCGAA AAAUACAU | 10396 |

TABLE II-continued

Human flt1 VEGF Receptor—Hammerhead Ribozyme and Substrate Sequence

| Pos | Substrate | Seq ID No | HH Ribozyme | Seq ID No |
|---|---|---|---|---|
| 5788 | AUGCGCCUA CUCUUCAG | 978 | CUGAAGAG CUGAUGAGGCCGUUAGGCCGAA AGGCGCAU | 10397 |
| 5791 | CGCCUACUC UUCAGGGU | 954 | ACCCUGAA CUGAUGAGGCCGUUAGGCCGAA AGUAGGCG | 10373 |
| 5793 | CCUACUCUU CAGGGUCU | 955 | AGACCCUG CUGAUGAGGCCGUUAGGCCGAA AGAGUAGG | 10374 |
| 5794 | CUACUCUUC AGGGUCUA | 956 | UAGACCOU CUGAUGAGGCCGUUAGGCCGAA AAGAGUAG | 10375 |
| 5800 | UUCAGGGUC UAAAGAUC | 957 | GAUCUUUA CUGAUGAGGCCGUUAGGCCGAA ACCCUGAA | 10376 |
| 5802 | CAGGGUCUA AAGAUCAA | 958 | UUGAUCUU CUGAUGAGGCCGUUAGGCCGAA AGACCCUG | 10377 |
| 5808 | CUAAAGAUC AAGUGGGC | 959 | GCCCACUU CUGAUGAGGCCGUUAGGCCGAA AUCUUUAG | 10378 |
| 5819 | GUGGGCCUU GGAUCGCU | 960 | AGCGAUCC CUGAUGAGGCCGUUAGGCCGAA AGGCCCAC | 10379 |
| 5824 | CCUUGGAUC GCUAAGCU | 961 | AGCUUAGC CUGAUGAGGCCGUUAGGCCGAA AUCCAAGG | 10380 |
| 5828 | GGAUCGCUA AGCUGGCU | 962 | AGCCAGCU CUGAUGAGGCCGUUAGGCCGAA AGCGAUCC | 10381 |
| 5837 | AGCUGGCUC UGUUUGAU | 963 | AUCAAACA CUGAUGAGGCCGUUAGGCCGAA AGCCAGCU | 10382 |
| 5841 | GGCUCUGUU UGAUGCUA | 964 | UAGCAUCA CUGAUGAGGCCGUUAGGCCGAA ACAGAGCC | 10383 |
| 5842 | GCUCUGUUU GAUGCUAU | 965 | AUAGCAUC CUGAUGAGGCCGUUAGGCCGAA AACAGAGC | 10384 |
| 5849 | UUGAUGCUA UUUAUGCA | 966 | UGCAUAAA CUGAUGAGGCCGUUAGGCCGAA AGCAUCAA | 10385 |
| 5851 | GAUGCUAUU UAUGCAAG | 967 | CUUGCAUA CUGAUGAGGCCGUUAGGCCGAA AUAGCAUC | 10386 |
| 5852 | AUGCUAUUU AUGCAAGU | 968 | ACUUCCAU CUGAUGAGGCCGUUAGGCCGAA AAUAGCAU | 10387 |
| 5853 | UGCUAUUUA UGCAAGUU | 969 | AACUUGCA CUGAUGAGGCCGUUAGGCCGAA AAAUAGCA | 10388 |
| 5861 | AUGCAAGUU AGGGUCUA | 970 | UAGACCCU CUGAUGAGGCCGUUAGGCCGAA ACUUGCAU | 10389 |
| 5862 | UGCAAGUUA GGGUCUAU | 971 | AUAGACCC CUGAUGAGGCCGUUAGGCCGAA AACUUGCA | 10390 |
| 5867 | GUUAGGGUC UAUGUAUU | 972 | AAUACAUA CUGAUGAGGCCGUUAGGCCGAA ACCCUAAC | 10391 |
| 5869 | UAGGGUCUA UGUAUUUA | 973 | UAAAUACA CUGAUGAGGCCGUUAGGCCGAA AGACCCUA | 10392 |
| 5873 | GUCUAUGUA UUUAGGAU | 974 | AUCCUAAA CUGAUGAGGCCGUUAGGCCGAA ACAUAGAC | 10393 |
| 5875 | CUAUGUAUU UAGGAUGU | 979 | ACAUCCUA CUGAUGAGGCCGUUAGGCCGAA AUACAUAG | 10398 |
| 5876 | UAUGUAUUU AGGAUGUC | 980 | GACAUCCU CUGAUGAGGCCGUUAGGCCGAA AAUACAUA | 10399 |
| 5877 | AUGUAUUUA GGAUGUCU | 981 | AGACAUCC CUGAUGAGGCCGUUAGGCCGAA AAAUACAU | 10400 |
| 5884 | UAGGAUGUC UGCACCUU | 982 | AAGGUGCA CUGAUGAGGCCGUUAGGCCGAA ACAUCCUA | 10401 |
| 5892 | CUGCACCUU CUGCAGCC | 983 | GGCUGCAG CUGAUGAGGCCGUUAGGCCGAA AGGUGCAG | 10402 |
| 5893 | UGCACCUUC UGCAGCCA | 984 | UGGCUGCA CUGAUGAGGCCGUUAGGCCGAA AAGGUGCA | 10403 |
| 5904 | CAGCCAGUC AGAAGCUG | 985 | CAGCUUCU CUGAUGAGGCCGUUAGGCCGAA ACUGGCUG | 10404 |
| 5930 | CAGUGGAUU GCUGCUUC | 986 | GAAGCAGC CUGAUGAGGCCGUUAGGCCGAA AUCCACUG | 10405 |
| 5937 | UUGCUGCUU CUUGGGGA | 987 | UCCCCAAG CUGAUGAGGCCGUUAGGCCGAA AGCAGCAA | 10406 |
| 5938 | UGCUGCUUC UUGGGGAG | 988 | CUCCCCAA CUGAUGAGGCCGUUAGGCCGAA AAGCAGCA | 10407 |
| 5940 | CUGCUUCUU GGGGAGAA | 989 | UUCUCCCC CUGAUGAGGCCGUUAGGCCGAA AGAAGCAG | 10408 |
| 5953 | AGAAGAGUA UGCUUCCU | 990 | AGGAAGCA CUGAUGAGGCCGUUAGGCCGAA ACUCUUCU | 10409 |
| 5958 | AGUAUGCUU CCUUUUAU | 991 | AUAAAAGG CUGAUGAGGCCGUUAGGCCGAA AGCAUACU | 10410 |
| 5959 | GUAUGCUUC CUUUUAUC | 992 | GAUAAAAG CUGAUGAGGCCGUUAGGCCGAA AAGCAUAC | 10411 |
| 5962 | UGCUUCCUU UUAUCCAU | 993 | AUGGAUAA CUGAUGAGGCCGUUAGGCCGAA AGGAAGCA | 10412 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 5963 | GCUUCCUUU UAUCCAUG | 994 | CAUGGAUA CUGAUGAGGCCGUUAGGCCGAA AAGGAAGC | 10413 |
| 5964 | CUUCCUUUU AUCCAUGU | 995 | ACAUGGAU CUGAUGAGGCCGUUAGGCCGAA AAAGGAAG | 10414 |
| 5965 | UUCCUUUUA UCCAUGUA | 996 | UACAUGGA CUGAUGAGGCCGUUAGGCCGAA AAAAGGAA | 10415 |
| 5967 | CCUUUUAUC CAUGUAAU | 997 | AUUACAUG CUGAUGAGGCCGUUAGGCCGAA AUAAAAGG | 10416 |
| 5973 | AUCCAUGUA AUUUAACU | 998 | AGUUAAAU CUGAUGAGGCCGUUAGGCCGAA ACAUGGAU | 10417 |
| 5976 | CAUGUAAUU UAACUGUA | 999 | UACAGUUA CUGAUGAGGCCGUUAGGCCGAA AUUACAUG | 10418 |
| 5977 | AUGUAAUUU AACUGUAG | 1000 | CUACAGUU CUGAUGAGGCCGUUAGGCCGAA AAUUACAU | 10419 |
| 5978 | UGUAAUUUA ACUGUAGA | 1001 | UCUACAGU CUGAUGAGGCCGUUAGGCCGAA AAAUUACA | 10420 |
| 5984 | UUAACUGUA GAACCUGA | 1002 | UCAGGUUC CUGAUGAGGCCGUUAGGCCGAA ACAGUUAA | 10421 |
| 5996 | CCUGAGCUC UAAGUAAC | 1003 | GUUACUUA CUGAUGAGGCCGUUAGGCCGAA AGCUCAGG | 10422 |
| 5998 | UGAGCUCUA AGUAACCG | 1004 | CGGUUACU CUGAUGAGGCCGUUAGGCCGAA AGAGCUCA | 10423 |
| 6002 | CUCUAAGUA ACCGAAGA | 1005 | UCUUCGGU CUGAUGAGGCCGUUAGGCCGAA ACUUAGAG | 10424 |
| 6015 | AAGAAUGUA UGCCUCUG | 1006 | CAGAGGCA CUGAUGAGGCCGUUAGGCCGAA ACAUUCUU | 10425 |
| 6021 | GUAUGCCUC UGUUCUUA | 1007 | UAAGAACA CUGAUGAGGCCGUUAGGCCGAA AGGCAUAC | 10426 |
| 6025 | GCCUCUGUU CUUAUGUG | 1008 | CACAUAAG CUGAUGAGGCCGUUAGGCCGAA ACAGAGGC | 10427 |
| 6026 | CCUCUGUUC UUAUGUGC | 1009 | GCACAUAA CUGAUGAGGCCGUUAGGCCGAA AACAGAGG | 10428 |
| 6028 | UCUGUUCUU AUGUGCCA | 1010 | UGGCACAU CUGAUGAGGCCGUUAGGCCGAA AGAACAGA | 10429 |
| 6029 | CUGUUCUUA UGUGCCAC | 1011 | GUGGCACA CUGAUGAGGCCGUUAGGCCGAA AAGAACAG | 10430 |
| 6040 | UGCCACAUC CUUGUUUA | 1012 | UAAACAAG CUGAUGAGGCCGUUAGGCCGAA AUGUGGCA | 10431 |
| 6043 | CACAUCCUU GUUUAAAG | 1013 | CUUUAAAC CUGAUGAGGCCGUUAGGCCGAA AGGAUGUG | 10432 |
| 6046 | AUCCUUGUU UAAAGGCU | 1014 | AGCCUUUA CUGAUGAGGCCGUUAGGCCGAA ACAAGGAU | 10433 |
| 6047 | UCCUUGUUU AAAGGCUC | 1015 | GAGCCUUU CUGAUGAGGCCGUUAGGCCGAA AACAAGGA | 10434 |
| 6048 | CCUUGUUUA AAGGCUCU | 1016 | AGAGCCUU CUGAUGAGGCCGUUAGGCCGAA AAACAAGG | 10435 |
| 6055 | UAAAGGCUC UCUGUAUG | 1017 | CAUACAGA CUGAUGAGGCCGUUAGGCCGAA AGCCUUUA | 10436 |
| 6057 | AAGGCUCUC UGUAUGAA | 1018 | UUCAUACA CUGAUGAGGCCGUUAGGCCGAA AGAGCCUU | 10437 |
| 6061 | CUCUCUGUA UGAAGAGA | 1019 | UCUCUUCA CUGAUGAGGCCGUUAGGCCGAA ACAGAGAG | 10438 |
| 6079 | GGGACCGUC AUCAGCAC | 1020 | GUGCUGAU CUGAUGAGGCCGUUAGGCCGAA ACGGUCCC | 10439 |
| 6082 | ACCGUCAUC AGCACAUU | 1021 | AAUGUGCU CUGAUGAGGCCGUUAGGCCGAA AUGACGGU | 10440 |
| 6090 | CAGCACAUU CCCUAGUG | 1022 | CACUAGGG CUGAUGAGGCCGUUAGGCCGAA AUGUGCUG | 10441 |
| 6091 | AGCACAUUC CCUAGUGA | 1023 | UCACUAGG CUGAUGAGGCCGUUAGGCCGAA AAUGUGCU | 10442 |
| 6095 | CAUUCCCUA GUGAGCCU | 1024 | AGGCUCAC CUGAUGAGGCCGUUAGGCCGAA AGGGAAUG | 10443 |
| 6104 | GUGAGCCUA CUGGCUCC | 1025 | GGAGCCAG CUGAUGAGGCCGUUAGGCCGAA AGGCUCAC | 10444 |
| 6111 | UACUGGCUC CUGGCAGC | 1026 | GCUGCCAG CUGAUGAGGCCGUUAGGCCGAA AGCCAGUA | 10445 |
| 6124 | CAGCGGCUU UUGUGGAA | 1027 | UUCCACAA CUGAUGAGGCCGUUAGGCCGAA AGCCGCUG | 10446 |
| 6125 | AGCGGCUUU UGUGGAAG | 1028 | CUUCCACA CUGAUGAGGCCGUUAGGCCGAA AAGCCGCU | 10447 |
| 6126 | GCGGCUUUU GUGGAAGA | 1029 | UCUUCCAC CUGAUGAGGCCGUUAGGCCGAA AAAGCCGC | 10448 |
| 6137 | GGAAGACUC ACUAGCCA | 1030 | UGGCUAGU CUGAUCAGGCCGUUAGGCCGAA AGUCUUCC | 10449 |

TABLE II-continued

Human flt1 VEGF Receptor—Hammerhead Ribozyme and Substrate Sequence

| Pos | Substrate | Seq ID No | HH Ribozyme | Seq ID No |
|---|---|---|---|---|
| 6141 | GACUCACUA GCCAGAAG | 1031 | CUUCUGGC CUGAUGAGGCCGUUAGGCCGAA AGUGAGUC | 10450 |
| 6166 | GGGACAGUC CUCUCCAC | 1032 | GUGGAGAG CUGAUGAGGCCGUUAGGCCGAA ACUGUCCC | 10451 |
| 6169 | ACAGUCCUC UCCACCAA | 1033 | UUGGUGGA CUGAUGAGGCCGUUAGGCCGAA AGGACUGU | 10452 |
| 6171 | AGUCCUCUC CACCAAGA | 1034 | UCUUCGUG CUGAUGAGGCCGUUAGGCCGAA AGAGGACU | 10453 |
| 6181 | ACCAAGAUC UAAAUCCA | 1035 | UGGAUUUA CUGAUGAGGCCGUUAGGCCGAA AUCUUGGU | 10454 |
| 6183 | CAAGAUCUA AAUCCAAA | 1036 | UUUGGAUU CUGAUGAGGCCGUUAGGCCGAA AGAUCUUG | 10455 |
| 6187 | AUCUAAAUC CAAACAAA | 1037 | UUUGUUUG CUGAUGAGGCCGUUAGGCCGAA AUUUAGAU | 10456 |
| 6204 | AGCAGGCUA GAGCCAGA | 1038 | UCUGGCUC CUGAUGAGGCCGUUAGGCCGAA AGCCUGCU | 10457 |
| 6226 | GGACAAAUC UUUGUUGU | 1039 | ACAACAAA CUGAUGAGGCCGUUAGGCCGAA AUUUGUCC | 10458 |
| 6228 | ACAAAUCUU UGUUGUUC | 1040 | GAACAACA CUGAUGAGGCCGUUAGGCCGAA AGAUUUGU | 10459 |
| 6229 | CAAAUCUUU GUUGUUCC | 1041 | GGAACAAC CUGAUGAGGCCGUUAGGCCGAA AAGAUUUG | 10460 |
| 6232 | AUCUUUGUU GUUCCUCU | 1042 | AGAGGAAC CUGAUGAGGCCGUUAGGCCGAA ACAAAGAU | 10461 |
| 6235 | UUUGUUGUU CCUCUUCU | 1043 | AGAAGAGG CUGAUGAGGCCGUUAGGCCGAA ACAACAAA | 10462 |
| 6236 | UUGUUGUUC CUCUUCUU | 1044 | AAGAAGAG CUGAUGAGGCCGUUAGGCCGAA AACAACAA | 10463 |
| 6239 | UUGUUCCUC UUCUUUAC | 1045 | GUAAAGAA CUGAUGAGGCCGUUAGGCCGAA AGGAACAA | 10464 |
| 6241 | GUUCCUCUU CUUUACAC | 1046 | GUGUAAAG CUGAUGAGGCCGUUAGGCCGAA AGAGGAAC | 10465 |
| 6242 | UUCCUCUUC UUUACACA | 1047 | UGUGUAAA CUGAUGAGGCCGUUAGGCCGAA AAGAGGAA | 10466 |
| 6244 | CCUCUUCUU UACACAUA | 1048 | UAUGUGUA CUGAUGAGGCCGUUAGGCCGAA AGAAGAGG | 10467 |
| 6245 | CUCUUCUUU ACACAUAC | 1049 | GUAUGUGU CUGAUGAGGCCGUUAGGCCGAA AAGAAGAG | 10468 |
| 6246 | UCUUCUUUA CACAUACG | 1050 | CGUAUGUG CUGAUGAGGCCGUUAGGCCGAA AAAGAAGA | 10469 |
| 6252 | UUACACAUA CGCAAACC | 1051 | GGUUUGCG CUGAUGAGGCCGUUAGGCCGAA AUGUGUAA | 10470 |
| 6280 | CUGGCAAUU UUAUAAAU | 1052 | AUUUAUAA CUGAUGAGGCCGUUAGGCCGAA AUUGCCAG | 10471 |
| 6281 | UGGCAAUUU UAUAAAUC | 1053 | GAUUUAUA CUGAUGAGGCCGUUAGGCCGAA AAUUGCCA | 10472 |
| 6282 | GGCAAUUUU AUAAAUCA | 1054 | UGAUUUAU CUGAUGAGGCCGUUAGGCCGAA AAAUUGCC | 10473 |
| 6283 | GCAAUUUUA UAAAUCAG | 1055 | CUGAUUUA CUGAUGAGGCCGUUAGGCCGAA AAAAUUGC | 10474 |
| 6285 | AAUUUUAUA AAUCAGGU | 1056 | ACCUGAUU CUGAUGAGGCCGUUAGGCCGAA AUAAAAUU | 10475 |
| 6289 | UUAUAAAUC AGGUAACU | 1057 | AGUUACCU CUGAUGAGGCCGUUAGGCCGAA AUUUAUAA | 10476 |
| 6294 | AAUCAGGUA ACUGGAAG | 1058 | CUUCCAGU CUGAUGAGGCCGUUAGGCCGAA ACCUGAUU | 10477 |
| 6308 | AAGGAGGUU AAACUCAG | 1059 | CUGAGUUU CUGAUGAGGCCGUUAGGCCGAA ACCUCCUU | 10478 |
| 6309 | AGGAGGUUA AACUCAGA | 1060 | UCUGAGUU CUGAUGAGGCCGUUAGGCCGAA AACCUCCU | 10479 |
| 6314 | GUUAAACUC AGAAAAAA | 1061 | UUUUUUCU CUGAUGAGGCCGUUAGGCCGAA AGUUUAAC | 10480 |
| 6331 | GAAGACCUC AGUCAAUU | 1062 | AAUUGACU CUGAUGAGGCCGUUAGGCCGAA AGGUCUUC | 10481 |
| 6335 | ACCUCAGUC AAUUCUCU | 1063 | AGAGAAUU CUGAUGAGGCCGUUAGGCCGAA ACUGAGGU | 10482 |
| 6339 | CAGUCAAUU CUCUACUU | 1064 | AAGUAGAG CUGAUGAGGCCGUUAGGCCGAA AUUGACUG | 10483 |
| 6340 | AGUCAAUUC UCUACUUU | 1065 | AAAGUAGA CUGAUGAGGCCGUUAGGCCGAA AAUUGACU | 10484 |
| 6342 | UCAAUUCUC UACUUUUU | 1066 | AAAAAGUA CUGAUGAGGCCGUUAGGCCGAA AGAAUUGA | 10485 |
| 6344 | AAUUCUCUA CUUUUUUU | 1067 | AAAAAAAG CUGAUGAGGCCGUUAGGCCGAA AGAGAAUU | 10486 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 6347 | UCUCUACUU UUUUUUUU | 1068 | AAAAAAAA CUGAUGAGGCCGUUAGGCCGAA AGUAGAGA | 10487 |
| 6348 | CUCUACUUU UUUUUUUU | 1069 | AAAAAAAA CUGAUGAGGCCGUUAGGCCGAA AAGUAGAG | 10488 |
| 6349 | UCUACUUUU UUUUUUUU | 1070 | AAAAAAAA CUGAUGAGGCCGUUAGGCCGAA AAAGUAGA | 10489 |
| 6350 | CUACUUUUU UUUUUUUU | 1071 | AAAAAAAA CUGAUGAGGCCGUUAGGCCGAA AAAAGUAG | 10490 |
| 6351 | UACUUUUUU UUUUUUUU | 1072 | AAAAAAAA CUGAUGAGGCCGUUAGGCCGAA AAAAAGUA | 10491 |
| 6352 | ACUUUUUUU UUUUUUUU | 1073 | AAAAAAAA CUGAUGAGGCCGUUAGGCCGAA AAAAAAGU | 10492 |
| 6353 | CUUUUUUUU UUUUUUUU | 1074 | AAAAAAAA CUGAUGAGGCCGUUAGGCCGAA AAAAAAAG | 10493 |
| 6354 | UUUUUUUUU UUUUUUUC | 1075 | GAAAAAAA CUGAUGAGGCCGUUAGGCCGAA AAAAAAAA | 10494 |
| 6355 | UUUUUUUUU UUUUUUCC | 1076 | GGAAAAAA CUGAUGAGGCCGUUAGGCCGAA AAAAAAAA | 10495 |
| 6356 | UUUUUUUUU UUUUUCCA | 1077 | UGGAAAAA CUGAUGAGGCCGUUAGGCCGAA AAAAAAAA | 10496 |
| 6357 | UUUUUUUUU UUUUCCAA | 1078 | UUGGAAAA CUGAUGAGGCCGUUAGGCCGAA AAAAAAAA | 10497 |
| 6358 | UUUUUUUUU UUUCCAAA | 1079 | UUUGGAAA CUGAUGAGGCCGUUAGGCCGAA AAAAAAAA | 10498 |
| 6359 | UUUUUUUUU UUCCAAAU | 1080 | AUUUGGAA CUGAUGAGGCCGUUAGGCCGAA AAAAAAAA | 10499 |
| 6360 | UUUUUUUUU UCCAAAUC | 1081 | GAUUUGGA CUGAUGAGGCCGUUAGGCCGAA AAAAAAAA | 10500 |
| 6361 | UUUUUUUUU CCAAAUCA | 1082 | UGAUUUGG CUGAUGAGGCCGUUAGGCCGAA AAAAAAAA | 10501 |
| 6362 | UUUUUUUUC CAAAUCAG | 1083 | CUGAUUUG CUGAUGAGGCCGUUAGGCCGAA AAAAAAAA | 10502 |
| 6368 | UUCCAAAUC AGAUAAUA | 1084 | UAUUAUCU CUGAUGAGGCCGUUAGGCCGAA AUUUGGAA | 10503 |
| 6373 | AAUCAGAUA AUAGCCCA | 1085 | UGGGCUAU CUGAUGAGGCCGUUAGGCCGAA AUCUGAUU | 10504 |
| 6376 | CAGAUAAUA GCCCAGCA | 1086 | UGCUGGGC CUGAUGAGGCCGUUAGGCCGAA AUUAUCUG | 10505 |
| 6388 | CAGCAAAUA GUGAUAAC | 1087 | GUUAUCAC CUGAUGAGGCCGUUAGGCCGAA AUUUGCUG | 10506 |
| 6394 | AUAGUGAUA ACAAAUAA | 1088 | UUAUUUGU CUGAUGAGGCCGUUAGGCCGAA AUCACUAU | 10507 |
| 6401 | UAACAAAUA AAACCUUA | 1089 | UAAGGUUU CUGAUGAGGCCGUUAGGCCGAA AUUUGUUA | 10508 |
| 6408 | UAAAACCUU AGCUGUUC | 1090 | GAACAGCU CUGAUGAGGCCGUUAGGCCGAA AGGUUUUA | 10509 |
| 6409 | AAAACCUUA GCUGUUCA | 1091 | UGAACAGC CUGAUGAGGCCGUUAGGCCGAA AAGGUUUU | 10510 |
| 6415 | UUAGCUGUU CAUGUCUU | 1092 | AAGACAUG CUGAUGAGGCCGUUAGGCCGAA ACAGCUAA | 10511 |
| 6416 | UAGCUGUUC AUGUCUUG | 1093 | CAAGACAU CUGAUGAGGCCGUUAGGCCGAA AACAGCUA | 10512 |
| 6421 | GUUCAUGUC UUGAUUUC | 1094 | GAAAUCAA CUGAUGAGGCCGUUAGGCCGAA ACAUGAAC | 10513 |
| 6423 | UCAUGUCUU GAUUUCAA | 1095 | UUGAAAUC CUGAUGAGGCCGUUAGGCCGAA AGACAUGA | 10514 |
| 6427 | GUCUUGAUU UCAAUAAU | 1096 | AUUAUUGA CUGAUGAGGCCGUUAGGCCGAA AUCAAGAC | 10515 |
| 6428 | UUCUGAUUU CAAUAAUU | 1097 | AAUUAUUG CUGAUGAGGCCGUUAGGCCGAA AAUCAAGA | 10516 |
| 6429 | CUUGAUUUC AAUAAUUA | 1098 | UAAUUAUU CUGAUGAGGCCGUUAGGCCGAA AAAUCAAG | 10517 |
| 6433 | AUUUCAAUA AUUAAUUC | 1099 | GAAUUAAU CUGAUGAGGCCGUUAGGCCGAA AUUGAAAU | 10518 |
| 6436 | UCAAUAAUU AAUUCUUA | 1100 | UAAGAAUU CUGAUGAGGCCGUUAGGCCGAA AUUAUUGA | 10519 |
| 6437 | CAAUAAUUA AUUCUUAA | 1101 | UUAAGAAU CUGAUGAGGCCGUUAGGCCGAA AAUUAUUG | 10520 |
| 6440 | UAAUUAAUU CUUAAUCA | 1102 | UGAUUAAG CUGAUGAGGCCGUUAGGCCGAA AUUAAUUA | 10521 |
| 6441 | AAUUAAUUC UUAAUCAU | 1103 | AUGAUUAA CUGAUGAGGCCGUUAGGCCGAA AAUUAAUU | 10522 |
| 6443 | UUAAUUCUU AAUCAUUA | 1104 | UAAUGAUU CUGAUGAGGCCGUUAGGCCGAA AGAAUUAA | 10523 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 6444 | UAAUUCUUA AUCAUUAA | 1105 | UUAAUGAU CUGAUGAGGCCGUUAGGCCGAA AAGAAUUA | 10524 |
| 6447 | UUCUUAAUC AUUAAGAG | 1106 | CUCUUAAU CUGAUGAGGCCGUUAGGCCGAA AUUAAGAA | 10525 |
| 6450 | UUAAUCAUU AAGAGACC | 1107 | GGUCUCUU CUGAUGAGGCCGUUAGGCCGAA AUGAUUAA | 10526 |
| 6451 | UAAUCAUUA AGAGACCA | 1108 | UGGUCUCU CUGAUGAGGCCGUUAGGCCGAA AAUGAUUA | 10527 |
| 6461 | GAGACCAUA AUAAAUAC | 1109 | GUAUUUAU CUGAUGAGGCCGUUAGGCCGAA AUGGUCUC | 10528 |
| 6464 | ACCAUAAUA AAUACUCC | 1110 | GGAGUAUU CUGAUGAGGCCGUUAGGCCGAA AUUAUGGU | 10529 |
| 6468 | UAAUAAAUA CUCCUUUU | 1111 | AAAAGGAG CUGAUGAGGCCGUUAGGCCGAA AUUUAUUA | 10530 |
| 6471 | UAAAUACUC CUUUUCAA | 1112 | UUGAAAAG CUGAUGAGGCCGUUAGGCCGAA AGUAUUUA | 10531 |
| 6474 | AUACUCCUU UUCAAGAG | 1113 | CUCUUGAA CUGAUGAGGCCGUUAGGCCGAA AGGAGUAU | 10532 |
| 6475 | UACUCCUUU UCAAGAGA | 1114 | UCUCUUGA CUGAUGAGGCCGUUAGGCCGAA AAGGAGUA | 10533 |
| 6476 | ACUCCUUUU CAAGAGAA | 1115 | UUCUCUUG CUGAUGAGGCCGUUAGGCCGAA AAAGGAGU | 10534 |
| 6477 | CUCCUUUUC AAGAGAAA | 1116 | UUUCUCUU CUGAUGAGGCCGUUAGGCCGAA AAAAGGAG | 10535 |
| 6497 | AAAACCAUU AGAAUUGU | 1117 | ACAAUUCU CUGAUGAGGCCGUUAGGCCGAA AUGGUUUU | 10536 |
| 6498 | AAACCAUUA GAAUUGUU | 1118 | AACAAUUC CUGAUGAGGCCGUUAGGCCGAA AAUGGUUU | 10537 |
| 6503 | AUUAGAAUU GUUACUCA | 1119 | UGAGUAAC CUGAUGAGGCCGUUAGGCCGAA AUUCUAAU | 10538 |
| 6506 | AGAAUUGUU ACUCAGCU | 1120 | AGCUGAGU CUGAUGAGGCCGUUAGGCCGAA ACAAUUCU | 10539 |
| 6507 | GAAUUGUUA CUCAGCUC | 1121 | GACCUGAG CUGAUGAGGCCGUUAGGCCGAA AACAAUUC | 10540 |
| 6510 | UUGUUACUC AGCUCCUU | 1122 | AAGGAGCU CUGAUGAGGCCGUUAGGCCGAA AGUAACAA | 10541 |
| 6515 | ACUCAGCUC CUUCAAAC | 1123 | GUUUGAAG CUGAUGAGGCCGUUAGGCCGAA AGCUGAGU | 10542 |
| 6518 | CAGCUCCUU CAAACUCA | 1124 | UGAGUUUG CUGAUGAGGCCGUUAGGCCGAA AGGAGCUG | 10543 |
| 6519 | AGCUCCUUC AAACUCAG | 1125 | CUGAGUUU CUGAUGAGGCCGUUAGGCCGAA AAGGAGCU | 10544 |
| 6525 | UUCAAACUC AGGUUUGU | 1126 | ACAAACCU CUGAUGAGGCCGUUAGGCCGAA AGUUUGAA | 10545 |
| 6530 | ACUCAGGUU UGUAGCAU | 1127 | AUGCUACA CUGAUGAGGCCGUUAGGCCGAA ACCUGAGU | 10546 |
| 6531 | CUCAGGUUU GUAGCAUA | 1128 | UAUGCUAC CUGAUGAGGCCGUUAGGCCGAA AACCUGAG | 10547 |
| 6534 | AGGUUUGUA GCAUACAU | 1129 | AUGUAUGC CUGAUGAGGCCGUUAGGCCGAA ACAAACCU | 10548 |
| 6539 | UUGUAGCAUA CAUGAGUC | 1130 | GACUCAUG CUGAUGAGGCCGUUAGGCCGAA AUGCUACA | 10549 |
| 6547 | ACAUGAGUC CAUCCAUC | 1131 | GAUGGAUG CUGAUGAGGCCGUUAGGCCGAA ACUCAUGU | 10550 |
| 6551 | GAGUCCAUC CAUCAGUC | 1132 | GACUGAUG CUGAUGAGGCCGUUAGGCCGAA AUGGACUC | 10551 |
| 6555 | CCAUCCAUC AGUCAAAG | 1133 | CUUUGACU CUGAUGAGGCCGUUAGGCCGAA AUGGAUGG | 10552 |
| 6559 | CCAUCAGUC AAAGAAUG | 1134 | CAUUCUUU CUGAUGAGGCCGUUAGGCCGAA ACUGAUGG | 10553 |
| 6570 | AGAAUGGUU CCAUCUGG | 1135 | CCAGAUGG CUGAUGAGGCCGUUAGGCCGAA ACCAUUCU | 10554 |
| 6571 | GAAUGGUUC CAUCUGGA | 1136 | UCCAGAUG CUGAUGAGGCCGUUAGGCCGAA AACCAUUC | 10555 |
| 6575 | GGUUCCAUC UGGAGUCU | 1137 | AGACUCCA CUGAUGAGGCCGUUAGGCCGAA AUGGAACC | 10556 |
| 6582 | UCUGCAGUC UUAAUGUA | 1138 | UACAUUAA CUGAUGAGGCCGUUAGGCCGAA ACUCCAGA | 10557 |
| 6584 | UGGAGUCUU AAUGUAGA | 1139 | UCUACAUU CUGAUGAGGCCGUUAGGCCGAA AGACUCCA | 10558 |
| 6585 | GGAGUCUUA AUGUAGAA | 1140 | UUCUACAU CUGAUGAGGCCGUUAGGCCGAA AAGACUCC | 10559 |
| 6590 | CUUAAUGUA GAAAGAAA | 1141 | UUUCUUUC CUGAUGAGGCCGUUAGGCCGAA ACAUUAAG | 10560 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 6609 | UGGAGACUU GUAAUAAU | 1142 | AUUAUUAC CUGAUGAG<u>GCCGUUAGGCC</u>GAA AGUCUCCA | 10561 |
| 6612 | AGACUUGUA AUAAUGAG | 1143 | CUCAUUAU CUGAUGAG<u>GCCGUUAGGCC</u>GAA ACAAGUCU | 10562 |
| 6615 | CUUGUAAUA AUGAGCUA | 1144 | UAGCUCAU CUGAUGAG<u>GCCGUUAGGCC</u>GAA AUUACAAG | 10563 |
| 6623 | AAUGAGCUA GUUACAAA | 1145 | UUUGUAAC CUGAUGAG<u>GCCGUUAGGCC</u>GAA AGCUCAUU | 10564 |
| 6626 | GAGCUAGUU ACAAAGUG | 1146 | CACUUUGU CUGAUGAG<u>GCCGUUAGGCC</u>GAA ACUAGCUC | 10565 |
| 6627 | AGCUAGUUA CAAAGUGC | 1147 | GCACUUUG CUGAUGAG<u>GCCGUUAGGCC</u>GAA AACUAGCU | 10566 |
| 6637 | AAAGUGCUU GUUCAUUA | 1148 | UAAUGAAC CUGAUGAG<u>GCCGUUAGGCC</u>GAA AGCACUUU | 10567 |
| 6640 | GUGCUUGUU CAUUAAAA | 1149 | UUUUAAUG CUGAUGAG<u>GCCGUUAGGCC</u>GAA ACAAGCAC | 10568 |
| 6641 | UGCUUGUUC AUUAAAAU | 1150 | AUUUUAAU CUGAUGAG<u>GCCGUUAGGCC</u>GAA AACAAGCA | 10569 |
| 6644 | UUGUUCAUU AAAAUAGC | 1151 | GCUAUUUU CUGAUGAG<u>GCCGUUAGGCC</u>GAA AUGAACAA | 10570 |
| 6645 | UGUUCAUUA AAAUAGCA | 1152 | UGCUAUUU CUGAUGAG<u>GCCGUUAGGCC</u>GAA AAUGAACA | 10571 |
| 6650 | AUUAAAAUA GCACUGAA | 1153 | UUCAGUGC CUGAUGAG<u>GCCGUUAGGCC</u>GAA AUUUUAAU | 10572 |
| 6662 | CUGAAAAUU GAAACAUG | 1154 | CAUGUUUC CUGAUGAG<u>GCCGUUAGGCC</u>GAA AUUUUCAG | 10573 |
| 6674 | ACAUGAAUU AACUGAUA | 1155 | UAUCAGUU CUGAUGAG<u>GCCGUUAGGCC</u>GAA AUUCAUGU | 10574 |
| 6675 | CAUGAAUUA ACUGAUAA | 1156 | UUAUCAGU CUGAUGAG<u>GCCGUUAGGCC</u>GAA AAUUCAUG | 10575 |
| 6682 | UAACUGAUA AUAUUCCA | 1157 | UGGAAUAU CUGAUGAG<u>GCCGUUAGGCC</u>GAA AUCAGUUA | 10576 |
| 6685 | CUGAUAAUA UUCCAAUC | 1158 | GAUUGGAA CUGAUGAG<u>GCCGUUAGGCC</u>GAA AUUAUCAG | 10577 |
| 6687 | GAUAAUAUU CCAAUCAU | 1159 | AUGAUUGG CUGAUGAG<u>GCCGUUAGGCC</u>GAA AUAUUAUC | 10578 |
| 6688 | AUAAUAUUC CAAUCAUU | 1160 | AAUGAUUG CUGAUGAG<u>GCCGUUAGGCC</u>GAA AAUAUUAU | 10579 |
| 6693 | AUUCCAAUC AUUUGCCA | 1161 | UGGCAAAU CUGAUGAG<u>GCCGUUAGGCC</u>GAA AUUGGAAU | 10580 |
| 6696 | CCAAUCAUU UGCCAUUU | 1162 | AAAUGGCA CUGAUGAG<u>GCCGUUAGGCC</u>GAA AUGAUUGG | 10581 |
| 6697 | CAAUCAUUU GCCAUUUA | 1163 | UAAAUGGC CUGAUGAG<u>GCCGUUAGGCC</u>GAA AAUGAUUG | 10582 |
| 6703 | UUUGCCAUU UAUGACAA | 1164 | UUGUCAUA CUGAUGAG<u>GCCGUUAGGCC</u>GAA AUGGCAAA | 10583 |
| 6704 | UUGCCAUUU AUGACAAA | 1165 | UUUGUCAU CUGAUGAG<u>GCCGUUAGGCC</u>GAA AAUGGCAA | 10584 |
| 6705 | UGCCAUUUA UGACAAAA | 1166 | UUUUGUCA CUGAUGAG<u>GCCGUUAGGCC</u>GAA AAAUGGCA | 10585 |
| 6719 | AAAAUGGUU GGCACUAA | 1167 | UUAGUGCC CUGAUGAG<u>GCCGUUAGGCC</u>GAA ACCAUUUU | 10586 |
| 6726 | UUGGCACUA ACAAAGAA | 1168 | UUCUUUGU CUGAUGAG<u>GCCGUUAGGCC</u>GAA AGUGCCAA | 10587 |
| 6743 | CGAGCACUU CCUUUCAG | 1169 | CUGAAAGG CUGAUGAG<u>GCCGUUAGGCC</u>GAA AGUGCUCG | 10588 |
| 6744 | GAGCACUUC CUUUCAGA | 1170 | UCUGAAAG CUGAUGAG<u>GCCGUUAGGCC</u>GAA AAGUGCUC | 10589 |
| 6747 | CACUUCCUU UCAGAGUU | 1171 | AACUCUGA CUGAUGAG<u>GCCGUUAGGCC</u>GAA AGGAAGUG | 10590 |
| 6748 | ACUUCCUUU CAGAGUUU | 1172 | AAACUCUG CUGAUGAG<u>GCCGUUAGGCC</u>GAA AAGGAAGU | 10591 |
| 6749 | CUUCCUUUC AGAGUUUC | 1173 | GAAACUCU CUGAUGAG<u>GCCGUUAGGCC</u>GAA AAAGGAAG | 10592 |
| 6755 | UUCAGAGUU UCUGAGAU | 1174 | AUCUCAGA CUGAUGAG<u>GCCGUUAGGCC</u>GAA ACUCUGAA | 10593 |
| 6756 | UCAGAGUUU CUGAGAUA | 1175 | CAUCUCAG CUGAUGAG<u>GCCGUUAGGCC</u>GAA AACUCUGA | 10594 |
| 6757 | CAGAGUUUC UGAGAUAA | 1176 | UUAUCUCA CUGAUGAG<u>GCCGUUAGGCC</u>GAA AAACUCUG | 10595 |
| 6764 | UCUGAGAUA AUGUACGU | 1177 | ACGUACAU CUGAUGAG<u>GCCGUUAGGCC</u>GAA AUCUCAGA | 10596 |
| 6769 | GAUAAUGUA CGUGGAAC | 1178 | GUUCCACG CUGAUGAG<u>GCCGUUAGGCC</u>GAA ACAUUAUC | 10597 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 6781 | GGAACAGUC UGGGUGGA | 1179 | UCCACCCA CUGAUGAGGCCGUUAGGCCGAA ACUGUUCC | 10598 |
| 6814 | GUGCAAGUC UGUGUCUU | 1180 | AAGACACA CUGAUGAGGCCGUUAGGCCGAA ACUUGCAC | 10599 |
| 6820 | GUCUGUGUC UUGUCAGU | 1181 | ACUGACAA CUGAUGAGGCCGUUAGGCCGAA ACACAGAC | 10600 |
| 6822 | CUGUGUCUU GUCAGUCC | 1182 | GGACUGAC CUGAUGAGGCCGUUAGGCCGAA AGACACAG | 10601 |
| 6825 | UGUCCUGUC AGUCCAAG | 1183 | CUUGGACU CUGAUGAGGCCGUUAGGCCGAA ACAAGACA | 10602 |
| 6829 | UUGUCAGUC CAAGAAGU | 1184 | ACUUCUUG CUGAUGAGGCCGUUAGGCCGAA ACUGACAA | 10603 |
| 6851 | CGAGAUGUU AAUUUUAG | 1185 | CUAAAAUU CUGAUGAGGCCGUUAGGCCGAA ACAUCUCG | 10604 |
| 6852 | GAGAUGUUA AUUUUAGG | 1186 | CCUAAAAU CUGAUGAGGCCGUUAGGCCGAA AACAUCUC | 10605 |
| 6855 | AUGUUAAUU UUAGGGAC | 1187 | GUCCCUAA CUGAUGAGGCCGUUAGGCCGAA AUUAACAU | 10606 |
| 6856 | UGUUAAUUU UAGGGACC | 1188 | GGUCCCUA CUGAUGAGGCCGUUAGGCCGAA AAUUAACA | 10607 |
| 6857 | GUUAAUUUU AGGGACCC | 1189 | GGGUCCCU CUGAUGAGGCCGUUAGGCCGAA AAAUUAAC | 10608 |
| 6858 | UUAAUUUUA GGGACCCG | 1190 | CGGGUCCC CUGAUGAGGCCGUUAGGCCGAA AAAAUUAA | 10609 |
| 6872 | CCGUGCCUU GUUUCCUA | 1191 | UAGGAAAC CUGAUGAGGCCGUUAGGCCGAA AGGCACGG | 10610 |
| 6875 | UGCCUUGUU UCCUAGCC | 1192 | GGCUAGGA CUGAUGAGGCCGUUAGGCCGAA ACAAGGCA | 10611 |
| 6876 | GCCUUGUUU CCUAGCCC | 1193 | GGGCUAGG CUGAUGAGGCCGUUAGGCCGAA AACAAGGC | 10612 |
| 6877 | CCUUGUUUC CUAGCCCA | 1194 | UGGGCUAG CUGAUGAGGCCGUUAGGCCGAA AAACAAGG | 10613 |
| 6880 | UGUUUCCUA GCCCACAA | 1195 | UUGUGGGC CUGAUGAGGCCGUUAGGCCGAA AGGAAACA | 10614 |
| 6901 | GCAAACAUC AAACAGAU | 1196 | AUCUGUUU CUGAUGAGGCCGUUAGGCCGAA AUGUUUGC | 10615 |
| 6910 | AAACAGAUA CUCGCUAG | 1197 | CUAGCGAG CUGAUGAGGCCGUUAGGCCGAA AUCUGUUU | 10616 |
| 6913 | CAGAUACUC GCUAGCCU | 1198 | AGGCUAGC CUGAUGAGGCCGUUAGGCCGAA AGUAUCUG | 10617 |
| 6917 | UACUCGCUA GCCUCAUU | 1199 | AAUGAGGC CUGAUGAGGCCGUUAGGCCGAA AGCGAGUA | 10618 |
| 6922 | GCUAGCCUC AUUUAAAU | 1200 | AUUUAAAU CUGAUGAGGCCGUUAGGCCGAA AGGCUAGC | 10619 |
| 6925 | AGCCUCAUU UAAAUUGA | 1201 | UCAAUUUA CUGAUGAGGCCGUUAGGCCGAA AUGAGGCU | 10620 |
| 6926 | GCCUCAUUU AAAUUGAU | 1202 | AUCAAUUU CUGAUGAGGCCGUUAGGCCGAA AAUGAGGC | 10621 |
| 6927 | CCUCAUUUA AAUUGAUU | 1203 | AAUCAAUU CUGAUGAGGCCGUUAGGCCGAA AAAUGAGG | 10622 |
| 6931 | AUUUAAAUU GAUUAAAG | 1204 | CUUUAAUC CUGAUGAGGCCGUUAGGCCGAA AUUUAAAU | 10623 |
| 6935 | AAAUUGAUU AAAGGAGG | 1205 | CCUCCUUU CUGAUGAGGCCGUUAGGCCGAA AUCAAUUU | 10624 |
| 6936 | AAUUGAUUA AAGGAGGA | 1206 | UCCUCCUU CUGAUGAGGCCGUUAGGCCGAA AAUCAAUU | 10625 |
| 6951 | GAGUGCAUC UUUGGCCG | 1207 | CGGCCAAA CUGAUGAGGCCGUUAGGCCGAA AUGCACUC | 10626 |
| 6953 | GUGCAUCUU UGGCCGAC | 1208 | GUCGGCCA CUGAUGAGGCCGUUAGGCCGAA AGAUGCAC | 10627 |
| 6954 | UGCAUCUUU GGCCGACA | 1209 | UGUCGGCC CUGAUGAGGCCGUUAGGCCGAA AAGAUGCA | 10628 |
| 6970 | AGUGGUGUA ACUGUGUG | 1210 | CACACAGU CUGAUGAGGCCGUUAGGCCGAA ACACCACU | 10629 |
| 7026 | GUGGGUGUA UGUGUGUU | 1211 | AACACACA CUGAUGAGGCCGUUAGGCCGAA ACACCCAC | 10630 |
| 7034 | AUGUGUGUU UUGUGCAU | 1212 | AUGCACAA CUGAUGAGGCCGUUAGGCCGAA ACACACAU | 10631 |
| 7035 | UGUGUGUUU UGUGCAUA | 1213 | UAUGCACA CUGAUGAGGCCGUUAGGCCGAA AACACACA | 10632 |
| 7036 | GUGUGUUUU GUGCAUAA | 1214 | UUAUGCAC CUGAUGAGGCCGUUAGGCCGAA AAACACAC | 10633 |
| 7043 | UUGUGCAUA ACUAUUUA | 1215 | UAAAUAGU CUGAUGAGGCCGUUAGGCCGAA AUGCACAA | 10634 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 7047 | GCAUAACUA UUUAAGGA | 1216 | UCCUUAAA CUGAUGAGGCCGUUAGGCCGAA AGUUAUGC | 10635 |
| 7049 | AUAACUAUU UAAGGAAA | 1217 | UUUCCUUA CUGAUGAGGCCGUUAGGCCGAA AUAGUUAU | 10636 |
| 7050 | UAACUAUUU AAGGAAAC | 1218 | GUUUCCUU CUGAUGAGGCCGUUAGGCCGAA AAUAGUUA | 10637 |
| 7051 | AACUAUUUA AGGAAACU | 1219 | AGUUUCCU CUGAUGAGGCCGUUAGGCCGAA AAAUAGUU | 10638 |
| 7065 | ACUGGAAUU UUAAAGUU | 1220 | AACUUUAA CUGAUGAGGCCGUUAGGCCGAA AUUCCAGU | 10639 |
| 7066 | CUGGAAUUU UAAAGUUA | 1221 | UAACUUUA CUGAUGAGGCCGUUAGGCCGAA AAUUCCAG | 10640 |
| 7067 | UGGAAUUUU AAAGUUAC | 1222 | GUAACUUU CUGAUGAGGCCGUUAGGCCGAA AAAUUCCA | 10641 |
| 7068 | GGAAUUUUA AAGUUACU | 1223 | AGUAACUU CUGAUGAGGCCGUUAGGCCGAA AAAAUUCC | 10642 |
| 7073 | UUUAAAGUU ACUUUUAU | 1224 | AUAAAAGU CUGAUGAGGCCGUUAGGCCGAA ACUUUAAA | 10643 |
| 7074 | UUAAAGUUA CUUUUAUA | 1225 | UAUAAAAG CUGAUGAGGCCGUUAGGCCGAA AACUUUAA | 10644 |
| 7077 | AAGUUACUU UUAUACAA | 1226 | UUGUAUAA CUGAUGAGGCCGUUAGGCCGAA AGUAACUU | 10645 |
| 7078 | AGUUACUUU UAUACAAA | 1227 | UUUGUAUA CUCAUGAGGCCGUUAGGCCGAA AAGUAACU | 10646 |
| 7079 | GUUACUUUU AUACAAAC | 1228 | GUUUGUAU CUGAUGAGGCCGUUAGGCCGAA AAAGUAAC | 10647 |
| 7080 | UUACUUUUA UACAAACC | 1229 | GGUUUGUA CUGAUGAGGCCGUUAGGCCGAA AAAAGUAA | 10648 |
| 7082 | ACUUUUAUA CAAACCAA | 1230 | UUGGUUUG CUGAUGAGGCCGUUAGGCCGAA AUAAAAGU | 10649 |
| 7095 | CCAAGAAUA UAUGCUAC | 1231 | GUAGCAUA CUGAUGAGGCCGUUAGGCCGAA AUUCUUGG | 10650 |
| 7097 | AAGAAUAUA UGCUACAG | 1232 | CUGUAGCA CUGAUGAGGCCGUUAGGCCGAA AUAUUCUU | 10651 |
| 7102 | UAUAUGCUA CAGAUAUA | 1233 | UAUAUCUG CUGAUGAGGCCGUUAGGCCGAA AGCAUAUA | 10652 |
| 7108 | CUACAGAUA UAAGACAG | 1234 | CUGUCUUA CUGAUGAGGCCGUUAGGCCGAA AUCUGUAG | 10653 |
| 7110 | ACAGAUAUA AGACAGAC | 1235 | GUCUGUCU CUGAUGAGGCCGUUAGGCCGAA AUAUCUGU | 10654 |
| 7124 | GACAUGGUU UGGUCCUA | 1236 | UAGGACCA CUGAUGAGGCCGUUAGGCCGAA ACCAUGUC | 10655 |
| 7125 | ACAUGGUUU GGUCCUAU | 1237 | AUAGGACC CUGAUGAGGCCGUUAGGCCGAA AACCAUGU | 10656 |
| 7129 | GGUUUGGUC UAUAUUU | 1238 | AAAUAUAG CUGAUGAGGCCGUUAGGCCGAA ACCAAACC | 10657 |
| 7132 | UUGGUCCUA UAUUUCUA | 1239 | UAGAAAUA CUGAUGAGGCCGUUAGGCCGAA AGGACCAA | 10658 |
| 7134 | UGUCCUAUA UUUCUAGU | 1240 | ACUAGAAA CUGAUGAGGCCGUUAGGCCGAA AUAGGACC | 10659 |
| 7136 | UCCUAUAUU UCUAGUCA | 1241 | UGACUAGA CUGAUGAGGCCGUUAGGCCGAA AUAUAGGA | 10660 |
| 7137 | CCUAUAUUU CUAGUCAU | 1242 | AUGACUAG CUGAUGAGGCCGUUAGGCCGAA AAUAUAGG | 10661 |
| 7138 | CUAUAUUUC UAGUCAUG | 1243 | CAUGACUA CUGAUGAGGCCGUUAGGCCGAA AAAUAUAG | 10662 |
| 7140 | AUAUUUCUA GUCAUGAU | 1244 | AUCAUGAC CUGAUGAGGCCGUUAGGCCGAA AGAAAUAU | 10663 |
| 7143 | UUUCUAGUC AUGAUGAA | 1245 | UUCAUCAU CUGAUGAGGCCGUUAGGCCGAA ACUAGAAA | 10664 |
| 7155 | AUGAAUGUA UUUUGUAU | 1246 | AUACAAAA CUGAUGAGGCCGUUAGGCCGAA ACAUUCAU | 10665 |
| 7157 | GAAUGUAUU UUGUAUAC | 1247 | GUAUACAA CUGAUGAGGCCGUUAGGCCGAA AUACAUUC | 10666 |
| 7158 | AAUGUAUUU UGUAUACC | 1248 | GGUAUACA CUGAUGAGGCCGUUAGGCCGAA AAUACAUU | 10667 |
| 7159 | AUGUAUUUU GUAUACCA | 1249 | UGGUAUAC CUGAUGAGGCCGUUAGGCCGAA AAAUACAU | 10668 |
| 7162 | UAUUUUGUA UACCAUCU | 1250 | AGAUGGUA CUGAUGAGGCCGUUAGGCCGAA ACAAAAUA | 10669 |
| 7164 | UUUUGUAUA CCAUCUUC | 1251 | GAAGAUGG CUGAUGAGGCCGUUAGGCCGAA AUACAAAA | 10670 |
| 7169 | UAUACCAUC UUCAUAUA | 1252 | UAUAUGAA CUGAUGAGGCCGUUAGGCCGAA AUGGUAUA | 10671 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 7171 | UACCAUCUU CAUAUAAU | 1253 | AUUAUAUG CUGAUGAGGCCGUUAGGCCGAA AGAUGGUA | 10672 |
| 7172 | ACCAUCUUC AUAUAAUA | 1254 | UAUUAUAU CUGAUGAGGCCGUUAGGCCGAA AAGAUGGU | 10673 |
| 7175 | AUCUUCAUA UAAUAUAC | 1255 | GUAUAUUA CUGAUGAGGCCGUUAGGCCGAA AUGAAGAU | 10674 |
| 7177 | CUUCAUAUA AUAUACUU | 1256 | AAGUAUAU CUGAUGAGGCCGUUAGGCCGAA AUAUGAAG | 10675 |
| 7180 | CAUAUAAUA UACUUAAA | 1257 | UUUAAGUA CUGAUGAGGCCGUUAGGCCGAA AUUAUAUG | 10676 |
| 7182 | UAUAAUAUA CUUAAAAA | 1258 | UUUUUAAG CUGAUGAGGCCGUUAGGCCGAA AUAUUAUA | 10677 |
| 7185 | AAUAUACUU AAAAAUAU | 1259 | AUAUUUUU CUGAUGAGGCCGUUAGGCCGAA AGUAUAUU | 10678 |
| 7186 | AUAUACUUA AAAAUAUU | 1260 | AAUAUUUU CUGAUGAGGCCGUUAGGCCGAA AAGUAUAU | 10679 |
| 7192 | UUAAAAAUA UUUCUUAA | 1261 | UUAAGAAA CUGAUGAGGCCGUUAGGCCGAA AUUUUUAA | 10680 |
| 7194 | AAAAAUAUU UCUUAAUU | 1262 | AAUUAAGA CUGAUGAGGCCGUUAGGCCGAA AUAUUUUU | 10681 |
| 7195 | AAAAUAUUU CUUAAUUG | 1263 | CAAUUAAG CUGAUGAGGCCGUUAGGCCGAA AAUAUUUU | 10682 |
| 7196 | AAAUAUUUC UUAAUUGG | 1264 | CCAAUUAA CUGAUGAGGCCGUUAGGCCGAA AAAUAUUU | 10683 |
| 7198 | AUAUUUCUU AAUUGGGA | 1265 | UCCCAAUU CUGAUGAGGCCGUUAGGCCGAA AGAAAUAU | 10684 |
| 7199 | UAUUUCUUA AUGGGAU | 1266 | AUCCCAAU CUGAUGAGGCCGUUAGGCCGAA AAGAAAUA | 10685 |
| 7202 | UUCUUAAUU GGGAUUUG | 1267 | CAAAUCCC CUGAUGAGGCCGUUAGGCCGAA AUUAAGAA | 10686 |
| 7208 | AUUGGGAUU UGUAAUCG | 1268 | CGAUUACA CUGAUGAGGCCGUUAGGCCGAA AUCCCAAU | 10687 |
| 7209 | UUGGGAUUU GUAAUCGU | 1269 | ACGAUUAC CUGAUGAGGCCGUUAGGCCGAA AAUCCCAA | 10688 |
| 7212 | GGAUUUGUA AUCGUACC | 1270 | GGUACGAU CUGAUGAGGCCGUUAGGCCGAA ACAAAUCC | 10689 |
| 7215 | UUUGUAAUC GUACCAAC | 1271 | GUUGGUAC CUGAUGAGGCCGUUAGGCCGAA AUUACAAA | 10690 |
| 7218 | GUAAUCGUA CCAACUUA | 1272 | UAAGUUGG CUGAUGAGGCCGUUAGGCCGAA ACGAUUAC | 10691 |
| 7225 | UACCAACUU AAUUGAUA | 1273 | UAUCAAUU CUGAUGAGGCCGUUAGGCCGAA AGUUGGUA | 10692 |
| 7226 | ACCAACUUA AUUGAUAA | 1274 | UUAUCAAU CUGAUGAGGCCGUUAGGCCGAA AAGUUGGU | 10693 |
| 7229 | AACUUAAUU GAUAAACU | 1275 | AGUUUAUC CUGAUGAGGCCGUUAGGCCGAA AUUAAGUU | 10694 |
| 7233 | UAAUUGAUA AACUUGGC | 1276 | GCCAAGUU CUGAUGAGGCCGUUAGGCCGAA AUCAAUUA | 10695 |
| 7238 | GAUAAACUU GGCAACUG | 1277 | CAGUUGCC CUGAUGAGGCCGUUAGGCCGAA AGUUUAUC | 10696 |
| 7249 | CAACUGCUU UUAUGUUC | 1278 | GAACAUAA CUGAUGAGGCCGUUAGGCCGAA AGCAGUUG | 10697 |
| 7250 | AACUGCUUU UAUGUUCU | 1279 | AGAACAUA CUGAUGAGGCCGUUAGGCCGAA AAGCAGUU | 10698 |
| 7251 | ACUGCUUUU AUGUUCUG | 1280 | CAGAACAU CUGAUGAGGCCGUUAGGCCGAA AAAGCAGU | 10699 |
| 7252 | CUGCUUUUA UGUUCUGU | 1281 | ACAGAACA CUGAUGAGGCCGUUAGGCCGAA AAAAGCAG | 10700 |
| 7256 | UUUUAUGUU CUGUCUCC | 1282 | GGAGACAG CUGAUGAGGCCGUUAGGCCGAA ACAUAAAA | 10701 |
| 7257 | UUUAUGUUC UGUCUCCU | 1283 | AGGAGACA CUGAUGAGGCCGUUAGGCCGAA AACAUAAA | 10702 |
| 7261 | UGUUCUGUC UCCUUCCA | 1284 | UGGAAGGA CUGAUGAGGCCGUUAGGCCGAA ACAGAACA | 10703 |
| 7263 | UUCUGUCUC CUUCCAUA | 1285 | UAUGGAAG CUGAUGAGGCCGUUAGGCCGAA AGACAGAA | 10704 |
| 7266 | UGUCCCUU CCAUAAAU | 1286 | AUUUAUGG CUGAUGAGGCCGUUAGGCCGAA AGGAGACA | 10705 |
| 7267 | GUCUCCUUC CAUAAAUU | 1287 | AAUUUAUG CUGAUGAGGCCGUUAGGCCGAA AAGGAGAC | 10706 |
| 7271 | CCUUCCAUA AAUUUUUC | 1288 | GAAAAAUU CUGAUGAGGCCGUUAGGCCGAA AUGGAAGG | 10707 |
| 7275 | CCAUAAAUU UUUCAAAA | 1289 | UUUUGAAA CUGAUGAGGCCGUUAGGCCGAA AUUUAUGG | 10708 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 7276 | CAUAAAUUU UUCAAAAU | 1290 | AUUUUGAA CUGAUGAGGCCGUUAGGCCGAA AAUUUAUG | 10709 |
| 7277 | AUAAAUUUU UCAAAAUA | 1291 | UAUUUUGA CUGAUGAGGCCGUUAGGCCGAA AAAUUUAU | 10710 |
| 7278 | UAAAUUUUU CAAAAUAC | 1292 | GUAUUUUG CUGAUGAGGCCGUUAGGCCGAA AAAAUUUA | 10711 |
| 7279 | AAAUUUUUC AAAAUACU | 1293 | AGUAUUUU CUGAUGAGGCCGUUAGGCCGAA AAAAAUUU | 10712 |
| 7285 | UUCAAAAUA CUAAUUCA | 1294 | UGAAUUAG CUGAUGAGGCCGUUAGGCCGAA AUUUUGAA | 10713 |
| 7288 | AAAAUACUA AUUCAACA | 1295 | UGUUGAAU CUGAUGAGGCCGUUAGGCCGAA AGUAUUUU | 10714 |
| 7291 | AUACUAAUU CAACAAAG | 1296 | CUUUGUUG CUGAUGAGGCCGUUAGGCCGAA AUUAGUAU | 10715 |
| 7292 | UACUAAUUC AACAAAGA | 1297 | UCUUUGUU CUGAUGAGGCCGUUAGGCCGAA AAUUAGUA | 10716 |
| 7308 | AAAAAGCUC UUUUUUUU | 1298 | AAAAAAAA CUGAUGAGGCCGUUAGGCCGAA AGCUUUUU | 10717 |
| 7310 | AAAGCUCUU UUUUUUCC | 1299 | GGAAAAAA CUGAUGAGGCCGUUAGGCCGAA AGAGCUUU | 10718 |
| 7311 | AAGCUCUUU UUUUUCCU | 1300 | AGGAAAAA CUGAUGAGGCCGUUAGGCCGAA AAGAGCUU | 10719 |
| 7312 | AGCUCUUUU UUUUCCUA | 1301 | UAGGAAAA CUGAUGAGGCCGUUAGGCCGAA AAAGAGCU | 10720 |
| 7313 | GCUCUUUUU UUUCCUAA | 1302 | UUAGGAAA CUGAUGAGGCCGUUAGGCCGAA AAAAGAGC | 10721 |
| 7314 | CUCUUUUUU UUCCUAAA | 1303 | UUUAGGAA CUGAUGAGGCCGUUAGGCCGAA AAAAAGAG | 10722 |
| 7315 | UCUUUUUUU UCCUAAAA | 1304 | UUUUAGGA CUGAUGAGGCCGUUAGGCCGAA AAAAAAGA | 10723 |
| 7316 | CUUUUUUUU CCUAAAAU | 1305 | AUUUUAGG CUGAUGAGGCCGUUAGGCCGAA AAAAAAAG | 10724 |
| 7317 | UUUUUUUUC CUAAAAUA | 1306 | UAUUUUAG CUGAUGAGGCCGUUAGGCCGAA AAAAAAAA | 10725 |
| 7320 | UUUUUCCUA AAAUAAAC | 1307 | GUUUAUUU CUGAUGAGGCCGUUAGGCCGAA AGGAAAAA | 10726 |
| 7325 | CCUAAAAUA AACUCAAA | 1308 | UUUGAGUU CUGAUGAGGCCGUUAGGCCGAA AUUUUAGG | 10727 |
| 7330 | AAUAAACUC AAAUUUAU | 1309 | AUAAAUUU CUGAUGAGGCCGUUAGGCCGAA AGUUUAUU | 10728 |
| 7335 | ACUCAAAUU UAUCCUUG | 1310 | CAAGGAUA CUGAUGAGGCCGUUAGGCCGAA AUUUGAGU | 10729 |
| 7336 | CUCAAAUUU AUCCUUGU | 1311 | ACAAGGAU CUGAUGAGGCCGUUAGGCCGAA AAUUUGAG | 10730 |
| 7337 | UCAAAUUUA UCCUUGUU | 1312 | AACAAGGA CUGAUGAGGCCGUUAGGCCGAA AAAUUUGA | 10731 |
| 7339 | AAAUUUAUC CUUGUUUA | 1313 | UAAACAAG CUGAUGAGGCCGUUAGGCCGAA AUAAAUUU | 10732 |
| 7342 | UUUAUCCUU GUUUAGAG | 1314 | CUCUAAAC CUGAUGAGGCCGUUAGGCCGAA AGGAUAAA | 10733 |
| 7345 | AUCCUUGUU UAGAGCAG | 1315 | CUGCUCUA CUGAUGAGGCCGUUAGGCCGAA ACAAGGAU | 10734 |
| 7346 | UCCUUGUUU AGAGCAGA | 1316 | UCUGCUCU CUGAUGAGGCCGUUAGGCCGAA AACAAGGA | 10735 |
| 7347 | CCUUGUUUA GAGCAGAG | 1317 | CUCUGCUC CUGAUGAGGCCGUUAGGCCGAA AAACAAGG | 10736 |
| 7362 | AGAAAAAUU AAGAAAAA | 1318 | UUUUUCUU CUGAUGAGGCCGUUAGGCCGAA AUUUUUCU | 10737 |
| 7363 | GAAAAAUUA AGAAAAAC | 1319 | GUUUUUCU CUGAUGAGGCCGUUAGGCCGAA AAUUUUUC | 10738 |
| 7373 | GAAAACUU UGAAAUGG | 1320 | CCAUUUCA CUGAUGAGGCCGUUAGGCCGAA AGUUUUUC | 10739 |
| 7374 | AAAAACUUU GAAAUGGU | 1321 | ACCAUUUC CUGAUGAGGCCGUUAGGCCGAA AAGUUUUU | 10740 |
| 7383 | GAAAUGGUC UCAAAAAA | 1322 | UUUUUUGA CUGAUGAGGCCGUUAGGCCGAA ACCAUUUC | 10741 |
| 7385 | AAUGGUCUC AAAAAAUU | 1323 | AAUUUUUU CUGAUGAGGCCGUUAGGCCGAA AGACCAUU | 10742 |
| 7393 | CAAAAAAUU GCUAAAUA | 1324 | UAUUUAGC CUGAUGAGGCCGUUAGGCCGAA AUUUUUUG | 10743 |
| 7397 | AAAUGCUA AAUAUUUU | 1325 | AAAAUAUU CUGAUGAGGCCGUUAGGCCGAA AGCAAUUU | 10744 |
| 7401 | UGCUAAAUA UUUUCAAU | 1326 | AUUGAAAA CUGAUGAGGCCGUUAGGCCGAA AUUUAGCA | 10745 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 7403 | CUAAAUAUU UUCAAUGG | 1327 | CCAUUGAA CUGAUGAGGCCGUUAGGCCGAA AUAUUUAG | 10746 |
| 7404 | UAAAUAUUU UCAAUGGA | 1328 | UCCAUUGA CUGAUGAGGCCGUUAGGCCGAA AAUAUUUA | 10747 |
| 7405 | AAAUAUUUU CAAUGGAA | 1329 | UUCCAUUG CUGAUGAGGCCGUUAGGCCGAA AAAUAUUU | 10748 |
| 7406 | AAUAUUUUC AAUGGAAA | 1330 | UUUCCAUU CUGAUGAGGCCGUUAGGCCGAA AAAAUAUU | 10749 |
| 7418 | GGAAAACUA AAUGUUAG | 1331 | CUAACAUU CUGAUGAGGCCGUUAGGCCGAA AGUUUUCC | 10750 |
| 7424 | CUAAAUGUU AGUUUAGC | 1332 | GCUAAACU CUGAUGAGGCCGUUAGGCCGAA ACAUUUAG | 10751 |
| 7425 | UAAAUGUUA GUUUAGCU | 1333 | AGCUAAAC CUGAUGAGGCCGUUAGGCCGAA AACAUUUA | 10752 |
| 7428 | AUGUUAGUU UAGCUGAU | 1334 | AUCAGCUA CUGAUGAGGCCGUUAGGCCGAA ACUAACAU | 10753 |
| 7429 | UGUUAGUUU AGCUGAUU | 1335 | AAUCAGCU CUGAUGAGGCCGUUAGGCCGAA AACUAACA | 10754 |
| 7430 | GUUAGUUUA GCUGAUUG | 1336 | CAAUCAGC CUGAUGAGGCCGUUAGGCCGAA AAACUAAC | 10755 |
| 7437 | UAGCUGAUU GUAUGGGG | 1337 | CCCCAUAC CUGAUGAGGCCGUUAGGCCGAA AUCAGCUA | 10756 |
| 7440 | CUGAUUGUA UGGGGUUU | 1338 | AAACCCCA CUGAUGAGGCCGUUAGGCCGAA ACAAUCAG | 10757 |
| 7447 | UAUGGGGUU UUCGAACC | 1339 | GGUUCGAA CUGAUGAGGCCGUUAGGCCGAA ACCCCAUA | 10758 |
| 7448 | AUGGGGUUU UCGAACCU | 1340 | AGGUUCGA CUGAUGAGGCCGUUAGGCCGAA AACCCCAU | 10759 |
| 7449 | UGGGGUUUU CGAACCUU | 1341 | AAGGUUCG CUGAUGAGGCCGUUAGGCCGAA AAACCCCA | 10760 |
| 7450 | GGGGUUUUC GAACCUUU | 1342 | AAAGGUUC CUGAUGAGGCCGUUAGGCCGAA AAAACCCC | 10761 |
| 7457 | UCGAACCUU UCACUUUU | 1343 | AAAAGUGA CUGAUGAGGCCGUUAGGCCGAA AGGUUCGA | 10762 |
| 7458 | CGAACCUUU CACUUUUU | 1344 | AAAAAGUG CUGAUGAGGCCGUUAGGCCGAA AAGGUUCG | 10763 |
| 7459 | GAACCUUUC ACUUUUUG | 1345 | CAAAAAGU CUGAUGAGGCCGUUAGGCCGAA AAAGGUUC | 10764 |
| 7463 | CUUUCACUU UUUGUUUG | 1346 | CAAACAAA CUGAUGAGGCCGUUAGGCCGAA AGUGAAAG | 10765 |
| 7464 | UUUCACUUU UUGUUUGU | 1347 | ACAAACAA CUGAUGAGGCCGUUAGGCCGAA AAGUGAAA | 10766 |
| 7465 | UUCACUUUU UGUUUGUU | 1348 | AACAAACA CUGAUGAGGCCGUUAGGCCGAA AAAGUGAA | 10767 |
| 7466 | UCACUUUUU GUUUGUUU | 1349 | AAACAAAC CUGAUGAGGCCGUUAGGCCGAA AAAAGUGA | 10768 |
| 7469 | CUUUUUGUU UGUUUUAC | 1350 | GUAAAACA CUGAUGAGGCCGUUAGGCCGAA ACAAAAAG | 10769 |
| 7470 | UUUUUGUUU GUUUUACC | 1351 | GGUAAAAC CUGAUGAGGCCGUUAGGCCGAA AACAAAAA | 10770 |
| 7473 | UUGUUUGUU UUACCUAU | 1352 | AUAGGUAA CUGAUGAGGCCGUUAGGCCGAA ACAAACAA | 10771 |
| 7474 | UGUUUGUUU UACCUAUU | 1353 | AAUAGGUA CUGAUGAGGCCGUUAGGCCGAA AACAAACA | 10772 |
| 7475 | GUUUGUUUU ACCUAUUU | 1354 | AAAUAGGU CUGAUGAGGCCGUUAGGCCGAA AAACAAAC | 10773 |
| 7476 | UUUGUUUUA CCUAUUUC | 1355 | GAAAUAGG CUGAUGAGGCCGUUAGGCCGAA AAAACAAA | 10774 |
| 7480 | UUUUACCUA UUUCACAA | 1356 | UUGUGAAA CUGAUGAGGCCGUUAGGCCGAA AGGUAAAA | 10775 |
| 7482 | UUACCUAUU UCACAACU | 1357 | AGUUGUGA CUGAUGAGGCCGUUAGGCCGAA AUAGGUAA | 10776 |
| 7483 | UACCUAUUU CACAACUG | 1358 | CAGUUGUG CUGAUGAGGCCGUUAGGCCGAA AAUAGGUA | 10777 |
| 7484 | ACCUAUUUC ACAACUGU | 1359 | ACAGUUGU CUGAUGAGGCCGUUAGGCCGAA AAAUAGGU | 10778 |
| 7495 | AACUGUGUA AAUUGCCA | 1360 | UGGCAAUU CUGAUGAGGCCGUUAGGCCGAA ACACAGUU | 10779 |
| 7499 | GUGUAAAUU GCCAAUAA | 1361 | UUAUUGGC CUGAUGAGGCCGUUAGGCCGAA AUUUACAC | 10780 |
| 7506 | UUGCCAAUA AUUCCUGU | 1362 | ACAGGAAU CUGAUGAGGCCGUUAGGCCGAA AUUGGCAA | 10781 |
| 7509 | CCAAUAUUU CCUGUCCA | 1363 | UGGACAGG CUGAUGAGGCCGUUAGGCCGAA AUUAUUGG | 10782 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 7510 | CAAUAAUUC CUGUCCAU | 1364 | AUGGACAG CUGAUGAGGCCGUUAGGCCGAA AAUUAUUG | 10783 |
| 7515 | AUUCCUGUC CAUGAAAA | 1365 | UUUUCAUG CUGAUGAGGCCGUUAGGCCGAA ACAGGAAU | 10784 |
| 7531 | AUGCAAAUU AUCCAGUG | 1366 | CACUGGAU CUGAUGAGGCCGUUAGGCCGAA AUUUGCAU | 10785 |
| 7532 | UGCAAAUUA UCCAGUGU | 1367 | ACACUGGA CUGAUGAGGCCGUUAGGCCGAA AAUUUGCA | 10786 |
| 7534 | CAAAUUAUC CAGUGUAG | 1368 | CUACACUG CUGAUGAGGCCGUUAGGCCGAA AUAAUUUG | 10787 |
| 7541 | UCCAGUGUA GAUAUAUU | 1369 | AAUAUAUC CUGAUGAGGCCGUUAGGCCGAA ACACUGGA | 10788 |
| 7545 | GUGUAGAUA UAUUUGAC | 1370 | GUCAAAUA CUGAUGAGGCCGUUAGGCCGAA AUCUACAC | 10789 |
| 7547 | GUAGAUAUA UUUGACCA | 1371 | UGGUCAAA CUGAUGAGGCCGUUAGGCCGAA AUAUCUAC | 10790 |
| 7549 | AGAUAUAUU UGACCAUC | 1372 | GAUGGUCA CUGAUGAGGCCGUUAGGCCGAA AUAUAUCU | 10791 |
| 7550 | GAUAUAUUU GACCAUCA | 1373 | UGAUGGUC CUGAUGAGGCCGUUAGGCCGAA AAUAUAUC | 10792 |
| 7557 | UUGACCAUC ACCCUAUG | 1374 | CAUAGGGU CUGAUGAGGCCGUUAGGCCGAA AUGGUCAA | 10793 |
| 7563 | AUCACCCUA UGGAUAUU | 1375 | AAUAUCCA CUGAUGAGGCCGUUAGGCCGAA AGGGUGAU | 10794 |
| 7569 | CUAUGGAUA UUGGCUAG | 1376 | CUAGCCAA CUGAUGAGGCCGUUAGGCCGAA AUCCAUAG | 10795 |
| 7571 | AUGGAUAUU GGCUAGUU | 1377 | AACUAGCC CUGAUGAGGCCGUUAGGCCGAA AUAUCCAU | 10796 |
| 7576 | UAUUGGCUA GUUUUGCC | 1378 | GGCAAAAC CUGAUGAGGCCGUUAGGCCGAA AGCCAAUA | 10797 |
| 7579 | UGGCUAGUU UUGCCUUU | 1379 | AAAGGCAA CUGAUGAGGCCGUUAGGCCGAA ACUAGCCA | 10798 |
| 7580 | GGCUAGUUU UGCCUUUA | 1380 | UAAAGGCA CUGAUGAGGCCGUUAGGCCGAA AACUAGCC | 10799 |
| 7581 | GCUAGUUUU GCCUUUAU | 1381 | AUAAAGGC CUGAUGAGGCCGUUAGGCCGAA AAACUAGC | 10800 |
| 7586 | UUUUGCCUU UAUUAAGC | 1382 | GCUUAAUA CUGAUGAGGCCGUUAGGCCGAA AGGCAAAA | 10801 |
| 7587 | UUUGCCUUU AUUAAGCA | 1383 | UGCUUAAU CUGAUGAGGCCGUUAGGCCGAA AAGGCAAA | 10802 |
| 7588 | UUGCCUUUA UUAAGCAA | 1384 | UUGCUUAA CUGAUGAGGCCGUUAGGCCGAA AAAGGCAA | 10803 |
| 7590 | GCCUUUAUU AAGCAAAU | 1385 | AUUUGCUU CUGAUGAGGCCGUUAGGCCGAA AUAAAGGC | 10804 |
| 7591 | CCUUUAUUA AGCAAAUU | 1386 | AAUUUGCU CUGAUGAGGCCGUUAGGCCGAA AAUAAAGG | 10805 |
| 7599 | AAGCAAAUU CAUUUCAG | 1387 | CUGAAAUG CUGAUGAGGCCGUUAGGCCGAA AUUUGCUU | 10806 |
| 7600 | AGCAAAUUC AUUUCAGC | 1388 | GCUGAAAU CUGAUGAGGCCGUUAGGCCGAA AAUUUGCU | 10807 |
| 7603 | AAAUUCAUU UCAGCCUG | 1389 | CAGGCUGA CUGAUGAGGCCGUUAGGCCGAA AUGAAUUU | 10808 |
| 7604 | AAUUCAUUU CAGCCUGA | 1390 | UCAGGCUG CUGAUGAGGCCGUUAGGCCGAA AAUGAAUU | 10809 |
| 7605 | AUUCAUUUC AGCCUGAA | 1391 | UUCAGGCU CUGAUGAGGCCGUUAGGCCGAA AAAUGAAU | 10810 |
| 7617 | CUGAAUGUC UGCCUAUA | 1392 | UAUAGGCA CUGAUGAGGCCGUUAGGCCGAA ACAUUCAG | 10811 |
| 7623 | GUCUGCCUA UAUAUUCU | 1393 | AGAAUAUA CUGAUGAGGCCGUUAGGCCGAA AGGCAGAC | 10812 |
| 7625 | CUGCCUAUA UAUUCUCU | 1394 | AGAGAAUA CUGAUGAGGCCGUUAGGCCGAA AUAGGCAG | 10813 |
| 7627 | GCCUAUAUA UUCUCUGC | 1395 | GCAGAGAA CUGAUGAGGCCGUUAGGCCGAA AUAUAGGC | 10814 |
| 7629 | CUAUAUAUU CUCUGCUC | 1396 | GAGCAGAG CUGAUGAGGCCGUUAGGCCGAA AUAUAUAG | 10815 |
| 7630 | UAUAUAUUC UCUGCUCU | 1397 | AGAGCAGA CUGAUGAGGCCGUUAGGCCGAA AAUAUAUA | 10816 |
| 7632 | UAUAUUCUC UGCUCUUU | 1398 | AAAGAGCA CUGAUGAGGCCGUUAGGCCGAA AGAAUAUA | 10817 |
| 7637 | UCUCUGCUC UUUGUAUU | 1399 | AAUACAAA CUGAUGAGGCCGUUAGGCCGAA AGCAGAGA | 10818 |
| 7639 | UCUGCUCUU UGUAUUCU | 1400 | AGAAUACA CUGAUGAGGCCGUUAGGCCGAA AGAGCAGA | 10819 |

TABLE II-continued

Human flt1 VEGF Receptor-Hammerhead Ribozyme and Substrate Sequence

| Pos | Substrate | Seq ID No | HH Ribozyme | Seq ID No |
|---|---|---|---|---|
| 7640 | CUGCUCUUU GUAUUCUC | 1401 | GAGAAUAC CUGAUGAG<u>GCCGUUAGGCC</u>GAA AAGAGCAG | 10820 |
| 7643 | CUCUUUGUA UUCUCCUU | 1402 | AAGGAGAA CUGAUGAG<u>GCCGUUAGGCC</u>GAA ACAAAGAG | 10821 |
| 7645 | CUUUGUAUU CUCCUUUG | 1403 | CAAAGGAG CUGAUGAG<u>GCCGUUAGGCC</u>GAA AUACAAAG | 10822 |
| 7646 | UUUGUAUUC UCCUUUGA | 1404 | UCAAAGGA CUGAUGAG<u>GCCGUUAGGCC</u>GAA AAUACAAA | 10823 |
| 7648 | UGUAUUCUC CUUUGAAC | 1405 | GUUCAAAG CUGAUGAG<u>GCCGUUAGGCC</u>GAA AGAAUACA | 10824 |
| 7651 | AUUCUCCUU UGAACCCG | 1406 | CGGGUUCA CUGAUGAG<u>GCCGUUAGGCC</u>GAA AGGAGAAU | 10825 |
| 7652 | UUCUCCUUU GAACCCGU | 1407 | ACGGGUUC CUGAUGAG<u>GCCGUUAGGCC</u>GAA AAGGAGAA | 10826 |
| 7661 | GAACCCGUU AAAACAUC | 1408 | GAUGUUUU CUGAUGAG<u>GCCGUUAGGCC</u>GAA ACGGGUUC | 10827 |
| 7662 | AACCCGUUA AAACAUCC | 1409 | GGAUGUUU CUGAUGAG<u>GCCGUUAGGCC</u>GAA AACGGGUU | 10828 |
| 7669 | UAAAACAUC CUGUGGCA | 1410 | UGCCACAG CUGAUGAG<u>GCCGUUAGGCC</u>GAA AUGUUUUA | 10829 |

Where "X" represents stem II region of a HH ribozyme (Hertel et al., 1992 Nucleic Acids Res. 20 3252). The length of stem II may be 2 base-pairs.
Underlined region can be any X sequence or linker, as described herein.

TABLE III

Human flt1 VEGF Receptor-Hairpin Ribozyme and Substrate sequence

| Pos | Substrate | Seq ID No | HP Ribozyme Sequence | Seq ID No |
|---|---|---|---|---|
| 16 | CCUCUCG GCU CCUCCCCG | 1411 | CGGGGAGG AGAA GAGAGG ACCAGAGAAACACACGUUGUGGUACAUUACCUGGUA | 10830 |
| 39 | GGCGGCG GCU CGGAGCGC | 1412 | CCGCUCCG AGAA GCCGCC ACCAGAGAAACACACGUUGUGGUACAUUACCUGGUA | 10831 |
| 180 | GACGACG GAC UCUGGCGG | 1413 | CCCCCAGA AGAA GUCCUC ACCAGAGAAACACACGUUGUGGUACAUUACCUGGUA | 10832 |
| 190 | UCUGGCG GCC GGGUCGUU | 1414 | AACGACCC AGAA GCCAGA ACCAGAGAAACACACGUUGUGGUACAUUACCUGGUA | 10833 |
| 278 | GGGUCCU GCU GUGCGCGC | 1415 | GCGCGCAC AGAA GGACCC ACCAGAGAAACACACGUUGUGGUACAUUACCUGGUA | 10834 |
| 290 | GCGCGCU GCU CAGCUGUC | 1416 | GACAUCUG AGAA GCGCGC ACCAGAGAAACACACGUUGUGGUACAUUACCUGGUA | 10835 |
| 295 | CUCCUCA GCU GUCUGCUU | 1417 | AAGCAGAC AGAA GAGCAG ACCAGAGAAACACACGUUGUGGUACAUUACCUGGUA | 10836 |
| 298 | CUCAGCU GUC UGCUUCUC | 1418 | GAGAAGCA AGAA GCUGAG ACCAGAGAAACACACGUUGUGGUACAUUACCUGGUA | 10837 |
| 302 | GCUGUCU GCU UCUCACAG | 1419 | CUGUGAGA AGAA GACAGC ACCAGAGAAACACACGUUGUGGUACAUUACCUGGUA | 10838 |
| 420 | GGAAGCA GCC CAUAAAUG | 1420 | CAUUUAUG AGAA GCUUCC ACCAGAGAAACACACGUUGUGGUACAUUACCUGGUA | 10839 |
| 486 | UAAAUCU GCC UGUGGAAG | 1421 | CUUCCACA AGAA GAUUUA ACCAGAGAAACACACGUUGUGGUACAUUACCUGGUA | 10840 |
| 537 | GAACACA GCU CAAGCAAA | 1422 | UUUGCUUG AGAA GUGUUC ACCAGAGAAACACACGUUGUGGUACAUUACCUGGUA | 10841 |
| 565 | UUCUACA GCU GCAAAUAU | 1423 | AUAUUUGC AGAA GUAGAA ACCAGAGAAACACACGUUGUGGUACAUUACCUGGUA | 10842 |
| 721 | AUUCCCU CCC GGGUUACG | 1424 | CGUAACCC AGAA GGGAAU ACCAGAGAAACACACGUUGUGGUACAUUACCUGGUA | 10843 |
| 786 | GAUCCCU GAU GGAAAACG | 1425 | CGUUUUCC AGAA GGGAUC ACCAGAGAAACACACGUUGUGGUACAUUACCUGGUA | 10844 |
| 863 | GGCUUCU GAC CUGUGAAG | 1426 | CUUCACAG AGAA GAAGCC ACCAGAGAAACACACGUUGUGGUACAUUACCUGGUA | 10845 |
| 1056 | UUACCCU GAU GAAAAAAA | 1427 | UUUUUUUC AGAA GGGUAA ACCAGAGAAACACACGUUGUGGUACAUUACCUGGUA | 10846 |
| 1301 | GCAAGCG GUC UUACCGGC | 1428 | GCCGGUAA AGAA GCUUGC ACCAGAGAAACACACGUUGUGGUACAUUACCUGGUA | 10847 |
| 1310 | CUUACCG GCU CUCUAUGA | 1429 | UCAUAGAG AGAA GGUAAG ACCAGAGAAACACACGUUGUGGUACAUUACCUGGUA | 10848 |
| 1389 | GAAAUCU GCU CGCUAUUU | 1430 | AAAUAGCG AGAA GAUUUC ACCAGAGAAACACACGUUGUGGUACAUUACCUGGUA | 10849 |

TABLE III-continued

Human flt1 VEGF Receptor-Hairpin Ribozyme and Substrate sequence

| Pos | Substrate | Seq ID No | HP Ribozyme Sequence | Seq ID No |
|---|---|---|---|---|
| 1535 | AACCCCA GAU UUACGAAA | 1431 | UUUCGUAA AGAA GGGGUU ACCAGAGAAACACACGUUGUGGUACAUUACCUGGUA | 10850 |
| 1566 | GUUUCCA GAC CCGGCUCU | 1432 | AGAGCCGG AGAA GGAAAC ACCAGAGAAACACACGUUGUGGUACAUUACCUGGUA | 10851 |
| 1572 | AGACCCG GCU CUCUACCC | 1433 | GGGUAGAG AGAA GGGUCU ACCAGAGAAACACACGUUGUGGUACAUUACCUGGUA | 10852 |
| 1604 | AAAUCCU GAC UUGUACCG | 1434 | CGGUACAA AGAA GGAUUU ACCAGAGAAACACACGUUGUGGUACAUUACCUGGUA | 10853 |
| 1824 | UGUGGCU GAC UCUAGAAU | 1435 | AUUCUAGA AGAA GCCACA ACCAGAGAAACACACGUUGUGGUACAUUACCUGGUA | 10854 |
| 1908 | UAUCACA GAU GUGCCAAA | 1436 | UUUGGCAC AGAA GUGAUA ACCAGAGAAACACACGUUGUGGUACAUUACCUGGUA | 10855 |
| 1949 | AAAUGCC GAC GGAAGGAG | 1437 | CUCCUUCC AGAA GCAUUU ACCAGAGAAACACACGUUGUGGUACAUUACCUGGUA | 10856 |
| 1973 | UGAAACU GUC UUGCACAG | 1438 | CUGUGCAA AGAA GUUUCA ACCAGAGAAACACACGUUGUGGUACAUUACCUGGUA | 10857 |
| 2275 | AUCACCA GUU CCACCACU | 1439 | AGUGGUGG AGAA GCUGAU ACCAGAGAAACACACGUUGUGGUACAUUACCUGGUA | 10858 |
| 2321 | AGCCUCA GAU CACUUGGU | 1440 | ACCAAGUG AGAA GAGGCU ACCAGAGAAACACACGUUGUGGUACAUUACCUGGUA | 10859 |
| 2396 | GCACGCU GUU UAUUGAAA | 1441 | UUUCAAUA AGAA GCGUGC ACCAGAGAAACACACGUUGUGGUACAUUACCUGGUA | 10860 |
| 2490 | CCUCACU GUU CAAGGAAC | 1442 | GUUCCUUG AGAA GUGAGG ACCAGAGAAACACACGUUGUGGUACAUUACCUGGUA | 10861 |
| 2525 | UGGAGCU GAU CACUCUAA | 1443 | UUAGAGUG AGAA GCUCCA ACCAGAGAAACACACGUUGUGGUACAUUACCUGGUA | 10862 |
| 2625 | AAAGACU GAC UACCUAUC | 1444 | GAUAGGUA AGAA GUCUUU ACCAGAGAAACACACGUUGUGGUACAUUACCUGGUA | 10863 |
| 2652 | GGACCCA GAU GAAGUUCC | 1445 | GGAACUUC AGAA GGGUCC ACCAGAGAAACACACGUUGUGGUACAUUACCUGGUA | 10864 |
| 2684 | GUGAGCG GCU CCCUUAUG | 1446 | CAUAAGGG AGAA GCUCAC ACCAGAGAAACACACGUUGUGGUACAUUACCUGGUA | 10865 |
| 2816 | CGUGCCG GAC UGUGGCUG | 1447 | CAGCCACA AGAA GGCACG ACCAGAGAAACACACGUUGUGGUACAUUACCUGGUA | 10866 |
| 2873 | AAGCUCU GAU GACUGAGC | 1448 | GCUCAGUC AGAA GAGCUU ACCAGAGAAACACACGUUGUGGUACAUUACCUGGUA | 10867 |
| 2930 | UUAACCU GCU GGGAGCCU | 1449 | AGGCUCCC AGAA GGUUAA ACCAGAGAAACACACGUUGUGGUACAUUACCUGGUA | 10868 |
| 2963 | GGCCUCU GAU GGUGAUUG | 1450 | CAAUCACC AGAA GAGGCC ACCAGAGAAACACACGUUGUGGUACAUUACCUGGUA | 10869 |
| 3157 | AGCUCCG GCU UUCAGGAA | 1451 | UUCCUGAA AGAA GGAGCU ACCAGAGAAACACACGUUGUGGUACAUUACCUGGUA | 10870 |
| 3207 | GGAUUCU GAC GGUUUCUA | 1452 | UAGAAACC AGAA GAAUCC ACCAGAGAAACACACGUUGUGGUACAUUACCUGGUA | 10871 |
| 3211 | UCUGACG GUU UCUACAAG | 1453 | CUUGUAGA AGAA GUCAGA ACCAGAGAAACACACGUUGUGGUACAUUACCUGGUA | 10872 |
| 3245 | AAGAUCU GAU UUCUUACA | 1454 | UGUAAGAA AGAA GAUCUG ACCAGAGAAACACACGUUGUGGUACAUUACCUGGUA | 10873 |
| 3256 | UCUUACA GUU UUCAAGUG | 1455 | CACUUGAA AGAA GUAAGA ACCAGAGAAACACACGUUGUGGUACAUUACCUGGUA | 10874 |
| 3287 | AGUUCCU GUC UUCCAGAA | 1456 | UUCUGGAA AGAA GGAACU ACCAGAGAAACACACGUUGUGGUACAUUACCUGGUA | 10875 |
| 3402 | GAACCCC GAU UAUGUGAG | 1457 | CUCACAUA AGAA GGGUUC ACCAGAGAAACACACGUUGUGGUACAUUACCUGGUA | 10876 |
| 3580 | UUUUGCA GUC GCCUGAGG | 1458 | CCUCAGGC AGAA GCAAAA ACCAGAGAAACACACGUUGUGGUACAUUACCUGGUA | 10877 |
| 3641 | UCUAUCA GAU CAUGCUGG | 1459 | CCAGCAUG AGAA GAUAGA ACCAGAGAAACACACGUUGUGGUACAUUACCUGGUA | 10878 |
| 3655 | CUGGACU GCU GGCACAGA | 1460 | UCUGUGCC AGAA GUCCAG ACCAGAGAAACACACGUUGUGGUACAUUACCUGGUA | 10879 |
| 3810 | AACUCCU GCC UUCUCUGA | 1461 | UCAGAGAA AGAA GGAGUU ACCAGAGAAACACACGUUGUGGUACAUUACCUGGUA | 10880 |
| 3846 | UAUUUCA GCU CCGAAGUU | 1462 | AACUUCGG AGAA GAAAUA ACCAGAGAAACACACGUUGUGGUACAUUACCUGGUA | 10881 |
| 3873 | AAGCUCU GAU GAUGUCAG | 1463 | CUGACAUC AGAA GAGCUU ACCAGAGAAACACACGUUGUGGUACAUUACCUGGUA | 10882 |
| 3995 | GCACUCU GUU GGCCUCUC | 1464 | GAGAGGCC AGAA GAGUGC ACCAGAGAAACACACGUUGUGGUACAUUACCUGGUA | 10883 |
| 4100 | CGGGGCU GUC UGAUGUCA | 1465 | UGACAUCA AGAA GCCCCG ACCAGAGAAACACACGUUGUGGUACAUUACCUGGUA | 10884 |
| 4104 | GCUGUCU GAU GUCAGCAG | 1466 | CUGCUGAC AGAA GACAGC ACCAGAGAAACACACGUUGUGGUACAUUACCUGGUA | 10885 |

TABLE III-continued

Human flt1 VEGF Receptor-Hairpin Ribozyme and Substrate sequence

| Pos | Substrate | Seq ID No | HP Ribozyme Sequence | Seq ID No |
|-----|-----------|-----------|----------------------|-----------|
| 4120 | AGGCCCA GUU UCUGCCAU | 1467 | AUGGCAGA AGAA GGGCCU ACCAGAGAAACACACGUUGUGGUACAUUACCUGGUA | 10886 |
| 4135 | CAUUCCA GCU GUGGGCAC | 1468 | GUGCCCAC AGAA GGAAUG ACCAGAGAAACACACGUUGUGGUACAUUACCUGGUA | 10887 |
| 4210 | GCGUGCU GCU CCCCGCCC | 1469 | GGGCGGGG AGAA GCACGC ACCAGAGAAACACACGUUGUGGUACAUUACCUGGUA | 10888 |
| 4217 | GCUCCCC GCC CCCAGACU | 1470 | AGUCUGG AGAA GGGAGC ACCAGAGAAACACACGUUGUGGUACAUUACCUGGUA | 10889 |
| 4224 | GCCCCCA GAC UACAACUC | 1471 | GAGUUGUA AGAA GGGGGC ACCAGAGAAACACACGUUGUGGUACAUUACCUGGUA | 10890 |
| 4382 | GGAGCCA GCU GCUUUUUG | 1472 | CAAAAAGC AGAA GGCUCC ACCAGAGAAACACACGUUGUGGUACAUUACCUGGUA | 10891 |
| 4385 | GCCAGCU GCU UUUUGUGA | 1473 | UCACAAAA AGAA GCUGGC ACCAGAGAAACACACGUUGUGGUACAUUACCUGGUA | 10892 |
| 4537 | CUUCCCU GCU CCAACCCC | 1474 | GGGGUUGG AGAA GGGAAG ACCAGAGAAACACACGUUGUGGUACAUUACCUGGUA | 10893 |
| 4573 | AGGACCA GUU UGAUUGAG | 1475 | CUCAAUCA AGAA GGUCCU ACCAGAGAAACACACGUUGUGGUACAUUACCUGGUA | 10894 |
| 4594 | CUGCACU GAU CACCCAAU | 1476 | AUUGGGUG AGAA GUGCAG ACCAGAGAAACACACGUUGUGGUACAUUACCUGGUA | 10895 |
| 4628 | UGGGCCA CCC CUGCAGCC | 1477 | GGCUGCAG AGAA GGCCCA ACCAGAGAAACACACGUUGUGGUACAUUACCUGGUA | 10896 |
| 4636 | CCCUGCA GCC CAAAACCC | 1478 | GGGUUUUG ACAA GCAGGG ACCAGACAAACACACGUUGUGGUACAUUACCUGGUA | 10897 |
| 4866 | CUUCCCA GCU CUGACCCU | 1479 | ACGGUCAG AGAA GGGAAG ACCACAGAAACACACQUUGUGGUACAUUACCUGGUA | 10898 |
| 4871 | CACCUCU CAC CCUUCUAC | 1480 | GUACAAGG AGAA GAGCUG ACCAGAGAAACACACGUUGUGGUACAUUACCUGGUA | 10899 |
| 4905 | AGGACCA GAU GGACAGCG | 1481 | CGCUGUCC AGAA GCUCCU ACCAGAGAAACACACGUUGUGGUACAUUACCUGGUA | 10900 |
| 5233 | UUAUUCU GUU UUCCACAG | 1482 | CUGUGCAA AGAA GAAUAA ACCAGAGAAACACACGUUGUGGUACAUUACCUGGUA | 10901 |
| 5281 | AAAUGCA GUC CUGAGGAG | 1483 | CUCCUCAG AGAA GCAUUU ACCAGAGAAACACACGUUGUGGUACAUUACCUGGUA | 10902 |
| 5319 | GAGGGCU GAU GGAGGAAA | 1484 | UUUCCUCC AGAA GCCCUC ACCAGAGAAACACACGUUGUGGUACAUUACCUGGUA | 10903 |
| 5358 | AGACCCC GUC UCUAUACC | 1485 | GGUAUAGA AGAA GGGUCU ACCAGAGAAACACACGUUGUGGUACAUUACCUGGUA | 10904 |
| 5392 | CAACACA GUU GGGACCCA | 1486 | UGGGUCCC AGAA GUGUUG ACCAGAGAAACACACGUUGUGGUACAUUACCUGGUA | 10905 |
| 5563 | UUCUCCA GUU GGGACUCA | 1487 | UGAGUCCC AGAA GGAGAA ACCAGAGAAACACACGUUGUGGUACAUUACCUGGUA | 10906 |
| 5622 | UUCAACU GCU UUGAAACU | 1488 | AGUUUCAA AGAA GUUGAA ACCAGAGAAACACACGUUGUGGUACAUUACCUGGUA | 10907 |
| 5738 | UGGCUCU GUU UGAUGCUA | 1489 | UAGCAUCA AGAA GAGCCA ACCAGAGAAACACACGUUGUGGUACAUUACCUGGUA | 10908 |
| 5838 | UGGCUCU GUU UGAUGCUA | 1489 | UAGCAUCA AGAA GAGCCA ACCAGAGAAACACACGUUGUGGUACAUUACCUGGUA | 10908 |
| 5933 | GAUUGCU GCU UCUGGGG | 1490 | CCCCAAGA AGAA GCAAUC ACCAGAGAAACACACGUUGUGGUACAUUACCUGGUA | 10909 |
| 6022 | UGCCUCU GUU CUUAUGUG | 1491 | CACAUAAG AGAA GAGGCA ACCAGAGAAACACACGUUGUGGUACAUUACCUGGUA | 10910 |
| 6120 | GGCAGCG GCU UCUGUGGA | 1492 | UCCACAAA AGAA GCUGCC ACCAGAGAAACACACGUUGUGGUACAUUACCUGGUA | 10911 |
| 6163 | UGGGACA GUC CUCUCCAC | 1493 | GUGGAGAG AGAA GUCCCA ACCAGAGAAACACACGUUGUGGUACAUUACCUGGUA | 10912 |
| 6270 | UGUGACA GCU GGCAAUUU | 1494 | AAAUUGCC AGAA GUCACA ACCAGAGAAACACACGUUGUGGUACAUUACCUGGUA | 10913 |
| 6412 | CUUAGCU GUU CAUGUCUU | 1495 | AAGACAUG AGAA GCUAAG ACCAGAGAAACACACGUUGUGGUACAUUACCUGGUA | 10914 |
| 6511 | UUACUCA GCU CCUUCAAA | 1496 | UUUGAAGG AGAA GAGUAA ACCAGAGAAACACACGUUGUGGUACAUUACCUGGUA | 10915 |
| 6778 | UGGAACA GUC UGGGUGGA | 1497 | UCCACCCA AGAA GUUCCA ACCAGAGAAACACACGUUGUGGUACAUUACCUGGUA | 10916 |
| 6826 | CUUGUCA GUC CAAGAAGU | 1498 | ACUUCUUG AGAA GACAAG ACCAGAGAAACACACGUUGUGGUACAUUACCUGGUA | 10917 |
| 7245 | GGCAACU GCU UUUAUGUU | 1499 | AACAUAAA AGAA GUUGCC ACCAGAGAAACACACGUUGUGGUACAUUACCUGGUA | 10918 |
| 7258 | AUGUUCU GUC UCCUUCCA | 1500 | UGGAAGGA AGAA GAACAU ACCAGAGAAACACACGUUGUGGUACAUUACCUGGUA | 10919 |
| 7433 | UUUAGCU GAU UGUAUGGG | 1501 | CCCAUACA AGAA GCUAAA ACCAGAGAAACACACGUUGUGGUACAUUACCUGGUA | 10920 |
| 7512 | AAUUCCU GUC CAUGAAAA | 1502 | UUUUCAUG AGAA GGAAUU ACCAGAGAAACACACGUUGUGGUACAUUACCUGGUA | 10921 |

TABLE III-continued

Human flt1 VEGF Receptor-Hairpin Ribozyme and Substrate sequence

| Pos | Substrate | Seq ID No | HP Ribozyme Sequence | Seq ID No |
|---|---|---|---|---|
| 7606 | CAUUUCA CCC UGAAUGUC | 1503 | GACAUUCA AGAA GAAAUG ACCAGAGAAACACACGUUGUGGUACAUUACCUGGUA | 10922 |
| 7618 | AAUGUCU CCC UAUAUAUU | 1504 | AAUAUAUA AGAA GACAUU ACCAGAGAAACACACGUUGUGGUACAUUACCUGGUA | 10923 |
| 7633 | AUUCUCU GCU CUUUGUAU | 1505 | AUACAAAG AGAA GAGAAU ACCAGAGAAACACACGUUGUGGUACAUUACCUGGUA | 10924 |

TABLE IV

Human KDR VEGF Receptor-Hammerhead Ribozyme and Substrate Sequence

| Pos | Substrate | Seq ID No | HH Ribozyme Sequence | Seq ID No |
|---|---|---|---|---|
| 21 | CUGGCCGUC GCCCUGUG | 1506 | CACAGGGC CUGAUGAGGCCGUUAGGCCGAA ACGGCCAG | 10925 |
| 33 | CUGUGGCUC UGCGUGGA | 1507 | UCCACGCA CUGAUGAGGCCGUUAGGCCGAA AGCCACAG | 10926 |
| 56 | GGCCGCCUC UGUGGGUU | 1508 | AACCCACA CUGAUGAGGCCGUUAGGCCGAA AGGCGGCC | 10927 |
| 64 | CUGUGGGUU UGCCUAGU | 1509 | ACUAGGCA CUGAUGAGGCCGUUAGGCCGAA ACCCACAG | 10928 |
| 65 | UGUGGGUUU GCCUAGUG | 1510 | CACUAGGC CUGAUGAGGCCGUUAGGCCGAA AACCCACA | 10929 |
| 70 | GUUUGCCUA GUGUUUCU | 1511 | AGAAACAC CUGAUGAGGCCGUUAGGCCGAA AGGCAAAC | 10930 |
| 75 | CCUAGUGUU UCUCUUGA | 1512 | UCAAGAGA CUGAUGAGGCCGUUAGGCCGAA ACACUAGG | 10931 |
| 76 | CUAGUGUUU CUCUUGAU | 1513 | AUCAAGAG CUGAUGAGGCCGUUAGGCCGAA AACACUAG | 10932 |
| 77 | UAGUGUUUC UCUUGAUC | 1514 | GAUCAAGA CUGAUGAGGCCGUUAGGCCGAA AAACACUA | 10933 |
| 79 | GUGUUUCUC UUGAUCUG | 1515 | CAGAUCAA CUGAUGAGGCCGUUAGGCCGAA AGAAACAC | 10934 |
| 81 | GUUUCUCUU GAUCUGCC | 1516 | GGCAGAUC CUGAUGAGGCCGUUAGGCCGAA AGAGAAAC | 10935 |
| 85 | CUCUUGAUC UGCCCAGG | 1517 | CCUGGGCA CUGAUGAGGCCGUUAGGCCGAA AUCAAGAG | 10936 |
| 96 | CCCAGGCUC AGCAUACA | 1518 | UGUAUGCU CUGAUGAGGCCGUUAGGCCGAA AGCCUGGG | 10937 |
| 102 | CUCAGCAUA CAAAAGA | 1519 | UCUUUUG CUGAUGAGGCCGUUAGGCCGAA AUGCUGAG | 10938 |
| 114 | AAAGACAUA CUUACAAU | 1520 | AUUGUAAG CUGAUGAGGCCGUUAGGCCGAA AUGUCUUU | 10939 |
| 117 | GACAUACUU ACAAUUAA | 1521 | UUAAUUGU CUGAUGAGGCCGUUAGGCCGAA AGUAUGUC | 10940 |
| 118 | ACAUACUUA CAAUUAAG | 1522 | CUUAAUUG CUGAUGAGGCCGUUAGGCCGAA AAGUAUGU | 10941 |
| 123 | CUUACAAUU AAGGCUAA | 1523 | UUAGCCUU CUGAUGAGGCCGUUAGGCCGAA AUUGUAAG | 10942 |
| 124 | UUACAAUUA AGGCUAAU | 1524 | AUUAGCCU CUGAUGAGGCCGUUAGGCCGAA AAUUGUAA | 10943 |
| 130 | UUAAGGCUA AUACAACU | 1525 | AGUUGUAU CUGAUGAGGCCGUUAGGCCGAA AGCCUUAA | 10944 |
| 133 | AGGCUAAUA CAACUCUU | 1526 | AAGAGUUG CUGAUGAGGCCGUUAGGCCGAA AUUAGCCU | 10945 |
| 139 | AUACAACUC UUCAAAUU | 1527 | AAUUUGAA CUGAUGAGGCCGUUAGGCCGAA AGUUGUAU | 10946 |
| 141 | ACAACUCUU CAAAUUAC | 1528 | GUAAUUUG CUGAUGAGGCCGUUAGGCCGAA AGAGUUGU | 10947 |
| 142 | CAACUCUUC AAAUUACU | 1529 | AGUAAUUU CUGAUGAGGCCGUUAGGCCGAA AAGAGUUG | 10948 |
| 147 | CUUCAAAUU ACUUGCAG | 1530 | CUGCAAGU CUGAUGAGGCCGUUAGGCCGAA AUUUGAAG | 10949 |
| 148 | UUCAAAUUA CUUGCAGG | 1531 | CCUGCAAG CUGAUGAGGCCGUUAGGCCGAA AAUUUGAA | 10950 |
| 151 | AAAUUACUU GCAGGGA | 1532 | UCCCCGC CUGAUGAGGCCGUUAGGCCGAA AGUAAUUU | 10951 |
| 170 | GAGGGACUU GGACUGGC | 1533 | GCCAGUCC CUGAUGAGGCCGUUAGGCCGAA AGUCCCUC | 10952 |

TABLE IV-continued

Human KDR VEGF Receptor-Hammerhead Ribozyme and Substrate Sequence

| Pos | Substrate | Seq ID No | HH Ribozyme Sequence | Seq ID No |
|-----|-----------|-----------|----------------------|-----------|
| 180 | GACUGGCUU UGGCCCAA | 1534 | UUGGGCCA CUGAUGAGGCCGUUAGGCCGAA AGCCAGUC | 10953 |
| 181 | ACUGGCUUU GGCCCAAU | 1535 | AUUGGGCC CUGAUGAGGCCGUUAGGCCGAA AAGCCAGU | 10954 |
| 190 | GGCCCAAUA AUCAGAGU | 1536 | ACUCUGAU CUGAUGAGGCCGUUAGGCCGAA AUUGGGCC | 10955 |
| 193 | CCAAUAAUC AGAGUGGC | 1537 | GCCACUCU CUGAUGAGGCCGUUAGGCCGAA AUUAUUGG | 10956 |
| 243 | GAUGGCCUC UUCUGUAA | 1538 | UUACAGAA CUGAUGAGGCCGUUAGGCCGAA AGGCCAUC | 10957 |
| 245 | UGGCCUCUU CUGUAAGA | 1539 | UCUUACAG CUGAUGAGGCCGUUAGGCCGAA AGAGGCCA | 10958 |
| 246 | GGCCUCUUC UGUAAGAC | 1540 | GUCUUACA CUGAUGAGGCCGUUAGGCCGAA AAGAGGCC | 10959 |
| 250 | UCUUCUGUA AGACACUC | 1541 | GAGUGUCU CUGAUGAGGCCGUUAGGCCGAA ACAGAAGA | 10960 |
| 258 | AAGACACUC ACAAUUCC | 1542 | GGAAUUGU CUGAUGAGGCCGUUAGGCCGAA AGUGUCUU | 10961 |
| 264 | CUCACAAUU CCAAAAGU | 1543 | ACUUUUGG CUGAUGAGGCCGUUAGGCCGAA AUUGUGAG | 10962 |
| 265 | UCACAAUUC CAAAAGUG | 1544 | CACUUUUG CUGAUGAGGCCGUUAGGCCGAA AAUUGUGA | 10963 |
| 276 | AAAGUGAUC GGAAAUGA | 1545 | UCAUUUCC CUGAUGAGGCCGUUAGGCCGAA AUCACUUG | 10964 |
| 296 | UGGAGCCUA CAAGUGCU | 1546 | AGCACUUG CUGAUGAGGCCGUUAGGCCGAA AGGCUCCA | 10965 |
| 305 | CAAGUGCUU CUACCGGG | 1547 | CCCGGUAG CUGAUGAGGCCGUUAGGCCGAA AGCACUUG | 10966 |
| 306 | AAGUGCUUC UACCGGGA | 1548 | UCCCGGUA CUGAUGAGGCCGUUAGGCCGAA AAGCACUU | 10967 |
| 308 | GUGCUUCUA CCGGGAAA | 1549 | UUUCCCGG CUGAUGAGGCCGUUAGGCCGAA AGAAGCAC | 10968 |
| 323 | AACUGACUU GGCCUCGG | 1550 | CCGAGGCC CUGAUGAGGCCGUUAGGCCGAA AGUCAGUU | 10969 |
| 329 | CUUGGCCUC GGUCAUUU | 1551 | AAAUGACC CUGAUGAGGCCGUUAGGCCGAA AGGCCAAG | 10970 |
| 333 | GCCUCGGUC AUUUAUGU | 1552 | ACAUAAAU CUGAUGAGGCCGUUAGGCCGAA ACCGAGGC | 10971 |
| 336 | UCGGUCAUU UAUGUCUA | 1553 | UAGACAUA CUGAUGAGGCCGUUAGGCCGAA AUGACCGA | 10972 |
| 337 | CGGUCAUUU AUGUCUAU | 1554 | AUAGACAU CUGAUGAGGCCGUUAGGCCGAA AAUGACCG | 10973 |
| 338 | GGUCAUUUA UGUCUAUG | 1555 | CAUAGACA CUGAUGAGGCCGUUAGGCCGAA AAAUGACC | 10974 |
| 342 | AUUUAUGUC UAUGUUCA | 1556 | UGAACAUA CUGAUGAGGCCGUUAGGCCGAA ACAUAAAU | 10975 |
| 344 | UUAUGUCUA UGUUCAAG | 1557 | CUUGAACA CUGAUGAGGCCGUUAGGCCGAA AGACAUAA | 10976 |
| 348 | GUCUAUGUU CAAGAUUA | 1558 | UAAUCUUG CUGAUGAGGCCGUUAGGCCGAA ACAUAGAC | 10977 |
| 349 | UCUAUGUUC AAGAUUAC | 1559 | GUAAUCUU CUGAUGAGGCCGUUAGGCCGAA AACAUAGA | 10978 |
| 355 | UUCAAGAUU ACAGAUCU | 1560 | AGAUCUGU CUGAUGAGGCCGUUAGGCCGAA AUCUUGAA | 10979 |
| 356 | UCAAGAUUA CAGAUCUC | 1561 | GAGAUCUG CUGAUGAGGCCGUUAGGCCGAA AAUCUUGA | 10980 |
| 362 | UUACAGAUC UCCAUUUA | 1562 | UAAAUGGA CUGAUGAGGCCGUUAGGCCGAA AUCUGUAA | 10981 |
| 364 | ACAGAUCUC CAUUUAUU | 1563 | AAUAAAUG CUGAUGAGGCCGUUAGGCCGAA AGAUCUGU | 10982 |
| 368 | AUCUCCAUU UAUUGCUU | 1564 | AAGCAAUA CUGAUGAGGCCGUUAGGCCGAA AUGGAGAU | 10983 |
| 369 | UCUCCAUUU AUUGCUUC | 1565 | GAAGCAAU CUGAUGAGGCCGUUAGGCCGAA AAUGGAGA | 10984 |
| 370 | CUCCAUUUA UUGCUUCU | 1566 | AGAAGCAA CUGAUGAGGCCGUUAGGCCGAA AAAUGGAG | 10985 |
| 372 | CCAUUUAUU GCUUCUGU | 1567 | ACAGAAGC CUGAUGAGGCCGUUAGGCCGAA AUAAAUGG | 10986 |
| 376 | UUAUUGCUU CUGUUAGU | 1568 | ACUAACAG CUGAUGAGGCCGUUAGGCCGAA AGCAAUAA | 10987 |
| 377 | UAUUGCUUC UGUUAGUG | 1569 | CACUAACA CUGAUGAGGCCGUUAGGCCGAA AAGCAAUA | 10988 |
| 381 | GCUUCUGUU AGUGACCA | 1570 | UGGUCACU CUGAUGAGGCCGUUAGGCCGAA ACAGAAGC | 10989 |

TABLE IV-continued

Human KDR VEGF Receptor-Hammerhead Ribozyme and Substrate Sequence

| Pos | Substrate | Seq ID No | HH Ribozyme Sequence | Seq ID No |
|-----|-----------|-----------|----------------------|-----------|
| 382 | CUUCUGUUA GUGACCAA | 1571 | UUGGUCAC CUGAUGAGGCCGUUAGGCCGAA AACAGAAG | 10990 |
| 399 | CAUGGAGUC GUGUACAU | 1572 | AUGUACAC CUGAUGAGGCCGUUAGGCCGAA ACUCCAUG | 10991 |
| 404 | AGUCGUGUA CAUUACUG | 1573 | CAGUAAUG CUGAUGAGGCCGUUAGGCCGAA ACACGACU | 10992 |
| 408 | GUGUACAUU ACUGAGAA | 1574 | UUCUCAGU CUGAUGAGGCCGUUAGGCCGAA AUGUACAC | 10993 |
| 409 | UGUACAUUA CUGAGAAC | 1575 | GUUCUCAG CUGAUGAGGCCGUUAGGCCGAA AAUGUACA | 10994 |
| 438 | GUGGUGAUU CCAUGUCU | 1576 | AGACAUGG CUGAUGAGGCCGUUAGGCCGAA AUCACCAC | 10995 |
| 439 | UGGUGAUUC CAUGUCUC | 1577 | GAGACAUG CUGAUGAGGCCGUUAGGCCGAA AAUCACCA | 10996 |
| 445 | UUCCAUGUC UCGGGUCC | 1578 | GGACCCGA CUGAUGAGGCCGUUAGGCCGAA ACAUGGAA | 10997 |
| 447 | CCAUGUCUC GGGUCCAU | 1579 | AUGGACCC CUGAUGAGGCCGUUAGGCCGAA AGACAUGG | 10998 |
| 452 | UCUCGGGUC CAUUUCAA | 1580 | UUGAAAUG CUGAUGAGGCCGUUAGGCCGAA ACCCGAGA | 10999 |
| 456 | GGGUCCAUU UCAAAUCU | 1581 | AGAUUUGA CUGAUGAGGCCGUUAGGCCGAA AUGGACCC | 11000 |
| 457 | GGUCCAUUU CAAAUCUC | 1582 | GAGAUUUG CUGAUGAGGCCGUUAGGCCGAA AAUGGACC | 11001 |
| 458 | GUCCAUUUC AAAUCUCA | 1583 | UGAGAUUU CUGAUGAGGCCGUUAGGCCGAA AAAUGGAC | 11002 |
| 463 | UUUCAAAUC UCAACGUG | 1584 | CACGUUGA CUGAUGAGGCCGUUAGGCCGAA AUUUGAAA | 11003 |
| 465 | UCAAAUCUC AACGUGUC | 1585 | GACACGUU CUGAUGAGGCCGUUAGGCCGAA AGAUUUGA | 11004 |
| 473 | CAACGUGUC ACUUUGUG | 1586 | CACAAAGU CUGAUGAGGCCGUUAGGCCGAA ACACGUUG | 11005 |
| 477 | GUGUCACUU UGUGCAAG | 1587 | CUUGCACA CUGAUGAGGCCGUUAGGCCGAA AGUGACAC | 11006 |
| 478 | UGUCACUUU GUGCAAGA | 1588 | UCUUGCAC CUGAUGAGGCCGUUAGGCCGAA AAGUGACA | 11007 |
| 488 | UGCAAGAUA CCCAGAAA | 1589 | UUUCUGGG CUGAUGAGGCCGUUAGGCCGAA AUCUUGCA | 11008 |
| 503 | AAAGAGAUU GUUCCUG | 1590 | CAGGAACA CUGAUGAGGCCGUUAGGCCGAA AUCUCUUU | 11009 |
| 504 | AAGAGAUUU GUUCCUGA | 1591 | UCAGGAAC CUGAUGAGGCCGUUAGGCCGAA AAUCUCUU | 11010 |
| 507 | AGAUUUGUU CCUGAUGG | 1592 | CCAUCAGG CUGAUGAGGCCGUUAGGCCGAA ACAAAUCU | 11011 |
| 508 | GAUUUGUUC CUGAUGGU | 1593 | ACCAUCAG CUGAUGAGGCCGUUAGGCCGAA AACAAAUC | 11012 |
| 517 | CUGAUGGUA ACAGAAUU | 1594 | AAUUCUGU CUGAUGAGGCCGUUAGGCCGAA ACCAUCAG | 11013 |
| 525 | AACAGAAUU UCCUGGGA | 1595 | UCCCAGGA CUGAUGAGGCCGUUAGGCCGAA AUUCUGUU | 11014 |
| 526 | ACAGAAUUU CCUGGGAC | 1596 | GUCCCAGG CUGAUGAGGCCGUUAGGCCGAA AAUUCUGU | 11015 |
| 527 | CAGAAUUUC CUGGGACA | 1597 | UGUCCCAG CUGAUGAGGCCGUUAGGCCGAA AAAUUCUG | 11016 |
| 548 | GAAGGGCUU UACUAUUC | 1598 | GAAUAGUA CUGAUGAGGCCGUUAGGCCGAA AGCCCUUC | 11017 |
| 549 | AAGGGCUUU ACUAUUCC | 1599 | GGAAUAGU CUGAUGAGGCCGUUAGGCCGAA AAGCCCUU | 11018 |
| 550 | AGGGCUUUA CUAUUCCC | 1600 | GGGAAUAG CUGAUGAGGCCGUUAGGCCGAA AAAGCCCU | 11019 |
| 553 | GCUUUACUA UUCCCAGC | 1601 | GCUGGGAA CUGAUGAGGCCGUUAGGCCGAA AGUAAAGC | 11020 |
| 555 | UUUACUAUU CCCAGCUA | 1602 | UAGCUGGG CUGAUGAGGCCGUUAGGCCGAA AUAGUAAA | 11021 |
| 556 | UUACUAUUC CCAGCUAC | 1603 | GUAGCUGG CUGAUGAGGCCGUUAGGCCGAA AAUAGUAA | 11022 |
| 563 | UCCCAGCUA CAUGAUCA | 1604 | UGAUCAUG CUGAUGAGGCCGUUAGGCCGAA AGCUGGGA | 11023 |
| 570 | UACAUGAUC AGCUAUGC | 1605 | GCAUAGCU CUGAUGAGGCCGUUAGGCCGAA AUCAUGUA | 11024 |
| 575 | GAUCAGCUA UGCUGGCA | 1606 | UGCCAGCA CUGAUGAGGCCGUUAGGCCGAA AGCUGAUC | 11025 |
| 588 | GGCAUGGUC UUCUGUGA | 1607 | UCACAGAA CUGAUGAGGCCGUUAGGCCGAA ACCAUGCC | 11026 |

TABLE IV-continued

Human KDR VEGF Receptor-Hammerhead Ribozyme and Substrate Sequence

| Pos | Substrate | Seq ID No | HH Ribozyme Sequence | Seq ID No |
|-----|-----------|-----------|----------------------|-----------|
| 590 | CAUGGUCUU CUGUGAAG | 1608 | CUUCACAG CUGAUGAGGCCGUUAGGCCGAA AGACCAUG | 11027 |
| 591 | AUGGUCUUC UGUGAAGC | 1609 | GCUUCACA CUGAUGAGGCCGUUAGGCCGAA AAGACCAU | 11028 |
| 606 | GCAAAAAUU AAUGAUGA | 1610 | UCAUCAUU CUGAUGAGGCCGUUAGGCCGAA AUUUUUGC | 11029 |
| 607 | CAAAAAUUA AUGAUGAA | 1611 | UUCAUCAU CUGAUGAGGCCGUUAGGCCGAA AAUUUUUG | 11030 |
| 619 | AUGAAAGUU ACCAGUCU | 1612 | AGACUGGU CUGAUGAGGCCGUUAGGCCGAA ACUUUCAU | 11031 |
| 620 | UGAAAGUUA CCAGUCUA | 1613 | UAGACUGG CUGAUGAGGCCGUUAGGCCGAA AACUUUCA | 11032 |
| 626 | UUACCAGUC UAUUAUGU | 1614 | ACAUAAUA CUGAUGAGGCCGUUAGGCCGAA ACUGGUAA | 11033 |
| 628 | ACCAGUCUA UUAUGUAC | 1615 | GUACAUAA CUGAUGAGGCCGUUAGGCCGAA AGACUGGU | 11034 |
| 630 | CAGUCUAUU AUGUACAU | 1616 | AUGUACAU CUGAUGAGGCCGUUAGGCCGAA AUAGACUG | 11035 |
| 631 | AGUCUAUUA UGUACAUA | 1617 | UAUGUACA CUGAUGAGGCCGUUAGGCCGAA AAUAGACU | 11036 |
| 635 | UAUUAUGUA CAUAGUUG | 1618 | CAACUAUG CUGAUGAGGCCGUUAGGCCGAA ACAUAAUA | 11037 |
| 639 | AUGUACAUA GUUGUCGU | 1619 | ACGACAAC CUGAUGAGGCCGUUAGGCCGAA AUGUACAU | 11038 |
| 642 | UACAUAGUU GUCGUUGU | 1620 | ACAACGAC CUGAUGAGGCCGUUAGGCCGAA ACUAUGUA | 11039 |
| 645 | AUAGUUGUC GUUGUAGG | 1621 | CCUACAAC CUGAUGAGGCCGUUAGGCCGAA ACAACUAU | 11040 |
| 648 | GUUGUCGUU GUAGGGUA | 1622 | UACCCUAC CUGAUGAGGCCGUUAGGCCGAA ACGACAAC | 11041 |
| 651 | GUCGUUGUA GGGUAUAG | 1623 | CUAUACCC CUGAUGAGGCCGUUAGGCCGAA ACAACGAC | 11042 |
| 656 | UGUAGGGUA UAGGAUUU | 1624 | AAAUCCUA CUGAUGAGGCCGUUAGGCCGAA ACCCUACA | 11043 |
| 658 | UAGGGUAUA GGAUUUAU | 1625 | AUAAAUCC CUGAUGAGGCCGUUAGGCCGAA AUACCCUA | 11044 |
| 663 | UAUAGGAUU UAUGAUGU | 1626 | ACAUCAUA CUGAUGAGGCCGUUAGGCCGAA AUCCUAUA | 11045 |
| 664 | AUAGGAUUU AUGAUGUG | 1627 | CACAUCAU CUGAUGAGGCCGUUAGGCCGAA AAUCCUAU | 11046 |
| 665 | UAGGAUUUA UGAUGUGG | 1628 | CCACAUCA CUGAUGAGGCCGUUAGGCCGAA AAAUCCUA | 11047 |
| 675 | GAUGUGGUU CUGAGUCC | 1629 | GGACUCAG CUGAUGAGGCCGUUAGGCCGAA ACCACAUC | 11048 |
| 676 | AUGUGGUUC UGAGUCCG | 1630 | CGGACUCA CUGAUGAGGCCGUUAGGCCGAA AACCACAU | 11049 |
| 682 | UUCUGAGUC CGUCUCAU | 1631 | AUGAGACG CUGAUGAGGCCGUUAGGCCGAA ACUCAGAA | 11050 |
| 686 | GAGUCCGUC UCAUGGAA | 1632 | UUCCAUGA CUGAUGAGGCCGUUAGGCCGAA ACGGACUC | 11051 |
| 688 | GUCCGUCUC AUGGAAUU | 1633 | AAUUCCAU CUGAUGAGGCCGUUAGGCCGAA AGACGGAC | 11052 |
| 696 | CAUGGAAUU GAACUAUC | 1634 | GAUAGUUC CUGAUGAGGCCGUUAGGCCGAA AUUCCAUG | 11053 |
| 702 | AUUGAACUA UCUGUUGG | 1635 | CCAACAGA CUGAUGAGGCCGUUAGGCCGAA AGUUCAAU | 11054 |
| 704 | UGAACUAUC UGUUGGAG | 1636 | CUCCAACA CUGAUGAGGCCGUUAGGCCGAA AUAGUUCA | 11055 |
| 708 | CUAUCUGUU GGAGAAAA | 1637 | UUUUCUCC CUGAUGAGGCCGUUAGGCCGAA ACAGAUAG | 11056 |
| 720 | GAAAAGCUU GUCUUAAA | 1638 | UUUAAGAC CUGAUGAGGCCGUUAGGCCGAA AGCUUUUC | 11057 |
| 723 | AAGCUUGUC UUAAAUUG | 1639 | CAAUUUAA CUGAUGAGGCCGUUAGGCCGAA ACAAGCUU | 11058 |
| 725 | GCUUGUCUU AAAUUGUA | 1640 | UACAAUUU CUGAUGAGGCCGUUAGGCCGAA AGACAAGC | 11059 |
| 726 | CUUGUCUUA AAUUGUAC | 1641 | GUACAAUU CUGAUGAGGCCGUUAGGCCGAA AAGACAAG | 11060 |
| 730 | UCUUAAAUU GUACAGCA | 1642 | UGCUGUAC CUGAUGAGGCCGUUAGGCCGAA AUUUAAGA | 11061 |
| 733 | UAAAUUGUA CAGCAAGA | 1643 | UCUUGCUG CUGAUGAGGCCGUUAGGCCGAA ACAAUUUA | 11062 |
| 750 | ACUGAACUA AAUGUGGG | 1644 | CCCACAUU CUGAUGAGGCCGUUAGGCCGAA AGUUCAGU | 11063 |

TABLE IV-continued

Human KDR VEGF Receptor-Hammerhead Ribozyme and Substrate Sequence

| Pos | Substrate | Seq ID No | HH Ribozyme Sequence | Seq ID No |
|-----|-----------|-----------|----------------------|-----------|
| 762 | GUGGGGAUU GACUUCAA | 1645 | UUGAAGUC CUGAUGAGGCCGUUAGGCCGAA AUCCCCAC | 11064 |
| 767 | GAUUGACUU CAACUGGG | 1646 | CCCAGUUG CUGAUGAGGCCGUUAGGCCGAA AGUCAAUC | 11065 |
| 768 | AUUGACUUC AACUGGGA | 1647 | UCCCAGUU CUGAUGAGGCCGUUAGGCCGAA AAGUCAAU | 11066 |
| 779 | CUGGGAAUA CCCUUCUU | 1648 | AAGAAGGG CUGAUGAGGCCGUUAGGCCGAA AUUCCCAG | 11067 |
| 784 | AAUACCCUU CUUCGAAG | 1649 | CUUCGAAG CUGAUGAGGCCGUUAGGCCGAA AGGGUAUU | 11068 |
| 785 | AUACCCUUC UUCGAAGC | 1650 | GCUUCGAA CUGAUGAGGCCGUUAGGCCGAA AAGGGUAU | 11069 |
| 787 | ACCCUUCUU CGAAGCAU | 1651 | AUGCUUCG CUGAUGAGGCCGUUAGGCCGAA AGAAGGGU | 11070 |
| 788 | CCCUUCUUC GAAGCAUC | 1652 | GAUGCUUC CUGAUGAGGCCGUUAGGCCGAA AAGAAGGG | 11071 |
| 796 | CGAAGCAUC AGCAUAAG | 1653 | CUUAUGCU CUGAUGAGGCCGUUAGGCCGAA AUGCUUCG | 11072 |
| 802 | AUCAGCAUA AGAAACUU | 1654 | AAGUUUCU CUGAUGAGGCCGUUAGGCCGAA AUGCUGAU | 11073 |
| 810 | AAGAAACUU GUAAACCG | 1655 | CGGUUUAC CUGAUGAGGCCGUUAGGCCGAA AGUUUCUU | 11074 |
| 813 | AAACUUGUA AACCGAGA | 1656 | UCUCGGUU CUGAUGAGGCCGUUAGGCCGAA ACAAGUUU | 11075 |
| 825 | CGAGACCUA AAAACCCA | 1657 | UGGGUUUU CUGAUGAGGCCGUUAGGCCGAA AGGUCUCG | 11076 |
| 836 | AACCCAGUC UGGGAGUG | 1658 | CACUCCCA CUGAUGAGGCCGUUAGGCCGAA ACUGGGUU | 11077 |
| 857 | GAAGAAAUU UUUGAGCA | 1659 | UGCUCAAA CUGAUGAGGCCGUUAGGCCGAA AUUUCUUC | 11078 |
| 858 | AAGAAAUUU UUGAGCAC | 1660 | GUGCUCAA CUGAUGAGGCCGUUAGGCCGAA AAUUUCUU | 11079 |
| 859 | AGAAAUUUU UGAGCACC | 1661 | GGUGCUCA CUGAUGAGGCCGUUAGGCCGAA AAAUUUCU | 11080 |
| 860 | GAAAUUUUU GAGCACCU | 1662 | AGGUGCUC CUGAUGAGGCCGUUAGGCCGAA AAAAUUUC | 11081 |
| 869 | GAGCACCUU AACUAUAG | 1663 | CUAUAGUU CUGAUGAGGCCGUUAGGCCGAA AGGUGCUC | 11082 |
| 870 | AGCACCUUA ACUAUAGA | 1664 | UCUAUAGU CUGAUGAGGCCGUUAGGCCGAA AAGGUGCU | 11083 |
| 874 | CCUUAACUA UAGAUGGU | 1665 | ACCAUCUA CUGAUGAGGCCGUUAGGCCGAA AGUUAAGG | 11084 |
| 876 | UUAACUAUA GAUGGUGU | 1666 | ACACCAUC CUGAUGAGGCCGUUAGGCCGAA AUAGUUAA | 11085 |
| 885 | GAUGGUGUA ACCCGGAG | 1667 | CUCCGGGU CUGAUGAGGCCGUUAGGCCGAA ACACCAUC | 11086 |
| 905 | CCAAGGAUU GUACACCU | 1668 | AGGUGUAC CUGAUGAGGCCGUUAGGCCGAA AUCCUUGG | 11087 |
| 908 | AGGAUUGUA CACCUGUG | 1669 | CACAGGUG CUGAUGAGGCCGUUAGGCCGAA ACAAUCCU | 11088 |
| 923 | UGCAGCAUC CAGUGGGC | 1670 | GCCCACUG CUGAUGAGGCCGUUAGGCCGAA AUGCUGCA | 11089 |
| 956 | CAGCACAUU UGUCAGGG | 1671 | CCCUGACA CUGAUGAGGCCGUUAGGCCGAA AUGUGCUG | 11090 |
| 957 | AGCACAUUU GUCAGGGU | 1672 | ACCCUGAC CUGAUGAGGCCGUUAGGCCGAA AAUGUGCU | 11091 |
| 960 | ACAUUUGUC AGGGUCCA | 1673 | UGGACCCU CUGAUGAGGCCGUUAGGCCGAA ACAAAUGU | 11092 |
| 966 | GUCAGGGUC CAUGAAAA | 1674 | UUUUCAUG CUGAUGAGGCCGUUAGGCCGAA ACCCUGAC | 11093 |
| 979 | AAAAACCUU UUGUUGCU | 1675 | AGCAACAA CUGAUGAGGCCGUUAGGCCGAA AGGUUUUU | 11094 |
| 980 | AAAACCUUU UGUUGCUU | 1676 | AAGCAACA CUGAUGAGGCCGUUAGGCCGAA AAGGUUUU | 11095 |
| 981 | AAACCUUUU GUUGCUUU | 1677 | AAAGCAAC CUGAUGAGGCCGUUAGGCCGAA AAAGGUUU | 11096 |
| 984 | CCUUUUGUU GCUUUUGG | 1678 | CCAAAAGC CUGAUGAGGCCGUUAGGCCGAA ACAAAAGG | 11097 |
| 988 | UUGUUGCUU UUGGAAGU | 1679 | ACUUCCAA CUGAUGAGGCCGUUAGGCCGAA AGCAACAA | 11098 |
| 989 | UGUUGCUUU UGGAAGUG | 1680 | CACUUCCA CUGAUGAGGCCGUUAGGCCGAA AAGCAACA | 11099 |
| 990 | GUUGCUUUU GGAAGUGG | 1681 | CCACUUCC CUGAUGAGGCCGUUAGGCCGAA AAAGCAAC | 11100 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 1007 | CAUGGAAUC UCUGGUGG | 1682 | CCACCAGA CUGAUGAGGCCGUUAGGCCGAA AUUCCAUG | 11101 |
| 1009 | UGGAAUCUC UGGUGGAA | 1683 | UUCCACCA CUGAUGAGGCCGUUAGGCCGAA AGAUUCCA | 11102 |
| 1038 | GAGCGUGUC AGAAUCCC | 1684 | GGGAUUCU CUGAUGAGGCCGUUAGGCCGAA ACACGCUC | 11103 |
| 1044 | GUCAGAAUC CUGCGAA | 1685 | UUCGCAGG CUGAUGAGGCCGUUAGGCCGAA AUUCUGAC | 11104 |
| 1055 | UGCGAAGUA CCUUGGUU | 1686 | AACCAAGG CUGAUGAGGCCGUUAGGCCGAA ACUUCGCA | 11105 |
| 1059 | AAGUACCUU GGUUACCC | 1687 | GGGUAACC CUGAUGAGGCCGUUAGGCCGAA AGGUACUU | 11106 |
| 1063 | ACCUUGGUU ACCCACCC | 1688 | GGGUGGGU CUGAUGAGGCCGUUAGGCCGAA ACCAAGGU | 11107 |
| 1064 | CCUUGGUUA CCCACCCC | 1689 | GGGGUGGG CUGAUGAGGCCGUUAGGCCGAA AACCAAGG | 11108 |
| 1080 | CCAGAAAUA AAAUGGUA | 1690 | UACCAUUU CUGAUGAGGCCGUUAGGCCGAA AUUUCUGG | 11109 |
| 1088 | AAAUGGUA UAAAAAUG | 1691 | CAUUUUUA CUGAUGAGGCCGUUAGGCCGAA ACCAUUUU | 11110 |
| 1090 | AAUGGUAUA AAAUGGA | 1692 | UCCAUUUU CUGAUGAGGCCGUUAGGCCGAA AUACCAUU | 11111 |
| 1101 | AAUGGAAUA CCCCUUGA | 1693 | UCAAGGGG CUGAUGAGGCCGUUAGGCCGAA AUUCCAUU | 11112 |
| 1107 | AUACCCCUU GAGUCCAA | 1694 | UUGGACUC CUGAUGAGGCCGUUAGGCCGAA AGGGGUAU | 11113 |
| 1112 | CCUUGAGUC CAAUCACA | 1695 | UGUGAUUG CUGAUGAGGCCGUUAGGCCGAA ACUCAAGG | 11114 |
| 1117 | AGUCCAAUC ACACAAUU | 1696 | AAUUGUGU CUGAUGAGGCCGUUAGGCCGAA AUUGGACU | 11115 |
| 1125 | CACACAAUU AAAGCGGG | 1697 | CCCGCUUU CUGAUGAGGCCGUUAGGCCGAA AUUGUGUG | 11116 |
| 1126 | ACACAAUUA AAGCGGGG | 1698 | CCCCGCUU CUGAUGAGGCCGUUAGGCCGAA AAUUGUGU | 11117 |
| 1140 | GGGCAUGUA CUGACGAU | 1699 | AUCGUCAG CUGAUGAGGCCGUUAGGCCGAA ACAUGCCC | 11118 |
| 1149 | CUGACGAUU AUGGAAGU | 1700 | ACUUCCAU CUGAUGAGGCCGUUAGGCCGAA AUCGUCAG | 11119 |
| 1150 | UGACGAUUA UGGAAGUG | 1701 | CACUUCCA CUGAUGAGGCCGUUAGGCCGAA AAUCGUCA | 11120 |
| 1180 | CAGGAAAUU ACACUGUC | 1702 | GACAGUGU CUGAUGAGGCCGUUAGGCCGAA AUUUCCUG | 11121 |
| 1181 | AGGAAAUUA CACUGUCA | 1703 | UGACAGUG CUGAUGAGGCCGUUAGGCCGAA AAUUUCCU | 11122 |
| 1188 | UACACUGUC AUCCUUAC | 1704 | GUAAGGAU CUGAUGAGGCCGUUAGGCCGAA ACAGUGUA | 11123 |
| 1191 | ACUGUCAUC CUUACCAA | 1705 | UUGGUAAG CUGAUGAGGCCGUUAGGCCGAA AUGACAGU | 11124 |
| 1194 | GUCAUCCUU ACCAAUCC | 1706 | GGAUUGGU CUGAUGAGGCCGUUAGGCCGAA AGGAUGAC | 11125 |
| 1195 | UCAUCCUUA CCAAUCCC | 1707 | GGGAUUGG CUGAUGAGGCCGUUAGGCCGAA AAGGAUGA | 11126 |
| 1201 | UUACCAAUC CAUUUCA | 1708 | UGAAAUGG CUGAUGAGGCCGUUAGGCCGAA AUUGGUAA | 11127 |
| 1206 | AAUCCCAUU UCAAAGGA | 1709 | UCCUUUGA CUGAUGAGGCCGUUAGGCCGAA AUGGGAUU | 11128 |
| 1207 | AUCCCAUUU CAAAGGAG | 1710 | CUCCUUUG CUGAUGAGGCCGUUAGGCCGAA AAUGGGAU | 11129 |
| 1208 | UCCCAUUUC AAAGGAGA | 1711 | UCUCCUUU CUGAUGAGGCCGUUAGGCCGAA AAAUGGGA | 11130 |
| 1233 | CAUGUGGUC UCUCUGGU | 1712 | ACCAGAGA CUGAUGAGGCCGUUAGGCCGAA ACCACAUG | 11131 |
| 1235 | UGUGGUCUC UCUGGUUG | 1713 | CAACCAGA CUGAUGAGGCCGUUAGGCCGAA AGACCACA | 11132 |
| 1237 | UGGUCUCUC UGGUUGUG | 1714 | CACAACCA CUGAUGAGGCCGUUAGGCCGAA AGAGACCA | 11133 |
| 1242 | UCUCUGGUU GUGUAUGU | 1715 | ACAUACAC CUGAUGAGGCCGUUAGGCCGAA ACCAGAGA | 11134 |
| 1247 | GGUUGUGUA UGUCCCAC | 1716 | GUGGGACA CUGAUGAGGCCGUUAGGCCGAA ACACAACC | 11135 |
| 1251 | GUGUAUGUC CCACCCCA | 1717 | UGGGGUGG CUGAUGAGGCCGUUAGGCCGAA ACAUACAC | 11136 |
| 1263 | CCCCAGAUU GGUGAGAA | 1718 | UUCUCACC CUGAUGAGGCCGUUAGGCCGAA AUCUGGGG | 11137 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 1274 | UGAGAAAUC UCUAAUCU | 1719 | AGAUUAGA CUGAUGAGGCCGUUAGGCCGAA AUUUCUCA | 11138 |
| 1276 | AGAAAUCUC UAAUCUCU | 1720 | AGAGAUUA CUGAUGAGGCCGUUAGGCCGAA AGAUUUCU | 11139 |
| 1278 | AAAUCUCUA AUCUCUCC | 1721 | GGAGAGAU CUGAUGAGGCCGUUAGGCCGAA AGAGAUUU | 11140 |
| 1281 | UCUCUAAUC UCUCCUGU | 1722 | ACAGGAGA CUGAUGAGGCCGUUAGGCCGAA AUUAGAGA | 11141 |
| 1283 | UCUAAUCUC UCCUGUGG | 1723 | CCACAGGA CUGAUGAGGCCGUUAGGCCGAA AGAUUAGA | 11142 |
| 1285 | UAAUCUCUC CUGUGGAU | 1724 | AUCCACAG CUGAUGAGGCCGUUAGGCCGAA AGAGAUUA | 11143 |
| 1294 | CUGUGGAUU CCUACCAG | 1725 | CUGGUAGG CUGAUGAGGCCGUUAGGCCGAA AUCCACAG | 11144 |
| 1295 | UGUGGAUUC CUACCAGU | 1726 | ACUGGUAG CUGAUGAGGCCGUUAGGCCGAA AAUCCACA | 11145 |
| 1298 | GGAUUCCUA CCAGUACG | 1727 | CGUACUGG CUGAUGAGGCCGUUAGGCCGAA AGGAAUCC | 11146 |
| 1304 | CUACCAGUA CGGCACCA | 1728 | UGGUGCCG CUGAUGAGGCCGUUAGGCCGAA ACUGGUAG | 11147 |
| 1315 | GCACCACUC AAACGCUG | 1729 | CAGCGUUU CUGAUGAGGCCGUUAGGCCGAA AGUGGUGC | 11148 |
| 1330 | UGACAUGUA CGGUCUAU | 1730 | AUAGACCG CUGAUGAGGCCGUUAGGCCGAA ACAUGUCA | 11149 |
| 1335 | UGUACGGUC UAUGCCAU | 1731 | AUGGCAUA CUGAUGAGGCCGUUAGGCCGAA ACCGUACA | 11150 |
| 1337 | UACGGUCUA UGCCAUUC | 1732 | GAAUGGCA CUGAUGAGGCCGUUAGGCCGAA AGACCGUA | 11151 |
| 1344 | UAUGCCAUU CCUCCCCC | 1733 | GGGGGAGG CUGAUGAGGCCGUUAGGCCGAA AUGGCAUA | 11152 |
| 1345 | AUGCCAUUC CUCCCCCG | 1734 | CGGGGGAG CUGAUGAGGCCGUUAGGCCGAA AAUGGCAU | 11153 |
| 1348 | CCAUUCCUC CCCGCAU | 1735 | AUGCGGGG CUGAUGAGGCCGUUAGGCCGAA AGGAAUGG | 11154 |
| 1357 | CCCCGCAUC ACAUCCAC | 1736 | GUGGAUGU CUGAUGAGGCCGUUAGGCCGAA AUGCGGGG | 11155 |
| 1362 | CAUCACAUC CACUGGUA | 1737 | UACCAGUG CUGAUGAGGCCGUUAGGCCGAA AUGUGAUG | 11156 |
| 1370 | CCACUGGUA UUGGCAGU | 1738 | ACUGCCAA CUGAUGAGGCCGUUAGGCCGAA ACCAGUGG | 11157 |
| 1372 | ACUGGUAUU GGCAGUUG | 1739 | CAACUGCC CUGAUGAGGCCGUUAGGCCGAA AUACCAGU | 11158 |
| 1379 | UUGGCAGUU GGAGGAAG | 1740 | CUUCCUCC CUGAUGAGGCCGUUAGGCCGAA ACUGCCAA | 11159 |
| 1416 | CAAGCUGUC UCAGUGAC | 1741 | GUCACUGA CUGAUGAGGCCGUUAGGCCGAA ACAGCUUG | 11160 |
| 1418 | AGCUGUCUC AGUGACAA | 1742 | UUGUCACU CUGAUGAGGCCGUUAGGCCGAA AGACAGCU | 11161 |
| 1433 | AAACCCAUA CCCUUGUG | 1743 | CACAAGGG CUGAUGAGGCCGUUAGGCCGAA AUGGGUUU | 11162 |
| 1438 | CAUACCCUU GUGAAGAA | 1744 | UUCUUCAC CUGAUGAGGCCGUUAGGCCGAA AGGGUAUG | 11163 |
| 1466 | GGAGGACUU CCAGGGAG | 1745 | CUCCCUGG CUGAUGAGGCCGUUAGGCCGAA AGUCCUCC | 11164 |
| 1467 | GAGGACUUC CAGGGAGG | 1746 | CCUCCCUG CUGAUGAGGCCGUUAGGCCGAA AAGUCCUC | 11165 |
| 1480 | GAGGAAAUA AAAUUGAA | 1747 | UUCAAUUU CUGAUGAGGCCGUUAGGCCGAA AUUUCCUC | 11166 |
| 1485 | AAUAAAAUU GAAGUUAA | 1748 | UUAACUUC CUGAUGAGGCCGUUAGGCCGAA AUUUUAUU | 11167 |
| 1491 | AUUGAAGUU AAUAAAAA | 1749 | UUUUUAUU CUGAUGAGGCCGUUAGGCCGAA ACUUCAAU | 11168 |
| 1492 | UUGAAGUUA AUAAAAAU | 1750 | AUUUUUAU CUGAUGAGGCCGUUAGGCCGAA AACUUCAA | 11169 |
| 1495 | AAGUUAAUA AAAUCAA | 1751 | UUGAUUUU CUGAUGAGGCCGUUAGGCCGAA AUUAACUU | 11170 |
| 1501 | AUAAAAUC AAUUUGCU | 1752 | AGCAAAUU CUGAUGAGGCCGUUAGGCCGAA AUUUUUAU | 11171 |
| 1505 | AAAUCAAUU UGCUCUAA | 1753 | UUAGAGCA CUGAUGAGGCCGUUAGGCCGAA AUUGAUUU | 11172 |
| 1506 | AAUCAAUUU GCUCUAAU | 1754 | AUUAGAGC CUGAUGAGGCCGUUAGGCCGAA AAUUGAUU | 11173 |
| 1510 | AAUUUGCUC UAAUUGAA | 1755 | UUCAAUUA CUGAUGAGGCCGUUAGGCCGAA AGCAAAUU | 11174 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 1512 | UUUGCUCUA AUUGAAGG | 1756 | CCUUCAAU CUGAUGAGGCCGUUAGGCCGAA AGAGCAAA | 11175 |
| 1515 | GCUCUAAUU GAAGGAAA | 1757 | UUUCCUUC CUGAUGAGGCCGUUAGGCCGAA AUUAGAGC | 11176 |
| 1536 | AAAACUGUA AGUACCCU | 1758 | AGGGUACU CUGAUGAGGCCGUUAGGCCGAA ACAGUUUU | 11177 |
| 1540 | CUGUAAGUA CCCUUGUU | 1759 | AACAAGGG CUGAUGAGGCCGUUAGGCCGAA ACUUACAG | 11178 |
| 1545 | AGUACCCUU GUUAUCCA | 1760 | UGGAUAAC CUGAUGAGGCCGUUAGGCCGAA AGGGUACU | 11179 |
| 1548 | ACCCUUGUU AUCCAAGC | 1761 | GCUUGGAU CUGAUGAGGCCGUUAGGCCGAA ACAAGGGU | 11180 |
| 1549 | CCCUUGUUA UCCAAGCG | 1762 | CGCUUGGA CUGAUGAGGCCGUUAGGCCGAA AACAAGGG | 11181 |
| 1551 | CUUGUUAUC CAAGCGGC | 1763 | GCCGCUUG CUGAUGAGGCCGUUAGGCCGAA AUAACAAG | 11182 |
| 1568 | AAAUGUGUC AGCUUUGU | 1764 | ACAAAGCU CUGAUGAGGCCGUUAGGCCGAA ACACAUUU | 11183 |
| 1573 | UGUCAGCUU UGUACAAA | 1765 | UUUGUACA CUGAUGAGGCCGUUAGGCCGAA AGCUGACA | 11184 |
| 1574 | GUCAGCUUU GUACAAAU | 1766 | AUUUGUAC CUGAUGAGGCCGUUAGGCCGAA AAGCUGAC | 11185 |
| 1577 | AGCUUUGUA CAAAUGUG | 1767 | CACAUUUG CUGAUGAGGCCGUUAGGCCGAA ACAAAGCU | 11186 |
| 1593 | GAAGCGGUC AACAAAGU | 1768 | ACUUUGUU CUGAUGAGGCCGUUAGGCCGAA ACCGCUUC | 11187 |
| 1602 | AACAAAGUC GGGAGAGG | 1769 | CCUCUCCC CUGAUGAGGCCGUUAGGCCGAA ACUUUGUU | 11188 |
| 1623 | AGGGUGAUC UCCUUCCA | 1770 | UGGAAGGA CUGAUGAGGCCGUUAGGCCGAA AUCACCCU | 11189 |
| 1625 | GGUGAUCUC CUUCCACG | 1771 | CGUGGAAG CUGAUGAGGCCGUUAGGCCGAA AGAUCACC | 11190 |
| 1628 | GAUCUCCUU CCACGUGA | 1772 | UCACGUGG CUGAUGAGGCCGUUAGGCCGAA AGGAGAUC | 11191 |
| 1629 | AUCUCCUUC CACGUGAC | 1773 | GUCACGUG CUGAUGAGGCCGUUAGGCCGAA AAGGAGAU | 11192 |
| 1645 | CCAGGGGUC UGAAAUU | 1774 | AAUUUCAG CUGAUGAGGCCGUUAGGCCGAA ACCCCUGG | 11193 |
| 1653 | CCUGAAAUU ACUUUGCA | 1775 | UGCAAAGU CUGAUGAGGCCGUUAGGCCGAA AUUUCAGG | 11194 |
| 1654 | CUGAAAUUA CUUUGCAA | 1776 | UUGCAAAG CUGAUGAGGCCGUUAGGCCGAA AAUUUCAG | 11195 |
| 1657 | AAAUUACUU UGCAACCU | 1777 | AGGUUGCA CUGAUGAGGCCGUUAGGCCGAA AGUAAUUU | 11196 |
| 1658 | AAUUACUUU GCAACCUG | 1778 | CAGGUUGC CUGAUGAGGCCGUUAGGCCGAA AAGUAAUU | 11197 |
| 1697 | GAGCGUGUC UUUGUGGU | 1779 | ACCACAAA CUGAUGAGGCCGUUAGGCCGAA ACACGCUC | 11198 |
| 1699 | GCGUGUCUU UGUGGUGC | 1780 | GCACCACA CUGAUGAGGCCGUUAGGCCGAA AGACACGC | 11199 |
| 1700 | CGUGUCUUU GUGGUGCA | 1781 | UGCACCAC CUGAUGAGGCCGUUAGGCCGAA AAGACACG | 11200 |
| 1721 | AGACAGAUC UACGUUUG | 1782 | CAAACGUA CUGAUGAGGCCGUUAGGCCGAA AUCUGUCU | 11201 |
| 1723 | ACAGAUCUA CGUUUGAG | 1783 | CUCAAACG CUGAUGAGGCCGUUAGGCCGAA AGAUCUGU | 11202 |
| 1727 | AUCUACGUU UGAGAACC | 1784 | GGUUCUCA CUGAUGAGGCCGUUAGGCCGAA ACGUAGAU | 11203 |
| 1728 | UCUACGUUU GAGAACCU | 1785 | AGGUUCUC CUGAUGAGGCCGUUAGGCCGAA AACGUAGA | 11204 |
| 1737 | GAGAACCUC ACAUGGUA | 1786 | UACCAUGU CUGAUGAGGCCGUUAGGCCGAA AGGUUCUC | 11205 |
| 1745 | CACAUGGUA CAAGCUUG | 1787 | CAAGCUUG CUGAUGAGGCCGUUAGGCCGAA ACCAUGUG | 11206 |
| 1752 | UACAAGCUU GGCCCACA | 1788 | UGUGGGCC CUGAUGAGGCCGUUAGGCCGAA AGCUUGUA | 11207 |
| 1765 | CACAGCCUC UGCCAAUC | 1789 | GAUUGGCA CUGAUGAGGCCGUUAGGCCGAA AGGCUGUG | 11208 |
| 1773 | CUGCCAAUC CAUGUGGG | 1790 | CCCACAUG CUGAUGAGGCCGUUAGGCCGAA AUUGGCAG | 11209 |
| 1787 | GGGAGAGUU GCCCACAC | 1791 | GUGUGGGC CUGAUGAGGCCGUUAGGCCGAA ACUCUCCC | 11210 |
| 1800 | ACACCUGUU UGCAAGAA | 1792 | UUCUUGCA CUGAUGAGGCCGUUAGGCCGAA ACAGGUGU | 11211 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 1801 | CACCUGUUU GCAAGAAC | 1793 | GUUCUUGC CUGAUGAGGCCGUUAGGCCGAA AACAGGUG | 11212 |
| 1811 | CAAGAACUU GGAUACUC | 1794 | GAGUAUCC CUGAUGAGGCCGUUAGGCCGAA AGUUCUUG | 11213 |
| 1816 | ACUUGGAUA CUCUUUGG | 1795 | CCAAAGAG CUGAUGAGGCCGUUAGGCCGAA AUCCAAGU | 11214 |
| 1819 | UGGAUACUC UUUGGAAA | 1796 | UUUCCAAA CUGAUGAGGCCGUUAGGCCGAA AGUAUCCA | 11215 |
| 1821 | GAUACUCUU UGGAAAUU | 1797 | AAUUUCCA CUGAUGAGGCCGUUAGGCCGAA AGAGUAUC | 11216 |
| 1822 | AUACUCUUU GGAAAUUG | 1798 | CAAUUUCC CUGAUGAGGCCGUUAGGCCGAA AAGAGUAU | 11217 |
| 1829 | UUGGAAAUU GAAUGCCA | 1799 | UGGCAUUC CUGAUGAGGCCGUUAGGCCGAA AUUUCCAA | 11218 |
| 1844 | CACCAUGUU CUCUAAUA | 1800 | UAUUAGAG CUGAUGAGGCCGUUAGGCCGAA ACAUGGUG | 11219 |
| 1845 | ACCAUGUUC UCUAAUAG | 1801 | CUAUUAGA CUGAUGAGGCCGUUAGGCCGAA AACAUGGU | 11220 |
| 1847 | CAUGUUCUC UAAUAGCA | 1802 | UGCUAUUA CUGAUGAGGCCGUUAGGCCGAA AGAACAUG | 11221 |
| 1849 | UGUUCUCUA AUAGCACA | 1803 | UGUGCUAU CUGAUGAGGCCGUUAGGCCGAA AGAGAACA | 11222 |
| 1852 | UCUCUAAUA GCACAAAU | 1804 | AUUUGUGC CUGAUGAGGCCGUUAGGCCGAA AUUAGAGA | 11223 |
| 1866 | AAUGACAUU UUGAUCAU | 1805 | AUGAUCAA CUGAUGAGGCCGUUAGGCCGAA AUGUCAUU | 11224 |
| 1867 | AUGACAUUU UGAUCAUG | 1806 | CAUGAUCA CUGAUGAGGCCGUUAGGCCGAA AAUGUCAU | 11225 |
| 1868 | UGACAUUUC GAUCAUGG | 1807 | CCAUGAUC CUGAUGAGGCCGUUAGGCCGAA AAAUGUCA | 11226 |
| 1872 | AUUUUGAUC AUGGAGCU | 1808 | AGCUCCAU CUGAUGAGGCCGUUAGGCCGAA AUCAAAAU | 11227 |
| 1881 | AUGGAGCUU AAGAAUGC | 1809 | GCAUUCUU CUGAUGAGGCCGUUAGGCCGAA AGCUCCAU | 11228 |
| 1882 | UGGACCUUA AGAAUGCA | 1810 | UGCAUUCU CUGAUGAGGCCGUUAGGCCGAA AAGCUCCA | 11229 |
| 1892 | GAAUGCAUC CUUGCAGG | 1811 | CCUGCAAG CUGAUGAGGCCGUUAGGCCGAA AUGCAUUC | 11230 |
| 1895 | UGCAUCCUU GCAGGACC | 1812 | GGUCCUGC CUGAUGAGGCCGUUAGGCCGAA AGGAUGCA | 11231 |
| 1913 | AGGAGACUA UGUCUGCC | 1813 | GGCAGACA CUGAUGAGGCCGUUAGGCCGAA AGUCUCCU | 11232 |
| 1917 | GACUAUGUC UGCCUUGC | 1814 | GCAAGGCA CUGAUGAGGCCGUUAGGCCGAA ACAUAGUC | 11233 |
| 1923 | GUCUGCCUU GCUCAAGA | 1815 | UCUUGAGC CUGAUGAGGCCGUUAGGCCGAA AGGCAGAC | 11234 |
| 1927 | GCCUUGCUC AAGACAGG | 1816 | CCUGUCUU CUGAUGAGGCCGUUAGGCCGAA AGCAAGGC | 11235 |
| 1954 | AAAGACAUU GCGUGGUC | 1817 | GACCACGC CUGAUGAGGCCGUUAGGCCGAA AUGUCUUU | 11236 |
| 1962 | UGCGUGGUC AGGCAGCU | 1818 | AGCUGCCU CUGAUGAGGCCGUUAGGCCGAA ACCACGCA | 11237 |
| 1971 | AGGCAGCUC ACAGUCCU | 1819 | AGGACUGU CUGAUGAGGCCGUUAGGCCGAA AGCUGCCU | 11238 |
| 1977 | CUCACAGUC CUAGAGCG | 1820 | CGCUCUAG CUGAUGAGGCCGUUAGGCCGAA ACUGUGAG | 11239 |
| 1980 | ACAGUCCUA GAGCGUGU | 1821 | ACACGCUC CUGAUGAGGCCGUUAGGCCGAA AGGACUGU | 11240 |
| 2001 | CCCACGAUC ACAGGAAA | 1822 | UUUCCUGU CUGAUGAGGCCGUUAGGCCGAA AUCGUGGG | 11241 |
| 2020 | UGGAGAAUC AGACGACA | 1823 | UGUCGUCU CUGAUGAGGCCGUUAGGCCGAA AUUCUCCA | 11242 |
| 2032 | CGACAAGUA UUGGGAA | 1824 | UUCCCCAA CUGAUGAGGCCGUUAGGCCGAA ACUUGUCG | 11243 |
| 2034 | ACAAGUAUU GGGAAAG | 1825 | CUUUCCCC CUGAUGAGGCCGUUAGGCCGAA AUACUUGU | 11244 |
| 2046 | GAAAGCAUC GAAGUCUC | 1826 | GAGACUUC CUGAUGAGGCCGUUAGGCCGAA AUGCUUUC | 11245 |
| 2052 | AUCGAAGUC UCAUGCAC | 1827 | GUGCAUGA CUGAUGAGGCCGUUAGGCCGAA ACUUCGAU | 11246 |
| 2054 | CGAAGUCUC AUGCACGG | 1828 | CCGUGCAU CUGAUGAGGCCGUUAGGCCGAA AGACUUCG | 11247 |
| 2066 | CACGGCAUC UGGGAAUC | 1829 | GAUUCCCA CUGAUGAGGCCGUUAGGCCGAA AUGCCGUG | 11248 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 2074 | CUGGGAAUC CCCCUCCA | 1830 | UGGAGGGG CUGAUGAGGCCGUUAGGCCGAA AUUCCCAG | 11249 |
| 2080 | AUCCCCCUC CACAGAUC | 1831 | GAUCUGUG CUGAUGAGGCCGUUAGGCCGAA AGGGGGAU | 11250 |
| 2088 | CCACAGAUC AUGUGGUU | 1832 | AACCACAU CUGAUGAGGCCGUUAGGCCGAA AUCUGUGG | 11251 |
| 2096 | CAUGUGGUU UAAAGAUA | 1833 | UAUCUUUA CUGAUGAGGCCGUUAGGCCGAA ACCACAUG | 11252 |
| 2097 | AUGUGGUUU AAAGAUAA | 1834 | UUAUCUUU CUGAUGAGGCCGUUAGGCCGAA AACCACAU | 11253 |
| 2098 | UGUGGUUUA AAGAUAAU | 1835 | AUUAUCUU CUGAUGAGGCCGUUAGGCCGAA AAACCACA | 11254 |
| 2104 | UUAAAGAUA AUGAGACC | 1836 | GGUCUCAU CUGAUGAGGCCGUUAGGCCGAA AUCUUUAA | 11255 |
| 2115 | GAGACCCUU GUAGAAGA | 1837 | UCUUCUAC CUGAUGAGGCCGUUAGGCCGAA AGGGUCUC | 11256 |
| 2118 | ACCCUUGUA GAAGACUC | 1838 | GAGUCCUC CUGAUGAGGCCGUUAGGCCGAA ACAAGGGU | 11257 |
| 2126 | AGAAGACUC AGGCAUUG | 1839 | CAAUGCCU CUGAUGAGGCCGUUAGGCCGAA AGUCUUCU | 11258 |
| 2133 | UCAGGCAUU GUAUUGAA | 1840 | UUCAAUAC CUGAUGAGGCCGUUAGGCCGAA AUGCCUGA | 11259 |
| 2136 | GGCAUUGUA UUGAAGGA | 1841 | UCCUUCAA CUGAUGAGGCCGUUAGGCCGAA ACAAUGCC | 11260 |
| 2138 | CAUUGUAUU GAAGGAUG | 1842 | CAUCCUUC CUGAUGAGGCCGUUAGGCCGAA AUACAAUG | 11261 |
| 2160 | CGGAACCUC ACUAUCCG | 1843 | CGGAUAGU CUGAUGAGGCCGUUAGGCCGAA AGGUUCCG | 11262 |
| 2164 | ACCUCACUA UCCGCAGA | 1844 | UCUGCGGA CUGAUGAGGCCGUUAGGCCGAA AGUGAGGU | 11263 |
| 2166 | CUCACUAUC CGCAGAGU | 1845 | ACUCUGCG CUGAUGAGGCCGUUAGGCCGAA AUAGUGAG | 11264 |
| 2196 | GAAGGCCUC UACACCUG | 1846 | CAGGUGUA CUGAUGAGGCCGUUAGGCCGAA AGGCCUUC | 11265 |
| 2198 | AGGCCUCUA CACCUGCC | 1847 | GGCAGGUG CUGAUGAGGCCGUUAGGCCGAA AGAGGCCU | 11266 |
| 2220 | UGCAGUGUU CUUGGCUG | 1848 | CAGCCAAG CUGAUGAGGCCGUUAGGCCGAA ACACUCCA | 11267 |
| 2221 | GCAGUGUUC UUGGCUGU | 1849 | ACAGCCAA CUGAUGAGGCCGUUAGGCCGAA AACACUGC | 11268 |
| 2223 | AGUGUUCUU GGCUGUGC | 1850 | GCACAGCC CUGAUGAGGCCGUUAGGCCGAA AGAACACU | 11269 |
| 2246 | GGAGGCAUU UUUCAUAA | 1851 | UUAUGAAA CUGAUGAGGCCGUUAGGCCGAA AUGCCUCC | 11270 |
| 2247 | GAGGCAUUU UUCAUAAU | 1852 | AUUAUGAA CUGAUGAGGCCGUUAGGCCGAA AAUGCCUC | 11271 |
| 2248 | AGGCAUUUU UCAUAAUA | 1853 | UAUUAUGA CUGAUGAGGCCGUUAGGCCGAA AAAUGCCU | 11272 |
| 2249 | GGCAUUUUU CAUAAUAG | 1854 | CUAUUAUG CUGAUGAGGCCGUUAGGCCGAA AAAAUGCC | 11273 |
| 2250 | GCAUUUUUC AUAAUAGA | 1855 | UCUAUUAU CUGAUGAGGCCGUUAGGCCGAA AAAAAUGC | 11274 |
| 2253 | UUUUUCAUA AUAGAAGG | 1856 | CCUUCUAU CUGAUGAGGCCGUUAGGCCGAA AUGAAAAA | 11275 |
| 2256 | UUCAUAAUA GAAGGUGC | 1857 | GCACCUUC CUGAUGAGGCCGUUAGGCCGAA AUUAUGAA | 11276 |
| 2282 | GACGAACUU GGAAAUCA | 1858 | UGAUUUCC CUGAUGAGGCCGUUAGGCCGAA AGUUCGUC | 11277 |
| 2289 | UUGGAAAUC AUUAUUCU | 1859 | AGAAUAAU CUGAUGAGGCCGUUAGGCCGAA AUUUCCAA | 11278 |
| 2292 | GAAAUCAUU AUUCUAGU | 1860 | ACUAGAAU CUGAUGAGGCCGUUAGGCCGAA AUGAUUUC | 11279 |
| 2293 | AAAUCAUUA UUCUAGUA | 1861 | UACUAGAA CUGAUGAGGCCGUUAGGCCGAA AAUGAUUU | 11280 |
| 2295 | AUCAUUAUU CUAGUAGG | 1862 | CCUACUAG CUGAUGAGGCCGUUAGGCCGAA AUAAUGAU | 11281 |
| 2296 | UCAUUAUUC UAGUAGGC | 1863 | GCCUACUA CUGAUGAGGCCGUUAGGCCGAA AAUAAUGA | 11282 |
| 2298 | AUUAUUCUA GUAGGCAC | 1864 | GUGCCUAC CUGAUGAGGCCGUUAGGCCGAA AGAAUAAU | 11283 |
| 2301 | AUUCUAGUA GGCACGAC | 1865 | GUCGUGCC CUGAUGAGGCCGUUAGGCCGAA ACUAGAAU | 11284 |
| 2316 | ACGGUGAUU GCCAUGUU | 1866 | AACAUGGC CUGAUGAGGCCGUUAGGCCGAA AUCACCGU | 11285 |

TABLE IV-continued

Human KDR VEGF Receptor-Hammerhead Ribozyme and Substrate Sequence

| Pos | Substrate | Seq ID No | HH Ribozyme Sequence | Seq ID No |
|-----|-----------|-----------|----------------------|-----------|
| 2324 | UGCCAUGUU CUUCUGGC | 1867 | GCCAGAAG CUGAUGAGGCCGUUAGGCCGAA ACAUGGCA | 11286 |
| 2325 | GCCAUGUUC UUCUGGCU | 1868 | AGCCAGAA CUGAUGAGGCCGUUAGGCCGAA AACAUGGC | 11287 |
| 2327 | CAUGUUCUU CUGGCUAC | 1869 | GUAGCCAG CUGAUGAGGCCGUUAGGCCGAA AGAACAUG | 11288 |
| 2328 | AUGUUCUUC UGGCUACU | 1870 | AGUAGCCA CUGAUGAGGCCGUUAGGCCGAA AAGAACAU | 11289 |
| 2334 | UUCUGGCUA CUUCUUGU | 1871 | ACAAGAAG CUGAUGAGGCCGUUAGGCCGAA AGCCAGAA | 11290 |
| 2337 | UGGCUACUU CUUGUCAU | 1872 | AUGACAAG CUGAUGAGGCCGUUAGGCCGAA AGUAGCCA | 11291 |
| 2338 | GGCUACUUC UUGUCAUC | 1873 | GAUGACAA CUGAUGAGGCCGUUAGGCCGAA AAGUAGCC | 11292 |
| 2340 | CUACUUCUU GUCAUCAU | 1874 | AUGAUGAC CUGAUGAGGCCGUUAGGCCGAA AGAAGUAG | 11293 |
| 2343 | CUUCUUGUC AUCACCU | 1875 | AGGAUGAU CUGAUGAGGCCGUUAGGCCGAA ACAAGAAG | 11294 |
| 2346 | CUUGUCAUC AUCCUAGG | 1876 | CCUAGGAU CUGAUGAGGCCGUUAGGCCGAA AUGACAAG | 11295 |
| 2349 | GUCAUCAUC CUAGGGAC | 1877 | GUCCCUAG CUGAUGAGGCCGUUAGGCCGAA AUGAUGAC | 11296 |
| 2352 | AUCAUCCUA GGGACCGU | 1878 | ACGGUCCC CUGAUGAGGCCGUUAGGCCGAA AGGAUGAU | 11297 |
| 2361 | GGGACCGUU AAGCGGGC | 1879 | GCCCGCUU CUGAUGAGGCCGUUAGGCCGAA ACGGUCCC | 11298 |
| 2362 | GGACCGUUA AGCGGGCC | 1880 | GGCCCGCU CUGAUGAGGCCGUUAGGCCGAA AACGGUCC | 11299 |
| 2396 | GACAGGCUA CUUGUCCA | 1881 | UGGACAAG CUGAUGAGGCCGUUAGGCCGAA AGCCUGUC | 11300 |
| 2399 | AGGCUACUU GUCCAUCG | 1882 | CGAUGGAC CUGAUGAGGCCGUUAGGCCGAA AGUAGCCU | 11301 |
| 2402 | CUACUUGUC CAUCGUCA | 1883 | UGACGAUG CUGAUGAGGCCGUUAGGCCGAA ACAAGUAG | 11302 |
| 2406 | UUGUCCAUC GUCAUGGA | 1884 | UCCAUGAC CUGAUGAGGCCGUUAGGCCGAA AUGGACAA | 11303 |
| 2409 | UCCAUCGUC AUGGAUCC | 1885 | GGAUCCAU CUGAUGAGGCCGUUAGGCCGAA ACGAUGGA | 11304 |
| 2416 | UCAUGGAUC CAGAUGAA | 1886 | UUCAUCUG CUGAUGAGGCCGUUAGGCCGAA AUCCAUGA | 11305 |
| 2427 | GAUGAACUC CAUUGGA | 1887 | UCCAAUGG CUGAUGAGGCCGUUAGGCCGAA AGUUCAUC | 11306 |
| 2432 | ACUCCCAUU GGAUGAAC | 1888 | GUUCAUCC CUGAUGAGGCCGUUAGGCCGAA AUGGGAGU | 11307 |
| 2443 | AUGAACAUU GUGAACGA | 1889 | UCGUUCAC CUGAUGAGGCCGUUAGGCCGAA AUGUUCAU | 11308 |
| 2458 | GACUGCCUU AUGAUGCC | 1890 | GGCAUCAU CUGAUGAGGCCGUUAGGCCGAA AGGCAGUC | 11309 |
| 2459 | ACUGCCUUA UGAUGCCA | 1891 | UGGCAUCA CUGAUGAGGCCGUUAGGCCGAA AAGGCAGU | 11310 |
| 2480 | AUGGGAAUU CCCCAGAG | 1892 | CUCUGGGG CUGAUGAGGCCGUUAGGCCGAA AUUCCCAU | 11311 |
| 2481 | UGGGAAUUC CCCAGAGA | 1893 | UCUCUGGG CUGAUGAGGCCGUUAGGCCGAA AAUUCCCA | 11312 |
| 2502 | CUGAACCUA GGUAAGCC | 1894 | GGCUUACC CUGAUGAGGCCGUUAGGCCGAA AGGUUCAG | 11313 |
| 2506 | ACCUAGGUA AGCCUCUU | 1895 | AAGAGGCU CUGAUGAGGCCGUUAGGCCGAA ACCUAGGU | 11314 |
| 2512 | GUAAGCCUC UUGGCCGU | 1896 | ACGGCCAA CUGAUGAGGCCGUUAGGCCGAA AGGCUUAC | 11315 |
| 2514 | AAGCCUCUU GGCCGUGG | 1897 | CCACGGCC CUGAUGAGGCCGUUAGGCCGAA AGAGGCUU | 11316 |
| 2528 | UGGUGCCUU UGGCCAAG | 1898 | CUUGGCCA CUGAUGAGGCCGUUAGGCCGAA AGGCACCA | 11317 |
| 2529 | GGUGCCUUU GGCCAAGA | 1899 | UCUUGGCC CUGAUGAGGCCGUUAGGCCGAA AAGGCACC | 11318 |
| 2541 | CAAGAGAUU GAAGCAGA | 1900 | UCUGCUUC CUGAUGAGGCCGUUAGGCCGAA AUCUCUUG | 11319 |
| 2555 | AGAUGCCUU UGGAAUUG | 1901 | CAAUUCCA CUGAUGAGGCCGUUAGGCCGAA AGGCAUCU | 11320 |
| 2556 | GAUGCCUUU GGAAUUGA | 1902 | UCAAUUCC CUGAUGAGGCCGUUAGGCCGAA AAGGCAUC | 11321 |
| 2562 | UUUGGAAUU GACAAGAC | 1903 | GUCUUGUC CUGAUGAGGCCGUUAGGCCGAA AUUCCAAA | 11322 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 2578 | CAGCAACUU GCAGGACA | 1904 | UGUCCUGC CUGAUGAGGCCGUUAGGCCGAA AGUUGCUG | 11323 |
| 2589 | AGGACAGUA GCAGUCAA | 1905 | UUGACUGC CUGAUGAGGCCGUUAGGCCGAA ACUGUCCU | 11324 |
| 2595 | GUAGCAGUC AAAAUGUU | 1906 | AACAUUUU CUGAUGAGGCCGUUAGGCCGAA ACUGCUAC | 11325 |
| 2603 | CAAAAUGUU GAAAGAAG | 1907 | CUUCUUUC CUGAUGAGGCCGUUAGGCCGAA ACAUUUUG | 11326 |
| 2632 | GUGAGCAUC GAGCUCUC | 1908 | GAGAGCUC CUGAUGAGGCCGUUAGGCCGAA AUGCUCAC | 11327 |
| 2638 | AUCGAGCUC UCAUGUCU | 1909 | AGACAUGA CUGAUGAGGCCGUUAGGCCGAA AGCUCGAU | 11328 |
| 2640 | CGAGCUCUC AUGUCUGA | 1910 | UCAGACAU CUGAUGAGGCCGUUAGGCCGAA AGAGCUCG | 11329 |
| 2645 | UCUCAUGUC UGAACUCA | 1911 | UGAGUUCA CUGAUGAGGCCGUUAGGCCGAA ACAUGAGA | 11330 |
| 2652 | UCUGAACUC AAGAUCCU | 1912 | AGGAUCUU CUGAUGAGGCCGUUAGGCCGAA AGUUCAGA | 11331 |
| 2658 | CUCAAGAUC UCAUUCA | 1913 | UGAAUGAG CUGAUGAGGCCGUUAGGCCGAA AUCUUGAG | 11332 |
| 2661 | AAGAUCCUC AUUCAUAU | 1914 | AUAUGAAU CUGAUGAGGCCGUUAGGCCGAA AGGAUCUU | 11333 |
| 2664 | AUCCUCAUU CAUAUUGG | 1915 | CCAAUAUG CUGAUGAGGCCGUUAGGCCGAA AUGAGGAU | 11334 |
| 2665 | UCCUCAUUC AUAUUGGU | 1916 | ACCAAUAU CUGAUGAGGCCGUUAGGCCGAA AAUGAGGA | 11335 |
| 2668 | UCAUUCAUA UUGGUCAC | 1917 | GUGACCAA CUGAUGAGGCCGUUAGGCCGAA AUGAAUGA | 11336 |
| 2670 | AUUCAUAUU GGUCACCA | 1918 | UGGUGACC CUGAUGAGGCCGUUAGGCCGAA AUAUGAAU | 11337 |
| 2674 | AUAUUGGUC ACCAUCUC | 1919 | GAGAUGGU CUGAUGAGGCCGUUAGGCCGAA ACCAAUAU | 11338 |
| 2680 | GUCACCAUC UCAAUGUG | 1920 | CACAUUGA CUGAUGAGGCCGUUAGGCCGAA AUGGUGAC | 11339 |
| 2682 | CACCAUCUC AAUGUGGU | 1921 | ACCACAUU CUGAUGAGGCCGUUAGGCCGAA AGAUGGUG | 11340 |
| 2691 | AAUGUGGUC AACCUUCU | 1922 | AGAAGGUU CUGAUGAGGCCGUUAGGCCGAA ACCACAUU | 11341 |
| 2697 | GUCAACCUU CUAGGUGC | 1923 | GCACCUAG CUGAUGAGGCCGUUAGGCCGAA AGGUUUAC | 11342 |
| 2698 | UCAACCUUC UAGGUGCC | 1924 | GGCACCUA CUGAUGAGGCCGUUAGGCCGAA AAGGUUGA | 11343 |
| 2700 | AACCUUCUA GGUGCCUG | 1925 | CAGGCACC CUGAUGAGGCCGUUAGGCCGAA AGAAGGUU | 11344 |
| 2710 | GUGCCUGUA CCAAGCCA | 1926 | UGGCUUGG CUGAUGAGGCCGUUAGGCCGAA ACAGGCAC | 11345 |
| 2730 | GGGCCACUC AUGGUGAU | 1927 | AUCACCAU CUGAUGAGGCCGUUAGGCCGAA AGUGGCCC | 11346 |
| 2739 | AUGGUGAUU GUGGAAUU | 1928 | AAUUCCAC CUGAUGAGGCCGUUAGGCCGAA AUCACCAU | 11347 |
| 2747 | UGUGGAAUU CUGCAAAU | 1929 | AUUUGCAG CUGAUGAGGCCGUUAGGCCGAA AUUCCACA | 11348 |
| 2748 | GUGGAAUUC UGCAAAUU | 1930 | AAUUUGCA CUGAUGAGGCCGUUAGGCCGAA AAUUCCAC | 11349 |
| 2756 | CUGCAAAUU GGAAACC | 1931 | GGUUUCCA CUGAUGAGGCCGUUAGGCCGAA AUUUGCAG | 11350 |
| 2757 | UGCAAAUUU GGAAACCU | 1932 | AGGUUUCC CUGAUGAGGCCGUUAGGCCGAA AAUUUGCA | 11351 |
| 2768 | AAACCUGUC CACUUACC | 1933 | GGUAAGUG CUGAUGAGGCCGUUAGGCCGAA ACAGGUUU | 11352 |
| 2773 | UGUCCACUU ACCUGAGG | 1934 | CCUCAGGU CUGAUGAGGCCGUUAGGCCGAA AGUGGACA | 11353 |
| 2774 | GUCCACUUA CCUGAGGA | 1935 | UCCUCAGG CUGAUGAGGCCGUUAGGCCGAA AAGUGGAC | 11354 |
| 2798 | AAAUGAAUU GUCCCCU | 1936 | AGGGGACA CUGAUGAGGCCGUUAGGCCGAA AUUCAUUU | 11355 |
| 2799 | AAUGAAUUU GUCCCUA | 1937 | UAGGGGAC CUGAUGAGGCCGUUAGGCCGAA AAUUCAUU | 11356 |
| 2802 | GAAUUUGUC CCUACAA | 1938 | UUGUAGGG CUGAUGAGGCCGUUAGGCCGAA ACAAAUUC | 11357 |
| 2807 | UGUCCCCUA CAAGACCA | 1939 | UGGUCUUG CUGAUGAGGCCGUUAGGCCGAA AGGGGACA | 11358 |
| 2828 | GGCACGAUU CCGUCAAG | 1940 | CUUGACGG CUGAUGAGGCCGUUAGGCCGAA AUCGUGCC | 11359 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 2829 | GCACGAUUC CGUCAAGG | 1941 | CCUUGACG CUGAUGAGGCCGUUAGGCCGAA AAUCGUGC | 11360 |
| 2833 | GAUUCCGUC AAGGGAAA | 1942 | UUUCCCUU CUGAUGAGGCCGUUAGGCCGAA ACGGAAUC | 11361 |
| 2846 | GAAAGACUA CGUUGGAG | 1943 | CUCCAACG CUGAUGAGGCCGUUAGGCCGAA AGUCUUUC | 11362 |
| 2850 | GACUACGUU GGAGCAAU | 1944 | AUUGCUCC CUGAUGAGGCCGUUAGGCCGAA ACGUAGUC | 11363 |
| 2859 | GGAGCAAUC CCUGUGGA | 1945 | UCCACAGG CUGAUGAGGCCGUUAGGCCGAA AUUGCUCC | 11364 |
| 2869 | CUGUGGAUC UGAAACGG | 1946 | CCGUUUCA CUGAUGAGGCCGUUAGGCCGAA AUCCACAG | 11365 |
| 2882 | ACGGCGCUU GGACAGCA | 1947 | UGCUGUCC CUGAUGAGGCCGUUAGGCCGAA AGCGCCGU | 11366 |
| 2892 | GACAGCAUC ACCAGUAG | 1948 | CUACUGGU CUGAUGAGGCCGUUAGGCCGAA AUGCUGUC | 11367 |
| 2899 | UCACCAGUA GCCAGAGC | 1949 | GCUCUGGC CUGAUGAGGCCGUUAGGCCGAA ACUGGUGA | 11368 |
| 2909 | CCAGAGCUC AGCCAGCU | 1950 | AGCUGGCU CUGAUGAGGCCGUUAGGCCGAA AGCUCUGG | 11369 |
| 2918 | AGCCAGCUC UGGAUUUG | 1951 | CAAAUCCA CUGAUGAGGCCGUUAGGCCGAA AGCUGGCU | 11370 |
| 2924 | CUCUGGAUU UGUGGAGG | 1952 | CCUCCACA CUGAUGAGGCCGUUAGGCCGAA AUCCAGAG | 11371 |
| 2925 | UCUGGAUUU GUGGAGGA | 1953 | UCCUCCAC CUGAUGAGGCCGUUAGGCCGAA AAUCCAGA | 11372 |
| 2939 | GGAGAAGUC CCUCAGUG | 1954 | CACUGAGG CUGAUGAGGCCGUUAGGCCGAA ACUUCUCC | 11373 |
| 2943 | AAGUCCCUC AGUGAUGU | 1955 | ACAUCACU CUGAUGAGGCCGUUAGGCCGAA AGGGACUU | 11374 |
| 2952 | AGUGAUGUA GAAGAAGA | 1956 | UCUUCUUC CUGAUGAGGCCGUUAGGCCGAA ACAUCACU | 11375 |
| 2968 | AGGAAGCUC CUGAAGAU | 1957 | AUCUUCAG CUGAUGAGGCCGUUAGGCCGAA AGCUUCCU | 11376 |
| 2977 | CUGAAGAUC UGUAUAAG | 1958 | CUUAUACA CUGAUGAGGCCGUUAGGCCGAA AUCUUCAG | 11377 |
| 2981 | AGAUCUGUA UAAGGACU | 1959 | AGUCCUUA CUGAUGAGGCCGUUAGGCCGAA ACAGAUCU | 11378 |
| 2983 | AUCUGUAUA AGGACUUC | 1960 | GAAGUCCU CUGAUGAGGCCGUUAGGCCGAA AUACAGAU | 11379 |
| 2990 | UAAGGACUU CCUGACCU | 1961 | AGGUCAGG CUGAUGAGGCCGUUAGGCCGAA AGUCCUUA | 11380 |
| 2991 | AAGGACUUC CUGACCUU | 1962 | AAGGUCAG CUGAUGAGGCCGUUAGGCCGAA AAGUCCUU | 11381 |
| 2999 | CCUGACCUU GGAGCAUC | 1963 | GAUGCUCC CUGAUGAGGCCGUUAGGCCGAA AGGUCAGG | 11382 |
| 3007 | UGGAGCAUC UCAUCUGU | 1964 | ACAGAUGA CUGAUGAGGCCGUUAGGCCGAA AUGCUCCA | 11383 |
| 3009 | GAGCAUCUC AUCUGUUA | 1965 | UAACAGAU CUGAUGAGGCCGUUAGGCCGAA AGAUGCUC | 11384 |
| 3012 | CAUCUCAUC UGUUACAG | 1966 | CUGUAACA CUGAUGAGGCCGUUAGGCCGAA AUGAGAUG | 11385 |
| 3016 | UCAUCUGUU ACAGCUUC | 1967 | GAAGCUGU CUGAUGAGGCCGUUAGGCCGAA ACAGAUGA | 11386 |
| 3017 | CAUCUGUUA CAGCUUCC | 1968 | GGAAGCUG CUGAUGAGGCCGUUAGGCCGAA AACAGAUG | 11387 |
| 3023 | UUACAGCUU CCAAGUGG | 1969 | CCACUUGG CUGAUGAGGCCGUUAGGCCGAA AGCUGUAA | 11388 |
| 3024 | UACAGCUUC CAAGUGGC | 1970 | GCCACUUG CUGAUGAGGCCGUUAGGCCGAA AAGCUGUA | 11389 |
| 3034 | AAGUGGCUA AGGCAUG | 1971 | CAUGCCCU CUGAUGAGGCCGUUAGGCCGAA AGCCACUU | 11390 |
| 3047 | CAUGGAGUU CUUGGCAU | 1972 | AUGCCAAG CUGAUGAGGCCGUUAGGCCGAA ACUCCAUG | 11391 |
| 3048 | AUGGAGGUC UUGGCAUC | 1973 | GAUGCCAA CUGAUGAGGCCGUUAGGCCGAA AACUCCAU | 11392 |
| 3050 | GGAGUUCUU GGCAUCGC | 1974 | GCGAUGCC CUGAUGAGGCCGUUAGGCCGAA AGAACUCC | 11393 |
| 3056 | CUUGGCAUC GCGAAAGU | 1975 | ACUUUCGC CUGAUGAGGCCGUUAGGCCGAA AUGCCAAG | 11394 |
| 3067 | GAAAGUGUA UCCACAGG | 1976 | CCUGUGGA CUGAUGAGGCCGUUAGGCCGAA ACACUUUC | 11395 |
| 3069 | AAGUGUAUC CACAGGGA | 1977 | UCCCUGUG CUGAUGAGGCCGUUAGGCCGAA AUACACUU | 11396 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 3094 | CACGAAAUA UCCUCUUA | 1978 | UAAGAGGA CUGAUGAGGCCGUUAGGCCGAA AUUUCCUG | 11397 |
| 3096 | CGAAAUAUC CUCUGAUC | 1979 | GAUAAGAG CUGAUGAGGCCGUUAGGCCGAA AUAUUUCG | 11398 |
| 3099 | AAUAUCCUC UUAUCGGA | 1980 | UCCGAUAA CUGAUGAGGCCGUUAGGCCGAA AGGAUAUU | 11399 |
| 3101 | UAUCCUCUU AUCGGAGA | 1981 | UCUCCGAU CUGAUGAGGCCGUUAGGCCGAA AGAGGAUA | 11400 |
| 3102 | AUCCUCUUA UCGGAGAA | 1982 | UUCUCCGA CUGAUGAGGCCGUUAGGCCGAA AAGAGGAU | 11401 |
| 3104 | CCUCUUAUC GGAGAAGA | 1983 | UCUUCUCC CUGAUGAGGCCGUUAGGCCGAA AUAAGAGG | 11402 |
| 3120 | AACGUGGUU AAAAUCUG | 1984 | CAGAUUUU CUGAUGAGGCCGUUAGGCCGAA ACCACGUU | 11403 |
| 3121 | ACGUGGUUA AAAUCUGU | 1985 | ACAGAUUU CUGAUGAGGCCGUUAGGCCGAA AACCACGU | 11404 |
| 3126 | GUUAAAAUC UGUGACUU | 1986 | AAGUCACA CUGAUGAGGCCGUUAGGCCGAA AUUUUAAC | 11405 |
| 3134 | CUGUGACUU UGGCUUGG | 1987 | CCAAGCCA CUGAUGAGGCCGUUAGGCCGAA AGUCACAG | 11406 |
| 3135 | UGUGACUUU GGCUUGGC | 1988 | GCCAAGCC CUGAUGAGGCCGUUAGGCCGAA AAGUCACA | 11407 |
| 3140 | CUUUGGCUU GGCCCGGG | 1989 | CCCGGGCC CUGAUGAGGCCGUUAGGCCGAA AGCCAAAG | 11408 |
| 3151 | CCCGGGAUA UUUAUAAA | 1990 | UUUAUAAA CUGAUGAGGCCGUUAGGCCGAA AUCCCGGG | 11409 |
| 3153 | CGGGAUAUU UAUAAAGA | 1991 | UCUUUAUA CUGAUGAGGCCGUUAGGCCGAA AUAUCCCG | 11410 |
| 3154 | GGGAUAUUU AUAAAGAU | 1992 | AUCUUUAU CUGAUGAGGCCGUUAGGCCGAA AAUAUCCC | 11411 |
| 3155 | GGAUAUUUA UAAAGAUC | 1993 | GAUCUUUA CUGAUGAGGCCGUUAGGCCGAA AAAUAUCC | 11412 |
| 3157 | AUAUUUAUA AAGAUCCA | 1994 | UGGAUCUU CUGAUGAGGCCGUUAGGCCGAA AUAAAUAU | 11413 |
| 3163 | AUAAAGAUC CAGAUUAU | 1995 | AUAAUCUG CUGAUGAGGCCGUUAGGCCGAA AUCUUUAU | 11414 |
| 3169 | AUCCAGAUU AUGUCAGA | 1996 | UCUGACAU CUGAUGAGGCCGUUAGGCCGAA AUCUGGAU | 11415 |
| 3170 | UCCAGAUUA UGUCAGAA | 1997 | UUCUGACA CUGAUGAGGCCGUUAGGCCGAA AAUCUGGA | 11416 |
| 3174 | GAUUAUGUC AGAAAGG | 1998 | CCUUUUCU CUGAUGAGGCCGUUAGGCCGAA ACAUAAUC | 11417 |
| 3190 | GAGAUGCUC GCCUCCCU | 1999 | AGGGAGGC CUGAUGAGGCCGUUAGGCCGAA AGCAUCUC | 11418 |
| 3195 | GCUCGCCUC CCUUUGAA | 2000 | UUCAAAGG CUGAUGAGGCCGUUAGGCCGAA AGGCGAGC | 11419 |
| 3199 | GCCUCCCUU UGAAAUGG | 2001 | CCAUUUCA CUGAUGAGGCCGUUAGGCCGAA AGGGAGGC | 11420 |
| 3200 | CCUCCCUUU GAAAUGGA | 2002 | UCCAUUUC CUGAUGAGGCCGUUAGGCCGAA AAGGGAGG | 11421 |
| 3225 | GAAACAAUU UUGACAG | 2003 | CUGUCAAA CUGAUGAGGCCGUUAGGCCGAA AUUGUUUC | 11422 |
| 3226 | AAACAAUUU UGACAGA | 2004 | UCUGUCAA CUGAUGAGGCCGUUAGGCCGAA AAUUGUUU | 11423 |
| 3227 | AACAAUUUU UGACAGAG | 2005 | CUCUGUCA CUGAUGAGGCCGUUAGGCCGAA AAAUUGUU | 11424 |
| 3228 | ACAAUUUUU GACAGAGU | 2006 | ACUCUGUC CUGAUGAGGCCGUUAGGCCGAA AAAAUUGU | 11425 |
| 3239 | CAGAGUGUA CACAAUCC | 2007 | GGAUUGUG CUGAUGAGGCCGUUAGGCCGAA ACACUCUG | 11426 |
| 3246 | UACACAAUC CAGAGUGA | 2008 | UCACUCUG CUGAUGAGGCCGUUAGGCCGAA AUUGUGUA | 11427 |
| 3258 | AGUGACGUC UGGUCUUU | 2009 | AAAGACCA CUGAUGAGGCCGUUAGGCCGAA ACGUCACU | 11428 |
| 3263 | CGUCUGGUC UUUUGGUG | 2010 | CACCAAAA CUGAUGAGGCCGUUAGGCCGAA ACCAGACG | 11429 |
| 3265 | UCUGGUCUU UUGGUGUU | 2011 | AACACCAA CUGAUGAGGCCGUUAGGCCGAA AGACCAGA | 11430 |
| 3266 | CUGGUCUUU UGGUGUUU | 2012 | AAACACCA CUGAUGAGGCCGUUAGGCCGAA AAGACCAG | 11431 |
| 3267 | UGGUCUUUU GGUGUUUU | 2013 | AAAACACC CUGAUGAGGCCGUUAGGCCGAA AAAGACCA | 11432 |
| 3273 | UUUGGUGUU UUGCUGUG | 2014 | CACAGCAA CUGAUGAGGCCGUUAGGCCGAA ACACCAAA | 11433 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 3274 | UUGGUGUUU UGCUGUGG | 2015 | CCACAGCA CUGAUGAGGCCGUUAGGCCGAA AACACCAA | 11434 |
| 3275 | UGGUGUUUU GCUGUGGG | 2016 | CCCACAGC CUGAUGAGGCCGUUAGGCCGAA AAACACCA | 11435 |
| 3288 | UGGGAAAUA UUUUCCUU | 2017 | AAGGAAAA CUGAUGAGGCCGUUAGGCCGAA AUUUCCCA | 11436 |
| 3290 | GGAAAUAUU UUCCUUAG | 2018 | CUAAGGAA CUGAUGAGGCCGUUAGGCCGAA AUAUUUCC | 11437 |
| 3291 | GAAAUAUUU UCCUUAGG | 2019 | CCUAAGGA CUGAUGAGGCCGUUAGGCCGAA AAUAUUUC | 11438 |
| 3292 | AAAUAUUUU CCUUAGGU | 2020 | ACCUAAGG CUGAUGAGGCCGUUAGGCCGAA AAAUAUUU | 11439 |
| 3293 | AAUAUUUUC CUUAGGUG | 2021 | CACCUAAG CUGAUGAGGCCGUUAGGCCGAA AAAAUAUU | 11440 |
| 3296 | AUUUUCCUU AGGUGCUU | 2022 | AAGCACCU CUGAUGAGGCCGUUAGGCCGAA AGGAAAAU | 11441 |
| 3297 | UUUUCCUUA GGUGCUUC | 2023 | GAAGCACC CUGAUGAGGCCGUUAGGCCGAA AAGGAAAA | 11442 |
| 3304 | UAGGUGCUU CUCCAUAU | 2024 | AUAUGGAG CUGAUGAGGCCGUUAGGCCGAA AGCACCUA | 11443 |
| 3305 | AGGUGCUUC UCCAUAUC | 2025 | GAUAUGGA CUGAUGAGGCCGUUAGGCCGAA AAGCACCU | 11444 |
| 3307 | GUGCUUCUC CAUAUCCU | 2026 | AGGAUAUG CUGAUGAGGCCGUUAGGCCGAA AGAAGCAC | 11445 |
| 3311 | UUCUCCAUA UCCUGGGG | 2027 | CCCCAGGA CUGAUGAGGCCGUUAGGCCGAA AUGGAGAA | 11446 |
| 3313 | CUCCAUAUC CUGGGGUA | 2028 | UACCCCAG CUGAUGAGGCCGUUAGGCCGAA AUAUGGAG | 11447 |
| 3321 | CCUGGGGUA AAGAUUGA | 2029 | UCAAUCUU CUGAUGAGGCCGUUAGGCCGAA ACCCCAGG | 11448 |
| 3327 | GUAAAGAUU GAUGAAGA | 2030 | UCUUCAUC CUGAUGAGGCCGUUAGGCCGAA AUCUUUAC | 11449 |
| 3338 | UGAAGAAUU UUGUAGGC | 2031 | GCCUACAA CUGAUGAGGCCGUUAGGCCGAA AUUCUUCA | 11450 |
| 3339 | GAAGAAUUU UGUAGGCG | 2032 | CGCCUACA CUGAUGAGGCCGUUAGGCCGAA AAUUCUUC | 11451 |
| 3340 | AAGAAUUUU GUAGGCGA | 2033 | UCGCCUAC CUGAUGAGGCCGUUAGGCCGAA AAAUUCUU | 11452 |
| 3343 | AAUUUUGUA GGCGAUUG | 2034 | CAAUCGCC CUGAUGAGGCCGUUAGGCCGAA ACAAAAUU | 11453 |
| 3350 | UAGGCGAUU GAAAGAAG | 2035 | CUUCUUUC CUGAUGAGGCCGUUAGGCCGAA AUCGCCUA | 11454 |
| 3364 | AAGGAACUA GAAUGAGG | 2036 | CCUCAUUC CUGAUGAGGCCGUUAGGCCGAA AGUUCCUU | 11455 |
| 3382 | CCCCUGAUU AUACUACA | 2037 | UGUAGUAU CUGAUGAGGCCGUUAGGCCGAA AUCAGGGG | 11456 |
| 3383 | CCCUGAUUA UACUACAC | 2038 | GUGUAGUA CUGAUGAGGCCGUUAGGCCGAA AAUCAGGG | 11457 |
| 3385 | CUGAUUAUA CUACACCA | 2039 | UGGUGUAG CUGAUGAGGCCGUUAGGCCGAA AUAAUCAG | 11458 |
| 3388 | AUUAUACUA CACCAGAA | 2040 | UUCUGGUG CUGAUGAGGCCGUUAGGCCGAA AGUAUAAU | 11459 |
| 3401 | AGAAAUGUA CCAGACCA | 2041 | UGGUCUGG CUGAUGAGGCCGUUAGGCCGAA ACAUUUCU | 11460 |
| 3439 | AGCCCAGUC AGAGACCC | 2042 | GGGUCUCU CUGAUGAGGCCGUUAGGCCGAA ACUGGGCU | 11461 |
| 3452 | ACCCACGUU UUCAGAGU | 2043 | ACUCUGAA CUGAUGAGGCCGUUAGGCCGAA ACGUGGGU | 11462 |
| 3453 | CCCACGUUU UCAGAGUU | 2044 | AACUCUGA CUGAUGAGGCCGUUAGGCCGAA AACGUGGG | 11463 |
| 3454 | CCACGUUUU CAGAGUUG | 2045 | CAACUCUG CUGAUGAGGCCGUUAGGCCGAA AAACGUGG | 11464 |
| 3455 | CACGUUUUC AGAGUUGG | 2046 | CCAACUCU CUGAUGAGGCCGUUAGGCCGAA AAAACGUG | 11465 |
| 3461 | UUCAGAGUU GGUGGAAC | 2047 | GUUCCACC CUGAUGAGGCCGUUAGGCCGAA ACUCUGAA | 11466 |
| 3472 | UGGAACAUU UGGGAAAU | 2048 | AUUUCCCA CUGAUGAGGCCGUUAGGCCGAA AUGUUCCA | 11467 |
| 3473 | GGAACAUUU GGGAAAUC | 2049 | GAUUUCCC CUGAUGAGGCCGUUAGGCCGAA AAUGUUCC | 11468 |
| 3481 | UGGGAAAUC UCUUGCAA | 2050 | UUGCAAGA CUGAUGAGGCCGUUAGGCCGAA AUUUCCCA | 11469 |
| 3483 | GGAAAUCUC UUGCAAGC | 2051 | GCUUGCAA CUGAUGAGGCCGUUAGGCCGAA AGAUUUCC | 11470 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 3485 | AAAUCUCUU GCAAGCUA | 2052 | UAGCUUGC CUGAUGAGGCCGUUAGGCCGAA AGAGAUUU | 11471 |
| 3493 | UGCAAGCUA AUGGUCAG | 2053 | CUGAGCAU CUGAUGAGGCCGUUAGGCCGAA AGCUUGCA | 11472 |
| 3499 | CUAAUGCUC AGCAGGAU | 2054 | AUCCUGCU CUGAUGAGGCCGUUAGGCCGAA AGCAUUAG | 11473 |
| 3518 | CAAAGACUA CAUUGUUC | 2055 | GAACAAUG CUGAUGAGGCCGUUAGGCCGAA AGUCUUUG | 11474 |
| 3522 | GACUACAUU GUUCUUCC | 2056 | GGAAGAAC CUGAUGAGGCCGUUAGGCCGAA AUGUAGUC | 11475 |
| 3525 | UACAUUGUU CUUCCGAU | 2057 | AUCGGAAG CUGAUGAGGCCGUUAGGCCGAA ACAAUGUA | 11476 |
| 3526 | ACAUUGUUC UUCCGAUA | 2058 | UAUCGGAA CUGAUGAGGCCGUUAGGCCGAA AACAAUGU | 11477 |
| 3528 | AUUGUUCUU CCGAUAUC | 2059 | GAUAUCGG CUGAUGAGGCCGUUAGGCCGAA AGAACAAU | 11478 |
| 3529 | UUGUUCUUC CGAUAUCA | 2060 | UGAUAUCG CUGAUGAGGCCGUUAGGCCGAA AAGAACAA | 11479 |
| 3534 | CUUCCGAUA UCAGAGAC | 2061 | GUCUCUGA CUGAUGAGGCCGUUAGGCCGAA AUCGGAAG | 11480 |
| 3536 | UCCGAUAUC AGAGACUU | 2062 | AAGUCUCU CUGAUGAGGCCGUUAGGCCGAA AUAUCGGA | 11481 |
| 3544 | CAGAGACUU UGAGCAUG | 2063 | CAUGCUCA CUGAUGAGGCCGUUAGGCCGAA AGUCUCUG | 11482 |
| 3545 | AGAGACUUU GAGCAUGG | 2064 | CCAUGCUC CUGAUGAGGCCGUUAGGCCGAA AAGUCUCU | 11483 |
| 3562 | AAGAGGAUU CUGGACUC | 2065 | GAGUCCAG CUGAUGAGGCCGUUAGGCCGAA AUCCUCUU | 11484 |
| 3563 | AGAGGAUUC UGGACUCU | 2066 | AGAGUCCA CUGAUGAGGCCGUUAGGCCGAA AAUCCUCU | 11485 |
| 3570 | UCGGACUC UCUCUGCC | 2067 | GGCAGAGA CUGAUGAGGCCGUUAGGCCGAA AGUCCAGA | 11486 |
| 3572 | UGGACUCUC UCUGCCUA | 2068 | UAGGCAGA CUGAUGAGGCCGUUAGGCCGAA AGAGUCCA | 11487 |
| 3574 | GACUCUCUC UGCCUACC | 2069 | GGUAGGCA CUGAUGAGGCCGUUAGGCCGAA AGAGAGUC | 11488 |
| 3580 | CUCUGCCUA CCUCACCU | 2070 | AGGUGAGG CUGAUGAGGCCGUUAGGCCGAA AGGCAGAG | 11489 |
| 3584 | GCCUACCUC ACCUGUUU | 2071 | AAACAGGU CUGAUGAGGCCGUUAGGCCGAA AGGUAGGC | 11490 |
| 3591 | UCACCUGUU UCCUGUAU | 2072 | AUACAGGA CUGAUGAGGCCGUUAGGCCGAA ACAGGUGA | 11491 |
| 3592 | CACCUGUUU CCUGUAUG | 2073 | CAUACAGG CUGAUGAGGCCGUUAGGCCGAA AACAGGUG | 11492 |
| 3593 | ACCUGUUUC CUGUAUGG | 2074 | CCAUACAG CUGAUGAGGCCGUUAGGCCGAA AAACAGGU | 11493 |
| 3598 | UUUCCUGUA UGGAGGAG | 2075 | CUCCUCCA CUGAUGAGGCCGUUAGGCCGAA ACAGGAAA | 11494 |
| 3615 | GAGGAAGUA UGUGACCC | 2076 | GGGUCACA CUGAUGAGGCCGUUAGGCCGAA ACUUCCUC | 11495 |
| 3629 | CCCCAAAUU CCAUUAUG | 2077 | CAUAAUGG CUGAUGAGGCCGUUAGGCCGAA AUUUGGGG | 11496 |
| 3630 | CCCAAAUUC CAUUAUGA | 2078 | UCAUAAUG CUGAUGAGGCCGUUAGGCCGAA AAUUUGGG | 11497 |
| 3634 | AAUUCCAUU AUGACAAC | 2079 | GUUGUCAU CUGAUGAGGCCGUUAGGCCGAA AUGGAAUU | 11498 |
| 3635 | AUUCCAUUA UGACAACA | 2080 | UGUUGUCA CUGAUGAGGCCGUUAGGCCGAA AAUGGAAU | 11499 |
| 3654 | GCAGGAAUC AGUCAGUA | 2081 | UACUGACU CUGAUGAGGCCGUUAGGCCGAA AUUCCUGC | 11500 |
| 3658 | GAAUCAGUC AGUAUCUG | 2082 | CAGAUACU CUGAUGAGGCCGUUAGGCCGAA ACUGAUUC | 11501 |
| 3662 | CAGUCAGUA UCUGCAGA | 2083 | UCUGCAGA CUGAUGAGGCCGUUAGGCCGAA ACUGACUG | 11502 |
| 3664 | GUCAGUAUC UGCAGAAC | 2084 | GUUCUGCA CUGAUGAGGCCGUUAGGCCGAA AUACUGAC | 11503 |
| 3676 | AGAACAGUA AGCGAAAG | 2085 | CUUUCGCU CUGAUGAGGCCGUUAGGCCGAA ACUGUUCU | 11504 |
| 3702 | GUGAGUGUA AAAACAUU | 2086 | AAUGUUUU CUGAUGAGGCCGUUAGGCCGAA ACACUCAC | 11505 |
| 3710 | AAAACAUU UGAAGAUA | 2087 | UAUCUUCA CUGAUGAGGCCGUUAGGCCGAA AUGUUUUU | 11506 |
| 3711 | AAAACAUUU GAAGAUAU | 2088 | AUAUCUUC CUGAUGAGGCCGUUAGGCCGAA AAUGUUUU | 11507 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 3718 | UUGAAGAUA UCCCGUUA | 2089 | UAACGGGA CUGAUGAGGCCGUUAGGCCGAA AUCUUCAA | 11508 |
| 3720 | GAAGAUAUC CGUUAGA | 2090 | UCUAACGG CUGAUGAGGCCGUUAGGCCGAA AUAUCUUC | 11509 |
| 3725 | UAUCCCGUU AGAAGAAC | 2091 | GUUCUUCU CUGAUGAGGCCGUUAGGCCGAA ACGGGAUA | 11510 |
| 3726 | AUCCCGUUA GAAGAACC | 2092 | GGUUCUUC CUGAUGAGGCCGUUAGGCCGAA AACGGGAU | 11511 |
| 3741 | CCAGAAGUA AAAGUAAU | 2093 | AUUACUUU CUGAUGAGGCCGUUAGGCCGAA ACUUCUGG | 11512 |
| 3747 | GUAAAGUA AUCCCAGA | 2094 | UCUGGGAU CUGAUGAGGCCGUUAGGCCGAA ACUUUUAC | 11513 |
| 3750 | AAAGUAAUC CCAGAUGA | 2095 | UCAUCUGG CUGAUGAGGCCGUUAGGCCGAA AUUACUUU | 11514 |
| 3778 | ACAGUGGUA UGGUUCUU | 2096 | AAGAACCA CUGAUGAGGCCGUUAGGCCGAA ACCACUGU | 11515 |
| 3783 | GGUAUGGUU CUUGCCUC | 2097 | GAGGCAAG CUGAUGAGGCCGUUAGGCCGAA ACCAUACC | 11516 |
| 3784 | GUAUGGUUC UUGCCUCA | 2098 | UGAGGCAA CUGAUGAGGCCGUUAGGCCGAA AACCAUAC | 11517 |
| 3786 | AUGGUUCUU GCCUCAGA | 2099 | UCUGAGGC CUGAUGAGGCCGUUAGGCCGAA AGAACCAU | 11518 |
| 3791 | UCUUGCCUC AGAAGAGC | 2100 | GCUCUUCU CUGAUGAGGCCGUUAGGCCGAA AGGCAAGA | 11519 |
| 3808 | UGAAAACUU UGGAAGAC | 2101 | GUCUUCCA CUGAUGAGGCCGUUAGGCCGAA AGUUUUCA | 11520 |
| 3809 | GAAAACUUU GGAAGACA | 2102 | UGUCUUCC CUGAUGAGGCCGUUAGGCCGAA AAGUUUUC | 11521 |
| 3827 | AACCAAAUU AUCUCCAU | 2103 | AUGGAGAU CUGAUGAGGCCGUUAGGCCGAA AUUUGGUU | 11522 |
| 3828 | ACCAAAUUA UCUCCAUC | 2104 | GAUGGAGA CUGAUGAGGCCGUUAGGCCGAA AAUUUGGU | 11523 |
| 3830 | CAAAUUAUC UCCAUCUU | 2105 | AAGAUGGA CUGAUGAGGCCGUUAGGCCGAA AUAAUUUG | 11524 |
| 3832 | AAUUAUCUC CAUCUUUU | 2106 | AAAAGAUG CUGAUGAGGCCGUUAGGCCGAA AGAUAAUU | 11525 |
| 3836 | AUCUCCAUC UUUUGGUG | 2107 | CACCAAAA CUGAUGAGGCCGUUAGGCCGAA AUGGAGAU | 11526 |
| 3838 | CUCCAUCUU UUGGUGGA | 2108 | UCCACCAA CUGAUGAGGCCGUUAGGCCGAA AGAUGGAG | 11527 |
| 3839 | UCCAUCUUU UGGUGGAA | 2109 | UUCCACCA CUGAUGAGGCCGUUAGGCCGAA AAGAUGGA | 11528 |
| 3840 | CCAUCUUUU GGUGGAAU | 2110 | AUUCCACC CUGAUGAGGCCGUUAGGCCGAA AAAGAUGG | 11529 |
| 3872 | CAGGGAGUC UGUGGCAU | 2111 | AUGCCACA CUGAUGAGGCCGUUAGGCCGAA ACUCCCUG | 11530 |
| 3881 | UGUGGCAUC UGAAGGCU | 2112 | AGCCUUCA CUGAUGAGGCCGUUAGGCCGAA AUGCCACA | 11531 |
| 3890 | UGAAGGCUC AAACCAGA | 2113 | UCUGGUUU CUGAUGAGGCCGUUAGGCCGAA AGCCUUCA | 11532 |
| 3908 | AAGCGGCUA CCAGUCCG | 2114 | CGGACUGG CUGAUGAGGCCGUUAGGCCGAA AGCCGCUU | 11533 |
| 3914 | CUACCAGUC GGAUAUC | 2115 | GAUAUCCG CUGAUGAGGCCGUUAGGCCGAA ACUGGUAG | 11534 |
| 3920 | GUCCGGAUA UCACUCCG | 2116 | CGGAGUGA CUGAUGAGGCCGUUAGGCCGAA AUCCGGAC | 11535 |
| 3922 | CCGGAUAUC ACUCCGAU | 2117 | AUCGGAGU CUGAUGAGGCCGUUAGGCCGAA AUAUCCGG | 11536 |
| 3926 | AUAUCACUC CGAUGACA | 2118 | UGUCAUCG CUGAUGAGGCCGUUAGGCCGAA AGUGAUAU | 11537 |
| 3950 | CACCGUGUA CUCCAGUG | 2119 | CACUGGAG CUGAUGAGGCCGUUAGGCCGAA ACACGGUG | 11538 |
| 3953 | CGUGUACUC CAGUGAGG | 2120 | CCUCACUG CUGAUGAGGCCGUUAGGCCGAA AGUACACG | 11539 |
| 3972 | GCAGAACUU UUAAAGCU | 2121 | AGCUUUAA CUGAUGAGGCCGUUAGGCCGAA AGUUCUGC | 11540 |
| 3973 | CAGAACUUU UAAAGCUG | 2122 | CAGCUUUA CUGAUGAGGCCGUUAGGCCGAA AAGUUCUG | 11541 |
| 3974 | AGAACUUUU AAAGCUGA | 2123 | UCAGCUUU CUGAUGAGGCCGUUAGGCCGAA AAAGUUCU | 11542 |
| 3975 | GAACUUUUA AAGCUGAU | 2124 | AUCAGCUU CUGAUGAGGCCGUUAGGCCGAA AAAAGUUC | 11543 |
| 3984 | AAGCUGAUA GAGAUUGG | 2125 | CCAAUCUC CUGAUGAGGCCGUUAGGCCGAA AUCAGCUU | 11544 |

TABLE IV-continued

Human KDR VEGF Receptor-Hammerhead Ribozyme and Substrate Sequence

| Pos | Substrate | Seq ID No | HH Ribozyme Sequence | Seq ID No |
|---|---|---|---|---|
| 3990 | AUAGAGAUU GGAGUGCA | 2126 | UGCACUCC CUGAUGAG<u>GCCGUUAGGCC</u>GAA AUCUCUAU | 11545 |
| 4006 | AAACCGGUA GCACAGCC | 2127 | GGCUGUGC CUGAUGAG<u>GCCGUUAGGCC</u>GAA ACCGGUUU | 11546 |
| 4020 | GCCCAGAUU CUCCAGCC | 2128 | GGCUGGAG CUGAUGAG<u>GCCGUUAGGCC</u>GAA AUCUGGGC | 11547 |
| 4021 | CCCAGAUUC UCCAGCCU | 2129 | AGGCUGGA CUGAUGAG<u>GCCGUUAGGCC</u>GAA AAUCUGGG | 11548 |
| 4023 | CAGAUUCUC CAGCCUGA | 2130 | UCAGGCUG CUGAUGAG<u>GCCGUUAGGCC</u>GAA AGAAUCUG | 11549 |
| 4052 | ACUGAGCUC UCCUCCUG | 2131 | CAGGAGGA CUGAUGAG<u>GCCGUUAGGCC</u>GAA AGCUCAGU | 11550 |
| 4054 | UGAGCUCUC CUCCUGUU | 2132 | AACAGGAG CUGAUGAG<u>GCCGUUAGGCC</u>GAA AGAGCUCA | 11551 |
| 4057 | GCUCUCCUC CUGUUUAA | 2133 | UUAAACAG CUGAUGAG<u>GCCGUUAGGCC</u>GAA AGGAGAGC | 11552 |
| 4062 | CCUCCUGUU UAAAAGGA | 2134 | UCCUUUUA CUGAUGAG<u>GCCGUUAGGCC</u>GAA ACAGGAGG | 11553 |
| 4063 | CUCCUGUUU AAAAGGAA | 2135 | UUCCUUUU CUGAUGAG<u>GCCGUUAGGCC</u>GAA AACAGGAG | 11554 |
| 4064 | UCCUGUUUA AAAGGAAG | 2136 | CUUCCUUU CUGAUGAG<u>GCCGUUAGGCC</u>GAA AAACAGGA | 11555 |
| 4076 | GGAAGCAUC CACACCCC | 2137 | GGGGUGUG CUGAUGAG<u>GCCGUUAGGCC</u>GAA AUGCUUCC | 11556 |
| 4089 | CCCCAACUC CCGGACAU | 2138 | AUGUCCGG CUGAUGAG<u>GCCGUUAGGCC</u>GAA AGUUGGGG | 11557 |
| 4098 | CCGGACAUC ACAUGAGA | 2139 | UCUCAUGU CUGAUGAG<u>GCCGUUAGGCC</u>GAA AUGUCCGG | 11558 |
| 4110 | UGAGAGGUC UGCUCAGA | 2140 | UCUGAGCA CUGAUGAG<u>GCCGUUAGGCC</u>GAA ACCUCUCA | 11559 |
| 4115 | GGUCUGCUC AGAUUUUG | 2141 | CAAAAUCU CUGAUGAG<u>GCCGUUAGGCC</u>GAA AGCAGACC | 11560 |
| 4120 | GCUCAGAUU UUGAAGUG | 2142 | CACUUCAA CUGAUGAG<u>GCCGUUAGGCC</u>GAA AUCUGAGC | 11561 |
| 4121 | CUCAGAUUU UGAAGUGU | 2143 | ACACUUCA CUGAUGAG<u>GCCGUUAGGCC</u>GAA AAUCUGAG | 11562 |
| 4122 | UCAGAUUUU GAAGUGUU | 2144 | AACACUUC CUGAUGAG<u>GCCGUUAGGCC</u>GAA AAAUCUGA | 11563 |
| 4130 | UGAAGUGUU GUUCUUUC | 2145 | GAAAGAAC CUGAUGAG<u>GCCGUUAGGCC</u>GAA ACACUUCA | 11564 |
| 4133 | AGUGUUGUU CUUUCCAC | 2146 | GUGGAAAG CUGAUGAG<u>GCCGUUAGGCC</u>GAA ACAACACU | 11565 |
| 4134 | GUGUUGUUC UUUCCACC | 2147 | GGUGGAAA CUGAUGAG<u>GCCGUUAGGCC</u>GAA AACAACAC | 11566 |
| 4136 | GUUGUUCUU UCCACCAG | 2148 | CUGGUGGA CUGAUGAG<u>GCCGUUAGGCC</u>GAA AGAACAAC | 11567 |
| 4137 | UUGUUCUUU CCACCAGC | 2149 | GCUGGUGG CUGAUGAG<u>GCCGUUAGGCC</u>GAA AAGAACAA | 11568 |
| 4138 | UGUUCUUUC CACCAGCA | 2150 | UGCUGGUG CUGAUGAG<u>GCCGUUAGGCC</u>GAA AAAGAACA | 11569 |
| 4153 | CAGGAAGUA GCCGCAUU | 2151 | AAUGCGGC CUGAUGAG<u>GCCGUUAGGCC</u>GAA ACUUCCUG | 11570 |
| 4161 | AGCCGCAUU UGAUUUUC | 2152 | GAAAAUCA CUGAUGAG<u>GCCGUUAGGCC</u>GAA AUGCGGCU | 11571 |
| 4162 | GCCGCAUUU GAUUUUCA | 2153 | UGAAAAUC CUGAUGAG<u>GCCGUUAGGCC</u>GAA AAUGCGGC | 11572 |
| 4166 | CAUUUGAUU UUCAUUUC | 2154 | GAAAUGAA CUGAUGAG<u>GCCGUUAGGCC</u>GAA AUCAAAUG | 11573 |
| 4167 | AUUUGAUUU UCAUUUCG | 2155 | CGAAAUGA CUGAUGAG<u>GCCGUUAGGCC</u>GAA AAUCAAAU | 11574 |
| 4168 | UUUGAUUUU CAUUUCGA | 2156 | UCGAAAUG CUGAUGAG<u>GCCGUUAGGCC</u>GAA AAAUCAAA | 11575 |
| 4169 | UUGAUUUUC AUUUCGAC | 2157 | GUCGAAAU CUGAUGAG<u>GCCGUUAGGCC</u>GAA AAAAUCAA | 11576 |
| 4172 | AUUUUCAUU UCGACAAC | 2158 | GUUGUCGA CUGAUGAG<u>GCCGUUAGGCC</u>GAA AUGAAAAU | 11577 |
| 4173 | UUUUCAUUU CGACAACA | 2159 | UGUUGUCG CUGAUGAG<u>GCCGUUAGGCC</u>GAA AAUGAAAA | 11578 |
| 4174 | UUUCAUUUC GACAACAG | 2160 | CUGUUGUC CUGAUGAG<u>GCCGUUAGGCC</u>GAA AAAUGAAA | 11579 |
| 4194 | AAGGACCUC GGACUGCA | 2161 | UGCAGUCC CUGAUGAG<u>GCCGUUAGGCC</u>GAA AGGUCCUU | 11580 |
| 4214 | AGCCAGCUC UUCUAGGC | 2162 | GCCUAGAA CUGAUGAG<u>GCCGUUAGGCC</u>GAA AGCUGGCU | 11581 |

TABLE IV-continued

Human KDR VEGF Receptor-Hammerhead Ribozyme and Substrate Sequence

| Pos | Substrate | Seq ID No | HH Ribozyme Sequence | Seq ID No |
|-----|-----------|-----------|----------------------|-----------|
| 4216 | CCAGCUCUU CUAGGCUU | 2163 | AAGCCUAG CUGAUGAG<u>GCCGUUAGGC</u>CGAA AGAGCUGG | 11582 |
| 4217 | CAGCUCUUC UAGGCUUG | 2164 | CAAGCCUA CUGAUGAG<u>GCCGUUAGGC</u>CGAA AAGAGCUG | 11583 |
| 4219 | GCUCUUCUA GGCUUGUG | 2165 | CACAAGCC CUGAUGAG<u>GCCGUUAGGC</u>CGAA AGAAGAGC | 11584 |

Where "X" represents stem II region of a HH ribozyme (Hertel et al., 1992 Nucleic Acids Res. 20 3252).
The length of stem II maybe 2 base-pairs.
Underlined region can be any X sequence or linker, as described herein.

TABLE V

Human KDR VEGF Receptor-Hairpin Ribozyme and Substrate Sequences

| Pos | Substrate | Seq ID No | Hairpin Ribozyme Sequence | Seq ID No |
|-----|-----------|-----------|---------------------------|-----------|
| 11 | AGGUGCU GCU GGCCGUCG | 2166 | CGACGGCC AGAA GCACCU ACCAGAGAAACACACGUUGUGGUACAUUACCUGGUA | 11585 |
| 18 | GCUGGCC GUC GCCCUGUG | 2167 | CACAGGGC AGAA GCCAGC ACCAGAGAAACACACGUUGUGGUACAUUACCUGGUA | 11586 |
| 51 | CCGGGCC GCC UCUGUGGG | 2168 | CCCACAGA AGAA GCCCGG ACCAGAGAAACACACGUUGUGGUACAUUACCUGGUA | 11587 |
| 86 | UUGAUCU CCC CAGGCUCA | 2169 | UGAGCCUG AGAA GAUCAA ACCAGAGAAACACACGUUGUGGUACAUUACCUGGUA | 11588 |
| 318 | GGAAACU GAC UUGGCCUC | 2170 | GAGGCCAA AGAA GUUUCC ACCAGAGAAACACACGUUGUGGUACAUUACCUGGUA | 11589 |
| 358 | GAUUACA GAU CUCCAUUU | 2171 | AAAUGGAG AGAA GUAAUC ACCAGAGAAACACACGUUGUGGUACAUUACCUGGUA | 11590 |
| 510 | UGUUCCU GAU GGUAACAG | 2172 | CUGUUACC AGAA GGAACA ACCAGAGAAACACACGUUGUGGUACAUUACCUGGUA | 11591 |
| 623 | GUUACCA GUC UAUUAUGU | 2173 | ACAUAAUA AGAA GGUAAC ACCAGAGAAACACACGUUGUGGUACAUUACCUGGUA | 11592 |
| 683 | UGAGUCC GUC UCAUGGAA | 2174 | UUCCAUGA AGAA CACUCA ACCAGAGAAACACACGUUGUGGUACAUUACCUGGUA | 11593 |
| 705 | ACUAUCU GUU GGAGAAAA | 2175 | UUUUCUCC AGAA GAUAGU ACCAGAGAAACACACGUUGUGGUACAUUACCUGGUA | 11594 |
| 833 | AAACCCA GUC UGGGAGUG | 2176 | CACUCCCA AGAA GGGUUU ACCAGAGAAACACACGUUGUGGUACAUUACCUGGUA | 11595 |
| 932 | GUGGGCU GAU GACCAACA | 2177 | UCUUGGUC AGAA GCCCAC ACCAGAGAAACACACGUUGUGGUACAUUACCUGGUA | 11596 |
| 1142 | AUGUACU GAC GAUUAUGG | 2178 | CCAUAAUC AGAA GUACAU ACCAGAGAAACACACGUUGUGGUACAUUACCUGGUA | 11597 |
| 1259 | CACCCCA GAU UGGUGAGA | 2179 | UCUCACCA AGAA GGGGUG ACCAGAGAAACACACGUUGUGGUACAUUACCUGGUA | 11598 |
| 1332 | AUGUACG GUC UAUGCCAU | 2180 | AUGGCAUA AGAA GUACAU ACCAGAGAAACACACGUUGUGGUACAUUACCUGGUA | 11599 |
| 1376 | AUUGGCA GUU GGAGGAAG | 2181 | CUUCCUCC AGAA GCCAAU ACCAGAGAAACACACGUUGUGGUACAUUACCUGGUA | 11600 |
| 1413 | CCAAGCU GUC UCAGUGAC | 2182 | GUCACUGA AGAA GCUUGG ACCAGAGAAACACACGUUGUGGUACAUUACCUGGUA | 11601 |
| 1569 | UGUGUCA GCU UUGUACAA | 2183 | UUGUACAA AGAA GACACA ACCAGAGAAACACACGUUGUGGUACAUUACCUGGUA | 11602 |
| 1673 | ACAUGCA GCC CACUGAGC | 2184 | GCUCAGUG AGAA GCAUGU ACCAGAGAAACACACGUUGUGGUACAUUACCUGGUA | 11603 |
| 1717 | GCAGACA GAU CUACGUUU | 2185 | AAACGUAG AGAA GUCUGC ACCAGAGAAACACACGUUGUGGUACAUUACCUGGUA | 11604 |
| 1760 | GCCCACA CCC UCUGCCAA | 2186 | UUGGCAGA AGAA GUGGGC ACCAGAGAAACACACGUUGUGGUACAUUACCUGGUA | 11605 |
| 1797 | CACACCU GUU UGCAAGAA | 2187 | UUCUUGCA AGAA GGUGUG ACCAGAGAAACACACGUUGUGGUACAUUACCUGGUA | 11606 |
| 1918 | UAUGUCU GCC UUGCUCAA | 2188 | UUGAGCAA AGAA GACAUA ACCAGAGAAACACACGUUGUGGUACAUUACCUGGUA | 11607 |
| 1967 | UCAGGCA GCU CACAGUCC | 2189 | GGACUGUG AGAA GCCUGA ACCAGAGAAACACACGUUGUGGUACAUUACCUGGUA | 11608 |
| 1974 | GCUCACA GUC CUAGAGCG | 2190 | CGCUCUAG AGAA GUGAGC ACCAGAGAAACACACGUUGUGGUACAUUACCUGGUA | 11609 |
| 2021 | AGAAUCA GAC GACAAGUA | 2191 | UACUUGUC AGAA GAUUCU ACCAGAGAAACACACGUUGUGGUACAUUACCUGGUA | 11610 |
| 2084 | CUCCACA GAU CAUGUGGU | 2192 | ACCACAUG AGAA GUGGAG ACCAGAGAAACACACGUUGUGGUACAUUACCUGGUA | 11611 |

TABLE V-continued

Human KDR VEGF Receptor-Hairpin Ribozyme and Substrate Sequences

| Pos | Substrate | Seq ID No | Hairpin Ribozyme Sequence | Seq ID No |
|---|---|---|---|---|
| 2418 | GGAUCCA GAU GAACUCCC | 2193 | GGGAGUUC AGAA GGAUCC ACCAGAGAAACACACGUUGUGGUACAUUACCUGGUA | 11612 |
| 2453 | AACGACU GCC UUAUGAUG | 2194 | CAUCAUAA AGAA GUCGUU ACCAGAGAAACACACGUUGUGGUACAUUACCUGGUA | 11613 |
| 2492 | GAGACCG GCU GAACCUAG | 2195 | CUAGGUUC AGAA GGUCUC ACCAGAGAAACACACGUUGUGGUACAUUACCUGGUA | 11614 |
| 2547 | UGAAGCA GAU GCCUUUGG | 2196 | CCAAAGGC AGAA GCUUCA ACCAGAGAAACACACGUUGUGGUACAUUACCUGGUA | 11615 |
| 2765 | GAAACCU CUC CACUUACC | 2197 | GGUAAGUG AGAA GGUUUC ACCAGAGAAACACACGUUGUGGUACAUUACCUGGUA | 11616 |
| 2914 | UCAGCCA GCU CUGGAUUU | 2198 | AAAUCCAG AGAA GGCUGA ACCAGAGAAACACACGUUGUGGUACAUUACCUGGUA | 11617 |
| 2993 | ACUUCCU GAC CUUGGAGC | 2199 | GCUCCAAG AGAA GGAAGU ACCAGAGAAACACACGUUGUGGUACAUUACCUGGUA | 11618 |
| 3019 | UGUUACA GCU UCCAAGUG | 2200 | CACUUGGA AGAA GUAACA ACCAGAGAAACACACGUUGUGGUACAUUACCUGGUA | 11619 |
| 3165 | AGAUCCA GAU UAUGUCAG | 2201 | CUGACAUA AGAA GGAUCU ACCAGAGAAACACACGUUGUGGUACAUUACCUGGUA | 11620 |
| 3378 | GGCCCCU GAU UAUACUAC | 2202 | GUAGUAUA AGAA GGGGCC ACCAGAGAAACACACGUUGUGGUACAUUACCUGGUA | 11621 |
| 3404 | UGUACCA GAC CAUGCUGG | 2203 | CCAGCAUG AGAA GGUACA ACCAGAGAAACACACGUUGUGGUACAUUACCUGGUA | 11622 |
| 3418 | CUGGACU GCU GGCACGGG | 2204 | CCCGUGCC AGAA GUCCAG ACCAGAGAAACACACGUUGUGGUACAUUACCUGGUA | 11623 |
| 3575 | UCUCUCU GCC UACCUCAC | 2205 | GUGAGGUA AGAA GAGAGA ACCAGAGAAACACACGUUGUGGUACAUUACCUGGUA | 11624 |
| 3588 | CUCACCU GUU UCCUGUAU | 2206 | AUACAGGA AGAA GGUGAG ACCAGAGAAACACACGUUGUGGUACAUUACCUGGUA | 11625 |
| 3689 | AGAGCCG GCC UGUGAGUG | 2207 | CACUCACA AGAA GGCUCU ACCAGAGAAACACACGUUGUGGUACAUUACCUGGUA | 11626 |
| 3753 | AAUCCCA GAU GACAACCA | 2208 | UGGUUGUC AGAA GGGAUU ACCAGAGAAACACACGUUGUGGUACAUUACCUGGUA | 11627 |
| 3764 | ACAACCA GAC GGACAGUG | 2209 | CACUGUCC AGAA GGUUGU ACCAGAGAAACACACGUUGUGGUACAUUACCUGGUA | 11628 |
| 3911 | GCUACCA GUC CGGAUAUC | 2210 | GAUAUCCG AGAA GGUAGC ACCAGAGAAACACACGUUGUGGUACAUUACCUGGUA | 11629 |
| 3927 | UCACUCC GAU GACACAGA | 2211 | UCUGUGUC AGAA GAGUGA ACCAGAGAAACACACGUUGUGGUACAUUACCUGGUA | 11630 |
| 4011 | UAGCACA GCC CAGAUUCU | 2212 | AGAAUCUG AGAA GUGCUA ACCAGAGAAACACACGUUGUGGUACAUUACCUGGUA | 11631 |
| 4016 | CAGCCCA GAU UCUCCAGC | 2213 | GCUGGAGA AGAA GGGCUG ACCAGAGAAACACACGUUGUGGUACAUUACCUGGUA | 11632 |
| 4025 | UUCUCCA GCC UGACACGG | 2214 | CCGUGUCA AGAA GGAGAA ACCAGAGAAACACACGUUGUGGUACAUUACCUGGUA | 11633 |
| 4059 | UCCUCCU GUU UAAAAGGA | 2215 | UCCUUUUA AGAA GGAGGA ACCAGAGAAACACACGUUGUGGUACAUUACCUGGUA | 11634 |
| 4111 | GAGGUCU GCU CAGAUUUU | 2216 | AAAAUCUG AGAA GACCUC ACCAGAGAAACACACGUUGUGGUACAUUACCUGGUA | 11635 |
| 4116 | CUGCUCA GAU UUUGAAGU | 2217 | ACUUCAAA AGAA GAGCAG ACCAGAGAAACACACGUUGUGGUACAUUACCUGGUA | 11636 |
| 4195 | GACCUCG GAC UGCAGGGA | 2218 | UCCCUGCA AGAA GAGGUC ACCAGAGAAACACACGUUGUGGUACAUUACCUGGUA | 11637 |
| 4210 | GGAGCCA GCU CUUCUAGG | 2219 | CCUAGAAG AGAA GGCUCC ACCAGAGAAACACACGUUGUGGUACAUUACCUGGUA | 11638 |

TABLE VI

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 13 | GGGCGAAUU GGGUACGG | 2220 | CCGUACCC CUGAUGAGGCCGUUAGGCCGAA AUUCGCCC | 11639 |
| 18 | AAUUGGGUA CGGGACCC | 2221 | GGGUCCCG CUGAUGAGGCCGUUAGGCCGAA ACCCAAUU | 11640 |
| 31 | ACCCCCUC GAGGUCGA | 2222 | UCGACCUC CUGAUGAGGCCGUUAGGCCGAA AGGGGGGU | 11641 |
| 37 | CUCGAGGUC GACGGUAU | 2223 | AUACCGUC CUGAUGAGGCCGUUAGGCCGAA ACCUCGAG | 11642 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 44 | UCGACGGUA UCGAUAAG | 2224 | CUUAUCGA CUGAUGAGGCCGUUAGGCCGAA ACCGUCGA | 11643 |
| 46 | GACGGUAUC GAUAAGCU | 2225 | AGCUUAUC CUGAUGAGGCCGUUAGGCCGAA AUACCGUC | 11644 |
| 50 | GUAUCGAUA AGCUUGAU | 2226 | AUCAAGCU CUGAUGAGGCCGUUAGGCCGAA AUCGAUAC | 11645 |
| 55 | GAUAAGCUU GAUAUCGA | 2227 | UCGAUAUC CUGAUGAGGCCGUUAGGCCGAA AGCUUAUC | 11646 |
| 59 | AGCUUGAUA UCGAAUUC | 2228 | GAAUUCGA CUGAUGAGGCCGUUAGGCCGAA AUCAAGCU | 11647 |
| 61 | CUUGAUAUC GAAUUCGG | 2229 | CCGAAUUC CUGAUGAGGCCGUUAGGCCGAA AUAUCAAG | 11648 |
| 66 | UAUCGAAUU CGGGCCCA | 2230 | UGGGCCCG CUGAUGAGGCCGUUAGGCCGAA AUUCGAUA | 11649 |
| 67 | AUCGAAUUC GGGCCCAG | 2231 | CUGGGCCC CUGAUGAGGCCGUUAGGCCGAA AAUUCGAU | 11650 |
| 83 | GACUGUGUC CCGCAGCC | 2232 | GGCUGCGG CUGAUGAGGCCGUUAGGCCGAA ACACAGUC | 11651 |
| 97 | GCCGGGAUA ACCUGGCU | 2233 | AGCCAGGU CUGAUGAGGCCGUUAGGCCGAA AUCCCGGC | 11652 |
| 114 | GACCCGAUU CCGCGGAC | 2234 | GUCCGCGG CUGAUGAGGCCGUUAGGCCGAA AUCGGGUC | 11653 |
| 115 | ACCCGAUUC CGCGGACA | 2235 | UGUCCGCG CUGAUGAGGCCGUUAGGCCGAA AAUCGGGU | 11654 |
| 169 | CCCGCGCUC UCCCCGGU | 2236 | ACCGGGGA CUGAUGAGGCCGUUAGGCCGAA AGCGCGGG | 11655 |
| 171 | CGCGCUCUC CCCGGUCU | 2237 | AGACCGGG CUGAUGAGGCCGUUAGGCCGAA AGAGCGCG | 11656 |
| 178 | UCCCCGGUC UUGCGCUG | 2238 | CAGCGCAA CUGAUGAGGCCGUUAGGCCGAA ACCGGGGA | 11657 |
| 180 | CCCGGUCUU GCGCUGCG | 2239 | CGCAGCGC CUGAUGAGGCCGUUAGGCCGAA AGACCGGG | 11658 |
| 197 | GGGGCCAUA CCGCCUCU | 2240 | AGAGGCGG CUGAUGAGGCCGUUAGGCCGAA AUGGCCCC | 11659 |
| 204 | UACCGCCUC UGUGACUU | 2241 | AAGUCACA CUGAUGAGGCCGUUAGGCCGAA AGGCGGUA | 11660 |
| 212 | CUGUGACUU CUUUGCGG | 2242 | CCGCAAAG CUGAUGAGGCCGUUAGGCCGAA AGUCACAG | 11661 |
| 213 | UGUGACUUC UUUGCGGG | 2243 | CCCGCAAA CUGAUGAGGCCGUUAGGCCGAA AAGUCACA | 11662 |
| 215 | UGACUUCUU UGCGGGCC | 2244 | GGCCCGCA CUGAUGAGGCCGUUAGGCCGAA AGAAGUCA | 11663 |
| 216 | GACUUCUUU GCGGGCCA | 2245 | UGGCCCGC CUGAUGAGGCCGUUAGGCCGAA AAGAAGUC | 11664 |
| 241 | GAAGGAGUC UGUGCCUG | 2246 | CAGGCACA CUGAUGAGGCCGUUAGGCCGAA ACUCCUUC | 11665 |
| 262 | ACUGGGCUC UGUGCCCA | 2247 | UGGGCACA CUGAUGAGGCCGUUAGGCCGAA AGCCCAGU | 11666 |
| 306 | GCGCUGCUA GCUGUCGC | 2248 | GCGACAGC CUGAUGAGGCCGUUAGGCCGAA AGCAGCGC | 11667 |
| 312 | CUAGCUGUC GCUCUGUG | 2249 | CACAGAGC CUGAUGAGGCCGUUAGGCCGAA ACAGCUAG | 11668 |
| 316 | CUGUCGCUC UGUGGUUC | 2250 | GAACCACA CUGAUGAGGCCGUUAGGCCGAA AGCGACAG | 11669 |
| 323 | UCUGUGGUU CUGCGUGG | 2251 | CCACGCAG CUGAUGAGGCCGUUAGGCCGAA ACCACAGA | 11670 |
| 324 | CUGUGGUUC UGCGUGGA | 2252 | UCCACGCA CUGAUGAGGCCGUUAGGCCGAA AACCACAG | 11671 |
| 347 | AGCCGCCUC UGUGGGUU | 2253 | AACCCACA CUGAUGAGGCCGUUAGGCCGAA AGGCGGCU | 11672 |
| 355 | CUGUGGGUU UGACUGGC | 2254 | GCCAGUCA CUGAUGAGGCCGUUAGGCCGAA ACCCACAG | 11673 |
| 356 | UGUGGGUUU GACUGGCG | 2255 | CGCCAGUC CUGAUGAGGCCGUUAGGCCGAA AACCCACA | 11674 |
| 367 | CUGGCGAUU UUCUCCAU | 2256 | AUGGAGAA CUGAUGAGGCCGUUAGGCCGAA AUCGCCAG | 11675 |
| 368 | UGGCGAUUU UCUCCAUC | 2257 | GAUGGAGA CUGAUGAGGCCGUUAGGCCGAA AAUCGCCA | 11676 |
| 369 | GGCGAUUUU CUCCAUCC | 2258 | GGAUGGAG CUGAUGAGGCCGUUAGGCCGAA AAAUCGCC | 11677 |
| 370 | GCGAUUUUC UCCAUCCC | 2259 | GGGAUGGA CUGAUGAGGCCGUUAGGCCGAA AAAAUCGC | 11678 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 372 | GAUUUCUC CAUCCCCC | 2260 | GGGGGAUG CUGAUGAGGCCGUUAGGCCGAA AGAAAAUC | 11679 |
| 376 | UUCUCCAUC CCCCCAAG | 2261 | CUUGGGGG CUGAUGAGGCCGUUAGGCCGAA AUGGAGAA | 11680 |
| 387 | CCCAAGCUC AGCACACA | 2262 | UGUGUGCU CUGAUGAGGCCGUUAGGCCGAA AGCUUGGG | 11681 |
| 405 | AAAGACAUA CUGACAAU | 2263 | AUUGUCAG CUGAUGAGGCCGUUAGGCCGAA AUGUCUUU | 11682 |
| 414 | CUGACAAUU UUGGCAAA | 2264 | UUUGCCAA CUGAUGAGGCCGUUAGGCCGAA AUUGUCAG | 11683 |
| 415 | UGACAAUUU UGGCAAAU | 2265 | AUUUGCCA CUGAUGAGGCCGUUAGGCCGAA AAUUGUCA | 11684 |
| 416 | GACAAUUUU GGCAAAUA | 2266 | UAUUUGCC CUGAUGAGGCCGUUAGGCCGAA AAAUUGUC | 11685 |
| 424 | UGGCAAAUA CAACCCUU | 2267 | AAGGGUUG CUGAUGAGGCCGUUAGGCCGAA AUUUGCCA | 11686 |
| 432 | ACAACCCUU CAGAUUAC | 2268 | GUAAUCUG CUGAUGAGGCCGUUAGGCCGAA AGGGUUGU | 11687 |
| 433 | CAACCCUUC AGAUUACU | 2269 | AGUAAUCU CUGAUGAGGCCGUUAGGCCGAA AAGGGUUG | 11688 |
| 438 | CUUCAGAUU ACUUGCAG | 2270 | CUGCAAGU CUGAUGAGGCCGUUAGGCCGAA AUCUGAAG | 11689 |
| 439 | UUCAGAUUA CUUGCAGG | 2271 | CCUGCAAG CUGAUGAGGCCGUUAGGCCGAA AAUCUGAA | 11690 |
| 442 | AGAUUACUU GCAGGGA | 2272 | UCCCCUGC CUGAUGAGGCCGUUAGGCCGAA AGUAAUCU | 11691 |
| 471 | GACUGGCUU UGGCCCAA | 1534 | UUGGGCCA CUGAUGAGGCCGUUAGGCCGAA AGCCAGUC | 10953 |
| 472 | ACUGGCUUU GGCCCAAU | 1535 | AUUGGGCC CUGAUGAGGCCGUUAGGCCGAA AAGCCAGU | 10954 |
| 484 | CCAAUGCUC AGCGUGAU | 2273 | AUCACGCU CUGAUGAGGCCGUUAGGCCGAA AGCAUUGG | 11692 |
| 493 | AGCGUGAUU CUGAGGAA | 2274 | DUCCUCAG CUGAUGAGGCCGUUAGGCCGAA AUCACGCU | 11693 |
| 494 | GCGUGAUUC UGAGGAAA | 2275 | UUUCCUCA CUGAUGAGGCCGUUAGGCCGAA AAUCACGC | 11694 |
| 507 | GAAAGGGUA UUGGUGAC | 2276 | GUCACCAA CUGAUGAGGCCGUUAGGCCGAA ACCCUUUC | 11695 |
| 509 | AAGGGUAUU GGUGACUG | 2277 | CAGUCACC CUGAUGAGGCCGUUAGGCCGAA AUACCCUU | 11696 |
| 538 | GUGACAGUA UCUUCUGC | 2278 | GCAGAAGA CUGAUGAGGCCGUUAGGCCGAA ACUGUCAC | 11697 |
| 540 | GACAGUAUC UUCUGCAA | 2279 | UUGCAGAA CUGAUGAGGCCGUUAGGCCGAA AUACUGUC | 11698 |
| 542 | CAGUAUCUU CUGCAAAA | 2280 | UUUUGCAG CUGAUGAGGCCGUUAGGCCGAA AGAUACUG | 11699 |
| 543 | AGUAUCUUC UGCAAAAC | 2281 | GUUUUGCA CUGAUGAGGCCGUUAGGCCGAA AAGAUACU | 11700 |
| 555 | AAAACACUC ACCAUUCC | 2282 | GGAAUGGU CUGAUGAGGCCGUUAGGCCGAA AGUGUUUU | 11701 |
| 561 | CUCACCAUU CCCAGGGU | 2283 | ACCCUGGG CUGAUGAGGCCGUUAGGCCGAA AUGGUGAG | 11702 |
| 562 | UCACCAUUC CCAGGGUG | 2284 | CACCCUGG CUGAUGAGGCCGUUAGGCCGAA AAUGGUGA | 11703 |
| 573 | AGGGUGGUU GGAAAUGA | 2285 | UCAUUUCC CUGAUGAGGCCGUUAGGCCGAA ACCACCCU | 11704 |
| 583 | GAAAUGAUA CUGGAGCC | 2286 | GGCUCCAG CUGAUGAGGCCGUUAGGCCGAA AUCAUUUC | 11705 |
| 593 | UGGAGCCUA CAAGUGCU | 1546 | AGCACUUG CUGAUGAGGCCGUUAGGCCGAA AGGCUCCA | 10965 |
| 602 | CAAGUGCUC GUACCGGG | 2287 | CCCGGUAC CUGAUGAGGCCGUUAGGCCGAA AGCACUUG | 11706 |
| 605 | GUGCUCGUA CCGGGACG | 2288 | CGUCCCGG CUGAUGAGGCCGUUAGGCCGAA ACGAGCAC | 11707 |
| 615 | CGGGACGUC GACAUAGC | 2289 | GCUAUGUC CUGAUGAGGCCGUUAGGCCGAA ACGUCCCG | 11708 |
| 621 | GUCGACAUA GCCUCCAC | 2290 | GUGGAGGC CUGAUGAGGCCGUUAGGCCGAA AUGUCGAC | 11709 |
| 626 | CAUAGCCUC CACUGUUU | 2291 | AAACAGUG CUGAUGAGGCCGUUAGGCCGAA AGGCUAUG | 11710 |
| 633 | UCCACUGUU UAUGUCUA | 2292 | UAGACAUA CUGAUGAGGCCGUUAGGCCGAA ACAGUGGA | 11711 |
| 634 | CCACUGUUU AUGUCUAU | 2293 | AUAGACAU CUGAUGAGGCCGUUAGGCCGAA AACAGUGG | 11712 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 635 | CACUGUUUA UGUCUAUG | 2294 | CAUAGACA CUGAUGAGGCCGUUAGGCCGAA AAACAGUG | 11713 |
| 639 | GUUUAUGUC UAUGUUCG | 2295 | CGAACAUA CUGAUGAGGCCGUUAGGCCGAA ACAUAAAC | 11714 |
| 641 | UUAUGUCUA UGUUCGAG | 2296 | CUCGAACA CUGAUGAGGCCGUUAGGCCGAA AGACAUAA | 11715 |
| 645 | GUCUAUGUU CGAGAUUA | 2297 | UAAUCUCG CUGAUGAGGCCGUUAGGCCGAA ACAUAGAC | 11716 |
| 646 | UCUAUGUUC GAGAUUAC | 2298 | GUAAUCUC CUGAUGAGGCCGUUAGGCCGAA AACAUAGA | 11717 |
| 652 | UUCGAGAUU ACAGAUCA | 2299 | UGAUCUGU CUGAUGAGGCCGUUAGGCCGAA AUCUCGAA | 11718 |
| 653 | UCGAGAUUA CAGAUCAC | 2300 | GUGAUCUG CUGAUGAGGCCGUUAGGCCGAA AAUCUCGA | 11719 |
| 659 | UUACAGAUC ACCAUUCA | 2301 | UGAAUGGU CUGAUGAGGCCGUUAGGCCGAA AUCUGUAA | 11720 |
| 665 | AUCACCAUU CAUCGCCU | 2302 | AGGCGAUG CUGAUGAGGCCGUUAGGCCGAA AUGGUGAU | 11721 |
| 666 | UCACCAUUC AUCGCCUC | 2303 | GAGGCGAU CUGAUGAGGCCGUUAGGCCGAA AAUGGUGA | 11722 |
| 669 | CCAUUCAUC GCCUCUGU | 2304 | ACAGAGGC CUGAUGAGGCCGUUAGGCCGAA AUGAAUGG | 11723 |
| 674 | CAUCGCCUC UGUCAGUG | 2305 | CACUGACA CUGAUGAGGCCGUUAGGCCGAA AGGCGAUG | 11724 |
| 678 | GCCUCUGUC AGUGACCA | 2306 | UGGUCACU CUGAUGAGGCCGUUAGGCCGAA ACAGAGGC | 11725 |
| 696 | CAUGGCAUC GUGUACAU | 2307 | AUGUACAC CUGAUGAGGCCGUUAGGCCGAA AUGCCAUG | 11726 |
| 701 | CAUCGUGUA CAUCACCG | 2308 | CGGUGAUG CUGAUGAGGCCGUUAGGCCGAA ACACGAUG | 11727 |
| 705 | GUGUACAUC ACCGAGAA | 2309 | UUCUCGGU CUGAUGAGGCCGUUAGGCCGAA AUGUACAC | 11728 |
| 735 | GUGGUGAUC CCCUGCCG | 2310 | CGGCAGGG CUGAUGAGGCCGUUAGGCCGAA AUCACCAC | 11729 |
| 749 | CCGAGGGUC GAUUUCAA | 2311 | UUGAAAUC CUGAUGAGGCCGUUAGGCCGAA ACCCUCGG | 11730 |
| 753 | GGGUCGAUU UCAAACCU | 2312 | AGGUUUGA CUGAUGAGGCCGUUAGGCCGAA AUCGACCC | 11731 |
| 754 | GGUCGAUUU CAAACCUC | 2313 | GAGGUUUG CUGAUGAGGCCGUUAGGCCGAA AAUCGACC | 11732 |
| 755 | GUCGAUUUC AAACCUCA | 2314 | UGAGGUUU CUGAUGAGGCCGUUAGGCCGAA AAAUCGAC | 11733 |
| 762 | UCAAACCUC AAUGUGUC | 2315 | GACACAUU CUGAUGAGGCCGUUAGGCCGAA AGGUUUGA | 11734 |
| 770 | CAAUGUGUC UCUUUGCG | 2316 | CGCAAAGA CUGAUGAGGCCGUUAGGCCGAA ACACAUUG | 11735 |
| 772 | AUGUGUCUC UUUGCGCU | 2317 | AGCGCAAA CUGAUGAGGCCGUUAGGCCGAA AGACACAU | 11736 |
| 774 | GUGUCUCUU UGCGCUAG | 2318 | CUAGCGCA CUGAUGAGGCCGUUAGGCCGAA AGAGACAC | 11737 |
| 775 | UGUCUCUUU GCGCUAGG | 2319 | CCUAGCGC CUGAUGAGGCCGUUAGGCCGAA AAGAGACA | 11738 |
| 781 | UUUGCGCUA GGUAUCCA | 2320 | UGGAUACC CUGAUGAGGCCGUUAGGCCGAA AGCGCAAA | 11739 |
| 785 | CGCUAGGUA UCCAGAAA | 2321 | UUUCUGGA CUGAUGAGGCCGUUAGGCCGAA ACCUAGCG | 11740 |
| 787 | CUAGGUAUC CAGAAAAG | 2322 | CUUUUCUG CUGAUGAGGCCGUUAGGCCGAA AUACCUAG | 11741 |
| 800 | AAAGAGAUU GUUCCGG | 2323 | CCGGAACA CUGAUGAGGCCGUUAGGCCGAA AUCUCUUU | 11742 |
| 801 | AAGAGAUUU GUUCCGGA | 2324 | UCCGGAAC CUGAUGAGGCCGUUAGGCCGAA AAUCUCUU | 11743 |
| 804 | AGAUUUGUU CCGGAUGG | 2325 | CCAUCCGG CUGAUGAGGCCGUUAGGCCGAA ACAAAUCU | 11744 |
| 805 | GAUUUGUUC CGGAUGGA | 2326 | UCCAUCCG CUGAUGAGGCCGUUAGGCCGAA AACAAAUC | 11745 |
| 822 | AACAGAAUU UCCUGGGA | 1595 | UCCCAGGA CUGAUGAGGCCGUUAGGCCGAA AUUCUGUU | 11014 |
| 823 | ACAGAAUUU CCUGGGAC | 1596 | GUCCCAGG CUGAUGAGGCCGUUAGGCCGAA AAUUCUGU | 11015 |
| 824 | CAGAAUUUC CUGGGACA | 1597 | UGUCCCAG CUGAUGAGGCCGUUAGGCCGAA AAAUUCUG | 11016 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 840 | AGCGAGAUA GGCUUUAC | 2327 | GUAAAGCC CUGAUGAGGCCGUUAGGCCGAA AUCUCGCU | 11746 |
| 845 | GAUAGGCUU UACUCUCC | 2328 | GGAGAGUA CUGAUGAGGCCGUUAGGCCGAA AGCCUAUC | 11747 |
| 846 | AUAGGCUUU ACUCUCCC | 2329 | GGGAGAGU CUGAUGAGGCCGUUAGGCCGAA AAGCCUAU | 11748 |
| 847 | UAGGCUUUA CUCUCCCC | 2330 | GGGGAGAG CUGAUGAGGCCGUUAGGCCGAA AAAGCCUA | 11749 |
| 850 | GCUUUACUC UCCCAGU | 2331 | ACUGGGGA CUGAUGAGGCCGUUAGGCCGAA AGUAAAGC | 11750 |
| 852 | UUUACUCUC CCAGUUA | 2332 | UAACUGGG CUGAUGAGGCCGUUAGGCCGAA AGAGUAAA | 11751 |
| 859 | UCCCCAGUU ACAUGAUC | 2333 | GAUCAUGU CUGAUGAGGCCGUUAGGCCGAA ACUGGGGA | 11752 |
| 860 | CCCCAGUUA CAUGAUCA | 2334 | UGAUCAUG CUGAUGAGGCCGUUAGGCCGAA AACUGGGG | 11753 |
| 867 | UACAUGAUC AGCUAUGC | 1605 | GCAUAGCU CUGAUGAGGCCGUUAGGCCGAA AUCAUGUA | 11024 |
| 872 | GAUCAGCUA UGCCGGCA | 2335 | UGCCGGCA CUGAUGAGGCCGUUAGGCCGAA AGCUGAUC | 11754 |
| 885 | GGCAUGGUC UUCUGUGA | 1607 | UCACAGAA CUGAUGAGGCCGUUAGGCCGAA ACCAUGCC | 11026 |
| 887 | CAUGGUCUU CUGUGAGG | 2336 | CCUCACAG CUGAUGAGGCCGUUAGGCCGAA AGACCAUG | 11755 |
| 888 | AUGGUCUUC UGUGAGGC | 2337 | GCCUCACA CUGAUGAGGCCGUUAGGCCGAA AAGACCAU | 11756 |
| 903 | GCAAAGAUC AAUGAUGA | 2338 | UCAUCAUU CUGAUGAGGCCGUUAGGCCGAA AUCUUUGC | 11757 |
| 917 | UGAAACCUA UCAGUCUA | 2339 | UAGACUGA CUGAUGAGGCCGUUAGGCCGAA AGGUUUCA | 11758 |
| 919 | AAACCUAUC AGUCUAUC | 2340 | GAUAGACU CUGAUGAGGCCGUUAGGCCGAA AUAGGUUU | 11759 |
| 923 | CUAUCAGUC UAUCAUGU | 2341 | ACAUGAUA CUGAUGAGGCCGUUAGGCCGAA ACUGAUAG | 11760 |
| 925 | AUCAGUCUA UCAUGUAC | 2342 | GUACAUGA CUGAUGAGGCCGUUAGGCCGAA AGACUGAU | 11761 |
| 927 | CAGUCUAUC AUGUACAU | 2343 | AUGUACAU CUGAUGAGGCCGUUAGGCCGAA AUAGACUG | 11035 |
| 932 | UAUCAUGUA CAUAGUUG | 2344 | CAACUAUG CUGAUGAGGCCGUUAGGCCGAA ACAUGAUA | 11762 |
| 936 | AUGUACAUA GUUGUGGU | 2345 | ACCACAAC CUGAUGAGGCCGUUAGGCCGAA AUGUACAU | 11763 |
| 939 | UACAUAGUU GUGGUUGU | 2346 | ACAACCAC CUGAUGAGGCCGUUAGGCCGAA ACUAUGUA | 11764 |
| 945 | GUUGUGGUU GUAGGAUA | 2347 | UAUCCUAC CUGAUGAGGCCGUUAGGCCGAA ACCACAAC | 11765 |
| 948 | GUGGUUGUA GGAUAUAG | 2348 | CUAUAUCC CUGAUGAGGCCGUUAGGCCGAA ACAACCAC | 11766 |
| 953 | UGUAGGAUA UAGGAUUU | 2349 | AAAUCCUA CUGAUGAGGCCGUUAGGCCGAA AUCCUACA | 11767 |
| 955 | UAGGAUAUA GGAUUUAU | 2350 | AUAAAUCC CUGAUGAGGCCGUUAGGCCGAA AUAUCCUA | 11768 |
| 960 | UAUAGGAUU UAUGAUGU | 1626 | ACAUCAUA CUGAUGAGGCCGUUAGGCCGAA AUCCUAUA | 11045 |
| 961 | AUAGGAUUU AUGAUGUG | 1627 | CACAUCAU CUGAUGAGGCCGUUAGGCCGAA AAUCCUAU | 11046 |
| 962 | UAGGAUUUA UGAUGUGA | 2351 | UCACAUCA CUGAUGAGGCCGUUAGGCCGAA AAAUCCUA | 11769 |
| 972 | GAUGUGAUU CUGAGCCC | 2352 | GGGCUCAG CUGAUGAGGCCGUUAGGCCGAA AUCACAUC | 11770 |
| 973 | AUGUGAUUC UGAGCCCC | 2353 | GGGGCUCA CUGAUGAGGCCGUUAGGCCGAA AAUCACAU | 11771 |
| 993 | CAUGAAAUU GAGCUAUC | 2354 | GAUAGCUC CUGAUGAGGCCGUUAGGCCGAA AUUUCAUG | 11772 |
| 999 | AUUGAGCUA UCUGCCGG | 2355 | CCGGCAGA CUGAUGAGGCCGUUAGGCCGAA AGCUCAAU | 11773 |
| 1001 | UGAGCUAUC UGCCGGAG | 2356 | CUCCGGCA CUGAUGAGGCCGUUAGGCCGAA AUAGCUCA | 11774 |
| 1017 | GAAAACUU GUCUUAAA | 2357 | UUUAAGAC CUGAUGAGGCCGUUAGGCCGAA AGUUUUUC | 11775 |
| 1020 | AACUUGUC UUAAAUUG | 2358 | CAAUUUAA CUGAUGAGGCCGUUAGGCCGAA ACAAGUUU | 11776 |
| 1022 | ACUUGUCUU AAAUUGUA | 2359 | UACAAUUU CUGAUGAGGCCGUUAGGCCGAA AGACAAGU | 11777 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 1023 | CUUGUCUUA AAUUGUAC | 1641 | GUACAAUU CUGAUGAGGCCGUUAGGCCGAA AAGACAAG | 11060 |
| 1027 | UCUUAAAUU GUACAGCG | 2360 | CGCUGUAC CUGAUGAGGCCGUUAGGCCGAA AUUUAAGA | 11778 |
| 1030 | UAAAUUGUA CAGCGAGA | 2361 | UCUCGCUG CUGAUGAGGCCGUUAGGCCGAA ACAAUUUA | 11779 |
| 1047 | ACAGAGCUC AAUGUGGG | 2362 | CCCACAUU CUGAUGAGGCCGUUAGGCCGAA AGCUCUGU | 11780 |
| 1059 | GUGGGGCUU GAUUUCAC | 2363 | GUGAAAUC CUGAUGAGGCCGUUAGGCCGAA AGCCCCAC | 11781 |
| 1063 | GGCUUGAUU UCACCUGG | 2364 | CCAGGUGA CUGAUGAGGCCGUUAGGCCGAA AUCAAGCC | 11782 |
| 1064 | GCUUGAUUU CACCUGGC | 2365 | GCCAGGUG CUGAUGAGGCCGUUAGGCCGAA AAUCAAGC | 11783 |
| 1065 | CUUGAUUUC ACCUGGCA | 2366 | UGCCAGGU CUGAUGAGGCCGUUAGGCCGAA AAAUCAAG | 11784 |
| 1076 | CUGGCACUC UCCACCUU | 2367 | AAGGUGGA CUGAUGAGGCCGUUAGGCCGAA AGUGCCAG | 11785 |
| 1078 | GGCACUCUC CACCUUCA | 2368 | UGAAGGUG CUGAUGAGGCCGUUAGGCCGAA AGAGUGCC | 11786 |
| 1084 | CUCCACCUU CAAAGUCU | 2369 | AGACUUUG CUGAUGAGGCCGUUAGGCCGAA AGGUGGAG | 11787 |
| 1085 | UCCACCUUC AAAGUCUC | 2370 | GAGACUUU CUGAUGAGGCCGUUAGGCCGAA AAGGUGGA | 11788 |
| 1091 | UUCAAAGUC UCAUCAUA | 2371 | UAUGAUGA CUGAUGAGGCCGUUAGGCCGAA ACUUUGAA | 11789 |
| 1093 | CAAAGUCUC AUCAUAAG | 2372 | CUUAUGAU CUGAUGAGGCCGUUAGGCCGAA AGACUUUG | 11790 |
| 1096 | AGUCUCAUC AUAAGAAG | 2373 | CUUCUUAU CUGAUGAGGCCGUUAGGCCGAA AUGAGACU | 11791 |
| 1099 | CUCAUCAUA AGAAGAUU | 2374 | AAUCUUCU CUGAUGAGGCCGUUAGGCCGAA AUGAUGAG | 11792 |
| 1107 | AAGAAGAUU GUAAACCG | 2375 | CGGUUUAC CUGAUGAGGCCGUUAGGCCGAA AUCUUCUU | 11793 |
| 1110 | AAGAUUGUA AACCGGGA | 2376 | UCCCGGUU CUGAUGAGGCCGUUAGGCCGAA ACAAUCUU | 11794 |
| 1130 | GAAACCCUU UCCUGGGA | 2377 | UCCCAGGA CUGAUGAGGCCGUUAGGCCGAA AGGGUUUC | 11795 |
| 1131 | AAACCCUUU CCUGGGAC | 2378 | GUCCCAGG CUGAUGAGGCCGUUAGGCCGAA AAGGGUUU | 11796 |
| 1132 | AACCCUUUC CUGGGACU | 2379 | AGUCCCAG CUGAUGAGGCCGUUAGGCCGAA AAAGGGUU | 11797 |
| 1154 | GAAGAUGUU UUUGAGCA | 2380 | UGCUCAAA CUGAUGAGGCCGUUAGGCCGAA ACAUCUUC | 11798 |
| 1155 | AAGAUGUUU UUGAGCAC | 2381 | GUGCUCAA CUGAUGAGGCCGUUAGGCCGAA AACAUCUU | 11799 |
| 1156 | AGAUGUUUU UGAGCACC | 2382 | GGUGCUCA CUGAUGAGGCCGUUAGGCCGAA AAACAUCU | 11800 |
| 1157 | GAUGUUUUU GAGCACCU | 2383 | AGGUGCUC CUGAUGAGGCCGUUAGGCCGAA AAAACAUC | 11801 |
| 1166 | GAGCACCUU GACAAUAG | 2384 | CUAUUGUC CUGAUGAGGCCGUUAGGCCGAA AGGUGCUC | 11802 |
| 1173 | UUGACAAUA GAAAGUGU | 2385 | ACACUUUC CUGAUGAGGCCGUUAGGCCGAA AUUGUCAA | 11803 |
| 1205 | AGGGGAAUA CACCUGUG | 2386 | CACAGGUG CUGAUGAGGCCGUUAGGCCGAA AUUCCCCU | 11804 |
| 1215 | ACCUGUGUA GCGUCCAG | 2387 | CUGGACGC CUGAUGAGGCCGUUAGGCCGAA ACACAGGU | 11805 |
| 1220 | UGUAGCGUC CAGUGGAC | 2388 | GUCCACUG CUGAUGAGGCCGUUAGGCCGAA ACGCUACA | 11806 |
| 1236 | CGGAUGAUC AAGAGAAA | 2389 | UUUCUCUU CUGAUGAGGCCGUUAGGCCGAA AUCAUCCG | 11807 |
| 1246 | AGAGAAAUA GAACAUUU | 2390 | AAAUGUUC CUGAUGAGGCCGUUAGGCCGAA AUUUCUCU | 11808 |
| 1253 | UAGAACAUU UGUCCGAG | 2391 | CUCGGACA CUGAUGAGGCCGUUAGGCCGAA AUGUUCUA | 11809 |
| 1254 | AGAACAUUU GUCCGAGU | 2392 | ACUCGGAC CUGAUGAGGCCGUUAGGCCGAA AAUGUUCU | 11810 |
| 1257 | ACAUUUGUC CGAGUUCA | 2393 | UGAACUCG CUGAUGAGGCCGUUAGGCCGAA ACAAAUGU | 11811 |
| 1263 | GUCCGAGUU CACACAAA | 2394 | UUUGUGUG CUGAUGAGGCCGUUAGGCCGAA ACUCGGAC | 11812 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 1264 | UCCGAGUUC ACACAAAG | 2395 | CUUUGUGU CUGAUGAGGCCGUUAGGCCGAA AACUCGGA | 11813 |
| 1276 | CAAAGCCUU UUAUUGCU | 2396 | AGCAAUAA CUGAUGAGGCCGUUAGGCCGAA AGGCUUUG | 11814 |
| 1277 | AAAGCCUUU UAUUGCUU | 2397 | AAGCAAUA CUGAUGAGGCCGUUAGGCCGAA AAGGCUUU | 11815 |
| 1278 | AAGCCUUUU AUUGCUUU | 2398 | AAAGCAAU CUGAUGAGGCCGUUAGGCCGAA AAAGGCUU | 11816 |
| 1279 | AGCCUUUUA UUGCUUUC | 2399 | GAAAGCAA CUGAUGAGGCCGUUAGGCCGAA AAAAGGCU | 11817 |
| 1281 | CCUUUUAUU GCUUUCGG | 2400 | CCGAAAGC CUGAUGAGGCCGUUAGGCCGAA AUAAAAGG | 11818 |
| 1285 | UUAUUGCUU UCGGUAGU | 2401 | ACUACCGA CUGAUGAGGCCGUUAGGCCGAA AGCAAUAA | 11819 |
| 1286 | UAUUGCUUU CGGUAGUG | 2402 | CACUACCG CUGAUGAGGCCGUUAGGCCGAA AAGCAAUA | 11820 |
| 1287 | AUUGCUUUC GGUAGUGG | 2403 | CCACUACC CUGAUGAGGCCGUUAGGCCGAA AAAGCAAU | 11821 |
| 1291 | CUUUCGGUA GUGGGAUG | 2404 | CAUCCCAC CUGAUGAGGCCGUUAGGCCGAA ACCGAAAG | 11822 |
| 1304 | GAUGAAAUC UUGGUGG | 2405 | CCACCAAA CUGAUGAGGCCGUUAGGCCGAA AUUUCAUC | 11823 |
| 1306 | UGAAAUCUU GGUGGAA | 2406 | UUCCACCA CUGAUGAGGCCGUUAGGCCGAA AGAUUUCA | 11824 |
| 1307 | GAAAUCUUU GGUGGAAG | 2407 | CUUCCACC CUGAUGAGGCCGUUAGGCCGAA AAGAUUUC | 11825 |
| 1330 | UGGGCAGUC AAGUCCGA | 2408 | UCGGACUU CUGAUGAGGCCGUUAGGCCGAA ACUGCCCA | 11826 |
| 1335 | AGUCAAGUC CGAAUCCC | 2409 | GGGAUUCG CUGAUGAGGCCGUUAGGCCGAA ACUUGACU | 11827 |
| 1341 | GUCCGAAUC CUGUGAA | 2410 | UUCACAGG CUGAUGAGGCCGUUAGGCCGAA AUUCGGAC | 11828 |
| 1352 | UGUGAAGUA UCUCAGUU | 2411 | AACUGAGA CUGAUGAGGCCGUUAGGCCGAA ACUUCACA | 11829 |
| 1354 | UGAAGUAUC UCAGUUAC | 2412 | GUAACUGA CUGAUGAGGCCGUUAGGCCGAA AUACUUCA | 11830 |
| 1356 | AAGUAUCUC AGUUACCC | 2413 | GGGUAACU CUGAUGAGGCCGUUAGGCCGAA AGAUACUU | 11831 |
| 1360 | AUCUCAGUU ACCCAGCU | 2414 | AGCUGGGU CUGAUGAGGCCGUUAGGCCGAA ACUGAGAU | 11832 |
| 1361 | UCUCAGUUA CCCAGCUC | 2415 | GAGCUGGG CUGAUGAGGCCGUUAGGCCGAA AACUGAGA | 11833 |
| 1369 | ACCCAGCUC UGAUAUC | 2416 | GAUAUCAG CUGAUGAGGCCGUUAGGCCGAA AGCUGGGU | 11834 |
| 1375 | CUCCUGAUA UCAAAUGG | 2417 | CCAUUUGA CUGAUGAGGCCGUUAGGCCGAA AUCAGGAG | 11835 |
| 1377 | CCUGAUAUC AAAUGGUA | 2418 | UACCAUUU CUGAUGAGGCCGUUAGGCCGAA AUAUCAGG | 11836 |
| 1385 | CAAAUGGUA CAGAAAUG | 2419 | CAUUUCUG CUGAUGAGGCCGUUAGGCCGAA ACCAUUUG | 11837 |
| 1404 | AGGCCCAUU GAGUCCAA | 2420 | UUGGACUC CUGAUGAGGCCGUUAGGCCGAA AUGGGCCU | 11838 |
| 1409 | CAUUGAGUC CAACUACA | 2421 | UGUAGUUG CUGAUGAGGCCGUUAGGCCGAA ACUCAAUG | 11839 |
| 1415 | GUCCAACUA CACAAUGA | 2422 | UCAUUGUG CUGAUGAGGCCGUUAGGCCGAA AGUUGGAC | 11840 |
| 1425 | ACAAUGAUU GUUGGCGA | 2423 | UCGCCAAC CUGAUGAGGCCGUUAGGCCGAA AUCAUUGU | 11841 |
| 1428 | AUGAUUGUU GGCGAUGA | 2424 | UCAUCGCC CUGAUGAGGCCGUUAGGCCGAA ACAAUCAU | 11842 |
| 1440 | GAUGAACUC ACCAUCAU | 2425 | AUGAUGGU CUGAUGAGGCCGUUAGGCCGAA AGUUCAUC | 11843 |
| 1446 | CUCACCAUC AUGGAAGU | 2426 | ACUUCCAU CUGAUGAGGCCGUUAGGCCGAA AUGGUGAG | 11844 |
| 1478 | AGGAAACUA CACGGUCA | 2427 | UGACCGUG CUGAUGAGGCCGUUAGGCCGAA AGUUUCCU | 11845 |
| 1485 | UACACGGUC AUCCUCAC | 2428 | GUGAGGAU CUGAUGAGGCCGUUAGGCCGAA ACCGUGUA | 11846 |
| 1488 | ACGGUCAUC CUCACCAA | 2429 | UUGGUGAG CUGAUGAGGCCGUUAGGCCGAA AUGACCGU | 11847 |
| 1491 | GUCAUCCUC ACCAACCC | 2430 | GGGUUGGU CUGAUGAGGCCGUUAGGCCGAA AGGAUGAC | 11848 |
| 1503 | AACCCCAUU UCAAUGGA | 2431 | UCCAUUGA CUGAUGAGGCCGUUAGGCCGAA AUGGGGUU | 11849 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 1504 | ACCCCAUUU CAAUGGAG | 2432 | CUCCAUUG CUGAUGAGGCCGUUAGGCCGAA AAUGGGGU | 11850 |
| 1505 | CCCCAUUUC AAUGGAGA | 2433 | UCUCCAUU CUGAUGAGGCCGUUAGGCCGAA AAAUGGGG | 11851 |
| 1530 | CACAUGGUC UCUCUGGU | 2434 | ACCAGAGA CUGAUGAGGCCGUUAGGCCGAA ACCAUGUG | 11852 |
| 1532 | CAUGGUCUC UCUGGUUG | 2435 | CAACCAGA CUGAUGAGGCCGUUAGGCCGAA AGACCAUG | 11853 |
| 1534 | UGGUCUCUC UGGUUGUG | 1714 | CACAACCA CUGAUGAGGCCGUUAGGCCGAA AGAGACCA | 11133 |
| 1539 | UCUCUGGUU GUGAAUGU | 2436 | ACAUUCAC CUGAUGAGGCCGUUAGGCCGAA ACCAGAGA | 11854 |
| 1548 | GUGAAUGUC CCACCCCA | 2437 | UGGGGUGG CUGAUGAGGCCGUUAGGCCGAA ACAUUCAC | 11855 |
| 1560 | CCCCAGAUC GGUGAGAA | 2438 | UUCUCACC CUGAUGAGGCCGUUAGGCCGAA AUCUGGGG | 11137 |
| 1574 | GAAAGCCUU GAUCUCGC | 2439 | GCGAGAUC CUGAUGAGGCCGUUAGGCCGAA AGGCUUUC | 11856 |
| 1578 | GCCUUGAUC UCGCCUAU | 2440 | AUAGGCGA CUGAUGAGGCCGUUAGGCCGAA AUCAAGGC | 11857 |
| 1580 | CUUGAUCUC GCCUAUGG | 2441 | CCAUAGGC CUGAUGAGGCCGUUAGGCCGAA AGAUCAAG | 11858 |
| 1585 | UCUCGCCUA UGGAUUCC | 2442 | GGAAUCCA CUGAUGAGGCCGUUAGGCCGAA AGGCGAGA | 11859 |
| 1591 | CUAUGGAUU CCUACCAG | 2443 | CUGGUAGG CUGAUGAGGCCGUUAGGCCGAA AUCCAUAG | 11860 |
| 1592 | UAUGGAUUC CUACCAGU | 2444 | ACUGGUAG CUGAUGAGGCCGUUAGGCCGAA AAUCCAUA | 11861 |
| 1595 | GGAUUCCUA CCAGUAUG | 2445 | CAUACUGG CUGAUGAGGCCGUUAGGCCGAA AGGAAUCC | 11862 |
| 1601 | CUACCAGUA UGGGACCA | 2446 | UGGUCCCA CUGAUGAGGCCGUUAGGCCGAA ACUGGUAG | 11863 |
| 1619 | GCAGACAUU GACAUGCA | 2447 | UGCAUGUC CUGAUGAGGCCGUUAGGCCGAA AUGUCUGC | 11864 |
| 1632 | UCCACAGUC UACGCCAA | 2448 | UUGGCGUA CUGAUGAGGCCGUUAGGCCGAA ACUGUGGA | 11865 |
| 1634 | CACAGUCUA CGCCAACC | 2449 | GGUUGGCG CUGAUGAGGCCGUUAGGCCGAA AGACUGUG | 11866 |
| 1645 | CCAACCCUC CCCUGCAC | 2450 | GUGCAGGG CUGAUGAGGCCGUUAGGCCGAA AGGGUUGG | 11867 |
| 1659 | CACCACAUC CAGUGGUA | 2451 | UACCACUG CUGAUGAGGCCGUUAGGCCGAA AUGUGGUG | 11868 |
| 1667 | CCAGUGGUA CUGGCAGC | 2452 | GCUGCCAG CUGAUGAGGCCGUUAGGCCGAA ACCACUGG | 11869 |
| 1677 | UGGCAGCUA AAGAAGC | 2453 | GCUUCUUC CUGAUGAGGCCGUUAGGCCGAA AGCUGCCA | 11870 |
| 1691 | AGCCUGCUC CUACAGAC | 2454 | GUCUGUAG CUGAUGAGGCCGUUAGGCCGAA AGCAGGCU | 11871 |
| 1694 | CUGCUCCUA CAGACCCG | 2455 | CGGGUCUG CUGAUGAGGCCGUUAGGCCGAA AGGAGCAG | 11872 |
| 1718 | AAGCCCGUA UGCUUGUA | 2456 | UACAAGCA CUGAUGAGGCCGUUAGGCCGAA ACGGGCUU | 11873 |
| 1723 | CGUAUGCUU GUAAAGAA | 2457 | UUCUUUAC CUGAUGAGGCCGUUAGGCCGAA AGCAUACG | 11874 |
| 1726 | AUGCUUGUA AGAAUGG | 2458 | CCAUUCUU CUGAUGAGGCCGUUAGGCCGAA ACAAGCAU | 11875 |
| 1750 | UGGAGGAUU UCCAGGGG | 2459 | CCCCUGGA CUGAUGAGGCCGUUAGGCCGAA AUCCUCCA | 11876 |
| 1751 | GGAGGAUUU CCAGGGGG | 2460 | CCCCCUGG CUGAUGAGGCCGUUAGGCCGAA AAUCCUCC | 11877 |
| 1752 | GAGGAUUUC CAGGGGGU | 2461 | CCCCCCUG CUGAUGAGGCCGUUAGGCCGAA AAAUCCUC | 11878 |
| 1770 | AACAAGAUC GAAGUCAC | 2462 | GUGACUUC CUGAUGAGGCCGUUAGGCCGAA AUCUUGUU | 11879 |
| 1776 | AUCGAAGUC ACCAAAAA | 2463 | UUUUUGGU CUGAUGAGGCCGUUAGGCCGAA ACUUCGAU | 11880 |
| 1790 | AAACCAAUA UGCCCUGA | 2464 | UCAGGGCA CUGAUGAGGCCGUUAGGCCGAA AUUGGUUU | 11881 |
| 1800 | GCCCUGAUU GAAGGAAA | 2465 | UUUCCUUC CUGAUGAGGCCGUUAGGCCGAA AUCAGGGC | 11882 |
| 1821 | AAAACUGUA AGUACGCU | 2466 | AGCGUACU CUGAUGAGGCCGUUAGGCCGAA ACAGUUUU | 11883 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 1825 | CUGUAAGUA CGCUGGUC | 2467 | GACCAGCG CUGAUGAGGCCGUUAGGCCGAA ACUUACAG | 11884 |
| 1833 | ACGCUGGUC AUCCAAGC | 2468 | GCUUGGAU CUGAUGAGGCCGUUAGGCCGAA ACCAGCGU | 11885 |
| 1836 | CUGGUCAUC CAAGCUGC | 2469 | GCAGCUUG CUGAUGAGGCCGUUAGGCCGAA AUGACCAG | 11886 |
| 1853 | CAACGUGUC AGCGUUGU | 2470 | ACAACGCU CUGAUGAGGCCGUUAGGCCGAA ACACGUUG | 11887 |
| 1859 | GUCAGCGUU GUACAAAU | 2471 | AUUUGUAC CUGAUGAGGCCGUUAGGCCGAA ACGCUGAC | 11888 |
| 1862 | AGCGUUGUA CAAAUGUG | 2472 | CACAUUUG CUGAUGAGGCCGUUAGGCCGAA ACAACGCU | 11889 |
| 1878 | GAAGCCAUC AACAAAGC | 2473 | GCUUUGUU CUGAUGAGGCCGUUAGGCCGAA AUGGCUUC | 11890 |
| 1905 | GAGAGGGUC AUCUCCUU | 2474 | AAGGAGAU CUGAUGAGGCCGUUAGGCCGAA ACCCUCUC | 11891 |
| 1908 | AGGGUCAUC UCCUUCCA | 2475 | UGGAAGGA CUGAUGAGGCCGUUAGGCCGAA AUGACCCU | 11892 |
| 1910 | GGUCAUCUC CUUCCAUG | 2476 | CAUGGAAG CUGAUGAGGCCGUUAGGCCGAA AGAUGACC | 11893 |
| 1913 | CAUCUCCUU CCAUGUGA | 2477 | UCACAUGG CUGAUGAGGCCGUUAGGCCGAA AGGAGAUG | 11894 |
| 1914 | AUCUCCUUC CAUGUGAU | 2478 | AUCACAUG CUGAUGAGGCCGUUAGGCCGAA AAGGAGAU | 11895 |
| 1923 | CAUGUGAUC AGGGUCC | 2479 | GGACCCCU CUGAUGAGGCCGUUAGGCCGAA AUCACAUG | 11896 |
| 1930 | UCAGGGGUC UGAAAUU | 2480 | AAUUUCAG CUGAUGAGGCCGUUAGGCCGAA ACCCCUGA | 11897 |
| 1938 | CCUGAAAUU ACUGUGCA | 2481 | UGCACAGU CUGAUGAGGCCGUUAGGCCGAA AUUUCAGG | 11898 |
| 1939 | CUGAAAUUA CUGUGCAA | 2482 | UUGCACAG CUGAUGAGGCCGUUAGGCCGAA AAUUUCAG | 11899 |
| 1982 | GAGUGUGUC CUGUUUGU | 2483 | ACAACAGG CUGAUGAGGCCGUUAGGCCGAA ACACACUC | 11900 |
| 1988 | GUCCCUGUU GUGCACUG | 2484 | CAGUGCAC CUGAUGAGGCCGUUAGGCCGAA ACAGGGAC | 11901 |
| 2008 | ACAGAAAUA CGUUUGAG | 2485 | CUCAAACG CUGAUGAGGCCGUUAGGCCGAA AUUUCUGU | 11902 |
| 2012 | AAAUACGUU UGAGAACC | 2486 | GGUUCUCA CUGAUGAGGCCGUUAGGCCGAA ACGUAUUU | 11903 |
| 2013 | AAUACGUUU GAGAACCU | 2487 | AGGUUCUC CUGAUGAGGCCGUUAGGCCGAA AACGUAUU | 11904 |
| 2022 | GAGAACCUC ACGUGGUA | 2488 | UACCACGU CUGAUGAGGCCGUUAGGCCGAA AGGUUCUC | 11905 |
| 2030 | CACGUGGUA CAAGCUUG | 2489 | CAAGCUUG CUGAUGAGGCCGUUAGGCCGAA ACCACGUG | 11906 |
| 2037 | UACAAGCUU GGCUCACA | 2490 | UGUGAGCC CUGAUGAGGCCGUUAGGCCGAA AGCUUGUA | 11907 |
| 2042 | GCUUGGCUC ACAGGCAA | 2491 | UUGCCUGU CUGAUGAGGCCGUUAGGCCGAA AGCCAAGC | 11908 |
| 2054 | GGCAACAUC GGUCCACA | 2492 | UGUGGACC CUGAUGAGGCCGUUAGGCCGAA AUGUUGCC | 11909 |
| 2058 | ACAUCGGUC CACAUGGG | 2493 | CCCAUGUG CUGAUGAGGCCGUUAGGCCGAA ACCGAUGU | 11910 |
| 2072 | GGGCGAAUC ACUCACAC | 2494 | GUGUGAGU CUGAUGAGGCCGUUAGGCCGAA AUUCGCCC | 11911 |
| 2076 | GAAUCACUC ACACCAGU | 2495 | ACUGGUGU CUGAUGAGGCCGUUAGGCCGAA AGUGAUUC | 11912 |
| 2085 | ACACCAGUU UGCAAGAA | 2496 | UUCUUGCA CUGAUGAGGCCGUUAGGCCGAA ACUGGUGU | 11913 |
| 2086 | CACCAGUUU GCAAGAAC | 2497 | GUUCUUGC CUGAUGAGGCCGUUAGGCCGAA AACUGGUG | 11914 |
| 2096 | CAAGAACUU GGAUGCUC | 2498 | GAGCAUCC CUGAUGAGGCCGUUAGGCCGAA AGUUCUUG | 11915 |
| 2104 | UGGAUGCUC UUUGGAAA | 2499 | UUUCCAAA CUGAUGAGGCCGUUAGGCCGAA AGCAUCCA | 11916 |
| 2106 | GAUGCUCUU UGGAAACU | 2500 | AGUUUCCA CUGAUGAGGCCGUUAGGCCGAA AGACCAUC | 11917 |
| 2107 | AUGCUCUUU GGAAACUG | 2501 | CAGUUUCC CUGAUGAGGCCGUUAGGCCGAA AAGAGCAU | 11918 |
| 2129 | CACCAUGUU UUCUAACA | 2502 | UGUUAGAA CUGAUGAGGCCGUUAGGCCGAA ACAUGGUG | 11919 |
| 2130 | ACCAUGUUU UCUAACAG | 2503 | CUGUUAGA CUGAUGAGGCCGUUAGGCCGAA AACAUGGU | 11920 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 2131 | CCAUGUUUU CUAACAGC | 2504 | GCUGUUAG CUGAUGAGGCCGUUAGGCCGAA AAACAUGG | 11921 |
| 2132 | CAUGUUUUC UAACAGCA | 2505 | UGCUGUUA CUGAUGAGGCCGUUAGGCCGAA AAAACAUG | 11922 |
| 2134 | UGUUUUCUA ACAGCACA | 2506 | UGUGCUGU CUGAUGAGGCCGUUAGGCCGAA AGAAAACA | 11923 |
| 2151 | AAUGACAUC UUGAUUGU | 2507 | ACAAUCAA CUGAUGAGGCCGUUAGGCCGAA AUGUCAUU | 11924 |
| 2153 | UGACAUCUU GAUUGUGG | 2508 | CCACAAUC CUGAUGAGGCCGUUAGGCCGAA AGAUGUCA | 11925 |
| 2157 | AUCUUGAUU GUGGCAUU | 2509 | AAUGCCAC CUGAUGAGGCCGUUAGGCCGAA AUCAAGAU | 11926 |
| 2165 | UGUGGCAUU UCAGAAUG | 2510 | CAUUCUGA CUGAUGAGGCCGUUAGGCCGAA AUGCCACA | 11927 |
| 2166 | GUGGCAUUU CAGAAUGC | 2511 | GCAUUCUG CUGAUGAGGCCGUUAGGCCGAA AAUGCCAC | 11928 |
| 2167 | UGGCAUUUC AGAAUGCC | 2512 | GGCAUUCU CUGAUGAGGCCGUUAGGCCGAA AAAUGCCA | 11929 |
| 2177 | GAAUGCCUC UCUGCAGG | 2513 | CCUGCAGA CUGAUGAGGCCGUUAGGCCGAA AGGCAUUC | 11930 |
| 2179 | AUGCCUCUC UGCAGGAC | 2514 | GUCCUGCA CUGAUGAGGCCGUUAGGCCGAA AGAGGCAU | 11931 |
| 2198 | AGGCGACUA UGUUUGCU | 2515 | AGCAAACA CUGAUGAGGCCGUUAGGCCGAA AGUCGCCU | 11932 |
| 2202 | GACUAUGUU UGCUCUGC | 2516 | GCAGAGCA CUGAUGAGGCCGUUAGGCCGAA ACAUAGUC | 11933 |
| 2203 | ACUAUGUUU GCUCUGCU | 2517 | AGCAGAGC CUGAUGAGGCCGUUAGGCCGAA AACAUAGU | 11934 |
| 2207 | UGUUUGCUC UGCUCAAG | 2518 | CUUGAGCA CUGAUGAGGCCGUUAGGCCGAA AGCAAACA | 11935 |
| 2212 | GCUCUGCUC AAGAUAAG | 2519 | CUUAUCUU CUGAUGAGGCCGUUAGGCCGAA AGCAGAGC | 11936 |
| 2218 | CUCAAGAUA AGAAGACC | 2520 | GGUCUUCU CUGAUGAGGCCGUUAGGCCGAA AUCUUGAG | 11937 |
| 2239 | AAAGACAUU GCCUGGUC | 2521 | GACCAGGC CUGAUGAGGCCGUUAGGCCGAA AUGUCUUU | 11938 |
| 2247 | UGCCUGGUC AAACAGCU | 2522 | AGCUGUUU CUGAUGAGGCCGUUAGGCCGAA ACCAGGCA | 11939 |
| 2256 | AAACAGCUC AUCAUCCU | 2523 | AGGAUGAU CUGAUGAGGCCGUUAGGCCGAA AGCUGUUU | 11940 |
| 2259 | CAGCUCAUC AUCCUAGA | 2524 | UCUAGGAU CUGAUGAGGCCGUUAGGCCGAA AUGAGCUG | 11941 |
| 2262 | CUCAUCAUC CUAGAGCG | 2525 | CGCUCUAG CUGAUGAGGCCGUUAGGCCGAA AUGAUGAG | 11942 |
| 2265 | AUCAUCCUA GAGCGCAU | 2526 | AUGCGCUC CUGAUGAGGCCGUUAGGCCGAA AGGAUGAU | 11943 |
| 2286 | CCCAUGAUC ACCGGAAA | 2527 | UUUCCGGU CUGAUGAGGCCGUUAGGCCGAA AUCAUGGG | 11944 |
| 2296 | CCGGAAAUC UGGAGAAU | 2528 | AUUCUCCA CUGAUGAGGCCGUUAGGCCGAA AUUUCCGG | 11945 |
| 2305 | UGGAGAAUC AGACAACA | 2529 | UGUUGUCU CUGAUGAGGCCGUUAGGCCGAA AUUCUCCA | 11946 |
| 2319 | ACAACCAUU GGCGAGAC | 2530 | GUCUCGCC CUGAUGAGGCCGUUAGGCCGAA AUGGUUGU | 11947 |
| 2331 | GAGACCAUU GAAGUGAC | 2531 | GUCACUUC CUGAUGAGGCCGUUAGGCCGAA AUGGUCUC | 11948 |
| 2341 | AAGUGACUU GCCCAGCA | 2532 | UGCUGGGC CUGAUGAGGCCGUUAGGCCGAA AGUCACUU | 11949 |
| 2351 | CCCAGCAUC UGGAAAUC | 2533 | GAUUUCCA CUGAUGAGGCCGUUAGGCCGAA AUGCUGGG | 11950 |
| 2359 | CUGGAAAUC UACCCCA | 2534 | UGGGGUAG CUGAUGAGGCCGUUAGGCCGAA AUUUCCAG | 11951 |
| 2362 | GAAAUCCUA CCCCACAC | 2535 | GUGUGGGG CUGAUGAGGCCGUUAGGCCGAA AGGAUUUC | 11952 |
| 2373 | CCACACAUU ACAUGGUU | 2536 | AACCAUGU CUGAUGAGGCCGUUAGGCCGAA AUGUGUGG | 11953 |
| 2374 | CACACAUUA CAUGGUUC | 2537 | GAACCAUG CUGAUGAGGCCGUUAGGCCGAA AAUGUGUG | 11954 |
| 2381 | UACAUGGUU CAAAGACA | 2538 | UGUCUUUG CUGAUGAGGCCGUUAGGCCGAA ACCAUGUA | 11955 |
| 2382 | ACAUGGUUC AAAGACAA | 2539 | UUGUCUUU CUGAUGAGGCCGUUAGGCCGAA AACCAUGU | 11956 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 2403 | ACCCUGGUA GAAGAUUC | 2540 | GAAUCUUC CUGAUGAGGCCGUUAGGCCGAA ACCAGGGU | 11957 |
| 2410 | UAGAAGAUU CAGGCAUU | 2541 | AAUGCCUG CUGAUGAGGCCGUUAGGCCGAA AUCUUCUA | 11958 |
| 2411 | AGAAGAUUC AGGCAUUG | 2542 | CAAUGCCU CUGAUGAGGCCGUUAGGCCGAA AAUCUUCU | 11959 |
| 2418 | UCAGGCAUU GUACUGAG | 2543 | CUCAGUAC CUGAUGAGGCCGUUAGGCCGAA AUGCCUGA | 11960 |
| 2421 | GGCAUUGUA CUGAGAGA | 2544 | UCUCUCAG CUGAUGAGGCCGUUAGGCCGAA ACAAUGCC | 11961 |
| 2449 | ACCUGACUA UCCGCAGG | 2545 | CCUGCGGA CUGAUGAGGCCGUUAGGCCGAA AGUCAGGU | 11962 |
| 2451 | CUGACUAUC CGCAGGGU | 2546 | ACCCUGCG CUGAUGAGGCCGUUAGGCCGAA AUAGUCAG | 11963 |
| 2481 | GGAGGCCUC UACACCUG | 2547 | CAGGUGUA CUGAUGAGGCCGUUAGGCCGAA AGGCCUCC | 11964 |
| 2483 | AGGCCUCUA CACCUGCC | 1847 | GGCAGGUG CUGAUGAGGCCGUUAGGCCGAA AGAGGCCU | 11266 |
| 2505 | UGCAAUGUC CUUGGCUG | 2548 | CAGCCAAG CUGAUGAGGCCGUUAGGCCGAA ACAUUGCA | 11965 |
| 2508 | AAUGUCCUU GGCUGUGC | 2549 | GCACAGCC CUGAUGAGGCCGUUAGGCCGAA AGGACAUU | 11966 |
| 2532 | GAGACGCUC UUCAUAAU | 2550 | AUUAUGAA CUGAUGAGGCCGUUAGGCCGAA AGCGUCUC | 11967 |
| 2534 | GACGCUCUU CAUAAUAG | 2551 | CUAUUAUG CUGAUGAGGCCGUUAGGCCGAA AGAGCGUC | 11968 |
| 2535 | ACGCUCUUC AUAAUAGA | 2552 | UCUAUUAU CUGAUGAGGCCGUUAGGCCGAA AAGAGCGU | 11969 |
| 2538 | CUCUUCAUA AUAGAAGG | 2553 | CCUUCUAU CUGAUGAGGCCGUUAGGCCGAA AUGAAGAG | 11970 |
| 2541 | UUCAUAAUA GAAGGUGC | 1857 | GCACCUUC CUGAUGAGGCCGUUAGGCCGAA AUUAUGAA | 11276 |
| 2567 | GACCAACUU GGAAGUCA | 2554 | UGACUUCC CUGAUGAGGCCGUUAGGCCGAA AGUUGGUC | 11971 |
| 2574 | UUGGAAGUC AUUAUCCU | 2555 | AGGAUAAU CUGAUGAGGCCGUUAGGCCGAA ACUUCCAA | 11972 |
| 2577 | GAAGUCAUU AUCCUCGU | 2556 | ACGAGGAU CUGAUGAGGCCGUUAGGCCGAA AUGACUUC | 11973 |
| 2578 | AAGUCAUUA UCCUCGUC | 2557 | GACGAGGA CUGAUGAGGCCGUUAGGCCGAA AAUGACUU | 11974 |
| 2580 | GUCAUUAUC CUCGUCGG | 2558 | CCGACGAG CUGAUGAGGCCGUUAGGCCGAA AUAAUGAC | 11975 |
| 2583 | AUUAUCCUC GUCGGCAC | 2559 | GUGCCGAC CUGAUGAGGCCGUUAGGCCGAA AGGAUAAU | 11976 |
| 2586 | AUCCUCGUC GGCACUGC | 2560 | GCAGUGCC CUGAUGAGGCCGUCAGGCCGAA ACGAGGAU | 11977 |
| 2601 | GCAGUGAUU GCCAUGUU | 2561 | AACAUGGC CUGAUGAGGCCGUUAGGCCGAA AUCACUGC | 11978 |
| 2609 | UGCCAUGUU CUUCUGGC | 1867 | GCCAGAAG CUGAUGAGGCCGUUAGGCCGAA ACAUGGCA | 11286 |
| 2610 | GCCAUGUUC UUCUGGCU | 1868 | AGCCAGAA CUGAUGAGGCCGUUAGGCCGAA AACAUGGC | 11287 |
| 2612 | CAUGUUCUU CUGGCUCC | 2562 | GGAGCCAG CUGAUGAGGCCGUUAGGCCGAA AGAACAUG | 11979 |
| 2613 | AUGUUCUUC UGGCUCCU | 2563 | AGGAGCCA CUGAUGAGGCCGUUAGGCCGAA AAGAACAU | 11980 |
| 2619 | UUCUGGCUC CUUCUUGU | 2564 | ACAAGAAG CUGAUGAGGCCGUUAGGCCGAA AGCCAGAA | 11290 |
| 2622 | UGGCUCCUU CUUGUCAU | 2565 | AUGACAAG CUGAUGAGGCCGUUAGGCCGAA AGGAGCCA | 11981 |
| 2623 | GGCUCCUUC UUGUCAUU | 2566 | AAUGACAA CUGAUGAGGCCGUUAGGCCGAA AAGGAGCC | 11982 |
| 2625 | CUCCUUCUU GUCAUUGU | 2567 | ACAAUGAC CUGAUGAGGCCGUUAGGCCGAA AGAAGGAG | 11983 |
| 2628 | CUUCUUGUC AUUGUCCU | 2568 | AGGACAAU CUGAUGAGGCCGUUAGGCCGAA ACAAGAAG | 11984 |
| 2631 | CUUGUCAUU GUCCUACG | 2569 | CGUAGGAC CUGAUGAGGCCGUUAGGCCGAA AUGACAAG | 11985 |
| 2634 | GUCAUUGUC CUACGGAC | 2570 | GUCCGUAG CUGAUGAGGCCGUUAGGCCGAA ACAAUGAC | 11986 |
| 2637 | AUUGUCCUA CGGACCGU | 2571 | ACGGUCCG CUGAUGAGGCCGUUAGGCCGAA AGGACAAU | 11987 |
| 2646 | CGGACCGUU AAGCGGGC | 2572 | GCCCGCUU CUGAUGAGGCCGUUAGGCCGAA ACGGUCCG | 11988 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 2647 | GGACCGUUA AGCGGGCC | 1880 | GGCCCGCU CUGAUGAGGCCGUUAGGCCGAA AACGGUCC | 11299 |
| 2681 | GACAGGCUA CUUGUCUA | 2573 | UAGACAAG CUGAUGAGGCCGUUAGGCCGAA AGCCUGUC | 11989 |
| 2684 | AGGCUACUU GUCUAUUG | 2574 | CAAUAGAC CUGAUGAGGCCGUUAGGCCGAA AGUAGCCU | 11990 |
| 2687 | CUACUUGUC UAUUGUCA | 2575 | UGACAAUA CUGAUGAGGCCGUUAGGCCGAA ACAAGUAG | 11991 |
| 2689 | ACUUGUCUA UUGUCAUG | 2576 | CAUGACAA CUGAUGAGGCCGUUAGGCCGAA AGACAAGU | 11992 |
| 2691 | UUGUCUAUU GUCAUGGA | 2577 | UCCAUGAC CUGAUGAGGCCGUUAGGCCGAA AUAGACAA | 11993 |
| 2694 | UCUAUUGUC AUGGAUCC | 2578 | GGAUCCAU CUGAUGAGGCCGUUAGGCCGAA ACAAUAGA | 11994 |
| 2701 | UCAUGGAUC CAGAUGAA | 1886 | UUCAUCUG CUGAUGAGGCCGUUAGGCCGAA AUCCAUGA | 11305 |
| 2711 | AGAUGAAUU GCCCUUGG | 2579 | CCAAGGGC CUGAUGAGGCCGUUAGGCCGAA AUUCAUCU | 11995 |
| 2717 | AUUGCCCUU GGAUGAGC | 2580 | GCUCAUCC CUGAUGAGGCCGUUAGGCCGAA AGGGCAAU | 11996 |
| 2738 | UGAACGCUU GCCUUAUG | 2581 | CAUAAGGC CUGAUGAGGCCGUUAGGCCGAA AGCGUUCA | 11997 |
| 2743 | GCUUGCCUU AUGAUGCC | 2582 | GGCAUCAU CUGAUGAGGCCGUUAGGCCGAA AGGCAAGC | 11998 |
| 2744 | CUUGCCUUA UGAUGCCA | 2583 | UGGCAUCA CUGAUGAGGCCGUUAGGCCGAA AAGGCAAG | 11999 |
| 2765 | GUGGGAAUU CCCCAGGG | 2584 | CCCUGGGG CUGAUGAGGCCGUUAGGCCGAA AUUCCCAC | 12000 |
| 2766 | UGGGAAUUC CCCAGGGA | 2585 | UCCCUGGG CUGAUGAGGCCGUUAGGCCGAA AAUUCCCA | 12001 |
| 2787 | CUGAAACUA GGAAAACC | 2586 | GGUUUUCC CUGAUGAGGCCGUUAGGCCGAA AGUUUCAG | 12002 |
| 2797 | GAAAACCUC UUGGCCGC | 2587 | GCGGCCAA CUGAUGAGGCCGUUAGGCCGAA AGGUUUUC | 12003 |
| 2799 | AAACCUCUU GGCCGCGG | 2588 | CCGCGGCC CUGAUGAGGCCGUUAGGCCGAA AGAGGUUU | 12004 |
| 2813 | CGGUGCCUU CGGCCAAG | 2589 | CUUGGCCG CUGAUGAGGCCGUUAGGCCGAA AGGCACCG | 12005 |
| 2814 | GGUGCCUUC GGCCAAGU | 2590 | ACUUGGCC CUGAUGAGGCCGUUAGGCCGAA AAGGCACC | 12006 |
| 2826 | CAAGUGAUU GAGGCAGA | 2591 | UCUGCCUC CUGAUGAGGCCGUUAGGCCGAA AUCACUUG | 12007 |
| 2839 | CAGACGCUU UUGGAAUU | 2592 | AAUUCCAA CUGAUGAGGCCGUUAGGCCGAA AGCGUCUG | 12008 |
| 2840 | AGACGCUUU UGGAAUUG | 2593 | CAAUUCCA CUGAUGAGGCCGUUAGGCCGAA AAGCGUCU | 12009 |
| 2841 | GACGCUUUU GGAAUUGA | 2594 | UCAAUUCC CUGAUGAGGCCGUUAGGCCGAA AAAGCGUC | 12010 |
| 2847 | UUUGGAAUU GACAAGAC | 1903 | GUCUUGUC CUGAUGAGGCCGUUAGGCCGAA AUUCCAAA | 11322 |
| 2863 | CAGCGACUU GCAAAACA | 2595 | UGUUUUGC CUGAUGAGGCCGUUAGGCCGAA AGUCGCUG | 12011 |
| 2874 | AAAACAGUA GCCGUCAA | 2596 | UUGACGGC CUGAUGAGGCCGUUAGGCCGAA ACUGUUUU | 12012 |
| 2880 | GUAGCCGUC AAGAUGUU | 2597 | AACAUCUU CUGAUGAGGCCGUUAGGCCGAA ACGGCUAC | 12013 |
| 2888 | CAAGAUGUU GAAAGAAG | 2598 | CUUCUUUC CUGAUGAGGCCGUUAGGCCGAA ACAUCUUG | 12014 |
| 2917 | GCGAGCAUC GAGCCCUC | 2599 | GAGGGCUC CUGAUGAGGCCGUUAGGCCGAA AUGCUCGC | 12015 |
| 2925 | CGAGCCCUC AUGUCUGA | 2600 | UCAGACAU CUGAUGAGGCCGUUAGGCCGAA AGGGCUCG | 12016 |
| 2930 | CCUCAUGUC UGAACUCA | 2601 | UGAGUUCA CUGAUGAGGCCGUUAGGCCGAA ACAUGAGG | 12017 |
| 2937 | UCUGAACUC AAGAUCCU | 1912 | AGGAUCUU CUGAUGAGGCCGUUAGGCCGAA AGUUCAGA | 11331 |
| 2943 | CUCAAGAUC CUCAUCCA | 2602 | UGGAUGAG CUGAUGAGGCCGUUAGGCCGAA AUCUUGAG | 12018 |
| 2946 | AAGAUCCUC AUCCACAU | 2603 | AUGUGGAU CUGAUGAGGCCGUUAGGCCGAA AGGAUCUU | 12019 |
| 2949 | AUCCUCAUC CACAUUGG | 2604 | CCAAUGUG CUGAUGAGGCCGUUAGGCCGAA AUGAGGAU | 12020 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 2955 | AUCCACAUU GGUCACCA | 2605 | UGGUGACC CUGAUGAGGCCGUUAGGCCGAA AUGUGGAU | 12021 |
| 2959 | ACAUUGGUC ACCAUCUC | 2606 | GAGAUGGU CUGAUGAGGCCGUUAGGCCGAA ACCAAUGU | 12022 |
| 2965 | GUCACCAUC UCAAUGUG | 1920 | CACAUUGA CUGAUGAGGCCGUUAGGCCGAA AUGGUGAC | 11339 |
| 2967 | CACCAUCUC AAUGUGGU | 1921 | ACCACAUU CUGAUGAGGCCGUUAGGCCGAA AGAUGGUG | 11340 |
| 2982 | GUGAACCUC CUAGGCGC | 2607 | GCGCCUAG CUGAUGAGGCCGUUAGGCCGAA AGGUUCAC | 12023 |
| 2985 | AACCUCCUA GGCGCCUG | 2808 | CAGGCGCC CUGAUGAGGCCGUUAGGCCGAA AGGAGGUU | 12024 |
| 3013 | GAGGGCCUC UCAUGGUG | 2609 | CACCAUGA CUGAUGAGGCCGUUAGGCCGAA AGGCCCUC | 12025 |
| 3015 | GGGCCUCUC AUGGUGAU | 2610 | AUCACCAU CUGAUGAGGCCGUUAGGCCGAA AGAGGCCC | 12026 |
| 3024 | AUGGUGAUU GUGGAAUU | 1928 | AAUUCCAC CUGAUGAGGCCGUUAGGCCGAA AUCACCAU | 11347 |
| 3032 | UGUGGAAUU CUGCAAGU | 2611 | ACUUGCAG CUGAUGAGGCCGUUAGGCCGAA AUUCCACA | 12027 |
| 3033 | GUGGAAUUC UGCAAGUU | 2612 | AACUUGCA CUGAUGAGGCCGUUAGGCCGAA AAUUCCAC | 12028 |
| 3041 | CUGCAAGUU UGGAAACC | 2613 | GGUUUCCA CUGAUGAGGCCGUUAGGCCGAA ACUUGCAG | 12029 |
| 3042 | UGCAAGUUU GGAAACCU | 2614 | AGGUUUCC CUGAUGAGGCCGUUAGGCCGAA AACUUGCA | 12030 |
| 3051 | GGAAACCUA UCAACUUA | 2615 | UAAGUUGA CUGAUGAGGCCGUUAGGCCGAA AGGUUUCC | 12031 |
| 3053 | AAACCUAUC AACUUACU | 2616 | AGUAAGUU CUGAUGAGGCCGUUAGGCCGAA AUAGGUUU | 12032 |
| 3058 | UAUCAACUU ACUUACGG | 2617 | CCGUAAGU CUGAUGAGGCCGUUAGGCCGAA AGUUGAUA | 12033 |
| 3059 | AUCAACUUA CUUACGGG | 2618 | CCCGUAAG CUGAUGAGGCCGUUAGGCCGAA AAGUUGAU | 12034 |
| 3062 | AACUUACUU ACGGGCA | 2619 | UGCCCCGU CUGAUGAGGCCGUUAGGCCGAA AGUAAGUU | 12035 |
| 3063 | ACUUACUUA CGGGCAA | 2620 | UUGCCCCG CUGAUGAGGCCGUUAGGCCGAA AAGUAAGU | 12036 |
| 3083 | AAAUGAAUU GUUCCCU | 2621 | AGGGAACA CUGAUGAGGCCGUUAGGCCGAA AUUCAUUU | 12037 |
| 3084 | AAUGAAUUU GUUCCUA | 2622 | UAGGGAAC CUGAUGAGGCCGUUAGGCCGAA AAUUCAUU | 12038 |
| 3087 | GAAUUUGUU CCUAUAA | 2623 | UUAUAGGG CUGAUGAGGCCGUUAGGCCGAA ACAAAUUC | 12039 |
| 3088 | AAUUUGUUC CUAUAAG | 2624 | CUUAUAGG CUGAUGAGGCCGUUAGGCCGAA AACAAAUU | 12040 |
| 3092 | UGUUCCCUA UAAGCA | 2625 | UGCUCUUA CUGAUGAGGCCGUUAGGCCGAA AGGGAACA | 12041 |
| 3094 | UUCCCUAUA AGAGCAAA | 2626 | UUUGCUCU CUGAUGAGGCCGUUAGGCCGAA AUAGGGAA | 12042 |
| 3113 | GGCACGCUU CCGCCAGG | 2627 | CCUGGCGG CUGAUGAGGCCGUUAGGCCGAA AGCGUGCC | 12043 |
| 3114 | GCACGCUUC CGCCAGGG | 2628 | CCCUGGCG CUGAUGAGGCCGUUAGGCCGAA AAGCGUGC | 12044 |
| 3131 | CAAGGACUA CGUUGGGG | 2629 | CCCCAACG CUGAUGAGGCCGUUAGGCCGAA AGUCCUUG | 12045 |
| 3135 | GACUACGUU GGGGAGCU | 2630 | AGCUCCCC CUGAUGAGGCCGUUAGGCCGAA ACGUAGUC | 12046 |
| 3144 | GGGGAGCUC UCCGUGGA | 2631 | UCCACGGA CUGAUGAGGCCGUUAGGCCGAA AGCUCCCC | 12047 |
| 3146 | GGAGCUCUC CGUGGAUC | 2632 | GAUCCACG CUGAUGAGGCCGUUAGGCCGAA AGAGCUCC | 12048 |
| 3154 | CCGUGGAUC UGAAAGA | 2633 | UCUUUUCA CUGAUGAGGCCGUUAGGCCGAA AUCCACGG | 12049 |
| 3167 | AAGACGCUU GGACAGCA | 2634 | UGCUGUCC CUGAUGAGGCCGUUAGGCCGAA AGCGUCUU | 12050 |
| 3177 | GACAGCAUC ACCAGCAG | 2635 | CUGCUGGU CUGAUGAGGCCGUUAGGCCGAA AUGCUGUC | 12051 |
| 3194 | CCAGAGCUC UGCCAGCU | 2636 | AGCUGGCA CUGAUGAGGCCGUUAGGCCGAA AGCUCUGG | 12052 |
| 3203 | UGCCAGCUC AGGCUUUG | 2637 | CAAAGCCU CUGAUGAGGCCGUUAGGCCGAA AGCUGGCA | 12053 |
| 3209 | CUCAGGCUU UGUUGAGG | 2638 | CCUCAACA CUGAUGAGGCCGUUAGGCCGAA AGCCUGAG | 12054 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 3210 | UCAGGCUUU GUUGAGGA | 2639 | UCCUCAAC CUGAUGAGGCCGUUAGGCCGAA AAGCCUGA | 12055 |
| 3213 | GGCUUUGUU GAGGAGAA | 2640 | UUCUCCUC CUGAUGAGGCCGUUAGGCCGAA ACAAAGCC | 12056 |
| 3224 | GGAGAAAUC GCUCAGUG | 2641 | CACUGAGC CUGAUGAGGCCGUUAGGCCGAA AUUUCUCC | 12057 |
| 3228 | AAAUCGCUC AGUGAUGU | 2642 | ACAUCACU CUGAUGAGGCCGUUAGGCCGAA AGCGAUUU | 12058 |
| 3237 | AGUGAUGUA GAGGAAGA | 2643 | UCUUCCUC CUGAUGAGGCCGUUAGGCCGAA ACAUCACU | 9921 |
| 3253 | AAGAAGCUU CUGAAGAA | 2644 | UUCUUCAG CUGAUGAGGCCGUUAGGCCGAA AGCUUCUU | 12059 |
| 3254 | AGAAGCUUC UGAAGAAC | 2645 | GUUCUUCA CUGAUGAGGCCGUUAGGCCGAA AAGCUUCU | 12060 |
| 3266 | AGAACUGUA CAAGGACU | 2646 | AGUCCUUG CUGAUGAGGCCGUUAGGCCGAA ACAGUUCU | 12061 |
| 3275 | CAAGGACUU CCUGACCU | 2647 | AGGUCAGG CUGAUGAGGCCGUUAGGCCGAA AGUCCUUG | 12062 |
| 3276 | AAGGACUUC CUGACCUU | 1962 | AAGGUCAG CUGAUGAGGCCGUUAGGCCGAA AAGUCCUU | 11381 |
| 3284 | CCUGACCUU GGAGCAUC | 1963 | GAUGCUCC CUGAUGAGGCCGUUAGGCCGAA AGGUCAGG | 11382 |
| 3292 | UGGAGCAUC UCAUCUGU | 1964 | ACAGAUGA CUGAUGAGGCCGUUAGGCCGAA AUGCUCCA | 11383 |
| 3294 | GACCAUCUC AUCUGUUA | 1965 | UAACAGAU CUGAUGAGGCCGUUAGGCCGAA AGAUGCUC | 11384 |
| 3297 | CAUCUCAUC UGUUACAG | 1966 | CUGUAACA CUGAUGAGGCCGUUAGGCCGAA AUGAGAUG | 11385 |
| 3301 | UCAUCUGUU ACAGCUUC | 1967 | GAAGCUGU CUGAUGAGGCCGUUAGGCCGAA ACAGAUGA | 11386 |
| 3302 | CAUCUGUUA CAGCUUCC | 1968 | GGAAGCUG CUGAUGAGGCCGUUAGGCCGAA AACAGAUG | 11387 |
| 3308 | UUACAGCUU CCAAGUGG | 1969 | CCACUUGG CUGAUGAGGCCGUUAGGCCGAA AGCUGUAA | 11388 |
| 3309 | UACAGCUUC CAAGUGGC | 1970 | GCCACUUG CUGAUGAGGCCGUUAGGCCGAA AAGCUGUA | 11389 |
| 3319 | AAGUGGCUA AGGGCAUG | 1971 | CAUGCCCU CUGAUGAGGCCGUUAGGCCGAA AGCCACUU | 11390 |
| 3332 | CAUGGAGUU CUUGGCAU | 1972 | AUGCCAAG CUGAUGAGGCCGUUAGGCCGAA ACUCCAUG | 11391 |
| 3333 | AUGGAGUUC UUGGCAUC | 1973 | GAUGCCAA CUGAUGAGGCCGUUAGGCCGAA AACUCCAU | 11392 |
| 3335 | GGAGUUCUU GGCAUCAA | 2648 | UUGAUGCC CUGAUGAGGCCGUUAGGCCGAA AGAACUCC | 12063 |
| 3341 | CUUGGCAUC AAGGAAGU | 2649 | ACUUCCUU CUGAUGAGGCCGUUAGGCCGAA AUGCCAAG | 12064 |
| 3352 | GGAAGUGUA UCCACAGG | 2650 | CCUGUGGA CUGAUGAGGCCGUUAGGCCGAA ACACUUCC | 12065 |
| 3354 | AAGUGUAUC CACAGGGA | 1977 | UCCCUGUG CUGAUGAGGCCGUUAGGCCGAA AUACACUU | 11396 |
| 3381 | CGAAACAUU CUCCUAUC | 2651 | GAUAGGAG CUGAUGAGGCCGUUAGGCCGAA AUGUUUCG | 12066 |
| 3382 | GAAACAUUC UCCUAUCG | 2652 | CGAUAGGA CUGAUGAGGCCGUUAGGCCGAA AAUGUUUC | 12067 |
| 3384 | AACAUUCUC CUAUCGGA | 2653 | UCCGAUAG CUGAUGAGGCCGUUAGGCCGAA AGAAUGUU | 12068 |
| 3387 | AUUCUCCUA UCGGAAA | 2654 | UUUCCGA CUGAUGAGGCCGUUAGGCCGAA AGGAGAAU | 12069 |
| 3389 | UCUCCUAUC GGAGAAGA | 2655 | UCUUCUCC CUGAUGAGGCCGUUAGGCCGAA AUAGGAGA | 12070 |
| 3405 | AAUGGGUU AAGAUCUG | 2656 | CAGAUCUU CUGAUGAGGCCGUUAGGCCGAA ACCACAUU | 12071 |
| 3406 | AUGUGGUUA AGAUCUGU | 2657 | ACAGAUCU CUGAUGAGGCCGUUAGGCCGAA AACCACAU | 12072 |
| 3411 | GUUAAGAUC UGUGACUU | 2658 | AAGUCACA CUGAUGAGGCCGUUAGGCCGAA AUCUUAAC | 12073 |
| 3419 | CUGUGACUU CGGCUUGG | 2659 | CCAAGCCG CUGAUGAGGCCGUUAGGCCGAA AGUCACAG | 12074 |
| 3420 | UGUGACUUC GGCUUGGC | 2660 | GCCAAGCC CUGAUGAGGCCGUUAGGCCGAA AAGUCACA | 11407 |
| 3425 | CUUCGGCUU GGCCCGGG | 2661 | CCCGGGCC CUGAUGAGGCCGUUAGGCCGAA AGCCGAAG | 12075 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 3438 | CGGGACAUU UAUAAAGA | 2662 | UCUUUAUA CUGAUGAGGCCGUUAGGCCGAA AUGUCCCG | 12076 |
| 3439 | GGGACAUUU AUAAAGAC | 2663 | GUCUUUAU CUGAUGAGGCCGUUAGGCCGAA AAUGUCCC | 12077 |
| 3440 | GGACAUUUA UAAAGACC | 2664 | GGUCUUUA CUGAUGAGGCCGUUAGGCCGAA AAAUGUCC | 12078 |
| 3442 | ACAUUUAUA AAGACCCG | 2665 | CGGGUCUU CUGAUGAGGCCGUUAGGCCGAA AUAAAUGU | 12079 |
| 3454 | ACCCGGAUU AUGUCAGA | 2666 | UCUGACAU CUGAUGAGGCCGUUAGGCCGAA AUCCGGGU | 12080 |
| 3455 | CCCGGAUUA UGUCAGAA | 2667 | UUCUGACA CUGAUGAGGCCGUUAGGCCGAA AAUCCGGG | 12081 |
| 3459 | GAUUAUGUC AGAAAAGG | 1998 | CCUUUUCU CUGAUGAGGCCGUUAGGCCGAA ACAUAAUC | 11417 |
| 3480 | GCCCGACUC CUUUGAA | 2668 | UUCAAAGG CUGAUGAGGCCGUUAGGCCGAA AGUCGGGC | 12082 |
| 3484 | GACUCCCUU UGAAGUGG | 2669 | CCACUUCA CUGAUGAGGCCGUUAGGCCGAA AGGGAGUC | 12083 |
| 3485 | ACUCCCUUU GAAGUGGA | 2670 | UCCACUUC CUGAUGAGGCCGUUAGGCCGAA AAGGGAGU | 12084 |
| 3510 | GAAACCAUU UUUGACAG | 2671 | CUGUCAAA CUGAUGAGGCCGUUAGGCCGAA AUGGUUUC | 12085 |
| 3511 | AAACCAUUU UGACAGA | 2672 | UCUGUCAA CUGAUGAGGCCGUUAGGCCGAA AAUGGUUU | 12086 |
| 3512 | AACCAUUUU UGACAGAG | 2673 | CUCUGUCA CUGAUGAGGCCGUUAGGCCGAA AAAUGGUU | 12087 |
| 3513 | ACCAUUUUU GACAGAGU | 2674 | ACUCUGUC CUGAUGAGGCCGUUAGGCCGAA AAAAUGGU | 12088 |
| 3522 | GACAGAGUA UACACAAU | 2675 | AUUGUGUA CUGAUGAGGCCGUUAGGCCGAA ACUCUGUC | 12089 |
| 3524 | CAGAGUAUA CACAAUUC | 2676 | GAAUUGUG CUGAUGAGGCCGUUAGGCCGAA AUACUCUG | 12090 |
| 3531 | UACACAAUU CAGAGCGA | 2677 | UCGCUCUG CUGAUGAGGCCGUUAGGCCGAA AUUGUGUA | 12091 |
| 3532 | ACACAAUUC AGAGCGAU | 2678 | AUCGCUCU CUGAUGAGGCCGUUAGGCCGAA AAUUGUGU | 12092 |
| 3548 | UGUGUGGUC UUUCGGUG | 2679 | CACCGAAA CUGAUGAGGCCGUUAGGCCGAA ACCACACA | 12093 |
| 3550 | UGUGGUCUU UCGGUGUG | 2680 | CACACCGA CUGAUGAGGCCGUUAGGCCGAA AGACCACA | 12094 |
| 3551 | GUGGUCUUU CGGUGUGU | 2681 | ACACACCG CUGAUGAGGCCGUUAGGCCGAA AAGACCAC | 12095 |
| 3552 | UGGUCUUUC GGUGUGUU | 2682 | AACACACC CUGAUGAGGCCGUUAGGCCGAA AAAGACCA | 12096 |
| 3560 | CGGUGUGUU GCUCUGGG | 2683 | CCCAGAGC CUGAUGAGGCCGUUAGGCCGAA ACACACCG | 12097 |
| 3564 | GUGUUGCUC UGGGAAAU | 2684 | AUUUCCCA CUGAUGAGGCCGUUAGGCCGAA AGCAACAC | 12098 |
| 3573 | UGGGAAAUA UUUUCCUU | 2017 | AAGGAAAA CUGAUGAGGCCGUUAGGCCGAA AUUUCCCA | 11436 |
| 3575 | GGAAAUAUU UUCCUUAG | 2018 | CUAAGGAA CUGAUGAGGCCGUUAGGCCGAA AUAUUUCC | 11437 |
| 3576 | GAAAUAUUU UCCUUAGG | 2019 | CCUAAGGA CUGAUGAGGCCGUUAGGCCGAA AAUAUUUC | 11438 |
| 3577 | AAAUAUUUU CCUUAGGU | 2020 | ACCUAAGG CUGAUGAGGCCGUUAGGCCGAA AAAUAUUU | 11439 |
| 3578 | AAUAUUUUC CUUAGGUG | 2021 | CACCUAAG CUGAUGAGGCCGUUAGGCCGAA AAAAUAUU | 11440 |
| 3581 | AUUUUCCUU AGGUGCCU | 2685 | AGGCACCU CUGAUGAGGCCGUUAGGCCGAA AGGAAAAU | 12099 |
| 3582 | UUUUCCUUA GGUGCCUC | 2686 | GAGGCACC CUGAUGAGGCCGUUAGGCCGAA AAGGAAAA | 12100 |
| 3590 | AGGUGCCUC CCCAUACC | 2687 | GGUAUGGG CUGAUGAGGCCGUUAGGCCGAA AGGCACCU | 12101 |
| 3596 | CUCCCCAUA CCCUGGGG | 2688 | CCCCAGGG CUGAUGAGGCCGUUAGGCCGAA AUGGGGAG | 12102 |
| 3606 | CCUGGGGUC AAGAUUGA | 2689 | UCAAUCUU CUGAUGAGGCCGUUAGGCCGAA ACCCCAGG | 11448 |
| 3612 | GUCAAGAUU GAUGAAGA | 2690 | UCUUCAUC CUGAUGAGGCCGUUAGGCCGAA AUCUUGAC | 12103 |
| 3623 | UGAAGAAUU UUGUAGGA | 2691 | UCCUACAA CUGAUGAGGCCGUUAGGCCGAA AUUCUUCA | 12104 |
| 3624 | GAAGAAUUU UGUAGGAG | 2692 | CUCCUACA CUGAUGAGGCCGUUAGGCCGAA AAUUCUUC | 12105 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 3625 | AAGAAUUUU GUAGGAGA | 2693 | UCUCCUAC CUGAUGAGGCCGUUAGGCCGAA AAAUUCUU | 12106 |
| 3628 | AAUUUUGUA GGAGAUUG | 2694 | CAAUCUCC CUGAUGAGGCCGUUAGGCCGAA ACAAAAUU | 12107 |
| 3635 | UAGGAGAUU GAAAGAAG | 2695 | CUUCUUUC CUGAUGAGGCCGUUAGGCCGAA AUCUCCUA | 12108 |
| 3649 | AAGGAACUA GAAUGCGG | 2696 | CCGCAUUC CUGAUGAGGCCGUUAGGCCGAA AGUUCCUU | 12109 |
| 3661 | UGCGGGCUC CUGACUAC | 2697 | GUAGUCAG CUGAUGAGGCCGUUAGGCCGAA AGCCCGCA | 12110 |
| 3668 | UCCGACUA CACUACCC | 2698 | GGGUAGUG CUGAUGAGGCCGUUAGGCCGAA AGUCAGGA | 12111 |
| 3673 | ACUACACUA CCCCAGAA | 2699 | UUCGGGG CUGAUGAGGCCGUUAGGCCGAA AGUGUAGU | 12112 |
| 3686 | AGAAAUGUA CCAGACCA | 2041 | UGGUCUGG CUGAUGAGGCCGUUAGGCCGAA ACAUUUCU | 11460 |
| 3734 | GAGACCCUC GUUUUCAG | 2700 | CUGAAAAC CUGAUGAGGCCGUUAGGCCGAA AGGGUCUC | 12113 |
| 3737 | ACCCUCGUU UUCAGAGU | 2701 | ACUCUGAA CUGAUGAGGCCGUUAGGCCGAA ACGAGGGU | 12114 |
| 3738 | CCCUCGUUU UCAGAGUU | 2702 | AACUCUGA CUGAUGAGGCCGUUAGGCCGAA AACGAGGG | 12115 |
| 3739 | CCUCGUUUU CAGAGUUG | 2703 | CAACUCUG CUGAUGAGGCCGUUAGGCCGAA AAACGAGG | 12116 |
| 3740 | CUCGUUUUC AGAGUUGG | 2704 | CCAACUCU CUGAUGAGGCCGUUAGGCCGAA AAAACGAG | 12117 |
| 3746 | UUCAGAGUU GGUGGAGC | 2705 | GCUCCACC CUGAUGAGGCCGUUAGGCCGAA ACUCUGAA | 12118 |
| 3757 | UGGAGCAUU UGGGAAAC | 2706 | GUUUCCCA CUGAUGAGGCCGUUAGGCCGAA AUGCUCCA | 12119 |
| 3758 | GGAGCAUUU GGGAAACC | 2707 | GGUUUCCC CUGAUGAGGCCGUUAGGCCGAA AAUGCUCC | 12120 |
| 3768 | GGAAACCUC CUGCAAGC | 2708 | GCUUGCAG CUGAUGAGGCCGUUAGGCCGAA AGGUUUCC | 12121 |
| 3803 | CAAAGACUA UAUUGUUC | 2709 | GAACAAUA CUGAUGAGGCCGUUAGGCCGAA AGUCUUUG | 12122 |
| 3805 | AAGACUAUA UUGUUCUU | 2710 | AAGAACAA CUGAUGAGGCCGUUAGGCCGAA AUAGUCUU | 12123 |
| 3807 | GACUAUAUU GUUCUUCC | 2711 | GGAAGAAC CUGAUGAGGCCGUUAGGCCGAA AUAUAGUC | 12124 |
| 3810 | UAUAUUGUU CUUCCAAU | 2712 | AUUGGAAG CUGAUGAGGCCGUUAGGCCGAA ACAAUAUA | 12125 |
| 3811 | AUAUUGUUC UUCCAAUG | 2713 | CAUUGGAA CUGAUGAGGCCGUUAGGCCGAA AACAAUAU | 12126 |
| 3813 | AUUGUUCUU CCAAUGUC | 2714 | GACAUUGG CUGAUGAGGCCGUUAGGCCGAA AGAACAAU | 12127 |
| 3814 | UUGUUCUUC CAAUGUCA | 2715 | UGACAUUG CUGAUGAGGCCGUUAGGCCGAA AGAACAA | 12128 |
| 3821 | UCCAAUGUC AGAGACAC | 2716 | GUGUCUCU CUGAUGAGGCCGUUAGGCCGAA ACAUUGGA | 12129 |
| 3847 | AAGAGGAUU CUGGACUC | 2065 | GAGUCCAG CUGAUGAGGCCGUUAGGCCGAA AUCCUCUU | 11484 |
| 3848 | AGAGGAUUC UGGACUCU | 2066 | AGAGUCCA CUGAUGAGGCCGUUAGGCCGAA AAUCCUCU | 11485 |
| 3855 | UCUGGACUC UCCCUGCC | 2717 | GGCAGGGA CUGAUGAGGCCGUUAGGCCGAA AGUCCAGA | 12130 |
| 3857 | UGGACUCUC CCUGCCUA | 2718 | UAGGCAGG CUGAUGAGGCCGUUAGGCCGAA AGAGUCCA | 12131 |
| 3865 | CCCUGCCUA CCUCACCU | 2719 | AGGUGAGG CUGAUGAGGCCGUUAGGCCGAA AGGCAGGG | 12132 |
| 3869 | GCCUACCUC ACCUGUUU | 2071 | AAACAGGU CUGAUGAGGCCGUUAGGCCGAA AGGUAGGC | 11490 |
| 3876 | UCACCUGUU UCCUGUAU | 2072 | AUACAGGA CUGAUGAGGCCGUUAGGCCGAA ACAGGUGA | 11491 |
| 3877 | CACCUGUUU CCUGUAUG | 2073 | CAUACAGG CUGAUGAGGCCGUUAGGCCGAA AACAGGUG | 11492 |
| 3878 | ACCUGUUUC CUGUAUGG | 2074 | CCAUACAG CUGAUGAGGCCGUUAGGCCGAA AAACAGGU | 11493 |
| 3883 | UUCCUGUA UGGAGGAA | 2720 | UUCCUCCA CUGAUGAGGCCGUUAGGCCGAA ACAGGAAA | 12133 |
| 3914 | CCCCAAAUU CCAUUAUG | 2077 | CAUAAUGG CUGAUGAGGCCGUUAGGCCGAA AUUUGGGG | 11496 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 3915 | CCCAAAUUC CAUUAUGA | 2078 | UCAUAAUG CUGAUGAGGCCGUUAGGCCGAA AAUUUGGG | 11497 |
| 3919 | AAUUCCAUU AUGACAAC | 2079 | GUUGUCAU CUGAUGAGGCCGUUAGGCCGAA AUGGAAUU | 11498 |
| 3920 | AUUCCAUUA UGACAACA | 2080 | UGUUGUCA CUGAUGAGGCCGUUAGGCCGAA AAUGGAAU | 11499 |
| 3939 | GCAGGAAUC AGUCAUUA | 2721 | UAAUGACU CUGAUGAGGCCGUUAGGCCGAA AUUCCUGC | 12134 |
| 3943 | GAAUCAGUC AUUAUCUC | 2722 | GAGAUAAU CUGAUGAGGCCGUUAGGCCGAA ACUGACUC | 12135 |
| 3946 | UCAGUCAUU AUCUCCAG | 2723 | CUGGAGAU CUGAUGAGGCCGUUAGGCCGAA AUGACUGA | 12136 |
| 3947 | CAGUCAUUA UCUCCAGA | 2724 | UCUGGAGA CUGAUGAGGCCGUUAGGCCGAA AAUGACUG | 12137 |
| 3949 | GUCAUUAUC UCCAGAAC | 2725 | GUUCUGGA CUGAUGAGGCCGUUAGGCCGAA AUAAUGAC | 12138 |
| 3951 | CAUUAUCUC CAGAACAG | 2726 | CUGUUCUG CUGAUGAGGCCGUUAGGCCGAA AGAUAAUG | 12139 |
| 3961 | AGAACAGUA AGCGAAAG | 2085 | CUUUCGCU CUGAUGAGGCCGUUAGGCCGAA ACUGUUCU | 11504 |
| 3987 | GUGAGUGUA AAAACAUU | 2086 | AAUGUUUU CUGAUGAGGCCGUUAGGCCGAA ACACUCAC | 11505 |
| 3995 | AAAAACAUU UGAAGAUA | 2087 | UAUCUUCA CUGAUGAGGCCGUUAGGCCGAA AUGUUUUU | 11506 |
| 3996 | AAAACAUUU GAAGAUAU | 2088 | AUAUCUUC CUGAUGAGGCCGUUAGGCCGAA AAUGUUUU | 11507 |
| 4003 | UUGAAGAUA UCCCAUUG | 2727 | CAAUGGGA CUGAUGAGGCCGUUAGGCCGAA AUCUUCAA | 12140 |
| 4005 | GAAGAUAUC CCAUUGGA | 2728 | UCCAAUGG CUGAUGAGGCCGUUAGGCCGAA AUAUCUUC | 12141 |
| 4010 | UAUCCCAUU GGAGGAAC | 2729 | GUUCCUCC CUGAUGAGGCCGUUAGGCCGAA AUGGGAUA | 12142 |
| 4026 | CCAGAAGUA AAAGUGAU | 2730 | AUCACUUU CUGAUGAGGCCGUUAGGCCGAA ACUUCUGG | 12143 |
| 4035 | AAAGUGAUC CAGAUGA | 2731 | UCAUCUGG CUGAUGAGGCCGUUAGGCCGAA AUCACUUU | 12144 |
| 4068 | GGGAUGGUC CUUGCAUC | 2732 | GAUGCAAG CUGAUGAGGCCGUUAGGCCGAA ACCAUCCC | 12145 |
| 4071 | AUGGUCCUU GCAUCAGA | 2733 | UCUGAUGC CUGAUGAGGCCGUUAGGCCGAA AGGACCAU | 12146 |
| 4076 | CCUUGCAUC AGAAGAGC | 2734 | GCUCUUCU CUGAUGAGGCCGUUAGGCCGAA AUGCAAGG | 12147 |
| 4093 | UGAAAACUC UGGAAGAC | 2735 | GUCUUCCA CUGAUGAGGCCGUUAGGCCGAA AGUUUUCA | 11520 |
| 4112 | GAACAAAUU AUCUCCAU | 2736 | AUGGAGAU CUGAUGAGGCCGUUAGGCCGAA AUUUGUUC | 12148 |
| 4113 | AACAAAUUA UCUCCAUC | 2737 | GAUGGAGA CUGAUGAGGCCGUUAGGCCGAA AAUUUGUU | 12149 |
| 4115 | CAAAUUAUC UCCAUCUU | 2105 | AAGAUGGA CUGAUGAGGCCGUUAGGCCGAA AUAAUUUG | 11524 |
| 4117 | AAUUAUCUC CAUCUUUU | 2106 | AAAAGAUG CUGAUGAGGCCGUUAGGCCGAA AGAUAAUU | 11525 |
| 4121 | AUCUCCAUC UUUUGGUG | 2107 | CACCAAAA CUGAUGAGGCCGUUAGGCCGAA AUGGAGAU | 11526 |
| 4123 | CUCCAUCUU UUGGUGGA | 2108 | UCCACCAA CUGAUGAGGCCGUUAGGCCGAA AGAUGGAG | 11527 |
| 4124 | UCCAUCUUU UGGUGGAA | 2109 | UUCCACCA CUGAUGAGGCCGUUAGGCCGAA AAGAUGGA | 11528 |
| 4125 | CCAUCUUUU GGUGGAAU | 2110 | AUUCCACC CUGAUGAGGCCGUUAGGCCGAA AAAGAUGG | 11529 |
| 4144 | UGCCCAGUA AAAGCAGG | 2738 | CCUGCUUU CUGAUGAGGCCGUUAGGCCGAA ACUGGGCA | 12150 |
| 4157 | CAGGGAGUC UGUGGCCU | 2739 | AGGCCACA CUGAUGAGGCCGUUAGGCCGAA ACUCCCUG | 12151 |
| 4166 | UGUGGCCUC GGAAGGCU | 2740 | AGCCUUCC CUGAUGAGGCCGUUAGGCCGAA AGGCCACA | 12152 |
| 4175 | GGAAGGCUC CAACCAGA | 2741 | UCUGGUUG CUGAUGAGGCCGUUAGGCCGAA AGCCUUCC | 12153 |
| 4193 | CAGUGGCUA CCAGUCUG | 2742 | CAGACUGG CUGAUGAGGCCGUUAGGCCGAA AGCCACUG | 12154 |
| 4199 | CUACCAGUC UGGGUAUC | 2743 | GAUACCCA CUGAUGAGGCCGUUAGGCCGAA ACUGGUAG | 12155 |
| 4205 | GUCUGGGUA UCACUCAG | 2744 | CUGAGUGA CUGAUGAGGCCGUUAGGCCGAA ACCCAGAC | 12156 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 4207 | CUGGGUAUC ACUCAGAU | 2745 | AUCUGAGU CUGAUGAGgccguuaggcCGAA AUACCCAG | 12157 |
| 4211 | GUAUCACUC AGAUGACA | 2746 | UGUCAUCU CUGAUGAGgccguuaggcCGAA AGUGAUAC | 12158 |
| 4235 | CACCGUGUA CUCCAGCG | 2747 | CGCUGGAG CUGAUGAGgccguuaggcCGAA ACACGGUG | 12159 |
| 4238 | CGUGUACUC CAGCGACG | 2748 | CGUCGCUG CUGAUGAGgccguuaggcCGAA AGUACACG | 12160 |
| 4257 | GCAGGACUU UUAAAGAU | 2749 | AUCUUUAA CUGAUGAGgccguuaggcCGAA AGUCCUGC | 12161 |
| 4258 | CAGGACUUU UAAAGAUG | 2750 | CAUCUUUA CUGAUGAGgccguuaggcCGAA AAGUCCUG | 12162 |
| 4259 | AGGACUUUU AAAGAUGG | 2751 | CCAUCUUU CUGAUGAGgccguuaggcCGAA AAAGUCCU | 12163 |
| 4260 | GGACUUUUA AAGAUGGU | 2752 | ACCAUCUG CUGAUGAGgccguuaggcCGAA AAAAGUCC | 12164 |
| 4281 | GCUGCAGUU CACGCUGA | 2753 | UCAGCGUG CUGAUGAGgccguuaggcCGAA ACUGCAGC | 12165 |
| 4282 | CUGCAGUUC ACGCUGAC | 2754 | GUCAGCGU CUGAUGAGgccguuaggcCGAA AACUGCAG | 12166 |
| 4292 | CGCUGACUC AGGGACCA | 2755 | UGGUCCCU CUGAUGAGgccguuaggcCGAA AGUCAGCG | 12167 |
| 4311 | CUGCAGCUC ACCUCCUG | 2756 | CAGGAGGU CUGAUGAGgccguuaggcCGAA AGCUGCAG | 12168 |
| 4316 | GCUCACCUC CUGUUUAA | 2757 | UUAAACAG CUGAUGAGgccguuaggcCGAA AGGUGAGC | 12169 |
| 4321 | CCUCCUGUU UAAAUGGA | 2758 | UCCAUUUA CUGAUGAGgccguuaggcCGAA ACAGGAGG | 12170 |
| 4322 | CUCCUGUUU AAAUGGAA | 2759 | UUCCAUUU CUGAUGAGgccguuaggcCGAA AACAGGAG | 12171 |
| 4323 | UCCUGUUUA AAUGGAAG | 2760 | CUUCCAUU CUGAUGAGgccguuaggcCGAA AAACAGGA | 12172 |
| 4336 | GAAGUGGUC UGUCCCG | 2761 | CGGGACAG CUGAUGAGgccguuaggcCGAA ACCACUUC | 12173 |
| 4341 | GGUCCUGUC CCGGCUCC | 2762 | GGAGCCGG CUGAUGAGgccguuaggcCGAA ACAGGACC | 12174 |
| 4348 | UCCCGGCUC CGCCCCCA | 2763 | UGGGGGCG CUGAUGAGgccguuaggcCGAA AGCCGGGA | 12175 |
| 4360 | CCCCAACUC CUGGAAAU | 2764 | AUUUCCAG CUGAUGAGgccguuaggcCGAA AGUUGGGG | 12176 |
| 4369 | CUGGAAAUC ACGAGAGA | 2765 | UCUCUCGU CUGAUGAGgccguuaggcCGAA AUUUCCAG | 12177 |
| 4387 | GUGCUGCUU AGAUUUUC | 2766 | GAAAAUCU CUGAUGAGgccguuaggcCGAA AGCAGCAC | 12178 |
| 4388 | UGCUGCUUA GAUUUUCA | 2767 | UGAAAAUC CUGAUGAGgccguuaggcCGAA AAGCAGCA | 12179 |
| 4392 | GCUUAGAUU UUCAAGUG | 2768 | CACUUGAA CUGAUGAGgccguuaggcCGAA AUCUAAGC | 12180 |
| 4393 | CUUAGAUUU UCAAGUGU | 2769 | ACACUUGA CUGAUGAGgccguuaggcCGAA AAUCUAAG | 12181 |
| 4394 | UUAGAUUUU CAAGUGUU | 2770 | AACACUUG CUGAUGAGgccguuaggcCGAA AAAUCUAA | 12182 |
| 4395 | UAGAUUUUC AAGUGUUG | 2771 | CAACACUG CUGAUGAGgccguuaggcCGAA AAAAUCUA | 12183 |
| 4402 | UCAAGUGUU GUUCUUUC | 2772 | GAAAGAAC CUGAUGAGgccguuaggcCGAA ACACUUGA | 12184 |
| 4405 | AGUGUUGUU CUUCCAC | 2146 | GUGGAAAG CUGAUGAGgccguuaggcCGAA ACAACACU | 11565 |
| 4406 | GUGUUGUUC UUUCCACC | 2147 | GGUGGAAA CUGAUGAGgccguuaggcCGAA AACAACAC | 11566 |
| 4408 | GUUGUUCUU UCCACCAC | 2773 | GUGGUGGA CUGAUGAGgccguuaggcCGAA AGAACAAC | 12185 |
| 4409 | UUGUUCUUU CCACCACC | 2774 | GGUGGUGG CUGAUGAGgccguuaggcCGAA AAGAACAA | 12186 |
| 4410 | UGUUCUUUC CACCACCC | 2775 | GGGUGGUG CUGAUGAGgccguuaggcCGAA AAAGAACA | 12187 |
| 4425 | CCGGAAGUA GCCACAUU | 2776 | AAUGUGGC CUGAUGAGgccguuaggcCGAA ACUUCCGG | 12188 |
| 4433 | AGCCACAUU UGAUUUUC | 2777 | GAAAAUCA CUGAUGAGgccguuaggcCGAA AUGGGCU | 12189 |
| 4434 | GCCACAUUU GAUUUUCA | 2778 | UGAAAAUC CUGAUGAGgccguuaggcCGAA AAUGUGGC | 12190 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 4438 | CAUUUGAUU UUCAUUUU | 2779 | AAAAUGAA CUGAUGAGGCCGUUAGGCCGAA AUCAAAUG | 12191 |
| 4439 | AUUUGAUUU UCAUUUUU | 2780 | AAAAAUGA CUGAUGAGGCCGUUAGGCCGAA AAUCAAAU | 12192 |
| 4440 | UUUGAUUUU CAUUUUUG | 2781 | CAAAAAUG CUGAUGAGGCCGUUAGGCCGAA AAAUCAAA | 12193 |
| 4441 | UUGAUUUUC AUUUUUGG | 2782 | CCAAAAAU CUGAUGAGGCCGUUAGGCCGAA AAAAUCAA | 12194 |
| 4444 | AUUUUCAUU UUUGGAGG | 2783 | CCUCCAAA CUGAUGAGGCCGUUAGGCCGAA AUGAAAAU | 12195 |
| 4445 | UUUUCAUUU UUGGAGGA | 2784 | UCCUCCAA CUGAUGAGGCCGUUAGGCCGAA AAUGAAAA | 12196 |
| 4446 | UUUCAUUUU UGGAGGAG | 2785 | CUCCUCCA CUGAUGAGGCCGUUAGGCCGAA AAAUGAAA | 12197 |
| 4447 | UUCAUUUUU GGAGGAGG | 2786 | CCUCCUCC CUGAUGAGGCCGUUAGGCCGAA AAAAUGAA | 12198 |
| 4461 | AGGGACCUC AGACUGCA | 2787 | UGCAGUCU CUGAUGAGGCCGUUAGGCCGAA AGUCCCU | 12199 |
| 4477 | AAGGAGCUU GUCCUCAG | 2788 | CUGAGGAC CUGAUGAGGCCGUUAGGCCGAA AGCUCCUU | 12200 |
| 4480 | GAGCUUGUC UCAGGGC | 2789 | GCCCUGAG CUGAUGAGGCCGUUAGGCCGAA ACAAGCUC | 12201 |
| 4483 | CUUGUCCUC AGGGCAUU | 2790 | AAUGCCCU CUGAUGAGGCCGUUAGGCCGAA AGGACAAG | 12202 |
| 4491 | CAGGGCAUU UCCAGAGA | 2791 | UCUCUGGA CUGAUGAGGCCGUUAGGCCGAA AUGCCCUG | 12203 |
| 4492 | AGGGCAUUU CCAGAGAA | 2792 | UUCUCUGG CUGAUGAGGCCGUUAGGCCGAA AAUGCCCU | 12204 |
| 4493 | GGGCAUUUC CAGAAGAAG | 2793 | CUUCUCUG CUGAUGAGGCCGUUAGGCCGAA AAAUGCCC | 12205 |
| 4525 | GAAUGUGUU GACUCUAC | 2794 | GUAGAGUC CUGAUGAGGCCGUUAGGCCGAA ACACAUUC | 12206 |
| 4530 | UGUUGACUC UACUCUCU | 2795 | AGAGAGUA CUGAUGAGGCCGUUAGGCCGAA AGUCAACA | 12207 |
| 4532 | UUGACUCUA CUCUCUUU | 2796 | AAAGAGAG CUGAUGAGGCCGUUAGGCCGAA AGAGUCAA | 12208 |
| 4535 | ACUCUACUC UCUUUUCC | 2797 | GGAAAAGA CUGAUGAGGCCGUUAGGCCGAA AGUAGAGU | 12209 |
| 4537 | UCUACUCUC UUUUCCAU | 2798 | AUGGAAAA CUGAUGAGGCCGUUAGGCCGAA AGAGUAGA | 12210 |
| 4539 | UACUCUCUU UUCCAUUC | 2799 | GAAUGGAA CUGAUGAGGCCGUUAGGCCGAA AGAGAGUA | 12211 |
| 4540 | ACUCUCUUU UCCAUUCA | 2800 | UGAAUGGA CUGAUGAGGCCGUUAGGCCGAA AAGAGAGU | 12212 |
| 4541 | CUCUCUUUU CCAUUCAU | 2801 | AUGAAUGG CUGAUGAGGCCGUUAGGCCGAA AAAGAGAG | 12213 |
| 4542 | UCUCUUUUC CAUUCAUU | 2802 | AAUGAAUG CUGAUGAGGCCGUUAGGCCGAA AAAAGAGA | 12214 |
| 4546 | UUUUCCAUU CAUUUAAA | 2803 | UUUAAAUG CUGAUGAGGCCGUUAGGCCGAA AUGGAAAA | 12215 |
| 4547 | UUUCCAUUC AUUUAAAA | 2804 | UUUUAAAU CUGAUGAGGCCGUUAGGCCGAA AAUGGAAA | 12216 |
| 4550 | CCAUUCAUU UAAAAGUC | 2805 | GACUUUUA CUGAUGAGGCCGUUAGGCCGAA AUGAAUGG | 12217 |
| 4551 | CAUUCAUUU AAAAGUCC | 2806 | GGACUUUU CUGAUGAGGCCGUUAGGCCGAA AAUGAAUG | 12218 |
| 4552 | AUUCAUUUA AAAGUCCU | 2807 | AGGACUUU CUGAUGAGGCCGUUAGGCCGAA AAAUGAAU | 12219 |
| 4558 | UUAAAAGUC UAUAUAA | 2808 | UUAUAUAG CUGAUGAGGCCGUUAGGCCGAA ACUUUUAA | 12220 |
| 4561 | AAAGUCCUA UAUAAUGU | 2809 | ACAUUAUA CUGAUGAGGCCGUUAGGCCGAA AGGACUUU | 12221 |
| 4563 | AGUCCUAUA UAAUGUGC | 2810 | GCACAUUA CUGAUGAGGCCGUUAGGCCGAA AUAGGACU | 12222 |
| 4565 | UCCUAUAUA AUGUGCCC | 2811 | GGGCACAU CUGAUGAGGCCGUUAGGCCGAA AUAUAGGA | 12223 |
| 4583 | GCUGUGGUC UCACUACC | 2812 | GGUAGUGA CUGAUGAGGCCGUUAGGCCGAA ACCACAGC | 12224 |
| 4585 | UGUGGUCUC ACUACCAG | 2813 | CUGGUAGU CUGAUGAGGCCGUUAGGCCGAA AGACCACA | 12225 |
| 4589 | GUCUCACUA CCAGUUAA | 2814 | UUAACUGG CUGAUGAGGCCGUUAGGCCGAA AGUGAGAC | 12226 |
| 4595 | CUACCAGUU AAAGCAAA | 2815 | UUUGCUUU CUGAUGAGGCCGUUAGGCCGAA ACUGGUAG | 12227 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 4596 | UACCAGUUA AAGCAAAA | 2816 | UUUUGCUU CUGAUGAGGCCGUUAGGCCGAA AACUGGUA | 12228 |
| 4609 | AAAAGACUU UCAAACAC | 2817 | GUGUUUGA CUGAUGAGGCCGUUAGGCCGAA AGUCUUUU | 12229 |
| 4610 | AAAGACUUU CAAACACG | 2818 | CGUGUUUG CUGAUGAGGCCGUUAGGCCGAA AAGUCUUU | 12230 |
| 4611 | AAGACUUUC AAACACGU | 2819 | ACGUGUUU CUGAUGAGGCCGUUAGGCCGAA AAAGUCUU | 12231 |
| 4625 | CGUGGACUC UGUCCUCC | 2820 | GGAGGACA CUGAUGAGGCCGUUAGGCCGAA AGUCCACG | 12232 |
| 4629 | GACUCUGUC CUCCAAGA | 2821 | UCUUGGAG CUGAUGAGGCCGUUAGGCCGAA ACAGAGUC | 12233 |
| 4632 | UCUGUCCUC CAAGAAGU | 2822 | ACUUCUUG CUGAUGAGGCCGUUAGGCCGAA AGGACAGA | 12234 |
| 4654 | CGGCACCUC UGUGAAAC | 2823 | GUUUCACA CUGAUGAGGCCGUUAGGCCGAA AGGUGCCG | 12235 |
| 4668 | AACUGGAUC GAAUGGGC | 2824 | GCCCAUUC CUGAUGAGGCCGUUAGGCCGAA AUCCAGUU | 12236 |
| 4683 | GCAAUGCUU UGUGUGUU | 2825 | AACACACA CUGAUGAGGCCGUUAGGCCGAA AGCAUUGC | 12237 |
| 4684 | CAAUGCUUU GUGUGUUG | 2826 | CAACACAC CUGAUGAGGCCGUUAGGCCGAA AAGCAUUG | 12238 |
| 4691 | UUGUGUGUU GAGGAUGG | 2827 | CCAUCCUC CUGAUGAGGCCGUUAGGCCGAA ACACACAA | 12239 |
| 4709 | UGAGAUGUC CCAGGGCC | 2828 | GGCCCUGG CUGAUGAGGCCGUUAGGCCGAA ACAUCUCA | 12240 |
| 4722 | GGCCGAGUC UGUCUACC | 2829 | GGUAGACA CUGAUGAGGCCGUUAGGCCGAA ACUCGGCC | 12241 |
| 4726 | GAGUCUGUC UACCUUGG | 2830 | CCAAGGUA CUGAUGAGGCCGUUAGGCCGAA ACAGACUC | 12242 |
| 4728 | GUCUGUCUA CCUUGGAG | 2831 | CUCCAAGG CUGAUGAGGCCGUUAGGCCGAA AGACAGAC | 12243 |
| 4732 | GUCUACCUU GGAGGCUU | 2832 | AAGCCUCC CUGAUGAGGCCGUUAGGCCGAA AGGUAGAC | 12244 |
| 4740 | UGGAGGCUU UGUGGAGG | 2833 | CCUCCACA CUGAUGAGGCCGUUAGGCCGAA AGCCUCCA | 12245 |
| 4741 | GGAGGCUUU GUGGAGGA | 2834 | UCCUCCAC CUGAUGAGGCCGUUAGGCCGAA AAGCCUCC | 12246 |
| 4758 | UGCGGGCUA UGAGCCAA | 2835 | UUGGCUCA CUGAUGAGGCCGUUAGGCCGAA AGCCCGCA | 12247 |
| 4771 | CCAAGUGUU AAGUGUGG | 2836 | CCACACUU CUGAUGAGGCCGUUAGGCCGAA ACACUUGG | 12248 |
| 4772 | CAAGUGUUA AGUGUGGG | 2837 | CCCACACU CUGAUGAGGCCGUUAGGCCGAA AACACUUG | 12249 |
| 4811 | GCGCAAGUC GCUCGGAG | 2838 | CUCCGAGC CUGAUGAGGCCGUUAGGCCGAA ACUUGCGC | 12250 |
| 4815 | AAGUCGCUC GGAGAGCG | 2839 | CGCUCUCC CUGAUGAGGCCGUUAGGCCGAA AGCGACUU | 12251 |
| 4826 | AGAGCGGUU GGAGCCUG | 2840 | CAGGCUCC CUGAUGAGGCCGUUAGGCCGAA ACCGCUCU | 12252 |
| 4844 | AGAUGCAUU GUGCUGGC | 2841 | GCCAGCAC CUGAUGAGGCCGUUAGGCCGAA AUGCAUCU | 12253 |
| 4854 | UGCUGGCUC UGGUGGAG | 2842 | CUCCACCA CUGAUGAGGCCGUUAGGCCGAA AGCCAGCA | 12254 |
| 4870 | GGUGGGCUU UGGGCCUG | 2843 | CAGGCCAC CUGAUGAGGCCGUUAGGCCGAA AGCCCACC | 12255 |
| 4880 | UGGCCUGUC AGGAAACG | 2844 | CGUUUCCU CUGAUGAGGCCGUUAGGCCGAA ACAGGCCA | 12256 |
| 4908 | GGCAGGGUU UGGUUUUG | 2845 | CAAAACCA CUGAUGAGGCCGUUAGGCCGAA ACCCUGCC | 12257 |
| 4909 | GCAGGGUUU GGUUUUGG | 2846 | CCAAAACC CUGAUGAGGCCGUUAGGCCGAA AACCCUGC | 12258 |
| 4913 | GGUUUGGUU UUGGAAGG | 2847 | CCUUCCAA CUGAUGAGGCCGUUAGGCCGAA ACCAAACC | 12259 |
| 4914 | GUUUGGUUU UGGAAGGU | 2848 | ACCUUCCA CUGAUGAGGCCGUUAGGCCGAA AACCAAAC | 12260 |
| 4915 | UUUGGUUUU GGAAGGUU | 2849 | AACCUUCC CUGAUGAGGCCGUUAGGCCGAA AAACCAAA | 12261 |
| 4923 | UGGAAGGUU UGCGUGCU | 2850 | AGCACGCA CUGAUGAGGCCGUUAGGCCGAA ACCUUCCA | 12262 |
| 4924 | GGAAGGUUU GCGUGCUC | 2851 | GAGCACGC CUGAUGAGGCCGUUAGGCCGAA AACCUUCC | 12263 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 4932 | UGCGUGCUC UUCACAGU | 2852 | ACUGUGAA CUGAUGAGGCCGUUAGGCCGAA AGCACGCA | 12264 |
| 4934 | CGUGCUCUU CACAGUCG | 2853 | CGACUGUG CUGAUGAGGCCGUUAGGCCGAA AGAGCACG | 12265 |
| 4935 | GUGCUCUUC ACAGUCGG | 2854 | CCGACUGU CUGAUGAGGCCGUUAGGCCGAA AAGAGCAC | 12266 |
| 4941 | UUCACAGUC GGGUUACA | 2855 | UGUAACCC CUGAUGAGGCCGUUAGGCCGAA ACUGUGAA | 12267 |
| 4946 | AGUCGGGUU ACAGGCGA | 2856 | UCGCCUGU CUGAUGAGGCCGUUAGGCCGAA ACCCGACU | 12268 |
| 4947 | GUCGGGUUA CAGGCGAG | 2857 | CUCGCCUG CUGAUGAGGCCGUUAGGCCGAA AACCCGAC | 12269 |
| 4957 | AGGCGAGUU CCCUGUGG | 2858 | CCACAGGG CUGAUGAGGCCGUUAGGCCGAA ACUCGCCU | 12270 |
| 4958 | GGCGAGUUC CCUGUGGC | 2859 | GCCACAGG CUGAUGAGGCCGUUAGGCCGAA AACUCGCC | 12271 |
| 4969 | UGGCGUUU UCCUACUC | 2860 | GAGUAGGA CUGAUGAGGCCGUUAGGCCGAA ACGCCACA | 12272 |
| 4970 | GUGGCGUUU CCUACUCC | 2861 | GGAGUAGG CUGAUGAGGCCGUUAGGCCGAA AACGCCAC | 12273 |
| 4971 | UGGCGUUUC CUACUCCU | 2862 | AGGAGUAG CUGAUGAGGCCGUUAGGCCGAA AAACGCCA | 12274 |
| 4974 | CGUUUCCUA CUCCUAAU | 2863 | AUUAGGAG CUGAUGAGGCCGUUAGGCCGAA AGGAAACG | 12275 |
| 4977 | UUCCUACUC CUAAUGAG | 2864 | CUCAUUAG CUGAUGAGGCCGUUAGGCCGAA AGUAGGAA | 12276 |
| 4980 | CUACUCCUA AUGAGAGU | 2865 | ACUCUCAU CUGAUGAGGCCGUUAGGCCGAA AGGAGUAG | 12277 |
| 4989 | AUGAGAGUU CCUUCCGG | 2866 | CCGGAAGG CUGAUGAGGCCGUUAGGCCGAA ACUCUCAU | 12278 |
| 4990 | UGAGAGUUC CUUCCGGA | 2867 | UCCGGAAG CUGAUGAGGCCGUUAGGCCGAA AACUCUCA | 12279 |
| 4993 | GAGUUCCUU CCGGACUC | 2868 | GAGUCCGG CUGAUGAGGCCGUUAGGCCGAA AGGAACUC | 12280 |
| 4994 | AGUUCCUUC CGGACUCU | 2869 | AGAGUCCG CUGAUGAGGCCGUUAGGCCGAA AAGGAACU | 12281 |
| 5001 | UCCGGACUC UUACGUGU | 2870 | ACACGUAA CUGAUGAGGCCGUUAGGCCGAA AGUCCGGA | 12282 |
| 5003 | CGGACUCUU ACGUGUCU | 2871 | AGACACGU CUGAUGAGGCCGUUAGGCCGAA AGAGUCCG | 12283 |
| 5004 | GGACUCUUA CGUGUCUC | 2872 | GAGACACG CUGAUGAGGCCGUUAGGCCGAA AAGAGUCC | 12284 |
| 5010 | UUACGUGUC UCCUGGCC | 2873 | GGCCAGGA CUGAUGAGGCCGUUAGGCCGAA ACACGUAA | 12285 |
| 5012 | ACGUGUCUC CUGGCCUG | 2874 | CAGGCCAG CUGAUGAGGCCGUUAGGCCGAA AGACACGU | 12286 |
| 5046 | AUGCAGCUU GCUCCUUC | 2875 | GAAGGAGC CUGAUGAGGCCGUUAGGCCGAA AGCUGCAU | 12287 |
| 5050 | AGCUUGCUC CUUCCUCA | 2876 | UGAGGAAG CUGAUGAGGCCGUUAGGCCGAA AGCAAGCU | 12288 |
| 5053 | UUGCUCCUU CCUCAUCU | 2877 | AGAUGAGG CUGAUGAGGCCGUUAGGCCGAA AGGAGCAA | 12289 |
| 5054 | UGCUCCUUC CUCAUCUC | 2878 | GAGAUGAG CUGAUGAGGCCGUUAGGCCGAA AAGGAGCA | 12290 |
| 5057 | UCCUUCCUC AUCUCUCA | 2879 | UGAGAGAU CUGAUGAGGCCGUUAGGCCGAA AGGAAGGA | 12291 |
| 5060 | UUCCUCAUC UCUCAGGC | 2880 | GCCUGAGA CUGAUGAGGCCGUUAGGCCGAA AUGAGGAA | 12292 |
| 5062 | CCUCAUCUC UCAGGCUG | 2881 | CAGCCUGA CUGAUGAGGCCGUUAGGCCGAA AGAUGAGG | 12293 |
| 5064 | UCAUCUCUC AGGCUGUG | 2882 | CACAGCCU CUGAUGAGGCCGUUAGGCCGAA AGAGAUGA | 12294 |
| 5076 | CUGUGCCUU AAUUCAGA | 2883 | UCUGAAUU CUGAUGAGGCCGUUAGGCCGAA AGGCACAG | 12295 |
| 5077 | UGUGCCUUA AUUCAGAA | 2884 | UUCUGAAU CUGAUGAGGCCGUUAGGCCGAA AAGGCACA | 12296 |
| 5080 | GCCUUAAUU CAGAACAC | 2885 | GUGUUCUG CUGAUGAGGCCGUUAGGCCGAA AUUAAGGC | 12297 |
| 5081 | CCUUAAUUC AGAACACC | 2886 | GGUGUUCU CUGAUGAGGCCGUUAGGCCGAA AAUUAAGG | 12298 |
| 5105 | AGGAACGUC GGCAGAGG | 2887 | CCUCUGCC CUGAUGAGGCCGUUAGGCCGAA ACGUUCCU | 12299 |
| 5116 | CAGAGGCUC UGACGGG | 2888 | CCCGUCAG CUGAUGAGGCCGUUAGGCCGAA AGCCUCUG | 12300 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 5135 | CGAAGAAUU GUGAGAAC | 2889 | GUUCUCAC CUGAUGAGGCCGUUAGGCCGAA AUUCUUCG | 12301 |
| 5156 | CAGAAACUC AGGGUUUC | 2890 | GAAACCCU CUGAUGAGGCCGUUAGGCCGAA AGUUUCUG | 12302 |
| 5162 | CUCAGGGUU UCUGCUGG | 2891 | CCAGCAGA CUGAUGAGGCCGUUAGGCCGAA ACCCUGAG | 12303 |
| 5163 | UCAGGGUUU CUGCUGGG | 2892 | CCCAGCAG CUGAUGAGGCCGUUAGGCCGAA AACCCUGA | 12304 |
| 5164 | CAGGGUUUC UGCUGGGU | 2893 | ACCCAGCA CUGAUGAGGCCGUUAGGCCGAA AAACCCUG | 12305 |
| 5203 | UGGCAGGUC UGAGGGUU | 2894 | AACCCUCA CUGAUGAGGCCGUUAGGCCGAA ACCUGCCA | 12306 |
| 5211 | CUGAGGGUU CUCUGUCA | 2895 | UGACAGAG CUGAUGAGGCCGUUAGGCCGAA ACCCUCAG | 12307 |
| 5212 | UGAGGGUUC UCUGUCAA | 2896 | UUGACAGA CUGAUGAGGCCGUUAGGCCGAA AACCCUCA | 12308 |
| 5214 | AGGGUUCUC UGUCAAGU | 2897 | ACUUGACA CUGAUGAGGCCGUUAGGCCGAA AGAACCCU | 12309 |
| 5218 | UUCUCUGUC AAGUGGCG | 2898 | CGCCACUU CUGAUGAGGCCGUUAGGCCGAA ACAGAGAA | 12310 |
| 5229 | GUGGCGGUA AAGGCUCA | 2899 | UGAGCCUU CUGAUGAGGCCGUUAGGCCGAA ACCGCCAC | 12311 |
| 5236 | UAAAGGCUC AGGCUGGU | 2900 | ACCAGCCU CUGAUGAGGCCGUUAGGCCGAA AGCCUUUA | 12312 |
| 5247 | GCUGGUGUU CUUCCUCU | 2901 | AGAGGAAG CUGAUGAGGCCGUUAGGCCGAA ACACCAGC | 12313 |
| 5248 | CUGGUGUUC UUCCUCUA | 2902 | UAGAGGAA CUGAUGAGGCCGUUAGGCCGAA AACACCAG | 12314 |
| 5250 | GGUGUUCUU CCUCUAUC | 2903 | GAUAGAGG CUGAUGAGGCCGUUAGGCCGAA AGAACACC | 12315 |
| 5251 | GUGUUCUUC CUCUAUCU | 2904 | AGAUAGAG CUGAUGAGGCCGUUAGGCCGAA AAGAACAC | 12316 |
| 5254 | UUCUUCCUC UAUCUCCA | 2905 | UGGAGAUA CUGAUGAGGCCGUUAGGCCGAA AGGAAGAA | 12317 |
| 5256 | CUUCCUCUA UCUCCACU | 2906 | AGUGGAGA CUGAUGAGGCCGUUAGGCCGAA AGAGGAAG | 12318 |
| 5258 | UCCUCUAUC UCCACUCC | 2907 | GGAGUGGA CUGAUGAGGCCGUUAGGCCGAA AUAGAGGA | 12319 |
| 5260 | CUCUAUCUC CACUCCUG | 2908 | CAGGAGUG CUGAUGAGGCCGUUAGGCCGAA AGAUAGAG | 12320 |
| 5265 | UCCCACUC CUGUCAGG | 2909 | CCUGACAG CUGAUGAGGCCGUUAGGCCGAA AGUGGAGA | 12321 |
| 5270 | ACUCCUGUC AGGCCCCC | 2910 | GGGGGCCU CUGAUGAGGCCGUUAGGCCGAA ACAGGAGU | 12322 |
| 5283 | CCCCAAGUC UCAGUAU | 2911 | AUACUGAG CUGAUGAGGCCGUUAGGCCGAA ACUUGGGG | 12323 |
| 5286 | CAAGUCCUC AGUAUUUU | 2912 | AAAAUACU CUGAUGAGGCCGUUAGGCCGAA AGGACUUG | 12324 |
| 5290 | UCCUCAGUA UUUUAGCU | 2913 | AGCUAAAA CUGAUGAGGCCGUUAGGCCGAA ACUGAGGA | 12325 |
| 5292 | CUCAGUAUU UUAGCUUU | 2914 | AAAGCUAA CUGAUGAGGCCGUUAGGCCGAA AUACUGAG | 12326 |
| 5293 | UCAGUAUUU UAGCUUUG | 2915 | CAAAGCUA CUGAUGAGGCCGUUAGGCCGAA AAUACUGA | 12327 |
| 5294 | CAGUAUUUU AGCUUUGU | 2916 | ACAAAGCU CUGAUGAGGCCGUUAGGCCGAA AAAUACUG | 12328 |
| 5295 | AGUAUUUUA GCUUUGUG | 2917 | CACAAAGC CUGAUGAGGCCGUUAGGCCGAA AAAAUACU | 12329 |
| 5299 | UUUUAGCUU UGUGGCUU | 2918 | AAGCCACA CUGAUGAGGCCGUUAGGCCGAA AGCUAAAA | 12330 |
| 5300 | UUUAGCUUU GUGGCUUC | 2919 | GAAGCCAC CUGAUGAGGCCGUUAGGCCGAA AAGCUAAA | 12331 |
| 5307 | UUGUGGCUU CCUGAUGG | 2920 | CCAUCAGG CUGAUGAGGCCGUUAGGCCGAA AGCCACAA | 12332 |
| 5308 | UGUGGCUUC CUGAUGGC | 2921 | GCCAUCAG CUGAUGAGGCCGUUAGGCCGAA AAGCCACA | 12333 |
| 5325 | AGAAAAAUC UUAAUUGG | 2922 | CCAAUUAA CUGAUGAGGCCGUUAGGCCGAA AUUUUUCU | 12334 |
| 5327 | AAAAAUCUU AAUUGGUU | 2923 | AACCAAUU CUGAUGAGGCCGUUAGGCCGAA AGAUUUUU | 12335 |
| 5328 | AAAAUCUUA AUUGGUUG | 2924 | CAACCAAU CUGAUGAGGCCGUUAGGCCGAA AAGAUUUU | 12336 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 5331 | AUCUUAAUU GGUUGGUU | 2925 | AACCAACC CUGAUGAGGCCGUUAGGCCGAA AUUAAGAU | 12337 |
| 5335 | UAAUUGGUU GGUUUGCU | 2926 | AGCAAACC CUGAUGAGGCCGUUAGGCCGAA ACCAAUUA | 12338 |
| 5339 | UGGUUGGUU UGCUCUCC | 2927 | GGAGAGCA CUGAUGAGGCCGUUAGGCCGAA ACCAACCA | 12339 |
| 5340 | GGUUGGUUU GCUCUCCA | 2928 | UGGAGAGC CUGAUGAGGCCGUUAGGCCGAA AACCAACC | 12340 |
| 5344 | GGUUUGCUC UCCAGAUA | 2929 | UAUCUGGA CUGAUGAGGCCGUUAGGCCGAA AGCAAACC | 12341 |
| 5346 | UUUGCUCUC CAGAUAAU | 2930 | AUUAUCUG CUGAUGAGGCCGUUAGGCCGAA AGAGCAAA | 12342 |
| 5352 | CUCCAGAUA AUCACUAG | 2931 | CUAGUGAU CUGAUGAGGCCGUUAGGCCGAA AUCUGGAG | 12343 |
| 5355 | CAGAUAAUC ACUAGCCA | 2932 | UGGCUAGU CUGAUGAGGCCGUUAGGCCGAA AUUAUCUG | 12344 |
| 5359 | UAAUCACUA GCCAGAUU | 2933 | AAUCUGGC CUGAUGAGGCCGUUAGGCCGAA AGUGAUUA | 12345 |
| 5367 | AGCCAGAUU UCGAAAUU | 2934 | AAUUUCGA CUGAUGAGGCCGUUAGGCCGAA AUCUGGCU | 12346 |
| 5368 | GCCAGAUUU CGAAAUUA | 2935 | UAAUUUCG CUGAUGAGGCCGUUAGGCCGAA AAUCUGGC | 12347 |
| 5369 | CCAGAUUUC GAAAUUAC | 2936 | GUAAUUUC CUGAUGAGGCCGUUAGGCCGAA AAAUCUGG | 12348 |
| 5375 | UUCGAAAUU ACUUUUUA | 2937 | UAAAAAGU CUGAUGAGGCCGUUAGGCCGAA AUUUCGAA | 12349 |
| 5376 | UCGAAAUUA CUUUUUAG | 2938 | CUAAAAAG CUGAUGAGGCCGUUAGGCCGAA AAUUUCGA | 12350 |
| 5379 | AAAUUACUU UUAGCCG | 2939 | CGGCUAAA CUGAUGAGGCCGUUAGGCCGAA AGUAAUUU | 12351 |
| 5380 | AAUUACUUU UUAGCCGA | 2940 | UCGGCUAA CUGAUGAGGCCGUUAGGCCGAA AAGUAAUU | 12352 |
| 5381 | AUUACUUUU UAGCCGAG | 2941 | CUCGGCUA CUGAUGAGGCCGUUAGGCCGAA AAAGUAAU | 12353 |
| 5382 | UUACUUUUU AGCCGAGG | 2942 | CCUCGGCU CUGAUGAGGCCGUUAGGCCGAA AAAAGUAA | 12354 |
| 5383 | UACUUUUUA GCCGAGGU | 2943 | ACCUCGGC CUGAUGAGGCCGUUAGGCCGAA AAAAAGUA | 12355 |
| 5392 | GCCGAGGUU AUGAUAAC | 2944 | GUUAUCAU CUGAUGAGGCCGUUAGGCCGAA ACCUCGGC | 12356 |
| 5393 | CCGAGGUUA UGAUAACA | 2945 | UGUUAUCA CUGAUGAGGCCGUUAGGCCGAA AACCUCGG | 12357 |
| 5398 | GUUAUGAUA ACAUCUAC | 2946 | GUAGAUGU CUGAUGAGGCCGUUAGGCCGAA AUCAUAAC | 12358 |
| 5403 | GAUAACAUC UACGUAU | 2947 | AUACAGUA CUGAUGAGGCCGUUAGGCCGAA AUGUUAUC | 12359 |
| 5405 | UAACAUCUA CUGUAUCC | 2948 | GGAUACAG CUGAUGAGGCCGUUAGGCCGAA AGAUGUUA | 12360 |
| 5410 | UCUACUGUA UCCUUUAG | 2949 | CUAAAGGA CUGAUGAGGCCGUUAGGCCGAA ACAGUAGA | 12361 |
| 5412 | UACUGUAUC CUUUAGAA | 2950 | UUCUAAAG CUGAUGAGGCCGUUAGGCCGAA AUACAGUA | 12362 |
| 5415 | UGUACCUU UAGAAUUU | 2951 | AAAUUCUA CUGAUGAGGCCGUUAGGCCGAA AGGAUACA | 12363 |
| 5416 | GUAUCCUUU AGAAUUUU | 2952 | AAAAUUCU CUGAUGAGGCCGUUAGGCCGAA AAGGAUAC | 12364 |
| 5417 | UAUCCUUUA GAAUUUUA | 2953 | UAAAAUUC CUGAUGAGGCCGUUAGGCCGAA AAAGGAUA | 12365 |
| 5422 | UUUAGAAUU UUAACCUA | 2954 | UAGGUUAA CUGAUGAGGCCGUUAGGCCGAA AUUCUAAA | 12366 |
| 5423 | UUAGAAUUU UAACCUAU | 2955 | AUAGGUUA CUGAUGAGGCCGUUAGGCCGAA AAUUCUAA | 12367 |
| 5424 | UAGAAUUUU AACCUAUA | 2956 | UAUAGGUU CUGAUGAGGCCGUUAGGCCGAA AAAUUCUA | 12368 |
| 5425 | AGAAUUUUA ACCUAUAA | 2957 | UUAUAGGU CUGAUGAGGCCGUUAGGCCGAA AAAAUUCU | 12369 |
| 5430 | UUUAACCUA UAAACUA | 2958 | UAGUUUUA CUGAUGAGGCCGUUAGGCCGAA AGGUUAAA | 12370 |
| 5432 | UAACCUAUA AAACUAUG | 2959 | CAUAGUUU CUGAUGAGGCCGUUAGGCCGAA AUAGGUUA | 12371 |
| 5438 | AUAAACUA UGUCUACU | 2960 | AGUAGACA CUGAUGAGGCCGUUAGGCCGAA AGUUUUAU | 12372 |
| 5442 | AACUAUGUC UACGGUU | 2961 | AACCAGUA CUGAUGAGGCCGUUAGGCCGAA ACAUAGUU | 12373 |

TABLE VI-continued

Mouse flk-1 VEGF Receptor-Hammerhead Ribozyme and Substrate Sequence

| Pos | Substrate | Seq ID No | HH Ribozyme Sequence | Seq ID No |
|---|---|---|---|---|
| 5444 | CUAUGUCUA CUGGUUUC | 2962 | GAAACCAG CUGAUGACgccguuaggcCGAA AGACAUAG | 12374 |
| 5450 | CUACUGGUU UCUGCCUG | 2963 | CAGGCAGA CUGAUGAGgccguuaggcCGAA ACCAGUAG | 12375 |
| 5451 | UACUGGUUU CUGCCUGU | 2964 | ACAGGCAG CUGAUGAGgccguuaggcCGAA AACCAGUA | 12376 |
| 5452 | ACUGGUUUC UGCCUGUG | 2965 | CACAGGCA CUGAUGAGgccguuaggcCGAA AAACCAGU | 12377 |

Where "X" represents stem II region of a HH ribozyme (Hertel et al., 1992 Nucleic Acids Res. 20 3252).
The length of stem II may be 2 base-pairs.
Underlined region can be any X sequence or linker, as described herein.

TABLE VII

Mouse flk-1 VEGF Receptor-Hairpin Ribozyme and Substrate Sequences

| Pos | Substrate | Seq ID No | HP Ribozyme Sequences | Seq ID No |
|---|---|---|---|---|
| 74 | GGGCCCA GAC UGUGUCCC | 2966 | GGGACACA AGAA GGGCCC ACCAGAGAAACACACGUUGUGGUACAUUACCUGGUA | 12378 |
| 88 | UCCCGCA GCC GGGAUAAC | 2967 | GUUAUCCC AGAA GCGGGA ACCAGAGAAACACACGUUGUGGUACAUUACCUGGUA | 12379 |
| 105 | CCUGGCU GAC CCGAUUCC | 2968 | GGAAUCGG AGAA GCCAGG ACCAGAGAAACACACGUUGUGGUACAUUACCUGGUA | 12380 |
| 110 | GUGACCC GAU UCCGCGGA | 2969 | UCCGCGGA AGAA GGUCAG ACCAGAGAAACACACGUUGUGGUACAUUACCUGGUA | 12381 |
| 125 | GGACACC GCU GACAGCCG | 2970 | GGGCUGUC AGAA GUGUGC ACCAGAGAAACACACGUUGUGGUACAUUACCUGGUA | 12382 |
| 132 | GCUGACA GCC GCGGCUGG | 2971 | CCAGCCGC AGAA GUCAGC ACCAGAGAAACACACGUUGUGGUACAUUACCUGGUA | 12383 |
| 138 | AGCCGCG GCU GGAGCCAG | 2972 | CUGGCUCC AGAA GCGGCU ACCAGAGAAACACACGUUGUGGUACAUUACCUGGUA | 12384 |
| 175 | CUCCCCG GUC UUGCGCUG | 2973 | CAGCGCAA AGAA GGGGAG ACCAGAGAAACACACGUUGUGGUACAUUACCUGGUA | 12385 |
| 199 | CCAUACC GCC UCUGUGAC | 2974 | GUCACAGA AGAA GUAUGG ACCAGAGAAACACACGUUGUGGUACAUUACCUGGUA | 12386 |
| 309 | GCUAGCU GUC GCUCUGUG | 2975 | CACAGAGC AGAA GCUAGC ACCAGAGAAACACACGUUGUGGUACAUUACCUGGUA | 12387 |
| 342 | CCGAGCC CCC UCUGUGGG | 2976 | CCCACAGA AGAA GCUCGG ACCAGAGAAACACACGUUGUGGUACAUUACCUGGUA | 12388 |
| 434 | CCCUUCA GAU UACUUGCA | 2977 | UGCAAGUA AGAA GAAGGG ACCAGAGAAACACACGUUGUGGUACAUUACCUGGUA | 12389 |
| 630 | GUCCACU GUU UAUGUCUA | 2978 | UAGACAUA AGAA GUGGAG ACCAGAGAAACACACGUUGUGGUACAUUACCUGGUA | 12390 |
| 655 | GAUUACA GAU CACCAUUC | 2979 | GAAUGGUG AGAA GUAAUC ACCAGAGAAACACACGUUGUGGUACAUUACCUGGUA | 12391 |
| 739 | AUCCCCU GCC GAGGGUCG | 2980 | GGACCCUC AGAA GGGGAU ACCAGAGAAACACACGUUGUGGUACAUUACCUGGUA | 12392 |
| 807 | UGUUCCG GAU GGAAACAG | 2981 | CUGUUUCC AGAA GGAACA ACCAGAGAAACACACGUUGUGGUACAUUACCUGGUA | 12393 |
| 920 | GCUAUCA GUC UAUCAUGU | 2982 | ACAUGAUA AGAA GAUAGG ACCAGAGAAACACACGUUGUGGUACAUUACCUGGUA | 12394 |
| 1002 | GCUAUCU GCC GGAGAAAA | 2983 | UUUUCUCC AGAA GAUAGC ACCAGAGAAACACACGUUGUGGUACAUUACCUGGUA | 12395 |
| 1229 | GUGGACG GAU GAUCAAGA | 2984 | UCUUGAUC AGAA GUCCAC ACCAGAGAAACACACGUUGUGGUACAUUACCUGGUA | 12396 |
| 1365 | UUACCCA GCU CCUGAUAU | 2985 | AUAUCAGG AGAA GGGUAA ACCAGAGAAACACACGUUGUGGUACAUUACCUGGUA | 12397 |
| 1556 | CACCCCA GAU COGUGAGA | 2986 | UCUCACCG AGAA GGGGUG ACCAGAGAAACACACGUUGUGGUACAUUACCUGGUA | 12398 |
| 1629 | AUCCACA GUC UACGCCAA | 2987 | UUGGCGUA AGAA GUGCAU ACCAGAGAAACACACGUUGUGGUACAUUACCUGGUA | 12399 |
| 1687 | GAAGCCU GCU CCUACAGA | 2988 | UCUGUAGG AGAA GGCUUC ACCAGAGAAACACACGUUGUGGUACAUUACCUGGUA | 12400 |
| 1696 | UCCUACA GAC CCGGCCAA | 2989 | UUGGCCGG AGAA GUAGGA ACCAGAGAAACACACGUUGUGGUACAUUACCUGGUA | 12401 |
| 1795 | AUGCCCU GAU UGAAGGAA | 2990 | UUCCUUCA AGAA GGGCAU ACCAGAGAAACACACGUUGUGGUACAUUACCUGGUA | 12402 |

TABLE VII-continued

Mouse flk-1 VEGF Receptor-Hairpin Ribozyme and Substrate Sequences

| Pos | Substrate | Seq ID No | HP Ribozyme Sequences | Seq ID No |
|---|---|---|---|---|
| 1950 | GCAACCU GCU GCCCAGCC | 2991 | GGCUGGGC AGAA GGUUGC ACCAGAGAAACACACGUUGUGGUACAUUACCUGGUA | 12403 |
| 1953 | ACCUGCU GCC CAGCCAAC | 2992 | GUUGGCUG AGAA GCAGGU ACCAGAGAAACACACGUUGUGGUACAUUACCUGGUA | 12404 |
| 1985 | UGUCCCU GUU GUCCACUG | 2993 | CAGUGGAC AGAA GGGACA ACCAGAGAAACACACGUUGUGGUACAUUACCUGGUA | 12405 |
| 2055 | AACAUCG GUC CACAUGGG | 2994 | CCCAUGUG AGAA GAUGUU ACCAGAGAAACACACGUUGUGGUACAUUACCUGGUA | 12406 |
| 2082 | CACACCA GUU UGCAAGAA | 2995 | UUCUUGCA AGAA GGUGUG ACCAGAGAAACACACGUUGUGGUACAUUACCUGGUA | 11606 |
| 2208 | UUGCUCU GCU CAAGAUAA | 2996 | UUAUCUUG AGAA GAGCAA ACCAGAGAAACACACGUUGUGGUACAUUACCUGGUA | 12407 |
| 2252 | UCAAACA GCU CAUCAUCC | 2997 | GGAUGAUG AGAA GUUUGA ACCAGAGAAACACACGUUGUGGUACAUUACCUGGUA | 12408 |
| 2444 | GGAACCU GAC UAUCCGCA | 2998 | UGCGGAUA AGAA GGUUCC ACCAGAGAAACACACGUUGUGGUACAUUACCUGGUA | 12409 |
| 2639 | UCCUACG GAC CGUUAAGC | 2999 | GCUUAACG AGAA GUAGGA ACCAGAGAAACACACGUUGUGGUACAUUACCUGGUA | 12410 |
| 2703 | GGAUCCA GAU GAAUUGCC | 3000 | GGCAAUUC AGAA GGAUCC ACCAGAGAAACACACGUUGUGGUACAUUACCUGGUA | 12411 |
| 2777 | GGGACCG GCU GAAACUAG | 3001 | CUAGUUUC AGAA GGUCCC ACCAGAGAAACACACGUUGUGGUACAUUACCUGGUA | 12412 |
| 2832 | UGAGGCA GAC GCUUUUGG | 3002 | CCAAAAGC AGAA GCCUCA ACCAGAGAAACACACGUUGUGGUACAUUACCUGGUA | 12413 |
| 3199 | UCUGCCA GCU CAGGCUUU | 3003 | AAAGCCUG AGAA GGCAGA ACCAGAGAAACACACGUUGUGGUACAUUACCUGGUA | 12414 |
| 3278 | ACUUCCU GAC CUUGGAGC | 2199 | GCUCCAAG AGAA GGAAGU ACCAGAGAAACACACGUUGUGGUACAUUACCUGGUA | 11618 |
| 3304 | UGUUACA GCU UCCAAGUG | 2200 | GACUUGGA AGAA GUAACA ACCAGAGAAACACACGUUGUGGUACAUUACCUGGUA | 11619 |
| 3421 | GACUUCG GCU UGGCCCGG | 3004 | CCGGGCCA AGAA GAAGUC ACCAGAGAAACACACGUUGUGGUACAUUACCUGGUA | 12415 |
| 3450 | AGACCCG GAU UAUGUCAG | 3005 | CUGACAUA AGAA GGGUCU ACCAGAGAAACACACGUUGUGGUACAUUACCUGGUA | 12416 |
| 3475 | GAUGCCC GAC UCCCUUUG | 3006 | CAAAGGGA AGAA GGCAUC ACCAGAGAAACACACGUUGUGGUACAUUACCUGGUA | 12417 |
| 3663 | GGCUCCU GAC UACACUAC | 3007 | GUAGUGUA AGAA GGAGCC ACCAGAGAAACACACGUUGUGGUACAUUACCUGGUA | 12418 |
| 3689 | UGUACCA GAC CAUGCUGG | 2203 | CCAGCAUG AGAA GGUACA ACCAGAGAAACACACGUUGUGGUACAUUACCUGGUA | 11622 |
| 3703 | CUGGACU GCU GGCAUGAG | 3008 | CUCAUGCC AGAA GUCCAG ACCAGAGAAACACACGUUGUGGUACAUUACCUGGUA | 12419 |
| 3860 | UCUCCCU GCC UACCUCAC | 3009 | GUGAGGUA AGAA GGGAGA ACCAGAGAAACACACGUUGUGGUACAUUACCUGGUA | 12420 |
| 3873 | CUCACCU GUU UCCUGUAU | 2205 | AUACAGGA AGAA GGUGAG ACCAGAGAAACACACGUUGUGGUACAUUACCUGGUA | 11625 |
| 4038 | GAUCCCA GAU GACAGCCA | 3010 | UGGCUGUC AGAA GGGAUC ACCAGAGAAACACACGUUGUGGUACAUUACCUGGUA | 12421 |
| 4181 | CCAACCA GAC CAGUGGCU | 3011 | AGCCACUG AGAA GGUUGG ACCAGAGAAACACACGUUGUGGUACAUUACCUGGUA | 12422 |
| 4196 | GCUACCA GUC UGGGUAUC | 3012 | GAUACCCA AGAA GGUAGC ACCAGAGAAACACACGUUGUGGUACAUUACCUGGUA | 12423 |
| 4212 | UCACUCA GAU GACACAGA | 3013 | UCUGUGUC AGAA GAGUGA ACCAGAGAAACACACGUUGUGGUACAUUACCUGGUA | 11630 |
| 4278 | UGCUGCA GUC CACGCUGA | 3014 | UCAGCGUG AGAA GCAGCA ACCAGAGAAACACACGUUGUGGUACAUUACCUGGUA | 12424 |
| 4287 | UCACGCU GAC UCAGGGAC | 3015 | GUCCCUGA AGAA GCGUGA ACCAGAGAAACACACGUUGUGGUACAUUACCUGGUA | 12425 |
| 4307 | CACUGCA GCU CACCUCCU | 3015 | AGGAGGUG AGAA GCAGUG ACCAGAGAAACACACGUUGUGGUACAUUACCUGGUA | 12426 |
| 4318 | ACCUCCU GUU UAAAUGGA | 3017 | UCCAUUUA AGAA GGAGGU ACCAGAGAAACACACGUUGUGGUACAUUACCUGGUA | 12427 |
| 4338 | UGGUCCU GUC CCGGCUCC | 3018 | GGAGCCGG AGAA GGACCA ACCAGAGAAACACACGUUGUGGUACAUUACCUGGUA | 12428 |
| 4344 | UGUCCCG GCU CCGCCCCC | 3019 | GGGGGCGG AGAA GGGACA ACCAGAGAAACACACGUUGUGGUACAUUACCUGGUA | 12429 |
| 4349 | CGGCUCC GCC CCCAACUC | 3020 | GAGUUGGG AGAA GAGCCG ACCAGAGAAACACACGUUGUGGUACAUUACCUGGUA | 12430 |
| 4383 | AGGUGCU GCU UAGAUUUU | 3021 | AAAAUCUA AGAA GCACCU ACCAGAGAAACACACGUUGUGGUACAUUACCUGGUA | 12431 |
| 4462 | GACCUCA GAC UGCAAGGA | 3022 | UCCUUGCA AGAA GAGGUC ACCAGAGAAACACACGUUGUGGUACAUUACCUGGUA | 12432 |

TABLE VII-continued

Mouse flk-1 VEGF Receptor-Hairpin Ribozyme and Substrate Sequences

| Pos | Substrate | Seq ID No | HP Ribozyme Sequences | Seq ID No |
|---|---|---|---|---|
| 4574 | GUGCCCU GCU GUGGUCUC | 3023 | GAGACCAC AGAA GGGCAC ACCAGAGAAACACACGUUGUGGUACAUUACCUGGUA | 12433 |
| 4626 | GGACUCU GUC CUCCAAGA | 3024 | UCUUGGAG AGAA GAGUCC ACCAGAGAAACACACGUUGUGGUACAUUACCUGGUA | 12434 |
| 4723 | CGAGUCU GUC UACCUUGG | 3025 | CCAAGGUA AGAA GACUCG ACCAGAGAAACACACGUUGUGGUACAUUACCUGGUA | 12435 |
| 4823 | GAGAGCG GUU GGAGCCUG | 3026 | CAGGCUCC AGAA GCUCUC ACCAGAGAAACACACGUUGUGGUACAUUACCUGGUA | 12436 |
| 4836 | GCCUGCA GAU GCAUUGUG | 3027 | CACAAUGC AGAA GCAGGC ACCAGAGAAACACACGUUGUGGUACAUUACCUGGUA | 12437 |
| 4895 | AAAGGCG CCC GGCAGGGU | 3028 | ACCCUGCC AGAA CCCUUU ACCAGAGAAACACACGUUGUGGUACAUUACCUGGUA | 12438 |
| 4938 | CUUCACA GUC GGGUUACA | 3029 | UGUAACCC AGAA GUGAAG ACCAGAGAAACACACGUUGUGGUACAUUACCUGGUA | 12439 |
| 4996 | CCUUCCG GAC UCUUACGU | 3030 | ACGUAAGA AGAA GGAAGG ACCAGAGAAACACACGUUGUGGUACAUUACCUGGUA | 12440 |
| 5042 | UGAUCCA GCU UGCUCCUU | 3031 | AAGGAGCA AGAA GCAUCA ACCAGAGAAACACACGUUGUGGUACAUUACCUGGUA | 12441 |
| 5118 | GGCUCCU GAC GGGGCCGA | 3032 | UCGGCCCC AGAA GGAGCC ACCAGAGAAACACACGUUGUGGUACAUUACCUGGUA | 12442 |
| 5165 | GGUUUCU GCU GUGUGGAG | 3033 | CUCCACCC AGAA GAAACC ACCAGAGAAACACACGUUGUGGUACAUUACCUGGUA | 12443 |
| 5310 | GCUUCCU GAU GGCAGAAA | 3034 | UUUCUGCC AGAA GGAAGC ACCAGAGAAACACACGUUGUGGUACAUUACCUGGUA | 12444 |
| 5363 | CUAGCCA GAU UUCGAAAU | 3035 | AUUUCGAA AGAA GGCUAG ACCAGAGAAACACACGUUGUGGUACAUUACCUGGUA | 12445 |
| 5453 | GGUUUCU CCC UGUGUGCU | 3035 | AGCACACA AGAA GAAACC ACCAGAGAAACACACGUUGUGGUACAUUACCUGGUA | 12446 |

TABLE VIII

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 17 | GGCCGCGUC UUGCUCAC | 3037 | GUGAGCAA CUGAUGAGGCCGUUAGGCCGAA ACGCGGCC | 12447 |
| 19 | CCGCGUCUU GCUCACCA | 3038 | UGGUGAGC CUGAUGAGGCCGUUAGGCCGAA AGACGCGG | 12448 |
| 23 | GUCUUGCUC ACCAUGGU | 3039 | ACCAUGGU CUGAUGAGGCCGUUAGGCCGAA AGCAAGAC | 12449 |
| 32 | ACCAUGGUC AGCUGCUG | 3040 | CAGCAGCU CUGAUGAGGCCGUUAGGCCGAA ACCAUGGU | 12450 |
| 53 | ACCGCGGUC UUGCCUUA | 3041 | UAAGGCAA CUGAUGAGGCCGUUAGGCCGAA ACCGCGGU | 12451 |
| 55 | CGCGGUCUU GCCUUACG | 3042 | CGUAAGGC CUGAUGAGGCCGUUAGGCCGAA AGACCGCG | 12452 |
| 60 | UCUUGCCUU ACGCGCUG | 3043 | CAGCGCGU CUGAUGAGGCCGUUAGGCCGAA AGGCAAGA | 12453 |
| 61 | CUUGCCUUA CGCGCUGC | 3044 | GCAGCGCG CUGAUGAGGCCGUUAGGCCGAA AAGGCAAG | 12454 |
| 71 | GCGCUGCUC GGGUGUCU | 3045 | AGACACCC CUGAUGAGGCCGUUAGGCCGAA AGCAGCGC | 12455 |
| 78 | UCGGGUGUC UGCUUCUC | 3046 | GAGAAGCA CUGAUGAGGCCGUUAGGCCGAA ACACCCGA | 12456 |
| 83 | UGUCUGCUU CUCACAGG | 25 | CCUGUGAG CUGAUGAGGCCGUUAGGCCGAA AGCAGACA | 9444 |
| 84 | GUCUGCUUC UCACAGGA | 26 | UCCUGUGA CUGAUGAGGCCGUUAGGCCGAA AAGCAGAC | 9445 |
| 86 | CUGCUUCUC ACAGGAUA | 3047 | UAUCCUGU CUGAUGAGGCCGUUAGGCCGAA AGAAGCAG | 12457 |
| 94 | CACAGGAUA UGGCUCAG | 3048 | CUGAGCCA CUGAUGAGGCCGUUAGGCCGAA AUCCUGUG | 12458 |
| 100 | AUAUGGCUC AGGGUCGA | 3049 | UCGACCCU CUGAUGAGGCCGUUAGGCCGAA AGCCAUAU | 12459 |
| 106 | CUCAGGGUC GAAGUUAA | 3050 | UUAACUUC CUGAUGAGGCCGUUAGGCCGAA ACCCUGAG | 12460 |
| 112 | GUCGAAGUU AAAAGUGC | 3051 | GCACUUUU CUGAUGAGGCCGUUAGGCCGAA ACUUCGAC | 12461 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 113 | UCGAAGUUA AAAGUGCC | 3052 | GGCACUUU CUGAUGAGGCCGUUAGGCCGAA AACUUCGA | 12462 |
| 132 | AACUGAGUU UAAAAGGC | 37 | GCCUUUUA CUGAUGAGGCCGUUAGGCCGAA ACUCAGUU | 9456 |
| 133 | ACUGAGUUU AAAAGGCA | 38 | UGCCUUUU CUGAUGAGGCCGUUAGGCCGAA AACUCAGU | 9457 |
| 134 | CUGAGUUUA AAGGCAC | 39 | GUGCCUUU CUGAUGAGGCCGUUAGGCCGAA AAACUCAG | 9458 |
| 152 | CAGCAUGUC AUGCAAGC | 3053 | GCUUGCAU CUGAUGAGGCCGUUAGGCCGAA ACAUGCUG | 12463 |
| 171 | GCCAGACUC UCUUUCUC | 3054 | GAGAAAGA CUGAUGAGGCCGUUAGGCCGAA AGUCUGGC | 12464 |
| 173 | CAGACUCUC UUUCUCAA | 3055 | UUGAGAAA CUGAUGAGGCCGUUAGGCCGAA AGAGUCUG | 12465 |
| 175 | GACUCUCUU UCUCAAGU | 3056 | ACUUGAGA CUGAUGAGGCCGUUAGGCCGAA AGAGAGUC | 12466 |
| 176 | ACUCUCUUU CUCAAGUG | 3057 | CACUUGAG CUGAUGAGGCCGUUAGGCCGAA AAGAGAGU | 12467 |
| 177 | CUCUCUUUC UCAAGUGC | 3058 | GCACUUGA CUGAUGAGGCCGUUAGGCCGAA AAAGAGAG | 12468 |
| 179 | CUCUUUCUC AAGUGCAG | 3059 | CUGCACUU CUGAUGAGGCCGUUAGGCCGAA AGAAAGAG | 12469 |
| 205 | AGCCCACUC AUGGUCUC | 3060 | GAGACCAU CUGAUGAGGCCGUUAGGCCGAA AGUGGGCU | 12470 |
| 211 | CUCAUGGUC UCUGCCCA | 3061 | UGGGCAGA CUGAUGAGGCCGUUAGGCCGAA ACCAUGAG | 12471 |
| 213 | CAUGGUCUC UGCCCACG | 3062 | CGUGGGCA CUGAUGAGGCCGUUAGGCCGAA AGACCAUG | 12472 |
| 254 | CUGAGCAUC ACUCCCCC | 3063 | GGGGGAGU CUGAUGAGGCCGUUAGGCCGAA AUGCUCAG | 12473 |
| 258 | GCAUCACUC CCCAUCG | 3064 | CGAUGGGG CUGAUGAGGCCGUUAGGCCGAA AGUGAUGC | 12474 |
| 265 | UCCCCAUC GGCCUGUG | 3065 | CACAGGCC CUGAUGAGGCCGUUAGGCCGAA AUGGGGA | 12475 |
| 282 | GGAGGGAUA ACAGGCAA | 3066 | UUGCCUGU CUGAUGAGGCCGUUAGGCCGAA AUCCCUCC | 12476 |
| 292 | CAGGCAAUU CUGCAGCA | 3067 | UGCUGCAG CUGAUGAGGCCGUUAGGCCGAA AUUGCCUG | 12477 |
| 293 | AGGCAAUUC UGCAGCAC | 3068 | GUGCUGCA CUGAUGAGGCCGUUAGGCCGAA AAUUGCCU | 12478 |
| 304 | CAGCACCUU GACCUUGG | 3069 | CCAAGGUC CUGAUGAGGCCGUUAGGCCGAA AGGUGCUG | 12479 |
| 310 | CUUGACCUU GGACACGG | 3070 | CCGUGUCC CUGAUGAGGCCGUUAGGCCGAA AGGUCAAG | 12480 |
| 341 | ACGGCCUC UACACCUG | 3071 | CAGGUGUA CUGAUGAGGCCGUUAGGCCGAA AGGCCCGU | 12481 |
| 343 | GGCCUCUA CACCUGUA | 3072 | UACAGGUG CUGAUGAGGCCGUUAGGCCGAA AGAGGCCC | 12482 |
| 351 | ACACCUGUA GAUACCUC | 3073 | GAGGUAUC CUGAUGAGGCCGUUAGGCCGAA ACAGGUGU | 12483 |
| 355 | CUGUAGAUA CCUCCCUA | 3074 | UAGGGAGG CUGAUGAGGCCGUUAGGCCGAA AUCUACAG | 12484 |
| 359 | AGAUACCUC CUACAUC | 3075 | GAUGUAGG CUGAUGAGGCCGUUAGGCCGAA AGGUAUCU | 12485 |
| 363 | ACCUCCCUA CAUCUACU | 3076 | AGUAGAUG CUGAUGAGGCCGUUAGGCCGAA AGGGAGGU | 12486 |
| 367 | CCCUACAUC UACUUCGA | 3077 | UCGAAGUA CUGAUGAGGCCGUUAGGCCGAA AUGUAGGG | 12487 |
| 369 | CUACAUCUA CUUCGAAG | 3078 | CUUCGAAG CUGAUGAGGCCGUUAGGCCGAA AGAUGUAG | 12488 |
| 372 | CAUCUACUU CGAAGAAA | 3079 | UUUCUUCG CUGAUGAGGCCGUUAGGCCGAA AGUAGAUG | 12489 |
| 373 | AUCUACUUC GAAGAAAA | 3080 | UUUUCUUC CUGAUGAGGCCGUUAGGCCGAA AAGUAGAU | 12490 |
| 394 | AGCGGAAUC UUCAAUCU | 3081 | AGAUUGAA CUGAUGAGGCCGUUAGGCCGAA AUUCCGCU | 12491 |
| 396 | CGGAAUCUU CAAUCUAC | 3082 | GUAGAUUG CUGAUGAGGCCGUUAGGCCGAA AGAUUCCG | 12492 |
| 397 | GGAAUCUUC AAUCUACA | 3083 | UGUAGAUU CUGAUGAGGCCGUUAGGCCGAA AAGAUUCC | 12493 |
| 401 | UCUUCAAUC UACAUAUU | 3084 | AAUAUGUA CUGAUGAGGCCGUUAGGCCGAA AUUGAAGA | 12494 |
| 403 | AUCAAUCUA CAUAUUUG | 3085 | CAAAUAUG CUGAUGAGGCCGUUAGGCCGAA AGAUUGAA | 12495 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 407 | AUCUACAUA UUUGUUAG | 3086 | CUAACAAA CUGAUGAGGCCGUUAGGCCGAA AUGUAGAU | 12496 |
| 409 | CUACAUAUU UGUUAGUG | 3087 | CACUAACA CUGAUGAGGCCGUUAGGCCGAA AUAUGUAG | 12497 |
| 410 | UACAUAUUU GUUAGUGA | 3088 | UCACUAAC CUGAUGAGGCCGUUAGGCCGAA AAUAUGUA | 12498 |
| 413 | AUAUUUGUU AGUGAUGC | 3089 | GCAUCACU CUGAUGAGGCCGUUAGGCCGAA ACAAAUAU | 12499 |
| 414 | UAUUUGUUA GUGAUGCA | 3090 | UGCAUCAC CUGAUGAGGCCGUUAGGCCGAA AACAAAUA | 12500 |
| 429 | CAGGGAGUC CUUUCAUA | 3091 | UAUGAAAG CUGAUGAGGCCGUUAGGCCGAA ACUCCCUG | 12501 |
| 432 | GGAGUCCUU UCAUAGAG | 3092 | CUCUAUGA CUGAUGAGGCCGUUAGGCCGAA AGGACUCC | 12502 |
| 433 | GAGUCCUUU CAUAGAGA | 3093 | UCUCUAUG CUGAUGAGGCCGUUAGGCCGAA AAGGACUC | 12503 |
| 434 | AGUCCUUUC AUAGAGAU | 3094 | AUCUCUAU CUGAUGAGGCCGUUAGGCCGAA AAAGGACU | 12504 |
| 437 | CCUUUCAUA GAGAUGCA | 3095 | UGCAUCUC CUGAUGAGGCCGUUAGGCCGAA AUGAAAGG | 12505 |
| 455 | ACUGACAUA CCCAAACU | 3096 | AGUUUGGG CUGAUGAGGCCGUUAGGCCGAA AUGUCAGU | 12506 |
| 464 | CCCAAACUU GUGCACAU | 3097 | AUGUGCAC CUGAUGAGGCCGUUAGGCCGAA AGUUUGGG | 12507 |
| 491 | AGACAGCUC AUCAUCCC | 3098 | GGGAUGAU CUGAUGAGGCCGUUAGGCCGAA AGCUGUCU | 12508 |
| 494 | CAGCUCAUC AUCCCCUG | 3099 | CAGGGGAU CUGAUGAGGCCGUUAGGCCGAA AUGAGCUG | 12509 |
| 497 | CUCAUCAUC CCCUGCCG | 3100 | CGGCAGGG CUGAUGAGGCCGUUAGGCCGAA AUGAUGAG | 12510 |
| 514 | GGUGACGUC ACCCAACG | 3101 | CGUUGGGU CUGAUGAGGCCGUUAGGCCGAA ACGUCACC | 12511 |
| 524 | CCCAACGUC ACAGUCAC | 3102 | GUGACUGU CUGAUGAGGCCGUUAGGCCGAA ACGUUGGG | 12512 |
| 530 | GUCACAGUC ACCCUAAA | 3103 | UUUAGGGU CUGAUGAGGCCGUUAGGCCGAA ACUGUGAC | 12513 |
| 536 | GUCACCCUA AAAAAGUU | 3104 | AACUUUUU CUGAUGAGGCCGUUAGGCCGAA AGGGUGAC | 12514 |
| 544 | AAAAAGUU UCCAUUUG | 3105 | CAAAUGGA CUGAUGAGGCCGUUAGGCCGAA ACUUUUUU | 12515 |
| 545 | AAAAAGUUU CCAUUUGA | 3106 | UCAAAUGG CUGAUGAGGCCGUUAGGCCGAA AACUUUUU | 12516 |
| 546 | AAAGUUUC CAUUUGAU | 3107 | AUCAAAUG CUGAUGAGGCCGUUAGGCCGAA AAACUUUU | 12517 |
| 550 | GUUUCCAUU UGAUACUC | 3108 | GAGUAUCA CUGAUGAGGCCGUUAGGCCGAA AUGGAAAC | 12518 |
| 551 | UUUCCAUUU GAUACUCU | 3109 | AGAGUAUC CUGAUGAGGCCGUUAGGCCGAA AAUGGAAA | 12519 |
| 555 | CAUUUGAUA CUCUUACC | 3110 | GGUAAGAG CUGAUGAGGCCGUUAGGCCGAA AUCAAAUG | 12520 |
| 558 | UUGAUACUC UUACCCCU | 3111 | AGGGGUAA CUGAUGAGGCCGUUAGGCCGAA AGUAUCAA | 12521 |
| 560 | GAUACUCUU ACCCUGA | 3112 | UCAGGGGU CUGAUGAGGCCGUUAGGCCGAA AGAGUAUC | 12522 |
| 561 | AUACUCUUA CCCUGAU | 3113 | AUCAGGGG CUGAUGAGGCCGUUAGGCCGAA AAGAGUAU | 12523 |
| 581 | CAAAGAAUA ACAUGGGA | 3114 | UCCCAUGU CUGAUGAGGCCGUUAGGCCGAA AUUCUUUG | 12524 |
| 594 | GGGACAGUA GGAGAGGC | 3115 | GCCUCUCC CUGAUGAGGCCGUUAGGCCGAA ACUGUCCC | 12525 |
| 604 | GAGAGGCUU UAUAAUAG | 3116 | CUAUUAUA CUGAUGAGGCCGUUAGGCCGAA AGCCUCUC | 12526 |
| 605 | AGAGGCUUU AUAAUAGC | 3117 | GCUAUUAU CUGAUGAGGCCGUUAGGCCGAA AAGCCUCU | 12527 |
| 606 | GAGGCUUUA UAAUAGCA | 3118 | UGCUAUUA CUGAUGAGGCCGUUAGGCCGAA AAAGCCUC | 12528 |
| 608 | GGCUUUAUA AUAGCAAA | 3119 | UUUGCUAU CUGAUGAGGCCGUUAGGCCGAA AUAAAGCC | 12529 |
| 611 | UUUAUAAUA GCAAAUGC | 3120 | GCAUUUGC CUGAUGAGGCCGUUAGGCCGAA AUUAUAAA | 12530 |
| 625 | UGCAACGUA CAAAGAGA | 3121 | UCUCUUUG CUGAUGAGGCCGUUAGGCCGAA ACGUUGCA | 12531 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|-----|-----------|-----------|----------------------|-----------|
| 635 | AAAGAGAUA GGACUGCU | 3122 | AGCAGUCC CUGAUGAGGCCGUUAGGCCGAA AUCUCUUU | 12532 |
| 662 | GCCACCGUC AACGGGCA | 3123 | UGCCCGUU CUGAUGAGGCCGUUAGGCCGAA ACGCUGGC | 12533 |
| 676 | GCACCUGUA CCAGACAA | 3124 | UUGUCUGG CUGAUGAGGCCGUUAGGCCGAA ACAGGUGC | 12534 |
| 688 | GACAAACUA UCUGACCC | 3125 | GGGUCAGA CUGAUGAGGCCGUUAGGCCGAA AGUUUGUC | 12535 |
| 690 | CAAACUAUC UGACCCAU | 3126 | AUGGGUCA CUGAUGAGGCCGUUAGGCCGAA AUAGUUUG | 12536 |
| 699 | UGACCCAUC GGCAGACC | 3127 | GGUCUGCC CUGAUGAGGCCGUUAGGCCGAA AUGGGUCA | 12537 |
| 711 | AGACCAAUA CAAUCCUA | 3128 | UAGGAUUG CUGAUGAGGCCGUUAGGCCGAA AUUGGUCU | 12538 |
| 716 | AAUACAAUC UAGAUGU | 3129 | ACAUCUAG CUGAUGAGGCCGUUAGGCCGAA AUUGUAUU | 12539 |
| 719 | ACAAUCCUA GAUGUCCA | 3130 | UGGACAUC CUGAUGAGGCCGUUAGGCCGAA AGGAUUGU | 12540 |
| 725 | CUAGAUGUC CAAAUACG | 3131 | CGUAUUUG CUGAUGAGGCCGUUAGGCCGAA ACAUCUAG | 12541 |
| 731 | GUCCAAAUA CGCCCGCC | 3132 | GGCGGGCG CUGAUGAGGCCGUUAGGCCGAA AUUUGGAC | 12542 |
| 758 | AGACUGCUC CACGGGCA | 3133 | UGCCCGUG CUGAUGAGGCCGUUAGGCCGAA AGCAGUCU | 12543 |
| 771 | GGCAGACUC UUGUCCUC | 3134 | GAGGACAA CUGAUGAGGCCGUUAGGCCGAA AGUCUGCC | 12544 |
| 773 | CAGACUCUU GUCCUCAA | 3135 | UUGAGGAC CUGAUGAGGCCGUUAGGCCGAA AGAGUCUG | 12545 |
| 776 | ACUCUUGUC CUCAACUG | 3136 | CAGUUGAG CUGAUGAGGCCGUUAGGCCGAA ACAAGAGU | 12546 |
| 779 | CUUGUCCUC AACUGCAC | 3137 | GUGCAGUU CUGAUGAGGCCGUUAGGCCGAA AGGACAAG | 12547 |
| 803 | ACGGAGCUC AAUACGAG | 3138 | CUCGUAUU CUGAUGAGGCCGUUAGGCCGAA AGCUCCGU | 12548 |
| 807 | AGCUCAAUA CGAGGGUG | 3139 | CACCCUCG CUGAUGAGGCCGUUAGGCCGAA AUUGAGCU | 12549 |
| 831 | GCUGGAAUU ACCCUGGU | 3140 | ACCAGGGU CUGAUGAGGCCGUUAGGCCGAA AUUCCAGC | 12550 |
| 832 | CUGGAAUUA CCCUGGUA | 3141 | UACCAGGG CUGAUGAGGCCGUUAGGCCGAA AAUUCCAG | 12551 |
| 840 | ACCCUGGUA AAGCAACU | 3142 | AGUUGCUU CUGAUGAGGCCGUUAGGCCGAA ACCAGGGU | 12552 |
| 849 | AAGCAACUA AGAGAUCA | 3143 | UGCUCUCU CUGAUGAGGCCGUUAGGCCGAA AGUUGCUU | 12553 |
| 859 | GAGAGCAUC UAUAAGGC | 3144 | GCCUUAUA CUGAUGAGGCCGUUAGGCCGAA AUGCUCUC | 12554 |
| 861 | GAGCAUCUA UAAGGCAG | 3145 | CUGCCUUA CUGAUGAGGCCGUUAGGCCGAA AGAUGCUC | 12555 |
| 863 | GCAUCUAUA AGGCAGCG | 3146 | CGCUGCCU CUGAUGAGGCCGUUAGGCCGAA AUAGAUGC | 12556 |
| 875 | CAGCGGAUU GACCGGAG | 3147 | CUCCGGUC CUGAUGAGGCCGUUAGGCCGAA AUCCGCUG | 12557 |
| 888 | GGAGCCAUU CCCACAAC | 3148 | GUUGUGGG CUGAUGAGGCCGUUAGGCCGAA AUGGCUCC | 12558 |
| 889 | GAGCCAUUC CCACAACA | 3149 | UGUUGUGG CUGAUGAGGCCGUUAGGCCGAA AAUGGCUC | 12559 |
| 904 | CAAUGUGUU CCACAGUG | 3150 | CACUGUGG CUGAUGAGGCCGUUAGGCCGAA ACACAUUG | 12560 |
| 905 | AAUGUGUUC CACAGUGU | 3151 | ACACUGUG CUGAUGAGGCCGUUAGGCCGAA AACACAUU | 12561 |
| 914 | CACAGUGUU CUUAAGAU | 3152 | AUCUUAAG CUGAUGAGGCCGUUAGGCCGAA ACACUGUG | 12562 |
| 915 | ACAGUGUUC UUAAGAUC | 3153 | GAUCUUAA CUGAUGAGGCCGUUAGGCCGAA AACACUGU | 12563 |
| 917 | AGUGUUCUU AAGAUCAA | 3154 | UUGAUCUU CUGAUGAGGCCGUUAGGCCGAA AGAACACU | 12564 |
| 918 | GUGUUCUUA AGAUCAAC | 3155 | GUUGAUCU CUGAUGAGGCCGUUAGGCCGAA AAGAACAC | 12565 |
| 923 | CUUAAGAUC AACAAUGU | 3156 | ACAUUGUU CUGAUGAGGCCGUUAGGCCGAA AUCUUAAG | 12566 |
| 953 | AAGGGCUC UACACCUG | 3157 | CAGGUGUA CUGAUGAGGCCGUUAGGCCGAA AGCCCUU | 12567 |
| 955 | GGGCUCUA CACCUGUC | 3158 | GACAGGUG CUGAUGAGGCCGUUAGGCCGAA AGAGCCCC | 12568 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 963 | ACACCUGUC GCGUGAAG | 3159 | CUUCACGC CUGAUGAGGCCGUUAGGCCGAA ACAGGUGU | 12569 |
| 979 | GAGUGGGUC CUCGUUCC | 3160 | GGAACGAG CUGAUGAGGCCGUUAGGCCGAA ACCCACUC | 12570 |
| 982 | UGGGUCCUC GUUCCAGU | 3161 | ACUGGAAC CUGAUGAGGCCGUUAGGCCGAA AGGACCCA | 12571 |
| 985 | GUCCUCGUU CCAGUCUU | 3162 | AAGACUGG CUGAUGAGGCCGUUAGGCCGAA ACGAGGAC | 12572 |
| 986 | UCCUCGUUC CAGUCUUU | 3163 | AAAGACUG CUGAUGAGGCCGUUAGGCCGAA AACGAGGA | 12573 |
| 991 | GUUCCAGUC UUUCAACA | 3164 | UGUUGAAA CUGAUGAGGCCGUUAGGCCGAA ACUGGAAC | 12574 |
| 993 | UCCAGUCUU UCAACACC | 3165 | GGUGUUGA CUGAUGAGGCCGUUAGGCCGAA AGACUGGA | 12575 |
| 994 | CCAGUCUUU CAACACCU | 3166 | AGGUGUUG CUGAUGAGGCCGUUAGGCCGAA AAGACUGG | 12576 |
| 995 | CAGUCUUUC AACACCUC | 3167 | GAGGUGUU CUGAUGAGGCCGUUAGGCCGAA AAAGACUG | 12577 |
| 1003 | CAACACCUC CGUGCAUG | 3168 | CAUGCACG CUGAUGAGGCCGUUAGGCCGAA AGGUGUUG | 12578 |
| 1015 | GCAUGUGUA UGAAAAAG | 3169 | CUUUUUCA CUGAUGAGGCCGUUAGGCCGAA ACACAUGC | 12579 |
| 1027 | AAAAGGAUU CAUCAGUG | 3170 | CACUGAUG CUGAUGAGGCCGUUAGGCCGAA AUCCUUUU | 12580 |
| 1028 | AAAGGAUUC AUCAGUGU | 3171 | ACACUGAU CUGAUGAGGCCGUUAGGCCGAA AAUCCUUU | 12581 |
| 1031 | GGAUUCAUC AGUGUGAA | 3172 | UUCACACU CUGAUGAGGCCGUUAGGCCGAA AUGAAUCC | 12582 |
| 1044 | UGAAACAUC GGAAGCAG | 3173 | CUGCUUCC CUGAUGAGGCCGUUAGGCCGAA AUGUUUCA | 12583 |
| 1084 | AAGACGGUC CUAUCGGC | 3174 | GCCGAUAG CUGAUGAGGCCGUUAGGCCGAA ACCGUCUU | 12584 |
| 1087 | ACGGUCCUA UCGGCUGU | 3175 | ACAGCCGA CUGAUGAGGCCGUUAGGCCGAA AGGACCGU | 12585 |
| 1089 | GGUCCUAUC GGCUGUCC | 3176 | GGACAGCC CUGAUGAGGCCGUUAGGCCGAA AUAGGACC | 12586 |
| 1096 | UCGGCUGUC CAUGAAAG | 3177 | CUUUCAUG CUGAUGAGGCCGUUAGGCCGAA ACAGCCGA | 12587 |
| 1114 | GAAGGCCUU CCCCUCCC | 3178 | GGGAGGGG CUGAUGAGGCCGUUAGGCCGAA AGGCCUUC | 12588 |
| 1115 | AAGGCCUUC CCCUCCCC | 3179 | GGGGAGGG CUGAUGAGGCCGUUAGGCCGAA AAGGCCUU | 12589 |
| 1120 | CUUCCCCUC CCAGAAAU | 3180 | UUUCUGGG CUGAUGAGGCCGUUAGGCCGAA AGGGGAAG | 12590 |
| 1130 | CCAGAAAUC GUAUGGUU | 3181 | AACCAUAC CUGAUGAGGCCGUUAGGCCGAA AUUUCUGG | 12591 |
| 1133 | GAAAUCGUA UGGUUAAA | 3182 | UUUAACCA CUGAUGAGGCCGUUAGGCCGAA ACGAUUUC | 12592 |
| 1138 | CGUAUGGUU AAAGAUG | 3183 | CAUCUUUU CUGAUGAGGCCGUUAGGCCGAA ACCAUACG | 12593 |
| 1139 | GUAUGGUUA AAGAUGG | 210 | CCAUCUUU CUGAUGAGGCCGUUAGGCCGAA AACCAUAC | 9629 |
| 1150 | AGAUGGCUC GCCUGCAA | 3184 | UUGCAGGC CUGAUGAGGCCGUUAGGCCGAA AGCCAUCU | 12594 |
| 1162 | UGCAACAUU GAAGUCUG | 3185 | CAGACUUC CUGAUGAGGCCGUUAGGCCGAA AUGUUGCA | 12595 |
| 1168 | AUUGAAGUC UGCUCGCU | 3186 | AGCGAGCA CUGAUGAGGCCGUUAGGCCGAA ACUUCAAU | 12596 |
| 1173 | AGUCUGCUC GCUAUUUG | 3187 | CAAAUAGC CUGAUGAGGCCGUUAGGCCGAA AGCAGACU | 12597 |
| 1177 | UGCUCGCUA UUUGGUAC | 3188 | GUACCAAA CUGAUGAGGCCGUUAGGCCGAA AGCGAGCA | 12598 |
| 1179 | CUCGCUAUU UGGUACAU | 3189 | AUGUACCA CUGAUGAGGCCGUUAGGCCGAA AUAGCGAG | 12599 |
| 1180 | UCGCUAUUU GGUACAUG | 3190 | CAUGUACC CUGAUGAGGCCGUUAGGCCGAA AAUAGCGA | 12600 |
| 1184 | UAUUUGGUA CAUGGCUA | 3191 | UAGCCAUG CUGAUGAGGCCGUUAGGCCGAA ACCAAAUA | 12601 |
| 1192 | ACAUGGCUA CUCAUUAA | 3192 | UUAAUGAG CUGAUGAGGCCGUUAGGCCGAA AGCCAUGU | 12602 |
| 1195 | UGGCUACUC AUUAAUUA | 3193 | UAAUUAAU CUGAUGAGGCCGUUAGGCCGAA AGUAGCCA | 12603 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 1198 | CUACUCAUU AAUUAUCA | 3194 | UGAUAAUU CUGAUGAGGCCGUUAGGCCGAA AUGAGUAG | 12604 |
| 1199 | UACUCAUUA AUUAUCAA | 3195 | UUGAUAAU CUGAUGAGGCCGUUAGGCCGAA AAUGAGUA | 12605 |
| 1202 | UCAUUAAUU AUCAAAGA | 3196 | UCUUUGAU CUGAUGAGGCCGUUAGGCCGAA AUUAAUGA | 12606 |
| 1203 | CAUUAAUUA UCAAAGAU | 3197 | AUCUUUGA CUGAUGAGGCCGUUAGGCCGAA AAUUAAUG | 12607 |
| 1205 | UUAAUUAUC AAAGAUGU | 3198 | ACAUCUUU CUGAUGAGGCCGUUAGGCCGAA AUAAUUAA | 12608 |
| 1237 | AGGGGACUA UACGAUCU | 3199 | AGAUCGUA CUGAUGAGGCCGUUAGGCCGAA AGUCCCCU | 12609 |
| 1239 | GGGACUAUA CGAUCUUG | 3200 | CAAGAUCG CUGAUGAGGCCGUUAGGCCGAA AUAGUCCC | 12610 |
| 1244 | UAUACGAUC UUGCUGGG | 3201 | CCCAGCAA CUGAUGAGGCCGUUAGGCCGAA AUCGUAUA | 12611 |
| 1246 | UACGAUCUU GCUGGGCA | 3202 | UGCCCAGC CUGAUGAGGCCGUUAGGCCGAA AGAUCGUA | 12612 |
| 1256 | CUGGGCAUA AAGCAGUC | 3203 | GACUGCUU CUGAUGAGGCCGUUAGGCCGAA AUGCCCAG | 12613 |
| 1264 | AAAGCAGUC AAGGCUAU | 3204 | AUAGCCUU CUGAUGAGGCCGUUAGGCCGAA ACUGCUUU | 12614 |
| 1271 | UCAAGGCUA UUUAAAAA | 3205 | UUUUUAAA CUGAUGAGGCCGUUAGGCCGAA AGCCUUGA | 12615 |
| 1273 | AAGGCUAUU UAAAACC | 3206 | GGUUUUUA CUGAUGAGGCCGUUAGGCCGAA AUAGCCUU | 12616 |
| 1274 | AGGCUAUUU AAAACCU | 3207 | AGGUUUUU CUGAUGAGGCCGUUAGGCCGAA AAUAGCCU | 12617 |
| 1275 | GGCUAUUUA AAACCUC | 3208 | GAGGUUUU CUGAUGAGGCCGUUAGGCCGAA AAAUAGCC | 12618 |
| 1283 | AAAACCUC ACUGCCAC | 237 | GUGGCAGU CUGAUGAGGCCGUUAGGCCGAA AGGUUUUU | 9656 |
| 1293 | CUGCCACUC UCAUUGUA | 3209 | UACAAUGA CUGAUGAGGCCGUUAGGCCGAA AGUGGCAG | 12619 |
| 1295 | GCCACUCUC AUUGUAAA | 3210 | UUUACAAU CUGAUGAGGCCGUUAGGCCGAA AGAGUGGC | 12620 |
| 1298 | ACUCAUU GUAAACGU | 3211 | ACGUUUAC CUGAUGAGGCCGUUAGGCCGAA AUGAGAGU | 12621 |
| 1301 | CUCAUUGUA AACGUGAA | 3212 | UUCACGUU CUGAUGAGGCCGUUAGGCCGAA ACAAUGAG | 12622 |
| 1314 | UGAAACCUC AGAUCUAC | 3213 | GUAGAUCU CUGAUGAGGCCGUUAGGCCGAA AGGUUUCA | 12623 |
| 1319 | CCUCAGAUC UACGAAAA | 3214 | UUUUCGUA CUGAUGAGGCCGUUAGGCCGAA AUCUGAGG | 12624 |
| 1321 | UCAGAUCUA CGAAAAGU | 3215 | ACUUUUCG CUGAUGAGGCCGUUAGGCCGAA AGAUCUGA | 12625 |
| 1330 | CGAAAAGUC CGUGUCCU | 3216 | AGGACACG CUGAUGAGGCCGUUAGGCCGAA ACUUUUCG | 12626 |
| 1336 | GUCCGUGUC CUCGCUUC | 3217 | GAAGCGAG CUGAUGAGGCCGUUAGGCCGAA ACACGGAC | 12627 |
| 1339 | CGUGUCCUC GCUUCCAA | 3218 | UUGGAAGC CUGAUGAGGCCGUUAGGCCGAA AGGACACG | 12628 |
| 1343 | UCCUCGCUU CCAAGCCC | 3219 | GGGCUUGG CUGAUGAGGCCGUUAGGCCGAA AGCGAGGA | 12629 |
| 1344 | CCUCGCUUC CAAGCCCA | 3220 | UGGGCUUG CUGAUGAGGCCGUUAGGCCGAA AAGCGAGG | 12630 |
| 1356 | GCCCACCUC UCUAUCCG | 3221 | CGGAUAGA CUGAUGAGGCCGUUAGGCCGAA AGGUGGGC | 12631 |
| 1358 | CCACCUCUC UAUCCGCU | 3222 | AGCGGAUA CUGAUGAGGCCGUUAGGCCGAA AGAGGUGG | 12632 |
| 1360 | ACCUCUCUA UCCGCUGG | 3223 | CCAGCGGA CUGAUGAGGCCGUUAGGCCGAA AGAGAGGU | 12633 |
| 1362 | CUCUCUAUC CGCUGGGC | 3224 | GCCCAGCG CUGAUGAGGCCGUUAGGCCGAA AUAGAGAG | 12634 |
| 1382 | AGACAAGUC UCACUUG | 3225 | CAAGUGAG CUGAUGAGGCCGUUAGGCCGAA ACUUGUCU | 12635 |
| 1385 | CAAGUCCUC ACUUGCAC | 3226 | GUGCAAGU CUGAUGAGGCCGUUAGGCCGAA AGGACUUG | 12636 |
| 1389 | UCCUCACUU GCACCGUG | 3227 | CACGGUGC CUGAUGAGGCCGUUAGGCCGAA AGUGAGGA | 12637 |
| 1399 | CACCGUGUA UGGCAUCC | 3228 | GGAUGCCA CUGAUGAGGCCGUUAGGCCGAA ACACGGUG | 12638 |
| 1406 | UAUGGCAUC CCUCGGCC | 3229 | GGCCGAGG CUGAUGAGGCCGUUAGGCCGAA AUGCCAUA | 12639 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 1410 | GCAUCCCUC GGCCAACA | 3230 | UGUUGGCC CUGAUGAGGCCGUUAGGCCGAA AGGGAUGC | 12640 |
| 1421 | CCAACAAUC ACGUGGCU | 3231 | AGCCACGU CUGAUGAGGCCGUUAGGCCGAA AUUGUUGG | 12641 |
| 1430 | ACGUGGCUC UGGCACCC | 3232 | GGGUGCCA CUGAUGAGGCCGUUAGGCCGAA AGCCACGU | 12642 |
| 1443 | ACCCCUGUC ACCACAAU | 3233 | AUUGUGGU CUGAUGAGGCCGUUAGGCCGAA ACAGGGGU | 12643 |
| 1452 | ACCACAAUC ACUCCAAA | 3234 | UUUGGAGU CUGAUGAGGCCGUUAGGCCGAA AUUGUGGU | 12644 |
| 1456 | CAAUCACUC CAAAGAAA | 3235 | UUUCUUUG CUGAUGAGGCCGUUAGGCCGAA AGUGAUUG | 12645 |
| 1468 | AGAAAGGUA UGACUUCU | 3236 | AGAAGUCA CUGAUGAGGCCGUUAGGCCGAA ACCUUUCU | 12646 |
| 1474 | GUAUGACUU CUGCACUG | 3237 | CAGUGCAG CUGAUGAGGCCGUUAGGCCGAA AGUCAUAC | 12647 |
| 1475 | UAUGACUUC UGCACUGA | 3238 | UCAGUGCA CUGAUGAGGCCGUUAGGCCGAA AAGUCAUA | 12648 |
| 1495 | UGAAGAAUC CUUUAUCC | 3239 | GGAUAAAG CUGAUGAGGCCGUUAGGCCGAA AUUCUUCA | 12649 |
| 1498 | AGAAUCCUU UAUCCUGG | 3240 | CCAGGAUA CUGAUGAGGCCGUUAGGCCGAA AGGAUUCU | 12650 |
| 1499 | GAAUCCUUU AUCCUGGA | 3241 | UCCAGGAU CUGAUGAGGCCGUUAGGCCGAA AAGGAUUC | 12651 |
| 1500 | AAUCCUUUA UCCUGGAU | 3242 | AUCCAGGA CUGAUGAGGCCGUUAGGCCGAA AAAGGAUU | 12652 |
| 1502 | UCCUUUAUC CUGGAUCC | 3243 | GGAUCCAG CUGAUGAGGCCGUUAGGCCGAA AUAAAGGA | 12653 |
| 1509 | UCCUGGAUC CCAGCAGC | 3244 | GCUGCUGG CUGAUGAGGCCGUUAGGCCGAA AUCCAGGA | 12654 |
| 1522 | CAGCAACUU AGGAAACA | 3245 | UGUUUCCU CUGAUGAGGCCGUUAGGCCGAA AGUUGCUG | 12655 |
| 1523 | AGCAACUUA GGAAACAG | 3246 | CUGUUUCC CUGAUGAGGCCGUUAGGCCGAA AAGUUGCU | 12656 |
| 1535 | AACAGAAUU GAGAGCAU | 280 | AUGCUCUC CUGAUGAGGCCGUUAGGCCGAA AUUCUGUU | 9699 |
| 1544 | GAGAGCAUC UCUCAGCG | 3247 | CGCUGAGA CUGAUGAGGCCGUUAGGCCGAA AUGCUCUC | 12657 |
| 1546 | GAGCAUCUC UCAGCGCA | 3248 | UGCGCUGA CUGAUGAGGCCGUUAGGCCGAA AGAUGCUC | 12658 |
| 1548 | GCAUCUCUC AGCGCAUG | 3249 | CAUGCGCU CUGAUGAGGCCGUUAGGCCGAA AGAGAUGC | 12659 |
| 1562 | AUGACGGUC UAUAGAAGG | 3250 | CCUUCUAU CUGAUGAGGCCGUUAGGCCGAA ACCGUCAU | 12660 |
| 1565 | ACGGUCAUA GAAGGAAC | 3251 | GUUCCUUC CUGAUGAGGCCGUUAGGCCGAA AUGACCGU | 12661 |
| 1578 | GAACAAAUA AGACGGUU | 3252 | AACCGUCU CUGAUGAGGCCGUUAGGCCGAA AUUUGUUC | 12662 |
| 1586 | AAGACGGUU AGCACAUU | 3253 | AAUGUGCU CUGAUGAGGCCGUUAGGCCGAA ACCGUCUU | 12663 |
| 1587 | AGACGGUUA GCACAUUG | 3254 | CAAUGUGC CUGAUGAGGCCGUUAGGCCGAA AACCGUCU | 12664 |
| 1594 | UAGCACAUU GGUGGUGG | 3255 | CCACCACC CUGAUGAGGCCGUUAGGCCGAA AUGUGCUA | 12665 |
| 1609 | GGCUGACUC UCAGACCC | 3256 | GGGUCUGA CUGAUGAGGCCGUUAGGCCGAA AGUCAGCC | 12666 |
| 1611 | CUGACUCUC AGACCCCU | 3257 | AGGGGUCU CUGAUGAGGCCGUUAGGCCGAA AGAGUCAG | 12667 |
| 1625 | CCUGGAAUC UACAGCUG | 3258 | CAGCUGUA CUGAUGAGGCCGUUAGGCCGAA AUUCCAGG | 12668 |
| 1627 | UGGAAUCUA CAGCUGCC | 3259 | GGCAGCUG CUGAUGAGGCCGUUAGGCCGAA AGAUUCCA | 12669 |
| 1642 | CCGGGCCUU CAAUAAAA | 3260 | UUUUAUUG CUGAUGAGGCCGUUAGGCCGAA AGGCCCGG | 12670 |
| 1643 | CGGGCCUUC AAUAAAAU | 3261 | AUUUUAUU CUGAUGAGGCCGUUAGGCCGAA AAGGCCCG | 12671 |
| 1647 | CCUUCAAUA AAAUAGGG | 3262 | CCCUAUUU CUGAUGAGGCCGUUAGGCCGAA AUUGAAGG | 12672 |
| 1652 | AAUAAAAUA GGGACUGU | 3263 | ACAGUCCC CUGAUGAGGCCGUUAGGCCGAA AUUUUAUU | 12673 |
| 1673 | AGAAACAUA AAAUUUUA | 3264 | UAAAAUUU CUGAUGAGGCCGUUAGGCCGAA AUGUUUCU | 12674 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 1678 | CAUAAAAUU UUAUGUCA | 3265 | UGACAUAA CUGAUGAGgccGUUAGGCcCGAA AUUUUAUG | 12675 |
| 1679 | AUAAAAUUU UAUGUCAC | 3266 | GUGACAUA CUGAUGAGgccGUUAGGCcCGAA AAUUUUAU | 12676 |
| 1680 | UAAAAUUUU AUGUCACA | 3267 | UGUGACAU CUGAUGAGgccGUUAGGCcCGAA AAAUUUUA | 12677 |
| 1681 | AAAAUUUUA UGUCACAG | 3268 | CUGUGACA CUGAUGAGgccGUUAGGCcCGAA AAAAUUUU | 12678 |
| 1685 | UUUUAUGUC ACAGAUGU | 3269 | ACAUCUGU CUGAUGAGgccGUUAGGCcCGAA ACAUAAAA | 12679 |
| 1705 | GAAUGGCUU UCACGUUU | 3270 | AAACGUGA CUGAUGAGgccGUUAGGCcCGAA AGCCAUUC | 12680 |
| 1706 | AAUGGCUUU CACGUUUC | 3271 | GAAACGUG CUGAUGAGgccGUUAGGCcCGAA AAGCCAUU | 12681 |
| 1707 | AUGGCUUUC ACGUUUCC | 3272 | GGAAACGU CUGAUGAGgccGUUAGGCcCGAA AAAGCCAU | 12682 |
| 1712 | UUUCACGUU UCCUUGGA | 3273 | UCCAAGGA CUGAUGAGgccGUUAGGCcCGAA ACGUGAAA | 12683 |
| 1713 | UUCACGUUU CCUUGGAA | 3274 | UUCCAAGG CUGAUGAGgccGUUAGGCcCGAA AACGUGAA | 12684 |
| 1714 | UCACGUUUC CUUGGAAA | 3275 | UUUCCAAG CUGAUGAGgccGUUAGGCcCGAA AAACGUGA | 12685 |
| 1717 | CGUUUCCUU GGAAAGA | 3276 | UCUUUUCC CUGAUGAGgccGUUAGGCcCGAA AGGAAACG | 12686 |
| 1756 | GAAACUGUC CUGUGUGG | 3277 | CCACACAG CUGAUGAGgccGUUAGGCcCGAA ACAGUUUC | 12687 |
| 1766 | UGUGUGGUC AAUAAAUU | 3278 | AAUUUAUU CUGAUGAGgccGUUAGGCcCGAA ACCACACA | 12688 |
| 1770 | UGGUCAAUA AAUUCCUG | 3279 | CAGGAAUU CUGAUGAGgccGUUAGGCcCGAA AUUGACCA | 12689 |
| 1774 | CAAUAAAUU CCUGUACA | 3280 | UGUACAGG CUGAUGAGgccGUUAGGCcCGAA AUUUAUUG | 12690 |
| 1775 | AAUAAAUUC CUGUACAG | 3281 | CUGUACAG CUGAUGAGgccGUUAGGCcCGAA AAUUUAUU | 12691 |
| 1780 | AUUCCUGUA CAGAGACA | 3282 | UGUCUCUG CUGAUGAGgccGUUAGGCcCGAA ACAGGAAU | 12692 |
| 1790 | AGAGACAUG ACCUGGAU | 3283 | AUCCAGGU CUGAUGAGgccGUUAGGCcCGAA AUGUCUCU | 12693 |
| 1791 | GAGACAUUA CCUGGAUU | 3284 | AAUCCAGG CUGAUGAGgccGUUAGGCcCGAA AAUGUCUC | 12694 |
| 1799 | ACCUGGAUU CUGCUACG | 3285 | CGUAGCAG CUGAUGAGgccGUUAGGCcCGAA AUCCAGGU | 12695 |
| 1800 | CCUGGAUUC UGCUACGG | 3286 | CCGUAGCA CUGAUGAGgccGUUAGGCcCGAA AAUCCAGG | 12696 |
| 1805 | AUUCUGCUA CGGACAGU | 3287 | ACUGUCCG CUGAUGAGgccGUUAGGCcCGAA AGCAGAAU | 12697 |
| 1814 | CGGACAGUU AACAACAG | 3288 | CUGUUGUU CUGAUGAGgccGUUAGGCcCGAA ACUGUCCG | 12698 |
| 1815 | GGACAGUUA ACAACAGA | 3289 | UCUGUUGU CUGAUGAGgccGUUAGGCcCGAA AACUGUCC | 12699 |
| 1836 | UGCACCAUA GUAUCAGC | 3290 | GCUGAUAC CUGAUGAGgccGUUAGGCcCGAA AUGGUGCA | 12700 |
| 1839 | ACCAUAGUA UCAGCAAG | 3291 | CUUGCUGA CUGAUGAGgccGUUAGGCcCGAA ACUAUGGU | 12701 |
| 1841 | CAUAGUAUC AGCAAGCA | 3292 | UGCUUGCU CUGAUGAGgccGUUAGGCcCGAA AUACUAUG | 12702 |
| 1866 | CCACCACUC AAGAUUAC | 3293 | GUAAUCUU CUGAUGAGgccGUUAGGCcCGAA AGUGGUGG | 12703 |
| 1872 | CUCAAGAUU ACUCCAUC | 3294 | GAUGGAGU CUGAUGAGgccGUUAGGCcCGAA AUCUUGAG | 12704 |
| 1873 | UCAAGAUUA CUCCAUCA | 3295 | UGAUGGAG CUGAUGAGgccGUUAGGCcCGAA AAUCUUGA | 12705 |
| 1876 | AGAUUACUC CAUCACUC | 3296 | GAGUGAUG CUGAUGAGgccGUUAGGCcCGAA AGUAAUCU | 12706 |
| 1880 | UACUCCAUC ACUCUGAA | 3297 | UUCAGAGU CUGAUGAGgccGUUAGGCcCGAA AUGGAGUA | 12707 |
| 1884 | CCAUCACUC UGAACCUU | 3298 | AAGGUUCA CUGAUGAGgccGUUAGGCcCGAA AGUGAUGG | 12708 |
| 1892 | CUGAACCUU GUCAUCAA | 3299 | UUGAUGAC CUGAUGAGgccGUUAGGCcCGAA AGGUUCAG | 12709 |
| 1895 | AACCUUGUC AUCAAGAA | 3300 | UUCUUGAU CUGAUGAGgccGUUAGGCcCGAA ACAAGGUU | 12710 |
| 1898 | CUUGUCAUC AAGAACGU | 3301 | ACGUUCUU CUGAUGAGgccGUUAGGCcCGAA AUGACAAG | 12711 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 1909 | GAACGUGUC UCUAGAAG | 3302 | CUUCUAGA CUGAUGAGGCCGUUAGGCCGAA ACACGUUC | 12712 |
| 1911 | ACGUGUCUC UAGAAGAC | 3303 | GUCUUCUA CUGAUGAGGCCGUUAGGCCGAA AGACACGU | 12713 |
| 1913 | GUGUCUCUA GAAGACUC | 3304 | GAGUCUUC CUGAUGAGGCCGUUAGGCCGAA AGAGACAC | 12714 |
| 1921 | AGAAGACUC GGGCACCU | 3305 | AGGUGCCC CUGAUGAGGCCGUUAGGCCGAA AGUCUUCU | 12715 |
| 1930 | GGGCACCUA UGCGUGCA | 3306 | UGCACGCA CUGAUGAGGCCGUUAGGCCGAA AGGUGCCC | 12716 |
| 1952 | AGGAACAUA UACACAGG | 3307 | CCUGUGUA CUGAUGAGGCCGUUAGGCCGAA AUGUUCCU | 12717 |
| 1954 | GAACAUAUA CACAGGGG | 3308 | CCCCUGUG CUGAUGAGGCCGUUAGGCCGAA AUAUGUUC | 12718 |
| 1970 | GAAGACAUC CUUCGAA | 3309 | UUCCGAAG CUGAUGAGGCCGUUAGGCCGAA AUGUCUUC | 12719 |
| 1973 | GACAUCCUU CGGAAGAC | 3310 | GUCUUCCG CUGAUGAGGCCGUUAGGCCGAA AGGAUGUC | 12720 |
| 1974 | ACAUCCUUC GGAAGACA | 3311 | UGUCUUCC CUGAUGAGGCCGUUAGGCCGAA AAGGAUGU | 12721 |
| 1988 | ACAGAAGUU CUCGUUAG | 3312 | CUAACGAG CUGAUGAGGCCGUUAGGCCGAA ACUUCUGU | 12722 |
| 1989 | CAGAAGUUC UCGUUAGA | 3313 | UCUAACGA CUGAUGAGGCCGUUAGGCCGAA AACUUCUG | 12723 |
| 1991 | GAAGUUCUC GUUAGAGA | 3314 | UCUCUAAC CUGAUGAGGCCGUUAGGCCGAA AGAACUUC | 12724 |
| 1994 | GUUCUCGUU AGAGAUUC | 3315 | GAAUCUCU CUGAUGAGGCCGUUAGGCCGAA ACGAGAAC | 12725 |
| 1995 | UUCUCGUUA GAGAUUCG | 3316 | CGAAUCUC CUGAUGAGGCCGUUAGGCCGAA AACGAGAA | 12726 |
| 2001 | UUAGAGAUU CGGAAGCG | 3317 | CGCUUCCG CUGAUGAGGCCGUUAGGCCGAA AUCUCUAA | 12727 |
| 2002 | UAGAGAUUC GGAAGCGC | 3318 | GCGCUUCC CUGAUGAGGCCGUUAGGCCGAA AAUCUCUA | 12728 |
| 2021 | CACCUGCUU CAAAACCU | 3319 | AGGUUUUG CUGAUGAGGCCGUUAGGCCGAA AGCAGGUG | 12729 |
| 2022 | ACCUGCUUC AAAACCUC | 3320 | GAGGUUUU CUGAUGAGGCCGUUAGGCCGAA AAGCAGGU | 12730 |
| 2030 | CAAAACCUC AGUGACUA | 3321 | UAGUCACU CUGAUGAGGCCGUUAGGCCGAA AGGUUUUG | 12731 |
| 2038 | CAGUGACUA CGAGGUCU | 3322 | AGACCUCG CUGAUGAGGCCGUUAGGCCGAA AGUCACUG | 12732 |
| 2045 | UACGAGGUC UCCAUCAG | 3323 | CUGAUGGA CUGAUGAGGCCGUUAGGCCGAA ACCUCGUA | 12733 |
| 2047 | CGAGGUCUC CAUCAGUG | 3324 | CACUGAUG CUGAUGAGGCCGUUAGGCCGAA AGACCUCG | 12734 |
| 2051 | GUCUCCAUC AGUGGCUC | 3325 | GAGCCACU CUGAUGAGGCCGUUAGGCCGAA AUGGAGAC | 12735 |
| 2059 | CAGUGGCUC UACGACCU | 3326 | AGGUCGUA CUGAUGAGGCCGUUAGGCCGAA AGCCACUG | 12736 |
| 2061 | GUGGCUCUA CGACCUUA | 3327 | UAAGGUCG CUGAUGAGGCCGUUAGGCCGAA AGAGCCAC | 12737 |
| 2068 | UACGACCUU AGACUGUC | 3328 | GACAGUCU CUGAUGAGGCCGUUAGGCCGAA AGGUCGUA | 12738 |
| 2069 | ACGACCUUA GACUGUCA | 3329 | UGACAGUC CUGAUGAGGCCGUUAGGCCGAA AAGGUCGU | 12739 |
| 2076 | UAGACUGUC AAGCUAGA | 3330 | UCUAGCUU CUGAUGAGGCCGUUAGGCCGAA ACAGUCUA | 12740 |
| 2082 | GUCAAGCUA GAGGUGUC | 3331 | GACACCUC CUGAUGAGGCCGUUAGGCCGAA AGCUUGAC | 12741 |
| 2090 | AGAGGUGUC CCCGCGCC | 3332 | GGCGCGGG CUGAUGAGGCCGUUAGGCCGAA ACACCUCU | 12742 |
| 2100 | CCGCGCCUC AGAUCACU | 3333 | AGUGAUCU CUGAUGAGGCCGUUAGGCCGAA AGGCGCGG | 12743 |
| 2105 | CCUCAGAUC ACUUGGUU | 378 | AACCAAGU CUGAUGAGGCCGUUAGGCCGAA AUCUGAGG | 9797 |
| 2109 | AGAUCACUU GGUUCAAA | 3334 | UUUGAACC CUGAUGAGGCCGUUAGGCCGAA AGUGAUCU | 12744 |
| 2113 | CACUUGGUU CAAAACA | 3335 | UGUUUUUG CUGAUGAGGCCGUUAGGCCGAA ACCAAGUG | 12745 |
| 2114 | ACUUGGUUC AAAACAA | 3336 | UUGUUUUU CUGAUGAGGCCGUUAGGCCGAA AACCAAGU | 9800 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 2132 | CACAAAAUA CAACAAGA | 383 | UCUUGUUG CUGAUGAGGCCGUUAGGCCGAA AUUUUGUG | 9802 |
| 2150 | CCGGGAAUU AUUUUAGG | 3337 | CCUAAAAU CUGAUGAGGCCGUUAGGCCGAA AUUCCCGG | 12746 |
| 2151 | CGGGAAUUA UUUUAGGA | 3338 | UCCUAAAA CUGAUGAGGCCGUUAGGCCGAA AAUUCCCG | 12747 |
| 2153 | GGAAUUAUU UUAGGACC | 386 | GGUCCUAA CUGAUGAGGCCGUUAGGCCGAA AUAAUUCC | 9805 |
| 2154 | GAAUUAUUU UAGGACCA | 387 | UGGUCCUA CUGAUGAGGCCGUUAGGCCGAA AAUAAUUC | 9806 |
| 2155 | AAUUAUUUU AGGACCAG | 388 | CUGGUCCU CUGAUGAGGCCGUUAGGCCGAA AAAUAAUU | 9807 |
| 2156 | AUUAUUUUA GGACCAGG | 389 | CCUGGUCC CUGAUGAGGCCGUUAGGCCGAA AAAAUAAU | 9808 |
| 2179 | CACGCUGUU UAUUGAAA | 390 | UUUCAAUA CUGAUGAGGCCGUUAGGCCGAA ACAGCGUG | 9809 |
| 2180 | ACGCUGUUU AUUGAAAG | 391 | CUUUCAAU CUGAUGAGGCCGUUAGGCCGAA AACAGCGU | 9810 |
| 2181 | CGCUGUUUA UUGAAAGA | 392 | UCUUUCAA CUGAUGAGGCCGUUAGGCCGAA AAACAGCG | 9811 |
| 2183 | CUGUUUAUU GAAAGAGU | 393 | ACUCUUUC CUGAUGAGGCCGUUAGGCCGAA AUAAACAG | 9812 |
| 2192 | GAAAGAGUC ACAGAGGA | 3339 | UCCUCUGU CUGAUGAGGCCGUUAGGCCGAA ACUCUUUC | 12748 |
| 2213 | GAGGGUGUC UAUAGGUG | 3340 | CACCUAUA CUGAUGAGGCCGUUAGGCCGAA ACACCCUC | 12749 |
| 2215 | GGGUGUCUA UAGGUGCC | 3341 | GGCACCUA CUGAUGAGGCCGUUAGGCCGAA AGACACCC | 12750 |
| 2217 | GUGUCUAUA GGUGCCGA | 3342 | UCGGCACC CUGAUGAGGCCGUUAGGCCGAA AUAGACAC | 12751 |
| 2263 | CGCAGCCUA CCUCACCG | 3343 | CGGUGAGG CUGAUGAGGCCGUUAGGCCGAA AGGCUGCG | 12752 |
| 2267 | GCCUACCUC ACCGUGCA | 3344 | UGCACGGU CUGAUGAGGCCGUUAGGCCGAA AGGUAGGC | 12753 |
| 2284 | AGGAACCUC AGACAAGU | 3345 | ACUUGUCU CUGAUGAGGCCGUUAGGCCGAA AGGUUCCU | 12754 |
| 2293 | AGACAAGUC AAACCUGG | 3346 | CCAGGUUU CUGAUGAGGCCGUUAGGCCGAA ACUUGUCU | 12755 |
| 2309 | GAGCUGAUC ACGCUCAC | 3347 | GUGAGCGU CUGAUGAGGCCGUUAGGCCGAA AUCAGCUC | 12756 |
| 2315 | AUCACGCUC ACGUGCAC | 3348 | GUGCACGU CUGAUGAGGCCGUUAGGCCGAA AGCGUGAU | 12757 |
| 2342 | GCGACCCUC UUUUGGCU | 3349 | AGCCAAAA CUGAUGAGGCCGUUAGGCCGAA AGGGUCGC | 12758 |
| 2344 | GACCCUCUU UUGGCUCC | 3350 | GGAGCCAA CUGAUGAGGCCGUUAGGCCGAA AGAGGGUC | 12759 |
| 2345 | ACCCUCUUU UGGCUCCU | 3351 | AGGAGCCA CUGAUGAGGCCGUUAGGCCGAA AAGAGGGU | 12760 |
| 2346 | CCCUCUUUU GGCUCCUU | 3352 | AAGGAGCC CUGAUGAGGCCGUUAGGCCGAA AAAGAGGG | 12761 |
| 2351 | UUUUGGCUC CUUCUAAC | 3353 | GUUAGAAG CUGAUGAGGCCGUUAGGCCGAA AGCCAAAA | 12762 |
| 2354 | UGGCUCCUU CUAACUCU | 3354 | AGAGUUAG CUGAUGAGGCCGUUAGGCCGAA AGGAGCCA | 12763 |
| 2355 | GGCUCCUUC UAACUCUC | 3355 | GAGAGUUA CUGAUGAGGCCGUUAGGCCGAA AAGGAGCC | 12764 |
| 2357 | CUCCUUCUA ACUCUCUU | 3356 | AAGAGAGU CUGAUGAGGCCGUUAGGCCGAA AGAAGGAG | 12765 |
| 2361 | UUCUAACUC UCUUCAUC | 3357 | GAUGAAGA CUGAUGAGGCCGUUAGGCCGAA AGUUAGAA | 12766 |
| 2363 | CUAACUCUC UUCAUCAG | 3358 | CUGAUGAA CUGAUGAGGCCGUUAGGCCGAA AGAGGUAG | 12767 |
| 2365 | AACUCUCUU CAUCAGAA | 3359 | UUCUGAUG CUGAUGAGGCCGUUAGGCCGAA AGAGAGUU | 12768 |
| 2366 | ACUCUCUUC AUCAGAAA | 3360 | UUUCUGAU CUGAUGAGGCCGUUAGGCCGAA AAGAGAGU | 12769 |
| 2369 | CUCUUCAUC AGAAACU | 3361 | AGUUUUCU CUGAUGAGGCCGUUAGGCCGAA AUGAAGAG | 12770 |
| 2386 | GAAGCGGUC UUCUUCCG | 3362 | CGGAAGAA CUGAUGAGGCCGUUAGGCCGAA ACCGCUUC | 12771 |
| 2388 | AGCGGUCUU CUUCCGAA | 3363 | UUCGGAAG CUGAUGAGGCCGUUAGGCCGAA AGACCGCU | 12772 |
| 2389 | GCGGUCUUC UUCCGAAG | 3364 | CUUCGGAA CUGAUGAGGCCGUUAGGCCGAA AAGACCGC | 12773 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 2391 | GGUCUUCUU CCGAAGUA | 3365 | UACUUCGG CUGAUGAGGCCGUUAGGCCGAA AGAAGACC | 12774 |
| 2392 | GUCUUCUUC CGAAGUAA | 3366 | UUACUUCG CUGAUGAGGCCGUUAGGCCGAA AAGAAGAC | 12775 |
| 2399 | UCCGAAGUA AAGACAGA | 3367 | UCUGUCUU CUGAUGAGGCCGUUAGGCCGAA ACUUCGGA | 12776 |
| 2410 | GACAGACUA CCUGUCAA | 3368 | UUGACAGG CUGAUGAGGCCGUUAGGCCGAA AGUCUGUC | 12777 |
| 2416 | CUACCUGUC AAUCAUUA | 3369 | UAAUGAUU CUGAUGAGGCCGUUAGGCCGAA ACAGGUAG | 12778 |
| 2420 | CUGUCAAUC AUUAUGGA | 3370 | UCCAUAAU CUGAUGAGGCCGUUAGGCCGAA AUUGACAG | 12779 |
| 2423 | UCAAUCAUU AUGGACCC | 3371 | GGGUCCAU CUGAUGAGGCCGUUAGGCCGAA AUGAUUGA | 12780 |
| 2424 | CAAUCAUUA UGGACCCA | 3372 | UGGGUCCA CUGAUGAGGCCGUUAGGCCGAA AAUGAUUG | 12781 |
| 2441 | GAUGAAGUU CCCCUGGA | 3373 | UCCAGGGG CUGAUGAGGCCGUUAGGCCGAA ACUUCAUC | 12782 |
| 2442 | AUGAAGUUC CCCUGGAU | 3374 | AUCCAGGG CUGAUGAGGCCGUUAGGCCGAA AACUUCAU | 12783 |
| 2473 | GCUGCCCUA UGAUGCCA | 3375 | UGGCAUCA CUGAUGAGGCCGUUAGGCCGAA AGGGCAGC | 12784 |
| 2494 | GUGGGAGUU UGCACGGG | 3376 | CCCGUGCA CUGAUGAGGCCGUUAGGCCGAA ACUCCCAC | 12785 |
| 2495 | UGGGAGUUU GCACGGGA | 3377 | UCCCGUGC CUGAUGAGGCCGUUAGGCCGAA AACUCCCA | 12786 |
| 2916 | CUGAAACUA GGCAAAUC | 3378 | GAUUUGCC CUGAUGAGGCCGUUAGGCCGAA AGUUUCAG | 12787 |
| 2524 | AGGCAAAUC GCUCGGAA | 3379 | UUCCGAGC CUGAUGAGGCCGUUAGGCCGAA AUUUGCCU | 12788 |
| 2528 | AAAUCGCUC GGAAGAGG | 3380 | CCUCUUCC CUGAUGAGGCCGUUAGGCCGAA AGCGAUUU | 12789 |
| 2541 | GAGGGCUUU UUGGGAAA | 3381 | UUUCCCAA CUGAUGAGGCCGUUAGGCCGAA AGCCCCUC | 12790 |
| 2542 | AGGGCUUUU UGGGAAAG | 3382 | CUUUCCCA CUGAUGAGGCCGUUAGGCCGAA AAGCCCCU | 12791 |
| 2543 | GGGGCUUUU GGGAAAGU | 3383 | ACUUUCCC CUGAUGAGGCCGUUAGGCCGAA AAAGCCCC | 12792 |
| 2552 | GGGAAAGUC GUUCAAGC | 3384 | GCUUGAAC CUGAUGAGGCCGUUAGGCCGAA ACUUUCCC | 12793 |
| 2555 | AAAGUCGUU CAAGCCUC | 3385 | GAGGCUUG CUGAUGAGGCCGUUAGGCCGAA ACGACUUU | 12794 |
| 2556 | AAGUCGUUC AAGCCUCU | 3386 | AGAGGCUU CUGAUGAGGCCGUUAGGCCGAA AACGACUU | 12795 |
| 2563 | UCAAGCCUC UGCAUUUG | 3387 | CAAAUGCA CUGAUGAGGCCGUUAGGCCGAA AGGCUUGA | 12796 |
| 2569 | CUCUGCAUU UGGCAUUA | 3388 | UAAUGCCA CUGAUGAGGCCGUUAGGCCGAA AUGCAGAG | 12797 |
| 2570 | UCUGCAUUU GGCAUUAA | 3389 | UUAAUGCC CUGAUGAGGCCGUUAGGCCGAA AAUGCAGA | 12798 |
| 2576 | UUUGGCAUU AAGAAAUC | 457 | GAUUUCUU CUGAUGAGGCCGUUAGGCCGAA AUGCCAAA | 9876 |
| 2577 | UUGGCAUUA AGAAAUCA | 458 | UGAUUUCU CUGAUGAGGCCGUUAGGCCGAA AAUGCCAA | 9877 |
| 2584 | UAAGAAAUC ACCCACCU | 3390 | AGGUGGGU CUGAUGAGGCCGUUAGGCCGAA AUUUCUUA | 12799 |
| 2617 | GAAGAUGUU GAAAGAGG | 3391 | CCUCUUUC CUGAUGAGGCCGUUAGGCCGAA ACAUCUUC | 12800 |
| 2644 | CAGUGAGUA CAAAGCUC | 3392 | GAGCUUUG CUGAUGAGGCCGUUAGGCCGAA ACUCACUG | 12801 |
| 2652 | ACAAAGCUC UGAUGACC | 3393 | GGUCAUCA CUGAUGAGGCCGUUAGGCCGAA AGCUUUGU | 12802 |
| 2666 | ACCGAACUC AAGAUCUU | 3394 | AAGAUCUU CUGAUGAGGCCGUUAGGCCGAA AGUUCGGU | 12803 |
| 2672 | CUCAAGAUC UUGACCCA | 3395 | UGGGUCAA CUGAUGAGGCCGUUAGGCCGAA AUCUUGAG | 12804 |
| 2674 | CAAGAUCUU GACCCACA | 3396 | UGUGGGUC CUGAUGAGGCCGUUAGGCCGAA AGAUCUUG | 12805 |
| 2684 | ACCCACAUC GGCCAUCA | 3397 | UGAUGGCC CUGAUGAGGCCGUUAGGCCGAA AUGUGGGU | 12806 |
| 2691 | UCGGCCAUC AUCUGAAU | 3398 | AUUCAGAU CUGAUGAGGCCGUUAGGCCGAA AUGGCCGA | 12807 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 2694 | GCCAUCAUC UGAAUGUG | 3399 | CACAUUCA CUGAUGAGGCCGUUAGGCCGAA AUGAUGGC | 12808 |
| 2705 | AAUGUGGUU AACCUCCU | 3400 | AGGAGGUU CUGAUGAGGCCGUUAGGCCGAA ACCACAUU | 12809 |
| 2706 | AUGUGGUUA ACCUCCUG | 3401 | CAGGAGGU CUGAUGAGGCCGUUAGGCCGAA AACCACAU | 12810 |
| 2711 | GUUAACCUC CUGGGAGC | 3402 | GCUCCCAG CUGAUGAGGCCGUUAGGCCGAA AGGUUAAC | 12811 |
| 2742 | GAGGGCCUC UGAUGGUG | 470 | CACCAUCA CUGAUGAGGCCGUUAGGCCGAA AGGCCCUC | 9889 |
| 2753 | AUGGUGAUC GUGGAAUA | 3403 | UAUUCCAC CUGAUGAGGCCGUUAGGCCGAA AUCACCAU | 12812 |
| 2761 | CGUGGAAUA CUGCAAAU | 3404 | AUUUGCAG CUGAUGAGGCCGUUAGGCCGAA AUUCCACG | 12813 |
| 2770 | CUGCAAAUA CGGAAACC | 3405 | GGUUUCCG CUGAUGAGGCCGUUAGGCCGAA AUUUGCAG | 12814 |
| 2782 | AAACCUGUC CAACUACC | 3406 | GGUAGUUG CUGAUGAGGCCGUUAGGCCGAA ACAGGUUU | 12815 |
| 2788 | GUCCAACUA CCUCAAGA | 3407 | UCUUGAGG CUGAUGAGGCCGUUAGGCCGAA AGUUGGAC | 12816 |
| 2792 | AACUACCUC AAGAGCAA | 479 | UUGCUCUU CUGAUGAGGCCGUUAGGCCGAA AGGUAGUU | 9898 |
| 2809 | ACGUGACUU AUUCUGUC | 3408 | GACAGAAU CUGAUGAGGCCGUUAGGCCGAA AGUCACGU | 12817 |
| 2810 | CGUGACUUA UUCUGUCU | 3409 | AGACAGAA CUGAUGAGGCCGUUAGGCCGAA AAGUCACG | 12818 |
| 2812 | UGACUUAUU CUGUCUCA | 3410 | UGAGACAG CUGAUGAGGCCGUUAGGCCGAA AUAAGUCA | 12819 |
| 2813 | GACUUAUUC UGUCUCAA | 3411 | UUGAGACA CUGAUGAGGCCGUUAGGCCGAA AAUAAGUC | 12820 |
| 2817 | UAUUCUGUC UCAACAAG | 3412 | CUUGUUGA CUGAUGAGGCCGUUAGGCCGAA ACAGAAUA | 12821 |
| 2819 | UUCUGUCUC AACAAGGA | 3413 | UCCUUGUU CUGAUGAGGCCGUUAGGCCGAA AGACAGAA | 12822 |
| 2836 | CGCAGCCUU GCAUAUGG | 3414 | CCAUAUGC CUGAUGAGGCCGUUAGGCCGAA AGGCUGCG | 12823 |
| 2841 | CCUUGCAUA UGGAGCUC | 3415 | GAGCUCCA CUGAUGAGGCCGUUAGGCCGAA AUGCAAGG | 12824 |
| 2849 | AUGGAGCUC AAGAAAGA | 3416 | UCUUUCUU CUGAUGAGGCCGUUAGGCCGAA AGCUCCAU | 12825 |
| 2900 | CCCCGCCUA GACAGUGU | 3417 | ACACUGUC CUGAUGAGGCCGUUAGGCCGAA AGGCGGGG | 12826 |
| 2909 | GACAGUGUC AGCAGCUC | 3418 | GAGCUGCU CUGAUGAGGCCGUUAGGCCGAA ACACUGUC | 12827 |
| 2917 | CAGCAGCUC AAGUGUCA | 3419 | UGACACUU CUGAUGAGGCCGUUAGGCCGAA AGCUGCUG | 12828 |
| 2924 | UCAAGUGUC ACCAGCUC | 3420 | GAGCUGGU CUGAUGAGGCCGUUAGGCCGAA ACACUUGA | 12829 |
| 2932 | CACCAGCUC CAGCUUCC | 3421 | GGAAGCUG CUGAUGAGGCCGUUAGGCCGAA AGCUGGUG | 12830 |
| 2938 | CUCCAGCUU CCCUGAAG | 3422 | CUUCAGGG CUGAUGAGGCCGUUAGGCCGAA AGCUGGAG | 12831 |
| 2939 | UCCAGCUUC CCUGAAGA | 3423 | UCUUCAGG CUGAUGAGGCCGUUAGGCCGAA AAGCUGGA | 12832 |
| 2982 | ACGAGGAUU ACAGUGAG | 3424 | CUCACUGU CUGAUGAGGCCGUUAGGCCGAA AUCCUCGU | 12833 |
| 2983 | CGAGGAUUA CAGUGAGA | 3425 | UCUCACUG CUGAUGAGGCCGUUAGGCCGAA AAUCCUCG | 12834 |
| 2993 | AGUGAGAUC UCCAAGCA | 3426 | UGCUUGGA CUGAUGAGGCCGUUAGGCCGAA AUCUCACU | 12835 |
| 2995 | UGAGAUCUC CAAGCAGC | 3427 | GCUGCUUG CUGAUGAGGCCGUUAGGCCGAA AGAUCUCA | 12836 |
| 3008 | CAGCCCCUC ACCAUGGA | 3428 | UCCAUGGU CUGAUGAGGCCGUUAGGCCGAA AGGGGCUG | 12837 |
| 3026 | GACCUGAUU UCCUACAG | 3429 | CUGUAGGA CUGAUGAGGCCGUUAGGCCGAA AUCAGGUC | 12838 |
| 3027 | ACCUGAUUU CCUACAGU | 3430 | ACUGUAGG CUGAUGAGGCCGUUAGGCCGAA AAUCAGGU | 12839 |
| 3028 | CCUGAUUUC CUACAGUU | 3431 | AACUGUAG CUGAUGAGGCCGUUAGGCCGAA AAAUCAGG | 12840 |
| 3031 | GAUUUCCUA CAGUUCC | 3432 | GGAAACUG CUGAUGAGGCCGUUAGGCCGAA AGGAAAUC | 12841 |
| 3036 | CCUACAGUU UCCAAGUG | 3433 | CACUUGGA CUGAUGAGGCCGUUAGGCCGAA ACUGUAGG | 12842 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 3037 | CUACAGUUU CCAAGUGG | 3434 | CCACUUGG CUGAUGAGGCCGUUAGGCCGAA AACUGUAG | 12843 |
| 3038 | UACAGUUUC CAAGUGGC | 3435 | GCCACUUG CUGAUGAGGCCGUUAGGCCGAA AAACUGUA | 9938 |
| 3061 | CAUGGAGUU UCUGUCCU | 3436 | AGGACAGA CUGAUGAGGCCGUUAGGCCGAA ACUCCAUG | 12844 |
| 3062 | AUGGAGUUU CUGUCCUC | 3437 | GAGGACAG CUGAUGAGGCCGUUAGGCCGAA AACUCCAU | 12845 |
| 3063 | UGGAGUUUC UGUCCUCC | 3438 | GGAGGACA CUGAUGAGGCCGUUAGGCCGAA AAACUCCA | 12846 |
| 3067 | GUUUCUGUC CUCCAGAA | 3439 | UUCUGGAG CUGAUGAGGCCGUUAGGCCGAA ACAGAAAC | 12847 |
| 3070 | UCUGUCCUC CAGAAAGU | 3440 | ACUUUCUG CUGAUGAGGCCGUUAGGCCGAA AGGACAGA | 12848 |
| 3083 | AAGUGCAUU CAUCGGGA | 526 | UCCCGAUG CUGAUGAGGCCGUUAGGCCGAA AUGCACUU | 9945 |
| 3084 | AGUGCAUUC AUCGGGAC | 527 | GUCCCGAU CUGAUGAGGCCGUUAGGCCGAA AAUGCACU | 9946 |
| 3087 | GCAUUCAUC GGGACCUG | 528 | CAGGUCCC CUGAUGAGGCCGUUAGGCCGAA AUGAAUGC | 9947 |
| 3110 | AGAAACAUC CUUUUAUC | 3441 | GAUAAAAG CUGAUGAGGCCGUUAGGCCGAA AUGUUUCU | 9948 |
| 3113 | AACAUCCUU UUAUCUGA | 3442 | UCAGAUAA CUGAUGAGGCCGUUAGGCCGAA AGGAUGUU | 12849 |
| 3114 | ACAUCCUUU UAUCUGAG | 3443 | CUCAGAUA CUGAUGAGGCCGUUAGGCCGAA AAGGAUGU | 12850 |
| 3115 | CAUCCUUUU AUCUGAGA | 3444 | UCUCAGAU CUGAUGAGGCCGUUAGGCCGAA AAAGGAUG | 12851 |
| 3116 | AUCCUUUUA UCUGAGAA | 3445 | UUCUCAGA CUGAUGAGGCCGUUAGGCCGAA AAAAGGAU | 12852 |
| 3118 | CCUUUUAUC UGAGAACA | 3446 | UGUUCUCA CUGAUGAGGCCGUUAGGCCGAA AUAAAAGG | 12853 |
| 3140 | GUGAAGAUU UGCGACUU | 3447 | AAGUCGCA CUGAUGAGGCCGUUAGGCCGAA AUCUUCAC | 12854 |
| 3141 | UGAAGAUUU GCGACUUU | 3448 | AAAGUCGC CUGAUGAGGCCGUUAGGCCGAA AAUCUUCA | 12855 |
| 3148 | UUGCGACUU UGGCCUGG | 3449 | CCAGGCCA CUGAUGAGGCCGUUAGGCCGAA AGUCGCAA | 12856 |
| 3149 | UGCGACUUU GGCCUGGC | 3450 | GCCAGGCC CUGAUGAGGCCGUUAGGCCGAA AAGUCGCA | 12857 |
| 3165 | CCCGGGAUA UUUAUAAG | 542 | CUUAUAAA CUGAUGAGGCCGUUAGGCCGAA AUCCCGGG | 9961 |
| 3167 | CGGGAUAUU UAUAAGAA | 543 | UUCUUAUA CUGAUGAGGCCGUUAGGCCGAA AUAUCCCG | 9962 |
| 3168 | GGGAUAUUU AUAAGAAC | 544 | GUUCUUAU CUGAUGAGGCCGUUAGGCCGAA AAUAUCCC | 9963 |
| 3169 | GGAUAUUUA UAAGAACC | 545 | GGUUCUUA CUGAUGAGGCCGUUAGGCCGAA AAAUAUCC | 9964 |
| 3171 | AUAUUUAUA AGAACCCU | 3451 | AGGGUUCU CUGAUGAGGCCGUUAGGCCGAA AUAAAUAU | 12858 |
| 3183 | ACCCUGAUU AUGUGAGG | 3452 | CCUCACAU CUGAUGAGGCCGUUAGGCCGAA AUCAGGGU | 12859 |
| 3184 | CCCUGAUUA UGUGAGGA | 3453 | UCCUCACA CUGAUGAGGCCGUUAGGCCGAA AAUCAGGG | 12860 |
| 3201 | GAGGAGAUA CUCGACUU | 3454 | AAGUCGAG CUGAUGAGGCCGUUAGGCCGAA AUCUCCUC | 12861 |
| 3204 | GAGAUACUC GACUUCCC | 3455 | GGGAAGUC CUGAUGAGGCCGUUAGGCCGAA AGUAUCUC | 12862 |
| 3209 | ACUCGACUU CCCCUAAA | 3456 | UUUAGGGG CUGAUGAGGCCGUUAGGCCGAA AGUCGAGU | 12863 |
| 3210 | CUCGACUUC CCCUAAAA | 3457 | UUUUAGGG CUGAUGAGGCCGUUAGGCCGAA AAGUCGAG | 12864 |
| 3215 | CUUCCCCUA AAAUGGAU | 3458 | AUCCAUUU CUGAUGAGGCCGUUAGGCCGAA AGGGGAAG | 12865 |
| 3228 | GGAUGGCUC CUGAAUCC | 3459 | GGAUUCAG CUGAUGAGGCCGUUAGGCCGAA AGCCAUCC | 12866 |
| 3235 | UCCUGAAUC CAUCUUUG | 3460 | CAAAGAUG CUGAUGAGGCCGUUAGGCCGAA AUUCAGGA | 12867 |
| 3239 | GAAUCCAUC UUUGACAA | 3461 | UUGUCAAA CUGAUGAGGCCGUUAGGCCGAA AUGGAUUC | 12868 |
| 3241 | AUCCAUCUU UGACAAGG | 3462 | CCUUGUCA CUGAUGAGGCCGUUAGGCCGAA AGAUGGAU | 12869 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 3242 | UCCAUCUUU GACAAGGU | 3463 | ACCUUGUC CUGAUGAGGCCGUUAGGCCGAA AAGAUGGA | 12870 |
| 3251 | GACAAGGUC UACAGCAC | 3464 | GUGCUGUA CUGAUGAGGCCGUUAGGCCGAA ACCUUGUC | 12871 |
| 3253 | CAAGGUCUA CAGCACCA | 3465 | UGGUGCUG CUGAUGAGGCCGUUAGGCCGAA AGACCUUG | 12872 |
| 3277 | UGUGUGGUC CUAUGGCG | 3466 | CGCCAUAG CUGAUGAGGCCGUUAGGCCGAA ACCACACA | 12873 |
| 3280 | GUGGUCCUA UGGCGUGU | 3467 | ACACGCCA CUGAUGAGGCCGUUAGGCCGAA AGGACCAC | 12874 |
| 3289 | UGGCGUGUU GCUGUGGG | 3468 | CCCACAGC CUGAUGAGGCCGUUAGGCCGAA ACACGCCA | 12875 |
| 3302 | UGGGAGAUC UUCUCCUU | 3469 | AAGGAGAA CUGAUGAGGCCGUUAGGCCGAA AUCUCCCA | 12876 |
| 3304 | GGAGAUCUU CUCCUUAG | 3470 | CUAAGGAG CUGAUGAGGCCGUUAGGCCGAA AGAUCUCC | 12877 |
| 3305 | GAGAUCUUC UCCUUAGG | 3471 | CCUAAGGA CUGAUGAGGCCGUUAGGCCGAA AAGAUCUC | 12878 |
| 3307 | GAUCUUCUC CUUAGGGG | 3472 | CCCCUAAG CUGAUGAGGCCGUUAGGCCGAA AGAAGAUC | 12879 |
| 3310 | CUUCUCCUU AGGGGUU | 3473 | AACCCCCU CUGAUGAGGCCGUUAGGCCGAA AGGAGAAG | 12880 |
| 3311 | UUCUCCUUA GGGGUUC | 3474 | GAACCCCC CUGAUGAGGCCGUUAGGCCGAA AAGGAGAA | 12881 |
| 3328 | UAGGGGUU CUCCAUAC | 3475 | GUAUGGAG CUGAUGAGGCCGUUAGGCCGAA ACCCCCUA | 12882 |
| 3319 | AGGGGUUC UCCAUACC | 3476 | GGUAUGGA CUGAUGAGGCCGUUAGGCCGAA AACCCCCU | 12883 |
| 3321 | GGGUUCUC CAUACCCA | 3477 | UGGGUAUG CUGAUGAGGCCGUUAGGCCGAA AGAACCCC | 12884 |
| 3325 | UUCUCCAUA CCCAGGAG | 3478 | CUCCUGGG CUGAUGAGGCCGUUAGGCCGAA AUGGAGAA | 12885 |
| 3352 | UGAAGACUU CUGCAGCC | 3479 | GGCUGCAG CUGAUGAGGCCGUUAGGCCGAA AGUCUUCA | 12886 |
| 3353 | GAAGACUUC UGCAGCCG | 3480 | CGGCUGCA CUGAUGAGGCCGUUAGGCCGAA AAGUCUUC | 12887 |
| 3397 | CCCGGAGUA UGCCACAC | 3481 | GUGUGGCA CUGAUGAGGCCGUUAGGCCGAA ACUCCGGG | 12888 |
| 3413 | CCUGAAAUC UACCAAAU | 3482 | AUUUGGUA CUGAUGAGGCCGUUAGGCCGAA AUUUCAGG | 12889 |
| 3415 | UGAAAUCUA CCAAAUCA | 3483 | UGAUUUGG CUGAUGAGGCCGUUAGGCCGAA AGAUUUCA | 12890 |
| 3422 | UACCAAAUC AUGGUGGA | 3484 | UCCAACAU CUGAUGAGGCCGUUAGGCCGAA AUUUGGUA | 12891 |
| 3427 | AAUCAUGUU GGAUUGCU | 3485 | AGCAAUCC CUGAUGAGGCCGUUAGGCCGAA ACAUGAUU | 12892 |
| 3432 | UGUUGGAUU GCUGGCAC | 3486 | GUGCCAGC CUGAUGAGGCCGUUAGGCCGAA AUCCAACA | 12893 |
| 3466 | GCCCCGGUU UGCUGAAC | 3487 | GUUCAGCA CUGAUGAGGCCGUUAGGCCGAA ACCGGGGC | 12894 |
| 3467 | CCCCGGUUU GCUGAACU | 3488 | AGUUCAGC CUGAUGAGGCCGUUAGGCCGAA AACCGGGG | 12895 |
| 3476 | GCUGAACUU GUGGAGAA | 3489 | UUCUCCAC CUGAUGAGGCCGUUAGGCCGAA AGUUCAGC | 12896 |
| 3488 | GAGAAACUU GGUGACCU | 3490 | AGGUCACC CUGAUGAGGCCGUUAGGCCGAA AGUUUCUC | 12897 |
| 3500 | GACCUGCUU CAAGCCAA | 3491 | UUGGCUUG CUGAUGAGGCCGUUAGGCCGAA AGCAGGUC | 12898 |
| 3501 | ACCUGCUUC AAGCCAAC | 3492 | GUUGGCUU CUGAUGAGGCCGUUAGGCCGAA AAGCAGGU | 12899 |
| 3512 | GCCAACGUC CAACAGGA | 3493 | UCCUGUUG CUGAUGAGGCCGUUAGGCCGAA ACGUUGGC | 12900 |
| 3531 | GGAAAGAUU ACAUCCCC | 3494 | GGGGAUGU CUGAUGAGGCCGUUAGGCCGAA AUCUUUCC | 12901 |
| 3532 | GAAAGAUUA CAUCCCCC | 3495 | GGGGGAUG CUGAUGAGGCCGUUAGGCCGAA AAUCUUUC | 12902 |
| 3536 | GAUUACAUC CCCUCAA | 3496 | UUGAGGGG CUGAUGAGGCCGUUAGGCCGAA AUGUAAUC | 12903 |
| 3542 | AUCCCCCUC AAUGCCAU | 3497 | AUGGCAUU CUGAUGAGGCCGUUAGGCCGAA AGGGGGAU | 12904 |
| 3551 | AAUGCCAUA CUGACUAG | 3498 | CUAGUCAG CUGAUGAGGCCGUUAGGCCGAA AUGGCAUU | 12905 |
| 3558 | UACUGACUA GAAACAGU | 3499 | ACUGUUUC CUGAUGAGGCCGUUAGGCCGAA AGUCAGUA | 12906 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 3567 | GAAACAGUA GCUUCACA | 3500 | UGUGAAGC CUGAUGAGGCCGUUAGGCCGAA ACUGUUUC | 12907 |
| 3571 | CAGUAGCUU CACAUACU | 3501 | AGUAUGUG CUGAUGAGGCCGUUAGGCCGAA AGCUACUG | 12908 |
| 3572 | AGUAGCUUC ACAUACUC | 3502 | GAGUAUGU CUGAUGAGGCCGUUAGGCCGAA AAGCUACU | 12909 |
| 3577 | CUUCACAUA CUCGACCC | 3503 | GGGUCGAG CUGAUGAGGCCGUUAGGCCGAA AUGUGAAG | 12910 |
| 3580 | CACAUACUC GACCCCCA | 3504 | UGGGGGUC CUGAUGAGGCCGUUAGGCCGAA AGUAUGUG | 12911 |
| 3592 | CCCCACCUU CUCUGAGG | 3505 | CCUCAGAG CUGAUGAGGCCGUUAGGCCGAA AGGUGGGG | 12912 |
| 3593 | CCCACCUUC UCUGAGGA | 3506 | UCCUCAGA CUGAUGAGGCCGUUAGGCCGAA AAGGUGGG | 12913 |
| 3595 | CACCUUCUC UGAGGACC | 3507 | GGUCCUCA CUGAUGAGGCCGUUAGGCCGAA AGAAGGUG | 12914 |
| 3605 | GAGGACCUU UUCAAGGA | 3508 | UCCUUGAA CUGAUGAGGCCGUUAGGCCGAA AGGUCCUC | 12915 |
| 3606 | AGGACCUUU UCAAGGAC | 3509 | GUCCUUGA CUGAUGAGGCCGUUAGGCCGAA AAGGUCCU | 12916 |
| 3607 | GGACCUUUU CAAGGACG | 3510 | CGUCCUUG CUGAUGAGGCCGUUAGGCCGAA AAAGGUCC | 12917 |
| 3608 | GACCUUUUC AAGGACGG | 3511 | CCGUCCUU CUGAUGAGGCCGUUAGGCCGAA AAAAGGUC | 12918 |
| 3619 | GGACGGCUU UGCAGAUC | 3512 | GAUCUCCA CUGAUGAGGCCGUUAGGCCGAA AGCCGUCC | 12919 |
| 3620 | GACGGCUUU GCAGAUCC | 3513 | GGAUCUGC CUGAUGAGGCCGUUAGGCCGAA AAGCCGUC | 12920 |
| 3627 | UUGCAGAUC CACAUUUU | 3514 | AAAAUGUG CUGAUGAGGCCGUUAGGCCGAA AUCUGCAA | 12921 |
| 3633 | AUCCACAUU UUCAUUCC | 3515 | GGAAUGAA CUGAUGAGGCCGUUAGGCCGAA AUGUGGAU | 12922 |
| 3634 | UCCACAUUU UCAUUCCG | 3516 | CGGAAUGA CUGAUGAGGCCGUUAGGCCGAA AAUGUGGA | 12923 |
| 3635 | CCACAUUUU CAUUCCGG | 3517 | CCGGAAUG CUGAUGAGGCCGUUAGGCCGAA AAAUGUGG | 12924 |
| 3636 | CACAUUUUC AUUCCGGA | 3518 | UCCGGAAU CUGAUGAGGCCGUUAGGCCGAA AAAAUGUG | 12925 |
| 3639 | AUUUUCAUU CCGGAAGC | 3519 | GCUUCCGG CUGAUGAGGCCGUUAGGCCGAA AUGAAAAU | 12926 |
| 3640 | UUUUCAUUC CGGAAGCU | 3520 | AGCUUCCG CUGAUGAGGCCGUUAGGCCGAA AAUGAAAA | 12927 |
| 3649 | CGGAAGCUC UGAUGAUG | 3521 | CAUCAUCA CUGAUGAGGCCGUUAGGCCGAA AGCUUCCG | 12928 |
| 3664 | UGUGAGAUA UGUAAACG | 3522 | CGUUUACA CUGAUGAGGCCGUUAGGCCGAA AUCUCACA | 12929 |
| 3668 | AGAUAUGUA AACGCUUU | 3523 | AAAGCGUU CUGAUGAGGCCGUUAGGCCGAA ACAUAUCU | 12930 |
| 3675 | UAAACGCUU UCAAAUUC | 3524 | GAAUUUGA CUGAUGAGGCCGUUAGGCCGAA AGCGUUUA | 12931 |
| 3676 | AAACGCUUU CAAAUUCA | 3525 | UGAAUUUG CUGAUGAGGCCGUUAGGCCGAA AAGCGUUU | 12932 |
| 3677 | AACGCUUUC AAAUUCAU | 3526 | AUGAAUUU CUGAUGAGGCCGUUAGGCCGAA AAAGCGUU | 12933 |
| 3682 | UUUCAAAUU CAUGAGCC | 3527 | GGCUCAUG CUGAUGAGGCCGUUAGGCCGAA AUUUGAAA | 12934 |
| 3683 | UUCAAAUUC AUGAGCCU | 3528 | AGGCUCAU CUGAUGAGGCCGUUAGGCCGAA AAUUUGAA | 12935 |
| 3701 | GAAAGAAUC AAAACCUU | 637 | AAGGUUUU CUGAUGAGGCCGUUAGGCCGAA AUUCUUUC | 10056 |
| 3709 | CAAAACCUU UGAGGAGC | 3529 | GCUCCUCA CUGAUGAGGCCGUUAGGCCGAA AGGUUUUG | 12936 |
| 3710 | AAAACCUUU GAGGAGCU | 3530 | AGCUCCUC CUGAUGAGGCCGUUAGGCCGAA AAGGUUUU | 12937 |
| 3719 | GAGGAGCUU UCACCGAA | 3531 | UUCGGUGA CUGAUGAGGCCGUUAGGCCGAA AGCUCCUC | 12938 |
| 3720 | AGGAGCUUU CACCGAAC | 3532 | GUUCGGUG CUGAUGAGGCCGUUAGGCCGAA AAGCUCCU | 12939 |
| 3721 | GGAGCUUUC ACCGAACU | 3533 | AGUUCGGU CUGAUGAGGCCGUUAGGCCGAA AAAGCUCC | 12940 |
| 3730 | ACCGAACUC CACCUCCA | 3534 | UGGAGGUG CUGAUGAGGCCGUUAGGCCGAA AGUUCGGU | 12941 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 3736 | CUCCACCUC CAUGUUUG | 3535 | CAAACAUG CUGAUGAGGCCGUUAGGCCGAA AGGUGGAG | 12942 |
| 3742 | CUCCAUGUU UGAGGACU | 3536 | AGUCCUCA CUGAUGAGGCCGUUAGGCCGAA ACAUGGAG | 12943 |
| 3743 | UCCAUGUUU GAGGACUA | 3537 | UAGUCCUC CUGAUGAGGCCGUUAGGCCGAA AACAUGGA | 12944 |
| 3751 | UGAGGACUA UCAGCUGG | 3538 | CCAGCUGA CUGAUGAGGCCGUUAGGCCGAA AGUCCUCA | 12945 |
| 3753 | AGGACUAUC AGCUGGAC | 3539 | GUCCAGCU CUGAUGAGGCCGUUAGGCCGAA AUAGUCCU | 12946 |
| 3765 | UGGACACUA GCACUCUG | 3540 | CAGAGUGC CUGAUGAGGCCGUUAGGCCGAA AGUGUCCA | 12947 |
| 3771 | CUAGCACUC UGCUGGGC | 3541 | GCCCAGCA CUGAUGAGGCCGUUAGGCCGAA AGUGCUAG | 12948 |
| 3781 | GCUGGGCUC CCCCUUGC | 3542 | GCAAGGGG CUGAUGAGGCCGUUAGGCCGAA AGCCCAGC | 12949 |
| 3787 | CUCCCCCUU GCUGAAGC | 3543 | GCUUCAGC CUGAUGAGGCCGUUAGGCCGAA AGGGGGAG | 12950 |
| 3799 | GAAGCGGUU CACCUGGA | 3544 | UCCAGGUG CUGAUGAGGCCGUUAGGCCGAA ACCGCUUC | 12951 |
| 3800 | AAGCGGUUC ACCUGGAC | 3545 | GUCCAGGU CUGAUGAGGCCGUUAGGCCGAA AACCGCUU | 12952 |
| 3829 | CAAGGCCUC CAUGAAGA | 3546 | UCUUCAUG CUGAUGAGGCCGUUAGGCCGAA AGGCCUUG | 12953 |
| 3839 | AUGAAGAUA GACUUGAG | 3547 | CUCAAGUC CUGAUGAGGCCGUUAGGCCGAA AUCUUCAU | 12954 |
| 3844 | GAUAGACUU GAGAAUAG | 3548 | CUAUUCUC CUGAUGAGGCCGUUAGGCCGAA AGUCUAUC | 12955 |
| 3851 | UUGAGAAUA GCGAGUAA | 3549 | UUACUCGC CUGAUGAGGCCGUUAGGCCGAA AUUCUCAA | 12956 |
| 3858 | UAGCGAGUA AAAGCAAG | 3550 | CUUGCUUU CUGAUGAGGCCGUUAGGCCGAA ACUCGCUA | 12957 |
| 3878 | GCGGGACUU UCCGAUCU | 3551 | AGAUCGGA CUGAUGAGGCCGUUAGGCCGAA AGUCCCGC | 12958 |
| 3879 | CGGGACUUU CCGAUCUG | 3552 | CAGAUCGG CUGAUGAGGCCGUUAGGCCGAA AAGUCCCG | 12959 |
| 3880 | GGGACUUUC CGAUCUGC | 3553 | GCAGAUCG CUGAUGAGGCCGUUAGGCCGAA AAAGUCCC | 12960 |
| 3885 | UUUCCGAUC UGCCGAGG | 3554 | CCUCGGCA CUGAUGAGGCCGUUAGGCCGAA AUCGGAAA | 12961 |
| 3901 | GCCCAGCUU CUGCUUCU | 3555 | AGAAGCAG CUGAUGAGGCCGUUAGGCCGAA AGCUGGGC | 12962 |
| 3902 | CCCAGCUUC UGCUUCUC | 3556 | GAGAAGCA CUGAUGAGGCCGUUAGGCCGAA AAGCUGGG | 12963 |
| 3907 | CUUCUGCUU CUCCAGCU | 3557 | AGCUGGAG CUGAUGAGGCCGUUAGGCCGAA AGCAGAAG | 12964 |
| 3908 | UUCUGCUUC UCCAGCUG | 3558 | CAGCUGGA CUGAUGAGGCCGUUAGGCCGAA AAGCAGAA | 12965 |
| 3910 | CUGCUUCUC CAGCUGUG | 3559 | CACAGCUG CUGAUGAGGCCGUUAGGCCGAA AGAAGCAG | 12966 |
| 3926 | GGCCACAUC AGGCCCGU | 3560 | ACGGGCCU CUGAUGAGGCCGUUAGGCCGAA AUGUGGCC | 12967 |
| 3949 | CGAUGAAUC UGAGCUGG | 3561 | CCAGCUCA CUGAUGAGGCCGUUAGGCCGAA AUUCAUCG | 12968 |
| 3967 | AAAGGAGUC CUGCUGUU | 3562 | AACAGCAG CUGAUGAGGCCGUUAGGCCGAA ACUCCUUU | 12969 |
| 3975 | CCUGCUGUU CUCCACCC | 3563 | GGGUGGAG CUGAUGAGGCCGUUAGGCCGAA ACAGCAGG | 12970 |
| 3976 | CUGCUGUUC UCCACCCC | 3564 | GGGGUGGA CUGAUGAGGCCGUUAGGCCGAA AACAGCAG | 12971 |
| 3978 | GCUGUUCUC CACCCCCA | 3565 | UGGGGGUG CUGAUGAGGCCGUUAGGCCGAA AGAACAGC | 12972 |
| 3991 | CCCAGACUA CAACUCCG | 3566 | CGGAGUUG CUGAUGAGGCCGUUAGGCCGAA AGUCUGGG | 12973 |
| 3997 | CUACAACUC CGUGGUGU | 3567 | ACACCACG CUGAUGAGGCCGUUAGGCCGAA AGUUGUAG | 12974 |
| 4006 | CGUGGUGUU GUACCUCU | 3568 | AGGAGUAC CUGAUGAGGCCGUUAGGCCGAA ACACCACG | 12975 |
| 4009 | GGUGUUGUA CUCCUCCC | 3569 | GGGAGGAG CUGAUGAGGCCGUUAGGCCGAA ACAACACC | 12976 |
| 4012 | GUUGUACUC CUCCCGC | 3570 | GCGGGGAG CUGAUGAGGCCGUUAGGCCGAA AGUACAAC | 12977 |
| 4015 | GUACUCCUC CCCGCCCG | 3571 | CGGGCGGG CUGAUGAGGCCGUUAGGCCGAA AGGAGUAC | 12978 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 4027 | GCCCGCCUA AAGCUUCU | 3572 | AGAAGCUU CUGAUGAGGCCGUUAGGCCGAA AGGCGGGC | 12979 |
| 4033 | CUAAAGCUU CUCACCAG | 3573 | CUGGUGAG CUGAUGAGGCCGUUAGGCCGAA AGCUUUAG | 12980 |
| 4034 | UAAAGCUUC UCACCAGC | 3574 | GCUGGUGA CUGAUGAGGCCGUUAGGCCGAA AAGCUUUA | 12981 |
| 4036 | AGCUUCUC ACCAGCCC | 3575 | GGGCUGGU CUGAUGAGGCCGUUAGGCCGAA AGAAGCUU | 12982 |
| 4066 | CUGACAGUA UUAUACAU | 3576 | AUGUAUAA CUGAUGAGGCCGUUAGGCCGAA ACUGUCAG | 12983 |
| 4068 | GACAGUAUU AUACUCU | 3577 | AGAUGUAU CUGAUGAGGCCGUUAGGCCGAA AUACUGUC | 12984 |
| 4069 | ACAGUAUUA UACAUCUA | 3578 | UAGAUGUA CUGAUGAGGCCGUUAGGCCGAA AAUACUGU | 12985 |
| 4071 | AGUAUUAUA CAUCUAUG | 3579 | CAUAGAUG CUGAUGAGGCCGUUAGGCCGAA AUAAUACU | 12986 |
| 4075 | UUAUACAUC UAUGAGUU | 3580 | AACUCAUA CUGAUGAGGCCGUUAGGCCGAA AUGUAUAA | 12987 |
| 4077 | AUACAUCUA UGAGUUUA | 3581 | UAAACUCA CUGAUGAGGCCGUUAGGCCGAA AGAUGUAU | 12988 |
| 4083 | CUAUGAGUU UACACCUA | 3582 | UAGGUGUA CUGAUGAGGCCGUUAGGCCGAA ACUCAUAG | 12989 |
| 4084 | UAUGAGUUU ACACCUAU | 3583 | AUAGGUGU CUGAUGAGGCCGUUAGGCCGAA AACUCAUA | 12990 |
| 4085 | AUGAGUUUA CACCUAUU | 3584 | AAUAGGUG CUGAUGAGGCCGUUAGGCCGAA AAACUCAU | 12991 |
| 4091 | UUACACCUA UUCCGCUC | 3585 | GAGCGGAA CUGAUGAGGCCGUUAGGCCGAA AGGUGUAA | 12992 |
| 4093 | ACACCUAUU CCGCUCCA | 3586 | UGGAGCGG CUGAUGAGGCCGUUAGGCCGAA AUAGGUGU | 12993 |
| 4094 | CACCUAUUC CGCUCCAC | 3587 | GUGGAGCG CUGAUGAGGCCGUUAGGCCGAA AAUAGGUG | 12994 |
| 4099 | AUUCCGCUC CACAGGAG | 3588 | CUCCUGUG CUGAUGAGGCCGUUAGGCCGAA AGCGGAAU | 12995 |
| 4117 | CAGCUGCUU UUCGUGAC | 3589 | GUCACGAA CUGAUGAGGCCGUUAGGCCGAA AGCAGCUG | 12996 |
| 4118 | AGCUGCUUU UCGUGACC | 3590 | GGUCACGA CUGAUGAGGCCGUUAGGCCGAA AAGCAGCU | 12997 |
| 4119 | GCUGCUUUU CGUGACCU | 3591 | AGGUCACG CUGAUGAGGCCGUUAGGCCGAA AAAGCAGC | 12998 |
| 4120 | CUGCUUUUC GUGACCUU | 3592 | AAGGUCAC CUGAUGAGGCCGUUAGGCCGAA AAAAGCAG | 12999 |
| 4128 | CGUGACCUU UAAUCGUG | 3593 | CACGAUUA CUGAUGAGGCCGUUAGGCCGAA AGGUCACG | 13000 |
| 4129 | GUGACCUUU AAUCGUGC | 3594 | GCACGAUU CUGAUGAGGCCGUUAGGCCGAA AAGGUCAC | 13001 |
| 4130 | UGACCUUUA AUCGUGCU | 3595 | AGCACGAU CUGAUGAGGCCGUUAGGCCGAA AAAGGUCA | 13002 |
| 4133 | CCUUUAAUC GUGCUUUU | 3596 | AAAAGCAC CUGAUGAGGCCGUUAGGCCGAA AUUAAAGG | 13003 |
| 4139 | AUCGUGCUU UUUEGUUU | 3597 | AAACAAAA CUGAUGAGGCCGUUAGGCCGAA AGCACGAU | 13004 |
| 4140 | UCGUGCUUU UUUGUUUU | 3598 | AAAACAAA CUGAUGAGGCCGUUAGGCCGAA AAGCACGA | 13005 |
| 4141 | CGUGCUUUU UUGUUUUU | 3599 | AAAAACAA CUGAUGAGGCCGUUAGGCCGAA AAAGCACG | 13006 |
| 4142 | GUGCUUUUU UGUUUUUU | 3600 | AAAAAACA CUGAUGAGGCCGUUAGGCCGAA AAAAGCAC | 13007 |
| 4143 | UGCUUUUUU GUUUUUUG | 3601 | CAAAAAAC CUGAUGAGGCCGUUAGGCCGAA AAAAAGCA | 13008 |
| 4146 | UUUUUUGUU UUUUGUUU | 3602 | AAACAAAA CUGAUGAGGCCGUUAGGCCGAA ACAAAAAA | 13009 |
| 4147 | UUUUUGUUU UUUGUUJU | 3603 | AAAACAAA CUGAUGAGGCCGUUAGGCCGAA AACAAAAA | 13010 |
| 4148 | UUUUGUUUU UUGUUUUG | 3604 | CAAAACAA CUGAUGAGGCCGUUAGGCCGAA AAACAAAA | 13011 |
| 4149 | UUUGUUUUU UGUUUUGU | 3605 | ACAAAACA CUGAUGAGGCCGUUAGGCCGAA AAAACAAA | 13012 |
| 4150 | UUGUUUUUU GUUUUGUU | 3606 | AACAAAAC CUGAUGAGGCCGUUAGGCCGAA AAAAACAA | 13013 |
| 4153 | UUUUUUGUU UUGUUUGU | 3607 | ACAAACAA CUGAUGAGGCCGUUAGGCCGAA ACAAAAAA | 13014 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 4154 | UUUUUGUUU UGUUUGUU | 3608 | AACAAACA CUGAUGAGGCCGUUAGGCCGAA AACAAAAA | 13015 |
| 4255 | UUUUGUUUU GUUUGUUG | 3609 | CAACAAAC CUGAUGAGGCCGUUAGGCCGAA AAACAAAA | 13016 |
| 4258 | UGUUUGUU UGUUGUUG | 3610 | CAACAACA CUGAUGAGGCCGUUAGGCCGAA ACAAAACA | 13017 |
| 4259 | GUUUUGUUU GUUGUUGC | 3611 | GCAACAAC CUGAUGAGGCCGUUAGGCCGAA AACAAAAC | 13018 |
| 4162 | UUGUUUGUU GUUGCUGU | 3612 | ACAGCAAC CUGAUGAGGCCGUUAGGCCGAA ACAAACAA | 13019 |
| 4165 | UUUGUUGUU GCUGUUUU | 3613 | AAAACAGC CUGAUGAGGCCGUUAGGCCGAA ACAACAAA | 13020 |
| 4171 | GUUGCUGUU UUGACUAA | 3614 | UUAGUCAA CUGAUGAGGCCGUUAGGCCGAA ACAGCAAC | 13021 |
| 4172 | UUGCUGUUU UGACUAAC | 3615 | GUUAGUCA CUGAUGAGGCCGUUAGGCCGAA AACAGCAA | 13022 |
| 4173 | UGCUGUUUU GACUAACA | 3616 | UGUUAGUC CUGAUGAGGCCGUUAGGCCGAA AAACAGCA | 13023 |
| 4178 | UUUUGACUA ACAAGAAU | 737 | AUUCUUGU CUGAUGAGGCCGUUAGGCCGAA AGUCAAAA | 10156 |
| 4189 | AAGAAUGUA ACCCCAGU | 3617 | ACUGGGGU CUGAUGAGGCCGUUAGGCCGAA ACAUUCUU | 13024 |
| 4198 | ACCCCAGUU AGUGACGU | 3618 | ACGUCACU CUGAUGAGGCCGUUAGGCCGAA ACUGGGGU | 13025 |
| 4199 | CCCCAGUUA GUGACGUG | 3619 | CACGUCAC CUGAUGAGGCCGUUAGGCCGAA AACUGGGG | 13026 |
| 4216 | UGAAGAAUA CUAUUGUU | 3620 | AACAAUAG CUGAUGAGGCCGUUAGGCCGAA AUUCUUCA | 13027 |
| 4219 | AGAAUACUA UUGUUAGA | 3621 | UCUAACAA CUGAUGAGGCCGUUAGGCCGAA AGUAUUCU | 13028 |
| 4221 | AAUACUAUU GUUAGAGA | 3622 | UCUCUAAC CUGAUGAGGCCGUUAGGCCGAA AUAGUAUU | 13029 |
| 4224 | ACUAUUGUU AGAGAAAU | 3623 | AUUUCUCU CUGAUGAGGCCGUUAGGCCGAA ACAAUAGU | 13030 |
| 4225 | CUAUUGUUA GAGAAAUC | 3624 | GAUUUCUC CUGAUGAGGCCGUUAGGCCGAA AACAAUAG | 13031 |
| 4233 | AGAGAAAUC CCCCCGC | 3625 | GCGGGGGG CUGAUGAGGCCGUUAGGCCGAA AUUUCUCU | 13032 |
| 4249 | CAAAGCCUC AGGGUAAC | 3626 | GUUACCCU CUGAUGAGGCCGUUAGGCCGAA AGGCUUUG | 13033 |
| 4255 | CUCAGGGUA ACCUGGAC | 3627 | GUCCAGGU CUGAUGAGGCCGUUAGGCCGAA ACCCUGAG | 13034 |
| 4282 | AGGUGCCUC UGGCGACC | 3628 | GGUCGCCA CUGAUGAGGCCGUUAGGCCGAA AGGCACCU | 13035 |
| 4323 | CCCACCCUC CCUGCAGC | 3629 | GCUGCAGG CUGAUGAGGCCGUUAGGCCGAA AGGGUGGG | 13036 |
| 4341 | GUGGGACUA GAGGCAGU | 3630 | ACUGCCUC CUGAUGAGGCCGUUAGGCCGAA AGUCCCAC | 13037 |
| 4350 | GAGGCAGUA AGCCCAUU | 3631 | AAUGGGCU CUGAUGAGGCCGUUAGGCCGAA ACUGCCUC | 13038 |
| 4358 | AAGCCCAUU AGCUCAUG | 3632 | CAUGAGCU CUGAUGAGGCCGUUAGGCCGAA AUGGGCUU | 13039 |
| 4359 | AGCCCAUUA GCUCAUGG | 3633 | CCAUGAGC CUGAUGAGGCCGUUAGGCCGAA AAUGGGCU | 13040 |
| 4363 | CAUUAGCUC AUGGCUGC | 3634 | GCAGCCAU CUGAUGAGGCCGUUAGGCCGAA AGCUAAUG | 13041 |
| 4387 | GACCUGCUC UGUCUCUC | 3635 | GAGAGACA CUGAUGAGGCCGUUAGGCCGAA AGCAGGUC | 13042 |
| 4391 | UGCUCUGUC UCUCUUAU | 3636 | AUAAGAGA CUGAUGAGGCCGUUAGGCCGAA ACAGAGCA | 13043 |
| 4393 | CUCUGUCUC UCUUAUGG | 3637 | CCAUAAGA CUGAUGAGGCCGUUAGGCCGAA AGACAGAG | 13044 |
| 4395 | CUGUCUCUC UUAUGGAG | 3638 | CUCCAUAA CUGAUGAGGCCGUUAGGCCGAA AGAGACAG | 13045 |
| 4397 | GUCUCUCUU AUGGAGGA | 3639 | UCCUCCAU CUGAUGAGGCCGUUAGGCCGAA AGAGAGAC | 13046 |
| 4398 | UCUCUCUUA UGGAGGAA | 3640 | UUCCUCCA CUGAUGAGGCCGUUAGGCCGAA AAGAGAGA | 13047 |
| 4445 | AAAAGGCUU UGGGAUGC | 3641 | GCAUCCCA CUGAUGAGGCCGUUAGGCCGAA AGCCUUUU | 13048 |
| 4446 | AAAGGCUUU GGGAUGCG | 3642 | CGCAUCCC CUGAUGAGGCCGUUAGGCCGAA AAGCCUUU | 13049 |
| 4456 | GGAUGCGUC CGUCCUGU | 3643 | ACAGGACG CUGAUGAGGCCGUUAGGCCGAA ACGCAUCC | 13050 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 4460 | GCGUCCGUC CUGUGGAG | 3644 | CUCCACAG CUGAUGAGGCCGUUAGGCCGAA ACGGACGC | 13051 |
| 4487 | AGGGGGCUC CGCUAUGC | 3645 | GCAUAGCG CUGAUGAGGCCGUUAGGCCGAA AGCCCCCU | 13052 |
| 4492 | GCUCCGCUA UGCCACUU | 3646 | AAGUGGCA CUGAUGAGGCCGUUAGGCCGAA AGCGGAGC | 13053 |
| 4500 | AUGCCACUU CAGUGACU | 3647 | AGUCACUG CUGAUGAGGCCGUUAGGCCGAA AGUGGCAU | 13054 |
| 4501 | UGCCACUUC AGUGACUU | 3648 | AAGUCACU CUGAUGAGGCCGUUAGGCCGAA AAGUGGCA | 13055 |
| 4509 | CAGUGACUU CUCACUCC | 3649 | GGAGUGAG CUGAUGAGGCCGUUAGGCCGAA AGUCACUG | 13056 |
| 4510 | AGUGACUUC UCACUCCU | 3650 | AGGAGUGA CUGAUGAGGCCGUUAGGCCGAA AAGUCACU | 13057 |
| 4512 | UGACUUCUC ACUCCUGG | 3651 | CCAGGAGU CUGAUGAGGCCGUUAGGCCGAA AGAAGUCA | 13058 |
| 4516 | UUCUCACUC CUGGCCUC | 3652 | GAGGCCAG CUGAUGAGGCCGUUAGGCCGAA AGUGAGAA | 13059 |
| 4524 | CCUGGCCUC CGCUGUUU | 3653 | AAACAGCG CUGAUGAGGCCGUUAGGCCGAA AGGCCAGG | 13060 |
| 4531 | UCCGCUGUU UCGGGCCC | 3654 | GGGCCCGA CUGAUGAGGCCGUUAGGCCGAA ACAGCGGA | 13061 |
| 4532 | CCGCUGUUU CGGGCCCC | 3655 | GGGGCCCG CUGAUGAGGCCGUUAGGCCGAA AACAGCGG | 13062 |
| 4533 | CGCUGUUUC GGGCCCCC | 3656 | GGGGGCCC CUGAUGAGGCCGUUAGGCCGAA AAACAGCG | 13063 |
| 4543 | GGCCCCCUU CCAAGAGG | 3657 | CCUCUUGG CUGAUGAGGCCGUUAGGCCGAA AGGGGGCC | 13064 |
| 4544 | GCCCCCUUC CAAGAGGU | 3658 | ACCUCUUG CUGAUGAGGCCGUUAGGCCGAA AAGGGGGC | 13065 |
| 4553 | CAAGAGGUA UCAGAGCA | 3659 | UGCUCUGA CUGAUGAGGCCGUUAGGCCGAA ACCUCUUG | 13066 |
| 4555 | AGAGGUAUC AGAGCAGA | 3660 | UCUGCUCU CUGAUGAGGCCGUUAGGCCGAA AUACCUCU | 13067 |
| 4577 | AGGGACGUU UCCUAGAC | 3661 | GUCUAGGA CUGAUGAGGCCGUUAGGCCGAA ACGUCCCU | 13068 |
| 4578 | GGGACGUUU CCUAGACC | 3662 | GGUCUAGG CUGAUGAGGCCGUUAGGCCGAA AACGUCCC | 13069 |
| 4579 | GGACGUUUC CUAGACCA | 3663 | UGGUCUAG CUGAUGAGGCCGUUAGGCCGAA AAACGUCC | 13070 |
| 4582 | CGUUUCCUA GACCAGGG | 3664 | CCCUGGUC CUGAUGAGGCCGUUAGGCCGAA AGGAAACG | 13071 |
| 4598 | GCACAUGUU CUCGGGAA | 3665 | UUCCCGAG CUGAUGAGGCCGUUAGGCCGAA ACAUGUGC | 13072 |
| 4599 | CACAUGUUC UCGGGAAC | 3666 | GUUCCCGA CUGAUGAGGCCGUUAGGCCGAA AACAUGUG | 13073 |
| 4601 | CAUGUUCUC GGGAACCA | 3667 | UGGUUCCC CUGAUGAGGCCGUUAGGCCGAA AGAACAUG | 13074 |
| 4614 | ACCACAGUU AAUCUUAA | 3668 | UUAAGAUU CUGAUGAGGCCGUUAGGCCGAA ACUGUGGU | 13075 |
| 4615 | CCACAGUUA AUCUUAAA | 3669 | UUUAAGAU CUGAUGAGGCCGUUAGGCCGAA AACUGUGG | 13076 |
| 4618 | CAGUUAAUC UUAAAUCU | 3670 | AGAUUUAA CUGAUGAGGCCGUUAGGCCGAA AUUAACUG | 13077 |
| 4620 | GUUAAUCUU AAAUCUUU | 3671 | AAAGAUUU CUGAUGAGGCCGUUAGGCCGAA AGAUUAAC | 13078 |
| 4621 | UUAAUCUUA AAUCUUUU | 3672 | AAAAGAUU CUGAUGAGGCCGUUAGGCCGAA AAGAUUAA | 13079 |
| 4625 | UCUUAAAUC UUUUCCCG | 3673 | CGGGAAAA CUGAUGAGGCCGUUAGGCCGAA AUUUAAGA | 13080 |
| 4627 | UUAAAUCUU UUCCCGGG | 3674 | CCCGGGAA CUGAUGAGGCCGUUAGGCCGAA AGAUUUAA | 13081 |
| 4628 | UAAAUCUUU UCCCGGGA | 3675 | UCCCGGGA CUGAUGAGGCCGUUAGGCCGAA AAGAUUUA | 13082 |
| 4629 | AAAUCUUUU CCCGGGAG | 3676 | CUCCCGGG CUGAUGAGGCCGUUAGGCCGAA AAAGAUUU | 13083 |
| 4630 | AAUCUUUUC CCGGGAGU | 3677 | ACUCCCGG CUGAUGAGGCCGUUAGGCCGAA AAAAGAUU | 13084 |
| 4639 | CCGGGAGUC UUCUGUUG | 3678 | CAACAGAA CUGAUGAGGCCGUUAGGCCGAA ACUCCCGG | 13085 |
| 4641 | GGGAGUCUU CUGUUGUC | 3679 | GACAACAG CUGAUGAGGCCGUUAGGCCGAA AGACUCCC | 13086 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 4642 | GGAGUCUUC UGUUGUCU | 3680 | AGACAACA CUGAUGAGGCCGUUAGGCCGAA AAGACUCC | 13087 |
| 4646 | UCUUCUGUU GUCUGUUU | 3681 | AAACAGAC CUGAUGAGGCCGUUAGGCCGAA ACAGAAGA | 13088 |
| 4649 | UCUGUUGUC UGUUUACC | 3682 | GGUAAACA CUGAUGAGGCCGUUAGGCCGAA ACAACAGA | 13089 |
| 4653 | UUGUCUGUU UACCAUCC | 3683 | GGAUGGUA CUGAUGAGGCCGUUAGGCCGAA ACAGACAA | 13090 |
| 4654 | UGUCUGUUU ACCAUCCA | 3684 | UGGAUGGU CUGAUGAGGCCGUUAGGCCGAA AACAGACA | 13092 |
| 4655 | GUCUGUUUA CCAUCCAA | 3685 | UUGGAUGG CUGAUGAGGCCGUUAGGCCGAA AAACAGAC | 13092 |
| 4660 | UUUACCAUC CAAAGCAU | 3686 | AUGCUUUG CUGAUGAGGCCGUUAGGCCGAA AUGGUAAA | 13093 |
| 4669 | CAAAGCAUA UUUAACAU | 3687 | AUGUUAAA CUGAUGAGGCCGUUAGGCCGAA AUGCUUUG | 13094 |
| 4671 | AAGCAUAUU UAACAUGU | 3688 | ACAUGUUA CUGAUGAGGCCGUUAGGCCGAA AUAUGCUU | 13095 |
| 4672 | AGCAUAUUU AACAUGUG | 3689 | CACAUGUU CUGAUGAGGCCGUUAGGCCGAA AAUAUGCU | 13096 |
| 4673 | GCAUAUUUA ACAUGUGU | 3690 | ACACAUGU CUGAUGAGGCCGUUAGGCCGAA AAAUAUGC | 13097 |
| 4682 | ACAUGUGUC AGUGGGGG | 3691 | CCCCCACU CUGAUGAGGCCGUUAGGCCGAA ACACAUGU | 13098 |
| 4698 | GUGGCGCUU GGCUUCUG | 3692 | CAGAAGCC CUGAUGAGGCCGUUAGGCCGAA AGCGCCAC | 13099 |
| 4703 | GCUUGGCUU CUGAGGCC | 3693 | GGCCUCAG CUGAUGAGGCCGUUAGGCCGAA AGCCAAGC | 13100 |
| 4704 | CUUGGCUUC UGAGGCCA | 3694 | UGGCCUCA CUGAUGAGGCCGUUAGGCCGAA AAGCCAAG | 13101 |
| 4720 | AGAGCCAUC AUCAGUUC | 3695 | GAACUGAU CUGAUGAGGCCGUUAGGCCGAA AUGGCUCU | 13102 |
| 4723 | GCCAUCAUC AGUUCCUC | 3696 | GAGGAACU CUGAUGAGGCCGUUAGGCCGAA AUGAUGGC | 13103 |
| 4727 | UCAUCAGUU CCUCUAGU | 3697 | ACUAGAGG CUGAUGAGGCCGUUAGGCCGAA ACUGAUGA | 13104 |
| 4728 | CAUCAGUUC CUCUAGUG | 3698 | CACUAGAG CUGAUGAGGCCGUUAGGCCGAA AACUGAUG | 13105 |
| 4731 | CAGUUCCUC UAGUGAGA | 3699 | UCUCACUA CUGAUGAGGCCGUUAGGCCGAA AGGAACUG | 13106 |
| 4733 | GUUCCUCUA GUGAGAUG | 3700 | CAUCUCAC CUGAUGAGGCCGUUAGGCCGAA AGAGGAAC | 13107 |
| 4745 | AGAUGCAUU GAGGUCAU | 3701 | AUGACCUC CUGAUGAGGCCGUUAGGCCGAA AUGCAUCU | 13108 |
| 4751 | AUUGAGGUC AUACCCAA | 3702 | UUGGGUAU CUGAUGAGGCCGUUAGGCCGAA ACCUCAAU | 13109 |
| 4754 | GAGGUCAUA CCCAAGCU | 3703 | AGCUUGGG CUGAUGAGGCCGUUAGGCCGAA AUGACCUC | 13110 |
| 4763 | CCCAAGCUU GCAGGCCU | 3704 | AGGCCUGC CUGAUGAGGCCGUUAGGCCGAA AGCUUGGG | 13111 |
| 4777 | CCUGACCUU CGCAUACU | 3705 | AGUAUGCG CUGAUGAGGCCGUUAGGCCGAA AGGUCAGG | 13112 |
| 4778 | CUGACCUUC GCAUACUG | 3706 | CAGUAUGC CUGAUGAGGCCGUUAGGCCGAA AAGGUCAG | 13113 |
| 4783 | CUUCGCAUA CUGCUCAC | 3707 | GUGAGCAG CUGAUGAGGCCGUUAGGCCGAA AUGCGAAG | 13114 |
| 4789 | AUACUGCUC ACGGGAG | 3708 | CUCCCCGU CUGAUGAGGCCGUUAGGCCGAA AGCAGUAU | 13115 |
| 4799 | CGGGGAGUU AAGUGGUC | 3709 | GACCACUU CUGAUGAGGCCGUUAGGCCGAA ACUCCCCG | 13116 |
| 4800 | GGGGAGUUA AGUGGUCC | 3710 | GGACCACU CUGAUGAGGCCGUUAGGCCGAA AACUCCCC | 13117 |
| 4807 | UAAGUGGUC CAGUUUGG | 3711 | CCAAACUG CUGAUGAGGCCGUUAGGCCGAA ACCACUUA | 13118 |
| 4812 | GGUCCAGUU UGGCCUAG | 3712 | CUAGGCCA CUGAUGAGGCCGUUAGGCCGAA ACUGGACC | 13119 |
| 4813 | GUCCAGUUU GGCCUAGU | 3713 | ACUAGGCC CUGAUGAGGCCGUUAGGCCGAA AACUGGAC | 13120 |
| 4819 | UUGGCCUAG UAAGGUU | 3714 | AACCUUAC CUGAUGAGGCCGUUAGGCCGAA AGGCCAAA | 13121 |
| 4822 | GGCCUAGUA AGGUUGCC | 3715 | GGCAACCU CUGAUGAGGCCGUUAGGCCGAA ACUAGGCC | 13122 |
| 4827 | AGUAAGGUU GCCUACUG | 3716 | CAGUAGGC CUGAUGAGGCCGUUAGGCCGAA ACCUUACU | 13123 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 4832 | GGUUGCCUA CUGAUGGG | 3717 | CCCAUCAG CUGAUGAGGCCGUUAGGCCGAA AGGCAACC | 13124 |
| 4843 | GAUGGGCUC AAAAGCCA | 3718 | UGGCUUUU CUGAUGAGGCCGUUAGGCCGAA AGCCCAUC | 13125 |
| 4855 | AGCCACAUU UAAACAG | 3719 | CUGUUUAA CUGAUGAGGCCGUUAGGCCGAA AUGUGGCU | 13126 |
| 4855 | GCCACAUUU UAAACAGG | 3720 | CCUGUUUA CUGAUGAGGCCGUUAGGCCGAA AAUGUGGC | 13127 |
| 4857 | CCACAUUUU AAACAGGU | 3721 | ACCUGUUU CUGAUGAGGCCGUUAGGCCGAA AAAUGUGG | 13128 |
| 4858 | CACAUUUUA AACAGGUU | 3722 | AACCUGUU CUGAUGAGGCCGUUAGGCCGAA AAAAUGUG | 13129 |
| 4866 | AAACAGGUU UAUCUCA | 3723 | UGAGAUAA CUGAUGAGGCCGUUAGGCCGAA ACCUGUUU | 13130 |
| 4867 | AACAGGUUU UAUCUCAA | 3724 | UUGAGAUA CUGAUGAGGCCGUUAGGCCGAA AACCUGUU | 13131 |
| 4868 | ACAGGUUUU AUCUCAAG | 3725 | CUUGAGAU CUGAUGAGGCCGUUAGGCCGAA AAACCUGU | 13132 |
| 4869 | CAGGUUUUA UCUCAAGU | 3726 | ACUUGAGA CUGAUGAGGCCGUUAGGCCGAA AAAACCUG | 13133 |
| 4871 | GGUUUUAUC UCAAGUAU | 3727 | AUACUUGA CUGAUGAGGCCGUUAGGCCGAA AUAAAACC | 13134 |
| 4873 | UUUUAUCUC AAGUAUUA | 3728 | UAAUACUU CUGAUGAGGCCGUUAGGCCGAA AGAUAAAA | 13135 |
| 4878 | UCUCAAGUA UUAAUAUA | 3729 | UAUAUUAA CUGAUGAGGCCGUUAGGCCGAA ACUUGAGA | 13136 |
| 4880 | UCAAGUAUU AAUAUAUA | 3730 | UAUAUAUU CUGAUGAGGCCGUUAGGCCGAA AUACUUGA | 13137 |
| 4881 | CAAGUAUUA AUAUAUAG | 3731 | CUAUAUAU CUGAUGAGGCCGUUAGGCCGAA AAUACUUG | 13138 |
| 4884 | GUAUUAAUA UAUAGACA | 3732 | UGUCUAUA CUGAUGAGGCCGUUAGGCCGAA AUUAAUAC | 13139 |
| 4886 | AUUAAUAUA UAGACAAG | 3733 | CUUGUCUA CUGAUGAGGCCGUUAGGCCGAA AUAUUAAU | 13140 |
| 4888 | UAAUAUAUA GACAAGAC | 3734 | GUCUUGUC CUGAUGAGGCCGUUAGGCCGAA AUAUAUUA | 13141 |
| 4900 | AAGACACUU AUGCAUUA | 3735 | UAAUGCAU CUGAUGAGGCCGUUAGGCCGAA AGUGUCUU | 13142 |
| 4901 | AGACACUUA UGCAUUAU | 3736 | AUAAUGCA CUGAUGAGGCCGUUAGGCCGAA AAGUGUCU | 13143 |
| 4907 | UUAUGCAUU AUCCUGUU | 3737 | AACAGGAU CUGAUGAGGCCGUUAGGCCGAA AUGCAUAA | 13144 |
| 4908 | UAUGCAUUA UCCUGUUU | 3738 | AAACAGGA CUGAUGAGGCCGUUAGGCCGAA AAUGCAUA | 13145 |
| 4910 | UGCAUUAUC CUGUUUUA | 3739 | UAAAACAG CUGAUGAGGCCGUUAGGCCGAA AUAAUGCA | 13146 |
| 4915 | UAUCCUGUU UUAUAUAU | 3740 | AUAUAUAA CUGAUGAGGCCGUUAGGCCGAA ACAGGAUA | 13147 |
| 4916 | AUCCUGUUU UAUAUAUC | 3741 | GAUAUAUA CUGAUGAGGCCGUUAGGCCGAA AACAGGAU | 13148 |
| 4917 | UCCUGUUUU AUAUAUCC | 3742 | GGAUAUAU CUGAUGAGGCCGUUAGGCCGAA AAACAGGA | 13149 |
| 4918 | CCUGUUUUA UAUAUCCA | 3743 | UGGAUAUA CUGAUGAGGCCGUUAGGCCGAA AAAACAGG | 13150 |
| 4920 | UGUUUUAUA UAUCCAAU | 3744 | AUUGGAUA CUGAUGAGGCCGUUAGGCCGAA AUAAAACA | 13151 |
| 4922 | UUUUAUAUA UCCAAUGA | 3745 | UCAUUGGA CUGAUGAGGCCGUUAGGCCGAA AUAUAAAA | 13152 |
| 4924 | UUAUAUAUC CAAUGAAU | 3746 | AUUCAUUG CUGAUGAGGCCGUUAGGCCGAA AUAUAUAA | 13153 |
| 4933 | CAAUGAAUA UAACUGGG | 3747 | CCCAGUUA CUGAUGAGGCCGUUAGGCCGAA AUUCAUUG | 13154 |
| 4935 | AUGAAUAUA ACUGGGGC | 3748 | GCCCCAGU CUGAUGAGGCCGUUAGGCCGAA AUAUUCAU | 13155 |
| 4948 | GGGCGAGUU AAGAGUCA | 3749 | UGACUCUU CUGAUGAGGCCGUUAGGCCGAA ACUCGCCC | 13156 |
| 4949 | GGCGAGUUA AGAGUCAU | 3750 | AUGACUCU CUGAUGAGGCCGUUAGGCCGAA AACUCGCC | 13157 |
| 4955 | UUAAGAGUC AUGGUCUA | 3751 | UAGACCAU CUGAUGAGGCCGUUAGGCCGAA ACUCUUAA | 13158 |
| 4961 | GUCAUGGUC UAGAAAAG | 3752 | CUUUUCUA CUGAUGAGGCCGUUAGGCCGAA ACCAUGAC | 13159 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 4963 | CAUGGUCUA GAAAAGGG | 3753 | CCCUUUUC CUGAUGAGGCCGUUAGGCCGAA AGACCAUG | 13160 |
| 4974 | AAAGGGGUU UCUCUGUA | 3754 | UACAGAGA CUGAUGAGGCCGUUAGGCCGAA ACCCCUUU | 13161 |
| 4975 | AAGGGGUUU CUCUGUAC | 3755 | GUACAGAG CUGAUGAGGCCGUUAGGCCGAA AACCCCUU | 13162 |
| 4976 | AGGGGUUUC UCUGUACC | 3756 | GGUACAGA CUGAUGAGGCCGUUAGGCCGAA AAACCCCU | 13163 |
| 4978 | GGGUUUCUC UGUACCCA | 3757 | UGGGUACA CUGAUGAGGCCGUUAGGCCGAA AGAAACCC | 13164 |
| 4982 | UUCUCUGUA CCCAAAUC | 3758 | GAUUUGGG CUGAUGAGGCCGUUAGGCCGAA ACAGAGAA | 13165 |
| 4990 | ACCCAAAUC GGGCUGGU | 3759 | ACCAGCCC CUGAUGAGGCCGUUAGGCCGAA AUUUGGGU | 13166 |
| 4999 | GGGCUGGUU GGACCAAG | 3760 | CUUGGUCC CUGAUGAGGCCGUUAGGCCGAA ACCAGCCC | 13167 |
| 5029 | AGAGUGGUU GUCCCAGC | 3761 | GCUGGGAC CUGAUGAGGCCGUUAGGCCGAA ACCACUCU | 13168 |
| 5032 | GUGGUUGUC CCAGCUAU | 3762 | AUAGCUGG CUGAUGAGGCCGUUAGGCCGAA ACAACCAC | 13169 |
| 5039 | UCCCAGCUA UAGUUACU | 3763 | AGUAACUA CUGAUGAGGCCGUUAGGCCGAA AGCUGGGA | 13170 |
| 5041 | CCAGCUAUA GUUACUAA | 3764 | UUAGUAAC CUGAUGAGGCCGUUAGGCCGAA AUAGCUGG | 13171 |
| 5044 | GCUAUAGUU ACUAAACU | 3765 | AGUUUAGU CUGAUGAGGCCGUUAGGCCGAA ACUAUAGC | 13172 |
| 5045 | CUAUAGUUA CUAAACUA | 3766 | UAGUUUAG CUGAUGAGGCCGUUAGGCCGAA AACUAUAG | 13173 |
| 5048 | UAGUUACUA AACUACUC | 3767 | GAGUAGUU CUGAUGAGGCCGUUAGGCCGAA AGUAACUA | 13174 |
| 5053 | ACUAAACUA CUCACCCA | 3768 | UGGGUGAG CUGAUGAGGCCGUUAGGCCGAA AGUUUAGU | 13175 |
| 5056 | AAACUACUC ACCCAAAG | 3769 | CUUUGGGU CUGAUGAGGCCGUUAGGCCGAA AGUAGUUU | 13176 |
| 5066 | CCCAAAGUU GGGACCUC | 3770 | GAGGUCCC CUGAUGAGGCCGUUAGGCCGAA ACUUUGGG | 13177 |
| 5074 | UGGGACCUC ACUGGCUU | 3771 | AAGCCAGU CUGAUGAGGCCGUUAGGCCGAA AGGUCCCA | 13178 |
| 5082 | CACUGGCUU CUCUUUAC | 3772 | GUAAAGAG CUGAUGAGGCCGUUAGGCCGAA AGCCAGUG | 13179 |
| 5083 | ACUGGCUUC UCUUUACU | 3773 | AGUAAAGA CUGAUGAGGCCGUUAGGCCGAA AAGCCAGU | 13180 |
| 5085 | UGGCUUCUC UUUACUUC | 3774 | GAAGUAAA CUGAUGAGGCCGUUAGGCCGAA AGAAGCCA | 13181 |
| 5087 | GCUUCUCUU UACUUCAU | 3775 | AUGAAGUA CUGAUGAGGCCGUUAGGCCGAA AGAGAAGC | 13182 |
| 5088 | CUUCUCUUU ACUUCAUC | 3776 | GAUGAAGU CUGAUGAGGCCGUUAGGCCGAA AAGAGAAG | 13183 |
| 5089 | UUCUCUUUA CUUCAUCA | 3777 | UGAUGAAG CUGAUGAGGCCGUUAGGCCGAA AAAGAGAA | 13184 |
| 5092 | UCUUUACUU CAUCAUGG | 3778 | CCAUGAUG CUGAUGAGGCCGUUAGGCCGAA AGUAAAGA | 13185 |
| 5093 | CUUUACUUC AUCAUGGA | 3779 | UCCAUGAU CUGAUGAGGCCGUUAGGCCGAA AAGUAAAG | 13186 |
| 5096 | UACUUCAUC AUGGAUUU | 3780 | AAAUCCAU CUGAUGAGGCCGUUAGGCCGAA AUGAAGUA | 13187 |
| 5103 | UCAUGGAUU UCACCAUC | 3781 | GAUGGUGA CUGAUGAGGCCGUUAGGCCGAA AUCCAUGA | 13188 |
| 5104 | CAUGGAUUU CACCAUCC | 3782 | GGAUGGUG CUGAUGAGGCCGUUAGGCCGAA AAUCCAUG | 13189 |
| 5105 | AUGGAUUUC ACCAUCCC | 3783 | GGGAUGGU CUGAUGAGGCCGUUAGGCCGAA AAAUCCAU | 13190 |
| 5111 | UUCACCAUC CCAAGGCA | 3784 | UGCCUUGG CUGAUGAGGCCGUUAGGCCGAA AUGGUGAA | 13191 |
| 5122 | AAGGCAGUC UGAGGA | 3785 | UCCUCUCA CUGAUGAGGCCGUUAGGCCGAA ACUGCCUU | 13192 |
| 5134 | GAGGAGCUA AAGAGUAU | 3786 | AUACUCUU CUGAUGAGGCCGUUAGGCCGAA AGCUCCUC | 13193 |
| 5141 | UAAAGAGUA UCAGCCCA | 3787 | UGGGCUGA CUGAUGAGGCCGUUAGGCCGAA ACUCUUUA | 13194 |
| 5143 | AAGAGUAUC AGCCCAUA | 3788 | UAUGGGCU CUGAUGAGGCCGUUAGGCCGAA AUACUCUU | 13195 |
| 5151 | CAGCCCAUA UUUAUUAA | 3789 | UUAAUAAA CUGAUGAGGCCGUUAGGCCGAA AUGGGCUG | 13196 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 5153 | GCCCAUAUU UAUUAAGC | 3790 | GCUUAAUA CUGAUGAGGCCGUUAGGCCGAA AUAUGGGC | 13197 |
| 5154 | CCCAUAUUU AUUAAGCA | 3791 | UGCUUAAU CUGAUGAGGCCGUUAGGCCGAA AAUAUGGG | 13198 |
| 5155 | CCAUAUUUA UUAAGCAC | 3792 | GUGCUUAA CUGAUGAGGCCGUUAGGCCGAA AAAUAUGG | 13199 |
| 5157 | AUAUUUAUU AAGCACUU | 3793 | AAGUGCUU CUGAUGAGGCCGUUAGGCCGAA AUAAAUAU | 13200 |
| 5158 | UAUUUAUUA AGCACUUU | 3794 | AAAGUGCU CUGAUGAGGCCGUUAGGCCGAA AAUAAAUA | 13201 |
| 5165 | UAAGCACUU UAUGCUCC | 3795 | GGAGCAUA CUGAUGAGGCCGUUAGGCCGAA AGUGCUUA | 13202 |
| 5166 | AAGCACUUU AUGCUCCU | 3796 | AGGAGCAU CUGAUGAGGCCGUUAGGCCGAA AAGUGCUU | 13203 |
| 5167 | AGCACUUUA UGCUCCUU | 3797 | AAGGAGCA CUGAUGAGGCCGUUAGGCCGAA AAAGUGCU | 13204 |
| 5172 | UUUAUGCUC CUUGGCAC | 3798 | GUGCCAAG CUGAUGAGGCCGUUAGGCCGAA AGCAUAAA | 13205 |
| 5175 | AUGCUCCUU GGCACAGC | 3799 | GCUGUGCC CUGAUGAGGCCGUUAGGCCGAA AGGAGCAU | 13206 |
| 5195 | UGAUGUGUA AUUUAUGC | 3800 | GCAUAAAU CUGAUGAGGCCGUUAGGCCGAA ACACAUCA | 13207 |
| 5198 | UGUGUAAUU UAUGCAAG | 3801 | CUUGCAUA CUGAUGAGGCCGUUAGGCCGAA AUUACACA | 13208 |
| 5199 | GUGUAAUUU AUGCAAGC | 3802 | GCUUGCAU CUGAUGAGGCCGUUAGGCCGAA AAUUACAC | 13209 |
| 5200 | UGUAAUUUA UGCAAGCU | 3803 | AGCUUGCA CUGAUGAGGCCGUUAGGCCGAA AAAUUACA | 13210 |
| 5209 | UGCAAGCUC CCUCUCCA | 3804 | UGGAGAGG CUGAUGAGGCCGUUAGGCCGAA AGCUUGCA | 13211 |
| 5213 | AGCUCCCUC UCCAGCUA | 3805 | UAGCUGGA CUGAUGAGGCCGUUAGGCCGAA AGGGAGCU | 13212 |
| 5215 | CUCCCUCUC CAGCUAGG | 3806 | CCUAGCUG CUGAUGAGGCCGUUAGGCCGAA AGAGGGAG | 13213 |
| 5221 | CUCCAGCUA GGACUCAG | 3807 | CUGAGUCC CUGAUGAGGCCGUUAGGCCGAA AGCUGGAG | 13214 |
| 5227 | CUAGGACUC AGGAUAUU | 3808 | AAUAUCCU CUGAUGAGGCCGUUAGGCCGAA AGUCCUAG | 13215 |
| 5233 | CUCAGGAUA UUAGUCAA | 3809 | UUGACUAA CUGAUGAGGCCGUUAGGCCGAA AUCCUGAG | 13216 |
| 5235 | CAGGAUAUU AGUCAAUG | 3810 | CAUUGACU CUGAUGAGGCCGUUAGGCCGAA AUAUCCUG | 13217 |
| 5236 | AGGAUAUUA GUCAAUGA | 3811 | UCAUUGAC CUGAUGAGGCCGUUAGGCCGAA AAUAUCCU | 13218 |
| 5239 | AUAUUAGUC AAUGAGCC | 3812 | GGCUCAUU CUGAUGAGGCCGUUAGGCCGAA ACUAAUAU | 10358 |
| 5250 | UGAGCCAUC AAAAGGAA | 3813 | UUCCUUUU CUGAUGAGGCCGUUAGGCCGAA AUGGCUCA | 13219 |
| 5273 | AAAACCUA UCUUAUUU | 3814 | AAAUAAGA CUGAUGAGGCCGUUAGGCCGAA AGGUUUUU | 13220 |
| 5275 | AAACCUAUC UUAUUUUC | 3815 | GAAAAUAA CUGAUGAGGCCGUUAGGCCGAA AUAGGUUU | 13221 |
| 5277 | ACCUAUCUU AUUUCAU | 3816 | AUGAAAAU CUGAUGAGGCCGUUAGGCCGAA AGAUAGGU | 13222 |
| 5278 | CCUAUCUUA UUUCAUC | 3817 | GAUGAAAA CUGAUGAGGCCGUUAGGCCGAA AAGAUAGG | 13223 |
| 5280 | UAUCUUAUU UUCAUCUG | 3818 | CAGAUGAA CUGAUGAGGCCGUUAGGCCGAA AUAAGAUA | 13224 |
| 5281 | AUCUUAUUU UCAUCUGU | 3819 | ACAGAUGA CUGAUGAGGCCGUUAGGCCGAA AAUAAGAU | 13225 |
| 5282 | UCUGAUGUG CAUCUGUG | 3820 | AACAGAUG CUGAUGAGGCCGUUAGGCCGAA AAAUAAGA | 13226 |
| 5283 | CUUAUUUUC AUCUGUUU | 3821 | AAACAGAU CUGAUGAGGCCGUUAGGCCGAA AAAAUAAG | 13227 |
| 5286 | AUGGUCAUC UGUUUCAU | 3822 | AUGAAACA CUGAUGAGGCCGUUAGGCCGAA AUGAAAAU | 13228 |
| 5290 | UCAUCUGUU UCAUACCU | 3823 | AGGUAUGA CUGAUGAGGCCGUUAGGCCGAA ACAGAUGA | 13229 |
| 5291 | CAUCUGUUU CAUACCUU | 3824 | AAGGUAUG CUGAUGAGGCCGUUAGGCCGAA AACAGAUG | 13230 |
| 5292 | AUCUGUGUC AUACCUUG | 3825 | CAAGGUAU CUGAUGAGGCCGUUAGGCCGAA AAACAGAU | 13231 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 5295 | UGUUUCAUA CCUUGUCU | 3826 | AGACAAGG CUGAUGAGGCCGUUAGGCCGAA AUGAAACA | 13232 |
| 5299 | UCAUACCUU GUCUGGGG | 3827 | CCCCAGAC CUGAUGAGGCCGUUAGGCCGAA AGGUAGGA | 13233 |
| 5302 | UACCUUGUC UGGGGUCU | 3828 | AGACCCCA CUGAUGAGGCCGUUAGGCCGAA ACAAGGUA | 13234 |
| 5309 | UCUGGGGUC UAAUGACG | 3829 | CGUCAUUA CUGAUGAGGCCGUUAGGCCGAA ACCCCAGA | 13235 |
| 5311 | UGGGGUCUA AUGACGAU | 3830 | AUCGUCAU CUGAUGAGGCCGUUAGGCCGAA AGACCCCA | 13236 |
| 5331 | AACAGGGUA GACAUGGG | 3831 | CCCAUGUC CUGAUGAGGCCGUUAGGCCGAA ACCCUGUU | 13237 |
| 5350 | GACAGGGUA GAAAAGGG | 3832 | CCCUUUUC CUGAUGAGGCCGUUAGGCCGAA ACCCUGUC | 13238 |
| 5367 | UGCCCGCUC UUUGGGGU | 3833 | ACCCCAAA CUGAUGAGGCCGUUAGGCCGAA AGCGGGCA | 13239 |
| 5369 | CCCGCUCUU UGGGGUCU | 3834 | AGACCCCA CUGAUGAGGCCGUUAGGCCGAA AGAGCGGG | 13240 |
| 5370 | CCGCUCUUU GGGGUCUA | 3835 | UAGACCCC CUGAUGAGGCCGUUAGGCCGAA AAGAGCGG | 13241 |
| 5376 | UUUGGGGUC UAGAGAUG | 3836 | CAUCUCUA CUGAUGAGGCCGUUAGGCCGAA ACCCCAAA | 13242 |
| 5378 | UGGGGUCUA GAGAUGAG | 3837 | CUCAUCUC CUGAUGAGGCCGUUAGGCCGAA AGACCCCA | 13243 |
| 5395 | CCCUGGGUC UCUAAAAU | 3838 | AUUUUAGA CUGAUGAGGCCGUUAGGCCGAA ACCCAGGG | 13244 |
| 5397 | CUGGGUCUC UAAAAUGG | 3839 | CCAUUUUA CUGAUGAGGCCGUUAGGCCGAA AGACCCAG | 13245 |
| 5399 | GGGUCUCUA AAAUGGCU | 3840 | AGCCAUUU CUGAUGAGGCCGUUAGGCCGAA AGAGACCC | 13246 |
| 5408 | AAAUGGCUC UCUUAGAA | 3841 | UUCUAAGA CUGAUGAGGCCGUUAGGCCGAA AGCCAUUU | 13247 |
| 5410 | AUGGCUCUC UUAGAAGU | 3842 | ACUUCUAA CUGAUGAGGCCGUUAGGCCGAA AGAGCCAU | 13248 |
| 5412 | GGCUCUCUU AGAAGUUG | 3843 | CAACUUCU CUGAUGAGGCCGUUAGGCCGAA AGAGAGCC | 13249 |
| 5413 | GCUCUCUUA GAAGUUGU | 3844 | ACAACUGC CUGAUGAGGCCGUUAGGCCGAA AAGAGAGC | 13250 |
| 5419 | UUAGAAGUU GUAUGUGC | 3845 | GCACAUAC CUGAUGAGGCCGUUAGGCCGAA ACUUCUAA | 13251 |
| 5422 | GAAGUUGUA UGUGCAAA | 3846 | UUUGCACA CUGAUGAGGCCGUUAGGCCGAA ACAACUUC | 13252 |
| 5432 | GUGCAAAUU AUGGUCUG | 3847 | CAGACCAG CUGAUGAGGCCGUUAGGCCGAA AUUUGCAC | 13253 |
| 5433 | UGCAAAUUA UGGUCUGU | 3848 | ACAGACCA CUGAUGAGGCCGUUAGGCCGAA AAUUUGCA | 13254 |
| 5438 | AUUAUGGUC UGUGUGCU | 3849 | AGCACACA CUGAUGAGGCCGUUAGGCCGAA ACCAUAAU | 13255 |
| 5447 | UGUGUGCUU AGGUCGUG | 3850 | CACGACCU CUGAUGAGGCCGUUAGGCCGAA AGCACACA | 13256 |
| 5448 | GUGUGCUUA GGUCGUGC | 3851 | GCACGACC CUGAUGAGGCCGUUAGGCCGAA AAGCACAC | 13257 |
| 5452 | GCUUAGGUC GUGCACAC | 3852 | GUGUGCAC CUGAUGAGGCCGUUAGGCCGAA ACCUAAGC | 13258 |
| 5475 | GAGCCGGUC ACAGCUGG | 3853 | CCAGCUGU CUGAUGAGGCCGUUAGGCCGAA ACCGGCUC | 13259 |
| 5497 | CGAUGAAUA GCUGCUUU | 3854 | AAAGCAGC CUGAUGAGGCCGUUAGGCCGAA AUUCAUCG | 13260 |
| 5504 | UAGCUGCUU UGGGAGAG | 3855 | CUCUCCCA CUGAUGAGGCCGUUAGGCCGAA AGCAGCUA | 13261 |
| 5505 | AGCUGCUUU GGGAGAGC | 3856 | GCUCUCCC CUGAUGAGGCCGUUAGGCCGAA AAGCAGCU | 13262 |
| 5524 | AGCAUGCUA GCCACUUA | 3857 | UAAGUGGC CUGAUGAGGCCGUUAGGCCGAA AGCAUGCU | 13263 |
| 5531 | UAGCCACUU AAUUCUCU | 3858 | AGAGAAUU CUGAUGAGGCCGUUAGGCCGAA AGUGGCUA | 13264 |
| 5532 | AGCCACUUA AUUCUCUG | 3859 | CAGAGAAU CUGAUGAGGCCGUUAGGCCGAA AAGUGGCU | 13265 |
| 5535 | CACUUAAUU CUCUGACC | 3860 | GGUCAGAG CUGAUGAGGCCGUUAGGCCGAA AUUAAGUG | 13266 |
| 5536 | ACUUAAUUC UCUGACCG | 3861 | CGGUCAGA CUGAUGAGGCCGUUAGGCCGAA AAUUAAGU | 13267 |
| 5538 | UUAAUUCUC UGACCGGG | 3862 | CCCGGUCA CUGAUGAGGCCGUUAGGCCGAA AGAAUUAA | 13268 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 5554 | GCCAGCAUC AUGGGUAC | 3863 | GUACCCAU CUGAUGAGGCCGUUAGGCCGAA AUGCUGGC | 13269 |
| 5561 | UCAUGGGUA CCUGCUCC | 3864 | GGAGCAGG CUGAUGAGGCCGUUAGGCCGAA ACCCAUGA | 13270 |
| 5568 | UACCUGCUC CCCUGUGU | 3865 | ACACAGGG CUGAUGAGGCCGUUAGGCCGAA AGCAGGUA | 13271 |
| 5577 | CCCUGUGUA CCCCAUCC | 3866 | GGAUGGGG CUGAUGAGGCCGUUAGGCCGAA ACACAGGG | 13272 |
| 5584 | UACCCCAUC CUUAAGGU | 3867 | ACCUUAAG CUGAUGAGGCCGUUAGGCCGAA AUGGGGUA | 13273 |
| 5587 | CCCAUCCUU AAGGUUUU | 3868 | AAAACCUU CUGAUGAGGCCGUUAGGCCGAA AGGAUGGG | 13274 |
| 5588 | CCAUCCUUA AGGUUUUC | 3869 | GAAAACCU CUGAUGAGGCCGUUAGGCCGAA AAGGAUGG | 13275 |
| 5593 | CUUAAGGUU UUCUGUCU | 3870 | AGACAGAA CUGAUGAGGCCGUUAGGCCGAA ACCUUAAG | 13276 |
| 5594 | UUAAGGUUU UCUGUCUG | 3871 | CAGACAGA CUGAUGAGGCCGUUAGGCCGAA AACCUUAA | 13277 |
| 5595 | UAAGGUUUU CUGUCUGA | 3872 | UCAGACAG CUGAUGAGGCCGUUAGGCCGAA AAACCUUA | 13278 |
| 5596 | AAGGUUUUC UGUCUGAU | 3873 | AUCAGACA CUGAUGAGGCCGUUAGGCCGAA AAAACCUU | 13279 |
| 5600 | UUUUCUGUC UGAUGAGA | 3874 | UCUCAUCA CUGAUGAGGCCGUUAGGCCGAA ACAGAAAA | 13280 |
| 5627 | AGUGCAAUC CCCACUGA | 3875 | UCAGUGGG CUGAUGAGGCCGUUAGGCCGAA AUUGCACU | 13281 |
| 5660 | CUGUGGCUC UUGGUGCA | 3876 | UGCACCAA CUGAUGAGGCCGUUAGGCCGAA AGCCACAG | 13282 |
| 5662 | GUGGCUCUU GGUGCACU | 3877 | AGUGCACC CUGAUGAGGCCGUUAGGCCGAA AGAGCCAC | 13283 |
| 5671 | GGUGCACUC ACCAGCCA | 3878 | UGGCUGGU CUGAUGAGGCCGUUAGGCCGAA AGUGCACC | 13284 |
| 5685 | CCAGGACUA GACAAGUA | 3879 | UACUUGUC CUGAUGAGGCCGUUAGGCCGAA AGUCCUGG | 13285 |
| 5693 | AGACAAGUA GGAAAGGG | 3880 | CCCUUUCC CUGAUGAGGCCGUUAGGCCGAA ACUUGUCU | 13286 |
| 5704 | AAAGGGCUU CUAGCCAC | 3881 | GUGGCUAG CUGAUGAGGCCGUUAGGCCGAA AGCCCUUU | 13287 |
| 5705 | AAGGGCUUC UAGCCACA | 3882 | UGUGGCUA CUGAUGAGGCCGUUAGGCCGAA AAGCCCUU | 13288 |
| 5707 | GGGCUUCUA GCCACACU | 3883 | AGUGUGGC CUGAUGAGGCCGUUAGGCCGAA AGAAGCCC | 13289 |
| 5731 | AAGAAAAUC AGGUAGGG | 3884 | CCCUACCU CUGAUGAGGCCGUUAGGCCGAA AUUUUCUU | 13290 |
| 5736 | AAUCAGGUA GGGCUGGC | 3885 | GCCAGCCC CUGAUGAGGCCGUUAGGCCGAA ACCUGAUU | 13291 |
| 5754 | AAAGACAUC UUUGUCCA | 3886 | UGGACAAA CUGAUGAGGCCGUUAGGCCGAA AUGUCUUU | 13292 |
| 5756 | AGACAUCUU UGUCCAUU | 3887 | AAUGGACA CUGAUGAGGCCGUUAGGCCGAA AGAUGUCU | 13293 |
| 5757 | GACAUCUUU GUCCAUUC | 3888 | GAAUGGAC CUGAUGAGGCCGUUAGGCCGAA AAGAUGUC | 13294 |
| 5760 | AUCUUUGUC CAUUCGCA | 3889 | UGCGAAUG CUGAUGAGGCCGUUAGGCCGAA ACAAAGAU | 13295 |
| 5764 | UUGUCCAUU CGCAAAAG | 3890 | CUUUUGCG CUGAUGAGGCCGUUAGGCCGAA AUGGACAA | 13296 |
| 5765 | UGUCCAUUC GCAAAAGC | 3891 | GCUUUUGC CUGAUGAGGCCGUUAGGCCGAA AAUGGACA | 13297 |
| 5775 | CAAAAGCUC UUGUCGGC | 3892 | GCCGACAA CUGAUGAGGCCGUUAGGCCGAA AGCUUUUG | 13298 |
| 5777 | AAAGCUCUU GUCGGCUG | 3893 | CAGCCGAC CUGAUGAGGCCGUUAGGCCGAA AGAGCUUU | 13299 |
| 5780 | GCUCUUGUC GGCUGCAG | 3894 | CUGCAGCC CUGAUGAGGCCGUUAGGCCGAA ACAAGAGC | 13300 |
| 5794 | CAGUGUGUA AGUCAGGC | 3895 | GCCUGACU CUGAUGAGGCCGUUAGGCCGAA ACACACUG | 13301 |
| 5798 | GUGUAAGUC AGGCGAUG | 3896 | CAUCGCCU CUGAUGAGGCCGUUAGGCCGAA ACUUACAC | 13302 |
| 5818 | CAGAGGCUA CCAGAGAA | 3897 | UUCUCUGG CUGAUGAGGCCGUUAGGCCGAA AGCCUCUG | 13303 |
| 5852 | CCUGAGGUU UCUCAUCC | 3898 | GGAUGAGA CUGAUGAGGCCGUUAGGCCGAA ACCUCAGG | 13304 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 5853 | CUGAGGUUU CUCAUCCA | 3899 | UGGAUGAG CUGAUGAGGCCGUUAGGCCGAA AACCUCAG | 13305 |
| 5854 | UGAGGUUUC UCAUCCAG | 3900 | CUGGAUGA CUGAUGAGGCCGUUAGGCCGAA AAACCUCA | 13306 |
| 5856 | AGGUUUCUC AUCCAGAU | 3901 | AUCUGGAU CUGAUGAGGCCGUUAGGCCGAA AGAAACCU | 13307 |
| 5859 | UUUCUCAUC CAGAUAUC | 3902 | GAUAUCUG CUGAUGAGGCCGUUAGGCCGAA AUGAGAAA | 13308 |
| 5865 | AUCCAGAUA UCCAGCAA | 3903 | UUGCUGGA CUGAUGAGGCCGUUAGGCCGAA AUCUGGAU | 13309 |
| 5867 | CCAGAUAUC CAGCAAUU | 3904 | AAUUGCUG CUGAUGAGGCCGUUAGGCCGAA AUAUCUGG | 13310 |
| 5875 | CCAGCAAUU GGGGGGUG | 3905 | CACCCCCC CUGAUGAGGCCGUUAGGCCGAA AUUGCUGG | 13311 |
| 5896 | AAGACCAUA GAUGGUCC | 3906 | GGACCAUC CUGAUGAGGCCGUUAGGCCGAA AUGGUCUU | 13312 |
| 5903 | UAGAUGGUC CUGUAUUA | 3907 | UAAUACAG CUGAUGAGGCCGUUAGGCCGAA ACCAUCUA | 13313 |
| 5908 | GGUCCUGUA UUAUUCCG | 3908 | CGGAAUAA CUGAUGAGGCCGUUAGGCCGAA ACAGGACC | 13314 |
| 5910 | UCCUGUAUU AUUCCGAU | 3909 | AUCGGAAU CUGAUGAGGCCGUUAGGCCGAA AUACAGGA | 13315 |
| 5911 | CCUGUAUUA UUCCGAUU | 3910 | AAUCGGAA CUGAUGAGGCCGUUAGGCCGAA AAUACAGG | 13316 |
| 5913 | UGUAUUAUU CCGAUUUU | 3911 | AAAAUCGG CUGAUGAGGCCGUUAGGCCGAA AUAAUACA | 13317 |
| 5914 | GUAUUAUUC CGAUUUUA | 3912 | UAAAAUCG CUGAUGAGGCCGUUAGGCCGAA AAUAAUAC | 13318 |
| 5919 | AUUCCGAUU UUAAUAAU | 3913 | AUUAUUAA CUGAUGAGGCCGUUAGGCCGAA AUCGGAAU | 13319 |
| 5920 | UUCCGAUUU UAAUAAUC | 3914 | GAUUAUUA CUGAUGAGGCCGUUAGGCCGAA AAUCGGAA | 13320 |
| 5921 | UCCGAUUUU AAUAAUCU | 3915 | AGAUUAUU CUGAUGAGGCCGUUAGGCCGAA AAAUCGGA | 13321 |
| 5922 | CCGAUUUUA AUAAUCUA | 3916 | UAGAUUAU CUGAUGAGGCCGUUAGGCCGAA AAAAUCGG | 13322 |
| 5925 | AUUUUAAUA AUCUAAUU | 3917 | AAUUAGAU CUGAUGAGGCCGUUAGGCCGAA AUUAAAAU | 13323 |
| 5928 | UUAAUAAUC UAAUUCGU | 3918 | ACGAAUUA CUGAUGAGGCCGUUAGGCCGAA AUUAUUAA | 13324 |
| 5930 | AAUAAUCUA AUUCGUGA | 3919 | UCACGAAU CUGAUGAGGCCGUUAGGCCGAA AGAUUAUU | 13325 |
| 5933 | AAUCUAAUU CGUGAUCA | 3920 | UGAUCACG CUGAUGAGGCCGUUAGGCCGAA AUUAGAUU | 13326 |
| 5934 | AUCUAAUUC GUGAUCAU | 3921 | AUGAUCAC CUGAUGAGGCCGUUAGGCCGAA AAUUAGAU | 13327 |
| 5940 | UUCGUGAUC AUUAAGAG | 3922 | CUCUUAAU CUGAUGAGGCCGUUAGGCCGAA AUCACGAA | 13328 |
| 5943 | GUGAUCAUU AAGAGACU | 3923 | AGUCUCUU CUGAUGAGGCCGUUAGGCCGAA AUGAUCAC | 13329 |
| 5944 | UGAUCAUUA AGAGACUU | 3924 | AAGUCUCU CUGAUGAGGCCGUUAGGCCGAA AAUGAUCA | 13330 |
| 5952 | AAGAGACUU UAGUAAAU | 3925 | AUUUACUA CUGAUGAGGCCGUUAGGCCGAA AGUCUCUU | 13331 |
| 5953 | AGAGACUUU AGUAAAUG | 3926 | CAUUUACU CUGAUGAGGCCGUUAGGCCGAA AAGUCUCU | 13332 |
| 5954 | GAGACUUUA GUAAAUGU | 3927 | ACAUUUAC CUGAUGAGGCCGUUAGGCCGAA AAAGUCUC | 13333 |
| 5957 | ACUUUAGUA AAUGUCCC | 3928 | GGGACAUU CUGAUGAGGCCGUUAGGCCGAA ACUAAAGU | 13334 |
| 5963 | GUAAAUGUC CCUUUUCC | 3929 | GGAAAAGG CUGAUGAGGCCGUUAGGCCGAA ACAUUUAC | 13335 |
| 5967 | AUGUCCCUU UUCCCACA | 3930 | UGUGGGAA CUGAUGAGGCCGUUAGGCCGAA AGGGACAU | 13336 |
| 5968 | UGUCCCUUU UCCCACAA | 3931 | UUGUGGGA CUGAUGAGGCCGUUAGGCCGAA AAGGGACA | 13337 |
| 5969 | GUCCCUUUU CCCACAAA | 3932 | UUUGUGGG CUGAUGAGGCCGUUAGGCCGAA AAAGGGAC | 13338 |
| 5970 | UCCCUUUUC CCACAAAA | 3933 | UUUUGUGG CUGAUGAGGCCGUUAGGCCGAA AAAAGGGA | 13339 |
| 5981 | ACAAAAGUA AAGAAAAG | 3934 | CUUUUCUU CUGAUGAGGCCGUUAGGCCGAA ACUUUUGU | 13340 |
| 5992 | GAAAAGCUA UCGGGAUU | 3935 | AAUCCCGA CUGAUGAGGCCGUUAGGCCGAA AGCUUUUC | 13341 |

TABLE VIII-continued

Mouse flt-1 VEGF Receptor-Hammerhead Ribozyme and Substrate Sequence

| Pos | Substrate | Seq ID No | HH Ribozyme Sequence | Seq ID No |
|---|---|---|---|---|
| 5994 | AAAGCUAUC GGGAUUCU | 3936 | AGAAUCCC CUGAUGAGGCCGUUAGGCCGAA AUAGCUUU | 13342 |
| 6000 | AUCGGGAUU CUCUGGUU | 3937 | AACCAGAG CUGAUGAGGCCGUUAGGCCGAA AUCCCGAU | 13343 |
| 6001 | UCGGGAUUC UCUGGUUC | 3938 | GAACCAGA CUGAUGAGGCCGUUAGGCCGAA AAUCCCGA | 13344 |
| 6003 | GGGAUUCUC UGGUUCUG | 3939 | CAGAACCA CUGAUGAGGCCGUUAGGCCGAA AGAAUCCC | 13345 |
| 6008 | UCUCUGGUU CUGCUUAA | 3940 | UUAAGCAG CUGAUGAGGCCGUUAGGCCGAA ACCAGAGA | 13346 |
| 6009 | CUCUGGUUC UGCUUAAA | 3941 | UUUAAGCA CUGAUGAGGCCGUUAGGCCGAA AACCAGAG | 13347 |
| 6014 | GUUCUGCUU AAAGACUU | 3942 | AAGUCUUU CUGAUGAGGCCGUUAGGCCGAA AGCAGAAC | 13348 |
| 6015 | UUCUGCUUA AAGACUUA | 3943 | UAAGUCUU CUGAUGAGGCCGUUAGGCCGAA AAGCAGAA | 13349 |
| 6022 | UAAAGACUU AGCUUUGG | 3944 | CCAAAGCU CUGAUGAGGCCGUUAGGCCGAA AGUCUUUA | 13350 |
| 6023 | AAAGACUUA GCUUUGGA | 3945 | UCCAAAGC CUGAUGAGGCCGUUAGGCCGAA AAGUCUUU | 13351 |
| 6027 | ACUUAGCUU UGGAGCCU | 3946 | AGGCUCCA CUGAUGAGGCCGUUAGGCCGAA AGCUAAGU | 13352 |
| 6028 | CUUAGCUUU GGAGCCUA | 3947 | UAGGCUCC CUGAUGAGGCCGUUAGGCCGAA AAGCUAAG | 13353 |
| 6036 | UGGAGCCUA UGAAAGUU | 3948 | AACUUUCA CUGAUGAGGCCGUUAGGCCGAA AGGCUCCA | 13354 |
| 6044 | AUGAAAGUU GAUCAGCC | 3949 | GGCUGAUC CUGAUGAGGCCGUUAGGCCGAA ACUUUCAU | 13355 |

Where "X" represents stem II region of a HH ribozyme (Hertel et al., 1992 Nucleic Acids Res. 20 3252).
The length of stem II may be 2 base-pairs.
Underlined region can be any X sequence or linker, as described herein.

TABLE IX

Mouse flt1 VEGF Receptor-Hairpin Ribozyme and Substrate Sequence

| Pos | Substrate | Seq ID No | HP Ribozyme | Seq ID No |
|---|---|---|---|---|
| 33 | AUGGUCA GCU GCUGGGAC | 3950 | GUCCCAGC AGAA GACCAC ACCAGAGAAACACACGUUGUGGUACAUUACCUGGUA | 13356 |
| 36 | GUCAGCU GCU GGGACACC | 3951 | GGUGUCCC AGAA GCUGAC ACCAGAGAAACACACGUUGUGGUACAUUACCUGGUA | 13357 |
| 50 | CACCGCG GUC UUGCCUUA | 3952 | UAAGGCAA AGAA GCGGUG ACCAGAGAAACACACGUUGUGGUACAUUACCUGGUA | 13358 |
| 67 | ACGCGCU GCU CGGGUGUC | 3953 | GACACCCG AGAA GCGCGU ACCAGAGAAACACACGUUGUGGUACAUUACCUGGUA | 13359 |
| 79 | GGUGUCU GCU UCUCACAG | 3954 | CUGUGAGA AGAA GACACC ACCAGAGAAACACACGUUGUGGUACAUUACCUGGUA | 13360 |
| 166 | CAGGCCA GAC UCUCUUUC | 3955 | GAAAGAGA AGAA GGCCUG ACCAGAGAAACACACGUUGUGGUACAUUACCUGGUA | 13361 |
| 197 | GGAGGCA GCC CACUCAUG | 3956 | CAUGAGUG AGAA GCCUCC ACCAGAGAAACACACGUUGUGGUACAUUACCUGGUA | 13362 |
| 214 | GGUCUCU GCC CACGACCG | 3957 | GGGUCGUG AGAA GAGACC ACCAGAGAAACACACGUUGUGGUACAUUACCUGGUA | 13363 |
| 266 | CCCAUCG GCC UGUGGGAG | 3958 | CUCCCACA AGAA GAUGGG ACCAGAGAAACACACGUUGUGGUACAUUACCUGGUA | 13364 |
| 487 | GAAGACA GCU CAUCAUCC | 3959 | GGAUGAUG AGAA GUCUUC ACCAGAGAAACACACGUUGUGGUACAUUACCUGGUA | 13365 |
| 501 | AUCCCCU GCC GGGUGACG | 3960 | CGUCACCC AGAA GGGGAU ACCAGAGAAACACACGUUGUGGUACAUUACCUGGUA | 13366 |
| 566 | UACCCCU GAU GGGCAAAG | 3961 | CUUUGCCC AGAA GGGGUA ACCAGAGAAACACACGUUGUGGUACAUUACCUGGUA | 13367 |
| 640 | UAGGACU GCU GAACUGCG | 3962 | CGCAGUUC AGAA GUCCUA ACCAGAGAAACACACGUUGUGGUACAUUACCUGGUA | 13368 |
| 691 | ACUAUCU GAC CCAUCGGC | 3963 | GCCGAUGG AGAA GAUAGU ACCAGAGAAACACACGUUGUGGUACAUUACCUGGUA | 13369 |
| 703 | AUCGGCA GAC CAAUACAA | 3964 | UUGUAUUG AGAA GCCGAU ACCAGAGAAACACACGUUGUGGUACAUUACCUGGUA | 13370 |

TABLE IX-continued

Mouse flt1 VEGF Receptor-Hairpin Ribozyme and Substrate Sequence

| Pos | Substrate | Seq ID No | HP Ribozyme | Seq ID No |
|---|---|---|---|---|
| 736 | UACGCCC GCC GAGCCCAG | 3965 | CUGGGCUC AGAA GGCGUA ACCAGAGAAACACACGUUGUGGUACAUUACCUGGUA | 13371 |
| 754 | UGAGACU GCU CCACGGGC | 3966 | GCCCGUGG AGAA GUCUCA ACCAGAGAAACACACGUUGUGGUACAUUACCUGGUA | 13372 |
| 766 | ACGGGCA GAC UCUUGUCC | 3967 | GGACAAGA AGAA GCCCGU ACCAGAGAAACACACGUUGUGGUACAUUACCUGGUA | 13373 |
| 871 | GGCAGCG GAU UGACCGGA | 3968 | UCCGGUCA AGAA GCUGCC ACCAGAGAAACACACGUUGUGGUACAUUACCUGGUA | 13374 |
| 960 | UACACCU GUC GCGUGAAG | 3969 | CUUCACGC AGAA GGUGUA ACCAGAGAAACACACGUUGUGGUACAUUACCUGGUA | 13375 |
| 988 | CGUUCCA GUC UUUCAACA | 3970 | UGUUGAAA AGAA GGAACG ACCAGAGAAACACACGUUGUGGUACAUUACCUGGUA | 13376 |
| 1051 | GGAAGCA GCC GGUGCAGG | 3971 | CCUGCACC AGAA GCUUCC ACCAGAGAAACACACGUUGUGGUACAUUACCUGGUA | 13377 |
| 1081 | GAAGACG GUC CUAUCGGC | 3972 | GCCGAUAG AGAA GUCUUC ACCAGAGAAACACACGUUGUGGUACAUUACCUGGUA | 13378 |
| 1090 | CCUAUCG GCU GUCCAUGA | 3973 | UCAUGGAC AGAA GAUAGG ACCAGAGAAACACACGUUGUGGUACAUUACCUGGUA | 13379 |
| 1093 | AUCGGCU GUC CAUGAAAG | 3974 | CUUUCAUG AGAA GCCGAU ACCAGAGAAACACACGUUGUGGUACAUUACCUGGUA | 13380 |
| 1169 | GAAGUCU GCU CGCUAUUU | 3975 | AAAUAGCG AGAA GACUUC ACCAGAGAAACACACGUUGUGGUACAUUACCUGGUA | 13381 |
| 1315 | AACCUCA GAU CUACGAAA | 3976 | UUUCGUAG AGAA GAGGUU ACCAGAGAAACACACGUUGUGGUACAUUACCUGGUA | 13382 |
| 1363 | UCUAUCC GCU GGGCAGCA | 3977 | UGCUGCCC AGAA GAUAGA ACCAGAGAAACACACGUUGUGGUACAUUACCUGGUA | 13383 |
| 1604 | GGUGGCU GAC UCUCAGAC | 3978 | GUCUGAGA AGAA GCCACC ACCAGAGAAACACACGUUGUGGUACAUUACCUGGUA | 13384 |
| 1612 | ACUCUCA GAC CCCUGGAA | 3979 | UUCCAGGG AGAA GAGAGU ACCAGAGAAACACACGUUGUGGUACAUUACCUGGUA | 13385 |
| 1629 | AUCUACA GCU GCCGGGCC | 3980 | GGCCCGGC AGAA GUAGAU ACCAGAGAAACACACGUUGUGGUACAUUACCUGGUA | 13386 |
| 1632 | UACAGCU GCC GGGCCUUC | 3981 | GAAGCCCC AGAA GCUGUA ACCAGACAAACACACGUUGUGGUACAUUACCUGGUA | 13387 |
| 1688 | UGUCACA GAU GUGCCGAA | 3982 | UUCGGCAC AGAA GUGACA ACCAGAGAAACACACGUUCUGGUACAUUACCUCGUA | 13388 |
| 1730 | GAUGCCA GCC CAAGGAGA | 3983 | UCUCCUUC AGAA GGCAUC ACCACAGAAACACACGUUCUGGUACAUUACCUGGUA | 13389 |
| 1753 | UCAAACU CUC CUCUCUGG | 3984 | CCACACAG AGAA GUUUCA ACCAGAGUAACACGUUGUGGUACAUUACCUGGUA | 13390 |
| 2017 | CACACCU GCU UCAAAACC | 3985 | GGUUUUGA AGAA GGUGUG ACCAGAGAAACACACGUUGUGGUACAUUACCUGGUA | 13391 |
| 2101 | CGCCUCA GAU CACUUGGU | 3986 | ACCAAGUG AGAA GAGGCC ACCAGAGAAACACACGUUGUGGUACAUUACCUGGUA | 13392 |
| 2176 | GCACGCU GUU UAUUCAAA | 1441 | UUUCAAUA AGAA GCGUCC ACCAGAGAAACACACGUUGUGGUACAUUACCUGGUA | 10860 |
| 2258 | AACCGCA GCC UACCUCAC | 3987 | GUCAGGUA AGAA GCGCUU ACCAGAGAAACACACGUUGUGGUACAUUACCUGGUA | 13393 |
| 2305 | UGGAGCU GAU CACGCUCA | 3988 | UGAGCGUG AGAA GCUCCA ACCAGAGAAACACACGUUGUGGUACAUUACCUGGUA | 13394 |
| 2383 | UGAAGCG GUC UUCUUCCG | 3989 | CGGAAGAA AGAA GCUUCA ACCAGAGAAACACACGUUGUCCUACAUUACCUGGUA | 13395 |
| 2405 | AAACACA GAC UACCUGUC | 3990 | GACACGUA AGAA GUCUUU ACCAGAGAAACACACGUUGUGGUACAUUACCUGGUA | 13396 |
| 2432 | GGACCCA GAU GAAGUUCC | 1445 | GGAACUUC AGAA GGGUCC ACCAGAGAAACACACGUUGUGGUACAUUACCUGGUA | 10864 |
| 2464 | GUGAACG GCU GCCCUAUG | 3991 | CAUAGGCC AGAA GUUCAC ACCAGAGAAACACACGUUGUGGUACAUUACCUGGUA | 13397 |
| 2467 | AACGGCU GCC CUAUGAUC | 3992 | CAUCAUAG AGAA GCCGUU ACCAGAGAAACACACGUUGUGGUACAUUACCUGGUA | 13398 |
| 2592 | CCCACCU GCC GGACUGUG | 3993 | CACAGUCC AGAA GGUGCG ACCAGAGAAACACACCUUGUGGUACAUUACCUGGUA | 13399 |
| 2596 | CCUGCCG GAC UGUGGCUG | 3994 | CAGCCACA AGAA GGCACG ACCAGAGAAACACACCUUGUGGUACAUUACCUGGUA | 13400 |
| 2653 | AAGCUCU GAU GACCGAAC | 3995 | GUUCGGUC AGAA GAGCUC ACCAGAGAAACACACGUUGUGGUACAUUACCUGGUA | 13401 |
| 2743 | GGCCUCU GAU GGUGAUCG | 3996 | CGAUCACC AGAA GAGGCC ACCAGAGAAACACACGUUGUGGUACAUUACCUGGUA | 13402 |
| 2779 | GAAACCU GUC CAACUACC | 3997 | GGUAGUUG AGAA GGUUUC ACCAGAGAAACACACGUUGUGGUACAUUACCUGGUA | 13403 |
| 2814 | UUAUUCU GUC UCAACAAG | 3998 | CUUGUUGA AGAA GAAUAA ACCAGAGAAACACACGUUGUGGUACAUUACCUGGUA | 13404 |

TABLE IX-continued

Mouse flt1 VEGF Receptor-Hairpin Ribozyme and Substrate Sequence

| Pos | Substrate | Seq ID No | HP Ribozyme | Seq ID No |
|---|---|---|---|---|
| 2831 | GGACGCA GCC UUGCAUAU | 3999 | AUAUGCAA AGAA GCGUCC ACCAGAGAAACACACGUUCUGGUACAUUACCUGGUA | 13405 |
| 2895 | AACCCCC CCC UAGACAGU | 4000 | ACUGUCUA AGAA GGGCUU ACCAGAGAAACACACGUUCUGGUACAUUACCUGGUA | 13406 |
| 2913 | GUCAGCA GCU CAACUGUC | 4001 | GACACUUG AGAA GCUGAC ACCAGAGAAACACACGUUCUGGUACAUUACCUGGUA | 13407 |
| 2928 | GUCACCA GCU CCACCUUC | 4002 | GAACCUGG AGAA GGUGAC ACCAGAGAAACACACGUUCUGGUACAUUACCUGGUA | 13408 |
| 2934 | AGCUCCA GCU UCCCUGAA | 4003 | UUCAGGGA AGAA GGAGCU ACCAGAGAAACACACGUUCUGGUACAUUACCUGGUA | 13409 |
| 3001 | CCAAGCA GCC CCUCACCA | 4004 | UGGUCACC AGAA GCUUCG ACCAGAGAAACACACGUUGUGGUACAUUACCUGGUA | 13410 |
| 3022 | AACACCU GAU UUCCUACA | 4005 | UGUAGGAA AGAA GGUCUU ACCAGACAAACACACGUUGUGGUACAUUACCUGGUA | 13411 |
| 3033 | UCCUACA GUU UCCAAGUG | 4006 | CACUUCGA AGAA GUAGGA ACCAGACAAACACACGUUGUGGUACAUUACCUGGUA | 13412 |
| 3064 | ACUUUCU GUC CUCCACAA | 4007 | UUCUGGAG AGAA GAAACU ACCAGACAAACACACGUUGUGGUACAUUACCUGGUA | 13413 |
| 3179 | GAACCCU GAU UAUGUGAG | 4008 | CUCACAUA AGAA GGCUUC ACCAGACAAACACACGUUCUGGUACAUUACCUGGUA | 10876 |
| 3357 | UUCUGCA GCC GCCUGAAG | 4009 | CUUCAGGC AGAA GCAGAA ACCAGACAAACACACGUUCUGGUACAUUACCUGGUA | 13414 |
| 3360 | UGCAGCC GCC UGAAGGAA | 4010 | UUCCUUCA AGAA GCUGCA ACCAGACAAACACACGUUCUGGUACAUUACCUGGUA | 13415 |
| 3379 | GCAUGCG GAU GAGAACCC | 4011 | GGGUUCUC AGAA GCAUGC ACCAGACAAACACACGUUCUGGUACAUUACCUGGUA | 13416 |
| 3463 | GGCCCCG GUU UGCUGAAC | 4012 | GUUCAGCA AGAA GGGGCC ACCAGACAAACACACGUUCUGGUACAUUACCUGGUA | 13417 |
| 3496 | GUGACCU GCU UCAAGCCA | 4013 | UGGCUUGA AGAA GGUCAC ACCAGACAAACACACGUUCUGGUACAUUACCUGGUA | 13418 |
| 3553 | CCAUACU GAC UAGAAACA | 4014 | UGUUUCUA AGAA GUAUGG ACCAGACAAACACACGUUCUGGUACAUUACCUGGUA | 13419 |
| 3615 | AAGGACG CU UUGCAGAU | 4015 | AUCUGCAA AGAA GUCCUU ACCAGAGAAACACACGUUGUGGUACAUUACCUGGUA | 13420 |
| 3623 | CUUUGCA GAU CCACAUUU | 4016 | AAAUGUGG AGAA GCAAAG ACCAGAGAAACACACGUUGUGGUACAUUACCUGGUA | 13421 |
| 3650 | AAGCUCU GAU GAUGUGAG | 4017 | CUCACAUC AGAA GAGCUU ACCAGAGAAACACACGUUGUGGUACAUUACCUGGUA | 13422 |
| 3754 | ACUAUCA GCU GGACACUA | 4018 | UAGUGUCC AGAA GAUAGU ACCAGAGAAACACACGUUGUGGUACAUUACCUGGUA | 13423 |
| 3772 | GCACUCU GCU GGGCUCCC | 4019 | GGGAGCCC AGAA GAGUGC ACCAGAGAAACACACGUUGUGGUACAUUACCUGGUA | 13424 |
| 3796 | UGAAGCG GUU CACCUGGA | 4020 | UCCAGGUG AGAA GCUUCA ACCAGAGAAACACACGUUGUGGUACAUUACCUGGUA | 13425 |
| 3881 | ACUUUCC GAU CUGCCGAG | 4021 | CUCGGCAG AGAA GAAAGU ACCAGAGAAACACACGUUGUGGUACAUUACCUGGUA | 13426 |
| 3886 | CCGAUCU GCC GAGGCCCA | 4022 | UGGGCCUC AGAA GAUCGG ACCAGAGAAACACACGUUGUGGUACAUUACCUGGUA | 13427 |
| 3897 | AGGCCCA GCU UCUGCUUC | 4023 | GAAGCAGA AGAA GGGCCU ACCAGAGAAACACACGUUGUGGUACAUUACCUGGUA | 13428 |
| 3903 | AGCUUCU GCU UCUCCAGC | 4024 | GCUGGAGA AGAA GAAGCU ACCAGAGAAACACACGUUGUGGUACAUUACCUGGUA | 13429 |
| 3912 | UUCUCCA GCU GUGGCCAC | 4025 | GUGGCCAC AGAA GGAGAA ACCAGAGAAACACACGUUGUGGUACAUUACCUGGUA | 13430 |
| 3969 | GAGUCCU GCU GUUCUCCA | 4026 | UGGAGAAC AGAA GGACUC ACCAGAGAAACACACGUUGUGGUACAUUACCUGGUA | 13431 |
| 3972 | UCCUGCU GUU CUCCACCC | 4027 | GGGUGGAG AGAA GCAGGA ACCAGAGAAACACACGUUGUGGUACAUUACCUGGUA | 13432 |
| 3986 | ACCCCCA GAC UACAACUC | 4028 | GAGUUGUA AGAA GGGGGU ACCAGAGAAACACACGUUGUGGUACAUUACCUGGUA | 13433 |
| 4018 | CCUCCCC GCC CGCCUAAA | 4029 | UUUAGGCG AGAA GGGAGG ACCAGAGAAACACACGUUGUGGUACAUUACCUGGUA | 13434 |
| 4022 | CCCGCCC GCC UAAAGCUU | 4030 | AAGCUUUA AGAA GGCGGG ACCAGAGAAACACACGUUGUGGUACAUUACCUGGUA | 13435 |
| 4040 | CUCACCA GCC CCGACAAC | 4031 | GUUGUCGG AGAA GGUGAG ACCAGAGAAACACACGUUGUGGUACAUUACCUGGUA | 13436 |
| 4053 | ACAACCA GCC CCUGACAG | 4032 | CUGUCAGG AGAA GGUUGU ACCAGAGAAACACACGUUGUGGUACAUUACCUGGUA | 13437 |
| 4095 | CUAUUCC GCU CCACAGGA | 4033 | UCCUGUGG AGAA GAAUAG ACCAGAGAAACACACGUUGUGGUACAUUACCUGGUA | 13438 |
| 4110 | GGAGCCA GCU GCUUUUCG | 4034 | CGAAAAGC AGAA GGCUCC ACCAGAGAAACACACGUUGUGGUACAUUACCUGGUA | 13439 |
| 4113 | GCCAGCU GCU UUUCGUGA | 4035 | UCACGAAA AGAA GCUGGC ACCAGAGAAACACACGUUGUGGUACAUUACCUGGUA | 13440 |

TABLE IX-continued

Mouse flt1 VEGF Receptor-Hairpin Ribozyme and Substrate Sequence

| Pos | Substrate | Seq ID No | HP Ribozyme | Seq ID No |
|---|---|---|---|---|
| 4168 | UGUUGCU GUU UUGACUAA | 4036 | UUAGUCAA AGAA GCAACA ACCAGAGAAACACACGUUGUGGUACAUUACCUGGUA | 13441 |
| 4290 | GGCGACC GCC CGCCCACC | 4037 | GGUGGGCG AGAA GUCGCC ACCAGAGAAACACACGUUGUGGUACAUUACCUGGUA | 13442 |
| 4294 | ACCGCCC GCC CACCGGCC | 4038 | GGCCGGUG AGAA GGCGGU ACCAGAGAAACACACGUUGUGGUACAUUACCUGGUA | 13443 |
| 4329 | CCCUGCA GCU GUGGGACU | 4039 | AGUCCCAC AGAA GCAGGG ACCAGAGAAACACACGUUGUGGUACAUUACCUGGUA | 13444 |
| 4378 | AUGCACU GAC CUGGUCUG | 4040 | CAGACCAG AGAA GUCCAG ACCAGAGAAACACACGUUGUGGUACAUUACCUGGUA | 13445 |
| 4383 | CUGACCU GCU CUGUCUCU | 4041 | AGAGACAG AGAA GGUCAG ACCAGAGAAACACACGUUGUGGUACAUUACCUGGUA | 13446 |
| 4388 | CUGCUCU GUC UCUCUUAU | 4042 | AUAAGAGA AGAA GAGCAG ACCAGAGAAACACACGUUGUGGUACAUUACCUGGUA | 13447 |
| 4457 | UGCGUCC GUC CUGUGGAG | 4043 | CUCCACAG AGAA GACGCA ACCAGAGAAACACACGUUGUGGUACAUUACCUGGUA | 13448 |
| 4525 | GGCCUCC GCU GUUUCGGG | 4044 | CCCGAAAC AGAA GAGGCC ACCAGAGAAACACACGUUGUGGUACAUUACCUGGUA | 13449 |
| 4528 | CUCCGCU GUU UCGGGCCC | 4045 | GGGCCCGA AGAA GCGGAG ACCAGAGAAACACACGUUGUGGUACAUUACCUGGUA | 13450 |
| 4643 | GUCUUCU GUU GUCUGUUU | 4046 | AAACAGAC AGAA GAAGAC ACCAGAGAAACACACGUUGUGGUACAUUACCUGGUA | 13451 |
| 4650 | GUUGUCU GUU UACCAUCC | 4047 | GGAUGGUA AGAA GACAAC ACCAGAGAAACACACGUUGUGGUACAUUACCUGGUA | 13452 |
| 4724 | AUCAUCA GUU CCUCUAGU | 4048 | ACUAGAGG AGAA GAUGAG ACCAGAGAAACACACGUUGUGGUACAUUACCUGGUA | 13453 |
| 4771 | CAGGCCU GAC CUUCGCAU | 4049 | AUGCGAAG AGAA GGCCUG ACCAGAGAAACACACGUUGUGGUACAUUACCUGGUA | 13454 |
| 4785 | GCAUACU GCU CACGGGGA | 4050 | UCCCCGUG AGAA GUAUGC ACCAGAGAAACACACGUUGUGGUACAUUACCUGGUA | 13455 |
| 4809 | UGGUCCA GUU UGGCCUAG | 4051 | CUAGGCCA AGAA GGACCA ACCAGAGAAACACACGUUGUGGUACAUUACCUGGUA | 13456 |
| 4834 | GCCUACU GAU GGGCUCAA | 4052 | UUGAGCCC AGAA GUAGGC ACCAGAGAAACACACGUUGUGGUACAUUACCUGGUA | 13457 |
| 4912 | UUAUCCU GUU UUAUAUAU | 4053 | AUAUAUAA AGAA GGAUAA ACCAGAGAAACACACGUUGUGGUACAUUACCUGGUA | 13458 |
| 5119 | CAAGGCA GUC UGAGAGGA | 4054 | UCCUCUCA AGAA GCCUUG ACCAGAGAAACACACGUUGUGGUACAUUACCUGGUA | 13459 |
| 5144 | AGUAUCA GCC CAUAUUUA | 4055 | UAAAUAUG AGAA GAUACU ACCAGAGAAACACACGUUGUGGUACAUUACCUGGUA | 13460 |
| 5287 | UUCAUCU GUU UCAUACCU | 4056 | AGGUAUGA AGAA GAUGAA ACCAGAGAAACACACGUUGUGGUACAUUACCUGGUA | 13461 |
| 5363 | GGUGCCC GCU CUUUGGGG | 4057 | CCCCAAAG AGAA GGCACC ACCAGAGAAACACACGUUGUGGUACAUUACCUGGUA | 13462 |
| 5462 | CACACCU GCC GGAGCCGG | 4058 | CCGGCUCC AGAA GGUGUG ACCAGAGAAACACACGUUGUGGUACAUUACCUGGUA | 13463 |
| 5478 | GGUCACA GCU GGGCAGAC | 4059 | GUCUGCCC AGAA GUGACC ACCAGAGAAACACACGUUGUGGUACAUUACCUGGUA | 13464 |
| 5486 | CUGGGCA GAC GAUGAAUA | 4060 | UAUUCAUC AGAA GCCCAG ACCAGAGAAACACACGUUGUGGUACAUUACCUGGUA | 13465 |
| 5500 | AAUAGCU GCU UUGGGAGA | 4061 | UCUCCCAA AGAA GCUAUU ACCAGAGAAACACACGUUGUGGUACAUUACCUGGUA | 13466 |
| 5539 | AUUCUCU GAC CGGGCCAG | 4062 | CUGGCCCG AGAA GAGAAU ACCAGAGAAACACACGUUGUGGUACAUUACCUGGUA | 13467 |
| 5564 | GGUACCU GCU CCCCUGUG | 4063 | CACAGGGG AGAA GGUACC ACCAGAGAAACACACGUUGUGGUACAUUACCUGGUA | 13468 |
| 5597 | GUUUUCU GUC UGAUGAGA | 4064 | UCUCAUCA AGAA GAAAAC ACCAGAGAAACACACGUUGUGGUACAUUACCUGGUA | 13469 |
| 5601 | UCUGUCU GAU GAGACUGG | 4065 | CCAGUCUC AGAA GACAGA ACCAGAGAAACACACGUUGUGGUACAUUACCUGGUA | 13470 |
| 5639 | UGAGACA GCC UGCAGCCC | 4066 | GGGCUGCA AGAA GUCUCA ACCAGAGAAACACACGUUGUGGUACAUUACCUGGUA | 13471 |
| 5646 | GCCUGCA GCC CACUGUGG | 4067 | CCACAGUG AGAA GCAGGC ACCAGAGAAACACACGUUGUGGUACAUUACCUGGUA | 13472 |
| 5781 | CUUGUCG GCU GCAGUGUG | 4068 | CACACUGC AGAA GACAAG ACCAGAGAAACACACGUUGUGGUACAUUACCUGGUA | 13473 |
| 5829 | AGAAACG GAU GAGAACAG | 4069 | CUGUUCUC AGAA GUUUCU ACCAGAGAAACACACGUUGUGGUACAUUACCUGGUA | 13474 |
| 5842 | AACAGCA GCC UGAGGUUU | 4070 | AAACCUCA AGAA GCUGUU ACCAGAGAAACACACGUUGUGGUACAUUACCUGGUA | 13475 |
| 5915 | UUAUUCC GAU UUUAAUAA | 4071 | UUAUUAAA AGAA GAAUAA ACCAGAGAAACACACGUUGUGGUACAUUACCUGGUA | 13476 |

TABLE IX-continued

Mouse flt1 VEGF Receptor-Hairpin Ribozyme and Substrate Sequence

| Pos | Substrate | Seq ID No | HP Ribozyme | Seq ID No |
|---|---|---|---|---|
| 6010 | UGGUUCU GCU UAAAGACU | 4072 | AGUCUUUA AGAA GAACCA ACCAGAGAAACACACGUUGUGGUACAUUACCUGGUA | 13477 |

TABLE X

Homologous Hammerhead Ribozyme Target Sites Between Human flt-1 and KDR RNA

| nt. Position | flt-1 Target Sequence | Seq ID No | nt. Position | KDR Target Sequence | Seq ID No |
|---|---|---|---|---|---|
| 3388 | CCGGGAU A UUUAUAA | 4073 | 3151 | CCGGGAU A UUUAUAA | 4073 |
| 2174 | AAUGUAU A CACAGGG | 4074 | 3069 | AgUGUAU c CACAGGG | 4116 |
| 2990 | UCCAAAU A UGGAAAU | 4075 | 2756 | UGCAAAU u UGGAAAc | 4117 |
| 2693 | CUCCCUU A UGAUGCC | 4076 | 2459 | CUgCCUU A UGAUGCC | 4118 |
| 2981 | GUUGAAU A CUGCAAA | 4077 | 2747 | GUgGAAU u CUGCAAA | 4119 |
| 1359 | UAUGGUU A AAAGAUG | 4078 | 2097 | U9UGGUU u AAAGAUa | 4120 |
| 3390 | GGGAUAU U UAUAAGA | 4079 | 3153 | GGGAUAU U UAUAAag | 4121 |
| 3391 | GGAUAUU U AUAAGAA | 4080 | 3154 | GGAUAUU U AUAAagA | 4122 |
| 2925 | ACGUGGU U AACCUGC | 4081 | 2691 | AuGUGGU c AACCUuC | 4123 |
| 7140 | UAUUUCU A GUCAUGA | 4082 | 2340 | UAcUUCU u GUCAUCA | 4124 |
| 1785 | CAAUAAU A GAAGGAA | 4083 | 1515 | CucUAAU U GAAGGAA | 4125 |
| 2731 | GAGACUU A AACUGGG | 4084 | 768 | uuGACUU c AACUGGG | 4126 |
| 3974 | GAUGACU A CCAGGGC | 4085 | 1466 | GAgGACU u CCAGGGa | 4127 |
| 6590 | UUAAUGU A GAAAGAA | 4086 | 2603 | aaAAUGU u GAAAGAA | 4128 |
| 6705 | GCCAUUU A UGACAAA | 4087 | 3227 | aCaAUUU u UGACAgA | 4129 |
| 974 | GUCAAAU U ACUUAGA | 4088 | 147 | uUCAAAU U ACUUgcA | 4130 |
| 1872 | AUAAAGU U GGGACUG | 4089 | 1602 | ACAAAGU c GGGAgaG | 4131 |
| 2333 | ACUUGGU U UAAAAAC | 4090 | 1088 | AaaUGGU a UAAAAAu | 4132 |
| 2775 | AAGUGGU U CAAGCAU | 4091 | 1745 | AcaUGGU a CAAGCuU | 4133 |
| 3533 | UUCUCCU U AGGUGGG | 4092 | 3296 | UUuUCCU U AGGUGcu | 4134 |
| 3534 | UCUCCUU A GGUGGGU | 4093 | 3297 | UuUCCUU A GGUGcuU | 4135 |
| 3625 | GUACUCU A CUCCUGA | 4094 | 4054 | GagCUCU c CUCCUGu | 4136 |
| 1814 | AGCACCU U GGUUGUG | 4095 | 1059 | AGuACCU U GGUUacc | 4137 |
| 2744 | GGCAAAU C ACUUGGA | 4096 | 147 | uuCAAAU u ACUUGcA | 4130 |
| 2783 | CAAGCAU C AGCAUUU | 4097 | 796 | gAAGCAU C AGCAUaa | 4138 |
| 3613 | GAGAGCU C CUGAGGA | 4098 | 2968 | GgaAGCU C CUGAagA | 4139 |
| 4052 | AAGGCCU C GCUCAAG | 4099 | 1923 | ucuGCCU u GCUCAAG | 4140 |
| 5305 | UCUCCAU A UCAAAAC | 4100 | 456 | ggUCCAU u UCAAAuC | 4141 |
| 7155 | AUGUAUU U UGUAUAC | 4101 | 631 | gUcUAUU a UGUAcAu | 4142 |
| 1836 | CUAGAAU U UCUGGAA | 4102 | 1007 | aUgGAAU c UCUGGug | 4143 |

TABLE X-continued

Homologous Hammerhead Ribozyme Target Sites Between Human flt-1 and KDR RNA

| nt. Position | flt-1 Target Sequence | Seq ID No | nt. Position | KDR Target Sequence | Seq ID No |
|---|---|---|---|---|---|
| 2565 | CUCUCUU C UGGCUCC | 4103 | 2328 | uguUCUU C UGGCUaC | 4144 |
| 4250 | CUGUACU C CACCCCA | 4104 | 3388 | uUaUACU a CACCagA | 4145 |
| 7124 | ACAUGGU U UGGUCCU | 4105 | 3778 | cagUGGU a UGGUuCU | 4146 |
| 436 | AUGGUCU U UGCCUGA | 4106 | 1337 | AcGGUCU a UGCCauu | 4147 |
| 2234 | GCACCAU A CCUCCUG | 4107 | 1344 | augCCAU u CCUCCcc | 4148 |
| 2763 | GGGCUUU U GGAAAAG | 4108 | 990 | uuGCUUU U GGAAgUG | 4149 |
| 4229 | CCAGACU A CAACUCG | 4109 | 767 | auuGACU u CAACUgG | 4150 |
| 5301 | GUUUUCU C CAUAUCA | 4110 | 3307 | ugcUUCU C CAUAUCc | 4151 |
| 6015 | AGAAUGU A UGCCUCU | 4111 | 1917 | AcuAUGU c UGCCUug | 4152 |
| 6095 | AUUCCCU A GUGAGCC | 4112 | 1438 | AUaCCCU u GUGAaya | 4153 |
| 6236 | UGUUGUU C CUCUUCU | 4113 | 76 | UagUGUU u CUCUUga | 4154 |
| 5962 | GCUUCCU U UUAUCCA | 4114 | 3099 | auaUCCU c UUAUCgg | 4155 |
| 7629 | UAUAUAU U CUCUGCU | 4115 | 3096 | gAaAUAU c CUCUuaU | 4156 |

Lowercase letters are used to represent sequence variance between flt-1 and KDR RNA

TABLE XI

| Reagent | Equivalents | Amount | Wait Time* DNA | Wait Time* 2'-O-methyl | Wait Time* RNA |
|---|---|---|---|---|---|
| A. 2.5 μmol Synthesis Cycle ABI 394 Instrument | | | | | |
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |
| B. 0.2 μmol Synthesis Cycle ABI 394 Instrument | | | | | |
| Phosphoramidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-Methyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |
| Beaucage | 7.7 | 232 μL | 100 sec | 300 sec | 300 sec |
| Acetonitrile | NA | 2.64 mL | NA | NA | NA |

| Reagent | Equivalents DNA/2'-O-methyl/Ribo | Amount DNA/2'-O-methyl/Ribo | Wait Time* DNA | Wait Time* 2'-O-methyl | Wait Time* Ribo |
|---|---|---|---|---|---|
| C. 0.2 μmol Synthesis Cycle 96 well Instrument | | | | | |
| Phosphoramidites | 22/33/66 | 40/60/120 μL | 60 sec | 180 sec | 360 sec |
| S-Ethyl Tetrazole | 70/105/210 | 40/60/120 μL | 60 sec | 180 min | 360 sec |
| Acetic Anhydride | 265/265/265 | 50/50/50 μL | 10 sec | 10 sec | 10 sec |
| N-Methyl Imidazole | 502/502/502 | 50/50/50 μL | 10 sec | 10 sec | 10 sec |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 | 100 sec | 200 sec | 200 sec |
| Acetonitrile | NA | 1150/1150/1150 μL | NA | NA | NA |

*Wait time does not include contact time during delivery.

TABLE XII

Ribozyme and attenuated control sequences and locations of modified nucleotides.

| Target Site* | RPI No. | Ribozyme Sequence†(5'–3') | Activity | Seq. ID No. |
|---|---|---|---|---|
| Flt-1358-amino | RPI 4118 | 5' $a_s u_s c_s u_s$uuu cUGAUGaggcgaaagccGaa AccauacB 3' | Active | 13478 |
| Flt-1358-amino (att.) | RPI 4581 | $a_s u_s c_s u_s$uuu cU<u>u</u>AUGaggcgaaagccGa<u>u</u> AccauacB | Attenuated | 13479 |
| Flt-1358-allyl | RPI 4159 | 5' $a_s u_s c_s U_s$uuu cUGAuGaggcgaaagccGaa AccauacB 3' | Active | 13480 |
| Flt-1358-allyl (att.) | RPI 4583 | $a_s u_s c_s u_s$uuu cU<u>u</u>AuGaggcgaaagccGa<u>u</u> AccauacB | Attenuated | 13481 |
| Flt-4229-amino | RPI 4131 | $g_s a_s g_s u_s$ug cUGAUGaggcgaaagccGaa AgucugB | Active | 13482 |
| Flt-4229-amino (att.) | RPI 4582 | $g_s a_s g_s u_s$ug cU<u>u</u>AUGaggcgaaagccGa<u>u</u> AgucugB | Attenuated | 13483 |
| Flt-4229-allyl | RPI 4172 | $g_s a_s g_s u_s$ug cUGAuGaggcgaaagccGaa AgucugB | Active | 13484 |
| Flt-4229-allyl (att.) | RPI 4584 | $g_s a_s g_s u_s$ug cU<u>U</u>AuGaggcgaaagccGa<u>u</u> AgucugB | Attenuated | 13485 |
| KDR-726-amino | RPI 4097 | $u_s a_s c_s a_s$auu cUGAUCaggcgaagccGaa AagacaaB | Active | 13486 |
| KDR-726-amino (att.) | RPI 4674 | $u_s a_s c_s a_s$auu cU<u>u</u>AUGaggcgaaagccGa<u>u</u> Aagacaab | Attenuated | 13487 |
| KDR-726-allyl | RPI 4138 | $u_s a_s c_s a_s$auu cUGAuGaggcgaaagccGaa AagacaaB | Active | 13488 |
| KDR-726allyl (att.) |  | $u_s a_s c_s a_s$auu cUuAuGaggcgaagccGau AagacaaB | Attenuated | 13489 |
| KDR-3950-amino | RPI 4110 | $c_s u_s g_s g_s$ag cUGAUGaggcgaaagccGaa AcacggB | Active | 13490 |
| KDR-3950-amino (att.) | RPI 4677 | $c_s u_s g_s g_s$ag cUuAUGaggcgaaagccGau AcacggB | Attenuated | 13491 |
| KDR-3950-allyl | RPI 4151 | $c_s u_s g_s g_s$ag cUcAuGaggcgaaagccGaa AcacggB | Active | 13492 |
| KDR-3950-allyl (att.) |  | $c_s u_s g_s g_s$ag cUuAuGaggcgaaagccGau AcacggB | Attenuated | 13493 | binding arm/catalytic core & stem II/binding arm

*Ribozyme target sites are named according to the cleavage position in human Flt-1 (EMBL accession no. X51602) or human KDR mRNA (EMBL accession no. L0497).
† Modifications are indicated as follows: 2'-O-methyl nucleotides, lowercase; ribonucleotides, uppercase G, A; inverted 3'-3'deoxyabasic, B. Two ribozyme motifs were tested[23]. For the $NH_2$-modified ribozymes, U indicates the two core positions where 2'-$NH_2$ uridines are present. U indicates 2'-C-allyl-uridine modification. The positions of four phosphorothioate linkages at the 5' end are indicated by a subscript "s". Changes in the attenuated controls are underlined. Nucleotides comprising the base paired region of stem II are in *italics*. A 3 bp stem II is shown above. Ribozymes or attenuated controls referred to in the text with a 4 bp stem II have one additional base pair such that the stem II/loop sequence is ggccgaaaggcc. (SEQ ID NO. 20823)

TABLE XIII

Ribozyme and attenuated control sequences with locations of modified nucleotides.

| Ribozyme | Sequence† (5'—3') | Activity | Seq ID Nos. |
|---|---|---|---|
| RPI.4610 (ANGIOZYME ™) | $g_s a_s g_s u_s$ug cUGAuGaggccgaaaggccGaa AgucugB | Active | 13494 |
| RPI.13141 | $g_s a_s g_s u_s$ug cUAGaGaggccgaaaggccGau AgucugB | BAC‡ | 13495 |
| RPI.13030 | $g_s a_s a_s g_s$gu cUAGuGaggccgaaaggccGau AugucB binding arm/core & stem II/binding arm | BAC* | 13496 |

†Modifications are indicated as follows: 2'-O-methyl nucleotides, lowercase; ribonucleotides, uppercase G, A; 2'-C-allyl uridine, U; inverted 3'-3' deoxyabasic, B. The positions of four phosphorothioate linkages at the 5' end are indicated by a subscript "s". Nucleotides comprising the base paired region of stem II are in *italics*. Nucleotide changes in the core of the attenuated controls are underlined. ANGIOZYME ribozyme is targeted to cleave site 4229 in human flt-1 RNA and is identical to Flt-4229-allyl ribozyme (Table XII) except that the ANGIOZYME has a stem II of length 4 bps.
‡BAc: Binding arm, Attenuated core Control.
*SAC: Scrambled arm, Attenuated core Control.

TABLE XIV

NCH Ribozyme and Target Sequences

| Pos | Target | Seq ID No | NCH Ribozyme | Seq ID No |
|---|---|---|---|---|
| 9 | GCGGACAC U CCUCUCGG | 4157 | CCGAGAGG CUGAUGAGGCCGUUAGGCCGAA IUGUCCGC | 13497 |
| 11 | GGACACUC C UCUCGGCU | 4158 | AGCCGAGA CUGAUGAGGCCGUUAGGCCGAA IAGUGUCC | 13498 |
| 12 | GACACUCC U CUCGGCUC | 4159 | GAGCCGAG CUGAUGAGGCCGUUAGGCCGAA IGAGUGUC | 13499 |
| 14 | CACUCCUC U CGGCUCCU | 4160 | AGGAGCCG CUGAUGAGGCCGUUAGGCCGAA IAGGAGUG | 13500 |
| 19 | CUCUCGGC U CCUCCCCG | 4161 | CGGGGAGG CUGAUGAGGCCGUUAGGCCGAA ICCGAGAG | 13501 |
| 21 | CUCGGCUC C UCCCCGGC | 4162 | GCCGGGGA CUGAUGAGGCCGUUAGGCCGAA IAGCCGAG | 13502 |
| 22 | UCGGCUCC U CCCCGGCA | 4163 | UGCCGGGG CUGAUGAGGCCGUUAGGCCGAA IGAGCCGA | 13503 |
| 24 | GGCUCCUC C CCGGCAGC | 4164 | GCUGCCGG CUGAUGAGGCCGUUAGGCCGAA IAGGAGCC | 13504 |
| 25 | GCUCCUCC C CGGCAGCG | 4165 | CGCUGCCG CUGAUGAGGCCGUUAGGCCGAA IGAGGAGC | 13505 |
| 26 | CUCCUCCC C GGCAGCGG | 4166 | CCGCUGCC CUGAUGAGGCCGUUAGGCCGAA IGGAGGAG | 13506 |
| 30 | UCCCCGGC A GCGGCGGC | 4167 | GCCGCCGC CUGAUGAGGCCGUUAGGCCGAA ICCGGGGA | 13507 |
| 42 | GCGGCGGC U CGGAGCGG | 4168 | CCGCUCCG CUGAUGAGGCCGUUAGGCCGAA ICCGCCGC | 13508 |
| 53 | GAGCGGGC U CCGGGGCU | 4169 | AGCCCCGG CUGAUGAGGCCGUUAGGCCGAA ICCCGCUC | 13509 |
| 55 | GCGGGCUC C GGGGCUCG | 4170 | CGAGCCCC CUGAUGAGGCCGUUAGGCCGAA IAGCCCGC | 13510 |
| 61 | UCCGGGGC U CGGGUGCA | 4171 | UGCACCCG CUGAUGAGGCCGUUAGGCCGAA ICCCCGGA | 13511 |
| 69 | UCGGGUGC A GCGGCCAG | 4172 | CUGGCCGC CUGAUGAGGCCGUUAGGCCGAA ICACCCGA | 13512 |
| 75 | GCAGCGGC C AGCGGGCC | 4173 | GGCCCGCU CUGAUGAGGCCGUUAGGCCGAA ICCGCUGC | 13513 |
| 76 | CAGCGGCC A GCGGGCCU | 4174 | AGGCCCGC CUGAUGAGGCCGUUAGGCCGAA IGCCGCUG | 13514 |
| 83 | CAGCGGGC C UGGCGGCG | 4175 | CGCCGCCA CUGAUGAGGCCGUUAGGCCGAA ICCCGCUG | 13515 |
| 84 | AGCGGGCC U GGCGGCGA | 4176 | UCGCCGCC CUGAUGAGGCCGUUAGGCCGAA IGCCCGCU | 13516 |
| 100 | AGGAUUAC C CGGGGAAG | 4177 | CUUCCCCG CUGAUGAGGCCGUUAGGCCGAA IUAAUCCU | 13517 |
| 101 | GGAUUACC C GGGGAAGU | 4178 | ACUUCCCC CUGAUGAGGCCGUUAGGCCGAA IGUAAUCC | 13518 |
| 117 | UGGUUGUC U CCUGGCUG | 4179 | CAGCCAGG CUGAUGAGGCCGUUAGGCCGAA IACAACCA | 13519 |
| 119 | GUUGUCUC C UGGCUGGA | 4180 | UCCAGCCA CUGAUGAGGCCGUUAGGCCGAA IAGACAAC | 13520 |
| 120 | UUGUCUCC U GGCUGGAG | 4181 | CUCCAGCC CUGAUGAGGCCGUUAGGCCGAA IGAGACAA | 13521 |
| 124 | CUCCUGGC U GGAGCCGC | 4182 | GCGGCUCC CUGAUGAGGCCGUUAGGCCGAA ICCAGGAG | 13522 |
| 130 | GCUGGAGC C GCGAGACG | 4183 | CGUCUCGC CUGAUGAGGCCGUUAGGCCGAA ICUCCAGC | 13523 |
| 144 | ACGGGCGC U CAGGCGC | 4184 | GCGCCCUG CUGAUGAGGCCGUUAGGCCGAA ICGCCCGU | 13524 |
| 146 | GGGCGCUC A GGCGCGG | 4185 | CCGCGCCC CUGAUGAGGCCGUUAGGCCGAA IAGCGCCC | 13525 |
| 158 | CGCGGGGC C GGCGGCGG | 4186 | CCGCCGCC CUGAUGAGGCCGUUAGGCCGAA ICCCCGCG | 13526 |
| 184 | GGACGGAC U CUGGCGGC | 4187 | GCCGCCAG CUGAUGAGGCCGUUAGGCCGAA IUCCGUCC | 13527 |
| 186 | ACGGACUC U GCGGCCG | 4188 | CGGCCGCC CUGAUGAGGCCGUUAGGCCGAA IAGUCCGU | 13528 |
| 193 | CUGGCGGC C GGGUCGUU | 4189 | AACGACCC CUGAUGAGGCCGUUAGGCCGAA ICCGCCAG | 13529 |
| 205 | UCGUUGGC C GGGGAGC | 4190 | GCUCCCCC CUGAUGAGGCCGUUAGGCCGAA ICCAACGA | 13530 |
| 220 | GCGCGGGC A CCGGGCGA | 4191 | UCGCCCGG CUGAUGAGGCCGUUAGGCCGAA ICCCGCGC | 13531 |
| 222 | GCGGGCAC C GGGCGAGC | 4192 | GCUCGCCC CUGAUGAGGCCGUUAGGCCGAA IUGCCCGC | 13532 |
| 231 | GGGCGAGC A GGCCGCGU | 4193 | ACGCGGCC CUGAUGAGGCCGUUAGGCCGAA ICUCGCCC | 13533 |

TABLE XIV-continued

NCH Ribozyme and Target Sequences

| Pos | Target | Seq ID No | NCH Ribozyme | Seq ID No |
|-----|--------|-----------|--------------|-----------|
| 235 | GAGCAGGC C GCGUCGCG | 4194 | CGCGACGC CUGAUGAGGCCGUUAGGCCGAA ICCUGCUC | 13534 |
| 245 | CGUCGCGC U CACCAUGG | 4195 | CCAUGGUG CUGAUGAGGCCGUUAGGCCGAA ICGCGACG | 13535 |
| 247 | UCGCGCUC A CCAUGGUC | 4196 | GACCAUGG CUGAUGAGGCCGUUAGGCCGAA IAGCGCGA | 13536 |
| 249 | GCGCUCAC C AUGGUCAG | 4197 | CUGACCAU CUGAUGAGGCCGUUAGGCCGAA IUGAGCGC | 13537 |
| 250 | CGCUCACC A UGGUCAGC | 4198 | GCUGACCA CUGAUGAGGCCGUUAGGCCGAA IGUGAGCG | 13538 |
| 256 | CCAUGGUC A GCUACUGG | 4199 | CCAGUAGC CUGAUGAGGCCGUUAGGCCGAA IACCAUGG | 13539 |
| 259 | UGGUCAGC U ACUGGGAC | 4200 | GUCCCAGU CUGAUGAGGCCGUUAGGCCGAA ICUGACCA | 13540 |
| 262 | UCAGCUAC U GGGACACC | 4201 | GGUGUCCC CUGAUGAGGCCGUUAGGCCGAA IUAGCUGA | 13541 |
| 268 | ACUGGGAC A CCGGGGUC | 4202 | GACCCCGG CUGAUGAGGCCGUUAGGCCGAA IUCCCAGU | 13542 |
| 270 | UGGGACAC C GCGGUCCU | 4203 | AGGACCCC CUGAUGAGGCCGUUAGGCCGAA IGUCCCA | 13543 |
| 277 | CCGGGGUC C UGCUGUGC | 4204 | GCACAGCA CUGAUGAGGCCGUUAGGCCGAA IACCCCGG | 13544 |
| 278 | CGGGGUCC U GCUGUGCG | 4205 | CGCACAGC CUGAUGAGGCCGUUAGGCCGAA IGACCCCG | 13545 |
| 281 | GGUCCUGC U GUGCGCGC | 4206 | GCGCGCAC CUGAUGAGGCCGUUAGGCCGAA ICAGGACC | 13546 |
| 290 | GUGCGCGC U GCUCAGCU | 4207 | AGCUGAGC CUGAUGAGGCCGUUAGCCCGAA ICGCGCAC | 13547 |
| 293 | CGCGCUGC U CAGCUGUC | 4208 | GACAGCUG CUGAUGAGGCCGUUAGGCCGAA ICAGCGCG | 13548 |
| 295 | CGCUGCUC A GCUGUCUG | 4209 | CAGACAGC CUGAUGAGGCCGUUAGGCCGAA IAGCAGCG | 13549 |
| 298 | UGCUCAGC U GUCUGCUU | 4210 | AAGCAGAC CUGAUGAGGCCGUUAGGCCGAA ICUGAGCA | 13550 |
| 302 | CAGCUGUC U GCUUCUCA | 4211 | UGAGAAGC CUGAUGAGGCCGUUAGCCCGAA IACAGCUG | 13551 |
| 305 | CUGUCUGC U UCUCACAG | 4212 | CUGUGAGA CUGAUGAGGCCGUUAGGCCGAA ICAGACAG | 13552 |
| 308 | UCUGCUUC U CACAGGAU | 4213 | AUCCUGUG CUGAUGAGGCCGUUAGGCCGAA IAAGCAGA | 13553 |
| 310 | UGCUUCUC A CAGGAUCU | 4214 | AGAUCCUG CUGAUGAGGCCGUUAGGCCGAA IAGAAGCA | 13554 |
| 312 | CUUCUCAC A GGAUCUAG | 4215 | CUAGAUCC CUGAUGAGGCCGUUAGGCCGAA IUGAGAAG | 13555 |
| 318 | ACAGGAUC U AGUUCAGG | 4216 | CCUGAACU CUGAUGAGGCCGUUAGGCCGAA IAUCCUGU | 13556 |
| 324 | UCUAGUUC A GGUUCAAA | 4217 | UUUGAACC CUGAUGAGGCCGUUAGGCCGAA IAACUAGA | 13557 |
| 330 | UCAGGUUC A AAAUUAAA | 4218 | UUUAAUUU CUGAUGAGGCCGUUAGGCCGAA IAACCUGA | 13558 |
| 344 | AAAAGAUC C UGAACUGA | 4219 | UCAGUUCA CUGAUGAGGCCGUUAGGCCGAA IAUCUUUU | 13559 |
| 345 | AAAGAUCC U GAACUGAG | 4220 | CUCAGUUC CUGAUGAGGCCGUUAGGCCGAA IGAUCUUU | 13560 |
| 350 | UCCUGAAC U GAGUUUAA | 4221 | UUAAACUC CUGAUGAGGCCGUUAGGCCGAA IUUCAGGA | 13561 |
| 364 | UAAAAGGC A CCCAGCAC | 4222 | GUGCUGGG CUGAUGAGGCCGUUAGGCCGAA ICCUUUUA | 13562 |
| 366 | AAAGGCAC C CAGCACAU | 4223 | AUGUGCUG CUGAUGAGGCCGUUAGGCCGAA IUGCCUUU | 13563 |
| 367 | AAGGCACC C AGCACAUC | 4224 | GAUGUGCU CUGAUGAGGCCGUUAGGCCGAA IGUGCCUU | 13564 |
| 368 | AGGCACCC A GCACAUCA | 4225 | UGAUGUGC CUGAUGAGGCCGUUAGGCCGAA IGGUGCCU | 13565 |
| 371 | CACCCAGC A CAUCAUGC | 4226 | GCAUGAUG CUGAUGAGGCCGUUAGGCCGAA ICUGGGUG | 13566 |
| 373 | CCCAGCAC A UCAUGCAA | 4227 | UUGCAUGA CUGAUGAGGCCGUUAGGCCGAA IUGCUGGG | 13567 |
| 376 | AGCACAUC A UGCAAGCA | 4228 | UGCUUGCA CUGAUGAGGCCGUUAGGCCGAA IAUGUGCU | 13568 |
| 380 | CAUCAUGC A AGCAGGCC | 4229 | GGCCUGCU CUGAUGAGGCCGUUAGGCCGAA ICAUGAUG | 13569 |
| 384 | AUGCAAGC A GGCCAGAC | 4230 | GUCUGGCC CUGAUGAGGCCGUUAGGCCGAA ICUUGCAU | 13570 |

TABLE XIV-continued

NCH Ribozyme and Target Sequences

| Pos | Target | Seq ID No | NCH Ribozyme | Seq ID No |
|---|---|---|---|---|
| 388 | AAGCAGGC C AGACACUG | 4231 | CAGUGUCU CUGAUGAGGCCGUUAGGCCGAA ICCUGCUU | 13571 |
| 389 | AGCAGGCC A GACACUGC | 4232 | GCAGUGUC CUGAUGAGGCCGUUAGGCCGAA IGCCUGCU | 13572 |
| 393 | GGCCAGAC A CUGCAUCU | 4233 | AGAUGCAG CUGAUGAGGCCGUUAGGCCGAA IUCUGGCC | 13573 |
| 395 | CCAGACAC U GCAUCUCC | 4234 | GGAGAUGC CUGAUGAGGCCGUUAGGCCGAA IUGUCUGG | 13574 |
| 398 | GACACUGC A UCUCCAAU | 4235 | AUUGGAGA CUGAUGAGGCCGUUAGGCCGAA ICAGUGUC | 13575 |
| 401 | ACUGCAUC U CCAAUGCA | 4236 | UGCAUUGG CUGAUGAGGCCGUUAGGCCGAA IAUGCAGU | 13576 |
| 403 | UGCAUCUC C AAUGCAGG | 4237 | CCUGCAUU CUGAUGAGGCCGUUAGGCCGAA IAGAUGCA | 13577 |
| 404 | GCAUCUCC A AUGCAGGG | 4238 | CCCUGCAU CUGAUGAGGCCGUUAGGCCGAA IGAGAUGC | 13578 |
| 409 | UCCAAUGC A GGGGGAA | 4239 | UUCCCCCC CUGAUGAGGCCGUUAGGCCGAA ICAUUGGA | 13579 |
| 420 | GGGGAAGC A GCCCAUAA | 4240 | UUAUGGGC CUGAUGAGGCCGUUAGGCCGAA ICUUCCCC | 13580 |
| 423 | GAAGCAGC C CAUAAAUG | 4241 | CAUUUAUG CUGAUGAGGCCGUUAGGCCGAA ICUGCUUC | 13581 |
| 424 | AAGCAGCC C AUAAAUGG | 4242 | CCAUUUAU CUGAUGAGGCCGUUAGGCCGAA IGCUGCUU | 13582 |
| 425 | AGCAGCCC A UAAAUGGU | 4243 | ACCAUUUA CUGAUGAGGCCGUUAGGCCGAA IGGCUGCU | 13583 |
| 435 | AAAUGGUC U UUGCCUGA | 4244 | UCAGGCAA CUGAUGAGGCCGUUAGGCCGAA IACCAUUU | 13584 |
| 440 | GUCUUUGC C UGAAAUGG | 4245 | CCAUUUCA CUGAUGAGGCCGUUAGGCCGAA ICAAAGAC | 13585 |
| 441 | UCUUUGCC U GAAAUGGU | 4246 | ACCAUUUC CUGAUGAGGCCGUUAGGCCGAA IGCAAAGA | 13586 |
| 470 | CGAAAGGC U GAGCAUAA | 4247 | UUAUGCUC CUGAUGAGGCCGUUAGGCCGAA ICCUUUCG | 13587 |
| 475 | GGCUGAGC A UAACUAAA | 4248 | UUUAGUUA CUGAUGAGGCCGUUAGGCCGAA ICUCAGCC | 13588 |
| 480 | AGCAUAAC U AAAUCUGC | 4249 | GCAGAUUU CUGAUGAGGCCGUUAGGCCGAA IUUAUGCU | 13589 |
| 486 | ACUAAAUC U GCCUGUGG | 4250 | CCACAGGC CUGAUGAGGCCGUUAGGCCGAA IAUUUAGU | 13590 |
| 489 | AAAUCUGC C UGUGGAAG | 4251 | CUUCCACA CUGAUGAGGCCGUUAGGCCGAA ICAGAUUU | 13591 |
| 490 | AAUCUGCC U GUGGAAGA | 4252 | UCUUCCAC CUGAUGAGGCCGUUAGGCCGAA IGCAGAUU | 13592 |
| 505 | GAAAUGGC A AACAAUUC | 4253 | GAAUUGUU CUGAUGAGGCCGUUAGGCCGAA ICCAUUUC | 13593 |
| 509 | UGGCAAAC A AUUCUGCA | 4254 | UGCAGAAU CUGAUGAGGCCGUUAGGCCGAA IUUUGCCA | 13594 |
| 514 | AACAAUUC U GCAGUACU | 4255 | AGUACUGC CUGAUGAGGCCGUUAGGCCGAA IAAUUGUU | 13595 |
| 517 | AAUUCUGC A GUACUUUA | 4256 | UAAAGUAC CUGAUGAGGCCGUUAGGCCGAA ICAGAAUU | 13596 |
| 522 | UGCAGUAC U UUAACCUU | 4257 | AAGGUUAA CUGAUGAGGCCGUUAGGCCGAA IACUGCA | 13597 |
| 528 | ACUUAAC C UUGAACAC | 4258 | CUGUUCAA CUGAUGAGGCCGUUAGGCCGAA IUUAAAGU | 13598 |
| 529 | CUUUAACC U UGAACACA | 4259 | UGUGUUCA CUGAUGAGGCCGUUAGGCCGAA IGUUAAAG | 13599 |
| 535 | CCUUGAAC A CAGCUCAA | 4260 | UUGAGCUG CUGAUGAGGCCGUUAGGCCGAA IUUCAAGG | 13600 |
| 537 | UUGAACAC A GCUCAAGC | 4261 | GCUUGAGC CUGAUGAGGCCGUUACGCCGAA IUGUUCAA | 13601 |
| 540 | AACACAGC U CAAGCAAA | 4262 | UUUGCUUG CUGAUGAGGCCGUUAGGCCGAA ICUGUGUU | 13602 |
| 542 | CACAGCUC A AGCAAACC | 4263 | GGUUUGCU CUGAUGAGGCCGUUAGGCCGAA IAGCUGUG | 13603 |
| 546 | GCUCAAGC A AACCACAC | 4264 | GUGUGGUU CUGAUCAGGCCGUUAGGCCGAA ICUUGAGC | 13604 |
| 550 | AAGCAAAC C ACACUGGC | 4265 | GCCAGUGU CUGAUGAGGCCGUUAGGCCGAA IUUUGCUU | 13605 |
| 551 | AGCAAACC A CACUGGCU | 4266 | AGCCAGUG CUGAUGAGGCCGUUAGGCCGAA IGUUUGCU | 13606 |
| 553 | CAAACCAC A CUGGCUUC | 4267 | GAAGCCAG CUGAUGAGGCCGUUAGGCCGAA IUGGUUUG | 13607 |

TABLE XIV-continued

NCH Ribozyme and Target Sequences

| Pos | Target | Seq ID No | NCH Ribozyme | Seq ID No |
|-----|--------|-----------|--------------|-----------|
| 555 | AACCACAC U GGCUUCUA | 4268 | UAGAAGCC CUGAUGAGGCCGUUAGGCCGAA IUGUGGUU | 13608 |
| 559 | ACACUGUC U UCUACAGC | 4269 | GCUGUAGA CUGAUGAGGCCGUUAGGCCGAA ICCAGUGU | 13609 |
| 562 | CUGGCUUC U ACAGCGC | 4270 | GCAGCUGU CUGAUGAGGCCGUUAGGCCGAA IAAGCCAG | 13610 |
| 565 | GCUUCUAC A GCUGCAAA | 4271 | UUUGCAGC CUGAUGAGGCCGUUAGGCCGAA IUAGAAGC | 13611 |
| 568 | UCUACAGC U GCAAAUAU | 4272 | AUAUUUGC CUGAUGAGGCCGUUAGGCCGAA ICUGUAGA | 13612 |
| 571 | ACAGCUGC A AAUAUCUA | 4273 | UAGAUAUU CUGAUGAGGCCGUUAGGCCGAA ICAGCUGU | 13613 |
| 578 | CAAAUAUC U AGCUGUAC | 4274 | GUACAGCU CUGAUGAGGCCGUUAGGCCGAA IAUAUUUG | 13614 |
| 582 | UAUCUAGC U GUACCUAC | 4275 | GUAGGUAC CUGAUGAGGCCGUUAGGCCGAA ICUAGAUA | 13615 |
| 587 | AGGUGUAC C UACUUCAA | 4276 | UUGAAGUA CUGAUGAGGCCGUUAGGCCGAA IUACAGCU | 13616 |
| 588 | GCUGUACC U ACUUCAAA | 4277 | UUUGAAGU CUGAUGAGGCCGUUAGGCCGAA IGUACAGC | 13617 |
| 591 | GUACCUAC U UCAAAGAA | 4278 | UUCUUUGA CUGAUGAGGCCGUUAGGCCGAA IAGGUAC | 13618 |
| 594 | CCUACUUC A AAGAAGAA | 4279 | UUCUUCUU CUGAUGAGGCCGUUAGGCCGAA IAAGUAGG | 13619 |
| 609 | AAGGAAAC A GAAUCUGC | 4280 | GCAGAUUC CUGAUGAGGCCGUUAGGCCGAA IUUUCCUU | 13620 |
| 615 | ACAGAAUC U GCAAUCUA | 4281 | UAGAUUGC CUGAUGAGGCCGUUAGGCCGAA IAUUCUGU | 13621 |
| 618 | GAAUCUGC A AUCUAUAU | 4282 | AUAUAGAU CUGAUGAGGCCGUUAGGCCGAA ICAGACUC | 13622 |
| 622 | CUGCAAUC U AUAUAUUU | 4283 | AAAUAUAU CUGAUGAGGCCGUUAGGCCGAA IAUUGCAG | 13623 |
| 642 | AGUGAUAC A GGUAGACC | 4284 | GGUCUACC CUGAUGAGGCCGUUAGGCCGAA IUAUCACU | 13624 |
| 650 | AGGUAGAC C UUUCGUAG | 4285 | CUACGAAA CUGAUGAGGCCGUUAGGCCGAA IUCUACCU | 13625 |
| 651 | GGUAGACC U UUCGUAGA | 4286 | UCUACGAA CUGAUGAGGCCGUUAGGCCGAA IGUCUACC | 13626 |
| 667 | AGAUGUAC A GUGAAAUC | 4287 | GAUUUCAC CUGAUGAGGCCGUUAGGCCGAA IUACAUCU | 13627 |
| 676 | GUGAAAUC C CGAAAUU | 4288 | AAUUUCGG CUGAUGAGGCCGUUAGGCCGAA IAUUUCAC | 13628 |
| 677 | UGAAAUCC C GAAAUUA | 4289 | UAAUUUCG CUGAUGAGGCCGUUAGGCCGAA IGAUUUCA | 13629 |
| 678 | GAAAUCCC C GAAAUUAU | 4290 | AUAAUUUC CUGAUGAGGCCGUUAGGCCGAA IGGAUUUC | 13630 |
| 689 | AAUUAUAC A CAUGACUG | 4291 | CAGUCAUG CUGAUGAGGCCGUUAGGCCGAA IUAUAAUU | 13631 |
| 691 | UUAUACAC A UGACUGAA | 4292 | UUCAGUCA CUGAUGAGGCCGUUAGGCCGAA IUGUAUAA | 13632 |
| 696 | CACAUGAC U GAAGGAAG | 4293 | CUUCCUUC CUGAUGAGGCCGUUAGGCCGAA ICAUGUG | 13633 |
| 710 | AAGGGAGC U CGUCAUUC | 4294 | GAAUGACG CUGAUGAGGCCGUUAGGCCGAA ICUCCCUU | 13634 |
| 715 | AGCUCGUC A UUCCCUGC | 4295 | GCAGGGAA CUGAUGAGGCCGUUAGGCCGAA IACGAGCU | 13635 |
| 719 | CGUCAUUC C CUGCCGGG | 4296 | CCCGGCAG CUGAUGAGGCCGUUAGGCCGAA IAAUGACG | 13636 |
| 720 | GUCAUUCC C UGCCGGGU | 4297 | ACCCGGCA CUGAUGAGGCCGUUAGGCCGAA IGAAUGAC | 13637 |
| 721 | UCAUUCCC U GCCGGGUU | 4298 | AACCCGGC CUGAUGAGGCCGUUAGGCCGAA IGGAAUGA | 13638 |
| 724 | UUCCCUGC C GGGUUACG | 4299 | CGUAACCC CUGAUGAGGCCGUUAGGCCGAA ICAGGGAA | 13639 |
| 735 | GUUACGUC A CCUAACAU | 4300 | AUGUUAGG CUGAUGAGGCCGUUAGGCCGAA IACGUAAC | 13640 |
| 737 | UACGUCAC C UAACAUCA | 4301 | UGAUGUUA CUGAUGAGGCCGUUAGGCCGAA IUGACGUA | 13641 |
| 738 | ACGUCACC U AACAUCAC | 4302 | GUGAUGUU CUGAUGAGGCCGUUAGGCCGAA IGUGACGU | 13642 |
| 742 | CACCUAAC A UCACUGUU | 4303 | AACAGUGA CUGAUGAGGCCGUUAGGCCGAA IUUAGGUG | 13643 |
| 745 | CUUACAUC A CUGUUACU | 4304 | AGUAACAG CUGAUGAGGCCGUUAGGCCGAA IAUGUUAG | 13644 |

TABLE XIV-continued

NCH Ribozyme and Target Sequences

| Pos | Target | Seq ID No | NCH Ribozyme | Seq ID No |
|-----|--------|-----------|--------------|-----------|
| 747 | AACAUCAC U GUUACUUU | 4305 | AAAGUAAC CUGAUGAGgccguuaggccGAA IUGAUGUU | 13645 |
| 753 | ACUGUGAC U UUAAAAAA | 4306 | UUUUUUAA CUGAUGAGgccguuaggccGAA IUAACAGU | 13646 |
| 767 | AAAGUUUC C ACUUGACA | 4307 | UGUCAAGU CUGAUGAGgccguuaggccGAA IAAACUUU | 13647 |
| 768 | AAGUUUCC A CUUGACAC | 4308 | GUGUCAAG CUGAUGAGgccguuaggccGAA IGAAACUU | 13648 |
| 770 | GUUUCCAC U UGACACUU | 4309 | AAGUGUCA CUGAUGAGgccguuaggccGAA IUGGAAAC | 13649 |
| 775 | CACUUGAC A CUUUGAUC | 4310 | GAUCAAAG CUGAUGAGgccguuaggccGAA IUCAAGUG | 13650 |
| 777 | CUUGACAC U UUGAUCCC | 4311 | GGGAUCAA CUGAUGAGgccguuaggccGAA IUGUCAAG | 13651 |
| 784 | CUUUGAUC C CUGAUGGA | 4312 | UCCAUCAG CUGAUGAGgccguuaggccGAA IAUCAAAG | 13652 |
| 785 | UUUGAUCC C UGAUGGAA | 4313 | UUCCAUCA CUGAUGAGgccguuaggccGAA IGAUCAAA | 13653 |
| 786 | UUGAUCCC U GAUGGAAA | 4314 | UUUCCAUC CUGAUGAGgccguuaggccGAA IGGAUCAA | 13654 |
| 799 | GAAAACGC A UAAUCUGG | 4315 | UCAGAUUA CUGAUGAGgccguuaggccGAA ICGUUUUC | 13655 |
| 805 | GCAUAAUC U GGGACAGU | 4316 | ACUGUCCC CUGAUGAGgccguuaggccGAA IAUUAUGC | 13656 |
| 811 | UCGGGAC A GUAGAAAG | 4317 | CUUUCUAC CUGAUGAGgccguuaggccGAA IUCCCAGA | 13657 |
| 823 | GAAAGGGC U UCAUCAUA | 4318 | UAUGAUGA CUGAUGAGgccguuaggccGAA ICCCUUUC | 13658 |
| 826 | AGGGCUUC A UCAUAUCA | 4319 | UGAUAUGA CUGAUGAGgccguuaggccGAA IAAGCCCU | 13659 |
| 829 | GCUUCAUC A UAUCAAAU | 4320 | AUUUGAUA CUGAUGAGgccguuaggccGAA IAUGAAGC | 13660 |
| 834 | AUCAUAUC A AAUGCAAC | 4321 | GUUGCAUU CUGAUGAGgccguuaggccGAA IAUAUGAU | 13661 |
| 840 | UCAAAUGC A ACGUACAA | 4322 | UUGUACGU CUGAUGAGgccguuaggccGAA ICAGUUGA | 13662 |
| 847 | CAACGUAC A AAGAAAUA | 4323 | UAUUUCUU CUGAUGAGgccguuaggccGAA IUAGGUUG | 13663 |
| 860 | AAUAGGGC U UCUGACCU | 4324 | AGGUCAGA CUGAUGAGgccguuaggccGAA ICCCUAUU | 13664 |
| 863 | AGGGCUUC U GACCUGUG | 4325 | CACAGGUC CUGAUGAGgccguuaggccGAA IAAGCCCU | 13665 |
| 867 | CUUCUGAC C UGUGAAGC | 4326 | GCUUCACA CUGAUGAGgccguuaggccGAA IUCAGAAG | 13666 |
| 868 | UUCUGACC U GUGAAGCA | 4327 | UGCUUCAC CUGAUGAGgccguuaggccGAA IGUCAGAA | 13667 |
| 876 | UGUGAAGC A ACAGUCAA | 4328 | UUGACUGU CUGAUGAGgccguuaggccGAA ICUUCACA | 13668 |
| 879 | GAAGCAAC A GUCAAUGG | 4329 | CCAUUGAC CUGAUGAGgccguuaggccGAA IUUGCUUC | 13669 |
| 883 | CAACAGUC A AUGGGCAU | 4330 | AUGCCCAU CUGAUGAGgccguuaggccGAA IACUGUUG | 13670 |
| 890 | CAAUGGGC A UUUGUAUA | 4331 | UAUACAAA CUGAUGAGgccguuaggccGAA ICCCAUUG | 13671 |
| 903 | UAUAAGAC A AACUAUCU | 4332 | AGAUAGUU CUGAUGAGgccguuaggccGAA IUCUUAUA | 13672 |
| 907 | AGACAAAC U AUCUCACA | 4333 | UGUGAGAU CUGAUGAGgccguuaggccGAA IUUUGUCU | 13673 |
| 911 | AAACUAUC U CACACAUC | 4334 | GAUGUGUG CUGAUGAGgccguuaggccGAA IAUAGUUU | 13674 |
| 913 | ACUAUCUC A CACAUCGA | 4335 | UCGAUGUG CUGAUGAGgccguuaggccGAA IAGAUAGU | 13675 |
| 915 | UAUCUCAC A CAUCGACA | 4336 | UGUCGAUG CUGAUGAGgccguuaggccGAA IUGAGAUA | 13676 |
| 917 | UCUCACAC A UCGACAAA | 4337 | UUUGUCGA CUGAUGAGgccguuaggccGAA IUGUGAGA | 13677 |
| 923 | ACAUCGAC A AACCAAUA | 4338 | UAUUGGUU CUGAUGAGgccguuaggccGAA IUCCAUGU | 13678 |
| 927 | CGACAAAC C AAUACAAU | 4339 | AUUGUAUU CUGAUGAGgccguuaggccGAA IUUUGUCG | 13679 |
| 928 | GACAAACC A AUACAAUC | 4340 | GAUUGUAU CUGAUGAGgccguuaggccGAA IGUUUGUC | 13680 |
| 933 | ACCAAUAC A AUCAUAGA | 4341 | UCUAUGAU CUGAUGAGgccguuaggccGAA IAUUGGUU | 13681 |

TABLE XIV-continued

NCH Ribozyme and Target Sequences

| Pos | Target | Seq ID No | NCH Ribozyme | Seq ID No |
|---|---|---|---|---|
| 937 | AUACAAUC A UAGAUGUC | 4342 | GACAUCUA CUGAUGAGGCCGUUAGGCCGAA IAUUGUAU | 13682 |
| 946 | UAGAUGUC C AAAUAAGC | 4343 | GCUUAUUU CUGAUGAGGCCGUUAGGCCGAA IACAUCUA | 13683 |
| 947 | AGAUGUCC A AAUAAGCA | 4344 | UGCUUAUU CUGAUGAGGCCGUUAGGCCGAA IGACAUCU | 13684 |
| 955 | AAAUAAGC A CACCACGC | 4345 | GCGUGGUG CUGAUGAGGCCGUUAGGCCGAA ICUUAUUU | 13685 |
| 957 | AUAAGCAC A CCACGCCC | 4346 | GGGCGUGG CUGAUGAGGCCGUUAGGCCGAA IUGCUUAU | 13686 |
| 959 | AAGCACAC C ACGCCCAG | 4347 | CUGGGCGU CUGAUGAGGCCGUUAGGCCGAA IUGUGCUU | 13687 |
| 960 | AGCACACC A CGCCCAGU | 4348 | ACUGGGCG CUGAUGAGGCCGUUAGGCCGAA IGUGUGCU | 13688 |
| 964 | CACCACGC C CAGUCAAA | 4349 | UUUGACUG CUGAUGAGGCCGUUAGGCCGAA ICGUGGUG | 13689 |
| 965 | ACCACGCC C AGUCAAAU | 4350 | AUUUGACU CUGAUGAGGCCGUUAGGCCGAA ICGUGGU | 13690 |
| 966 | CCACGCCC A GUCAAAUU | 4351 | AAUUUGAC CUGAUGAGGCCGUUAGGCCGAA IGGCGUGG | 13691 |
| 970 | GCCCAGUC A AAUUACUU | 4352 | AAGUAAUU CUGAUGAGGCCGUUAGGCCGAA IACUGGGC | 13692 |
| 977 | CAAAUUAC U UAGAGGCC | 4353 | GGCCUCUA CUGAUGAGGCCGUUAGGCCGAA IUAAUUUG | 13693 |
| 985 | UUAGAGGC C AUACUCUU | 4354 | AAGAGUAU CUGAUGAGGCCGUUAGGCCGAA ICCUCUAA | 13694 |
| 986 | UAGAGGCC A UACUCUUG | 4355 | CAAGAGUA CUGAUGAGGCCGUUAGGCCGAA IGCCUCUA | 13695 |
| 990 | GGCCAUAC U CUUGUCCU | 4356 | AGGACAAG CUGAUGAGGCCGUUAGGCCGAA IUAUGGCC | 13696 |
| 992 | CCAUACUC U UGUCCUCA | 4337 | UGAGGACA CUGAUGAGGCCGUUAGGCCGAA IAGUAUGG | 13697 |
| 997 | CUCUUGUC C UCAAUUGU | 4358 | ACAAUUGA CUGAUGAGGCCGUUAGGCCGAA IACAAGAG | 13698 |
| 998 | UCUUGUCC U CAAUUGUA | 4359 | UACAAUUG CUGAUGAGGCCGUUAGGCCGAA IGACAAGA | 13699 |
| 1000 | UUGUCCUC A AUUGUACU | 4360 | AGUACAAU CUGAUGAGGCCGUUAGGCCGAA IAGGACAA | 13700 |
| 1008 | AAUUGUAC U GCUACCAC | 4361 | GUGGUAGC CUGAUGAGGCCGUUAGGCCGAA IUACAAUU | 13701 |
| 1011 | UGUACUGC U ACCACUCC | 4362 | GGAGUGGU CUGAUGAGGCCGUUAGGCCGAA ICAGUACA | 13702 |
| 1014 | ACUGCUAC C ACUCCCUU | 4363 | AAGGGAGU CUGAUGAGGCCGUUAGGCCGAA IUAGCAGU | 13703 |
| 1015 | CUGCUACC A CUCCCUUG | 4364 | CAAGGGAG CUGAUGAGGCCGUUAGGCCGAA IGUAGCAG | 13704 |
| 1017 | GCUACCAC U CCCUUGAA | 4365 | UUCAAGGG CUGAUGAGGCCGUUAGGCCGAA IUGGUAGC | 13705 |
| 1019 | UACCACUC C CUUGAACA | 4366 | UGUUCAAG CUGAUGAGGCCGUUAGGCCGAA IAGUGGUA | 13706 |
| 1020 | ACCACUCC C UUGAACAC | 4367 | GUGUUCAA CUGAUGAGGCCGUUAGGCCGAA IGAGUGGU | 13707 |
| 1021 | CCACUCCC U UGAACACG | 4368 | CGUGUUCA CUGAUGAGGCCGUUAGGCCGAA IGGAGUGG | 13708 |
| 1027 | CCUUGAAC A CGAGAGUU | 4369 | AACUCUCG CUGAUGAGGCCGUUAGGCCGAA IUUCAAGG | 13709 |
| 1037 | GAGAGUUC A AAUGACCU | 4370 | AGGUCAUU CUGAUGAGGCCGUUAGGCCGAA IAACUCUC | 13710 |
| 1044 | CAAAUGAC C UGGAGUUA | 4371 | UAACUCCA CUGAUGAGGCCGUUAGGCCGAA IUCAUUUG | 13711 |
| 1045 | AAAUGACC U GGAGUUAC | 4372 | GUAACUCC CUGAUGAGGCCGUUAGGCCGAA IGUCAUUU | 13712 |
| 1054 | GGAGUUAC C CUGAUGAA | 4373 | UUCAUCAG CUGAUGAGGCCGUUAGGCCGAA IUAACUCC | 13713 |
| 1055 | GAGUUACC C UGAUGAAA | 4374 | UUUCAUCA CUGAUGAGGCCGUUAGGCCGAA IGUAACUC | 13714 |
| 1056 | AGUUACCC U GAUGAAAA | 4375 | UUUUCAUC CUGAUGAGGCCGUUAGGCCGAA IGGUAACU | 13715 |
| 1077 | AAGAGAGC U UCCGUAAG | 4376 | CUUACGGA CUGAUGAGGCCGUUAGGCCGAA ICUCUCUU | 13716 |
| 1080 | AGAGCUUC C GUAAGGCG | 4377 | CGCCUUAC CUGAUGAGGCCGUUAGGCCGAA IAAGCUCU | 13717 |
| 1099 | GAAUUGAC C AAAGCAAU | 4378 | AUUGCUUU CUGAUGAGGCCGUUAGGCCGAA IUCAAUUC | 13718 |

TABLE XIV-continued

NCH Ribozyme and Target Sequences

| Pos | Target | Seq ID No | NCH Ribozyme | Seq ID No |
|---|---|---|---|---|
| 1100 | AAUUGACC A AAGCAAUU | 4379 | AAUUGCUU CUGAUGAGGCCGUUAGGCCGAA IGUCAAUU | 13719 |
| 1105 | ACCAAAGC A AUUCCCAU | 4380 | AUGGGAAU CUGAUGAGGCCGUUAGGCCGAA ICUUUGGU | 13720 |
| 1110 | AGCAAUUC C CAUGCCAA | 4381 | UUGGCAUG CUGAUGAGGCCGUUAGGCCGAA IAAUUGCU | 13721 |
| 1111 | GCAAUUCC C AUGCCAAC | 4382 | GUUGGCAU CUGAUGAGGCCGUUAGGCCGAA IGAAUUGC | 13722 |
| 1112 | CAAUUCCC A UGCCAACA | 4383 | UGUUGGCA CUGAUGAGGCCGUUAGGCCGAA IGGAAUUG | 13723 |
| 1116 | UCCCAUGC C AACAUAUU | 4384 | AAUAUGUU CUGAUGAGGCCGUUAGGCCGAA ICAUGGGA | 13724 |
| 1117 | CCCAUGCC A ACAUAUUC | 4385 | GAAUAUGU CUGAUGAGGCCGUUAGGCCGAA IGCAUGGG | 13725 |
| 1120 | AUGCCAAC A UAUUCUAC | 4386 | GUAGAAUA CUGAUGAGGCCGUUAGGCCGAA IUUGGCAU | 13726 |
| 1126 | ACAUAUUC U ACAGUGUU | 4387 | AACACUGU CUGAUGAGGCCGUUAGGCCGAA IAAUAUGU | 13727 |
| 1129 | UAUUCUAC A GUGUUCUU | 4388 | AAGAACAC CUGAUGAGGCCGUUAGGCCGAA IUAGAAUA | 13728 |
| 1136 | CAGUGUUC U UACUAUUG | 4389 | CAAUAGUA CUGAUGAGGCCGUUAGGCCGAA IAACACUG | 13729 |
| 1140 | GUUCUUAC U AUUGACAA | 4390 | UUGUCAAU CUGAUGAGGCCGUUAGGCCGAA IUAAGAAC | 13730 |
| 1147 | CUAUUGAC A AAAUGCAG | 4391 | CUGCAUUU CUGAUGAGGCCGUUAGGCCGAA IUCAAUAG | 13731 |
| 1154 | CAAAAUGC A GAACAAAG | 4392 | CUUUGUUC CUGAUGAGGCCGUUAGGCCGAA ICAUUUUG | 13732 |
| 1159 | UGCAGAAC A AAGACAAA | 4393 | UUUGUCUU CUGAUGAGGCCGUUAGGCCGAA IUUCUGCA | 13733 |
| 1165 | ACAAAGAC A AAGGACUU | 4394 | AAGUCCUU CUGAUGAGGCCGUUAGGCCGAA IUCUUUGU | 13734 |
| 1172 | CAAAGGAC U UUAUACUU | 4395 | AAGUAUAA CUGAUGAGGCCGUUAGGCCGAA IUCCUCUG | 13735 |
| 1179 | CUUUAUAC U UGUCGUGU | 4396 | ACACGACA CUGAUGAGGCCGUUAGGCCGAA IUAUAAAG | 13736 |
| 1199 | GAGUGGAC C AUCAUCCA | 4397 | UGAAUGAU CUGAUGAGGCCGUUAGGCCGAA UUCCACUC | 13737 |
| 1200 | AGUGGACC A UCAUCCAA | 4398 | UUGAAUGA CUGAUGAGGCCGUUAGGCCGAA IGUCCACU | 13738 |
| 1203 | GGACCAUC A UUCAAAUC | 4399 | GAUUUGAA CUGAUGAGGCCGUUAGGCCGAA IAUGGUCC | 13739 |
| 1207 | CAUCAUUC A AAUCUGUU | 4400 | AACAGAUU CUGAUGAGGCCGUUAGGCCGAA IAAUGAUG | 13740 |
| 1212 | UUCAAAUC U GUUAACAC | 4401 | GUGUUAAC CUGAUGAGGCCGUUAGGCCGAA IAUUUGAA | 13741 |
| 1219 | CUGUUAAC A CCUCAGUG | 4402 | CACUGAGG CUGAUGAGGCCGUUAGGCCGAA IUUAACAG | 13742 |
| 1221 | GUUAACAC C UCAGUGCA | 4403 | UGCACUGA CUGAUGAGGCCGUUAGGCCGAA IUGUUAAC | 13743 |
| 1222 | UUAACACC U CAGUGCAU | 4404 | AUGCACUG CUGAUGAGGCCGUUAGGCCGAA IGUGUUAA | 13744 |
| 1224 | AACACCUC A GUGCAUAU | 4405 | AUAUGCAC CUGAUGAGGCCGUUAGGCCGAA IAGGUGUU | 13745 |
| 1229 | CUCAGUGC A UAUAUAUG | 4406 | CAUAUAUA CUGAUGAGGCCGUUAGGCCGAA ICACUGAG | 13746 |
| 1245 | GAUAAAGC A UUCAUCAC | 4407 | GUGAUGAA CUGAUGAGGCCGUUAGGCCGAA ICUUUAUC | 13747 |
| 1249 | AAGCAUUC A UCACUGUG | 4408 | CACAGUGA CUGAUGAGGCCGUUAGGCCGAA IAAUGCUU | 13748 |
| 1252 | CAUUCAUC A CUGUGAAA | 4409 | UUUCACAG CUGAUGAGGCCGUUAGGCCGAA IAUGAAUG | 13749 |
| 1254 | UUCAUCAC U GUGAAACA | 4410 | UGUUUCAC CUGAUGAGGCCGUUAGGCCGAA IUGAUGAA | 13750 |
| 1262 | UGUGAAAC A UCGAAAAC | 4411 | GUUUUCGA CUGAUGAGGCCGUUAGGCCGAA IUUUCACA | 13751 |
| 1271 | UCGAAAAC A GCAGGUGC | 4412 | GCACCUGC CUGAUGAGGCCGUUAGGCCGAA IUUUUCGA | 13752 |
| 1274 | AAAACAGC A GGUGCUUG | 4413 | CAAGCACC CUGAUGAGGCCGUUAGGCCGAA ICUGUUUU | 13753 |
| 1280 | GCAGGUGC U UGAAACCG | 4414 | CGGUUUCA CUGAUGAGGCCGUUAGGCCGAA ICACCUGC | 13754 |
| 1287 | CUUGAAAC C GUAGCUGG | 4415 | CCAGCUAC CUGAUGAGGCCGUUAGGCCGAA IUUUCAAG | 13755 |

TABLE XIV-continued

NCH Ribozyme and Target Sequences

| Pos | Target | Seq ID No | NCH Ribozyme | Seq ID No |
|---|---|---|---|---|
| 1293 | ACCGUAGC U GGCAAGCG | 4416 | CGCUUGCC CUGAUGAGGCCGUUAGGCCGAA ICUACGGU | 13756 |
| 1297 | UAGCUGGC A AGCGGUCU | 4417 | AGACCGCU CUGAUGAGGCCGUUAGGCCGAA ICCAGCUA | 13757 |
| 1305 | AAGCGGUC U UACCGGCU | 4418 | AGCCGGUA CUGAUGAGGCCGUUAGGCCGAA IACCGCUU | 13758 |
| 1309 | GGUCUUAC C GGCUCUCU | 4419 | AGAGAGCC CUGAUGAGGCCGUUAGGCCGAA IUAAGACC | 13759 |
| 1313 | UUACCGGC U CUCUAUGA | 4420 | UCAUAGAG CUGAUGAGGCCGUUAGGCCGAA ICCGGUAA | 13760 |
| 1315 | ACCGGCUC U CUAUGAAA | 4421 | UUUCAUAG CUGAUGAGGCCGUUAGGCCGAA IAGCCGGU | 13761 |
| 1317 | CGGCUCUC U AUGAAAGU | 4422 | ACUUUCAU CUGAUGAGGCCGUUAGGCCGAA IAGAGCCG | 13762 |
| 1332 | GUGAAGGC A UUUCCCUC | 4423 | GAGGGAAA CUGAUGAGGCCGUUAGGCCGAA ICCUUCAC | 13763 |
| 1337 | GGCAUUUC C CUCGCCGG | 4424 | CCGGCGAG CUGAUGAGGCCGUUAGGCCGAA IAAAUGCC | 13764 |
| 1338 | GCAUUUCC C UCGCCGGA | 4425 | UCCGGCGA CUGAUGAGGCCGUUAGGCCGAA IGAAAUGC | 13765 |
| 1339 | CAUUUCCC U CGCCGGAA | 4426 | UUCCGGCG CUGAUGAGGCCGUUAGGCCGAA IGCAAAUC | 13766 |
| 1343 | UCCCUCGC C GGAAGUUG | 4427 | CAACUUCC CUGAUGAGGCCGUUAGGCCGAA ICGAGGGA | 13767 |
| 1373 | UGGGUUAC C UGCGACUG | 4428 | CAGUCGCA CUGAUGAGGCCGUUAGGCCGAA IUAACCCA | 13768 |
| 1374 | GGGUUACC U GCGACUGA | 4429 | UCAGUCGC CUGAUGAGGCCGUUAGGCCGAA IGUAACCC | 13769 |
| 1380 | CCUGCGAC U GAGAAAUC | 4430 | GAUUUCUC CUGAUGAGGCCGUUAGGCCGAA ICGCAGG | 13770 |
| 1389 | GAGAAAUC U GCUCGCUA | 4431 | UAGCGAGC CUGAUGAGGCCGUUAGGCCGAA IAUUUCUC | 13771 |
| 1392 | AAAUCUGC U CGCUAUUU | 4432 | AAAUAGCG CUGAUGAGGCCGUUAGGCCGAA ICAGAUUU | 13772 |
| 1396 | CUGCUCGC U AUUUGACU | 4433 | AGUCAAAU CUGAUGAGGCCGUUAGGCCGAA ICGAGCAG | 13773 |
| 1404 | UAUUUGAC U CGUGGCUA | 4434 | UAGCCACG CUGAUGAGGCCGUUAGGCCGAA IUCAAAUA | 13774 |
| 1411 | CUCGUGGC U ACUCGUUA | 4435 | UAACGAGU CUGAUGAGGCCGUUAGGCCGAA ICCACGAG | 13775 |
| 1414 | GUGGCUAC U CGUUAAUU | 4436 | AAUUAACG CUGAUGAGGCCGUUAGGCCGAA IUAGCCAC | 13776 |
| 1426 | UAAUUAUC A AGGACGUA | 4437 | UACGUCCU CUGAUGAGGCCGUUAGGCCGAA IAUAAUUA | 13777 |
| 1437 | GACGUAAC U GAAGAGGA | 4438 | UCCUCUUC CUGAUGAGGCCGUUAGGCCGAA IUUACGUC | 13778 |
| 1449 | GAGGAUGC A GGGAAUUA | 4439 | UAAUUCCC CUGAUGAGGCCGUUAGGCCGAA ICAUCCUC | 13779 |
| 1461 | AAUUAUAC A AUCUUGCU | 4440 | AGCAAGAU CUGAUGAGGCCGUUAGGCCGAA IUAUAAUU | 13780 |
| 1465 | AUACAAUC U UGCUGAGC | 4441 | GCUCAGCA CUGAUGAGGCCGUUAGGCCGAA IAUUGUAU | 13781 |
| 1469 | AAUCUUGC U GAGCAUAA | 4442 | UUAUGCUC CUGAUGAGGCCGUUAGGCCGAA ICAAGAUU | 13782 |
| 1474 | UGCUGAGC A UAAAACAG | 4443 | CUGUUUUA CUGAUGAGGCCGUUAGGCCGAA ICUCAGCA | 13783 |
| 1481 | CAUAAAAC A GUCAAAUG | 4444 | CAUUUGAC CUGAUGAGGCCGUUAGGCCGAA IUUUUAUG | 13784 |
| 1485 | AAACAGUC A AAUGUGUU | 4445 | AACACAUU CUGAUGAGGCCGUUAGGCCGAA IACUGUUU | 13785 |
| 1501 | UUAAAAAC C UCACUGCC | 4446 | GGCAGUGA CUGAUGAGGCCGUUAGGCCGAA IUUUUUAA | 13786 |
| 1502 | UAAAAACC U CACUGCCA | 4447 | UGGCAGUG CUGAUGAGGCCGUUAGGCCGAA IGUUUUUA | 13787 |
| 1504 | AAAACCUC A CUGCCACU | 4448 | AGUGGCAG CUGAUGAGGCCGUUAGGCCGAA IAGGUUUU | 13788 |
| 1506 | AACCUCAC U GCCACUCU | 4449 | AGAGUGGC CUGAUGAGGCCGUUAGGCCGAA IUGAGGUU | 13789 |
| 1509 | CUCACUGC C ACUCUAAU | 4450 | AUUAGAGU CUGAUGAGGCCGUUAGGCCGAA ICAGUGAG | 13790 |
| 1510 | UCACUGCC A CUCUAAUU | 4451 | AAUUAGAG CUGAUGAGGCCGUUAGGCCGAA IGCAGUGA | 13791 |
| 1512 | ACUGCCAC U CUAAUUGU | 4452 | ACAAUUAG CUGAUGAGGCCGUUAGGCCGAA IUGGCAGU | 13792 |

TABLE XIV-continued

NCH Ribozyme and Target Sequences

| Pos | Target | Seq ID No | NCH Ribozyme | Seq ID No |
|-----|--------|-----------|--------------|-----------|
| 1514 | UGCCACUC U AAUUGUCA | 4453 | UGACAAUU CUGAUGAGGCCGUUAGGCCGAA IAGUGGCA | 13793 |
| 1522 | UAAUUGUC A AUGUGAAA | 4454 | UUUCACAU CUGAUGAGGCCGUUAGGCCGAA IACAAUUA | 13794 |
| 1532 | UGUGAAAC C CCAGAUUU | 4455 | AAAUCUGG CUGAUGAGGCCGUUAGGCCGAA IUUUCACA | 13795 |
| 1533 | GUGAAACC C CAGAUUUA | 4456 | UAAAUCUG CUGAUGAGGCCGUUAGGCCGAA IGUUUCAC | 13796 |
| 1534 | UGAAACCC C AGAUUUAC | 4457 | GUAAAUCU CUGAUGAGGCCGUUAGGCCGAA IGGUUUCA | 13797 |
| 1535 | GAAACCCC A GAUUUACG | 4458 | CGUAAAUC CUGAUGAGGCCGUUAGGCCGAA IGGGUUUC | 13798 |
| 1551 | GAAAAGGC C GUGUCAUC | 4459 | GAUGACAC CUGAUGAGGCCGUUAGGCCGAA ICCUUUUC | 13799 |
| 1557 | GCCGUGUC A UCGUUUCC | 4460 | GGAAACGA CUGAUGAGGCCGUUAGGCCGAA IACACGGC | 13800 |
| 1565 | AUCGUUUC C AGACCCGG | 4461 | CCGGGUCU CUGAUGAGGCCGUUAGGCCGAA IAAACGAU | 13801 |
| 1566 | UCGUUUCC A GACCCGGC | 4462 | GCCGGGUC CUGAUGAGGCCGUUAGGCCGAA IGAAACGA | 13802 |
| 1570 | UUCCAGAC C CGGCUCUC | 4463 | GAGAGCCG CUGAUGAGGCCGUUAGGCCGAA IUCUGGAA | 13803 |
| 1571 | UCCAGACC C GGCUCUCU | 4464 | AGAGAGCC CUGAUGAGGCCGUUAGGCCGAA IGUCUGGA | 13804 |
| 1575 | GACCCGGC U CUCUACCC | 4465 | GGGUAGAG CUGAUGAGGCCGUUAGGCCGAA ICCGGGUC | 13805 |
| 1577 | CCCGGCUC U CUACCCAC | 4466 | GUGGGUAG CUGAUGAGGCCGUUAGGCCGAA IAGCCGGG | 13806 |
| 1579 | CGGCUCUC U ACCCACUG | 4467 | CAGUGGGU CUGAUGAGGCCGUUAGGCCGAA IAGAGCCG | 13807 |
| 1582 | CUCUCUAC C CACUGGGC | 4468 | GCCCAGUG CUGAUGAGGCCGUUAGGCCGAA IUAGAGAG | 13808 |
| 1583 | UCUCUACC C ACUGGGCA | 4469 | UGCCCAGU CUGAUGAGGCCGUUAGGCCGAA IGUAGAGA | 13809 |
| 1584 | CUCUACCC A CUGGGCAG | 4470 | CUGCCCAG CUGAUGAGGCCGUUAGGCCGAA IGGUAGAG | 13810 |
| 1586 | CUACCCAC U GGGCAGCA | 4471 | UGCUGCCC CUGAUGAGGCCGUUAGGCCGAA IUGGGUAG | 13811 |
| 1591 | CACUGGGC A GCAGACAA | 4472 | UUGUCUGC CUGAUGAGGCCGUUAGGCCGAA ICCCAGUG | 13812 |
| 1594 | UGGGCAGC A GACAAAUC | 4473 | GAUUUGUC CUGAUGAGGCCGUUAGGCCGAA ICUGCCCA | 13813 |
| 1598 | CAGCAGAC A AAUCCUGA | 4474 | UCAGGAUU CUGAUGAGGCCGUUAGGCCGAA IUCUGCUG | 13814 |
| 1603 | GACAAAUC C UGACUUGU | 4475 | ACAAGUCA CUGAUGAGGCCGUUAGGCCGAA IAUUUGUC | 13815 |
| 1604 | ACAAAUCC U GACUUGUA | 4476 | UACAAGUC CUGAUGAGGCCGUUAGGCCGAA IGAUUUGU | 13816 |
| 1608 | AUCCUGAC U UGUACCGC | 4477 | GCGGUACA CUGAUGAGGCCGUUAGGCCGAA IUCAGGAU | 13817 |
| 1614 | ACUUGUAC C GCAUAUGG | 4478 | CCAUAUGC CUGAUGAGGCCGUUAGGCCGAA IUACAAGU | 13818 |
| 1617 | UGUACCGC A UAUGGUAU | 4479 | AUACCAUA CUGAUGAGGCCGUUAGGCCGAA ICGGUACA | 13819 |
| 1627 | AUGGUAUC C CUCAACCU | 4480 | AGGUUGAG CUGAUGAGGCCGUUAGGCCGAA IAUACCAU | 13820 |
| 1628 | UGGUAUCC C UCAACCUA | 4481 | UAGGUUGA CUGAUGAGGCCGUUAGGCCGAA IGAUACCA | 13821 |
| 1629 | GGUAUCCC U CAACCUAC | 4482 | GUAGGUUG CUGAUGAGGCCGUUAGGCCGAA IGGAUACC | 13822 |
| 1631 | UAUCCCUC A ACCUACAA | 4483 | UUGUAGGU CUGAUGAGGCCGUUAGGCCGAA IAGGGAUA | 13823 |
| 1634 | CCCUCAAC C UACAAUCA | 4484 | UGAUUGUA CUGAUGAGGCCGUUAGGCCGAA IUUGAGGG | 13824 |
| 1635 | CCUCAACC U ACAAUCAA | 4485 | UUGAUUGU CUGAUGAGGCCGUUAGGCCGAA IGUUGAGG | 13825 |
| 1638 | CAACCUAC A AUCAAGUG | 4486 | CACUUGAU CUGAUGAGGCCGUUAGGCCGAA IUAGGUUG | 13826 |
| 1642 | CUACAAUC A AGUGGUUC | 4487 | GAACCACU CUGAUGAGGCCGUUAGGCCGAA IAUUGUAG | 13827 |
| 1651 | AGUGGUUC U GGCACCCC | 4488 | GGGGUGCC CUGAUGAGGCCGUUAGGCCGAA IAACCACU | 13828 |
| 1655 | GUUCUGGC A CCCCUGUA | 4489 | UACAGGGG CUGAUGAGGCCGUUAGGCCGAA ICCAGAAC | 13829 |

TABLE XIV-continued

NCH Ribozyme and Target Sequences

| Pos | Target | Seq ID No | NCH Ribozyme | Seq ID No |
|---|---|---|---|---|
| 1657 | UCUGGCAC C CCUGUAAC | 4490 | GUUACAGG CUGAUGAGGCCGUUAGGCCGAA IUGCCAGA | 13830 |
| 1658 | CUGGCACC C CUGUAACC | 4491 | GGUUACAG CUGAUGAGGCCGUUAGGCCGAA IGUGCCAG | 13831 |
| 1659 | UGGCACCC C UGUAACCA | 4492 | UGGUUACA CUGAUGAGGCCGUUAGGCCGAA IGGUGCCA | 13832 |
| 1660 | GGCACCCC U GUAACCAU | 4493 | AUGGUUAC CUGAUGAGGCCGUUAGGCCGAA IGGGUGCC | 13833 |
| 1666 | CCUGUAAC C AUAAUCAU | 4494 | AUGAUUAU CUGAUGAGGCCGUUAGGCCGAA IUUACAGG | 13834 |
| 1667 | CUGUAACC A UAAUCAUU | 4495 | AAUGAUUA CUGAUGAGGCCGUUAGGCCGAA IGUUACAG | 13835 |
| 1673 | CCAUAAUC A UUCCGAAG | 4496 | CUUCGGAA CUGAUGAGGCCGUUAGGCCGAA IAUUAUGG | 13836 |
| 1677 | AAUCAUUC C GAAGCAAG | 4497 | CUUGCUUC CUGAUGAGGCCGUUAGGCCGAA IAAUGAUU | 13837 |
| 1683 | UCCGAAGC A AGGUGUGA | 4498 | UCACACCU CUGAUGAGGCCGUUAGGCCGAA ICUUCGGA | 13838 |
| 1693 | GGUGUGAC U UUEUUUCC | 4499 | GGAACAAA CUGAUGAGGCCGUUAGGCCGAA IUCACACC | 13839 |
| 1701 | UUUUGUUC C AAUAAUGA | 4500 | UCAUUAUU CUGAUGAGGCCGUUAGGCCGAA IAACAAAA | 13840 |
| 1702 | UUUGUUCC A AUAAUGAA | 4501 | UUCAUUAU CUGAUGAGGCCGUUAGGCCGAA IGAACAAA | 13841 |
| 1716 | GAAGAGUC C UUUAUCCU | 4502 | AGGAUAAA CUGAUGAGGCCGUUAGGCCGAA IACUCUUC | 13842 |
| 1717 | AAGAGUCC U UUAUCCUG | 4503 | CAGGAUAA CUGAUGAGGCCGUUAGGCCGAA IGACUCUU | 13843 |
| 1723 | CCUUUAUC C UGGAUGCU | 4504 | AGCAUCCA CUGAUGAGGCCGUUAGGCCGAA IAUAAAGG | 13844 |
| 1724 | CUUUAUCC U GGAUGCUG | 4505 | CAGCAUCC CUGAUGAGGCCGUUAGGCCGAA IGAUAAAG | 13845 |
| 1731 | CUGGAUGC U GACAGCAA | 4506 | UUGCUGUC CUGAUGAGGCCGUUAGGCCGAA ICAUCCAG | 13846 |
| 1735 | AUGCUGAC A GCAACAUG | 4507 | CAUGUUGC CUGAUGAGGCCGUUAGGCCGAA IUCAGCAU | 13847 |
| 1738 | CUGACAGC A ACAUGGGA | 4508 | UCCCAUGU CUGAUGAGGCCGUUAGGCCGAA ICUGUCAG | 13848 |
| 1741 | ACAGCAAC A UGGGAAAC | 4509 | GUUUCCCA CUGAUGAGGCCGUUAGGCCGAA IUUGCUGU | 13849 |
| 1750 | UGGGAAAC A GAAUUGAG | 4510 | CUCAAUUC CUGAUGAGGCCGUUAGGCCGAA IUUUCCCA | 13850 |
| 1762 | UUGAGAGC A UCACUCAG | 4511 | CUGAGUGA CUGAUGAGGCCGUUAGGCCGAA ICUCUCAA | 13851 |
| 1765 | AGAGCAUC A CUCAGCGC | 4512 | GCGCUGAG CUGAUGAGGCCGUUAGGCCGAA IAUGCUCU | 13852 |
| 1767 | AGGAUCAC U CAGCGCAU | 4513 | AUGCGCUG CUGAUGAGGCCGUUAGGCCGAA IUGAUGCU | 13853 |
| 1769 | CAUCACUC A GCGCAUGG | 4514 | CCAUGCGC CUGAUGAGGCCGUUAGGCCGAA IAGUGAUG | 13854 |
| 1774 | CUCAGCGC A UGGCAAUA | 4515 | UAUUGCCA CUGAUGAGGCCGUUAGGCCGAA ICGCUGAG | 13855 |
| 1779 | CGCAUGGC A AUAAUAGA | 4516 | UCUAUUAU CUGAUGAGGCCGUUAGGCCGAA ICCAUGCG | 13856 |
| 1806 | AAGAUGGU U AGCACCUU | 4517 | AAGGUGCU CUGAUGAGGCCGUUAGGCCGAA ICCAUCUU | 13857 |
| 1810 | UGGCUAGC A CCUUGGUU | 4518 | AACCAAGG CUGAUGAGGCCGUUAGGCCGAA ICUAGCCA | 13858 |
| 1812 | GCUAGCAC C UUGGUUGU | 4519 | ACAACCAA CUGAUGAGGCCGUUAGGCCGAA IUGCUAGC | 13859 |
| 1813 | CUAGCACC U UGGUUGUG | 4520 | CACAACCA CUGAUGAGGCCGUUAGGCCGAA IGUGCUAG | 13860 |
| 1824 | GUUGUGGC U GACUCUAG | 4521 | CUAGAGUC CUGAUGAGGCCGUUAGGCCGAA ICCACAAC | 13861 |
| 1828 | UGGCUGAC U CUAGAAUU | 4522 | AAUUCUAG CUGAUGAGGCCGUUAGGCCGAA IUCAGCCA | 13862 |
| 1830 | GCUGACUC U AGAAUUUC | 4523 | GAAAUUCU CUGAUGAGGCCGUUAGGCCGAA IAGUCAGC | 13863 |
| 1839 | AGAAUUUC U GGAAUCUA | 4524 | UAGAUUCC CUGAUGAGGCCGUUAGGCCGAA IAAAUUCU | 13864 |
| 1846 | CUGGAAUC U ACAUUUGC | 4525 | GCAAAUGU CUGAUGAGGCCGUUAGGCCGAA IAUUCCAG | 13865 |
| 1849 | GAAUCUAC A UUUGCAUA | 4526 | UAUGCAAA CUGAUGAGGCCGUUAGGCCGAA IUAGAUUC | 13866 |

TABLE XIV-continued

NCH Ribozyme and Target Sequences

| Pos | Target | Seq ID No | NCH Ribozyme | Seq ID No |
|---|---|---|---|---|
| 1855 | ACAUUUGC A UAGCUUCC | 4527 | GGAAGCUA CUGAUGAGGCCGUUAGGCCGAA ICAAAUGU | 13867 |
| 1860 | UGCAUAGC U UCCAAUAA | 4528 | UUAUUGGA CUGAUGAGGCCGUUAGGCCGAA ICUAUGCA | 13868 |
| 1863 | AUAGCUUC C AAUAAAGU | 4529 | ACUUUAUU CUGAUGAGGCCGUUAGGCCGAA IAAGCUAU | 13869 |
| 1864 | UAGCUUCC A AUAAAGUU | 4530 | AACUUUAU CUGAUGAGGCCGUUAGGCCGAA IGAAGCUA | 13870 |
| 1878 | GUUGGGAC U GUGGGAAG | 4531 | CUUCCCAC CUGAUGAGGCCGUUAGGCCGAA IUCCCAAC | 13871 |
| 1891 | GAAGAAAC A UAAGCUUU | 4532 | AAAGCUUA CUGAUGAGGCCGUUAGGCCGAA IUUUCUUC | 13872 |
| 1897 | ACAUAAGC U UUUAUAUC | 4533 | GAUAUAAA CUGAUGAGGCCGUUAGGCCGAA ICUUAUGU | 13873 |
| 1906 | UUUAUAUC A CAGAUGUG | 4534 | CACAUCUG CUGAUGAGGCCGUUAGGCCGAA IAUAUAAA | 13874 |
| 1908 | UAUAUCAC A GAUGUGCC | 4535 | GGCACAUC CUGAUGAGGCCGUUAGGCCGAA IUGAUAUA | 13875 |
| 1916 | AGAUGUGC C AAAUGGGU | 4536 | ACCCAUUU CUGAUGAGGCCGUUAGGCCGAA ICACAUCU | 13876 |
| 1917 | GAUGUGCC A AAUGGGUU | 4537 | AACCCAUU CUGAUGAGGCCGUUAGGCCGAA IGCACAUC | 13877 |
| 1928 | UGGGUUUC A UGUUAACU | 4538 | AGUUAACA CUGAUGAGGCCGUUAGGCCGAA IAAACCCA | 13878 |
| 1936 | AUGUUAAC U UGGAAAAA | 4539 | UUUUUCCA CUGAUGAGGCCGUUAGGCCGAA IUUAACAU | 13879 |
| 1949 | AAAAUGC C GACGGAAG | 4540 | CUUCCGUC CUGAUGAGGCCGUUAGGCCGAA ICAUUUUU | 13880 |
| 1966 | GAGAGGAC C UGAAACUG | 4541 | CAGUUUCA CUGAUGAGGCCGUUAGGCCGAA IUCCUCUC | 13881 |
| 1967 | AGAGGACC U GAAACUGU | 4542 | ACAGUUUC CUGAUGAGGCCGUUAGGCCGAA IGUCCUCU | 13882 |
| 1973 | CCUGAAAC U GUCUUGCA | 4543 | UGCAAGAC CUGAUGAGGCCGUUAGGCCGAA IUUUCAGG | 13883 |
| 1977 | AAACUGUC U UGCACAGU | 4544 | ACUGUGCA CUGAUGAGGCCGUUAGGCCGAA IACAGUUU | 13884 |
| 1981 | UGUCUUGC A CAGUUAAC | 4545 | GUUAACUG CUGAUGAGGCCGUUAGGCCGAA ICAAGACA | 13885 |
| 1983 | UCUUGCAC A GUUAACAA | 4546 | UUGUUAAC CUGAUGAGGCCGUUAGGCCGAA IUGCAAGA | 13886 |
| 1990 | CAGUUAAC A AGUUCUUA | 4547 | UAAGAACU CUGAUGAGGCCGUUAGGCCGAA IUUAACUG | 13887 |
| 1996 | ACAAGUUC U UAUACAGA | 4548 | UCUGUAUA CUGAUGAGGCCGUUAGGCCGAA IAACUUGU | 13888 |
| 2002 | UCUUAUAC A GAGACGUU | 4549 | AACGUCUC CUGAUGAGGCCGUUAGGCCGAA IUAUAAGA | 13889 |
| 2013 | GACGUUAC U UGGAUUUU | 4550 | AAAAUCCA CUGAUGAGGCCGUUAGGCCGAA IUAACGUC | 13890 |
| 2024 | GAUUUUAC U GCGGACAG | 4551 | CUGUCCGC CUGAUGAGGCCGUUAGGCCGAA IUAAAAUC | 13891 |
| 2031 | CUGCGGAC A GUUAAUAA | 4552 | UUAUUAAC CUGAUGAGGCCGUUAGGCCGAA IUCCGCAG | 13892 |
| 2041 | UUAAUAAC A GAACAAUG | 4553 | CAUUGUUC CUGAUGAGGCCGUUAGGCCGAA IUUAUUAA | 13893 |
| 2046 | AACAGAAC A AUGCACUA | 4554 | UAGUGCAU CUGAUGAGGCCGUUAGGCCGAA IUUCUGUU | 13894 |
| 2051 | AACAAUGC A CUACAGUA | 4555 | UACUGUAG CUGAUGAGGCCGUUAGGCCGAA ICAUUGUU | 13895 |
| 2053 | CAAUGCAC U ACAGUAUU | 4556 | AAUACUGU CUGAUGAGGCCGUUAGGCCGAA IUGCAUUG | 13896 |
| 2056 | UGCACUAC A GUAUUAGC | 4557 | GCUAAUAC CUGAUGAGGCCGUUAGGCCGAA IUAGUGCA | 13897 |
| 2065 | GUAUUAGC A AGCAAAAA | 4558 | UUUUUGCU CUGAUGAGGCCGUUAGGCCGAA ICUAAUAC | 13898 |
| 2069 | UAGCAAGC A AAAAUGG | 4559 | CCAUUUUU CUGAUGAGGCCGUUAGGCCGAA ICUUGCUA | 13899 |
| 2079 | AAAAUGGC C AUCACUAA | 4560 | UUAGUGAU CUGAUGAGGCCGUUAGGCCGAA ICCAUUUU | 13900 |
| 2080 | AAAUGGCC A UCACUAAG | 4561 | CUUAGUGA CUGAUGAGGCCGUUAGGCCGAA IGCCAUUU | 13901 |
| 2083 | UGGCCAUC A CUAAGGAG | 4562 | CUCCUUAG CUGAUGAGGCCGUUAGGCCGAA IAUGGCCA | 13902 |
| 2085 | GCCAUCAC U AAGGAGCA | 4563 | UGCUCCUU CUGAUGAGGCCGUUAGGCCGAA IUGAUGGC | 13903 |

TABLE XIV-continued

NCH Ribozyme and Target Sequences

| Pos | Target | Seq ID No | NCH Ribozyme | Seq ID No |
|---|---|---|---|---|
| 2093 | UAAGGAGC A CUCCAUCA | 4564 | UGAUGGAG CUGAUGAGGCCGUUAGGCCGAA ICUCCUUA | 13904 |
| 2095 | AGGAGCAC U CCAUCACU | 4565 | AGUGAUGG CUGAUGAGGCCGUUAGGCCGAA IUGCUCCU | 13905 |
| 2097 | GAGCACUC C AUCACUCU | 4566 | AGAGUGAU CUGAUGAGGCCGUUAGGCCGAA IAGUGCUC | 13906 |
| 2098 | AGCACUCC A UCACUCUU | 4567 | AAGAGUGA CUGAUGAGGCCGUUAGGCCGAA IGAGUGCU | 13907 |
| 2101 | ACUCCAUC A CUCUUAAU | 4568 | AUUAAGAG CUGAUGAGGCCGUUAGGCCGAA IAUGGAGU | 13908 |
| 2103 | UCCAUCAC U CUUAAUCU | 4569 | AGAUUAAG CUGAUGAGGCCGUUAGGCCGAA IUGAUGGA | 13909 |
| 2105 | CAUCACUC U UAAUCUUA | 4570 | UAAGAUUA CUGAUGAGGCCGUUAGGCCGAA IAGUGAUG | 13910 |
| 2111 | UCUUAAUC U UACCAUCA | 4571 | UGAUGGUA CUGAUGAGGCCGUUAGGCCGAA IAUUAAGA | 13911 |
| 2115 | AAUCUUAC C AUCAUGAA | 4572 | UUCAUGAU CUGAUGAGGCCGUUAGGCCGAA IUAAGAUU | 13912 |
| 2116 | AUCUUACC A UCAUGAAU | 4573 | AUUCAUGA CUGAUGAGGCCGUUAGGCCGAA IGUAAGAU | 13913 |
| 2119 | UUACCAUC A UGAAUGUU | 4574 | AACAUUCA CUGAUGAGGCCGUUAGGCCGAA IAUGGUAA | 13914 |
| 2130 | AAUGUUUC C CUGCAAGA | 4575 | UCUUGCAG CUGAUGAGGCCGUUAGGCCGAA IAAACAUU | 13915 |
| 2131 | AUGUUUCC C UGCAAGAU | 4576 | AUCUUGCA CUGAUGAGGCCGUUAGGCCGAA IGAAACAU | 13916 |
| 2132 | UGUUUCCC U GCAAGAUU | 4577 | AAUCUUGC CUGAUGAGGCCGUUAGGCCGAA IGGAAACA | 13917 |
| 2135 | UUCCCUGC A AGAUUCAG | 4578 | CUGAAUCU CUGAUGAGGCCGUUAGGCCGAA ICAGGGAA | 13918 |
| 2142 | CAAGAUUC A GGCACCUA | 4579 | UAGGUGCC CUGAUGAGGCCGUUAGGCCGAA IAAUCUUG | 13919 |
| 2146 | AUUCAGGC A CCUAUGCC | 4580 | GGCAUAGG CUGAUGAGGCCGUUAGGCCGAA ICCUGAAU | 13920 |
| 2148 | UCAGGCAC C UAUGCCUG | 4581 | CAGGCAUA CUGAUGAGGCCGUUAGGCCGAA IUGCCUGA | 13921 |
| 2149 | CAGGCACC U AUGCCUGC | 4582 | GCAGGCAU CUGAUGAGGCCGUUAGGCCGAA IGUGCCUG | 13922 |
| 2154 | ACCUAUGC C UGCAGAGC | 4583 | GCUCUGCA CUGAUGAGGCCGUUAGGCCGAA ICAUAGGU | 13923 |
| 2155 | CCUAUGCC U GCAGAGCC | 4584 | GGCUCUGC CUGAUGAGGCCGUUAGGCCGAA IGCAUAGG | 13924 |
| 2158 | AUGCCUGC A GAGCCAGG | 4585 | CCUGGCUC CUGAUGAGGCCGUUAGGCCGAA ICAGGCAU | 13925 |
| 2163 | UGCAGAGC C AGGAAUGU | 4586 | ACAUUCCU CUGAUGAGGCCGUUAGGCCGAA ICUCUGCA | 13926 |
| 2164 | GCAGAGCC A GGAAUGUA | 4587 | UACAUUCC CUGAUGAGGCCGUUAGGCCGAA IGCUCUGC | 13927 |
| 2176 | AUGUAUAC A CAGGGGAA | 4588 | UUCCCCUG CUGAUGAGGCCGUUAGGCCGAA IUAUACAU | 13928 |
| 2178 | GUAUACAC A GGGGAAGA | 4589 | UCUUCCCC CUGAUGAGGCCGUUAGGCCGAA IUGUAUAC | 13929 |
| 2191 | AAGAAAUC C UCCAGAAG | 4590 | CUUCUGGA CUGAUGAGGCCGUUAGGCCGAA IAUUUCUU | 13930 |
| 2192 | AGAAAUCC U CCAGAAGA | 4591 | UCUUCUGG CUGAUGAGGCCGUUAGGCCGAA IGAUUUCU | 13931 |
| 2194 | AAAUCCUC C AGAAGAAA | 4592 | UUUCUUCU CUGAUGAGGCCGUUAGGCCGAA IAGGAUUU | 13932 |
| 2195 | AAUCCUCC A GAAGAAAG | 4593 | CUUUCUUC CUGAUGAGGCCGUUAGGCCGAA IGAGGAUU | 13933 |
| 2211 | GAAAUUAC A AUCAGAGA | 4594 | UCUCUGAU CUGAUGAGGCCGUUAGGCCGAA IUAAUUUC | 13934 |
| 2215 | UUACAAUC A GAGAUCAG | 4595 | CUGAUCUC CUGAUGAGGCCGUUAGGCCGAA IAUUGUAA | 13935 |
| 2222 | CAGAGAUC A GGAAGCAC | 4596 | GUGCUUCC CUGAUGAGGCCGUUAGGCCGAA IAUCUCUG | 13936 |
| 2229 | CAGGAAGC A CCAUACCU | 4597 | AGGUAUGG CUGAUGAGGCCGUUAGGCCGAA ICUUCCUG | 13937 |
| 2231 | GGAAGCAC C AUACCUCC | 4598 | GGAGGUAU CUGAUGAGGCCGUUAGGCCGAA IUGCUUCC | 13938 |
| 2232 | GAAGCACC A UACCUCCU | 4599 | AGGAGGUA CUGAUGAGGCCGUUAGGCCGAA IGUGCUUC | 13939 |
| 2236 | CACCAUAC C UCCUGCGA | 4600 | UCGCAGGA CUGAUGAGGCCGUUAGGCCGAA IUAUGGUG | 13940 |

TABLE XIV-continued

NCH Ribozyme and Target Sequences

| Pos | Target | Seq ID No | NCH Ribozyme | Seq ID No |
|---|---|---|---|---|
| 2237 | ACCAUACC U CCUGCGAA | 4601 | UUCGCAGG CUGAUGAGGCCGUUAGGCCGAA IGUAUGGU | 13941 |
| 2239 | CAUACCUC C UGCGAAAC | 4602 | GUUUCGCA CUGAUGAGGCCGUUAGGCCGAA IAGGUAUG | 13942 |
| 2240 | AUACCUCC U GCGAAACC | 4603 | GGUUUCGC CUGAUGAGGCCGUUAGGCCGAA IGAGGUAU | 13943 |
| 2248 | UGCGAAAC C UCAGUGAU | 4604 | AUCACUGA CUGAUGAGGCCGUUAGGCCGAA IUUUCGCA | 13944 |
| 2249 | GCGAAACC U CAGUGAUC | 4605 | GAUCACUG CUGAUGAGGCCGUUAGGCCGAA IGUUUCGC | 13945 |
| 2251 | GAAACCUC A GUGAUCAC | 4606 | GUGAUCAC CUGAUGAGGCCGUUAGGCCGAA IAGGUUUC | 13946 |
| 2258 | CAGUGAUC A CACAGUGG | 4607 | CCACUGUG CUGAUGAGGCCGUUAGGCCGAA IAUCACUG | 13947 |
| 2260 | GUGAUCAC A CACUGGCC | 4608 | GGCCACUG CUGAUGAGGCCGUUAGGCCGAA IGAUCAC | 13948 |
| 2262 | GAUCACAC A GUGGCCAU | 4609 | AUGGCCAC CUGAUGAGGCCGUUAGGCCGAA IGUGAUC | 13949 |
| 2268 | ACAGUGGC C AUCAGCAG | 4610 | CUGCUGAU CUGAUGAGGCCGUUAGGCCGAA ICCACUGU | 13950 |
| 2269 | CAGUGGCC A UCAGCAGU | 4611 | ACUGCUGA CUGAUGAGGCCGUUAGGCCGAA IGCCACUG | 13951 |
| 2272 | UGGCCAUC A GCAGUUCC | 4612 | GGAACUGC CUGAUGAGGCCGUUAGGCCGAA IAUGGCCA | 13952 |
| 2275 | CCAUCAGC A GUUCCACC | 4613 | GGUGGAAC CUGAUGAGGCCGUUAGGCCGAA ICUGAUGG | 13953 |
| 2280 | AGCAGUUC C ACCACUUU | 4614 | AAAGUGGU CUGAUGAGGCCGUUAGGCCGAA IAACUGCU | 13954 |
| 2281 | GCAGUUCC A CCACUUUA | 4615 | UAAAGUGG CUGAUGAGGCCGUUAGGCCGAA IGAACUGC | 13955 |
| 2283 | AGUUCCAC C ACUUUAGA | 4616 | UCUAAAGU CUGAUGAGGCCGUUAGGCCGAA IUGGAACU | 13956 |
| 2284 | GUUCCACC A CUUUAGAC | 4617 | GUCUAAAG CUGAUGAGGCCGUUAGGCCGAA IGUGGAAC | 13957 |
| 2286 | UCCACCAC U UUAGACUG | 4618 | CAGUCUAA CUGAUGAGGCCGUUAGGCCGAA IUGGUGGA | 13958 |
| 2293 | CUUUAGAC U GUCAUGCU | 4619 | AGCAUGAC CUGAUGAGGCCGUUAGGCCGAA IUCUAAAG | 13959 |
| 2297 | AGACUGUC A UGCUAAUG | 4620 | CAUUAGCA CUGAUGAGGCCGUUAGGCCGAA IACAGUCU | 13960 |
| 2301 | UGUCAUGC U AAUGGUGU | 4621 | ACACCAUU CUGAUGAGGCCGUUAGGCCGAA ICAUGACA | 13961 |
| 2311 | AUGGUGUC C CCGAGCCU | 4622 | AGGCUCGG CUGAUGAGGCCGUUAGGCCGAA IACACCAU | 13962 |
| 2312 | UGGUGUCC C CGAGCCUC | 4623 | GAGGCUCG CUGAUGAGGCCGUUAGGCCGAA IGACACCA | 13963 |
| 2313 | GGUGUCCC C GAGCCUCA | 4624 | UGAGGCUC CUGAUGAGGCCGUUAGGCCGAA IGGACACC | 13964 |
| 2318 | CCCCGAGC C UCAGAUCA | 4625 | UGAUCUGA CUGAUGAGGCCGUUAGGCCGAA ICUCGGGG | 13965 |
| 2319 | CCCGAGCC U CAGAUCAC | 4626 | GUGAUCUG CUGAUGAGGCCGUUAGGCCGAA IGCUCGGG | 13966 |
| 2321 | CGAGCCUC A GAUCACUU | 4627 | AAGUGAUC CUGAUGAGGCCGUUAGGCCGAA IAGGCUCG | 13967 |
| 2326 | CUCAGAUC A CUUGGUUU | 4628 | AAACCAAG CUGAUGAGGCCGUUAGGCCGAA IAUCUGAG | 13968 |
| 2328 | CAGAUCAC U UGGUUUAA | 4629 | UUAAACCA CUGAUGAGGCCGUUAGGCCGAA IUGAUCUG | 13969 |
| 2341 | UUAAAAAC A ACCACAAA | 4630 | UUUGUGGU CUGAUGAGGCCGUUAGGCCGAA IUUUUUAA | 13970 |
| 2344 | AAAACAAC C ACAAAUA | 4631 | UAUUUGU CUGAUGAGGCCGUUAGGCCGAA IUUGUUUU | 13971 |
| 2345 | AAACAACC A CAAAUAC | 4632 | GUAUUUG CUGAUGAGGCCGUUAGGCCGAA IGUUGUUU | 13972 |
| 2347 | ACAACCAC A AAUACAA | 4633 | UUGUAUUU CUGAUGAGGCCGUUAGGCCGAA IGGUUGU | 13973 |
| 2354 | CAAAUAC A ACAAGAGC | 4634 | GCUCUUGU CUGAUGAGGCCGUUAGGCCGAA IAUUUUG | 13974 |
| 2357 | AAUACAAC A AGAGCCUG | 4635 | CAGGCUCU CUGAUGAGGCCGUUAGGCCGAA IUUGUAUU | 13975 |
| 2363 | ACAAGAGC C UGGAAUUA | 4636 | UAAUUCCA CUGAUGAGGCCGUUAGGCCGAA ICUCUUGU | 13976 |
| 2364 | CAAGAGCC U GGAAUUAU | 4637 | AUAAUUCC CUGAUGAGGCCGUUAGGCCGAA IGCUCUUG | 13977 |

TABLE XIV-continued

NCH Ribozyme and Target Sequences

| Pos | Target | Seq ID No | NCH Ribozyme | Seq ID No |
|---|---|---|---|---|
| 2381 | UUUAGGAC C AGGAAGCA | 4638 | UGCUUCCU CUGAUGAGGCCGUUAGGCCGAA IUCCUAAA | 13978 |
| 2382 | UUAGGACC A GGAAGCAG | 4639 | CUGCUUCC CUGAUGAGGCCGUUAGGCCGAA IGUCCUAA | 13979 |
| 2389 | CAGGAAGC A GCACGCUG | 4640 | CAGCGUGC CUGAUGAGGCCGUUAGGCCGAA ICUUCCUG | 13980 |
| 2392 | GAAGCAGC A CGCUGUUU | 4641 | AAACAGCG CUGAUGAGGCCGUUAGGCCGAA ICUGCUUC | 13981 |
| 2396 | CAGCACGC U GUUUAUUG | 4642 | CAAUAAAC CUGAUGAGGCCGUUAGGCCGAA ICGUGCUG | 13982 |
| 2413 | AAAGAGUC A CAGAAGAG | 4643 | CUCUUCUG CUGAUGAGGCCGUUAGGCCGAA IACUCUUU | 13983 |
| 2415 | AGAGUCAC A GAAGAGGA | 4644 | UCCUCUUC CUGAUGAGGCCGUUAGGCCGAA IUGACUCU | 13984 |
| 2434 | AAGGUGUC U AUCACUGC | 4645 | GCAGUGAU CUGAUGAGGCCGUUAGGCCGAA IACACCUU | 13985 |
| 2438 | UGUCUAUC A CUGCAAAG | 4646 | CUUUGCAG CUGAUGAGGCCGUUAGGCCGAA IAUAGACA | 13986 |
| 2440 | UCUAUCAC U GCAAAGCC | 4647 | GGCUUUGC CUGAUGAGGCCGUUAGGCCGAA IUGAUAGA | 13987 |
| 2443 | AUCACUGC A AAGCCACC | 4648 | GGUGGCUU CUGAUGAGGCCGUUAGGCCGAA ICAGUGAU | 13988 |
| 2448 | UGCAAAGC C ACCAACCA | 4649 | UGGUUGGU CUGAUGAGGCCGUUAGGCCGAA ICUUUGCA | 13989 |
| 2449 | GCAAAGCC A CCAACCAG | 4650 | CUGGUUGG CUGAUGAGGCCGUUAGGCCGAA IGCUUUGC | 13990 |
| 2451 | AAAGCCAC C AACCAGAA | 4651 | UUCUGGUU CUGAUGAGGCCGUUAGGCCGAA IUGGCUUU | 13991 |
| 2452 | AAGCCACC A ACCAGAAG | 4652 | CUUCUGGU CUGAUGAGGCCGUUAGGCCGAA IGUGGCUU | 13992 |
| 2455 | CCACCAAC C AGAAGGGC | 4653 | GCCCUUCU CUGAUGAGGCCGUUAGGCCGAA IUUGGUGG | 13993 |
| 2456 | CACCAACC A GAAGGGCU | 4654 | AGCCCUUC CUGAUGAGGCCGUUAGGCCGAA IGUUGGUG | 13994 |
| 2464 | AGAAGGGC U CUGUGGAA | 4655 | UUCCACAG CUGAUGAGGCCGUUAGGCCGAA ICCCUUCU | 13995 |
| 2466 | AAGGGCUC U GUGGAAAG | 4656 | CUUUCCAC CUGAUGAGGCCGUUAGGCCGAA IAGCCCUU | 13996 |
| 2478 | GAAAGUUC A GCAUACCU | 4657 | AGGUAUGC CUGAUGAGGCCGUUAGGCCGAA IAACUUUC | 13997 |
| 2481 | AGUUCAGC A UACCUCAC | 4658 | GUGAGGUA CUGAUGAGGCCGUUAGGCCGAA ICUGAACU | 13998 |
| 2485 | CAGCAUAC C UCACUGUU | 4659 | AACAGUGA CUGAUGAGGCCGUUAGGCCGAA IUAUGCUG | 13999 |
| 2486 | AGCAUACC U CACUGUUC | 4660 | GAACAGUG CUGAUGAGGCCGUUAGGCCGAA IGUAUGCU | 14000 |
| 2488 | CAUACCUC A CUGUUCAA | 4661 | UUGAACAG CUGAUGAGGCCGUUAGGCCGAA IAGGUAUG | 14001 |
| 2490 | UACCUCAC U GUUCAAGG | 4662 | CCUUGAAC CUGAUGAGGCCGUUAGGCCGAA IUGAGGUA | 14002 |
| 2495 | CACUGUUC A AGGAACCU | 4663 | AGGUUCCU CUGAUGAGGCCGUUAGGCCGAA IAACACUG | 14003 |
| 2502 | CAAGGAAC C UCGGACAA | 4664 | UUGUCCGA CUGAUGAGGCCGUUAGGCCGAA IUUCCUUG | 14004 |
| 2503 | AAGGAACC U CGGACAAG | 4665 | CUUGUCCG CUGAUGAGGCCGUUAGGCCGAA IGUUCCUU | 14005 |
| 2509 | CCUCGGAC A AGUCUAAU | 4666 | AUUAGACU CUGAUGAGGCCGUUAGGCCGAA IUCCGAGG | 14006 |
| 2514 | GACAAGUC U AAUCUGGA | 4667 | UCCAGAUU CUGAUGAGGCCGUUAGGCCGAA IACUUGUC | 14007 |
| 2519 | GUCUAAUC U GGAGCUGA | 4668 | UCAGCUCC CUGAUGAGGCCGUUAGGCCGAA IAUUAGAC | 14008 |
| 2525 | UCGGAGC U GAUCACUC | 4669 | GAGUGAUC CUGAUGAGGCCGUUAGGCCGAA ICUCCAGA | 14009 |
| 2530 | AGCUGAUC A CUCUAACA | 4670 | UGUUAGAG CUGAUGAGGCCGUUAGGCCGAA IAUCAGCU | 14010 |
| 2532 | CUGAUCAC U CUAACAUG | 4671 | CAUGUUAG CUGAUGAGGCCGUUAGGCCGAA IUGAUCAG | 14011 |
| 2534 | GAUCACUC U AACAUGCA | 4672 | UGCAUGUU CUGAUGAGGCCGUUAGGCCGAA IAGUGAUC | 14012 |
| 2538 | ACUCUAAC A UGCACCUG | 4673 | CAGGUGCA CUGAUGAGGCCGUUAGGCCGAA IUUAGAGU | 14013 |
| 2542 | UAACAUGC A CCUGUGUG | 4674 | CACACAGG CUGAUGAGGCCGUUAGGCCGAA ICAUGUUA | 14014 |

TABLE XIV-continued

NCH Ribozyme and Target Sequences

| Pos | Target | Seq ID No | NCH Ribozyme | Seq ID No |
|---|---|---|---|---|
| 2544 | ACAUGCAC C UGUGUGGC | 4675 | GCCACACA CUGAUGAGGCCGUUAGGCCGAA IUGCAUGU | 14015 |
| 2545 | CAUGCACC U GUGUGGCU | 4676 | AGCCACAC CUGAUGAGGCCGUUAGGCCGAA IGUGCAUG | 14016 |
| 2553 | UGUGUGGC U GCGACUCU | 4677 | AGAGUCGC CUGAUGAGGCCGUUAGGCCGAA ICCACACA | 14017 |
| 2559 | GCUGCGAC U CUCUUCUG | 4678 | CAGAAGAG CUGAUGAGGCCGUUAGGCCGAA IUCGCAGC | 14018 |
| 2561 | UGCGACUC U CUUCUGGC | 4679 | GCCAGAAG CUGAUGAGGCCGUUAGGCCGAA IAGUCGCA | 14019 |
| 2563 | CGACUCUC U UCUGGCUC | 4680 | GAGCCAGA CUGAUGAGGCCGUUAGGCCGAA IAGAGUCG | 14020 |
| 2566 | CUCUCUUC U GGCUCCUA | 4681 | UAGGAGCC CUGAUGAGGCCGUUAGGCCGAA IAAGAGAG | 14021 |
| 2570 | CUUCUGGC U CCUAUUAA | 4682 | UUAAUAGG CUGAUGAGGCCGUUAGGCCGAA ICCAGAAG | 14022 |
| 2572 | UCUGGCUC C UAUUAACC | 4683 | GGUUAAUA CUGAUGAGGCCGUUAGGCCGAA IAGCCAGA | 14023 |
| 2573 | CUGGCUCC U AUUAACCC | 4684 | GGGUUAAU CUGAUGAGGCCGUUAGGCCGAA IGAGCCAG | 14024 |
| 2580 | CUAUUAAC C CUCCUUAU | 4685 | AUAAGGAG CUGAUGAGGCCGUUAGGCCGAA IUUAAUAG | 14025 |
| 2581 | UAUUAACC C UCCUUAUC | 4686 | GAUAAGGA CUGAUGAGGCCGUUAGGCCGAA IGUUAAUA | 14026 |
| 2582 | AUUAACCC U CCUUAUCC | 4687 | GGAUAAGG CUGAUGAGGCCGUUAGGCCGAA IGGUUAAU | 14027 |
| 2584 | UAACCCUC C UUAUCCGA | 4688 | UCGGAUAA CUGAUGAGGCCGUUAGGCCGAA IAGGGUUA | 14028 |
| 2585 | AACCCUCC U UAUCCGAA | 4689 | UUCGGAUA CUGAUGAGGCCGUUAGGCCGAA IGAGGGUU | 14029 |
| 2590 | UCCUUAUC C GAAAAAUG | 4690 | CAUUUUUC CUGAUGAGGCCGUUAGGCCGAA IAUAAGGA | 14030 |
| 2607 | AAAAGGUC U UCUUCUGA | 4691 | UCAGAAGA CUGAUGAGGCCGUUAGGCCGAA IACCUUUU | 14031 |
| 2610 | AGGUCUUC U UCUGAAAU | 4692 | AUUUCAGA CUGAUGAGGCCGUUAGGCCGAA IAAGACCU | 14032 |
| 2613 | UCUUCUUC U GAAAUAAA | 4693 | UUUAUUUC CUGAUGAGGCCGUUAGGCCGAA IAAGAAGA | 14033 |
| 2625 | AUAAAGAC U GACUACCU | 4694 | AGGUAGUC CUGAUGAGGCCGUUAGGCCGAA IUCUUUAU | 14034 |
| 2629 | AGACUGAC U ACCAUCA | 4695 | UGAUAGGU CUGAUGAGGCCGUUAGGCCGAA IUCAGUCU | 14035 |
| 2632 | CUGACUAC C UAUCAAUU | 4696 | AAUUGAUA CUGAUGAGGCCGUUAGGCCGAA IUAGUCAG | 14036 |
| 2633 | UGACUACC U AUCAAUUA | 4697 | UAAUUGAU CUGAUGAGGCCGUUAGGCCGAA IGUAGUCA | 14037 |
| 2637 | UACCUAUC A AUUAUAAU | 4698 | AUUAUAAU CUGAUGAGGCCGUUAGGCCGAA IAUAGGUA | 14038 |
| 2650 | UAAUGGAC C CAGAUGAA | 4699 | UUCAUCUG CUGAUGAGGCCGUUAGGCCGAA IUCCAUUA | 14039 |
| 2651 | AAUGGACC C AGAUGAAG | 4700 | CUUCAUCU CUGAUGAGGCCGUUAGGCCGAA IGUCCAUU | 14040 |
| 2652 | AUGGACCC A GAUGAAGU | 4701 | ACUUCAUC CUGAUGAGGCCGUUAGGCCGAA IGGUCCAU | 14041 |
| 2663 | UGAAGUUC C UUGGAUG | 4702 | CAUCCAAA CUGAUGAGGCCGUUAGGCCGAA IAACUUCA | 14042 |
| 2664 | GAAGUUCC U UGGAUGA | 4703 | UCAUCCAA CUGAUGAGGCCGUUAGGCCGAA IGAACUUC | 14043 |
| 2675 | GGAUGAGC A GUGUGAGC | 4704 | GCUCACAC CUGAUGAGGCCGUUAGGCCGAA ICUCAUCC | 14044 |
| 2687 | UGAGCGGC U CCCUUAUG | 4705 | CAUAAGGG CUGAUGAGGCCGUUAGGCCGAA ICCGCUCA | 14045 |
| 2689 | AGCGGCUC C CUUAUGAU | 4706 | AUCAUAAG CUGAUGAGGCCGUUAGGCCGAA IAGCCGCU | 14046 |
| 2690 | GCGGCUCC C UUAUGAUG | 4707 | CAUCAUAA CUGAUGAGGCCGUUAGGCCGAA IGAGCCGC | 14047 |
| 2691 | CGGCUCCC U UAUGAUGC | 4708 | GCAUCAUA CUGAUGAGGCCGUUAGGCCGAA IGGAGCCG | 14048 |
| 2700 | UAUGAUGC C AGCAAGUG | 4709 | CACUUGCU CUGAUGAGGCCGUUAGGCCGAA ICAUCAUA | 14049 |
| 2701 | AUGAUGCC A GCAAGUGG | 4710 | CCACUUGC CUGAUGAGGCCGUUAGGCCGAA IGCAUCAU | 14050 |
| 2704 | AUGCCAGC A AGUGGGAG | 4711 | CUCCCACU CUGAUGAGGCCGUUAGGCCGAA ICUGGCAU | 14051 |

TABLE XIV-continued

NCH Ribozyme and Target Sequences

| Pos | Target | Seq ID No | NCH Ribozyme | Seq ID No |
|---|---|---|---|---|
| 2718 | GAGUUUGC C CGGGAGAG | 4712 | CUCUCCCG CUGAUGAGGCCGUUAGGCCGAA ICAAACUC | 14052 |
| 2719 | AGUUUGCC C GGGAGAGA | 4713 | UCUCUCCC CUGAUGAGGCCGUUAGGCCGAA IGCAAACU | 14053 |
| 2729 | GGAGAGAC U UAAACUGG | 4714 | CCAGUUUA CUGAUGAGGCCGUUAGGCCGAA IUCUCUCC | 14054 |
| 2735 | ACUUAAAC U GGGCAAAU | 4715 | AUUUGCCC CUGAUGAGGCCGUUAGGCCGAA IUUUAAGU | 14055 |
| 2740 | AACUGGGC A AAUCACUU | 4716 | AAGUGAUU CUGAUGAGGCCGUUAGGCCGAA ICCCAGUU | 14056 |
| 2745 | GGCAAAUC A CUUGGAAG | 4717 | CUUCCAAG CUGAUGAGGCCGUUAGGCCGAA IAUUUGCC | 14057 |
| 2747 | CAAAUCAC U UGGAAGAG | 4718 | CUCUUCCA CUGAUGAGGCCGUUAGGCCGAA IUGAUUUG | 14058 |
| 2760 | AGAGGGGC U UUUGGAAA | 4719 | UUUCCAAA CUGAUGAGGCCGUUAGGCCGAA ICCCCUCU | 14059 |
| 2777 | AGUGGUUC A AGCAUCAG | 4720 | CUGAUGCU CUGAUGAGGCCGUUAGGCCGAA IAACCACU | 14060 |
| 2781 | GUUCAAGC A UCAGCAUU | 4721 | AAUGCUGA CUGAUGAGGCCGUUAGGCCGAA ICUUGAAC | 14061 |
| 2784 | CAAGCAUC A GCAUUUGG | 4722 | CCAAAUGC CUGAUGAGGCCGUUAGGCCGAA IAUGCUUG | 14062 |
| 2787 | GCAUCAGC A UUUGGCAU | 4723 | AUGCCAAA CUGAUGAGGCCGUUAGGCCGAA ICUGAUGC | 14063 |
| 2794 | CAUUUGGC A UUAAGAAA | 4724 | UUUCUUAA CUGAUGAGGCCGUUAGGCCGAA ICCAAAUG | 14064 |
| 2805 | AAGAAAUC A CCUACGUG | 4725 | CACGUAGG CUGAUGAGGCCGUUAGGCCGAA IAUUUCUU | 14065 |
| 2807 | GAAAUCAC C UACGUGCC | 4726 | GGCACGUA CUGAUGAGGCCGUUAGGCCGAA IUGAUUUC | 14066 |
| 2808 | AAAUCACC U ACGUGCCG | 4727 | CGGCACGU CUGAUGAGGCCGUUAGGCCGAA IGUGAUUU | 14067 |
| 2815 | CUACGUGC C GGACUGUG | 4728 | CACAGUCC CUGAUGAGGCCGUUAGGCCGAA ICACGUAG | 14068 |
| 2820 | UGCCGGAC U GUGGCUGU | 4729 | ACAGCCAC CUGAUGAGGCCGUUAGGCCGAA IUCCGGCA | 14069 |
| 2826 | ACUGUGGC U GUGAAAAU | 4730 | AUUUUCAC CUGAUGAGGCCGUUAGGCCGAA ICCACAGU | 14070 |
| 2837 | GAAAAUGC U GAAAGAGG | 4731 | CCUCUUUC CUGAUGAGGCCGUUAGGCCGAA ICAUUUUC | 14071 |
| 2850 | GAGGGGGC C ACGGCCAG | 4732 | CUGGCCGU CUGAUGAGGCCGUUAGGCCGAA ICCCCCUC | 14072 |
| 2851 | AGGGGGCC A CGGCCAGC | 4733 | GCUGGCCG CUGAUGAGGCCGUUAGGCCGAA IGCCCCCU | 14073 |
| 2856 | GCCACGGC C AGCGAGUA | 4734 | UACUCGCU CUGAUGAGGCCGUUAGGCCGAA ICCGUGGC | 14074 |
| 2857 | CCACGGCC A GCGAGUAC | 4735 | GUACUCGC CUGAUGAGGCCGUUAGGCCGAA IGCCGUGG | 14075 |
| 2866 | GCGAGUAC A AAGCUCUG | 4736 | CAGAGCUU CUGAUGAGGCCGUUAGGCCGAA IUACUCGC | 14076 |
| 2871 | UACAAAGC U CUGAUGAC | 4737 | GUCAUCAG CUGAUGAGGCCGUUAGGCCGAA ICUUUGUA | 14077 |
| 2873 | CAAAGCUC U GAUGACUG | 4738 | CAGUCAUC CUGAUGAGGCCGUUAGGCCGAA IAGCUUUG | 14078 |
| 2880 | CUGAUGAC U GAGCUAAA | 4739 | UUUAGCUC CUGAUGAGGCCGUUAGGCCGAA IUCAUCAG | 14079 |
| 2885 | GACUGAGC U AAAAAUCU | 4740 | AGAUUUUU CUGAUGAGGCCGUUAGGCCGAA ICUCAGUC | 14080 |
| 2893 | UAAAAAUC U UGACCCAC | 4741 | GUGGGUCA CUGAUGAGGCCGUUAGGCCGAA IAUUUUUA | 14081 |
| 2898 | AUCUUGAC C CACAUUGG | 4742 | CCAAUGUG CUGAUGAGGCCGUUAGGCCGAA IUCAAGAU | 14082 |
| 2899 | UCUUGACC C ACAUUGGC | 4743 | GCCAAUGU CUGAUGAGGCCGUUAGGCCGAA IGUCAAGA | 14083 |
| 2900 | CUUGACCC A CAUUGGCC | 4744 | GGCCAAUG CUGAUGAGGCCGUUAGGCCGAA IGGUCAAG | 14084 |
| 2902 | UGACCCAC A UUGGCCAC | 4745 | GUGGCCAA CUGAUGAGGCCGUUAGGCCGAA IUGGGUCA | 14085 |
| 2908 | ACAUUGGC C ACCAUCUG | 4746 | CAGAUGGU CUGAUGAGGCCGUUAGGCCGAA ICCAAUGU | 14086 |
| 2909 | CAUUGGCC A CCAUCGA | 4747 | UCAGAUGG CUGAUGAGGCCGUUAGGCCGAA IGCCAAUG | 14087 |
| 2911 | UUGGCCAC C AUCUGAAC | 4748 | GUUCAGAU CUGAUGAGGCCGUUAGGCCGAA IUGGCCAA | 14088 |

TABLE XIV-continued

NCH Ribozyme and Target Sequences

| Pos | Target | Seq ID No | NCH Ribozyme | Seq ID No |
|---|---|---|---|---|
| 2912 | UGGCCACC A UCUGAACG | 4749 | CGUUCAGA CUGAUGAGGCCGUUAGGCCGAA IGUGGCCA | 14089 |
| 2915 | CCACCAUC U GAACGUGG | 4750 | CCACGUUC CUGAUGAGGCCGUUAGGCCGAA IAUGGUGG | 14090 |
| 2929 | UGGUUAAC C UGCUGGGA | 4751 | UCCCAGCA CUGAUGAGGCCGUUAGGCCGAA IUUAACCA | 14091 |
| 2930 | GGUUAACC U GCUGGGAG | 4752 | CUCCCAGC CUGAUGAGGCCGUUAGGCCGAA IGUUAACC | 14092 |
| 2933 | UAACCUGC U GGGAGCCU | 4753 | AGGCUCCC CUGAUGAGGCCGUUAGGCCGAA ICAGGUUA | 14093 |
| 2940 | CUGGGAGC C UGCACCAA | 4754 | UUGGUGCA CUGAUGAGGCCGUUAGGCCGAA ICUCCCAG | 14094 |
| 2941 | UGGGAGCC U GCACCAAG | 4755 | CUUGGUGC CUGAUGAGGCCGUUAGGCCGAA IGCUCCCA | 14095 |
| 2944 | GAGCCUGC A CCAAGCAA | 4756 | UUGCUUGG CUGAUGAGGCCGUUAGGCCGAA ICAGGCUC | 14096 |
| 2946 | GCCUGCAC C AAGCAAGG | 4757 | CCUUGCUU CUGAUGAGGCCGUUAGGCCGAA IUGCAGGC | 14097 |
| 2947 | CCUGCACC A AGCAAGGA | 4758 | UCCUUGCU CUGAUGAGGCCGUUAGGCCGAA IGUGCAGG | 14098 |
| 2951 | CACCAAGC A AGGAGGGC | 4759 | GCCCUCCU CUGAUGAGGCCGUUAGGCCGAA ICUUGGUG | 14099 |
| 2960 | AGGAGGGC C UCUGAUGG | 4760 | CCAUCAGA CUGAUGAGGCCGUUAGGCCGAA ICCCUCCU | 14100 |
| 2961 | GGAGGGCC U CUGAUGGU | 4761 | ACCAUCAG CUGAUGAGGCCGUUAGGCCGAA IGCCCUCC | 14101 |
| 2963 | AGGGCCUC U GAUGGUGA | 4762 | UCACCAUC CUGAUGAGGCCGUUAGGCCGAA IAGGCCCU | 14102 |
| 2983 | UUGAAUAC U GCAAAUAU | 4763 | AUAUUUGC CUGAUGAGGCCGUUAGGCCGAA IUAUUCAA | 14103 |
| 2986 | AAUACUGC A AAUAUGGA | 4764 | UCCAUAUU CUGAUGAGGCCGUUAGGCCGAA ICAGUAUU | 14104 |
| 2999 | UGGAAAUC U CUCCAACU | 4765 | AGUUGGAG CUGAUGAGGCCGUUAGGCCGAA IAUUUCCA | 14105 |
| 3001 | GAAAUCUC U CCAACUAC | 4766 | GUAGUUGG CUGAUGAGGCCGUUAGGCCGAA IAGAUUUC | 14106 |
| 3003 | AAUCUCUC C AACUACCU | 4767 | AGGUAGUU CUGAUGAGGCCGUUAGGCCGAA IAGAGAUU | 14107 |
| 3004 | AUCUCUCC A ACUACCUC | 4768 | GAGGUAGU CUGAUGAGGCCGUUAGGCCCAA IGAGAGAU | 14108 |
| 3007 | UCUCCAAC U ACCUCAAG | 4769 | CUUGAGGU CUGAUGAGGCCGUUAGGCCGAA IUUGGAGA | 14109 |
| 3010 | CCAACUAC C UCAAGAGC | 4770 | GCUCUUGA CUGAUGAGGCCGUUAGGCCGAA IUAGUUGG | 14110 |
| 3011 | CAACUACC U CAAGAGCA | 4771 | UGCUCUUG CUGAUGAGGCCGUUAGGCCGAA IGUAGUUG | 14111 |
| 3013 | ACUACCUC A AGAGCAAA | 4772 | UUUGCUCU CUGAUGAGGCCGUUAGGCCGAA IAGGUAGU | 14112 |
| 3019 | UCAAGAGC A AACGUGAC | 4773 | GUCACGUU CUGAUGAGGCCGUUAGGCCGAA ICUCUUGA | 14113 |
| 3028 | AACGUGAC U UAUUUUUU | 4774 | AAAAAAUA CUGAUGAGGCCGUUAGGCCGAA IUCACGUU | 14114 |
| 3038 | AUUUUUUU U CAACAAGG | 4775 | CCUUGUUG CUGAUGAGGCCGUUAGGCCGAA IAAAAAAU | 14115 |
| 3040 | UUUUUCUC A ACAAGGAU | 4776 | AUCCUUGU CUGAUGAGGCCGUUAGGCCGAA IAGAAAAA | 14116 |
| 3043 | UUCUCAAC A AGGAUGCA | 4777 | UGCAUCCU CUGAUGAGGCCGUUAGGCCGAA IUUGAGAA | 14117 |
| 3051 | AAGGAUGC A GCACUACA | 4778 | UGUAGUGC CUGAUGAGGCCGUUAGGCCGAA ICAUCCUU | 14118 |
| 3054 | GAUGCAGC A CUACACAU | 4779 | AUGUGUAG CUGAUGAGGCCGUUAGGCCGAA ICUGCAUC | 14119 |
| 3056 | UGCAGCAC U ACACAUGG | 4780 | CCAUGUGU CUGAUGAGGCCGUUAGGCCGAA IUGCUGCA | 14120 |
| 3059 | AGCACUAC A CAUGGAGC | 4781 | GCUCCAUG CUGAUGAGGCCGUUAGGCCGAA IUAGUGCU | 14121 |
| 3061 | CACUACAC A UGGAGCCU | 4782 | AGGCUCCA CUGAUGAGGCCGUUAGGCCGAA IGUAGUG | 14122 |
| 3068 | CAUGGAGC C UAAGAAAG | 4783 | CUUUCUUA CUGAUGAGGCCGUUAGGCCGAA ICUCCAUG | 14123 |
| 3069 | AUGGAGCC U AAGAAAGA | 4784 | UCUUUCUU CUGAUGAGGCCGUUAGGCCGAA IGCUCCAU | 14124 |
| 3089 | AAUGGAGC C AGGCCUGG | 4785 | CCAGGCCU CUGAUGAGGCCGUUAGGCCGAA ICUCCAUU | 14125 |

TABLE XIV-continued

NCH Ribozyme and Target Sequences

| Pos | Target | Seq ID No | NCH Ribozyme | Seq ID No |
|-----|--------|-----------|--------------|-----------|
| 3090 | AUGGAGCC A GGCCUGGA | 4786 | UCCAGGCC CUGAUGAGgccguuaggccGAA IGCUCCAU | 14126 |
| 3094 | AGCCAGGC C UGGAACAA | 4787 | UUGUUCCA CUGAUGAGgccguuaggccGAA ICCUGGCU | 14127 |
| 3095 | GCCAGGCC U GGAACAAG | 4788 | CUUGUUCC CUGAUGAGgccguuaggccGAA IGCCUGGC | 14128 |
| 3101 | CCUGGAAC A AGGCAAGA | 4789 | UCUUGCCU CUGAUGAGgccguuaggccGAA IUUCCAGG | 14129 |
| 3106 | AACAAGGC A AGAAACCA | 4790 | UGGUUUCU CUGAUGAGgccguuaggccGAA ICCUUGUU | 14130 |
| 3113 | CAAGAAAC C AAGACUAG | 4791 | CUAGUCUU CUGAUGAGgccguuaggccGAA IUUUCUUG | 14131 |
| 3114 | AAGAAACC A AGACUAGA | 4792 | UCUAGUCU CUGAUGAGgccguuaggccGAA IGUUUCUU | 14132 |
| 3119 | ACCAAGAC U AGAUAGCG | 4793 | CGCUAUCU CUGAUGAGgccguuaggccGAA IUCUUGGU | 14133 |
| 3130 | AUAGCGUC A CCAGCAGC | 4794 | GCUGCUGG CUGAUGAGgccguuaggccGAA IACGCUAU | 14134 |
| 3132 | AGCGUCAC C AGCAGCGA | 4795 | UCGCUGCU CUGAUGAGgccguuaggccGAA IUGACGCU | 14135 |
| 3133 | GCGUCACC A GCAGCAA | 4796 | UUCGCUGC CUGAUGAGgccguuaggccGAA IGUGACGC | 14136 |
| 3136 | UCACCAGC A GCGAAAGC | 4797 | GCUUUCGC CUGAUGAGgccguuaggccGAA ICUGGUGA | 14137 |
| 3145 | GCGAAAGC U UUGCGAGC | 4798 | GCUCGCAA CUGAUGAGgccguuaggccGAA ICUUUCGC | 14138 |
| 3154 | UUGCGAGC U CCGGCUUU | 4799 | AAAGCCGG CUGAUGAGgccguuaggccGAA ICUCGCAA | 14139 |
| 3156 | GCGAGCUC C GGCUUUCA | 4800 | UGAAAGCC CUGAUGAGgccguuaggccGAA IAGCUCGC | 14140 |
| 3160 | GCUCCGGC U UUCAGGAA | 4801 | UUCCUGAA CUGAUGAGgccguuaggccGAA ICCGGAGC | 14141 |
| 3164 | CGGCUUUC A GGAAGAUA | 4802 | UAUCUUCC CUGAUGAGgccguuaggccGAA IAAAGCCG | 14142 |
| 3179 | UAAAAGUC U GAGUGAUG | 4803 | CAUCACUC CUGAUGAGgccguuaggccGAA IACUUUUA | 14143 |
| 3207 | GAGGAUUC U GACGGUUU | 4804 | AAACCGUC CUGAUGAGgccguuaggccGAA IAAUCCUC | 14144 |
| 3217 | ACGGUUUC U ACAAGGAG | 4805 | CUCCUUGU CUGAUGAGgccguuaggccGAA IAAACCGU | 14145 |
| 3220 | GUUUCUAC A AGGAGCCC | 4806 | GGGCUCCU CUGAUGAGgccguuaggccGAA IUAGAAAC | 14146 |
| 3227 | CAAGGAGC C CAUCACUA | 4807 | UAGUGAUG CUGAUGAGgccguuaggccGAA ICUCCUUG | 14147 |
| 3228 | AAGGAGCC C AUCACUAU | 4808 | AUAGUGAU CUGAUGAGgccguuaggccGAA IGCUCCUU | 14148 |
| 3229 | AGGAGCCC A UCACUAUG | 4809 | CAUAGUGA CUGAUGAGgccguuaggccGAA IGGCUCCU | 14149 |
| 3232 | AGCCCAUC A CUAUGGAA | 4810 | UUCCAUAG CUGAUGAGgccguuaggccGAA IUGGGCU | 14150 |
| 3234 | CCCAUCAC U AUGGAAGA | 4811 | UCUUCCAU CUGAUGAGgccguuaggccGAA IUGAUGGG | 14151 |
| 3245 | GGAAGAUC U GAUUUCUU | 4812 | AAGAAAUC CUGAUGAGgccguuaggccGAA IAUCUUCC | 14152 |
| 3252 | CUGAUUUC U UACAGUUU | 4813 | AAACUGUA CUGAUGAGgccguuaggccGAA IAAAUCAG | 14153 |
| 3256 | UUUCUUAC A GUUUCAA | 4814 | UUGAAAAC CUGAUGAGgccguuaggccGAA IUAAGAAA | 14154 |
| 3263 | CAGUUUC A AGUGGCCA | 4815 | UGGCCACU CUGAUGAGgccguuaggccGAA IAAAACUG | 14155 |
| 3270 | CAAGUGGC C AGAGGCAU | 4816 | AUGCCUCU CUGAUGAGgccguuaggccGAA ICCACUUG | 14156 |
| 3271 | AAGUGGCC A GAGGCAUG | 4817 | CAUGCCUC CUGAUGAGgccguuaggccGAA IGCCACUU | 14157 |
| 3277 | CCAGAGGC A UGGAGUUC | 4818 | GAACUCCA CUGAUGAGgccguuaggccGAA ICCUCUGG | 14158 |
| 3286 | UGGAGUUC C UGUCUUCC | 4819 | GGAAGACA CUGAUGAGgccguuaggccGAA IAACUCCA | 14159 |
| 3287 | GGAGUUCC U GUCUUCCA | 4820 | UGGAAGAC CUGAUGAGgccguuaggccGAA IGAACUCC | 14160 |
| 3291 | UUCCUGUC U UCCAGAAA | 4821 | UUUCUGGA CUGAUGAGgccguuaggccGAA IACAGGAA | 14161 |
| 3294 | CUGUCUUC C AGAAAGUG | 4822 | CACUUUCU CUGAUGAGgccguuaggccGAA IAAGACAG | 14162 |

TABLE XIV-continued

NCH Ribozyme and Target Sequences

| Pos | Target | Seq ID No | NCH Ribozyme | Seq ID No |
|---|---|---|---|---|
| 3295 | UGUCUUCC A GAAAGUGC | 4823 | GCACUUUC CUGAUGAGGCCGUUAGGCCGAA IGAAGACA | 14163 |
| 3304 | GAAAGUGC A UUCAUCGG | 4824 | CCGAUGAA CUGAUGAGGCCGUUAGGCCGAA ICACUUUC | 14164 |
| 3308 | GUGCAUUC A UCGGGACC | 4825 | GGUCCCGA CUGAUGAGGCCGUUAGGCCGAA IAAUGCAC | 14165 |
| 3316 | AUCGGGAC C UGGCAGCG | 4826 | CGCUGCCA CUGAUGAGGCCGUUAGGCCGAA IUCCCGAU | 14166 |
| 3317 | UCGGGACC U GGCAGCGA | 4827 | UCGCUGCC CUGAUGAGGCCGUUAGGCCGAA IGUCCCGA | 14167 |
| 3321 | GACCUGGC A GCGAGAAA | 4828 | UUUCUCGC CUGAUGAGGCCGUUAGGCCGAA ICCAGGUC | 14168 |
| 3331 | CGAGAAAC A UUCUUUUA | 4829 | UAAAAGAA CUGAUGAGGCCGUUAGGCCGAA IUUUCUCG | 14169 |
| 3335 | AAACAUUC U UUUAUCUG | 4830 | CAGAUAAA CUGAUGAGGCCGUUAGGCCGAA IAAUGUUU | 14170 |
| 3342 | CUUUUAUC U GAGAACAA | 4831 | UUGUUCUC CUGAUGAGGCCGUUAGGCCGAA IAUAAAAG | 14171 |
| 3349 | CUGAGAAC A ACGUGGUG | 4832 | CACCACGU CUGAUGAGGCCGUUAGGCCGAA IUUCUCAG | 14172 |
| 3376 | AUUUUGGC C UUGCCCGG | 4833 | CCGGGCAA CUGAUGAGGCCGUUAGGCCGAA ICCAAAAU | 14173 |
| 3377 | UUUUGGCC U UGCCCGGG | 4834 | CCCGGGCA CUGAUGAGGCCGUUAGGCCGAA IGCCAAAA | 14174 |
| 3381 | GGCCUUGC C CGGGAUAU | 4835 | AUAUCCCG CUGAUGAGGCCGUUAGGCCGAA ICAAGGCC | 14175 |
| 3382 | GCCUUGCC C GGGAUAUU | 4836 | AAUAUCCC CUGAUGAGGCCGUUAGGCCGAA IGCAAGGC | 14176 |
| 3400 | AUAAGAAC C CCGAUUAU | 4837 | AUAAUCGG CUGAUGAGGCCGUUAGGCCGAA IUUCUUAU | 14177 |
| 3401 | UAAGAACC C CGAUUAUG | 4838 | CAUAAUCG CUGAUGAGGCCGUUAGGCCGAA IGUUCUUA | 14178 |
| 3402 | AAGAACCC C GAUUAUGU | 4839 | ACAUAAUC CUGAUGAGGCCGUUAGGCCGAA IGGUUCUU | 14179 |
| 3426 | GGAGAUAC U CGACUUCC | 4840 | GGAAGUCG CUGAUGAGGCCGUUAGGCCGAA IUAUCUCC | 14180 |
| 3431 | UACUCGAC U UCCUCUGA | 4841 | UCAGAGGA CUGAUGAGGCCGUUAGGCCGAA IUCGAGUA | 14181 |
| 3434 | UCGACUUC C UCUGAAAU | 4842 | AUUUCAGA CUGAUGAGGCCGUUAGGCCGAA IAAGUCGA | 14182 |
| 3435 | CGACUUCC U CUGAAAUG | 4843 | CAUUUCAG CUGAUGAGGCCGUUAGGCCGAA IGAAGUCG | 14183 |
| 3437 | ACUUCCUC U GAAAUGGA | 4844 | UCCAUUUC CUGAUGAGGCCGUUAGGCCGAA IAGGAAGU | 14184 |
| 3450 | UGGAUGGC U CCCGAAUC | 4845 | GAUUCGGG CUGAUGAGGCCGUUAGGCCGAA ICCAUCCA | 14185 |
| 3452 | CAUGGCUC C CGAAUCUA | 4846 | UAGAUUCG CUGAUGAGGCCGUUAGGCCGAA IAGCCAUC | 14186 |
| 3453 | AUGGCUCC C GAAUCUAU | 4847 | AUAGAUUC CUGAUGAGGCCGUUAGGCCGAA IGAGCCAU | 14187 |
| 3459 | CCCGAAUC U AUCUUUGA | 4848 | UCAAAGAU CUGAUGAGGCCGUUAGGCCGAA IAUUCGGG | 14188 |
| 3463 | AAUCUAUC U UUGACAAA | 4849 | UUUGUCAA CUGAUGAGGCCGUUAGGCCGAA IAUAGAUU | 14189 |
| 3469 | UCUUUGAC A AAUCUAC | 4850 | GUAGAUUU CUGAUGAGGCCGUUAGGCCGAA IUCAAAGA | 14190 |
| 3475 | ACAAAAUC U ACAGCACC | 4851 | GGUGCUGU CUGAUGAGGCCGUUAGGCCGAA IAUUUUGU | 14191 |
| 3478 | AAUCUAC A GCACCAAG | 4852 | CUUGGUGC CUGAUGAGGCCGUUAGGCCGAA IUAGAUUU | 14192 |
| 3481 | UCUACAGC A CCAAGAGC | 4853 | GCUCUUGG CUGAUGAGGCCGUUAGGCCGAA ICUGUAGA | 14193 |
| 3483 | UACAGCAC C AAGAGCGA | 4854 | UCGCUCUU CUGAUGAGGCCGUUAGGCCGAA IUGCUGUA | 14194 |
| 3484 | ACAGCACC A AGAGCGAC | 4855 | GUCGCUCU CUGAUGAGGCCGUUAGGCCGAA IGUGCUGU | 14195 |
| 3501 | GUGUGGUC U UACGGAGU | 4856 | ACUCCGUA CUGAUGAGGCCGUUAGGCCGAA IACCACAC | 14196 |
| 3515 | AGUAUUGC U GUGGGAAA | 4857 | UUUCCCAC CUGAUGAGGCCGUUAGGCCGAA ICAAUACU | 14197 |
| 3526 | GGGAAAUC U UCUCCUUA | 4858 | UAAGGAGA CUGAUGAGGCCGUUAGGCCGAA IAUUUCCC | 14198 |
| 3529 | AAAUCUUC U CCUUAGGU | 4859 | ACCUAAGG CUGAUGAGGCCGUUAGGCCGAA IAAGAUUU | 14199 |

TABLE XIV-continued

NCH Ribozyme and Target Sequences

| Pos | Target | Seq ID No | NCH Ribozyme | Seq ID No |
|---|---|---|---|---|
| 3531 | AUCUUCUC C UUAGGUGG | 4860 | CCACCUAA CUGAUGAGgccGUUAGGCCGAA IAGAAGAU | 14200 |
| 3532 | UCUUCUCC U UAGGUGGG | 4861 | CCCACCUA CUGAUGAGgccGUUAGGCCGAA IGAGAAGA | 14201 |
| 3543 | GGUGGGUC U CCAUACCC | 4862 | GGGUAUGG CUGAUGAGgccGUUAGGCCGAA IACCCACC | 14202 |
| 3545 | UGGGUCUC C AUACCCAG | 4863 | CUGGGUAU CUGAUGAGgccGUUAGGCCGAA IAGACCCA | 14203 |
| 3546 | GGGUCUCC A UACCCAGG | 4864 | CCUGGGUA CUGAUGAGgccGUUAGGCCGAA IGAGACCC | 14204 |
| 3550 | CUCCAUAC C CAGGAGUA | 4865 | UACUCCUG CUGAUGAGgccGUUAGGCCGAA IUAUGGAG | 14205 |
| 3551 | UCCAUACC C AGGAGUAC | 4866 | GUACUCCU CUGAUGAGgccGUUAGGCCGAA IGUAUGGA | 14206 |
| 3552 | CCAUACCC A GGAGUACA | 4867 | UGUACUCC CUGAUGAGgccGUUAGGCCGAA IGGUAUGG | 14207 |
| 3560 | AGGAGUAC A AAUGGAUG | 4868 | CAUCCAUU CUGAUGAGgccGUUAGGCCGAA IUACUCCU | 14208 |
| 3574 | AUGAGGAC U UUUGCAGU | 4869 | ACUGCAAA CUGAUGAGgccGUUAGGCCGAA IUCCUCAU | 14209 |
| 3580 | ACUUUUGC A GUCGCCUG | 4870 | CAGGCGAC CUGAUGAGgccGUUAGGCCGAA ICAAAAGU | 14210 |
| 3586 | GCAGUCGC C UGAGGGAA | 4871 | UUCCCUCA CUGAUGAGgccGUUAGGCCGAA ICGACUGC | 14211 |
| 3587 | CAGUCGCC U GAGGGAAG | 4872 | CUUCCCUC CUGAUGAGgccGUUAGGCCGAA IGCGACUG | 14212 |
| 3598 | GGGAAGGC A UGAGGAUG | 4873 | CAUCCUCA CUGAUGAGgccGUUAGGCCGAA ICCUUCCC | 14213 |
| 3612 | AUGAGAGC U CCUGAGUA | 4874 | UACUCAGG CUGAUGAGgccGUUAGGCCGAA ICUCUCAU | 14214 |
| 3614 | GAGAGCUC C UGAGUACU | 4875 | AGUACUCA CUGAUGAGgccGUUAGGCCGAA IAGCUCUC | 14215 |
| 3615 | AGAGCUCC U GAGUACUC | 4876 | GAGUACUC CUGAUGAGgccGUUAGGCCGAA IGAGCUCU | 14216 |
| 3622 | CUGAGUAC U CUACUCCU | 4877 | AGGAGUAG CUGAUGAGgccGUUAGGCCGAA IUACUCAG | 14217 |
| 3624 | GAGUACUC U ACUCCUGA | 4878 | UCAGGAGU CUGAUGAGgccGUUAGGCCGAA IAGUACUC | 14218 |
| 3627 | UACUCUAC U CCUGAAAU | 4879 | AUUUCAGG CUGAUGAGgccGUUAGGCCGAA IUAGAGUA | 14219 |
| 3629 | CUCUACUC C UGAAAUCU | 4880 | AGAUUUCA CUGAUGAGgccGUUAGGCCGAA IAGUAGAG | 14220 |
| 3630 | UCUACUCC U GAAAUCUA | 4881 | UAGAUUUC CUGAUGAGgccGUUAGGCCGAA IGAGUAGA | 14221 |
| 3637 | CUGAAAUC U AUCAGAUC | 4882 | GAUCUGAU CUGAUGAGgccGUUAGGCCGAA IAUUUCAG | 14222 |
| 3641 | AAUCUAUC A GAUCAUGC | 4883 | GCAUGAUC CUGAUGAGgccGUUAGGCCGAA IAUAGAUU | 14223 |
| 3646 | AUCAGAUC A UGCUGGAC | 4884 | GUCCAGCA CUGAUGAGgccGUUAGGCCGAA IAUCUGAU | 14224 |
| 3650 | GAUCAUGC U GGACUGCU | 4885 | AGCAGUCC CUGAUGAGgccGUUAGGCCGAA ICAUGAUC | 14225 |
| 3655 | UGCUGGAC U GCUGGCAC | 4886 | GUGCCAGC CUGAUGAGgccGUUAGGCCGAA IUCCAGCA | 14226 |
| 3658 | UGGACUGC U GGCACAGA | 4887 | UCUGUGCC CUGAUGAGgccGUUAGGCCGAA ICAGUCCA | 14227 |
| 3662 | CUGCUGGC A CAGAGACC | 4888 | GGUCUCUG CUGAUGAGgccGUUAGGCCGAA ICCAGCAG | 14228 |
| 3664 | GCUGGCAC A GAGACCCA | 4889 | UGGGUCUC CUGAUGAGgccGUUAGGCCGAA IUGCCAGC | 14229 |
| 3670 | ACAGAGAC C CAAAAGAA | 4890 | UUCUUUUG CUGAUGAGgccGUUAGGCCGAA IUCUCUGU | 14230 |
| 3671 | CAGAGACC C AAAAGAAA | 4891 | UUUCUUUU CUGAUGAGgccGUUAGGCCGAA IGUCUCUG | 14231 |
| 3672 | AGAGACCC A AAAGAAAG | 4892 | CUUUCUUU CUGAUGAGgccGUUAGGCCGAA IGGUCUCU | 14232 |
| 3683 | AGAAAGGC C AAGAUUUG | 4893 | CAAAUCUU CUGAUGAGgccGUUAGGCCGAA ICCUUUCU | 14233 |
| 3684 | GAAAGGCC A AGAUUUGC | 4894 | GCAAAUCU CUGAUGAGgccGUUAGGCCGAA IGCCUUUC | 14234 |
| 3693 | AGAUUUGC A GAACUUGU | 4895 | ACAAGUUC CUGAUGAGgccGUUAGGCCGAA ICAAAUCU | 14235 |
| 3698 | UGCAGAAC U UGUGGAAA | 4896 | UUUCCACA CUGAUGAGgccGUUAGGCCGAA IUUCUGCA | 14236 |

TABLE XIV-continued

NCH Ribozyme and Target Sequences

| Pos | Target | Seq ID No | NCH Ribozyme | Seq ID No |
|---|---|---|---|---|
| 3710 | GGAAAAAC U AGGUGAUU | 4897 | AAUCACCU CUGAUGAGGCCGUUAGGCCGAA IUUUUUCC | 14237 |
| 3722 | UGAUUUGC U UCAAGCAA | 4898 | UUCCACA CUGAUGAGGCCGUUAGGCCGAA ICAAAUCA | 14238 |
| 3725 | UUUGCUUC A AGCAAAUG | 4899 | CAUUUGCU CUGAUGAGGCCGUUAGGCCGAA IAAGCAAA | 14239 |
| 3729 | CUUCAAGC A AAUGUACA | 4900 | UGUACAUU CUGAUGAGGCCGUUAGGCCGAA ICUUGAAG | 14240 |
| 3737 | AAAUGUAC A ACAGGAUG | 4901 | CAUCCUGU CUGAUGAGGCCGUUAGGCCGAA IUACAUUU | 14241 |
| 3740 | UGUACAAC A GGAUGGUA | 4902 | UACCAUCC CUGAUGAGGCCGUUAGGCCGAA IUUGUACA | 14242 |
| 3754 | GUAAAGAC U ACAUCCCA | 4903 | UGGGAUGU CUGAUGAGGCCGUUAGGCCGAA IUCUUUAC | 14243 |
| 3757 | AAGACUAC A UCCCAAUC | 4904 | GAUUGGGA CUGAUGAGGCCGUUAGGCCGAA IAGUCUU | 14244 |
| 3760 | ACUACAUC C CAAUCAAU | 4905 | AUUGAUUG CUGAUGAGGCCGUUAGGCCGAA IAUGUAGU | 14245 |
| 3761 | CUACAUCC C AAUCAAUG | 4906 | CAUUGAUU CUGAUGAGGCCGUUAGGCCGAA IGAUGUAG | 14246 |
| 3762 | UACAUCCC A UACUGACA | 4907 | GCAUUGAU CUGAUGAGGCCGUUAGGCCGAA IGGAUGUA | 14247 |
| 3766 | UCCCAAUC A AUGCCAUA | 4908 | UAUGGCAU CUGAUGAGGCCGUUAGGCCGAA IAUUGGGA | 14248 |
| 3771 | AUCAAUGC C AUACUGAC | 4909 | GUCAGUAU CUGAUGAGGCCGUUAGGCCGAA ICAUUGAU | 14249 |
| 3772 | UCAAUGCC A UACUGACA | 4910 | UGUCAGUA CUGAUGAGGCCGUUAGGCCGAA IGCAUUGA | 14250 |
| 3776 | UGCCAUAC U GACAGGAA | 4911 | UUCCUGUC CUGAUGAGGCCGUUAGGCCGAA IUAUGGCA | 14251 |
| 3780 | AUACUGAC A GGAAAUAG | 4912 | CUAUUUCC CUGAUGAGGCCGUUAGGCCGAA IUCAGUAU | 14252 |
| 3798 | GGGUUUAC A UACUCAAC | 4913 | GUUGAGUA CUGAUGAGGCCGUUAGGCCGAA IUAAACCC | 14253 |
| 3802 | UUACAUAC U CAACUCCU | 4914 | AGGAGUUG CUGAUGAGGCCGUUAGGCCGAA IUAUGUAA | 14254 |
| 3804 | ACAUACUC A ACUCCUGC | 4915 | GCAGGAGU CUGAUGAGGCCGUUAGGCCGAA IAGUAUGU | 14255 |
| 3807 | UACUCAAC U CCUGCCUU | 4916 | AAGGCAGG CUGAUGAGGCCGUUAGGCCGAA IUUGAGUA | 14256 |
| 3809 | CUCAACUC C UGCCUUCU | 4917 | AGAAGGCA CUGAUGAGGCCGUUAGGCCGAA IAGUUGAG | 14257 |
| 3810 | UCAACUCC U GCCUUCUC | 4918 | GAGAAGGC CUGAUGAGGCCGUUAGGCCGAA IGAGUUGA | 14258 |
| 3813 | ACUCCUGC C UUCUUUGA | 4919 | UCAGAGAA CUGAUGAGGCCGUUAGGCCGAA ICAGGAGU | 14259 |
| 3814 | CUCCUGCC U UCUCUGAG | 4920 | CUCAGAGA CUGAUGAGGCCGUUAGGCCGAA IGCAGGAG | 14260 |
| 3817 | CUGCCUUC U CUGAGGAC | 4921 | GUCCUCAG CUGAUGAGGCCGUUAGGCCGAA IAAGGCAG | 14261 |
| 3819 | GCCUUCUC U GAGGACUU | 4922 | AAGUCCUC CUGAUGAGGCCGUUAGGCCGAA IAGAAGGC | 14262 |
| 3826 | CUGAGGAC U UCUUCAGG | 4923 | CUUGAAGA CUGAUGAGGCCGUUAGGCCGAA IUCCUCAG | 14263 |
| 3829 | AGGACUUC U UCAAGGAA | 4924 | UUCCUUGA CUGAUGAGGCCGUUAGGCCGAA IAAGUCCU | 14264 |
| 3832 | ACUUCUUC A AGGAAAGU | 4925 | ACUUUCCU CUGAUGAGGCCGUUAGGCCGAA IAAGAAGU | 14265 |
| 3846 | AGUAUUUC A GCUCCGAA | 4926 | UUCGGAGC CUGAUGAGGCCGUUAGGCCGAA IAAAUACU | 14266 |
| 3849 | AUUUCAGC U CCGAAGUU | 4927 | AACUUCGG CUGAUGAGGCCGUUAGGCCGAA ICUGAAAU | 14267 |
| 3851 | UUCAGCUC C GAAGUUUA | 4928 | UAAACUUC CUGAUGAGGCCGUUAGGCCGAA IAGCUGAA | 14268 |
| 3864 | UUUAAUUC A GGAAGCUC | 4929 | GAGCUUCC CUGAUGAGGCCGUUAGGCCGAA IAAUUAAA | 14269 |
| 3871 | CAGGAAGC U CUGAUGAU | 4930 | AUCAUCAG CUGAUGAGGCCGUUAGGCCGAA ICUUCCUG | 14270 |
| 3873 | GGAAGCUC U GAUGAUGU | 4931 | ACAUCAUC CUGAUGAGGCCGUUAGGCCGAA IAGCUUCC | 14271 |
| 3883 | AUGAUGUC A GAUAUGUA | 4932 | UACAUAUC CUGAUGAGGCCGUUAGGCCGAA IACAUCAU | 14272 |
| 3897 | GUAAAUGC U UUCAAGUU | 4933 | AACUUGAA CUGAUGAGGCCGUUAGGCCGAA ICAUUUAC | 14273 |

TABLE XIV-continued

NCH Ribozyme and Target Sequences

| Pos | Target | Seq ID No | NCH Ribozyme | Seq ID No |
|---|---|---|---|---|
| 3901 | AUGCUUUC A AGUUCAUG | 4934 | CAUGAACU CUGAUGAGGCCGUUAGGCCGAA IAAAGCAU | 14274 |
| 3907 | UCAAGUUC A UGAGCCUG | 4935 | CAGGCUCA CUGAUGAGGCCGUUAGGCCGAA IAACUUGA | 14275 |
| 3913 | UCAUGAGC C UGGAAAGA | 4936 | UCUUUCCA CUGAUGAGGCCGUUAGGCCGAA ICUCAUGA | 14276 |
| 3914 | CAUGAGCC U GGAAAGAA | 4937 | UUCUUUCC CUGAUGAGGCCGUUAGGCCGAA IGCUCAUG | 14277 |
| 3925 | AAAGAAUC A AAACCUUU | 4938 | AAAGGUUU CUGAUGAGGCCGUUAGGCCGAA IAUUCUUU | 14278 |
| 3930 | AUCAAAAC C UUUGAAGA | 4939 | UCUUCAAA CUGAUGAGGCCGUUAGGCCGAA IUUUUGAU | 14279 |
| 3931 | UCAAAACC U UUGAAGAA | 4940 | UUCUUCAA CUGAUGAGGCCGUUAGGCCGAA IGUUUUGA | 14280 |
| 3941 | UGAAGAAC U UUUACCGA | 4941 | UCGGUAAA CUGAUGAGGCCGUUAGGCCGAA IUUCUUCA | 14281 |
| 3947 | ACUUUUAC C GAAUGCCA | 4942 | UGGCAUUC CUGAUGAGGCCGUUAGGCCGAA IAAAAGU | 14282 |
| 3954 | CCGAAUGC C ACCUCCAU | 4943 | AUGGAGGU CUGAUGAGGCCGUUAGGCCGAA ICAUUCGG | 14283 |
| 3955 | CGAAUGCC A CCUCCAUG | 4944 | CAUGGAGG CUGAUGAGGCCGUUAGGCCGAA IGCAUUCG | 14284 |
| 3957 | AAUGCCAC C UCCAUGUU | 4945 | AACAUGGA CUGAUGAGGCCGUUAGGCCGAA IUGGCAUU | 14285 |
| 3958 | AUGCCACC U CCAUGUUU | 4946 | AAACAUGG CUGAUGAGGCCGUUAGGCCGAA IGUGGCAU | 14286 |
| 3960 | GCCACCUC C AUGUUUGA | 4947 | UCAAACAU CUGAUGAGGCCGUUAGGCCGAA IAGGUGGC | 14287 |
| 3961 | CCACCUCC A UGUUUGAU | 4948 | AUCAAACA CUGAUGAGGCCGUUAGGCCGAA IGAGGUGG | 14288 |
| 3973 | UUGAUGAC U ACCAGGGC | 4949 | GCCCUGGU CUGAUGAGGCCGUUAGGCCGAA IUCAUCAA | 14289 |
| 3976 | AUGACUAC C AGGGCGAC | 4950 | GUCGCCCU CUGAUGAGGCCGUUAGGCCGAA IUAGUCAU | 14290 |
| 3977 | UGACUACC A GGGCGACA | 4951 | UGUCGCCC CUGAUGAGGCCGUUAGGCCGAA IGUAGUCA | 14291 |
| 3985 | AGGGCGAC A GCAGCACU | 4952 | AGUGCUGC CUGAUGAGGCCGUUAGGCCGAA IUCGCCCU | 14292 |
| 3988 | GCGACAGC A GCACUCUG | 4953 | CAGAGUGC CUGAUGAGGCCGUUAGGCCGAA ICUGUCGC | 14293 |
| 3991 | ACAGCAGC A CUCUGUUG | 4954 | CAACAGAG CUGAUGAGGCCGUUAGGCCGAA ICUGCUGU | 14294 |
| 3993 | AGCAGCAC U CUGUUGGC | 4955 | GCCAACAG CUGAUGAGGCCGUUAGGCCGAA IUGCUGCU | 14295 |
| 3995 | CAGCACUC U GUUGGCCU | 4956 | AGGCCAAC CUGAUGAGGCCGUUAGGCCGAA IAGUGCUG | 14296 |
| 4002 | CUGUUGGC C UCUCCCAU | 4957 | AUGGGAGA CUGAUGAGGCCGUUAGGCCGAA ICCAACAG | 14297 |
| 4003 | UGUUGGCC U CUCCCAUG | 4958 | CAUGGGAG CUGAUGAGGCCGUUAGGCCGAA IGCCAACA | 14298 |
| 4005 | UUGGCCUC U CCCAUGCU | 4959 | AGCAUGGG CUGAUGAGGCCGUUAGGCCGAA IAGGCCAA | 14299 |
| 4007 | GGCCUCUC C CAUGCUGA | 4960 | UCAGCAUG CUGAUGAGGCCGUUAGGCCGAA IAGAGGCC | 14300 |
| 4008 | GCCUCUCC C AUGCUGAA | 4961 | UUCAGCAU CUGAUGAGGCCGUUAGGCCGAA IGAGAGGC | 14301 |
| 4009 | CCUCUCCC A UGCUGAAG | 4962 | CUUCAGCA CUGAUGAGGCCGUUAGGCCGAA IGGAGAGG | 14302 |
| 4013 | UCCCAUGC U GAAGCGCU | 4963 | AGCGCUUC CUGAUGAGGCCGUUAGGCCGAA ICAUGGGA | 14303 |
| 4021 | UGAAGCGC U UCACCUGG | 4964 | CCAGGUGA CUGAUGAGGCCGUUAGGCCGAA ICGCUUCA | 14304 |
| 4024 | AGCGCUUC A CCUGGACU | 4965 | AGUCCAGG CUGAUGAGGCCGUUAGGCCGAA IAAGCGCU | 14305 |
| 4026 | CGCUUCAC C UGGACUGA | 4966 | UCAGUCCA CUGAUGAGGCCGUUAGGCCGAA IUGAAGCG | 14306 |
| 4027 | GCUUCACC U GGACUGAC | 4967 | GUCAGUCC CUGAUGAGGCCGUUAGGCCGAA IGUGAAGC | 14307 |
| 4032 | ACCUGGAC U GACAGCAA | 4968 | UUGCUGUC CUGAUGAGGCCGUUAGGCCGAA IUCCAGGU | 14308 |
| 4036 | GGACUGAC A GCAAACCC | 4969 | GGGUUUGC CUGAUGAGGCCGUUAGGCCGAA ICAGUCC | 14309 |
| 4039 | CUGACAGC A AACCCAAG | 4970 | CUUGGGUU CUGAUGAGGCCGUUAGGCCGAA ICUGUCAG | 14310 |

TABLE XIV-continued

NCH Ribozyme and Target Sequences

| Pos | Target | Seq ID No | NCH Ribozyme | Seq ID No |
|---|---|---|---|---|
| 4043 | CAGCAAAC C CAAGGCCU | 4971 | AGGCCUUG CUGAUGAGGCCGUUAGGCCGAA IUUUGCUG | 14311 |
| 4044 | AGCAAACC C AAGGCCUC | 4972 | GAGGCCUU CUGAUGAGGCCGUUAGGCCGAA IGUUUGCU | 14312 |
| 4045 | GCAAACCC A AGGCCUCG | 4973 | CGAGGCCU CUGAUGAGGCCGUUAGGCCGAA IGGUUUGC | 14313 |
| 4050 | CCCAAGGC C UCGCUCAA | 4974 | UUGAGCGA CUGAUGAGGCCGUUAGGCCGAA ICCUUGGG | 14314 |
| 4051 | CCAAGGCC U CGCUCAAG | 4975 | CUUGAGCG CUGAUGAGGCCGUUAGGCCGAA IGCCUUGG | 14315 |
| 4055 | GGCCUCGC U CAAGAUUG | 4976 | CAAUCUUG CUGAUGAGGCCGUUAGGCCGAA ICGAGGCC | 14316 |
| 4057 | CCUCGCUC A AGAUUGAC | 4977 | GUCAAUCU CUGAUGAGGCCGUUAGGCCGAA IAGCGAGG | 14317 |
| 4066 | AGAUUGAC U UGAGAGUA | 4978 | UACUCUCA CUGAUGAGGCCGUUAGGCCGAA IUCAAUCU | 14318 |
| 4077 | AGAGUAAC C AGUAAAAG | 4979 | CUUUUACU CUGAUGAGGCCGUUAGGCCGAA IUUACUCU | 14319 |
| 4078 | GAGUAACC A GUAAAAGU | 4980 | ACUUUUAC CUGAUGAGGCCGUUAGGCCGAA IGUUACUC | 14320 |
| 4100 | GUCGGGGC U GUCUGAUG | 4981 | CAUCAGAC CUGAUGAGGCCGUUAGGCCGAA ICCCCGAC | 14321 |
| 4104 | GGGCUGUC U GAUGUCAG | 4982 | CUGACAUC CUGAUGAGGCCGUUAGGCCGAA IACAGCCC | 14322 |
| 4111 | CUGAUGUC A GCAGGCCC | 4983 | GGGCCUGC CUGAUGAGGCCGUUAGGCCGAA IACAUCAG | 14323 |
| 4114 | AUGUCAGC A GGCCCAGU | 4984 | ACUGGGCC CUGAUGAGGCCGUUAGGCCGAA ICUGACAU | 14324 |
| 4118 | CAGCAGGC C CAGUUUCU | 4985 | AGAAACUG CUGAUGAGGCCGUUAGGCCGAA ICCUGCUG | 14325 |
| 4119 | AGCAGGCC C AGUUUCUG | 4986 | CAGAAACU CUGAUGAGGCCGUUAGGCCGAA IGCCUGCU | 14326 |
| 4120 | GCAGGCCC A GUUUCUGC | 4987 | GCAGAAAC CUGAUGAGGCCGUUAGGCCGAA IGGCCUGC | 14327 |
| 4126 | CCAGUUUC U GCCAUUCC | 4988 | GGAAUGGC CUGAUGAGGCCGUUAGGCCGAA IAAACUGG | 14328 |
| 4129 | GUUUCUGC C AUUCCAGC | 4989 | GCUGGAAU CUGAUGAGGCCGUUAGGCCGAA ICAGAAAC | 14329 |
| 4130 | UUUCUGCC A UUCCAGCU | 4990 | AGCUGGAA CUGAUGAGGCCGUUAGGCCGAA IGCAGAAA | 14330 |
| 4134 | UGCCAUUC C AGCUGUGG | 4991 | CCACAGCU CUGAUGAGGCCGUUAGGCCGAA IAAUGGCA | 14331 |
| 4135 | GCCAUUCC A GCUGUGGG | 4992 | CCCACAGC CUGAUGAGGCCGUUAGGCCGAA IGAAUGGC | 14332 |
| 4138 | AUUCCAGC U GUGGGCAC | 4993 | GUGCCCAC CUGAUGAGGCCGUUAGGCCGAA ICUGGAAU | 14333 |
| 4145 | CUGUGGGC A CGUCAGCG | 4994 | CGCUGACG CUGAUGAGGCCGUUAGGCCGAA ICCCACAG | 14334 |
| 4150 | GGCACGUC A GCGAAGGC | 4995 | GCCUUCGC CUGAUGAGGCCGUUAGGCCGAA IACGUGCC | 14335 |
| 4159 | GCGAAGGC A AGCGCAGG | 4996 | CCUGCGCU CUGAUGAGGCCGUUAGGCCGAA ICCUUCGC | 14336 |
| 4165 | GCAAGCGC A GGUUCACC | 4997 | GGUGAACC CUGAUGAGGCCGUUAGGCCGAA ICGCUUGC | 14337 |
| 4171 | GCAGGUUC A CCUACGAC | 4998 | GUCGUAGG CUGAUGAGGCCGUUAGGCCGAA IAACCUGC | 14338 |
| 4173 | AGGUUCAC C UACGACCA | 4999 | UGGUCGUA CUGAUGAGGCCGUUAGGCCGAA IUGAACCU | 14339 |
| 4174 | GGUUCACC U ACGACCAC | 5000 | GUGGUCGU CUGAUGAGGCCGUUAGGCCGAA IGUGAACC | 14340 |
| 4180 | CCUACGAC C ACGCUGAG | 5001 | CUCAGCGU CUGAUGAGGCCGUUAGGCCGAA IUCGUAGG | 14341 |
| 4181 | CUACGACC A CGCUGAGC | 5002 | GCUCAGCG CUGAUGAGGCCGUUAGGCCGAA IGUCGUAG | 14342 |
| 4185 | GACCACGC U GAGCUGGA | 5003 | UCCAGCUC CUGAUGAGGCCGUUAGGCCGAA ICGUGGUC | 14343 |
| 4190 | CGCUGAGC U GGAAGGA | 5004 | UCCUUCC CUGAUGAGGCCGUUAGGCCGAA ICUCAGCG | 14344 |
| 4210 | UCGCGUGC U GCUCCCCG | 5005 | CGGGGAGC CUGAUGAGGCCGUUAGGCCGAA ICACGCGA | 14345 |
| 4213 | CGUGCUGC U CCCCGCCC | 5006 | GGGCGGGG CUGAUGAGGCCGUUAGGCCGAA ICAGCACG | 14346 |
| 4215 | UGCUGCUC C CCGCCCCC | 5007 | GGGGGCGG CUGAUGAGGCCGUUAGGCCGAA IAGCAGCA | 14347 |

TABLE XIV-continued

NCH Ribozyme and Target Sequences

| Pos | Target | Seq ID No | NCH Ribozyme | Seq ID No |
|---|---|---|---|---|
| 4216 | GCUGCUCC C CGCCCCA | 5008 | UGGGGGCG CUGAUGAGGCCGUUAGGCCGAA IGAGCAGC | 14348 |
| 4217 | CUGCUCCC C GCCCCAG | 5009 | CUGGGGGC CUGAUGAGGCCGUUAGGCCGAA IGGAGCAG | 14349 |
| 4220 | CUCCCCGC C CCAGACU | 5010 | AGUCUGG CUGAUGAGGCCGUUAGGCCGAA ICGGGGAG | 14350 |
| 4221 | UCCCCGCC C CAGACUA | 5011 | UAGUCUGG CUGAUGAGGCCGUUAGGCCGAA IGCGGGA | 14351 |
| 4222 | CCCCGCCC C CAGACUAC | 5012 | GUAGUCUG CUGAUGAGGCCGUUAGGCCGAA IGGCGGGG | 14352 |
| 4223 | CCCGCCCC C AGACUACA | 5013 | UGUAGUCU CUGAUGAGGCCGUUAGGCCGAA IGGGCGGG | 14353 |
| 4224 | CCGCCCCC A GACUACAA | 5014 | UUGUAGUC CUGAUGAGGCCGUUAGGCCGAA IGGGGCGG | 14354 |
| 4228 | CCCCAGAC U ACAACUCG | 5015 | CGAGUUGU CUGAUGAGGCCGUUAGGCCGAA IUCUGGGG | 14355 |
| 4231 | CAGACUAC A ACUCGGUG | 5016 | CACCGAGU CUGAUGAGGCCGUUAGGCCGAA IAGUCUG | 14356 |
| 4234 | ACUACAAC U CGGUGGUC | 5017 | GACCACCG CUGAUGAGGCCGUUAGGCCGAA IUUGUAGU | 14357 |
| 4243 | CGGUGGUC C UGUACUCC | 5018 | GGAGUACA CUGAUGAGGCCGUUAGGCCGAA IACCACCG | 14358 |
| 4244 | GGUGGUCC U GUACUCCA | 5019 | UGGAGUAC CUGAUGAGGCCGUUAGGCCGAA IGACCACC | 14359 |
| 4249 | UCCUGUAC U CCACCCCA | 5020 | UGGGGUGG CUGAUGAGGCCGUUAGGCCGAA IUACAGGA | 14360 |
| 4251 | CUGUACUC C ACCCCACC | 5021 | GGUGGGGU CUGAUGAGGCCGUUAGGCCGAA IAGUACAG | 14361 |
| 4252 | UGUACUCC A CCCCACCC | 5022 | GGGUGGGG CUGAUGAGGCCGUUAGGCCGAA IGAGUACA | 14362 |
| 4254 | UACUCCAC C CCACCCAU | 5023 | AUGGGUGG CUGAUGAGGCCGUUAGGCCGAA IUGGAGUA | 14363 |
| 4255 | ACUCCACC C CACCCAUC | 5024 | GAUGGGUG CUGAUGAGGCCGUUAGGCCGAA IGUGGAGU | 14364 |
| 4256 | CUCCACCC C ACCCAUCU | 5025 | AGAUGGGU CUGAUGAGGCCGUUAGGCCGAA IGGUGGAG | 14365 |
| 4257 | UCCACCCC A CCCAUCUA | 5026 | UAGAUGGG CUGAUGAGGCCGUUAGGCCGAA IGGGUGGA | 14366 |
| 4259 | CACCCCAC C CAUCUAGA | 5027 | UCUAGAUG CUGAUGAGGCCGUUAGGCCGAA IUGGGGUG | 14367 |
| 4260 | ACCCCACC C AUCUAGAG | 5028 | CUCUAGAU CUGAUGAGGCCGUUAGGCCGAA IGUGGGGU | 14368 |
| 4261 | CCCCACCC A UCUAGAGU | 5029 | ACUCUAGA CUGAUGAGGCCGUUAGGCCGAA IGGUGGGG | 14369 |
| 4264 | CACCCAUC U AGAGUUUG | 5030 | CAAACUCU CUGAUGAGGCCGUUAGGCCGAA IAUGGGUG | 14370 |
| 4275 | AGUUUGAC A CGAAGCCU | 5031 | AGGCUUCG CUGAUGAGGCCGUUAGGCCGAA IUCAAACU | 14371 |
| 4282 | CACGAAGC C UUAUUUCU | 5032 | AGAAAUAA CUGAUGAGGCCGUUAGGCCGAA ICUUCGUG | 14372 |
| 4283 | ACGAAGCC U UAUUUCUA | 5033 | UAGAAAUA CUGAUGAGGCCGUUAGGCCGAA IGCUUCGU | 14373 |
| 4290 | CUUAUUUC U AGAAGCAC | 5034 | GUGCUUCU CUGAUGAGGCCGUUAGGCCGAA IAAAUAAG | 14374 |
| 4297 | CUAGAAGC A CAUGUGUA | 5035 | UACACAUG CUGAUGAGGCCGUUAGGCCGAA ICUUCUAG | 14375 |
| 4299 | AGAAGCAC A UGUGUAUU | 5036 | AAUACACA CUGAUGAGGCCGUUAGGCCGAA IUGCUUCU | 14376 |
| 4313 | AUUUAUAC C CCAGGAA | 5037 | UUCCUGGG CUGAUGAGGCCGUUAGGCCGAA IUAUAAAU | 14377 |
| 4314 | UUUAUACC C CAGGAAA | 5038 | UUUCCUGG CUGAUGAGGCCGUUAGGCCGAA IGUAUAAA | 14378 |
| 4315 | UUAUACCC C CAGGAAAC | 5039 | GUUUCCUG CUGAUGAGGCCGUUAGGCCGAA IGGUAUAA | 14379 |
| 4316 | UAUACCCC C AGGAAACU | 5040 | AGUUUCCU CUGAUGAGGCCGUUAGGCCGAA IGGGUAUA | 14380 |
| 4317 | AUACCCCC A GGAAACUA | 5041 | UAGUUUCC CUGAUGAGGCCGUUAGGCCGAA IGGGGUAU | 14381 |
| 4324 | CAGGAAAC U AGCUUUUG | 5042 | CAAAAGCU CUGAUGAGGCCGUUAGGCCGAA IUUUCCUG | 14382 |
| 4328 | AAACUAGC U UUGCCAG | 5043 | CUGGCAAA CUGAUGAGGCCGUUAGGCCGAA ICUAGUUU | 14383 |
| 4334 | GCUUUUGC C AGUAUUAU | 5044 | AUAAUACU CUGAUGAGGCCGUUAGGCCGAA ICAAAAGC | 14384 |

TABLE XIV-continued

NCH Ribozyme and Target Sequences

| Pos | Target | Seq ID No | NCH Ribozyme | Seq ID No |
|---|---|---|---|---|
| 4335 | CUUUUGCC A GUAUUAUG | 5045 | CAUAAUAC CUGAUGAGgccGUUAGGCCGAA IGCAAAAG | 14385 |
| 4345 | UAUUAUGC A UAUAUAAG | 5046 | CUUAUAUA CUGAUGAGgccGUUAGGCCGAA ICAUAAUA | 14386 |
| 4359 | AAGUUUAC A CCUUUAUC | 5047 | GAUAAAGG CUGAUGAGgccGUUAGGCCGAA IUAAACUU | 14387 |
| 4361 | GUUUACAC C UUUAUCUU | 5048 | AAGAUAAA CUGAUGAGgccGUUAGGCCGAA IGUAAAC | 14388 |
| 4362 | UUUACACC U UAUCUUU | 5049 | AAAGAUAA CUGAUGAGgccGUUAGGCCGAA IGUGUAAA | 14389 |
| 4368 | CCUUUAUC U UUCCAUGG | 5050 | CCAUGGAA CUGAUGAGgccGUUAGGCCGAA IAUAAAGG | 14390 |
| 4372 | UAUCUUUC C AUGGGAGC | 5051 | GCUCCCAU CUGAUGAGgccGUUAGGCCGAA IAAAGAUA | 14391 |
| 4373 | AUCUUUCC A UGGGAGCC | 5052 | GGCUCCCA CUGAUGAGgccGUUAGGCCGAA IGAAAGAU | 14392 |
| 4381 | AUGGGAGC C AGCUGCUU | 5053 | AAGCAGCU CUGAUGAGgccGUUAGGCCGAA ICUCCCAU | 14393 |
| 4382 | UGGGAGCC A GCUGCUUU | 5054 | AAAGCAGC CUGAUGAGgccGUUAGGCCGAA IGCUCCCA | 14394 |
| 4385 | GAGCCAGC U GCUUUUG | 5055 | CAAAAGC CUGAUGAGgccGUUAGGCCGAA ICUGGCUC | 14395 |
| 4388 | CCAGCUGC U UUUGUGA | 5056 | UCACAAAA CUGAUGAGgccGUUAGGCCGAA ICAGCUGG | 14396 |
| 4412 | AAUAGUGC U UUUUUUU | 5057 | AAAAAAAA CUGAUGAGgccGUUAGGCCGAA ICACUAUU | 14397 |
| 4426 | UUUUUGAC U AACAAGAA | 5058 | UUCUUGUU CUGAUGAGgccGUUAGGCCGAA IUCAAAAA | 14398 |
| 4430 | UGACUAAC A AGAAUGUA | 5059 | UACAUUCU CUGAUGAGgccGUUAGGCCGAA IUUAGUCA | 14399 |
| 4441 | AAUGUAAC U CCAGAUAG | 5060 | CUAUCUGG CUGAUGAGgccGUUAGGCCGAA IUUACAUU | 14400 |
| 4443 | UGUAACUC C AGAUAGAG | 5061 | CUCUAUCU CUGAUGAGgccGUUAGGCCGAA IAGUUACA | 14401 |
| 4444 | GUAACUCC A GAUAGAGA | 5062 | UCUCUAUC CUGAUGAGgccGUUAGGCCGAA IGAGUUAC | 14402 |
| 4462 | AUAGUGAC A AGUGAAGA | 5063 | UCUUCACU CUGAUGAGgccGUUAGGCCGAA IUCACUAU | 14403 |
| 4473 | UGAAGAAC A CUACUGCU | 5064 | AGCAGUAG CUGAUGAGgccGUUAGGCCGAA IUUCUUCA | 14404 |
| 4475 | AAGAACAC U ACUGCUAA | 5065 | UUAGCAGU CUGAUGAGgccGUUAGGCCGAA IUGUUCUU | 14405 |
| 4478 | AACACUAC U GCUAAAUC | 5066 | GAUUUAGC CUGAUGAGgccGUUAGGCCGAA IUAGUGUU | 14406 |
| 4481 | ACUACUGC U AAAUCCUC | 5067 | GAGGAUUU CUGAUGAGgccGUUAGGCCGAA ICAGUAGU | 14407 |
| 4487 | GCUAAAUC C UCAUGUUA | 5068 | UACAUGA CUGAUGAGgccGUUAGGCCGAA IAUUUAGC | 14408 |
| 4488 | CUAAAUCC U CAUGUUAC | 5069 | GUAACAUG CUGAUGAGgccGUUAGGCCGAA IGAUUUAG | 14409 |
| 4490 | AAUCCUC A UGUUACUC | 5070 | GAGUAACA CUGAUGAGgccGUUAGGCCGAA IAGGAUUU | 14410 |
| 4497 | CAUGUUAC U CAGUGUUA | 5071 | UAACACUG CUGAUGAGgccGUUAGGCCGAA IUAACAUG | 14411 |
| 4499 | UGUUACUC A GUGUUAGA | 5072 | UCUAACAC CUGAUGAGgccGUUAGGCCGAA IAGUAACA | 14412 |
| 4514 | GAGAAAUC C UUCCUAAA | 5073 | UUUAGGAA CUGAUGAGgccGUUAGGCCGAA IAUUUCUC | 14413 |
| 4515 | AGAAAUCC U UCCUAAAC | 5074 | GUUUAGGA CUGAUGAGgccGUUAGGCCGAA IGAUUUCU | 14414 |
| 4518 | AAUCCUUC C UAAACCCA | 5075 | UUGGGUUA CUGAUGAGgccGUUAGGCCGAA IAAGGAUU | 14415 |
| 4519 | AUCCUUCC U AAACCCAA | 5076 | UUGGGUUU CUGAUGAGgccGUUAGGCCGAA IGAAGGAU | 14416 |
| 4524 | UCCUAAAC C CAAUGACU | 5077 | AGUCAUUG CUGAUGAGgccGUUAGGCCGAA IUUUAGGA | 14417 |
| 4525 | CCUAAACC C AAUGACUU | 5078 | AAGUCAUU CUGAUGAGgccGUUAGGCCGAA IGUUUAGG | 14418 |
| 4526 | CUAAACCC A AUGACUUC | 5079 | GAAGUCAU CUGAUGAGgccGUUAGGCCGAA IGGUUUAG | 14419 |
| 4532 | CCAAUGAC U UCCCUGCU | 5080 | AGCAGGGA CUGAUGAGgccGUUAGGCCGAA IUCAUUGG | 14420 |
| 4535 | AUGACUUC C CUGGUCCA | 5081 | UGGAGCAG CUGAUGAGgccGUUAGGCCGAA IAAGUCAU | 14421 |

TABLE XIV-continued

NCH Ribozyme and Target Sequences

| Pos | Target | Seq ID No | NCH Ribozyme | Seq ID No |
|---|---|---|---|---|
| 4536 | UGACUUCC C UGCUCCAA | 5082 | UUGGAGCA CUGAUGAG<u>GCCGUUAGGC</u>CGAA IGAAGUCA | 14422 |
| 4537 | GACUUCCC U GCUCCAAC | 5083 | GUUGGAGC CUGAUGAG<u>GCCGUUAGGC</u>CGAA IGGAAGUC | 14423 |
| 4540 | UUCCCUGC U CCAACCCC | 5084 | GGGGUUGG CUGAUGAG<u>GCCGUUAGGC</u>CGAA ICAGGGAA | 14424 |
| 4542 | CCCUGCUC C AACCCCCG | 5085 | CGGGGGUU CUGAUGAG<u>GCCGUUAGGC</u>CGAA IAGCAGGG | 14425 |
| 4543 | CCUGCUCC A ACCCCGC | 5086 | GCGGGGGU CUGAUGAG<u>GCCGUUAGGC</u>CGAA IGAGCAGG | 14426 |
| 4546 | GCUCCAAC C CCCGCCAC | 5087 | GUGGCGGG CUGAUGAG<u>GCCGUUAGGC</u>CGAA IUUGGAGC | 14427 |
| 4547 | CUCCAACC C CCGCCACC | 5088 | GGUGGCGG CUGAUGAG<u>GCCGUUAGGC</u>CGAA IGUUGGAG | 14428 |
| 4548 | UCCAACCC C CGCCACCU | 5089 | AGGUGGCG CUGAUGAG<u>GCCGUUAGGC</u>CGAA IGGUUGGA | 14429 |
| 4549 | CCAACCCC C GCCACCUC | 5090 | GAGGUGGC CUGAUGAG<u>GCCGUUAGGC</u>CGAA IGGGUUGG | 14430 |
| 4552 | ACCCCGC C ACCUCAGG | 5091 | CCUGAGGU CUGAUGAG<u>GCCGUUAGGC</u>CGAA ICGGGGGU | 14431 |
| 4553 | CCCCCGCC A CCUCAGGG | 5092 | CCCUGAGG CUGAUGAG<u>GCCGUUAGGC</u>CGAA IGCGGGGG | 14432 |
| 4555 | CCCGCCAC C UCAGGGCA | 5093 | UGCCCUGA CUGAUGAG<u>GCCGUUAGGC</u>CGAA IUGGCGGG | 14433 |
| 4556 | CCGCCACC U CAGGGCAC | 5094 | GUGCCCUG CUGAUGAG<u>GCCGUUAGGC</u>CGAA IGUGGCGG | 14434 |
| 4558 | GCCACCUC A GGGCACGC | 5095 | GCGUGCCC CUGAUGAG<u>GCCGUUAGGC</u>CGAA IAGGUGGC | 14435 |
| 4563 | CUCAGGGC A CGCAGGAC | 5096 | GUCCUGCG CUGAUGAG<u>GCCGUUAGGC</u>CGAA ICCCUGAG | 14436 |
| 4567 | GGGCACGC A GGACCAGU | 5097 | ACUGGUCC CUGAUGAG<u>GCCGUUAGGC</u>CGAA ICGUGCCC | 14437 |
| 4572 | CGCAGGAC C AGUUUGAU | 5098 | AUCAAACU CUGAUGAG<u>GCCGUUAGGC</u>CGAA IUCCUGCG | 14438 |
| 4573 | GCAGGACC A GUUUGAUU | 5099 | AAUCAAAC CUGAUGAG<u>GCCGUUAGGC</u>CGAA IGUCCUGG | 14439 |
| 4589 | UGAGGAGC U GCACUGAU | 5100 | AUCAGUGC CUGAUGAG<u>GCCGUUAGGC</u>CGAA ICUCCUCA | 14440 |
| 4592 | GGAGCUGC A CUGAUCAC | 5101 | GUGAUCAG CUGAUGAG<u>GCCGUUAGGC</u>CGAA ICAGCUCC | 14441 |
| 4594 | AGCUGCAC U GAUCACCC | 5102 | GGGUGAUC CUGAUGAG<u>GCCGUUAGGC</u>CGAA IUGCAGCU | 14442 |
| 4599 | CACUGAUC A CCCAAUGC | 5103 | GCAUUGGG CUGAUGAG<u>GCCGUUAGGC</u>CGAA IAUCAGUG | 14443 |
| 4601 | CUGAUCAC C CAAUGCAU | 5104 | AUGCAUUG CUGAUGAG<u>GCCGUUAGGC</u>CGAA IUGAUCAG | 14444 |
| 4602 | UGAUCACC C AAUGCAUC | 5105 | GAUGCAUU CUGAUGAG<u>GCCGUUAGGC</u>CGAA IGUGAUCA | 14445 |
| 4603 | GAUCACCC A AUGCAUCA | 5106 | UGAUGCAU CUGAUGAG<u>GCCGUUAGGC</u>CGAA IGGUGAUC | 14446 |
| 4608 | CCCAAUGC A UCACGUAC | 5107 | GUACGUGA CUGAUGAG<u>GCCGUUAGGC</u>CGAA ICAUUGGG | 14447 |
| 4611 | AAUGCAUC A CGUACCCC | 5108 | GGGGUACG CUGAUGAG<u>GCCGUUAGGC</u>CGAA IAUGCAUU | 14448 |
| 4617 | UCACGUAC C CCACUGGG | 5109 | CCCAGUGG CUGAUGAG<u>GCCGUUAGGC</u>CGAA IUACGUGA | 14449 |
| 4618 | CACGUACC C CACUGGGC | 5110 | GCCCAGUG CUGAUGAG<u>GCCGUUAGGC</u>CGAA IGUACGUG | 14450 |
| 4619 | ACGUACCC C ACUGGGCC | 5111 | GGCCCAGU CUGAUGAG<u>GCCGUUAGGC</u>CGAA IGGUACGU | 14451 |
| 4620 | CGUACCCC A CUGGGCCA | 5112 | UGGCCCAG CUGAUGAG<u>GCCGUUAGGC</u>CGAA IGGGUACG | 14452 |
| 4622 | UACCCCAC U GGGCCAGC | 5113 | GCUGGCCC CUGAUGAG<u>GCCGUUAGGC</u>CGAA IUGGGGUA | 14453 |
| 4627 | CACUGGGC C AGCCCUGC | 5114 | GCAGGGCU CUGAUGAG<u>GCCGUUAGGC</u>CGAA ICCCAGUG | 14454 |
| 4628 | ACUGGGCC A GCCCUGCA | 5115 | UGCAGGGC CUGAUGAG<u>GCCGUUAGGC</u>CGAA IGCCAGU | 14455 |
| 4631 | GGGCCAGC C CUGCAGCC | 5116 | GGCUGCAG CUGAUGAG<u>GCCGUUAGGC</u>CGAA ICUGGCCC | 14456 |
| 4632 | GGCCAGCC C UGCAGCCC | 5117 | GGGCUGCA CUGAUGAG<u>GCCGUUAGGC</u>CGAA IGCUGGCC | 14457 |
| 4633 | GCCAGCCC U GCAGCCCA | 5118 | UGGGCUGC CUGAUGAG<u>GCCGUUAGGC</u>CGAA IGGCUGGC | 14458 |

TABLE XIV-continued

NCH Ribozyme and Target Sequences

| Pos | Target | Seq ID No | NCH Ribozyme | Seq ID No |
|---|---|---|---|---|
| 4636 | AGCCCUGC A GCCCAAAA | 5119 | UUUUGGGC CUGAUGAGGCCGUUAGGCCGAA ICAGGGCU | 14459 |
| 4639 | CCUGCAGC C CAAAACCC | 5120 | GGGUUUUG CUGAUGAGGCCGUUAGGCCGAA ICUGCAGG | 14460 |
| 4640 | CUGCAGCC C AAAACCCA | 5121 | UGGGUUUU CUGAUGAGGCCGUUAGGCCGAA IGCUGCAG | 14461 |
| 4641 | UGCAGCCC A AAACCCAG | 5122 | CUGGGUUU CUGAUGAGGCCGUUAGGCCGAA IGGCUGCA | 14462 |
| 4646 | CCCAAAAC C CAGGGCAA | 5123 | UUGCCCUG CUGAUGAGGCCGUUAGGCCGAA IUUUUGGG | 14463 |
| 4647 | CCAAAACC C AGGGCAAC | 5124 | GUUGCCCU CUGAUGAGGCCGUUAGGCCGAA IGUUUUGG | 14464 |
| 4648 | CAAAACCC A GGGCAACA | 5125 | UGUUGCCC CUGAUGAGGCCGUUAGGCCGAA IGGUUUUG | 14465 |
| 4653 | CCCAGGGC A CAAGCCC | 5126 | GGGCUUGU CUGAUGAGGCCGUUAGGCCGAA ICCCUGGG | 14466 |
| 4656 | AGGGCAAC A AGCCCGUU | 5127 | AACGGGCU CUGAUGAGGCCGUUAGGCCGAA IUUGCCCU | 14467 |
| 4660 | CAACAAGC C CGUUAGCC | 5128 | GGCUAACG CUGAUGAGGCCGUUAGGCCGAA ICUUGUUG | 14468 |
| 4661 | AACAAGCC C GUUAGCCC | 5129 | GGGCUAAC CUGAUGAGGCCGUUAGGCCGAA IGCUUGUU | 14469 |
| 4668 | CCGUUAGC C CCAGGGGA | 5130 | UCCCCUGG CUGAUGAGGCCGUUAGGCCGAA ICUAACGG | 14470 |
| 4669 | CGUUAGCC C CAGGGGAU | 5131 | AUCCCCUG CUGAUGAGGCCGUUAGGCCGAA IGCUAACG | 14471 |
| 4670 | GUUAGCCC C AGGGGAUC | 5132 | GAUCCCCU CUGAUGAGGCCGUUAGGCCGAA IGGCUAAC | 14472 |
| 4671 | UUAGCCCC A GGGGAUCA | 5133 | UGAUCCCC CUGAUGAGGCCGUUAGGCCGAA IGGGCUAA | 14473 |
| 4679 | AGGGGAUC A CUGGCUGG | 5134 | CCAGCCAG CUGAUGAGGCCGUUAGGCCGAA IAUCCCCU | 14474 |
| 4681 | GGGAUCAC U GGCUGGCC | 5135 | GGCCAGCC CUGAUGAGGCCGUUAGGCCGAA IUGAUCCC | 14475 |
| 4685 | UCACUGGC U GGCCUGAG | 5136 | CUCAGGCC CUGAUGAGGCCGUUAGGCCGAA ICCAGUGA | 14476 |
| 4689 | UGGCUGGC C UGAGCAAC | 5137 | GUUGCUCA CUGAUGAGGCCGUUAGGCCGAA ICCAGCCA | 14477 |
| 4690 | GGCUGGCC U GAGCAACA | 5138 | UGUUGCUC CUGAUGAGGCCGUUAGGCCGAA IGCCAGCC | 14478 |
| 4695 | GCCUGAGC A ACAUCUCG | 5139 | CGAGAUGU CUGAUGAGGCCGUUAGGCCGAA ICUCAGGC | 14479 |
| 4698 | UGAGCAAC A UCUCGGGA | 5140 | UCCCGAGA CUGAUGAGGCCGUUAGGCCGAA IUUGCUCA | 14480 |
| 4701 | GCAACAUC U CGGGAGUC | 5141 | GACUCCCG CUGAUGAGGCCGUUAGGCCGAA IAUGUUGC | 14481 |
| 4710 | CGGGAGUC C UCUAGCAG | 5142 | CUGCUAGA CUGAUGAGGCCGUUAGGCCGAA IACUCCCG | 14482 |
| 4711 | GGGAGUCC U CUAGCAGG | 5143 | CCUGCUAG CUGAUGAGGCCGUUAGGCCGAA IGACUCCC | 14483 |
| 4713 | GAGUCCUC U AGCAGGCC | 5144 | GGCCUGCU CUGAUGAGGCCGUUAGGCCGAA IAGGACUC | 14484 |
| 4717 | CCUCUAGC A GGCCUAAG | 5145 | CUUAGGCC CUGAUGAGGCCGUUAGGCCGAA ICUAGAGG | 14485 |
| 4721 | UAGCAGGC C UAAGACAU | 5146 | AUGUCUUA CUGAUGAGGCCGUUAGGCCGAA ICCUGCUA | 14486 |
| 4722 | AGCAGGCC U AAGACAUG | 5147 | CAUGUCUU CUGAUGAGGCCGUUAGGCCGAA IGCCUGCU | 14487 |
| 4728 | CCUAAGAC A UGUGAGGA | 5148 | UCCUCACA CUGAUGAGGCCGUUAGGCCGAA IUCUUAGG | 14488 |
| 4754 | AAAAAAGC A AAAGCAA | 5149 | UUGCUUUU CUGAUGAGGCCGUUAGGCCGAA ICUUUUUU | 14489 |
| 4761 | CAAAAAGC A AGGGAGAA | 5150 | UUCUCCCU CUGAUGAGGCCGUUAGGCCGAA ICUUUUUG | 14490 |
| 4779 | AGAGAAAC C GGGAGAAG | 5151 | CUUCUCCC CUGAUGAGGCCGUUAGGCCGAA IUUUCUCU | 14491 |
| 4790 | GAGAAGGC A UGAGAAAG | 5152 | CUUUCUCA CUGAUGAGGCCGUUAGGCCGAA ICCUUCUC | 14492 |
| 4811 | UGAGACGC A CCAUGUGG | 5153 | CCACAUGG CUGAUGAGGCCGUUAGGCCGAA ICGUCUCA | 14493 |
| 4813 | AGACGCAC C AUGGGGC | 5154 | GCCCACAU CUGAUGAGGCCGUUAGGCCGAA IUGCGUCU | 14494 |
| 4814 | GACGCACC A UGUGGGCA | 5155 | UGCCCACA CUGAUGAGGCCGUUAGGCCGAA IGUGCGUC | 14495 |

TABLE XIV-continued

NCH Ribozyme and Target Sequences

| Pos | Target | Seq ID No | NCH Ribozyme | Seq ID No |
|---|---|---|---|---|
| 4822 | AUGUGGGC A CGGAGGGG | 5156 | CCCCUCCG CUGAUGAGGCCGUUAGGCCGAA ICCCACAU | 14496 |
| 4839 | GACGGGGC U CAGCAAUG | 5157 | CAUUGCUG CUGAUGAGGCCGUUAGGCCGAA ICCCCGUC | 14497 |
| 4841 | CGGGGCUC A GCAAUGCC | 5158 | GGCAUUGC CUGAUGAGGCCGUUAGGCCGAA IAGCCCCG | 14498 |
| 4844 | GGCUCAGC A AUGCCAUU | 5159 | AAUGGCAU CUGAUGAGGCCGUUAGGCCGAA ICUGAGCC | 14499 |
| 4849 | AGCAAUGC C AUUUCAGU | 5160 | ACUGAAAU CUGAUGAGGCCGUUAGGCCGAA ICAUUGCU | 14500 |
| 4850 | GCAAUGCC A UUUCAGUG | 5161 | CACUGAAA CUGAUGAGGCCGUUAGGCCGAA IGCAUUGC | 14501 |
| 4855 | GCCAUUUC A GUGGCUUC | 5162 | GAAGCCAC CUGAUGAGGCCGUUAGGCCGAA IAAAUGGC | 14502 |
| 4861 | UCAGUGGC U UCCCAGCU | 5163 | AGCUGGGA CUGAUGAGGCCGUUAGGCCGAA ICCACUGA | 14503 |
| 4864 | GUGGCUUC C CAGCUCUG | 5164 | CAGAGCUG CUGAUGAGGCCGUUAGGCCGAA IAAGCCAC | 14504 |
| 4865 | UGGCUUCC C AGCUCUGA | 5165 | UCAGAGCU CUGAUGAGGCCGUUAGGCCGAA IGAAGCCA | 14505 |
| 4866 | GGCUUCCC A GCUCUGAC | 5166 | GUCAGAGC CUGAUGAGGCCGUUAGGCCGAA IGGAAGCC | 14506 |
| 4869 | UUCCCAGC U CUGACCCU | 5167 | AGGGUCAG CUGAUGAGGCCGUUAGGCCGAA ICUGGGAA | 14507 |
| 4871 | CCCAGCUC U GACCCUUC | 5168 | GAAGGGUC CUGAUGAGGCCGUUAGGCCGAA IAGCUGGG | 14508 |
| 4875 | GCUCUGAC C CUUCUACA | 5169 | UGUAGAAG CUGAUGAGGCCGUUAGGCCGAA ICAGAGC | 14509 |
| 4876 | CUCUGACC C UUCUACAU | 5170 | AUGUAGAA CUGAUGAGGCCGUUAGGCCGAA IGUCAGAG | 14510 |
| 4877 | UCUGACCC U UCUACAUU | 5171 | AAUGUAGA CUGAUGAGGCCGUUAGGCCGAA IGGUCAGA | 14511 |
| 4880 | GACCCUUC U ACAUUUGA | 5172 | UCAAAUGU CUGAUGAGGCCGUUAGGCCGAA IAAGGGUC | 14512 |
| 4883 | CCUUCUAC A UUUGAGGG | 5173 | CCCUCAAA CUGAUGAGGCCGUUAGGCCGAA IUAGAAGG | 14513 |
| 4893 | UUGAGGGC C CAGCCAGG | 5174 | CCUGGCUG CUGAUGAGGCCGUUAGGCCGAA ICCCUCAA | 14514 |
| 4894 | UGAGGGCC C AGCCAGGA | 5175 | UCCUGGCU CUGAUGAGGCCGUUAGGCCGAA IGCCCUCA | 14515 |
| 4895 | GAGGGCCC A GCCAGGAG | 5176 | CUCCUGGC CUGAUGAGGCCGUUAGGCCGAA IGGCCCUC | 14516 |
| 4898 | GGCCCAGC C AGGAGCAG | 5177 | CUGCUCCU CUGAUGAGGCCGUUAGGCCGAA ICUGGGCC | 14517 |
| 4899 | GCCCAGCC A GGAGCAGA | 5178 | UCUGCUCC CUGAUGAGGCCGUUAGGCCGAA IGCUGGGC | 14518 |
| 4905 | CCAGGAGC A GAUGGACA | 5179 | UGUCCAUC CUGAUGAGGCCGUUAGGCCGAA ICUCCUGG | 14519 |
| 4913 | AGAUGGAC A GCGAUGAG | 5180 | CUCAUCGC CUGAUGAGGCCGUUAGGCCGAA IUCCAUCU | 14520 |
| 4927 | GAGGGGAC A UUUUCUGG | 5181 | CCAGAAAA CUGAUGAGGCCGUUAGGCCGAA IUCCCCUC | 14521 |
| 4933 | ACAUUUUC U GGAUUCUG | 5182 | CAGAAUCC CUGAUGAGGCCGUUAGGCCGAA IAAAAUGU | 14522 |
| 4940 | CUGGAUUC U GGGAGGCA | 5183 | UGCCUCCC CUGAUGAGGCCGUUAGGCCGAA IAAUCCAG | 14523 |
| 4948 | UGGGAGGC A AGAAAAGG | 5184 | CCUUUUCU CUGAUGAGGCCGUUAGGCCGAA ICCUCCCA | 14524 |
| 4959 | AAAAGGAC A AAUAUCUU | 5185 | AAGAUAUU CUGAUGAGGCCGUUAGGCCGAA IUCCUUUU | 14525 |
| 4966 | CAAAUAUC U UUUUGGA | 5186 | UCCAAAAA CUGAUGAGGCCGUUAGGCCGAA IAUAUUUG | 14526 |
| 4977 | UUUGGAAC U AAAGCAAA | 5187 | UUUGCUUU CUGAUGAGGCCGUUAGGCCGAA IUUCCAAA | 14527 |
| 4983 | ACUAAAGC A AAUUUUAG | 5188 | CUAAAAUU CUGAUGAGGCCGUUAGGCCGAA ICUUUAGU | 14528 |
| 4994 | UUUUAGAC C UUUACCUA | 5189 | UAGGUAAA CUGAUGAGGCCGUUAGGCCGAA ICUAAAA | 14529 |
| 4995 | UUUAGACC U UUACCUAU | 5190 | AUAGGUAA CUGAUGAGGCCGUUAGGCCGAA IGUCUAAA | 14530 |
| 5000 | ACCUUUAC C UAUGGAAG | 5191 | CUUCCAUA CUGAUGAGGCCGUUAGGCCGAA IUAAAGGU | 14531 |
| 5001 | CCUUUACC U AUGGAAGU | 5192 | ACUUCCAU CUGAUGAGGCCGUUAGGCCGAA IGUAAAGG | 14532 |

TABLE XIV-continued

NCH Ribozyme and Target Sequences

| Pos | Target | Seq ID No | NCH Ribozyme | Seq ID No |
|---|---|---|---|---|
| 5015 | AGUGGUUC U AUGUCCAU | 5193 | AUGGACAU CUGAUGAGGCCGUUAGGCCGAA IAACCACU | 14533 |
| 5021 | UCUAUGUC C AUUCUCAU | 5194 | AUGAGAAU CUGAUGAGGCCGUUAGGCCGAA IACAUAGA | 14534 |
| 5022 | CUAUGUCC A UUCUCAUU | 5195 | AAUGAGAA CUGAUGAGGCCGUUAGGCCGAA IGACAUAG | 14535 |
| 5026 | GUCCAUUC U CAUUCGUG | 5196 | CACGAAUG CUGAUGAGGCCGUUAGGCCGAA IAAUGGAC | 14536 |
| 5028 | CCAUUCUC A UUCGUGGC | 5197 | GCCACGAA CUGAUGAGGCCGUUAGGCCGAA IAGAAUGG | 14537 |
| 5037 | UUCGUGGC A UGUUUUGA | 5198 | UCAAAACA CUGAUGAGGCCGUUAGGCCGAA ICCACGAA | 14538 |
| 5054 | UUUGUAGC A CUGAGGGU | 5199 | ACCCUCAG CUGAUGAGGCCGUUAGGCCGAA ICUACAAA | 14539 |
| 5056 | UGUAGCAC U GAGGGUGG | 5200 | CCACCCUC CUGAUGAGGCCGUUAGGCCGAA IUGCUACA | 14540 |
| 5066 | AGGGUGGC A CUCAACUC | 5201 | GAGUUGAG CUGAUGAGGCCGUUAGGCCGAA ICCACCCU | 14541 |
| 5068 | GGUGGCAC U CAACUCUG | 5202 | CAGAGUUG CUGAUGAGGCCGUUAGGCCGAA IUGCCACC | 14542 |
| 5070 | UGGCACUC A ACUCUGAG | 5203 | CUCAGAGU CUGAUGAGGCCGUUAGGCCGAA IAGUGCCA | 14543 |
| 5073 | CACUCAAC U CUGAGCCC | 5204 | GGGCUCAG CUGAUGAGGCCGUUAGGCCGAA IUUGAGUG | 14544 |
| 5075 | CUCAACUC U GAGCCCAU | 5205 | AUGGGCUC CUGAUGAGGCCGUUAGGCCGAA IAGUUGAG | 14545 |
| 5080 | CUCUGAGC C CAUACUUU | 5206 | AAAGUAUG CUGAUGAGGCCGUUAGGCCGAA ICUCAGAG | 14546 |
| 5081 | UCUGAGCC C AUACUUUU | 5207 | AAAAGUAU CUGAUGAGGCCGUUAGGCCGAA IGCUCAGA | 14547 |
| 5082 | CUGAGCCC A UACUUUUG | 5208 | CAAAAGUA CUGAUGAGGCCGUUAGGCCGAA IGGCUCAG | 14548 |
| 5086 | GCCCAUAC U UUGGCUC | 5209 | GAGCCAAA CUGAUGAGGCCGUUAGGCCGAA IUAUGGGC | 14549 |
| 5093 | CUUUUGGC U CCUCUAGU | 5210 | ACUAGAGG CUGAUGAGGCCGUUAGGCCGAA ICCAAAAG | 14550 |
| 5095 | UUUGGCUC C UCUAGUAA | 5211 | UUACUAGA CUGAUGAGGCCGUUAGGCCGAA IAGCCAAA | 14551 |
| 5096 | UUGGCUCC U CUAGUAAG | 5212 | CUUACUAG CUGAUGAGGCCGUUAGGCCGAA IGAGCCAA | 14552 |
| 5098 | GGCUCCUC U AGUAAGAU | 5213 | AUCUUACU CUGAUGAGGCCGUUAGGCCGAA IAGGAGCC | 14553 |
| 5109 | UAAGAUGC A CUGAAAAC | 5214 | GUUUUCAG CUGAUGAGGCCGUUAGGCCGAA ICAUCUUA | 14554 |
| 5111 | AGAUGCAC U GAAAACUU | 5215 | AAGUUUUC CUGAUGAGGCCGUUAGGCCGAA IUGCAUCU | 14555 |
| 5118 | CUGAAAAC U UAGCCAGA | 5216 | UCUGGCUA CUGAUGAGGCCGUUAGGCCGAA IUUUUCAG | 14556 |
| 5123 | AACUUAGC C AGAGUUAG | 5217 | CUAACUCU CUGAUGAGGCCGUUAGGCCGAA ICUAAGUU | 14557 |
| 5124 | ACUUAGCC A GAGUUAGG | 5218 | CCUAACUC CUGAUGAGGCCGUUAGGCCGAA IGCUAAGU | 14558 |
| 5138 | AGGUUGUC U CCAGGCCA | 5219 | UGGCCUGG CUGAUGAGGCCGUUAGGCCGAA IACAACCU | 14559 |
| 5140 | GUUGUCUC C AGGCCAUG | 5220 | CAUGGCCU CUGAUGAGGCCGUUAGGCCGAA IAGACAAC | 14560 |
| 5141 | UUGUCUCC A GGCCAUGA | 5221 | UCAUGGCC CUGAUGAGGCCGUUAGGCCGAA IGAGACAA | 14561 |
| 5145 | CUCCAGGC C AUGAUGGC | 5222 | GCCAUCAU CUGAUGAGGCCGUUAGGCCGAA ICCUGGAG | 14562 |
| 5146 | UCCAGGCC A UGAUGGCC | 5223 | GGCCAUCA CUGAUGAGGCCGUUAGGCCGAA IGCCUGGA | 14563 |
| 5154 | AUGAUGGC C UUACACUG | 5224 | CAGUGUAA CUGAUGAGGCCGUUAGGCCGAA ICCAUCAU | 14564 |
| 5155 | UGAUGGCC U UACACUGA | 5225 | UCAGUGUA CUGAUGAGGCCGUUAGGCCGAA IGCCAUCA | 14565 |
| 5159 | GGCCUUAC A CUGAAAAU | 5226 | AUUUUCAG CUGAUGAGGCCGUUAGGCCGAA IUAAGGCC | 14566 |
| 5161 | CCUUACAC U GAAAAUGU | 5227 | ACAUUUUC CUGAUGAGGCCGUUAGGCCGAA IUGUAAGG | 14567 |
| 5171 | AAAAUGUC A CAUUCUAU | 5228 | AUAGAAUG CUGAUGAGGCCGUUAGGCCGAA ICAUUUUU | 14568 |
| 5173 | AAUGUCAC A UUCUAUUU | 5229 | AAAUAGAA CUGAUGAGGCCGUUAGGCCGAA IUGACAUU | 14569 |

TABLE XIV-continued

NCH Ribozyme and Target Sequences

| Pos | Target | Seq ID No | NCH Ribozyme | Seq ID No |
|---|---|---|---|---|
| 5177 | UCACAUUC U AUUUUGGG | 5230 | CCCAAAAU CUGAUGAGGCCGUUAGGCCGAA IAAUGUGA | 14570 |
| 5201 | AUAUAGUC C AGACACUU | 5231 | AAGUGUCU CUGAUGAGGCCGUUAGGCCGAA IACUAUAU | 14571 |
| 5202 | UAUAGUCC A GACACUUA | 5232 | UAAGUGUC CUGAUGAGGCCGUUAGGCCGAA IGACUAUA | 14572 |
| 5206 | GUCCAGAC A CUUAACUC | 5233 | GAGUUAAG CUGAUGAGGCCGUUAGGCCGAA IUCUGGAC | 14573 |
| 5208 | CCAGACAC U UAACUCAA | 5234 | UUGAGUUA CUGAUGAGGCCGUUAGGCCGAA IGUGUCUGG | 14574 |
| 5213 | CACUUAAC U CAAUUUCU | 5235 | AGAAAUUG CUGAUGAGGCCGUUAGGCCGAA IUUAAGUG | 14575 |
| 5215 | CUUAACUC A AUUUCUUG | 5236 | CAAGAAAU CUGAUGAGGCCGUUAGGCCGAA IAGUUAAG | 14576 |
| 5221 | UCAAUUUC U UGGUAUUA | 5237 | UAAUACCA CUGAUGAGGCCGUUAGGCCGAA IAAAUUGA | 14577 |
| 5233 | UAUUAUUC U GUUUUGCA | 5238 | UGCAAAAC CUGAUGAGGCCGUUAGGCCGAA IAAUAAUA | 14578 |
| 5241 | UGUUUUGC A CAGUUAGU | 5239 | ACUAACUG CUGAUGAGGCCGUUAGGCCGAA ICAAAACA | 14579 |
| 5243 | UUUUGCAC A GUUAGUUG | 5240 | CAACUAAC CUGAUGAGGCCGUUAGGCCGAA IUGCAAAA | 14580 |
| 5263 | AAGAAAGC U GAGAAGAA | 5241 | UUCUUCUC CUGAUGAGGCCGUUAGGCCGAA ICUUUCUU | 14581 |
| 5281 | GAAAAUGC A GUCCUGAG | 5242 | CUCAGGAC CUGAUGAGGCCGUUAGGCCGAA ICAUUUUC | 14582 |
| 5285 | AUGCAGUC C UGAGGAGA | 5243 | UCUCCUCA CUGAUGAGGCCGUUAGGCCGAA IACUGCAU | 14583 |
| 5286 | UGCAGUCC U GAGGAGAG | 5244 | CUCUCCUC CUGAUGAGGCCGUUAGGCCGAA IGACUGCA | 14584 |
| 5300 | GAGUUUUC U CCAUAUCA | 5245 | UGAUAUGG CUGAUGAGGCCGUUAGGCCGAA IAAAACUC | 14585 |
| 5302 | GUUUUCUC C AUAUCAAA | 5246 | UUUGAUAU CUGAUGAGGCCGUUAGGCCGAA IAGAAAAC | 14586 |
| 5303 | UUUUCUCC A UAUCAAAA | 5247 | UUUUGAUA CUGAUGAGGCCGUUAGGCCGAA IGAGAAAA | 14587 |
| 5308 | UCCAUAUC A AAACGAGG | 5248 | CCUCGUUU CUGAUGAGGCCGUUAGGCCGAA IAUAUGGA | 14588 |
| 5319 | ACGAGGGC U GAUGGAGG | 5249 | CCUCCAUC CUGAUGAGGCCGUUAGGCCGAA ICCCUCGU | 14589 |
| 5337 | AAAAGGUC A AUAAGGUC | 5250 | GACCUUAU CUGAUGAGGCCGUUAGGCCGAA IACCUUUU | 14590 |
| 5346 | AUAAGGUC A AGGGAAGA | 5251 | UCUUCCCU CUGAUGAGGCCGUUAGGCCGAA IACCUUAU | 14591 |
| 5356 | GGGAAGAC C CCGUCUCU | 5252 | AGAGACGG CUGAUGAGGCCGUUAGGCCGAA IUCUUCCC | 14592 |
| 5357 | GGAAGACC C CGUCUCUA | 5253 | UAGAGACG CUGAUGAGGCCGUUAGGCCGAA IGUCUUCC | 14593 |
| 5358 | GAAGACCC C GUCUCUAU | 5254 | AUAGAGAC CUGAUGAGGCCGUUAGGCCGAA IGGUCUUC | 14594 |
| 5362 | ACCCGUC U CUAUACCA | 5255 | UGGUAUAG CUGAUGAGGCCGUUAGGCCGAA IACGGGU | 14595 |
| 5364 | CCCGUCUC U AUACCAAC | 5256 | GUUGGUAU CUGAUGAGGCCGUUAGGCCGAA IAGACGGG | 14596 |
| 5369 | CUCUAUAC C AACCAAAC | 5257 | GUUUGGUU CUGAUGAGGCCGUUAGGCCGAA IUAUAGAG | 14597 |
| 5370 | UCUAUACC A ACCAAACC | 5258 | GGUUUGGU CUGAUGAGGCCGUUAGGCCGAA IGUAUAGA | 14598 |
| 5373 | AUACCAAC C AAACCAAU | 5259 | AUUGGUUU CUGAUGAGGCCGUUAGGCCGAA IUUGGUAU | 14599 |
| 5374 | UACCAACC A AACCAAUU | 5260 | AAUUGGUU CUGAUGAGGCCGUUAGGCCGAA IGUUGGUA | 14600 |
| 5378 | AACCAAAC C AAUUCACC | 5261 | GGUGAAUU CUGAUGAGGCCGUUAGGCCGAA IUUUGGUU | 14601 |
| 5379 | ACCAAACC A AUUCACCA | 5262 | UGGUGAAU CUGAUGAGGCCGUUAGGCCGAA IGUUUGGU | 14602 |
| 5384 | ACCAAUUC A CCAACACA | 5263 | UGUGUUGG CUGAUGAGGCCGUUAGGCCGAA IAAUUGGU | 14603 |
| 5386 | CAAUUCAC C AACACAGU | 5264 | ACUGUGUU CUGAUGAGGCCGUUAGGCCGAA IUGAAUUG | 14604 |
| 5387 | AAUUCACC A ACACAGUU | 5265 | AACUGUGU CUGAUGAGGCCGUUAGGCCGAA IGUGAAUU | 14605 |
| 5390 | UCACCAAC A CAGUUGGG | 5266 | CCCAACUG CUGAUGAGGCCGUUAGGCCGAA IUUGGUGA | 14606 |

TABLE XIV-continued

NCH Ribozyme and Target Sequences

| Pos | Target | Seq ID No | NCH Ribozyme | Seq ID No |
|---|---|---|---|---|
| 5392 | ACCAACAC A GUUGGGAC | 5267 | GUCCCAAC CUGAUGAGGCCGUUAGGCCGAA IUGUUGGU | 14607 |
| 5401 | GUUGGGAC C CAAAACAC | 5268 | GUGUUUUG CUGAUGAGGCCGUUAGGCCGAA IUCCCAAC | 14608 |
| 5402 | UUGGGACC C AAAACACA | 5269 | UGUGUUUU CUGAUGAGGCCGUUAGGCCGAA IGUCCCAA | 14609 |
| 5403 | UGGGACCC A AAACACAG | 5270 | CUGUGUUU CUGAUGAGGCCGUUAGGCCGAA IGGUCCCA | 14610 |
| 5408 | CCCAAAAC A CAGGAAGU | 5271 | ACUUCCUG CUGAUGAGGCCGUUAGGCCGAA IUUUUGGG | 14611 |
| 5410 | CAAAACAC A GGAAGUCA | 5272 | UGACUUCC CUGAUGAGGCCGUUAGGCCGAA IGUGUUUG | 14612 |
| 5418 | AGGAAGUC A GUCACGUU | 5273 | AACGUGAC CUGAUGAGGCCGUUAGGCCGAA IACUUCCU | 14613 |
| 5422 | AGUCAGUC A CGUUCCU | 5274 | AGGAAACG CUGAUGAGGCCGUUAGGCCGAA IACUGACU | 14614 |
| 5429 | CACGUUUC C UUUUCAUU | 5275 | AAUGAAAA CUGAUGAGGCCGUUAGGCCGAA IAAACGUG | 14615 |
| 5430 | ACGUUUCC U UUUCAUUU | 5276 | AAAUGAAA CUGAUGAGGCCGUUAGGCCGAA IGAAACGU | 14616 |
| 5435 | UCCUUUUC A UUUAAUGG | 5277 | CCAUUAAA CUGAUGAGGCCGUUAGGCCGAA IAAAAGGA | 14617 |
| 5450 | GGGAUUC C ACUAUCUC | 5278 | GAGAUAGU CUGAUGAGGCCGUUAGGCCGAA IAAUCCCC | 14618 |
| 5451 | GGGAUUCC A CUAUCCA | 5279 | UGAGAUAG CUGAUGAGGCCGUUAGGCCGAA IGAAUCCC | 14619 |
| 5453 | GAUUCCAC U AUCUCACA | 5280 | UGUGAGAU CUGAUGAGGCCGUUAGGCCGAA IUGGAAUC | 14620 |
| 5457 | CCACUAUC U CACACUAA | 5281 | UUAGUGUG CUGAUGAGGCCGUUAGGCCGAA IAUAGUGG | 14621 |
| 5459 | ACUAUCUC A CACUAAUC | 5282 | GAUUAGUG CUGAUGAGGCCGUUAGGCCGAA IAGAUAGU | 14622 |
| 5461 | UAUCUCAC A CUAAUCUG | 5283 | CAGACUAG CUGAUGAGGCCGUUAGGCCGAA IUGAGAUA | 14623 |
| 5463 | UCUCACAC U AAUCUGAA | 5284 | UUCAGAUU CUGAUGAGGCCGUUAGGCCGAA IUGUGAGA | 14624 |
| 5468 | CACUAAUC U GAAAGGAU | 5285 | AUCCUUUC CUGAUGAGGCCGUUAGGCCGAA IAUUAGUG | 14625 |
| 5487 | GGAAGAGC A UUAGCUGG | 5286 | CCAGCUAA CUGAUGAGGCCGUUAGGCCGAA ICUCUUCC | 14626 |
| 5493 | GCAUUAGC U GGCGCAUA | 5287 | UAUGCGCC CUGAUGAGGCCGUUAGGCCGAA ICUAAUGC | 14627 |
| 5499 | GCUGGCGC A UAUUAAGC | 5288 | GCUUAAUA CUGAUGAGGCCGUUAGGCCGAA ICGCCAGC | 14628 |
| 5508 | UAUUAAGC A CUUUAAGC | 5289 | GCUUAAAG CUGAUGAGGCCGUUAGGCCGAA ICUUAAUA | 14629 |
| 5510 | UUAAGCAC U UUAAGCUC | 5290 | GAGCUUAA CUGAUGAGGCCGUUAGGCCGAA IUGCUUAA | 14630 |
| 5517 | CUUUAAGC U CCUUGAGU | 5291 | ACUCAAGG CUGAUGAGGCCGUUAGGCCGAA ICUUAAAG | 14631 |
| 5519 | UUAAGCUC C UUGAGUAA | 5292 | UUACUCAA CUGAUGAGGCCGUUAGGCCGAA IAGCUUAA | 14632 |
| 5520 | UAAGCUCC U UGAGUAAA | 5293 | UUUACUCA CUGAUGAGGCCGUUAGGCCGAA IGAGCUUA | 14633 |
| 5550 | AUUUAUGC A AGGUAUUU | 5294 | AAAUACCU CUGAUGAGGCCGUUAGGCCGAA ICAUAAAU | 14634 |
| 5560 | GGUAUUUC U CCAGUUGG | 5295 | CCAACUGG CUGAUGAGGCCGUUAGGCCGAA IAAAUACC | 14635 |
| 5562 | UAUUUCUC C AGUUGGGA | 5296 | UCCCAACU CUGAUGAGGCCGUUAGGCCGAA IAGAAAUA | 14636 |
| 5563 | AUUUCUCC A GUUGGGAC | 5297 | GUCCCAAC CUGAUGAGGCCGUUAGGCCGAA IGAGAAAU | 14637 |
| 5572 | GUUGGGAC U CAGGAUAU | 5298 | AUACCUG CUGAUGAGGCCGUUAGGCCGAA IUCCCAAC | 14638 |
| 5574 | UGGGACUC A GGAUAUUA | 5299 | UAAUAUCC CUGAUGAGGCCGUUAGGCCGAA IAGUCCCA | 14639 |
| 5593 | UAAUGAGC C AUCACUAG | 5300 | CUAGUGAU CUGAUGAGGCCGUUAGGCCGAA ICUCAUUA | 14640 |
| 5594 | AAUGAGCC A UCACUAGA | 5301 | UCUAGUGA CUGAUGAGGCCGUUAGGCCGAA IGCUCAUU | 14641 |
| 5597 | GAGCCAUC A CUAGAAGA | 5302 | UCUUCUAG CUGAUGAGGCCGUUAGGCCGAA IAUGGCUC | 14642 |
| 5599 | GCCAUCAC U AGAAGAAA | 5303 | UUUCUUCU CUGAUGAGGCCGUUAGGCCGAA IUGAUGGC | 14643 |

TABLE XIV-continued

NCH Ribozyme and Target Sequences

| Pos | Target | Seq ID No | NCH Ribozyme | Seq ID No |
|---|---|---|---|---|
| 5611 | AGAAAAGC C CAUUUUCA | 5304 | UGAAAAUG CUGAUGAGGCCGUUAGGCCGAA ICUUUUCU | 14644 |
| 5612 | GAAAAGCC C AUUUUCAA | 5305 | UUGAAAAU CUGAUGAGGCCGUUAGGCCGAA IGCUUUUC | 14645 |
| 5613 | AAAAGCCC A UUUUCAAC | 5306 | GUUGAAAA CUGAUGAGGCCGUUAGGCCGAA IGGCUUUU | 14646 |
| 5619 | CCAUUUUC A ACUGCUUU | 5307 | AAAGCAGU CUGAUGAGGCCGUUAGGCCGAA IAAAAUGG | 14647 |
| 5622 | UUUUCAAC U GCUUUGAA | 5308 | UUCAAAGC CUGAUGAGGCCGUUAGGCCGAA IUUGAAAA | 14648 |
| 5625 | UCAACUGC U UUGAAACU | 5309 | AGUUUCAA CUGAUGAGGCCGUUAGGCCGAA ICAGUUGA | 14649 |
| 5633 | UUUGAAAC U UGCCUGGG | 5310 | CCCAGGCA CUGAUGAGGCCGUUAGGCCGAA IUUUCAAA | 14650 |
| 5637 | AAACUUGC C UGGGUCU | 5311 | AGACCCCA CUGAUGAGGCCGUUAGGCCGAA ICAAGUUU | 14651 |
| 5638 | AACUUGCC U GGGUCUG | 5312 | CAGACCCC CUGAUGAGGCCGUUAGGCCGAA IGCAAGUU | 14652 |
| 5645 | CUGGGGUC U GAGCAUGA | 5313 | UCAUGCUC CUGAUGAGGCCGUUAGGCCGAA IACCCCAG | 14653 |
| 5650 | GUCUGAGC A UGAUGGGA | 5314 | UCCCAUCA CUGAUGAGGCCGUUAGGCCGAA ICUCAGAC | 14654 |
| 5669 | AGGGAGAC A GGGUAGGA | 5315 | UCCUACCC CUGAUGAGGCCGUUAGGCCGAA IUCUCCCU | 14655 |
| 5686 | AAGGGCGC C UACUCUUC | 5316 | GAAGAGUA CUGAUGAGGCCGUUAGGCCGAA ICGCCCUU | 14656 |
| 5687 | AGGGCGCC U ACUCUUCA | 5317 | UGAAGAGU CUGAUGAGGCCGUUAGGCCGAA IGCGCCCU | 14657 |
| 5690 | GCGCCUAC U CUUCAGGG | 5318 | CCCUGAAG CUGAUGAGGCCGUUAGGCCGAA IUAGGCGC | 14658 |
| 5692 | GCCUACUC U UCAGGGUC | 5319 | GACCCUGA CUGAUGAGGCCGUUAGGCCGAA IAGUAGGC | 14659 |
| 5695 | UACUCUUC A GGGUCUAA | 5320 | UUAGACCC CUGAUGAGGCCGUUAGGCCGAA IAAGAGUA | 14660 |
| 5701 | UCAGGGUC U AAAGAUCA | 5321 | UGAUCUUU CUGAUGAGGCCGUUAGGCCGAA IACCCUGA | 14661 |
| 5709 | UAAAGAUC A AGUGGGCC | 5322 | GGCCCACU CUGAUGAGGCCGUUAGGCCGAA IAUCUUUA | 14662 |
| 5717 | AAGUGGGC C UUGGAUCG | 5323 | CGAUCCAA CUGAUGAGGCCGUUAGGCCGAA ICCCACUU | 14663 |
| 5718 | AGUGGGCC U UGGAUCGC | 5324 | GCGAUCCA CUGAUGAGGCCGUUAGGCCGAA IGCCCACU | 14664 |
| 5727 | UGGAUCGC U AAGCUGGC | 5325 | GCCAGCUU CUGAUGAGGCCGUUAGGCCGAA ICGAUCCA | 14665 |
| 5732 | CGCUAAGC U GGCUCUGU | 5326 | ACAGAGCC CUGAUGAGGCCGUUAGGCCGAA ICUUAGCG | 14666 |
| 5736 | AAGCUGGC U CUGUUUGA | 5327 | UCAAACAG CUGAUGAGGCCGUUAGGCCGAA ICCAGCUU | 14667 |
| 5738 | GCUGGCUC U GUUUGAUG | 5328 | CAUCAAAC CUGAUGAGGCCGUUAGGCCGAA IAGCCAGC | 14668 |
| 5748 | UUUGAUGC U AUUUAUGC | 5329 | GCAUAAAU CUGAUGAGGCCGUUAGGCCGAA ICAUCAAA | 14669 |
| 5757 | AUUUAUGC A AGUUAGGG | 5330 | CCCUAACU CUGAUGAGGCCGUUAGGCCGAA ICAUAAAU | 14670 |
| 5768 | UUAGGGUC U AUGUAUUU | 5331 | AAAUACAU CUGAUGAGGCCGUUAGGCCGAA IACCCUAA | 14671 |
| 5786 | GGAUGCGC C UACUCUUC | 5332 | GAAGAGUA CUGAUGAGGCCGUUAGGCCGAA ICGCAUCC | 14672 |
| 5787 | GAUGCGCC U ACUCUUCA | 5333 | UGAAGAGU CUGAUGAGGCCGUUAGGCCGAA IGCGCAUC | 14673 |
| 5790 | GCGCCUAC U CUUCAGGG | 5318 | CCCUGAAG CUGAUGAGGCCGUUAGGCCGAA IUAGGCGC | 14658 |
| 5792 | GCCUACUC U UCAGGGUC | 5319 | GACCCUGA CUGAUGAGGCCGUUAGGCCGAA IAGUAGGC | 14659 |
| 5795 | UACUCUUC A GGGUCUAA | 5320 | UUAGACCC CUGAUGAGGCCGUUAGGCCGAA IAAGAGUA | 14660 |
| 5801 | UCAGGGUC U AAAGAUCA | 5321 | UGAUCUUU CUGAUGAGGCCGUUAGGCCGAA IACCCUGA | 14661 |
| 5809 | UAAAGAUC A AGUGGGCC | 5322 | GGCCCACU CUGAUGAGGCCGUUAGGCCGAA IAUCUUUA | 14662 |
| 5817 | AAGUGGGC C UUGGAUCG | 5323 | CGAUCCAA CUGAUGAGGCCCUUAGGCCGAA ICCCACUU | 14663 |
| 5818 | AGUGGGCC U UGGAUCGC | 5324 | GCGAUCCA CUGAUGAGGCCGUUAGGCCGAA IGCCCACU | 14664 |

TABLE XIV-continued

NCH Ribozyme and Target Sequences

| Pos | Target | Seq ID No | NCH Ribozyme | Seq ID No |
|---|---|---|---|---|
| 5827 | UGGAUCGC U AAGCUGGC | 5325 | GCCAGCUU CUGAUGAGGCCGUUAGGCCGAA ICGAUCCA | 14665 |
| 5832 | CGCUAAGC U GGCUCUGU | 5326 | ACAGAGCC CUGAUGAGGCCGUUAGGCCGAA ICUUAGCG | 14666 |
| 5836 | AAGCUGGC U CUGUUUGA | 5327 | UCAAACAG CUGAUGAGGCCGUUACGCCGAA ICCAGCUU | 14667 |
| 5838 | GCUGGCUC U GUUUGAUG | 5328 | CAUCAAAC CUGAUGAGGCCGUUAGGCCGAA IAGCCAGC | 14668 |
| 5848 | UUUGAUGC U AUUUAUGC | 5329 | GCAUAAAU CUGAUGAGGCCCUUAGGCCGAA ICAUCAAA | 14669 |
| 5857 | AUUUAUGC A AGUUAGGG | 5330 | CCCUAACU CUGAUGAGGCCGUUAGGCCGAA ICAUAAAU | 14670 |
| 5868 | UUAGGGUC U AUGUAUUU | 5331 | AAAUACAU CUGAUGAGGCCGUUAGGCCGAA IACCCUAA | 14671 |
| 5885 | AGGAUGUC U GCACCUUC | 5334 | GAAGGUGC CUGAUGAGGCCGUUAGGCCGAA IACAUCCU | 14674 |
| 5888 | AUGUCUGC A CCUUCGC | 5335 | GCAGAAGG CUGAUGAGGCCCUUAGGCCGAA ICAGACAU | 14675 |
| 5890 | GUCUGCAC C UUCUGCAG | 5336 | CUGCAGAA CUGAUGAGGCCGUUAGGCCGAA IUGCAGAC | 14676 |
| 5891 | UCUGCACC U UCUGCAGC | 5337 | GCUGCAGA CUGAUGAGGCCGUUAGGCCGAA IGUGCAGA | 14677 |
| 5894 | GCACCUUC U GCAGCCAG | 5338 | CUGGCUGC CUGAUGAGGCCGUUAGGCCGAA IAAGGUGC | 14678 |
| 5897 | CCUUCUGC A GCCAGUCA | 5339 | UGACUGGC CUGAUGAGGCCGUUAGGCCGAA ICAGAAGG | 14679 |
| 5900 | UCUGCAGC C AGUCAGAA | 5340 | UUCUGACU CUGAUGAGGCCGUUAGGCCGAA ICUGCAGA | 14680 |
| 5901 | CUGCAGCC A GUCAGAAG | 5341 | CUUCUGAC CUGAUGAGGCCGUUAGGCCGAA IGCUGCAG | 14681 |
| 5905 | AGCCAGUC A GAAGCUGG | 5342 | CCAGCUUC CUGAUGAGGCCGUUAGGCCGAA IACUGGCU | 14682 |
| 5911 | UCAGAAGC U GGAGAGGC | 5343 | GCCUCUCC CUGAUGAGGCCGUUAGGCCGAA ICUUCUGA | 14683 |
| 5920 | GGAGAGGC A ACAGUGGA | 5344 | UCCACUGU CUGAUGAGGCCGUUAGGCCGAA ICCUCUCC | 14684 |
| 5923 | GAGGCAAC A GUGGAUUG | 5345 | CAAUCCAC CUGAUGAGGCCGUUAGGCCGAA IUUGCCUC | 14685 |
| 5933 | UGGAUUGC U GCUUCUUG | 5346 | CAAGAAGC CUGAUGAGGCCGUUAGGCCGAA ICAAUCCA | 14686 |
| 5936 | AUUGCUGC U UCUUGGGG | 5347 | CCCCAAGA CUGAUGAGGCCGUUAGGCCGAA ICAGCAAU | 14687 |
| 5939 | GCUGCUUC U UGGGGAGA | 5348 | UCUCCCCA CUGAUGAGGCCGUUAGGCCGAA IAAGCAGC | 14688 |
| 5957 | GAGUAUGC U UCCUUUUA | 5349 | UAAAAGGA CUGAUGAGGCCGUUAGGCCGAA ICAUACUC | 14689 |
| 5960 | UAUGCUUC C UUUUAUCC | 5350 | GGAUAAAA CUGAUGAGGCCGUUAGGCCGAA IAAGCAUA | 14690 |
| 5961 | AUGCUUCC U UUUAUCCA | 5351 | UGGAUAAA CUGAUGAGGCCGUUAGGCCGAA IGAAGCAU | 14691 |
| 5968 | CUUUUAUC C AUGUAAUU | 5352 | AAUUACAU CUGAUGAGGCCGUUAGGCCGAA IAUAAAAG | 14692 |
| 5969 | UUUUAUCC A UGUAAUUU | 5353 | AAAUUACA CUGAUGAGGCCGUUAGGCCGAA IGAUAAAA | 14693 |
| 5981 | AAUUUAAC U GUAGAACC | 5354 | GGUUCUAC CUGAUGAGGCCGUUAGGCCGAA IUUAAAUU | 14694 |
| 5989 | UGUAGAAC C UGAGCUCU | 5355 | AGAGCUCA CUGAUGAGGCCGUUACGCCGAA IUUCUACA | 14695 |
| 5990 | GUAGAACC U GAGCUCUA | 5356 | UAGAGCUC CUGAUGAGGCCGUUAGGCCGAA IGUUCUAC | 14696 |
| 5995 | ACCUGAGC U CUAAGUAA | 5357 | UUACUUAG CUGAUGAGGCCGUUAGGCCGAA ICUCAGGU | 14697 |
| 5997 | CUGAGCUC U AAGUAACC | 5358 | GGUUACUU CUGAUGAGGCCGUUAGGCCGAA IACCUCAG | 14698 |
| 6005 | UAAGUAAC C GAAGAAUG | 5359 | CAUUCUUC CUGAUGAGGCCGUUAGGCCGAA IUUACUUA | 14699 |
| 6019 | AUGUAUGC C UCUGUUCU | 5360 | AGAACAGA CUGAUGAGGCCGUUAGGCCGAA ICAUACAU | 14700 |
| 6020 | UGUAUGCC U CUGUUCUU | 5361 | AAGAACAG CUGAUGAGGCCGUUAGGCCGAA IGCAUACA | 14701 |
| 6022 | UAUGCCUC U GUUCUUAU | 5362 | AUAAGAAC CUGAUGAGGCCGUUAGGCCGAA IAGGCAUA | 14702 |
| 6027 | CUCUGUUC U UAUGUGCC | 5363 | GGCACAUA CUGAUGAGGCCGUUAGGCCGAA IAACAGAG | 14703 |

TABLE XIV-continued

NCH Ribozyme and Target Sequences

| Pos | Target | Seq ID No | NCH Ribozyme | Seq ID No |
|---|---|---|---|---|
| 6035 | UUAUGUGC C ACAUCCUU | 5364 | AAGGAUGU CUGAUGAGGCCGUUAGGCCGAA ICACAUAA | 14704 |
| 6036 | UAUGUGCC A CAUCCUUG | 5365 | CAAGGAUG CUGAUGAGGCCGUUAGGCCGAA IGCACAUA | 14705 |
| 6038 | UGUGCCAC A UCCUUGUU | 5366 | AACAAGGA CUGAUGAGGCCGUUAGGCCGAA IUGGCACA | 14706 |
| 6041 | GCCACAUC C UUGUUAA | 5367 | UUAAACAA CUGAUGAGGCCGUUAGGCCGAA IAUGUGGC | 14707 |
| 6042 | CCACAUCC U UGUUUAAA | 5368 | UUUAAACA CUGAUGAGGCCGUUAGGCCGAA ICAUGUGG | 14708 |
| 6054 | UUAAAGGC U CUCUGUAU | 5369 | AUACAGAG CUGAUGAGGCCGUUAGGCCGAA ICCUUUAA | 14709 |
| 6056 | AAAGGCUC U CUGUAUGA | 5370 | UCAUACAG CUGAUGAGGCCGUUAGGCCGAA IAGCCUUU | 14710 |
| 6058 | AGGCUCUC U GUAUGAAG | 5371 | CUUCAUAC CUGAUGAGGCCGUUAGGCCGAA IAGAGCCU | 14711 |
| 6076 | GAUGGGAC C GUCAUCAG | 5372 | CUGAUGAC CUGAUGAGGCCGUUAGGCCGAA IUCCCAUC | 14712 |
| 6080 | GGACCGUC A UCAGCACA | 5373 | UGUGCUGA CUGAUGAGGCCGUUAGGCCGAA IACGGUCC | 14713 |
| 6083 | CCGUCAUC A GCACAUUC | 5374 | GAAUGUGC CUGAUGAGGCCGUUAGGCCGAA IAUGACGG | 14714 |
| 6086 | UCAUCAGC A CAUUCCCU | 5375 | AGGGAAUG CUGAUGAGGCCGUUAGGCCGAA ICUGAUGA | 14715 |
| 6088 | AUCAGCAC A UUCCCUAG | 5376 | CUAGGGAA CUGAUGAGGCCGUUAGGCCGAA IUGCUGAU | 14716 |
| 6092 | GCACAUUC C CUAGUGAG | 5377 | CUCACUAG CUGAUGAGGCCGUUAGGCCGAA IAAUGUGC | 14717 |
| 6093 | CACAUUCC C UAGUGAGC | 5378 | GCUCACUA CUGAUGAGGCCGUUAGGCCGAA IGAAUGUG | 14718 |
| 6094 | ACAUUCCC U AGUGAGCC | 5379 | GGCUCACU CUGAUGAGGCCGUUAGGCCGAA IGGAAUGU | 14719 |
| 6102 | UAGUGAGC C UACUGGCU | 5380 | AGCCAGUA CUGAUGAGGCCGUUAGGCCGAA ICUCACUA | 14720 |
| 6103 | AGUGAGCC U ACUGGCUC | 5381 | GAGCCAGU CUGAUGAGGCCGUUAGGCCGAA IGCUCACU | 14721 |
| 6106 | GAGCCUAC U GGCUCCUG | 5382 | CAGGAGCC CUGAUGAGGCCGUUAGGCCGAA IUAGGCUC | 14722 |
| 6110 | CUACUGGC U CCUGGCAG | 5383 | CUGCCAGG CUGAUGAGGCCGUUAGGCCGAA ICCAGUAG | 14723 |
| 6112 | ACUGGCUC C UGGCAGCG | 5384 | CGCUGCCA CUGAUGAGGCCGUUAGGCCGAA IAGCCAGU | 14724 |
| 6113 | CUGGCUCC U GGCAGCGG | 5385 | CCGCUGCC CUGAUGAGGCCGUUAGGCCGAA IGAGCCAG | 14725 |
| 6117 | CUCCUGGC A GCGGCUUU | 5386 | AAAGCCGC CUGAUGAGGCCGUUAGGCCGAA ICCAGGAG | 14726 |
| 6123 | GCAGCGGC U UUGUGGA | 5387 | UCCACAAA CUGAUGAGGCCGUUAGGCCGAA ICCGCUGC | 14727 |
| 6136 | UGGAAGAC U CACUAGCC | 5388 | GGCUAGUG CUGAUGAGGCCGUUAGGCCGAA IUCUUCCA | 14728 |
| 6138 | GAAGACUC A CUAGCCAG | 5389 | CUGGCUAG CUGAUGAGGCCGUUAGGCCGAA IAGUCUUC | 14729 |
| 6140 | AGACUCAC U AGCCAGAA | 5390 | UUCUGGCU CUGAUGAGGCCGUUAGGCCGAA IUGAGUCU | 14730 |
| 6144 | UCACUAGC C AGAAGAGA | 5391 | UCUCUUCU CUGAUGAGGCCGUUAGGCCGAA ICUAGUGA | 14731 |
| 6145 | CACUAGCC A GAAGAGAG | 5392 | CUCUCUUC CUGAUGAGGCCGUUAGGCCGAA IGCUAGUG | 14732 |
| 6163 | AGUGGGAC A GUCCUCUC | 5393 | GAGAGGAC CUGAUGAGGCCGUUAGGCCGAA IUCCCACU | 14733 |
| 6167 | GGACAGUC C UCUCCACC | 5394 | GGUGGAGA CUGAUGAGGCCGUUAGGCCGAA IACUGUCC | 14734 |
| 6168 | GACAGUCC U CUCCACCA | 5395 | UGGUGGAG CUGAUGAGGCCGUUAGGCCGAA IGACUGUC | 14735 |
| 6170 | CAGUCCUC U CCACCAAG | 5396 | CUUGGUGG CUGAUGAGGCCGUUAGGCCGAA IAGGACUG | 14736 |
| 6172 | GUCCUCUC C ACCAAGAU | 5397 | AUCUUGGU CUGAUGAGGCCGUUAGGCCGAA IAGAGGAC | 14737 |
| 6173 | UCCUCUCC A CCAAGAUC | 5398 | GAUCUUGG CUGAUGAGGCCGUUAGGCCGAA IGAGAGGA | 14738 |
| 6175 | CUCUCCAC C AAGAUCUA | 5399 | UAGAUCUU CUGAUGAGGCCGUUAGGCCGAA IUGGAGAG | 14739 |
| 6176 | UCUCCACC A AGAUCUAA | 5400 | UUAGAUCU CUGAUGAGGCCGUUAGGCCGAA IGUGGAGA | 14740 |

TABLE XIV-continued

NCH Ribozyme and Target Sequences

| Pos | Target | Seq ID No | NCH Ribozyme | Seq ID No |
|---|---|---|---|---|
| 6182 | CCAAGAUC U AAAUCCAA | 5401 | UUGGAUUU CUGAUGAGGCCGUUAGGCCGAA IAUCUUGG | 14741 |
| 6188 | UCUAAAUC C AAACAAAA | 5402 | UUUUGUUU CUGAUGAGGCCGUUAGGCCGAA IAUUUAGA | 14742 |
| 6189 | CUAAAUCC A AACAAAAG | 5403 | CUUUUGUU CUGAUGAGGCCGUUAGGCCGAA IGAUUUAG | 14743 |
| 6193 | AUCCAAAC A AAGCAGG | 5404 | CCUGCUUU CUGAUGAGGCCGUUAGGCCGAA IUUUGGAU | 14744 |
| 6199 | ACAAAAGC A GGCUAGAG | 5405 | CUCUAGCC CUGAUGAGGCCGUUAGGCCGAA ICUUUUGU | 14745 |
| 6203 | AAGCAGGC U AGAGCCAG | 5406 | CUGGCUCU CUGAUGAGGCCGUUAGGCCGAA ICCUGCUU | 14746 |
| 6209 | GCUAGAGC C AGAAGAGA | 5407 | UCUCUUCU CUGAUGAGGCCGUUAGGCCGAA ICUCUAGC | 14747 |
| 6210 | CUAGAGCC A GAAGAGAG | 5408 | CUCUCUUC CUGAUGAGGCCGUUAGGCCGAA IGCUCUAG | 14748 |
| 6222 | GAGAGGAC A AAUCUUUG | 5409 | CAAAGAUU CUGAUGAGGCCGUUAGGCCGAA IUCCUCUC | 14749 |
| 6227 | GACAAAUC U UUGUUGUU | 5410 | AACAACAA CUGAUGAGGCCGUUAGGCCGAA IAUUGGUC | 14750 |
| 6237 | UGUUGUUC C UCUUCUUU | 5411 | AAAGAAGA CUGAUGAGGCCGUUAGGCCGAA IAACAACA | 14751 |
| 6238 | GUUGUUCC U CUUCUUUA | 5412 | UAAAGAAG CUGAUGAGGCCGUUAGGCCGAA IGAACAAC | 14752 |
| 6240 | UGUUCCUC U UCUUUACA | 5413 | UGUAAAGA CUGAUGAGGCCGUUAGGCCGAA IAGGAACA | 14753 |
| 6243 | UCCUCUUC U UUACACAU | 5414 | AUGUGUAA CUGAUGAGGCCGUUAGGCCGAA IAAGAGGA | 14754 |
| 6248 | UUCUUUAC A CAUACGCA | 5415 | UGCGUAUG CUGAUGAGGCCGUUAGGCCGAA IUAAAGAA | 14755 |
| 6250 | CUUUACAC A UACGCAAA | 5416 | UUUGCGUA CUGAUGAGGCCGUUAGGCCGAA IUGUAAAG | 14756 |
| 6256 | ACAUACGC A AACCACCU | 5417 | AGGUGGUU CUGAUGAGGCCGUUAGGCCGAA ICGUAUGU | 14757 |
| 6260 | ACGCAAAC C ACCUGUGA | 5418 | UCACAGGU CUGAUGAGGCCGUUAGGCCGAA IUUUGCGU | 14758 |
| 6261 | CGCAAACC A CCUGUGAC | 5419 | GUCACAGG CUGAUGAGGCCGUUAGGCCGAA IGUUUGCG | 14759 |
| 6263 | CAAACCAC C UGUGACAG | 5420 | CUGUCACA CUGAUGAGGCCGUUAGGCCGAA IUGGUUUG | 14760 |
| 6264 | AAACCACC U GUGACAGC | 5421 | GCUGUCAC CUGAUGAGGCCGUUAGGCCGAA IGUGGUUU | 14761 |
| 6270 | CCUGUGAC A GCUGGCAA | 5422 | UUGCCAGC CUGAUGAGGCCGUUAGGCCGAA IUCACAGG | 14762 |
| 6273 | GUGACAGC U GGCAAUUU | 5423 | AAAUUGCC CUGAUGAGGCCGUUAGGCCGAA ICUGUCAC | 14763 |
| 6277 | CAGCUGGC A AUUUUAUA | 5424 | UAUAAAAU CUGAUGAGGCCGUUAGGCCGAA ICCAGCUG | 14764 |
| 6290 | UAUAAAUC A GGUAACUG | 5425 | CAGUUACC CUGAUGAGGCCGUUAGGCCGAA IAUUUAUA | 14765 |
| 6297 | CAGGUAAC U GGAAGGAG | 5426 | CUCCUUCC CUGAUGAGGCCGUUAGGCCGAA IUUACCUG | 14766 |
| 6313 | GGUUAAAC U CAGAAAAA | 5427 | UUUUUCUG CUGAUGAGGCCGUUAGGCCGAA IUUUAACC | 14767 |
| 6315 | UUAAACUC A GAAAAAAG | 5428 | CUUUUUUC CUGAUGAGGCCGUUAGGCCGAA IAGUUUAA | 14768 |
| 6329 | AAGAAGAC C UCAGUCAA | 5429 | UUGACUGA CUGAUGAGGCCGUUAGGCCGAA IUCUUCUU | 14769 |
| 6330 | AGAAGACC U CAGUCAAA | 5430 | AUUGACUG CUGAUGAGGCCGUUAGGCCGAA IGUCUUCU | 14770 |
| 6332 | AAGACCUC A GUCAAUUC | 5431 | GAAUUGAC CUGAUGAGGCCGUUAGGCCGAA IAGGUCUU | 14771 |
| 6336 | CCUCAGUC A AUUCUCUA | 5432 | UAGAGAAU CUGAUGAGGCCGUUAGGCCGAA IACUGAGG | 14772 |
| 6341 | GUCAAUUC U CUACUUUU | 5433 | AAAAGUAG CUGAUGAGGCCGUUAGGCCGAA IAAUUGAC | 14773 |
| 6343 | CAAUUCUC U ACUUUUUU | 5434 | AAAAAAGU CUGAUGAGGCCGUUAGGCCGAA IAGAAUUG | 14774 |
| 6346 | UUCUCUAC U UUUUUUU | 5435 | AAAAAAAA CUGAUGAGGCCGUUAGGCCGAA IUAGAGAA | 14775 |
| 6363 | UUUUUUUC C AAAUCAGA | 5436 | UCUGAUUU CUGAUGAGGCCGUUAGGCCGAA IAAAAAAA | 14776 |
| 6364 | UUUUUUCC A AAUCAGAU | 5437 | AUCUGAUU CUGAUGAGGCCGUUAGGCCGAA IGAAAAAA | 14777 |

TABLE XIV-continued

NCH Ribozyme and Target Sequences

| Pos | Target | Seq ID No | NCH Ribozyme | Seq ID No |
|---|---|---|---|---|
| 6369 | UCCAAAUC A GAUAAUAG | 5438 | CUAUUAUC CUGAUGAGGCCGUUAGGCCGAA IAUUUGGA | 14778 |
| 6379 | AUAAUAGC C CAGCAAAU | 5439 | AUUUGCUG CUGAUGAGGCCGUUAGGCCGAA ICUAUUAU | 14779 |
| 6380 | UAAUAGCC C AGCAAAUA | 5440 | UAUUUGCU CUGAUGAGGCCGUUAGGCCGAA IGCUAUUA | 14780 |
| 6381 | AAUAGCCC A GCAAAUAG | 5441 | CUAUUUGC CUGAUGAGGCCGUUAGGCCGAA IGGCUAUU | 14781 |
| 6384 | AGCCCAGC A AAUAGUGA | 5442 | UCACUAUU CUGAUGAGGCCGUUAGGCCGAA ICUGGGCU | 14782 |
| 6397 | GUGAUAAC A AAUAAAAC | 5443 | GUUUUAUU CUGAUGAGGCCGUUAGGCCGAA IUUAUCAC | 14783 |
| 6406 | AAUAAAAC C UUAGCUGU | 5444 | ACAGCUAA CUGAUGAGGCCGUUAGGCCGAA IUUUUAUU | 14784 |
| 6407 | AUAAAACC U UAGCUGUU | 5445 | AACAGCUA CUGAUGAGGCCGUUAGGCCGAA IGUUUUAU | 14785 |
| 6412 | ACCUUAGC U GUUCAUGU | 5446 | ACAUGAAC CUGAUGAGGCCGUUAGGCCGAA ICUAAGGU | 14786 |
| 6417 | AGCUGUUC A UGUCUUGA | 5447 | UCAAGACA CUGAUGAGGCCGUUAGGCCGAA IAACAGCU | 14787 |
| 6422 | UUCAUGUC U UGAUUUCA | 5448 | UGAAAUCA CUGAUGAGGCCGUUAGGCCGAA IACAUGAA | 14788 |
| 6430 | UUGAUUUC A AUAAUUAA | 5449 | UUAAUUAU CUGAUGAGGCCGUUAGGCCGAA IAAAUCAA | 14789 |
| 6442 | AUUAAUUC U UAAUCAUU | 5450 | AAUGAUUA CUGAUGAGGCCGUUAGGCCGAA IAAUUAAU | 14790 |
| 6448 | UCUUAAUC A UUAAGAGA | 5451 | UCUCUUAA CUGAUGAGGCCGUUAGGCCGAA IAUUAAGA | 14791 |
| 6458 | UAAGAGAC C AUAAUAAA | 5452 | UUUAUUAU CUGAUGAGGCCGUUAGGCCGAA IUCUCUUA | 14792 |
| 6459 | AAGAGACC A UAAUAAAU | 5453 | AUUUAUUA CUGAUGAGGCCGUUAGGCCGAA IGUCUCUU | 14793 |
| 6470 | AUAAAUAC U CCUUUUCA | 5454 | UGAAAAGG CUGAUGAGGCCGUUAGGCCGAA IUAUUUAU | 14794 |
| 6472 | AAAUACUC C UUUUCAAG | 5455 | CUUGAAAA CUGAUGAGGCCGUUAGGCCGAA IAGUAUUU | 14795 |
| 6473 | AAUACUCC U UUUCAAGA | 5456 | UCUUGAAA CUGAUGAGGCCGUUAGGCCGAA IGAGUAUU | 14796 |
| 6478 | UCCUUUUC A AGAGAAAA | 5457 | UUUUCUCU CUGAUGAGGCCGUUAGGCCGAA IAAAAGGA | 14797 |
| 6489 | AGAAAAGC A AACCAUU | 5458 | AAUGGUUU CUGAUGAGGCCGUUAGGCCGAA ICUUUUCU | 14798 |
| 6494 | AGCAAAAC C AUUAGAAU | 5459 | AUUCUAAU CUGAUGAGGCCGUUAGGCCGAA IUUUUGCU | 14799 |
| 6495 | GCAAAACC A UUAGAAUU | 5460 | AAUUCUAA CUGAUGAGGCCGUUAGGCCGAA IGUUUUGC | 14800 |
| 6509 | AUUGUUAC U CAGCUCCU | 5461 | AGGAGCUG CUGAUGAGGCCGUUAGGCCGAA IUAACAAU | 14801 |
| 6511 | UGUUACUC A GCUCCUUC | 5462 | GAAGGAGC CUGAUGAGGCCGUUAGGCCGAA IAGUAACA | 14802 |
| 6514 | UACUCAGC U CCUUCAAA | 5463 | UUUGAAGG CUGAUGAGGCCGUUAGGCCGAA ICUGAGUA | 14803 |
| 6516 | CUCAGCUC C UUCAAACU | 5464 | AGUUUGAA CUGAUGAGCCCGUUAGGCCGAA IAGCUGAG | 14804 |
| 6517 | UCAGCUCC U UCAAACUC | 5465 | GAGUUUGA CUGAUGAGGCCGUUAGGCCGAA IGAGOUGA | 14805 |
| 6520 | GCUCCUUC A AACUCAGG | 5466 | CCUGAGUU CUGAUGAGGCCGUUAGGCCGAA IAAGGAGC | 14806 |
| 6524 | CUUCAAAC U CAGGUUUG | 5467 | CAAACCUG CUGAUGAGGCCGUUAGGCCGAA IUUUGAAG | 14807 |
| 6526 | UCAAACUC A GGUUUGUA | 5468 | UACAAACC CUGAUGAGGCCGUUAGGCCGAA IAGUUUGA | 14808 |
| 6537 | UUUGUAGC A UACAUGAG | 5469 | CUCAUGUA CUGAUGAGGCCGUUAGGCCGAA ICUACAAA | 14809 |
| 6541 | UAGCAUAC A UGAGUCCA | 5470 | UGGACUCA CUGAUGAGGCCGUUAGGCCGAA IUAUGCUA | 14810 |
| 6548 | CAUGAGUC C AUCCAUCA | 5471 | UGAUGGAU CUGAUGAGGCCGUUAGGCCGAA IACUCAUG | 14811 |
| 6549 | AUGAGUCC A UCCAUCAG | 5472 | CUGAUGGA CUGAUGAGGCCGUUAGGCCGAA IGACUCAU | 14812 |
| 6552 | AGUCCAUC C AUCAGUCA | 5473 | UGACUGAU CUGAUGAGGCCGUUAGGCCGAA IAUGGACU | 14813 |
| 6553 | GUCCAUCC A UCAGUCAA | 5474 | UUGACUGA CUGAUGAGGCCGUUAGGCCGAA IGAUGGAC | 14814 |

TABLE XIV-continued

NCH Ribozyme and Target Sequences

| Pos | Target | Seq ID No | NCH Ribozyme | Seq ID No |
|---|---|---|---|---|
| 6556 | CAUCCAUC A GUCAAAGA | 5475 | UCUUUGAC CUGAUGAGgccguuaggcCGAA IAUGGAUG | 14815 |
| 6560 | CAUCAGUC A AAGAAUGG | 5476 | CCAUUCUU CUGAUGAGgccguuaggcCGAA IACUGAUG | 14816 |
| 6572 | AAUGGUUC C AUCUGGAG | 5477 | CUCCAGAU CUGAUGAGgccguuaggcCGAA IAACCAUU | 14817 |
| 6573 | AUGGUUCC A UCUGGAGU | 5478 | ACUCCAGA CUGAUGAGgccguuaggcCGAA IGAACCAU | 14818 |
| 6576 | GUUCCAUC U GGAGUCUU | 5479 | AAGACUCC CUGAUGAGgccguuaggcCGAA IAUGGAAC | 14819 |
| 6583 | CUGGAGUC U UAAUGUAG | 5480 | CUACAUUA CUGAUGAGgccguuaggcCGAA IACUCCAG | 14820 |
| 6608 | AUGGAGAC U UGUAAUAA | 5481 | UUAUUACA CUGAUGAGgccguuaggcCGAA IUCUCCAU | 14821 |
| 6622 | UAAUGAGC U AGUUACAA | 5482 | UUGUAACU CUGAUGAGgccguuaggcCGAA ICUCAUUA | 14822 |
| 6629 | CUAGUUAC A AAGUGCUU | 5483 | AAGCACUU CUGAUGAGgccguuaggcCGAA IUAACUAG | 14823 |
| 6636 | CAAAGUGC U UGUUCAUU | 5484 | AAUGAACA CUGAUGAGgccguuaggcCGAA ICACUUUG | 14824 |
| 6642 | GCUUGUUC A UUAAAAUA | 5485 | UAUUUUAA CUGAUGAGgccguuaggcCGAA IAACAAGC | 14825 |
| 6653 | AAAAUAGC A CUGAAAAU | 5486 | AUUUUCAG CUGAUGAGgccguuaggcCGAA ICUAUUUU | 14826 |
| 6655 | AAUAGCAC U GAAAAUUG | 5487 | CAAUUUUC CUGAUGAGgccguuaggcCGAA IUGCUAUU | 14827 |
| 6668 | AUUGAAAC A UGAAUUAA | 5488 | UUAAUUCA CUGAUGAGgccguuaggcCGAA IUUUCAAU | 14828 |
| 6678 | GAAUUAAC U GAUAAUAU | 5489 | AUAUUAUC CUGAUGAGgccguuaggcCGAA IUUAAUUC | 14829 |
| 6689 | UAAUAUUC C AAUCACAU | 5490 | AAAUGAUU CUGAUGAGgccguuaggcCGAA IAAUAUUA | 14830 |
| 6690 | AAUAUUCC A AUCAUUUG | 5491 | CAAAUGAU CUGAUGAGgccguuaggcCGAA IGAAUAUU | 14831 |
| 6694 | UUCCAAUC A UUUGCCAU | 5492 | AUGGCAAA CUGAUGAGgccguuaggcCGAA IAUUGGAA | 14832 |
| 6700 | UCAUUUGC C AUUUAUGA | 5493 | UCAUAAAU CUGAUGAGgccguuaggcCGAA ICAAAUGA | 14833 |
| 6701 | CAUUUGCC A UUUAUGAC | 5494 | GUCAUAAA CUGAUGAGgccguuaggcCGAA IGCAAAUG | 14834 |
| 6710 | UUUAUGAC A AAAAUGGU | 5495 | ACCAUUUU CUGAUGAGgccguuaggcCGAA IUCAUAAA | 14835 |
| 6723 | UGGUUGGC A CUAACAAA | 5496 | UUUGUUAG CUGAUGAGgccguuaggcCGAA ICCAACCA | 14836 |
| 6725 | GUUGGCAC U AACAAAGA | 5497 | UCUUUGUU CUGAUGAGgccguuaggcCGAA IUGCCAAC | 14837 |
| 6729 | GCACUAAC A AAGAACGA | 5498 | UCGUUCUU CUGAUGAGgccguuaggcCGAA IUUAGUGC | 14838 |
| 6740 | GAACGAGC A CUUCCUUU | 5499 | AAAGGAAG CUGAUGAGgccguuaggcCGAA ICUCGUUC | 14839 |
| 6742 | ACGAGCAC U UCCUUUCA | 5500 | UGAAAGGA CUGAUGAGgccguuaggcCGAA IUGCUCGU | 14840 |
| 6745 | AGCACUUC C UUUCAGAG | 5501 | CUCUGAAA CUGAUGAGgccguuaggcCGAA IAAGUGCU | 14841 |
| 6746 | GCACUUCC U UUCAGAGU | 5502 | ACUCUGAA CUGAUGAGgccguuaggcCGAA IGAAGUGC | 14842 |
| 6750 | UUCCUUUC A GAGUUUCU | 5503 | AGAAACUC CUGAUGAGgccguuaggcCGAA IAAAGGAA | 14843 |
| 6758 | AGAGUUUC U GAGAUAAU | 5504 | AUUAUCUC CUGAUGAGgccguuaggcCGAA IAAACUCU | 14844 |
| 6778 | CGUGGAAC A GUCUGGGU | 5505 | ACCCAGAC CUGAUGAGgccguuaggcCGAA IUUCCACG | 14845 |
| 6782 | GAACAGUC U GGGUGGAA | 5506 | UUCCACCC CUGAUGAGgccguuaggcCGAA IACUGUUC | 14846 |
| 6797 | AAUGGGGC U GAAACCAU | 5507 | AUGGUUUC CUGAUGAGgccguuaggcCGAA ICCCCAUU | 14847 |
| 6803 | GCUGAAAC C AUGUGCAA | 5508 | UUGCACAU CUGAUGAGgccguuaggcCGAA IUUUCAGC | 14848 |
| 6804 | CUGAAACC A UGUGCAAG | 5509 | CUUGCACA CUGAUGAGgccguuaggcCGAA IGUUUCAG | 14849 |
| 6810 | CCAUGUGC A AGUCUGUG | 5510 | CACAGACU CUGAUGAGgccguuaggcCGAA ICACAUGG | 14850 |
| 6815 | UGCAAGUC U GUGUCUUG | 5511 | CAAGACAC CUGAUGAGgccguuaggcCGAA IACUUGCA | 14851 |

TABLE XIV-continued

NCH Ribozyme and Target Sequences

| Pos | Target | Seq ID No | NCH Ribozyme | Seq ID No |
|---|---|---|---|---|
| 6821 | UCUGUGUC U UGUCAGUC | 5512 | GACUGACA CUGAUGAGGCCGUUAGGCCGAA IACACAGA | 14852 |
| 6826 | GCUUUGUC A GUCCAAGA | 5513 | UCUUGGAC CUGAUGAGGCCGUUAGGCCGAA IACAAGAC | 14853 |
| 6830 | UGUCAGUC C AAGAAGUG | 5514 | CACUUCUU CUGAUGAGGCCGUUAGGCCGAA IACUGACA | 14854 |
| 6831 | GUCAGUCC A AGAAGUGA | 5515 | UCACUUCU CUGAUGAGGCCGUUAGGCCGAA IGACUGAC | 14855 |
| 6841 | GAAGUGAC A CCGAGAUG | 5516 | CAUCUCGG CUGAUGAGGCCGUUAGGCCGAA IUCACUUC | 14856 |
| 6843 | AGUGACAC C GAGAUGUU | 5517 | AACAUCUC CUGAUGAGGCCGUUAGGCCGAA IUGUCACU | 14857 |
| 6864 | UUAGGGAC C CGUGCCUU | 5518 | AAGGCACG CUGAUGAGGCCGUUAGGCCGAA IUCCCUAA | 14858 |
| 6865 | UAGGGACC C GUGCCUUG | 5519 | CAAGGCAC CUGAUGAGGCCGUUAGGCCGAA IGUCCCUA | 14859 |
| 6870 | ACCCGUGC C UUGUUUCC | 5520 | GGAAACAA CUGAUGAGGCCGUUAGGCCGAA ICACGGGU | 14860 |
| 6871 | CCCGUGCC U UGUUUCCU | 5521 | AGGAAACA CUGAUGAGGCCGUUAGGCCGAA IGCACGGG | 14861 |
| 6878 | CUUGUUUC C UAGCCCAC | 5522 | GUGGGCUA CUGAUGAGGCCGUUAGGCCGAA IAAACAAG | 14862 |
| 6879 | UUGUUUCC U AGCCCACA | 5523 | UGUGGGCU CUGAUGAGGCCGUUAGGCCGAA IGAAACAA | 14863 |
| 6883 | UUCCUAGC C CACAAGAA | 5524 | UUCUUGUG CUGAUGAGGCCGUUAGGCCGAA ICUAGGAA | 14864 |
| 6884 | UCCUAGCC C ACAAGAAU | 5525 | AUUCUUGU CUGAUGAGGCCGUUAGGCCGAA IGCUAGGA | 14865 |
| 6885 | CCUAGCCC A CAAGAAUG | 5526 | CAUUCUUG CUGAUGAGGCCGUUAGGCCGAA IGGCUAGG | 14866 |
| 6887 | UAGCCCAC A AGAAUGCA | 5527 | UGCAUUCU CUGAUGAGGCCGUUAGGCCGAA IUGGGCUA | 14867 |
| 6895 | AAGAAUGC A AACAUCAA | 5528 | UUGAUGUU CUGAUGAGGCCGUUAGGCCGAA ICAUUCUU | 14868 |
| 6899 | AUGCAAAC A UCAAACAG | 5529 | CUGUUUGA CUGAUGAGGCCGUUAGGCCGAA IUUUGCAU | 14869 |
| 6902 | CAAACAUC A AACAGAUA | 5530 | UAUCUGUU CUGAUGAGGCCGUUAGGCCGAA IAUGUUUG | 14870 |
| 6906 | CAUCAAAC A GAUACUCG | 5531 | CGAGUAUC CUGAUGAGGCCGUUAGGCCGAA IUUUGAUG | 14871 |
| 6912 | ACAGAUAC U CGCUAGCC | 5532 | GGCUAGCG CUGAUGAGGCCGUUAGGCCGAA IUAUCUGU | 14872 |
| 6916 | AUACUCGC U AGCCUCAU | 5533 | AUGAGGCU CUGAUGAGGCCGUUAGGCCGAA ICGAGUAU | 14873 |
| 6920 | UCGCUAGC C UCAUUUAA | 5534 | UUAAAUGA CUGAUGAGGCCGUUAGGCCGAA ICUAGCGA | 14874 |
| 6921 | CGCUAGCC U CAUUUAAA | 5535 | UUUAAAUG CUGAUGAGGCCGUUAGGCCGAA IGCUAGCG | 14875 |
| 6923 | CUAGCCUC A UUUAAAUU | 5536 | AAUUUAAA CUGAUGAGGCCGUUAGGCCGAA IAGGCUAG | 14876 |
| 6949 | AGGAGUGC A UCUUUGGC | 5537 | GCCAAAGA CUGAUGAGGCCGUUAGGCCGAA ICACUCCU | 14877 |
| 6952 | AGUGCAUC U UUGGCCGA | 5538 | UCGGCCAA CUGAUGAGGCCGUUAGGCCGAA IAUGCACU | 14878 |
| 6958 | UCUUUGGC C GACAGUGG | 5539 | CCACUGUC CUGAUGAGGCCGUUAGGCCGAA ICCAAAGA | 14879 |
| 6962 | UGGCCGAC A GUGGUGUA | 5540 | UACACCAC CUGAUGAGGCCGUUAGGCCGAA IUCGGCCA | 14880 |
| 6973 | GGUGUAAC U GUGUGUGU | 5541 | ACACACAC CUGAUGAGGCCGUUAGGCCGAA IUUACACC | 14881 |
| 7041 | UUUUGUGC A UAACUAUU | 5542 | AAUAGUUA CUGAUGAGGCCGUUAGGCCGAA ICACAAAA | 14882 |
| 7046 | UGCAUAAC U AUUUAAGG | 5543 | CCUUAAAU CUGAUGAGGCCGUUAGGCCGAA IUUAUGCA | 14883 |
| 7059 | AAGGAAAC U GGAAUUUU | 5544 | AAAAUUCC CUGAUGAGGCCGUUAGGCCGAA IUUUCCUU | 14884 |
| 7076 | AAAGUUAC U UUUAUACA | 5545 | UGUAUAAA CUGAUGAGGCCGUUAGGCCGAA IUAACUUU | 14885 |
| 7084 | UUUUAUAC A AACCAAGA | 5546 | UCUUGGUU CUGAUGAGGCCGUUAGGCCGAA IUAUAAAA | 14886 |
| 7088 | AUACAAAC C AAGAAUAU | 5547 | AUAUUCUU CUGAUGAGGCCGUUAGGCCGAA IUUUGUAU | 14887 |
| 7089 | UACAAACC A AGAAUAUA | 5548 | UAUAUUCU CUGAUGAGGCCGUUAGGCCGAA IGUUUGUA | 14888 |

TABLE XIV-continued

NCH Ribozyme and Target Sequences

| Pos | Target | Seq ID No | NCH Ribozyme | Seq ID No |
|---|---|---|---|---|
| 7101 | AUAUAUGC U ACAGAUAU | 5549 | AUAUCUGU CUGAUGAGGCCGUUAGGCCGAA ICAUAUAU | 14889 |
| 7104 | UAUGCUAC A GAUAUAAG | 5550 | CUUAUAUC CUGAUGAGGCCGUUAGGCCGAA IUAGCAUA | 14890 |
| 7115 | UAUAAGAC A GACAUGGU | 5551 | ACCAUGUC CUGAUGAGGCCGUUAGGCCGAA IUCUUAUA | 14891 |
| 7119 | AGACAGAC A UGGUUUGG | 5552 | CCAAACCA CUGAUGAGGCCGUUAGGCCGAA IUCUGUCU | 14892 |
| 7130 | GUUUGGUC C UAUAUUUC | 5553 | GAAAUAUA CUGAUGAGGCCGUUAGGCCGAA IACCAAAC | 14893 |
| 7131 | UUUGGUCC U AUAUUUCU | 5554 | AGAAAUAU CUGAUGAGGCCGUUAGGCCGAA IGACCAAA | 14894 |
| 7139 | UAUAUUUC U AGCAUGA | 5555 | UCAUGACU CUGAUGAGGCCGUUAGGCCGAA IAAAUAUA | 14895 |
| 7144 | UUCUAGUC A UGAUGAAU | 5556 | AUUCAUCA CUGAUGAGGCCGUUAGGCCGAA IACUAGAA | 14896 |
| 7166 | UUGUAUAC C AUCUUCAU | 5557 | AUGAAGAU CUGAUGAGGCCGUUAGGCCGAA IUAUACAA | 14897 |
| 7167 | UGUAUACC A UCUUCAUA | 5558 | UAUGAAGA CUGAUGAGGCCGUUAGGCCGAA IGUAUACA | 14898 |
| 7170 | AUACCAUC U UCAUAUAA | 5559 | UUAUAUGA CUGAUGAGGCCGUUAGGCCGAA IAUGGUAU | 14899 |
| 7173 | CCAUCUUC A UAUAAUAU | 5560 | AUAUUAUA CUGAUGAGGCCGUUAGGCCGAA IAAGAUGG | 14900 |
| 7184 | UAAUAUAC U UAAAAAUA | 5561 | UAUUUUUA CUGAUGAGGCCGUUAGGCCGAA IUAUAUUA | 14901 |
| 7197 | AAUAUUUC U UAAUUGGG | 5562 | CCCAAUUA CUGAUGAGGCCGUUAGGCCGAA IAAAUAUU | 14902 |
| 7220 | AAUCGUAC C AACUUAAU | 5563 | AUUAAGUU CUGAUGAGGCCGUUAGGCCGAA IUACGAUU | 14903 |
| 7221 | AUCGUACC A ACUUAAUU | 5564 | AAUUAAGU CUGAUGAGGCCGUUAGGCCGAA IGUACGAU | 14904 |
| 7224 | GUACCAAC U UAAUUGAU | 5565 | AUCAAUUA CUGAUGAGGCCGUUAGGCCGAA IUUGGUAC | 14905 |
| 7237 | UGAUAAAC U UGGCAACU | 5566 | AGUUGCCA CUGAUGAGGCCGUUAGGCCGAA ICUUAUCA | 14906 |
| 7242 | AACUUGGC A ACUGCUUU | 5567 | AAAGCAGU CUCAUGAGGCCGUUAGGCCGAA ICCAAGUU | 14907 |
| 7245 | UUGGCAAC U GCUUUUAU | 5568 | AUAAAAGC CUGAUGAGGCCGUUAGGCCGAA IUUGCCAA | 14908 |
| 7248 | GCAACUGC U UUUAUGUU | 5569 | AACAUAAA CUGAUGAGGCCGUUAGGCCGAA ICAGUUGC | 14909 |
| 7258 | UUAUGUUC U GUCUCCUU | 5570 | AAGGAGAC CUGAUGAGGCCGUUAGGCCGAA IAACAUAA | 14910 |
| 7262 | GUUCUGUC U CCUUCCAU | 5571 | AUGGAAGG CUGAUGAGGCCGUUAGGCCGAA IACAGAAC | 14911 |
| 7264 | UCUGUCUC C UUCCAUAA | 5572 | UUAUGGAA CUGAUGAGGCCGUUAGGCCGAA IAGACAGA | 14912 |
| 7265 | CUGUCUCC U UCCAUAAA | 5573 | UUUAUGGA CUGAUGAGGCCGUUAGGCCGAA IGAGACAG | 14913 |
| 7268 | UCUCCUUC C AUAAAUUU | 5574 | AAAUUUAU CUGAUGAGGCCGUUAGGCCGAA IAAGGAGA | 14914 |
| 7269 | CUCCUUCC A UAAAUUUU | 5575 | AAAAUUUA CUGAUGAGGCCGUUAGGCCGAA IGAAGGAG | 14915 |
| 7280 | AAUUUUUC A AAAUACUA | 5576 | UAGUAUUU CUGAUGAGGCCGUUAGGCCGAA IAAAAAUU | 14916 |
| 7287 | CAAAAUAC U AAUUCAAC | 5577 | GUUGAAUU CUGAUGAGGCCGUUAGGCCGAA IUAUUUUG | 14917 |
| 7293 | ACUAAUUC A ACAAAGAA | 5578 | UUCUUUGU CUGAUGAGGCCGUUAGGCCGAA IAAUUAGU | 14918 |
| 7296 | AAUUCAAC A AGAAAAA | 5579 | UUUUUCUU CUGAUGAGGCCGUUAGGCCGAA IUUGAAUU | 14919 |
| 7307 | GAAAAGC U CUUUUUUU | 5580 | AAAAAAG CUGAUGAGGCCGUUAGGCCGAA ICUUUUUC | 14920 |
| 7309 | AAAGCUC U UUUUUUC | 5581 | GAAAAAAA CUGAUGAGGCCGUUAGGCCGAA IAGCUUUU | 14921 |
| 7318 | UUUUUUUC C UAAAAUAA | 5582 | UUAUUUUA CUGAUGAGGCCGUUAGGCCGAA IAAAAAAA | 14922 |
| 7319 | UUUUUUCC U AAAUAAA | 5583 | UUUAUUUU CUGAUGAGGCCGUUAGGCCGAA IGAAAGAA | 14923 |
| 7329 | AAUAAAC U CAAAUUUA | 5584 | UAAAUUUG CUGAUGAGGCCGUUAGGCCGAA IUUUAUUU | 14924 |
| 7331 | AUAAACUC A AAUUUAUC | 5585 | GAUAAAUU CUGAUGAGGCCGUUAGGCCGAA IAGUUUAU | 14925 |

TABLE XIV-continued

NCH Ribozyme and Target Sequences

| Pos | Target | Seq ID No | NCH Ribozyme | Seq ID No |
|---|---|---|---|---|
| 7340 | AAUUUAUC C UUGUUUAG | 5586 | CUAAACAA CUGAUGAGgccguuaggCCGAA IAUAAAUU | 14926 |
| 7341 | AUUUAUCC U UGUUUAGA | 5587 | UCUAAACA CUGAUGAGgccguuaggCCGAA IGAUAAAU | 14927 |
| 7352 | UUUAGAGC A GAGAAAAA | 5588 | UUUUUCUC CUGAUGAGgccguuaggCCGAA ICUCUAAA | 14928 |
| 7372 | AGAAAAAC U UUGAAAUG | 5589 | CAUUUCAA CUGAUGAGgccguuaggCCGAA IUUUUUCU | 14929 |
| 7384 | AAAUGGUC U CAAAAAAU | 5590 | AUUUUUUG CUGAUGAGgccguuaggCCGAA IACCAUUU | 14930 |
| 7386 | AUGGUCUC A AAAAUUG | 5591 | CAAUUUUU CUGAUGAGgccguuaggCCGAA IAGACCAU | 14931 |
| 7396 | AAAAUUGC U AAAUAUUU | 5592 | AAAUAUUU CUGAUGAGgccguuaggCCGAA ICAAUUUU | 14932 |
| 7407 | AUAUUUUC A AUGGAAAA | 5593 | UUUUCCAU CUGAUGAGgccguuaggCCGAA IAAAAUAU | 14933 |
| 7417 | UGGAAAAC U AAAUGUUA | 5594 | UAACAUUU CUGAUGAGgccguuaggCCGAA IUUUUCCA | 14934 |
| 7433 | AGUUUAGC U GAUUGUAU | 5595 | AUACAAUC CUGAUGAGgccguuaggCCGAA ICUAAACU | 14935 |
| 7455 | UUUCGAAC C UUUCACUU | 5596 | AAGUGAAA CUGAUGAGgccguuaggCCGAA IUUCGAAA | 14936 |
| 7456 | UUCGAACC U UUCACUUU | 5597 | AAAGUGAA CUGAUGAGgccguuaggCCGAA IGUUCGAA | 14937 |
| 7460 | AACCUUUC A CUUUUUGU | 5598 | ACAAAAAG CUGAUGAGgccguuaggCCGAA IAAAGGUU | 14938 |
| 7462 | CCUUUCAC U UUUUGUUU | 5599 | AAACAAAA CUGAUGAGgccguuaggCCGAA IGAAAGG | 14939 |
| 7478 | UGUUUUAC C UAUUUCAC | 5600 | GUGAAAUA CUGAUGAGgccguuaggCCGAA IUAAAACA | 14940 |
| 7479 | GUUUUACC U AUUUCACA | 5601 | UGUGAAAU CUGAUGAGgccguuaggCCGAA IGUAAAAC | 14941 |
| 7485 | CCUAUUUC A CAACUGUG | 5602 | CACAGUUG CUGAUGAGgccguuaggCCGAA IAAAUAGG | 14942 |
| 7487 | UAUUUCAC A ACUGUGUA | 5603 | UACACAGU CUGAUGAGgccguuaggCCGAA IUGAAAUA | 14943 |
| 7490 | UUCACAAC U GUGUAAAU | 5604 | AUUUACAC CUGAUGAGgccguuaggCCGAA IUUGUGAA | 14944 |
| 7502 | UAAAUUGC C AAUAAUUC | 5605 | GAAUUAUU CUGAUGAGgccguuaggCCGAA ICAAUUUA | 14945 |
| 7503 | AAAUUGCC A AUAAUUCC | 5606 | GGAAUUAU CUGAUGAGgccguuaggCCGAA IGCAAUUU | 14946 |
| 7511 | AAUAAUUC C UGUCCAUG | 5607 | CAUGGACA CUGAUGAGgccguuaggCCGAA IAAUUAUU | 14947 |
| 7512 | AUAAUUCC U GUCCAUGA | 5608 | UCAUGGAC CUGAUGAGgccguuaggCCGAA IGAAUUAU | 14948 |
| 7516 | UUCCUGUC C AUGAAAAU | 5609 | AUUUUCAU CUGAUGAGgccguuaggCCGAA IACAGGAA | 14949 |
| 7517 | UCCUGUCC A UGAAAAUG | 5610 | CAUUUUCA CUGAUGAGgccguuaggCCGAA IGACAGGA | 14950 |
| 7527 | GAAAAUGC A AAUUAUCC | 5611 | GGAUAAUU CUGAUGAGgccguuaggCCGAA ICAUUUUC | 14951 |
| 7535 | AAAUUAUC C AGUGUAGA | 5612 | UCUACACU CUGAUGAGgccguuaggCCGAA IAUAAUUU | 14952 |
| 7536 | AAUUAUCC A GUGUAGAU | 5613 | AUCUACAC CUGAUGAGgccguuaggCCGAA IGAUAAUU | 14953 |
| 7554 | UAUUUGAC C AUCACCCU | 5614 | AGGGUGAU CUGAUGAGgccguuaggCCGAA IUCAAAUA | 14954 |
| 7555 | AUUUGACC A UCACCCUA | 5615 | UAGGGUGA CUGAUGAGgccguuaggCCGAA IGUCAAAU | 14955 |
| 7558 | UGACCAUC A CCCUAUGG | 5616 | CCAUAGGG CUGAUGAGgccguuaggCCGAA IAUGGUCA | 14956 |
| 7560 | ACCAUCAC C CUAUGGAU | 5617 | AUCCAUAG CUGAUGAGgccguuaggCCGAA IUGAUGGU | 14957 |
| 7561 | CCAUCACC C UAUGGAUA | 5618 | UAUCCAUA CUGAUGAGgccguuaggCCGAA IGUGAUGG | 14958 |
| 7562 | CAUCACCC U AUGGAUAU | 5619 | AUAUCCAU CUGAUGAGgccguuaggCCGAA IGGUGAUG | 14959 |
| 7575 | AUAUUGGC U AGUUUGC | 5620 | GCAAAACU CUGAUGAGgccguuaggCCGAA ICCAAUAU | 14960 |
| 7584 | AGUUUUGC C UUUAUUAA | 5621 | UUAAUAAA CUGAUGAGgccguuaggCCGAA ICAAACU | 14961 |
| 7585 | GUUUUGCC U UUAUUAAG | 5622 | CUUAAUAA CUGAUGAGgccguuaggCCGAA IGCAAACU | 14962 |

TABLE XIV-continued

NCH Ribozyme and Target Sequences

| Pos | Target | Seq ID No | NCH Ribozyme | Seq ID No |
|---|---|---|---|---|
| 7595 | UAUUAAGC A AAUUCAUU | 5623 | AAUGAAUU CUGAUGAGGCCGUUAGGCCGAA ICUUAUA | 14963 |
| 7601 | GCAAAUUC A UUUCAGCC | 5624 | GGCUGAAA CUGAUGAGGCCGUUAGGCCGAA IAAUUUGC | 14964 |
| 7606 | UUCAUUUC A GCCUGAAU | 5625 | AUUCAGGC CUGAUGAGGCCGUUAGGCCGAA IAAAUGAA | 14965 |
| 7609 | AUUUCAGC C UGAAUGUC | 5626 | GACAUUCA CUGAUGAGGCCGUUAGGCCGAA ICUGAAAU | 14966 |
| 7610 | UUUCAGCC U GAAUGUCU | 5627 | AGACAUUC CUGAUGAGGCCGUUAGGCCGAA IGCUGAAA | 14967 |
| 7618 | UGAAUGUC U GCCUAUAU | 5628 | AUAUAGGC CUGAUGAGGCCGUUAGGCCGAA IACAUUCA | 14968 |
| 7621 | AUGUCUGC C UAUAUAUU | 5629 | AAUAUAUA CUGAUGAGGCCGUUAGGCCGAA ICAGACAU | 14969 |
| 7622 | UGUCUGCC U AUAUAUUC | 5630 | GAAUAUAU CUGAUGAGGCCGUUAGGCCGAA IGCAGACA | 14970 |
| 7631 | AUAUAUUC U CUGCUCUU | 5631 | AAGAGCAG CUGAUGAGGCCGUUAGGCCGAA IAAUAUAU | 14971 |
| 7633 | AUAUUCUC U GCUCUUUG | 5632 | CAAAGAGC CUGAUGAGGCCGUUAGGCCGAA IAGAAUAU | 14972 |
| 7636 | UUCUCUGC U CUUUGUAU | 5633 | AUACAAAG CUGAUGAGGCCGUUAGGCCGAA ICAGAGAA | 14973 |
| 7638 | CUCUGCUC U UUGUAUUC | 5634 | GAAUACAA CUGAUGAGGCCGUUAGGCCGAA IAGCAGAG | 14974 |
| 7647 | UUGUAUUC U CCUUUGAA | 5635 | UUCAAAGG CUGAUGAGGCCGUUAGGCCGAA IAAUACAA | 14975 |
| 7649 | GUAUUCUC C UUUGAACC | 5636 | GGUUCAAA CUGAUGAGGCCGUUAGGCCGAA IAGAAUAC | 14976 |
| 7650 | UAUUCUCC U UUGAACCC | 5637 | GGGUUCAA CUGAUGAGGCCGUUAGGCCGAA IGAGAAUA | 14977 |
| 7657 | CUUUGAAC C CGUUAAAA | 5638 | UUUUAACG CUGAUGAGGCCGUUAGGCCGAA IUUCAAAG | 14978 |
| 7658 | UUUGAACC C GUUAAAAC | 5639 | GUUUUAAC CUGAUGAGGCCGUUAGGCCGAA IGUUCAAA | 14979 |
| 7667 | GUUAAAAC A UCCUGUGG | 5640 | CCACAGGA CUGAUGAGGCCGUUAGGCCGAA IUUUUAAC | 14980 |
| 7670 | AAAACAUC C UGUGGCAC | 5641 | GUGCCACA CUGAUGAGGCCGUUAGGCCGAA IAUGUUUU | 14981 |
| 7671 | AAACAUCC U GUGGCACU | 5642 | AGUGCCAC CUGAUGAGGCCGUUAGGCCGAA IGAUGUUU | 14982 |

Core Sequence = CUGAUGAG GCCGUUAGGC CGAA (SEQ ID NO. 20827).
Underlined region can be any X sequence or linker, as described herein.
"I" represents Inosine.

TABLE XV

G-Cleaver Ribozyme and Target Sequences

| Pos | Target | Seq ID No | Ribozyme Sequence | Seq ID No |
|---|---|---|---|---|
| 67 | GGGCUCGGGU G CAGCG | 5643 | CGCUG UGAUG GCAUGCACUAUGC GCG ACCCGAGCCC | 14983 |
| 91 | GCCUGGCGGC G AGGAU | 5644 | AUCCU UGAUG GCAUGCACUAUGC GCG GCCGCCAGGC | 14984 |
| 114 | GGAAGUGGUU G UCUCC | 5645 | GGAGA UGAUG GCAUGCACUAUGC GCG AACCACUUCC | 14985 |
| 131 | GGCUGGAGCC G CGAGA | 5646 | UCUCG UGAUG GCAUGCACUAUGC GCG GCUCCAGCC | 14986 |
| 133 | CUGGAGCCGC G AGACG | 5647 | CGUCU UGAUG GCAUGCACUAUGC GCG GCGGCUCCAG | 14987 |
| 142 | CGAGACGGGC G CUCAG | 5648 | CUGAG UGAUG GCAUGCACUAUGC GCG GCCCGUCUCG | 14988 |
| 151 | CGCUCAGGGC G CGGGG | 5649 | CCCCG UGAUG GCAUGCACUAUGC GCG GCCCUGAGCG | 14989 |
| 168 | CGGCGGCGGC G AACGA | 5650 | UCGUU UGAUG GCAUGCACUAUGC GCG GCCGCCGCCG | 14990 |
| 172 | GGCGGCGAAC G AGAGG | 5651 | CCUCU UGAUG GCAUGCACUAUGC GCG GUUCGCCGCC | 14991 |
| 214 | CCGGGGGAGC G CGGGC | 5652 | GCCCG UGAUG GCAUGCACUAUGC GCG GCUCCCCCGG | 14992 |
| 227 | GGCACCGGGC G AGCAG | 5653 | CUGCU UGAUG GCAUGCACUAUGC GCG GCCCGGUGCC | 14993 |

TABLE XV-continued

G-Cleaver Ribozyme and Target Sequences

| Pos | Target | Seq ID No | Ribozyme Sequence | Seq ID No |
|-----|--------|-----------|-------------------|-----------|
| 236 | CGAGCAGGCC G CGUCG | 5654 | CGACG UGAUG GCAUGCACUAUGC GCG GGCCUGCUCG | 14994 |
| 241 | AGGCCGCGUC G CGCUC | 5655 | GAGCG UGAUG GCAUGCACUAUGC GCG GACGCGGCCU | 14995 |
| 243 | GCCGCGUCGC G CUCAC | 5656 | GUGAG UGAUG GCAUGCACUAUGC GCG GCGACGCGGC | 14996 |
| 279 | CCGGGGUCCU G CUGUG | 5657 | CACAG UGAUG GCAUGCACUAUGC GCG AGGACCCCGG | 14997 |
| 282 | GGGUCCUGCU G UGCGC | 5658 | GCGCA UGAUG GCAUGCACUAUGC GCG AGCAGGACCC | 14998 |
| 284 | GUCCUGCUGU G CGCGC | 5659 | GCGCG UGAUG GCAUGCACUAUGC GCG ACAGCAGGAC | 14999 |
| 286 | CCUGCUGUGC G CGCUG | 5660 | CAGCG UGAUG GCAUGCACUAUGC GCG GCACAGCAGG | 15000 |
| 288 | UGCUGUGCGC G CUGCU | 5661 | AGCAG UGAUG GCAUGCACUAUGC GCG GCGCACAGCA | 15001 |
| 291 | UGUGCGCGCU G CUCAG | 5662 | CUGAG UGAUG GCAUGCACUAUGC GCG AGCGCGCACA | 15002 |
| 299 | CUGCUCAGCU G UCUGC | 5663 | GCAGA UGAUG GCAUGCACUAUGC GCG AGCUGAGCAG | 15003 |
| 303 | UCAGCUGUCU G CUUCU | 5664 | AGAAG UGAUG GCAUGCACUAUGC GCG AGACAGCUGA | 15004 |
| 346 | AAAAGAUCCU G AACUG | 5665 | CAGUU UGAUG GCAUGCACUAUGC GCG AGGAUCUUUU | 15005 |
| 351 | AUCCUGAACU G AGUUU | 5666 | AAACU UGAUG GCAUGCACUAUGC GCG AGUUCAGGAU | 15006 |
| 378 | AGCACAUCAU G CAAGC | 5667 | GCUUG UGAUG GCAUGCACUAUGC GCG AUGAUGUGCU | 15007 |
| 396 | GCCAGACACU G CAUCU | 5668 | AGAUG UGAUG GCAUGCACUAUGC GCG AGUGUCUGGC | 15008 |
| 407 | CAUCUCCAAU G CAGGG | 5669 | CCCUG UGAUG GCAUGCACUAUGC GCG AUUGGAGAUG | 15009 |
| 438 | AAUGGUCUUU G CCUGA | 5670 | UCAGG UGAUG GCAUGCACUAUGC GCG AAAGACCAUU | 15010 |
| 442 | GUCUUUGCCU G AAAUG | 5671 | CAUUU UGAUG GCAUGCACUAUGC GCG AGGCAAAGAC | 15011 |
| 450 | CUGAAAUGGU G AGUAA | 5672 | UUACU UGAUG GCAUGCACUAUGC GCG ACCAUUUCAG | 15012 |
| 463 | UAAGGAAAGC G AAAGG | 5673 | CCUUU UGAUG GCAUGCACUAUGC GCG GCUUUCCUUA | 15013 |
| 471 | GCGAAAGGCU G AGCAU | 5674 | AUGCU UGAUG GCAUGCACUAUGC GCG AGCCUUUCGC | 15014 |
| 487 | AACUAAAUCU G CCUGU | 5675 | ACAGG UGAUG GCAUGCACUAUGC GCG AGAUUUAGUU | 15015 |
| 491 | AAAUCUGCCU G UGGAA | 5676 | UUCCA UGAUG GCAUGCACUAUGC GCG AGGCAGAUUU | 15016 |
| 515 | AAACAAUUCU G CAGUA | 5677 | UACUG UGAUG GCAUGCACUAUGC GCG AGAAUUGUUU | 15017 |
| 531 | CUUUAACCUU G AACAC | 5678 | GUGUU UGAUG GCAUGCACUAUGC GCG AAGGUUAAAG | 15018 |
| 569 | UUCUACAGCU G CAAAU | 5679 | AUUUG UGAUG GCAUGCACUAUGC GCG AGCUGUAGAA | 15019 |
| 583 | AUAUCUAGCU G UACCU | 5680 | AGGUA UGAUG GCAUGCACUAUGC GCG AGCUAGAUAU | 15020 |
| 616 | AACAGAAUCU G CAAUC | 5681 | GAUUG UGAUG GCAUGCACUAUGC GCG AGAUUCUGUU | 15021 |
| 637 | AUUUAUUAGU G AUACA | 5682 | UGUAU UGAUG GCAUGCACUAUGC GCG ACUAAUAAAU | 15022 |
| 663 | UCGUAGAGAU G UACAG | 5683 | CUGUA UGAUG GCAUGCACUAUGC GCG AUCUCUACGA | 15023 |
| 670 | GAUGUACAGU G AAAUC | 5684 | GAUUU UGAUG GCAUGCACUAUGC GCG ACUGUACAUC | 15024 |
| 679 | UGAAAUCCCC G AAAUU | 5685 | AAUUU UGAUG GCAUGCACUAUGC GCG GGGGAUUUCA | 15025 |
| 693 | UUAUACACAU G ACUGA | 5686 | UCAGU UGAUG GCAUGCACUAUGC GCG AUGUGUAUAA | 15026 |
| 697 | ACACAUGACU G AAGGA | 5687 | UCCUU UGAUG GCAUGCACUAUGC GCG AGUCAUGUGU | 15027 |
| 722 | GUCAUUCCCU G CCGGG | 5688 | CCCGG UGAUG GCAUGCACUAUGC GCG AGGGAAUGAC | 15028 |
| 748 | UAACAUCACU G UUACU | 5689 | AGUAA UGAUG GCAUGCACUAUGC GCG AGUGAUGUUA | 15029 |
| 772 | GUUCCACUU G ACACU | 5690 | AGUGU UGAUG GCAUGCACUAUGC GCG AAGUGGAAAC | 15030 |

TABLE XV-continued

G-Cleaver Ribozyme and Target Sequences

| Pos | Target | Seq ID No | Ribozyme Sequence | Seq ID No |
|---|---|---|---|---|
| 780 | UUGACACUUU G AUCCC | 5691 | GCGAU UGAUG GCAUGCACUAUGC GCG AAAGUGUCAA | 15031 |
| 787 | UUUGAUCCCU G AUGGA | 5692 | UCCAU UGAUG GCAUGCACUAUGC GCG AGGGAUCAAA | 15032 |
| 797 | GAUGGAAAAC G CAUAA | 5693 | UUAUC UGAUG GCAUGCACUAUGC GCG GUUUUCCAUC | 15033 |
| 838 | CAUAUCAAAU G CAACG | 5694 | CGUUG UGAUG GCAUGCACUAUGC GCG AUUUGAUAUG | 15034 |
| 864 | UAGGGCUUCU G ACCUG | 5695 | CAGGU UGAUG GCAUGCACUAUGC GCG AGAAGCCCUA | 15035 |
| 869 | CUUCUGACCU G UGAAG | 5696 | CUUCA UGAUG GCAUGCACUAUGC GCG AGGUCAGAAG | 15036 |
| 871 | UCUGACCUGU G AAGCA | 5697 | UGCUU UGAUG GCAUGCACUAUGC GCG ACAGGUCAGA | 15037 |
| 894 | AUGGGCAUUU G UAUAA | 5698 | UUAUA UGAUG GCAUGCACUAUGC GCG AAAUGCCCAU | 15038 |
| 920 | CUCACACAUC G ACAAA | 5699 | UUUGU UGAUG GCAUGCACUAUCC GCG GAUGUGUGAG | 15039 |
| 943 | AAUCAUAGAU G UCCAA | 5700 | UUGGA UGAUG GCAUGCACUAUGC GCG AUCUAUGAUU | 15040 |
| 962 | AGCACACCAC G CCCAG | 5701 | CUGGG UGAUG GCAUGCACUAUGC GCG GUGGUGUGCU | 15041 |
| 994 | CCAUACUCUU G UCCUC | 5702 | GAGGA UGAUG GCAUGCACUAUGC GCG AAGAGUAUGG | 15042 |
| 1004 | GUCCUCAAUU G UACUG | 5703 | CAGUA UGAUG GCAUGCACUAUGC GCG AAUUGAGGAC | 15043 |
| 1009 | CAAUUGUACU G CUACC | 5704 | GGUAG UGAUG GCAUGCACUAUGC GCG AGUACAAUUG | 15044 |
| 1023 | CCACUCCCUU G AACAC | 5705 | GUGUU UGAUG GCAUGCACUAUGC GCG AAGGGAGUGG | 15045 |
| 1029 | CCUUGAACAC G AGAGU | 5706 | ACUCU UGAUG GCAUGCACUAUGC GCG GUGUUCAAGG | 15046 |
| 1041 | GAGUUCAAAU G ACCUG | 5707 | CAGGU UGAUG GCAUGCACUAUGC GCG AUUUGAACUC | 15047 |
| 1057 | GAGUUACCCU G AUGAA | 5708 | UUCAU UGAUG GCAUGCACUAUGC GCG AGGGUAACUC | 15048 |
| 1060 | UUACCCUGAU G AAAAA | 5709 | UUUUU UGAUG GCAUGCACUAUGC GCG AUCAGGGUAA | 15049 |
| 1088 | UCCGUAAGGC G ACGAA | 5710 | UUCGU UGAUG GCAUGCACUAUGC GCG GCCUUACGGA | 15050 |
| 1091 | GUAAGGCGAC G AAUUG | 5711 | CAAUU UGAUG GCAUGCACUAUGC GCG GUCGCCUUAC | 15051 |
| 1096 | GCGACGAAUU G ACCAA | 5712 | UUGGU UGAUG GCAUGCACUAUGC GCG AAUUCGUCGC | 15052 |
| 1114 | CAAUUCCCAU G CCAAC | 5713 | GUUGG UGAUG GCAUGCACUAUGC GCG AUGGGAAUUG | 15053 |
| 1132 | AUUCUACAGU G UUCUU | 5714 | AAGAA UGAUG GCAUGCACUAUGC GCG ACUGUAGAAU | 15054 |
| 1144 | UCUUACUAUU G ACAAA | 5715 | UUUGU UGAUG GCAUGCACUAUGC GCG AAUAGUAAGA | 15055 |
| 1152 | UUGACAAAAU G CAGAA | 5716 | UUCUG UGAUG GCAUGCACUAUGC GCG AUUUUGUCAA | 15056 |
| 1181 | CUUUAUACUU G UCGUG | 5717 | CACGA UGAUG GCAUGCACUAUGC GCG AAGUAUAAAG | 15057 |
| 1186 | UACUUGUCGU G UAAGG | 5718 | CCUUA UGAUG GCAUGCACUAUGC GCG ACGACAAGUA | 15058 |
| 1213 | AUUCAAAUCU G UUAAC | 5719 | GUUAA UGAUG GCAUGCACUAUGC GCG AGAUUUGAAU | 15059 |
| 1227 | ACACCUCAGU G CAUAU | 5720 | AUAUG UGAUG GCAUGCACUAUGC GCG ACUGAGGUGU | 15060 |
| 1237 | GCAUAUAUAU G AUAAA | 5721 | UUUAU UGAUG GCAUGCACUAUGC GCG AUAUAUAUGC | 15061 |
| 1255 | AUUCAUCACU G UGAAA | 5722 | UUUCA UGAUG GCAUGCACUAUGC GCG AGUGAUGAAU | 15062 |
| 1257 | UCAUCACUGU G AAACA | 5723 | UGUUU UGAUG GCAUGCACUAUGC GCG ACAGUGAUGA | 15063 |
| 1265 | GUGAAACAUC G AAAAC | 5724 | GUUUU UGAUG GCAUGCACUAUGC GCG GAUGUUUCAC | 15064 |
| 1278 | AACAGCAGGU G CUUGA | 5725 | UCAAG UGAUG GCAUGCACUAUGC GCG ACCUGCUGUU | 15065 |
| 1282 | GCAGGUGCUU G AAACC | 5726 | GGUUU UGAUG GCAUGCACUAUGC GCG AAGCACCUGC | 15066 |
| 1320 | GGCUCUCUAU G AAAGU | 5727 | ACUUU UGAUG GCAUGCACUAUGC GCG AUAGAGAGCC | 15067 |

TABLE XV-continued

G-Cleaver Ribozyme and Target Sequences

| Pos | Target | Seq ID No | Ribozyme Sequence | Seq ID No |
|---|---|---|---|---|
| 1326 | CUAUGAAAGU G AAGGC | 5728 | GCCUU UGAUG GCAUGCACUAUGC GCG ACUUUCAUAG | 15068 |
| 1341 | CAUUUCCCUC G CCGGA | 5729 | UCCGG UGAUG GCAUGCACUAUGC GCG GAGGGAAAUG | 15069 |
| 1351 | GCCGGAAGUU G UAUGG | 5730 | CCAUA UGAUG GCAUGCACUAUGC GCG AACUUCCGGC | 15070 |
| 1375 | UGGGUUACCU G CGACU | 5731 | AGUCG UGAUG GCAUGCACUAUGC GCG AGGUAACCCA | 15071 |
| 1377 | GGUUACCUGC G ACUGA | 5732 | UCAGU UGAUG GCAUGCACUAUGC GCG GCAGGUAACC | 15072 |
| 1381 | ACCUGCGACU G AGAAA | 5733 | UUUCU UGAUG GCAUGCACUAUGC GCG AGUCGCAGGU | 15073 |
| 1390 | UGAGAAAUCU G CUCGC | 5734 | GCGAG UGAUG GCAUGCACUAUGC GCG AGAUUUCUCA | 15074 |
| 1394 | AAAUCUGCUC G CUAUU | 5735 | AAUAG UGAUG GCAUGCACUAUGC GCG GAGCAGAUUU | 15075 |
| 1401 | CUCGCUAUUU G ACUCG | 5736 | CGAGU UGAUG GCAUGCACUAUGC GCG AAAUAGCGAG | 15076 |
| 1438 | GGACGUAACU G AAGAG | 5737 | CUCUU UGAUG GCAUGCACUAUGC GCG AGUUACGUCC | 15077 |
| 1447 | UGAAGAGGAU G CAGGG | 5738 | CCCUG UGAUG GCAUGCACUAUGC GCG AUCCUCUUCA | 15078 |
| 1467 | AUACAAUCUU G CUGAG | 5739 | CUCAG UGAUG GCAUGCACUAUGC GCG AAGAUUGUAU | 15079 |
| 1470 | CAAUCUUGCU G AGCAU | 5740 | AUGCU UGAUG GCAUGCACUAUGC GCG AGCAAGAUUG | 15080 |
| 1489 | ACAGUCAAAU G UGUUU | 5741 | AAACA UGAUG GCAUGCACUAUGC GCG AUUUGACUGU | 15081 |
| 1491 | AGUCAAAUGU G UUUAA | 5742 | UUAAA UGAUG GCAUGCACUAUGC GCG ACAUUUGACU | 15082 |
| 1507 | AAACCUCACU G CCACU | 5743 | AGUGG UGAUG GCAUGCACUAUGC GCG AGUGAGGUUG | 15083 |
| 1519 | CACUCUAAUU G UCAAU | 5744 | AUUGA UGAUG GCAUGCACUAUGC GCG AAUUAGAGUG | 15084 |
| 1525 | AAUUGUCAAU G UGAAA | 5745 | UGUCA UGAUG GCAUGCACUAUGC GCG AUUGACAAUU | 15085 |
| 1527 | UUGUCAAUGU G AAACC | 5746 | GGUUU UGAUG GCAUGCACUAUGC GCG ACAUUGACAA | 15086 |
| 1543 | CCAGAUUUAC G AAAAG | 5747 | CUUUU UGAUG GCAUGCACUAUGC GCG GUAAAUCUGG | 15087 |
| 1554 | AAAAGGCCGU G UCAUC | 5748 | GAUGA UGAUG GCAUGCACUAUGC GCG ACGGCCUUUU | 15088 |
| 1605 | GACAAAUCCU G ACUUG | 5749 | CAAGU UGAUG GCAUGCACUAUGC GCG AGGAUUUGUC | 15089 |
| 1610 | AUCCUGACUU G UACCG | 5750 | CGGUA UGAUG GCAUGCACUAUGC GCG AAGUCAGGAU | 15090 |
| 1615 | GACUUGUACC G CAUAU | 5751 | AUAUG UGAUG GCAUGCACUAUGC GCG GGUACAAGUC | 15091 |
| 1661 | UGGCACCCCU G UAACC | 5752 | GGUUA UGAUG GCAUGCACUAUGC GCG AGGGGUGCCA | 15092 |
| 1678 | UAAUCAUUCC G AAGCA | 5753 | UGCUU UGAUG GCAUGCACUAUGC GCG GGAAUGAUUA | 15093 |
| 1688 | GAAGCAAGGU G UGACU | 5754 | AGUCA UGAUG GCAUGCACUAUGC GCG ACCUUGCUUC | 15094 |
| 1690 | AGCAAGGUGU G ACUUU | 5755 | AAAGU UGAUG GCAUGCACUAUGC GCG ACACCUUGCU | 15095 |
| 1697 | UGUGACUUUU G UUCCA | 5756 | UGGAA UGAUG GCAUGCACUAUGC GCG AAAAGUCACA | 15096 |
| 1708 | UUCCAAUAAU G AAGAG | 5757 | CUCUU UGAUG GCAUGCACUAUGC GCG AUUAUUGGAA | 15097 |
| 1729 | UAUCCUGGAU G CUGAC | 5758 | GUCAG UGAUG GCAUGCACUAUGC GCG AUCCAGGAUA | 15098 |
| 1732 | CCUGGAUGCU G ACAGC | 5759 | GCUGU UGAUG GCAUGCACUAUGC GCG AGCAUCCAGG | 15099 |
| 1756 | AAACAGAAUU G AGAGC | 5760 | GCUCU UGAUG GCAUGCACUAUGC GCG AAUUCUGUUU | 15100 |
| 1772 | AUCACUCAGC G CAUGG | 5761 | CCAUG UGAUG GCAUGCACUAUGC GCG GCUGAGUGAU | 15101 |
| 1819 | CACCUGGGUU G UGGCU | 5762 | AGCCA UGAUG GCAUGCACUAUGC GCG AACCAAGGUG | 15102 |
| 1825 | GGUUGUGGCU G ACUCU | 5763 | AGAGU UGAUG GCAUGCACUAUGC GCG AGCCACAACC | 15103 |
| 1853 | AUCUACAUUU G CAUAG | 5764 | CUAUG UGAUG GCAUGCACUAUGC GCG AAAUGUAGAU | 15104 |

TABLE XV-continued

G-Cleaver Ribozyme and Target Sequences

| Pos | Target | Seq ID No | Ribozyme Sequence | Seq ID No |
|---|---|---|---|---|
| 1879 | AGUUGGGACU G UGGGA | 5765 | UCCCA UGAUG GCAUGCACUAUGC GCG AGUCCCAACU | 15105 |
| 1912 | UAUCACAGAU G UGCCA | 5766 | UGGCA UGAUG GCAUGCACUAUGC GCG AUCUGUGAUA | 15106 |
| 1914 | UCACAGAUGU G CCAAA | 5767 | UUUGG UGAUG GCAUGCACUAUGC GCG ACAUCUGUGA | 15107 |
| 1930 | UGGGUUUCAU G UUAAC | 5768 | GUUAA UGAUG GCAUGCACUAUGC GCG AUGAAACCCA | 15108 |
| 1947 | UGGAAAAAAU G CCGAC | 5769 | GUCGG UGAUG GCAUGCACUAUGC GCG AUUUUUUCCA | 15109 |
| 1950 | AAAAAAUGCC G ACGGA | 5770 | UCCGU UGAUG GCAUGCACUAUGC GCG GGCAUUUUUU | 15110 |
| 1968 | GAGAGGACCU G AAACU | 5771 | AGUUU UGAUG GCAUGCACUAUGC GCG AGGUCCUCUC | 15111 |
| 1974 | ACCUGAAACU G UCUUG | 5772 | CAAGA UGAUG GCAUGCACUAUGC GCG AGUUUCAGGU | 15112 |
| 1979 | AAACUGUCUU G CACAG | 5773 | CUGUG UGAUG GCAUGCACUAUGC GCG AAGACAGUUU | 15113 |
| 2025 | GGAUUUUACU G CGGAC | 5774 | GUCCG UGAUG GCAUGCACUAUGC GCG AGUAAAAUCC | 15114 |
| 2049 | ACAGAACAAU G CACUA | 5775 | UAGUG UGAUG GCAUGCACUAUGC GCG AUUGUUCUGU | 15115 |
| 2121 | UUACCAUCAU G AAUGU | 5776 | ACAUU UGAUG GCAUGCACUAUGC GCG AUGAUGGUAA | 15116 |
| 2125 | CAUCAUGAAU G UUUCC | 5777 | GGAAA UGAUG GCAUGCACUAUGC GCG AUUCAUGAUG | 15117 |
| 2133 | AUGUUUCCCU G CAAGA | 5778 | UCUUG UGAUG GCAUGCACUAUGC GCG AGGGAAACAU | 15118 |
| 2152 | AGGCACCUAU G CCUGC | 5779 | GCAGG UGAUG GCAUGCACUAUGC GCG AUAGGUGCCU | 15119 |
| 2156 | ACCUAUGCCU G CAGAG | 5780 | CUCUG UGAUG GCAUGCACUAUGC GCG AGGGAUAGGU | 15120 |
| 2170 | AGCCAGGAAU G UAUAC | 5781 | GUAUA UGAUG GCAUGCACUAUGC GCG AUUCCUGGCU | 15121 |
| 2241 | CAUACCUCCU G CGAAA | 5782 | UUUCG UGAUG GCAUGCACUAUGC GCG AGGAGGUAUG | 15122 |
| 2243 | UACCUCCUGC G AAACC | 5783 | GGUUU UGAUG GCAUGCACUAUGC GCG GCAGGAGGUA | 15123 |
| 2254 | AAACCUCAGU G AUCAC | 5784 | GUGAU UGAUG GCAUGCACUAUGC GCG ACUGAGGUUU | 15124 |
| 2294 | ACUUAGACU G UCAUG | 5785 | CAUGA UGAUG GCAUGCACUAUGC GCG AGUCUAAAGU | 15125 |
| 2299 | AGACUGUCAU G CUAAU | 5786 | AUUAG UGAUG GCAUGCACUAUGC GCG AUGACAGUCU | 15126 |
| 2308 | UGCUAAUGGU G UCCCC | 5787 | GGGGA UGAUG GCAUGCACUAUGC GCG ACCAUUAGCA | 15127 |
| 2314 | UGGUGUCCCC G AGCCU | 5788 | AGGCU UGAUG GCAUGCACUAUGC GCG GGGGACACCA | 15128 |
| 2394 | GAAGCAGCAC G CUGUU | 5789 | AACAG UGAUG GCAUGCACUAUGC GCG GUGCUGCUUC | 15129 |
| 2397 | GCAGCACGCU G UUUAU | 5790 | AUAAA UGAUG GCAUGCACUAUGC GCG AGCGUGCUGC | 15130 |
| 2404 | GCUGUUUAUU G AAAGA | 5791 | UCUUU UGAUG GCAUGCACUAUGC GCG AAUAAACAGC | 15131 |
| 2425 | AGAAGAGGAU G AAGGU | 5792 | ACCUU UGAUG GCAUGCACUAUGC GCG AUCCUCUUCU | 15132 |
| 2431 | GGAUGAAGGU G UCUAU | 5793 | AUAGA UGAUG GCAUGCACUAUGC GCG ACCUUCAUCC | 15133 |
| 2441 | GUCUAUCACU G CAAAG | 5794 | CUUUG UGAUG GCAUGCACUAUGC GCG AGUGAUAGAC | 15134 |
| 2467 | GAAGGGCUCU G UGGAA | 5795 | UUCCA UGAUG GCAUGCACUAUGC GCG AGAGCCCUUC | 15135 |
| 2491 | AUACCUCACU G UUCAA | 5796 | UUGAA UGAUG GCAUGCACUAUGC GCG AGUGAGGUAU | 15136 |
| 2526 | AUCUGGAGCU G AUCAC | 5797 | GUGAU UGAUG GCAUGCACUAUGC GCG AGCUCCAGAU | 15137 |
| 2540 | ACUCUAACAU G CACCU | 5798 | AGGUG UGAUG GCAUGCACUAUGC GCG AUGUUAGAGU | 15138 |
| 2546 | ACAUGCACCU G UGGG | 5799 | CCACA UGAUG GCAUGCACUAUGC GCG AGGUGCAUGU | 15139 |
| 2548 | AUGCACCUGU G GGCU | 5800 | AGCCA UGAUG GCAUGCACUAUGC GCG ACAGGUGCAU | 15140 |
| 2554 | CUGUGUGGCU G CGACU | 5801 | AGUCG UGAUG GCAUGCACUAUGC GCG AGCCACACAG | 15141 |

TABLE XV-continued

G-Cleaver Ribozyme and Target Sequences

| Pos | Target | Seq ID No | Ribozyme Sequence | Seq ID No |
|---|---|---|---|---|
| 2556 | GUGUGGCUGC G ACUCU | 5802 | AGAGU UGAUG GCAUGCACUAUGC GCG GCAGCCACAC | 15142 |
| 2591 | CUCCUUAUCC G AAAAA | 5803 | UUUUU UGAUG GCAUGCACUAUGC GCG GGAUAAGGAG | 15143 |
| 2598 | UCCGAAAAAU G AAAAG | 5804 | CUUUU UGAUG GCAUGCACUAUGC GCG AUUUUCGGA | 15144 |
| 2614 | GUCUUCUUCU G AAAUA | 5805 | UAUUU UGAUG GCAUGCACUAUGC GCG AGAAGAAGAC | 15145 |
| 2626 | AAUAAAGACU G ACUAC | 5806 | GUAGU UGAUG GCAUGCACUAUGC GCG AGUCUUUAUU | 15146 |
| 2656 | GGACCCAGAU G AAGUU | 5807 | AACUU UGAUG GCAUGCACUAUGC GCG AUCUGGGUCC | 15147 |
| 2671 | UCCUUUGGAU G AGCAG | 5808 | CUGCU UGAUG GCAUGCACUAUGC GCG AUCCAAAGGA | 15148 |
| 2678 | GAUGAGCAGU G UGAGC | 5809 | GCUCA UGAUG GCAUGCACUAUGC GCG ACUGCUCAUC | 15149 |
| 2680 | UGAGCAGUGU G AGCGG | 5810 | CCGCU UGAUG GCAUGCACUAUGC GCG ACACUGCUCA | 15150 |
| 2695 | GCUCCCUUAU G AUGCC | 5811 | GGCAU UGAUG GCAUGCACUAUGC GCG AUAAGGGAGC | 15151 |
| 2698 | CCCUUAUGAU G CCAGC | 5812 | GCUGG UGAUG GCAUGCACUAUGC GCG AUCAUAAGGG | 15152 |
| 2716 | GUGGGAGUUU G CCCGG | 5813 | CCGGG UGAUG GCAUGCACUAUGC GCG AAACUCCCAC | 15153 |
| 2813 | UCACCUACGU G CCGGA | 5814 | UCCGG UGAUG GCAUGCACUAUGC GCG ACGUAGGUGA | 15154 |
| 2821 | GUGCCGGACU G UGGCU | 5815 | AGCCA UGAUG GCAUGCACUAUGC GCG AGUCCGGCAC | 15155 |
| 2827 | GACUGUGGCU G UGAAA | 5816 | UUUCA UGAUG GCAUGCACUAUGC GCG AGCCACAGUC | 15156 |
| 2829 | CUGUGGCUGU G AAAAU | 5817 | AUUUU UGAUG GCAUGCACUAUGC GCG ACAGCCACAG | 15157 |
| 2835 | CUGUGAAAAU G CUGAA | 5818 | UUCAG UGAUG GCAUGCACUAUGC GCG AUUUUCACAG | 15158 |
| 2838 | UGAAAAUGCU G AAAGA | 5819 | UCUUU UGAUG GCAUGCACUAUGC GCG AGCAUUUUCA | 15159 |
| 2860 | CACGGCCAGC G AGUAC | 5820 | GUACU UGAUG GCAUGCACUAUGC GCG GCUGGCCGUG | 15160 |
| 2874 | ACAAAGCUCU G AUGAC | 5821 | GUCAU UGAUG GCAUGCACUAUGC GCG AGAGCUUUGU | 15161 |
| 2877 | AAGCUCUGAU G ACUGA | 5822 | UCAGU UGAUG GCAUGCACUAUGC GCG AUCAGAGCUU | 15162 |
| 2881 | UCUGAUGACU G AGCUA | 5823 | UAGCU UGAUG GCAUGCACUAUGC GCG AGUCAUCAGA | 15163 |
| 2895 | UAAAAAUCUU G ACCCA | 5824 | UGGGU UGAUG GCAUGCACUAUGC GCG AAGAUUUUUA | 15164 |
| 2916 | GCCACCAUCU G AACGU | 5825 | ACGUU UGAUG GCAUGCACUAUGC GCG AGAUGGUGGC | 15165 |
| 2931 | UGGUUAACCU G CUGGG | 5826 | CCCAG UGAUG GCAUGCACUAUGC GCG AGGUUAACCA | 15166 |
| 2942 | CUGGGAGCCU G CACCA | 5827 | UGGUG UGAUG GCAUGCACUAUGC GCG AGGCUCCCAG | 15167 |
| 2964 | GAGGGCCUCU G AUGGU | 5828 | ACCAU UGAUG GCAUGCACUAUGC GCG AGAGGCCCUC | 15168 |
| 2970 | CUCUGAUGGU G AUUGU | 5829 | ACAAU UGAUG GCAUGCACUAUGC GCG ACCAUCAGAG | 15169 |
| 2974 | GAUGGUGAUU G UUGAA | 5830 | UUCAA UGAUG GCAUGCACUAUGC GCG AAUCACCAUC | 15170 |
| 2977 | GGUGAUUGUU G AAUAC | 5831 | GUAUU UGAUG GCAUGCACUAUGC GCG AACAAUCACC | 15171 |
| 2984 | GUUGAAUACU G CAAAU | 5832 | AUUUG UGAUG GCAUGCACUAUGC GCG AGUAUUCAAC | 15172 |
| 3025 | GAGCAAACGU G ACUUA | 5833 | UAAGU UGAUG GCAUGCACUAUGC GCG ACGUUUGCUC | 15173 |
| 3049 | CAACAAGGAU G CAGCA | 5834 | UGCUG UGAUG GCAUGCACUAUGC GCG AUCCUUGUUG | 15174 |
| 3139 | CACCAGCAGC G AAAGC | 5835 | GCUUU UGAUG GCAUGCACUAUGC GCG GCUGCUGGUG | 15175 |
| 3148 | CGAAAGCUUU G CGAGC | 5838 | GCUCG UGAUG GCAUGCACUAUGC GCG AAAGCUUUCG | 15176 |
| 3150 | AAAGCUUUGC G AGCUC | 5837 | GAGCU UGAUG GCAUGCACUAUGC GCG GCAAAGCUUU | 15177 |
| 3180 | AUAAAAGUCU G AGUGA | 5838 | UCACU UGAUG GCAUGCACUAUGC GCG AGACUUUUAU | 15178 |

TABLE XV-continued

G-Cleaver Ribozyme and Target Sequences

| Pos | Target | Seq ID No | Ribozyme Sequence | Seq ID No |
|---|---|---|---|---|
| 3184 | AAGUCUGAGU G AUGUU | 5839 | AACAU UGAUG GCAUGCACUAUGC GCG ACUCAGACUU | 15179 |
| 3187 | UCUGAGUGAU G UUGAG | 5840 | CUCAA UGAUG GCAUGCACUAUGC GCG AUCACUCAGA | 15180 |
| 3190 | GAGUGAUGUU G AGGAA | 5841 | UUCCU UGAUG GCAUGCACUAUGC GCG AACAUCACUC | 15181 |
| 3208 | GGAGGAUUCU G ACGGU | 5842 | ACCGU UGAUG GCAUGCACUAUGC GCG AGAAUCCUCC | 15182 |
| 3246 | UGGAAGAUCU G AUUUC | 5843 | GAAAU UGAUG GCAUGCACUAUGC GCG AGAUCUUCCA | 15183 |
| 3288 | UGGAGUUCCU G UCUUC | 5844 | GAAGA UGAUG GCAUGCACUAUGC GCG AGGAACUCCA | 15184 |
| 3302 | UCCAGAAAGU G CAUUC | 5845 | GAAUG UGAUG GCAUGCACUAUGC GCG ACUUUCUGGA | 15185 |
| 3324 | ACCUGGCAGC G AGAAA | 5846 | UUUCU UGAUG GCAUGCACUAUGC GCG GCUGCCAGGU | 15186 |
| 3343 | UCUUUUAUCU G AGAAC | 5847 | GUUCU UGAUG GCAUGCACUAUGC GCG AGAUAAAAGA | 15187 |
| 3357 | ACAACGUGGU G AAGAU | 5848 | AUCUU UGAUG GCAUGCACUAUGC GCG ACCACGUUGU | 15188 |
| 3365 | GUGAGAUUU G UGAUU | 5849 | AAUCA UGAUG GCAUGCACUAUGC GCG AAAUCUUCAC | 15189 |
| 3367 | GAAGAUUUGU G AUUUU | 5850 | AAAAU UGAUG GCAUGCACUAUGC GCG ACAAAUCUUC | 15190 |
| 3379 | UUUUGGCCUU G CCCGG | 5851 | CCGGG UGAUG GCAUGCACUAUGC GCG AAGGCCAAAA | 15191 |
| 3403 | UAAGAACCCC G AUUAU | 5852 | AUAAU UGAUG GCAUGCACUAUGC GCG GGGUUCUUA | 15192 |
| 3409 | CCCCGAUUAU G UGAGA | 5853 | UCUCA UGAUG GCAUGCACUAUGC GCG AUAAUCGGGG | 15193 |
| 3411 | CCGAUUAUGU G AGAAA | 5854 | UUUCU UGAUG GCAUGCACUAUGC GCG ACAUAAUCGG | 15194 |
| 3428 | GGAGAUACUC G ACUUC | 5855 | GAAGU UGAUG GCAUGCACUAUGC GCG GAGUAUCUCC | 15195 |
| 3438 | GACUUCCUCU G AAAUG | 5856 | CAUUU UGAUG GCAUGCACUAUGC GCG AGAGGAAGUC | 15196 |
| 3454 | GAUGGCUCCC G AAUCU | 5857 | AGAUU UGAUG GCAUGCACUAUGC GCG GGGAGCCAUC | 15197 |
| 3466 | AUCUAUCUUU G ACAAA | 5858 | UUUGU UGAUG GCAUGCACUAUGC GCG AAAGAUAGAU | 15198 |
| 3490 | CACCAAGAGC G ACGUG | 5859 | CACGU UGAUG GCAUGCACUAUGC GCG GCUCUUGGUG | 15199 |
| 3495 | AGAGCGACGU G UGGUC | 5860 | GACCA UGAUG GCAUGCACUAUGC GCG ACGUGCCUCU | 15200 |
| 3513 | ACGGAGUAUU G CUGUG | 5861 | CACAG UGAUG GCAUGCACUAUGC GCG AAUACUCCGU | 15201 |
| 3516 | GAGUAUUGCU G UGGGA | 5862 | UCCCA UGAUG GCAUGCACUAUGC GCG AGCAAUACUC | 15202 |
| 3568 | ACAAAUGGAU G AGGAC | 5863 | GUCCU UGAUG GCAUGCACUAUGC GCG AUCCAUUUGU | 15203 |
| 3578 | GAGGACUUUU G CAGUC | 5864 | GACUG UGAUG GCAUGCACUAUGC GCG AAAAGUCCUC | 15204 |
| 3584 | UUUUGCAGUC G CCUGA | 5865 | UCAGG UGAUG GCAUGCACUAUGC GCG GACUGCAAAA | 15205 |
| 3588 | GCAGUCGCCU G AGGGA | 5866 | UCCCU UGAUG GCAUGCACUAUGC GCG AGGCGACUGC | 15206 |
| 3600 | GGGAAGGCAU G AGGAU | 5867 | AUCCU UGAUG GCAUGCACUAUGC GCG AUGCCUUCCC | 15207 |
| 3606 | GCAUCAGGAU G AGAGC | 5868 | GCUCU UGAUG GCAUGCACUAUGC GCG AUCCUGAUGC | 15208 |
| 3616 | GAGAGCUCCU G AGUAC | 5869 | CUACU UGAUG GCAUGCACUAUGC GCG AGGAGCUCUC | 15209 |
| 3631 | CUCUACUCCU G AAAUC | 5870 | GAUUU UGAUG GCAUGCACUAUGC GCG AGGAGUAGAG | 15210 |
| 3648 | AUCAGAUCAU G CUGGA | 5871 | UCCAG UGAUG GCAUGCACUAUGC GCG AUGAUCUGAU | 15211 |
| 3656 | AUGCUGGACU G CUGGC | 5872 | GCCAG UGAUG GCAUGCACUAUGC GCG AGUCCAGCAU | 15212 |
| 3691 | GCCAAGAUUU G CAGAA | 5873 | UUCUG UGAUG GCAUGCACUAUGC GCG AAAUCUUGGC | 15213 |
| 3700 | UGCAGAACUU G UGGAA | 5874 | UUCCA UGAUG GCAUGCACUAUGC GCG AAGUUCUGCA | 15214 |
| 3715 | AAAACUAGGU G AUUUG | 5875 | CAAAU UGAUG GCAUGCACUAUGC GCG ACCAGUUUU | 15215 |

TABLE XV-continued

G-Cleaver Ribozyme and Target Sequences

| Pos | Target | Seq ID No | Ribozyme Sequence | Seq ID No |
|---|---|---|---|---|
| 3720 | UAGGUGAUUU G CUUCA | 5876 | UGAAG UGAUG GCAUGCACUAUGC GCG AAAUCACCUA | 15216 |
| 3733 | UCAAGCAAAU G UACAA | 5877 | UUGUA UGAUG GCAUGCACUAUGC GCG AUUUGCUUGA | 15217 |
| 3769 | CCCAAUCAAU G CCAUA | 5878 | UAUGG UGAUG GCAUGCACUAUGC GCG AUUGAUUGGG | 15218 |
| 3777 | AUGCCAUACU G ACAGG | 5879 | CCUGU UGAUG GCAUGCACUAUGC GCG AGUAUGGCAU | 15219 |
| 3811 | CUCAACUCCU G CCUUC | 5880 | GAAGG UGAUG GCAUGCACUAUGC GCG AGGAGUUGAG | 15220 |
| 3820 | UGCCUUCUCU G AGGAC | 5881 | GUCCU UGAUG GCAUGCACUAUGC GCG AGAGAAGGCA | 15221 |
| 3852 | UUUCAGCUCC G AAGUU | 5882 | AACUU UGAUG GCAUGCACUAUGC GCG GGAGCUGAAA | 15222 |
| 3874 | AGGAAGCUCU G AUGAU | 5883 | AUCAU UGAUG GCAUGCACUAUGC GCG AGAGCUUCCU | 15223 |
| 3877 | AAGCUCUGAU G AUGUC | 5884 | GACAU UGAUG GCAUGCACUAUGC GCG AUCAGAGCUU | 15224 |
| 3880 | CUCUGAUGAU G UCAGA | 5885 | UCUGA UGAUG GCAUGCACUAUGC GCG AUCAUCAGAG | 15225 |
| 3889 | UGUCAGAUAU G UAAAU | 5886 | AUUUA UGAUG GCAUGCACUAUGC GCG AUAUCUGACA | 15226 |
| 3895 | AUAUGUAAAU G CUUUC | 5887 | GAAAG UGAUG GCAUGCACUAUGC GCG AUUUACAUAU | 15227 |
| 3909 | UCAAGUUCAU G AGCCU | 5888 | AGGCU UGAUG GCAUGCACUAUGC GCG AUGAACUUGA | 15228 |
| 3934 | CAAAACCUUU G AAGAA | 5889 | UUCUU UGAUG GCAUGCACUAUGC GCG AAAGGUUUUG | 15229 |
| 3948 | AACUUUUACC G AAUGC | 5890 | GCAUU UGAUG GCAUGCACUAUGC GCG GGUAAAAGUU | 15230 |
| 3952 | UUUACCGAAU G CCACC | 5891 | GGUGG UGAUG GCAUGCACUAUGC GCG AUUCGGUAAA | 15231 |
| 3963 | CCACCUCCAU G UUUGA | 5892 | UCAAA UGAUG GCAUGCACUAUGC GCG AUGGAGGUGG | 15232 |
| 3967 | CUCCAUGUUU G AUGAC | 5893 | GUCAU UGAUG GCAUGCACUAUGC GCG AAACAUGGAG | 15233 |
| 3970 | CAUGUUUGAU G ACUAC | 5894 | GUAGU UGAUG GCAUGCACUAUGC GCG AUCAAACAUG | 15234 |
| 3982 | CUACCAGGGC G ACAGC | 5895 | GCUGU UGAUG GCAUGCACUAUGC GCG GCCCUGGUAG | 15235 |
| 3996 | GCAGCACUCU G UUGGC | 5896 | GCCAA UGAUG GCAUGCACUAUGC GCG AGAGUGCUGC | 15236 |
| 4011 | CCUCUCCCAU G CUGAA | 5897 | UUCAG UGAUG GCAUGCACUAUGC GCG AUGGGAGAGG | 15237 |
| 4014 | CUCCCAUGCU G AAGCG | 5898 | CGCUU UGAUG GCAUGCACUAUGC GCG AGCAUGGGAG | 15238 |
| 4019 | AUGCUGAAGC G CUUCA | 5899 | UGAAG UGAUG GCAUGCACUAUGC GCG GCUUCAGCAU | 15239 |
| 4033 | CACCUGGACU G ACAGC | 5900 | GCUGU UGAUG GCAUGCACUAUGC GCG AGUCCAGGUG | 15240 |
| 4053 | CCAAGGCCUC G CUCAA | 5901 | UUGAG UGAUG GCAUGCACUAUGC GCG GAGGCCUUGG | 15241 |
| 4063 | GCUCAAGAUU G ACUUG | 5902 | CAAGU UGAUG GCAUGCACUAUGC GCG AAUCUUGAGC | 15242 |
| 4068 | AGAUUGACUU G AGAGU | 5903 | ACUCU UGAUG GCAUGCACUAUGC GCG AAGUCAAUCU | 15243 |
| 4101 | AGUCGGGGCU G UCUGA | 5904 | UCAGA UGAUG GCAUGCACUAUGC GCG AGCCCCGACU | 15244 |
| 4105 | GGGGCUGUCU G AUGUC | 5905 | GACAU UGAUG GCAUGCACUAUGC GCG AGACAGCCCC | 15245 |
| 4108 | GCUGUCUGAU G UCAGC | 5906 | GCUGA UGAUG GCAUGCACUAUGC GCG AUCAGACAGC | 15246 |
| 4127 | CCCAGUUUCU G CCAUU | 5907 | AAUGG UGAUG GCAUGCACUAUGC GCG AGAAACUGGG | 15247 |
| 4139 | CAUUCCAGCU G UGGGC | 5908 | GCCCA UGAUG GCAUGCACUAUGC GCG AGCUGGAAUG | 15248 |
| 4153 | GCACGUCAGC G AAGGC | 5909 | GCCUU UGAUG GCAUGCACUAUGC GCG GCUGACGUGC | 15249 |
| 4163 | GAAGGCAAGC G CAGGU | 5910 | ACCUG UGAUG GCAUGCACUAUGC GCG GCUUGCCUUC | 15250 |
| 4177 | GUUCACCUAC G ACCAC | 5911 | GUGGU UGAUG GCAUGCACUAUGC GCG GUAGGUGAAC | 15251 |
| 4183 | CUACGACCAC G CUGAG | 5912 | CUCAG UGAUG GCAUGCACUAUGC GCG GUGGUCGUAG | 15252 |

TABLE XV-continued

G-Cleaver Ribozyme and Target Sequences

| Pos | Target | Seq ID No | Ribozyme Sequence | Seq ID No |
|-----|--------|-----------|-------------------|-----------|
| 4186 | CGACCACGCU G AGCUG | 5913 | CAGCU UGAUG GCAUGCACUAUGC GCG AGCGUGGUCG | 15253 |
| 4204 | AAGGAAAAUC G CGUGC | 5914 | GCACG UGAUG GCAUGCACUAUGC GCG GAUUUUCCUU | 15254 |
| 4208 | AAAAUCGCGU G CUGCU | 5915 | AGCAG UGAUG GCAUGCACUAUGC GCG ACGCGAUUUU | 15255 |
| 4211 | AUCGCGUGCU G CUCCC | 5916 | GGGAG UGAUG GCAUGCACUAUGC GCG AGCACGCGAU | 15256 |
| 4218 | GCUGCUCCCC G CCCCC | 5917 | GGGGG UGAUG GCAUGCACUAUGC GCG GGGGAGCAGC | 15257 |
| 4245 | CGGUGGUCCU G UACUC | 5918 | GAGUA UGAUG GCAUGCACUAUGC GCG AGGACCACCG | 15258 |
| 4272 | UCUAGAGUUU G ACACG | 5919 | CGUGU UGAUG GCAUGCACUAUGC GCG AAACUCUAGA | 15259 |
| 4277 | AGUUUGACAC G AAGCC | 5920 | GGCUU UGAUG GCAUGCACUAUGC GCG GUGUCAAACU | 15260 |
| 4301 | AGAAGCACAU G UGUAU | 5921 | AUACA UGAUG GCAUGCACUAUGC GCG AUGUGCUUCU | 15261 |
| 4303 | AAGCACAUGU G UAUUU | 5922 | AAAUA UGAUG GCAUGCACUAUGC GCG ACAUGUGCUU | 15262 |
| 4332 | ACUAGCUUUU G CCAGU | 5923 | ACUGG UGAUG GCAUGCACUAUGC GCG AAAAGCUAGU | 15263 |
| 4343 | CCAGUAUUAU G CAUAU | 5924 | AUAUG UGAUG GCAUGCACUAUGC GCG AUAAUACUGG | 15264 |
| 4386 | GGAGCCAGCU G CUUUU | 5925 | AAAAG UGAUG GCAUGCACUAUGC GCG AGCUGGCUCC | 15265 |
| 4393 | GCUGCUUUUU G UGAUU | 5926 | AAUCA UGAUG GCAUGCACUAUGC GCG AAAAAGCAGC | 15266 |
| 4395 | UGCUUUUUGU G AUUUU | 5927 | AAAAU UGAUG GCAUGCACUAUGC GCG ACAAAAAGCA | 15267 |
| 4410 | UUUUAAUAGU G CUUUU | 5928 | AAAAG UGAUG GCAUGCACUAUGC GCG ACUAUUAAAA | 15268 |
| 4423 | UUUUUUUUUU G ACUAA | 5929 | UUAGU UGAUG GCAUGCACUAUGC GCG AAAAAAAAAA | 15269 |
| 4436 | UAACAAGAAU G UAACU | 5930 | AGUUA UGAUG GCAUGCACUAUGC GCG AUUCUUGUUA | 15270 |
| 4459 | GAGAAAUAGU G ACAAG | 5931 | CUUGU UGAUG GCAUGCACUAUGC GCG ACUAUUUCUC | 15271 |
| 4466 | AGUGACAAGU G AAGAA | 5932 | UUCUU UGAUG GCAUGCACUAUGC GCG ACUUGUCACU | 15272 |
| 4479 | GAACACUACU G CUAAA | 5933 | UUUAG UGAUG GCAUGCACUAUGC GCG AGUAGUGUC | 15273 |
| 4492 | AAAUCCUCAU G UUACU | 5934 | AGUAA UGAUG GCAUGCACUAUGC GCG AUGAGGAUUU | 15274 |
| 4502 | GUUACUCAGU G UUAGA | 5935 | UCUAA UGAUG GCAUGCACUAUGC GCG ACUGAGUAAC | 15275 |
| 4529 | UAAACCCAAU G ACUUC | 5936 | GAAGU UGAUG GCAUGCACUAUGC GCG AUUGGGUUUA | 15276 |
| 4538 | UGACUUCCCU G CUCCA | 5937 | UGGAG UGAUG GCAUGCACUAUGC GCG AGGGAAGUCA | 15277 |
| 4550 | UCCAACCCCC G CCACC | 5938 | GGUGG UGAUG GCAUGCACUAUGC GCG GGGGGUUGGA | 15278 |
| 4565 | CUCAGGGCAC G CAGGA | 5939 | UCCUG UGAUG GCAUGCACUAUGC GCG GUGCCCUGAG | 15279 |
| 4578 | GGACCAGUUU G AUUGA | 5940 | UCAAU UGAUG GCAUGCACUAUGC GCG AAACUGGUCC | 15280 |
| 4582 | CAGUUUGAUU G AGGAG | 5941 | CUCCU UGAUG GCAUGCACUAUGC GCG AAUCAAACUG | 15281 |
| 4590 | UUGAGGAGCU G CACUG | 5942 | CAGUG UGAUG GCAUGCACUAUGC GCG AGCUCCUCAA | 15282 |
| 4595 | GAGCUGCACU G AUCAC | 5943 | GUGAU UGAUG GCAUGCACUAUGC GCG AGUGCAGCUC | 15283 |
| 4606 | AUCACCCAAU G CAUCA | 5944 | UGAUG UGAUG GCAUGCACUAUGC GCG AUUGGGUGAU | 15284 |
| 4634 | GGCCAGCCCU G CAGCC | 5945 | GGCUG UGAUG GCAUGCACUAUGC GCG AGGGCUGGCC | 15285 |
| 4691 | UGGCUGGCCU G AGCAA | 5946 | UUGCU UGAUG GCAUGCACUAUGC GCG AGGCCAGCCA | 15286 |
| 4730 | CCUAAGACAU G UGAGG | 5947 | CCUCA UGAUG GCAUGCACUAUGC GCG AUGUCUUAGG | 15287 |
| 4732 | UAAGACAUGU G AGGAG | 5948 | CUCCU UGAUG GCAUGCACUAUGC GCG ACAUGUCUUA | 15288 |
| 4792 | GAGAAGGCAU G AGAAA | 5949 | UUUCU UGAUG GCAUGCACUAUGC GCG AUGCCUUCUC | 15289 |

TABLE XV-continued

G-Cleaver Ribozyme and Target Sequences

| Pos | Target | Seq ID No | Ribozyme Sequence | Seq ID No |
|---|---|---|---|---|
| 4804 | GAAAGAAUUU G AGACG | 5950 | CGUCU UGAUG GCAUGCACUAUGC GCG AAAUUCUUUC | 15290 |
| 4809 | AAUUUGAGAC G CACCA | 5951 | UGGUG UGAUG GCAUGCACUAUGC GCG GUCUCAAAUU | 15291 |
| 4816 | GACGCACCAU G UGGGC | 5952 | GCCCA UGAUG GCAUGCACUAUGC GCG AUGGUGCGUC | 15292 |
| 4847 | GCUCAGCAAU G CCAUU | 5953 | AAUGG UGAUG GCAUGCACUAUGC GCG AUUGCUGAGC | 15293 |
| 4872 | UCCCAGCUCU G ACCCU | 5954 | AGGGU UGAUG GCAUGCACUAUGC GCG AGAGCUGGGA | 15294 |
| 4887 | UUCUACAUUU G AGGGC | 5955 | GCCCU UGAUG GCAUGCACUAUGC GCG AAAUGUAGAA | 15295 |
| 4916 | GAUGGACAGC G AUGAG | 5956 | CUCAU UGAUG GCAUGCACUAUGC GCG GCUGUCCAUC | 15296 |
| 4919 | GGACAGCGAU G AGGGG | 5957 | CCCCU UGAUG GCAUGCACUAUGC GCG AUCGCUGUCC | 15297 |
| 5018 | GUGGUUCUAU G UCCAU | 5958 | AUGGA UGAUG GCAUGCACUAUGC GCG AUAGAACCAC | 15298 |
| 5039 | UUCGUGGCAU G UUUUG | 5959 | CAAAA UGAUG GCAUGCACUAUGC GCG AUGCCACGAA | 15299 |
| 5044 | GGCAUGUUUU G AUUUG | 5960 | CAAAU UGAUG GCAUGCACUAUGC GCG AAAACAUGCC | 15300 |
| 5049 | GUUUUGAUUU G UAGCA | 5961 | UGCUA UGAUG GCAUGCACUAUGC GCG AAAUCAAAAC | 15301 |
| 5057 | UUGUAGCACU G AGGGU | 5962 | ACCCU UGAUG GCAUGCACUAUGC GCG AGUGCUACAA | 15302 |
| 5076 | ACUCAACUCU G AGCCC | 5963 | GGCCU UGAUG GCAUGCACUAUGC GCG AGAGUUGAGU | 15303 |
| 5107 | CUAGUAAGAU G CACUG | 5964 | CAGUG UGAUG GCAUGCACUAUGC GCG AUCUUACUAG | 15304 |
| 5112 | AAGAUGCACU G AAAAC | 5965 | GUUUU UGAUG GCAUGCACUAUGC GCG AGUGCAUCUU | 15305 |
| 5135 | GAGUUAGGUU G UCUCC | 5966 | GGAGA UGAUG GCAUGCACUAUGC GCG AACCUAACUC | 15306 |
| 5148 | UCCAGGCCAU G AUGGC | 5967 | GCCAU UGAUG GCAUGCACUAUGC GCG AUGGCCUGGA | 15307 |
| 5162 | GCCUUACACU G AAAAU | 5968 | AUUUU UGAUG GCAUGCACUAUGC GCG AGUGUAAGGC | 15308 |
| 5168 | CACUGAAAAU G UCACA | 5969 | UGUGA UGAUG GCAUGCACUAUGC GCG AUUUUCAGUG | 15309 |
| 5234 | GUAUUAUUCU G UUUUG | 5970 | CAAAA UGAUG GCAUGCACUAUGC GCG AGAAUAAUAC | 15310 |
| 5239 | AUUCUGUUUU G CACAG | 5971 | CUGUG UGAUG GCAUGCACUAUGC GCG AAAACAGAAU | 15311 |
| 5251 | ACAGUUAGUU G UGAAA | 5972 | UUUCA UGAUG GCAUGCACUAUGC GCG AACUAACUGU | 15312 |
| 5253 | AGUUAGUUGU G AAAGA | 5973 | UCUUU UGAUG GCAUGCACUAUGC GCG ACAACUAACU | 15313 |
| 5264 | AAAGAAAGCU G AGAAG | 5974 | CUUCU UGAUG GCAUGCACUAUGC GCG AGCUUUCUUU | 15314 |
| 5273 | UGAGAAGAAU G AAAAU | 5975 | AUUUU UGAUG GCAUGCACUAUGC GCG AUUCUUCUCA | 15315 |
| 5279 | GAAUGAAAAU G CAGUC | 5976 | GACUG UGAUG GCAUGCACUAUGC GCG AUUUUCAUUC | 15316 |
| 5287 | AUGCAGUCCU G AGGAG | 5977 | CUCCU UGAUG GCAUGCACUAUGC GCG AGGACUGCAU | 15317 |
| 5313 | AUAUCAAAAC G AGGGC | 5978 | GCCCU UGAUG GCAUGCACUAUGC GCG GUUUUGAUAU | 15318 |
| 5320 | AACGAGGGCU G AUGGA | 5979 | UCCAU UGAUG GCAUGCACUAUGC GCG AGCCCUCGUU | 15319 |
| 5469 | ACACUAAUCU G AAAGG | 5980 | CCUUU UGAUG GCAUGCACUAUGC GCG AGAUUAGUGU | 15320 |
| 5477 | CUGAAAGGAU G UGGAA | 5981 | UUCCA UGAUG GCAUGCACUAUGC GCG AUCCUUUCAG | 15321 |
| 5497 | AUUAGCUGGC G CAUAU | 5982 | AUAUG UGAUG GCAUGCACUAUGC GCG GCCAGCUAAU | 15322 |
| 5522 | UAAGCUCCUU G AGUAA | 5983 | UUACU UGAUG GCAUGCACUAUGC GCG AAGGAGCUUA | 15323 |
| 5539 | AAGGUGGUAU G UAAUU | 5984 | AAUUA UGAUG GCAUGCACUAUGC GCG AUACCACCUU | 15324 |
| 5548 | UGUAAUUUAU G CAAGG | 5985 | CCUUG UGAUG GCAUGCACUAUGC GCG AUAAAUUACA | 15325 |
| 5589 | AUUAGUUAAU G AGCCA | 5986 | UGGCU UGAUG GCAUGCACUAUGC GCG AUUAACUAAU | 15326 |

TABLE XV-continued

G-Cleaver Ribozyme and Target Sequences

| Pos | Target | Seq ID No | Ribozyme Sequence | Seq ID No |
|---|---|---|---|---|
| 5623 | AUUUUCAACU G CUUUG | 5987 | CAAAG UGAUG GCAUGCACUAUGC GCG AGUUGAAAAU | 15327 |
| 5628 | CAACUGCUUU G AAACU | 5988 | AGUUU UGAUG GCAUGCACUAUGC GCG AAAGCAGUUG | 15328 |
| 5635 | UUUGAAACUU G CCUGG | 5989 | CCAGG UGAUG GCAUGCACUAUGC GCG AAGUUUCAAA | 15329 |
| 5646 | CCUGGGGUCU G AGCAU | 5990 | AUGCU UGAUG GCAUGCACUAUGC GCG AGACCCCAGG | 15330 |
| 5652 | GUCUGAGCAU G AUGGG | 5991 | CCCAU UGAUG GCAUGCACUAUGC GCG AUGCUCAGAC | 15331 |
| 5684 | AGGAAAGGGC G CCUAC | 5992 | GUAGG UGAUG GCAUGCACUAUGC GCG GCCCUUUCCU | 15332 |
| 5725 | GCCUUGGAUC G CUAAG | 5993 | CUUAG UGAUG GCAUGCACUAUGC GCG GAUCCAAGGC | 15333 |
| 5739 | AGCUGGCUCU G UUUGA | 5994 | UCAAA UGAUG GCAUGCACUAUGC GCG AGAGCCAGCU | 15334 |
| 5743 | GGCUCUGUUU G AUGCU | 5995 | AGCAU UGAUG GCAUGCACUAUGC GCG AAACAGAGCC | 15335 |
| 5746 | UCUGUUUGAU G CUAUU | 5996 | AAUAG UGAUG GCAUGCACUAUGC GCG AUCAAACAGA | 15336 |
| 5755 | UGCUAUUUAU G CAAGU | 5997 | ACUUG UGAUG GCAUGCACUAUGC GCG AUAAAUAGCA | 15337 |
| 5771 | UAGGGUCUAU G UAUUU | 5998 | AAAUA UGAUG GCAUGCACUAUGC GCG AUAGACCCUA | 15338 |
| 5782 | UAUUUAGGAU G CGCCU | 5999 | AGGCG UGAUG GCAUGCACUAUGC GCG AUCCUAAAUA | 15339 |
| 5784 | UUUAGGAUGC G CCUAC | 6000 | GUAGG UGAUG GCAUGCACUAUGC GCG GCAUCCUAAA | 15340 |
| 5825 | GCCUUGGAUC G CUAAG | 5993 | CUUAG UGAUG GCAUGCACUAUGC GCG GAUCCAAGGC | 15333 |
| 5839 | AGCUGGCUCU G UUUGA | 5994 | UCAAA UGAUG GCAUGCACUAUGC GCG AGAGCCAGCU | 15334 |
| 5843 | GGCUCUGUUU G AUGCU | 5995 | AGCAU UGAUG GCAUGCACUAUGC GCG AAACAGAGCC | 15335 |
| 5846 | UCUGUUUGAU G CUAUU | 5996 | AAUAG UGAUG GCAUGCACUAUGC GCG AUCAAACAGA | 15336 |
| 5855 | UGCUAUUUAU G CAAGU | 5997 | ACUUG UGAUG GCAUGCACUAUGC GCG AUAAAUAGCA | 15337 |
| 5871 | UAGGGUCUAU G UAUUU | 5998 | AAAUA UGAUG GCAUGCACUAUGC GCG AUAGACCCUA | 15338 |
| 5882 | UAUUUAGGAU G UCUGC | 6001 | GCAGA UGAUG GCAUGCACUAUGC GCG AUCCUAAAUA | 15341 |
| 5886 | UAGGAUGUCU G CACCU | 6002 | AGGUG UGAUG GCAUGCACUAUGC GCG AGACAUCCUA | 15342 |
| 5895 | UGCACCUUCU G CAGCC | 6003 | GCCUG UGAUG GCAUGCACUAUGC GCG AGAAGGUGCA | 15343 |
| 5931 | ACAGUGGAUU G CUGCU | 6004 | AGCAG UGAUG GCAUGCACUAUGC GCG AAUCCACUGU | 15344 |
| 5934 | GUGGAUUGCU G CUUCU | 6005 | AGAAG UGAUG GCAUGCACUAUGC GCG AGCAAUCCAC | 15345 |
| 5955 | AGAAGAGUAU G CUUCC | 6006 | GGAAG UGAUG GCAUGCACUAUGC GCG AUACUCUUCU | 15346 |
| 5971 | UUUUAUCCAU G UAAUU | 6007 | AAUUA UGAUG GCAUGCACUAUGC GCG AUGGAUAAAA | 15347 |
| 5982 | UAAUUUAACU G UAGAA | 6008 | UUCUA UGAUG GCAUGCACUAUGC GCG AGUUAAAUUA | 15348 |
| 5991 | UGUAGAACCU G AGCUC | 6009 | GAGCU UGAUG GCAUGCACUAUGC GCG AGGUUCUACA | 15349 |
| 6006 | CUAAGUAACC G AAGAA | 6010 | UUCUU UGAUG GCAUGCACUAUGC GCG GGUUACUUAG | 15350 |
| 6013 | ACCGAAGAAU G UAUGC | 6011 | GCAUA UGAUG GCAUGCACUAUGC GCG AUUCUUCGGU | 15351 |
| 6017 | AAGAAUGUAU G CCUCU | 6012 | AGAGG UGAUG GCAUGCACUAUGC GCG AUACAUUCUU | 15352 |
| 6023 | GUAUGCCUCU G UUCUU | 6013 | AAGAA UGAUG GCAUGCACUAUGC GCG AGAGGCAUAC | 15353 |
| 6031 | CUGUUCUAU G UGCCA | 6014 | UGGCA UGAUG GCAUGCACUAUGC GCG AUAAGAACAG | 15354 |
| 6033 | GUUCUUAUGU G CCACA | 6015 | UGUGG UGAUG GCAUGCACUAUGC GCG ACAUAAGAAC | 15355 |
| 6044 | CCACAUCCUU G UUUAA | 6016 | UUAAA UGAUG GCAUGCACUAUGC GCG AAGGAUGUGG | 15356 |
| 6059 | AAGGCUCUCU G UAUGA | 6017 | UCAUA UGAUG GCAUGCACUAUGC GCG AGAGAGCCUU | 15357 |

TABLE XV-continued

G-Cleaver Ribozyme and Target Sequences

| Pos | Target | Seq ID No | Ribozyme Sequence | Seq ID No |
|---|---|---|---|---|
| 6063 | CUCUCUGUAU G AAGAG | 6018 | CUCUU UGAUG GCAUGCACUAUGC GCG AUACAGAGAG | 15358 |
| 6098 | AUUCCCUAGU G AGCCU | 6019 | AGGCU UGAUG GCAUGCACUAUGC GCG ACUAGGGAAU | 15359 |
| 6127 | AGCGGCUUUU G UGGAA | 6020 | UUCCA UGAUG GCAUGCACUAUGC GCG AAAAGCCGCU | 15360 |
| 6230 | ACAAAUCUUU G UUGUU | 6021 | AACAA UGAUG GCAUGCACUAUGC GCG AAAGAUUUCU | 15361 |
| 6233 | AAUCUUUGUU G UUCCU | 6022 | AGGAA UGAUG GCAUGCACUAUGC GCG AACAAAGAUU | 15362 |
| 6254 | UUACACAUAC G CAAAC | 6023 | GUUUG UGAUG GCAUGCACUAUGC GCG GUAUGUGUAA | 15363 |
| 6265 | CAAACCACCU G UGACA | 6024 | UGUCA UGAUG GCAUGCACUAUGC GCG AGGUGGUUUG | 15364 |
| 6267 | AACCACCUGU G ACAGC | 6025 | GCUGU UGAUG GCAUGCACUAUGC GCG ACAGGUGGUU | 15265 |
| 6391 | AGCAAAUAGU G AUAAC | 6026 | GUUAU UGAUG GCAUGCACUAUGC GCG ACUAUUUGCU | 15366 |
| 6413 | AACCUUAGCU G UUCAU | 6027 | AUGAA UGAUG GCAUGCACUAUGC GCG AGCUAAGGUU | 15367 |
| 6419 | AGCUGUUCAU G UCUUG | 6028 | CAAGA UGAUG GCAUGCACUAUGC GCG AUGAACAGCU | 15368 |
| 6424 | UUCAUGUCUU G AUUUC | 6029 | GAAAU UGAUG GCAUGCACUAUGC GCG AAGACAUGAA | 15369 |
| 6504 | CAUUAGAAUU G UUACU | 6030 | AGUAA UGAUG GCAUGCACUAUGC GCG AAUUCUAAUG | 15370 |
| 6532 | ACUCAGGUUU G UAGCA | 6031 | UGCUA UGAUG GCAUGCACUAUGC GCG AAACCUGAGU | 15371 |
| 6543 | UAGCAUACAU G AGUCC | 6032 | GGACU UGAUG GCAUGCACUAUGC GCG AUGUAUGCUA | 15372 |
| 6588 | GAGUCUUAAU G UAGAA | 6033 | UUCUA UGAUG GCAUGCACUAUGC GCG AUUAAGACUC | 15373 |
| 6610 | AUGGAGACUU G UAAUA | 6034 | UAUUA UGAUG GCAUGCACUAUGC GCG AAGUCUCCAU | 15374 |
| 6618 | UUGUAAUAAU G AGCUA | 6035 | UAGCU UGAUG GCAUGCACUAUGC GCG AUUAUUACAA | 15375 |
| 6634 | GUUACAAAGU G CUUGU | 6036 | ACAAG UGAUG GCAUGCACUAUGC GCG ACUUUGUAAC | 15376 |
| 6638 | CAAAGUGCUU G UUCAU | 6037 | AUGAA UGAUG GCAUGCACUAUGC GCG AAGCACUUUG | 15377 |
| 6656 | AAAUAGCACU G AAAAU | 6038 | AUUUU UGAUG GCAUGCACUAUGC GCG AGUGCUAUUU | 15378 |
| 6663 | ACUGAAAAUU G AAACA | 6039 | UGUUU UGAUG GCAUGCACUAUGC GCG AAUUUUCAGU | 15379 |
| 6670 | AUUGAAACAU G AAUUA | 6040 | UAAUU UGAUG GCAUGCACUAUGC GCG AUGUUUCAAU | 15380 |
| 6679 | UGAAUUAACU G AUAAU | 6041 | AUUAU UGAUG GCAUGCACUAUGC GCG AGUUAAUUCA | 15381 |
| 6698 | CCAAUCAUUU G CCAUU | 6042 | AAUGG UGAUG GCAUGCACUAUGC GCG AAAUGAUUGG | 15382 |
| 6707 | UGCCAUUUAU G ACAAA | 6043 | UUUGU UGAUG GCAUGCACUAUGC GCG AUAAAUGGCA | 15383 |
| 6736 | AACAAAGAAC G AGCAC | 6044 | GUGCU UGAUG GCAUGCACUAUGC GCG GUUCUUUGUU | 15384 |
| 6759 | CAGAGUUUCU G AGAUA | 6045 | UAUCU UGAUG GCAUGCACUAUGC GCG AGAAACUCUG | 15385 |
| 6767 | CUGAGAUAAU G UACGU | 6046 | ACGUA UGAUG GCAUGCACUAUGC GCG AUUAUCUCAG | 15386 |
| 6798 | GAAUGGGGCU G AAACC | 6047 | GGUUU UGAUG GCAUGCACUAUGC GCG AGCCCCAUUC | 15387 |
| 6806 | CUGAAACCAU G UGCAA | 6048 | UUGCA UGAUG GCAUGCACUAUGC GCG AUGGUUUCAG | 15388 |
| 6808 | GAAACCAUGU G CAAGU | 6049 | ACUUG UGAUG GCAUGCACUAUGC GCG ACAUGGUUUC | 15389 |
| 6816 | GUGCAAGUCU G UGUCU | 6050 | AGACA UGAUG GCAUGCACUAUGC GCG AGACUUGCAC | 15390 |
| 6818 | GCAAGUCUGU G UCUUG | 6051 | CAAGA UGAUG GCAUGCACUAUGC GCG ACAGACUUGC | 15391 |
| 6823 | UCUGUGUCUU G UCAGU | 6052 | ACUGA UGAUG GCAUGCACUAUGC GCG AAGACACAGA | 15392 |
| 6838 | UCCAAGAAGU G ACACC | 6053 | GGUGU UGAUG GCAUGCACUAUGC GCG ACUUCUUGGA | 15393 |
| 6844 | AAGUGACACC G AGAUG | 6054 | CAUCU UGAUG GCAUGCACUAUGC GCG GGUGUCACUU | 15394 |

TABLE XV-continued

G-Cleaver Ribozyme and Target Sequences

| Pos | Target | Seq ID No | Ribozyme Sequence | Seq ID No |
|---|---|---|---|---|
| 6849 | ACACCGAGAU G UUAAU | 6055 | AUUAA UGAUG GCAUGCACUAUGC GCG AUCUCGGUGU | 15395 |
| 6868 | AGGGACCCGU G CCUUG | 6056 | CAAGG UGAUG GCAUGCACUAUGC GCG ACGGGUCCCU | 15396 |
| 6873 | CCCGUGCCUU G UUUCC | 6057 | GGAAA UGAUG GCAUGCACUAUGC GCG AAGGCACGGG | 15397 |
| 6893 | CCACAAGAAU G CAAAC | 6058 | GUUUG UGAUG GCAUGCACUAUGC GCG AUUCUUGUGG | 15398 |
| 6914 | ACAGAUACUC G CUAGC | 6059 | GCUAG UGAUG GCAUGCACUAUGC GCG GAGUAUCUGU | 15399 |
| 6932 | CAUUUAAAUU G AUUAA | 6060 | UUAAU UGAUG GCAUGCACUAUGC GCG AAUUUAAAUG | 15400 |
| 6947 | AAGGAGGAGU G CAUCU | 6061 | AGAUG UGAUG GCAUGCACUAUGC GCG ACUCCUCCUU | 15401 |
| 6959 | AUCUUUGGCC G ACAGU | 6062 | ACUGU UGAUG GCAUGCACUAUGC GCG GGCCAAAGAU | 15402 |
| 6968 | CGACAGUGGU G UAACU | 6063 | AGUUA UGAUG GCAUGCACUAUGC GCG ACCACUGUCG | 15403 |
| 6974 | UGGUGUAACU G UGUGU | 6064 | ACACA UGAUG GCAUGCACUAUGC GCG AGUUACACCA | 15404 |
| 6976 | GUGUAACUGU G UGUGU | 6065 | ACACA UGAUG GCAUGCACUAUGC GCG ACAGUUACAC | 15405 |
| 6978 | GUAACUGUGU G UGUGU | 6066 | ACACA UGAUG GCAUGCACUAUGC GCG ACACAGUUAC | 15406 |
| 6980 | AACUGUGUGU G UGUGU | 6067 | ACACA UGAUG GCAUGCACUAUGC GCG ACACACAGUU | 15407 |
| 6982 | CUGUGUGUGU G UGUGU | 6068 | ACACA UGAUG GCAUGCACUAUGC GCG ACACACACAG | 15408 |
| 6984 | GUGUGUGUGU G UGUGU | 6069 | ACACA UGAUG GCAUGCACUAUGC GCG ACACACACAC | 15409 |
| 6986 | GUGUGUGUGU G UGUGU | 6069 | ACACA UGAUG GCAUGCACUAUGC GCG ACACACACAC | 15409 |
| 6988 | GUGUGUGUGU G UGUGU | 6069 | ACACA UGAUG GCAUGCACUAUGC GCG ACACACACAC | 15409 |
| 6990 | GUGUGUGUGU G UGUGU | 6069 | ACACA UGAUG GCAUGCACUAUGC GCG ACACACACAC | 15409 |
| 6992 | GUGUGUGUGU G UGUGU | 6069 | ACACA UGAUG GCAUGCACUAUGC GCG ACACACACAC | 15409 |
| 6994 | GUGUGUGUGU G UGUGU | 6069 | ACACA UGAUG GCAUGCACUAUGC GCG ACACACACAC | 15409 |
| 6996 | GUGUGUGUGU G UGUGU | 6069 | ACACA UGAUG GCAUGCACUAUGC GCG ACACACACAC | 15409 |
| 6998 | GUGUGUGUGU G UGUGU | 6069 | ACACA UGAUG GCAUGCACUAUGC GCG ACACACACAC | 15409 |
| 7000 | GUGUGUGUGU G UGUGU | 6069 | ACACA UGAUG GCAUGCACUAUGC GCG ACACACACAC | 15409 |
| 7002 | GUGUGUGUGU G UGUGU | 6069 | ACACA UGAUG GCAUGCACUAUGC GCG ACACACACAC | 15409 |
| 7004 | GUGUGUGUGU G UGUGU | 6069 | ACACA UGAUG GCAUGCACUAUGC GCG ACACACACAC | 15409 |
| 7006 | GUGUGUGUGU G UGUGU | 6069 | ACACA UGAUG GCAUGCACUAUGC GCG ACACACACAC | 15409 |
| 7008 | GUGUGUGUGU G UGUGU | 6069 | ACACA UGAUG GCAUGCACUAUGC GCG ACACACACAC | 15409 |
| 7010 | GUGUGUGUGU G UGUGG | 6070 | CCACA UGAUG GCAUGCACUAUGC GCG ACACACACAC | 15410 |
| 7012 | GUGUGUGUGU G UGGGU | 6071 | ACCCA UGAUG GCAUGCACUAUGC GCG ACACACACAC | 15411 |
| 7018 | GUGUGUGGGU G UGGGU | 6072 | ACCCA UGAUG GCAUGCACUAUGC GCG ACCCACACAC | 15412 |
| 7024 | GGGUGUGGGU G UAUGU | 6073 | ACAUA UGAUG GCAUGCACUAUGC GCG ACCCACACCC | 19413 |
| 7028 | GUGGGUGUAU G UGUGU | 6074 | ACACA UGAUG GCAUGCACUAUGC GCG AUACCCCAC | 15414 |
| 7030 | GGGUGUAUGU G UGUUU | 6075 | AAACA UGAUG GCAUGCACUAUGC GCG ACAUACACCC | 15415 |
| 7032 | GUGUAUGUGU G UUUUG | 6076 | CAAAA UGAUG GCAUGCACUAUGC GCG ACACAUACAC | 15416 |
| 7037 | UGUGUGUUUU G UGCAU | 6077 | AUGCA UGAUG GCAUGCACUAUGC GCG AAAACACACA | 15417 |
| 7039 | UGUGUUUUGU G CAUAA | 6078 | UUAUG UGAUG GCAUGCACUAUGC GCG ACAAAACACA | 15418 |
| 7099 | AAGAAUAUAU G CUACA | 6079 | UGUAG UGAUG GCAUGCACUAUGC GCG AUAUAUUCUU | 15419 |

TABLE XV-continued

G-Cleaver Ribozyme and Target Sequences

| Pos | Target | Seq ID No | Ribozyme Sequence | Seq ID No |
|---|---|---|---|---|
| 7146 | UUCUAGUCAU G AUGAA | 6080 | UUCAU UGAUG GCAUGCACUAUGC GCG AUGACUAGAA | 15420 |
| 7149 | UAGUCAUGAU G AAUGU | 6081 | ACAUU UGAUG GCAUGCACUAUGC GCG AUCAUGACUA | 15421 |
| 7153 | CAUGAUGAAU G UAUUU | 6082 | AAAUA UGAUG GCAUGCACUAUGC GCG AUUCAUCAUG | 15422 |
| 7160 | AAUGUAUUUU G UAUAC | 6083 | GUAUA UGAUG GCAUGCACUAUGC GCG AAAAUACAUU | 15423 |
| 7210 | AUUGGGAUUU G UAAUC | 6084 | GAUUA UGAUG GCAUGCACUAUGC GCG AAAUCCCAAU | 15424 |
| 7230 | CAACUUAAUU G AUAAA | 6085 | UUUAU UGAUG GCAUGCACUAUGC GCG AAUUAAGUUG | 15425 |
| 7246 | CUUGGCAACU G CUUUU | 6086 | AAAAG UGAUG GCAUGCACUAUGC GCG AGUUGCCAAG | 15426 |
| 7254 | CUGCUUUUAU G UUCUG | 6087 | CAGAA UGAUG GCAUGCACUAUGC GCG AUAAAAGCAG | 15427 |
| 7259 | UUUAUGUUCU G UCUCC | 6088 | GGAGA UGAUG GCAUGCACUAUGC GCG AGAACAUAAA | 15428 |
| 7343 | AUUUAUCCUU G UUUAC | 6089 | CUAAA UGAUG GCAUGCACUAUGC GCG AAGGAUAAAU | 15429 |
| 7375 | GAAAAACUUU G AAAUG | 6090 | CAUUU UGAUG GCAUGCACUAUGC GCG AAAGUUUUUC | 15430 |
| 7394 | UCAAAAAAUU G CUAAA | 6091 | UUUAG UGAUG GCAUGCACUAUGC GCG AAUUUUUGA | 15431 |
| 7422 | AAAACUAAAU G UUAGU | 6092 | ACUAA UGAUG GCAUGCACUAUGC GCG AUUUAGUUUU | 15432 |
| 7434 | UAGUUUAGCU G AUUGU | 6093 | ACAAU UGAUG GCAUGCACUAUGC GCG AGCUAAACUA | 15433 |
| 7438 | UUAGCUGAUU G UAUGG | 6094 | CCAUA UGAUG GCAUGCACUAUGC GCG AAUCAGCUAA | 15434 |
| 7451 | UGGGGUUUUC G AACCU | 6095 | AGGUU UGAUG GCAUGCACUAUGC GCG GAAAACCCCA | 15435 |
| 7467 | UUCACUUUUU G UUUGU | 6096 | ACAAA UGAUG GCAUGCACUAUGC GCG AAAAAGUGAA | 15436 |
| 7471 | CUUUUUGUUU G UUUUA | 6097 | UAAAA UGAUG GCAUGCACUAUGC GCG AAACAAAAAG | 15437 |
| 7491 | UUUCACAACU G UGUAA | 6098 | UUACA UGAUG GCAUGCACUAUGC GCG AGUUGUGAAA | 15438 |
| 7493 | UCACAACUGU G UAAAU | 6099 | AUUUA UGAUG GCAUGCACUAUGC GCG ACAGUUGUGA | 15439 |
| 7500 | UGUGUAAAUU G CCAAU | 6100 | AUUGG UGAUG GCAUGCACUAUGC GCG AAUUUACACA | 15440 |
| 7513 | AAUAAUUCCU G UCCAU | 6101 | AUGGA UGAUG GCAUGCACUAUGC GCG AGGAAUUAUU | 15441 |
| 7519 | UCCUGUCCAU G AAAAU | 6102 | AUUUU UGAUG GCAUGCACUAUGC GCG AUGGACAGGA | 15442 |
| 7525 | CCAUGAAAAU G CAAAU | 6103 | AUUUG UGAUG GCAUGCACUAUGC GCG AUUUUCAUGG | 15443 |
| 7539 | AUUAUCCAGU G UAGAU | 6104 | AUCUA UGAUG GCAUGCACUAUGC GCG ACUGGAUAAU | 15444 |
| 7551 | AGAUAUAUUU G ACCAU | 6105 | AUGGU UGAUG GCAUGCACUAUGC GCG AAAUAUAUCU | 15445 |
| 7582 | GGCUAGUUUU G CCUUU | 6106 | AAAGG UGAUG GCAUGCACUAUGC GCG AAAACUAGCC | 15446 |
| 7611 | AUUUCAGCCU G AAUGU | 6107 | ACAUU UGAUG GCAUGCACUAUGC GCG AGGCUGAAAU | 15447 |
| 7615 | CAGCCUGAAU G UCUGC | 6108 | GCAGA UGAUG GCAUGCACUAUGC GCG AUUCAGGCUG | 15448 |
| 7619 | CUGAAUGUCU G CCUAU | 6109 | AUAGG UGAUG GCAUGCACUAUGC GCG AGACAUUCAG | 15449 |
| 7634 | UAUAUUCUCU G CUCUU | 6110 | AAGAG UGAUG GCAUGCACUAUGC GCG AGAGAAUAUA | 15450 |
| 7641 | UCUGCUCUUU G UAUUC | 6111 | GAAUA UGAUG GCAUGCACUAUGC GCG AAAGAGCAGA | 15451 |
| 7653 | AUUCUCCUUU G AACCC | 6112 | GGGUU UGAUG GCAUGCACUAUGC GCG AAAGGAGAAU | 15452 |
| 7672 | AAAACAUCCU G UGGCA | 6113 | UGCCA UGAUG GCAUGCACUAUGC GCG AGGAUGUUUU | 15453 |

TABLE XVI

Human KDR NCH Ribozyme and Target Sequences

| Pos | Target | Seq ID No | Ribozyme Sequence | Seq ID No. |
|---|---|---|---|---|
| 11 | CAAGGUGC U GCUGGCCG | 6114 | CGGCCAGC CUGAUGAGGCCGUUAGGCCGAA ICACCUUG | 15454 |
| 14 | GGUGCUGC U GGCCGUCG | 6115 | CGACGGCC CUGAUGAGGCCGUUAGGCCGAA ICAGCACC | 15455 |
| 18 | CUGCUGGC C GUCGCCCU | 6116 | AGGGCGAC CUGAUGAGGCCGUUAGGCCGAA ICCAGCAG | 15456 |
| 24 | GCCGUCGC C CUGUGGCU | 6117 | AGCCACAG CUGAUGAGGCCGUUAGGCCGAA ICGACGGC | 15457 |
| 25 | CCGUCGCC C UGUGGCUC | 6118 | GAGCCACA CUGAUGAGGCCGUUAGGCCGAA IGCGACGG | 15458 |
| 26 | CGUCGCCC U GUGGCUCU | 6119 | AGAGCCAC CUGAUGAGGCCGUUAGGCCGAA IGGCGACG | 15459 |
| 32 | CCUGUGGC U CUGCGUGG | 6120 | CCACGCAG CUGAUGAGGCCGUUAGGCCGAA ICCACAGG | 15460 |
| 34 | UGUGGCUC U GCGUGGAG | 6121 | CUCCACGC CUGAUGAGGCCGUUAGGCCGAA IAGCCACA | 15461 |
| 45 | GUGGAGAC C CGGGCCGC | 6122 | GCGGCCCG CUGAUGAGGCCGUUAGGCCGAA IUCUCCAC | 15462 |
| 46 | UGGAGACO C GGGCCGCC | 6123 | GGCGGCCC CUGAUGAGGCCGUUAGGCCGAA IGUCUCCA | 15463 |
| 51 | ACCCGGGC C GCCUCUGU | 6124 | ACAGAGGC CUGAUGAGGCCGUUAGGCCGAA ICCCGGGU | 15464 |
| 54 | CGGGCCGC C UCUGUGGG | 6125 | CCCACAGA CUGAUGAGGCCGUUAGGCCGAA ICGGCCCG | 15465 |
| 55 | GGGCCGCC U CUGUGGGU | 6126 | ACCCACAG CUGAUGAGGCCGUUAGGCCGAA IGCGGCCC | 15466 |
| 57 | GCCGCCUC U GUGGGUUU | 6127 | AAACCCAC CUGAUGAGGCCGUUAGGCCGAA IAGGCGGC | 15467 |
| 68 | GGGUUUGC C UAGUGUUU | 6128 | AAACACUA CUGAUGAGGCCGUUAGGCCGAA ICAAACCC | 15468 |
| 69 | GGUUUGCC U AGUGUUUC | 6129 | GAAACACU CUGAUGAGGCCGUUAGGCCGAA IGCAAACC | 15469 |
| 78 | AGUGUUUC U CUUGAUCU | 6130 | AGAUCAAG CUGAUGAGGCCGUUAGGCCGAA IAAACACU | 15470 |
| 80 | UGUUUCUC U UGAUCUGC | 6131 | GCAGAUCA CUGAUGAGGCCGUUAGGCCGAA IAGAAACA | 15471 |
| 86 | UCIUGAUC U GCCCAGGC | 6132 | GCCUGGGC CUGAUGAGGCCGUUAGGCCGAA IAUCAAGA | 15472 |
| 89 | UGAUCUGC C CAGUCUCA | 6133 | UGAGCCUG CUGAUGAGGCCGUUAGGCCGAA ICAGAUCA | 15473 |
| 90 | GAUCUGCC C AGGCUCAG | 6134 | CUGAGCCU CUGAUGAGGCCGUUAGGCCGAA IGCAGAUC | 15474 |
| 91 | AUCUGCCC A GGCUCAGC | 6135 | GCUGAGCC CUGAUGAGGCCGUUAGGCCGAA IGGCAGAU | 15475 |
| 95 | GCCCAGGC U CAGCAUAC | 6136 | GUAUGCUG CUGAUGAGGCCGUUAGGCCGAA ICCUGGGC | 15476 |
| 97 | CCAGGCUC A GCAUACAA | 6137 | UUGUAUGC CUGAUGAGGCCGUUAGGCCGAA IAGCCUGG | 15477 |
| 100 | GGCUCAGC A UACAAAAA | 6138 | UUUUUGUA CUGAUGAGGCCGUUAGGCCGAA ICUGAGCC | 15478 |
| 104 | CAGCAUAC A AAAAGACA | 6139 | UGUCUUUU CUGAUGAGGCCGUUAGGCCGAA IUAUGCUG | 15479 |
| 112 | AAAAAGAC A UACUUACA | 6140 | UGUAAGUA CUGAUGAGGCCGUUAGGCCGAA IUCUUUUU | 15480 |
| 116 | AGACAUAC U UACAAUUA | 6141 | UAAUUGUA CUGAUGAGGCCGUUAGGCCGAA IUAUGUCU | 15481 |
| 120 | AUACUUAC A AUUAAGGC | 6142 | GCCUUAAU CUGAUGAGGCCGUUAGGCCGAA IUAAGUAU | 15482 |
| 129 | AUUAAGGC U AAUACAAC | 6143 | GUUGUAUU CUGAUGAGGCCGUUAGGCCGAA ICCUUAAU | 15483 |
| 135 | GCUAAUAC A ACUCUUCA | 6144 | UGAAGAGU CUGAUGAGGCCGUUAGGCCGAA IUAUUAGC | 15484 |
| 138 | AAUACAAC U CUUCAAAU | 6145 | AUUUGAAG CUGAUGAGGCCGUUAGGCCGAA IUUGUAUU | 15485 |
| 140 | UACAACUC U UCAAAUUA | 6146 | UAAUUUGA CUGAUGAGGCCGUUAGGCCGAA IAGUUGUA | 15486 |
| 143 | AACUCUUC A AAUUACUU | 6147 | AAGUAAUU CUGAUGAGGCCGUUAGGCCGAA IAAGAGUU | 15487 |
| 150 | CAAAUUAC U UGCAGGGG | 6148 | CCCCUGCA CUGAUGAGGCCGUUAGGCCGAA IUAAUUUG | 15488 |
| 154 | UUACUUGC A GGGGACAG | 6149 | CUGUCCCC CUGAUGAGGCCGUUAGGCCGAA ICAAGUAA | 15489 |
| 161 | CAGGGGAC A GAGGGACU | 6150 | AGUCCCUC CUGAUGAGGCCGUUAGGCCGAA IUCCCCUG | 15490 |

TABLE XVI-continued

Human KDR NCH Ribozyme and Target Sequences

| Pos | Target | Seq ID No | Ribozyme Sequence | Seq ID No. |
|---|---|---|---|---|
| 169 | AGAGGGAC U UGGACUGG | 6151 | CCAGUCCA CUGAUGAGgccguuaggCCGAA IUCCCUCU | 15491 |
| 175 | ACUUGGAC U GGCUUUGG | 6152 | CCAAAGCC CUGAUGAGgccguuaggCCGAA IUCCAAGU | 15492 |
| 179 | GGACUGGC U JUGGCCCA | 6153 | UGGGCCAA CUGAUGAGgccguuaggCCGAA ICCAGUCC | 15493 |
| 185 | GCUUUGGC C CAAUAAUC | 6154 | GAUUAUUG CUGAUGAGgccguuaggCCGAA ICCAAAGC | 15494 |
| 186 | CUUUGGCC C AAUAAUCA | 6155 | UGAUUAUU CUGAUGAGgccguuaggCCGAA IGCCAAAG | 15495 |
| 187 | UUUGGCCC A AUAAUCAG | 6156 | CUGAUUAU CUGAUGAGgccguuaggCCGAA IGGCCAAA | 15496 |
| 194 | CAAUAAUC A GAGUGGCA | 6157 | UGCCACUC CUGAUGAGgccguuaggCCGAA IAUUAUUG | 15497 |
| 202 | AGAGUGGC A GUGAGCAA | 6158 | UUGCUCAC CUGAUGAGgccguuaggCCGAA ICCACUCU | 15498 |
| 209 | CAGUGAGC A AAGGGUGG | 6159 | CCACCCUU CUGAUGAGgccguuaggCCGAA ICUCACUG | 15499 |
| 225 | GAGGUGAC U GAGUGCAG | 6160 | CUGCACUC CUGAUGAGgccguuaggCCGAA IUCACCUC | 15500 |
| 232 | CUGAGUGC A GCGAUGGC | 6161 | GCCAUCGC CUGAUGAGgccguuaggCCGAA ICACUCAG | 15501 |
| 241 | GCGAUGGC C UCUUCUGU | 6162 | ACAGAAGA CUGAUGAGgccguuaggCCGAA ICCAUCGC | 15502 |
| 242 | CGAUGGCC U CUUCUGUA | 6163 | UACAGAAG CUGAUGAGgccguuaggCCGAA IGCCAUCG | 15503 |
| 244 | AUGGCCUC U UCUGUAAG | 6164 | CUUACAGA CUGAUGAGgccguuaggCCGAA IAGGCCAU | 15504 |
| 247 | GCCUCUUC U GUAAGACA | 6165 | UGUCUUAC CUGAUGAGgccguuaggCCGAA IAAGAGGC | 15505 |
| 255 | UGUAAGAC A CUCACAAU | 6166 | AUUGUGAG CUGAUGAGgccguuaggCCGAA IUCUUACA | 15506 |
| 257 | UAAGACAC U CACAAUUC | 6167 | GAAUUGUG CUGAUGAGgccguuaggCCGAA IUGUCUUA | 15507 |
| 259 | AGACACUC A CAAUUCCA | 6168 | UGGAAUUG CUGAUGAGgccguuaggCCGAA IAGUGUCU | 15508 |
| 261 | ACACUCAC A AUUCCAAA | 6169 | UUUGGAAU CUGAUGAGgccguuaggCCGAA IUGAGUGU | 15509 |
| 266 | CACAAUUC C AAAAGUGA | 6170 | UCACUUEU CUGAUGAGgccguuaggCCGAA IAAUUGUG | 15510 |
| 267 | ACAAUUCC A AAAGUGAU | 6171 | AUCACUUU CUGAUGAGgccguuaggCCGAA IGAAUUGU | 15511 |
| 286 | GAAAUGAC A CUGGAGCC | 6172 | GGCUCCAG CUGAUGAGgccguuaggCCGAA IUCAUUUC | 15512 |
| 288 | AAUGACAC U GGAGCCUA | 6173 | UAGGCUCC CUGAUGAGgccguuaggCCGAA IUGUCAUU | 15513 |
| 294 | ACUGGAGC C UACAAGUG | 6174 | CACUUGUA CUGAUGAGgccguuaggCCGAA ICUCCAGU | 15514 |
| 295 | CUGGAGCC U ACAAGUGC | 6175 | GCACUUGU CUGAUGAGgccguuaggCCGAA IGCUCCAG | 15515 |
| 298 | GAGCCUAC A AGUGCUUC | 6176 | GAAGCACU CUGAUGAGgccguuaggCCGAA IUAGGCUC | 15516 |
| 304 | ACAAGUGC U UCUACCGG | 6177 | CCGGUAGA CUGAUGAGgccguuaggCCGAA ICACUUGU | 15517 |
| 307 | AGUGCUUC U ACCGGGAA | 6178 | UUCCCGGU CUGAUGAGgccguuaggCCGAA IAAGCACU | 15518 |
| 310 | GCUUCUAC C GGGAAACU | 6179 | AGUUUCCC CUGAUGAGgccguuaggCCGAA IUAGAAGC | 15519 |
| 318 | CGGGAAAC U GACUUGGC | 6180 | GCCAAGUC CUGAUGAGgccguuaggCCGAA IUUUCCCG | 15520 |
| 322 | AAACUGAC U UGGCCUCG | 6181 | CGAGGCCA CUGAUGAGgccguuaggCCGAA IUCAGUUU | 15521 |
| 327 | GACUUGGC C UCGGUCAU | 6182 | AUGACCGA CUGAUGAGgccguuaggCCGAA ICCAAGUC | 15522 |
| 328 | ACUUGGCC U CGGUCAUU | 6183 | AAUGACCG CUGAUGAGgccguuaggCCGAA IGCCAAGU | 15523 |
| 334 | CCUCGGUC A UUUAUGUC | 6184 | GACAUAAA CUGAUGAGgccguuaggCCGAA IACCGAGG | 15524 |
| 343 | UUUAUGUC U AUGUUCAA | 6185 | UUGAACAU CUGAUGAGgccguuaggCCGAA IACAUAAA | 15525 |
| 350 | CUAUGUUC A AGAUUACA | 6186 | UGUAAUCU CUGAUGAGgccguuaggCCGAA IAACAUAG | 15526 |
| 358 | AAGAUUAC A GAUCUCCA | 6187 | UGGAGAUC CUGAUGAGgccguuaggCCGAA IUAAUCUU | 15527 |

TABLE XVI-continued

Human KDR NCH Ribozyme and Target Sequences

| Pos | Target | Seq ID No | Ribozyme Sequence | Seq ID No. |
|---|---|---|---|---|
| 363 | UACAGAUC U CCAUUUAU | 6188 | AUAAAUGG CUGAUGAGGCCGUUAGGCCGAA IAUCUGUA | 15528 |
| 365 | CAGAUCUC C AUUUAUUG | 6189 | CAAUAAAU CUGAUGAGGCCGUUAGGCCGAA IAGAUCUG | 15529 |
| 366 | AGAUCUCC A UUUAUUGC | 6190 | GCAAUAAA CUGAUGAGGCCGUUAGGCCGAA IGAGAUCU | 15530 |
| 375 | UUUAUUGC U UCUGUUAG | 6191 | CUAACAGA CUGAUGAGGCCGUUAGGCCGAA ICAAUAAA | 15531 |
| 378 | AUUGCUUC U GUUAGUGA | 6192 | UCACUAAC CUGAUGAGGCCGUUAGGCCGAA IAAGCAAU | 15532 |
| 388 | UUAGUGAC C AACAUGGA | 6193 | UCCAUGUU CUGAUGAGGCCGUUAGGCCGAA IUCACUAA | 15533 |
| 389 | UAGUGACC A ACAUGGAG | 6194 | CUCCAUGU CUGAUGAGGCCGUUAGGCCGAA IGUCACUA | 15534 |
| 392 | UGACCAAC A UGGAGUCG | 6195 | CGACUCCA CUGAUGAGGCCGUUAGGCCGAA IUUGGUCA | 15535 |
| 406 | UCGUGUAC A UUACUGAG | 6196 | CUCAGUAA CUGAUGAGGCCGUUAGGCCGAA IACACGA | 15536 |
| 411 | UACAUUAC U GAGAACAA | 6197 | UUGUUCUC CUGAUGAGGCCGUUAGGCCGAA IUAAUGUA | 15537 |
| 418 | CUGAGAAC A AAAACAAA | 6198 | UUUGUUUU CUGAUGAGGCCGUUAGGCCGAA IUUCUCAG | 15538 |
| 424 | ACAAAAAC A AAACUGUG | 6199 | CACAGUUU CUGAUGAGGCCGUUAGGCCGAA IUUUUUGU | 15539 |
| 429 | AACAAAAC U GUGGUGAU | 6200 | AUCACCAC CUGAUGAGGCCGUUAGGCCGAA IUUUUGUU | 15540 |
| 440 | GGUGAUUC C AUGUCUCG | 6201 | CGAGACAU CUGAUGAGGCCGUUAGGCCGAA IAAUCACC | 15541 |
| 441 | GUGAUUCC A UGUCUCGG | 6202 | CCGAGACA CUGAUGAGGCCGUUAGGCCGAA IGAAUCAC | 15542 |
| 446 | UCCAUGUC U CGGGUCCA | 6203 | UGGACCCG CUGAUGAGGCCGUUAGGCCGAA IACAUGGA | 15543 |
| 453 | CUCGGGUC C AUUUCAAA | 6204 | UUUGAAAU CUGAUGAGGCCGUUAGGCCGAA IACCCGAG | 15544 |
| 454 | UCGGGUCC A UUUCAAAU | 6205 | AUUUGAAA CUGAUGAGGCCGUUAGGCCGAA IGACCCGA | 15545 |
| 459 | UCCAUUUC A AAUCUCAA | 6206 | UUGAGAUU CUGAUGAGGCCGUUAGGCCGAA IAAAUGGA | 15546 |
| 464 | UUCAAAUC U CAACGUGU | 6207 | ACACGUUG CUGAUGAGGCCGUUAGGCCGAA IAUUUGAA | 15547 |
| 466 | CAAAUCUC A ACGUGUCA | 6208 | UGACACGU CUGAUGAGGCCGUUAGGCCGAA IAGAUUUG | 15548 |
| 474 | AACGUGUC A CUUUGUGC | 6209 | GCACAAAG CUGAUGAGGCCGUUAGGCCGAA IACACGUU | 15549 |
| 476 | CGUGUCAC U UUGUGCAA | 6210 | UUGCACAA CUGAUGAGGCCGUUAGGCCGAA IUGACACG | 15550 |
| 483 | CUUUGUGC A AGAUACCC | 6211 | GGGUAUCU CUGAUGAGGCCGUUAGGCCGAA ICACAAAG | 15551 |
| 490 | CAAGAUAC C CAGAAAAG | 6212 | CUUUUCUG CUGAUGAGGCCGUUAGGCCGAA ICAUCCUG | 15552 |
| 491 | AAGAUACC C AGAAAAGA | 6213 | UCUUUUCU CUGAUGAGGCCGUUAGGCCGAA IGUAUCUU | 15553 |
| 492 | AGAUACCC A GAAAAGAG | 6214 | CUCUUUUC CUGAUGAGGCCGUUAGGCCGAA IGGUAUCU | 15554 |
| 509 | AUUUGUUC C UGAUGGUA | 6215 | UACCAUCA CUGAUGAGGCCGUUAGGCCGAA IAACAAAU | 15555 |
| 510 | UUUGUUCC U GAUGGUAA | 6216 | UUACCAUC CUGAUGAGGCCGUUAGGCCGAA IGAACAAA | 15556 |
| 520 | AUGGUAAC A GAAUUUCC | 6217 | GGAAAUUC CUGAUGAGGCCGUUAGGCCGAA IUUACCAU | 15557 |
| 528 | AGAAUUUC C UGGGACAG | 6218 | CUGUCCCA CUGAUGAGGCCGUUAGGCCGAA IAAAUUCU | 15558 |
| 529 | GAAUUUCC U GGGACAGC | 6219 | GCUGUCCC CUGAUGAGGCCGUUAGGCCGAA IGAAAUUC | 15559 |
| 535 | CCUGGGAC A GCAAGAAG | 6220 | CUUCUUGC CUGAUGAGGCCGUUAGGCCGAA IUCCCAGG | 15560 |
| 538 | GGGACAGC A AGAAGGGC | 6221 | GCCCUUCU CUGAUGAGGCCGUUAGGCCGAA ICUGUCCC | 15561 |
| 547 | AGAAGGGC U UUACUAUU | 6222 | AAUAGUAA CUGAUGAGGCCGUUAGGCCGAA ICCCUUCU | 15562 |
| 552 | GGCUUUAC U AUUCCCAG | 6223 | CUGGGAAU CUGAUGAGGCCGUUAGGCCGAA IUAAAGCC | 15563 |
| 557 | UACUAUUC C CAGCUACA | 6224 | UGUAGCUG CUGAUGAGGCCGUUAGGCCGAA IAAUAGUA | 15564 |

TABLE XVI-continued

Human KDR NCH Ribozyme and Target Sequences

| Pos | Target | Seq ID No | Ribozyme Sequence | Seq ID No. |
|---|---|---|---|---|
| 558 | ACUAUUCC C AGCUACAU | 6225 | AUGUAGCU CUGAUGAGGCCGUUAGGCCGAA IGAAUAGU | 15565 |
| 559 | CUAUUCCC A GCUACAUG | 6226 | CAUGUAGC CUGAUGAGGCCGUUAGGCCGAA IGGAAUAG | 15566 |
| 562 | UUCCCAGC U ACAUGAUC | 6227 | GAUCAUGU CUGAUGAGGCCGUUAGGCCGAA ICUGGGAA | 15567 |
| 565 | CCAGCUAC A UGAUCAGC | 6228 | GCUGAUCA CUGAUGAGGCCGUUAGGCCGAA IUAGCUGG | 15568 |
| 571 | ACAUGAUC A GCUAUGCU | 6229 | AGCAUAGC CUGAUGAGGCCGUUAGGCCGAA IAUCAUGU | 15569 |
| 574 | UGAUCAGC U AUGCUGGC | 6230 | GCCAGCAU CUGAUGAGGCCGUUAGGCCGAA ICUGAUCA | 15570 |
| 579 | AGCUAUGC U GGCAUGGU | 6231 | ACCAUGCC CUGAUGAGGCCGUUAGGCCGAA ICAUAGCU | 15571 |
| 583 | AUGCUGGC A UGGUCUUC | 6232 | GAAGACCA CUGAUGAGGCCGUUAGGCCGAA ICCAGCAU | 15572 |
| 589 | GCAUGGUC U UCUGUGAA | 6233 | UUCACAGA CUGAUGAGGCCGUUAGGCCGAA IACCAUGC | 15573 |
| 592 | UGGUCUUC U GUGAAGCA | 6234 | UGCUUCAC CUGAUGAGGCCGUUAGGCCGAA IAAGACCA | 15574 |
| 600 | UGUGAAGC A AAAAUUAA | 6235 | UUAAUUUU CUGAUGAGGCCGUUAGGCCGAA ICUUCACA | 15575 |
| 622 | AAAGUUAC C AGUCUAUU | 6236 | AAUAGACU CUGAUGAGGCCGUUAGGCCGAA IUAACUUU | 15576 |
| 623 | AAGUUACC A GUCUAUUA | 6237 | UAAUAGAC CUGAUGAGGCCGUUAGGCCGAA IGUAACUU | 15577 |
| 627 | UACCAGUC U AUUAUGUA | 6238 | UACAUAAU CUGAUGAGGCCGUUAGGCCGAA IACUGGUA | 15578 |
| 637 | UUAUGUAC A UAGUUGUC | 6239 | GACAACUA CUGAUGAGGCCGUUAGGCCGAA IUACAUAA | 15579 |
| 677 | UGUGGUUC U GAGUCCGU | 6240 | ACGGACUC CUGAUGAGGCCGUUAGGCCGAA IAACCACA | 15580 |
| 683 | UCUGAGUC C GUCUCAUG | 6241 | CAUGAGAC CUGAUGAGGCCGUUAGGCCGAA IACUCAGA | 15581 |
| 687 | AGUCCGUC U CAUGGAAU | 6242 | AUUCCAUG CUGAUGAGGCCGUUAGGCCGAA IACGGACU | 15582 |
| 689 | UCCGUCUC A UGGAAUUG | 6243 | CAAUUCCA CUGAUGAGGCCGUUAGGCCGAA IAGACGGA | 15583 |
| 701 | AAUUGAAC U AUCUGUUG | 6244 | CAACAGAU CUGAUGAGGCCGUUAGGCCGAA IUUCAAUU | 15584 |
| 705 | GAACUAUC U GUUGGAGA | 6245 | UCUCCAAC CUGAUGAGGCCGUUAGGCCGAA IAUAGUUC | 15585 |
| 719 | AGAAAGC U UGUCUUAA | 6246 | UUAAGACA CUGAUGAGGCCGUUAGGCCGAA ICUUUUCU | 15586 |
| 724 | AGCUUGUC U UAAAUUGU | 6247 | ACAAUUUA CUGAUGAGGCCGUUAGGCCGAA IACAAGCU | 15587 |
| 735 | AAUUGUAC A GCAAGAAC | 6248 | GUUCUUGC CUGAUGAGGCCGUUAGGCCGAA IUACAAUU | 15588 |
| 738 | UGUACAGC A AGAACUGA | 6249 | UCAGUUCU CUGAUGAGGCCGUUAGGCCGAA ICUGUACA | 15589 |
| 744 | GCAAGAAC U GAACUAAA | 6250 | UUUAGUUC CUGAUGAGGCCGUUAGGCCGAA IUUCUUGC | 15590 |
| 749 | AACUGAAC U AAAUGUGG | 6251 | CCACAUUU CUGAUGAGGCCGUUAGGCCGAA IUUCAGUU | 15591 |
| 766 | GGAUUGAC U UCAACGG | 6252 | CCAGUUGA CUGAUGAGGCCGUUAGGCCGAA IUCAAUCC | 15592 |
| 769 | UUGACUUC A ACGGGAA | 6253 | UUCCCAGU CUGAUGAGGCCGUUAGGCCGAA IAAGUCAA | 15593 |
| 772 | ACUUCAAC U GGGAAUAC | 6254 | GUAUUCCC CUGAUGAGGCCGUUAGGCCGAA IUUGAAGU | 15594 |
| 781 | GGGAAUAC C UUCUUCG | 6255 | CGAAGAAG CUGAUGAGGCCGUUAGGCCGAA IAUUCCC | 15595 |
| 782 | GGAAUACC C UUCUUCGA | 6256 | UCGAAGAA CUGAUGAGGCCGUUAGGCCGAA IGUAUUCC | 15596 |
| 783 | GAAUACCC U UCUUCGAA | 6257 | UUCGAAGA CUGAUGAGGCCGUUAGGCCGAA IGGUAUUC | 15597 |
| 786 | UACCCUUC U UCGAAGCA | 6258 | UGCUUCGA CUGAUGAGGCCGUUAGGCCGAA IAAGGGUA | 15598 |
| 794 | UUCGAAGC A UCAGCAUA | 6259 | UAUGCUGA CUGAUGAGGCCGUUAGGCCGAA ICUUCGAA | 15599 |
| 797 | GAAGCAUC A GCAUAAGA | 6260 | UCUUAUGC CUGAUGAGGCCGUUAGGCCGAA IAUGCUUC | 15600 |
| 800 | GCAUCAGC A UAAGAAAC | 6261 | GUUUCUUA CUGAUGAGGCCGUUAGGCCGAA ICUGAUGC | 15601 |

TABLE XVI-continued

Human KDR NCH Ribozyme and Target Sequences

| Pos | Target | Seq ID No | Ribozyme Sequence | Seq ID No. |
|---|---|---|---|---|
| 809 | UAAGAAAC U UGUAAACC | 6262 | GGUUUACA CUGAUGAGGCCGUUAGGCCGAA IUUUCUUA | 15602 |
| 817 | UUGUAAAC C CAGACCUA | 6263 | UAGGUCUC CUGAUGAGGCCGUUAGGCCGAA IUUUACAA | 15603 |
| 823 | ACCGAGAC C UAAAAACC | 6264 | GGUUUUUA CUGAUGAGGCCGUUAGGCCGAA IUCUCGGU | 15604 |
| 824 | CCGAGACC U AAAAACCC | 6265 | GGGUUUUU CUGAUGAGGCCGUUAGGCCGAA IGUCUCGG | 15605 |
| 831 | CUAAAAAC C CAGUCUGG | 6266 | CCAGACUG CUGAUGAGGCCGUUAGGCCGAA IUUUUUAG | 15606 |
| 832 | UAAAAACC C AGUCUGGG | 6267 | CCCAGACU CUGAUGAGGCCGUUAGGCCGAA IGUUUUUA | 15607 |
| 833 | AAAAACCC A GUCUGGGA | 6268 | UCCCAGAC CUGAUGAGGCCGUUAGGCCGAA IGGUUUUU | 15608 |
| 837 | ACCCAGUC U GGGAGUGA | 6269 | UCACUCCC CUGAUGAGGCCGUUAGGCCGAA IACUGGGU | 15609 |
| 865 | UUUUGAGC A CCUUAACU | 6270 | AGUUAAGG CUGAUGAGGCCGUUAGGCCGAA ICUCAAAA | 15610 |
| 867 | UUGAGCAC C UUAACUAU | 6271 | AUAGUUAA CUGAUGAGGCCGUUAGGCCGAA IUGCUCAA | 15611 |
| 868 | UGAGCACC U UAACUAUA | 6272 | UAUAGUUA CUGAUGAGGCCGUUAGGCCGAA IGUGCUCA | 15612 |
| 873 | ACCUUAAC U AUAGAUGG | 6273 | CCAUCUAU CUGAUGAGGCCGUUAGGCCGAA IUUAAGGU | 15613 |
| 888 | GGUGUAAC C CGGAGUGA | 6274 | UCACUCCG CUGAUGAGGCCGUUAGGCCGAA IUUACACC | 15614 |
| 889 | GUGUAACC C CGAGUGAC | 6275 | GUCACUCC CUGAUGAGGCCGUUAGGCCGAA IGUUACAC | 15615 |
| 898 | GGAGUGAC C AAGGAUUG | 6276 | CAAUCCUU CUGAUGAGGCCGUUAGGCCGAA IUCACUCC | 15616 |
| 899 | GAGUGACC A AGGAUUGU | 6277 | ACAAUCCU CUGAUGAGGCCGUUAGGCCGAA ICUCACUC | 15617 |
| 910 | GAUUGUAC A CCUGUGCA | 6278 | UGCACAGG CUGAUGAGGCCGUUAGGCCGAA IUACAAUC | 15618 |
| 912 | UUGUACAC C UGUGCAGC | 6279 | GCUGCACA CUGAUGAGGCCGUUAGGCCGAA IUGUACAA | 15619 |
| 913 | UGUACACC U GUGCAGCA | 6280 | UGCUGCAC CUGAUCAGGCCGUUAGGCCGAA IGUGUACA | 15620 |
| 918 | ACCUGUGC A GCAUCCAG | 6281 | CUGGAUGC CUGAUGAGGCCGUUAGGCCGAA ICACAGGU | 15621 |
| 921 | UGUGCAGC A UCCAGUGG | 6282 | CCACUGGA CUGAUGAGGCCGUUAGGCCGAA ICUGCACA | 15622 |
| 924 | GCAGCAUC C AGUGGGCU | 6283 | AGCCCACU CUGAUGAGGCCGUUAGGCCGAA IAUGCUGC | 15623 |
| 925 | CAGCAUCC A GUGGGCUG | 6284 | CAGCCCAC CUGAUGAGGCCGUUAGGCCGAA IGAUGCUG | 15624 |
| 932 | CAGUGGGC U GAUGACCA | 6285 | UGGUCAUC CUGAUGAGGCCGUUAGGCCGAA ICCCACUG | 15625 |
| 939 | CUGAUGAC C AAGAAGAA | 6286 | UUCUUCUU CUGAUGAGGCCGUUAGGCCGAA IUCAUCAG | 15626 |
| 940 | UGAUGACC A AGAAGAAC | 6287 | GUUCUUCU CUGAUGAGGCCGUUAGGCCGAA IGUCAUCA | 15627 |
| 949 | AGAAGAAC A GCACAUUU | 6288 | AAAUGUGC CUGAUGAGGCCGUUAGGCCGAA IUUCUUCU | 15628 |
| 952 | AGAACAGC A CAUUUGUC | 6289 | GACAAAUG CUGAUGAGGCCGUUAGGCCGAA ICUGUUCU | 15629 |
| 954 | AACAGCAC A UUUGUCAG | 6290 | CUGACAAA CUGAUGAGGCCGUUAGGCCGAA IUGCUGUU | 15630 |
| 961 | CAUUUGUC A GGGUCCAU | 6291 | AUGGACCC CUGAUGAGGCCGUUAGGCCGAA IACAAAUG | 15631 |
| 967 | UCAGGGUC C AUGAAAAA | 6292 | UUUUUCAU CUGAUGAGGCCGUUAGGCCGAA IACCCUGA | 15632 |
| 968 | CAGGGUCC A UGAAAAAC | 6293 | GUUUUUCA CUGAUGAGGCCGUUAGGCCGAA IGACCCUG | 15633 |
| 977 | UGAAAAAC C UUUGUUG | 6294 | CAACAAAA CUGAUGAGGCCGUUAGGCCGAA IUUUUUCA | 15634 |
| 978 | GAAAAACC U UUGUUGC | 6295 | GCAACAAA CUGAUGAGGCCGUUAGGCCGAA IGUUUUUC | 15635 |
| 987 | UUUGUUGC U UUGGAAG | 6296 | CUUCCAAA CUGAUGAGGCCGUUAGGCCGAA ICAACAAA | 15636 |
| 1000 | GAAGUGGC A UGGAAUCU | 6297 | AGAUUCCA CUGAUGAGGCCGUUAGGCCGAA ICCACUUC | 15637 |
| 1008 | AUGGAAUC U CUGGUGGA | 6298 | UCCACCAG CUGAUGAGGCCGUUAGGCCGAA IAUUCCAU | 15638 |

TABLE XVI-continued

Human KDR NCH Ribozyme and Target Sequences

| Pos | Target | Seq ID No | Ribozyme Sequence | Seq ID No. |
|---|---|---|---|---|
| 1010 | GGAAUCUC U GGUGGAAG | 6299 | CUUCCACC CUGAUGAGGCCGUUAGGCCGAA IAGAUUCC | 15639 |
| 1020 | GUGGAAGC C ACGGUGGG | 6300 | CCCACCGU CUGAUGAGGCCGUUAGGCCGAA ICUUCCAC | 15640 |
| 1021 | UGGAAGCC A CGGUGGGG | 6301 | CCCCACCG CUGAUGAGGCCGUUAGGCCGAA IGCUUCCA | 15641 |
| 1039 | AGCGUGUC A GAAUCCCU | 6302 | AGGGAUUC CUGAUGAGGCCGUUAGGCCGAA IACACGCU | 15642 |
| 1045 | UCAGAAUC C CUGCGAAG | 6303 | CUUCGCAG CUGAUGAGGCCGUUAGGCCGAA IAUUCUGA | 15643 |
| 1046 | CAGAAUCC C UGCGAAGU | 6304 | ACUUCGCA CUGAUGAGGCCGUUAGGCCGAA IGAUUCUG | 15644 |
| 1047 | AGAAUCCC U GCGAAGUA | 6305 | UACUUCGC CUGAUGAGGCCGUUAGGCCGAA IGGAUUCU | 15645 |
| 1057 | CGAAGUAC C UUGGUUAC | 6306 | GUAACCAA CUGAUGAGGCCGUUAGGCCGAA IACUUCG | 15646 |
| 1058 | GAAGUACC U UGGUUACC | 6307 | GGUAACCA CUGAUGAGGCCGUUAGGCCGAA IGUACUUC | 15647 |
| 1066 | UUGGUUAC C CACCCCCA | 6308 | UGGGGGUG CUGAUGAGGCCGUUAGGCCGAA IUAACCAA | 15648 |
| 1067 | UGGUUACC C ACCCCCAG | 6309 | CUGGGGGU CUGAUGAGGCCGUUAGGCCGAA IGUAACCA | 15649 |
| 1068 | GGUUACCC A CCCCCAGA | 6310 | UCUGGGGG CUGAUGAGGCCGUUAGGCCGAA IGGUAACC | 15650 |
| 1070 | UUACCCAC C CCCAGAAA | 6311 | UUUCUGGG CUGAUGAGGCCGUUAGGCCGAA IUGGGUAA | 15651 |
| 1071 | UACCCACC C CAGAAAU | 6312 | AUUUCUGG CUGAUGAGGCCGUUAGGCCGAA IGUGGGUA | 15652 |
| 1072 | ACCCACCC C AGAAAUA | 6313 | UAUUUCUG CUGAUGAGGCCGUUAGGCCGAA IGGUGGGU | 15653 |
| 1073 | CCCACCCC C AGAAAUAA | 6314 | UUAUUUCU CUGAUGAGGCCGUUAGGCCGAA IGGGUGGG | 15654 |
| 1074 | CCACCCCC A GAAAUAAA | 6315 | UUUAUUUC CUGAUGAGGCCGUUAGGCCGAA IGGGGUGG | 15655 |
| 1103 | UGGAAUAC C CUUGAGU | 6316 | ACUCAAGG CUGAUGAGGCCGUUAGGCCGAA IUAUUCCA | 15656 |
| 1104 | GGAAUACC C UUGAGUC | 6317 | GACUCAAG CUGAUGAGGCCGUUAGGCCGAA IGUAUUCC | 15657 |
| 1105 | GAAUACCC C UUGAGUCC | 6318 | GGACUCAA CUGAUGAGGCCGUUAGGCCGAA IGGUAUUC | 15658 |
| 1106 | AAUACCCC U UGAGUCCA | 6319 | UGGACUCA CUGAUGAGGCCGUUAGGCCGAA IGGGUAUU | 15659 |
| 1113 | CUUGAGUC C AAUCACAC | 6320 | GUGUGAUU CUGAUGAGGCCGUUAGGCCGAA IACUCAAG | 15660 |
| 1114 | UUGAGUCC A AUCACACA | 6321 | UGUGUGAU CUGAUGAGGCCGUUAGGCCGAA IGACUCAA | 15661 |
| 1118 | GUCCAAUC A CACAAUUA | 6322 | UAAUUGUG CUGAUGAGGCCGUUAGGCCGAA IAUUGGAC | 15662 |
| 1120 | CCAAUCAC A CAAUUAAA | 6323 | UUUAAUUG CUGAUGAGGCCGUUAGGCCGAA IUGAUUGG | 15663 |
| 1122 | AAUCACAC A AUUAAAGC | 6324 | GCUUUAAU CUGAUGAGGCCGUUAGGCCGAA IUGUGAUU | 15664 |
| 1136 | AGCGGGGC A UGUACUGA | 6325 | UCAGUACA CUGAUGAGGCCGUUAGGCCGAA ICCCCGCU | 15665 |
| 1142 | GCAUGUAC U GACGAUUA | 6326 | UAAUCGUC CUGAUGAGGCCGUUAGGCCGAA IUACAUGC | 15666 |
| 1171 | AAAGAGAC A CAGGAAAU | 6327 | AUUUCCUG CUGAUGAGGCCGUUAGGCCGAA IUCUCUUU | 15667 |
| 1173 | AGAGACAC A GGAAAUUA | 6328 | UAAUUUCC CUGAUGAGGCCGUUAGGCCGAA IGUGUCUCU | 15668 |
| 1183 | GAAAUUAC A CUGUCAUC | 6329 | GAUGACAG CUGAUGAGGCCGUUAGGCCGAA IUAAUUUC | 15669 |
| 1185 | AAUUACAC U GUCAUCCU | 6330 | AGGAUGAC CUGAUGAGGCCGUUAGGCCGAA IGUAAUU | 15670 |
| 1189 | ACACUGUC A UCCUUACC | 6331 | GGUAAGGA CUGAUGAGGCCGUUAGGCCGAA IACAGUGU | 15671 |
| 1192 | CUGUCAUC C UUACCAAU | 6332 | AUUGGUAA CUGAUGAGGCCGUUAGGCCGAA IAUGACAG | 15672 |
| 1193 | UGUCAUCC U UACCAAUC | 6333 | GAUUGGUA CUGAUGAGGCCGUUAGGCCGAA IGAUGACA | 15673 |
| 1197 | AUCCUUAC C AAUCCCAU | 6334 | AUGGGAUU CUGAUGAGGCCGUUAGGCCGAA IUAAGGAU | 15674 |
| 1198 | UCCUUACC A AUCCCAUU | 6335 | AAUGGGAU CUGAUGAGGCCGUUAGGCCGAA IGUAAGGA | 15675 |

TABLE XVI-continued

Human KDR NCH Ribozyme and Target Sequences

| Pos | Target | Seq ID No | Ribozyme Sequence | Seq ID No. |
|---|---|---|---|---|
| 1202 | UACCAAUC C CAUUUCAA | 6336 | UUGAAAUG CUGAUGAGGCCGUUAGGCCGAA IAUUGGUA | 15676 |
| 1203 | ACCAAUCC C AUUUCAAA | 6337 | UUUGAAAU CUGAUGAGGCCGUUAGGCCGAA IGAUUGGU | 15677 |
| 1204 | CCAAUCCC A UUUCAAAG | 6338 | CUUUGAAA CUGAUGAGGCCGUUAGGCCGAA IGGAUUGG | 15678 |
| 1209 | CCCAUUUC A AAGGAGAA | 6339 | UUCUCCUU CUGAUGAGGCCGUUAGGCCGAA IAAAUGGG | 15679 |
| 1220 | GGAGAAGC A GAGCCAUG | 6340 | CAUGGCUC CUGAUGAGGCCGUUAGGCCGAA ICUUCUCC | 15680 |
| 1225 | AGCAGAGC C AUGGGUC | 6341 | GACCACAU CUGAUGAGGCCGUUAGGCCGAA ICUCUGCU | 15681 |
| 1226 | GCAGAGCC A UGUGGCU | 6342 | AGACCACA CUGAUGAGGCCGUUAGGCCGAA IGCUCUGC | 15682 |
| 1234 | AUGUGGUC U CUCUGGUU | 6343 | AACCAGAG CUGAUGAGGCCGUUAGGCCGAA IACCACAU | 15683 |
| 1236 | GUGGUCUC U CUGGUUGU | 6344 | ACAACCAG CUGAUGAGGCCGUUAGGCCGAA IAGACCAC | 15684 |
| 1238 | GGUCUCUC U GGUUGUGU | 6345 | ACACAACC CUGAUGAGGCCGUUAGGCCGAA IAGAGACC | 15685 |
| 1252 | UGUAUGUC C CACCCCAG | 6346 | CUGGGGUG CUGAUGAGGCCGUUAGGCCGAA IACAUACA | 15686 |
| 1253 | GUAUGUCC C ACCCCAGA | 6347 | UCUGGGGU CUGAUGAGGCCGUUAGGCCGAA IGACAUAC | 15687 |
| 1254 | UAUGUCCC A CCCCAGAU | 6348 | AUCUGGGG CUGAUGAGGCCGUUAGGCCGAA IGGACAUA | 15688 |
| 1256 | UGUCCCAC C CCAGAUUG | 6349 | CAAUCUGG CUGAUGAGGCCGUUAGGCCGAA IUGGGACA | 15689 |
| 1257 | GUCCCACC C CAGAUUGG | 6350 | CCAAUCUG CUGAUGAGGCCGUUAGGCCGAA IGUGGGAC | 15690 |
| 1258 | UCCCACCC C AGAUUGGU | 6351 | ACCAAUCU CUGAUGAGGCCGUUAGGCCGAA IGGUGGGA | 15691 |
| 1259 | CCCACCCC A GAUUGGUG | 6352 | CACCAAUC CUGAUGAGGCCGUUAGGCCGAA IGGGUGUG | 15692 |
| 1275 | GAGAAAUC U CUAAUCUC | 6353 | GAGAUUAG CUGAUGAGGCCGUUAGGCCGAA IAUUUCUC | 15693 |
| 1277 | GAAAUCUC U AAUCUCUC | 6354 | GAGAGAUU CUGAUGAGGCCGUUAGGCCGAA IAGAUUUC | 15694 |
| 1282 | CUCUAAUC U CUCCUGUG | 6355 | CACAGGAG CUGAUGAGGCCGUUAGGCCGAA IAUUAGAG | 15695 |
| 1284 | CUAAUCUC U CCUGUGGA | 6356 | UCCACAGG CUGAUGAGGCCGUUAGGCCGAA IAGAUUAG | 15696 |
| 1286 | AAUCUCUC C UGGGAUU | 6357 | AAUCCACA CUGAUGAGGCCGUUAGGCCGAA IAGAGAUU | 15697 |
| 1287 | AUCUCUCC U GGGAUUC | 6358 | GAAUCCAC CUGAUGAGGCCGUUAGGCCGAA IGAGAGAU | 15698 |
| 1296 | GUGGAUUC C UACCAGUA | 6359 | UACUGGUA CUGAUGAGGCCGUUAGGCCGAA IAAUCCAC | 15699 |
| 1297 | UGGAUUCC U ACCAGUAC | 6360 | GUACUGGU CUGAUGAGGCCGUUAGGCCGAA IGAAUCCA | 15700 |
| 1300 | AUUCCUAC C AGUACGGC | 6361 | GCCGUACU CUGAUGAGGCCGUUAGGCCGAA IUAGGAAU | 15701 |
| 1301 | UUCCUACC A GUACGGCA | 6362 | UGCCGUAC CUGAUGAGGCCGUUAGGCCGAA IGUAGGAA | 15702 |
| 1309 | AGUACGGC A CCACUCAA | 6363 | UUGAGUGG CUGAUGAGGCCGUUAGGCCGAA ICCGUACU | 15703 |
| 1311 | UACGGCAC C ACUCAAAC | 6364 | GUUUGAGU CUGAUGAGGCCGUUAGGCCGAA IUGCCGUA | 15704 |
| 1312 | ACGGCACC A CUCAAACG | 6365 | CGUUUGAG CUGAUGAGGCCGUUAGGCCGAA IGUGCCGU | 15705 |
| 1314 | GGCACCAC U CAAACGCU | 6366 | AGCGUUUG CUGAUGAGGCCGUUAGGCCGAA IUGGUGCC | 15706 |
| 1316 | CACCACUC A AACGCUGA | 6367 | UCAGCGUU CUGAUGAGGCCGUUAGGCCGAA IAGUGGUG | 15707 |
| 1322 | UCAAACGC U GACAUGUA | 6368 | UACAUGUC CUGAUGAGGCCGUUAGGCCGAA ICGUUUGA | 15708 |
| 1326 | ACGCUGAC A UGUACGGU | 6369 | ACCGUACA CUGAUGAGGCCGUUAGGCCGAA IUCAGCGU | 15709 |
| 1336 | GUACGGUC U AUGCCAUU | 6370 | AAUGGCAU CUGAUGAGGCCGUUAGGCCGAA IACCGUAC | 15710 |
| 1341 | GUCUAUGC C AUUCCUCC | 6371 | GGAGGAAU CUGAUGAGGCCGUUAGGCCGAA ICAUAGAC | 15711 |
| 1342 | UCUAUGCC A UUCCUCCC | 6372 | GGGAGGAA CUGAUGAGGCCGUUAGGCCGAA IGCAUAGA | 15712 |

TABLE XVI-continued

Human KDR NCH Ribozyme and Target Sequences

| Pos | Target | Seq ID No | Ribozyme Sequence | Seq ID No. |
|-----|--------|-----------|-------------------|------------|
| 1346 | UGCCAUUC C UCCCCCGC | 6373 | GCGGGGGA CUGAUGAGGCCGUUAGGCCGAA IAAUGGCA | 15713 |
| 1347 | GCCAUUCC U CCCCCGCA | 6374 | UGCGGGGG CUGAUGAGGCCGUUAGGCCGAA IGAAUGGC | 15714 |
| 1349 | CAUUCCUC C CCCGCAUC | 6375 | GAUGCGGG CUGAUGAGGCCGUUAGGCCGAA IAGGAAUG | 15715 |
| 1350 | AUUCCUCC C CCCCAUCA | 6376 | UGAUGCGG CUGAUGAGGCCGUUAGGCCGAA IGAGGAAU | 15716 |
| 1351 | UUCCUCCC C CCCAUCAC | 6377 | GUGAUGCG CUGAUGAGGCCGUUAGGCCGAA IGGAGGAA | 15717 |
| 1352 | UCCUCCCC C GCAUCACA | 6378 | UGUGAUGC CUGAUGAGGCCGUUAGGCCGAA IGGGAGGA | 15718 |
| 1355 | UCCCCCGC A UCACAUCC | 6379 | GGAUGUGA CUGAUGAGGCCGUUAGGCCGAA ICGGGGGA | 15719 |
| 1358 | CCCGCAUC A CAUCCACU | 6380 | AGUGGAUG CUGAUGAGGCCGUUAGGCCGAA IAUGCGGG | 15720 |
| 1360 | CGCAUCAC A UCCACUGG | 6381 | CCAGUGGA CUGAUGAGGCCGUUAGGCCGAA IUGAUGCG | 15721 |
| 1363 | AUCACAUC C ACUGGUAU | 6382 | AUACCAGU CUGAUGAGGCCGUUAGGCCGAA IAUGUGAU | 15722 |
| 1364 | UCACAUCC A CUGGUAUU | 6383 | AAUACCAG CUGAUGAGGCCGUUAGGCCGAA IGAUGUGA | 15723 |
| 1366 | ACAUCCAC U GGUAUUGG | 6384 | CCAAUACC CUGAUGAGGCCGUUAGGCCGAA IUGGAUGU | 15724 |
| 1376 | GUAUUGGC A GUUGGAGG | 6385 | CCUCCAAC CUGAUGAGGCCGUUAGGCCGAA ICCAAUAC | 15725 |
| 1395 | GAGUGCGC C AACGAGCC | 6386 | GGCUCGUU CUGAUGAGGCCGUUAGGCCGAA ICGCACUC | 15726 |
| 1396 | AGUGCGCC A ACGAGCCC | 6387 | GGGCUCGU CUGAUGAGGCCGUUAGGCCGAA IGCGCACU | 15727 |
| 1403 | CAACGAGC C CAGCCAAG | 6388 | CUUGGCUG CUGAUGAGGCCGUUAGGCCGAA ICUCGUUG | 15728 |
| 1404 | AACGAGCC C AGCCAAGC | 6389 | GCUUGGCU CUGAUGAGGCCGUUAGGCCGAA IGCUCGUU | 15729 |
| 1405 | ACGAGCCC A GCCAAGCU | 6390 | AGCUUGGC CUGAUGAGGCCGUUAGGCCGAA IGGCUCGU | 15730 |
| 1408 | AGCCCAGC C AAGCUGUC | 6391 | GACAGCUU CUGAUGAGGCCGUUAGGCCGAA ICUGGGCU | 15731 |
| 1409 | GCCCAGCC A AGCUGUCU | 6392 | AGACAGCU CUGAUGAGGCCGUUAGGCCGAA IGCUGGGC | 15732 |
| 1413 | AGCCAAGC U GUCUCAGU | 6393 | ACUGAGAC CUGAUGAGGCCGUUAGGCCGAA ICUUGGCU | 15733 |
| 1417 | AAGCUGUC U CAGUGACA | 6394 | UGUCACUG CUGAUGAGGCCGUUAGGCCGAA IACAGCUU | 15734 |
| 1419 | GCUGUCUC A GUGACAAA | 6395 | UUUGUCAC CUGAUGAGGCCGUUAGGCCGAA IAGACAGC | 15735 |
| 1425 | UCAGUGAC A AACCCAUA | 6396 | UAUGGGUU CUGAUGAGGCCGUUAGGCCGAA IUCACUGA | 15736 |
| 1429 | UGACAAAC C CAUACCCU | 6397 | AGGGUAUG CUGAUGAGGCCGUUAGGCCGAA IUUUGUCA | 15737 |
| 1430 | GACAAACC C AUACCCUU | 6398 | AAGGGUAU CUGAUGAGGCCGUUAGGCCGAA IGUUUGUC | 15738 |
| 1431 | ACAAACCC A UACCCUUG | 6399 | CAAGGGUA CUGAUGAGGCCGUUAGGCCGAA IGGUUUGU | 15739 |
| 1435 | ACCCAUAC C CUUGUGAA | 6400 | UUCACAAG CUGAUGAGGCCGUUAGGCCGAA IUAUGGGU | 15740 |
| 1436 | CCCAUACC C UUGUGAAG | 6401 | CUUCACAA CUGAUGAGGCCGUUAGGCCGAA IGUAUGGG | 15741 |
| 1437 | CCAUACCC U UGUGAAGA | 6402 | UCUUCACA CUGAUGAGGCCGUUAGGCCGAA IGGUAUGG | 15742 |
| 1465 | UGGAGGAC U UCCAGGGA | 6403 | UCCCUGGA CUGAUGAGGCCGUUAGGCCGAA IUCCUCCA | 15743 |
| 1468 | AGGACUUC C AGGGAGGA | 6404 | UCCUCCCU CUGAUGAGGCCGUUAGGCCGAA IAAGUCCU | 15744 |
| 1469 | GGACUUCC A GGGAGGAA | 6405 | UUCCUCCC CUGAUGAGGCCGUUAGGCCGAA IGAAGUCC | 15745 |
| 1502 | UAAAAAUC A AUUUGCUC | 6406 | GAGCAAAU CUGAUGAGGCCGUUAGGCCGAA IAUUUUUA | 15746 |
| 1509 | CAAUUUGC U CUAAUUGA | 6407 | UCAAUUAG CUGAUGAGGCCGUUAGGCCGAA ICAAAUUG | 15747 |
| 1511 | AUUUGCUC U AAUUGAAG | 6408 | CUUCAAUU CUGAUGAGGCCGUUAGGCCGAA IAGCAAAU | 15748 |
| 1528 | GAAAAAAC A AAACUGUA | 6409 | UACAGUUU CUGAUGAGGCCGUUAGGCCGAA IUUUUUUC | 15749 |

TABLE XVI-continued

Human KDR NCH Ribozyme and Target Sequences

| Pos | Target | Seq ID No | Ribozyme Sequence | Seq ID No. |
|---|---|---|---|---|
| 1533 | AACAAAAC U GUAAGUAC | 6410 | GUACUUAC CUGAUGAGGCCGUUAGGCCGAA IUUUUGUU | 15750 |
| 1542 | GUAAGUAC C CUUGUUAU | 6411 | AUAACAAG CUGAUGAGGCCGUUAGGCCGAA IUACUUAC | 15751 |
| 1543 | UAAGUACC C UUGUUAUC | 6412 | GAUAACAA CUGAUGAGGCCGUUAGGCCGAA IGUACUUA | 15752 |
| 1544 | AAGUACCC U UGUUAUCC | 6413 | GGAUAACA CUGAUGAGGCCGUUAGGCCGAA IGGUACUU | 15753 |
| 1552 | UUGUUAUC C AAGCGGCA | 6414 | UGCCGCUU CUGAUGAGGCCGUUAGGCCGAA IAUAACAA | 15754 |
| 1553 | UGUUAUCC A AGCGGCAA | 6415 | UUGCCGCU CUGAUGAGGCCGUUAGGCCGAA IGAUAACA | 15755 |
| 1560 | CAAGCGGC A AAUGUGUC | 6416 | GACACAUU CUGAUGAGGCCGUUAGGCCGAA ICCGCUUG | 15756 |
| 1569 | AAUGUGUC A GCUUUGUA | 6417 | UACAAAGC CUGAUGAGGCCGUUAGGCCGAA IACACAUU | 15757 |
| 1572 | GUGUCAGC U UUGUACAA | 6418 | UUGUACAA CUGAUGAGGCCGUUAGGCCGAA ICUGACAC | 15758 |
| 1579 | CUUUGUAC A AAUGUGAA | 6419 | UUCACAUU CUGAUGAGGCCGUUAGGCCGAA IUACAAAG | 15759 |
| 1594 | AAGCGGUC A ACAAAGUC | 6420 | GACUUUGU CUGAUGAGGCCGUUAGGCCGAA IACCGCUU | 15760 |
| 1597 | CGGUCAAC A AAGUCGGG | 6421 | CCCGACUU CUGAUGAGGCCGUUAGGCCGAA IUUGACCG | 15761 |
| 1624 | GGGUGAUC U CCUUCCAC | 6422 | GUGGAAGG CUGAUGAGGCCGUUAGGCCGAA IAUCACCC | 15762 |
| 1626 | GUGAUCUC C UUCCACGU | 6423 | ACGUGGAA CUGAUGAGGCCGUUAGGCCGAA IAGAUCAC | 15763 |
| 1627 | UGAUCUCC U UCCACGUG | 6424 | CACGUGGA CUGAUGAGGCCGUUAGGCCGAA IGAGAUCA | 15764 |
| 1630 | UCUCCUUC C ACGUGACC | 6425 | GGUCACGU CUGAUGAGGCCGUUAGGCCGAA IAAGGAGA | 15765 |
| 1631 | CUCCUUCC A CGUGACCA | 6426 | UGGUCACG CUGAUGAGGCCGUUAGGCCGAA IGAAGGAG | 15766 |
| 1638 | CACGUGAC C AGGGGUCC | 6427 | GGACCCCU CUGAUGAGGCCGUUAGGCCGAA IUCACGUG | 15767 |
| 1639 | ACGUGACC A GGGGUCCU | 6428 | AGGACCCC CUGAUGAGGCCGUUAGGCCGAA IGUCACGU | 15768 |
| 1646 | CAGGGGUC C UGAAAUUA | 6429 | UAAUUUCA CUGAUGAGGCCGUUAAGCCCGA IACCCCUG | 15769 |
| 1647 | AGGGGUCC U GAAAUUAC | 6430 | GUAAUUUC CUGAUGAGGCCGUUAGGCCGAA IGACCCCU | 15770 |
| 1656 | GAAAUUAC U UUGCAACC | 6431 | GGUUGCAA CUGAUGAGGCCGUUAGGCCGAA IUAAUUUC | 15771 |
| 1661 | UACUUUGC A ACCUGACA | 6432 | UGUCAGGU CUGAUGAGGCCGUUAGGCCGAA ICAAAGUA | 15772 |
| 1664 | UUUGCAAC C UGACAUGC | 6433 | GCAUGUCA CUGAUGAGGCCGUUAGGCCGAA IUUGCAAA | 15773 |
| 1665 | UUGCAACC U GACAUGCA | 6434 | UGCAUGUC CUGAUGAGGCCGUUAGGCCGAA IGUUGCAA | 15774 |
| 1669 | AACCUGAC A UGCAGCCC | 6435 | GGGCUGCA CUGAUGAGGCCGUUAGGCCGAA IUCAGGUU | 15775 |
| 1673 | UGACAUGC A GCCCACUG | 6436 | CAGUGGGC CUGAUGAGGCCGUUAGGCCGAA ICAUGUCA | 15776 |
| 1676 | CAUGCAGC C CACUGAGC | 6437 | GCUCAGUG CUGAUGAGGCCGUUAGGCCGAA ICUGCAUG | 15777 |
| 1677 | AUGCAGCC C ACUGAGCA | 6438 | UGCUCAGU CUGAUGAGGCCGUUAGGCCGAA IGCUGCAU | 15778 |
| 1678 | UGCAGCCC A CUGAGCAG | 6439 | CUGCUCAG CUGAUGAGGCCGUUAGGCCGAA IGGCUGCA | 15779 |
| 1680 | CAGCCCAC U GAGCAGGA | 6440 | UCCUGCUC CUGAUGAGGCCGUUAGGCCGAA IUGGGCUG | 15780 |
| 1685 | CACUGAGC A GGAGAGCG | 6441 | CGCUCUCC CUGAUGAGGCCGUUAGGCCGAA ICUCAGUG | 15781 |
| 1698 | AGCGUGUC U UUGUGGUG | 6442 | CACCACAA CUGAUGAGGCCGUUAGGCCGAA IACACGCU | 15782 |
| 1708 | UGUGGUGC A CUGCAGAC | 6443 | GUCUGCAG CUGAUGAGGCCGUUAGGCCGAA ICACCACA | 15783 |
| 1710 | UGGUGCAC U GCAGACAG | 6444 | CUGUCUGC CUGAUGAGGCCGUUAGGCCGAA IUGCACCA | 15784 |
| 1713 | UGCACUGC A GACAGAUC | 6445 | GAUCUGUC CUGAUGAGGCCGUUAGGCCGAA ICAGUGCA | 15785 |
| 1717 | CUGCAGAC A GAUCUACG | 6446 | CGUAGAUC CUGAUGAGGCCGUUAGGCCGAA IUCUGCAG | 15786 |

TABLE XVI-continued

Human KDR NCH Ribozyme and Target Sequences

| Pos | Target | Seq ID No | Ribozyme Sequence | Seq ID No. |
|---|---|---|---|---|
| 1722 | GACAGAUC U ACGUUUGA | 6447 | UCAAACGU CUGAUGAGGCCGUUAGGCCGAA IAUCUGUC | 15787 |
| 1735 | UUGAGAAC C UCACAUGG | 6448 | CCAUGUGA CUGAUGAGGCCGUUAGGCCGAA IUUCUCAA | 15788 |
| 1736 | UGAGAACC U CACAUGGU | 6449 | ACCAUGUG CUGAUGAGGCCGUUAGGCCGAA IGUUCUCA | 15789 |
| 1738 | AGAACCUC A CAUGGUAC | 6450 | GUACCAUG CUGAUGAGGCCGUUAGGCCGAA IAGGUUCU | 15790 |
| 1740 | AACCUCAC A UGGUACAA | 6451 | UUGUACCA CUGAUGAGGCCGUUAGGCCGAA IUGAGGUU | 15791 |
| 1747 | CAUGGUAC A AGCUUGGC | 6452 | GCCAAGCU CUGAUGAGGCCGUUAGGCCGAA IUACCAUG | 15792 |
| 1751 | GUACAAGC U UGGCCCAC | 6453 | GUGGGCCA CUGAUGAGGCCGUUAGGCCGAA ICUUGUAC | 15793 |
| 1756 | AGCUUGGC C CACAGCCU | 6454 | AGGCUGUG CUGAUGAGGCCGUUAGGCCGAA ICCAAGCU | 15794 |
| 1757 | GCUUGGCC C ACAGCCUC | 6455 | GAGGCUGU CUGAUGAGGCCGUUAGGCCGAA IGCCAAGC | 15795 |
| 1758 | CUUGGCCC A CAGCCUCU | 6456 | AGAGGCUG CUGAUGAGGCCGUUAGGCCGAA IGGCCAAG | 15796 |
| 1760 | UGGCCCAC A GCCUCUGC | 6457 | GCAGAGGC CUGAUGAGGCCGUUAGGCCGAA IUGGGCCA | 15797 |
| 1763 | CCCACAGC C UCUGCCAA | 6458 | UUGGCAGA CUGAUGAGGCCGUUAGGCCGAA ICUGUGGG | 15798 |
| 1764 | CCACAGCC U CUGCCAAU | 6459 | AUUGGCAG CUGAUGAGGCCGUUAGGCCGAA IGCUGUGG | 15799 |
| 1766 | ACAGCCUC U GCCAAUCC | 6460 | GGAUUGGC CUGAUGAGGCCGUUAGGCCGAA IAGGCUGU | 15800 |
| 1769 | GCCUCUGC C AAUCCAUG | 6461 | CAUGGAUU CUGAUGAGGCCGUUAGGCCGAA ICAGAGGC | 15801 |
| 1770 | CCUCUGCC A AUCCAUGU | 6462 | ACAUGGAU CUGAUGAGGCCGUUAGGCCGAA IGCAGAGG | 15802 |
| 1774 | UGCCAAUC C AUGGGGA | 6463 | UCCCACAU CUGAUGAGGCCGUUAGGCCGAA IAUUGGCA | 15803 |
| 1775 | GCCAAUCC A UGUGGGAG | 6464 | CUCCCACA CUGAUGAGGCCGUUAGGCCGAA IGAUUGGC | 15804 |
| 1790 | AGAGUUGC C CACACCUG | 6465 | CAGGUGUG CUGAUGAGGCCGUUAGGCCGAA ICAACUCU | 15805 |
| 1791 | GAGUUGCC C ACACCGUU | 6466 | ACAGGUGU CUGAUGAGGCCGUUAGGCCGAA IGCAACUC | 15806 |
| 1792 | AGUUGCCC A CACCUGUU | 6467 | AACAGGUG CUGAUGAGGCCGUUAGGCCGAA IGGCAACU | 15807 |
| 1794 | UUGCCCAC A CCUGUUUG | 6468 | CAAACAGG CUGAUGAGGCCGUUAGGCCGAA IUGGGCAA | 15808 |
| 1796 | GCCCACAC C UGUUUGCA | 6469 | UGCAAACA CUGAUGAGGCCGUUAGGCCGAA IUGUGGGC | 15809 |
| 1797 | CCCACACC U GUUUGCAA | 6470 | UUGCAAAC CUGAUGAGGCCGUUAGGCCGAA IGUGUGGG | 15810 |
| 1804 | CUGUUUGC A AGAACUUG | 6471 | CAAGUUCU CUGAUGAGGCCGUUAGGCCGAA ICAAACAG | 15811 |
| 1810 | GCAAGAAC U UGGAUACU | 6472 | AGUAUCCA CUGAUGAGGCCGUUAGGCCGAA IUUCUUGC | 15812 |
| 1818 | UUGGAUAC U CUUUGGAA | 6473 | UUCCAAAG CUGAUGAGGCCGUUAGGCCGAA IUAUCCAA | 15813 |
| 1820 | GGAUACUC U UUGGAAAU | 6474 | AUUUCCAA CUGAUGAGGCCGUUAGGCCGAA IAGUAUCC | 15814 |
| 1836 | UUGAAUGC C ACCAUGUU | 6475 | AACAUGGU CUGAUGAGGCCGUUAGGCCGAA ICAUUCAA | 15815 |
| 1837 | UGAAUGCC A CCAUGUUC | 6476 | GAACAUGG CUGAUGAGGCCGUUAGGCCGAA IGCAUUCA | 15816 |
| 1839 | AAUGCCAC C AUGUUCUC | 6477 | GAGAACAU CUGAUGAGGCCGUUAGGCCGAA IUGGCAUU | 15817 |
| 1840 | AUGCCACC A UGUUCUCU | 6478 | AGAGAACA CUGAUGAGGCCGUUAGGCCGAA IGUGGCAU | 15818 |
| 1846 | CCAUGUUC U CUAAUAGC | 6479 | GCUAUUAG CUGAUGAGGCCGUUAGGCCGAA IAACAUGG | 15819 |
| 1848 | AUGUUCUC U AAUAGCAC | 6480 | GUGCUAUU CUGAUGAGGCCGUUAGGCCGAA IAGAACAU | 15820 |
| 1855 | CUAAUAGC A CAAAUGAC | 6481 | GUCAUUUG CUGAUGAGGCCGUUAGGCCGAA ICUAUUAG | 15821 |
| 1857 | AAUAGCAC A AAUGACAU | 6482 | AUGUCAUU CUGAUGAGGCCGUUAGGCCGAA IUGCUAUU | 15822 |
| 1864 | CAAAUGAC A UUUUGAUC | 6483 | GAUCAAAA CUGAUGAGGCCGUUAGGCCGAA IUCAUUUG | 15823 |

TABLE XVI-continued

Human KDR NCH Ribozyme and Target Sequences

| Pos | Target | Seq ID No | Ribozyme Sequence | Seq ID No. |
|---|---|---|---|---|
| 1873 | UUUUGAUC A UGGAGCUU | 6484 | AAGCUCCA CUGAUGAG<u>GCCGUUAGGCC</u>GAA IAUCAAAA | 15824 |
| 1880 | CAUGGAGC U UAAGAAUG | 6485 | CAUUCUUA CUGAUGAG<u>GCCGUUAGGCC</u>GAA ICUCCAUG | 15825 |
| 1890 | AAGAAUGC A UCCUUGCA | 6486 | UGCAAGGA CUGAUGAG<u>GCCGUUAGGCC</u>GAA ICAUUCUU | 15826 |
| 1893 | AAUGCAUC C UUGCAGGA | 6487 | UCCUGCAA CUGAUGAG<u>GCCGUUAGGCC</u>GAA IAUGCAUU | 15827 |
| 1894 | AUGCAUCC U UGCAGGAC | 6488 | GUCCUGCA CUGAUGAG<u>GCCGUUAGGCC</u>GAA IGAUGCAU | 15828 |
| 1898 | AUCCUUGC A GGACCAAG | 6489 | CUUGGUCC CUGAUGAG<u>GCCGUUAGGCC</u>GAA ICAAGGAU | 15829 |
| 1903 | UGCAGGAC C AAGGAGAC | 6490 | GUCUCCUU CUGAUGAG<u>GCCGUUAGGCC</u>GAA IUCCUGCA | 15830 |
| 1904 | GCAGGACC A AGGAGACU | 6491 | AGUCUCCU CUGAUGAG<u>GCCGUUAGGCC</u>GAA IGUCCUGC | 15831 |
| 1912 | AAGGAGAC U AUGUCUGC | 6492 | GCAGACAU CUGAUGAG<u>GCCGUUAGGCC</u>GAA IUCUCCUU | 15832 |
| 1918 | ACUAUGUC U GCCUUGCU | 6493 | AGCAAGGC CUGAUGAG<u>GCCGUUAGGCC</u>GAA IACAUAGU | 15833 |
| 1921 | AUGUCUGC C UUGCUCAA | 6494 | UUGAGCAA CUGAUGAG<u>GCCGUUAGGCC</u>GAA ICAGACAU | 15834 |
| 1922 | UGUCUGCC U UGCUCAAG | 6495 | CUUGAGCA CUGAUGAG<u>GCCGUUAGGCC</u>GAA IGCAGACA | 15835 |
| 1926 | UGCCUUGC U CAAGACAG | 6496 | CUGUCUUG CUGAUGAG<u>GCCGUUAGGCC</u>GAA ICAAGGCA | 15836 |
| 1928 | CCUUGCUC A AGACAGGA | 6497 | UCCUGUCU CUGAUGAG<u>GCCGUUAGGCC</u>GAA IAGCAAGG | 15837 |
| 1933 | CUCAAGAC A GGAAGACC | 6498 | GGUCUUCC CUGAUGAG<u>GCCGUUAGGCC</u>GAA IUCUUGAG | 15838 |
| 1941 | AGGAAGAC C AAGAAAAG | 6499 | CUUUCUUU CUGAUGAG<u>GCCGUUAGGCC</u>GAA IUCUUCCU | 15839 |
| 1942 | GGAAGACC A AGAAAAGA | 6500 | UCUUUUCU CUGAUGAG<u>GCCGUUAGGCC</u>GAA IGUCUUCC | 15840 |
| 1952 | GAAAAGAC A UUGCGUGG | 6501 | CCACGCAA CUGAUGAG<u>GCCGUUAGGCC</u>GAA IUCUUUUC | 15841 |
| 1963 | GCGUGGUC A GGCAGCUC | 6502 | GAGCUGCC CUGAUGAG<u>GCCGUUAGGCC</u>GAA IACCACGC | 15842 |
| 1967 | GGUCAGGC A GCUCACAG | 6503 | CUGUGAGC CUGAUGAG<u>GCCGUUAGGCC</u>GAA ICCUGACC | 15843 |
| 1970 | CAGGCAGC U CACAGUCC | 6504 | GGACUGUG CUGAUGAG<u>GCCGUUAGGCC</u>GAA ICUGCCUG | 15844 |
| 1972 | GCAGCUC A CAGUCCUA | 6505 | UAGGACUG CUGAUGAG<u>GCCGUUAGGCC</u>GAA IAGCUGCC | 15845 |
| 1974 | CAGCUCAC A GUCCUAGA | 6506 | UCUAGGAC CUGAUGAG<u>GCCGUUAGGCC</u>GAA IUGAGCUG | 15846 |
| 1978 | UCACAGUC C UAGAGCGU | 6507 | ACGCUCUA CUGAUGAG<u>GCCGUUAGGCC</u>GAA IACUGUGA | 15847 |
| 1979 | CACAGUCC U AGAGCGUG | 6508 | CACGCUCU CUGAUGAG<u>GCCGUUAGGCC</u>GAA IGACUGUG | 15848 |
| 1992 | CGUGUGGC A CCCACGAU | 6509 | AUCGUGGG CUGAUGAG<u>GCCGUUAGGCC</u>GAA ICCACACG | 15849 |
| 1994 | UGUGGCAC C CACGAUCA | 6510 | UGAUCGUG CUGAUGAG<u>GCCGUUAGGCC</u>GAA IUGCCACA | 15850 |
| 1995 | GUGGCACC C ACGAUCAC | 6511 | GUGAUCGU CUGAUGAG<u>GCCGUUAGGCC</u>GAA IGUGCCAC | 15851 |
| 1996 | UGGCACCC A CGAUCACA | 6512 | UGUGAUCG CUGAUGAG<u>GCCGUUAGGCC</u>GAA IGGUGCCA | 15852 |
| 2002 | CCACGAUC A CAGGAAAC | 6513 | GUUUCCUG CUGAUGAG<u>GCCGUUAGGCC</u>GAA IAUCGUGG | 15853 |
| 2004 | ACGAUCAC A GGAAACCU | 6514 | AGGUUUCC CUGAUGAG<u>GCCGUUAGGCC</u>GAA IUGAUCGU | 15854 |
| 2011 | CAGGAAAC C UGGAGAAU | 6515 | AUUCUCCA CUGAUGAG<u>GCCGUUAGGCC</u>GAA IUUUCCUG | 15855 |
| 2012 | AGGAAACC U GGAGAAUC | 6516 | GAUUCUCC CUGAUGAG<u>GCCGUUAGGCC</u>GAA IGUUUCCU | 15856 |
| 2021 | GGAGAAUC A GACGACAA | 6517 | UUGUCGUC CUGAUGAG<u>GCCGUUAGGCC</u>GAA IAUUCUCC | 15857 |
| 2028 | CAGACGAC A AGUAUUGG | 6518 | CCAAUACU CUGAUGAG<u>GCCGUUAGGCC</u>GAA ICGUCUG | 15858 |
| 2044 | GGGAAAGC A UCGAAGUC | 6519 | GACUUCGA CUGAUGAG<u>GCCGUUAGGCC</u>GAA ICUUUCCC | 15859 |
| 2053 | UCGAAGUC U CAUGCACG | 6520 | CGUGCAUG CUGAUGAG<u>GCCGUUAGGCC</u>GAA IACUUCGA | 15860 |

TABLE XVI-continued

Human KDR NCH Ribozyme and Target Sequences

| Pos | Target | Seq ID No | Ribozyme Sequence | Seq ID No. |
|---|---|---|---|---|
| 2055 | GAAGUCUC A UGCACGGC | 6521 | GCCGUGCA CUGAUGAGGCCGUUAGGCCGAA IAGACUUC | 15861 |
| 2059 | UCUCAUGC A CGGCAUCU | 6522 | AGAUGCCG CUGAUGAGGCCGUUAGGCCGAA ICAUGAGA | 15862 |
| 2064 | UGCACGGC A UCUGGGAA | 6523 | UUCCCAGA CUGAUGAGGCCGUUAGGCCGAA ICCGUGCA | 15863 |
| 2067 | ACGGCAUC U GGGAAUCC | 6524 | GGAUUCCC CUGAUGAGGCCGUUAGGCCGAA IAUGCCGU | 15864 |
| 2075 | UGGGAAUC C CCCUCCAC | 6525 | GUGGAGGG CUGAUGAGGCCGUUAGGCCGAA IAUUCCCA | 15865 |
| 2076 | GGGAAUCC C CCUCCACA | 6526 | UGUGGAGO CUGAUGAGGCCGUUAGGCCGAA IGAUUCCC | 15866 |
| 2077 | GGAAUCCC C CUCCACAG | 6527 | CUGUGGAG CUGAUGAGGCCGUUAGGCCGAA IGGAUUCC | 15867 |
| 2078 | GAAUCCCC C UCCACAGA | 6528 | UCUGUGGA CUGAUGAGGCCGUUAGGCCGAA IGGGAUUC | 15868 |
| 2079 | AAUCCCCC U CCACAGAU | 6529 | AUCUGUGG CUGAUGAGGCCGUUAGGCCGAA IGGGGAUU | 15869 |
| 2081 | UCCCCCUC C ACAGAUCA | 6530 | UGAUCUGU CUGAUGAGGCCGUUAGGCCGAA IAGGGGGA | 15870 |
| 2082 | CCCCCUCC A CAGAUCAU | 6531 | AUGAUCUG CUGAUGAGGCCGUUAGGCCGAA IGAGGGGG | 15871 |
| 2084 | CCCUCCAC A GAUCAUGU | 6532 | ACAUGAUC CUGAUGAGGCCGUUAGGCCGAA IUGGAGGG | 15872 |
| 2089 | CACAGAUC A UGUGGUUU | 6533 | AAACCACA CUGAUGAGGCCGUUAGGCCGAA IAUCUGUG | 15873 |
| 2112 | AAUGAGAC C CUUGUAGA | 6534 | UCUACAAG CUGAUGAGGCCGUUAGGCCGAA IUCUCAUU | 15874 |
| 2113 | AUGAGACC C UUGUAGAA | 6535 | UUCUACAA CUGAUGAGGCCGUUAGGCCGAA IGUCUCAU | 15875 |
| 2114 | UGAGACCC U UGUAGAAG | 6536 | CUUCUACA CUGAUGAGGCCGUUAGGCCGAA IGGUCUCA | 15876 |
| 2125 | UAGAAGAC U CAGGCAUU | 6537 | AAUGCCUG CUGAUGAGGCCGUUAGGCCGAA IUCUUCUA | 15877 |
| 2127 | GAAGACUC A GGCAUUGU | 6538 | ACAAUGCC CUGAUGAGGCCGUUAGGCCGAA IAGUCUUC | 15878 |
| 2131 | ACUCAGGC A UUGUAUUG | 6539 | CAAUACAA CUGAUGAGGCCGUUAGGCCGAA ICCUGAGU | 15879 |
| 2152 | AUGGGAAC C GGAACCUC | 6540 | GAGGUUCC CUGAUGAGGCCGUUAGGCCGAA IUUCCCAU | 15880 |
| 2158 | ACCGGAAC C UCACUAUC | 6541 | GAUAGUGA CUGAUGAGGCCGUUAGGCCGAA IUUCCGGU | 15881 |
| 2159 | CCGGAACC U CACUAUCC | 6542 | GGAUAGUG CUGAUGAGGCCGUUAGGCCGAA IGUUCCGG | 15882 |
| 2161 | GGAACCUC A CUAUCCGC | 6543 | GCGGAUAG CUGAUGAGGCCGUUAGGCCGAA IAGGUUCC | 15883 |
| 2163 | AACCUCAC U AUCCGCAG | 6544 | CUGCGGAU CUGAUGAGGCCGUUAGGCCGAA IUGAGGUU | 15884 |
| 2167 | UCACUAUC C GCAGAGUG | 6545 | CACUCUGC CUGAUGAGGCCGUUAGGCCGAA IAUAGUGA | 15885 |
| 2170 | CUAUCCGC A GAGUGAGG | 6546 | CCUCACUC CUGAUGAGGCCGUUAGGCCGAA ICGGAUAG | 15886 |
| 2194 | ACGAAGGC C UCUACACC | 6547 | GGUGUAGA CUGAUGAGGCCGUUAGGCCGAA ICCUUCGU | 15887 |
| 2195 | CGAAGGCC U CUACACCU | 6548 | AGGUGUAG CUGAUGAGGCCGUUAGGCCGAA IGCCUUCG | 15888 |
| 2197 | AAGGCCUC U ACACCUGC | 6549 | GCAGGUGU CUGAUGAGGCCGUUAGGCCGAA IAGGCCUU | 15889 |
| 2200 | GCCUCUAC A CCUGCCAG | 6550 | CUGGCAGG CUGAUGAGGCCGUUAGGCCGAA IUAGAGGC | 15890 |
| 2202 | CUCUACAC C UGCCAGGC | 6551 | GCCUGGCA CUGAUGAGGCCGUUAGGCCGAA IUGUAGAG | 15891 |
| 2203 | UCUACACC U GCCAGGCA | 6552 | UGCCUGGC CUGAUGAGGCCGUUAGGCCGAA IGUGUAGA | 15892 |
| 2206 | ACACCUGC C AGGCAUGC | 6553 | GCAUGCCU CUGAUGAGGCCGUUAGGCCGAA ICAGGUGU | 15893 |
| 2207 | CACCUGCC A GGCAUGCA | 6554 | UGCAUGCC CUGAUGAGGCCGUUAGGCCGAA IGCAGGUG | 15894 |
| 2211 | UGCCAGGC A UGCAGUGU | 6555 | ACACUGCA CUGAUGAGGCCGUUAGGCCGAA ICCUGGCA | 15895 |
| 2215 | AGGCAUGC A GUGUUCUU | 6556 | AAGAACAC CUGAUGAGGCCGUUAGGCCGAA ICAUGCCU | 15896 |
| 2222 | CAGUGUUC U UGGCUGUG | 6557 | CACAGCCA CUGAUGAGGCCGUUAGGCCGAA IAACACUG | 15897 |

TABLE XVI-continued

Human KDR NCH Ribozyme and Target Sequences

| Pos | Target | Seq ID No | Ribozyme Sequence | Seq ID No. |
|---|---|---|---|---|
| 2227 | UUCUUGGC U GUGCAAAA | 6558 | UUUUGCAC CUGAUGAGGCCGUUAGGCCGAA ICCAAGAA | 15898 |
| 2232 | GGCUGUGC A AAAGUGGA | 6559 | UCCACUUU CUGAUGAGGCCGUUAGGCCGAA ICACAGCC | 15899 |
| 2244 | GUGGAGGC A UUUUUCAU | 6560 | AUGAAAAA CUGAUGAGGCCGUUAGGCCGAA ICCUCCAC | 15900 |
| 2251 | CAUUUUUC A UAAUAGAA | 6561 | UUCUAUUA CUGAUGAGGCCGUUAGGCCGAA IAAAAAUG | 15901 |
| 2265 | GAAGGUGC C CAGGAAAA | 6562 | UUUUCCUG CUGAUGAGGCCGUUAGGCCGAA ICACCUUC | 15902 |
| 2266 | AAGGUGCC C AGGAAAAG | 6563 | CUUUUCCU CUGAUGAGGCCGUUAGGCCGAA IGCACCUU | 15903 |
| 2267 | AGGUGCCC A GGAAAAGA | 6564 | UCUUUUCC CUGAUGAGGCCGUUAGGCCGAA IGGCACCU | 15904 |
| 2281 | AGACGAAC U UGGAAAUC | 6565 | GAUUUCCA CUGAUGAGGCCGUUAGGCCGAA IUUCGUCU | 15905 |
| 2290 | UGGAAAUC A UUAUUCUA | 6566 | UAGAAUAA CUGAUGAGGCCGUUAGGCCGAA IAUUUCCA | 15906 |
| 2297 | CAUUAUUC U AGUAGGCA | 6567 | UGCCUACU CUGAUGAGGCCGUUAGGCCGAA IAAUAAUG | 15907 |
| 2305 | UAGUAGGC A CGACGGUG | 6568 | CACCGUCG CUGAUGAGGCCGUUAGGCCGAA ICCUACUA | 15908 |
| 2319 | GUGAUUGC C AUGUUCUU | 6569 | AAGAACAU CUGAUGAGGCCGUUAGGCCGAA ICAAUCAC | 15909 |
| 2320 | UGAUUGCC A UGUUCUUC | 6570 | GAAGAACA CUGAUGAGGCCGUUAGGCCGAA IGCAAUCA | 15910 |
| 2326 | CCAUGUUC U UCUGGCUA | 6571 | UAGCCAGA CUGAUGAGGCCGUUAGGCCGAA IAACAUGG | 15911 |
| 2329 | UGUUCUUC U GGCUACUU | 6572 | AAGUAGCC CUGAUGAGGCCGUUAGGCCGAA IAAGAACA | 15912 |
| 2333 | CUUCUGGC U ACUUCUUG | 6573 | CAAGAAGU CUGAUGAGGCCGUUAGGCCGAA ICCAGAAG | 15913 |
| 2336 | CUGGCUAC U UCUUGUCA | 6574 | UGACAAGA CUGAUGAGGCCGUUAGGCCGAA IUAGCCAG | 15914 |
| 2339 | GCUACUUC U UGUCAUCA | 6575 | UGAUGACA CUGAUGAGGCCGUUAGGCCGAA IAAGUAGC | 15915 |
| 2344 | UUCUUGUC A UCAUCCUA | 6576 | UAGGAUGA CUGAUGAGGCCGUUAGGCCGAA IACAAGAA | 15916 |
| 2347 | UUGUCAUC A UCCUAGGG | 6577 | CCCUAGGA CUGAUGAGGCCGUUAGGCCGAA IAUGACAA | 15917 |
| 2350 | UCAUCAUC C UAGGGACC | 6578 | GGUCCCUA CUGAUGAGGCCGUUAGGCCGAA IAUGAUGA | 15918 |
| 2351 | CAUCAUCC U AGGGACCG | 6579 | CGGUCCCU CUGAUGAGGCCGUUAGGCCGAA IGAUGAUG | 15919 |
| 2358 | CUAGGGAC C GUUAAGCG | 6580 | CGCUUAAC CUGAUGAGGCCGUUAGGCCGAA IUCCCUAG | 15920 |
| 2370 | AAGCGGGC C AAUGGAGG | 6581 | CCUCCAUU CUGAUGAGGCCGUUAGGCCGAA ICCCGCUU | 15921 |
| 2371 | AGCGGGCC A AUGGAGGG | 6582 | CCCUCCAU CUGAUGAGGCCGUUAGGCCGAA IGCCCGCU | 15922 |
| 2384 | AGGGGAAC U GAAGACAG | 6583 | CUGUCUUC CUGAUGAGGCCGUUAGGCCGAA IUUCCCCU | 15923 |
| 2391 | CUGAAGAC A GGCUACUU | 6584 | AAGUAGCC CUGAUGAGGCCGUUAGGCCGAA IUCUUCAG | 15924 |
| 2395 | AGACAGGC U ACUUGUCC | 6585 | GGACAAGU CUGAUGAGGCCGUUAGGCCGAA ICCUGUCU | 15925 |
| 2398 | CAGGCUAC U UGUCCAUC | 6586 | GAUGGACA CUGAUGAGGCCGUUAGGCCGAA IUAGCCUG | 15926 |
| 2403 | UACUUGUC C AUCGUCAU | 6587 | AUGACGAU CUGAUGAGGCCGUUAGGCCGAA IACAAGUA | 15927 |
| 2404 | ACUUGUCC A UCGUCAUG | 6588 | CAUGACGA CUGAUGAGGCCGUUAGGCCGAA IGACAAGU | 15928 |
| 2410 | CCAUCGUC A UGGAUCCA | 6589 | UGGAUCCA CUGAUGAGGCCGUUAGGCCGAA IACGAUGG | 15929 |
| 2417 | CAUGGAUC C AGAUGAAC | 6590 | GUUCAUCU CUGAUGAGGCCGUUAGGCCGAA IAUCCAUG | 15930 |
| 2418 | AUGGAUCC A GAUGAACU | 6591 | AGUUCAUC CUGAUGAGGCCGUUAGGCCGAA IGAUCCAU | 15931 |
| 2426 | AGAUGAAC U CCCAUUGG | 6592 | CCAAUGGG CUGAUGAGGCCGUUAGGCCGAA IUUCAUCU | 15932 |
| 2428 | AUGAACUC C CAUUGGAU | 6593 | AUCCAAUG CUGAUGAGGCCGUUAGGCCGAA IAGUUCAU | 15933 |
| 2429 | UGAACUCC C AUUGGAUG | 6594 | CAUCCAAU CUGAUGAGGCCGUUAGGCCGAA IGAGUUCA | 15934 |

TABLE XVI-continued

Human KDR NCH Ribozyme and Target Sequences

| Pos | Target | Seq ID No | Ribozyme Sequence | Seq ID No. |
|---|---|---|---|---|
| 2430 | GAACUCCC A UUGGAUGA | 6595 | UCAUCCAA CUGAUGAGGCCGUUAGGCCGAA IGGAGUUC | 15935 |
| 2441 | GGAUGAAC A UUGUGAAC | 6596 | GUUCACAA CUGAUGAGGCCGUUAGGCCGAA IUUCAUCC | 15936 |
| 2453 | UGAACGAC U GCCUUAUG | 6597 | CAUAAGGC CUGAUGAGGCCGUUAGGCCGAA IUCGUUCA | 15937 |
| 2456 | ACGACUGC C UUAUGAUG | 6598 | CAUCAUAA CUGAUGAGGCCGUUAGGCCGAA ICAGUCGU | 15938 |
| 2457 | CGACUGCC U UAUGAUGC | 6599 | GCAUCAUA CUGAUGAGGCCGUUAGGCCGAA IGCAGUCG | 15939 |
| 2466 | UAUGAUGC C AGCAAAUG | 6600 | CAUUUGCU CUGAUGAGGCCGUUAGGCCGAA ICAUCAUA | 15940 |
| 2467 | AUGAUGCC A GCAAAUGG | 6601 | CCAUUUGC CUGAUGAGGCCGUUAGGCCGAA IGCAUCAU | 15941 |
| 2470 | AUGCCAGC A AAUGGGAA | 6602 | UUCCCAUU CUGAUGAGGCCGUUAGGCCGAA ICUGGCAU | 15942 |
| 2482 | GGGAAUUC C CCAGAGAC | 6603 | GUCUCUGG CUGAUGAGGCCGUUAGGCCGAA IAAUUCCC | 15943 |
| 2483 | GGAAUUCC C CAGAGACC | 6604 | GGUCUCUG CUGAUGAGGCCGUUAGGCCGAA IGAAUUCC | 15944 |
| 2484 | GAAUUCCC C AGAGACCG | 6605 | CGGUCUCU CUGAUGAGGCCGUUAGGCCGAA IGGAAUUC | 15945 |
| 2485 | AAUUCCCC A GAGACCGG | 6606 | CCGGUCUC CUGAUGAGGCCGUUAGGCCGAA IGGGAAUU | 15946 |
| 2491 | CCAGAGAC C GGCUGAAC | 6607 | GUUCAGCC CUGAUGAGGCCGUUAGGCCGAA IUCUCUGG | 15947 |
| 2495 | AGACCGGC U GAACCUAG | 6608 | CUAGGUUC CUGAUGAGGCCGUUAGGCCGAA ICCGGUCU | 15948 |
| 2500 | GGCUGAAC C UAGGUAAG | 6609 | CUUACCUA CUGAUGAGGCCGUUAGGCCGAA IUUCAGCC | 15949 |
| 2501 | GCUGAACC U AGGUAAGC | 6610 | GCUUACCU CUGAUGAGGCCGUUAGGCCGAA IGUUCAGC | 15950 |
| 2510 | AGGUAAGC C UCUUGGCC | 6611 | GGCCAAGA CUCAUGAGGCCGUUAGGCCGAA ICUUACCU | 15951 |
| 2511 | GGUAAGCC U CUUGGCCG | 6612 | CGGCCAAG CUGAUGAGGCCGUUAGGCCGAA IGCUUACC | 15952 |
| 2513 | UAAGCCUC U UGGCCGUG | 6613 | CACGGCCA CUGAUGAGGCCGUUAGGCCGAA IAGGCUUA | 15953 |
| 2518 | CUCUUGGC C GUGGUGCC | 6614 | GGCACCAC CUGAUGAGGCCGUUAGGCCGAA ICCAAGAG | 15954 |
| 2526 | CGUGGUGC C UUUGGCCA | 6615 | UGGCCAAA CUGAUGAGGCCGUUAGGCCGAA ICACCACO | 15955 |
| 2527 | GUGGUGCC U UUGGCCAA | 6616 | UUGGCCAA CUGAUGAGGCCGUUAGGCCGAA IGCACCAC | 15956 |
| 2533 | CCUUUGGC C AAGAGAUU | 6617 | AAUCUCUU CUGAUGAGGCCGUUAGGCCGAA ICCAAAGG | 15957 |
| 2534 | CUUUGGCC A AGAGACUG | 6618 | CAAUCUCU CUGAUGAGGCCGUUAGGCCGAA IGCCAAAG | 15958 |
| 2547 | AUUGAAGC A GAUGCCUU | 6619 | AAGGCAUC CUGAUGAGGCCGUUAGGCCGAA ICUUCAAU | 15959 |
| 2553 | GCAGAUGC C UUUGGAAU | 6620 | AUUCCAAA CUGAUGAGGCCGUUAGGCCGAA ICAUCUGC | 15960 |
| 2554 | CAGAUGCC U UUGGAAUU | 6621 | AAUUCCAA CUGAUGAGGCCGUUAGGCCGAA IGCAUCUG | 15961 |
| 2566 | GAAUUGAC A AGACAGCA | 6622 | UGCUGUCU CUGAUGAGGCCGUUAGGCCGAA IUCAAUUC | 15962 |
| 2571 | GACAAGAC A GCAACUUG | 6623 | CAAGUUGC CUGAUGAGGCCGUUAGGCCGAA IUCUUGUC | 15963 |
| 2574 | AAGACAGC A ACUUGCAG | 6624 | CUGCAAGU CUGAUGAGGCCGUUAGGCCGAA ICUGUCUU | 15964 |
| 2577 | ACAGCAAC U UGCAGGAC | 6625 | GUCCUGCA CUGAUGAGGCCGUUAGGCCGAA IUUGCUGU | 15965 |
| 2581 | CAACUUGC A GGACAGUA | 6626 | UACUGUCC CUGAUGAGGCCGUUAGGCCGAA ICAAGUUG | 15966 |
| 2586 | UGCAGGAC A GUAGCAGU | 6627 | ACUGCUAC CUGAUGAGGCCGUUAGGCCGAA IUCCUGCA | 15967 |
| 2592 | ACAGUAGC A GUCAAAAU | 6628 | AUUUUGAC CUGAUGAGGCCGUUAGGCCGAA ICUACUGU | 15968 |
| 2596 | UAGCAGUC A AAUGUUG | 6629 | CAACAUUU CUGAUGAGGCCGUUAGGCCGAA IACUGCUA | 15969 |
| 2616 | GAAGGAGC A ACACACAG | 6630 | CUGUGUGU CUGAUGAGGCCGUUAGGCCGAA ICUCCUUC | 15970 |
| 2619 | GGAGCAAC A CACAGUGA | 6631 | UCACUGUG CUGAUGAGGCCGUUAGGCCGAA IUUGCUCC | 15971 |

TABLE XVI-continued

Human KDR NCH Ribozyme and Target Sequences

| Pos | Target | Seq ID No | Ribozyme Sequence | Seq ID No. |
|---|---|---|---|---|
| 2621 | AGCAACAC A CAGUGAGC | 6632 | GCUCACUG CUGAUGAGGCCGUUAGGCCGAA IUGUUGCU | 15972 |
| 2623 | CAACACAC A GUGAGCAU | 6633 | AUGCUCAC CUGAUGAGGCCGUUAGGCCGAA IUGUGUUG | 15973 |
| 2630 | CAGUGAGC A UCGAGCUC | 6634 | GAGCUCGA CUGAUGAGGCCGUUAGGCCGAA ICUCACUG | 15974 |
| 2637 | CAUCGAGC U CUCAUGUC | 6635 | GACAUGAG CUGAUGAGGCCGUUAGGCCGAA ICUCGAUG | 15975 |
| 2639 | UCGAGCUC U CAUGUCUG | 6636 | CAGACAUG CUGAUGAGGCCGUUAGGCCGAA IAGCUCGA | 15976 |
| 2641 | GAGCUCUC A UGUCUGAA | 6637 | UUCAGACA CUGAUGAGGCCGUUAGGCCGAA IAGAGCUC | 15977 |
| 2646 | CUCAUGUC U GAACUCAA | 6638 | UUGAGUUC CUGAUGAGGCCGUUAGGCCGAA IACAUGAG | 15978 |
| 2651 | GUCUGAAC U CAAGAUCC | 6639 | GGAUCUUG CUGAUGAGGCCGUUAGGCCGAA IUUCAGAC | 15979 |
| 2653 | CUGAACUC A AGAUCCUC | 6640 | GAGGAUCU CUGAUGAGGCCGUUAGGCCGAA IAGUUCAG | 15980 |
| 2659 | UCAAGAUC C UCAUUCAU | 6641 | AUGAAUGA CUGAUGAGGCCGUUAGGCCGAA IAUCUUGA | 15981 |
| 2660 | CAAGAUCC U CAUUCAUA | 6642 | UAUGAAUG CUGAUGAGGCCGUUAGGCCGAA IGAUCUUG | 15982 |
| 2662 | AGAUCCUC A UUCAUAUU | 6643 | AAUAUGAA CUGAUGAGGCCGUUAGGCCGAA IAGGAUCU | 15983 |
| 2666 | CCUCAUUC A UAUUGGUC | 6644 | GACCAAUA CUGAUGAGGCCGUUAGGCCGAA IAAUGAGG | 15984 |
| 2675 | UAUUGGUC A CCAUCUCA | 6645 | UGAGAUGG CUGAUGAGGCCGUUAGGCCGAA IACCAAUA | 15985 |
| 2677 | UUGGUCAC C AUCUCAAU | 6646 | AUUGAGAU CUGAUGAGGCCGUUAGGCCGAA IUGACCAA | 15986 |
| 2678 | UGGUCACC A UCUCAAUG | 6647 | CAGUGAGA CUGAUGAGGCCGUUAGGCCGAA IGUGACCA | 15987 |
| 2681 | UCACCAUC U CAAUGUGG | 6648 | CCACAUUG CUGAUGAGGCCGUUAGGCCGAA IAUGGUGA | 15988 |
| 2683 | ACCAUCUC A AUGGGUC | 6649 | GACCACAU CUGAUGAGGCCGUUAGGCCGAA IAGAUGGU | 15989 |
| 2692 | AUGUGGUC A ACCUUCUA | 6650 | UAGAAGGU CUGAUGAGGCCGUUAGGCCGAA IACCACAU | 15990 |
| 2695 | UGGUCAAC C UUCUAGGU | 6651 | ACCUAGAA CUGAUGAGGCCGUUAGGCCGAA IUUGACCA | 15991 |
| 2696 | GGUCAACC U UCUAGGUG | 6652 | CACCUAGA CUGAUGAGGCCGUUAGGCCGAA IGUUGACC | 15992 |
| 2699 | CAACCUUC U AGGUGCCU | 6653 | AGGCACCU CUGAUGAGGCCGUUAGGCCGAA IAAGGUUG | 15993 |
| 2706 | CUAGGUGC C UGUACCAA | 6654 | UUGGUACA CUGAUGAGGCCGUUAGGCCGAA ICACCUAG | 15994 |
| 2707 | UAGGUGCC U GUACCAAG | 6655 | CUUGGUAC CUGAUGAGGCCGUUAGGCCGAA IGCACCUA | 15995 |
| 2712 | GCCUGUAC C AAGCCAGG | 6656 | CCUGGCUU CUGAUGAGGCCGUUAGGCCGAA IUACAGGC | 15996 |
| 2713 | CCUGUACC A AGCCAGGA | 6657 | UCCUGGCU CUGAUGAGGCCGUUAGGCCGAA IGUACAGG | 15997 |
| 2717 | UACCAAGC C AGGAGGGC | 6658 | GCCCUCCU CUGAUGAGGCCGUUAGGCCGAA ICUUGGUA | 15998 |
| 2718 | ACCAAGCC A GGAGGGCC | 6659 | GGCCCUCC CUGAUGAGGCCGUUAGGCCGAA IGCUUGGU | 15999 |
| 2726 | AGGAGGGC C ACUCAUGG | 6660 | CCAUGAGU CUGAUGAGGCCGUUAGGCCGAA ICCCUCCU | 16000 |
| 2727 | GGAGGGCC A CUCAUGGU | 6661 | ACCAUGAG CUGAUGAGGCCGUUAGGCCGAA IGCCCUCC | 16001 |
| 2729 | AGGGCCAC U CAUGGUGA | 6662 | UCACCAUG CUGAUGAGGCCGUUAGGCCGAA IUGGCCCU | 16002 |
| 2731 | GGCCACUC A UGGUGAUU | 6663 | AAUCACCA CUGAUGAGGCCGUUAGGCCGAA IAGUGGCC | 16003 |
| 2749 | UGGAAUUC U GCAAAUUU | 6664 | AAAUUUGC CUGAUGAGGCCGUUAGGCCGAA IAAUUCCA | 16004 |
| 2752 | AAUUCUGC A AAUUUGGA | 6665 | UCCAAAUU CUGAUGAGGCCGUUAGGCCGAA ICAGAAUU | 16005 |
| 2764 | UUGGAAAC C UGUCCACU | 6666 | AGUGGACA CUGAUGAGGCCGUUAGGCCGAA IUUUCCAA | 16006 |
| 2765 | UGGAAACC U GUCCACUU | 6667 | AAGUGGAC CUGAUGAGGCCGUUAGGCCGAA IGUUUCCA | 16007 |
| 2769 | AACCUGUC C ACUUACCU | 6668 | AGGUAAGU CUGAUGAGGCCGUUAGGCCGAA IACAGGUU | 16008 |

TABLE XVI-continued

Human KDR NCH Ribozyme and Target Sequences

| Pos | Target | Seq ID No | Ribozyme Sequence | Seq ID No. |
|---|---|---|---|---|
| 2770 | ACCUGUCC A CUUACCUG | 6669 | CAGGUAAG CUGAUGAGGCCGUUAGGCCGAA IGACAGGU | 16009 |
| 2772 | CUGUCCAC U UACCUGAG | 6670 | CUCAGGUA CUGAUGAGGCCGUUAGGCCGAA IUGGACAG | 16010 |
| 2776 | CCACUUAC C UGAGGAGC | 6671 | GCUCCUCA CUGAUGAGGCCGUUAGGCCGAA IUAAGUGG | 16011 |
| 2777 | CACUUACC U GAGGAGCA | 6672 | UGCUCCUC CUGAUGAGGCCGUUAGGCCGAA IGUAAGUG | 16012 |
| 2785 | UGAGGAGC A AGAGAAAU | 6673 | AUUUCUCU CUGAUGAGGCCGUUAGGCCGAA ICUCCUCA | 16013 |
| 2803 | AAUUUGUC C CCUACAAG | 6674 | CUUGUAGG CUGAUGAGGCCGUUAGGCCGAA IACAAAUU | 16014 |
| 2804 | AUUUGUCC C CUACAAGA | 6675 | UCUUGUAG CUGAUGAGGCCGUUAGGCCGAA IGACAAAU | 16015 |
| 2805 | UUUGUCCC C UACAAGAC | 6676 | GUCUUGUA CUGAUGAGGCCGUUAGGCCGAA IGGACAAA | 16016 |
| 2806 | UUGUCCCC U ACAAGACC | 6677 | GGUCUUGU CUGAUGAGGCCGUUAGGCCGAA IGGGACAA | 16017 |
| 2809 | UCCCCUAC A AGACCAAA | 6678 | UUUGGUCU CUGAUGAGGCCGUUAGGCCGAA IAGGGGA | 16018 |
| 2814 | UACAAGAC C AAAGGGC | 6679 | GCCCCUUU CUGAUGAGGCCGUUAGGCCGAA IUCUUGUA | 16019 |
| 2815 | ACAAGACC A AAGGGCA | 6680 | UGCCCCUU CUGAUGAGGCCGUUAGGCCGAA IGUCUUGU | 16020 |
| 2823 | AAAGGGGC A CGAUUCCG | 6681 | CGGAAUCG CUGAUGAGGCCGUUAGGCCGAA ICCCCUUU | 16021 |
| 2830 | CACGAUUC C GUCAAGGG | 6682 | CCCUUGAC CUGAUGAGGCCGUUAGGCCGAA IAAUCGUG | 16022 |
| 2834 | AUUCCGUC A AGGGAAAG | 6683 | CUUUCCCU CUGAUGAGGCCGUUAGGCCGAA IACGGAAU | 16023 |
| 2845 | GGAAAGAC U ACGUUGGA | 6684 | UCCAACGU CUGAUGAGGCCGUUAGGCCGAA IUCUUUCC | 16024 |
| 2856 | GUUGGAGC A AUCCCUGU | 6685 | ACAGGGAU CUGAUGAGGCCGUUAGGCCGAA ICUCCAAC | 16025 |
| 2860 | GAGCAAUC C CUGUGGAU | 6686 | AUCCACAG CUGAUGAGGCCGUUAGGCCGAA IAUUGCUC | 16026 |
| 2861 | AGCAAUCC C UGUGGAUC | 6687 | GAUCCACA CUGAUGAGGCCGUUAGGCCGAA IGAUUGCU | 16027 |
| 2862 | GCAAUCCC U GUGGAUCU | 6688 | AGAUCCAC CUGAUGAGGCCGUUAGGCCGAA IGGAUUGC | 16028 |
| 2870 | UGUGGAUC U GAAACGGC | 6689 | GCCGUUUC CUGAUGAGGCCGUUAGGCCGAA IAUCCACA | 16029 |
| 2881 | AACGGCGC U UGGACAGC | 6690 | GCUGUCCA CUGAUGAGGCCGUUAGGCCGAA ICGCCGUU | 16030 |
| 2887 | GCUUGGAC A GCAUCACC | 6691 | GGUGAUGC CUGAUGAGGCCGUUAGGCCGAA IUCCAAGC | 16031 |
| 2890 | UGGACAGC A UCACCAGU | 6692 | ACUGGUGA CUGAUGAGGCCGUUAGGCCGAA ICUGUCCA | 16032 |
| 2893 | ACAGCAUC A CCAGUAGC | 6693 | GCUACUGG CUGAUGAGGCCGUUAGGCCGAA IAUGCUGU | 16033 |
| 2895 | AGCAUCAC C AGUAGCCA | 6694 | UGGCUACU CUGAUGAGGCCGUUAGGCCGAA IUGAUGCU | 16034 |
| 2896 | GCAUCACC A GUAGCCAG | 6695 | CUGGCUAC CUGAUGAGGCCGUUAGGCCGAA IGUGAUGC | 16035 |
| 2902 | CCAGUAGC C AGAGCUCA | 6696 | UGAGCUCU CUGAUGAGGCCGUUAGGCCGAA ICUACUGG | 16036 |
| 2903 | CAGUAGCC A GAGCUCAG | 6697 | CUGAGCUC CUGAUGAGGCCGUUAGGCCGAA IGCUACUG | 16037 |
| 2908 | GCCAGAGC U CAGCCAGC | 6698 | GCUGGCUG CUGAUGAGGCCGUUAGGCCGAA ICUCUGGC | 16038 |
| 2910 | CAGAGCUC A GCCAGCUC | 6699 | GAGCUGGC CUGAUGAGGCCGUUAGGCCGAA IAGCUCUG | 16039 |
| 2913 | AGCUCAGC C AGCUCUGG | 6700 | CCAGAGCU CUGAUGAGGCCGUUAGGCCGAA ICUGAGCU | 16040 |
| 2914 | GCUCAGCC A GCUCUGGA | 6701 | UCCAGAGO CUGAUGAGGCCGUUAGGCCGAA IGCUGAGC | 16041 |
| 2917 | CAGCCAGC U CUGGAUUU | 6702 | AAAUCCAG CUGAUGAGGCCGUUAGGCCGAA ICUGGCUG | 16042 |
| 2919 | GCCAGCUC U GGAUUUGU | 6703 | ACAAAUCC CUGAUGAGGCCGUUAGGCCGAA IAGCUGGC | 16043 |
| 2940 | GAGAAGUC C CUCAGUGA | 6704 | UCACUGAG CUGAUGAGGCCGUUAGGCCGAA IACUUCUC | 16044 |
| 2941 | AGAAGUCC C UCAGUGAU | 6705 | AUCACUGA CUGAUGAGGCCGUUAGGCCGAA IGACUUCU | 16045 |

TABLE XVI-continued

Human KDR NCH Ribozyme and Target Sequences

| Pos | Target | Seq ID No | Ribozyme Sequence | Seq ID No. |
|---|---|---|---|---|
| 2942 | GAAGUCCC U CAGUGAUG | 6706 | CAUCACUG CUGAUGAGGCCGUUAGGCCGAA IGGACUUC | 16046 |
| 2944 | AGUCCUC A GUGAUGUA | 6707 | UACAUCAC CUGAUGAGGCCGUUAGGCCGAA IAGGGACU | 16047 |
| 2967 | GAGGAAGC U CCUGAAGA | 6708 | UCUUCAGG CUGAUGAGGCCGUUAGGCCGAA ICUUCCUC | 16048 |
| 2969 | GGAAGCUC C UGAAGAUC | 6709 | GAUCUUCA CUGAUGAGGCCGUUAGGCCGAA IAGCUUCC | 16049 |
| 2970 | GAAGCUCC U GAAGAUCU | 6710 | AGAUCUUC CUGAUGAGGCCGUUAGGCCGAA IGAGCUUC | 16050 |
| 2978 | UGAAGAUC U GUAUAAGG | 6711 | CCUUAUAC CUGAUGAGGCCGUUAGGCCGAA IAUCUUCA | 16051 |
| 2989 | AUAAGGAC U UCCUGACC | 6712 | GGUCAGGA CUGAUGAGGCCGUUAGGCCGAA IUCCUUAU | 16052 |
| 2992 | AGGACUUC C UGACCUUG | 6713 | CAAGGUCA CUGAUGAGGCCGUUAGGCCGAA IAAGUCCU | 16053 |
| 2993 | GGACUUCC U GACCUUGG | 6714 | CCAAGGUC CUGAUGAGGCCGUUAGGCCGAA IGAAGUCC | 16054 |
| 2997 | UUCCUGAC C UUGGAGCA | 6715 | UGCUCCAA CUGAUGAGGCCGUUAGGCCGAA ICAGGAA | 16055 |
| 2998 | UCCUGACC U UGGAGCAU | 6716 | AUGCUCCA CUGAUGAGGCCGUUAGGCCGAA IGUCAGGA | 16056 |
| 3005 | CUUGGAGC A UCUCAUCU | 6717 | AGAUGAGA CUGAUGAGGCCGUUAGGCCGAA ICUCCAAG | 16057 |
| 3008 | GGAGCAUC U CAUCUGUU | 6718 | AACAGAUG CUGAUGAGGCCGUUAGGCCGAA IAUGCUCC | 16058 |
| 3010 | AGCAUCUC A UCUGUUAC | 6719 | GUAACAGA CUGAUGAGGCCGUUAGGCCGAA IAGAUGCU | 16059 |
| 3013 | AUCUCAUC U GUUACAGC | 6720 | GCUGUAAC CUGAUGAGGCCGUUAGGCCGAA IAUGAGAU | 16060 |
| 3029 | UCUGUUAC A GCUUCCAA | 6721 | UUGGAAGC CUGAUGAGGCCGUUAGGCCGAA IUAACAGA | 16061 |
| 3022 | GUUACAGC U UCCAAGUG | 6722 | CACUUGGA CUGAUGAGGCCGUUAGGCCGAA ICUGUAAC | 16062 |
| 3025 | ACAGCUUC C AAGUGGCU | 6723 | AGCCACUU CUGAUGAGGCCGUUAGGCCGAA IAAGCUGU | 16063 |
| 3026 | CAGCUUCC A AGUGGCUA | 6724 | UAGCCACU CUGAUGAGGCCGUUAGGCCGAA IGAAGCUG | 16064 |
| 3033 | CAAGUGGC U AAGGGCAU | 6725 | AUGCCCUU CUGAUGAGGCCGUUAGGCCGAA ICCACUUG | 16065 |
| 3040 | CUAAGGGC A UGGAGUUC | 6726 | GAACUCCA CUGAUGAGGCCGUUAGGCCGAA ICCCUUAG | 16066 |
| 3049 | UGGAGUUC U UGGCAUCG | 6727 | CGAUGCCA CUGAUGAGGCCGUUAGGCCGAA IAACUCCA | 16067 |
| 3054 | UUCUUGGC A UCGCGAAA | 6728 | UUUCGCGA CUGAUGAGGCCGUUAGGCCGAA ICCAAGAA | 16068 |
| 3070 | AGUGUAUC C ACAGGGAC | 6729 | GUCCCUGU CUGAUGAGGCCGUUAGGCCGAA IAUACACU | 16069 |
| 3071 | GUGUAUCC A CAGGGACC | 6730 | GGUCCCUG CUGAUGAGGCCGUUAGGCCGAA IGAUACAC | 16070 |
| 3073 | GUAUCCAC A GGGACCUG | 6731 | CAGGUCCC CUGAUGAGGCCGUUAGGCCGAA IUGGAUAC | 16071 |
| 3079 | ACAGGGAC C UGGCGGCA | 6732 | UGCCGCCA CUGAUGAGGCCGUUAGGCCGAA IUCCCUGU | 16072 |
| 3080 | CAGGGACC U GGCGGCAC | 6733 | GUGCCGCC CUGAUGAGGCCGUUAGGCCGAA IGUCCCUG | 16073 |
| 3087 | CUGGCGGC A CGAAAUAU | 6734 | AUAUUUCG CUGAUGAGGCCGUUAGGCCGAA ICCGCCAG | 16074 |
| 3097 | GAAAUAUC C UCUUAUCG | 6735 | CGAUAAGA CUGAUGAGGCCGUUAGGCCGAA IAUAUUUC | 16075 |
| 3098 | AAAUAUCC U CUUAUCGG | 6736 | CCGAUAAG CUGAUGAGGCCGUUAGGCCGAA IGAUAUUU | 16076 |
| 3100 | AUAUCCUC U UAUCGGAG | 6737 | CUCCGAUA CUGAUGAGGCCGUUAGGCCGAA IAGGAUAU | 16077 |
| 3127 | UUAAAAUC U GUGACUUU | 6738 | AAAGUCAC CUGAUGAGGCCGUUAGGCCGAA IAUUUUAA | 16078 |
| 3133 | UCUGUGAC U UUGGCUUG | 6739 | CAAGCCAA CUGAUGAGGCCGUUAGGCCGAA IUCACAGA | 16079 |
| 3139 | ACUUGGC U UGGCCCGG | 6740 | CCGGGCCA CUGAUGAGGCCGUUAGGCCGAA ICCAAAGU | 16080 |
| 3144 | GGCUUGGC C CGGAUAU | 6741 | AUAUCCCG CUGAUGAGGCCGUUAGGCCGAA ICCAAGCC | 16081 |
| 3145 | GCUUGGCC C GGAUAUU | 6742 | AAUAUCCC CUGAUGAGGCCGUUAGGCCGAA IGCCAAGC | 16082 |

TABLE XVI-continued

Human KDR NCH Ribozyme and Target Sequences

| Pos | Target | Seq ID No | Ribozyme Sequence | Seq ID No. |
|---|---|---|---|---|
| 3164 | UAAAGAUC C AGAUUAUG | 6743 | CAUAAUCU CUGAUGAGgccGUUAGGCCGAA IAUCUUUA | 16083 |
| 3165 | AAAGAUCC A GAUUAUGU | 6744 | ACAUAAUC CUGAUGAGgccGUUAGGCCGAA IGAUCUUU | 16084 |
| 3175 | AUUAUGUC A GAAAAGGA | 6745 | UCCUUUUC CUGAUGAGgccGUUAGGCCGAA IACAUAAU | 16085 |
| 3189 | GGAGAUGC U CGCCUCCC | 6746 | GGGAGGCG CUGAUGAGgccGUUAGGCCGAA ICAUCUCC | 16086 |
| 3293 | AUGCUCGC C UCCCUUUG | 6747 | CAAAGGGA CUGAUGAGgccGUUAGGCCGAA ICGAGCAU | 16087 |
| 3294 | UGCUCGCC U CCCUUUGA | 6748 | UCAAAGGG CUGAUGAGgccGUUAGGCCGAA IGCGAGCA | 16088 |
| 3296 | CUCGCCUC C CUUUGAAA | 6749 | UUUCAAAG CUGAUGAGgccGUUAGGCCGAA IAGGCGAG | 16089 |
| 3297 | UCGCCUCC C UUUGAAAU | 6750 | AUUUCAAA CUGAUGAGgccGUUAGGCCGAA IGAGGCGA | 16090 |
| 3298 | CGCCUCCC U UUGAAAUG | 6751 | CAUUUCAA CUGAUGAGgccGUUAGGCCGAA IGGAGGCG | 16091 |
| 3213 | UGGAUGGC C CCAGAAAC | 6752 | CUUUCUGG CUGAUGAGgccGUUAGGCCGAA ICCAUCCA | 16092 |
| 3214 | GGAUGGCC C CAGAAACA | 6753 | UGUUUCUG CUGAUGAGgccGUUAGGCCGAA IGCCAUCC | 16093 |
| 3215 | GAUGGCCC C AGAAACAA | 6754 | UUGUUUCU CUGAUGAGgccGUUAGGCCGAA IGGCCAUC | 16094 |
| 3216 | AUGGCCCC A GAAACAAU | 6755 | AUUGUUUC CUGAUGAGgccGUUAGGCCGAA IGCGCCAU | 16095 |
| 3222 | CCAGAAAC A AUUUUGA | 6756 | UCAAAAAU CUGAUGAGgccGUUAGGCCGAA IUUUCUGG | 16096 |
| 3232 | UUUUUGAC A GAGUGUAC | 6757 | GUACACUC CUGAUGAGgccGUUAGGCCGAA IUCAAAAA | 16097 |
| 3241 | GAGUGUAC A CAAUCCAG | 6758 | CUGGAUUG CUGAUGAGgccGUUAGGCCGAA IUACACUC | 16098 |
| 3243 | GUGUACAC A AUCCAGAG | 6759 | CUCUGGAU CUGAUGAGgccGUUAGGCCGAA IUGUACAC | 16099 |
| 3247 | ACACAAUC C AGAGUGAC | 6760 | GUCACUCU CUGAUGAGgccGUUAGGCCGAA IAUUGUGU | 16100 |
| 3248 | CACAAUCC A GAGUGACG | 6761 | CGUCACUC CUGAUGAGgccGUUAGGCCGAA IGAUUGUG | 16101 |
| 3259 | GUGACGUC U GGUCUUUU | 6762 | AAAAGACC CUGAUGAGgccGUUAGGCCGAA IACGUCAC | 16102 |
| 3264 | GUCUGGUC U UUUGGUGU | 6763 | ACACCAAA CUGAUGAGgccGUUAGGCCGAA IACCAGAC | 16103 |
| 3278 | UGUUUUGC U GUGGGAAA | 6764 | UUUCCCAC CUGAUGAGgccGUUAGGCCGAA ICAAAACA | 16104 |
| 3294 | AUAUUUUC C UUAGGUGC | 6765 | GCACCUAA CUGAUGAGgccGUUAGGCCGAA IAAAAUAU | 16105 |
| 3295 | UAUUUUCC U UAGGUGCU | 6766 | AGCACCUA CUGAUGAGgccGUUAGGCCGAA IGAAAAUA | 16106 |
| 3303 | UUAGGUGC U UCUCCAUA | 6767 | UAUGGAGA CUGAUGAGgccGUUAGGCCGAA ICACCUAA | 16107 |
| 3306 | GGUGCUUC U CCAUAUCC | 6768 | GGAUAUGG CUGAUGAGgccGUUAGGCCGAA IAAGCACC | 16108 |
| 3308 | UGCUUCUC C AUAUCCUG | 6769 | CAGGAUAU CUGAUGAGgccGUUAGGCCGAA IAGAAGCA | 16109 |
| 3309 | GCUUCUCC A UAUCCUGG | 6770 | CCAGGAUA CUGAUGAGgccGUUAGGCCGAA IGAGAAGC | 16110 |
| 3314 | UCCAUAUC C UGGGUAA | 6771 | UUACCCCA CUGAUGAGgccGUUAGGCCGAA IAUAUGGA | 16111 |
| 3315 | CCAUAUCC U GGGUAAA | 6772 | UUUACCCC CUGAUGAGgccGUUAGGCCGAA IGAUAUGG | 16112 |
| 3363 | GAAGGAAC U AGAAUGAG | 6773 | CUCAUUCU CUGAUGAGgccGUUAGGCCGAA IUUCCUUC | 16113 |
| 3375 | AUGAGGGC C CCUGAUUA | 6774 | UAAUCAGG CUGAUGAGgccGUUAGGCCGAA ICCCUCAU | 16114 |
| 3376 | UGAGGGCC C CUGAUUAU | 6775 | AUAAUCAG CUGAUGAGgccGUUAGGCCGAA IGCCCUCA | 16115 |
| 3377 | GAGGGCCC C UGAUUAUA | 6776 | UAUAAUCA CUGAUGAGgccGUUAGGCCGAA IGGCCCUC | 16116 |
| 3378 | AGGGCCCC U GAUUAUAC | 6777 | GUAUAAUC CUGAUGAGgccGUUAGGCCGAA IGGGCCCU | 16117 |
| 3387 | GAUUAUAC U ACACCAGA | 6778 | UCUGGUGU CUGAUGAGgccGUUAGGCCGAA IUAUAAUC | 16118 |
| 3390 | UAUACUAC A CCAGAAAU | 6779 | AUUUCUGG CUGAUGAGgccGUUAGGCCGAA IUAGUAUA | 16119 |

TABLE XVI-continued

Human KDR NCH Ribozyme and Target Sequences

| Pos | Target | Seq ID No | Ribozyme Sequence | Seq ID No. |
|---|---|---|---|---|
| 3392 | UACUACAC C AGAAAUGU | 6780 | ACAUUUCU CUGAUGAGGCCGUUAGGCCGAA IUGUAGUA | 16120 |
| 3393 | ACUACACC A GAAAUGUA | 6781 | UACAUUUC CUGAUGAGGCCGUUAGGCCGAA IGUGUAGU | 16121 |
| 3403 | AAAUGUAC C AGACCAUG | 6782 | CAUGGUCU CUGAUGAGGCCGUUAGGCCGAA IUACAUUU | 16122 |
| 3404 | AAUGUACC A GACCAUGC | 6783 | GCAUGGUC CUGAUGAGGCCGUUAGGCCGAA IGUACAUU | 16123 |
| 3408 | UACCAGAC C AUGCUGGA | 6784 | UCCAGCAU CUGAUGAGGCCGUUAGGCCGAA IUCUGGUA | 16124 |
| 3409 | ACCAGACC A UGCUGGAC | 6785 | GUCCAGCA CUGAUGAGGCCGUUAGGCCGAA IGUCUGGU | 16125 |
| 3413 | GACCAUGC U GGACUGCU | 6786 | AGCAGUCC CUGAUGAGGCCGUUAGGCCGAA ICAUGGUC | 16126 |
| 3418 | UGCUGGAC U GCUGGCAC | 4886 | GUGCCAGC CUGAUGAGGCCGUUAGGCCGAA IUCCAGCA | 14226 |
| 3421 | UGGACUGC U GGCACGGG | 6787 | CCCGUGCC CUGAUGAGGCCGUUAGGCCGAA ICAGUCCA | 16127 |
| 3425 | CUGCUGGC A CGGGGAGC | 6788 | GCUCCCCG CUGAUGAGGCCGUUAGGCCGAA ICCAGCAG | 16128 |
| 3434 | CGGGGAGC C CAGUCAGA | 6789 | UCUGACUG CUGAUGAGGCCGUUAGGCCGAA ICUCCCCG | 16129 |
| 3435 | GGGGAGCC C AGUCAGAG | 6790 | CUCUGACU CUGAUGAGGCCGUUAGGCCGAA IGCUCCCC | 16130 |
| 3436 | GGGAGCCC A GUCAGAGA | 6791 | UCUCUGAC CUGAUGAGGCCGUUAGGCCGAA IGGCUCCC | 16131 |
| 3440 | GCCCAGUC A GAGACCCA | 6792 | UGGGUCUC CUGAUGAGGCCGUUAGGCCGAA IACUGGGC | 16132 |
| 3446 | UCAGAGAC C CACGUUUU | 6793 | AAAACGUG CUGAUGAGGCCGUUAGGCCGAA IUCUCUGA | 16133 |
| 3447 | CAGAGACC C ACGUUUUC | 6794 | GAAAACGU CUGAUGAGGCCGUUAGGCCGAA IGUCUCUG | 16134 |
| 3448 | AGAGACCC A CGUUUUCA | 6795 | UGAAAACG CUGAUGAGGCCGUUAGGCCGAA IGGUCUCU | 16135 |
| 3456 | ACGUUUUC A GAGUUGGU | 6796 | ACCAACUC CUGAUGAGGCCGUUAGGCCGAA IAAAACGU | 16136 |
| 3470 | GGUGGAAC A UUUGGGAA | 6797 | UUCCCAAA CUGAUGAGGCCGUUAGGCCGAA IUUCCACC | 16137 |
| 3482 | GGGAAAUC U CUUGCAAG | 6798 | CUUGCAAG CUGAUGAGGCCGUUAGGCCGAA IAUUUCCC | 16138 |
| 3484 | GAAAUCUC U UGCAAGCU | 6799 | AGCUUGCA CUGAUGAGGCCGUUAGGCCGAA IAGAUUUC | 16139 |
| 3488 | UCUCUUGC A AGCUAAUG | 6800 | CAUUAGCU CUGAUGAGGCCGUUAGGCCGAA ICAAGAGA | 16140 |
| 3492 | UUGCAAGC U AAUGCUCA | 6801 | UGAGCAUU CUGAUGAGGCCGUUAGGCCGAA ICUUGCAA | 16141 |
| 3498 | GCUAAUGC U CAGCAGGA | 6802 | UCCUGCUG CUGAUGAGGCCGUUAGGCCGAA ICAUUAGC | 16142 |
| 3500 | UAAUGCUC A GCAGGAUG | 6803 | CAUCCUGC CUGAUGAGGCCGUUAGGCCGAA IAGCAUUA | 16143 |
| 3503 | UGCUCAGC A GGAUGGCA | 6804 | UGCCAUCC CUGAUGAGGCCGUUAGGCCGAA ICUGAGCA | 16144 |
| 3511 | AGGAUGGC A AAGACUAC | 6805 | GUAGUCUU CUGAUGAGGCCGUUAGGCCGAA ICCAUCCU | 16145 |
| 3517 | GCAAAGAC U ACAUUGUU | 6806 | AACAAUGU CUGAUGAGGCCGUUAGGCCGAA IUCUUUGC | 16146 |
| 3520 | AAGACUAC A UUGUUCUU | 6807 | AAGAACAA CUGAUGAGGCCGUUAGGCCGAA IUAGUCUU | 16147 |
| 3527 | CAUUGUUC U UCCGAUAU | 6808 | AUAUCGGA CUGAUGAGGCCGUUAGGCCGAA IAACAAUG | 16148 |
| 3530 | UGUUCUUC C GAUAUCAG | 6809 | CUGAUAUC CUGAUGAGGCCGUUAGGCCGAA IAAGAACA | 16149 |
| 3537 | CCGAUAUC A GAGACUUU | 6810 | AAAGUCUC CUGAUGAGGCCGUUAGGCCGAA IAUAUCGG | 16150 |
| 3543 | UCAGAGAC U UUGAGCAU | 6811 | AUGCUCAA CUGAUGAGGCCGUUAGGCCGAA IUCUCUGA | 16151 |
| 3550 | CUUUGAGC A UGGAAGAG | 6812 | CUCUUCCA CUGAUGAGGCCGUUAGGCCGAA ICUCAAAG | 16152 |
| 3564 | GAGGAUUC U GUACUCUC | 6813 | GAGAGUCC CUGAUGAGGCCGUUAGGCCGAA IAAUCCUC | 16153 |
| 3569 | UUCUGGAC U CUCUCUGC | 6814 | GCAGAGAG CUGAUGAGGCCGUUAGGCCGAA IUCCAGAA | 16154 |
| 3571 | CUGGACUC U CUCUGCCU | 6815 | AGGCAGAG CUGAUGAGGCCGUUAGGCCGAA IAGUCCAG | 16155 |

TABLE XVI-continued

Human KDR NCH Ribozyme and Target Sequences

| Pos | Target | Seq ID No | Ribozyme Sequence | Seq ID No. |
|---|---|---|---|---|
| 3573 | GGACUCUC U CUGCCUAC | 6816 | GUAGGCAG CUGAUGAGGCCGUUAGGCCGAA IAGAGUCC | 16156 |
| 3575 | ACUCUCUC U GCCUACCU | 6817 | AGGUAGGC CUGAUGAGGCCGUUAGGCCGAA IAGAGAGU | 16157 |
| 3578 | CUCUCUGC C UACCUCAC | 6818 | GUGAGGUA CUGAUGAGGCCGUUAGGCCGAA ICAGAGAG | 16158 |
| 3579 | UCUCUGCC U ACCUCACC | 6819 | GGUGAGGU CUGAUGAGGCCGUUAGGCCGAA IGCAGAGA | 16159 |
| 3582 | CUGCCUAC C UCACCUGU | 6820 | ACAGGUGA CUGAUGAGGCCGUUAGGCCGAA IUAGGCAG | 16160 |
| 3583 | UGCCUACC U CACCUGUU | 6821 | AACAGGUG CUGAUGAGGCCGUUAGGCCGAA IGUAGGCA | 16161 |
| 3585 | CCUACCUC A CCUGUUUC | 6822 | GAAACAGG CUGAUGAGGCCGUUAGGCCGAA IAGGUAGG | 16162 |
| 3587 | UACCUCAC C UGUUUCCU | 6823 | AGGAAACA CUGAUGAGGCCGUUAGGCCGAA IUGAGGUA | 16163 |
| 3588 | ACCUCACC U GUUUCCUG | 6824 | CAGGAAAC CUGAUGAGGCCGUUAGGCCGAA IGUGAGGU | 16164 |
| 3594 | CCUGUiUC C UGUAUGGA | 6825 | UCCAUACA CUGAUGAGGCCGUUAGGCCGAA IAAACAGG | 16165 |
| 3595 | CUGUUUCC U GUAUGGAG | 6826 | CUCCAUAC CUGAUGAGGCCGUUAGGCCGAA IGAAACAG | 16166 |
| 3622 | UAUGUGAC C CCAAAUUC | 6827 | GAAUUUGG CUGAUGAGGCCGUUAGGCCGAA IUCACAUA | 16167 |
| 3623 | AUGUGACC C CAAAUUCC | 6828 | GGAAUUUG CUGAUGAGGCCGUUAGGCCGAA IGUCACAU | 16168 |
| 3624 | UGUGACCC C AAAUUCCA | 6829 | UGGAAUUU CUGAUGAGGCCGUUAGGCCGAA IGGUCACA | 16169 |
| 3625 | GUGACCCC A AAUUCCAU | 6830 | AUGGAAUU CUGAUGAGGCCGUUAGGCCGAA IGGGUCAC | 16170 |
| 3631 | CCAAAUUC C AUUAUGAC | 6831 | GUCAUAAU CUGAUGAGGCCGUUAGGCCGAA IAAUUUGG | 16171 |
| 3632 | CAAAUUCC A UUAUGACA | 6832 | UGUCAUAA CUGAUGAGGCCGUUAGGCCGAA IGAAUUUG | 16172 |
| 3640 | AUUAUGAC A ACACAGCA | 6833 | UGCUGUGU CUGAUGAGGCCGUUAGGCCGAA IUCAUAAU | 16173 |
| 3643 | AUGACAAC A CAGCAGGA | 6834 | UCCUGCUG CUGAUGAGGCCGUUAGGCCGAA IUUGUCAU | 16174 |
| 3645 | GACAACAC A GCAGGAAU | 6835 | AUUCCUGC CUGAUGAGGCCGUUAGGCCGAA IGUUGUC | 16175 |
| 3648 | AACACAGC A GGAAUCAG | 6836 | CUGAUUCC CUGAUGAGGCCGUUAGGCCGAA ICUGUGUU | 16176 |
| 3655 | CAGGAAUC A GUCAGUAU | 6837 | AUACUGAC CUGAUGAGGCCGUUAGGCCGAA IAUUCCUG | 16177 |
| 3659 | AAUCAGUC A GUAUCUGC | 6838 | GCAGAUAC CUGAUGAGGCCGUUAGGCCGAA IACUGAUU | 16178 |
| 3665 | UCAGUAUC U GCAGAACA | 6839 | UGUUCUGC CUGAUGAGGCCGUUAGGCCGAA IAUACUGA | 16179 |
| 3668 | GUAUCUGC A GAACAGUA | 6840 | UACUGUUC CUGAUGAGGCCGUUAGGCCGAA ICAGAUAC | 16180 |
| 3673 | UGCAGAAC A GUAAGCGA | 6841 | UCGCUUAC CUGAUGAGGCCGUUAGGCCGAA IUUCUGCA | 16181 |
| 3688 | GAAAGAGC C GGCCUGUG | 6842 | CACAGGCC CUGAUGAGGCCGUUAGGCCGAA ICUCUUUC | 16182 |
| 3692 | GAGCCGGC C UGUGAGUG | 6843 | CACUCACA CUGAUGAGGCCGUUAGGCCGAA ICCGGCUC | 16183 |
| 3693 | AGCCGGCC U GUGAGUGU | 6844 | ACACUCAC CUGAUGAGGCCGUUAGGCCGAA IGCCGGCU | 16184 |
| 3708 | GUAAAAAC A UUUGAAGA | 6845 | UCUUCAAA CUGAUGAGGCCGUUAGGCCGAA IUUUUUAC | 16185 |
| 3721 | AAGAUAUC C CCUUAGAA | 6846 | UUCUAACG CUGAUGAGGCCGUUAGGCCGAA IAUAUCUU | 16186 |
| 3722 | AGAUAUCC C GUUAGAAG | 6847 | CUUCUAAC CUGAUGAGGCCGUUAGGCCGAA IGAUAUCU | 16187 |
| 3734 | AGAAGAAC C AGAAGUAA | 6848 | UUACUUCU CUGAUGAGGCCGUUAGGCCGAA IUUCUUCU | 16188 |
| 3735 | GAAGAACC A GAAGUAAA | 6849 | UUUACUUC CUGAUGAGGCCGUUAGGCCGAA IGUUCUUC | 16189 |
| 3751 | AAGUAAUC C CAGAUGAC | 6850 | GUCAUCUG CUGAUGAGGCCGUUAGGCCGAA IAUUACUU | 16190 |
| 3752 | AGUAAUCC C AGAUGACA | 6851 | UGUCAUCU CUGAUGAGGCCGUUAGGCCGAA IGAUUACU | 16191 |
| 3753 | GUAAUCCC A GAUGACAA | 6852 | UUGUCAUC CUGAUGAGGCCGUUAGGCCGAA IGGAUUAC | 16192 |

TABLE XVI-continued

Human KDR NCH Ribozyme and Target Sequences

| Pos | Target | Seq ID No | Ribozyme Sequence | Seq ID No. |
|---|---|---|---|---|
| 3760 | CAGAUGAC A ACCAGACG | 6853 | CGUCUGGU CUGAUGAGGCCGUUAGGCCGAA IUCAUCUG | 16193 |
| 3763 | AUGACAAC C AGACGGAC | 6854 | GUCCGUCU CUGAUGAGGCCGUUAGGCCGAA IUUGUCAU | 16194 |
| 3764 | UGACAACC A GACGGACA | 6855 | UGUCCGUC CUGAUGAGGCCGUUAGGCCGAA IGUUGUCA | 16195 |
| 3772 | AGACGGAC A GUGGUAUG | 6856 | CAUACCAC CUGAUGAGGCCGUUAGGCCGAA IUCCGUCU | 16196 |
| 3785 | UAUGGUUC U UGCCUCAG | 6857 | CUGAGGCA CUGAUGAGGCCGUUAGGCCGAA IAACCAUA | 16197 |
| 3789 | GUUCUUGC C UCAGAAGA | 6858 | UCUUCUGA CUGAUGAGGCCGUUAGGCCGAA ICAAGAAC | 16198 |
| 3790 | UUCUUGCC U CAGAAGAG | 6859 | CUCCUCUG CUGAUGAGGCCGUUAGGCCGAA IGCAAGAA | 16199 |
| 3792 | CUUGCCUC A GAAGAGCU | 6860 | AGCUCUUC CUGAUGAGGCCGUUAGGCCGAA IAGGCAAG | 16200 |
| 3800 | AGAAGAGC U GAAAACUU | 6861 | AAGUUUUC CUGAUGAGGCCGUUAGGCCGAA ICUCUUCU | 16201 |
| 3807 | CUGAAAAC U UUGGAAGA | 6862 | UCUUCCAA CUGAUGAGGCCGUUAGGCCGAA IUUUUCAG | 16202 |
| 3817 | UGGAAGAC A GAACCAAA | 6863 | UUUGGUUC CUGAUGAGGCCGUUAGGCCGAA IUCUUCCA | 16203 |
| 3822 | GACAGAAC C AAAUUAUC | 6864 | GAUAAUUU CUGAUGAGGCCGUUAGGCCGAA IUUCUGUC | 16204 |
| 3823 | ACAGAACC A AAUUAUCU | 6865 | AGAUAAUU CUGAUGAGGCCGUUAGGCCGAA IGUUCUGU | 16205 |
| 3831 | AAAUUAUC U CCAUCUUU | 6866 | AAAGAUGG CUGAUGAGGCCGUUAGGCCGAA IAUAAUUU | 16206 |
| 3833 | AUUAUCUC C AUCUUUUG | 6867 | CAAAAGAU CUGAUGAGGCCGUUAGGCCGAA IAGAUAAU | 16207 |
| 3834 | UUAUCUCC A UCUUUUGG | 6868 | CCAAAAGA CUGAUGAGGCCGUUAGGCCGAA IGAGAUAA | 16208 |
| 3837 | UCUCCAUC U UUUGGUGG | 6869 | CCACCAAA CUGAUGAGGCCGUUAGGCCGAA IAUGGAGA | 16209 |
| 3854 | AAUGGUGC C CAGCAAAA | 6870 | UUUUGCUG CUGAUGAGGCCGUUAGGCCGAA ICACCAUU | 16210 |
| 3855 | AUGGUGCC C AGCAAAAG | 6871 | CUUUUGCU CUGAUGAGGCCGUUAGGCCGAA IGCACCAU | 16211 |
| 3856 | UGGUGCCC A GCAAAAGC | 6872 | GCUUUUGC CUGAUGAGGCCGUUAGGCCGAA IGGCACCA | 16212 |
| 3859 | UGCCCAGC A AAAGCAGG | 6873 | CCUGCUUU CUGAUGAGGCCGUUAGGCCGAA ICUGGGCA | 16213 |
| 3865 | GCAAAAGC A GGGAGUCU | 6874 | AGACUCCC CUGAUGAGGCCGUUAGGCCGAA ICU(UUGC | 16214 |
| 3873 | AGGGAGUC U GUGGCAUC | 6875 | GAUGCCAC CUGAUGAGGCCGUUAGGCCGAA IACUCCCU | 16215 |
| 3879 | UCUGUGGC A UCUGAAGG | 6876 | CCUUCAGA CUGAUGAGGCCGUUAGGCCGAA ICCACAGA | 16216 |
| 3882 | GUGGCAUC U GAAGGCUC | 6877 | GAGCCUUC CUGAUGAGGCCGUUAGGCCGAA IAUGCCAC | 16217 |
| 3889 | CUGAAGGC U CAAACCAG | 6878 | CUGGUUUG CUGAUGAGGCCGUUAGGCCGAA ICCUUCAG | 16218 |
| 3891 | GAAGGCUC A AACCAGAC | 6879 | GUCUGGUU CUGAUGAGGCCGUUAGGCCGAA IAGCCUUC | 16219 |
| 3895 | GCUCAAAC C AGACAAGC | 6880 | GCUUGUCU CUGAUGAGGCCGUUAGGCCGAA IUUUGAGC | 16220 |
| 3896 | CUCAAACC A GACAAGCG | 6881 | CGCUUGUC CUGAUGAGGCCGUUAGGCCGAA IGUUUGAG | 16221 |
| 3900 | AACCAGAC A AGCGGCUA | 6882 | UAGCCGCU CUGAUGAGGCCGUUAGGCCGAA IUCUGGUU | 16222 |
| 3907 | CAAGCGGC U ACCAGUCC | 6883 | GGACUGGU CUGAUGAGGCCGUUAGGCCGAA ICCGCUUG | 16223 |
| 3910 | GCGGCUAC C AGUCCGGA | 6884 | UCCGGACU CUGAUGAGGCCGUUAGGCCGAA IUAGCCGC | 16224 |
| 3911 | CGGCUACC A GUCCGGAU | 6885 | AUCCGGAC CUGAUGAGGCCGUUAGGCCGAA IGUAGCCG | 16225 |
| 3915 | UACCAGUC C GGAUAUCA | 6886 | UGAUAUCC CUGAUGAGGCCGUUAGGCCGAA IACUGGUA | 16226 |
| 3923 | CGGAUAUC A CUCCGAUG | 6887 | CAUCGGAG CUGAUGAGGCCGUUAGGCCGAA IAUAUCCG | 16227 |
| 3925 | GAUAUCAC U CCGAUGAC | 6888 | GUCAUCGG CUGAUGAGGCCGUUAGGCCGAA IUGAUAUC | 16228 |
| 3927 | UAUCACUC C GAUGACAC | 6889 | GUGUCAUC CUGAUGAGGCCGUUAGGCCGAA IAGUGAUA | 16229 |

TABLE XVI-continued

Human KDR NCH Ribozyme and Target Sequences

| Pos | Target | Seq ID No | Ribozyme Sequence | Seq ID No. |
|---|---|---|---|---|
| 3934 | CCGAUGAC A CAGACACC | 6890 | GGUGUCUG CUGAUGAGGCCGUUAGGCCGAA IUCAUCGG | 16230 |
| 3936 | GAUGACAC A GACACCAC | 6891 | GUGGUGUC CUGAUGAGGCCGUUAGGCCGAA IUGUCAUC | 16231 |
| 3940 | ACACAGAC A CCACCGUG | 6892 | CACGGUGG CUGAUGAGGCCGUUAGGCCGAA IUCUGUGU | 16232 |
| 3942 | ACAGACAC C ACCGUGUA | 6893 | UACACGGU CUGAUGAGGCCGUUAGGCCGAA IUGUCUGU | 16233 |
| 3943 | CAGACACC A CCGUGUAC | 6894 | GUACACGG CUGAUGAGGCCGUUAGGCCGAA IGUGUCUG | 16234 |
| 3945 | GACACCAC C GUGUACUC | 6895 | GAGUACAC CUGAUGAGGCCGUUAGGCCGAA IUGGUGUC | 16235 |
| 3952 | CCGUGUAC U CCAGUGAG | 6896 | CUCACUGG CUGAUGAGGCCGUUAGGCCGAA IUACACGG | 16236 |
| 3954 | GUGUACUC C AGUGAGGA | 6897 | UCCUCACU CUGAUGAGGCCGUUAGGCCGAA IAGUACAC | 16237 |
| 3955 | UGUACUCC A GUGAGGAA | 6898 | UUCCUCAC CUGAUGAGGCCGUUAGGCCGAA IGAGUACA | 16238 |
| 3966 | GAGGAAGC A GAACUUUU | 6899 | AAAAGUUC CUGAUGAGGCCGUUAGGCCGAA ICUUCCUC | 16239 |
| 3971 | AGCAGAAC U UUUAAAGC | 6900 | GCUUUAAA CUGAUGAGGCCGUUAGGCCGAA IUUCUGCU | 16240 |
| 3980 | UUUAAAGC U GAUAGAGA | 6901 | UCUCUAUC CUGAUGAGGCCGUUAGGCCGAA ICUUUAAA | 16241 |
| 3998 | UGGAGUGC A AACCGGUA | 6902 | UACCGGUU CUGAUGAGGCCGUUAGGCCGAA ICACUCCA | 16242 |
| 4002 | GUGCAAAC C GGUAGCAC | 6903 | GUGCUACC CUGAUGAGGCCGUUAGGCCGAA IUUUGCAC | 16243 |
| 4009 | CCGGUAGC A CAGCCCAG | 6904 | CUGGGCUG CUGAUGAGGCCGUUAGGCCGAA ICUACCGG | 16244 |
| 4011 | GGUAGCAC A GCCCAGAU | 6905 | AUCUGGGC CUGAUGAGGCCGUUAGGCCGAA IUGCUACC | 16245 |
| 4014 | AGCACAGC C CAGAUUCU | 6906 | AGAAUCUG CUGAUGAGGCCGUUAGGCCGAA ICUGUGCU | 16246 |
| 4015 | GCACAGCC C AGAUUCUC | 6907 | GAGAAUCU CUGAUGAGGCCGUUAGGCCGAA IGCUGUGC | 16247 |
| 4016 | CACAGCCC A GAUUCUCC | 6908 | GGAGAAUC CUGAUGAGGCCGUUAGGCCGAA IGGCUGUG | 16248 |
| 4022 | CCAGAUUC U CCAGCCUG | 6909 | CAGGCUGG CUGAUGAGGCCGUUAGGCCGAA IAAUCUGG | 16249 |
| 4024 | AGAUUCUC C AGCCUGAC | 6910 | GUCAGGCU CUGAUGAGGCCGUUAGGCCGAA IAGAAUCU | 16250 |
| 4025 | GAUUCUCC A GCCUGACA | 6911 | UGUCAGGC CUGAUGAGGCCGUUAGGCCGAA IGAGAAUC | 16251 |
| 4028 | UCUCCAGC C UGACACGG | 6912 | CCGUGUCA CUGAUGAGGCCGUUAGGCCGAA ICUGGAGA | 16252 |
| 4029 | CUCCAGCC U GACACGGG | 6913 | CCCGUGUC CUGAUGAGGCCGUUAGGCCGAA IGCUGGAG | 16253 |
| 4033 | AGCCUGAC A CGGGACC | 6914 | GGUCCCCG CUGAUGAGGCCGUUAGGCCGAA IUCAGGCU | 16254 |
| 4041 | ACGGGAC C ACACUGAG | 6915 | CUCAGUGU CUGAUGAGGCCGUUAGGCCGAA IUCCCCGU | 16255 |
| 4042 | CGGGGACC A CACUGAGC | 6916 | GCUCAGUG CUGAUGAGGCCGUUAGGCCGAA IGUCCCCG | 16256 |
| 4044 | GGGACCAC A CUGAGCUC | 6917 | GAGCUCAG CUGAUGAGGCCGUUAGGCCGAA IUGGUCCC | 16257 |
| 4046 | GACCACAC U GAGCUCUC | 6918 | GAGAGCUC CUGAUGAGGCCGUUAGGCCGAA IUGUGGUC | 16258 |
| 4051 | CACUGAGC U CUCCUCCU | 6919 | AGGAGGAG CUGAUGAGGCCGUUAGGCCGAA ICUCAGUG | 16259 |
| 4053 | CUGAGCUC U CCUCCUGU | 6920 | ACAGGAGG CUGAUGAGGCCGUUAGGCCGAA IAGCUCAG | 16260 |
| 4055 | GAGCUCUC C UCCUGUUU | 6921 | AAACAGGA CUGAUGAGGCCGUUAGGCCGAA IAGAGCUC | 16261 |
| 4056 | AGCUCUCC U CCUGUUUA | 6922 | UAAACAGG CUGAUGAGGCCGUUAGGCCGAA IGAGAGCU | 16262 |
| 4058 | CUCUCCUC C UGUUUAAA | 6923 | UUUAAACA CUGAUGAGGCCGUUAGGCCGAA IAGGAGAG | 16263 |
| 4059 | UCUCCCUC U GUUUAAAA | 6924 | UUUUAAAC CUGAUGAGGCCGUUAGGCCGAA IGAGGAGA | 16264 |
| 4074 | AAGGAAGC A UCCACACC | 6925 | GGUGUGGA CUGAUGAGGCCGUUAGGCCGAA ICUUCCUU | 16265 |
| 4077 | GAAGCAUC C ACACCCCA | 6926 | UGGGGUGU CUGAUGAGGCCGUUAGGCCGAA IAUGCUUC | 16266 |

TABLE XVI-continued

Human KDR NCH Ribozyme and Target Sequences

| Pos | Target | Seq ID No | Ribozyme Sequence | Seq ID No. |
|---|---|---|---|---|
| 4078 | AAGCAUCC A CACCCCAA | 6927 | UUGGGGUG CUGAUGAG<u>GCCGUUAGGC</u>CGAA IGAUGCUU | 16267 |
| 4080 | GCAUCCAC A CCCCAACU | 6928 | AGUUGGGG CUGAUGAG<u>GCCGUUAGGC</u>CGAA IUGGAUGC | 16268 |
| 4082 | AUCCACAC C CCAACUCC | 6929 | GGAGUUGG CUGAUGAG<u>GCCGUUAGGC</u>CGAA IUGUGGAU | 16269 |
| 4083 | UCCACACC C CAACUCCC | 6930 | GGGAGUUG CUGAUGAG<u>GCCGUUAGGC</u>CGAA IGUGUGGA | 16270 |
| 4084 | CCACACCC C AACUCCCG | 6931 | CGGGAGUU CUGAUGAG<u>GCCGUUAGGC</u>CGAA IGGUGUGG | 16271 |
| 4085 | CACACCCC A CUCCCGG | 6932 | CCGGGAGU CUGAUGAG<u>GCCGUUAGGC</u>CGAA IGGGUGUG | 16272 |
| 4088 | ACCCCAAC U CCCGGACA | 6933 | UGUCCGGG CUGAUGAG<u>GCCGUUAGGC</u>CGAA IUUGGGGU | 16273 |
| 4090 | CCCAACUC C CCGACAUC | 6934 | GAUGUCCG CUGAUGAG<u>GCCGUUAGGC</u>CGAA IAGUUGGG | 16274 |
| 4091 | CCAACUCC C GGACAUCA | 6935 | UGAUGUCC CUGAUGAG<u>GCCGUUAGGC</u>CGAA IGAGUUGG | 16275 |
| 4096 | UCCCGGAC A UCACAUGA | 6936 | UCAUGUGA CUGAUGAG<u>GCCGUUAGGC</u>CGAA IUCCGGGA | 16276 |
| 4099 | CGGACAUC A CAUGAGAG | 6937 | CUCUCAUG CUGAUGAG<u>GCCGUUAGGC</u>CGAA IAUGUCCG | 16277 |
| 4101 | GACAUCAC A UGAGAGGU | 6938 | ACCUCUCA CUGAUGAG<u>GCCGUUAGGC</u>CGAA IUGAUGUC | 16278 |
| 4111 | GAGAGGUC U GCUCAGAU | 6939 | AUCUGAGC CUGAUGAG<u>GCCGUUAGGC</u>CGAA IACCUCUC | 16279 |
| 4114 | AGGUCUGC U CAGAUUUU | 6940 | AAAAUCUG CUGAUGAG<u>GCCGUUAGGC</u>CGAA ICAGACCU | 16280 |
| 4116 | GUCUGCUC A GAUUUGA | 6941 | UCAAAAUC CUGAUGAG<u>GCCGUUAGGC</u>CGAA IAGCAGAC | 16281 |
| 4135 | UGUUGUUC U UUCCACCA | 6942 | UGGUGGAA CUGAUGAG<u>GCCGUUAGGC</u>CGAA IACAACA | 16282 |
| 4139 | GUUCUUUC C ACCAGCAG | 6943 | CUGCUGGU CUGAUGAG<u>GCCGUUAGGC</u>CGAA IAAAGAAC | 16283 |
| 4140 | UUCUUUCC A CCAGCAGG | 6944 | CCUGCUGG CUGAUGAG<u>GCCGUUAGGC</u>CGAA IGAAAGAA | 16284 |
| 4142 | CUUUCCAC C AGCAGGAA | 6945 | UUCCUGCU CUGAUGAG<u>GCCGUUAGGC</u>CGAA IUGGAAAG | 16285 |
| 4143 | UUUCCACC A GCAGGAAG | 6946 | CUUCCUGC CUGAUGAG<u>GCCGUUAGGC</u>CGAA IGUGGAAA | 16286 |
| 4146 | CCACCAGC A GGAAGUAG | 6947 | CUACUUCC CUGAUGAG<u>GCCGUUAGGC</u>CGAA ICUGGUGG | 16287 |
| 4156 | GAAGUAGC C CAUUUGA | 6948 | UCAAAUGC CUGAUGAG<u>GCCGUUAGGC</u>CGAA ICUACUUC | 16288 |
| 4159 | GUAGCCGC A UUUGAUUU | 6949 | AAAUCAAA CUGAUGAG<u>GCCGUUAGGC</u>CGAA ICGGCUAC | 16289 |
| 4170 | UGAUUUUC A UUCGACA | 6950 | UGUCGAAA CUGAUGAG<u>GCCGUUAGGC</u>CGAA IAAAAUCA | 16290 |
| 4178 | AUUUCGAC A ACAGAAAA | 6951 | UUUUCUGU CUGAUGAG<u>GCCGUUAGGC</u>CGAA IUCGAAAU | 16291 |
| 4181 | UCGACAAC A GAAAAGG | 6952 | CCUUUUUC CUGAUGAG<u>GCCGUUAGGC</u>CGAA IUUGUCGA | 16292 |
| 4192 | AAAAGGAC C UCGGACUG | 6953 | CAGUCCGA CUGAUGAG<u>GCCGUUAGGC</u>CGAA IUCCUUUU | 16293 |
| 4193 | AAAGGACC U CGGACUGC | 6954 | GCAGUCCG CUGAUGAG<u>GCCGUUAGGC</u>CGAA IGUCCUUU | 16294 |
| 4199 | CCUCGGAC U GCAGGGAG | 6955 | CUCCCUGC CUGAUGAG<u>GCCGUUAGGC</u>CGAA IUCCGAGG | 16295 |
| 4202 | CGGACUGC A GGGAGCCA | 6956 | UGGCUCCC CUGAUGAG<u>GCCGUUAGGC</u>CGAA ICAGUCCG | 16296 |
| 4209 | CAGGGAGC C AGCUCUUC | 6957 | GAAGAGCU CUGAUGAG<u>GCCGUUAGGC</u>CGAA ICUCCCUG | 16297 |
| 4210 | AGGGAGCC A GCUCUUCU | 6958 | AGAAGAGC CUGAUGAG<u>GCCGUUAGGC</u>CGAA IGCUCCCU | 16298 |
| 4213 | GAGCCAGC U CUUCUAGG | 6959 | CCUAGAAG CUGAUGAG<u>GCCGUUAGGC</u>CGAA ICUGGCUC | 16299 |
| 4215 | GCCAGCUC U UCUAGGCU | 6960 | AGCCUAGA CUGAUGAG<u>GCCGUUAGGC</u>CGAA IAGCUGGC | 16300 |
| 4218 | AGCUCUUC U AGGCUUGU | 6961 | ACAAGCCU CUGAUGAG<u>GCCGUUAGGC</u>CGAA IAAGAGCU | 16301 |

Core Sequence = CUGAUGAG <u>GCCGUUAGGC</u> CGAA (SEQ ID NO. 20827).
Underlined region can be any X sequence or linker, as described herein.
"I" represents Inosine

TABLE XVII

KDR G-Cleaver Ribozyme and Target Sequences

| Pos | Target | Seq ID No | Ribozyme Sequence | Seq ID No |
|---|---|---|---|---|
| 12 | GCAAGGUGCU G CUGGC | 6962 | GCCAG UGAUG GCAUGCACUAUGC GCG AGCACCUUGC | 16302 |
| 22 | GCUGGCCGUC G CCCUG | 6963 | CAGGG UGAUG GCAUGCACUAUGC GCG GACGGCCAGC | 16303 |
| 35 | CUGUGGCUCU G CGUGG | 6964 | CCACG UGAUG GCAUGCACUAUGC GCG AGAGCCACAG | 16304 |
| 52 | GACCCGGGCC G CCUCU | 6965 | AGAGG UGAUG GCAUGCACUAUGC GCG GGCCCGGGUC | 16305 |
| 66 | CUGUGGGUUU G CCUAG | 6966 | CUAGG UGAUG GCAUGCACUAUGC GCG AAACCCACAG | 16306 |
| 82 | UGUUUCUCUU G AUCUG | 6967 | CAGAU UGAUG GCAUGCACUAUGC GCG AAGAGAAACA | 16307 |
| 87 | CUCUUGAUCU G CCCAG | 6968 | CUGGG UGAUG GCAUGCACUAUGC GCG AGAUCAAGAG | 16308 |
| 152 | CAAAUUACUU G CAGGG | 6969 | CCCUG UGAUG GCAUGCACUAUGC GCG AAGUAAUUUG | 16309 |
| 205 | GAGUGGCAGU G AGCAA | 6970 | UUGCU UGAUG GCAUGCACUAUGC GCG ACUGCCACUC | 16310 |
| 222 | GGGUGGAGGU G ACUGA | 6971 | UCAGU UGAUG GCAUGCACUAUGC GCG ACCUCCACCC | 16311 |
| 226 | GGAGGUGACU G AGUGC | 6972 | GCACU UGAUG GCAUGCACUAUGC GCG AGUCACCUCC | 16312 |
| 230 | GUGACUGAGU G CAGCG | 6973 | CGCUG UGAUG GCAUGCACUAUGC GCG ACUCAGUCAC | 16313 |
| 235 | UGAGUGCAGC G AUGGC | 6974 | GCCAU UGAUG GCAUGCACUAUGC GCG GCUGCACUCA | 16314 |
| 273 | UUCCAAAAGU G AUCGG | 6975 | CCGAU UGAUG GCAUGCACUAUGC GCG ACUUUUGGAA | 16315 |
| 283 | GAUCGGAAAU G ACACU | 6976 | AGUGU UGAUG GCAUGCACUAUGC GCG AUUUCCGAUC | 16316 |
| 302 | GCCUACAAGU G CUUCU | 6977 | AGAAG UGAUG GCAUGCACUAUGC GCG ACUUGUAGGC | 16317 |
| 319 | CCGGGAAACU G ACUUG | 6978 | CAAGU UGAUG GCAUGCACUAUGC GCG AGUUUCCCGG | 16318 |
| 373 | UCCAUUUAUU C CUUCU | 6979 | AGAAG UGAUG GCAUGCACUAUGC GCG AAUAAAUGGA | 16319 |
| 385 | UUCUGUUAGU G ACCAA | 6980 | UUGGU UGAUG GCAUGCACUAUGC GCG ACUAACAGAA | 16320 |
| 412 | GUACAUUACU G AGAAC | 6981 | GUUCU UGAUG GCAUGCACUAUGC GCG AGUAAUGUAC | 16321 |
| 435 | AAACUGUGGU G AUUCC | 6982 | GGAAU UGAUG GCAUGCACUAUGC GCG ACCACAGUUU | 16322 |
| 481 | GUCACUUUGU G CAAGA | 6983 | UCUUG UGAUG GCAUGCACUAUGC GCG ACAAAGUGAC | 16323 |
| 511 | AUUUGUUCCU G AUGGU | 6984 | ACCAU UGAUG GCAUGCACUAUGC GCG AGGAACAAAU | 16324 |
| 567 | CCAGCUACAU G AUCAG | 6985 | CUGAU UGAUG GCAUGCACUAUGC GCG AUGUAGCUGG | 16325 |
| 577 | GAUCAGCUAU G CUGGC | 6986 | GCCAG UGAUG GCAUGCACUAUGC GCG AUAGCUGAUC | 16326 |
| 595 | GGUCUUCUGU G AAGCA | 6987 | UGCUU UGAUG GCAUGCACUAUGC GCG ACAGAAGACC | 16327 |
| 610 | AAAAAUUAAU G AUGAA | 6988 | UUCAU UGAUG GCAUGCACUAUGC GCG AUUAAUUUUU | 16328 |
| 613 | AAUUAAUGAU G AAAGU | 6989 | ACUUU UGAUG GCAUGCACUAUGC GCG AUCAUUAAUU | 16329 |
| 667 | UAGGAUUUAU G AUGUG | 6990 | CACAU UGAUG GCAUGCACUAUGC GCG AUAAAUCCUA | 16330 |
| 678 | AUGUGGUUCU G AGUCC | 6991 | GGACU UGAUG GCAUGCACUAUGC GCG AGAACCACAU | 16331 |
| 697 | UCAUGGAAUU G AACUA | 6992 | UAGUU UGAUG GCAUGCACUAUGC GCG AAUUCCAUGA | 16332 |
| 745 | AGCAAGAACU G AACUA | 6993 | UAGUU UGAUG GCAUGCACUAUGC GCG AGUUCUUGCU | 16333 |
| 763 | UGUGGGGAUU G ACUUC | 6994 | GAAGU UGAUG GCAUGCACUAUGC GCG AAUCCCCACA | 16334 |
| 789 | ACCCUUCUUC G AAGCA | 6995 | UGCUU UGAUG GCAUGCACUAUGC GCG GAAGAAGGGU | 16335 |
| 818 | CUUGUAAACC G AGACC | 6996 | GGUCU UGAUG GCAUGCACUAUGC GCG GGUUUACAAG | 16336 |
| 844 | GUCUGGGAGU G AGAUG | 6997 | CAUCU UGAUG GCAUGCACUAUGC GCG ACUCCCAGAC | 16337 |
| 849 | GGAGUGAGAU G AAGAA | 6998 | UUCUU UGAUG GCAUGCACUAUGC GCG AUCUCACUCC | 16338 |

TABLE XVII-continued

KDR G-Cleaver Ribozyme and Target Sequences

| Pos | Target | Seq ID No | Ribozyme Sequence | Seq ID No |
|---|---|---|---|---|
| 861 | AGAAAUUUUU G AGCAC | 6999 | GUGCU UGAUG GCAUGCACUAUGC GCG AAAAAUUUCU | 16339 |
| 895 | AACCCGGAGU G ACCAA | 7000 | UUGGU UGAUG GCAUGCACUAUGC GCG ACUCCGGGUU | 16340 |
| 916 | GUACACCUGU G CAGCA | 7001 | UGCUG UGAUG GCAUGCACUAUGC CCC ACACCUCUAC | 16341 |
| 933 | CCAGUGGGCU G AUGAC | 7002 | GUCAU UGAUC GCAUCCACUAUGC GCG AGCCCACUGG | 16342 |
| 936 | GUGGGCUGAU G ACCAA | 7003 | UUGGU UGAUG GCAUGCACUAUGC GCG AUCAGCCCAC | 16343 |
| 970 | CAGGGUCCAU G AAAAA | 7004 | UUUUU UGAUG GCAUGCACUAUGC GCG AUGGACCCUG | 16344 |
| 985 | ACCUUUUGUU G CUUUU | 7005 | AAAAG UGAUG GCAUGCACUAUGC GCG AACAAAAGGU | 16345 |
| 1048 | CAGAAUCCCU G CGAAG | 7006 | CUUCG UGAUG GCAUGCACUAUGC GCG AGGGAUUCUG | 16346 |
| 1050 | GAAUCCCUGC G AAGUA | 7007 | UACUU UGAUG GCAUGCACUAUCC CCC GCAGCGAUUC | 16347 |
| 1108 | AAUACCCCUU G AGUCC | 7008 | GGACU UGAUG GCAUGCACUAUGC GCG AAGGGGUAUU | 16348 |
| 1143 | GGCAUGUACU G ACGAU | 7009 | AUCGU UGAUG GCAUGCACUAUGC GCG AGUACAUGCC | 16349 |
| 1146 | AUGUACUGAC G AUUAU | 7010 | AUAAU UGAUG GCAUGCACUAUGC GCG GUCAGUACAU | 16350 |
| 1158 | UUAUGGAAGU G AGUGA | 7011 | UCACU UGAUG GCAUGCACUAUGC GCG ACUUCCAUAA | 16351 |
| 1162 | GGAAGUGAGU G AAAGA | 7012 | UCUUU UGAUG GCAUGCACUAUGC GCG ACUCACUUCC | 16352 |
| 1267 | CCAGAUUGGU G AGAAA | 7013 | UUUCU UGAUG GCAUGCACUAUGC GCG ACCAAUCUGG | 16353 |
| 1320 | CCACUCAAAC G CUGAC | 7014 | GUCAG UGAUG GCAUGCACUAUGC GCG GUUUGAGUGG | 16354 |
| 1323 | CUCAAACGCU G ACAUG | 7015 | CAUGU UGAUG GCAUGCACUAUGC GCG AGCGUUUGAG | 16355 |
| 1339 | UACGGUCUAU G CCAUU | 7016 | AAUGG UGAUG GCAUGCACUAUGC GCG AUAGACCGUA | 16356 |
| 1353 | UUCCUCCCCC G CAUCA | 7017 | UGAUG UGAUG GCAUGCACUAUGC GCG GGGGGAGGAA | 16357 |
| 1391 | GAGGAAGAGU G CGCCA | 7018 | UGGCG UGAUG GCAUGCACUAUGC GCG ACUCUUCCUC | 16358 |
| 1393 | GGAAGAGUGC G CCAAC | 7019 | GUGUG UGAUG GCAUGCACUAUGC GCG GCACUCUUCC | 16359 |
| 1399 | GUGCGCCAAC G AGCCC | 7020 | GGGCU UGAUG GCAUGCACUAUGC GCG GUUGGCGCAC | 16360 |
| 1422 | CUGUCUCAGU G ACAAA | 7021 | UUUGU UGAUG GCAUGCACUAUGC GCG ACUGAGACAG | 16361 |
| 1441 | AUACCCUUGU G AAGAA | 7022 | UUCUU UGAUG GCAUGCACUAUGC GCG ACAAGGGUAU | 16362 |
| 1486 | AAAUAAAAUU G AAGUU | 7023 | AACUU UGAUG GCAUGCACUAUGC GCG AAUUUUAUUU | 16363 |
| 1507 | AAAUCAAUUU G CUCUA | 7024 | UAGAG UGAUG GCAUGCACUAUGC GCG AAAUUGAUUU | 16364 |
| 1516 | UGCUCUAAUU G AAGGA | 7025 | UCCUU UGAUG GCAUGCACUAUGC GCG AAUUAGAGCA | 16365 |
| 1585 | GUACAAAUGU G AAGCG | 7026 | CGCUU UGAUG GCAUGCACUAUGC GCG ACAUUUGUAC | 16366 |
| 1620 | GAGAGAGGGU G AUCUC | 7027 | GAGAU UGAUG GCAUGCACUAUGC GCG ACCCUCUCUC | 16367 |
| 1635 | CCUUCCACGU G ACCAG | 7028 | CUGGU UGAUG GCAUGCACUAUGC GCG ACGUGGAAGG | 16368 |
| 1648 | CAGGGGUCCU G AAAUU | 7029 | AAUUU UGAUG GCAUGCACUAUGC GCG AGGACCCCUG | 16369 |
| 1659 | AAAUUACUUU G CAACC | 7030 | GGUUG UGAUG GCAUGCACUAUGC GCG AAAGUAAUUU | 16370 |
| 1666 | UUUGCAACCU G ACAUG | 7031 | CAUGU UGAUG GCAUGCACUAUGC GCG AGGUUGCAAA | 16371 |
| 1671 | AACCUGACAU G CAGCC | 7032 | GGCUG UGAUG GCAUGCACUAUGC GCG AUGUCAGGUU | 16372 |
| 1681 | GCAGCCCACU G AGCAG | 7033 | CUGCU UGAUG GCAUGCACUAUGC GCG AGUGGGCUGC | 16373 |
| 1706 | UCUUUGUGGU G CACUG | 7034 | CAGUG UGAUG GCAUGCACUAUGC GCG ACCACAAAGA | 16374 |
| 1711 | GUGGUGCACU G CAGAC | 7035 | GUCUG UGAUG GCAUGCACUAUGC GCG AGUGCACCAC | 16375 |

TABLE XVII-continued

KDR G-Cleaver Ribozyme and Target Sequences

| Pos | Target | Seq ID No | Ribozyme Sequence | Seq ID No |
|---|---|---|---|---|
| 1729 | AUCUACGUUU G AGAAC | 7036 | GUUCU UGAUG GCAUGCACUAUGC GCG AAACGUAGAU | 16376 |
| 1767 | CACAGCCUCU G CCAAU | 7037 | AUUGG UGAUG GCAUGCACUAUGC GCG AGAGGCUGUG | 16377 |
| 1788 | UGGGAGAGUU G CCCAC | 7038 | GUGGG UGAUG GCAUGCACUAUGC GCG AACUCUCCCA | 16378 |
| 1802 | ACACCUGUUU G CAAGA | 7039 | UCUUG UGAUG GCAUGCACUAUGC GCG AAACAGGUGU | 16379 |
| 1830 | UUUGGAAAUU G AAUGC | 7040 | GCAUU UGAUG GCAUGCACUAUGC GCG AAUUUCCAAA | 16380 |
| 1834 | GAAAUUGAAU G CCACC | 7041 | GGUGG UGAUG GCAUGCACUAUGC GCG AUUCAAUUUC | 16381 |
| 1861 | UAGCACAAAU G ACAUU | 7042 | AAUGU UGAUG GCAUGCACUAUGC GCG AUUUGUGCUA | 16382 |
| 1869 | AUGACAUUUU G AUCAU | 7043 | AUGAU UGAUG GCAUGCACUAUGC GCG AAAAUGUCAU | 16383 |
| 1888 | GCUUAAGAAU G CAUCC | 7044 | GGAUG UGAUG GCAUGCACUAUGC GCG AUUCUUAAGC | 16384 |
| 1896 | AUGCAUCCUU G CAGGA | 7045 | UCCUG UGAUG GCAUGCACUAUGC GCG AAGGAUGCAU | 16385 |
| 1919 | GACUAUGUCU G CCUUG | 7046 | CAAGG UGAUG GCAUGCACUAUGC GCG AGACAUAGUC | 16386 |
| 1924 | UGUCUGCCUU G CUCAA | 7047 | UUGAG UGAUG GCAUGCACUAUGC GCG AAGGCAGACA | 16387 |
| 1955 | AAAAGACAUU G CGUGG | 7048 | CCACG UGAUG GCAUGCACUAUGC GCG AAUGUCUUUU | 16388 |
| 1998 | UGGCACCCAC G AUCAC | 7049 | GUGAU UGAUG GCAUGCACUAUGC GCG GUGGGUGCCA | 16389 |
| 2025 | AGAAUCAGAC G ACAAG | 7050 | CUUGU UGAUG GCAUGCACUAUGC GCG GUCUGAUUCU | 16390 |
| 2047 | GGAAAGCAUC G AAGUC | 7051 | GACUU UGAUG GCAUGCACUAUGC GCG GAUGCUUUCC | 16391 |
| 2057 | GAAGUCUCAU G CACGG | 7052 | CCGUG UGAUG GCAUGCACUAUGC GCG AUGAGACUUC | 16392 |
| 2107 | UAAAGAUAAU G AGACC | 7053 | GGUCU UGAUG GCAUGCACUAUGC GCG AUUAUCUUUA | 16393 |
| 2139 | GCAUUGUAUU G AAGGA | 7054 | UCCUU UGAUG GCAUGCACUAUGC GCG AAUACAAUGC | 16394 |
| 2168 | CUCACUAUCC G CAGAG | 7055 | CUCUG UGAUG GCAUGCACUAUGC GCG GGAUAGUGAG | 16395 |
| 2175 | UCCGCAGAGU G AGGAA | 7056 | UUCCU UGAUG GCAUGCACUAUGC GCG ACUCUGCGGA | 16396 |
| 2188 | GAAGGAGGAC G AAGGC | 7057 | GCCUU UGAUG GCAUGCACUAUGC GCG GUCCUCCUUC | 16397 |
| 2204 | CUCUACACCU G CCAGG | 7058 | CCUGG UGAUG GCAUGCACUAUGC GCG AGGUGUAGAG | 16398 |
| 2213 | UGCCAGGCAU G CAGUG | 7059 | CACUG UGAUG GCAUGCACUAUGC GCG AUGCCUGGCA | 16399 |
| 2230 | UCUUGGCUGU G CAAAA | 7060 | UUUUG UGAUG GCAUGCACUAUGC GCG ACAGCCAAGA | 16400 |
| 2263 | AAUAGAAGGU G CCCAG | 7061 | CUGGG UGAUG GCAUGCACUAUGC GCG ACCUUCUAUU | 16401 |
| 2277 | AGGAAAAGAC G AACUU | 7062 | AAGUU UGAUG GCAUGCACUAUGC GCG GUCUUUUCCU | 16402 |
| 2307 | UAGUAGGCAC G ACGGU | 7063 | ACCGU UGAUG GCAUGCACUAUGC GCG GUGCCUACUA | 16403 |
| 2313 | GCACGACGGU G AUUGC | 7064 | GCAAU UGAUG GCAUGCACUAUGC GCG ACCGUCGUGC | 16404 |
| 2317 | GACGGUGAUU G CCAUG | 7065 | CAUGG UGAUG GCAUGCACUAUGC GCG AAUCACCGUC | 16405 |
| 2385 | GAGGGGAACU G AAGAC | 7066 | GUCUU UGAUG GCAUGCACUAUGC GCG AGUUCCCCUC | 16406 |
| 2422 | GGAUCCAGAU G AACUC | 7067 | GAGUU UGAUG GCAUGCACUAUGC GCG AUCUGGAUCC | 16407 |
| 2437 | CCCAUUGGAU G AACAU | 7068 | AUGUU UGAUG GCAUGCACUAUGC GCG AUCCAAUGGG | 16408 |
| 2446 | UGAACAUUGU G AACGA | 7069 | UCGUU UGAUG GCAUGCACUAUGC GCG ACAAUGUUCA | 16409 |
| 2450 | CAUUGUGAAC G ACUGC | 7070 | GCAGU UGAUG GCAUGCACUAUGC GCG GUUCACAAUG | 16410 |
| 2454 | GUGAACGACU G CCUUA | 7071 | UAAGG UGAUG GCAUGCACUAUGC GCG AGUCGUUCAC | 16411 |
| 2461 | ACUGCCUUAU G AUGCC | 7072 | GGCAU UGAUG GCAUGCACUAUGC GCG AUAAGGCAGU | 16412 |

TABLE XVII-continued

KDR G-Cleaver Ribozyme and Target Sequences

| Pos | Target | Seq ID No | Ribozyme Sequence | Seq ID No |
|---|---|---|---|---|
| 2464 | GCCUUAUGAU G CCAGC | 7073 | GCUGG UGAUG GCAUGCACUAUGC GCG AUCAUAAGGC | 16413 |
| 2496 | GAGACCGGCU G AACCU | 7074 | AGGUU UGAUG GCAUGCACUAUGC GCG AGCCGGUCUC | 16414 |
| 2524 | UGGCCGUGGU G CCUUU | 7075 | AAAGG UGAUG GCAUGCACUAUGC GCG ACCACGGCCA | 16415 |
| 2542 | CCAAGAGAUU G AAGCA | 7076 | UGCUU UGAUG GCAUGCACUAUGC GCG AAUCUCUUGG | 16416 |
| 2551 | UGAAGCAGAU G CCUUU | 7077 | AAAGG UGAUG GCAUGCACUAUGC GCG AUCUGCUUCA | 16417 |
| 2563 | CUUUGGAAUU G ACAAG | 7078 | CUUGU UGAUG GCAUGCACUAUGC GCG AAUUCCAAAG | 16418 |
| 2579 | ACAGCAACUU G CAGGA | 7079 | UCCUG UGAUG GCAUGCACUAUGC GCG AAGUUGCUGU | 16419 |
| 2604 | UCAAAAUGUU G AAAGA | 7080 | UCUUU UGAUG GCAUGCACUAUGC GCG AACAUUUUGA | 16420 |
| 2626 | AACACACAGU G AGCAU | 7081 | AUGCU UGAUG GCAUGCACUAUGC GCG ACUGUGUGUU | 16421 |
| 2633 | AGUGAGCAUC G ACCUC | 7082 | GAGCU UGAUG GCAUGCACUAUGC GCG GAUGCUCACU | 16422 |
| 2647 | UCUCAUGUCU G AACUC | 7083 | GAGUU UGAUG GCAUGCACUAUGC GCG AGACAUGAGA | 16423 |
| 2704 | CCUUCUAGGU G CCUGU | 7084 | ACAGG UGAUG GCAUGCACUAUGC GCG ACCUAGAAGG | 16424 |
| 2736 | CACUCAUGGU G AUUGU | 7085 | ACAAU UGAUG GCAUGCACUAUGC GCG ACCAUGAGUG | 16425 |
| 2750 | GUGGAAUUCU G CAAAU | 7086 | AUUUG UGAUG GCAUGCACUAUGC GCG AGAAUUCCAC | 16426 |
| 2778 | CCACUUACCU G AGGAG | 7087 | CUCCU UGAUG GCAUGCACUAUGC GCG AGGUAAGUGG | 16427 |
| 2794 | CAAGAGAAAU G AAUUU | 7088 | AAAUU UGAUG GCAUGCACUAUGC GCG AUUUCUCUUG | 16428 |
| 2825 | AAAGGGGCAC G AUUCC | 7089 | GGAAU UGAUG GCAUGCACUAUGC GCG GUGCCCCUUU | 16429 |
| 2871 | CUGUGGAUCU G AAACG | 7090 | CGUUU UGAUG GCAUGCACUAUGC GCG AGAUCCACAG | 16430 |
| 2879 | CUGAAACGGC G CUUGG | 7091 | CCAAG UGAUG GCAUGCACUAUGC GCG GCCGUUUCAG | 16431 |
| 2947 | GUCCCUCAGU G AUGUA | 7092 | UACAU UGAUG GCAUGCACUAUGC GCG ACUGAGGGAC | 16432 |
| 2971 | GGAAGCUCCU G AAGAU | 7093 | AUCUU UGAUG GCAUGCACUAUGC GCG AGGAGCUUCC | 16433 |
| 2994 | AGGACUUCCU G ACCUU | 7094 | AAGGU UGAUG GCAUGCACUAUGC GCG AGGAAGUCCU | 16434 |
| 3057 | UCUUGGCAUC G CGAAA | 7095 | UUUCG UGAUG GCAUGCACUAUGC GCG GAUGCCAAGA | 16435 |
| 3059 | UUGGCAUCGC G AAAGU | 7096 | ACUUU UGAUG GCAUGCACUAUGC GCG GCGAUGCCAA | 16436 |
| 3089 | CUGGCGGCAC G AAAUA | 7097 | UAUUU UGAUG GCAUGCACUAUGC GCG GUGCCGCCAG | 16437 |
| 3130 | UAAAAUCUGU G ACUUU | 7098 | AAAGU UGAUG GCAUGCACUAUGC GCG ACAGAUUUUA | 16438 |
| 3187 | AAAAGGAGAU G CUCGC | 7099 | GCGAG UGAUG GCAUGCACUAUGC GCG AUCUCCUUUU | 16439 |
| 3191 | GGAGAUGCUC G CCUCC | 7100 | GGAGG UGAUG GCAUGCACUAUGC GCG GAGCAUCUCC | 16440 |
| 3201 | GCCUCCCUUU G AAAUG | 7101 | CAUUU UGAUG GCAUGCACUAUGC GCG AAAGGGAGGC | 16441 |
| 3229 | AACAAUUUUU G ACAGA | 7102 | UCUGU UGAUG GCAUGCACUAUGC GCG AAAAAUUGUU | 16442 |
| 3253 | AAUCCAGAGU G ACUUC | 7103 | GACGU UGAUG GCAUGCACUAUGC GCG ACUCUGGAUU | 16443 |
| 3276 | UUGGUGUUUU G CUGUG | 7104 | CACAG UGAUG GCAUGCACUAUGC GCG AAAACACCAA | 16444 |
| 3301 | UUCCUUAGGU G CUUCU | 7105 | AGAAG UGAUG GCAUGCACUAUGC GCG ACCUAAGGAA | 16445 |
| 3328 | GGUAAAGAUU G AUGAA | 7106 | UUCAU UGAUG GCAUGCACUAUGC GCG AAUCUUUACC | 16446 |
| 3331 | AAAGAUUGAU G AAGAA | 7107 | UUCUU UGAUG GCAUGCACUAUGC GCG AUCAAUCUUU | 16447 |
| 3347 | UUUUGUAGGC G AUUGA | 7108 | UCAAU UGAUG GCAUGCACUAUGC GCG GCCUACAAAA | 16448 |
| 3351 | GUAGGCGAUU G AAAGA | 7109 | UCUUU UGAUG GCAUGCACUAUGC GCG AAUCGCCUAC | 16449 |

TABLE XVII-continued

KDR G-Cleaver Ribozyme and Target Sequences

| Pos | Target | Seq ID No | Ribozyme Sequence | Seq ID No |
|---|---|---|---|---|
| 3369 | GAACUAGAAU G AGGGC | 7110 | GCCCU UGAUG GCAUGCACUAUGC GCG AUUCUAGUUC | 16450 |
| 3379 | GAGGGCCCCU G AUUAU | 7111 | AUAAU UGAUG GCAUGCACUAUGC GCG AGGGGCCCUC | 16451 |
| 3411 | ACCAGACCAU G CUGGA | 7112 | UCCAG UGAUG GCAUGCACUAUGC GCG AUGGUCUGGU | 16452 |
| 3419 | AUGCUGGACU G CUGGC | 5872 | GCCAG UGAUG GCAUGCACUAUGC GCG AGUCCAGCAU | 15212 |
| 3486 | GAAAUCUCUU G CAAGC | 7113 | GCUUG UGAUG GCAUGCACUAUGC GCG AAGAGAUUUC | 16453 |
| 3496 | GCAAGCUAAU G CUCAG | 7114 | CUGAG UGAUG GCAUGCACUAUGC GCG AUUAGCUUGC | 16454 |
| 3531 | UUGUUCUUCC G AUAUC | 7115 | GAUAU UGAUG GCAUGCACUAUGC GCG GGAAGAACAA | 16455 |
| 3546 | CAGAGACUUU G AGCAU | 7116 | AUGCU UGAUG GCAUGCACUAUGC GCG AAAGUCUCUG | 16456 |
| 3576 | GACUCUCUCU G CCUAC | 7117 | GUAGG UGAUG GCAUGCACUAUGC GCG AGAGAGAGUC | 16457 |
| 3619 | GGAAGUAUGU G ACCCC | 7118 | GGGGU UGAUG GCAUGCACUAUGC GCG ACAUACUUCC | 16458 |
| 3637 | AUUCCAUUAU G ACAAC | 7119 | GUUGU UGAUG GCAUGCACUAUGC GCG AUAAUGGAAU | 16459 |
| 3666 | GUCAGUAUCU G CAGAA | 7120 | UCCUG UGAUG GCAUGCACUAUGC GCG AGAUACUGAC | 16460 |
| 3680 | AACAGUAAGC G AAAGA | 7121 | UCUUU UGAUG GCAUGCACUAUGC GCG GCUUACUGUU | 16461 |
| 3696 | GCCGGCCUGU G AGUGU | 7122 | ACACU UGAUG GCAUGCACUAUGC GCG ACAGGCCGGC | 16462 |
| 3712 | AAAAACAUUU G AAGAU | 7123 | AUCUU UGAUG GCAUGCACUAUGC GCG AAAUGUUUUU | 16463 |
| 3757 | AAUCCCAGAU G ACAAC | 7124 | GUUGU UGAUG GCAUGCACUAUGC GCG AUCUGGGAUU | 16464 |
| 3787 | UAUGGUUCUU G CCUCA | 7125 | UGAGG UGAUG GCAUGCACUAUGC GCG AAGAACCAUA | 16465 |
| 3801 | CAGAAGAGCU G AAAAC | 7126 | GUUUU UGAUG GCAUGCACUAUGC GCG AGCUCUUCUG | 16466 |
| 3852 | GUGGAAUGGU G CCCAG | 7127 | CUGGG UGAUG GCAUGCACUAUGC GCG ACCAUUCCAC | 16467 |
| 3883 | UGUGGCAUCU G AAGGC | 7128 | GCCUU UGAUG GCAUGCACUAUGC GCG AGAUGCCACA | 16468 |
| 3928 | AUAUCACUCC G AUGAC | 7129 | GUCAU UGAUG GCAUGCACUAUGC GCG GGAGUGAUAU | 16469 |
| 3931 | UCACUCCGAU G ACACA | 7130 | UGUGU UGAUG GCAUGCACUAUGC GCG AUCGGAGUGA | 16470 |
| 3958 | GUACUCCAGU G AGGAA | 7131 | UUCCU UGAUG GCAUGCACUAUGC GCG ACUGGAGUAC | 16471 |
| 3981 | UUUUAAAGCU G AGAGA | 7132 | UCUAU UGAUG GCAUGCACUAUGC GCG AGCUUUAAAA | 16472 |
| 3996 | AGAUUGGAGU G CAAAC | 7133 | GUUUG UGAUG GCAUGCACUAUGC GCG ACUCCAAUCU | 16473 |
| 4030 | UCUCCAGCCU G ACACG | 7134 | CGUGU UGAUG GCAUGCACUAUGC GCG AGGCUGGAGA | 16474 |
| 4047 | GGACCACACU G AGCUC | 7135 | GAGCU UGAUG GCAUGCACUAUGC GCG AGUGUGGUCC | 16475 |
| 4103 | GACAUCACAU G AGAGG | 7136 | CCUCU UGAUG GCAUGCACUAUGC GCG AUGUGAUGUC | 16476 |
| 4112 | UGAGAGGUCU G CUCAG | 7137 | CUGAG UGAUG GCAUGCACUAUGC GCG AGACCUCUCA | 16477 |
| 4123 | CUCAGAUUUU G AAGUG | 7138 | CACUU UGAUG GCAUGCACUAUGC GCG AAAAUCUGAG | 16478 |
| 4157 | GGAAGUAGCC G CAUUU | 7139 | AAAUG UGAUG GCAUGCACUAUGC GCG GGCUACUUCC | 16479 |
| 4163 | AGCCGCAUUU G AUUUU | 7140 | AAAAU UGAUG GCAUGCACUAUGC GCG AAAUGCGGCU | 16480 |
| 4175 | UUUUCAUUUC G ACAAC | 7141 | GUUGU UGAUG GCAUGCACUAUGC GCG GAAAUGAAAA | 16481 |
| 4200 | ACCUCGGACU G CAGGG | 7142 | CCCUG UGAUG GCAUGCACUAUGC GCG AGUCCGAGGU | 16482 |

TABLE XVIII

Human FLT DNAzyme and Substrate Sequence

| Pos | Substrate | Seq ID No | DNAzyme | Seq ID No |
|---|---|---|---|---|
| 17 | UCCUCUCG G CUCCUCCC | 7143 | GGGAGGAG GGCTAGCTACAACGA CGAGAGGA | 16483 |
| 28 | CCUCCCCG G CAGCGGCG | 7144 | CGCCGCTG GGCTAGCTACAACGA CGGGGAGG | 16484 |
| 31 | CCCCGGCA G CGGCGGCG | 7145 | CGCCGCCG GGCTAGCTACAACGA TGCCGGGG | 16485 |
| 34 | CGGCAGCG G CGGCGGCU | 7146 | AGCCGCCG GGCTAGCTACAACGA CGCTGCCG | 16486 |
| 37 | CAGCGGCG G CGGCUCGG | 7147 | CCGAGCCG GGCTAGCTACAACGA CGCCGCTG | 16487 |
| 40 | CGGCGGCG G CUCGGAGC | 7148 | GCTCCGAG GGCTAGCTACAACGA CGCCGCCG | 16488 |
| 47 | GGCUCGGA G CGGGCUCC | 7149 | GGAGCCCG GGCTAGCTACAACGA TCCGAGCC | 16489 |
| 51 | CGGAGCGG G CUCCGGGG | 7150 | CCCCGGAG GGCTAGCTACAACGA CCGCTCCG | 16490 |
| 59 | GCUCCGGG G CUCGGGUG | 7151 | CACCCGAG GGCTAGCTACAACGA CCCGGAGC | 16491 |
| 65 | GGGCUCGG G UGCAGCGG | 7152 | CCGCTGCA GGCTAGCTACAACGA CCGAGCCC | 16492 |
| 67 | GCUCGGGU G CAGCGGCC | 7153 | GGCCGCTG GGCTAGCTACAACGA ACCCGAGC | 16493 |
| 70 | CGGGUGCA G CGGCCAGC | 7154 | GCTGGCCG GGCTAGCTACAACGA TGCACCCG | 16494 |
| 73 | GUGCAGCG G CCAGCGGG | 7155 | CCCGCTGG GGCTAGCTACAACGA CGCTGCAC | 16495 |
| 77 | AGCGCCCA G CGGGCCUG | 7156 | CAGGCCCG GGCTAGCTACAACGA TGGCCGCT | 16496 |
| 81 | GCCAGCGG G CCUGGCGG | 7157 | CCGCCAGG GGCTAGCTACAACGA CCGCTGGC | 16497 |
| 86 | CGGGCCUG G CGGCGAGG | 7158 | CCTCGCCG GGCTAGCTACAACGA CAGGCCCG | 16498 |
| 89 | GCCUGGCG G CGAGGAUU | 7159 | AATCCTCG GGCTAGCTACAACGA CGCCAGGC | 16499 |
| 95 | CGGCGAGG A UUACCCGG | 7160 | CCGGGTAA GGCTAGCTACAACGA CCTCGCCG | 16500 |
| 98 | CGAGGAUU A CCCGGGGA | 10 | TCCCCGGG GGCTAGCTACAACGA AATCCTCG | 16501 |
| 108 | CCGGGGAA G UGGUUGUC | 7161 | GACAACCA GGCTAGCTACAACGA TTCCCCGG | 16502 |
| 111 | GGGAAGUG G UUGUCUCC | 7162 | GGAGACAA GGCTAGCTACAACGA CACTTCCC | 16503 |
| 114 | AAGUGGUU G UCUCCUGG | 7163 | CCAGGAGA GGCTAGCTACAACGA AACCACTT | 16504 |
| 122 | GUCUCCUG G CUGGAGCC | 7164 | GGCTCCAG GGCTAGCTACAACGA CAGGAGAC | 16505 |
| 128 | UGGCUGGA G CCGCGAGA | 7165 | TCTCGCGG GGCTAGCTACAACGA TCCAGCCA | 16506 |
| 131 | CUGGAGCC G CGAGACGG | 7166 | CCGTCTCG GGCTAGCTACAACGA GGCTCCAG | 16507 |
| 136 | GCCGCGAG A CGGGCGCU | 7167 | AGCGCCCG GGCTAGCTACAACGA CTCGCGGC | 16508 |
| 140 | CGAGACGG G CGCUCAGG | 7168 | CCTGAGCG GGCTAGCTACAACGA CCGTCTCG | 16509 |
| 142 | AGACGGGC G CUCAGGGC | 7169 | GCCCTGAG GGCTAGCTACAACGA GCCCGTCT | 16510 |
| 149 | CGCUCAGG G CGCGGGGC | 7170 | GCCCCGCG GGCTAGCTACAACGA CCTGAGCG | 16511 |
| 151 | CUCAGGGC G CGGGGCCG | 7171 | CGGCCCCG GGCTAGCTACAACGA GCCCTGAG | 16512 |
| 156 | GGCGCGGG G CCGGCGGC | 7172 | GCCGCCGG GGCTAGCTACAACGA CCCGCGCC | 16513 |
| 160 | CGGGGCCG G CGGCGGCG | 7173 | CGCCGCCG GGCTAGCTACAACGA CGGCCCCG | 16514 |
| 163 | GGCCGGCG G CGGCGAAC | 7174 | GTTCGCCG GGCTAGCTACAACGA CGCCGGCC | 16515 |
| 166 | CGGCGGCG G CGAACGAG | 7175 | CTCGTTCG GGCTAGCTACAACGA CGCCGCCG | 16516 |
| 170 | GGCGGCGA A CGAGAGGA | 7176 | TCCTCTCG GGCTAGCTACAACGA TCGCCGCC | 16517 |
| 178 | ACGAGAGG A CGGACUCU | 7177 | AGAGTCCG GGCTAGCTACAACGA CCTCTCGT | 16518 |
| 182 | GAGGACGG A CUCUGGCG | 7178 | CGCCAGAG GGCTAGCTACAACGA CCGTCCTC | 16519 |

TABLE XVIII-continued

Human FLT DNAzyme and Substrate Sequence

| Pos | Substrate | Seq ID No | DNAzyme | Seq ID No |
|---|---|---|---|---|
| 188 | GGACUCUG G CGGCCGGG | 7179 | CCCGGCCG GGCTAGCTACAACGA CAGAGTCC | 16520 |
| 191 | CUCUGGCG G CCGGGUCG | 7180 | CGACCCGG GGCTAGCTACAACGA CGCCAGAG | 16521 |
| 196 | GCGGCCGG G UCGUUGGC | 7181 | GCCAACGA GGCTAGCTACAACGA CCGGCCGC | 16522 |
| 199 | GCCGGGUC G UUGGCCGG | 7182 | CCGGCCAA GGCTAGCTACAACGA GACCCGGC | 16523 |
| 203 | GGUCGUUG G CCGGGGGA | 7183 | TCCCCCGG GGCTAGCTACAACGA CAACGACC | 16524 |
| 212 | CCGGGGGA G CGCGGGCA | 7184 | TGCCCGCG GGCTAGCTACAACGA TCCCCCGG | 16525 |
| 214 | GGGGGAGC G CGGGCACC | 7185 | GGTGCCCG GGCTAGCTACAACGA GCTCCCCC | 16526 |
| 218 | GAGCGCGG G CACCGGGC | 7186 | GCCCGGTG GGCTAGCTACAACGA CCGCGCTC | 16527 |
| 220 | GCGCGGGC A CCGGGCGA | 4191 | UCGCCCGG GGCTAGCTACAACGA GCCCGCGC | 16528 |
| 225 | GGCACCGG G CGAGCAGG | 7187 | CCTGCTCG GGCTAGCTACAACGA CCGGTGCC | 16529 |
| 229 | CCGGGCGA G CAGGCCGC | 7188 | GCGGCCTG GGCTAGCTACAACGA TCGCCCGG | 16530 |
| 233 | GCGAGCAG G CCGCGUCG | 7189 | CGACGCGG GGCTAGCTACAACGA CTGCTCGC | 16531 |
| 236 | AGCAGGCC G CGUCGCGC | 7190 | GCGCGACG GGCTAGCTACAACGA GGCCTGCT | 16532 |
| 238 | CAGGCCGC G UCGCGCUC | 7191 | GAGCGCGA GGCTAGCTACAACGA GCGGCCTG | 16533 |
| 241 | GCCGCGUC G CGCUCACC | 7192 | GGTGAGCG GGCTAGCTACAACGA GACGCGGC | 16534 |
| 243 | CGCGUCGC G CUCACCAU | 7193 | ATGGTGAG GGCTAGCTACAACGA GCGACGCG | 16535 |
| 247 | UCGCGCUC A CCAUGGUC | 4196 | GACCATGG GGCTAGCTACAACGA GAGCGCGA | 16536 |
| 250 | CGCUCACC A UGGUCAGC | 4198 | GCTGACCA GGCTAGCTACAACGA GGTGAGCG | 16537 |
| 253 | UCACCAUG C UCAGCUAC | 7194 | GTAGCTGA GGCTAGCTACAACGA CATGGTGA | 16538 |
| 257 | CAUGGUCA G CUACUGGG | 7195 | CCCAGTAG GGCTAGCTACAACGA TGACCATG | 16539 |
| 260 | GGUCAGCU A CUGGGACA | 21 | UGTCCCAG GGCTAGCTACAACGA AGCTGACC | 16540 |
| 266 | CUACUGGG A CACCGGGG | 7196 | CCCCGGTG GGCTAGCTACAACGA CCCAGTAG | 16541 |
| 268 | ACUGGGAC A CCGGGGUC | 4202 | GACCCCGG GGCTAGCTACAACGA GTCCCAGT | 16542 |
| 274 | ACACCGGG C UCCUGCUG | 7197 | CACCAGGA GGCTAGCTACAACGA CCCGGTGT | 16543 |
| 279 | GGGGUCCU G CUGUGCGC | 7198 | GCGCACAG GGCTAGCTACAACGA AGGACCCC | 16544 |
| 282 | GUCCUGCU G UGCGCGCU | 7199 | ACCGCGCA GGCTAGCTACAACGA AGCAGGAC | 16545 |
| 284 | CCUGCUGU G CGCGCUGC | 7200 | GCAGCGCG GGCTAGCTACAACGA ACAGCAGG | 16546 |
| 286 | UGCUGUGC G CGCUGCUC | 7201 | GAGCAGCG GGCTAGCTACAACGA GCACAGCA | 16547 |
| 288 | CUGUGCGC C CUCCUCAG | 7202 | CTGAGCAG GCCTAGCTACAACGA GCGCACAG | 16548 |
| 291 | UGCGCGCU C CUCAGCUG | 7203 | CAGCTGAG GGCTAGCTACAACGA AGCGCGCA | 16549 |
| 296 | GCUCCUCA C CUGUCUGC | 7204 | GCAGACAG CGCTAGCTACAACGA TGAGCAGC | 16550 |
| 299 | CCUCAGCU G UCUCCGUC | 7205 | GAAGCAGA GGCTAGCTACAACGA AGCTGAGC | 16551 |
| 303 | AGCUCUCU G CUUCUCAC | 7206 | GTGAGAAG CGCTAGCTACAACGA AGACAGCT | 16552 |
| 310 | UGCUUCUC A CACCAUCU | 4214 | AGATCCTG GGCTAGCTACAACGA GAGAAGCA | 16553 |
| 315 | CUCACACG A UCUAGUUC | 7207 | GAACTAGA CGCTACCTACAACGA CCTGTGAC | 16554 |
| 320 | ACCAUCUA G UUCAGCUU | 7208 | AACCTGAA GGCTAGCTACAACGA TACATCCT | 16555 |
| 326 | UAGUUCAG C UUCAAAAU | 7209 | ATTTTGAA GCCTAGCTACAACGA CTGAACTA | 16556 |

TABLE XVIII-continued

Human FLT DNAzyme and Substrate Sequence

| Pos | Substrate | Seq ID No | DNAzyme | Seq ID No |
|-----|-----------|-----------|---------|-----------|
| 333 | GGUUCAAA A UUAAAAGA | 7210 | TCTTTTAA GGCTAGCTACAACGA TTTGAACC | 16557 |
| 341 | AUUAAAAG A UCCUGAAC | 7211 | GTTCAGGA GGCTAGCTACAACGA CTTTTAAT | 16558 |
| 348 | GAUCCUCA A CUGACUUU | 7212 | AAACTCAG GGCTAGCTACAACGA TCAGGATC | 16559 |
| 353 | UGAACUGA G UUUAAAAG | 7213 | CTTTTAAA GGCTAGCTACAACGA TCAGTTCA | 16560 |
| 362 | UUUAAAAG C CACCCAGC | 7214 | GCTGGGTG GGCTAGCTACAACGA CTTTTAAA | 16561 |
| 364 | UAAAAGGC A CCCAGCAC | 4222 | CTCCTCCG GGCTAGCTACAACGA GCCTTTTA | 16562 |
| 369 | CCCACCCA C CACAUCAU | 7215 | ATCATGTC GGCTAGCTACAACGA TCCGTGCC | 16563 |
| 371 | CACCCAGC A CAUCAUGC | 4226 | GCATGATG GGCTAGCTACAACGA CCTCGGTG | 16564 |
| 373 | CCCAGCAC A UCAUGCAA | 4227 | TTGCATCA GGCTAGCTACAACGA GTCCTGCC | 16565 |
| 376 | ACCACAUC A UCCAAGCA | 4228 | TCCTTCCA GGCTAGCTACAACGA CATCTGCT | 16566 |
| 378 | CACAUCAU C CAAGCAGG | 7216 | CCTGCTTG GGCTACCTACAACGA ATGATGTG | 16567 |
| 382 | UCAUCCAA C CAGGCCAG | 7217 | CTGGCCTC GGCTAGCTACAACGA TTCCATGA | 16568 |
| 386 | GCAAGCAG C CCAGACAC | 7218 | GTCTCTGC GGCTAGCTACAACGA CTGCTTCC | 16569 |
| 391 | CACCCCAG A CACUGCAU | 7219 | ATCCAGTC GGCTACCTACAACGA CTCCCCTC | 16570 |
| 393 | GGCCACAC A CUGCAUCU | 4233 | ACATCCAC GGCTAGCTACAACGA CTCTGGCC | 16571 |
| 396 | CAGACACU C CAUCUCCA | 7220 | TGCACATC GGCTAGCTACAACGA ACTGTCTG | 16572 |
| 398 | CACACUGC A UCUCCAAU | 4235 | ATTGCAGA GGCTAGCTACAACGA GCACTCTC | 16573 |
| 405 | CAUCUCCA A UCCAGGGC | 7221 | CCCCTCCA GGCTAGCTACAACGA TGCACATG | 16574 |
| 407 | UCUCCAAU C CACGCCGC | 7222 | CCCCCCTG GGCTAGCTACAACGA ATTGCACA | 16575 |
| 418 | GGGGGGAA C CAGCCCAU | 7223 | ATCGCCTC GGCTAGCTACAACGA TTCCCCCC | 16576 |
| 421 | GGGAAGCA G CCCAUAAA | 7224 | TTTATGGG GGCTAGCTACAACGA TGCTTCCC | 16577 |
| 425 | AGCAGCCC A UAAAUGGU | 4243 | ACCATTTA GGCTAGCTACAACGA GGGCTGCT | 16578 |
| 429 | GCCCAUAA A UGGUCUUU | 7225 | AAAGACCA GGCTAGCTACAACGA TTATGGGC | 16579 |
| 432 | CAUAAAUG G UCUUUGCC | 7226 | GGCAAAGA GGCTAGCTACAACGA CATTTATG | 16580 |
| 438 | UGGUCUUU G CCUGAAAU | 7227 | ATTTCAGG GGCTAGCTACAACGA AAAGACCA | 16581 |
| 445 | UGCCUGAA A UGGUGAGU | 7228 | ACTCACCA GGCTAGCTACAACGA TTCAGGCA | 16582 |
| 448 | CUGAAAUG G UGAGUAAG | 7229 | CTTACTCA GGCTAGCTACAACGA CATTTCAG | 16583 |
| 452 | AAUGGUGA G UAAGGAAA | 7230 | TTTCCTTA GGCTAGCTACAACGA TCACCATT | 16584 |
| 461 | UAAGGAAA G CGAAAGGC | 7231 | GCCTTTCG GGCTAGCTACAACGA TTTCCTTA | 16585 |
| 468 | AGCGAAAG G CUGAGCAU | 7232 | ATGCTCAG GGCTAGCTACAACGA CTTTCGCT | 16586 |
| 473 | AAGGCUGA G CAUAACUA | 7233 | TAGTTATG GGCTAGCTACAACGA TCAGCCTT | 16587 |
| 475 | GGCUGAGC A UAACUAAA | 4248 | TTTAGTTA GGCTAGCTACAACGA GCTCAGCC | 16588 |
| 478 | UGAGCAUA A CUAAAUCU | 7234 | AGATTTAG GGCTAGCTACAACGA TATGCTCA | 16589 |
| 483 | AUAACUAA A UCUGCCUG | 7235 | CAGGCAGA GGCTAGCTACAACGA TTAGTTAT | 16590 |
| 487 | CUAAAUCU G CCUGUGGA | 7236 | TCCACAGG QGCTAGCTACAACGA AGATTTAG | 16591 |
| 491 | AUCUGCCU G UGGAAGAA | 7237 | TTCTTCCA GGCTAGCTACAACGA AGGCAGAT | 16592 |
| 500 | UGGAAGAA A UGGCAAAC | 7238 | GTTTGCCA GGCTAGCTACAACGA TTCTTCCA | 16593 |

TABLE XVIII-continued

Human FLT DNAzyme and Substrate Sequence

| Pos | Substrate | Seq ID No | DNAzyme | Seq ID No |
|---|---|---|---|---|
| 503 | AAGAAAUG G CAAACAAU | 7239 | ATTGTTTG GGCTAGCTACAACGA CATTTCTT | 16594 |
| 507 | AAUGGCAA A CAAUUCUG | 7240 | CAGAATTG GGCTAGCTACAACGA TTGCCATT | 16595 |
| 510 | GGCAAACA A UUCUGCAG | 7241 | CTGCAGAA GGCTAGCTACAACGA TGTTTGCC | 16596 |
| 515 | ACAAUUCU G CAGUACUU | 7242 | AAGTACTG GGCTAGCTACAACGA ACAATTGT | 16597 |
| 518 | AUUCUGCA G UACUUUAA | 7243 | TTAAAGTA GGCTAGCTACAACGA TGCAGAAT | 16598 |
| 520 | UCUGCAGU A CUUUAACC | 53 | GGTTAAAG GGCTAGCTACAACGA ACTGCAGA | 16599 |
| 526 | GUACUUUA A CCUUGAAC | 7244 | GTTCAAGG GGCTAGCTACAACGA TAAAGTAC | 16600 |
| 533 | AACCUUGA A CACAGCUC | 7245 | GAGCTGTG GGCTAGCTACAACGA TCAAGGTT | 16601 |
| 535 | CCUUGAAC A CAGCUCAA | 4260 | TTGAGCTG GGCTAGCTACAACGA GTTCAAGG | 16602 |
| 538 | UGAACACA G CUCAAGCA | 7246 | TGCTTGAG GGCTAGCTACAACGA TGTGTTCA | 16603 |
| 544 | CAGCUCAA G CAAACCAC | 7247 | GTGGTTTG GGCTAGCTACAACGA TTGAGCTG | 16604 |
| 548 | UCAAGCAA A CGACACUG | 7248 | CAGTGTGG GGCTAGCTACAACGA TTGCTTGA | 16605 |
| 551 | AGCAAACC A CACUGGCU | 4266 | AGCCAGTG GGCTAGCTACAACGA GGTTTGCT | 16606 |
| 553 | CAAACCAC A CUGGCUUC | 4267 | GAAGCCAG GGCTAGCTACAACGA GTGGTTTG | 16607 |
| 557 | CGACACUG G CUUCUACA | 7249 | TGTAGAAG GGCTAGCTACAACGA CAGTGTGG | 16608 |
| 563 | UGGCUUCU A CAGCUGCA | 61 | UGCAGCTG GGCTAGCTACAACGA AGAAGCCA | 16609 |
| 566 | CU1CUACA G CUGCAAAU | 7250 | ATTTGCAG GGCTAGCTACAACGA TGTAGAAG | 16610 |
| 569 | CUACAGCU G CAAAUAUC | 7251 | GATATTTG GGCTAGCTACAACGA AGCTGTAG | 16611 |
| 573 | AGCUGCAA A UAUCUAGC | 7252 | GCTAGATA GGCTAGCTACAACGA TTGCAGCT | 16612 |
| 575 | CUGCAAAU A UCUAGCUG | 62 | CAGCTAGA GGCTAGCTACAACGA ATTTGCAG | 16613 |
| 580 | AAUAUCUA G CUGUACCU | 7253 | AGGTACAG GGCTAGCTACAACGA TAGATATT | 16614 |
| 583 | AUCUAGCU G UACCUACU | 7254 | AGTAGGTA GGCTAGCTACAACGA AGCTAGAT | 16615 |
| 585 | CUAGCUGU A CCUACUUC | 65 | GAAGTAGG GGCTAGCTACAACGA ACAGCTAG | 16616 |
| 589 | CUGUACCU A CUUCAAAG | 66 | CTTTGAAG GGCTAGCTACAACGA AGGTACAG | 16617 |
| 607 | AGAAGGAA A CAGAAUCU | 7255 | AGATTCTG GGCTAGCTACAACGA TTCCTTCT | 16618 |
| 612 | GAAACAGA A UCCCAAU | 7256 | ATTGCAGA GGCTAGCTACAACGA TCTGTTTC | 16619 |
| 616 | CAGAAUCU G CAAUCUAU | 7257 | ATAGATTG GGCTAGCTACAACGA AGATTCTG | 16620 |
| 619 | AAUCUGCA A UCUAUAUA | 7258 | TATATAGA GGCTAGCTACAACGA TGCAGATT | 16621 |
| 623 | UGCAAUCU A UAUAUUUA | 71 | UAAATATA GGCTAGCTACAACGA AGATTGCA | 16622 |
| 625 | CAAUCUAU A UAUUUAUU | 72 | AATAAATA GGCTAGCTACAACGA ATAGATTG | 16623 |
| 627 | AUCUAUAU A UUUAUUAG | 73 | CTAATAAA GGCTAGCTACAACGA ATATAGAT | 16624 |
| 631 | AUAUAUUU A UUAGUGAU | 76 | ATCACTAA GGCTAGCTACAACGA AAATATAT | 16625 |
| 635 | AUUUAUUA G UGAUACAG | 7259 | CTGTATCA GGCTAGCTACAACGA TAATAAAT | 16626 |
| 638 | UAUUAGUG A UACAGGUA | 7260 | TACCTGTA GGCTAGCTACAACGA CACTAATA | 16627 |
| 640 | UUAGUGAU A CAGGUAGA | 79 | TCTACCTG GGCTAGCTACAACGA ATCACTAA | 16628 |
| 644 | UGAUACAG G UAGACCUU | 7261 | AAGGTCTA GGCTAGCTACAACGA CTGTATCA | 16629 |
| 648 | ACAGGUAG A CCUUUCGU | 7262 | ACGAAAGG GGCTAGCTACAACGA CTACCTGT | 16630 |

TABLE XVIII-continued

Human FLT DNAzyme and Substrate Sequence

| Pos | Substrate | Seq ID No | DNAzyme | Seq ID No |
|---|---|---|---|---|
| 655 | GACCUUUC G UAGAGAUG | 7263 | CATCTCTA GGCTAGCTACAACGA GAAAGGTC | 16631 |
| 661 | UCGUAGAG A UGUACAGU | 7264 | ACTGTACA GGCTAGCTACAACGA CTCTACGA | 16632 |
| 663 | GUAGAGAU G UACAGUGA | 7265 | TCACTGTA GGCTAGCTACAACGA ATCTCTAC | 16633 |
| 665 | AGAGAUGU A CAGUGAAA | 85 | TTTCACTG GGCTAGCTACAACGA ACATCTCT | 16634 |
| 668 | GAUGUACA G UGAAAUCC | 7266 | GGATTTCA GGCTAGCTACAACGA TGTACATC | 16635 |
| 673 | ACAGUGAA A UCCCCGAA | 7267 | TTCGGGGA GGCTAGCTACAACGA TTCACTGT | 16636 |
| 682 | UCCCCGAA A UUAUACAC | 7268 | GTGTATAA GGCTAGCTACAACGA TTCGGGGA | 16637 |
| 685 | CCGAAAUU A UACACAUG | 88 | CATGTGTA GGCTAGCTACAACGA AATTTCGG | 16638 |
| 687 | GAAAUUAU A CACAUGAC | 89 | GTCATGTG GGCTAGCTACAACGA ATAATTTC | 16639 |
| 689 | AAUUAUAC A CAUGACUG | 4291 | CAGTCATG GGCTAGCTACAACGA GTATAATT | 16640 |
| 691 | UUAUACAC A UGACUAA | 4292 | TTCAGTCA GGCTAGCTACAACGA GTGTATAA | 16641 |
| 694 | UACACAUG A CUGAAGGA | 7269 | TCCTTCAG GGCTAGCTACAACGA CATGTGTA | 16642 |
| 708 | GGAAGGGA G CUCGUCAU | 7270 | ATGACGAG GGCTAGCTACAACGA TCCCTTCC | 16643 |
| 712 | GGGAGCUC G UCAUUCCC | 7271 | GGGAATGA GGCTAGCTACAACGA GAGCTCCC | 16644 |
| 715 | AGCUCGUC A UUCCCUGC | 4295 | GCAGGGAA GGCTAGCTACAACGA GACGAGCT | 16645 |
| 722 | CAUUCCCU G CCGGGUUA | 7272 | TAACCCGG GGCTAGCTACAACGA AGGGAATG | 16646 |
| 727 | CCUGCCGG G UUACGUCA | 7273 | TGACGTAA GGCTAGCTACAACGA CCGGCAGG | 16647 |
| 730 | GCCGGGUU A CGUCACCU | 95 | AGGTGACG GGCTAGCTACAACGA AACCCGGC | 16648 |
| 732 | CGGGUUAC G UCACCUAA | 7274 | TTAGGTGA GGCTAGCTACAACGA GTAACCCG | 16649 |
| 735 | GUUACGUC A CCUAACAU | 4300 | ATGTTAGG GGCTAGCTACAACGA GACGTAAC | 16650 |
| 740 | GUCACCUA A CAUCACUG | 7275 | CAGTGATG GGCTAGCTACAACGA TAGGTGAC | 16651 |
| 742 | CACCUAAC A UCACUGUU | 4303 | AACAGTGA GGCTAGCTACAACGA GTTAGGTG | 16652 |
| 745 | CUAACAUC A CUGUUACU | 4304 | AGTAACAG GGCTAGCTACAACGA GATGTTAG | 16653 |
| 748 | ACAUCACU G UUACUUUA | 7276 | TAAAGTAA GGCTAGCTACAACQA AGTGATGT | 16654 |
| 751 | UCACUGUU A CUUUAAAA | 100 | TTTTAAAG GGCTAGCTACAACGA AACAGTGA | 16655 |
| 762 | UUAAAAAA G UUCCACU | 7277 | AGTGGAAA GGCTAGCTACAACGA TTTTTTAA | 16656 |
| 768 | AAGUUUCC A CUUGACAC | 4308 | GTGTCAAG GGCTAGCTACAACGA GGAAACTT | 16657 |
| 773 | UCCACUUG A CACUUUGA | 7278 | TCAAAGTG GGCTAGCTACAACGA CAAGTGGA | 16658 |
| 775 | CACUUGAC A CUUUGAUC | 4310 | GATCAAAG GGCTAGCTACAACGA GTCAAGTG | 16659 |
| 781 | ACACUUUG A UCCCUGAU | 7279 | ATCAGGGA GGCTAGCTACAACGA CAAAGTGT | 16660 |
| 788 | GAUCCCUG A UGGAAAAC | 7280 | GTTTTCCA GGCTAGCTACAACGA CAGGGATC | 16661 |
| 795 | GAUGGAAA A CGCAUAAU | 7281 | ATTATGCG GGCTAGCTACAACGA TTTCCATC | 16662 |
| 797 | UGGAAAAC G CAUAAUCU | 7282 | AGATTATG GGCTAGCTACAACGA GTTTTCCA | 16663 |
| 799 | GAAAACGC A UAAUCUGG | 4315 | CCAGATTA GGCTAGCTACAACGA GCGTTTTC | 16664 |
| 802 | AACGCAUA A UCUGGGAC | 7283 | GTCCCAGA GGCTAGCTACAACGA TATGCGTT | 16665 |
| 809 | AAUCUGGG A CAGUAGAA | 7284 | TTCTACTG GGCTAGCTACAACGA CCCAGATT | 16666 |
| 812 | CUGGGACA G UAGAAAGG | 7285 | CCTTTCTA GGCTAGCTACAACGA TGTCCCAG | 16667 |

TABLE XVIII-continued

Human FLT DNAzyme and Substrate Sequence

| Pos | Substrate | Seq ID No | DNAzyme | Seq ID No |
|---|---|---|---|---|
| 821 | UAGAAAGG C CUUCAUCA | 7286 | TGATGAAG GGCTAGCTACAACGA CCTTTCTA | 16668 |
| 826 | AGGGCUUC A UCAUAUCA | 4319 | TGATATGA GGCTAGCTACAACGA GAAGCCCT | 16669 |
| 829 | GCUUCAUC A UAUCAAAU | 4320 | ATTTGATA GGCTAGCTACAACGA GATGAAGC | 16670 |
| 831 | UUCAUCAU A UCAAAUGC | 117 | GCATTTGA GGCTAGCTACAACGA ATGATGAA | 16671 |
| 836 | CAUAUCAA A UGCAACGU | 7287 | ACGTTGCA GGCTAGCTACAACGA TTGATATG | 16672 |
| 838 | UAUCAAAU C CAACGUAC | 7288 | GTACGTTG GGCTAGCTACAACGA ATTTGATA | 16673 |
| 841 | CAAAUGCA A CGUACAAA | 7289 | TTTGTACG GGCTAGCTACAACGA TGCATTTG | 16674 |
| 843 | AAUGCAAC G UACAAAGA | 7290 | TCTTTGTA GGCTAGCTACAACGA GTTGCATT | 16675 |
| 845 | UGCAACGU A CAAAGAAA | 119 | TTTCTTTG GGCTAGCTACAACGA ACGTTGCA | 16676 |
| 853 | ACAAAGAA A UAGGGCUU | 7291 | AAGCCCTA GGCTAGCTACAACGA TTCTTTGT | 16677 |
| 858 | GAAAUAGG G CUUCUGAC | 7292 | GTCAGAAG GGCTAGCTACAACGA CCTATTTC | 16678 |
| 865 | GGCUUCUG A CCUGUGAA | 7293 | TTCACAGG GGCTAGCTACAACGA CAGAAGCC | 16679 |
| 869 | UCUGACCU G UGAAGCAA | 7294 | TTGCTTCA GGCTAGCTACAACGA AGGTCAGA | 16680 |
| 874 | CCUGUGAA C CAACAGUC | 7295 | GACTGTTG GGCTAGCTACAACGA TTCACAGG | 16681 |
| 877 | GUGAAGCA A CAGUCAAU | 7296 | ATTGACTG GGCTAGCTACAACGA TGCTTCAC | 16682 |
| 880 | AAGCAACA G UCAAUGGG | 7297 | CCCATTGA GGCTAGCTACAACGA TGTTGCTT | 16683 |
| 884 | AACAGUCA A UGGGCAUU | 7298 | AATGCCCA GGCTAGCTACAACGA TGACTGTT | 16684 |
| 888 | GUCAAUGG G CAUUUGUA | 7299 | TACAAATG GGCTAGCTACAACGA CCATTGAC | 16685 |
| 890 | CAAUGGGC A UUUGUAUA | 433 | UATACAAA GGCTAGCTACAACGA GCCCATTG | 16686 |
| 894 | GGGCAUUU G UAUAAGAC | 7300 | GTCTTATA GGCTAGCTACAACGA AAATGCCC | 16687 |
| 896 | GCAUUUGU A UAAGACAA | 126 | TTGTCTTA GGCTAGCTACAACGA ACAAATGC | 16688 |
| 901 | UGUAUAAG A CAAACUAU | 7301 | ATAGTTTG GGCTAGCTACAACGA CTTATACA | 16689 |
| 905 | UAAGACAA A CUAUCUCA | 7302 | TGAGATAG GGCTAGCTACAACGA TTGTCTTA | 16690 |
| 908 | GACAAACU A UCUCACAC | 128 | GTGTGAGA GGCTAGCTACAACGA AGTTTCTC | 16691 |
| 913 | ACUAUCUC A CACAUCCA | 4335 | TCGATGTG GGCTAGCTACAACGA GAGATAGT | 16692 |
| 915 | UAUCUCAC A CAUCGACA | 4336 | TGTCGATG GGCTAGCTACAACGA GTGAGATA | 16693 |
| 917 | UCUCACAC A UCGACAAA | 4337 | TTTGTCGA GGCTAGCTACAACGA GTGTGAGA | 16694 |
| 921 | ACACAUCG A CAAACCAA | 7303 | TTGGTTTG GGCTAGCTACAACGA CGATGTCT | 16695 |
| 925 | AUCGACAA A CCAAUACA | 7304 | TGTATTGG GGCTAGCTACAACGA TTGTCGAT | 16696 |
| 929 | ACAAACCA A UACAAUCA | 7305 | TGATTGTA GGCTAGCTACAACGA TGGTTTGT | 16697 |
| 931 | AAACCAAU A CAAUCAUA | 132 | TATGATTG GGCTAGCTACAACGA ATTGGTTT | 16698 |
| 934 | CCAAUACA A UCAUAGAU | 7306 | ATCTATGA GGCTAGCTACAACGA TGTATTCG | 16699 |
| 937 | AUACAAUC A UAGAUGUC | 4342 | GACATCTA GGCTAGCTACAACGA GATTGTAT | 16700 |
| 941 | AAUCAUAG A UGUCCAAA | 7307 | TTTGGACA GGCTAGCTACAACGA CTATGATT | 16701 |
| 943 | UCAUAGAU C UCCAAAUA | 7308 | TATTTGGA GGCTAGCTACAACGA ATCTATGA | 16702 |
| 949 | AUGUCCAA A UAAGCACA | 7309 | TGTCCTTA GGCTACCTACAACGA TTGGACAT | 16703 |
| 953 | CCAAAUAA G CACACCAC | 7310 | GTGGTGTG GGCTAGCTACAACGA TTATTTGG | 16704 |

TABLE XVIII-continued

Human FLT DNAzyme and Substrate Sequence

| Pos | Substrate | Seq ID No | DNAzyme | Seq ID No |
|---|---|---|---|---|
| 955 | AAAUAAGC A CACCACGC | 4345 | GCGTGGTG GGCTAGCTACAACGA GCTTATTT | 16705 |
| 957 | AUAAGCAC A CCACGCCC | 4346 | GGGCGTGG GCCTAGCTACAACGA GTGCTTAT | 16706 |
| 960 | AGCACACC A CGCCCAGU | 4348 | ACTGGCCG GCCTAGCTACAACGA GGTGTGCT | 16707 |
| 962 | CACACCAC C CCCAGUCA | 731 | UGACTGGG GGCTAGCTACAACGA GTGGTGTG | 16708 |
| 967 | CACGCCCA C UCAAAUUA | 7312 | TAATTTGA GGCTAGCTACAACGA TGGGCGTG | 16709 |
| 972 | CCAGUCAA A UUACUUAG | 7313 | CTAAGTAA GGCTAGCTACAACGA TTGACTGG | 16710 |
| 975 | GUCAAAUU A CUUAGAGG | 139 | CCTCTAAG GGCTAGCTACAACGA AATTTGAC | 16711 |
| 983 | ACUUAGAG G CCAUACUC | 7314 | GAGTATGG GGCTAGCTACAACGA CTCTAAGT | 16712 |
| 986 | UAGAGGCC A UACUCUUG | 4355 | CAAGAGTA CGCTAGCTACAACGA GGCCTCTA | 16713 |
| 988 | GAGGCCAU A CUCUUGUC | 142 | GACAACAG GGCTAGCTACAACGA ATGGCCTC | 16714 |
| 994 | AUACUCUU G UCCUCAAU | 7315 | ATTGAGGA GGCTAGCTACAACGA AAGAGTAT | 16715 |
| 1001 | UGUCCUCA A UUGUACUG | 7316 | CAGTACAA GGCTAGCTACAACGA TGAGGACA | 16716 |
| 1004 | CCUCAAUU G UACUGCUA | 7317 | TACCACTA GGCTAGCTACAACGA AATTGAGG | 16717 |
| 1006 | UCAAUUCU A CUGCUACC | 148 | GGTAGCAG CGCTAGCTACAACGA ACAATTGA | 16718 |
| 1009 | AUUCUACU C CUACCACU | 7318 | AGTGGTAC GGCTAGCTACAACGA AGTACAAT | 16719 |
| 1012 | GUACUGCU A CCACUCCC | 149 | GGGAGTGG GGCTAGCTACAACGA ACCACTAC | 16720 |
| 1015 | CUGCUACC A CUCCCUUC | 4364 | CAAGGGAG GGCTAGCTACAACGA GGTAGCAG | 16721 |
| 1025 | UCCCUUCA A CACGAGAG | 7319 | CTCTCGTC CGCTAGCTACAACGA TCAACGCA | 16722 |
| 1027 | CCUUGAAC A CGAGAGUU | 4369 | AACTCTCG GGCTACCTACAACGA CTTCAAGC | 16723 |
| 1033 | ACACGAGA G UUCAAAUG | 7320 | CATTTGAA GGCTAGCTACAACGA TCTCGTGT | 16724 |
| 1039 | GAGUUCAA A UGACCUGG | 7321 | CCAGGTCA GGCTAGCTACAACGA TTGAACTC | 16725 |
| 1042 | UUCAAAUG A CCUGGAGU | 7322 | ACTCCAGG GGCTAGCTACAACGA CATTTGAA | 16726 |
| 1049 | GACCUGGA G UUACCCUG | 7323 | CAGGGTAA GGCTAGCTACAACGA TCCAGGTC | 16727 |
| 1052 | CUGGAGUU A CCCUGAUG | 155 | CATCAGGG GGCTAGCTACAACGA AACTCCAG | 16728 |
| 1058 | UUACCCUG A UGAAAAAA | 7324 | TTTTTTCA GGCTAGCTACAACGA CAGGGTAA | 16729 |
| 1067 | UGAAAAAA A UAAGAGAG | 7325 | CTCTCTTA GGCTAGCTACAACGA TTTTTTCA | 16730 |
| 1075 | AUAAGAGA G CUUCCGUA | 7326 | TACGGAA3 GGCTAGCTACAACGA TCTCTTAT | 16731 |
| 1081 | GAGCUUCC G UAAGGCGA | 7327 | TCGCCTTA GGCTAGCTACAACGA GGAAGCTC | 16732 |
| 1086 | UCCGUAAG G CGACGAAU | 7328 | ATTCGTCG GGCTAGCTACAACGA CTTACGGA | 16733 |
| 1089 | GUAAGGCG A CGAAUUGA | 7329 | TCAATTCG GGCTAGCTACAACGA CGCCTTAC | 16734 |
| 1093 | GGCGACGA A UUGACCAA | 7330 | TTGGTCAA GGCTAGCTACAACGA TCGTCGCC | 16735 |
| 1097 | ACGAAUUG A CCAAAGCA | 733 | UGCTTTGG GGCTAGCTACAACGA CAATTCGT | 16736 |
| 1103 | UGACCAAA G CAAUUCCC | 7332 | GGGAATTG GGCTAGCTACAACGA TTTGGTCA | 16737 |
| 1106 | CCAAAGCA A UUCCCAUG | 7333 | CATGGGAA GGCTAGCTACAACGA TGCTTTGG | 16738 |
| 1112 | CAAUUCCC A UGCCAACA | 4383 | TGTTGGCA GGCTAGCTACAACGA GGGAATTG | 16739 |
| 1114 | AUUCCCAU G CCAACAUA | 7334 | TATGTTGG GGCTAGCTACAACGA ATGGGAAT | 16740 |
| 1118 | CCAUGCCA A CAUAUUCU | 7335 | AGAATATG GGCTAGCTACAACGA TGGCATGG | 16741 |

TABLE XVIII-continued

Human FLT DNAzyme and Substrate Sequence

| Pos | Substrate | Seq ID No | DNAzyme | Seq ID No |
|---|---|---|---|---|
| 1120 | AUGCCAAC A UAUUCUAC | 4386 | GTAGAATA GGCTAGCTACAACGA GTTGGCAT | 16742 |
| 1122 | GCCAACAU A UUCUACAG | 163 | CTGTAGAA GGCTAGCTACAACGA ATGTTGGC | 16743 |
| 1127 | CAUAUUCU A CAGUGUUC | 166 | GAACACTG GGCTAGCTACAACGA AGAATATG | 16744 |
| 1130 | AUUCUACA G UGUUCUUA | 7336 | TAAGAACA GGCTAGCTACAACGA TGTAGAAT | 16745 |
| 1132 | UCUACAGU G UUCUUACU | 7337 | AGTAAGAA GGCTAGCTACAACGA ACTGTAGA | 16746 |
| 1138 | GUGUUCUU A CUAUUGAC | 170 | GTCAATAG GGCTAGCTACAACGA AAGAACAC | 16747 |
| 1141 | UUCUUACU A UUGACAAA | 171 | TTTGTCAA GGCTAGCTACAACGA AGTAAGAA | 16748 |
| 1145 | UACUAUUG A CAAAAUGC | 7338 | GCATTTTG GGCTAGCTACAACGA CAATAGTA | 16749 |
| 1150 | UUGACAAA A UGCAGAAC | 7339 | GTTCTGCA GGCTAGCTACAACGA TTTGTCAA | 16750 |
| 1152 | GACAAAAU G CAGAACAA | 7340 | TTGTTCTG GGCTAGCTACAACGA ATTTTGTC | 16751 |
| 1157 | AAUGCAGA A CAAAGACA | 734 | UGTCTTTG GCCTAGCTACAACGA TCTGCATT | 16752 |
| 1163 | GAACAAAG A CAAAGGAC | 7342 | GTCCTTTG GGCTAGCTACAACGA CTTTGTTC | 16753 |
| 1170 | GACAAAGG A CUUUAUAC | 7343 | GTATAAAG GGCTAGCTACAACGA CCTTTGTC | 16754 |
| 1175 | AGGACUUU A UACUUGUC | 175 | GACAAGTA GGCTAGCTACAACGA AAAGTCCT | 16755 |
| 1177 | GACUUUAU A CUUGUCGU | 176 | ACGACAAG GGCTAGCTACAACGA ATAAAGTC | 16756 |
| 1181 | UUAUACUU G UCGUGUAA | 7344 | TTACACGA GGCTAGCTACAACGA AAGTATAA | 16757 |
| 1184 | UACUUGUC G UGUAAGGA | 7345 | TCCTTACA GGCTAGCTACAACGA GACAAGTA | 16758 |
| 1186 | CUUGUCGU G UAAGGAGU | 7346 | ACTCCTTA GGCTAGCTACAACGA ACGACAAG | 16759 |
| 1193 | UGUAAGGA G UGGACCAU | 7347 | ATGGTCCA GGCTAGCTACAACGA TCCTTACA | 16760 |
| 1197 | AGGAGUGG A CCAUCAUU | 7348 | AATGATGG GGCTAGCTACAACGA CCACTCCT | 16761 |
| 1200 | AGUGGACC A UCAUUCAA | 4398 | TTGAATGA GGCTAGCTACAACGA GGTCCACT | 16762 |
| 1203 | UGACCAUC A UUCAAAUC | 4399 | GATTTGAA GGCTAGCTACAACGA GATGGTCC | 16763 |
| 1209 | UCAUUCAA A UCUCUUAA | 7349 | TTAACAGA GGCTAGCTACAACGA TTGAATGA | 16764 |
| 1213 | UCAAAUCU G UUAACACC | 7350 | GGTGTTAA GGCTAGCTACAACGA AGATTTGA | 16765 |
| 1217 | AUCUGUUA A CACCUCAG | 7351 | CTGAGGTG GGCTAGCTACAACGA TAACAGAT | 16766 |
| 1219 | CUGUUAAC A CCUCAGUG | 4402 | CACTGAGG GGCTAGCTACAACGA GTTAACAG | 16767 |
| 1225 | ACACCUCA G UGCAUAUA | 7352 | TATATGCA GGCTAGCTACAACGA TGAGGTGT | 16768 |
| 1227 | ACCUCAGU G CAUAUAUA | 7353 | TATATATG GGCTAGCTACAACGA ACTGAGGT | 16769 |
| 1229 | CUCAGUGC A UAUAUAUG | 4406 | CATATATA GGCTAGCTACAACGA GCACTGAG | 16770 |
| 1231 | CAGUGCAU A UAUAUGAU | 187 | ATCATATA GGCTAGCTACAACGA ATGCACTG | 16771 |
| 1233 | GUGCAUAU A UAUGAUAA | 188 | TTATCATA GGCTAGCTACAACGA ATATGCAC | 16772 |
| 1235 | GCAUAUAU A UGAUAAAG | 189 | CTTTATCA GGCTAGCTACAACGA ATATATGC | 16773 |
| 1238 | UAUAUAUG A UAAAGCAU | 7354 | ATGCTTTA GGCTAGCTACAACGA CATATATA | 16774 |
| 1243 | AUGAUAAA G CAUUCAUC | 7355 | GATGAATG GGCTAGCTACAACGA TTTATCAT | 16775 |
| 1245 | GAUAAAGC A UUCAUCAC | 4407 | GTGATGAA GGCTAGCTACAACGA GCTTTATC | 16776 |
| 1249 | AAGCAUUC A UCACUGUG | 4408 | CACAGTGA GGCTAGCTACAACGA GAATGCTT | 16777 |
| 1252 | CAUUCAUC A CUGUGAAA | 4409 | TTTCACAG GGCTAGCTACAACGA GATGAATG | 16778 |

TABLE XVIII-continued

Human FLT DNAzyme and Substrate Sequence

| Pos | Substrate | Seq ID No | DNAzyme | Seq ID No |
|---|---|---|---|---|
| 1255 | UCAUCACU G UGAAACAU | 7356 | ATGTTTCA GGCTAGCTACAACGA AGTGATGA | 16779 |
| 1260 | ACUGUGAA A CAUCGAAA | 7357 | TTTCGATG GGCTAGCTACAACGA TTCACAGT | 16780 |
| 1262 | UGUGAAAC A UCGAAAAC | 4411 | GTTTTCGA GGCTAGCTACAACGA GTTTCACA | 16781 |
| 1269 | CAUCGAAA A CAGCAGGU | 7358 | ACCTGCTG GGCTAGCTACAACGA TTTCGATG | 16782 |
| 1272 | CGAAAACA G CAGGUGCU | 7359 | AGCACCTG GGCTAGCTACAACGA TGTTTTCG | 16783 |
| 1276 | AACAGCAG G UGCUUGAA | 7360 | TTCAAGCA GGCTAGCTACAACGA CTGCTGTT | 16784 |
| 1278 | CAGCAGGU G CUUGAAAC | 7361 | GTTTCAAG GGCTAGCTACAACGA ACCTGCTG | 16785 |
| 1285 | UGCUUGAA A CCGUAGCU | 7362 | AGCTACGG GGCTAGCTACAACGA TTCAAGCA | 16786 |
| 1288 | UUGAAACC C UACCGGGC | 7363 | GCCAGCTA GGCTAGCTACAACGA GCTTTCAA | 16787 |
| 1291 | AAACCGUA G CUGGCAAG | 7364 | CTTGCCAG GGCTAGCTACAACGA TACGGTTT | 16788 |
| 1295 | CGUAGCUG G CAACCGCU | 7365 | ACCGCTTG GGCTAGCTACAACGA CAGCTACG | 16789 |
| 1299 | GCUGGCAA C CGGUCUUA | 7366 | TAAGACCG GGCTAGCTACAACGA TTGCCAGC | 16790 |
| 1302 | GGCAAGCG G UCUUACCG | 7367 | CGGTAAGA GGCTAGCTACAACGA CGCTTGCC | 16791 |
| 1307 | GCGGUCUU A CCGGCUCU | 199 | AGAGCCGG GGCTAGCTACAACGA AAGACCGC | 16792 |
| 1311 | UCUUACCG G CUCUCUAU | 7368 | ATAGAGAG GGCTAGCTACAACGA CGGTAAGA | 16793 |
| 1318 | GGCUCUCU A UGAAAGUG | 202 | CACTTTCA GGCTAGCTACAACGA AGAGAGCC | 16794 |
| 1324 | CUAUGAAA G UGAAGGCA | 7369 | TGCCTTCA GGCTAGCTACAACGA TTTCATAG | 16795 |
| 1330 | AAGUGAAG G CAUUUCCC | 7370 | GGGAAATG GGCTAGCTACAACGA CTTCACTT | 16796 |
| 1332 | GUGAAGGC A UUUCCCUC | 4423 | GAGGGAAA GGCTAGCTACAACGA GCCTTCAC | 16797 |
| 1341 | UUUCCCUC G CCGGAAGU | 7371 | ACTTCCGG GGCTAGCTACAACGA GAGGGAAA | 16798 |
| 1348 | CGCCGGAA C UUGUAUGG | 7372 | CCATACAA GGCTAGCTACAACGA TTCCGGCG | 16799 |
| 1351 | CGGAAGUU G UAUGGUUA | 7373 | TAACCATA GGCTAGCTACAACGA AACTTCCG | 16800 |
| 1353 | GAAGUUGU A UGGUUAAA | 208 | TTTAACCA GGCTAGCTACAACGA ACAACTTC | 16801 |
| 1356 | GUUGUAUG C UUAAAAGA | 7374 | TCTTTTAA GGCTAGCTACAACGA CATACAAC | 16802 |
| 1364 | GUUAAAAG A UGGGUUAC | 7375 | GTAACCCA GGCTAGCTACAACGA CTTTTAAC | 16803 |
| 1368 | AAAGAUGG C UUACCUGC | 7376 | GCAGGTAA GGCTAGCTACAACGA CCATCTTT | 16804 |
| 1371 | GAUGGGUU A CCUGCGAC | 212 | GTCGCAGG GGCTAGCTACAACGA AACCCATC | 16805 |
| 1375 | GGUUACCU C CCACUGAC | 7377 | CTCAGTCG CGCTAGCTACAACGA ACGTAACC | 16806 |
| 1378 | UACCUGCG A CUGAGAAA | 7378 | TTTCTCAC GCCTAGCTACAACGA CGCAGGTA | 16807 |
| 1386 | ACUGAGAA A UCUCCUCC | 7379 | CGAGCACA GCCTAGCTACAACGA TTCTCACT | 16808 |
| 1390 | AGAAAUCU C CUCCCUAU | 7380 | ATACCGAG GCCTAGCTACAACGA AGATTTCT | 16809 |
| 1394 | AUCCUCC C CUAUUUGA | 738 | UCAAATAG GGCTAGCTACAACGA GAGCAGAT | 16810 |
| 1397 | UGCUCGCU A UUUCACUC | 215 | CAGTCAAA GGCTAGCTACAACGA AGCCAGCA | 16811 |
| 1402 | GCUAUUUC A CUCGUCCC | 7382 | CCCACGAG GGCTAGCTACAACGA CAAATACC | 16812 |
| 1406 | UUUGACUC C UGCCUACU | 7383 | AGTAGCCA GGCTAGCTACAACGA GAGTCAAA | 16813 |
| 1409 | CACUCCUC C CUACUCGU | 7384 | ACCAGTAC CGCTAGCTACAACGA CACGACTC | 16814 |
| 1412 | UCGUGCCU A CUCGUUAA | 219 | TTAACCAG CGCTAGCTACAACGA ACCCACCA | 16815 |

TABLE XVIII-continued

Human FLT DNAzyme and Substrate Sequence

| Pos | Substrate | Seq ID No | DNAzyme | Seq ID No |
|---|---|---|---|---|
| 1416 | GGCUACUC C UUAAUUAU | 7385 | ATAATTAA GGCTAGCTACAACGA GAGTAGCC | 16816 |
| 1420 | ACUCGUUA A UUAUCAAG | 7386 | CTTGATAA GGCTAGCTACAACGA TAACGAGT | 16817 |
| 1423 | CGUUAAUU A UCAAGGAC | 224 | CTCCTTGA GGCTAGCTACAACGA AATTAACG | 16818 |
| 1430 | UAUCAACC A CGUAACUC | 7387 | CAGTTACG GCCTAGCTACAACGA CCTTCATA | 16819 |
| 1432 | UCAACGAC C UAACUGAA | 7388 | TTCAGTTA GCCTAGCTACAACGA GTCCTTCA | 16820 |
| 1435 | AGCACCUA A CUCAACAC | 7389 | CTCTTCAG CCCTACCTACAACGA TACGTCCT | 16821 |
| 1445 | UGAAGAGG A UGCAGGGA | 7390 | TCCCTGCA GGCTAGCTACAACGA CCTCTTCA | 16822 |
| 1447 | AAGAGGAU G CAGGGAAU | 7391 | ATTCCCTG GGCTAGCTACAACGA ATCCTCTT | 16823 |
| 1454 | UGCAGGGA A UUAUACAA | 7392 | TTGTATAA GGCTAGCTACAACGA TCCCTGCA | 16824 |
| 1457 | AGGGAAUU A UACAAUCU | 228 | AGATTGTA GGCTAGCTACAACGA AATTCCCT | 16825 |
| 1459 | GGAAUUAU A CAAUCUUG | 229 | CAAGATTG GGCTAGCTACAACGA ATAATTCC | 16826 |
| 1462 | AUUAUACA A UCUUGCUG | 7393 | CAGCAAGA GGCTAGCTACAACGA TGTATAAT | 16827 |
| 1467 | ACAAUCUU G CUGAGCAU | 7394 | ATGCTCAG GGCTAGCTACAACGA AAGATTGT | 16828 |
| 1472 | CUUGCUGA G CAUAAAAC | 7395 | GTTTTATG GGCTAGCTACAACGA TCAGCAAG | 16829 |
| 1474 | UGCUGAGC A UAAAACAG | 4443 | CTGTTTTA GGCTAGCTACAACGA GCTCAGCA | 16830 |
| 1479 | AGCAUAAA A CAGUCAAA | 7396 | TTTGACTG GGCTAGCTACAACGA TTTATGCT | 16831 |
| 1482 | AUAAAACA G UCAAAUGU | 7397 | ACATTTGA GGCTAGCTACAACGA TGTTTTAT | 16832 |
| 1487 | ACAGUCAA A UGUGUUUA | 7398 | TAAACACA GGCTAGCTACAACGA TTGACTGT | 16833 |
| 1489 | AGUCAAAU G UGUUUAAA | 7399 | TTTAAACA GGCTAGCTACAACGA ATTTGACT | 16834 |
| 1491 | UCAAAUGU G UUUAAAAA | 7400 | TTTTTAAA GGCTAGCTACAACGA ACATTTGA | 16835 |
| 1499 | GUUUAAAA A CCUCACUG | 7401 | CAGTGAGG GGCTAGCTACAACGA TTTTAAAC | 16836 |
| 1504 | AAAACCUC A CUGCCACU | 4448 | AGTGGCAG GGCTAGCTACAACGA GAGGTTTT | 16837 |
| 1507 | ACCUCACU G CCACUCUA | 7402 | TAGAGTGG GGCTAGCTACAACGA AGTGAGGT | 16838 |
| 1510 | UCACUGCC A CUCUAAUU | 4451 | AATTAGAG GGCTAGCTACAACGA GGCAGTGA | 16839 |
| 1516 | CCACUCUA A UUGUCAAU | 7403 | ATTGACAA GGCTAGCTACAACGA TAGAGTGG | 16840 |
| 1519 | CUCUAAUU G UCAAUGUG | 7404 | CACATTGA GGCTAGCTACAACGA AATTAGAG | 16841 |
| 1523 | AAUUGUCA A UGUGAAAC | 7405 | GTTTCACA GGCTAGCTACAACGA TGACAATT | 16842 |
| 1525 | UUGUCAAU G UGAAACCC | 7406 | GGGTTTCA GGCTAGCTACAACGA ATTGACAA | 16843 |
| 1530 | AAUGUGAA A CCCCAGAU | 7407 | ATCTGGGG GGCTAGCTACAACGA TTCACATT | 16844 |
| 1537 | AACCCCAG A UUUACGAA | 7408 | TTCGTAAA GGCTAGCTACAACGA CTGGGGTT | 16845 |
| 1541 | CCAGAUUU A CGAAAAGG | 244 | CCTTTTCG GGCTAGCTACAACGA AAATCTGG | 16846 |
| 1549 | ACGAAAAG G CCGUGUCA | 7409 | TGACACGG GGCTAGCTACAACGA CTTTTCGT | 16847 |
| 1552 | AAAAGGCC G UGUCAUCG | 7410 | CGATGACA GGCTAGCTACAACGA GGCCTTTT | 16848 |
| 1554 | AAGGCCGU G UCAUCGUU | 7411 | AACGATGA GGCTAGCTACAACGA ACGGCCTT | 16849 |
| 1557 | GCCGUGUC A UCGUUUCC | 4460 | GGAAACGA GGCTAGCTACAACGA GACACGGC | 16850 |
| 1560 | GUGUCAUC G UUUCCAGA | 7412 | TCTGGAAA GGCTAGCTACAACGA GATGACAC | 16851 |
| 1568 | GUUUCCAG A GCCGGCUC | 7413 | GAGCCGGG GGCTAGCTACAACGA CTGGAAAC | 16852 |

TABLE XVIII-continued

Human FLT DNAzyme and Substrate Sequence

| Pos | Substrate | Seq ID No | DNAzyme | Seq ID No |
|---|---|---|---|---|
| 1573 | CAGACCCG G CUCUCUAC | 7414 | GTAGAGAG GGCTAGCTACAACGA CGGGTCTG | 16853 |
| 1580 | GGCUCUCG A CCCACUGG | 252 | CCAGTGGG GGCTAGCTACAACGA AGAGAGCC | 16854 |
| 1584 | CUCUACCC A CUGGGCAG | 4470 | CTGCCCAG GGCTAGCTACAACGA GGGTAGAG | 16855 |
| 1589 | CCCACUGG G CAGCAGAC | 7415 | GTCTGCTG GGCTAGCTACAACGA CCAGTGGG | 16856 |
| 1592 | ACUGGGCA G CAGACAAA | 7416 | TTTGTCTG GGCTAGCTACAACGA TGCCCAGT | 16857 |
| 1596 | GGCAGCAG A CAAAUCCU | 7417 | AGGATTTG GGCTAGCTACAACGA CTGCTGCC | 16858 |
| 1600 | GCAGACAA A UCCUGACU | 7418 | AGTCAGGA GGCTAGCTACAACGA TTGTCTGC | 16859 |
| 1606 | AAAUCCUG A CUUGUACC | 7419 | GGTACAAG GGCTAGCTACAACGA CAGGATTT | 16860 |
| 1610 | CCUGACUU G UACCGCAU | 7420 | ATGCGGTA GGCTAGCTACAACGA AAGTCAGG | 16861 |
| 1612 | UGACUUGU A CCGCAUAU | 255 | ATATGCGG GGCTAGCTACAACGA ACAAGTCA | 16862 |
| 1615 | CUUGUACC G CAUAUGGU | 7421 | ACCATATG GGCTAGCTACAACGA GGTACAAG | 16863 |
| 1617 | UGUACCGC A UAUGGUAU | 4479 | ATACCATA GGCTAGCTACAACGA GCGGTACA | 16864 |
| 1619 | UACCGCAU A UGGUAUCC | 256 | GGATACCA GGCTAGCTACAACGA ATGCCGTA | 16865 |
| 1622 | CGCAUAUG G UAUCCCUC | 7422 | GAGGGATA GGCTAGCTACAACGA CATATGCG | 16866 |
| 1624 | CAUAUGGU A UCCCUCAA | 257 | TTGAGGGA GGCTAGCTACAACGA ACCATATG | 16867 |
| 1632 | AUCCCUCA A CCUACAAU | 7423 | ATTGTAGG GGCTAGCTACAACGA TGAGGGAT | 16868 |
| 1636 | CUCAACCU A CAAUCAAG | 260 | CTTGATTG GGCTAGCTACAACGA AGGTTGAG | 16869 |
| 1639 | AACCUACA A UCAAGUGG | 7424 | CCACTTGA GGCTAGCTACAACGA TGTAGGTT | 16870 |
| 1644 | ACAAUCAA G UGGUUCUG | 7425 | CAGAACCA GGCTAGCTACAACGA TTGATTGT | 16871 |
| 1647 | AUCAAGUG G UUCUGGCA | 7426 | TGCCAGAA GGCTAGCTACAACGA CACTTGAT | 16872 |
| 1653 | UGGUUCUG G CACCCCUG | 7427 | CAGGGGTG GGCTAGCTACAACGA CAGAACCA | 16873 |
| 1655 | GUUCUGGC A CCCCUGUA | 4489 | TACAGGGG GGCTAGCTACAACGA GCCAGAAC | 16874 |
| 1661 | GCACCCCU G UAACCAUA | 7428 | TATGGTTA GGCTAGCTACAACGA AGGGGTGC | 16875 |
| 1664 | CCCCUGUA A CCAUAAUC | 7429 | GATTATGG GGCTAGCTACAACGA TACAGGGG | 16876 |
| 1667 | CUGUAACC A UAAUCAUU | 4495 | AATGATTA GGCTAGCTACAACGA GGTTACAG | 16877 |
| 1670 | UAACCAUA A UCAUUCCG | 7430 | CGGAATGA GGCTAGCTACAACGA TATGGTTA | 16878 |
| 1673 | CCAUAAUC A UUCCGAAG | 4496 | CTTCGGAA GGCTAGCTACAACGA GATTATCG | 16879 |
| 1681 | AUUCCGAA C CAAGGUGU | 7431 | ACACCTTG GGCTAGCTACAACGA TTCGGAAT | 16880 |
| 1686 | GAAGCAAG G UGUGACUU | 7432 | AAGTCACA GGCTAGCTACAACGA CTTCCTTC | 16881 |
| 1688 | AGCAAGGU G UGACUUUU | 7433 | AAAAGTCA GGCTAGCTACAACGA ACCTTGCT | 16882 |
| 1691 | AAGGUGUG A CUUUUGUU | 7434 | AACAAAAG GGCTAGCTACAACGA CACACCTT | 16883 |
| 1697 | UGACUUUU C UUCCAAUA | 7435 | TATTGGAA CGCTAGCTACAACGA AAAAGTCA | 16884 |
| 1703 | UUCUUCCA A UAAUGAAG | 7436 | CTTCATTA GGCTAGCTACAACGA TGGAACAA | 16885 |
| 1706 | UUCCAAUA A UGAAGAGU | 7437 | ACTCTTCA CGCTAGCTACAACGA TATTGCAA | 16886 |
| 1713 | AAUCAAGA G UCCUUUAU | 7438 | ATAAAGGA GGCTACCTACAACGA TCTTCATT | 16887 |
| 1720 | AGUCCUUU A UCCUGGAU | 278 | ATCCAGGA GGCTAGCTACAACGA AAAGGACT | 16888 |
| 1727 | UAUCCUGG A UCCUGACA | 7439 | TGTCAGCA GGCTAGCTACAACGA CCAGGATA | 16889 |

TABLE XVIII-continued

Human FLT DNAzyme and Substrate Sequence

| Pos | Substrate | Seq ID No | DNAzyme | Seq ID No |
|---|---|---|---|---|
| 1729 | UCCUCGAU C CUGACAGC | 7440 | GCTGTCAC GGCTAGCTACAACGA ATCCACCA | 16890 |
| 1733 | GCAUCCUG A CACCAACA | 744 | UGTTCCTG CCCTAGCTACAACGA CACCATCC | 16891 |
| 1736 | UCCUCACA C CAACAUGC | 7442 | CCATCTTC CCCTACCTACAACGA TGTCAGCA | 16892 |
| 1739 | UGACACCA A CAUCCGAA | 7443 | TTCCCATC CGCTACCTACAACGA TGCTCTCA | 16893 |
| 1741 | ACAGCAAC A UGGCAAAC | 4509 | GTTTCCCA GGCTAGCTACAACGA CTTGCTGT | 16894 |
| 1748 | CAUGGGAA A CACAAUUG | 7444 | CAATTCTC CCCTACCTACAACGA TTCCCATC | 16895 |
| 1753 | GAAACAGA A UUGACAGC | 7445 | CCTCTCAA GGCTAGCTACAACGA TCTGTTTC | 16896 |
| 1760 | AAUUGAGA C CAUCACUC | 7446 | GAGTGATG CGCTACCTACAACGA TCTCAATT | 16897 |
| 1762 | UUGAGAGC A UCACUCAG | 4511 | CTCAGTGA GGCTAGCTACAACGA CCTCTCAA | 16898 |
| 1765 | AGAGCAUC A CUCAGCGC | 4512 | GCGCTCAG GGCTAGCTACAACGA CATGCTCT | 16899 |
| 1770 | AUCACUCA C CGCAUCGC | 7447 | CCCATCCG GGCTAGCTACAACGA TGAGTGAT | 16900 |
| 1772 | CACUCAGC G CAUGGCAA | 7448 | TTGCCATC CGCTAGCTACAACGA GCTGAGTG | 16901 |
| 1774 | CUCACCGC A UGGCAAUA | 4515 | TATTGCCA GCCTAGCTACAACGA GCGCTCAC | 16902 |
| 1777 | AGCGCAUG C CAAUAAUA | 7449 | TATTATTC CGCTAGCTACAACGA CATGCGCT | 16903 |
| 1780 | GCAUGGCA A UAAUACAA | 7450 | TTCTATTA GGCTAGCTACAACGA TGCCATGC | 16904 |
| 1783 | UGCCAAUA A UAGAACGA | 745 | UCCTTCTA GGCTAGCTACAACGA TATTGCCA | 16905 |
| 1796 | ACGAAAGA A UAAGAUGG | 7452 | CCATCTTA GGCTAGCTACAACGA TCTTTCCT | 16906 |
| 1801 | ACAAUAAC A UCCCUACC | 7453 | GCTACCCA GCCTAGCTACAACGA CTTATTCT | 16907 |
| 1804 | AUAACAUG C CUAGCACC | 7454 | CCTCCTAG GCCTAGCTACAACGA CATCTTAT | 16908 |
| 1808 | GAUGGCUA C CACCUUGG | 7455 | CCAAGGTG CGCTAGCTACAACGA TACCCATC | 16909 |
| 1810 | UCGCUAGC A CCUUCCUU | 4518 | AACCAAGG GGCTAGCTACAACGA GCTAGCCA | 16910 |
| 1816 | CCACCUUC C UUCUCCCU | 7456 | ACCCACAA CCCTACCTACAACGA CAACCTCC | 16911 |
| 1819 | CCUUCCUU C UCCCUCAC | 7457 | CTCACCCA CCCTACCTACAACGA AACCAACC | 16912 |
| 1822 | UCCUUCUC C CUCACUCU | 7458 | AGAGTCAC CCCTACCTACAACGA CACAACCA | 16913 |
| 1826 | UCUCGCUC A CUCUACAA | 7459 | TTCTACAG GGCTAGCTACAACGA CACCCACA | 16914 |
| 1834 | ACUCUACA A UUUCUCGA | 7460 | TCCACAAA CCCTACCTACAACGA TCTACAGT | 16915 |
| 1843 | UUUCUCCA A UCUACAUU | 7461 | AATCTAGA CGCTAGCTACAACGA TCCACAAA | 16916 |
| 1847 | UCCAAUCU A CAUUCCA | 295 | TCCAAATC CCCTACCTACAACGA ACATTCCA | 16917 |
| 1849 | GAAUCUAC A UUCCAUA | 4526 | TATCCAAA CCCTACCTACAACGA CTACATTC | 16918 |
| 1853 | CUACAUUU C CAUACCUU | 7462 | AACCTATC CCCTACCTACAACGA AAATCTAC | 16919 |
| 1855 | ACAUUUGC A UAGCUUCC | 4527 | GGAAGCTA GGCTAGCTACAACGA GCAAATGT | 16920 |
| 1858 | UUUGCAUA G CUUCCAAU | 7463 | ATTGGAAG GGCTAGCTACAACGA TATGCAAA | 16921 |
| 1865 | AGCUUCCA A UAAAGUUG | 7464 | CAACTTTA GGCTAGCTACAACGA TGGAAGCT | 16922 |
| 1870 | CCAAUAAA G UUGGGACU | 7465 | AGTCCCAA GGCTAGCTACAACGA TTTATTGG | 16923 |
| 1876 | AAGUUGGG A CUGUGGGA | 7466 | TCCCACAG GGCTAGCTACAACGA CCCAACTT | 16924 |
| 1879 | UUGGGACU G UGGGAAGA | 7467 | TCTTCCCA GGCTAGCTACAACGA AGTCCCAA | 16925 |
| 1889 | GGGAAGAA A CAUAAGCU | 7468 | AGCTTATG GGCTAGCTACAACGA TTCTTCCC | 16926 |

TABLE XVIII-continued

Human FLT DNAzyme and Substrate Sequence

| Pos | Substrate | Seq ID No | DNAzyme | Seq ID No |
|---|---|---|---|---|
| 1891 | GAAGAAAC A UAAGCUUU | 4532 | AAAGCTTA GGCTAGCTACAACGA GTTTCTTC | 16927 |
| 1895 | AAACAUAA G CUUUUAUA | 7469 | TATAAAAG GGCTAGCTACAACGA TTATGTTT | 16928 |
| 1901 | AAGCUUUU A UAUCACAG | 307 | CTGTGATA GGCTAGCTACAACGA AAAAGCTT | 16929 |
| 1903 | GCUUUUAU A UCACAGAU | 308 | ATCTGTGA GGCTAGCTACAACGA ATAAAGC | 16930 |
| 1906 | UUUAUAUC A CAGAUGUG | 4534 | CACATCTG GGCTAGCTACAACGA GATATAAA | 16931 |
| 1910 | UAUCACAG A UGUGCCAA | 7470 | TTGGCACA GGCTAGCTACAACGA CTGTGATA | 16932 |
| 1912 | UCACAGAU G UGCCAAAU | 7471 | ATTTGGCA GGCTAGCTACAACGA ATCTGTGA | 16933 |
| 1914 | ACAGAUGU G CCAAAUGG | 7472 | CCATTTGG GGCTAGCTACAACGA ACATCTGT | 16934 |
| 1919 | UGUGCCAA A UGGGUUUC | 7473 | GAAACCCA GGCTAGCTACAACGA TTGGCACA | 16935 |
| 1923 | CCAAAUGG G UUUCAUGU | 7474 | ACATGAAA GGCTAGCTACAACGA CCATTTGG | 16936 |
| 1928 | UGGGUUUC A UGUUAACU | 4538 | AGTTAACA GGCTAGCTACAACGA GAAACCCA | 16937 |
| 1930 | GGUUUCAU G UUAACUUG | 7475 | CAAGTTAA GGCTAGCTACAACGA ATGAAACC | 16938 |
| 1934 | UCAUGUUA A CUUGGAAA | 7476 | TTTCCAAG GGCTAGCTACAACGA TAACATGA | 16939 |
| 1945 | UGGAAAAA A UGCCGACG | 7477 | CGTCGGCA GGCTAGCTACAACGA TTTTTCCA | 16940 |
| 1947 | GAAAAAAU G CCGACGGA | 7478 | TCCGTCGG GGCTAGCTACAACGA ATTTTTTC | 16941 |
| 1951 | AAAUGCCG A CGGAAGGA | 7479 | TCCTTCCG GGCTAGCTACAACGA CGGCATTT | 16942 |
| 1964 | AGGAGAGG A CCUGAAAC | 7480 | GTTTCAGG GGCTAGCTACAACGA CCTCTCCT | 16943 |
| 1971 | GACCUGAA A CUGUCUUG | 7481 | CAAGACAG GGCTAGCTACAACGA TTCAGGTC | 16944 |
| 1974 | CUGAAACU G UCUUGCAC | 7482 | GTGCAAGA GGCTAGCTACAACGA AGTTTCAG | 16945 |
| 1979 | ACUGUCUU G CACAGUUA | 7483 | TAACTGTG GGCTAGCTACAACGA AAGACAGT | 16946 |
| 1981 | UGUCUUGC A CAGUUAAC | 4545 | GTTAACTG GGCTAGCTACAACGA GCAAGACA | 16947 |
| 1984 | CUUGCACA G UUAACAAG | 7484 | CTTGTTAA GGCTAGCTACAACGA TGTGCAAG | 16948 |
| 1988 | CACAGUUA A CAAGUUCU | 7485 | AGAACTTG GGCTAGCTACAACGA TAACTGTG | 16949 |
| 1992 | GUUAACAA G UUCUUAUA | 7486 | TATAAGAA GGCTAGCTACAACGA TTGTTAAC | 16950 |
| 1998 | AAGUUCUU A UACAGAGA | 323 | TCTCTGTA GGCTAGCTACAACGA AAGAACTT | 16951 |
| 2000 | GUUCUUAU A CAGAGACG | 324 | CGTCTCTG GGCTAGCTACAACGA ATAAGAAC | 16952 |
| 2006 | AUACAGAG A CGUUACUU | 7487 | AAGTAACG GGCTAGCTACAACGA CTCTGTAT | 16953 |
| 2008 | ACAGAGAC G UUACUUGG | 7488 | CCAAGTAA GGCTAGCTACAACGA GTCTCTGT | 16954 |
| 2011 | GAGACGUU A CUUGGAUU | 326 | AATCCAAG GGCTAGCTACAACGA AACGTCTC | 16955 |
| 2017 | UUACUUGG A UUUUACUG | 7489 | CAGTAAAA GGCTAGCTACAACGA CCAAGTAA | 16956 |
| 2022 | UGGAUUUU A CUGCGGAC | 331 | GTCCGCAG GGCTAGCTACAACGA AAAATCCA | 16957 |
| 2025 | AUUUUACU G CGGACAGU | 7490 | ACTGTCCG GGCTAGCTACAACGA AGTAAAAT | 16958 |
| 2029 | UACUGCGG A CAGUUAAU | 7491 | ATTAACTG GGCTAGCTACAACGA CCGCAGTA | 16959 |
| 2032 | UGCGGACA G UUAAUAAC | 7492 | GTTATTAA GGCTAGCTACAACGA TGTCCGCA | 16960 |
| 2036 | GACAGUUA A UAACAGAA | 7493 | TTCTGTTA GGCTAGCTACAACGA TAACTGTC | 16961 |
| 2039 | AGUUAAUA A CAGAACAA | 7494 | TTGTTCTG GGCTAGCTACAACGA TATTAACT | 16962 |
| 2044 | AUAACAGA A CAAUGCAC | 7495 | GTGCATTG GGCTAGCTACAACGA TCTGTTAT | 16963 |

TABLE XVIII-continued

Human FLT DNAzyme and Substrate Sequence

| Pos | Substrate | Seq ID No | DNAzyme | Seq ID No |
|---|---|---|---|---|
| 2047 | ACAGAACA A UGCACUAC | 7496 | GTAGTGCA GGCTAGCTACAACGA TGTTCTGT | 16964 |
| 2049 | AGAACAAU G CACUACAG | 7497 | CTGTAGTG GGCTAGCTACAACGA ATTGTTCT | 16965 |
| 2051 | AACAAUGC A CUACAGUA | 4555 | TACTGTAG GGCTAGCTACAACGA GCATTGTT | 16966 |
| 2054 | AAUGCACU A CAGUAUUA | 335 | TAATACTG GGCTAGCTACAACGA AGTGCATT | 16967 |
| 2057 | GCACUACA G UAUUAGCA | 7498 | TGCTAATA GGCTAGCTACAACGA TGTAGTGC | 16968 |
| 2059 | ACUACAGU A UUAGCAAG | 336 | CTTGCTAA GGCTAGCTACAACGA ACTGTAGT | 16969 |
| 2063 | CAGUAUUA G CAAGCAAA | 7499 | TTTGCTTG GGCTAGCTACAACGA TAATACTG | 16970 |
| 2067 | AUUAGCAA G CAAAAAAU | 7500 | ATTTTTTG GGCTAGCTACAACGA TTGCTAAT | 16971 |
| 2074 | AGCAAAAA A UGGCCAUC | 7501 | GATGGCCA GGCTAGCTACAACGA TTTTTGCT | 16972 |
| 2077 | AAAAAAUG G CCAUCACU | 7502 | AGTGATGG GGCTAGCTACAACGA CATTTTTT | 16973 |
| 2080 | AAAUGGCC A UCACUAAG | 4561 | CTTAGTGA GGCTAGCTACAACGA GGCCATTT | 16974 |
| 2083 | UGGCCAUC A CUAAGGAG | 4562 | CTCCTTAG GGCTAGCTACAACGA GATGGCCA | 16975 |
| 2091 | ACUAAGGA G CACUCCAU | 7503 | ATGGAGTG GGCTAGCTACAACGA TCCTTAGT | 16976 |
| 2093 | UAAGGAGC A CUCCAUCA | 4564 | TGATGGAG GGCTAGCTACAACGA GCTCCTTA | 16977 |
| 2098 | AGCACUCC A UCACUCUU | 4567 | AAGAGTGA GGCTAGCTACAACGA GGAGTGCT | 16978 |
| 2101 | ACUCCAUC A CUCUUAAU | 4568 | ATTAAGAG GGCTAGCTACAACGA GATGGAGT | 16979 |
| 2108 | CACUCUUA A UCUUACCA | 7504 | TGGTAAGA GGCTAGCTACAACGA TAAGAGTG | 16980 |
| 2113 | UUAAUCUU A CCAUCAUG | 348 | CATGATGG GGCTAGCTACAACGA AAGATTAA | 16981 |
| 2116 | AUCUUACC A UCAUGAAU | 4573 | ATTCATGA GGCTAGCTACAACGA GGTAAGAT | 16982 |
| 2119 | UUACCAUC A UGAAUGUU | 4574 | AACATTCA GGCTAGCTACAACGA GATGGTAA | 16983 |
| 2123 | CAUCAUGA A UGUUUCCC | 7505 | GGGAAACA GGCTAGCTACAACGA TCATGATG | 16984 |
| 2125 | UCAUGAAU C UUUCCCUG | 7506 | CAGGGAAA GGCTAGCTACAACGA ATTCATGA | 16985 |
| 2133 | GUUUCCCU C CAAGAUUC | 7507 | GAATCTTG GGCTAGCTACAACGA AGGGAAAC | 16986 |
| 2138 | CCUGCAAG A UUCAGGCA | 7508 | TGCCTGAA GGCTAGCTACAACGA CTTGCAGG | 16987 |
| 2144 | AGAUUCAG G CACCUAUG | 7509 | CATAGGTG GGCTAGCTACAACGA CTGAATCT | 16988 |
| 2146 | AUUCAGGC A CCUAUGCC | 4580 | GGCATAGG GCCTAGCTACAACGA GCCTGAAT | 16989 |
| 2150 | AGGCACCU A UGCCUGCA | 355 | TGCAGGCA GGCTAGCTACAACGA AGGTGCCT | 16990 |
| 2152 | GCACCUAU G CCUGCAGA | 7510 | TCTCCAGG GGCTAGCTACAACGA ATACGTCC | 16991 |
| 2156 | CUAUGCCU G CAGAGCCA | 751 | UGGCTCTG GGCTAGCTACAACGA AGGCATAG | 16992 |
| 2161 | CCUGCAGA G CCAGGAAU | 7512 | ATTCCTGC CCCTAGCTACAACGA TCTGCAGG | 16993 |
| 2168 | ACCCAGGA A UGUAUACA | 7513 | TGTATACA GGCTAGCTACAACGA TCCTGGCT | 16994 |
| 2170 | CCAGGAAU G UAUACACA | 7514 | TGTGTATA GGCTAGCTACAACGA ATTCCTGG | 16995 |
| 2172 | AGGAAUGU A UACACAGG | 356 | CCTGTGTA GGCTAGCTACAACGA ACATTCCT | 16996 |
| 2174 | GAAUGUAU A CACAGCGG | 357 | CCCCTCTG GGCTAGCTACAACGA ATACATTC | 16997 |
| 2176 | AUGUAUAC A CAGGGGAA | 4588 | TTCCCCTG GGCTAGCTACAACGA GTATACAT | 16998 |
| 2188 | GGGAAGAA A UCCUCCAG | 7515 | CTGGAGGA GGCTAGCTACAACGA TTCTTCCC | 16999 |
| 2206 | AGAAAGAA A UUACAAUC | 7516 | GATTGTAA GGCTAGCTACAACGA TTCTTTCT | 17000 |

TABLE XVIII-continued

Human FLT DNAzyme and Substrate Sequence

| Pos | Substrate | Seq ID No | DNAzyme | Seq ID No |
|---|---|---|---|---|
| 2209 | AAGAAAUU A CAAUCAGA | 36 | UCTGATTG GGCTAGCTACAACGA AATTTCTT | 17001 |
| 2212 | AAAUUACA A UCAGAGAU | 7517 | ATCTCTGA GGCTAGCTACAACGA TGTAATTT | 17002 |
| 2219 | AAUCAGAG A UCAGGAAG | 7518 | CTTCCTGA GGCTAGCTACAACGA CTCTGATT | 17003 |
| 2227 | AUCAGGAA C CACCAUAC | 7519 | GTATGGTG GGCTAGCTACAACGA TTCCTCAT | 17004 |
| 2229 | CAGGAACC A CCAUACCU | 4597 | AGCTATGG GGCTAGCTACAACGA GCTTCCTG | 17005 |
| 2232 | GAAGCACC A UACCUCCU | 4599 | AGGACGTA CGCTAGCTACAACGA GGTGCTTC | 17006 |
| 2234 | AGCACCAU A CCUCCUGC | 364 | GCAGGAGG GGCTAGCTACAACGA ATGGTGCT | 17007 |
| 2241 | UACCUCCU C CGAAACCU | 7520 | AGGTTTCG GGCTACCTACAACGA ACCAGGTA | 17008 |
| 2246 | CCUGCGAA A CCUCAGUG | 7521 | CACTGAGG GGCTAGCTACAACGA TTCGCACG | 17009 |
| 2252 | AAACCUCA G UGAUCACA | 7522 | TGTCATCA GGCTAGCTACAACGA TGAGGTTT | 17010 |
| 2255 | CCUCAGUG A UCACACAG | 7523 | CTGTGTGA CGCTAGCTACAACGA CACTCAGG | 17011 |
| 2258 | CAGUGAUC A CACAGUGG | 4607 | CCACTGTG GGCTAGCTACAACGA GATCACTC | 17012 |
| 2260 | GUGAUCAC A CACUGCCC | 4608 | GGCCACTG CCCTAGCTACAACGA GTGATCAC | 17013 |
| 2263 | AUCACACA G UGGCCAUC | 7524 | GATCGCCA GCCTAGCTACAACGA TGTGTGAT | 17014 |
| 2266 | ACACAGUG G CCAUCAGC | 7525 | GCTGATCG CGCTAGCTACAACGA CACTGTCT | 17015 |
| 2269 | CAGUGGCC A UCAGCAGU | 4611 | ACTGCTCA GGCTAGCTACAACGA GCCCACTG | 17016 |
| 2273 | GGCCAUCA G CAGUUCCA | 7526 | TGCAACTG GGCTAGCTACAACGA TGATGGCC | 17017 |
| 2276 | CAUCAGCA G UUCCACCA | 7527 | TGGTGGAA GGCTAGCTACAACGA TGCTGATG | 17018 |
| 2281 | GCAGUUCC A CCACUUUA | 4615 | TAAAGTGG GGCTAGCTACAACGA GGAACTCC | 17019 |
| 2284 | GUUCCACC A CUUUAGAC | 4617 | GTCTAAAG GGCTAGCTACAACGA GGTGGAAC | 17020 |
| 2291 | CACUUUAG A CUGUCAUG | 7528 | CATGACAG GGCTAGCTACAACGA CTAAAGTG | 17021 |
| 2294 | UUUAGACU G UCAUGCUA | 7529 | TAGCATGA GGCTAGCTACAACGA AGTCTAAA | 17022 |
| 2297 | AGACUGUC A UGCUAAUG | 4620 | CATTAGCA GGCTAGCTACAACGA GACAGTCT | 17023 |
| 2299 | ACUGUCAU G CUAAUGGU | 7530 | ACCATTAG GGCTAGCTACAACGA ATGACAGT | 17024 |
| 2303 | UCAUGCUA A UGGUGUCC | 7531 | GGACACCA GGCTAGCTACAACGA TAGCATGA | 17025 |
| 2306 | UGCUAAUG G UGUCCCCG | 7532 | CGGGGACA GGCTAGCTACAACGA CATTAGCA | 17026 |
| 2308 | CUAAUGGU G UCCCGAG | 7533 | CTCGGGGA GGCTAGCTACAACGA ACCATTAG | 17027 |
| 2316 | GUCCCCGA G CCUCAGAU | 7534 | ATCTGAGG GGCTAGCTACAACGA TCGGGGAC | 17028 |
| 2323 | AGCCUCAG A UCACUUGG | 7535 | CCAAGTGA GGCTAGCTACAACGA CTGAGGCT | 17029 |
| 2326 | CUCAGAUC A CUUGGUUU | 4628 | AAACCAAG GGCTAGCTACAACGA GATCTGAG | 17030 |
| 2331 | AUCACUUG C UUUAAAAA | 7536 | TTTTTAAA GGCTAGCTACAACGA CAAGTGAT | 17031 |
| 2339 | GUUUAAAA A CAACCACA | 7537 | TGTGGTTG GGCTAGCTACAACGA TTTTAAAC | 17032 |
| 2342 | UAAAAACA A CCACAAAA | 7538 | TTTTGTGG GGCTAGCTACAACGA TGTTTTTA | 17033 |
| 2345 | AAACAACC A CAAAAUAC | 4632 | GTATTTTG GGCTAGCTACAACGA GGTTGTTT | 17034 |
| 2350 | ACCACAAA A UACAACAA | 7539 | TTGTTGTA GGCTAGCTACAACGA TTTGTGGT | 17035 |
| 2352 | CACAAAAU A CAACAAGA | 383 | TCTTGTTG GGCTAGCTACAACGA ATTTTGTG | 17036 |
| 2355 | AAAAUACA A CAAGAGCC | 7540 | GGCTCTTG GGCTAGCTACAACGA TGTATTTT | 17037 |

TABLE XVIII-continued

Human FLT DNAzyme and Substrate Sequence

| Pos | Substrate | Seq ID No | DNAzyme | Seq ID No |
|---|---|---|---|---|
| 2361 | CAACAAGA G CCUGGAAU | 7541 | ATTCCAGG GGCTAGCTACAACGA TCTTGTTG | 17038 |
| 2368 | AGCCUGGA A UUAUUUUA | 7542 | TAAAATAA GGCTAGCTACAACGA TCCAGGCT | 17039 |
| 2371 | CUGGAAUU A UUUUAGGA | 385 | TCCTAAAA GGCTAGCTACAACGA AATTCCAG | 17040 |
| 2379 | AUUUUAGG A CCAGGAAG | 7543 | CTTCCTGG GGCTAGCTACAACGA CCTAAAAT | 17041 |
| 2387 | ACCAGGAA G CAGCACGC | 7544 | GCGTGCTG GGCTAGCTACAACGA TTCCTGGT | 17042 |
| 2390 | AGGAAGCA G CACGCUGU | 7545 | ACAGCGTG GGCTAGCTACAACGA TGCTTCCT | 17043 |
| 2392 | GAAGCAGC A CGCUGUUU | 4641 | AAACAGCG GGCTAGCTACAACGA GCTGCTTC | 17044 |
| 2394 | AGCAGCAC G CUGUUUAU | 7546 | ATAAACAG GGCTAGCTACAACGA GTGCTGCT | 17045 |
| 2397 | AGCACGCU G UUUAUUGA | 7547 | TCAATAAA GGCTAGCTACAACGA AGCGTGCT | 17046 |
| 2401 | CGCUGUUU A UUGAAAGA | 392 | TCTTTCAA GGCTAGCTACAACGA AAACAGCG | 17047 |
| 2410 | UUGAAAGA G UCACAGAA | 7548 | TTCTGTGA GGCTAGCTACAACGA TCTTTCAA | 17048 |
| 2413 | AAAGAGUC A CAGAAGAG | 4643 | CTCTTCTG GGCTAGCTACAACGA GACTCTTT | 17049 |
| 2423 | AGAAGAGG A UGAAGGUG | 7549 | CACCTTCA GGCTAGCTACAACGA CCTCTTCT | 17050 |
| 2429 | GGAUGAAG G UGUCUAUC | 7550 | GATAGACA GGCTAGCTACAACGA CTTCATCC | 17051 |
| 2431 | AUGAAGGU G UCUAUCAC | 7551 | GTGATAGA GGCTAGCTACAACGA ACCTTCAT | 17052 |
| 2435 | AGGUGUCU A UCACUGCA | 396 | TGCAGTGA GGCTAGCTACAACGA AGACACCT | 17053 |
| 2438 | UGUCUAUC A CUGCAAAG | 4646 | CTTTGCAG GGCTAGCTACAACGA GATAGACA | 17054 |
| 2441 | CUAUCACU G CAAAGCCA | 7552 | TGGCTTTG GGCTAGCTACAACGA AGTGATAG | 17055 |
| 2446 | ACUGCAAA G CCACCAAC | 7553 | GTTGGTGG GGCTAGCTACAACGA TTTGCAGT | 17056 |
| 2449 | GCAAAGCC A CCAACCAG | 4650 | CTGGTTGG GGCTAGCTACAACGA GGCTTTGC | 17057 |
| 2453 | AGCCACCA A CCAGAAGG | 7554 | CCTTCTGG GGCTAGCTACAACGA TGGTGGCT | 17058 |
| 2462 | CCAGAAGG G CUCUGUGG | 7555 | CCACAGAG GGCTAGCTACAACGA CCTTCTGG | 17059 |
| 2467 | AGGGCUCU C UGGAAAGU | 7556 | ACTTTCCA GGCTAGCTACAACGA AGAGCCCT | 17060 |
| 2474 | UGUGGAAA G UUCAGCAU | 7557 | ATGCTGAA GGCTAGCTACAACGA TTTCCACA | 17061 |
| 2479 | AAAGUUCA C CAUACCUC | 7558 | GAGGTATG GGCTAGCTACAACGA TGAACTTT | 17062 |
| 2481 | AGUUCAGC A UACCUCAC | 4658 | GTGAGGTA GGCTAGCTACAACGA GCTGAACT | 17063 |
| 2483 | UUCAGCAU A CCUCACUG | 401 | CAGTGAGG GGCTAGCTACAACGA ATGCTGAA | 17064 |
| 2488 | CAUACCUC A CUGUUCAA | 466 | TTGAACAG GGCTAGCTACAACGA GAGGTATG | 17065 |
| 2491 | ACCUCACU C UUCAAGGA | 7559 | TCCTTGAA GGCTAGCTACAACGA AGTGAGGT | 17066 |
| 2500 | UUCAAGGA A CCUCGGAC | 7560 | GTCCGAGG GGCTAGCTACAACGA TCCTTGAA | 17067 |
| 2507 | AACCUCGG A CAAGUCUA | 756 | TAGACTTG GGCTAGCTACAACGA CCGAGGTT | 17068 |
| 2511 | UCGGACAA G UCUAAUCU | 7562 | AGATTAGA GGCTAGCTACAACGA TTGTCCGA | 17069 |
| 2516 | CAAGUCUA A UCUGGAGC | 7563 | GCTCCAGA GGCTAGCTACAACGA TAGACTTG | 17070 |
| 2523 | AAUCUGGA G CUGAUCAC | 7564 | GTGATCAG GGCTAGCTACAACGA TCCAGATT | 17071 |
| 2527 | UGGAGCUG A UCACUCUA | 7565 | TAGAGTGA GGCTAGCTACAACGA CAGCTCCA | 17072 |
| 2530 | AGCUGAUC A CUCUAACA | 4670 | TGTTAGAG GGCTAGCTACAACGA GATCAGCT | 17073 |
| 2536 | UCACUCUA A CAUGCACC | 7566 | GGTGCATG GGCTAGCTACAACGA TAGAGTGA | 17074 |

TABLE XVIII-continued

Human FLT DNAzyme and Substrate Sequence

| Pos | Substrate | Seq ID No | DNAzyme | Seq ID No |
|---|---|---|---|---|
| 2538 | ACUCUAAC A UGCACCUG | 4673 | CAGGTGCA GGCTAGCTACAACGA GTTAGAGT | 17075 |
| 2540 | UCUAACAU G CACCUGUG | 7567 | CACAGGTG GGCTAGCTACAACGA ATGTTAGA | 17076 |
| 2542 | UAACAUGC A CCUGUGUG | 4674 | CACACAGG GGCTAGCTACAACGA GCATGTTA | 17077 |
| 2546 | AUGCACCU G UGUGGCUG | 7568 | CAGCCACA GGCTAGCTACAACGA AGGTGCAT | 17078 |
| 2548 | GCACCUGU C UGGCUGCG | 7569 | CGCAGCCA GGCTAGCTACAACGA ACAGGTGC | 17079 |
| 2551 | GCUGUGUG C CUGCGACU | 7570 | AGTCGCAG GGCTAGCTACAACGA CACACAGG | 17080 |
| 2554 | GUGUGGCU G CGACUCUC | 7571 | GAGAGTCG GGCTAGCTACAACGA AGCCACAC | 17081 |
| 2557 | UGGCUGCG A CUCUCUUC | 7572 | GAAGACAG GGCTAGCTACAACGA CGCAGCCA | 17082 |
| 2568 | CUCCUCUG G CUCCUAUU | 7573 | AATAGGAG GGCTAGCTACAACGA CAGAAGAG | 17083 |
| 2574 | UGGCUCCU A UUAACCCU | 417 | AGGGTTAA GGCTAGCTACAACGA AGGAGCCA | 17084 |
| 2578 | UCCUAUUA A CCCUCCUU | 7574 | AAGGAGGG GGCTAGCTACAACGA TAATAGGA | 17085 |
| 2587 | CCCUCCUU A UCCGAAAA | 422 | TTTTCGGA GGCTAGCTACAACGA AAGGAGGG | 17086 |
| 2596 | UCCGAAAA A UGAAAAGG | 7575 | CCTTTTCA GGCTAGCTACAACGA TTTTCGGA | 17087 |
| 2604 | AUGAAAAC G CUUCUUC | 7576 | GAAGAAGA GGCTAGCTACAACGA CTTTTCAT | 17088 |
| 2617 | CUUCUGAA A UAAAGACU | 7577 | AGTCTTTA GGCTAGCTACAACGA TTCAGAAG | 17089 |
| 2623 | AAAUAAAG A CUGACUAC | 7578 | GTAGTCAG GGCTAGCTACAACGA CTTTATTT | 17090 |
| 2627 | AAAGACUG A CUACCUAU | 7579 | ATAGGTAG GGCTAGCTACAACGA CAGTCTTT | 17091 |
| 2630 | GACUGACU A CCUAUCAA | 430 | TTGATAGG GGCTAGCTACAACGA AGTCAGTC | 17092 |
| 2634 | GACUACCU A UCAAUUAU | 431 | ATAATTGA GGCTAGCTACAACGA AGGTAGTC | 17093 |
| 2638 | ACCUAUCA A UUAUAAUG | 7580 | CATTATAA GGCTAGCTACAACGA TGATAGGT | 17094 |
| 2641 | UAUCAAUU A UAAUGGAC | 434 | GTCCATTA GGCTAGCTACAACGA AATTGATA | 17095 |
| 2644 | CAAUUAUA A UGGACCCA | 758 | TGGGTCCA GGCTAGCTACAACGA TATAATTG | 17096 |
| 2648 | UAUAAUGG A CCCAGAUG | 7582 | CATCTGGG GGCTAGCTACAACGA CCATTATA | 17097 |
| 2654 | GGACCCAG A UGAAGUUC | 7583 | GAACTTCA GGCTAGCTACAACGA CTGGGTCC | 17098 |
| 2659 | CAGAUGAA C UUCCUUUG | 7584 | CAAAGGAA GGCTAGCTACAACGA TTCATCTG | 17099 |
| 2669 | UCCUUUGC A UGAGCAGU | 7585 | ACTGCTCA GGCTAGCTACAACGA CCAAAGGA | 17100 |
| 2673 | UUGGAUGA G CAGUGUGA | 7586 | TCACACTG GGCTAGCTACAACGA TCATCCAA | 17101 |
| 2676 | GAUGAGCA G UGUGAGCG | 7587 | CGCTCACA GGCTAGCTACAACGA TGCTCATC | 17102 |
| 2678 | UGAGCAGU G UGAGCGGC | 7588 | GCCGCTCA GGCTAGCTACAACGA ACTGCTCA | 17103 |
| 2682 | CAGUGUGA G CGGCUCCC | 7589 | GGGAGCCG GGCTAGCTACAACGA TCACACTG | 17104 |
| 2685 | UGUGAGCG G CUCCCUUA | 7590 | TAAGGCAG GGCTAGCTACAACGA CGCTCACA | 17105 |
| 2693 | GCUCCCUU A UGAUGCCA | 442 | TGGCATCA GGCTAGCTACAACGA AAGGGAGC | 17106 |
| 2696 | CCCUUAUG A UGCCAGCA | 759 | UGCTGGCA GGCTAGCTACAACGA CATAAGGG | 17107 |
| 2698 | CUUAUGAU G CCAGCAAG | 7592 | CTTGCTGG GGCTAGCTACAACGA ATCATAAG | 17108 |
| 2702 | UGAUGCCA C CAAGUGGG | 7593 | CCCACTTG GGCTAGCTACAACGA TGGCATCA | 17109 |
| 2706 | GCCAGCAA G UGGGAGUU | 7594 | AACTCCCA GGCTAGCTACAACGA TTGCTGGC | 17110 |
| 2712 | AAGUGGGA G UUUGCCCG | 7595 | CGGGCAAA GGCTAGCTACAACGA TCCCACTT | 17111 |

TABLE XVIII-continued

Human FLT DNAzyme and Substrate Sequence

| Pos | Substrate | Seq ID No | DNAzyme | Seq ID No |
|---|---|---|---|---|
| 2716 | CGGAGUUU C CCCGGGAC | 7596 | CTCCCGGG GGCTAGCTACAACGA AAACTCCC | 17112 |
| 2727 | CGCGAGAG A CUUAAACU | 7597 | AGTTTAAG GGCTAGCTACAACGA CTCTCCCG | 17113 |
| 2733 | AGACUUAA A CUGGGCAA | 7598 | TTGCCCAG GGCTAGCTACAACGA TTAAGTCT | 17114 |
| 2738 | UAAACUGG C CAAAUCAC | 7599 | CTGATTTG GGCTAGCTACAACGA CCAGTTTA | 17115 |
| 2742 | CUGGGCAA A UCACUUGG | 7600 | CCAAGTGA GGCTAGCTACAACGA TTGCCCAG | 17116 |
| 2745 | GGCAAAUC A CUUGGAAG | 4717 | CTTCCAAG GGCTAGCTACAACGA GATTTGCC | 17117 |
| 2758 | GAAGAGGG G CUUUUGGA | 760 | UCCAAAAG GGCTAGCTACAACGA CCCTCTTC | 17118 |
| 2770 | UUGGAAAA G UGGUUCAA | 7602 | TTGAACCA GGCTAGCTACAACGA TTTTCCAA | 17119 |
| 2773 | GAAAAGUG G UUCAAGCA | 7603 | TGCTTGAA GGCTAGCTACAACGA CACTTTTC | 17120 |
| 2779 | UGGUUCAA G CAUCAGCA | 7604 | TGCTGATG GGCTAGCTACAACGA TTGAACCA | 17121 |
| 2781 | GUUCAAGC A UCAGCAUU | 4721 | AATGCTGA GGCTAGCTACAACGA GCTTGAAC | 17122 |
| 2785 | AAGCAUCA G CAUUUGGC | 7605 | GCCAAATG GGCTAGCTACAACGA TGATGCTT | 17123 |
| 2787 | GCAUCAGC A UUUGGCAU | 4723 | ATGCCAAA GGCTAGCTACAACGA GCTGATGC | 17124 |
| 2792 | AGCAUUUG G CAUUAAGA | 7606 | TCTTAATG GGCTAGCTACAACGA CAAATGCT | 17125 |
| 2794 | CAUUUGGC A UUAAGAAA | 4724 | TTTCTTAA GGCTAGCTACAACGA GCCAAATG | 17126 |
| 2802 | AUUAAGAA A UCACCUAC | 7607 | GTAGGTGA GGCTAGCTACAACGA TTCTTAAT | 17127 |
| 2805 | AAGAAAUC A CCUACGUG | 4725 | CACGTAGG GGCTAGCTACAACGA GATTTCTT | 17128 |
| 2809 | AAUCACCU A CGUGCCGG | 460 | CCGGCACG GGCTAGCTACAACGA AGGTGATT | 17129 |
| 2811 | UCACCUAC C UCCCGCAC | 7608 | CTCCGGCA GGCTAGCTACAACGA GTAGGTGA | 17130 |
| 2813 | ACCUACGU C CCGGACUG | 7609 | CAGTCCGG GGCTAGCTACAACGA ACGTAGGT | 17131 |
| 2818 | CGUCCCGC A CUGUGGCU | 7610 | AGCCACAG GGCTAGCTACAACGA CCCCCACG | 17132 |
| 2821 | CCCCCACU C UGGCUGUG | 7611 | CACAGCCA GGCTAGCTACAACGA AGTCCGGC | 17133 |
| 2824 | GGACUCUG G CUGUCAAA | 7612 | TTTCACAG GGCTAGCTACAACGA CACAGTCC | 17134 |
| 2827 | CUGUGGCU G UGAAAAUG | 7613 | CATTTTCA GGCTAGCTACAACGA AGCCACAG | 17135 |
| 2833 | CUCUCAAA A UCCUCAAA | 7614 | TTTCACCA CGCTACCTACAACGA TTTCACAG | 17136 |
| 2835 | GUGAAAAU G CUGAAACA | 7615 | TCTTTCAG GGCTAGCTACAACGA ATTTTCAC | 17137 |
| 2848 | AACAGGGC G CCACGGCC | 7616 | GGCCCTGG GGCTACCTACAACGA CCCTCTT | 17138 |
| 2851 | AGGGCGCC A CCCCCAGC | 4733 | GCTGCCCC GGCTACCTACAACGA CCCCCCCT | 17139 |
| 2854 | GCCCCACC G CCAGCGAG | 7617 | CTCGCTCG GGCTAGCTACAACGA CGTCGCCC | 17140 |
| 2858 | CACCCCCA G CGACUACA | 7618 | TGTACTCC GGCTACCTACAACGA TCCCCCTG | 17141 |
| 2862 | GCCAGCGA G UACAAACC | 7619 | GCTTTGTA GCCTAGCTACAACGA TCCCTCGC | 17142 |
| 2864 | CAGCGAGU A CAAAGCUC | 461 | GAGCTTTC GGCTAGCTACAACGA ACTCCCTC | 17143 |
| 2869 | ACUACAAA C CUCUGAUC | 7620 | CATCAGAC GGCTACCTACAACGA TTTCTACT | 17144 |
| 2875 | AACCUCUG A UGACUGAC | 7621 | CTCAGTCA GCCTAGCTACAACGA CACACCTT | 17145 |
| 2878 | CUCUGAUG A CUGACCUA | 7622 | TACCTCAG GGCTAGCTACAACGA CATCAGAC | 17146 |
| 2883 | AUGACUGA C CUAAAAUU | 7623 | ATTTTTAG GGCTAGCTACAACGA TCAGTCAT | 17147 |
| 2890 | AGCUAAAA A UCUUGACC | 7624 | CCTCAACA GCCTAGCTACAACGA TTTTAGCT | 17148 |

TABLE XVIII-continued

Human FLT DNAzyme and Substrate Sequence

| Pos | Substrate | Seq ID No | DNAzyme | Seq ID No |
|---|---|---|---|---|
| 2896 | AAAUCUUG A CCCACAUU | 7625 | AATGTGGG GCCTAGCTACAACGA CAAGATTT | 17149 |
| 2900 | CUUGACCC A CAUUGGCC | 4744 | GGCCAATG GGCTAGCTACAACGA GGGTCAAG | 17150 |
| 2902 | UCACCCAC A UUGGCCAC | 4745 | GTCCCCAA GGCTAGCTACAACGA GTGGGTCA | 17151 |
| 2906 | CCACAUUG C CCACCAUC | 7626 | CATCGTGG GGCTACCTACAACGA CAATGTGG | 17152 |
| 2909 | CAUUCGCC A CCAUCUGA | 4747 | TCACATGC CCCTAGCTACAACGA CCCCAATG | 17153 |
| 2912 | UCGCCACC A UCUGAACG | 4749 | CGTTCAGA GCCTAGCTACAACGA GGTGGCCA | 17154 |
| 2918 | CCAUCUGA A CGUGCUUA | 7627 | TAACCACG CCCTAGCTACAACGA TCAGATGG | 17155 |
| 2920 | AUCUGAAC C UCCUUAAC | 7628 | CTTAACCA GGCTACCTACAACGA GTTCACAT | 17156 |
| 2923 | UGAACGUG C UUAACCUG | 7629 | CAGGTTAA GGCTAGCTACAACGA CACGTTCA | 17157 |
| 2927 | CCUCCUUA A CCUCCUCC | 7630 | CCAGCACC CGCTACCTACAACGA TAACCACC | 17158 |
| 2931 | GUUAACCU C CUCCGACC | 7631 | GCTCCCAC GGCTAGCTACAACGA AGCTTAAC | 17159 |
| 2938 | UCCUCCCA C CCUGCACC | 7632 | CCTCCACG CCCTACCTACAACGA TCCCACCA | 17160 |
| 2942 | CCCACCCU C CACCAAGC | 7633 | GCTTCCTG CGCTAGCTACAACGA AGGCTCCC | 17161 |
| 2944 | CACCCUCC A CCAAGCAA | 4756 | TTGCTTCG GCCTAGCTACAACGA GCAGGCTC | 17162 |
| 2949 | UCCACCAA C CAAGGACG | 7634 | CCTCCTTG CGCTAGCTACAACGA TTCCTCCA | 17163 |
| 2958 | CAAGCACG C CCUCUCAU | 7635 | ATCAGACC CCCTACCTACAACGA CCTCCTTC | 17164 |
| 2965 | GGCCUCUG A UGGUGAUU | 7636 | AATCACCA GGCTAGCTACAACGA CAGAGGCC | 17165 |
| 2968 | CUCUGAUG G UGAUUGUU | 7637 | AACAATCA GGCTAGCTACAACGA CATCAGAG | 17166 |
| 2971 | UGAUGGUG A UUGUUGAA | 7638 | TTCAACAA GGCTAGCTACAACGA CACCATCA | 17167 |
| 2974 | UGGUGAUU G UUGAAUAC | 7639 | GTATTCAA GGCTAGCTACAACGA AATCACCA | 17168 |
| 2979 | AUUGUUGA A UACUGCAA | 7640 | TTGCAGTA GGCTAGCTACAACGA TCAACAAT | 17169 |
| 2981 | UGUUGAAU A CUGCAAAU | 473 | ATTTGCAG GGCTAGCTACAACGA ATTCAACA | 17170 |
| 2984 | UGAAUACU G CAAAUAUG | 7641 | CATATTTG GGCTAGCTACAACGA AGTATTCA | 17171 |
| 2988 | UACUGCAA A UAUGGAAA | 7642 | TTTCCATA GGCTAGCTACAACGA TTGCAGTA | 17172 |
| 2990 | CUGCAAAU A UGGAAAUC | 474 | GATTTCCA GGCTAGCTACAACGA ATTTGCAG | 17173 |
| 2996 | AUAUGGAA A UCUCUCCA | 7643 | TGGAGAGA GGCTAGCTACAACGA TTCCATAT | 17174 |
| 3005 | UCUCUCCA A CUACCUCA | 7644 | TGAGGTAG GGCTAGCTACAACGA TGGAGAGA | 17175 |
| 3008 | CUCCAACU A CCUCAAGA | 478 | TCTTGAGG GGCTAGCTACAACGA AGTTGGAG | 17176 |
| 3017 | CCUCAAGA G CAAACGUG | 7645 | CACGTTTG GGCTAGCTACAACGA TCTTGAGG | 17177 |
| 3021 | AAGAGCAA A CGUGACUU | 7646 | AAGTCACG GGCTAGCTACAACGA TTGCTCTT | 17178 |
| 3023 | GAGCAAAC G UGACUUAU | 7647 | ATAAGTCA GGCTAGCTACAACGA GTTTGCTC | 17179 |
| 3026 | CAAACGUG A CUUAUUUU | 7648 | AAAATAAG GGCTAGCTACAACGA CACGTTTG | 17180 |
| 3030 | CGUGACUU A UUUUUUCU | 481 | AGAAAAAA GGCTAGCTACAACGA AAGTCACG | 17181 |
| 3041 | UUUUCUCA A CAAGGAUG | 7649 | CATCCTTG GGCTAGCTACAACGA TGAGAAAA | 17182 |
| 3047 | CAACAAGG A UGCAGCAC | 7650 | GTGCTGCA GGCTAGCTACAACGA CCTTGTTG | 17183 |
| 3049 | ACAAGGAU G CAGCACUA | 765 | UAGTGCTG GGCTAGCTACAACGA ATCCTTGT | 17184 |
| 3052 | AGGAUGCA G CACUACAC | 7652 | GTGTAGTG GGCTAGCTACAACGA TGCATCCT | 17185 |

TABLE XVIII-continued

Human FLT DNAzyme and Substrate Sequence

| Pos | Substrate | Seq ID No | DNAzyme | Seq ID No |
|---|---|---|---|---|
| 3054 | GAUGCAGC A CUACACAU | 4779 | ATGTGTAG GGCTAGCTACAACGA GCTGCATC | 17186 |
| 3057 | GCAGCACU A CACAUGGA | 489 | TCCATGTG GGCTAGCTACAACGA AGTGCTGC | 17187 |
| 3059 | AGCACUAC A CAUGGAGC | 4781 | GCTCCATG GGCTAGCTACAACGA GTAGTGCT | 17188 |
| 3061 | CACUACAC A UGGAGCCU | 4782 | AGGCTCCA GGCTAGCTACAACGA GTGTAGTG | 17189 |
| 3066 | CACAUGGA G CCUAAGAA | 7653 | TTCTTAGG GGCTAGCTACAACGA TCCATGTG | 17190 |
| 3082 | AAGAAAAA A UGGAGCCA | 7654 | TGGCTCCA GGCTAGCTACAACGA TTTTTCTT | 17191 |
| 3087 | AAAAUGGA G CCAGGCCU | 7655 | AGGCCTGG GGCTAGCTACAACGA TCCATTTT | 17192 |
| 3092 | GGAGCCAG G CCUGGAAC | 7656 | GTTCCAGG GGCTAGCTACAACGA CTGGCTCC | 17193 |
| 3099 | GGCCUGGA A CAAGGCAA | 7657 | TTGCCTTG GGCTAGCTACAACGA TCCAGGCC | 17194 |
| 3104 | GGAACAAG G CAAGAAAC | 7658 | GTTTCTTG GGCTAGCTACAACGA CTTGTTCC | 17195 |
| 3111 | GGCAAGAA A CCAAGACU | 7659 | AGTCTTGG GGCTAGCTACAACGA TTCTTGCC | 17196 |
| 3117 | AAACCAAG A CUAGAUAG | 7660 | CTATCTAG GGCTAGCTACAACGA CTTGGTTT | 17197 |
| 3122 | AAGACUAG A UAGCGUCA | 766 | UGACGCTA GGCTAGCTACAACGA CTAGTCTT | 17198 |
| 3125 | ACUAGAUA G CGUCACCA | 7662 | TGGTGACG GGCTAGCTACAACGA TATCTAGT | 17199 |
| 3127 | UAGAUAGC G UCACCAGC | 7663 | GCTGGTGA GGCTAGCTACAACGA GCTATCTA | 17200 |
| 3130 | AUAGCGUC A CCAGCAGC | 4794 | GCTGCTGG GGCTAGCTACAACGA GACGCTAT | 17201 |
| 3134 | CGUCACCA G CAGCGAAA | 7664 | TTTCGCTG GGCTAGCTACAACGA TGGTGACG | 17202 |
| 3137 | CACCAGCA G CGAAAGCU | 7665 | AGCTTTCG GGCTAGCTACAACGA TGCTGGTG | 17203 |
| 3143 | CAGCGAAA G CUUUGCGA | 7666 | TCGCAAAG GGCTAGCTACAACGA TTTCGCTG | 17204 |
| 3148 | AAAGCUUU G CGAGCUCC | 7667 | GGAGCTCG GGCTAGCTACAACGA AAAGCTTT | 17205 |
| 3152 | CUUUGCGA G CUCCGGCU | 7668 | AGCCGGAG GGCTAGCTACAACGA TCGCAAAG | 17206 |
| 3158 | GAGCUCCG G CUUUCAGG | 7669 | CCTGAAAG GGCTAGCTACAACGA CGGAGCTC | 17207 |
| 3170 | UCAGGAAG A UAAAAGUC | 7670 | GACTTTTA GGCTAGCTACAACGA CTTCCTGA | 17208 |
| 3176 | AGAUAAAA G UCUGAGUG | 7671 | CACTCAGA GGCTAGCTACAACGA TTTTATCT | 17209 |
| 3182 | AAGUCUGA G UGAUGUUG | 7672 | CAACATCA GGCTAGCTACAACGA TCAGACTT | 17210 |
| 3185 | UCUGAGUG A UGUUGAGG | 7673 | CCTCAACA GGCTAGCTACAACGA CACTCAGA | 17211 |
| 3187 | UGAGUGAU G UUGAGGAA | 7674 | TTCCTCAA GGCTAGCTACAACGA ATCACTCA | 17212 |
| 3203 | AGAGGAGG A UUCUGACG | 7675 | CGTCAGAA GGCTAGCTACAACGA CCTCCTCT | 17213 |
| 3209 | GGAUUCUG A CGGUUUCU | 7676 | AGAAACCG GGCTAGCTACAACGA CAGAATCC | 17214 |
| 3212 | UUCUGACG G UUUCUACA | 7677 | TGTAGAAA GGCTAGCTACAACGA CGTCAGAA | 17215 |
| 3218 | CGGUUUCU A CAAGGAGC | 508 | GCTCCTTG GGCTAGCTACAACGA AGAAACCG | 17216 |
| 3225 | UACAAGGA G CCCAUCAC | 7678 | GTGATGGG GGCTAGCTACAACGA TCCTTGTA | 17217 |
| 3229 | AGGAGCCC A UCACUAUG | 4809 | CATAGTGA GGCTAGCTACAACGA GGCCTCCT | 17218 |
| 3232 | AGCCCAUC A CUAUGGAA | 4810 | TTCCATAG GGCTAGCTACAACGA GATGGGCT | 17219 |
| 3235 | CCAUCACU A UGGAAGAU | 510 | ATCTTCCA GGCTAGCTACAACGA AGTGATGG | 17220 |
| 3242 | UAUGGAAG A UCUGAUUU | 7679 | AAATCAGA GGCTAGCTACAACGA CTTCCATA | 17221 |
| 3247 | AAGAUCUG A UUUCUUAC | 7680 | GTAAGAAA GGCTAGCTACAACGA CAGATCTT | 17222 |

TABLE XVIII-continued

Human FLT DNAzyme and Substrate Sequence

| Pos | Substrate | Seq ID No | DNAzyme | Seq ID No |
|---|---|---|---|---|
| 3254 | GAUUUCUU A CAGUUUUC | 516 | GAAAACTG GGCTAGCTACAACGA AAGAAATC | 17223 |
| 3257 | UUCUUACA G UUUUCAAG | 7681 | CTTGAAAA GGCTAGCTACAACGA TGTAAGAA | 17224 |
| 3265 | GUUUUCAA G UGGCCAGA | 7682 | TCTGGCCA GGCTAGCTACAACGA TTGAAAAC | 17225 |
| 3268 | UUCAAGUG G CCAGAGGC | 7683 | GCCTCTGG GGCTAGCTACAACGA CACTTGAA | 17226 |
| 3275 | GGCCAGAG G CAUGGAGU | 7684 | ACTCCATG GGCTAGCTACAACGA CTCTGGCC | 17227 |
| 3277 | CCAGAGGC A UGGAGUUC | 4818 | GAACTCCA GGCTAGCTACAACGA GCCTCTGG | 17228 |
| 3282 | GGCAUGGA G UUCCUGUC | 7685 | GACAGGAA GGCTAGCTACAACGA TCCATGCC | 17229 |
| 3288 | GAGUUCCU G UCUUCCAG | 7686 | CTGGAAGA GGCTAGCTACAACGA AGGAACTC | 17230 |
| 3300 | UCCAGAAA G UGCAUUCA | 7687 | TGAATGCA GGCTAGCTACAACGA TTTCTGGA | 17231 |
| 3302 | CAGAAAGU C CAUUCAUC | 7688 | GATGAATG GGCTAGCTACAACGA ACTTTCTG | 17232 |
| 3304 | GAAAGUGC A UUCAUCGG | 4824 | CCGATGAA GGCTAGCTACAACGA GCACTTTC | 17233 |
| 3308 | GUGCAUUC A UCGGGACC | 4825 | GGTCCCGA GGCTAGCTACAACGA GAATGCAC | 17234 |
| 3314 | UCAUCGGG A CCUGGCAG | 7689 | CTGCCAGG GGCTAGCTACAACGA CCCGATGA | 17235 |
| 3319 | GGGACCUG C CACCGACA | 7690 | TCTCCCTG GGCTAGCTACAACGA CAGGTCCC | 17236 |
| 3322 | ACCUGGCA G CCAGAAAC | 7691 | GTTTCTCC CGCTACCTACAACGA TGCCACGT | 17237 |
| 3329 | ACCCACAA A CAUUCUUU | 7692 | AAAGAATG GGCTAGCTACAACGA TTCTCGCT | 17238 |
| 3331 | CGAGAAAC A UUCUUUUA | 4829 | TAAAAGAA GGCTAGCTACAACGA GTTTCTCG | 17239 |
| 3339 | AUUCUUUU A UCUGAGAA | 534 | TTCTCAGA GGCTAGCTACAACGA AAAAGAAT | 17240 |
| 3347 | AUCUGAGA A CAACGUCG | 7693 | CCACGTTG GGCTAGCTACAACGA TCTCAGAT | 17241 |
| 3350 | UGAGAACA A CGUGGUCA | 7694 | TCACCACG CGCTAGCTACAACGA TGTTCTCA | 17242 |
| 3352 | AGAACAAC G UGGUGAAG | 7695 | CTTCACCA CCCTACCTACAACGA CTTCTTCT | 17243 |
| 3355 | ACAACGUG G UCAAGAUU | 7696 | AATCTTCA GGCTAGCTACAACGA CACGTTGT | 17244 |
| 3361 | UCCUGAAG A UUUCUGAU | 7697 | ATCACAAA GGCTAGCTACAACGA CTTCACCA | 17245 |
| 3365 | GAAGAUUU C UGAUUUUG | 7698 | CAAAATCA GGCTAGCTACAACGA AAATCTTC | 17246 |
| 3368 | CAUUUGUG A UUUUGGCC | 7699 | GGCCAAAA GCCTAGCTACAACGA CACAAATC | 17247 |
| 3374 | UGAUUUUG G CCUUGCCC | 7700 | GGGCAAGG GGCTAGCTACAACGA CAAAATCA | 17248 |
| 3379 | UUGGCCUU G CCCGGGAU | 7701 | ATCCCCCG GGCTAGCTACAACGA AAGGCCAA | 17249 |
| 3386 | UGCCCGGC A UAUUUAUA | 7702 | TATAAATA GGCTAGCTACAACGA CCCGGGCA | 17250 |
| 3388 | CCCGGGAU A UUUAUAAG | 542 | CTTATAAA GGCTAGCTACAACGA ATCCCGGG | 17251 |
| 3392 | GCAUAUUU A UAAGAACC | 545 | CGTTCTTA CGCTAGCTACAACGA AAATATCC | 17252 |
| 3398 | UUAUAAGA A CCCCGAUU | 7703 | AATCGGGG GGCTAGCTACAACGA TCTTATAA | 17253 |
| 3404 | CAACCCCG A UUAUGUCA | 7704 | TCACATAA CGCTAGCTACAACGA CGGGGTTC | 17254 |
| 3407 | CCCCGAUU A UGUCAGAA | 548 | TTCTCACA GGCTACCTACAACGA AATCGGGG | 17255 |
| 3409 | CCGAUUAU C UCACAAAA | 7705 | TTTTCTCA GGCTAGCTACAACGA ATAATCCG | 17256 |
| 3422 | AAAAGGAG A UACUCGAC | 7706 | GTCGAGTA GGCTAGCTACAACGA CTCCTTTT | 17257 |
| 3424 | AAGCAGAU A CUCGACUU | 549 | AAGTCGAG GGCTAGCTACAACGA ATCTCCTT | 17258 |
| 3429 | GAUACUCG A CUUCCUCU | 7707 | AGAGGAAG GGCTAGCTACAACGA CGAGTATC | 17259 |

TABLE XVIII-continued

Human FLT DNAzyme and Substrate Sequence

| Pos | Substrate | Seq ID No | DNAzyme | Seq ID No |
|---|---|---|---|---|
| 3441 | CCUCUGAA A UGGAUGGC | 7708 | GCCATCCA GGCTAGCTACAACGA TTCAGAGG | 17260 |
| 3445 | UGAAAUGG A UGGCUCCC | 7709 | CGGACCCA GGCTAGCTACAACGA CCATTTCA | 17261 |
| 3448 | AAUCCAUG G CUCCCGAA | 7710 | TTCGGGAG GGCTAGCTACAACGA CATCCATT | 17262 |
| 3456 | GCUCCCGA A UCUAUCUU | 7711 | AAGATAGA GGCTAGCTACAACGA TCGGGAGC | 17263 |
| 3460 | CCGAAUCU A UCUUUGAC | 556 | TCAAAGA GGCTAGCTACAACGA AGATTCGG | 17264 |
| 3467 | UAUCUUUG A CAAAAUCU | 7712 | AGATTTTG GGCTAGCTACAACGA CAAAGATA | 17265 |
| 3472 | UUGACAAA A UCUACAGC | 7713 | GCTGTAGA GGCTAGCTACAACGA TTTGTCAA | 17266 |
| 3476 | CAAAAUCU A CAGCACCA | 56 | UGGTGCTG GGCTAGCTACAACGA AGATTTTG | 17267 |
| 3479 | AAUCUACA G CACCAAGA | 7714 | TCTTGGTG GGCTAGCTACAACGA TGTAGATT | 17268 |
| 3481 | UCUACAGC A CCAAGAGC | 4853 | GCTCTTGG GGCTAGCTACAACGA GCTGTAGA | 17269 |
| 3488 | CACCAAGA G CGACGUGU | 7715 | ACACGTCG GGCTAGCTACAACGA TCTTGGTG | 17270 |
| 3491 | CAAGAGCG A CGUGGGU | 7716 | ACCACACG GGCTAGCTACAACGA CGCTCTTG | 17271 |
| 3493 | AGAGCGAC G UGGGUCU | 7717 | AGACCACA GGCTAGCTACAACGA GTCGCTCT | 17272 |
| 3495 | AGCGACGU C UGGUCUUA | 7718 | TAAGACCA GGCTAGCTACAACGA ACGTCGCT | 17273 |
| 3498 | GACGUGUG G UCUUACGG | 7719 | CCGTAAGA GGCTAGCTACAACGA CACACGTC | 17274 |
| 3503 | GUGGUCUG A CGGAGUAU | 564 | ATACTCCG GGCTAGCTACAACGA AAGACCAC | 17275 |
| 3508 | CUUACGGA C UAUUGCUG | 7720 | CAGCAATA GGCTAGCTACAACGA TCCGTAAG | 17276 |
| 3510 | UACGGAGU A UUGCUGUG | 565 | CACAGCAA GGCTAGCTACAACGA ACTCCGTA | 17277 |
| 3513 | GGAGUAUU G CUGUGGGA | 772 | UGCCACAG GGCTAGCTACAACGA AATACTCC | 17278 |
| 3516 | GUAUUGCU G UGGGAAAU | 7722 | ATTTCCCA GGCTAGCTACAACGA AGCAATAC | 17279 |
| 3523 | UGUGGGAA A UCUUCUCC | 7723 | GGAGAAGA GGCTAGCTACAACGA TTCCCACA | 17280 |
| 3536 | CUCCUUAG C UGGGCUC | 7724 | GAGACCCA GGCTAGCTACAACGA CTAAGGAG | 17281 |
| 3540 | UUAGGUGG G UCCAUA | 7725 | TATGGAGA GGCTAGCTACAACGA CCACCTAA | 17282 |
| 3546 | GGGUCUCC A UACCCAGG | 4864 | CCTGGGTA GGCTAGCTACAACGA GGACACCC | 17283 |
| 3548 | GUCUCCAC A CCCAGGAG | 575 | CTCCTGGG GGCTAGCTACAACGA ATGGAGAC | 17284 |
| 3556 | ACCCAGGA G UACAAAUG | 7726 | CATTTGTA GGCTAGCTACAACGA TCCTGGGT | 17285 |
| 3558 | CCAGGAGU A CAAAUGGA | 576 | TCCATTTG GGCTAGCTACAACGA ACTCCTGG | 17286 |
| 3562 | GAGUACAA A UGGAUGAG | 7727 | CTCATCCA GGCTAGCTACAACGA TTGTACTC | 17287 |
| 3566 | ACAAAUGG A UGAGGACU | 7728 | AGTCCTCA GGCTAGCTACAACGA CCATTTGT | 17288 |
| 3572 | GGAUGAGG A CUUUUGCA | 7729 | TGCAAAAG GGCTAGCTACAACGA CCTCATCC | 17289 |
| 3578 | GGACUUUU C CAGUCGCC | 7730 | GGCGACTG GGCTAGCTACAACGA AAAAGTCC | 17290 |
| 3581 | CUUUUGCA G UCGCCUGA | 7731 | UCAGGCGA GGCTAGCTACAACGA TGCAAAAG | 17291 |
| 3584 | UUGCAGUC G CCUGAGGG | 7732 | CCCTCAGG GGCTAGCTACAACGA GACTGCAA | 17292 |
| 3596 | GAGGGAAG G CAUGAGGA | 7733 | TCCTCATG GGCTAGCTACAACGA CTTCCCTC | 17293 |
| 3598 | GGGAAGGC A UGAGGAUG | 4873 | CATCCTCA GGCTAGCTACAACGA GCCTTCCC | 17294 |
| 3604 | GCAUGAGG A UGAGAGCU | 7734 | AGCTCTCA GGCTAGCTACAACGA CCTCATGC | 17295 |
| 3610 | GGAUGAGA G CUCCUGAG | 7735 | CTCAGGAG GGCTAGCTACAACGA TCTCATCC | 17296 |

TABLE XVIII-continued

Human FLT DNAzyme and Substrate Sequence

| Pos | Substrate | Seq ID No | DNAzyme | Seq ID No |
|---|---|---|---|---|
| 3618 | GCUCCUGA G UACUCUAC | 7736 | GTAGAGTA GGCTAGCTACAACGA TCAGGAGC | 17297 |
| 3620 | UCCUGAGU A CUCUACUC | 582 | GAGTAGAG GGCTAGCTACAACGA ACTCAGGA | 17298 |
| 3625 | AGUACUCU A CUCCUGAA | 584 | TTCAGGAG GGCTAGCTACAACGA AGAGTACT | 17299 |
| 3634 | CUCCUGAA A UCUAUCAG | 7737 | CTGATAGA GGCTAGCTACAACGA TTCAGGAG | 17300 |
| 3638 | UGAAAUCU A UCAGAUCA | 587 | TGATCTGA GGCTAGCTACAACGA AGATTTCA | 17301 |
| 3643 | UCUAUCAG A UCAUGCUG | 7738 | CAGCATGA GGCTAGCTACAACGA CTGATAGA | 17302 |
| 3646 | AUCAGAUC A UCCUGGAC | 4884 | GTCCAGCA GGCTAGCTACAACGA GATCTGAT | 17303 |
| 3648 | CAGAUCAU G CUGGACUG | 7739 | CAGTCCAG GGCTAGCTACAACGA ATGATCTG | 17304 |
| 3653 | CAUGCUGG A CUGCUGGC | 7740 | GCCAGCAG GGCTAGCTACAACGA CCAGCATG | 17305 |
| 3656 | GCUGGACU G CUGGCACA | 774 | UGTGCCAG GGCTAGCTACAACGA AGTCCAGC | 17306 |
| 3660 | GACUCCUG C CACACAGA | 7742 | TCTCTGTG GGCTAGCTACAACGA CAGCAGTC | 17307 |
| 3662 | CUGCUGGC A CAGAGACC | 4888 | GGTCTCTG GGCTACCTACAACGA GCCAGCAG | 17308 |
| 3668 | GCACAGAG A CCCAAAAG | 7743 | CTTTTGGG GGCTAGCTACAACGA CTCTGTGC | 17309 |
| 3681 | AAAGAAAG G CCAAGAUU | 7744 | AATCTTGG GGCTAGCTACAACGA CTTTCTTT | 17310 |
| 3687 | AGGCCAAG A UUUGCAGA | 7745 | TCTGCAAA GCCTAGCTACAACGA CTTGGCCT | 17311 |
| 3691 | CAAGAUUU G CAGAACUU | 7746 | AAGTTCTG GGCTAGCTACAACGA AAATCTTG | 17312 |
| 3696 | UUUGCAGA A CUUGUGGA | 7747 | TCCACAAG GGCTAGCTACAACGA TCTGCAAA | 17313 |
| 3700 | CAGAACUU G UGGAAAAA | 7748 | TTTTTCCA GGCTAGCTACAACGA AAGTTCTG | 17314 |
| 3708 | GUGGAAAA A CUAGGUGA | 7749 | TCACCTAG GGCTAGCTACAACGA TTTTCCAC | 17315 |
| 3713 | AAAACUAG G UGAUUUGC | 7750 | GCAAATCA GGCTAGCTACAACGA CTAGTTTT | 17316 |
| 3716 | ACUAGGUG A UUUGCUUC | 7751 | GAAGCAAA GGCTAGCTACAACGA CACCTAGT | 17317 |
| 3720 | GGUGAUUU C CUUCAAGC | 7752 | GCTTGAAG GGCTAGCTACAACGA AAATCACC | 17318 |
| 3727 | UGCUUCAA G CAAAUGUA | 7753 | TACATTTG GGCTAGCTACAACGA TTGAAGCA | 17319 |
| 3731 | UCAAGCAA A UGUACAAC | 7754 | GTTGTACA GGCTAGCTACAACGA TTGCTTGA | 17320 |
| 3733 | AAGCAAAU C UACAACAG | 7755 | CTGTTGTA GGCTAGCTACAACGA ATTTGCTT | 17321 |
| 3735 | GCAAAUGU A CAACAGGA | 598 | TCCTGTTG GGCTAGCTACAACGA ACATTTGC | 17322 |
| 3738 | AAUGUACA A CAGGAUGG | 7756 | CCATCCTG GGCTAGCTACAACGA TGTACATT | 17323 |
| 3743 | ACAACAGG A UGGUAAAG | 7757 | CTTTACCA GGCTAGCTACAACGA CCTGTTGT | 17324 |
| 3746 | ACAGGAUG C UAAAGACU | 7758 | AGTCTTTA GGCTAGCTACAACGA CATCCTGT | 17325 |
| 3752 | UGGUAAAG A CUACAUCC | 7759 | GGATGTAG GGCTAGCTACAACGA CTTTACCA | 17326 |
| 3755 | UAAAGACU A CAUCCCAA | 600 | TTGGGATG GGCTAGCTACAACGA AGTCTTTA | 17327 |
| 3757 | AAGACUAC A UCCCAAUC | 4904 | GATTGGGA GGCTAGCTACAACGA GTAGTCTT | 17328 |
| 3763 | ACAUCCCA A UCAAUGCC | 7760 | GGCATTGA GGCTACCTACAACGA TGGCATCT | 17329 |
| 3767 | CCCAAUCA A UGCCAUAC | 7761 | GTATGGCA GGCTAGCTACAACGA TGATTGGG | 17330 |
| 3769 | CAAUCAAU G CCAUACUG | 7762 | CAGTATGG GGCTAGCTACAACGA ATTGATTG | 17331 |
| 3772 | UCAAUGCC A UACUGACA | 4910 | TGTCAGTA GGCTAGCTACAACGA GGCATTGA | 17332 |
| 3774 | AAUGCCAU A CUGACAGG | 603 | CCTGTCAG GGCTAGCTACAACGA ATGGCATT | 17333 |

TABLE XVIII-continued

Human FLT DNAzyme and Substrate Sequence

| Pos | Substrate | Seq ID No | DNAzyme | Seq ID No |
|---|---|---|---|---|
| 3778 | CCAUACUG A CAGGAAAU | 7763 | ATTTCCTG GGCTAGCTACAACGA CAGTATGG | 17334 |
| 3785 | GACAGGAA A UAGUGGGU | 7764 | ACCCACTA GGCTAGCTACAACGA TTCCTGTC | 17335 |
| 3788 | AGGAAAUA G UGGGUUUA | 7765 | TAAACCCA CGCTAGCTACAACGA TATTTCCT | 17336 |
| 3792 | AAUAGUGG G UUUACAUA | 7766 | TATGTAAA GGCTAGCTACAACGA CCACTATT | 17337 |
| 3796 | GUGGGUUU A CAUACUCA | 607 | TGAGTATG GGCTAGCTACAACGA AAACCCAC | 17338 |
| 3798 | GGCUUUAC A UACUCAAC | 4913 | GTTGAGTA GGCTAGCTACAACGA GTAAACCC | 17339 |
| 3800 | GUUUACAU A CUCAACUC | 608 | GAGTTGAG GGCTAGCTACAACGA ATGTAAAC | 17340 |
| 3805 | CAUACUCA A CUCCUGCC | 7767 | GGCAGGAG GGCTAGCTACAACGA TGAGTATG | 17341 |
| 3811 | CAACUCCU G CCUUCUCU | 7768 | AGAGAAGG GGCTAGCTACAACGA AGGAGTTG | 17342 |
| 3824 | CUCUGAGG A CUUCUUCA | 7769 | TGAAGAAG GGCTAGCTACAACGA CCTCAGAG | 17343 |
| 3839 | CAAGGAAA C UAUUUCAG | 7770 | CTGAAATA GGCTAGCTACAACGA TTTCCTTG | 17344 |
| 3841 | AGGAAAGU A UUUCAGCU | 618 | AGCTGAAA GGCTAGCTACAACGA ACTTTCCT | 17345 |
| 3847 | GUAUUUCA C CUCCGAAG | 7771 | CTTCGGAG GGCTAGCTACAACGA TGAAATAC | 17346 |
| 3855 | GCUCCGAA G UUUAAUUC | 7772 | GAATTAAA GGCTAGCTACAACGA TTCGGAGC | 17347 |
| 3860 | GAAGUUUA A UUCAGGAA | 7773 | TTCCTGAA GGCTAGCTACAACGA TAAACTTC | 17348 |
| 3869 | UUCAGGAA C CUCUGAUG | 7774 | CATCAGAG GGCTAGCTACAACGA TTCCTGAA | 17349 |
| 3875 | AAGCUCUG A UGAUGUCA | 7775 | TCACATCA GCCTAGCTACAACGA CACACCTT | 17350 |
| 3878 | CUCUGAUG A UGUCAGAU | 7776 | ATCTGACA GGCTAGCTACAACGA CATCAGAG | 17351 |
| 3880 | CUGAUGAU C UCAGAUAU | 7777 | ATATCTGA GCCTAGCTACAACGA ATCATCAG | 17352 |
| 3885 | GAUGUCAC A UAUGUAAA | 7778 | TTTACATA GGCTAGCTACAACGA CTGACATC | 17353 |
| 3887 | UGUCAGAU A UCUAAAUG | 630 | CATTTACA GGCTAGCTACAACGA ATCTCACA | 17354 |
| 3889 | UCAGAUAU C UAAAUGCU | 7779 | ACCATTTA GGCTAGCTACAACGA ATATCTGA | 17355 |
| 3893 | AUAUGUAA A UCCUCUCA | 7780 | TGAAAGCA GGCTAGCTACAACGA TTACATAT | 17356 |
| 3895 | AUGUAAAU C CUUUCAAG | 7781 | CTTGAAAG GGCTAGCTACAACGA ATTTACAT | 17357 |
| 3903 | GCUUUCAA C UUCAUGAG | 7782 | CTCATGAA GGCTAGCTACAACGA TTGAAAGC | 17358 |
| 3907 | UCAAGUUC A UGAGCCUC | 4935 | CACGCTCA GCCTAGCTACAACGA CAACTTCA | 17359 |
| 3911 | GUUCAUGA C CCUGGAAA | 7783 | TTTCCAGG GGCTAGCTACAACGA TCATGAAC | 17360 |
| 3922 | UGGAAAGA A UCAAAACC | 7784 | GGTTTTGA GGCTAGCTACAACGA TCTTTCCA | 17361 |
| 3928 | GAAUCAAA A CCUUUGAA | 7785 | TTCAAAGG GGCTAGCTACAACGA TTTGATTC | 17362 |
| 3939 | UUUGAAGA A CUUUUACC | 7786 | GGTAAAAG GGCTAGCTACAACGA TCTTCAAA | 17363 |
| 3945 | GAACUUUU A CCGAAUGC | 643 | GCATTCGG GGCTAGCTACAACGA AAAAGTTC | 17364 |
| 3950 | UUUACCGA A UGCCACCU | 7787 | AGGTGGCA GGCTAGCTACAACGA TCGGTAAA | 17365 |
| 3952 | UACCGAAV C CCACCUCC | 7788 | GGAGGTGG GGCTAGCTACAACGA ATTCGGTA | 17366 |
| 3955 | CGAAUGCC A CCUCCAUG | 4944 | CATGGAGG GGCTAGCTACAACGA GGCATTCG | 17367 |
| 3961 | CCACCUCC A UGUUUGAU | 4948 | ATCAAACA GGCTAGCTACAACGA GGAGGTGG | 17368 |
| 3963 | ACCUCCAU G UUUGAUGA | 7789 | TCATCAAA GGCTAGCTACAACGA ATGCAGGT | 17369 |
| 3968 | CAUGUUUG A UGACUACC | 7790 | GGTAGTCA GGCTAGCTACAACGA CAAACATG | 17370 |

TABLE XVIII-continued

Human FLT DNAzyme and Substrate Sequence

| Pos | Substrate | Seq ID No | DNAzyme | Seq ID No |
|---|---|---|---|---|
| 3971 | GUUUGAUG A CUACCAGG | 7791 | CCTGGTAG GGCTAGCTACAACGA CATCAAAC | 17371 |
| 3974 | UGAUGACU A CCAGCGCC | 647 | CGCCCTGG CGCTAGCTACAACGA AGTCATCA | 17372 |
| 3980 | CUACCAGG C CGACAGCA | 7792 | TGCTGTCG GGCTAGCTACAACGA CCTGCTAG | 17373 |
| 3983 | CCAGGCCG A CAGCAGCA | 7793 | TGCTGCTG GGCTAGCTACAACGA CGCCCTGG | 17374 |
| 3986 | GGGCGACA G CAGCACUC | 7794 | GAGTGCTG GGCTAGCTACAACGA TGTCGCCC | 17375 |
| 3989 | CGACAGCA C CACUCUCU | 7795 | ACAGAGTG CGCTAGCTACAACGA TGCTGTCG | 17376 |
| 3991 | ACAGCACC A CUCUGUUG | 4954 | CAACAGAG GGCTAGCTACAACGA CCTGCTGT | 17377 |
| 3996 | ACCACUCU C UUGGCCUC | 7796 | GAGGCCAA GGCTAGCTACAACGA AGACTCCT | 17378 |
| 4000 | CUCUCUUG C CCUCUCCC | 7797 | CGCACACC GGCTACCTACAACGA CAACAGAC | 17379 |
| 4009 | CCUCUCCC A UGCUGAAG | 4962 | CTTCAGCA CGCTAGCTACAACGA GGGAGAGG | 17380 |
| 4011 | UCUCCCAU G CUGAAGCG | 7798 | CGCTTCAG GGCTACCTACAACGA ATGCCACA | 17381 |
| 4017 | AUGCUCAA G CGCUUCAC | 7799 | CTGAAGCG GGCTAGCTACAACGA TTCAGCAT | 17382 |
| 4019 | CCUCAACC G CUUCACCU | 7800 | ACGTCAAG CGCTAGCTACAACGA GCTTCAGC | 17383 |
| 4024 | ACCGCUUC A CCUGCACU | 4965 | ACTCCAGC GGCTAGCTACAACGA GAAGCGCT | 17384 |
| 4030 | UCACCUGC A CUGACAGC | 7801 | CCTCTCAC CCCTACCTACAACGA CCAGCTCA | 17385 |
| 4034 | CUGGACUG A CAGCAAAC | 7802 | GTTTGCTG GGCTACCTACAACGA CAGTCCAG | 17386 |
| 4037 | GACUGACA C CAAACCCA | 7803 | TGGGTTTC GGCTACCTACAACGA TCTCAGTC | 17387 |
| 4041 | GACAGCAA A CCCAAGGC | 7804 | GCCTTCCC GCCTAGCTACAACGA TTGCTGTC | 17388 |
| 4048 | AACCCAAC G CCUCGCUC | 7805 | CACCCACG GGCTAGCTACAACGA CTTCGCTT | 17389 |
| 4053 | AAGGCCUC C CUCAAGAU | 7806 | ATCTTCAG GGCTACCTACAACGA GAGGCCTT | 17390 |
| 4060 | CGCUCAAG A UUGACUUG | 7807 | CAACTCAA GGCTACCTACAACGA CTTCAGCC | 17391 |
| 4064 | CAACAUUG A CUCCACAG | 7808 | CTCTCAAC GGCTAGCTACAACGA CAATCTTG | 17392 |
| 4072 | ACUUCAGA C UAACCACU | 7809 | ACTCCTTA GGCTACCTACAACGA TCTCAAGT | 17393 |
| 4075 | UCACACCA A CCAGUAAA | 7810 | TTTACTGG GCCTAGCTACAACGA TACTCTCA | 17394 |
| 4079 | AGUAACCA C UAAAGUA | 781 | UACTTTTA GCCTAGCTACAACGA TGGTTACT | 17395 |
| 4085 | CAGUAAAA C UAAGCACU | 7812 | ACTCCTTA GGCTAGCTACAACGA TTTTACTC | 17396 |
| 4092 | ACUAACCA C UCCGCCCU | 7813 | ACCCCCGA GGCTACCTACAACGA TCCTTACT | 17397 |
| 4098 | CACUCCGC C CUCUCUGA | 7814 | TCACACAC CGCTAGCTACAACGA CCCCACTC | 17398 |
| 4101 | UCCCCGCU C UCUCAUGU | 7815 | ACATCAGA GGCTAGCTACAACGA AGCCCCGA | 17399 |
| 4106 | GCUCUCUC A UCUCAGCA | 7816 | TGCTCACA GGCTAGCTACAACGA CAGACACC | 17400 |
| 4108 | UCUCUCAU C UCACCACC | 7817 | CCTGCTCA GGCTAGCTACAACGA ATCAGACA | 17401 |
| 4112 | UCAUCUCA C CACCCCCA | 7818 | TCCGCCTC CCCTAGCTACAACGA TCACATCA | 17402 |
| 4116 | CUCACCAG C CCCAGUUU | 7819 | AAACTCGC GGCTAGCTACAACGA CTCCTGAC | 17403 |
| 4121 | CACCCCCA C UUUCUCCC | 7820 | GGCAGAAA GGCTAGCTACAACGA TCCCCCTC | 17404 |
| 4127 | CACUUUCU C CCAUUCCA | 782 | UCGAATCG GGCTAGCTACAACGA ACAAACTG | 17405 |
| 4130 | UUUCUCCC A UUCCACCU | 4990 | AGCTCGAA CGCTAGCTACAACGA CGCACAAA | 17406 |
| 4136 | CCAUUCCA C CUGUGGGC | 7822 | CCCCACAC CGCTAGCTACAACGA TGCAATGG | 17407 |

TABLE XVIII-continued

Human FLT DNAzyme and Substrate Sequence

| Pos | Substrate | Seq ID No | DNAzyme | Seq ID No |
|---|---|---|---|---|
| 4139 | UUCCACCU C UGCCCACC | 7823 | CGTCCCCA CCCTACCTACAACGA ACCTGCAA | 17408 |
| 4143 | AGCUGUGG C CACCUCAG | 7824 | CTCACGTG GGCTAGCTACAACGA CCACACCT | 17409 |
| 4145 | CUGUGGGC A CGUCAGCG | 4994 | CGCTGACG GGCTAGCTACAACGA CCCCACAG | 17410 |
| 4147 | GUGGGCAC G UCAGCGAA | 7825 | TTCGCTGA GGCTAGCTACAACGA GTGCCCAC | 17411 |
| 4151 | GCACGUCA G CGAAGGCA | 7826 | TGCCTTCG GGCTAGCTACAACGA TGACGTGC | 17412 |
| 4157 | CAGCGAAG G CAAGCGCA | 7827 | TGCGCTTG GGCTAGCTACAACGA CTTCGCTG | 17413 |
| 4161 | GAAGGCAA G CGCAGGUU | 7828 | AACCTGCG GGCTAGCTACAACGA TTGCCTTC | 17414 |
| 4163 | AGGCAAGC G CAGGUUCA | 7829 | TGAACCTG GGCTAGCTACAACGA GCTTGCCT | 17415 |
| 4167 | AAGCGCAG G UUCACCUA | 7830 | TAGGTGAA GGCTAGCTACAACGA CTGCGCTT | 17416 |
| 4171 | GCAGGUUC A CCUACGAC | 4998 | GTCGTAGG GGCTAGCTACAACGA GAACCTGC | 17417 |
| 4175 | GUUCACCU A CGACCACG | 672 | CGTGGTCG GGCTAGCTACAACGA AGGTGAAC | 17418 |
| 4178 | CACCUACG A CCACGCUG | 7831 | CAGCGTGG GGCTAGCTACAACGA CGTAGGTG | 17419 |
| 4181 | CUACGACC A CGCUGAGC | 5002 | GCTCAGCG GGCTAGCTACAACGA GGTCGTAG | 17420 |
| 4183 | ACGACCAC G CUGASCUG | 7832 | CAGCTCAG GGCTAGCTACAACGA GTGGTCGT | 17421 |
| 4188 | CACGCUGA G CUGGAAAG | 7833 | CTTTCCAG GGCTAGCTACAACGA TCASCGTG | 17422 |
| 4201 | AAAGGAAA A UCGCGUGC | 7834 | GCACGCGA GGCTAGCTACAACGA TTTCCTTT | 17423 |
| 4204 | GGAAAAUC G CGUGCUGC | 7835 | GCASCACG GGCTAGCTACAACGA GATTTTCC | 17424 |
| 4206 | AAAAUCSC G UGCUGCUC | 7836 | GAGCAGCA GGCTAGCTACAACGA GCGATTTT | 17425 |
| 4208 | AAUCGCGU G CUGCUCCC | 7837 | GGGAGCAG GGCTAGCTACAACSA ACGCGATT | 17426 |
| 4211 | CGCGUGCU G CUCCCCGC | 7838 | GCGGGGAG GGCTAGCTACAACGA AGCACGCG | 17427 |
| 4218 | UGCUCCCC G CCCCCAGA | 7839 | TCTGGGGG GGCTAGCTACAACSA SGGGAGCA | 17428 |
| 4226 | GCCCCCAG A CUACAACU | 7840 | AGTTGTAG SGCTAGCTACAACGA CTGGGGGC | 17429 |
| 4229 | CCCAGACU A CAACUCGG | 675 | CCGAGTTG GGCTAGCTACAACGA AGTCTGSG | 17430 |
| 4232 | AGACUACA A CUCGGUGG | 7841 | CCACCGAG GGCTAGCTACAACSA TGTAGTCT | 17431 |
| 4237 | ACAACUCG G UGGUCCUG | 7842 | CAGGACCA GGCTAGCTACAACGA CGAGTTGT | 17432 |
| 4240 | ACUCGGUG G UCCUGUAC | 7843 | GTACAGGA GGCTAGCTACAACGA CACCGAST | 17433 |
| 4245 | GUGGUCCU G UACUCCAC | 7844 | GTGGAGTA GGCTAGCTACAACSA AGGACCAC | 17434 |
| 4247 | GGUCCUGU A CUCCACCC | 678 | GGGTGGAG GGCTAGCTACAACGA ACAGGACC | 17435 |
| 4252 | UGUACUCC A CCCCACCC | 5022 | GGGTGGGG GGCTAGCTACAACGA GGAGTACA | 17436 |
| 4257 | UCCACCCC A CCCAUCUA | 5026 | TAGATGGG GGCTAGCTACAACGA GGGGTGGA | 17437 |
| 4261 | CCCCACCC A UCUAGAGU | 5029 | ACTCTAGA GGCTAGCTACAACGA SSSTGGGG | 17438 |
| 4268 | CAUCUAGA G UUUGACAC | 7845 | GTGTCAAA GGCTAGCTACAACGA TCTAGATG | 17439 |
| 4273 | AGAGUUUS A CACGAAGC | 7846 | GCTTCGTG GGCTAGCTACAACGA CAAACTCT | 17440 |
| 4275 | AGUUUGAC A CGAAGCCU | 5031 | AGGCTTCG GGCTAGCTACAACGA GTCAAACT | 17441 |
| 4280 | GACACGAA G CCUUAUUU | 7847 | AAATAAGG GGCTAGCTACAACGA TTCGTSTC | 17442 |
| 4285 | GAAGCCUU A UUUCUAGA | 685 | TCTAGAAA GGCTAGCTACAACGA AAGGCTTC | 17443 |
| 4295 | UUCUAGAA G CACAUGUG | 7848 | CACATGTG GGCTAGCTACAACGA TTCTAGAA | 17444 |

TABLE XVIII-continued

Human FLT DNAzyme and Substrate Sequence

| Pos | Substrate | Seq ID No | DNAzyme | Seq ID No |
|---|---|---|---|---|
| 4297 | CUAGAAGC A CAUGUGUA | 5035 | TACACATG GGCTAGCTACAACGA GCTTCTAG | 17445 |
| 4299 | AGAAGCAC A USUSUAUU | 5036 | AATACACA GGCTAGCTACAACGA STGCTTCT | 17446 |
| 4301 | AAGCACAU G USUAUUUA | 7849 | TAAATACA GGCTAGCTACAACGA ATSTGCTT | 17447 |
| 4303 | GCACAUGU G UAUUUAUA | 7850 | TATAAATA GGCTAGCTACAACGA ACATSTGC | 17448 |
| 4305 | ACAUGUGU A UUUAUACC | 690 | GGTATAAA GGCTAGCTACAACGA ACACATGT | 17449 |
| 4309 | GUGUAUUU A UACCCCCA | 693 | TSGGGGTA GGCTAGCTACAACGA AAATACAC | 17450 |
| 4311 | GUAUUUAU A CCCCCAGG | 694 | CCTGGGGG GGCTAGCTACAACGA ATAAATAC | 17451 |
| 4322 | CCCAGGAA A CUAGCUUU | 7851 | AAAGCTAG GGCTAGCTACAACGA TTCCTGGG | 17452 |
| 4326 | GGAAACUA G CUUUUGCC | 7852 | GGCAAAAG GGCTAGCTACAACGA TAGTTTCC | 17453 |
| 4332 | UAGCUUUU G CCAGUAUU | 7853 | AATACTGG GGCTAGCTACAACGA AAAAGCTA | 17454 |
| 4336 | UUUUGCCA G UAUUAUGC | 7854 | GCATAATA GGCTAGCTACAACGA TGGCAAAA | 17455 |
| 4338 | UUGCCAGU A UUAUGCAU | 699 | ATGCATAA GGCTAGCTACAACGA ACTGGCAA | 17456 |
| 4341 | CCAGUAUU A UGCAUAUA | 70 | UATATGCA GGCTAGCTAGAACGA AATACTGG | 17457 |
| 4343 | AGUAUUAU G CAUAUAUA | 7855 | TATATATG GGCTAGCTACAACGA ATAATACT | 17458 |
| 4345 | UAUUAUGC A UAUAUAAG | 5046 | CTTATATA GGCTAGCTACAACGA GCATAATA | 17459 |
| 4347 | UUAUGCAU A UAUAAGUU | 702 | AACTTATA GGCTAGCTACAACGA ATGCATAA | 17460 |
| 4349 | AUGCAUAU A UAAGUUUA | 703 | TAAACTTA GGCTAGCTACAACGA ATATGCAT | 17461 |
| 4353 | AUAUAUAA G UUUACACC | 7856 | GGTGTAAA GGCTAGCTACAACGA TTATATAT | 17462 |
| 4357 | AUAAGUUU A CACCUUUA | 707 | TAAAGGTG GGCTAGCTACAACGA AAACTTAT | 17463 |
| 4359 | AAGUUUAC A CCUUUAUC | 5047 | GATAAAGG GGCTAGCTACAACGA GTAAACTT | 17464 |
| 4365 | ACACCUUU A UCUUUCCA | 710 | TGGAAAGA GGCTAGCTACAACGA AAAGGTGT | 17465 |
| 4373 | AUCUUUCC A UGGGAGCC | 5052 | GGCTCCCA GGCTAGCTACAACGA GGAAAGAT | 17466 |
| 4379 | CCAUGGGA G CCAGCUGC | 7857 | GCAGCTGG GGCTAGCTACAACGA TCCCATGG | 17467 |
| 4383 | GGGAGCCA G CUGCUUUU | 7858 | AAAAGCAG GGCTAGCTACAACGA TGGCTCCC | 17468 |
| 4386 | AGCCAGCU G CUUUUUGU | 7859 | ACAAAAAG GGCTAGCTACAACGA AGCTGGCT | 17469 |
| 4393 | UGCUUUUU G UGAUUUUU | 7860 | AAAAATCA GGCTAGCTACAACGA AAAAAGCA | 17470 |
| 4396 | UUUUUGUG A UUUUUUUA | 786 | UAAAAAAA GGCTAGCTACAACGA CACAAAAA | 17471 |
| 4405 | UUUUUUUA A UAGUGCUU | 7862 | AAGCACTA GGCTAGCTACAACGA TAAAAAAA | 17472 |
| 4408 | UUUUAAUA G UGCUUUUU | 7863 | AAAAAGCA GGCTAGCTACAACGA TATTAAAA | 17473 |
| 4410 | UUAAUAGU G CUUUUUUU | 7864 | AAAAAAAG GGCTAGCTACAACGA ACTATTAA | 17474 |
| 4424 | UUUUUUUG A CUAACAAG | 7865 | CTTGTTAG GGCTAGCTACAACGA CAAAAAAA | 17475 |
| 4428 | UUUGACUA A CAAGAAUG | 7866 | CATTCTTG GGCTAGCTACAACGA TAGTCAAA | 17476 |
| 4434 | UAACAAGA A UGUAACUC | 7867 | GAGTTACA GGCTAGCTACAACGA TCTTGTTA | 17477 |
| 4436 | ACAAGAAU G UAACUCCA | 7868 | TGGAGTTA GGCTAGCTACAACGA ATTCTTGT | 17478 |
| 4439 | AGAAUGUA A CUCCAGAU | 7869 | ATCTGGAG GGCTAGCTACAACGA TACATTCT | 17479 |
| 4446 | AACUCCAG A UAGAGAAA | 7870 | TTTCTCTA GGCTAGCTACAACGA CTGGAGTT | 17480 |
| 4454 | AUAGAGAA A UAGUGACA | 787 | UGTCACTA GGCTAGCTACAACGA TTCTCTAT | 17481 |

TABLE XVIII-continued

Human FLT DNAzyme and Substrate Sequence

| Pos | Substrate | Seq ID No | DNAzyme | Seq ID No |
|---|---|---|---|---|
| 4457 | GAGAAAUA G UGACAAGU | 7872 | ACTTGTCA GGCTAGCTACAACGA TATTTCTC | 17482 |
| 4460 | AAAUAGUG A CAAGUGAA | 7873 | TTCACTTG GGCTAGCTACAACGA CACTATTT | 17483 |
| 4464 | AGUGACAA G UGAAGAAC | 7874 | GTTCTTCA GGCTAGCTACAACGA TTGTCACT | 17484 |
| 4471 | AGUGAAGA A CACUACUG | 7875 | CAGTAGTG GGCTAGCTACAACGA TCTTCACT | 17485 |
| 4473 | UGAAGAAC A CUACUGCU | 5064 | AGCAGTAG GGCTAGCTACAACGA GTTCTTCA | 17486 |
| 4476 | AGAACACU A CUGCUAAA | 742 | TTTAGCAG GGCTAGCTACAACGA AGTGTTCT | 17487 |
| 4479 | ACACUACU G CUAAAUCC | 7876 | GGATTTAG GGCTAGCTACAACGA AGTAGTGT | 17488 |
| 4484 | ACUGCUAA A UCCUCAUG | 7877 | CATGAGGA GGCTAGCTACAACGA TTAGCAGT | 17489 |
| 4490 | AAAUCCUC A UGUUACUC | 5070 | GAGTAACA GGCTAGCTACAACGA GAGGATTT | 17490 |
| 4492 | AUCCUCAU G UUACUCAG | 7878 | CTGAGTAA GGCTAGCTACAACGA ATGAGGAT | 17491 |
| 4495 | CUCAUGUU A CUCAGUGU | 747 | ACACTGAG GGCTAGCTACAACGA AACATGAG | 17492 |
| 4500 | GUUACUCA G UGUUAGAG | 7879 | CTCTAACA GGCTAGCTACAACGA TGAGTAAC | 17493 |
| 4502 | UACUCAGU G UUAGAAA | 7880 | TTCTCTAA GGCTAGCTACAACGA ACTGAGTA | 17494 |
| 4511 | UUAGAGAA A UCCUUCCU | 7881 | AGGAAGGA GGCTAGCTACAACGA TTCTCTAA | 17495 |
| 4522 | CUUCCUAA A CCCAAUGA | 7882 | TCATTGGG GGCTAGCTACAACGA TTAGGAAG | 17496 |
| 4527 | UAAACCCA A UGACUUCC | 7883 | GGAAGTCA GGCTAGCTACAACGA TGGGTTTA | 17497 |
| 4530 | ACCCAAUG A CUUCCCUG | 7884 | CAGGGAAG GGCTAGCTACAACGA CATTGGGT | 17498 |
| 4538 | ACUUCCCU G CUCCAACC | 7885 | GGTTGGAG GGCTAGCTACAACGA AGGGAAGT | 17499 |
| 4544 | CUGCUCCA A CCCCCGCC | 7886 | GGCGGGGG GGCTAGCTACAACGA TGGAGCAG | 17500 |
| 4550 | CAACCCCC G CCACCUCA | 7887 | TGAGGTGG GGCTAGCTACAACGA GGGGGTTG | 17501 |
| 4553 | CCCCCGCC A CCUCAGGG | 5092 | CCCTGAGG GGCTAGCTACAACGA GGCGGGGG | 17502 |
| 4561 | ACCUCAGG G CACGCAGG | 7888 | CCTGCGTG GGCTAGCTACAACGA CCTGAGGT | 17503 |
| 4563 | CUCAGGGC A CGCAGGAC | 5096 | GTCCTGCG GGCTAGCTACAACGA GCCCTGAG | 17504 |
| 4565 | CAGGGCAC G CAGGACCA | 7889 | TGGTCCTG GGCTAGCTACAACGA GTGCCCTG | 17505 |
| 4570 | CACGCAGG A CCAGUUUG | 7890 | CAAACTGG GGCTAGCTACAACGA CCTGCGTG | 17506 |
| 4574 | CAGGACCA G UUUGAUUG | 7891 | CAATCAAA GGCTAGCTACAACGA TGGTCCTG | 17507 |
| 4579 | CCAGUUUG A UUGAGGAG | 7892 | CTCCTCAA GGCTAGCTACAACGA CAAACTGG | 17508 |
| 4587 | AUUGAGGA G CUGCACUG | 7893 | CAGTGCAG GGCTAGCTACAACGA TCCTCAAT | 17509 |
| 4590 | GAGGAGCU G CACUGAUC | 7894 | GATCAGTG GGCTAGCTACAACGA AGCTCCTC | 17510 |
| 4592 | GGAGCUGC A CUGAUCAC | 5101 | GTGATCAG GGCTAGCTACAACGA GCAGCTCC | 17511 |
| 4596 | CUGCACUG A UCACCCAA | 7895 | TTGGGTGA GGCTAGCTACAACGA CAGTGCAG | 17512 |
| 4599 | CACUGAUC A CCCAAUGC | 5103 | GCATTGGG GGCTAGCTACAACGA GATCAGTG | 17513 |
| 4604 | AUCACCCA A UGCAUCAC | 7896 | GTGATGCA GGCTAGCTACAACGA TGGGTGAT | 17514 |
| 4606 | CACCCAAU G CAUCACGU | 7897 | ACGTGATG GGCTAGCTACAACGA ATTGGGTG | 17515 |
| 4608 | CCCAAUGC A UCACGUAC | 5107 | GTACGTGA GGCTAGCTACAACGA GCATTGGG | 17516 |
| 4611 | AAUGCAUC A CGUACCCC | 5108 | GGGGTACG GGCTAGCTACAACGA GATGCATT | 17517 |
| 4613 | UGCAUCAC G UACCCCAC | 7898 | GTGGGGTA GGCTAGCTACAACGA GTGATGCA | 17518 |

TABLE XVIII-continued

Human FLT DNAzyme and Substrate Sequence

| Pos | Substrate | Seq ID No | DNAzyme | Seq ID No |
|---|---|---|---|---|
| 4615 | CAUCACGU A CCCCACUG | 764 | CAGTGGGG GGCTAGCTACAACGA ACGTGATG | 17519 |
| 4620 | CGUACCCC A CUGGGCCA | 5112 | TGGCCCAG GGCTAGCTACAACGA GGGGTACG | 17520 |
| 4625 | CCCACUGG G CCAGCCCU | 7899 | AGGGCTGG GGCTAGCTACAACGA CCAGTGGG | 17521 |
| 4629 | CUGGGCCA G CCCUGCAG | 7900 | CTGCAGGG GGCTAGCTACAACGA TGGCCCAG | 17522 |
| 4634 | CCAGCCCU G CAGCCCAA | 7901 | UTGGGCTG GGCTAGCTACAACGA AGGGCTGG | 17523 |
| 4637 | GCCCUGCA G CCCAAAAC | 7902 | GTTTTGGG GGCTAGCTACAACGA TGCAGGGC | 17524 |
| 4644 | AGCCCAAA A CCCAGGGC | 7903 | GCCCTGGG GGCTAGCTACAACGA TTTGGGCT | 17525 |
| 4651 | AACCCAGG G CAACAAGC | 7904 | GCTTGTTG GGCTAGCTACAACGA CCTGGGTT | 17526 |
| 4654 | CCAGGGCA A CAAGCCCG | 7905 | CGGGCTTG GGCTAGCTACAACGA TGCCCTGG | 17527 |
| 4658 | GGCAACAA G CCCGUUAG | 7906 | CTAACGGG GGCTAGCTACAACGA TTGTTGCC | 17528 |
| 4662 | ACAAGCCC G UUAGCCCC | 7907 | GGGGCTAA GGCTAGCTACAACGA GGGCTTGT | 17529 |
| 4666 | GCCCGUUA G CCCCAGGG | 7908 | CCCTGGGG GGCTAGCTACAACGA TAACGGGC | 17530 |
| 4676 | CCCAGGGG A UCACUGGC | 7909 | GCCAGTGA GGCTAGCTACAACGA CCCCTGGG | 17531 |
| 4679 | AGGGGAUC A CUGGCUGG | 5134 | CCAGCCAG GGCTAGCTACAACGA GATCCCCT | 17532 |
| 4683 | GAUCACUG G CUGGCCUG | 7910 | CAGGCCAG GGCTAGCTACAACGA CAGTGATC | 17533 |
| 4687 | ACUGGCUG G CCUGAGCA | 791 | UGCTCAGG GGCTAGCTACAACGA CAGCCAGT | 17534 |
| 4693 | UGGCCUGA G CAACAUCU | 7912 | AGATGTTG GGCTAGCTACAACGA TCAGGCCA | 17535 |
| 4696 | CCUGAGCA A CAUCUCGG | 7913 | CCGAGATG GGCTAGCTACAACGA TGCTCAGG | 17536 |
| 4698 | UGAGCAAC A UCUCGGGA | 5140 | TCCCGAGA GGCTAGCTACAACGA GTTGCTCA | 17537 |
| 4707 | UCUCGGGA G UCCUCUAG | 7914 | CTAGAGGA GGCTAGCTACAACGA TCCCGAGA | 17538 |
| 4715 | GUCCUCUA G CAGGCCUA | 7915 | TAGGCCTG GGCTAGCTACAACGA TAGAGGAC | 17539 |
| 4719 | UCUAGCAG G CCUAAGAC | 7916 | GTCTTAGG GGCTAGCTACAACGA CTGCTAGA | 17540 |
| 4726 | GGCCUAAG A CAUGUGAG | 7917 | CTCACATG GGCTAGCTACAACGA CTTAGGCC | 17541 |
| 4728 | CCUAAGAC A UGUGAGGA | 5148 | TCCTCACA GGCTAGCTACAACGA GTCTTAGG | 17542 |
| 4730 | UAAGACAU G UGAGGAGG | 7918 | CCTCCTCA GGCTAGCTACAACGA ATGTCTTA | 17543 |
| 4752 | GAAAAAAA G CAAAAAGC | 7919 | GCTTTTTG GGCTAGCTACAACGA TTTTTTTC | 17544 |
| 4759 | AGCAAAAA G CAAGGGAG | 7920 | CTCCCTTG GGCTAGCTACAACGA TTTTTGCT | 17545 |
| 4777 | AAAGAGAA A CCGGGAGA | 792 | UCTCCCGG GGCTAGCTACAACGA TTCTCTTT | 17546 |
| 4788 | GGGAGAAG G CAUGAGAA | 7922 | TTCTCATG GGCTAGCTACAACGA CTTCTCCC | 17547 |
| 4790 | GAGAAGGC A UGAGAAAG | 5152 | CTTTCTCA GGCTAGCTACAACGA GCCTTCTC | 17548 |
| 4800 | GAGAAAGA A UUUGAGAC | 7923 | GTCTCAAA GGCTAGCTACAACGA TCTTTCTC | 17549 |
| 4807 | AAUUUGAG A CGCACCAU | 7924 | ATGGTGCG GGCTAGCTACAACGA CTCAAATT | 17550 |
| 4809 | UUUGAGAC G CACCAUGU | 7925 | ACATGGTG GGCTAGCTACAACGA GTCTCAAA | 17551 |
| 4811 | UGAGACGC A CCAUGUGG | 5153 | CCACATGG GGCTAGCTACAACGA GCGTCTCA | 17552 |
| 4814 | GACGCACC A UGUGGCA | 5155 | TGCCCACA GGCTAGCTACAACGA GGTGCGTC | 17553 |
| 4816 | CGCACCAU G UGGCACG | 7926 | CGTGCCCA GGCTAGCTACAACGA ATGGTGCG | 17554 |
| 4820 | CCAUGUGG G CACGGAGG | 7927 | CCTCCGTG GGCTAGCTACAACGA CCACATGG | 17555 |

TABLE XVIII-continued

Human FLT DNAzyme and Substrate Sequence

| Pos | Substrate | Seq ID No | DNAzyme | Seq ID No |
|---|---|---|---|---|
| 4822 | AUGUGGGC A CGGAGGGG | 5156 | CCCCTCCG GGCTAGCTACAACGA GCCCACAT | 17556 |
| 4832 | GGAGGGGG A CGGGGCUC | 7928 | GAGCCCCG GGCTAGCTACAACGA CCCCCTCC | 17557 |
| 4837 | GGGACGGG G CUCAGCAA | 7929 | TTGCTGAG GGCTAGCTACAACGA CCCGTCCC | 17558 |
| 4842 | GGGGCUCA G CAAUGCCA | 7930 | TGGCATTG GGCTAGCTACAACGA TGAGCCCC | 17559 |
| 4845 | GCUCAGCA A UGCCAUUU | 7931 | AAATGGCA GGCTAGCTACAACGA TGCTGAGC | 17560 |
| 4847 | UCAGCAAU G CCAUUUCA | 7932 | TGAAATGG GGCTAGCTACAACGA ATTGCTGA | 17561 |
| 4850 | GCAAUGCC A UUUCAGUG | 5161 | CACTGAAA GGCTAGCTACAACGA GGCATTGC | 17562 |
| 4856 | CCAUUUCA G UGGCUUCC | 7933 | GGAAGCCA GGCTAGCTACAACGA TGAAATGG | 17563 |
| 4859 | UUUCAGUG G CUUCCCAG | 7934 | CTGGGAAG GGCTAGCTACAACGA CACTGAAA | 17564 |
| 4867 | GCUUCCCA G CUCUGACC | 7935 | GGTCAGAG GGCTAGCTACAACGA TGGGAAGC | 17565 |
| 4873 | CAGCUCUG A CCCUUCUA | 7936 | TAGAAGGG GGCTAGCTACAACGA CAGAGCTG | 17566 |
| 4881 | ACCCUUCU A CAUUUGAG | 785 | CTCAAATG GGCTAGCTACAACGA AGAAGGGT | 17567 |
| 4883 | CCUUCUAC A UUUGAGGG | 5173 | CCCTCAAA GGCTAGCTACAACGA GTAGAAGG | 17568 |
| 4891 | AUUUGAGG G CCCAGCCA | 7937 | TGGCTGGG GGCTAGCTACAACGA CCTCAAAT | 17569 |
| 4896 | AGGGCCCA G CCAGGAGC | 7938 | GCTCCTGG GGCTAGCTACAACGA TGGGCCCT | 17570 |
| 4903 | AGCCAGGA G CAGAUGGA | 7939 | TCCATCTG GGCTAGCTACAACGA TCCTGGCT | 17571 |
| 4907 | AGGAGCAG A UGGACAGG | 7940 | GCTGTCCA GGCTAGCTACAACGA CTGCTCCT | 17572 |
| 4911 | GCAGAUGG A CAGCGAUG | 7941 | CATCGCTG GGCTAGCTACAACGA CCATCTGC | 17573 |
| 4914 | GAUGGACA G CGAUGAGG | 7942 | CCTCATCG GGCTAGCTACAACGA TGTCCATC | 17574 |
| 4917 | GGACAGCG A UGAGGGA | 7943 | TCCCCTCA GGCTAGCTACAACGA CGCTGTCC | 17575 |
| 4925 | AUGAGGGG A CAUUUUCU | 7944 | AGAAAATG GGCTAGCTACAACGA CCCCTCAT | 17576 |
| 4927 | GAGGGGAC A UUUUCUGG | 5181 | CCAGAAAA GGCTAGCTACAACGA GTCCCCTC | 17577 |
| 4936 | UUUUCUGG A UUCUGGGA | 7945 | TCCCAGAA GGCTAGCTACAACGA CCAGAAAA | 17578 |
| 4946 | UCUGGGAG G CAAGAAAA | 7946 | TTTTCTTG GGCTAGCTACAACGA CTCCCAGA | 17579 |
| 4957 | AGAAAAGG A CAAAUAUC | 7947 | GATATTTG GGCTAGCTACAACGA CCTTTTCT | 17580 |
| 4961 | AAGGACAA A UAUCUUUU | 7948 | AAAAGATA GGCTAGCTACAACGA TTGTCCTT | 17581 |
| 4963 | GGACAAAU A UCUUUUUU | 794 | AAAAAAGA GGCTAGCTACAACGA ATTTGTCC | 17582 |
| 4975 | UUUUUGGA A CUAAAGCA | 7949 | TGCTTTAG GGCTAGCTACAACGA TCCAAAAA | 17583 |
| 4981 | GAACUAAA G CAAAUUUU | 7950 | AAAATTTG GGCTAGCTACAACGA TTTAGTTC | 17584 |
| 4985 | UAAAGCAA A UUUUAGAC | 7951 | GTCTAAAA GGCTAGCTACAACGA TTGCTTTA | 17585 |
| 4992 | AAUUUUAG A CCUUUACC | 7952 | GGTAAAGG GGCTAGCTACAACGA CTAAAATT | 17586 |
| 4998 | AGACCUUU A CCUAUGGA | 808 | TCCATAGG GGCTAGCTACAACGA AAAGGTCT | 17587 |
| 5002 | CUUUACCU A UGGAAGUG | 809 | CACTTCCA GGCTAGCTACAACGA AGGTAAAG | 17588 |
| 5008 | CUAUGGAA G UGGUUCUA | 7953 | TAGAACCA GGCTAGCTACAACGA TTCCATAG | 17589 |
| 5011 | UGGAAGUG G UUCUAUGU | 7954 | ACATAGAA GGCTAGCTACAACGA CACTTCCA | 17590 |
| 5016 | GUGGUUCU A UGCCAUU | 812 | AATGGACA GGCTAGCTACAACGA AGAACCAC | 17591 |
| 5018 | GGUUCUAU G UCCAUUCU | 7955 | AGAATGGA GGCTAGCTACAACGA ATAGAACC | 17592 |

TABLE XVIII-continued

Human FLT DNAzyme and Substrate Sequence

| Pos | Substrate | Seq ID No | DNAzyme | Seq ID No |
|---|---|---|---|---|
| 5022 | CUAUGUCC A UUCUCAUU | 5195 | AATGAGAA GGCTAGCTACAACGA GGACATAG | 17593 |
| 5028 | CCAUUCUC A UUCGUGGC | 5197 | GCCACGAA GGCTAGCTACAACGA GAGAATGG | 17594 |
| 5032 | UCUCAUUC G UGGCAUGU | 7956 | ACATGCCA GGCTAGCTACAACGA GAATGAGA | 17595 |
| 5035 | CAUUCGUG G CAUGUUUU | 7957 | AAAACATG GGCTAGCTACAACGA CACGAATG | 17596 |
| 5037 | UUCGUGGC A UGUUUUGA | 5198 | TCAAAACA GGCTAGCTACAACGA GCCACGAA | 17597 |
| 5039 | CGUGGCAU G UUUUGAUU | 7958 | AATCAAAA GGCTAGCTACAACGA ATGCCACG | 17598 |
| 5045 | AUGUUUUG A UUUGUAGC | 7959 | GCTACAAA GGCTAGCTACAACGA CAAAACAT | 17599 |
| 5049 | UUUGAUUU G UAGCACUG | 7960 | CAGTGCTA GGCTAGCTACAACGA AAATCAAA | 17600 |
| 5052 | GAUUUGUA G CACUGAGG | 7961 | CCTCAGTG GGCTAGCTACAACGA TACAAATC | 17601 |
| 5054 | UUUGUAGC A CUGAGGGU | 5199 | ACCCTCAG GGCTAGCTACAACGA GCTACAAA | 17602 |
| 5061 | CACUGAGG G UGGCACUC | 7962 | GAGTGCCA GGCTAGCTACAACGA CCTCAGTG | 17603 |
| 5064 | UGAGGGUG G CACUCAAC | 7963 | GTTGAGTG GGCTAGCTACAACGA CACCCTCA | 17604 |
| 5066 | AGGGUGGC A CUCAACUC | 5201 | GAGTTGAG GGCTAGCTACAACGA GCCACCCT | 17605 |
| 5071 | GGCACUCA A CUCUGAGC | 7964 | GCTCAGAG GGCTAGCTACAACGA TGAGTGCC | 17606 |
| 5078 | AACUCUGA G CCCAUACU | 7965 | AGTATGGG GGCTAGCTACAACGA TCAGAGTT | 17607 |
| 5082 | CUGAGCCC A UACUUUUG | 5208 | CAAAAGTA GGCTAGCTACAACGA GGGCTCAG | 17608 |
| 5084 | GAGCCCAU A CUUUUGGC | 827 | GCCAAAG GGCTAGCTACAACGA ATGGGCTC | 17609 |
| 5091 | UACUUUUG G CUCCUCUA | 7966 | TAGAGGAG GGCTAGCTACAACGA CAAAAGTA | 17610 |
| 5100 | CUCCUCUA G UAAGAUGC | 7967 | GCATCTTA GGCTAGCTACAACGA TAGAGGAG | 17611 |
| 5105 | CUAGUAAG A UGCACUGA | 7968 | TCAGTGCA GGCTAGCTACAACGA CTTACTAG | 17612 |
| 5107 | AGUAAGAU G CACUGAAA | 7969 | TTTCAGTG GGCTAGCTACAACGA ATCTTACT | 17613 |
| 5109 | UAAGAUGC A CUGAAAAC | 5214 | GTTTTCAG GGCTAGCTACAACGA GCATCTTA | 17614 |
| 5116 | CACUGAAA A CUUAGCCA | 7970 | TGGCTAAG GGCTAGCTACAACGA TTTCAGTG | 17615 |
| 5121 | AAAACUUA G CCAGAGUU | 7971 | AACTCTGG GGCTAGCTACAACGA TAAGTTTT | 17616 |
| 5127 | UAGCCAGA G UUAGGUUG | 7972 | CAACCTAA GGCTAGCTACAACGA TCTGGCTA | 17617 |
| 5132 | AGAGUUAG G UUGUCUCC | 7973 | GGAGACAA GGCTAGCTACAACGA CTAACTCT | 17618 |
| 5135 | GUUAGGUU G UCUCCAGG | 7974 | CCTGGAGA GGCTAGCTACAACGA AACCTAAC | 17619 |
| 5143 | GUCUCCAG G CCAUGAUG | 7975 | CATCATGG GGCTAGCTACAACGA CTGGAGAC | 17620 |
| 5146 | UCCAGGCC A UGAUGGCC | 5223 | GGCCATCA GGCTAGCTACAACGA GGCCTGGA | 17621 |
| 5149 | AGGCCAUG A UGGCCUUA | 7976 | TAAGGCCA GGCTAGCTACAACGA CATGGCCT | 17622 |
| 5152 | CCAUGAUG G CCUUACAC | 7977 | GTGTAAGG GGCTAGCTACAACGA CATCATGG | 17623 |
| 5157 | AUGGCCUU A CACUGAAA | 843 | TTTCAGTG GGCTAGCTACAACGA AAGGCCAT | 17624 |
| 5159 | GGCCUUAC A CUGAAAAU | 5226 | ATTTTCAG GGCTAGCTACAACGA GTAAGGCC | 17625 |
| 5166 | CACUGAAA A UGUCACAU | 7978 | ATGTGACA GGCTAGCTACAACGA TTTCAGTG | 17626 |
| 5168 | CUGAAAAU G UCACAUUC | 7979 | GAATGTGA GGCTAGCTACAACGA ATTTTCAG | 17627 |
| 5171 | AAAAUGUC A CAUUCUAU | 5228 | ATAGAATG GGCTAGCTACAACGA GACATTTT | 17628 |
| 5173 | AAUGUCAC A UUCUAUUU | 5229 | AAATAGAA GGCTAGCTACAACGA GTGACATT | 17629 |

TABLE XVIII-continued

Human FLT DNAzyme and Substrate Sequence

| Pos | Substrate | Seq ID No | DNAzyme | Seq ID No |
|---|---|---|---|---|
| 5178 | CACAUUCU A UUUUGGGU | 847 | ACCCAAAA GGCTAGCTACAACGA AGAATGTG | 17630 |
| 5185 | UAUUUUGG G UAUUAAUA | 7980 | TATTAATA GGCTAGCTACAACGA CCAAAATA | 17631 |
| 5187 | UUUUGGGU A UUAAUAUA | 851 | UATATTAA GGCTAGCTACAACGA ACCCAAAA | 17632 |
| 5191 | GGGUAUUA A UAUAUAGU | 7981 | ACTATATA GGCTAGCTACAACGA TAATACCC | 17633 |
| 5193 | GUAUUAAU A UAUAGUCC | 854 | GGACTATA GGCTAGCTACAACGA ATTAATAC | 17634 |
| 5195 | AUUAAUAU A CAGUCCAG | 855 | CTGGACTA GGCTAGCTACAACGA ATATTAAT | 17635 |
| 5198 | AAUAUAUA G UCCAGACA | 7982 | TGTCTGGA GGCTAGCTACAACGA TATATATT | 17636 |
| 5204 | UAGUCCAG A CACUUAAC | 7983 | GTTAAGTG GGCTAGCTACAACGA CTGGACTA | 17637 |
| 5206 | GUCCAGAC A CUUAACUC | 5233 | GAGTTAAG GGCTAGCTACAACGA GTCTGGAC | 17638 |
| 5211 | GACACUUA A CUCAAUUU | 7984 | AAATTGAG GGCTAGCTACAACGA TAAGTGTC | 17639 |
| 5216 | UUAACUCA A UUUCUUGG | 7985 | CCAAGAAA GGCTAGCTACAACGA TGAGTTAA | 17640 |
| 5224 | AUUUCUUG G UAUUAUUC | 7986 | GAATAATA GGCTAGCTACAACGA CAAGAAAT | 17641 |
| 5226 | UUCUUGGU A UUAUUCUG | 865 | CAGAATAA GGCTAGCTACAACGA ACCAAGAA | 17642 |
| 5229 | UUGGUAUU A UUCUGUUU | 867 | AAACAGAA GGCTAGCTACAACGA AATACCAA | 17643 |
| 5234 | AUUAUUCU G UUUUGCAC | 7987 | GTGCAAAA GGCTAGCTACAACGA AGAATAAT | 17644 |
| 5239 | UCUGUUUU G CACAGUUA | 7988 | TAACTGTG GGCTAGCTACAACGA AAAACAGA | 17645 |
| 5241 | UGUUUUGC A CAGUUAGU | 5239 | ACTAACTG GGCTAGCTACAACGA GCAAAACA | 17646 |
| 5244 | UUUGCACA G UUAGUUGU | 7989 | ACAACTAA GGCTAGCTACAACGA TGTGCAAA | 17647 |
| 5248 | CACAGUUA G UUGUGAAA | 7990 | TTTCACAA GGCTAGCTACAACGA TAACTGTG | 17648 |
| 5251 | AGUUAGUU G UGAAAGAA | 799 | UCTTTCA GGCTAGCTACAACGA AACTAACT | 17649 |
| 5261 | GAAAGAAA G CUGAGAAG | 7992 | CTTCTCAG GGCTAGCTACAACGA TTTCTTTC | 17650 |
| 5271 | UGAGAAGA A UGAAAAUG | 7993 | CATTTTCA GGCTAGCTACAACGA TCTTCTCA | 17651 |
| 5277 | GAAUGAAA A UGCAGUCC | 7994 | GGACTGCA GGCTAGCTACAACGA TTTCATTC | 17652 |
| 5279 | AUGAAAAU G CAGUCCUG | 7995 | CAGGACTG GGCTAGCTACAACGA ATTTTCAT | 17653 |
| 5282 | AAAAUGCA G UCCUGAGG | 7996 | CCTCAGGA GGCTAGCTACAACGA TGCATTTT | 17654 |
| 5294 | UGAGGAGA G UUUUCUCC | 7997 | GGAGAAAA GGCTAGCTACAACGA TCTCCTCA | 17635 |
| 5303 | UUUUCUCC A UAUCAAAA | 5247 | TTTTGATA GGCTAGCTACAACGA GGAGAAAA | 17656 |
| 5305 | UUCUCCAU A UCAAAACG | 882 | CGTTTTGA GGCTAGCTACAACGA ATGGAGAA | 17657 |
| 5312 | AUAUCAAA A CGAGGGCU | 7998 | AGCCCTCG GGCTAGCTACAACGA TTTGATAT | 17658 |
| 5317 | AAACGAGG G CUGAUGGA | 7999 | TCCATCAG GGCTAGCTACAACGA CCTCGTTT | 17659 |
| 5321 | GAGGGCUG A UGGAGGAA | 8000 | TTCCTCCA GGCTAGCTACAACGA CAGCCCTC | 17660 |
| 5334 | GGAAAAAG G UCAAUAAG | 8001 | CTTATTGA GGCTAGCTACAACGA CTTTTTCC | 17661 |
| 5338 | AAAGGUCA A UAAGGUCA | 8002 | TGACCTTA GGCTAGCTACAACGA TGACCTTT | 17662 |
| 5343 | UCAAUAAG G UCAAGGGA | 8003 | TCCCTTGA GGCTAGCTACAACGA CTTATTGA | 17663 |
| 5354 | AAGGGAAG A CCCCGUCU | 8004 | AGACGGGG GGCTAGCTACAACGA CTTCCCTT | 17664 |
| 5359 | AAGACCCC G UCUCUAUA | 8005 | TATAGAGA GGCTAGCTACAACGA GGGGTCTT | 17665 |
| 5365 | CCGUCUCU A UACCAACC | 889 | GGTTGGTA GGCTAGCTACAACGA AGAGACGG | 17666 |

TABLE XVIII-continued

Human FLT DNAzyme and Substrate Sequence

| Pos | Substrate | Seq ID No | DNAzyme | Seq ID No |
|---|---|---|---|---|
| 5367 | GUCUCUAU A CCAACCAA | 890 | TTGGTTGG GGCTAGCTACAACGA ATAGAGAC | 17667 |
| 5371 | CUAUACCA A CCAAACCA | 8006 | TGGTTTGG GGCTAGCTACAACGA TGGTATAG | 17668 |
| 5376 | CCAACCAA A CCAAUUCA | 8007 | TGAATTGG GGCTAGCTACAACGA TTGGTTGG | 17669 |
| 5380 | CCAAACCA A UUCACCAA | 8008 | TTGGTGAA GGCTAGCTACAACGA TGGTTTGG | 17670 |
| 5384 | ACCAAUUC A CCAACACA | 5263 | TGTGTTGG GGCTAGCTACAACGA GAATTGGT | 17671 |
| 5388 | AUUCACCA A CACAGUUG | 8009 | CAACTGTG GGCTAGCTACAACGA TGGTGAAT | 17672 |
| 5390 | UCACCAAC A CAGUUGGG | 5266 | CCCAACTG GGCTAGCTACAACGA GTTGGTGA | 17673 |
| 5393 | CCAACACA G UUGGGACC | 8010 | GGTCCCAA GGCTAGCTACAACGA TGTGTTGG | 17674 |
| 5399 | CAGUUGGG A CCCAAAAC | 8011 | GTTTTGGG GGCTAGCTACAACGA CCCAACTG | 17675 |
| 5406 | GACCCAAA A CACAGGAA | 8012 | TTCCTGTG GGCTAGCTACAACGA TTTGGGTC | 17676 |
| 5408 | CCCAAAAC A CAGGAAGU | 5271 | ACTTCCTG GGCTAGCTACAACGA GTTTTGGG | 17677 |
| 5415 | CACAGGAA G UCAGUCAC | 8013 | GTGACTGA GGCTAGCTACAACGA TTCCTGTG | 17678 |
| 5419 | GGAAGUCA G UCACGUUU | 8014 | AAACGTGA GGCTAGCTACAACGA TGACTTCC | 17679 |
| 5422 | AGUCAGUC A CGUUUCCU | 5274 | AGGAAACG GGCTAGCTACAACGA GACTGACT | 17680 |
| 5424 | UCAGUCAC G UUUCCUUU | 8015 | AAAGGAAA GGCTAGCTACAACGA GTGACTGA | 17681 |
| 5435 | UCCUUUUC A UUUAAUGG | 5277 | CCATTAAA GGCTAGCTACAACGA GAAAAGGA | 17682 |
| 5440 | UUCAUUUA A UGGGGAUU | 8016 | AATCCCCA GGCTAGCTACAACGA TAAATGAA | 17683 |
| 5446 | UAAUGGGG A UUCCACUA | 8017 | TAGTGGAA GGCTAGCTACAACGA CCCCATTA | 17684 |
| 5451 | GGGAUUCC A CUAUCUCA | 5279 | TGAGATAG GGCTAGCTACAACGA GGAATCCC | 17685 |
| 5454 | AUUCCACU A UCUCACAC | 908 | GTGTGAGA GGCTAGCTACAACGA AGTGGAAT | 17686 |
| 5459 | ACUAUCUC A CACUAAUC | 5282 | GATTAGTG GGCTAGCTACAACGA GAGATAGT | 17687 |
| 5461 | UAUCUCAC A CUAAUCUG | 5283 | CAGATTAG GGCTAGCTACAACGA GTGAGATA | 17688 |
| 5465 | UCACACUA A UCUGAAAG | 8018 | CTTTCAGA GGCTAGCTACAACGA TAGTGTGA | 17689 |
| 5475 | CUGAAAGG A UGUGGAAG | 8019 | CTTCCACA GGCTAGCTACAACGA CCTTTCAG | 17690 |
| 5477 | GAAAGGAU G UGGAAGAG | 8020 | CTCTTCCA GGCTAGCTACAACGA ATCCTTTC | 17691 |
| 5485 | GUGGAAGA G CAUUAGCU | 8021 | AGCTAATG GGCTAGCTACAACGA TCTTCCAC | 17692 |
| 5487 | GGAAGAGC A UUAGCUGG | 5286 | CCAGCTAA GGCTAGCTACAACGA GCTCTTCC | 17693 |
| 5491 | GAGCAUUA G CUGGCGCA | 8022 | TGCGCCAG GGCTAGCTACAACGA TAATGCTC | 17694 |
| 5495 | AUUAGCUG G CGCAUAUU | 8023 | AATATGCG GGCTAGCTACAACGA CAGCTAAT | 17695 |
| 5497 | UAGCUGGC G CAUAUUAA | 8024 | TTAATATG GGCTAGCTACAACGA GCCAGCTA | 17696 |
| 5499 | GCUGGCGC A UAUUAAGC | 5288 | GCTTAATA GGCTAGCTACAACGA GCGCCAGC | 17697 |
| 5501 | UGGCGCAU A UUAAGCAC | 915 | GTGCTTAA GGCTAGCTACAACGA ATGCGCCA | 17698 |
| 5506 | CAUAUUAA G CACUUUAA | 8025 | TTAAAGTG GGCTAGCTACAACGA TTAATATG | 17699 |
| 5508 | UAUUAAGC A CUUUAGC | 5289 | GCTTAAAG GGCTAGCTACAACGA GCTTAATA | 17700 |
| 5515 | CACUUUAA G CUCCUUGA | 8026 | TCAAGGAG GGCTAGCTACAACGA TTAAAGTG | 17701 |
| 5524 | CUCCUUGA G UAAAAGG | 8027 | CCTTTTTA GGCTAGCTACAACGA TCAAGGAG | 17702 |
| 5532 | GUAAAAAG G UGGUAUGU | 8028 | ACATACCA GGCTAGCTACAACGA CTTTTTAC | 17703 |

TABLE XVIII-continued

Human FLT DNAzyme and Substrate Sequence

| Pos | Substrate | Seq ID No | DNAzyme | Seq ID No |
|---|---|---|---|---|
| 5535 | AAAAGGUG G UAUGUAAU | 8029 | ATTACATA GGCTAGCTACAACGA CACCTTTT | 17704 |
| 5537 | AAGGUGGU A UGUAAUUU | 924 | AAATTACA GGCTAGCTACAACGA ACCACCTT | 17705 |
| 5539 | GGUGGUAU G UAAUUUAU | 8030 | ATAAATTA GGCTAGCTACAACGA ATACCACC | 17706 |
| 5542 | GGUAUGUA A UUUAUGCA | 803 | UGCATAAA GGCTAGCTACAACGA TACATACC | 17707 |
| 5546 | UGUAAUUU A UGCAAGGU | 928 | ACCTTGCA GGCTAGCTACAACGA AAATTACA | 17708 |
| 5548 | UAAUUUAU G CAAGGUAU | 8032 | ATACCTTG GGCTAGCTACAACGA ATAAATTA | 17709 |
| 5553 | UAUGCAAG G UAUUUCUC | 8033 | GAGAAATA GGCTAGCTACAACGA CTTGCATA | 17710 |
| 5555 | UGCAAGGU A UUUCUCCA | 929 | TGGAGAAA GGCTAGCTACAACGA ACCTTGCA | 17711 |
| 5564 | UUUCUCCA G UUGGGACU | 8034 | AGTCCCAA GGCTAGCTACAACGA TGGAGAAA | 17712 |
| 5570 | CAGUUGGG A CUCAGGAU | 8035 | ATCCTGAG GGCTAGCTACAACGA CCCAACTG | 17713 |
| 5577 | GACUCAGG A UAUUAGUU | 8036 | AACTAATA GGCTAGCTACAACGA CCTGAGTC | 17714 |
| 5579 | CUCAGGAU A UUAGUUAA | 936 | TTAACTAA GGCTAGCTACAACGA ATCCTGAG | 17715 |
| 5583 | GGAUAUUA G UUAAUGAG | 8037 | CTCATTAA GGCTAGCTACAACGA TAATATCC | 17716 |
| 5587 | AUUAGUUA A UGAGCCAU | 8038 | ATGGCTCA GGCTAGCTACAACGA TAACTAAT | 17717 |
| 5591 | GUUAAUGA G CCAUCACU | 8039 | AGTGATGG GGCTAGCTACAACGA TCATTAAC | 17718 |
| 5594 | AAUGAGCC A UCACUAGA | 530 | UCTAGTGA GGCTAGCTACAACGA GGCTCATT | 17719 |
| 5597 | GAGCCAUC A CUAGAAGA | 5302 | TCTTCTAG GGCTAGCTACAACGA GATGGCTC | 17720 |
| 5609 | GAAGAAAA G CCCAUUUU | 8040 | AAAATGGG GGCTAGCTACAACGA TTTTCTTC | 17721 |
| 5613 | AAAAGCCC A UUUUCAAC | 5306 | GTTGAAAA GGCTAGCTACAACGA GGGCTTTT | 17722 |
| 5620 | CAUUUUCA A CUGCUUUG | 8041 | CAAAGCAG GGCTAGCTACAACGA TGAAAATG | 17723 |
| 5623 | UUUCAACU G CUUUGAAA | 8042 | TTTCAAAG GGCTAGCTACAACGA AGTTGAAA | 17724 |
| 5631 | GCUUUGAA A CUUGCCUG | 8043 | CAGGCAAG GGCTAGCTACAACGA TTCAAAGC | 17725 |
| 5635 | UGAAACUU G CCUGGGGU | 8044 | ACCCCAGG GGCTAGCTACAACGA AAGTTTCA | 17726 |
| 5642 | UGCCUGGG C UCUGACCA | 8045 | TGCTCAGA GGCTAGCTACAACGA CCCAGGCA | 17727 |
| 5648 | GGGUCUGA C CAUGAUGG | 8046 | CCATCATG GGCTAGCTACAACGA TCAGACCC | 17728 |
| 5650 | GUCUGAGC A UGAUGGGA | 5314 | TCCCATCA GGCTAGCTACAACGA GCTCAGAC | 17729 |
| 5653 | UGACCAUG A UGGGAAUA | 8047 | TATTCCCA GGCTAGCTACAACGA CATGCTCA | 17730 |
| 5659 | UGAUGGGA A UAGGGAGA | 8048 | TCTCCCTA GGCTAGCTACAACGA TCCCATCA | 17731 |
| 5667 | AUAGGGAG A CAGGGUAG | 8049 | CTACCCTG GGCTAGCTACAACGA CTCCCTAT | 17732 |
| 5672 | GAGACAGG G UAGGAAAG | 8050 | CTTTCCTA GGCTAGCTACAACGA CCTGTCTC | 17733 |
| 5682 | AGGAAAGG G CGCCUACU | 8051 | AGTAGGCG GGCTAGCTACAACGA CCTTTCCT | 17734 |
| 5684 | GAAAGGGC G CCUACUCU | 8052 | AGAGTAGG GGCTAGCTACAACGA GCCCTTTC | 17735 |
| 5688 | GGGCGCCU A CUCUUCAG | 953 | CTGAAGAG GGCTAGCTACAACGA AGGCGCCC | 17736 |
| 5698 | UCUUCAGG G UCUAAAGA | 8053 | TCTTTAGA GGCTAGCTACAACGA CCTGAAGA | 17737 |
| 5706 | GUCUAAAG A UCAAGUGG | 8054 | CCACTTGA GGCTAGCTACAACGA CTTTAGAC | 17738 |
| 5711 | AAGAUCAA G UGGGCCUU | 8055 | AAGGCCCA GGCTAGCTACAACGA TTGATCTT | 17739 |
| 5715 | UCAAGUGG G CCUUGGAU | 8056 | ATCCAAGG GGCTAGCTACAACGA CCACTTGA | 17740 |

TABLE XVIII-continued

Human FLT DNAzyme and Substrate Sequence

| Pos | Substrate | Seq ID No | DNAzyme | Seq ID No |
|---|---|---|---|---|
| 5722 | GGCCUUGG A UCGCUAAG | 8057 | CTTAGCGA GGCTAGCTACAACGA CCAAGGCC | 17741 |
| 5725 | CUUGGAUC G CUAAGCUG | 8058 | CAGCTTAG GGCTAGCTACAACGA GATCCAAG | 17742 |
| 5730 | AUCGCUAA C CUGGCUCU | 8059 | AGAGCCAG GGCTAGCTACAACGA TTAGCGAT | 17743 |
| 5734 | CUAAGCUG G CUCUGUUU | 8060 | AAACAGAG GGCTAGCTACAACGA CAGCTTAG | 17744 |
| 5739 | CUGGCUCU G UUUGAUGC | 8061 | GCATCAAA GGCTAGCTACAACGA AGAGCCAG | 17745 |
| 5744 | UCUGUUUG A UGCUAUUU | 8062 | AAATAGCA GGCTAGCTACAACGA CAAACAGA | 17746 |
| 5746 | UGUUUGAU G CUAUUUAU | 8063 | ATAAATAG GGCTAGCTACAACGA ATCAAACA | 17747 |
| 5749 | UUGAUGCU A UUUAUGCA | 966 | TGCATAAA GGCTAGCTACAACGA AGCATCAA | 17748 |
| 5753 | UCCUAUUU A UGCAAGUU | 969 | AACTTGCA GGCTAGCTACAACGA AAATAGCA | 17749 |
| 5755 | CUAUUUAU C CAAGUUAG | 8064 | CTAACTTG CGCTAGCTACAACGA ATAAATAG | 17750 |
| 5759 | UUAUGCAA G UUAGGGUC | 8065 | GACCCTAA GGCTAGCTACAACGA TTGCATAA | 17751 |
| 5765 | AAGUUAGG G UCUAUGUA | 8066 | TACATAGA GGCTAGCTACAACGA CCTAACTT | 17752 |
| 5769 | UAGGGUCU A UGUAUUUA | 973 | TAAATACA GGCTAGCTACAACGA AGACCCTA | 17753 |
| 5771 | GGGUCUAU G UAUUUAGG | 8067 | CCTAAATA GGCTAGCTACAACGA ATAGACCC | 17754 |
| 5773 | GUCUAUGU A UUUAGGAU | 974 | ATCCTAAA GGCTAGCTACAACGA ACATAGAC | 17755 |
| 5780 | UAUUUAGG A UGCGCCUA | 8068 | TAGGCGCA GGCTAGCTACAACGA CCTAAATA | 17756 |
| 5782 | UUUAGGAU G CGCCUACU | 8069 | AGTAGGCG GGCTAGCTACAACGA ATCCTAAA | 17757 |
| 5784 | UAGGAUGC G CCUACUCU | 8070 | AGAGTAGG GGCTAGCTACAACGA GCATCCTA | 17758 |
| 5788 | AUGCGCCU A CUCUUCAG | 978 | CTGAAGAG GGCTAGCTACAACGA AGGCGCAT | 17759 |
| 5798 | UCUUCAGG G UCUAAAGA | 8053 | TCTTTAGA GGCTAGCTACAACGA CCTGAAGA | 17737 |
| 5806 | GUCUAAAG A UCAAGUGG | 8054 | CCACTTCA GGCTAGCTACAACGA CTTTAGAC | 17738 |
| 5811 | AAGAUCAA G UGGGCCUU | 8055 | AAGGCCCA GGCTAGCTACAACGA TTGATCTT | 17739 |
| 5815 | UCAAGUGG G CCUUGGAU | 8056 | ATCCAAGG GGCTAGCTACAACGA CCACTTGA | 17740 |
| 5822 | GGCCUUGG A UCGCUAAG | 8057 | CTTAGCGA GGCTAGCTACAACGA CCAAGGCC | 17741 |
| 5825 | CUUGGAUC G CUAAGCUG | 8058 | CAGCTTAG GGCTAGCTACAACGA GATCCAAG | 17742 |
| 5830 | AUCGCUAA G CUGGCUCU | 8059 | AGAGCCAG GGCTAGCTACAACGA TTAGCGAT | 17743 |
| 5834 | CUAAGCUG G CUCUGUUU | 8060 | AAACAGAG GGCTAGCTACAACGA CAGCTTAG | 17744 |
| 5839 | CUGGCUCU G UUUGAUGC | 8061 | GCATCAAA GGCTAGCTACAACGA AGAGCCAG | 17745 |
| 5844 | UCUGUUUG A UGCUAUUU | 8062 | AAATAGCA GGCTAGCTACAACGA CAAACAGA | 17746 |
| 5846 | UGUUUGAU G CUAUUUAU | 8063 | ATAAATAG GGCTAGCTACAACGA ATCAAACA | 17747 |
| 5849 | UUGAUGCU A UUUAUGCA | 966 | TGCATAAA GGCTAGCTACAACGA AGCATCAA | 17748 |
| 5853 | UGCUAUUU A UGCAAGUU | 969 | AACTTGCA GGCTAGCTACAACGA AAATAGCA | 17749 |
| 5855 | CUAUUUAU G CAAGUUAG | 8064 | CTAACTTG GGCTAGCTACAACGA ATAAATAG | 17750 |
| 5859 | UUAUGCAA G UUAGGGUC | 8065 | GACCCTAA GGCTAGCTACAACGA TTGCATAA | 17751 |
| 5865 | AAGUUAGG G UCUAUGUA | 8066 | TACATAGA GGCTAGCTACAACGA CCTAACTT | 17752 |
| 5869 | UAGGGUCU A UGUAUUUA | 973 | TAAATACA GGCTAGCTACAACGA AGACCCTA | 17753 |
| 5871 | GGGUCUAU G UAUUUAGG | 8067 | CCTAAATA GGCTAGCTACAACGA ATAGACCC | 17754 |

TABLE XVIII-continued

Human FLT DNAzyme and Substrate Sequence

| Pos | Substrate | Seq ID No | DNAzyme | Seq ID No |
|---|---|---|---|---|
| 5873 | GUCUAUGU A UUUAGGAU | 974 | ATCCTAAA GGCTAGCTACAACGA ACATAGAC | 17755 |
| 5880 | UAUUUAGG A UGUCUGCA | 807 | UGCAGACA GGCTAGCTACAACGA CCTAAATA | 17760 |
| 5882 | UUUAGGAU G UCUGCACC | 8072 | GGTGCAGA GGCTAGCTACAACGA ATCCTAAA | 17761 |
| 5886 | GGAUGUCU G CACCUUCU | 8073 | AGAAGGTG GGCTAGCTACAACGA AGACATCC | 17762 |
| 5888 | AUGUCUGC A CCUUCUGC | 5335 | GCAGAAGG GGCTAGCTACAACGA GCAGACAT | 17763 |
| 5895 | CACCUUCU G CAGCCAGU | 8074 | ACTGGCTG GGCTAGCTACAACGA AGAAGGTG | 17764 |
| 5898 | CUUCUGCA G CCAGUCAG | 8075 | CTGACTGG GGCTAGCTACAACGA TGCAGAAG | 17765 |
| 5902 | UGCAGCCA G UCAGAAGC | 8076 | GCTTCTGA GGCTAGCTACAACGA TGGCTGCA | 17766 |
| 5909 | AGUCAGAA G CUGGAGAG | 8077 | CTCTCCAG GGCTAGCTACAACGA TTCTGACT | 17767 |
| 5918 | CUGGAGAG G CAACAGUG | 8078 | CACTGTTG GGCTAGCTACAACGA CTCTCCAG | 17768 |
| 5921 | GAGAGGCA A CAGUGGAU | 8079 | ATCCACTG GGCTAGCTACAACGA TGCCTCTC | 17769 |
| 5924 | AGGCAACA G UGGAUUGC | 8080 | GCAATCCA GGCTAGCTACAACGA TGTTGCCT | 17770 |
| 5928 | AACAGUGG A UUGCUGCU | 8081 | AGCAGCAA GGCTAGCTACAACGA CCACTGTT | 17771 |
| 5931 | AGUGGAUU G CUGCUUCU | 8082 | AGAAGCAG GGCTAGCTACAACGA AATCCACT | 17772 |
| 5934 | GGAUUGCU G CUUCUUGG | 8083 | CCAAGAAG GGCTAGCTACAACGA AGCAATCC | 17773 |
| 5951 | GGAGAAGA G UAUGCUUC | 8084 | GAAGCATA GGCTAGCTACAACGA TCTTCTCC | 17774 |
| 5953 | AGAAGAGU A UGCUUCCU | 990 | AGGAAGCA GGCTAGCTACAACGA ACTCTTCT | 17775 |
| 5955 | AAGAGUAU G CUUCCUUU | 8085 | AAAGGAAG GGCTAGCTACAACGA ATACTCTT | 17776 |
| 5965 | UUCCUUUU A UCCAUGUA | 996 | TACATGGA GGCTAGCTACAACGA AAAAGGAA | 17777 |
| 5969 | UUUUAUCC A UGUAAUUU | 5353 | AAATTACA GGCTAGCTACAACGA GGATAAAA | 17778 |
| 5971 | UUAUCCAU G UAAUUUAA | 8086 | TTAAATTA GGCTAGCTACAACGA ATGGATAA | 17779 |
| 5974 | UCCAUGUA A UUUAACUG | 8087 | CAGTTAAA GGCTAGCTACAACGA TACATGGA | 17780 |
| 5979 | GUAAUUUA A CUGUAGAA | 8088 | TTCTACAG GGCTAGCTACAACGA TAAATTAC | 17781 |
| 5982 | AUUUAACU G UAGAACCU | 8089 | AGGTTCTA GGCTAGCTACAACGA AGTTAAAT | 17782 |
| 5987 | ACUGUAGA A CCUGAGCU | 8090 | AGCTCAGG GGCTAGCTACAACGA TCTACAGT | 17783 |
| 5993 | GAACCUGA G CUCUAAGU | 8091 | ACTTAGAG GGCTAGCTACAACGA TCAGGTTC | 17784 |
| 6000 | AGCUCUAA G UAACCGAA | 8092 | TTCGGTTA GGCTAGCTACAACGA TTAGAGCT | 17785 |
| 6003 | UCUAAGUA A CCGAAGAA | 8093 | TTCTTCGG GGCTAGCTACAACGA TACTTAGA | 17786 |
| 6011 | ACCGAAGA A UGUAUGCC | 8094 | GGCATACA GGCTAGCTACAACGA TCTTCGGT | 17787 |
| 6013 | CGAAGAAU G UAUGCCUC | 8095 | GAGGCATA GGCTAGCTACAACGA ATTCTTCG | 17788 |
| 6015 | AAGAAUGU A UGCCUCUG | 1006 | CAGAGGCA GGCTAGCTACAACGA ACATTCTT | 17789 |
| 6017 | GAAUGUAU G CCUCUGUU | 8096 | AACAGAGG GGCTAGCTACAACGA ATACATTC | 17790 |
| 6023 | AUGCCUCU G UUCUUAUG | 8097 | CATAAGAA GGCTAGCTACAACGA AGAGGCAT | 17791 |
| 6029 | CUGUUCUU A UGUGCCAC | 1011 | GTGGCACA GGCTAGCTACAACGA AAGAACAG | 17792 |
| 6031 | GUUCUUAU G UGCCACAU | 8098 | ATGTGGCA GGCTAGCTACAACGA ATAAGAAC | 17793 |
| 6033 | UCUAUGU G CCACAUCC | 8099 | GGATGTGG GGCTAGCTACAACGA ACATAAGA | 17794 |
| 6036 | UAUGUGCC A CAUCCUUG | 5365 | CAAGGATG GGCTAGCTACAACGA GGCACATA | 17795 |

TABLE XVIII-continued

Human FLT DNAzyme and Substrate Sequence

| Pos | Substrate | Seq ID No | DNAzyme | Seq ID No |
|---|---|---|---|---|
| 6038 | UGUGCCAC A UCCUUGUU | 5366 | AACAAGGA GGCTAGCTACAACGA GTGGCACA | 17796 |
| 6044 | ACAUCCUU G UUUAAAGG | 8100 | CCTTTAAA GGCTAGCTACAACGA AAGGATGT | 17797 |
| 6052 | GUUUAAAG G CUCUCUGU | 8101 | ACAGAGAG GGCTAGCTACAACGA CTTTAAAC | 17798 |
| 6059 | GGCUCUCU G UAUGAAGA | 8102 | TCTTCATA GGCTAGCTACAACGA AGAGAGCC | 17799 |
| 6061 | CUCUCUGU A UGAAGAGA | 1019 | TCTCTTCA GGCTAGCTACAACGA ACAGAGAG | 17800 |
| 6069 | AUGAAGAG A UGGGACCG | 8103 | CGGTCCCA GGCTAGCTACAACGA CTCTTCAT | 17801 |
| 6074 | GAGAUGGG A CCGUCAUC | 8104 | GATGACGG GGCTAGCTACAACGA CCCATCTC | 17802 |
| 6077 | AUGGGACC G UCAUCAGC | 8105 | GCTGATGA GGCTAGCTACAACGA GGTCCCAT | 17803 |
| 6080 | GGACCGUC A UCAGCACA | 5373 | TGTGCTGA GGCTAGCTACAACGA GACGGTCC | 17804 |
| 6084 | CGUCAUCA G CACAUUCC | 8106 | GGAATGTG GGCTAGCTACAACGA TGATGACG | 17805 |
| 6086 | UCAUCAGC A CAUUCCCU | 5375 | AGGGAATG GGCTAGCTACAACGA GCTGATGA | 17806 |
| 6088 | AUCAGCAC A UUCCCUAG | 5376 | CTAGGGAA GGCTAGCTACAACGA GTGCTGAT | 17807 |
| 6096 | AUUCCCUA G UGAGCCUA | 8107 | TAGGCTCA GGCTAGCTACAACGA TAGGGAAT | 17808 |
| 6100 | CCUAGUGA G CCUACUGG | 8108 | CCAGTAGG GGCTAGCTACAACGA TCACTAGG | 17809 |
| 6104 | GUGAGCCU A CUGGCUCC | 1025 | GGAGCCAG GGCTAGCTACAACGA AGGCTCAC | 17810 |
| 6108 | GCCUACUG G CUCCUGGC | 8109 | GCCAGGAG GGCTAGCTACAACGA CAGTAGGC | 17811 |
| 6115 | GGCUCCUG G CAGCGGCU | 8110 | AGCCGCTG GGCTAGCTACAACGA CAGGAGCC | 17812 |
| 6118 | UCCUGGCA G CGGCUUUU | 8111 | AAAAGCCG GGCTAGCTACAACGA TGCCAGGA | 17813 |
| 6121 | UGGCAGCG G CUUUUGUG | 8112 | CACAAAAG GGCTAGCTACAACGA CGCTGCCA | 17814 |
| 6127 | CGGCUUUU G UGGAAGAC | 8113 | GTCTTCCA GGCTAGCTACAACGA AAAAGCCG | 17815 |
| 6134 | UGUGGAAG A CUCACUAG | 8114 | CTAGTGAG GGCTAGCTACAACGA CTTCCACA | 17816 |
| 6138 | GAAGACUC A CUAGCCAG | 5389 | CTGGCTAG GGCTAGCTACAACGA GAGTCTTC | 17817 |
| 6142 | ACUCACUA G CCAGAAGA | 8115 | TCTTCTGG GGCTAGCTACAACGA TAGTGAGT | 17818 |
| 6156 | AGAGAGGA G UGGGACAG | 8116 | CTGTCCCA GGCTAGCTACAACGA TCCTCTCT | 17819 |
| 6161 | GGAGUGGG A CAGUCCUC | 8117 | GAGGACTG GGCTAGCTACAACGA CCCACTCC | 17820 |
| 6164 | GUGGGACA G UCCUCUCC | 8118 | GGAGAGGA GGCTAGCTACAACGA TGTCCCAC | 17821 |
| 6173 | UCCUCUCC A CCAAGAUC | 5398 | GATCTTGG GGCTAGCTACAACGA GGAGAGGA | 17822 |
| 6179 | CCACCAAG A UCUAAAUC | 8119 | GATTTAGA GGCTAGCTACAACGA CTTGGTGG | 17823 |
| 6185 | AGAUCUAA A UCCAAACA | 8120 | TGTTTGGA GGCTAGCTACAACGA TTAGATCT | 17824 |
| 6191 | AAAUCCAA A CAAAAGCA | 812 | UGCTTTTG GGCTAGCTACAACGA TTGGATTT | 17825 |
| 6197 | AAACAAAA G CAGGCUAG | 8122 | CTAGCCTG GGCTAGCTACAACGA TTTTGTTT | 17826 |
| 6201 | AAAAGCAG G CUAGAGCC | 8123 | GGCTCTAG GGCTAGCTACAACGA CTGCTTTT | 17827 |
| 6207 | AGGCUAGA G CCAGAAGA | 8124 | TCTTCTGG GGCTAGCTACAACGA TCTAGCCT | 17828 |
| 6220 | AAGAGAGG A CAAAUCUU | 8125 | AAGATTTG GGCTAGCTACAACGA CCTCTCTT | 17829 |
| 6224 | GAGGACAA A UCUUUGUU | 8126 | AACAAAGA GGCTAGCTACAACGA TTGTCCTC | 17830 |
| 6230 | AAAUCUUU G UUGUUCCU | 8127 | AGGAACAA GGCTAGCTACAACGA AAAGATTT | 17831 |
| 6233 | UCUUUGUU G UUCCUCUU | 8128 | AAGAGGAA GGCTAGCTACAACGA AACAAAGA | 17832 |

TABLE XVIII-continued

Human FLT DNAzyme and Substrate Sequence

| Pos | Substrate | Seq ID No | DNAzyme | Seq ID No |
|---|---|---|---|---|
| 6246 | UCUUCUUU A CACAUACG | 1050 | CGTATGTG GGCTAGCTACAACGA AAAGAAGA | 17833 |
| 6248 | UUCUUUAC A CAUACGCA | 5415 | TGCGTATG GGCTAGCTACAACGA GTAAAGAA | 17834 |
| 6250 | CUUUACAC A UACGCAAA | 5416 | TTTGCGTA GGCTAGCTACAACGA GTGTAAAG | 17835 |
| 6252 | UUACACAU A CGCAAACC | 1051 | GGTTTGCG GGCTAGCTACAACGA ATGTGTAA | 17836 |
| 6254 | ACACAUAC G CAAACCAC | 8129 | GTGGTTTG GGCTAGCTACAACGA GTATGTGT | 17837 |
| 6258 | AUACGCAA A CCACCUGU | 8130 | ACAGGTGG GGCTAGCTACAACGA TTGCGTAT | 17838 |
| 6262 | CGCAAACC A CCUGUGAC | 5419 | GTCACAGG GGCTAGCTACAACGA GGTTTGCG | 17839 |
| 6265 | AACCACCU G UGACAGCU | 8131 | AGCTGTCA GGCTAGCTACAACGA AGGTGGTT | 17840 |
| 6268 | CACCUGUG A CACCUGGG | 8132 | GCCAGCTG GGCTAGCTACAACGA CACAGGTG | 17841 |
| 6271 | CUGUGACA G CUGGCAAU | 8133 | ATTGCCAG GGCTAGCTACAACGA TGTCACAG | 17842 |
| 6275 | GACACCUG G CAAUUUUA | 8134 | TAAAATTG GGCTAGCTACAACGA CAGCTGTC | 17843 |
| 6278 | AGCUGGCA A UUUUAUAA | 8135 | TTATAAAA GGCTAGCTACAACGA TGCCAGCT | 17844 |
| 6283 | GCAAUUUU A UAAAUCAG | 1055 | CTGATTTA GGCTAGCTACAACGA AAAATTGC | 17845 |
| 6287 | UUUUAUAA A UCAGGUAA | 8136 | TTACCTGA GGCTAGCTACAACGA TTATAAAA | 17846 |
| 6292 | UAAAUCAG G UAACUGGA | 8137 | TCCAGTTA GGCTAGCTACAACGA CTGATTTA | 17847 |
| 6295 | AUCAGGUA A CUGGAAGG | 8138 | CCTTCCAG GGCTAGCTACAACGA TACCTGAT | 17848 |
| 6306 | GGAAGGAG G UUAAACUC | 8139 | GAGTTTAA GGCTAGCTACAACGA CTCCTTCC | 17849 |
| 6311 | GAGGUUAA A CUCAGAAA | 8140 | TTTCTGAG GGCTAGCTACAACGA TTAACCTC | 17850 |
| 6327 | AAAAGAAG A CCUCAGUC | 8141 | GACTGAGG GGCTAGCTACAACGA CTTCTTTT | 17851 |
| 6333 | AGACCUCA G UCAAUUCU | 8142 | AGAATTGA GGCTAGCTACAACGA TGAGGTCT | 17852 |
| 6337 | CUCAGUCA A UUCUCUAC | 8143 | GTAGAGAA GGCTAGCTACAACGA TGACTGAG | 17853 |
| 6344 | AAUUCUCU A CUUUUUUU | 1067 | AAAAAAAG GGCTAGCTACAACGA AGAGAATT | 17854 |
| 6366 | UUUUCCAA A UCAGAUAA | 8144 | TTATCTGA GGCTAGCTACAACGA TTGGAAAA | 17855 |
| 6371 | CAAAUCAG A UAAUAGCC | 8145 | GGCTATTA GGCTAGCTACAACGA CTGATTTG | 17856 |
| 6374 | AUCAGAUA A UAGCCCAG | 8146 | CTGGGCTA GGCTAGCTACAACGA TATCTGAT | 17857 |
| 6377 | AGAUAAUA G CCCAGCAA | 8147 | TTGCTGGG GGCTAGCTACAACGA TATTATCT | 17858 |
| 6382 | AUAGCCCA G CAAAUAGU | 8148 | ACTATTTG GGCTAGCTACAACGA TGGGCTAT | 17859 |
| 6386 | CCCAGCAA A UAGUGAUA | 8149 | TATCACTA GGCTAGCTACAACGA TTGCTGGG | 17860 |
| 6389 | AGCAAAUA G UGAUAACA | 8150 | TGTTATCA GGCTAGCTACAACGA TATTTGCT | 17861 |
| 6392 | AAAUAGUG A UAACAAAU | 8151 | ATTTGTTA GGCTAGCTACAACGA CACTATTT | 17862 |
| 6395 | UAGUGAUA A CAAAUAAA | 8152 | TTTATTTG GGCTAGCTACAACGA TATCACTA | 17863 |
| 6399 | GAUAACAA A UAAACCU | 8153 | AGGTTTTA GGCTAGCTACAACGA TTGTTATC | 17864 |
| 6404 | CAAAUAAA A CCUUAGCU | 8154 | AGCTAAGG GGCTAGCTACAACGA TTTATTTG | 17865 |
| 6410 | AAACCUUA G CUGUUCAU | 8155 | ATGAACAG GGCTAGCTACAACGA TAAGGTTT | 17866 |
| 6413 | CCUUAGCU G UUCAUGUC | 8156 | GACATGAA GGCTAGCTACAACGA AGCTAAGG | 17867 |
| 6417 | AGCUGUUC A UGUCUUGA | 5447 | TCAAGACA GGCTAGCTACAACGA GAACAGCT | 17868 |
| 6419 | CUGUUCAU G UCUUGAUU | 8157 | AATCAAGA GGCTAGCTACAACGA ATGAACAG | 17869 |

TABLE XVIII-continued

Human FLT DNAzyme and Substrate Sequence

| Pos | Substrate | Seq ID No | DNAzyme | Seq ID No |
|---|---|---|---|---|
| 6425 | AUGUCUUG A UUUCAAUA | 8158 | TATTGAAA GGCTAGCTACAACGA CAAGACAT | 17870 |
| 6431 | UGAUUUCA A UAAUUAAU | 8159 | ATTAATTA GGCTAGCTACAACGA TGAAATCA | 17871 |
| 6434 | UUUCAAUA A UUAAUUCU | 8160 | AGAATTAA GGCTAGCTACAACGA TATTGAAA | 17872 |
| 6438 | AAUAAUUA A UUCUUAAU | 8161 | ATTAAGAA GGCTAGCTACAACGA TAATTATT | 17873 |
| 6445 | AAUUCUUA A UCAUUAAG | 8162 | CTTAATGA GGCTAGCTACAACGA TAAGAATT | 17874 |
| 6448 | UCUUAAUC A UUAAGAGA | 545 | UCTCTTAA GGCTAGCTACAACGA GATTAAGA | 17875 |
| 6456 | AUUAAGAG A CCAUAAUA | 8163 | TATTATGG GGCTAGCTACAACGA CTCTTAAT | 17876 |
| 6459 | AAGAGACC A UAAUAAAU | 5453 | ATTTATTA GGCTAGCTACAACGA GGTCTCTT | 17877 |
| 6462 | AGACCAUA A UAAAUACU | 8164 | AGTATTTA GGCTAGCTACAACGA TATGGTCT | 17878 |
| 6466 | CAUAAUAA A UACUCCUU | 8165 | AAGGAGTA GGCTAGCTACAACGA TTATTATG | 17879 |
| 6468 | UAAUAAAU A CUCCUUUU | 1111 | AAAAGGAG GGCTAGCTACAACGA ATTTATTA | 17880 |
| 6487 | AGAGAAAA G CAAAACCA | 8166 | TGGTTTTG GGCTAGCTACAACGA TTTTCTCT | 17881 |
| 6492 | AAAGCAAA A CCAUUAGA | 8167 | TCTAATGG GGCTAGCTACAACGA TTTGCTTT | 17882 |
| 6495 | GCAAAACC A UUAGAAUU | 5460 | AATTCTAA GGCTAGCTACAACGA GGTTTTGC | 17883 |
| 6501 | CCAUUAGA A UUGUUACU | 8168 | AGTAACAA GGCTAGCTACAACGA TCTAATGG | 17884 |
| 6504 | UUAGAAUU G UUACUCAG | 8169 | CTGAGTAA GGCTAGCTACAACGA AATTCTAA | 17885 |
| 6507 | GAAUUGUU A CUCAGCUC | 1121 | GAGCTGAG GGCTAGCTACAACGA AACAATTC | 17886 |
| 6512 | GUUACUCA G CUCCUUCA | 8170 | TGAAGGAG GGCTAGCTACAACGA TGAGTAAC | 17887 |
| 6522 | UCCUUCAA A CUCAGGUU | 8171 | AACCTGAG GGCTAGCTACAACGA TTGAAGGA | 17888 |
| 6528 | AAACUCAG G UUUGUAGC | 8172 | GCTACAAA GGCTAGCTACAACGA CTGAGTTT | 17889 |
| 6532 | UCAGGUUU G UAGCAUAC | 8173 | GTATGCTA GGCTAGCTACAACGA AAACCTGA | 17890 |
| 6535 | GGUUUGUA G CAUACAUG | 8174 | CATGTATG GGCTAGCTACAACGA TACAAACC | 17891 |
| 6537 | UUUGUAGC A UACAUGAG | 5469 | CTCATGTA GGCTAGCTACAACGA GCTACAAA | 17892 |
| 6539 | UGUAGCAU A CAUGAGUC | 1130 | GACTCATG GGCTAGCTACAACGA ATGCTACA | 17893 |
| 6541 | UAGCAUAC A UGAGUCCA | 5470 | TGGACTCA GGCTAGCTACAACGA GTATGCTA | 17894 |
| 6545 | AUACAUGA G UCCAUCCA | 8175 | TGGATGGA GGCTAGCTACAACGA TCATGTAT | 17895 |
| 6549 | AUGAGUCC A UCCAUCAG | 5472 | CTGATGGA GGCTAGCTACAACGA GGACTCAT | 17896 |
| 6553 | GUCCAUCC A UCAGUCAA | 5474 | TTGACTGA GGCTAGCTACAACGA GGATGGAC | 17897 |
| 6557 | AUCCAUCA G UCAAAGAA | 8176 | TTCTTTGA GGCTAGCTACAACGA TGATGGAT | 17898 |
| 6565 | GUCAAAGA A UGGUUCCA | 8177 | TGGAACCA GGCTAGCTACAACGA TCTTTGAC | 17899 |
| 6568 | AAAGAAUG G UUCCAUCU | 8178 | AGATGGAA GGCTAGCTACAACGA CATTCTTT | 17900 |
| 6573 | AUGGUUCC A UCUGGAGU | 5478 | ACTCCAGA GGCTAGCTACAACGA GGAACCAT | 17901 |
| 6580 | CAUCUGGA G UCUUAAUG | 8179 | CATTAAGA GGCTAGCTACAACGA TCCAGATG | 17902 |
| 6586 | GAGUCUUA A UGUAGAAA | 8180 | TTTCTACA GGCTAGCTACAACGA TAAGACTC | 17903 |
| 6588 | GUCUUAAU G UAGAAAGA | 818 | UCTTTCTA GGCTAGCTACAACGA ATTAAGAC | 17904 |
| 6600 | AAAGAAAA A UGGAGACU | 8182 | AGTCTCCA GGCTAGCTACAACGA TTTTCTTT | 17905 |
| 6606 | AAAUGGAG A CUUGUAAU | 8183 | ATTACAAG GGCTAGCTACAACGA CTCCATTT | 17906 |

TABLE XVIII-continued

Human FLT DNAzyme and Substrate Sequence

| Pos | Substrate | Seq ID No | DNAzyme | Seq ID No |
|---|---|---|---|---|
| 6610 | GGAGACUU G UAAUAAUG | 8184 | CATTATTA GGCTAGCTACAACGA AAGTCTCC | 17907 |
| 6613 | GACUUGUA A UAUGAGC | 8185 | GCTCATTA GGCTAGCTACAACGA TACAAGTC | 17908 |
| 6616 | UUGUAAUA A UGAGCUAG | 8186 | CTAGCTCA GGCTAGCTACAACGA TATTACAA | 17909 |
| 6620 | AAUAAUGA G CUAGUUAC | 8187 | GTAACTAG GGCTAGCTACAACGA TCATTATT | 17910 |
| 6624 | AUGAGCUA G UUACAAAG | 8188 | CTTTGTAA GGCTAGCTACAACGA TAGCTCAT | 17911 |
| 6627 | AGCUAGUU A CAAAGUGC | 1147 | GCACTTTG GGCTAGCTACAACGA AACTAGCT | 17912 |
| 6632 | GUUACAAA G UGCUUGUU | 8189 | AACAAGCA GGCTAGCTACAACGA TTTGTAAC | 17913 |
| 6634 | UACAAAGU G CUUGUUCA | 8190 | TGAACAAG GGCTAGCTACAACGA ACTTTGTA | 17914 |
| 6638 | AAGUGCUU G UUCAUUAA | 819 | UTAATGAA GGCTAGCTACAACGA AAGCACTT | 17915 |
| 6642 | GCUUGUUC A UUAAAAUA | 5485 | TATTTTAA GGCTAGCTACAACGA GAACAAGC | 17916 |
| 6648 | UCAUUAAA A UAGCACUG | 8192 | CAGTGCTA GGCTAGCTACAACGA TTTAATGA | 17917 |
| 6651 | UUAAAAUA G CACUGAAA | 8193 | TTTCAGTG GGCTAGCTACAACGA TATTTTAA | 17918 |
| 6653 | AAAAUAGC A CUGAAAAU | 5486 | ATTTTCAG GGCTAGCTACAACGA GCTATTTT | 17919 |
| 6660 | CACUGAAA A UUGAAACA | 8194 | TGTTTCAA GGCTAGCTACAACGA TTTCAGTG | 17920 |
| 6666 | AAAUUGAA A CAUGAAUU | 8195 | AATTCATG GGCTAGCTACAACGA TTCAATTT | 17921 |
| 6668 | AUUGAAAC A UGAAUUAA | 5488 | TTAATTCA GGCTAGCTACAACGA GTTTCAAT | 17922 |
| 6672 | AAACAUGA A UUAACUGA | 8196 | TCAGTTAA GGCTAGCTACAACGA TCATGTTT | 17923 |
| 6676 | AUGAAUUA A CUGAUAAU | 8197 | ATTATCAG GGCTAGCTACAACGA TAATTCAT | 17924 |
| 6680 | AUUAACUG A UAAUAUUC | 8198 | GAATATTA GGCTAGCTACAACGA CAGTTAAT | 17925 |
| 6683 | AACUGAUA A UAUUCCAA | 8199 | TTGGAATA GGCTAGCTACAACGA TATCAGTT | 17926 |
| 6685 | CUGAUAAU A UUCCAAUC | 1158 | GATTGGAA GGCTAGCTACAACGA ATTATCAG | 17927 |
| 6691 | AUAUUCCA A UCAUUUGC | 8200 | GCAAATGA GGCTAGCTACAACGA TGGAATAT | 17928 |
| 6694 | UUCCAAUC A UUUGCCAU | 5492 | ATGGCAAA GGCTAGCTACAACGA GATTGGAA | 17929 |
| 6698 | AAUCAUUU G CCAUUUAU | 8201 | ATAAATGG GGCTAGCTACAACGA AAATGATT | 17930 |
| 6701 | CAUUUGCC A UUUAUGAC | 5494 | GTCATAAA GGCTAGCTACAACGA GGCAAATG | 17931 |
| 6705 | UGCCAUUU A UGACAAAA | 1166 | TTTTGTCA GGCTAGCTACAACGA AAATGGCA | 17932 |
| 6708 | CAUUUAUG A CAAAAAUG | 8202 | CATTTTTG GGCTAGCTACAACGA CATAAATG | 17933 |
| 6714 | UGACAAAA A UGGUUGGC | 8203 | GCCAACCA GGCTAGCTACAACGA TTTTGTCA | 17934 |
| 6717 | CAAAAUUG G UUGGCACU | 8204 | AGTGCCAA GGCTAGCTACAACGA CATTTTTG | 17935 |
| 6721 | AAUGGUUG G CACUAACA | 8205 | TGTTAGTG GGCTAGCTACAACGA CAACCATT | 17936 |
| 6723 | UGGUUGGC A CUAACAAA | 5496 | TTTGTTAG GGCTAGCTACAACGA GCCAACCA | 17937 |
| 6727 | UGGCACUA A CAAAGAAC | 8206 | GTTCTTTG GGCTAGCTACAACGA TAGTGCCA | 17938 |
| 6734 | AACAAAGA A CGAGCACU | 8207 | AGTGCTCG GGCTAGCTACAACGA TCTTTGTT | 17939 |
| 6738 | AAGAACGA G CACUUCCU | 8208 | AGGAAGTG GGCTAGCTACAACGA TCGTTCTT | 17940 |
| 6740 | GAACGAGC A CUUCCUUU | 5499 | AAAGGAAG GGCTAGCTACAACGA GCTCGTTC | 17941 |
| 6753 | CUUUCAGA G UUUCUGAG | 8209 | CTCAGAAA GGCTAGCTACAACGA TCTGAAAG | 17942 |
| 6762 | UUUCUGAG A UAAUGUAC | 8210 | GTACATTA GGCTAGCTACAACGA CTCAGAAA | 17943 |

TABLE XVIII-continued

Human FLT DNAzyme and Substrate Sequence

| Pos | Substrate | Seq ID No | DNAzyme | Seq ID No |
|---|---|---|---|---|
| 6765 | CUGAGAUA A UGUACGUG | 8211 | CACGTACA GGCTAGCTACAACGA TATCTCAG | 17944 |
| 6767 | GAGAUAAU G UACGUGGA | 8212 | TCCACGTA GGCTAGCTACAACGA ATTATCTC | 17945 |
| 6769 | GAUAAUGU A CGUGGAAC | 1178 | GTTCCACG GGCTAGCTACAACGA ACATTATC | 17946 |
| 6771 | UAAUGUAC G UGGAACAG | 8213 | CTGTTCCA GGCTAGCTACAACGA GTACATTA | 17947 |
| 6776 | UACGUGGA A CAGUCUGG | 8214 | CCAGACTG GGCTAGCTACAACGA TCCACGTA | 17948 |
| 6779 | GUGGAACA G UCUGGGUG | 8215 | CACCCAGA GGCTAGCTACAACGA TGTTCCAC | 17949 |
| 6785 | CAGUCUGG G UGGAAUGG | 8216 | CCATTCCA GGCTAGCTACAACGA CCAGACTG | 17950 |
| 6790 | UGGGUGGA A UGGGGCUG | 8217 | CAGCCCCA GGCTAGCTACAACGA TCCACCCA | 17951 |
| 6795 | GGAAUGGG G CUGAAACC | 8218 | GGTTTCAG GGCTAGCTACAACGA CCCATTCC | 17952 |
| 6801 | GGGCUGAA A CCAUGUGC | 8219 | GCACATGG GGCTAGCTACAACGA TTCAGCCC | 17953 |
| 6804 | CUGAAACC A UGUGCAAG | 5509 | CTTGCACA GGCTAGCTACAACGA GGTTTCAG | 17954 |
| 6806 | GAAACCAU G UGCAAGUC | 8220 | GACTTGCA GGCTAGCTACAACGA ATGGTTTC | 17955 |
| 6808 | AACCAUGU G CAAGUCUG | 8221 | CAGACTTG GGCTAGCTACAACGA ACATGGTT | 17956 |
| 6812 | AUGUGCAA G UCUGUGUC | 8222 | GACACAGA GGCTAGCTACAACGA TTGCACAT | 17957 |
| 6816 | GCAAGUCU G UGUCUUGU | 8223 | ACAAGACA GGCTAGCTACAACGA AGACTTGC | 17958 |
| 6818 | AAGUCUGU G UCUUGUCA | 8224 | TGACAAGA GGCTAGCTACAACGA ACAGACTT | 17959 |
| 6823 | UGUGUCUU G UCAGUCCA | 8225 | TGGACTGA GGCTAGCTACAACGA AAGACACA | 17960 |
| 6827 | UCUUGUCA G UCCAAGAA | 8226 | TTCTTGGA GGCTAGCTACAACGA TGACAAGA | 17961 |
| 6836 | UCCAAGAA C UGACACCG | 8227 | CGGTGTCA GGCTAGCTACAACGA TTCTTGGA | 17962 |
| 6839 | AAGAAGUG A CACCGAGA | 8228 | TCTCGGTG GGCTAGCTACAACGA CACTTCTT | 17963 |
| 6841 | GAAGUGAC A CCGAGAUG | 5516 | CATCTCGG GGCTAGCTACAACGA GTCACTTC | 17964 |
| 6847 | ACACCGAG A UGUUAAUU | 8229 | AATTAACA GGCTAGCTACAACGA CTCGGTGT | 17965 |
| 6849 | ACCGAGAU C UUAAUUUU | 8230 | AAAATTAA GGCTAGCTACAACGA ATCTCGGT | 17966 |
| 6853 | AGAUGUUA A UUUUAGGG | 8231 | CCCTAAAA GGCTAGCTACAACGA TAACATCT | 17967 |
| 6862 | UUUUAGGG A CCCGUGCC | 8232 | GGCACGGG GGCTAGCTACAACGA CCCTAAAA | 17968 |
| 6866 | AGGGACCC G UGCCUUGU | 8233 | ACAAGCA GGCTAGCTACAACGA GGGTCCCT | 17969 |
| 6868 | GGACCCGU C CUUGUUU | 8234 | AAACAAGG GGCTAGCTACAACGA ACGGGTCC | 17970 |
| 6873 | CGUGCCUU G UUUCCUAG | 8235 | CTAGGAAA GGCTAGCTACAACGA AAGGCACG | 17971 |
| 6881 | GUUUCCUA G CCCACAAG | 8236 | CTTGTGGG GGCTAGCTACAACGA TAGGAAAC | 17972 |
| 6885 | CCUAGCCC A CAAGAAUG | 5526 | CATTCTTG GGCTAGCTACAACGA GCGCTAGG | 17973 |
| 6891 | CCACAAGA A UGCAAACA | 8237 | TGTTTGCA GGCTAGCTACAACGA TCTTGTGG | 17974 |
| 6893 | ACAAGAAU G CAAACAUC | 8238 | GATGTTTG GGCTAGCTACAACGA ATTCTTGT | 17975 |
| 6897 | GAAUGCAA A CAUCAAAC | 8239 | GTTTGATG GGCTAGCTACAACGA TTGCATTC | 17976 |
| 6899 | AUGCAAAC A UCAAACAG | 5529 | CTCTTTGA GGCTAGCTACAACGA GTTTGCAT | 17977 |
| 6904 | AACAUCAA A CAGAUACU | 8240 | AGTATCTG GGCTAGCTACAACGA TTGATGTT | 17978 |
| 6908 | UCAAACAG A UACUCGCU | 8241 | AGCGAGTA GGCTAGCTACAACGA CTGTTTGA | 17979 |
| 6910 | AAACAGAU A CUCGCUAG | 1197 | CTAGCGAG GGCTAGCTACAACGA ATCTGTTT | 17980 |

TABLE XVIII-continued

Human FLT DNAzyme and Substrate Sequence

| Pos | Substrate | Seq ID No | DNAzyme | Seq ID No |
|---|---|---|---|---|
| 6914 | AGAUACUC G CUAGCCUC | 8242 | GAGGCTAG GGCTAGCTACAACGA GAGTATCT | 17981 |
| 6918 | ACUCGCUA G CCUCAUUU | 8243 | AAATGAGG GGCTAGCTACAACGA TAGCGAGT | 17982 |
| 6923 | CUAGCCUC A UUUAAAUU | 5536 | AATTTAAA GGCTAGCTACAACGA GAGGCTAG | 17983 |
| 6929 | UCAUUUAA A UUGAUUAA | 8244 | TTAATCAA GGCTAGCTACAACGA TTAAATGA | 17984 |
| 6933 | UUAAAUUG A UUAAAGGA | 8245 | TCCTTTAA GGCTAGCTACAACGA CAATTTAA | 17985 |
| 6945 | AAGGAGGA G UGCAUCUU | 8246 | AAGATGCA GGCTAGCTACAACGA TCCTCCTT | 17986 |
| 6947 | GGAGGAGU G CAUCUUUG | 8247 | CAAAGATG GGCTAGCTACAACGA ACTCCTCC | 17987 |
| 6949 | AGGAGUGC A UCUUUGGC | 5537 | GCCAAAGA GGCTAGCTACAACGA GCACTCCT | 17988 |
| 6956 | CAUCUUUG G CCGACAGU | 8248 | ACTGTCGG GGCTAGCTACAACGA CAAAGATG | 17989 |
| 6960 | UUUGGCCG A CAGUGGUG | 8249 | CACCACTG GGCTAGCTACAACGA CGGCCAAA | 17990 |
| 6963 | GGCCGACA G UGGUGUAA | 8250 | TTACACCA GGCTAGCTACAACGA TGTCGGCC | 17991 |
| 6966 | CGACAGUG G UGUAACUG | 8251 | CAGTTACA GGCTAGCTACAACGA CACTGTCG | 17992 |
| 6968 | ACAGUGGU C UAACUGUG | 8252 | CACAGTTA GGCTAGCTACAACGA ACCACTGT | 17993 |
| 6971 | GUGGUGUA A CUGUGUGU | 8253 | ACACACAG GGCTAGCTACAACGA TACACCAC | 17994 |
| 6974 | GUGUAACU G UGUGUGU | 8254 | CACACACA GGCTAGCTACAACGA AGTTACAC | 17995 |
| 6976 | GUAACUGU G UGUGUGUG | 8255 | CACACACA GGCTAGCTACAACGA ACAGTTAC | 17996 |
| 6978 | AACUGUGU G UGUGUGUG | 8256 | CACACACA GGCTAGCTACAACGA ACACAGTT | 17997 |
| 6980 | CUGUGUGU G UGUGUGUG | 8257 | CACACACA GGCTAGCTACAACGA ACACACAG | 17998 |
| 6982 | GUGUGUGU G UGUGUGUG | 8258 | CACACACA GGCTAGCTACAACGA ACACACAC | 17999 |
| 6984 | GUGUGUGU G UGUGUGUG | 8258 | CACACACA GGCTAGCTACAACGA ACACACAC | 17999 |
| 6986 | GUGUGUGU G UGUGUGUG | 8258 | CACACACA GGCTAGCTACAACGA ACACACAC | 17999 |
| 6988 | GUGUGUGU G UGUGUGUG | 8258 | CACACACA GGCTAGCTACAACGA ACACACAC | 17999 |
| 6990 | GUGUGUGU G UGUGUGUG | 8258 | CACACACA GGCTAGCTACAACGA ACACACAC | 17999 |
| 6992 | GUGUGUGU G UGUGUGUG | 8258 | CACACACA GGCTAGCTACAACGA ACACACAC | 17999 |
| 6994 | GUGUGUGU G UGUGUGUG | 8258 | CACACACA GGCTAGCTACAACGA ACACACAC | 17999 |
| 6996 | GUGUGUGU G UGUGUGUG | 8258 | CACACACA GGCTAGCTACAACGA ACACACAC | 17999 |
| 6998 | GUGUGUGU G UGUGUGUG | 8258 | CACACACA GGCTAGCTACAACGA ACACACAC | 17999 |
| 7000 | GUGUGUGU C UGUGUGUG | 8258 | CACACACA GGCTAGCTACAACGA ACACACAC | 17999 |
| 7002 | GUGUGUGU G UGUGUGUG | 8258 | CACACACA GGCTAGCTACAACGA ACACACAC | 17999 |
| 7004 | GUGUGUGU G UGUGUGUG | 8258 | CACACACA GGCTAGCTACAACGA ACACACAC | 17999 |
| 7006 | GUGUGUGU G UGUGUGUG | 8258 | CACACACA GGCTAGCTACAACGA ACACACAC | 17999 |
| 7008 | GUGUGUGU C UGUGUGGG | 8259 | CCCACACA GGCTAGCTACAACGA ACACACAC | 18000 |
| 7010 | GUGUGUGU G UGUGGGUG | 8260 | CACCCACA GGCTAGCTACAACGA ACACACAC | 18001 |
| 7012 | GUGUGUGU G UGGGUGUG | 8261 | CACACCCA GGCTAGCTACAACGA ACACACAC | 18002 |
| 7016 | GUGUGUGG C UGUGGGUG | 8262 | CACCCACA GGCTAGCTACAACGA CCACACAC | 18003 |
| 7018 | GUGUGGGU G UGGGUGUA | 8263 | TACACCCA GGCTAGCTACAACGA ACCCACAC | 18004 |
| 7022 | GGGUGUGG C UGUAUGUG | 8264 | CACATACA GGCTAGCTACAACGA CCACACCC | 18005 |

TABLE XVIII-continued

Human FLT DNAzyme and Substrate Sequence

| Pos | Substrate | Seq ID No | DNAzyme | Seq ID No |
|---|---|---|---|---|
| 7024 | GUGUGGGU G UAUGUGUG | 8265 | CACACATA GGCTAGCTACAACGA ACCCACAC | 18006 |
| 7026 | GUGGGUGU A UGUGUGUU | 1211 | AACACACA GGCTAGCTACAACGA ACACCCAC | 18007 |
| 7028 | GGGUGUAU C UGUGUUUU | 8266 | AAAACACA GGCTAGCTACAACGA ATACACCC | 18008 |
| 7030 | GUGUAUGU C UGUUUUGU | 8267 | ACAAACA GGCTAGCTACAACGA ACATACAC | 18009 |
| 7032 | GUAUGUGU G UUUUGUGC | 8268 | GCACAAAA GGCTAGCTACAACGA ACACATAC | 18010 |
| 7037 | UGUGUUUU C UGCAUAAC | 8269 | GTTATGCA GGCTAGCTACAACGA AAAACACA | 18011 |
| 7039 | UGUUUUGU C CAUAACUA | 8270 | TAGTTATG GGCTAGCTACAACGA ACAAAACA | 18012 |
| 7041 | UUUUGUGC A UAACUAUU | 5542 | AATAGTTA GGCTAGCTACAACGA GCACAAAA | 18013 |
| 7044 | UGUGCAUA A CUAUUUAA | 827 | UTAAATAG GGCTAGCTACAACGA TATGCACA | 18014 |
| 7047 | GCAUAACU A UUUAAGGA | 1216 | TCCTTAAA GGCTAGCTACAACGA AGTTATGC | 18015 |
| 7057 | UUAAGGAA A CUGGAAUU | 8272 | AATTCCAG GGCTAGCTACAACGA TTCCTTAA | 18016 |
| 7063 | AAACUGGA A UUUAAAG | 8273 | CTTTAAAA GGCTAGCTACAACGA TCCAGTTT | 18017 |
| 7071 | AUUUAAAA G UUACUUUU | 8274 | AAAAGTAA GGCTAGCTACAACGA TTTAAAAT | 18018 |
| 7074 | UUAAAGUU A CUUUUAUA | 1225 | TATAAAAG GGCTAGCTACAACGA AACTTTAA | 18019 |
| 7080 | UUACUUUU A UACAAACC | 1229 | GGTTTGTA GGCTAGCTACAACGA AAAAGTAA | 18020 |
| 7082 | ACUUUUAU A CAAACCAA | 1230 | TTGGTTTG GGCTAGCTACAACGA ATAAAAGT | 18021 |
| 7086 | UUAUACAA A CCAAGAAU | 8275 | ATTCTTGG GGCTAGCTACAACGA TTGTATAA | 18022 |
| 7093 | AACCAAGA A UAUAUGCU | 8276 | AGCATATA GGCTAGCTACAACGA TCTTGGTT | 18023 |
| 7095 | CCAAGAAU A UAUGCUAC | 1231 | GTAGCATA GGCTAGCTACAACGA ATTCTTGG | 18024 |
| 7097 | AAGAAUAU A UGCUACAG | 1232 | CTGTAGCA GGCTAGCTACAACGA ATATTCTT | 18025 |
| 7099 | GAAUAUAU G CUACAGAU | 8277 | ATCTGTAG GGCTAGCTACAACGA ATATATTC | 18026 |
| 7102 | UAUAUGCU A CAGAUAUA | 1233 | TATATCTG GGCTAGCTACAACGA AGCATATA | 18027 |
| 7106 | UGCUACAG A UAUAAGAC | 8278 | GTCTTATA GGCTAGCTACAACGA CTGTAGCA | 18028 |
| 7108 | CUACAGAD A UAAGACAG | 1234 | CTGTCTTA GGCTAGCTACAACGA ATCTGTAG | 18029 |
| 7113 | GAUAUAAG A CAGACAUG | 8279 | CATGTCTG GGCTAGCTACAACGA CTTATATC | 18030 |
| 7117 | UAAGACAG A CAUGGUUU | 8280 | AAACCATG GGCTAGCTACAACGA CTGTCTTA | 18031 |
| 7119 | AGACAGAC A UGGUUUGG | 5552 | CCAAACCA GGCTAGCTACAACGA GTCTGTCT | 18032 |
| 7122 | CAGACAUG G UUUGGUCC | 8281 | GGACCAAA GGCTAGCTACAACGA CATGTCTG | 18033 |
| 7127 | AUGGUUUG G UCCUAUAU | 8282 | ATATAGGA GGCTAGCTACAACGA CAAACCAT | 18034 |
| 7132 | UUGGUCCU A UAUUUCUA | 1239 | TAGAAATA GGCTAGCTACAACGA AGGACCAA | 18035 |
| 7134 | GGUCCUAU A UUUCUAGU | 1240 | ACTAGAAA GGCTAGCTACAACGA ATAGGACC | 18036 |
| 7141 | UAUUUCUA G UCAUGAUG | 8283 | CATCATGA GGCTAGCTACAACGA TAGAAATA | 18037 |
| 7144 | UUCUAGUC A UGAUGAAU | 5556 | ATTCATCA GGCTAGCTACAACGA GACTAGAA | 18038 |
| 7147 | UAGUCAUG A UGAAUGUA | 8284 | TACATTCA GGCTAGCTACAACGA CATGACTA | 18039 |
| 7151 | CAUGAUGA A UGUAUUUU | 8285 | AAAATACA GGCTAGCTACAACGA TCATCATG | 18040 |
| 7153 | UGAUGAAU G UAUUUUGU | 8286 | ACAAAATA GGCTAGCTACAACGA ATTCATCA | 18041 |
| 7155 | AUGAAUGU A UUUUGUAU | 1246 | ATACAAAA GGCTAGCTACAACGA ACATTCAT | 18042 |

TABLE XVIII-continued

Human FLT DNAzyme and Substrate Sequence

| Pos | Substrate | Seq ID No | DNAzyme | Seq ID No |
|---|---|---|---|---|
| 7160 | UGUAUUUU G UAUACCAU | 8287 | ATGGTATA GGCTAGCTACAACGA AAAATACA | 18043 |
| 7162 | UAUUUUGU A UACCAUCU | 1250 | AGATGGTA GGCTAGCTACAACGA ACAAAATA | 18044 |
| 7164 | UUUUGUAU A CCAUCUUC | 1251 | GAAGATGG GGCTAGCTACAACGA ATACAAAA | 18045 |
| 7167 | UGUAUACC A UCUUCAUA | 5558 | TATGAAGA GGCTAGCTACAACGA GGTATACA | 18046 |
| 7173 | CCAUCUUC A UAUAAUAU | 5560 | ATATTATA GGCTAGCTACAACGA GAAGATGG | 18047 |
| 7175 | AUCUUCAU A UAAUAUAC | 1255 | GTATATTA GGCTAGCTACAACGA ATGAAGAT | 18048 |
| 7178 | UUCAUAUA A UAUACUUA | 8288 | TAAGTATA GGCTAGCTACAACGA TATATGAA | 18049 |
| 7180 | CAUAUAAU A UACUUAAA | 1257 | TTTAAGTA GGCTAGCTACAACGA ATTATATG | 18050 |
| 7182 | UAUAAUAU A CUUAAAAA | 1258 | TTTTTAAG GGCTAGCTACAACGA ATATTATA | 18051 |
| 7190 | ACUUAAAA A UAUUUCUU | 8289 | AAGAAATA GGCTAGCTACAACGA TTTTAAGT | 18052 |
| 7192 | UUAAAAAU A UUUCUUAA | 126 | UTAAGAAA GGCTAGCTACAACGA ATTTTTAA | 18053 |
| 7200 | AUUUCUUA A UUGGGAUU | 8290 | AATCCCAA GGCTAGCTACAACGA TAAGAAAT | 18054 |
| 7206 | UAAUUGGG A UUUGUAAU | 8291 | ATTACAAA GGCTAGCTACAACGA CCCAATTA | 18055 |
| 7210 | UGGGAUUU G UAAUCGUA | 8292 | TAGGATTA GGCTAGCTACAACGA AAATCCCA | 18056 |
| 7213 | GAUUUGUA A UCGUACCA | 8293 | TGGTACGA GGCTAGCTACAACGA TACAAATC | 18057 |
| 7216 | UUGUAAUC G UACCAACU | 8294 | AGTTGGTA GGCTAGCTACAACGA GATTACAA | 18058 |
| 7218 | GUAAUCGU A CCAACUUA | 1272 | TAAGTTGG GGCTAGCTACAACGA ACGATTAC | 18059 |
| 7222 | UCGUACCA A CUUAAUUG | 8295 | CAATTAAG GGCTAGCTACAACGA TGGTACGA | 18060 |
| 7227 | CCAACUUA A UUGAUAUA | 8296 | TTTATCAA GGCTAGCTACAACGA TAAGTTGG | 18061 |
| 7231 | CUUAAUUG A UAAACUUG | 8297 | CAAGTTTA GGCTAGCTACAACGA CAATTAAG | 18062 |
| 7235 | AUUGAUAA A CUUGGCAA | 8298 | TTGCCAAG GGCTAGCTACAACGA TTATCAAT | 18063 |
| 7240 | UAAACUUG G CAACUGCU | 8299 | AGCAGTTG GGCTAGCTACAACGA CAAGTTTA | 18064 |
| 7243 | ACUUGGCA A CUGCUUUU | 8300 | AAAAGCAG GGCTAGCTACAACGA TGCCAAGT | 18065 |
| 7246 | UGGCAACU G CUUUUAUG | 8301 | CATAAAAG GGCTAGCTACAACGA AGTTGCCA | 18066 |
| 7252 | CUGCUUUU A UGUUCUGU | 1281 | ACAGAACA GGCTAGCTACAACGA AAAAGCAG | 18067 |
| 7254 | GCUUUUAU G UUCUGUCU | 8302 | AGACAGAA GGCTAGCTACAACGA ATAAAAGC | 18068 |
| 7259 | UAUGUUCU G UCUCCUUC | 8303 | GAAGGAGA GGCTAGCTACAACGA AGAACATA | 18069 |
| 7269 | CUCCUUCC A UAAAUUUU | 5575 | AAAATTTA GGCTAGCTACAACGA GGAAGGAG | 18070 |
| 7273 | UUCCAUAA A UUUUUCAA | 8304 | TTGAAAAA GGCTAGCTACAACGA TTATGGAA | 18071 |
| 7283 | UUUUUCAA A UACUAAUU | 8305 | AATTAGTA GGCTAGCTACAACGA TTTGAAAA | 18072 |
| 7285 | UUCAAAAU A CUAAUUCA | 1294 | TGAATTAG GGCTAGCTACAACGA ATTTTGAA | 18073 |
| 7289 | AAAUACUA A UUCAACAA | 8306 | TTGTTGAA GGCTAGCTACAACGA TAGTATTT | 18074 |
| 7294 | CUAAUUCA A CAAAGAAA | 8307 | TTTCTTTG GGCTAGCTACAACGA TGAATTAG | 18075 |
| 7305 | AAGAAAAA G CUCUUUUU | 8308 | AAAAAGAG GGCTAGCTACAACGA TTTTTCTT | 18076 |
| 7323 | UUCCUAAA A UAAACUCA | 8309 | TGAGTTTA GGCTAGCTACAACGA TTTAGGAA | 18077 |
| 7327 | UAAAAUAA A CUCAAAUU | 8310 | AATTTGAG GGCTAGCTACAACGA TTATTTTA | 18078 |
| 7333 | AAACUCAA A UUUAUCCU | 8311 | AGGATAAA GGCTAGCTACAACGA TTGAGTTT | 18079 |

TABLE XVIII-continued

Human FLT DNAzyme and Substrate Sequence

| Pos | Substrate | Seq ID No | DNAzyme | Seq ID No |
|---|---|---|---|---|
| 7337 | UCAAAUUU A UCCUUGUU | 1312 | AACAAGGA GGCTAGCTACAACGA AAATTTGA | 18080 |
| 7343 | UUAUCCUU G UUUAGAGC | 8312 | GCTCTAAA GGCTAGCTACAACGA AAGGATAA | 18081 |
| 7350 | UGUUUAGA G CAGAGAAA | 8313 | TTTCTCTG GGCTAGCTACAACGA TCTAAACA | 18082 |
| 7360 | AGAGAAAA A UUAAGAAA | 8314 | TTTCTTAA GGCTAGCTACAACGA TTTTCTCT | 18083 |
| 7370 | UAAGAAAA A CUUUGAAA | 8315 | TTTCAAAG GGCTAGCTACAACGA TTTTCTTA | 18084 |
| 7378 | ACUUUGAA A UGGUCUCA | 8316 | TGAGACCA GGCTAGCTACAACGA TTCAAAGT | 18085 |
| 7381 | UUGAAAUG G UCUCAAAA | 8317 | TTTTGAGA GGCTAGCTACAACGA CATTTCAA | 18086 |
| 7391 | CUCAAAAA A UUGCUAAA | 8318 | TTTAGCAA GGCTAGCTACAACGA TTTTTGAG | 18087 |
| 7394 | AAAAAAUU G CUAAAUAU | 8319 | ATATTTAG GGCTAGCTACAACGA AATTTTTT | 18088 |
| 7399 | AUUGCUAA A UAUUUCA | 8320 | TGAAAATA GGCTAGCTACAACGA TTAGCAAT | 18089 |
| 7401 | UGCUAAAU A UUUUCAAU | 1326 | ATTGAAAA GGCTAGCTACAACGA ATTTAGCA | 18090 |
| 7408 | UAUUUUCA A UGGAAAAC | 8321 | GTTTTCCA GGCTAGCTACAACGA TGAAAATA | 18091 |
| 7415 | AAUGGAAA A CUAAAUGU | 8322 | ACATTTAG GGCTAGCTACAACGA TTTCCATT | 18092 |
| 7420 | AAAACUAA A UGUUAGUU | 8323 | AACTAACA GGCTAGCTACAACGA TTAGTTTT | 18093 |
| 7422 | AACUAAAU G UUAGUUUA | 8324 | TAAACTAA GGCTAGCTACAACGA ATTTAGTT | 18094 |
| 7426 | AAAUGUUA G UUUAGCUG | 8325 | CAGCTAAA GGCTAGCTACAACGA TAACATTT | 18095 |
| 7431 | UUAGUUUA G CUGAUUGU | 8326 | ACAATCAG GGCTAGCTACAACGA TAAACTAA | 18096 |
| 7435 | UUUAGCUG A UUGUAUGG | 8327 | CCATACAA GGCTAGCTACAACGA CAGCTAAA | 18097 |
| 7438 | AGCUGAUU G UAUGGGGU | 8328 | ACCCCATA GGCTAGCTACAACGA AATCAGCT | 18098 |
| 7440 | CUGAUUGU A UGGGGUUU | 1338 | AAACCCCA GGCTAGCTACAACGA ACAATCAG | 18099 |
| 7445 | UGUAUGGG G UUUCGAA | 8329 | TTCGAAAA GGCTAGCTACAACGA CCCATACA | 18100 |
| 7453 | GUUUCGA A CCUUUCAC | 8330 | GTGAAAGG GGCTAGCTACAACGA TCGAAAAC | 18101 |
| 7460 | AACCUUUC A CUUUUUGU | 5598 | ACAAAAAG GGCTAGCTACAACGA GAAAGGTT | 18102 |
| 7467 | CACUUUUU G UUUUGUUU | 8331 | AAAACAAA GGCTAGCTACAACGA AAAAAGTG | 18103 |
| 7471 | UUUUGUUU G UUUUACCU | 8332 | AGGTAAAA GGCTAGCTACAACGA AAACAAAA | 18104 |
| 7476 | UUUGUUUU A CCUAUUUC | 1355 | GAAATAGG GGCTAGCTACAACGA AAAACAAA | 18105 |
| 7480 | UUUUACCU A UUUCACAA | 1356 | TTGTGAAA GGCTAGCTACAACGA AGGTAAAA | 18106 |
| 7485 | CCUAUUUC A CAACUGUG | 5602 | CACAGTTG GGCTAGCTACAACGA GAAATAGG | 18107 |
| 7488 | AUUUCACA A CUGUGUAA | 8333 | TTACACAG GGCTAGCTACAACGA TGTGAAAT | 18108 |
| 7491 | UCACAACU G UGUAAAUU | 8334 | AATTTACA GGCTAGCTACAACGA AGTTGTGA | 18109 |
| 7493 | ACAACUGU G UAAAUUGC | 8335 | GCAATTTA GGCTAGCTACAACGA ACAGTTGT | 18110 |
| 7497 | CUGUGUAA A UUGCCAAU | 8336 | ATTGGCAA GGCTAGCTACAACGA TTACACAG | 18111 |
| 7500 | UGUAAAUU G CCAAUAAU | 8337 | ATTATTGG GGCTAGCTACAACGA AATTTACA | 18112 |
| 7504 | AAUUGCCA A UAAUUCCU | 8338 | AGGAATTA GGCTAGCTACAACGA TGGCAATT | 18113 |
| 7507 | UGCCAAUA A UUCCUGUC | 8339 | GACAGGAA GGCTAGCTACAACGA TATTGGCA | 18114 |
| 7513 | UAAUUCCU G UCCAUGAA | 8340 | TTCATGGA GGCTAGCTACAACGA AGGAATTA | 18115 |
| 7517 | UCCUGUCC A UGAAAUG | 5610 | CATTTTCA GGCTAGCTACAACGA GGACAGGA | 18116 |

TABLE XVIII-continued

Human FLT DNAzyme and Substrate Sequence

| Pos | Substrate | Seq ID No | DNAzyme | Seq ID No |
|---|---|---|---|---|
| 7523 | CCAUGAAA A UGCAAAUU | 8341 | AATTTGCA GGCTAGCTACAACGA TTTCATGG | 18117 |
| 7525 | AUGAAAAU G CAAAUUAU | 8342 | ATAATTTG GGCTAGCTACAACGA ATTTTCAT | 18118 |
| 7529 | AAAUGCAA A UUAUCCAG | 8343 | CTGGATAA GGCTAGCTACAACGA TTGCATTT | 18119 |
| 7532 | UGCAAAUU A UCCAGUGU | 1367 | ACACTGGA GGCTAGCTACAACGA AATTTGCA | 18120 |
| 7537 | AUUAUCCA G GUAGAUA | 8344 | TATCTACA GGCTAGCTACAACGA TGGATAAT | 18121 |
| 7539 | UAUCCAGU G UAGAUAUA | 8345 | TATATCTA GGCTAGCTACAACGA ACTGGATA | 18122 |
| 7543 | CAGUGUAG A UAUAUUUG | 8346 | CAAATATA GGCTAGCTACAACGA CTACACTG | 18123 |
| 7545 | GUGUAGAU A UAUUUGAC | 1370 | GTCAAATA GGCTAGCTACAACGA ATCTACAC | 18124 |
| 7547 | GUAGAUAU A UUUGACCA | 137 | UGGTCAAA GGCTAGCTACAACGA ATATCTAC | 18125 |
| 7552 | UAUAUUUG A CCAUCACC | 8347 | GGTGATGG GGCTAGCTACAACGA CAAATATA | 18126 |
| 7555 | AUUUGACC A UCACCCUA | 5615 | TAGGGTGA GGCTAGCTACAACGA GGTCAAAT | 18127 |
| 7558 | UGACCAUC A CCCUAUGG | 5616 | CCATAGGG GGCTAGCTACAACGA GATGGTCA | 18128 |
| 7563 | AUCACCCU A UGGAUAUU | 1375 | AATATCCA GGCTAGCTACAACGA AGGGTGAT | 18129 |
| 7567 | CCCUAUGG A UAUUGGCU | 8348 | AGCCAATA GGCTAGCTACAACGA CCATAGGG | 18130 |
| 7569 | CUAUGGAU A UUGGCUAG | 1376 | CTAGCCAA GGCTAGCTACAACGA ATCCATAG | 18131 |
| 7573 | GGAUAUUG G CUAGUUUU | 8349 | AAAACTAG GGCTAGCTACAACGA CAATATCC | 18132 |
| 7577 | AUUGGCUA G UUUUGCCU | 8350 | AGGCAAAA GGCTAGCTACAACGA TAGCCAAT | 18133 |
| 7582 | CUAGUUUU G CCUUUAUU | 8351 | AATAAAGG GGCTAGCTACAACGA AAAACTAG | 18134 |
| 7588 | UUGCCUUU A UUAAGCAA | 1384 | TTGCTTAA GGCTAGCTACAACGA AAAGGCAA | 18135 |
| 7593 | UUUAUUAA G CAAAUUCA | 8352 | TGAATTTG GGCTAGCTACAACGA TTAATAAA | 18136 |
| 7597 | UUAAGCAA A UUCAUUUC | 8353 | GAAATGAA GGCTAGCTACAACGA TTGCTTAA | 18137 |
| 7601 | GCAAAUUC A UUUCAGCC | 5624 | GGCTGAUA GGCTAGCTACAACGA GAATTTGC | 18138 |
| 7607 | UCAUUUCA G CCUGAAUG | 8354 | CATTCAGG GGCTAGCTACAACGA TGAAATGA | 18139 |
| 7613 | CAGGCUGA A UGUCUGCC | 8355 | GGCAGACA GGCTAGCTACAACGA TCAGGCTG | 18140 |
| 7615 | GCCUGAAU G UCUGCCUA | 8356 | TAGGGAGA GGCTAGCTACAACGA ATTCAGGC | 18141 |
| 7619 | GAAUGUCU G CCUAUAUA | 8357 | TATATAGG GGCTAGCTACAACGA AGACATTC | 18142 |
| 7623 | GUCUGCCU A UAUAUUCU | 1393 | AGAATATA GGCTAGCTACAACGA AGGCAGAC | 18143 |
| 7625 | CUGCCUAU A UAUUCUCU | 1394 | AGAGAATA GGCTAGCTACAACGA ATAGGCAG | 18144 |
| 7627 | GCCUAUAU A UUCUCUGC | 1395 | GCAGAGAA GGCTAGCTACAACGA ATATAGGC | 18145 |
| 7634 | UAUUCUCU G CUCUUUGU | 8358 | ACAAAGAG GGCTAGCTACAACGA AGAGAATA | 18146 |
| 7641 | UGCUCUUU G UAUUCUCC | 8359 | GGAGAATA GGCTAGCTACAACGA AAAGAGCA | 18147 |
| 7643 | CUCUUUGU A UUCUCCUU | 1402 | AAGGAGAA GGCTAGCTACAACGA ACAAAGAG | 18148 |
| 7655 | UCCUUUGA A CCCGUUAA | 8360 | TTAACGGG GGCTAGCTACAACGA TCAAAGGA | 18149 |
| 7659 | UUGAACCC G UUAAAACA | 836 | UGTTTTAA GGCTAGCTACAACGA GGGTTCAA | 18150 |
| 7665 | CCGUUAAA A CAUCCUGU | 8362 | ACAGGATG GGCTAGCTACAACGA TTTAACGG | 18151 |

TABLE XVIII-continued

Human FLT DNAzyme and Substrate Sequence

| Pos | Substrate | Seq ID No | DNAzyme | Seq ID No |
|---|---|---|---|---|
| 7667 | GUUAAAAC A UCCUGUGG | 5640 | CCACAGGA GGCTAGCTACAACGA GTTTTAAC | 18152 |
| 7672 | AACAUCCU G UGGCACUC | 8363 | GAGTGCCA GGCTAGCTACAACGA AGGATGTT | 18153 |

Input Sequence = HSFLT.
Cut Gite = R/Y
Arm Length = 8.
Core Sequence = GGCTAGCTACAACGA (SEQ ID NO. 20828)
HSFLT (Human flt mRNA for receptor-related tyrosine kinase.; Acc# X51602; 7680 bp)

TABLE XIX

Human FLT Zinzyme and Substrate Sequence

| Pos | Substrate | Seq ID No | Zinzyme | Seq ID No |
|---|---|---|---|---|
| 17 | UCCUCUCG G CUCCUCCC | 7143 | GGGAGGAG GCCGAAAGGCGAGUGAGGUCU CGAGAGGA | 18154 |
| 28 | CCUCCCCG G CAGCGGCG | 7144 | CGCCGCUG GCCGAAAGGCGAGUGAGGUCU CGGGGAGG | 18155 |
| 31 | CCCCGGCA G CGGCGGCG | 7145 | CGCCGCCG GCCGAAAGGCGAGUGAGGUCU UGCCGGGG | 18156 |
| 34 | CGGCAGCG G CGGCGGCU | 7146 | AGCCGCCG GCCGAAAGGCGAGUGAGGUCU CGCUGCCG | 18157 |
| 37 | CAGCGGCG G CGGCUCGG | 7147 | CCGAGCCG GCCGAAAGGCGAGUGAGGUCU CGCCGCUG | 18158 |
| 40 | CGGCGGCG G CUCGGAGC | 7148 | GCUCCGAG GCCGAAAGGCGAGUGAGGUCU CGCCGCCG | 18159 |
| 47 | GGCUCGGA G CGGGCUCC | 7149 | GGAGCCCG GCCGAAAGGCGAGUGAGGUCU UCCGAGCC | 18160 |
| 51 | CGGAGCGG G CUCCGGGG | 7150 | CCCCGGAG GCCGAAAGGCGAGUGAGGUCU CCGCUCCG | 18161 |
| 59 | GCUCCGGG G CUCGGGUG | 7151 | CACCCGAG GCCGAAAGGCGAGUGAGGUCU CCCGGAGC | 18162 |
| 65 | GGGCUCGG G UGCAGCGG | 7152 | CCGCUGCA GCCGAAAGGCGAGUGAGGUCU CCGAGCCC | 18163 |
| 67 | GCUCGGGU G CAGCGCC | 7153 | GGCCGCUG GCCGAAAGGCGAGUGAGGUCU ACCCGAGC | 18164 |
| 70 | CGGGUGCA G CGGCCAGC | 7154 | GCUGGCCG GCCGAAAGGCGAGUGAGGUCU UGCACCCG | 18165 |
| 73 | GUGCAGCG G CCAGCGGG | 7155 | CCCGCUGG GCCGAAAGGCGAGUGAGGUCU CGCUGCAC | 18166 |
| 77 | AGCGGCCA G CGGGCCUG | 7156 | CAGGCCCG GCCGAAAGGCGAGUGAGGUCU UGGCCGCU | 18167 |
| 81 | GCCAGCGG G CCUGGCGG | 7157 | CCGCCAGG GCCGAAAGGCGAGUGAGGUCU CCGCUGGC | 18168 |
| 86 | CGGGCCUG G CGGCGAGG | 7158 | CCUCGCCG GCCGAAAGGCGAGUGAGGUCU CAGGCCCG | 18169 |
| 89 | GCCUGGCG G CGAGGAUU | 7159 | AAUCCUCG GCCGAAAGGCGAGUGAGGUCU CGCCAGGC | 18170 |
| 108 | CCGGGGAA G UGGUUGUC | 7161 | CACAACCA GCCGAAAGGCGAGUGAGGUCU UUCCCCGG | 18171 |
| 111 | GGGAAGUG G UUGUCUCC | 7162 | GGAGACAA GCCGAAAGGCGAGUGAGGUCU CACUUCCC | 18172 |
| 114 | AAGUGGUU G UCUCCUGG | 7163 | CCAGGAGA GCCGAAAGGCGAGUGAGGUCU AACCACUU | 18173 |
| 122 | GUCUCCUG G CUGGAGCC | 7164 | GGCUCCAG GCCGAAAGGCGAGUGAGGUCU CAGGAGAC | 18174 |
| 128 | UGGCUGGA G CCGCGAGA | 7165 | UCUCGCGG GCCGAAAGGCGAGUGAGGUCU UCCAGCCA | 18175 |
| 131 | CUGGAGCC G CGAGACGG | 7166 | CCGUCUCG GCCGAAAGGCGAGUGAGGUCU GGCUCCAG | 18176 |
| 140 | CGAGACGG G CGCUCAGG | 7168 | CCUGAGCG GCCGAAAGGCGAGUGAGGUCU CCGUCUCG | 18177 |
| 142 | AGACGGGC G CUCAGGGC | 7169 | GCCCUGAG GCCGAAAGGCGAGUGAGGUCU GCCCGUCU | 18178 |
| 149 | CGCUCAGG G CGCGGGGC | 7170 | GCCCCGCG GCCGAAAGGCGAGUGAGGUCU CCUGAGCG | 18179 |
| 151 | CUCAGGGC G CGGGGCCG | 7171 | CGGCCCCG GCCGAAAGGCGAGUGAGGUCU GCCCUGAG | 18180 |

TABLE XIX-continued

Human FLT Zinzyme and Substrate Sequence

| Pos | Substrate | Seq ID No | Zinzyme | Seq ID No |
|---|---|---|---|---|
| 156 | GGCGCGGG G CCGGCGGC | 7172 | GCCGCCGG GCCGAAAGGCGAGUGAGGUCU CCCGCGCC | 18181 |
| 160 | CGGGGCCG G CGGCGGCG | 7173 | CGCCGCCG GCCGAAAGGCGAGUGAGGUCU CGGCCCCG | 18182 |
| 163 | GGCCGGCG G CGGCGAAC | 7174 | GUUCGCCG GCCGAAAGGCGAGUGAGGUCU CGCCGGCC | 18183 |
| 166 | CGGCGGCG G CGAACGAG | 7175 | CUCGUUCG GCCGAAAGGCGAGUGAGGUCU CGCCGGCC | 18184 |
| 188 | GCAGUCUG G CGGCCGGG | 7179 | CCCGGCCG GCCGAAAGGCGAGUGAGGUCU CAGAGUCC | 18185 |
| 191 | CUCUGGCG G CCGGGUCG | 7180 | CGACCCGG GCCGAAAGGCGAGUGAGGUCU CGCCAGAG | 18186 |
| 196 | GCGGCCGG G UCGUUGGC | 7181 | GCCAACGA GCCGAAAGGCGAGUGAGGUCU CCGGCCGC | 18187 |
| 199 | GCCGGGUC G UUGGCCGG | 7182 | CCGGCCAA GCCGAAAGGCGAGUGAGGUCU GACCCGGC | 18188 |
| 203 | GGUCGUUG G CCGGGGGA | 7183 | UCCCCCGG GCCGAAAGGCGAGUGAGGUCU CAACGACC | 18189 |
| 212 | CCGGGGGA G CGCGGGCA | 7184 | UGCCCGCG GCCGAAAGGCGAGUGAGGUCU UCCCCCGG | 18190 |
| 214 | GGGGGAGC G CGGGCACC | 7185 | GGUGCCCG GCCGAAAGGCGAGUGAGGUCU GCUCCCCC | 18191 |
| 218 | GAGCGCGG G CACCGGGC | 7186 | GCCCGGUG GCCGAAAGGCGAGUGAGGUCU CCGCGCUC | 18192 |
| 225 | GGCACCGG G CGAGCAGG | 7187 | CCUGCUCG GCCGAAAGGCGAGUGAGGUCU CCGGUGCC | 18193 |
| 229 | CCGGGCGA G CAGGCCGC | 7188 | GCGGCCUG GCCGAAAGGCGAGUGAGGUCU UCGCCCGG | 18194 |
| 233 | GCGAGCAG G CCGCGUCG | 7189 | CGACGCGG GCCGAAAGGCGAGUGAGGUCU CUGCUCGC | 18195 |
| 236 | AGCAGGCC G CGUCGCGC | 7190 | GCGCGACG GCCGAAAGGCGAGUGAGGUCU GGCCUGCU | 18196 |
| 238 | CAGGCCGC G UCGCGCUC | 7191 | GAGCGCGA GCCGAAAGGCGAGUGAGGUCU GCGGCCUG | 18197 |
| 241 | GCCGCGUC G CGCUCACC | 7192 | GGUGAGCG GCCGAAAGGCGAGUGAGGUCU GACGCGGC | 18198 |
| 243 | CGCGUCGC G CUCACCAU | 7193 | AUGGUGAG GCCGAAAGGCGAGUGAGGUCU GCGACGCG | 18199 |
| 253 | UCACCAUG G UCAGCUAC | 7194 | GUAGCUGA GCCGAAAGGCGAGUGAGGUCU CAUGGUGA | 18200 |
| 257 | CAUGGUCA G CUACUGGG | 7195 | CCCAGUAG GCCGAAAGGCGAGUGAGGUCU UGACCAUG | 18201 |
| 274 | ACACCGGG G UCCUGCUG | 7197 | CAGCAGGA GCCGAAAGGCGAGUGAGGUCU CCCGGUGU | 18202 |
| 279 | GGGGUCCU G CUGUGCGC | 7198 | GCGCACAG GCCGAAAGGCGAGUGAGGUCU AGGACCCC | 18203 |
| 282 | GUCCUGCU G UGCGCGCU | 7199 | AGCGCGCA GCCGAAAGGCGAGUGAGGUCU AGCAGGAC | 18204 |
| 284 | CCUGCUGU G CGCGCUGC | 7200 | GCAGCGCG GCCGAAAGGCGAGUGAGGUCU ACAGCAGG | 18205 |
| 286 | UGCUGUGC G CGCUGCUC | 7201 | GAGCAGCG GCCGAAAGGCGAGUGAGGUCU GCACAGCA | 18206 |
| 288 | CUGUGCGC G CUGCUCAG | 7202 | CUGAGCAG GCCGAAAGGCGAGUGAGGUCU GCGCACAG | 18207 |
| 291 | UGCGCGCU G CUCAGCUG | 7203 | CAGCUGAG GCCGAAAGGCGAGUGAGGUCU AGCGCGCA | 18208 |
| 296 | GCUGCUCA G CUGUCUGC | 7204 | GCAGACAG GCCGAAAGGCGAGUGAGGUCU UGAGCAGC | 18209 |
| 299 | GCUCAGCU G UCUGCUUC | 7205 | GAAGCAGA GCCGAAAGGCGAGUGAGGUCU AGCUGAGC | 18210 |
| 303 | AGCUGUCU G CUUCUCAC | 7206 | GUGAGAAG GCCGAAAGGCGAGUGAGGUCU AGACAGCU | 18211 |
| 320 | AGGAUCUA G UUCAGGUU | 7208 | AACCUGAA GCCGAAAGGCGAGUGAGGUCU UAGAUCCU | 18212 |
| 326 | UAGUUCAG G UUCAAAAU | 7209 | AUUUUGAA GCCGAAAGGCGACUGAGGUCU CUGAACUA | 18213 |
| 353 | UGAACUGA G UUUAAAAG | 7213 | CUUUUAAA GCCGAAAGGCGAGUGAGGUCU UCAGUUCA | 18214 |
| 362 | UUUAAAAG G CACCCAGC | 7214 | GCUGGGUG GCCGAAAGGCGAGUGAGGUCU CUUUUAAA | 18215 |
| 369 | GGCACCCA G CACAUCAU | 7215 | AUGAUGUG GCCGAAAGGCGAGUGAGGUCU UGGGUGCC | 18216 |
| 378 | CACAUCAU G CAAGCAGG | 7216 | CCUGCUUG GCCGAAAGGCGAGUGAGGUCU AUGAUGUG | 18217 |

TABLE XIX-continued

Human FLT Zinzyme and Substrate Sequence

| Pos | Substrate | Seq ID No | Zinzyme | Seq ID No |
|---|---|---|---|---|
| 382 | UCAUGCAA G CAGGCCAG | 7217 | CUGGCCUG GCCGAAAGGCGAGUGAGGUCU UUGCAUGA | 18218 |
| 386 | GCAAGCAG G CCAGACAC | 7218 | GUGUCUGG GCCGAAAGGCGAGUGAGGUCU CUGCUUGC | 18219 |
| 396 | CAGACACU G CAUCUCCA | 7220 | UGGAGAUG GCCGAAAGGCGACUGAGGUCU AGUGUCUG | 18220 |
| 407 | UCUCCAAU G CAGGGGGG | 7222 | CCCCCCUG GCCGAAAGGCGAGUGAGGUCU AUUGGAGA | 18221 |
| 418 | GGGGGGAA G CAGCCCAU | 7223 | AUGGGCUG GCCGAAAGGCGAGUGAGGUCU UUCCCCCC | 18222 |
| 421 | GGGAAGCA G CCCAUAAA | 7224 | UUUAUGGG GCCGAAAGGCGAGUGAGGUCU UGCUUCCC | 18223 |
| 432 | CAUAAAUG G UCUUUGCC | 7226 | GGCAAAGA GCCGAAAGGCGAGUGAGGUCU CAUUUAUG | 18224 |
| 438 | UGGUCUUU G CCUGAAAU | 7227 | AUUUCAGG GCCGAAAGGCGAGUGAGGUCU AAAGACCA | 18225 |
| 448 | CUGAAAUG G UGAGUAAG | 7229 | CUUACUCA GCCGAAAGGCGAGUGAGGUCU CAUUUCAG | 18226 |
| 452 | AAUGGUGA G UAAGGAAA | 7230 | UUUCCUUA GCCGAAAGGCGAGUGAGGUCU UCACCAUU | 18227 |
| 461 | UAAGGAAA G CGAAAGGC | 7231 | GCCUUUCG GCCGAAAGGCGACUGAGGUCU UUUCCUUA | 18228 |
| 468 | AGCGAAAG G CUGAGCAU | 7232 | AUGCUCAG GCCGAAAGGCGAGUGAGGUCU CUUUCGCU | 18229 |
| 473 | AAGGCUGA G CAUAACUA | 7233 | UAGUUAUG GCCGAAAGGCGAGUGAGGUCU UCAGCCUU | 18230 |
| 487 | CUAAAUCU G CCUGUGGA | 7236 | UCCACAGG GCCGAAAGGCGAGUGAGGUCU AGAUUUAG | 18231 |
| 491 | AUCUGCCU G UGGAAGAA | 7237 | UUCUUCCA GCCGAAAGGCGAGUGAGGUCU AGGCAGAU | 18232 |
| 503 | AAGAAAUG G CAAACAAU | 7239 | AUUGUUUG GCCGAAAGGCGAGUGAGGUCU CAUUUCUU | 18233 |
| 515 | ACAAUUCU G CAGUACUU | 7242 | AAGUACUG GCCGAAAGGCGAGUGAGGUCU AGAAUUGU | 18234 |
| 518 | AUUCUGCA G UACUUUAA | 7243 | UUAAAGUA GCCGAAAGGCGAGUGAGGUCU UGCAGAAU | 18235 |
| 538 | UGAACACA G CUCAAGCA | 7246 | UGCUUGAG GCCGAAAGGCGAGUGAGGUCU UGUGUUCA | 18236 |
| 544 | CAGCUCAA G CAAACCAC | 7247 | GUGGUUUG GCCGAAAGGCGAGUGAGGUCU UUGAGCUG | 18237 |
| 557 | CCACACUG G CUUCUACA | 7249 | UGUAGAAG GCCGAAAGGCGAGUGAGGUCU CAGUGUGG | 18238 |
| 566 | CUUCUACA G CUGCAAAU | 7250 | AUUUGCAG GCCGAAAGGCGAGUGAGGUCU UGUAGAAG | 18239 |
| 569 | CUACAGCU G CAAAUAUC | 7251 | GAUAUUUG GCCGAAAGGCGAGUGAGGUCU AGCUGUAG | 18240 |
| 580 | AAUAUCUA G CUGUACCU | 7253 | AGGUACAG GCCGAAAGGCGAGUGAGGUCU UAGAUAUU | 18241 |
| 583 | AUCUAGCU G UACCUACU | 7254 | AGUAGGUA GCCGAAAGGCGAGUGAGGUCU AGCUAGAU | 18242 |
| 616 | CAGAAUCU G CAAUCUAU | 7257 | AUAGAUUG GCCGAAAGGCGAGUGAGGUCU AGAUUCUG | 18243 |
| 635 | AUUUAUUA G UGAUACAG | 7259 | CUGUAUCA GCCGAAAGGCGAGUGAGGUCU UAAUAAAU | 18244 |
| 644 | UGAUACAG G UAGACCUU | 7261 | AAGGUCUA GCCGAAAGGCGAGUGAGGUCU CUGUAUCA | 18245 |
| 855 | GACCUUUC G UAGAGAUG | 7263 | CAUCUCUA GCCGAAAGGCGAGUGAGGUCU GAAAGGUC | 18246 |
| 663 | GUAGAGAU G UACAGUGA | 7265 | UCACUGUA GCCGAAAGGCGAGUGAGGUCU AUCUCUAC | 18247 |
| 668 | GAUGUACA G UGAAAUCC | 7266 | GGAUUUCA GCCGAAAGGCGAGUGAGGUCU UGUACAUC | 18248 |
| 708 | GGAAGGGA G CUCGUCAU | 7270 | AUGACGAG GCCGAAAGGCGAGUGAGGUCU UCCCUUCC | 18249 |
| 712 | GGGAGCUC G UCAUUCCC | 7271 | GGGAAUGA GCCGAAAGGCGAGUGAGGUCU GAGCUCCC | 18250 |
| 722 | CAUUCCCU G CCGGGUUA | 7272 | UAACCCGG GCCGAAAGGCGAGUGAGGUCU AGGGAAUG | 18251 |
| 727 | CCUGCCGG G UUACGUCA | 7273 | UGACGUAA GCCGAAAGGCGAGUGAGGUCU CCGGCAGG | 18252 |
| 732 | CGGGUUAC G UCACCUAA | 7274 | UUAGGUGA GCCGAAAGGCGAGUGAGGUCU GUAACCCG | 18253 |
| 748 | ACAUCACU G UUACUUUA | 7276 | UAAAGUAA GCCGAAAGGCGAGUGAGGUCU AGUGAUGU | 18254 |

TABLE XIX-continued

Human FLT Zinzyme and Substrate Sequence

| Pos | Substrate | Seq ID No | Zinzyme | Seq ID No |
|---|---|---|---|---|
| 762 | UUAAAAAA G UUUCCACU | 7277 | AGUGGAAA GCCGAAAGGCGAGUGAGGUCU UUUUUUAA | 18255 |
| 797 | UGGAAAAC G CAUAAUCU | 7282 | AGAUUAUG GCCGAAAGGCGAGUGAGGUCU GUUUUCCA | 18256 |
| 812 | CUGGGACA G UAGAAAGG | 7285 | CCUUUCUA GCCGAAAGGCGAGUGAGGUCU UGUCCCAG | 18257 |
| 821 | UAGAAAGG G CUUCAUCA | 7286 | UGAUGAAG GCCGAAAGGCGAGUGAGGUCU CCUUUCUA | 18258 |
| 838 | UAUCAAAU G CAACGUAC | 7288 | GUACGUUG GCCGAAAGGCGAGUGAGGUCU AUUUGAUA | 18259 |
| 843 | AAUGCAAC G UACAAAGA | 7290 | UCUUUGUA GCCGAAAGGCGAGUGAGGUCU GUUGCAUU | 18260 |
| 858 | GAAAUAGG G CUUCUGAC | 7292 | GUCAGAAG GCCGAAAGCCGAGUGAGGUCU CCUAUUUC | 18261 |
| 869 | UCUGACCU G UGAAGCAA | 7294 | UUGCUUCA GCCGAAAGGCGACUGAGGUCU AGGUCAGA | 18262 |
| 874 | CCUGUGAA G CAACAGUC | 7295 | GACUGUUG GCCGAAAGGCGAGUGAGGUCU UUCACAGG | 18263 |
| 880 | AAGCAACA G UCAAUGGG | 7297 | CCCAUUGA GCCGAAAGGCGAGUGAGGUCU UGUUGCUU | 18264 |
| 888 | GUCAAUGG G CAUUUGUA | 7299 | UACAAAUG GCCGAAAGGCGAGUGAGGUCU CCAUUGAC | 18265 |
| 894 | GGGCAUUU G UAUAAGAC | 7300 | GUCUUAUA GCCGAAAGGCGAGUGAGGUCU AAAUGCCC | 18266 |
| 943 | UCAUAGAU G UCCAAAUA | 7308 | UAUUUGGA GCCGAAAGGCGAGUGAGGUCU AUCUAUGA | 18267 |
| 953 | CCAAAUAA G CACACCAC | 7310 | GUGGUGUG GCCGAAAGGCGAGUGAGGUCU UUAUUUGG | 18268 |
| 962 | CACACCAC G CCCAGUCA | 7311 | UGACUGGG GCCGAAAGGCGAGUGAGGUCU GUGGUGUG | 18269 |
| 967 | CACGCCCA G UCAAAUUA | 7312 | UAAUUUGA GCCGAAAGCCGACUCAGCUCU UGGGCGUG | 18270 |
| 983 | ACUUAGAG G CCAUACUC | 7314 | GAGUAUGG GCCGAAAGGCGAGUGAGGUCU CUCUAAGU | 18271 |
| 994 | AUACUCUU G UCCUCAAU | 7315 | AUUGAGGA GCCGAAAGGCGAGUGAGGUCU AAGAGUAU | 18272 |
| 1004 | CCUCAAUU G UACUGCUA | 7317 | UAGCAGUA GCCGAAAGGCGAGUGAGGUCU AAUUGAGG | 18273 |
| 1009 | AUUGUACU G CUACCACU | 7318 | AGUGGUAG GCCGAAAGGCGAGUGAGGUCU AGUACAAU | 18274 |
| 1033 | ACACGAGA G UUCAAAUG | 7320 | CAUUUGAA GCCGAAAGGCGAGUGAGGUCU UCUCGUGU | 18275 |
| 1049 | GACCUGGA G UUACCCUG | 7323 | CAGGGUAA GCCGAAAGGCGAGUGAGGUCU UCCAGGUC | 18276 |
| 1075 | AUAAGAGA G CUUCCGUA | 7326 | UACGGAAG GCCGAAAGGCGAGUGAGGUCU UCUCUUAU | 18277 |
| 1081 | GAGCUUCC G UAAGGCGA | 7327 | UCGCCUUA GCCGAAAGGCGAGUGAGGUCU GGAAGCUC | 18278 |
| 1086 | UCCGUAAG G CGACGAAU | 7328 | AUUCGUCG GCCGAAAGGCGAGUGAGGUCU CUUACGGA | 18279 |
| 1103 | UGACCAAA G CAAUUCCC | 7332 | GGGAAUUG GCCGAAAGGCGAGUGAGGUCU UUUGGUCA | 18280 |
| 1114 | AUUCCCAU G CCAACAUA | 7334 | UAUGUUGG GCCGAAAGGCGAGUGAGGUCU AUGGGAAU | 18281 |
| 1130 | AUUCUACA G UGUUCUUA | 7336 | UAAGAACA GCCGAAAGGCGAGUGAGGUCU UGUAGAAU | 18282 |
| 1132 | UCUACAGU G UUCUUACU | 7337 | AGUAAGAA GCCGAAAGGCGAGUGAGGUCU ACUGUAGA | 18283 |
| 1152 | GACAAAAU G CAGAACAA | 7340 | UUGUUCUG GCCGAAAGGCGAGUGAGGUCU AUUUUGUC | 18284 |
| 1181 | UUAUACUU G UCGUGUAA | 7344 | UUACACGA GCCGAAAGGCGAGUGAGGUCU AAGUAUAA | 18285 |
| 1184 | UACUUGUC G UGUAAGGA | 7345 | UCCUUACA GCCGAAAGGCGAGUGAGGUCU GACAAGUA | 18286 |
| 1186 | CUUGUCGU G UAAGGAGU | 7346 | ACUCCUUA GCCGAAAGGCGAGUGAGGUCU ACGACAAG | 18287 |
| 1193 | UGUAAGGA G UGGACCAU | 7347 | AUGGUCCA GCCGAAAGGCGAGUGAGGUCU UCCUUACA | 18288 |
| 1213 | UCAAAUCU G UUAACACC | 7350 | GGUGUUAA GCCGAAAGGCGAGUGAGGUCU AGAUUUGA | 18289 |
| 1225 | ACACCUCA G UGCAUAUA | 7352 | UAUAUGCA GCCGAAAGGCGAGUGAGGUCU UGAGGUGU | 18290 |
| 1227 | ACCUCAGU G CAUAUAUA | 7353 | UAUAUAUG GCCGAAAGGCGAGUGAGGUCU ACUGAGGU | 18291 |

TABLE XIX-continued

Human FLT Zinzyme and Substrate Sequence

| Pos | Substrate | Seq ID No | Zinzyme | Seq ID No |
|---|---|---|---|---|
| 1243 | AUGAUAAA G CAUUCAUC | 7355 | GAUGAAUG GCCGAAAGGCGAGUGAGGUCU UUUAUCAU | 18292 |
| 1255 | UCAUCACU G UGAAACAU | 7356 | AUGUUUCA GCCGAAAGGCGACUGAGGUCU AGUGAUGA | 18293 |
| 1272 | CGAAAACA G CAGGUGCU | 7359 | AGCACCUG GCCGAAAGGCGAGUGAGGUCU UGUUUUCG | 18294 |
| 1276 | AACAGCAG G UGCUUGAA | 7360 | UUCAAGCA GCCGAAAGGCGAGUGAGGUCU CUGCUGUU | 18295 |
| 1278 | CAGCAGGU G CUUGAAAC | 7361 | GUUUCAAG GCCGAAAGGCGAGUGAGGUCU ACCUGCUG | 18296 |
| 1288 | UUGAAACC G UAGCUGGC | 7363 | GCCAGCUA GCCGAAAGGCGAGUGAGGUCU GGUUUCAA | 18297 |
| 1291 | AAACCGUA G CUGGCAAG | 7364 | CUUGCCAG GCCGAAAGGCGAGUGAGGUCU UACGGUUU | 18298 |
| 1295 | CGUAGCUG G CAAGCGGU | 7365 | ACCGCUUG GCCGAAAGGCGAGUGAGGUCU CAGCUACG | 18299 |
| 1299 | GCUGGCAA G CGGUCUUA | 7366 | UAAGACCG GCCGAAAGGCGAGUGAGGUCU UUGCCAGC | 18300 |
| 1302 | GGCAAGCG G UCUUACCG | 7367 | CGGUAAGA GCCGAAAGGCGAGUGAGGUCU CGCUUGCC | 18301 |
| 1311 | UCUUACCG G CUCUCUAU | 7368 | AUAGAGAG GCCGAAAGGCGAGUGAGGUCU CGGUAAGA | 18302 |
| 1324 | CUAUGAAA G UGAAGGCA | 7369 | UGCCUUCA GCCGAAAGGCGAGUGAGGUCU UUUCAUAG | 18303 |
| 1330 | AAGUGAAG G CAUUUCCC | 7370 | GGGAAAUG GCCGAAAGGCGAGUGAGGUCU CUUCACUU | 18304 |
| 1341 | UUUCCCUC G CCGGAAGU | 7371 | ACUUCCGG GCCGAAAGGCGAGUGAGGUCU GAGGGAAA | 18305 |
| 1348 | CGCCGGAA G UUGUAUGG | 7372 | CCAUACAA GCCGAAAGGCGAGUGAGGUCU UUCCGGCG | 18306 |
| 1351 | CGGAAGUU G UAUGGUUA | 7373 | UAACCAUA GCCGAAAGGCGAGUGAGGUCU AACUUCCG | 18307 |
| 1356 | GUUGUAUG G UUAAAAGA | 7374 | UCUUUUAA GCCGAAAGGCGAGUGAGGUCU CAUACAAC | 18308 |
| 1368 | AAAGAUGG G UUACCUGC | 7376 | GCAGGUAA GCCGAAAGGCGAGUGAGGUCU CCAUCUUU | 18309 |
| 1375 | GGUUACCU G CGACUGAG | 7377 | CUCAGUCG GCCGAAAGGCGAGUGAGGUCU AGGUAACC | 18310 |
| 1390 | AGAAAUCU G CUCGCUAU | 7380 | AUAGCGAG GCCGAAAGGCGAGUGAGGUCU AGAUUUCU | 18311 |
| 1394 | AUCUGCUC G CUAUUUGA | 7381 | UCAAAUAG GCCGAAAGGCGAGUGAGGUCU GAGCAGAU | 18312 |
| 1406 | UUUGACUC G UGGCUACU | 7383 | AGUAGCCA GCCGAAAGGCGAGUGAGGUCU GAGUCAAA | 18313 |
| 1409 | GACUCGUG G CUACUCGU | 7384 | ACGAGUAG GCCGAAAGGCGAGUUAGGUCU CACGAGUC | 18314 |
| 1416 | GGCUACUC G UUAAUUAU | 7385 | AUAAUUAA GCCGAAAGGCGAGUGAGGUCU GAGUAGCC | 18315 |
| 1432 | UCAAGGAC G UAACUGAA | 7388 | UUCAGUUA GCCGAAAGGCGAGUGAUGUCU GUCCUUGA | 18316 |
| 1447 | AAGAGGAU G CAGGGAAU | 7391 | AUUCCCUG GCCGAAAGGCGAGUGAGGUCU AUCCUCUU | 18317 |
| 1467 | ACAAUCUU G CUGAGCAU | 7394 | AUGCUCAG GCCGAAAGGCGAGUGAGGUCU AAGAUUGU | 18318 |
| 1472 | CUUGCUGA G CAUAAAAC | 7395 | GUUUUAUG GCCGAAAGGCGAGUGAGGUCU UCAGCAAG | 18319 |
| 1482 | AUAAAACA G UCAAAUGU | 7397 | ACAUUUGA GCCGAAAGGCGAGUGAGGUCU UGUUUUAU | 18320 |
| 1489 | AGUCAAAU G UGUUUAAA | 7399 | UUUAAACA GCCGAAAGGCGAGUGAGGUCU AUUUGACU | 18321 |
| 1491 | UCAAAUGU G UUUAAAAA | 7400 | UUUUUAAA GCCGAAAGGCGAGUGAGGUCU ACAUUUGA | 18322 |
| 1507 | ACCUCACU G CCACUCUA | 7402 | UAGAGUGG GCCGAAAGGCGAGUGAGGUCU AGUGAGGU | 18323 |
| 1519 | CUCUAAUU G UCAAUGUG | 7404 | CACAUUGA GCCGAAAGGCGAGUGAGGUCU AAUUAGAG | 18324 |
| 1525 | UUGUCAAU G UGAAACCC | 7406 | GGGUUUCA GCCGAAAGGCGAGUGAUGUCU AUUGACAA | 18325 |
| 1549 | ACGAAAAG G CCGUGUCA | 7409 | UGACACGG GCCGAAAGGCGAGUGAGGUCU CUUUUCGU | 18326 |
| 1552 | AAAAGGCC G UGUCAUCG | 7410 | CGAUGACA GCCGAAAGGCGAGUGAGGUCU GGCCUUUU | 18327 |
| 1554 | AAGGCCGU G UCAUCGUU | 7411 | AACGAUGA GCCGAAAGGCGAGUGAGGUCU ACGGCCUU | 18328 |

TABLE XIX-continued

Human FLT Zinzyme and Substrate Sequence

| Pos | Substrate | Seq ID No | Zinzyme | Seq ID No |
|---|---|---|---|---|
| 1560 | GUGUCAUC G UUUCCAGA | 7412 | UCUGGAAA GCCGAAAGGCGAGUGAGGUCU GAUGACAC | 18329 |
| 1573 | CAGACCCG G CUCUCUAC | 7414 | GUAGAGAG GCCGAAAGGCGAGUGAGGUCU CGGGUCUG | 18330 |
| 1589 | CCCACUGG G CAGCAGAC | 7415 | GUCUGCUG GCCGAAAGGCGAGUGAGGUCU CCAGUGGG | 18331 |
| 1592 | ACUGGGCA G CAGACAAA | 7416 | UUUGUCUG GCCGAAAGGCGAGUGAGGUCU UGCCCAGU | 18332 |
| 1610 | CCUGACUU G UACCGCAU | 7420 | AUGCGGUA GCCGAAAGGCGAGUGAGGUCU AAGUCAGG | 18333 |
| 1615 | CUUGUACC G CAUAUGGU | 7421 | ACCAUAUG GCCGAAAGGCGAGUGAGGUCU GGUACAAG | 18334 |
| 1622 | CGCAUAUU G UAUCCCUC | 7422 | GAGGGAUA GCCGAAAGGCGAGUGAGGUCU CAUAUGCG | 18335 |
| 1644 | ACAAUCAA G UGGUUCUG | 7425 | CAGAACCA GCCGAAAGGCGAGUGAGGUCU UUGAUUGU | 18336 |
| 1647 | AUCAAGUG G UUCGGUCA | 7426 | UGCCAGAA GCCGAAAGGCGAGUGAGGUCU CACUUGAU | 18337 |
| 1653 | UGGUUCUG G CACCCCUG | 7427 | CAGGGGUG GCCGAAAGGCGAGUGAGGUCU CAGAACCA | 18338 |
| 1661 | GCACCCCU G UAACCAUA | 7428 | UAUGGUUA GCCGAAAGGCGAGUGAGGUCU AGGGGUGC | 18339 |
| 1681 | AUUCCGAA G CAAGGUGU | 7431 | ACACCUUG GCCGAAAGGCGAGUGAGGUCU UUCGGAAU | 18340 |
| 1686 | GAAGCAAG G UGUGACUU | 7432 | AAGUCACA GCCGAAAGGCGAGUGAGGUCU CUUGCUUC | 18341 |
| 1688 | AGCAAGGU G UGACUUUU | 7433 | AAAAGUCA GCCGAAAGGCGAGUGAGGUCU ACCUUGCU | 18342 |
| 1697 | UGACUUUU G UUCCAAUA | 7435 | UAUUGGAA GCCGAAAGGCGAGUGAGGUCU AAAAGUCA | 18343 |
| 1713 | AAUGAAGA G UCCUUUAU | 7438 | AUAAAGGA GCCGAAAGGCGAGUGAGGUCU UCUUCAUU | 18344 |
| 1729 | UCCUGGAU G CUGACAGC | 7440 | GCUGUCAG GCCGAAAGGCGAGUGAGGUCU AUCCAGGA | 18345 |
| 1736 | UGCUGACA G CAACAUGG | 7442 | CCAUGUUG GCCGAAAGGCGAGUGAGGUCU UGUCAGCA | 18346 |
| 1760 | AAUUGAGA G CAUCACUC | 7446 | GAGUGAUG GCCGAAAGGCGAGUGAGGUCU UCUCAAUU | 18347 |
| 1770 | AUCACUCA G CGCAUGGC | 7447 | GCCAUGCG GCCGAAAGGCGAGUGAGGUCU UGAGUGAU | 18348 |
| 1772 | CACUCAGC G CAUGGCAA | 7448 | UUGCCAUG GCCGAAAGGCGAGUGAGGUCU GCUGAGUG | 18349 |
| 1777 | AGCGCAUG G CAAUAAUA | 7449 | UAUUAUUG GCCGAAAGGCGAGUGAGGUCU CAUGCGCU | 18350 |
| 1804 | AUAAGAUG G CUAGCACC | 7454 | GGUGCUAG GCCGAAAGGCGAGUGAGGUCU CAUCUUAU | 18351 |
| 1808 | GAUGGCUA G CACCUUGG | 7455 | CCAAGGUG GCCGAAAGGCGAGUGAGGUCU UAGCCAUC | 18352 |
| 1816 | GCACCUUG G UUGUGGCU | 7456 | AGCCACAA GCCGAAAGGCGAGUGAGGUCU CAAGGUGC | 18353 |
| 1819 | CCUUGGUU G UGGCUGAC | 7457 | GUCAGCCA GCCGAAAGGCGAGUGAGGUCU AACCAAGG | 18354 |
| 1822 | UGGUUGUG G CUGACUCU | 7458 | AGAGUCAG GCCGAAAGGCGAGUGAGGUCU CACAACCA | 18355 |
| 1853 | CUACAUUU G CAUAGCUU | 7462 | AAGCUAUG GCCGAAAGGCGAGUGAGGUCU AAAUGUAG | 18356 |
| 1858 | UUUGCAUA G CUUCCAAU | 7463 | AUUGGAAG GCCGAAAGGCGAGUGAGGUCU UAUGCAAA | 18357 |
| 1870 | CCAAUAAA G UUGGGACU | 7465 | AGUCCCAA GCCGAAAGGCGAGUGAGGUCU UUUAUUGG | 18358 |
| 1879 | UUGGGACU G UGGGAAGA | 7467 | UCUUCCCA GCCGAAAGGCGAGUGAGGUCU AGUCCCAA | 18359 |
| 1895 | AAACAUAA G CUUUUAUA | 7469 | UAUAAAAG GCCGAAAGGCGAGUGAGGUCU UUAUGUUU | 18360 |
| 1912 | UCACAGAU G UGCCAAAU | 7471 | AUUUGGCA GCCGAAAGGCGAGUGAGGUCU AUCUGUGA | 18361 |
| 1914 | ACAGAUGU G CCAAAUGG | 7472 | CCAUUUGG GCCGAAAGGCGAGUGAGGUCU ACAUCUGU | 18362 |
| 1923 | CCAAAUGG G UUUCAUGU | 7474 | ACAUGAAA GCCGAAAGGCGAGUGAGGUCU CCAUUUGG | 18363 |
| 1930 | GGUUUCAU G UUAACUUG | 7475 | CAAGUUAA GCCGAAAGGCGAGUGAGGUCU AUGAAACC | 18364 |
| 1947 | GAAAAAAU G CCGACGGA | 7478 | UCCGUCGG GCCGAAAGGCGAGUGAGGUCU AUUUUUUC | 18365 |

TABLE XIX-continued

Human FLT Zinzyme and Substrate Sequence

| Pos | Substrate | Seq ID No | Zinzyme | Seq ID No |
|---|---|---|---|---|
| 1974 | CUGAAACU G UCUUGCAC | 7482 | GUGCAAGA GCCGAAAGGCGAGUGAGGUCU AGUUUCAG | 18366 |
| 1979 | ACUGUCUU G CACAGUUA | 7483 | UAACUGUG GCCGAAAGGCGAGUGAGGUCU AAGACAGU | 18367 |
| 1984 | CUUGCACA G UUAACAAG | 7484 | CUUGUUAA GCCGAAAGGCGAGUGAGGUCU UGUGCAAG | 18368 |
| 1992 | GUUAACAA G UUCUUAUA | 7486 | UAUAAGAA GCCGAAAGGCGAGUGAGGUCU UUGUUAAC | 18369 |
| 2008 | ACAGAGAC G UUACUUGG | 7488 | CCAAGUAA GCCGAAAGGCGAGUGAGGUCU GUCUCUGU | 18370 |
| 2025 | AUUUUACU G CGGACAGU | 7490 | ACUGUCCG GCCGAAAGGCGAGUGAGGUCU AGUAAAAU | 18371 |
| 2032 | UGCGGACA G UUAAUAAC | 7492 | GUUAUUAA GCCGAAAGGCGAGUGAGGUCU UGUCCGCA | 18372 |
| 2049 | AGAACAAU G CACUACAG | 7497 | CUGUAGUG GCCGAAAGGCGAGUGAGGUCU AUUGUUCU | 18373 |
| 2057 | GCACUACA G UAUUAGCA | 7498 | UGCUAAUA GCCGAAAGGCGAGUGAGGUCU UGUAGUGC | 18374 |
| 2063 | CAGUAUUA G CAAGCAAA | 7499 | UUUGCUUG GCCGAAAGGCGAGUGAGGUCU UAAUACUG | 18375 |
| 2067 | AUUAGCAA G CAAAAAAU | 7500 | AUUUUUUG GCCGAAAGGCGAGUGAGGUCU UUGCUAAU | 18376 |
| 2077 | AAAAAAUG G CCAUCACU | 7502 | AGUGAUGG GCCGAAAGGCGAGUGAGGUCU CAUUUUUU | 18377 |
| 2091 | ACUAAGGA G CACUCCAU | 7503 | AUGGAGUG GCCGAAAGGCGAGUGAGGUCU UCCUUAGU | 18378 |
| 2125 | UCAUGAAU G UUUCCCUG | 7506 | CAGGGAAA GCCGAAAGGCGAGUGAGGUCU AUUCAUGA | 18379 |
| 2133 | GUUUCCCU G CAAGAUUC | 7507 | GAAUCUUG GCCGAAAGGCGAGUGAGGUCU AGGGAAAC | 18380 |
| 2144 | AGAUUCAG G CACCUAUG | 7509 | CAUAGGUG GCCGAAAGGCGAGUGAGGUCU CUGAAUCU | 18381 |
| 2152 | GCACCUAU G CCUGCAGA | 7510 | UCUGCAGG GCCGAAAGGCGAGUGAGGUCU AUAGGUGC | 18382 |
| 2156 | CUAUGCCU G CAGAGCCA | 7511 | UGGCUCUG GCCGAAAGGCGAGUGAGGUCU AGGCAUAG | 18383 |
| 2161 | CCUGCAGA G CCAGGAAU | 7512 | AUUCCUGG GCCGAAAGGCGAGUGAGGUCU UCUGCAGG | 18384 |
| 2170 | CCAGGAAU G UAUACACA | 7514 | UGUGUAUA GCCGAAAGGCGAGUGAGGUCU AUUCCUGG | 18385 |
| 2227 | AUCAGGAA G CACCAUAC | 7519 | GUAUGGUG GCCGAAAGGCGAGUGAGGUCU UUCCUGAU | 18386 |
| 2241 | UACCUCCU G CGAAACCU | 7520 | AGGUUUCG GCCGAAAGGCGAGUGAGGUCU AGGAGGUA | 18387 |
| 2252 | AAACCUCA G UGAUCACA | 7522 | UGUGAUCA GCCGAAAGGCGAGUGAGGUCU UGAGGUUU | 18388 |
| 2263 | AUCACACA G UGGCCAUC | 7524 | GAUGGCCA GCCGAAAGGCGAGUGAGGUCU UGUGUGAU | 18389 |
| 2266 | ACACAGUG G CCAUCAGC | 7525 | GCUGAUGG GCCGAAAGGCGAGUGAGGUCU CACUGUGU | 18390 |
| 2273 | GGCCAUCA G CAGUUCCA | 7526 | UGGAACUG GCCGAAAGGCGAGUGAGGUCU UGAUGGCC | 18391 |
| 2276 | CAUCAGCA G UUCCACCA | 7527 | UGGUGGAA GCCGAAAGGCGAGUGAGGUCU UGCUGAUG | 18392 |
| 2294 | UUUAGACU G UCAUGCUA | 7529 | UAGCAUGA GCCGAAAGGCGAGUGAGGUCU AGUCUAAA | 18393 |
| 2299 | ACUGUCAU G CUAAUGGU | 7530 | ACCAUUAG GCCGAAAGGCGAGUGAGGUCU AUGACAGU | 18394 |
| 2306 | UGCUAAUG G UGUCCCCG | 7532 | CGGGGACA GCCGAAAGGCGAGUGAGGUCU CAUUAGCA | 18395 |
| 2308 | CUAAUGGU G UCCCCGAG | 7533 | CUCGGGGA GCCGAAAGGCGAGUGAGGUCU ACCAUUAG | 18396 |
| 2316 | GUCCCCGA G CCUCAGAU | 7534 | AUCUGAGG GCCGAAAGGCGAGUGAGGUCU UCGGGGAC | 18397 |
| 2331 | AUCACUUG G UUUAAAAA | 7536 | UUUUUAAA GCCGAAAGGCGAGUGAGGUCU CAAGUGAU | 18398 |
| 2361 | CAACAAGA G CCUGGAAU | 7541 | AUUCCAGG GCCGAAAGGCGAGUGAGGUCU UCUUGUUG | 18399 |
| 2387 | ACCAGGAA G CAGCACGC | 7544 | GCGUGCUG GCCGAAAGGCGAGUGAGGUCU UUCCUGGU | 18400 |
| 2390 | AGGAAGCA G CACGCUGU | 7545 | ACAGCGUG GCCGAAAGGCGAGUGAGGUCU UGCUUCCU | 18401 |
| 2394 | AGCAGCAC G CUGUUUAU | 7546 | AUAAACAG GCCGAAAGGCGAGUGAGGUCU GUGCUGCU | 18402 |

TABLE XIX-continued

Human FLT Zinzyme and Substrate Sequence

| Pos | Substrate | Seq ID No | Zinzyme | Seq ID No |
|---|---|---|---|---|
| 2397 | AGCACGCU G UUUAUUGA | 7547 | UCAAUAAA GCCGAAAGGCGAGUGAGGUCU AGCGUGCU | 18403 |
| 2410 | UUGAAAGA G UCACAGAA | 7548 | UUCUGUGA GCCGAAAGGCGAGUGAGGUCU UCUUUCAA | 18404 |
| 2429 | GGAUGAAG G UGUCUAUC | 7550 | GAUAGACA GCCGAAAGGCGAGUGAGGUCU CUUCAUCC | 18405 |
| 2431 | AUGAAGGU G UCUAUCAC | 7551 | GUGAUAGA GCCGAAAGGCGAGUGAGGUCU ACCUUCAU | 18406 |
| 2441 | CUAUCACU G CAAAGCCA | 7552 | UGGCUUUG GCCGAAAGGCGAGUGAGGUCU AGUGAUAG | 18407 |
| 2446 | ACUGCAAA G CCACCAAC | 7553 | GUUGGUGG GCCGAAAGGCGAGUGAGGUCU UUUGCAGU | 18408 |
| 2462 | CCAGAAGG G CUCUGUGG | 7555 | CCACAGAG GCCGAAAGGCGAGUGAGGUCU CCUUCUGG | 18409 |
| 2467 | AGGGCUCU G UGGAAAGU | 7556 | ACUUUCCA GCCGAAAGGCGAGUGAGGUCU AGAGCCCU | 18410 |
| 2474 | UGUGGAAA G UUCAGCAU | 7557 | AUGCUGAA GCCGAAAGGCGAGUGAGGUCU UUUCCACA | 18411 |
| 2479 | AAAGUUCA G CAUACCUC | 7558 | GAGGUAUG GCCGAAAGGCGAGUGAGGUCU UGAACUUU | 18412 |
| 2491 | ACCUCACU G UUCAAGGA | 7559 | UCCUUGAA GCCGAAAGGCGAGUGAGGUCU AGUGAGGU | 18413 |
| 2511 | UCGGACAA G UCUAAUCU | 7562 | AGAUUAGA GCCGAAAGGCGAGUGAGGUCU UUGUCCGA | 18414 |
| 2523 | AAUCUGGA G CUGAUCAC | 7564 | GUGAUCAG GCCGAAAGGCGAGUGAGGUCU UCCAGAUU | 18415 |
| 2540 | UCUAACAU G CACCUGUG | 7567 | CACAGGUG GCCGAAAGGCGAGUGAGGUCU AUGUUAGA | 18416 |
| 2546 | AUGCACCU G UGUGGCUG | 7568 | CAGCCACA GCCGAAAGGCGAGUGAGGUCU AGGUGCAU | 18417 |
| 2548 | GCACCUGU G UGGCUGCG | 7569 | CGCAGCCA GCCGAAAGGCGAGUGAGGUCU ACAGGUGC | 18418 |
| 2551 | CCUGUGUG G CUGCGACU | 7570 | AGUCGCAG GCCGAAAGGCGAGUGAGGUCU CACACAGG | 18419 |
| 2554 | GUGUGGCU G CGACUCUC | 7571 | GAGAGUCG GCCGAAAGGCGAGUGAGGUCU AGCCACAC | 18420 |
| 2568 | CUCUUCUG G CUCCUAUU | 7573 | AAUAGGAG GCCGAAAGGCGAGUGAGGUCU CAGAAGAG | 18421 |
| 2604 | AUGAAAAG G UCUUCUUC | 7576 | GAAGAAGA GCCGAAAGGCGAGUGAGGUCU CUUUUCAU | 18422 |
| 2659 | CAGAUGAA G UUCCUUUG | 7584 | CAAAGGAA GCCGAAAGGCGAGUGAGGUCU UUCAUCUG | 18423 |
| 2673 | UUGGAUGA G CAGUGUGA | 7586 | UCACACUG GCCGAAAGGCGAGUGAGGUCU UCAUCCAA | 18424 |
| 2676 | GAUGAGCA G UGUGAGCG | 7587 | CGCUCACA GCCGAAAGGCGAGUGAGGUCU UGCUCAUC | 18425 |
| 2678 | UGAGCAGU G UGAGCGGC | 7588 | GCCGCUCA GCCGAAAGGCGAGUGAGGUCU ACUGCUCA | 18426 |
| 2682 | CAGUGUGA G CGGCUCCC | 7589 | GGGACCCG GCCGAAAGGCGAGUGAGGUCU UCACACUG | 18427 |
| 2685 | UGUGAGCG G CUCCCUUA | 7590 | UAAGGGAG GCCGAAAGGCGAGUGAGGUCU CGCUCACA | 18428 |
| 2698 | CUUAUGAU G CCAGCAAG | 7592 | CUUGCUGG GCCGAAAGGCGAGUGAGGUCU AUCAUAAG | 18429 |
| 2702 | UGAUGCCA G CAAGUGGG | 7593 | CCCACUUG GCCGAAAGGCGAGUGAGGUCU UGGCAUCA | 18430 |
| 2706 | GCCAGCAA G UGGGAGUU | 7594 | AACUCCCA GCCGAAAGGCGAGUGAGGUCU UUGCUGGC | 18431 |
| 2712 | AAGUGGGA G UUUGCCCG | 7595 | CGGGCAAA GCCGAAAGGCGAGUGAGGUCU UCCCACUU | 18432 |
| 2716 | GGGAGUUU G CCCGGGAG | 7596 | CUCCCGGG GCCGAAAGGCGAGUGAGGUCU AAACUCCC | 18433 |
| 2738 | UAAACUGG G CAAAUCAC | 7599 | GUGAUUUC GCCGAAAGGCGAGUGAGGUCU CCAGUUUA | 18434 |
| 2758 | GAAGAGGG G CUUUUGGA | 7601 | UCCAAAAG GCCGAAAGGCGAGUGAGGUCU CCCUCUUC | 18435 |
| 2770 | UUGGAAAA G UGGUUCAA | 7602 | UUGAACCA GCCGAAAGGCGAGUGAGGUCU UUUUCCAA | 18436 |
| 2773 | GAAAAGUG G UUCAAGCA | 7603 | UGCUUGAA GCCGAAAGGCGAGUGAGGUCU CACUUUUC | 18437 |
| 2779 | UGGUUCAA G CAUCAGCA | 7604 | UGCUGAUG GCCGAAAGGCGAGUGAGGUCU UUGAACCA | 18438 |
| 2785 | AAGCAUCA G CAUUUGGC | 7605 | GCCAAAUG GCCGAAAGGCGAGUGAGGUCU UGAUGCUU | 18439 |

TABLE XIX-continued

Human FLT Zinzyme and Substrate Sequence

| Pos | Substrate | Seq ID No | Zinzyme | Seq ID No |
|---|---|---|---|---|
| 2792 | AGCAUUUG G CAUUAAGA | 7606 | UCUUAAUG GCCGAAAGGCGAGUGAGGUCU CAAAUGCU | 18440 |
| 2811 | UCACCUAC G UGCCGGAC | 7608 | GUCCGGCA GCCGAAAGGCGAGUGAGGUCU GUAGGUGA | 18441 |
| 2813 | ACCUACGU G CCGGACUG | 7609 | CAGUCCGG GCCGAAAGGCGAGUGAGGUCU ACGUAGGU | 18442 |
| 2821 | GCCGGACU G UGGCUGUG | 7611 | CACAGCCA GCCGAAAGGCGAGUGAGGUCU AGUCCGGC | 18443 |
| 2824 | GGACUGUG G CUGUGAAA | 7612 | UUUCACAG GCCGAAAGGCGAGUGAGGUCU CACAGUCC | 18444 |
| 2827 | CUGUGGCU G UGAAAAUG | 7613 | CAUUUUCA GCCGAAAGGCGAGUGAGGUCU AGCCACAG | 18445 |
| 2835 | GUGAAAAU G CUGAAAGA | 7615 | UCUUUCAG GCCGAAAGGCGAGUGAGGUCU AUUUUCAC | 18446 |
| 2848 | AAGAGGGG G CCACGGCC | 7616 | GGCCGUGG GCCGAAAGGCGAGUGAGGUCU CCCCUCUU | 18447 |
| 2854 | GGGCCACG G CCAGCGAG | 7617 | CUCGCUGG GCCGAAAGGCGAGUGAGGUCU CGUGGCCC | 18448 |
| 2858 | CACGGCCA G CGAGUACA | 7618 | UGUACUCG GCCGAAAGGCGAGUGAGGUCU UGGCCGUG | 18449 |
| 2862 | GCCAGCGA G UACAAAGC | 7619 | GCUUUGUA GCCGAAAGGCGAGUGAGGUCU UCGCUGGC | 18450 |
| 2869 | AGUACAAA G CUCUGAUG | 7620 | CAUCAGAG GCCGAAAGGCGAGUGAGGUCU UUUGUACU | 18451 |
| 2883 | AUGACUGA G CUAAAAAU | 7623 | AUUUUUAG GCCGAAAGGCGAGUGAGGUCU UCAGUCAU | 18452 |
| 2906 | CCACAUUG G CCACCAUC | 7626 | GAUGGUGG GCCGAAAGGCGAGUGAGGUCU CAAUGUGG | 18453 |
| 2920 | AUCUGAAC G UGGUUAAC | 7628 | GUUAACCA GCCGAAAGGCGAGUGAGGUCU GUUCAGAU | 18454 |
| 2923 | UGAACGUG G UUAACCUG | 7629 | CAGGUUAA GCCGAAAGGCGAGUGAGGUCU CACGUUCA | 18455 |
| 2931 | GUUAACCU G CUGGGAGC | 7631 | GCUCCCAG GCCGAAAGGCGAGUGAGGUCU AGGUUAAC | 18456 |
| 2938 | UGCUGGGA G CCUGCACC | 7632 | GGUGCAGG GCCGAAAGGCGAGUGAGGUCU UCCCAGCA | 18457 |
| 2942 | GGGAGCCU G CACCAAGC | 7633 | GCUUGGUG GCCGAAAGGCGAGUGAGGUCU AGGCUCCC | 18458 |
| 2949 | UGCACCAA G CAAGGAGG | 7634 | CCUCCUUG GCCGAAAGGCGAGUGAGGUCU UUGGUGCA | 18459 |
| 2958 | CAAGGAGG G CCUCUGAU | 7635 | AUCAGAGG GCCGAAAGGCGAGUGAGGUCU CCUCCUUG | 18460 |
| 2968 | CUCUGAUG G UGAUUGUU | 7637 | AACAAUCA GCCGAAAGGCGAGUGAGGUCU CAUCAGAG | 18461 |
| 2974 | UGGUGAUU G UUGAAUAC | 7639 | GUAUUCAA GCCGAAAGGCGAGUGAGGUCU AAUCACCA | 18462 |
| 2984 | UGAAUACU G CAAAUAUG | 7641 | CAUAUUUG GCCGAAAGGCGAGUGAGGUCU AGUAUUCA | 18463 |
| 3017 | CCUCAAGA G CAAACGUG | 7645 | CACGUUUG GCCGAAAGGCGAGUGAGGUCU UCUUGAGG | 18464 |
| 3023 | GAGCAAAC G UGACUUAU | 7647 | AUAAGUCA GCCGAAAGGCGAGUGAGGUCU GUUUGCUC | 18465 |
| 3049 | ACAAGGAU G CAGCACUA | 7651 | UAGUGCUG GCCGAAAGGCGAGUGAGGUCU AUCCUUGU | 18466 |
| 3052 | AGGAUGCA G CACUACAC | 7652 | GUGUAGUG GCCGAAAGGCGAGUGAGGUCU UGCAUCCU | 18467 |
| 3066 | CACAUGGA G CCUAAGAA | 7653 | UUCUUAGG GCCGAAAGGCGAGUGAGGUCU UCCAUGUG | 18468 |
| 3087 | AAAAUGGA G CCAGGCCU | 7655 | AGGCCUGG GCCGAAAGGCGAGUGAGGUCU UCCAUUUU | 18469 |
| 3092 | GGAGCCAG G CCUGGAAC | 7656 | GUUCCAGG GCCGAAAGGCGAGUGAGGUCU CUGGCUCC | 18470 |
| 3104 | GGAACAAG G CAAGAAAC | 7658 | GUUUCUUG GCCGAAAGGCGAGUGAGGUCU CUUGUUCC | 18471 |
| 3125 | ACUAGAUA G CGUCACCA | 7662 | UGGUGACG GCCGAAAGGCGAGUGAGGUCU UAUCUAGU | 18472 |
| 3127 | UAGAUAGC G UCACCAGC | 7663 | GCUGGUGA GCCGAAAGGCGAGUGAGGUCU GCUAUCUA | 18473 |
| 3134 | CGUCACCA G CAGCGAAA | 7664 | UUUCGCUG GCCGAAAGGCGAGUGAGGUCU UGGUGACG | 18474 |
| 3137 | CACCAGCA G CGAAAGCU | 7665 | AGCUUUCG GCCGAAAGGCGAGUGAGGUCU UGCUGGUG | 18475 |
| 3143 | CAGCGAAA G CUUUGCGA | 7666 | UCGCAAAG GCCGAAAGGCGAGUGAGGUCU UUUCGCUG | 18476 |

TABLE XIX-continued

Human FLT Zinzyme and Substrate Sequence

| Pos | Substrate | Seq ID No | Zinzyme | Seq ID No |
|---|---|---|---|---|
| 3148 | AAAGCUUU G CGAGCUCC | 7667 | GGAGCUCG GCCGAAAGGCGAGUGAGGUCU AAAGCUUU | 18477 |
| 3152 | CUUUGCGA G CUCCGGCU | 7668 | AGCCGGAG GCCGAAAGGCGAGUGAGGUCU UCGCAAAG | 18478 |
| 3158 | GAGCUCCG G CUUUCAGG | 7669 | CCUGAAAG GCCGAAAGGCGAGUGAGGUCU CGGAGCUC | 18479 |
| 3176 | AGAUAAAA G UCUGAGUG | 7671 | CACUCAGA GCCGAAAGGCGAGUGAGGUCU UUUUAUCU | 18480 |
| 3182 | AAGUCUGA G UGAUGUUG | 7672 | CAACAUCA GCCGAAAGGCGAGUGAGGUCU UCAGACUU | 18481 |
| 3187 | UGAGUGAU G UUGAGGAA | 7674 | UUCCUCAA GCCGAAAGGCGAGUGAGGUCU AUCACUCA | 18482 |
| 3212 | UUCUGACG G UUUCUACA | 7677 | UGUAGAAA GCCGAAAGGCGAGUGAGGUCU CGUCAGAA | 18483 |
| 3225 | UACAAGGA G CCCAUCAC | 7678 | GUGAUGGG GCCGAAAGGCGAGUGAGGUCU UCCUUGUA | 18484 |
| 3257 | UUCUUACA G UUUUCAAG | 7681 | CUUGAAAA GCCGAAAGGCGAGUGAGGUCU UGUAAGAA | 18485 |
| 3265 | GUUUUCAA G UGGCCAGA | 7682 | UCUGGCCA GCCGAAAGGCGAGUGAGGUCU UUGAAAAC | 18486 |
| 3268 | UUCAAGUG G CCAGAGGC | 7683 | GCCUCUGG GCCGAAAGGCGAGUGAGGUCU CACUUGAA | 18487 |
| 3275 | GGCCAGAG G CAUGGAGU | 7684 | ACUCCAUG GCCGAAAGGCGAGUGAGGUCU CUCUGGCC | 18488 |
| 3282 | GGCAUGGA G UUCCUGUC | 7685 | GACAGGAA GCCGAAAGGCGAGUGAGGUCU UCCAUGCC | 18489 |
| 3288 | GAGUUCCU G UCUUCCAG | 7686 | CUGGAAGA GCCGAAAGGCGAGUGAGGUCU AGGAACUC | 18490 |
| 3300 | UCCAGAAA G UGCAUUCA | 7687 | UGAAUGCA GCCGAAAGGCGAGUGAGGUCU UUUCUGGA | 18491 |
| 3302 | CAGAAAGU G CAUUCAUC | 7688 | GAUGAAUG GCCGAAAGGCGAGUGAGGUCU ACUUUCUG | 18492 |
| 3319 | GGGACCUG G CAGCGAGA | 7690 | UCUCGCUG GCCGAAAGGCGAGUGAGGUCU CAGGUCCC | 18493 |
| 3322 | ACCUGGCA G CGAGAAAC | 7691 | GUUUCUCG GCCGAAAGGCGAGUGAGGUCU UGCCAGGU | 18494 |
| 3352 | AGAACAAC G UGGUGAAG | 7695 | CUUCACCA GCCGAAAGGCGAGUGAGGUCU GUUGUUCU | 18495 |
| 3355 | ACAACGUG G UGAAGAUU | 7696 | AAUCUUCA GCCGAAAGGCGAGUGAGGUCU CACGUUGU | 18496 |
| 3365 | GAAGAUUU G UGAUUUUG | 7698 | CAAAAUCA GCCGAAAGGCGAGUGAGGUCU AAAUCUUC | 18497 |
| 3374 | UGAUUUUG G CCUUGCCC | 7700 | GGGCAAGG GCCGAAAGGCGAGUGAGGUCU CAAAAUCA | 18498 |
| 3379 | UUGGCCUU G CCCGGGAU | 7701 | AUCCCGGG GCCGAAAGGCGAGUGAGGUCU AAGGCCAA | 18499 |
| 3409 | CCGAUUAU G UGAGAAAA | 7705 | UUUUCUCA GCCGAAAGGCGAGUGAGGUCU AUAAUCGG | 18500 |
| 3448 | AAUGGAUG G CUCCCGAA | 7710 | UUCGGGAG GCCGAAAGGCGAGUGAGGUCU CAUCCAUU | 18501 |
| 3479 | AAUCUACA G CACCAAGA | 7714 | UCUUGGUG GCCGAAAGGCGAGUGAGGUCU UGUAGAUU | 18502 |
| 3488 | CACCAAGA G CGACGUGU | 7715 | ACACGUCG GCCGAAAGGCGAGUGAGGUCU UCUUGGUG | 18503 |
| 3493 | AGAGCGAC G UGGUCUA | 7717 | AGACCACA GCCGAAAGGCGAGUGAGGUCU GUCGCUCU | 18504 |
| 3495 | AGCGACGU G GUCUUA | 7718 | UAAGACCA GCCGAAAGGCGAGUGAGGUCU ACGUCGCU | 18505 |
| 3498 | GACGUGUG G UCUUACGG | 7719 | CCGUAAGA GCCGAAAGGCGAGUGAGGUCU CACACGUC | 18506 |
| 3508 | CUUACGGA G UAUUGCUG | 7720 | CAGCAAUA GCCGAAAGGCGAGUGAGGUCU UCCGUAAG | 18507 |
| 3513 | GGAGUAUU G CUGUGGGA | 7721 | UCCCACAG GCCGAAAGGCGAGUGAGGUCU AAUACUCC | 18508 |
| 3516 | GUAUUGCU G UGGGAAAU | 7722 | AUUUCCCA GCCGAAAGGCGAGUGAGGUCU AGCAAUAC | 18509 |
| 3536 | CUCCUUAG G UGGGUCUC | 7724 | GAGACCCA GCCGAAAGGCGAGUGAGGUCU CUAAGGAG | 18510 |
| 3540 | UUAGGUGG G UCUCCAUA | 7725 | UAUGGAGA GCCGAAAGGCGAGUGAGGUCU CCACCUAA | 18511 |
| 3556 | ACCCAGGA G UACAAAUG | 7726 | CAUUUGUA GCCGAAAGGCGAGUGAGGUCU UCCUGGGU | 18512 |
| 3578 | GGACUUUU G CAGUCGCC | 7730 | GGCGACUG GCCGAAAGGCGAGUGAGGUCU AAAAGUCC | 18513 |

TABLE XIX-continued

Human FLT Zinzyme and Substrate Sequence

| Pos | Substrate | Seq ID No | Zinzyme | Seq ID No |
|---|---|---|---|---|
| 3581 | CUUUUGCA G UCGCCUGA | 7731 | UCAGGCGA GCCGAAAGGCGAGUGAGGUCU UGCAAAAG | 18514 |
| 3584 | UUGCAGUC G CCUGAGGG | 7732 | CCCUCAGG GCCGAAAGGCGAGUGAGGUCU GACUGCAA | 18515 |
| 3596 | GAGGGAAG G CAUGAGGA | 7733 | UCCUCAUG GCCGAAAGGCGAGUGAGGUCU CUUCCCUC | 18516 |
| 3610 | GGAUGAGA G CUCCUGAG | 7735 | CUCAGGAG GCCGAAAGGCGAGUGAGGUCU UCUCAUCC | 18517 |
| 3618 | GCUCCUGA G UACUCUAC | 7736 | GUAGAGUA GCCGAAAGGCGAGUGAGGUCU UCAGGAGC | 18518 |
| 3648 | CAGAUCAU G CUGGACUG | 7739 | CAGUCCAG GCCGAAAGGCGAGUGAGGUCU AUGAUCUG | 18519 |
| 3656 | GCUGGACU G CUGGCACA | 7741 | UGUGCCAG GCCGAAAGGCGAGUGAGGUCU AGUCCAGC | 18520 |
| 3660 | GACUGCUG G CACAGAGA | 7742 | UCUCUGUG GCCGAAAGGCGAGUGAGGUCU CAGCAGUC | 18521 |
| 3681 | AAAGAAAG G CCAAGAUU | 7744 | AAUCUUGG GCCGAAAGGCGAGUGAGGUCU CUUUCUUU | 18522 |
| 3691 | CAAGAUUU G CAGAACUU | 7746 | AAGUUCUG GCCGAAAGGCGAGUGAGGUCU AAAUCUUG | 18523 |
| 3700 | CAGAACUU G UGGAAAAA | 7748 | UUUUUCCA GCCGAAAGGCGAGUGAGGUCU AAGUUCUG | 18524 |
| 3713 | AAAACUAG G UGAUUUGC | 7750 | GCAAAUCA GCCGAAAGGCGAGUGAGGUCU CUAGUUUU | 18525 |
| 3720 | GGUGAUUU G CUUCAAGC | 7752 | GCUUGAAG GCCGAAAGGCGAGUGAGGUCU AAAUCACC | 18526 |
| 3727 | UGCUUCAA G CAAAUGUA | 7753 | UACAUUUG GCCGAAAGGCGAGUGAGGUCU UUGAAGCA | 18527 |
| 3733 | AAGCAAAU G UACAACAG | 7755 | CUGUUGUA GCCGAAAGGCGAGUGAGGUCU AUUUGCUU | 18528 |
| 3746 | ACAGGAUG G UAAAGACU | 7758 | AGUCUUUA GCCGAAAGGCGAGUGAGGUCU CAUCCUGU | 18529 |
| 3769 | CAAUCAAU G CCAUACUG | 7762 | CAGUAUGG GCCGAAAGGCGAGUGAGGUCU AUUGAUUG | 18530 |
| 3788 | AGGAAAUA G UGGGUUUA | 7765 | UAAACCCA GCCGAAAGGCGAGUGAGGUCU UAUUUCCU | 18531 |
| 3792 | AAUAGUGG G UUUACAUA | 7766 | UAUGUAAA GCCGAAAGGCGAGUGAGGUCU CCACUAUU | 18532 |
| 3811 | CAACUCCU G CCUUCUCU | 7768 | AGAGAAGG GCCGAAAGGCGAGUGAGGUCU AGGAGUUG | 18533 |
| 3839 | CAAGGAAA G UAUUUCAG | 7770 | CUGAAAUA GCCGAAAGGCGAGUGAGGUCU UUUCCUUG | 18534 |
| 3847 | GUAUUUCA G CUCCGAAG | 7771 | CUUCGGAG GCCGAAAGGCGAGUGAGGUCU UGAAAUAC | 18535 |
| 3855 | GCUCCGAA G UUUAAUUC | 7772 | GAAUUAAA GCCGAAAGGCGAGUGAGGUCU UUCGGAGC | 18536 |
| 3869 | UUCAGGAA G CUCUGAUG | 7774 | CAUCAGAG GCCGAAAGGCGAGUGAGGUCU UUCCUGAA | 18537 |
| 3880 | CUGAUGAU G UCAGAUAU | 7777 | AUAUCUGA GCCGAAAGGCGAGUGAGGUCU AUCAUCAG | 18538 |
| 3889 | UCAGAUAU G UAAAUGCU | 7779 | AGCAUUUA GCCGAAAGGCGAGUGAGGUCU AUAUCUGA | 18539 |
| 3895 | AUGUAAAU G CUUUCAAG | 7781 | CUUGAAAG GCCGAAAGGCGAGUGAGGUCU AUUUACAU | 18540 |
| 3903 | GCUUUCAA G UUCAUGAG | 7782 | CUCAUGAA GCCGAAAGGCGAGUGAGGUCU UUGAAAGC | 18541 |
| 3911 | GUUCAUGA G CCUGGAAA | 7783 | UUUCCAGG GCCGAAAGGCGAGUGAGGUCU UCAUGAAC | 18542 |
| 3952 | UACCGAAU G CCACCUCC | 7788 | GGAGGUGG GCCGAAAGGCGAGUGAGGUCU AUUCGGUA | 18543 |
| 3963 | ACCUCCAU G UUUGAUGA | 7789 | UCAUCAAA GCCGAAAGGCGAGUGAGGUCU AUGGAGGU | 18544 |
| 3980 | CUACCAGG G CGACAGCA | 7792 | UGCUGUCG GCCGAAAGGCGAGUGAGGUCU CCUGGUAG | 18545 |
| 3986 | GGGCGACA G CAGCACUC | 7794 | GAGUGCUG GCCGAAAGGCGAGUGAGGUCU UGUCGCCC | 18546 |
| 3989 | CGACAGCA G CACUCUGU | 7795 | ACAGAGUG GCCGAAAGGCGAGUGAGGUCU UGCUGUCG | 18547 |
| 3996 | AGCACUCU G UUGGCCUC | 7796 | GAGGCCAA GCCGAAAGGCGAGUGAGGUCU AGAGUGCU | 18548 |
| 4000 | CUCUGUUG G CCUCUCCC | 7797 | GGGAGAGG GCCGAAAGGCGAGUGAGGUCU CAACAGAG | 18549 |
| 4011 | UCUCCCAU G CUGAAGCG | 7798 | CGCUUCAG GCCGAAAGGCGAGUGAGGUCU AUGGGAGA | 18550 |

TABLE XIX-continued

Human FLT Zinzyme and Substrate Sequence

| Pos | Substrate | Seq ID No | Zinzyme | Seq ID No |
|---|---|---|---|---|
| 4017 | AUGCUGAA G CGCUUCAC | 7799 | GUGAAGCG GCCGAAAGGCGAGUGAGGUCU UUCAGCAU | 18551 |
| 4019 | GCUGAAGC G CUUCACCU | 7800 | AGGUGAAG GCCGAAAGGCGAGUGAGGUCU GCUUCAGC | 18552 |
| 4037 | GACUGACA G CAAACCCA | 7803 | UGGGUUUG GCCGAAAGGCGAGUGAGGUCU UGUCAGUC | 18553 |
| 4048 | AACCCAAG G CCUCGCUC | 7805 | GAGCGAGG GCCGAAAGGCGAGUGAGGUCU CUUGGGUU | 18554 |
| 4053 | AAGGCCUC G CUCAAGAU | 7806 | AUCUUGAG GCCGAAAGGCGAGUGAGGUCU GAGGCCUU | 18555 |
| 4072 | ACUUGAGA G UAACCAGU | 7809 | ACUGGUUA GCCGAAAGGCGAGUGAGGUCU UCUCAAGU | 18556 |
| 4079 | AGUAACCA G UAAAAGUA | 7811 | UACUUUUA GCCGAAAGGCGAGUGAGGUCU UGGUUACU | 18557 |
| 4085 | CAGUAAAA G UAAGGAGU | 7812 | ACUCCUUA GCCGAAAGGCGAGUGAGGUCU UUUUACUG | 18558 |
| 4092 | AGUAAGGA G UCGGGCU | 7813 | AGCCCCGA GCCGAAAGGCGAGUGAGGUCU UCCUUACU | 18559 |
| 4098 | GAGUCGGG G CUGUCUGA | 7814 | UCAGACAG GCCGAAAGGCGAGUGAGGUCU CCCGACUC | 18560 |
| 4101 | UCGGGGCU G UCUGAUGU | 7815 | ACAUCAGA GCCGAAAGGCGAGUGAGGUCU AGCCCCGA | 18561 |
| 4108 | UGUCUGAU G UCAGCAGG | 7817 | CCUGCUGA GCCGAAAGGCGAGUGAGGUCU AUCAGACA | 18562 |
| 4112 | UGAUGUCA G CAGGCCCA | 7818 | UGGGCCUG GCCGAAAGGCGAGUGAGGUCU UGACAUCA | 18563 |
| 4116 | GUCAGCAG G CCCAGUUU | 7819 | AAACUGGG GCCGAAAGGCGAGUGAGGUCU CUGCUGAC | 18564 |
| 4121 | CAGGCCCA G UUUCUGCC | 7820 | GGCAGAAA GCCGAAAGGCGAGUGAGGUCU UGGGCCUG | 18565 |
| 4127 | CAGUUUCU G CCAUUCCA | 7821 | UGGAAUGG GCCGAAAGGCGAGUGAGGUCU AGAAACUG | 18566 |
| 4136 | CCAUUCCA G CUGUGGGC | 7822 | GCCCACAG GCCGAAAGGCGAGUGAGGUCU UGGAAUGG | 18567 |
| 4139 | UUCCAGCU G UGGGCACG | 7823 | CGUGCCCA GCCGAAAGGCGAGUGAGGUCU AGCUGGAA | 18568 |
| 4143 | AGCUGUGG G CACGUCAG | 7824 | CUGACGUG GCCGAAAGGCGAGUGAGGUCU CCACAGCU | 18569 |
| 4147 | GUGGGCAC G UCAGCGAA | 7825 | UUCGCUGA GCCGAAAGGCGAGUGAGGUCU GUGCCCAC | 18570 |
| 4151 | GCACGUCA G CGAAGGCA | 7826 | UGCCUUCG GCCGAAAGGCGAGUGAGGUCU UGACGUGC | 18571 |
| 4157 | CAGCGAAG G CAAGCGCA | 7827 | UGCGCUUG GCCGAAAGGCGAGUGAGGUCU CUUCGCUG | 18572 |
| 4161 | GAAGGCAA G CGCAGGUU | 7828 | AACCUGCG GCCGAAAGGCGAGUGAGGUCU UUGCCUUC | 18573 |
| 4163 | AGGCAAGC G CAGGUUCA | 7829 | UGAACCUG GCCGAAAGGCGAGUGAGGUCU GCUUGCCU | 18574 |
| 4167 | AAGCGCAG G UUCACCUA | 7830 | UAGGUGAA GCCGAAAGGCGAGUGAGGUCU CUGCGCUU | 18575 |
| 4183 | ACGACCAC G CUGAGCUG | 7832 | CAGCUCAG GCCGAAAGGCGAGUGAGGUCU GUGGUCGU | 18576 |
| 4188 | CACGCUGA G CUGGAAAG | 7833 | CUUUCCAG GCCGAAAGGCGAGUGAGGUCU UCAGCGUG | 18577 |
| 4204 | GGAAAAUC G CGUGCUGC | 7835 | GCAGCACG GCCGAAAGGCGAGUGAGGUCU GAUUUUCC | 18578 |
| 4206 | AAAAUCGC G UGCUGCUC | 7836 | GAGCAGCA GCCGAAAGGCGAGUGAGGUCU GCGAUUUU | 18579 |
| 4208 | AAUCGCGU G CUGCUCCC | 7837 | GGGAGCAG GCCGAAAGGCGAGUGAGGUCU ACGCGAUU | 18580 |
| 4211 | CGCGUGCU G CUCCCCGC | 7838 | GCGGGGAG GCCGAAAGGCGAGUGAGGUCU AGCACGCG | 18581 |
| 4218 | UGCUCCCC G CCCCCAGA | 7839 | UCUGGGGG GCCGAAAGGCGAGUGAGGUCU GGGGAGCA | 18582 |
| 4237 | ACAACUCG G UGGUCCUG | 7842 | CAGGACCA GCCGAAAGGCGAGUGAGGUCU CGAGUUGU | 18583 |
| 4240 | ACUCGGUG G UCCUGUAC | 7843 | GUACAGGA GCCGAAAGGCGAGUGAGGUCU CACCGAGU | 18584 |
| 4245 | GUGGUCCU G UACCCAC | 7844 | GUGGAGUA GCCGAAAGGCGAGUGAGGUCU AGGACCAC | 18585 |
| 4268 | CAUCUAGA G UUUGACAC | 7845 | GUGUCAAA GCCGAAAGGCGAGUGAGGUCU UCUAGAUG | 18586 |
| 4280 | GACACGAA C CCUUAUUU | 7847 | AAAUAAGG GCCGAAAGGCGAGUGAGGUCU UUCGUGUC | 18587 |

TABLE XIX-continued

Human FLT Zinzyme and Substrate Sequence

| Pos | Substrate | Seq ID No | Zinzyme | Seq ID No |
|---|---|---|---|---|
| 4295 | UUCUAGAA G CACAUGUG | 7848 | CACAUGUG GCCGAAAGGCGAGUGAGGUCU UUCUAGAA | 18588 |
| 4301 | AAGCACAU G UGUAUUUA | 7849 | UAAAUACA GCCGAAAGGCGAGUGAGGUCU AUGUGCUU | 18589 |
| 4303 | GCACAUGU G UAUUUAUA | 7850 | UAUAAAUA GCCGAAAGGCGAGUGAGGUCU ACAUGUGC | 18590 |
| 4326 | GGAAACUA G CUUUUGCC | 7852 | GGCAAAAG GCCGAAAGGCGAGUGAGGUCU UAGUUUCC | 18591 |
| 4332 | UAGCUUUU G CCAGUAUU | 7853 | AAUACUGG GCCGAAAGGCGAGUGAGGUCU AAAAGCUA | 18592 |
| 4336 | UUUUGCCA G UAUUAUGC | 7854 | GCAUAAUA GCCGAAAGGCGAGUGAGGUCU UGGCAAAA | 18593 |
| 4343 | AGUAUUAU G CAUAUAUA | 7855 | UAUAUAUG GCCGAAAGGCGAGUGAGGUCU AUAAUACU | 18594 |
| 4353 | AUAUAUAA G UUUACACC | 7856 | GGUGUAAA GCCGAAAGGCGAGUGAGGUCU UUAUAUAU | 18595 |
| 4379 | CCAUGGGA G CCAGCUGC | 7857 | GCAGCUGG GCCGAAAGGCGAGUGAGGUCU UCCCAUGG | 18596 |
| 4383 | GGGAGCCA G CUGCUUUU | 7858 | AAAAGCAG GCCGAAAGGCGAGUGAGGUCU UGGCUCCC | 18597 |
| 4386 | AGCCAGCU G CUUUUUGU | 7859 | ACAAAAAG GCCGAAAGGCGAGUGAGGUCU AGCUGGCU | 18598 |
| 4393 | UGCUUUUU G UGAUUUUU | 7860 | AAAAAUCA GCCGAAAGGCGAGUGAGGUCU AAAAAGCA | 18599 |
| 4408 | UUUUAAUA G UGCUUUUU | 7863 | AAAAAGCA GCCGAAAGGCGAGUGAGGUCU UAUUAAAA | 18600 |
| 4410 | UUAAUAGU G CUUUUUUU | 7864 | AAAAAAAG GCCGAAAGGCGAGUGAGGUCU ACUAUUAA | 18601 |
| 4336 | ACAAGAAU G UAACUCCA | 7868 | UGGAGUUA GCCGAAAGGCGAGUGAGGUCU AUUCUUGU | 18602 |
| 4457 | GAGAAAUA G UGACAAGU | 7872 | ACUUGUCA GCCGAAAGGCGAGUGAGGUCU UAUUUCUC | 18603 |
| 4464 | AGUGACAA G UGAAGAAC | 7874 | GUUCUUCA GCCGAAAGGCGAGUGAGGUCU UUGUCACU | 18604 |
| 4479 | ACACUACU G CUAAAUCC | 7876 | GGAUUUAG GCCGAAAGGCGAGUGAGGUCU AGUAGUGU | 18605 |
| 4492 | AUCCUCAU G UUACUCAG | 7878 | CUGAGUAA GCCGAAAGGCGAGUGAGGUCU AUGAGGAU | 18606 |
| 4500 | GUUACUCA G UGUUAGAG | 7879 | CUCUAACA GCCGAAAGGCGAGUGAGGUCU UGAGUAAC | 18607 |
| 4502 | UACUCAGU G UUAGAGAA | 7880 | UUCUCUAA GCCGAAAGGCGACUGAGUCU ACUGAGUA | 18608 |
| 4538 | ACUUCCCU G CUCCAACC | 7885 | GGUUGGAG GCCGAAAGGCGAGUGAGGUCU AGGGAAGU | 18609 |
| 4550 | CAACCCCC G CCACCUCA | 7887 | UGAGGUGG GCCGAAAGGCGAGUGAGGUCU GGGGGUUG | 18610 |
| 4561 | ACCUCAGG G CACGCAGG | 7888 | CCUGCGUG GCCGAAAGGCGAGUGAGGUCU CCUGAGGU | 18611 |
| 4565 | CAGGGCAC G CAGGACCA | 7889 | UGGUCCUG GCCGAAAGGCGAGUGAGGUCU GUGCCCUG | 18612 |
| 4574 | CAGGACCA G UUUGAUUG | 7891 | CAAUCAAA GCCGAAAGGCGAGUGAGGUCU UGGUCCUG | 18613 |
| 4587 | AUUGAGGA G CUGCACUG | 7893 | CAGUGCAG GCCGAAAGGCGAGUGAGGUCU UCCUCAAU | 18614 |
| 4590 | GAGGAGCU G CACUGAUC | 7894 | GAUCAGUG GCCGAAAGGCGAGUGAGGUCU AGCUCCUC | 18615 |
| 4606 | CACCCAAU G CAUCACGU | 7897 | ACGUGAUG GCCGAAAGGCGAGUGAGGUCU AUUGGGUG | 18616 |
| 4613 | UGCAUCAC G UACCCCAC | 7898 | GUGGGGUA GCCGAAAGGCGAGUGAGGUCU GUGAUGCA | 18617 |
| 4625 | CCCACUGG G CCAGCCCU | 7899 | AGGGCUGG GCCGAAAGGCGAGUGAGGUCU CCAGUGGG | 18618 |
| 4629 | CUGGGCCA G CCCUGCAG | 7900 | CUGCAGGG GCCGAAAGGCGAGUGAGGUCU UGGCCCAG | 18619 |
| 4634 | CCAGCCCU G CAGCCCAA | 7901 | UUGGGCUG GCCGAAAGGCGAGUGAGGUCU AGGGCUGG | 18620 |
| 4637 | GCCCUGCA G CCCAAAAC | 7902 | GUUUUGGG GCCGAAAGGCGAGUGAGGUCU UGCAGGGC | 18621 |
| 4651 | AACCCAGG G CAACAAGC | 7904 | GCUUGUUG GCCGAAAGGCGAGUGAGGUCU CCUGGGUU | 18622 |
| 4658 | GGCAACAA G CCCGUUAG | 7906 | CUAACGGG GCCGAAAGGCGAGUGAGGUCU UUGUUGCC | 18623 |
| 4662 | ACAAGCCC G UUAGCCCC | 7907 | GGGGCUAA GCCGAAAGGCGAGUGAGGUCU GGGCUUGU | 18624 |

TABLE XIX-continued

Human FLT Zinzyme and Substrate Sequence

| Pos | Substrate | Seq ID No | Zinzyme | Seq ID No |
|---|---|---|---|---|
| 4666 | GCCCGUUA G CCCCAGGG | 7908 | CCCUGGGG GCCGAAAGGCGAGUGAGGUCU UAACGGGC | 18625 |
| 4683 | GAUCACUG G CUGGCCUG | 7910 | CAGGCCAC GCCGAAAGGCGAGUGAGGUCU CAGUGAUC | 18626 |
| 4687 | ACUGGCUG G CCUGAGCA | 7911 | UGCUCAGG GCCGAAAGGCGAGUGAGGUCU CAGCCAGU | 18627 |
| 4693 | UGGCCUGA G CAACAUCU | 7912 | AGAUGUUG GCCGAAAGGCGAGUGAGGUCU UCAGGCCA | 18628 |
| 4707 | UCUCGGGA G UCCUCUAC | 7914 | CUAGAGGA GCCGAAAGGCGAGUGAGGUCU UCCCGAGA | 18629 |
| 4715 | GUCCUCUA G CAGGCCUA | 7915 | UAGGCCUG GCCGAAAGGCGAGUGAGGUCU UAGAGGAC | 18630 |
| 4719 | UCUAGCAG G CCUAAGAC | 7916 | GUCUUAGG GCCGAAAGGCGAGUGAGGUCU CUGCUAGA | 18631 |
| 4730 | UAAGACAU G UGAGGAGG | 7918 | CCUCCUCA GCCGAAAGGCGAGUGAGGUCU AUGUCUUA | 18632 |
| 4752 | GAAAAAAA G CAAAAAGC | 7919 | GCUUUUUG GCCGAAAGGCGAGUGAGGUCU UUUUUUUC | 18633 |
| 4759 | AGCAAAAA G CAAGGGAG | 7920 | CUCCCUUG GCCGAAAGGCGAGUGAGGUCU UUUUUGCU | 18634 |
| 4788 | GGGAGAAG G CAUGAGAA | 7922 | UUCUCAUG GCCGAAAGGCGAGUGAGGUCU CUUCUCCC | 18635 |
| 4809 | UUUGAGAC G CACCAUGU | 7925 | ACAUGGUG GCCGAAAGGCGAGUGAGGUCU GUCUCAAA | 18636 |
| 4816 | CGCACCAU G UGGGCACG | 7926 | CGUGCCCA GCCGAAAGGCGAGUGAGGUCU AUGGUGCG | 18637 |
| 4820 | CCAUGUGG G CACGGAGG | 7927 | CCUCCGUG GCCGAAAGGCGAGUGAGGUCU CCACAUGG | 18638 |
| 4837 | GGGACGGG G CUCAGCAA | 7929 | UUGCUGAG GCCGAAAGGCGAGUGAGGUCU CCCGUCCC | 18639 |
| 4842 | GGGGCUCA G CAAUGCCA | 7930 | UGGCAUUG GCCGAAAGGCGAGUGAGGUCU UGAGCCCC | 18640 |
| 4847 | UCAGCAAU G CCAUUUCA | 7932 | UGAAAUGG GCCGAAAGGCGAGUGAGGUCU AUUGCUGA | 18641 |
| 4856 | CCAUUUCA G UGGCUUCC | 7933 | GGAAGCCA GCCGAAAGGCGAGUGAGGUCU UGAAAUGG | 18642 |
| 4859 | UUUCAGUG G CUUCCCAG | 7934 | CUGGGAAG GCCGAAAGGCGAGUGAGGUCU CACUGAAA | 18643 |
| 4867 | GCUUCCCA G CUCUGACC | 7935 | GGUCAGAG GCCGAAAGGCGAGUGAGGUCU UGGGAAGC | 18644 |
| 4891 | AUUUGAGG G CCCAGCCA | 7937 | UGGCUGGG GCCGAAAGGCGAGUGAGGUCU CCUCAAAU | 18645 |
| 4896 | AGGGCCCA G CCAGGAGC | 7938 | GCUCCUGG GCCGAAAGGCGAGUGAGGUCU UGGGCCCU | 18646 |
| 4903 | AGCCAGGA G CAGAUGGA | 7939 | UCCAUCUG GCCGAAAGGCGAGUGAGGUCU UCCUGGCU | 18647 |
| 4914 | GAUGGACA G CGAUGAGG | 7942 | CCUCAUCG GCCGAAAGGCGAGUGAGGUCU UGUCCAUC | 18648 |
| 4946 | UCUGGGAG G CAAGAAAA | 7946 | UUUUCUUG GCCGAAAGGCGAGUGAGGUCU CUCCCAGA | 18649 |
| 4981 | GAACUAAA G CAAAUUUU | 7950 | AAAAUUUG GCCGAAAGGCGAGUGAGGUCU UUUAGUUC | 18650 |
| 5008 | CUAUGGAA G UGGUUCUA | 7953 | UAGAACCA GCCGAAAGGCGAGUGAGGUCU UUCCAUAG | 18651 |
| 5011 | UGGAAGUG G UUCUAUGU | 7954 | ACAUAGAA GCCGAAAGGCGAGUGAGGUCU CACUUCCA | 18652 |
| 5018 | GGUUCUAU G UCCAUUCU | 7955 | AGAAUGGA GCCGAAAGGCGAGUGAGGUCU AUAGAACC | 18653 |
| 5032 | UCUCAUUC G UGGCAUGU | 7956 | ACAUGCCA GCCGAAAGGCGAGUGAGGUCU GAAUGAGA | 18654 |
| 5035 | CAUUCGUG G CAUGUUUU | 7957 | AAAACAUG GCCGAAAGGCGAGUGAGGUCU CACGAAUG | 18655 |
| 5039 | CGUGGCAU G UUUUGAUU | 7958 | AAUCAAAA GCCGAAAGGCGAGUGAGGUCU AUGCCACG | 18656 |
| 5049 | UUUGAUUU G UAGCACUG | 7960 | CAGUGCUA GCCGAAAGGCGAGUGAGGUCU AAAUCAAA | 18657 |
| 5052 | GAUUUGUA G CACUGAGG | 7961 | CCUCAGUG GCCGAAAGGCGAGUGAGGUCU UACAAAUC | 18658 |
| 5061 | CACUGAGG G UGGCACUC | 7962 | GAGUGCCA GCCGAAAGGCGAGUGAGGUCU CCUCAGUG | 18659 |
| 5064 | UGAGGGUG G CACUCAAC | 7963 | GUUGAGUG GCCGAAAGGCGAGUGAGGUCU CACCCUCA | 18660 |
| 5078 | AACUCUGA G CCCAUACU | 7965 | AGUAUGGG GCCGAAAGGCGAGUGAGGUCU UCAGAGUU | 18661 |

TABLE XIX-continued

Human FLT Zinzyme and Substrate Sequence

| Pos | Substrate | Seq ID No | Zinzyme | Seq ID No |
|---|---|---|---|---|
| 5091 | UACUUUUG G CUCCUCUA | 7966 | UAGAGGAG GCCGAAAGGCGAGUGAGGUCU CAAAAGUA | 18662 |
| 5100 | CUCCUCUA G UAAGAUGC | 7967 | GCAUCUUA GCCGAAAGGCGAGUGAGGUCU UAGAGGAG | 18663 |
| 5107 | AGUAAGAU G CACUGAAA | 7969 | UUUCAGUG GCCGAAAGGCGAGUGAGGUCU AUCUUACU | 18664 |
| 5121 | AAAACUUA G CCAGAGUU | 7971 | AACUCUGG GCCGAAAGGCGAGUGAGGUCU UAAGUUUU | 18665 |
| 5127 | UAGCCAGA G UUAGGUUG | 7972 | CAACCUAA GCCGAAAGGCGAGUGAGGUCU UCUGGCUA | 18666 |
| 5132 | AGAGUUAG G UUGUCUCC | 7973 | GGAGACAA GCCGAAAGGCGAGUGAGGUCU CUAACUCU | 18667 |
| 5135 | GUUAGGUU G UCUCCAGG | 7974 | CCUGGAGA GCCGAAAGGCGAGUGAGGUCU AACCUAAC | 18668 |
| 5143 | GUCUCCAG G CCAUGAUG | 7975 | CAUCAUGG GCCGAAAGGCGAGUGAGGUCU CUGGAGAC | 18669 |
| 5152 | CCAUGAUG G CCUUACAC | 7977 | GUGUAAGG GCCGAAAGGCGAGUGAGGUCU CAUCAUGG | 18670 |
| 5168 | CUGAAAAU G UCACAUUC | 7979 | GAAUGUGA GCCGAAAGGCGAGUGAGGUCU AUUUUCAG | 18671 |
| 5185 | UAUUUUGG G UAUUAAUA | 7980 | UAUUAAUA GCCGAAAGGCGAGUGAGGUCU CCAAAAUA | 18672 |
| 5198 | AAUAUAUA G UCCAGACA | 7982 | UGUCUGGA GCCGAAAGGCGAGUGAGGUCU UAUAUAUU | 18673 |
| 5224 | AUUUCUUG G UAUUAUUC | 7986 | GAAUAAUA GCCGAAAGGCGAGUGAGGUCU CAAGAAAU | 18674 |
| 5234 | AUUAUUCU G UUUUGCAC | 7987 | GUGCAAAA GCCGAAAGGCGAGUGAGGUCU AGAAUAAU | 18675 |
| 5239 | UCUGUUUU G CACAGUUA | 7988 | UAACUGUG GCCGAAAGGCGAGUGAGGUCU AAAACAGA | 18676 |
| 5244 | UUUGCACA G UUAGUUGU | 7989 | ACAACUAA GCCGAAAGGCGAGUGAGGUCU UGUGCAAA | 18677 |
| 5248 | CACAGUUA G UUGUGAAA | 7990 | UUUCACAA GCCGAAAGGCGAGUGAGGUCU UAACUGUG | 18678 |
| 5251 | AGUUAGUU G UGAAAGAA | 7991 | UUCUUUCA GCCGAAAGGCGAGUGAGGUCU AACUAACU | 18679 |
| 5261 | GAAAGAAA G CUGAGAAG | 7992 | CUUCUCAG GCCGAAAGGCGAGUGAGGUCU UUUCUUUC | 18680 |
| 5279 | AUGAAAAU G CAGUCCUG | 7995 | CAGGACUG GCCGAAAGGCGAGUGAGGUCU AUUUUCAU | 18681 |
| 5282 | AAAAUGCA G UCCUGAGG | 7996 | CCUCAGGA GCCGAAAGGCGAGUGAGGUCU UGCAUUUU | 18682 |
| 5294 | UGAGGAGA G UUUUCUCC | 7997 | GGAGAAAA GCCGAAAGGCGAGUGAGGUCU UCUCCUCA | 18683 |
| 5317 | AAACGAGG G CUGAUGGA | 7999 | UCCAUCAG GCCGAAAGGCGAGUGAGGUCU CCUCGUUU | 18684 |
| 5334 | GGAAAAAG G UCAAUAAG | 8001 | CUUAUUGA GCCGAAAGGCGAGUGAGGUCU CUUUUUCC | 18685 |
| 5343 | UCAAUAAG G UCAAGGGA | 8003 | UCCCUUGA GCCGAAAGGCGAGUGAGGUCU CUUAUUGA | 18686 |
| 5359 | AAGACCCC G UCUCUAUA | 8005 | UAUAGAGA GCCGAAAGGCGAGUGAGGUCU GGGGUCUU | 18687 |
| 5393 | CCAACACA G UUGGGACC | 8010 | GGUCCCAA GCCGAAAGGCGAGUGAGGUCU UGUGUUGG | 18688 |
| 5415 | CACAGGAA G UCAGUCAC | 8013 | GUGACUGA GCCGAAAGGCGAGUGAGGUCU UUCCUGUG | 18689 |
| 5419 | GGAAGUCA G UCACGUUU | 8014 | AAACGUGA GCCGAAAGGCGAGUGAGGUCU UGACUUCC | 18690 |
| 5424 | UCAGUCAC G UUUCCUUU | 8015 | AAAGGAAA GCCGAAAGGCGAGUGAGGUCU GUGACUGA | 18691 |
| 5477 | GAAAGGAU G UGGAAGAG | 8020 | CUCUUCCA GCCGAAAGGCGAGUGAGGUCU AUCCUUUC | 18692 |
| 5485 | GUGGAAGA G CAUUAGCU | 8021 | AGCUAAUG GCCGAAAGGCGAGUGAGGUCU UCUUCCAC | 18693 |
| 5491 | GAGCAUUA G CUGGCGCA | 8022 | UGCGCCAG GCCGAAAGGCGAGUGAGGUCU UAAUGCUC | 18694 |
| 5495 | AUUAGCUG G CGCAUAUU | 8023 | AAUAUGCG GCCGAAAGGCGAGUGAGGUCU CAGCUAAU | 18695 |
| 5497 | UAGCUGGC G CAUAUUAA | 8024 | UUAAUAUG GCCGAAAGGCGAGUGAGGUCU GCCAGCUA | 18696 |
| 5506 | CAUAUUAA G CACUUUAA | 8025 | UUAAAGUG GCCGAAAGGCGAGUGAGGUCU UUAAUAUG | 18697 |
| 5515 | CACUUUAA G CUCCUUGA | 8026 | UCAAGGAG GCCGAAAGGCGAGUGAGGUCU UUAAAGUG | 18698 |

TABLE XIX-continued

Human FLT Zinzyme and Substrate Sequence

| Pos | Substrate | Seq ID No | Zinzyme | Seq ID No |
|---|---|---|---|---|
| 5524 | CUCCUUGA G UAAAAAGG | 8027 | CCUUUUUA GCCGAAAGGCGAGUGAGGUCU UCAAGGAG | 18699 |
| 5532 | GUAAAAAG G UGGUAUGU | 8028 | ACAUACCA GCCGAAAGGCGAGUGAGGUCU CUUUUUAC | 18700 |
| 5535 | AAAAGGUG G UAUGUAAU | 8029 | AUUACAUA GCCGAAAGGCGAGUGAGGUCU CACCUUUU | 18701 |
| 5539 | GGUGGUAU G UAAUUUAU | 8030 | AUAAAUUA GCCGAAAGGCGAGUGAGGUCU AUACCACC | 18702 |
| 5548 | UAAUUUAU G CAAGGUAU | 8032 | AUACCUUG GCCGAAAGGCGAGUGAGGUCU AUAAAUUA | 18703 |
| 5553 | UAUGCAAG G UAUUUCUC | 8033 | GAGAAAUA GCCGAAAGGCGAGUGAGGUCU CUUGCAUA | 18704 |
| 5564 | UUUCUCCA G UUGGGACU | 8034 | AGUCCCAA GCCGAAAGGCGAGUGAGGUCU UGGAGAAA | 18705 |
| 5583 | GGAUAUUA G UUAAUGAG | 8037 | CUCAUUAA GCCGAAAGGCGAGUGAGGUCU UAAUAUCC | 18706 |
| 5591 | GUUAAUGA G CCAUCACU | 8039 | AGUGAUGG GCCGAAAGGCGAGUGAGGUCU UCAUUAAC | 18707 |
| 5609 | GAAGAAAA G CCCAUUUU | 8040 | AAAAUGGG GCCGAAAGGCGAGUGAGGUCU UUUUCUUC | 18708 |
| 5623 | UUUCAACU G CUUUGAAA | 8042 | UUUCAAAG GCCGAAAGGCGAGUGAGGUCU AGUUGAAA | 18709 |
| 5635 | UGAAACUU G CCUGGGGU | 8044 | ACCCCAGG GCCGAAAGGCGAGUGAGGUCU AAGUUUCA | 18710 |
| 5642 | UGCCUGGG G UCUGAGCA | 8045 | UGCUCAGA GCCGAAAGGCGAGUGAGGUCU CCCAGGCA | 18711 |
| 5648 | GGGUCUGA G CAUGAUGG | 8046 | CCAUCAUG GCCGAAAGGCGAGUGAGGUCU UCAGACCC | 18712 |
| 5672 | GAGACAGG G UAGGAAAG | 8050 | CUUUCCUA GCCGAAAGGCGAGUGAGGUCU CCUGUCUC | 18713 |
| 5682 | AGGAAAGG G CGCCUACU | 8051 | AGUAGGCG GCCGAAAGGCGAGUGAGGUCU CCUUUCCU | 18714 |
| 5684 | GAAAGGGC G CCUACUCU | 8052 | AGAGUAGG GCCGAAAGGCGAGUGAGGUCU GCCCUUUC | 18715 |
| 5698 | UCUUCAGG G UCUAAAGA | 8053 | UCUUUAGA GCCGAAAGGCGAGUGAGGUCU CCUGAAGA | 18716 |
| 5711 | AAGAUCAA G UGGGCCUU | 8055 | AAGGCCCA GCCGAAAGGCGAGUGAGGUCU UUGAUCUU | 18717 |
| 5715 | UCAAGUGG G CCUUGGAU | 8056 | AUCCAAGG GCCGAAAGGCGAGUGAGGUCU CCACUUGA | 18718 |
| 5725 | CUUGGAUC G CUAAGCUG | 8058 | CAGCUUAG GCCGAAAGGCGAGUGAGGUCU GAUCCAAG | 18719 |
| 5730 | AUCGCUAA G CUGGCUCU | 8059 | AGAGCCAG GCCGAAAGGCGAGUGAGGUCU UUAGCGAU | 18720 |
| 5734 | CUAAGCUG G CUCUGUUU | 8060 | AAACAGAG GCCGAAAGGCGAGUGAGGUCU CAGCUUAG | 18721 |
| 5739 | CUGGCUCU G UUUGAUGC | 8061 | GCAUCAAA GCCGAAAGGCGAGUGAGGUCU AGAGCCAG | 18722 |
| 5746 | UGUUUGAU G CUAUUUAU | 8063 | AUAAAUAG GCCGAAAGGCGAGUGAGGUCU AUCAAACA | 18723 |
| 5755 | CUAUUUAU G CAAGUUAG | 8064 | CUAACUUG GCCGAAAGGCGAGUGAGGUCU AUAAAUAG | 18724 |
| 5759 | UUAUGCAA G UUAGGGUC | 8065 | GACCCUAA GCCGAAAGGCGAGUGAGGUCU UUGCAUAA | 18725 |
| 5765 | AAGUUAGG G UCUAUGUA | 8066 | UACAUAGA GCCGAAAGGCGAGUGAGGUCU CCUAACUU | 18726 |
| 5771 | GGGUCUAU G UAUUUAGG | 8067 | CCUAAAUA GCCGAAAGGCGAGUGAGGUCU AUAGACCC | 18727 |
| 5782 | UUUAGGAU G CGCCUACU | 8069 | AGUAGGCG GCCGAAAGGCGAGUGAGGUCU AUCCUAAA | 18728 |
| 5784 | UAGGAUGC G CCUACUCU | 8070 | AGAGUAGG GCCGAAAGGCGAGUGAGGUCU GCAUCCUA | 18729 |
| 5798 | UCUUCAGG G UCUAAAGA | 8053 | UCUUUAGA GCCGAAAGGCGAGUGAGGUCU CCUGAAGA | 18716 |
| 5811 | AAGAUCAA G UGGGCCUU | 8055 | AAGGCCCA GCCGAAAGGCGAGUGAGGUCU UUGAUCUU | 18717 |
| 5815 | UCAAGUGG G CCUUGGAU | 8056 | AUCCAAGG GCCGAAAGGCGAGUGAGGUCU CCACUUGA | 18718 |
| 5825 | CUUGGAUC G CUAAGCUG | 8058 | CAGCUUAG GCCGAAAGGCGAGUGAGGUCU GAUCCAAG | 18719 |
| 5830 | AUCGCUAA G CUGGCUCU | 8059 | AGAGCCAG GCCGAAAGGCGAGUGAGGUCU UUAGCGAU | 18720 |
| 5834 | CUAAGCUG G CUCUGUUU | 8060 | AAACAGAG GCCGAAAGGCGAGUGAGGUCU CAGCUUAG | 18721 |

TABLE XIX-continued

Human FLT Zinzyme and Substrate Sequence

| Pos | Substrate | Seq ID No | Zinzyme | Seq ID No |
|---|---|---|---|---|
| 5839 | CUGGCUCU G UUUGAUGC | 8061 | GCAUCAAA GCCGAAAGGCGAGUGAGGUCU AGAGCCAG | 18722 |
| 5846 | UGUUUGAU G CUAUUUAU | 8063 | AUAAAUAG GCCGAAAGGCGAGUGAGGUCU AUCAAACA | 18723 |
| 5855 | CUAUUUAU G CAAGUUAG | 8064 | CUAACUUG GCCGAAAGGCGAGUGAGGUCU AUAAAUAG | 18724 |
| 5859 | UUAUGCAA G UUAGGGUC | 8065 | GACCCUAA GCCGAAAGGCGAGUGAGGUCU UUGCAUAA | 18725 |
| 5865 | AAGUUAGG G UCUAUGUA | 8066 | UACAUAGA GCCGAAAGGCGAGUGAGGUCU CCUAACUU | 18726 |
| 5871 | GGGUCUAU G UAUUUAGG | 8067 | CCUAAAUA GCCGAAAGGCGAGUGAGGUCU AUAGACCC | 18727 |
| 5882 | UUUAGGAU G UCUGCACC | 8072 | GGUGCAGA GCCGAAAGGCGAGUGAGGUCU AUCCUAAA | 18730 |
| 5886 | GGAUGUCU G CACCUUCU | 8073 | AGAAGGUG GCCGAAAGGCGACUGAGGUCU AGACAUCC | 18731 |
| 5895 | CACCUUCU G CAGCCAGU | 8074 | ACUGGCUG GCCGAAAGGCGAGUGAGGUCU AGAAGGUG | 18732 |
| 5898 | CUUCUGCA G CCAGUCAG | 8075 | CUGACUGG GCCGAAAGGCGAGUGAGGUCU UGCAGAAG | 18733 |
| 5902 | UGCAGCCA G UCAGAAGC | 8076 | GCUUCUGA GCCGAAAGGCGAGUGAGGUCU UGGCUGCA | 18734 |
| 5909 | AGUCAGAA G CUGGAGAG | 8077 | CUCUCCAG GCCGAAAGGCGAGUGAGGUCU UUCUGACU | 18735 |
| 5918 | CUGGAGAG G CAACAGUG | 8078 | CACUGUUG GCCGAAAGGCGAGUGAGGUCU CUCUCCAG | 18736 |
| 5924 | AGGCAACA G UGGAUUGC | 8080 | GCAAUCCA GCCGAAAGGCGAGUGAGGUCU UGUUGCCU | 18737 |
| 5931 | AGUGGAUU G CUGCUUCU | 8082 | AGAAGCAG GCCGAAAGGCGAGUGAGGUCU AAUCCACU | 18738 |
| 5934 | GGAUUGCU G CUUCUUGG | 8083 | CCAAGAAG GCCGAAAGGCGAGUGAGGUCU AGCAAUCC | 18739 |
| 5951 | GGAGAAGA G UAUGCUUC | 8084 | GAAGCAUA GCCGAAAGGCGAGUGAGGUCU UCUUCUCC | 18740 |
| 5955 | AAGAGUAU G CUUCCUUU | 8085 | AAAGGAAG GCCGAAAGGCGAGUGAGGUCU AUACUCUU | 18741 |
| 5971 | UUAUCCAU G UAAUUUAA | 8086 | UUAAAUUA GCCGAAAGGCGAGUGAGGUCU AUGGAUAA | 18742 |
| 5982 | AUUUAACU G UAGAACCU | 8089 | AGGUUCUA GCCGAAAGGCGAGUGAGGUCU AGUUAAAU | 18743 |
| 5993 | GAACCUGA G CUCUAAGU | 8091 | ACUUAGAG GCCGAAAGGCGAGUGAGGUCU UCAGGUUC | 18744 |
| 6000 | AGCUCUAA G UAACCGAA | 8092 | UUCGGUUA GCCGAAAGGCGAGUGAGGUCU UUAGAGCU | 18745 |
| 6013 | CGAAGAAU G UAUGCCUC | 8095 | GAGGCAUA GCCGAAAGGCGAGUGAGGUCU AUUCUUCG | 18746 |
| 6017 | GAAUGUAU G CCUCUGUU | 8096 | AACAGAGG GCCGAAAGGCGAGUGAGGUCU AUACAUUC | 18747 |
| 6023 | AUGCCUCU G UUCUUAUG | 8097 | CAUAAGAA GCCGAAAGGCGAGUGAGGUCU AGAGGCAU | 18748 |
| 6031 | GUUCUUAU G UGCACAU | 8098 | AUGUGGCA GCCGAAAGGCGAGUGAGGUCU AUAAGAAC | 18749 |
| 6033 | UCUUAUGU G CCACAUCC | 8099 | GGAUGUGG GCCGAAAGGCGAGUGAGGUCU ACAUAAGA | 18750 |
| 6044 | ACAUCCUU G UUUAAAGG | 8100 | CCUUUAAA GCCGAAAGGCGAGUGAGGUCU AAGGAUGU | 18751 |
| 6052 | GUUUAAAG G CUCUCUGU | 8101 | ACAGAGAG GCCGAAAGGCGAGUGAGGUCU CUUUAAAC | 18752 |
| 6059 | GGCUCUCU G UAUGAAGA | 8102 | UCUUCAUA GCCGAAAGGCGAGUGAGGUCU AGAGAGCC | 18753 |
| 6077 | AUGGGACC G UCAUCAGC | 8105 | GCUGAUGA GCCGAAAGGCGAGUGAGGUCU GGUCCCAU | 18754 |
| 6084 | CGUCAUCA G CACAUUCC | 8106 | GGAAUGUG GCCGAAAGGCGAGUGAGGUCU UGAUGACG | 18755 |
| 6096 | AUUCCCUA G UGAGCCUA | 8107 | UAGGCUCA GCCGAAAGGCGAGUGAGGUCU UAGGGAAU | 18756 |
| 6100 | CCUAGUGA G CCUACUGG | 8108 | CCAGUAGG GCCGAAAGGCGAGUGAGGUCU UCACUAGG | 18757 |
| 6108 | GCCUACUG G CUCCUGGC | 8109 | GCCAGGAG GCCGAAAGGCGAGUGAGGUCU CAGUAGGC | 18758 |
| 6115 | GGCUCCUG G CAGCGGCU | 8110 | AGCCGCUG GCCGAAAGGCGAGUGAGGUCU CAGGAGCC | 18759 |
| 6118 | UCCUGGCA G CGGCUUUU | 8111 | AAAAGCCG GCCGAAAGGCGAGUGAGGUCU UGCCAGGA | 18760 |

TABLE XIX-continued

Human FLT Zinzyme and Substrate Sequence

| Pos | Substrate | Seq ID No | Zinzyme | Seq ID No |
|---|---|---|---|---|
| 6121 | UGGCAGCG G CUUUUGUG | 8112 | CACAAAAG GCCGAAAGGCGAGUGAGGUCU CGCUGCCA | 18761 |
| 6127 | CGGCUUUU G UGGAAGAC | 8113 | GUCUUCCA GCCGAAAGGCGAGUGAGGUCU AAAAGCCG | 18762 |
| 6142 | ACUCACUA G CCAGAAGA | 8115 | UCUUCUGG GCCGAAAGGCGAGUGAGGUCU UAGUGAGU | 18763 |
| 6156 | AGAGAGGA G UGGGACAG | 8116 | CUGUCCCA GCCGAAAGGCGAGUGAGGUCU UCCUCUCU | 18764 |
| 6164 | GUGGGACA G UCCUCUCC | 8118 | GGAGAGGA GCCGAAAGGCGAGUGAGGUCU UGUCCCAC | 18765 |
| 6197 | AAACAAAA G CAGGCUAG | 8122 | CUAGCCUG GCCGAAAGGCGAGUGAGGUCU UUUUGUUU | 18766 |
| 6201 | AAAAGCAG G CUAGAGCC | 8123 | GGCUCUAG GCCGAAAGGCGAGUGAGGUCU CUGCUUUU | 18767 |
| 6207 | AGGCUAGA G CCAGAAGA | 8124 | UCUUCUGG GCCGAAAGGCGAGUGAGGUCU UCUAGCCU | 18768 |
| 6230 | AAAUCUUU G UUGUUCCU | 8127 | AGGAACAA GCCGAAAGGCGAGUGAGGUCU AAAGAUUU | 18769 |
| 6233 | UCUUUGUU G UUCCUCUU | 8128 | AAGAGGAA GCCGAAAGGCGAGUGAGGUCU AACAAAGA | 18770 |
| 6254 | ACACAUAC G CAAACCAC | 8129 | GUGGUUUG GCCGAAAGGCGAGUGAGGUCU GUAUGUGU | 18771 |
| 6265 | AACCACCU G UGACAGCU | 8131 | AGCUGUCA GCCGAAAGGCGAGUGAGGUCU AGGUGGUU | 18772 |
| 6271 | CUGUGACA G CUGGCAAU | 8133 | AUUGCCAG GCCGAAAGGCGAGUGAGGUCU UGUCACAG | 18773 |
| 6275 | GACAGCUG G CAAUUUUA | 8134 | UAAAAUUG GCCGAAAGGCGAGUGAGGUCU CAGCUGUC | 18774 |
| 6292 | UAAAUCAG G UAACUGGA | 8137 | UCCAGUUA GCCGAAAGGCGAGUGAGGUCU CUGAUUUA | 18775 |
| 6306 | GGAAGGAG G UUAAACUC | 8139 | GAGUUUAA GCCGAAAGGCGAGUGAGGUCU CUCCUUCC | 18776 |
| 6333 | AGACCUCA G UCAAUUCU | 8142 | AGAAUUGA GCCGAAAGGCGAGUGAGGUCU UGAGGUCU | 18777 |
| 6377 | AGAUAAUA G CCCAGCAA | 8147 | UUGCUGGG GCCGAAAGGCGAGUGAGGUCU UAUUAUCU | 18778 |
| 6382 | AUAGCCCA G CAAAUAGU | 8148 | ACUAUUUG GCCGAAAGGCGAGUGAGGUCU UGGGCUAU | 18779 |
| 6389 | AGCAAAUA G UGAUAACA | 8150 | UGUUAUCA GCCGAAAGGCGAGUGAGGUCU UAUUUGCU | 18780 |
| 6410 | AAACCUUA G CUGUUCAU | 8155 | AUGAACAG GCCGAAAGGCGAGUGAGGUCU UAAGGUUU | 18781 |
| 6413 | CCUUAGCU G UUCAUGUC | 8156 | GACAUGAA GCCGAAAGGCGAGUGAGGUCU AGCUAAGG | 18782 |
| 6419 | CUGUUCAU G UCUUGAUU | 8157 | AAUCAAGA GCCGAAAGGCGAGUGAGGUCU AUGAACAG | 18783 |
| 6487 | AGAGAAAA G CAAAACCA | 8166 | UGGUUUUG GCCGAAAGGCGAGUGAGGUCU UUUUCUCU | 18784 |
| 6504 | UUAGAAUU G UUACUCAG | 8169 | CUGAGUAA GCCGAAAGGCGAGUGAGGUCU AAUUCUAA | 18785 |
| 6512 | GUUACUCA G CUCCUUCA | 8170 | UGAAGGAG GCCGAAAGGCGAGUGAGGUCU UGAGUAAC | 18786 |
| 6528 | AAACUCAG G UUUGUAGC | 8172 | GCUACAAA GCCGAAAGGCGAGUGAGGUCU CUGAGUUU | 18787 |
| 6532 | UCAGGUUU G UAGCAUAC | 8173 | GUAUGCUA GCCGAAAGGCGAGUGAGGUCU AAACCUGA | 18788 |
| 6535 | GGUUUGUA G CAUACAUG | 8174 | CAUGUAUG GCCGAAAGGCGAGUGAGGUCU UACAAACC | 18789 |
| 6545 | AUACAUGA G UCCAUCCA | 8175 | UGGAUGGA GCCGAAAGGCGAGUGAGGUCU UCAUGUAU | 18790 |
| 6557 | AUCCAUCA G UCAAAGAA | 8176 | UUCUUUGA GCCGAAAGGCGAGUGAGGUCU UGAUGGAU | 18791 |
| 6568 | AAAGAAUG G UUCCAUCU | 8178 | AGAUGGAA GCCGAAAGGCGAGUGAGGUCU CAUUCUUU | 18792 |
| 6580 | CAUCUGGA G UCUUAAUG | 8179 | CAUUAAGA GCCGAAAGGCGAGUGAGGUCU UCCAGAUG | 18793 |
| 6588 | GUCUUAAU G UAGAAAGA | 8181 | UCUUUCUA GCCGAAAGGCGAGUGAGGUCU AUUAAGAC | 18794 |
| 6610 | GGAGACUU G UAAUAAUG | 8184 | CAUUAUUA GCCGAAAGGCGAGUGAGGUCU AAGUCUCC | 18795 |
| 6620 | AAUAAUGA G CUAGUCAC | 8187 | GUAACUAG GCCGAAAGGCGAGUGAGGUCU UCAUUAUU | 18796 |
| 6624 | AUGAGCUA G UUACAAAG | 8188 | CUUUGUAA GCCGAAAGGCGAGUGAGGUCU UAGCUCAU | 18797 |

TABLE XIX-continued

Human FLT Zinzyme and Substrate Sequence

| Pos | Substrate | Seq ID No | Zinzyme | Seq ID No |
|---|---|---|---|---|
| 6632 | GUUACAAA G UGCUUGUU | 8189 | AACAAGCA GCCGAAAGGCGAGUGAGGUCU UUUGUAAC | 18798 |
| 6634 | UACAAAGU G CUUGUUCA | 8190 | UGAACAAG GCCGAAAGGCGAGUGAGGUCU ACUUUGUA | 18799 |
| 6638 | AAGUGCUU G UUCAUUAA | 8191 | UUAAUGAA GCCGAAAGGCGAGUGAGGUCU AAGCACUU | 18800 |
| 6651 | UUAAAAUA G CACUGAAA | 8193 | UUUCAGUG GCCGAAAGGCGAGUGAGGUCU UAUUUUAA | 18801 |
| 6698 | AAUCAUUU G CCAUUUAU | 8201 | AUAAAUGG GCCGAAAGGCGAGUGAGGUCU AAAUGAUU | 18802 |
| 6717 | CAAAAAUG G UUGGCACU | 8204 | AGUGCCAA GCCGAAAGGCGAGUGAGGUCU CAUCUUUG | 18803 |
| 6721 | AAUGGUUG G CACUAACA | 8205 | UGUUAGUG GCCGAAAGGCGAGUGAGGUCU CAACCAUU | 18804 |
| 6738 | AAGAACGA G CACUUCCU | 8208 | AGGAAGUG GCCGAAAGGCGAGUGAGGUCU UCGUUCUU | 18805 |
| 6753 | CUUUCAGA G UCUCUGAG | 8209 | CUCAGAAA GCCGAAAGCCGAGUGAGGUCU UCUGAAAG | 18806 |
| 6767 | GAGAUAAU G UACGUGGA | 8212 | UCCACGUA GCCGAAAGGCGAGUGAGGUCU AUUAUCUC | 18807 |
| 6771 | UAAUGUAC G UGGAACAG | 8213 | CUGUUCCA GCCGAAAGGCGAGUGAGGUCU GUACAUUA | 18808 |
| 6779 | GUGGAACA G UCUGGGUG | 8215 | CACCCAGA GCCGAAAGGCGAGUGAGGUCU UGUUCCAC | 18809 |
| 6785 | CAGUCUGG G UGGAAUGG | 8216 | CCAUUCCA GCCGAAAGGCGAGUGAGGUCU CCAGACUG | 18810 |
| 6795 | GGAAUGGG G CUGAAACC | 8218 | GGUUUCAG GCCGAAAGGCGAGUGAGGUCU CCCAUUCC | 18811 |
| 6806 | GAAACCAU G UGCAAGUC | 8220 | GACUUGCA GCCGAAAGGCGAGUGAGGUCU AUGGUUUC | 18812 |
| 6808 | AACCAUGU G CAAGUCUG | 8221 | CAGACUUG GCCGAAAGGCGAGUGAGGUCU ACAUGGUU | 18813 |
| 6812 | AUGUGCAA G UCUGUGUC | 8222 | GACACAGA GCCGAAAGGCGAGUGAGGUCU UUGCACAU | 18814 |
| 6816 | GCAAGUCU G UGUCUUGU | 8223 | ACAAGACA GCCGAAAGGCGAGUGAGGUCU AGACUUGC | 18815 |
| 6818 | AAGUCUGU G UCUUGUCA | 8224 | UGACAAGA GCCGAAAGGCGAGUGAGGUCU ACAGACUU | 18816 |
| 6823 | UGUGUCUU G UCAGUCCA | 8225 | UGGACUGA GCCGAAAGGCGAGUGAGGUCU AAGACACA | 18817 |
| 6827 | UCUUGUCA G UCCAAGAA | 8226 | UUCUUGGA GCCGAAAGGCGAGUGAGGUCU UGACAAGA | 18818 |
| 6836 | UCCAAGAA G UGACACCG | 8227 | CGGUGUCA GCCGAAAGGCGAGUGAGGUCU UUCUUGGA | 18819 |
| 6849 | ACCGAGAU G UUAAUUUU | 8230 | AAAAUUAA GCCGAAAGGCGAGUGAGGUCU AUCUCGGU | 18820 |
| 6866 | AGGGACCC G UGCCUUGU | 8233 | ACAAGGCA GCCGAAAGGCGAGUGAGGUCU GGGUCCCU | 18821 |
| 6868 | GGACCCGU G CCUUGUUU | 8234 | AAACAAGG GCCGAAAGGCGAGUGAGGUCU ACGGGUCC | 18822 |
| 6873 | CGUGCCUU G UUUCCUAG | 8235 | CUAGGAAA GCCGAAAGGCGAGUGAGGUCU AAGGCACG | 18823 |
| 6881 | GUUUCCUA G CCCACAAG | 8236 | CUUGUGGG GCCGAAAGGCGAGUGAGGUCU UAGGAAAC | 18824 |
| 6893 | ACAAGAAU G CAAACAUC | 8238 | GAUGUUUG GCCGAAAGGCGAGUGAGGUCU AUUCUUGU | 18825 |
| 6914 | AGAUACUC G CUAGCCUC | 8242 | GAGGCUAG GCCGAAAGGCGAGUGAGGUCU CAGUAUCU | 18826 |
| 6918 | ACUCGCUA G CCUCAUUU | 8243 | AAAUGAGG GCCGAAAGGCGAGUGAGGUCU UAGCGAGU | 18827 |
| 6945 | AAGGAGGA G UGCAUCUU | 8246 | AAGAUGCA GCCGAAAGGCGAGUGAGGUCU UCCUCCUU | 18828 |
| 6947 | GGAGGAGU G CAUCUUUG | 8247 | CAAAGAUG GCCGAAAGGCGAGUGAGGUCU ACUCCUCC | 18829 |
| 6956 | CAUCUUUG G CCGACAGU | 8248 | ACUGUCGG GCCGAAAGGCGAGUGAGGUCU CAAAGAUG | 18830 |
| 6963 | GGCCGACA G UGGUGUAA | 8250 | UUACACCA GCCGAAAGGCGAGUGAGGUCU UGUCGGCC | 18831 |
| 6966 | CGACAGUG G UGUAACUG | 8251 | CAGUUACA GCCGAAAGGCGAGUGAGGUCU CACUGUCG | 18832 |
| 6968 | ACAGUGGU G UAACUGUG | 8252 | CACAGUUA GCCGAAAGGCGAGUGAGGUCU ACCACUGU | 18833 |
| 6974 | GUGUAACU G UGUGUGUG | 8254 | CACACACA GCCGAAAGGCGAGUGAGGUCU AGUUACAC | 18834 |

TABLE XIX-continued

Human FLT Zinzyme and Substrate Sequence

| Pos | Substrate | Seq ID No | Zinzyme | Seq ID No |
|---|---|---|---|---|
| 6976 | GUAACUGU G UGUGUGUG | 8255 | CACACACA GCCGAAAGGCGAGUGAGGUCU ACAGUUAC | 18835 |
| 6978 | AACUGUGU G UGUGUGUG | 8256 | CACACACA GCCGAAAGGCGAGUGAGGUCU ACACAGUU | 18836 |
| 6980 | CUGUGUGU G UGUGUGUG | 8257 | CACACACA GCCGAAAGGCGAGUGAGGUCU ACACACAG | 18837 |
| 6982 | GUGUGUGU G UGUGUGUG | 8258 | CACACACA GCCGAAAGGCGAGUGAGGUCU ACACACAC | 18838 |
| 6984 | GUGUGUGU G UGUGUGUG | 8258 | CACACACA GCCGAAAGGCGAGUGAGGUCU ACACACAC | 18838 |
| 6986 | GUGUGUGU G UGUCUGUG | 8258 | CACACACA GCCGAAAGGCGAGUGAGGUCU ACACACAC | 18838 |
| 6988 | GUGUGUGU G UGUGUGUG | 8258 | CACACACA GCCGAAAGGCGAGUGAGGUCU ACACACAC | 18838 |
| 6990 | GUGUGUGU G UGUGUGUG | 8258 | CACACACA GCCGAAAGGCGAGUGAGGUCU ACACACAC | 18838 |
| 6992 | GUGUGUGU G UGUGUGUG | 8258 | CACACACA GCCGAAAGGCGAGUGAGGUCU ACACACAC | 18838 |
| 6994 | GUGUGUGU G UGUGUGUG | 8258 | CACACACA GCCGAAAGGCGAGUGAGGUCU ACACACAC | 18838 |
| 6996 | GUGUGUGU G UGUGUGUG | 8258 | CACACACA GCCGAAAGGCGAGUGAGGUCU ACACACAC | 18838 |
| 6998 | GUGUGUGU G UGUGUGUG | 8258 | CACACACA GCCGAAAGGCGAGUGAGGUCU ACACACAC | 18838 |
| 7000 | GUCUGUGU G UGUGUGUC | 8258 | CACACACA GCCGAAAGGCGAGUGAGGUCU ACACACAC | 18838 |
| 7002 | GUGUGUGU G UGUGUGUG | 8258 | CACACACA GCCGAAAGGCGAGUGAGGUCU ACACACAC | 18838 |
| 7004 | GUGUGUGU G UGUCUGUG | 8258 | CACACACA GCCGAAAGGCGAGUGAGCUCU ACACACAC | 18838 |
| 7006 | GUGUGUGU G UGUCUGUG | 8258 | CACACACA GCCGAAAGGCGAGUGAGGUCU ACACACAC | 18838 |
| 7008 | GUGUGUGU G UGUGUGGG | 8259 | CCCACACA GCCGAAAGGCGAGUGAGGUCU ACACACAC | 18839 |
| 7010 | GUGUGUGU G UGUGGGUG | 8260 | CACCCACA GCCGAAAGGCGAGUGAGGUCU ACACACAC | 18840 |
| 7012 | GUGUGUGU G UGGGUGUG | 8261 | CACACCCA GCCGAAAGGCGAGUGAGGUCU ACACACAC | 18841 |
| 7016 | GUGUGUGG G UGUGGGUG | 8262 | CACCCACA GCCGAAAGGCGAGUGAGGUCU CCACACAC | 18842 |
| 7018 | GUGUGGGU G UGGGUGUA | 8263 | UACACCCA GCCGAAAGGCGAGUGAGGUCU ACCCACAC | 18843 |
| 7022 | GGGUGUGG G UGUAUGUG | 8264 | CACAUACA GCCGAAAGGCGAGUGAGGUCU CCACACCC | 18844 |
| 7024 | GUGUGGGU G UAUGUGUG | 8265 | CACACAUA GCCGAAAGGCGAGUGAGGUCU ACCCACAC | 18845 |
| 7028 | GGGUGUAU G UGUGUUUU | 8266 | AAAACACA GCCGAAAGGCGAGUGAGGUCU AUACACCC | 18846 |
| 7030 | GUGUAUGU G UGUUUUGU | 8267 | ACAAAACA GCCGAAAGGCGAGUGAGGUCU ACAUACAC | 18847 |
| 7032 | GUAUGUGU G UUUUGUGC | 8268 | GCACAAAA GCCGAAAGGCGAGUGAGGUCU ACACAUAC | 18848 |
| 7037 | UGUGUUUU G UGCAUAAC | 8269 | GUUAUGCA GCCGAAAGGCGAGUGAGGUCU AAAACACA | 18849 |
| 7039 | UGUUUUGU G CAUAACUA | 8270 | UAGUUAUG GCCGAAAGGCGAGUGAGGUCU ACAAAACA | 18850 |
| 7071 | AUUUUAAA G UUACUUUU | 8274 | AAAAGUAA GCCGAAAGGCGAGUGAGGUCU UUUAAAAU | 18851 |
| 7099 | GAAUAUAU G CUACAGAU | 8277 | AUCUGUAG GCCGAAAGGCGAGUGAGGUCU AUAUAUUC | 18852 |
| 7122 | CAGACAUG G UUUGGUCC | 8281 | GGACCAAA GCCGAAAGGCGAGUGAGGUCU CAUGUCUG | 18853 |
| 7127 | AUGGUUUG G UCCUAUAU | 8282 | AUAUAGGA GCCGAAAGGCGAGUGAGGUCU CAAACCAU | 18854 |
| 7141 | UAUUUCUA G UCAUGAUG | 8283 | CAUCAUGA GCCGAAAGGCGAGUGAGGUCU UAGAAAUA | 18855 |
| 7153 | UGAUGAAU G UAUUUUGU | 8286 | ACAAAAUA GCCGAAAGGCGAGUGAGGUCU AUUCAUCA | 18856 |
| 7160 | UGUAUUUU G UAUACCAU | 8287 | AUGGUAUA GCCGAAAGGCGAGUGAGGUCU AAAAUACA | 18857 |
| 7210 | UGGGAUUU G UAAUCGUA | 8292 | UACGAUUA GCCGAAAGGCGAGUGAGGUCU AAAUCCCA | 18858 |
| 7216 | UUGUAAUC G UACCAACU | 8294 | AGUUGGUA GCCGAAAGGCGAGUGAGGUCU GAUUACAA | 18859 |

TABLE XIX-continued

Human FLT Zinzyme and Substrate Sequence

| Pos | Substrate | Seq ID No | Zinzyme | Seq ID No |
|---|---|---|---|---|
| 7240 | UAAACUUG G CAACUGCU | 8299 | AGCAGUUG GCCGAAAGGCGAGUGAGGUCU CAAGUUUA | 18860 |
| 7246 | UGGCAACU G CUUUUAUG | 8301 | CAUAAAAG GCCGAAAGGCGAGUGAGGUCU AGUUGCCA | 18861 |
| 7254 | GCUUUUAU G UUCUGUCU | 8302 | AGACAGAA GCCGAAAGGCGAGUGAGGUCU AUAAAAGC | 18862 |
| 7259 | UAUGUUCU G UCUCCUUC | 8303 | GAAGGAGA GCCGAAAGGCGAGUGAGGUCU AGAACAUA | 18863 |
| 7305 | AAGAAAAA G CUCUUUUU | 8308 | AAAAAGAG GCCGAAAGGCGAGUGAGGUCU UUUUUCUU | 18864 |
| 7343 | UUAUCCUU G UUUAGAGC | 8312 | GCUCUAAA GCCGAAAGGCGAGUGAGGUCU AAGGAUAA | 18865 |
| 7350 | UGUUUAGA G CAGAGAAA | 8313 | UUUCUCUG GCCGAAAGGCGAGUGAGGUCU UCUAAACA | 18866 |
| 7381 | UUGAAAUG G UCUCAAAA | 8317 | UUUUGAGA GCCGAAAGGCGAGUGAGGUCU CAUUUCAA | 18867 |
| 7394 | AAAAAAUU G CUAAAUAU | 8319 | AUAUUUAG GCCGAAAGGCGAGUGAGGUCU AAUUUUUU | 18868 |
| 7422 | AACUAAAU G UUAGUUUA | 8324 | UAAACUAA GCCGAAAGGCGAGUGAGGUCU AUUUAGUU | 18869 |
| 7426 | AAAUGUUA G UUUAGCUG | 8325 | CAGCUAAA GCCGAAAGGCGAGUGAGGUCU UAACAUUU | 18870 |
| 7431 | UUAGUUUA G CUGAUUGU | 8326 | ACAAUCAG GCCGAAAGGCGAGUGAGGUCU UAAACUAA | 18871 |
| 7438 | AGCUGAUU G UAUGGGGU | 8328 | ACCCCAUA GCCGAAAGGCGAGUGAGGUCU AAUCAGCU | 18872 |
| 7445 | UGUAUGGG G UUUUCGAA | 8329 | UUCGAAAA GCCGAAAGGCGAGUGAGGUCU CCCAUACA | 18873 |
| 7467 | CACUUUUU G UUUGUUUU | 8331 | AAAACAAA GCCGAAAGGCGAGUGAGGUCU AAAAAGUG | 18874 |
| 7471 | UUUUGUUU G UUUUACCU | 8332 | AGGUAAAA GCCGAAAGGCGAGUGAGGUGU AAACAAAA | 18875 |
| 7491 | UCACAACU G UGUAAAUU | 8334 | AAUUUACA GCCGAAAGGCGAGUGAGGUCU AGUUGUGA | 18876 |
| 7493 | ACAACUGU G UAAAUUGC | 8335 | GCAAUUUA GCCGAAAGGCGAGUGAGGUCU ACAGUUGU | 18877 |
| 7500 | UGUAAAUU G CCAAUAAU | 8337 | AUUAUUGG GCCGAAAGGCGAGUGAGGUCU AAUUUACA | 18878 |
| 7513 | UAAUUCCU G UCCAUGAA | 8340 | UUCAUGGA GCCGAAAGGCGAGUGAGGUCU AGGAAUUA | 18879 |
| 7525 | AUGAAAAU G CAAAUUAU | 8342 | AUAAUUUG GCCGAAAGGCGAGUGAGGUCU AUUUUCAU | 18880 |
| 7537 | AUUAUCCA G UGUAGAUA | 8344 | UAUCUACA GCCGAAAGGCGAGUGAGGUCU UGGAUAAU | 18881 |
| 7539 | UAUCCAGU G UAGAUAUA | 8345 | UAUAUCUA GCCGAAAGGCGAGUGAGGUCU ACUGGAUA | 18882 |
| 7573 | GGAUAUUG G CUAGUUUU | 8349 | AAAACUAG GCCGAAAGGCGAGUGAGGUCU CAAUAUCC | 18883 |
| 7577 | AUUGGCUA G UUUUGCCU | 8350 | AGGCAAAA GCCGAAAGGCGAGUGAGGUCU UAGCCAAU | 18884 |
| 7582 | CUAGUUUU G CCUUUAUU | 8351 | AAUAAAGG GCCGAAAGGCGAGUGAGGUCU AAAACUAG | 18885 |
| 7593 | UUUAUUAA G CAAAUUCA | 8352 | UGAAUUUG GCCGAAAGGCGAGUGAGGUCU UUAAUAAA | 18886 |
| 7607 | UCAUUUCA G CCUGAAUG | 8354 | CAUUCAGG GCCGAAAGGCGAGUGAGGUCU UGAAAUGA | 18887 |
| 7615 | GCCUGAAU G UCUGCCUA | 8356 | UAGGCAGA GCCGAAAGGCGAGUGAGGUCU AUUCAGGC | 18888 |
| 7619 | GAAUGUCU G CCUAUAUA | 8357 | UAUAUAGG GCCGAAAGGCGAGUGAGGUCU AGACAGUC | 18889 |
| 7634 | UAUUCUCU G CUCUUUGU | 8358 | ACAAAGAG GCCGAAAGGCGAGUGAGGUCU AGAGAAUA | 18890 |
| 7641 | UGCUCUUU G UAUUCUCC | 8359 | GGAGAAUA GCCGAAAGGCGAGUGAGGUCU AAAGAGCA | 18891 |
| 7659 | UUGAACCC G UUAAAACA | 8361 | UGUUUUAA GCCGAAAGGCGAGUGAGGUCU GGGUUCAA | 18892 |
| 7672 | AACAUCCU G UGGCACUC | 8363 | GAGUGCCA GCCGAAAGGCGAGUGAGGUCU AGGAUGUU | 18893 |

Input Sequence = HSFLT. Cut Site = G/Y
Arm Length = 8. Core Sequence = GCcgaaagGCGaGuCaaGGuCu (SEQ ID NO. 20829).
HSFLT (Human flt mRNA for receptor-related tyrosine kinase; Acc# X51602; 7680 bp)

TABLE XX

Patient Demographics

| Dose cohort (mg/m²) | Pt# | Age | Sex | Diagnosis | Status | Doses |
|---|---|---|---|---|---|---|
| 10 | 1001 | 49 | F | NSC Lung | PD | 29 |
| 10 | 1002 | 65 | F | liposarcoma | PD | 120 |
| 10 | 1003 | 49 | M | nasopharyngeal CA | WD | 109 |
| 30 | 1004* | | | | | |
| 30 | 1005 | 45 | F | melanoma (ocular) | PD | 113 |
| 30 | 1006 | 57 | M | colon | PD | 199 |
| 30 | 1007 | 39 | F | epitheliod hemangioendothelioma | PD | 198 |
| 100 | 1008 | 52 | M | adrenal ca | PD | 57 |
| 100 | 1009 | 44 | F | breast | PD | 35 |
| 100 | 1010 | 62 | F | renal | PD | 134 |
| 300 | 1011 | 24 | F | melanoma | PD | 31 |
| 300 | 1012 | 57 | M | renal cell | PD | 178 |
| 300 | 1013 | 53 | M | nasopharyngeal SCCA | PD | 29 |
| 300 | 1014 | 64 | F | peritoneal mesothelioma | stable | 236** |
| 100 | 1015 | 65 | M | melanoma | PD | 140 |
| 100 | 1016 | 77 | F | breast | stable | 231** |
| 100 | 1017 | | F | melanoma | PD | 35 |
| 100 | 1018* | | | | | |
| 100 | 1019 | 69 | F | endometrial sarcoma | stable | 212** |
| 100 | 1020 | 65 | M | carcinoid | PD | 124 |
| 100 | 1021 | 59 | M | gallbladder adeno carcinoma | PD | 34 |
| 100 | 1022* | | | | | |
| 100 | 1023 | 78 | F | breast | PD | 50 |
| 100 | 1024 | 40 | F | parotid adenocarcinoma | stable | 161** |
| 100 | 1025 | 52 | F | breast | WD | 71 |
| 100 | 1026 | 39 | F | breast | PD | 34 |
| 100 | 1027 | 55 | F | breast | PD | 36 |
| 100 | 1028 | 52 | M | melanoma | PD | 29 |
| 100 | 1029 | 38 | M | pancreatic | PD | 36 |
| 100 | 1030 | 83 | M | melanoma | PD | 41 |
| 100 | 1031 | 50 | M | medullary thyroid | WD | 108 |

PD = progressive disease; WD = withdrawal. 4 patients remain on study.
*Inappropriate enrollment, patient withdrawn
**As of Jan. 11, 2000

TABLE XXI

Pharmacokinetic parameters of ANGIOZYME after bolus subcutaneous administration.

| | 10 mg/m² | | 30 mg/m² | | 100 mg/m² | | 300 mg/m² | |
|---|---|---|---|---|---|---|---|---|
| | Mean | SD | Mean | SD | Mean | SD | Mean | SD |
| Day 1 | | | | | | | | |
| Cmax (ug/mL) | 0.43 | 0.07 | 0.62 | 0.28 | 3.17 | 0.69 | 8.91 | 2.93 |
| AUCt (ug*hr/mL) | 2.60 | 1.43 | 6.04 | 2.70 | 34.14 | 2.28 | 89.87 | 21.68 |
| AUCinf (ug*hr/mL) | 4.40 | 0.06 | 7.99 | 1.66 | 37.51 | 1.91 | 101.57 | 13.47 |
| t(1/2) (hr) | 3.62 | 0.79 | 7.32 | 6.94 | 4.58 | 0.02 | 9.26 | 6.20 |
| CL/F (L/hr/m²) | 2.24 | 0.08 | 3.73 | 0.92 | 2.96 | 0.61 | 2.99 | 0.43 |
| Day 29 | | | | | | | | |
| Cmax (ug/mL) | 0.35 | 0.19 | 1.17 | 0.53 | 3.23 | 0.35 | 8.93 | 6.71 |
| AUCt (ug*hr/mL) | 2.11 | 1.31 | 7.29 | 1.16 | 31.87 | 1.91 | 119.42 | 65.84 |
| AUCinf (ug*hr/mL) | 3.38 | 1.31 | 8.54 | 2.46 | 33.61 | 2.16 | 132.73 | 67.82 |
| t(1/2) (hr) | 4.49 | 1.60 | 3.26 | 1.01 | 4.66 | 0.35 | 7.24 | 0.70 |
| CL/F (L/hr/m²) | 2.49 | 1.48 | 3.69 | 0.94 | 3.21 | 0.56 | 2.72 | 1.40 |

TABLE XXII

Human KDR DNAzyme and Substrate sequence

| Pos | Substrate | Seq ID No | DNAzyme | Seq ID No |
|---|---|---|---|---|
| 14 | GUCCCGGG A CCCCGGGA | 8364 | TCCCGGGG GGCTAGCTACAACGA CCCGGGAC | 18894 |
| 25 | CCGGGAGA G CGGUCAGU | 8365 | ACTGACCG GGCTAGCTACAACGA TCTCCCGG | 18895 |
| 28 | GGAGAGCG G UCAGUGUG | 8366 | CACACTGA GGCTAGCTACAACGA CGCTCTCC | 18896 |
| 32 | AGCGGUCA G UGUGGUGGU | 8367 | ACCACACA GGCTAGCTACAACGA TGACCGCT | 18897 |
| 34 | CGGUCAGU G UGGUCG | 8368 | CGACCACA GGCTAGCTACAACGA ACTGACCG | 18898 |
| 36 | GUCAGUGU G UGGUCGCU | 8369 | AGCGACCA GGCTAGCTACAACGA ACACTGAC | 18899 |
| 39 | AGUGUGUG G UCGCUGCG | 8370 | CGCAGCGA GGCTAGCTACAACGA CACACACT | 18900 |
| 42 | GUGUGGUC G CUGCGUUU | 8371 | AAACGCAG GGCTAGCTACAACGA GACCACAC | 18901 |
| 45 | UGGUCGCU G CGUUUCCU | 8372 | AGGAAACG GGCTAGCTACAACGA AGCGACCA | 18902 |
| 47 | GUCGCUGC G UUUCCUCU | 8373 | AGAGGAAA GGCTAGCTACAACGA GCAGCGAC | 18903 |

TABLE XXII-continued

Human KDR DNAzyme and Substrate sequence

| Pos | Substrate | Seq ID No | DNAzyme | Seq ID No |
|---|---|---|---|---|
| 56 | UUUCCUCU G CCUGCGCC | 8374 | GGCGCAGG GGCTAGCTACAACGA AGAGGAAA | 18904 |
| 60 | CUCUGCCU G CGCCGGGC | 8375 | GCCCGGCG GGCTAGCTACAACGA AGGCAGAG | 18905 |
| 62 | CUGCCUGC G CCGGGCAU | 8376 | ATGCCCGG GGCTAGCTACAACGA GCAGGCAG | 18906 |
| 67 | UGCGCCGG G CAUCACUU | 8377 | AAGTGATG GGCTAGCTACAACGA CCGGCGCA | 18907 |
| 69 | CGCCGGGC A UCACUUGC | 8378 | GCAAGTGA GGCTAGCTACAACGA GCCCGGCG | 18908 |
| 72 | CGGGCAUC A CUUGCGCG | 8379 | CGCGCAAG GGCTAGCTACAACGA GATGCCCG | 18909 |
| 76 | CAUCACUU G CGCCGCGC | 8380 | GCGGCGCG GGCTAGCTACAACGA AAGTGATG | 18910 |
| 78 | UCACUUGC G CGCCGCAG | 8381 | CTGCGGCG GGCTAGCTACAACGA GCAAGTGA | 18911 |
| 80 | ACUUGCGC G CCGCAGAA | 8382 | TTCTGCGG GGCTAGCTACAACGA GCGCAAGT | 18912 |
| 83 | UGCGCGCC G CAGAAAGU | 8383 | ACTTTCTG GGCTAGCTACAACGA GGCGCGCA | 18913 |
| 90 | CGCAGAAA G UCCGUCUG | 8384 | CAGACGGA GGCTAGCTACAACGA TTTCTGCG | 18914 |
| 94 | GAAAGUCC G UCUGGCAG | 8385 | CTGCCAGA GGCTAGCTACAACGA GGACTTTC | 18915 |
| 99 | UCCGUCUG G CAGCCUGG | 8386 | CCAGGCTG GGCTAGCTACAACGA CAGACGGA | 18916 |
| 102 | GUCUGGCA G CCUGGAUA | 8387 | TATCCAGG GGCTAGCTACAACGA TGCCAGAC | 18917 |
| 108 | CAGCCUGG A UAUCCUCU | 8388 | AGAGGATA GGCTAGCTACAACGA CCAGGCTG | 18918 |
| 110 | GCCUGGAU A UCCUCUCC | 8389 | GGAGAGGA GGCTAGCTACAACGA ATCCAGGC | 18919 |
| 120 | CCUCUCCU A CCGGCACC | 8390 | GGTGCCGG GGCTAGCTACAACGA AGGAGAGG | 18920 |
| 124 | UCCUACCG G CACCCGCA | 8391 | TGCGGGTG GGCTAGCTACAACGA CGGTAGGA | 18921 |
| 126 | CUACCGGC A CCCGCAGA | 8392 | TCTGCGGG GGCTAGCTACAACGA GCCGGTAG | 18922 |
| 130 | CGGCACCC G CAGACGCC | 8393 | GGCGTCTG GGCTAGCTACAACGA GGGTGCCG | 18923 |
| 134 | ACCCGCAG A CGCCCUG | 8394 | CAGGGGCG GGCTAGCTACAACGA CTGCGGGT | 18924 |
| 136 | CCGCAGAC G CCCCUGCA | 8395 | TGCAGGGG GGCTAGCTACAACGA GTCTGCGG | 18925 |
| 142 | ACGCCCCU G CAGCCGCC | 8396 | GGCGGCTG GGCTAGCTACAACGA AGGGGCGT | 18926 |
| 145 | CCCCUGCA G CCGCCGGU | 8397 | ACCGGCGG GGCTAGCTACAACGA TGCAGGGG | 18927 |
| 148 | CUGCAGCC G CCGGUCGG | 8398 | CCGACCGG GGCTAGCTACAACGA GGCTGCAG | 18928 |
| 152 | AGCCGCCG G UCGGCGCC | 8399 | GGCGCCGA GGCTAGCTACAACGA CGGCGGCT | 18929 |
| 156 | GCCGGUCG G CGCCCGGG | 8400 | CCCGGGCG GGCTAGCTACAACGA CGACCGGC | 18930 |
| 158 | CGGUCGGC G CCCGGGCU | 8401 | AGCCCGGG GGCTAGCTACAACGA GCCGACCG | 18931 |
| 164 | GCGCCCGG G CUCCCUAG | 8402 | CTAGGGAG GGCTAGCTACAACGA CCGGGCGC | 18932 |
| 172 | GCUCCCUA G CCCUGUGC | 8403 | GCACAGGG GGCTAGCTACAACGA TAGGGAGC | 18933 |
| 177 | CUAGCCCU G UGCGCUCA | 8404 | TGAGCGCA GGCTAGCTACAACGA AGGGCTAG | 18934 |
| 179 | AGCCCUGU G CGCUCAAC | 8405 | GTTGAGCG GGCTAGCTACAACGA ACAGGGCT | 18935 |
| 181 | CCCUGUGC G CUCAACUG | 8406 | CAGTTGAG GGCTAGCTACAACGA GCACAGGG | 18936 |
| 186 | UGCGCUCA A CUGUCCUG | 8407 | CAGGACAG GGCTAGCTACAACGA TGAGCGCA | 18937 |
| 189 | GCUCAACU G UCCGCGC | 8408 | GCGCAGGA GGCTAGCTACAACGA AGTTGAGC | 18938 |
| 194 | ACUGUCCU G CGCUGCGG | 8409 | CCGCAGCG GGCTAGCTACAACGA AGGACAGT | 18939 |
| 196 | UGUCCUGC G CUGCGGGG | 8410 | CCCCGCAG GGCTAGCTACAACGA GCAGGACA | 18940 |

TABLE XXII-continued

Human KDR DNAzyme and Substrate sequence

| Pos | Substrate | Seq ID No | DNAzyme | Seq ID No |
|---|---|---|---|---|
| 199 | CCUGCGCU G CGGGGUGC | 8411 | GCACCCCG GGCTAGCTACAACGA AGCGCAGG | 18941 |
| 204 | GCUGCGGG G UGCCGCGA | 8412 | TCGCGGCA GGCTAGCTACAACGA CCCGCAGC | 18942 |
| 206 | UGCGGGGU G CCGCGAGU | 8413 | ACTCGCGG GGCTAGCTACAACGA ACCCCGCA | 18943 |
| 209 | GGGGUGCC G CGAGUUCC | 8414 | GGAACTCG GGCTAGCTACAACGA GGCACCCC | 18944 |
| 213 | UGCCGCGA G UUCCACCU | 8415 | AGGTGGAA GGCTAGCTACAACGA TCGCGGCA | 18945 |
| 218 | CGAGUUCC A CCUCCGCG | 8416 | CGCGGAGG GGCTAGCTACAACGA GGAACTCG | 18946 |
| 224 | CCACCUCC G CGCCUCCU | 8417 | AGGAGGCG GGCTAGCTACAACGA GGAGGTGG | 18947 |
| 226 | ACCUCCGC G CCUCCUUC | 8418 | GAAGGAGG GGCTAGCTACAACGA GCGGAGGT | 18948 |
| 240 | UUCUCUAG A CAGGCGCU | 8419 | AGCGCCTG GGCTAGCTACAACGA CTAGAGAA | 18949 |
| 244 | CUAGACAG G CGCUGGGA | 8420 | TCCCAGCG GGCTAGCTACAACGA CTGTCTAG | 18950 |
| 246 | AGACAGGC G CUGGGAGA | 8421 | TCTCCCAG GGCTAGCTACAACGA GCCTGTCT | 18951 |
| 259 | GAGAAAGA A CCGGCUCC | 8422 | GGAGCCGG GGCTAGCTACAACGA TCTTTCTC | 18952 |
| 263 | AAGAACCG G CUCCCGAG | 8423 | CTCGGGAG GGCTAGCTACAACGA CGGTTCTT | 18953 |
| 271 | GCUCCCGA G UUCUGGGC | 8424 | GCCCAGAA GGCTAGCTACAACGA TCGGGAGC | 18954 |
| 278 | AGUUCUGG G CAUUUCGC | 8425 | GCGAAATG GGCTAGCTACAACGA CCAGAACT | 18955 |
| 280 | UUCUGGGC A UUUCGCCC | 8426 | GGGCGAAA GGCTAGCTACAACGA GCCCAGAA | 18956 |
| 285 | GGCAUUUC G CCCGGCUC | 8427 | GAGCCGGG GGCTAGCTACAACGA GAAATGCC | 18957 |
| 290 | UUCGCCCG G CUCGAGGU | 8428 | ACCTCGAG GGCTAGCTACAACGA CGGGCGAA | 18958 |
| 297 | GGCUCGAG G UGCAGGAU | 8429 | ATCCTGCA GGCTAGCTACAACGA CTCGAGCC | 18959 |
| 299 | CUCGAGGU G CAGGAUGC | 8430 | GCATCCTG GGCTAGCTACAACGA ACCTCGAG | 18960 |
| 304 | GGUGCAGG A UGCAGAGC | 8431 | GCTCTGCA GGCTAGCTACAACGA CCTGCACC | 18961 |
| 306 | UGCAGGAU G CAGAGCAA | 8432 | TTGCTCTG GGCTAGCTACAACGA ATCCTGCA | 18962 |
| 311 | GAUGCAGA G CAAGGUGC | 8433 | GCACCTTG GGCTAGCTACAACGA TCTGCATC | 18963 |
| 316 | AGAGCAAG G UGCUGCUG | 8434 | CAGCAGCA GGCTAGCTACAACGA CTTGCTCT | 18964 |
| 318 | AGCAAGGU G CUGCUGGC | 8435 | GCCAGCAG GGCTAGCTACAACGA ACCTTGCT | 18965 |
| 321 | AAGGUGCU G CUGGCCGU | 8436 | ACGGCCAG GGCTAGCTACAACGA AGCACCTT | 18966 |
| 325 | UGCUGCUG G CCGUCGCC | 8437 | GGCGACGG GGCTAGCTACAACGA CAGCAGCA | 18967 |
| 328 | UGCUGGCC G UCGCCCUG | 8438 | CAGGGCGA GGCTAGCTACAACGA GGCCAGCA | 18968 |
| 331 | UGGCCGUC G CCCUGUGG | 8439 | CCACAGGG GGCTAGCTACAACGA GACGGCCA | 18969 |
| 336 | GUCGCCCU G UGGCUCUG | 8440 | CAGAGCCA GGCTAGCTACAACGA AGGGCGAC | 18970 |
| 339 | GCCCUGUG G CUCUGCGU | 8441 | ACGCAGAG GGCTAGCTACAACGA CACAGGGC | 18971 |
| 344 | GUGGCUCU G CGUGGAGA | 8442 | TCTCCACG GGCTAGCTACAACGA AGAGCCAC | 18972 |
| 346 | GGCUCUGC G UGGAGACC | 8443 | GGTCTCCA GGCTAGCTACAACGA GCAGAGCC | 18973 |
| 352 | GCGUGGAG A CCCGGGCC | 8444 | GGCCCGGG GGCTAGCTACAACGA CTCCACGC | 18974 |
| 358 | AGACCCGG G CCGCCUCU | 8445 | AGAGGCGG GGCTAGCTACAACGA CCGGGTCT | 18975 |
| 361 | CCCGGGCC G CCUCUGUG | 8446 | CACAGAGG GGCTAGCTACAACGA GGCCCGGG | 18976 |
| 367 | CCGCCUCU G UGGGUUUG | 8447 | CAAACCCA GGCTAGCTACAACGA AGAGGCGG | 18977 |

TABLE XXII-continued

Human KDR DNAzyme and Substrate sequence

| Pos | Substrate | Seq ID No | DNAzyme | Seq ID No |
|---|---|---|---|---|
| 371 | CUCUGUGG G UUUGCCUA | 8448 | TAGGCAAA GGCTAGCTACAACGA CCACAGAG | 18978 |
| 375 | GUGGGUUU G CCUAGUGU | 8449 | ACACTAGG GGCTAGCTACAACGA AAACCCAC | 18979 |
| 380 | UUUGCCUA G UGUUUCUC | 8450 | GAGAAACA GGCTAGCTACAACGA TAGGCAAA | 18980 |
| 382 | UGCCUAGU G UUUCUCUU | 8451 | AAGAGAAA GGCTAGCTACAACGA ACTAGGCA | 18981 |
| 392 | UUCUCUUG A UCUGCCCA | 8452 | TGGGCAGA GGCTAGCTACAACGA CAAGAGAA | 18982 |
| 396 | CUUGAUCU G CCCAGGCU | 8453 | AGCCTGGG GGCTAGCTACAACGA AGATCAAG | 18983 |
| 402 | CUGCCCAG G CUCAGCAU | 8454 | ATGCTGAG CCCTAGCTACAACGA CTGGGCAG | 18984 |
| 407 | CAGGCUCA G CAUACAAA | 8455 | TTTCTATG GGCTAGCTACAACGA TGAGCCTG | 18985 |
| 409 | GGCUCAGC A UACAAAAU | 6138 | TTTTTGTA GGCTAGCTACAACGA GCTGAGCC | 18986 |
| 411 | CUCAGCAU A CAAAAGA | 1519 | TCTTTTTG GGCTAGCTACAACGA ATGCTGAG | 18987 |
| 419 | ACAAAAAG A CAUACUUA | 8456 | TAAGTATG GGCTAGCTACAACGA CTTTTTGT | 18988 |
| 421 | AAAAAGAC A UACUUACA | 6140 | TGTAAGTA GGCTAGCTACAACGA GTCTTTTT | 18989 |
| 423 | AAAGACAU A CUUACAAU | 1520 | ATTGTAAG GGCTAGCTACAACGA ATGTCTTT | 18990 |
| 427 | ACAUACUU A CAAUUAAG | 1522 | CTTAATTG GGCTAGCTACAACGA AAGTATGT | 18991 |
| 430 | UACUUACA A UUAAGGCU | 8457 | AGCCTTAA GGCTAGCTACAACGA TGTAAGTA | 18992 |
| 436 | CAAUUAAG G CUAAUACA | 8458 | TGTATTAG GGCTAGCTACAACGA CTTAATTG | 18993 |
| 440 | UAAGGCUA A UACAACUC | 8459 | GAGTTGTA GGCTAGCTACAACGA TAGCCTTA | 18994 |
| 442 | AGGCUAAU A CAACUCUU | 1526 | AAGAGTTG GGCTAGCTACAACGA ATTAGCCT | 18995 |
| 445 | CUAAUACA A CUCUUCAA | 8460 | TTGAAGAG GGCTAGCTACAACGA TGTATTAG | 18996 |
| 454 | CUCUUCAA A UUACUUGC | 8461 | GCAAGTAA GGCTAGCTACAACGA TTGAAGAG | 18997 |
| 457 | UUCAAAUU A CUUGCAGG | 1531 | CCTGCAAG GGCTAGCTACAACGA AATTTGAA | 18998 |
| 461 | AAUUACUU G CAGGGGAC | 8462 | GTCCCCTG GGCTAGCTACAACGA AAGTAATT | 18999 |
| 468 | UGCAGGGG A CAGAGGGA | 8463 | TCCCTCTG GGCTAGCTACAACGA CCCCTGCA | 19000 |
| 476 | ACAGAGGG A CUUGGACU | 8464 | AGTCCAAG GGCTAGCTACAACGA CCCTCTGT | 19001 |
| 482 | GGACUUGG A CUGGCUUU | 8465 | AAAGCCAG GGCTAGCTACAACGA CCAAGTCC | 19002 |
| 486 | UUGGACUG G CUUUGGCC | 8466 | GGCCAAAG GGCTAGCTACAACGA CAGTCCAA | 19003 |
| 492 | UGGCUUUG G CCCAAUAA | 8467 | TTATTGGG GGCTAGCTACAACGA CAAAGCCA | 19004 |
| 497 | UUGGCCCA A UAAUCAGA | 8468 | TCTGATTA GGCTAGCTACAACGA TGGGCCAA | 19005 |
| 500 | GCCCAAUA A UCAGAGUG | 8469 | CACTCTGA GGCTAGCTACAACGA TATTGGGC | 19006 |
| 506 | UAAUCAGA G UGGCAGUG | 8470 | CACTGCCA GGCTAGCTACAACGA TCTGATTA | 19007 |
| 509 | UCAGAGUG G CAGUGAGC | 8471 | GCTCACTG GGCTAGCTACAACGA CACTCTGA | 19008 |
| 512 | GAGUGGCA G UGAGCAAA | 8472 | TTTGCTCA GGCTAGCTACAACGA TGCCACTC | 19009 |
| 516 | GGCAGUGA G CAAAGGGU | 8473 | ACCCTTTG GGCTAGCTACAACGA TCACTGCC | 19010 |
| 523 | AGCAAAGG G UGGAGGUG | 8474 | CACCTCCA GGCTAGCTACAACGA CCTTTGCT | 19011 |
| 529 | GGGUGGAG G UGACUGAG | 8475 | CTCAGTCA GGCTAGCTACAACGA CTCCACCC | 19012 |
| 532 | UGGAGGUG A CUGAGUGC | 8476 | GCACTCAG GGCTAGCTACAACGA CACCTCCA | 19013 |
| 537 | GUGACUGA G UGCAGCGA | 8477 | TCGCTGCA GGCTAGCTACAACGA TCAGTCAC | 19014 |

TABLE XXII-continued

Human KDR DNAzyme and Substrate sequence

| Pos | Substrate | Seq ID No | DNAzyme | Seq ID No |
|-----|-----------|-----------|---------|-----------|
| 539 | GACUGAGU G CAGCGAUG | 8478 | CATCGCTG GGCTAGCTACAACGA ACTCAGTC | 19015 |
| 542 | UGAGUGCA G CGAUGGCC | 8479 | GGCCATCG GGCTAGCTACAACGA TGCACTCA | 19016 |
| 545 | GUGCAGCG A UGGCCUCU | 8480 | AGAGGCCA GGCTAGCTACAACGA CGCTGCAC | 19017 |
| 548 | CAGCGAUG G CCUCUUCU | 8481 | AGAAGAGG GGCTAGCTACAACGA CATCGCTG | 19018 |
| 557 | CCUCUUCU G UAAGACAC | 8482 | GTGTCTTA GGCTAGCTACAACGA AGAAGAGG | 19019 |
| 562 | UCUGUAAG A CACUCACA | 8483 | TGTGAGTG GGCTAGCTACAACGA CTTACAGA | 19020 |
| 564 | UGUAAGAC A CUCACAAU | 6166 | ATTGTGAG GGCTAGCTACAACGA GTCTTACA | 19021 |
| 568 | AGACACUC A CAAUUCCA | 6168 | TGGAATTG GGCTAGCTACAACGA GAGTGTCT | 19022 |
| 571 | CACUCACA A UUCCAAAA | 8484 | TTTTGGAA GGCTAGCTACAACGA TGTGAGTG | 19023 |
| 580 | UUCCAAAA G UGAUCGGA | 8485 | TCCGATCA GGCTAGCTACAACGA TTTTGGAA | 19024 |
| 583 | CAAAAGUG A UCGGAAAU | 8486 | ATTTCCGA GGCTAGCTACAACGA CACTTTTG | 19025 |
| 590 | GAUCGGAA A UGACACUG | 8487 | CAGTGTCA GGCTAGCTACAACGA TTCCGATC | 19026 |
| 593 | CGGAAAUG A CACUGGAG | 8488 | CTCCAGTG GGCTAGCTACAACGA CATTTCCG | 19027 |
| 595 | GAAAUGAC A CUGGAGCC | 6172 | GGCTCCAG GGCTAGCTACAACGA GTCATTTC | 19028 |
| 601 | ACACUGGA G CCUACAAG | 8489 | CTTGTAGG GGCTAGCTACAACGA TCCAGTGT | 19029 |
| 605 | UGGAGCCU A CAAGUGCU | 1546 | AGCACTTG GGCTAGCTACAACGA AGGCTCCA | 19030 |
| 609 | GCCUACAA G UGCUUCUA | 8490 | TAGAAGCA GGCTAGCTACAACGA TTGTAGGC | 19031 |
| 611 | CUACAAGU G CUUCUACC | 8491 | GGTAGAAG GGCTAGCTACAACGA ACTTGTAG | 19032 |
| 617 | GUGCUUCU A CCGGGAAA | 1549 | TTTCCCGG GGCTAGCTACAACGA AGAAGCAC | 19033 |
| 625 | ACCGGGAA A CUGACUUG | 8492 | CAAGTCAG GGCTAGCTACAACGA TTCCCGGT | 19034 |
| 629 | GGAAACUG A CUUGGCCU | 8493 | AGGCCAAG GGCTAGCTACAACGA CAGTTTCC | 19035 |
| 634 | CUGACUUG G CCUCGGUC | 8494 | GACCGAGG GGCTAGCTACAACGA CAAGTCAG | 19036 |
| 640 | UGGCCUCG G UCAUUUAU | 8495 | ATAAATGA GGCTAGCTACAACGA CGAGGCCA | 19037 |
| 643 | CCUCGGUC A UUUAUGUC | 6184 | GACATAAA GGCTAGCTACAACGA GACCGAGG | 19038 |
| 647 | GGUCAUUU A UGUCUAUG | 1555 | CATAGACA GGCTAGCTACAACGA AAATGACC | 19039 |
| 649 | UCAUUUAU G UCUAUGUU | 8496 | AACATAGA GGCTAGCTACAACGA ATAAATGA | 19040 |
| 653 | UUAUGUCU A UGUUCAAG | 1557 | CTTGAACA GGCTAGCTACAACCA AGACATAA | 19041 |
| 655 | AUGUCUAU G UUCAAGAU | 8497 | ATCTTGAA GGCTAGCTACAACGA ATAGACAT | 19042 |
| 662 | UGUUCAAG A UUACAGAU | 8498 | ATCTGTAA GGCTAGCTACAACGA CTTGAACA | 19043 |
| 665 | UCAAGAUU A CAGAUCUC | 1561 | GAGATCTG GGCTAGCTACAACGA AATCTTGA | 19044 |
| 669 | GAUUACAG A UCUCCAUU | 8499 | AATGGAGA GGCTAGCTACAACGA CTGTAATC | 19045 |
| 675 | AGAUCUCC A UUUAUUGC | 6190 | GCAATAAA GGCTAGCTACAACGA GGAGATCT | 19046 |
| 679 | CUCCAUUU A UUGCUUCU | 1566 | AGAAGCAA GGCTAGCTACAACGA AAATGGAG | 19047 |
| 682 | CAUUUAUU G CUUCUGUU | 8500 | AACAGAAG GGCTAGCTACAACGA AATAAATG | 19048 |
| 688 | UUGCUUCU G UUAGUGAC | 8501 | GTCACTAA GGCTAGCTACAACGA AGAAGCAA | 19049 |
| 692 | UUCUGUUA G UGACCAAC | 8502 | GTTGGTCA GGCTAGCTACAACGA TAACAGAA | 19050 |
| 695 | UGUUAGUG A CCAACAUG | 8503 | CATGTTGG GGCTAGCTACAACGA CACTAACA | 19051 |

TABLE XXII-continued

Human KDR DNAzyme and Substrate sequence

| Pos | Substrate | Seq ID No | DNAzyme | Seq ID No |
|---|---|---|---|---|
| 699 | AGUGACCA A CAUGGAGU | 8504 | ACTCCATG GGCTAGCTACAACGA TGGTCACT | 19052 |
| 701 | UGACCAAC A UGGAGUGG | 6195 | CGACTCCA GGCTAGCTACAACGA GTTGGTCA | 19053 |
| 706 | AACAUGGA G UCGUGUAC | 8505 | GTACACGA GGCTAGCTACAACGA TCCATGTT | 19054 |
| 709 | AUGGAGUC G UGUACAUU | 8506 | AATGTACA GGCTAGCTACAACGA GACTCCAT | 19055 |
| 711 | GGAGUCGU G UACAUUAC | 8507 | GTAATGTA GGCTAGCTACAACGA ACGACTCC | 19056 |
| 713 | AGUCGUGU A CAUUACUG | 1573 | CAGTAATG GGCTAGCTACAACGA ACACGACT | 19057 |
| 715 | UCGUGUAC A UUACUGAG | 6196 | CTCAGTAA GGCTAGCTACAACGA GTACACGA | 19058 |
| 718 | UGUACAUU A CUGAGAAC | 1575 | GTTCTCAG GGCTAGCTACAACGA AATGTACA | 19059 |
| 725 | UACUGAGA A CAAAACA | 8508 | TGTTTTTG GGCTAGCTACAACGA TCTCAGTA | 19060 |
| 731 | GAACAAAA A CAAAACUG | 8509 | CAGTTTTG GGCTAGCTACAACGA TTTTGTTC | 19061 |
| 736 | AAAACAAA A CUGUGGUG | 8510 | CACCACAG GGCTAGCTACAACGA TTTGTTTT | 19062 |
| 739 | ACAAAACU G UGGUGAUU | 8511 | AATCACCA GGCTAGCTACAACGA AGTTTTGT | 19063 |
| 742 | AAACUGUG G UGAUUCCA | 8512 | TGGAATCA GGCTAGCTACAACGA CACAGTTT | 19064 |
| 745 | CUGUGGUG A UUCCAUGU | 8513 | ACATGGAA GGCTAGCTACAACGA CACCACAG | 19065 |
| 750 | GUGAUUCC A UGUCUCGG | 6202 | CCGAGACA GGCTAGCTACAACGA GGAATCAC | 19066 |
| 752 | GAUUCCAU G UCUCGGGU | 8514 | ACCCGAGA GGCTAGCTACAACGA ATGGAATC | 19067 |
| 759 | UGUCUCGG G UCCAUUUC | 8515 | GAAATGGA GGCTAGCTACAACGA CCGAGACA | 19068 |
| 763 | UCGGGUCC A UUUCAAAU | 6205 | ATTTGAAA GGCTAGCTACAACGA GGACCCGA | 19069 |
| 770 | CAUUUCAA A UCUCAACG | 8516 | CGTTGAGA GGCTAGCTACAACGA TTGAAATG | 19070 |
| 776 | AAAUCUCA A CGUGUCAC | 8517 | GTGACACG GGCTAGCTACAACGA TGAGATTT | 19071 |
| 778 | AUCUCAAC G UGUCACUU | 8518 | AAGTGACA GGCTAGCTACAACGA GTTGAGAT | 19072 |
| 780 | CUCAACGU G UCACUUUG | 8519 | CAAAGTGA GGCTAGCTACAACGA ACGTTGAG | 19073 |
| 783 | AACGUGUC A CUUUGUGC | 6209 | GCACAAAG GGCTAGCTACAACGA GACACGTT | 19074 |
| 788 | GUCACUUU G UGCAAGAU | 8520 | ATCTTGCA GGCTAGCTACAACGA AAAGTGAC | 19075 |
| 790 | CACUUUGU G CAAGAUAC | 8521 | GTATCTTG GGCTAGCTACAACGA ACAAAGTG | 19076 |
| 795 | UGUGCAAG A UACCCAGA | 8522 | TCTGGGTA GGCTAGCTACAACGA CTTGCACA | 19077 |
| 797 | UGCAAGAU A CCCAGAAA | 1589 | TTTCTGGG GGCTAGCTACAACGA ATCTTGCA | 19078 |
| 810 | GAAAAGAG A UUUGUUCC | 8523 | GGAACAAA GGCTAGCTACAACGA CTCTTTTC | 19079 |
| 814 | AGAGAUUU G UUCCUGAU | 8524 | ATCAGGAA GGCTAGCTACAACGA AAATCTCT | 19080 |
| 821 | UGUUCCUG A UGGUAACA | 8525 | TGTTACCA GGCTAGCTACAACGA CAGGAACA | 19081 |
| 824 | UCCUGAUG G UAACAGAA | 8526 | TTCTGTTA GGCTAGCTACAACGA CATCAGGA | 19082 |
| 827 | UGAUGGUA A CAGAAUUU | 8527 | AAATTCTG GGCTAGCTACAACGA TACCATCA | 19083 |
| 832 | GUAACAGA A UUUCCUGG | 8528 | CCAGGAAA GGCTAGCTACAACGA TCTGTTAC | 19084 |
| 842 | UUCCUGGG A CAGCAAGA | 8529 | TCTTGCTG GGCTAGCTACAACGA CCCAGGAA | 19085 |
| 845 | CUGGGACA G CAAGAAGG | 8530 | CCTTCTTG GGCTAGCTACAACGA TGTCCCAG | 19086 |
| 854 | CAAGAAGG G CUUUACUA | 8531 | TAGTAAAG GGCTAGCTACAACGA CCTTCTTG | 19087 |
| 859 | AGGGCUUU A CUAUUCCC | 1600 | GGGAATAG GGCTAGCTACAACGA AAAGCCCT | 19088 |

TABLE XXII-continued

Human KDR DNAzyme and Substrate sequence

| Pos | Substrate | Seq ID No | DNAzyme | Seq ID No |
|---|---|---|---|---|
| 862 | GCUUUACU A UUCCCAGC | 1601 | GCTGGGAA GGCTAGCTACAACGA AGTAAAGC | 19089 |
| 869 | UAUUCCCA G CUACAUGA | 8532 | TCATGTAG GGCTAGCTACAACGA TGGGAATA | 19090 |
| 872 | UCCCAGCU A CAUGAUCA | 1604 | TGATCATG GGCTAGCTACAACGA AGCTGGGA | 19091 |
| 874 | CCAGCUAC A UGAUCAGC | 6228 | GCTGATCA GGCTAGCTACAACGA GTAGCTGG | 19092 |
| 877 | GCUACAUG A UCAGCUAU | 8533 | ATAGCTGA GGCTAGCTACAACGA CATGTAGC | 19093 |
| 881 | CAUGAUCA G CUAUGCUG | 8534 | CAGCATAG GGCTAGCTACAACGA TGATCATG | 19094 |
| 884 | GAUCAGCU A UGCUGGCA | 1606 | TGCCAGCA GGCTAGCTACAACGA AGCTGATC | 19095 |
| 886 | UCAGCUAU G CUGGCAUG | 8535 | CATGCCAG GGCTAGCTACAACGA ATAGCTGA | 19096 |
| 890 | CUAUGCUG G CAUGGUCU | 8536 | AGACCATG GGCTAGCTACAACGA CAGCATAG | 19097 |
| 892 | AUGCUGGC A UGGUCUUC | 6232 | GAAGACCA GGCTAGCTACAACGA GCCAGCAT | 19098 |
| 895 | CUGGCAUG G UCUUCUGU | 8537 | ACAGAAGA GGCTAGCTACAACGA CATGCCAG | 19099 |
| 902 | GGUCUUCU G UGAAGCAA | 8538 | TTGCTTCA GGCTAGCTACAACGA AGAAGACC | 19100 |
| 907 | UCUGUGAA G CAAAAAUU | 8539 | AATTTTTG GGCTAGCTACAACGA TTCACAGA | 19101 |
| 913 | AAGCAAAA A UUAAUGAU | 8540 | ATCATTAA GGCTAGCTACAACGA TTTTGCTT | 19102 |
| 917 | AAAAAUUA A UGAUGAAA | 8541 | TTTCATCA GGCTAGCTACAACGA TAATTTTT | 19103 |
| 920 | AAUUAAUG A UGAAAGUU | 8542 | AACTTTCA GGCTAGCTACAACGA CATTAATT | 19104 |
| 926 | UGAUGAAA G UUACCAGU | 8543 | ACTGGTAA GGCTAGCTACAACGA TTTCATCA | 19105 |
| 929 | UGAAAGUU A CCAGUCUA | 1613 | TAGACTGG GGCTAGCTACAACGA AACTTTCA | 19160 |
| 933 | AGUUACCA G UCUAUUAU | 8544 | ATAATAGA GGCTAGCTACAACGA TGGTAACT | 19107 |
| 937 | ACCAGUCU A UUAUGUAC | 1615 | GTACATAA GGCTAGCTACAACGA AGACTGGT | 19108 |
| 940 | AGUCUAUU A UGUACAUA | 1617 | TATGTACA GGCTAGCTACAACGA AATAGACT | 19109 |
| 942 | UCUAUUAU G UACAUAGU | 8545 | ACTATGTA GGCTAGCTACAACGA ATAATAGA | 19110 |
| 944 | UAUUAUGU A CAUAGUUG | 1618 | CAACTATG GGCTAGCTACAACGA ACATAATA | 19111 |
| 946 | UUAUGUAC A UAGUUGUC | 6239 | GACAACTA GGCTAGCTACAACGA GTACATAA | 19112 |
| 949 | UGUACAUA G UUGUCGUU | 8546 | AACGACAA GGCTAGCTACAACGA TATGTACA | 19113 |
| 952 | ACAUAGUU G UCGUUGUA | 8547 | TACAACGA GGCTAGCTACAACGA AACTATGT | 19114 |
| 955 | UAGUUGUC G UUGUAGGG | 8548 | CCCTACAA GGCTAGCTACAACGA GACAACTA | 19115 |
| 958 | UUGUCGUU G UAGGGUAU | 8549 | ATACCCTA GGCTAGCTACAACGA AACGACAA | 19116 |
| 963 | GUUGUAGG G UAUAGGAU | 8550 | ATCCTATA GGCTAGCTACAACGA CCTACAAC | 19117 |
| 965 | UGUAGGGU A UAGGAUUU | 1624 | AAATCCTA GGCTAGCTACAACGA ACCCTACA | 19118 |
| 970 | GGUAUAGG A UUUAUGAU | 8551 | ATCATAAA GGCTAGCTACAACGA CCTATACC | 19119 |
| 974 | UAGGAUUU A UGAUGUGG | 1628 | CCACATCA GGCTAGCTACAACGA AAATCCTA | 19120 |
| 977 | GAUUUAUG A UGUGGUUC | 8552 | GAACCACA GGCTAGCTACAACGA CATAAATC | 19121 |
| 979 | UUUAUGAU G UGGUUCUG | 8553 | CAGAACCA GGCTAGCTACAACGA ATCATAAA | 19122 |
| 982 | AUGAUGUG G UUCUGAGU | 8554 | ACTCAGAA GGCTAGCTACAACGA CACATCAT | 19123 |
| 989 | GGUUCUGA G UCCGUCUC | 8555 | GAGACGGA GGCTAGCTACAACGA TCAGAACC | 19124 |
| 993 | CUGAGUCC G UCUCAUGG | 8556 | CCATGAGA GGCTAGCTACAACGA GGACTCAG | 19125 |

TABLE XXII-continued

Human KDR DNAzyme and Substrate sequence

| Pos | Substrate | Seq ID No | DNAzyme | Seq ID No |
|---|---|---|---|---|
| 998 | UCCGUCUC A UGGAAUUG | 6243 | CAATTCCA GGCTAGCTACAACGA GAGACGGA | 19126 |
| 1003 | CUCAUGGA A UUGAACUA | 8557 | TAGTTCAA GGCTAGCTACAACGA TCCATGAG | 19127 |
| 1008 | GGAAUUGA A CUAUCUGU | 8558 | ACAGATAG GGCTAGCTACAACGA TCAATTCC | 19128 |
| 1011 | AUUGAACU A UCUGUUGG | 1635 | CCAACAGA GGCTAGCTACAACGA AGTTCAAT | 19129 |
| 1015 | AACUAUCU G UUGGAGAA | 8559 | TTCTCCAA GGCTAGCTACAACGA AGATAGTT | 19130 |
| 1026 | GGAGAAAA G CUUGUCUU | 8560 | AAGACAAG GGCTAGCTACAACGA TTTTCTCC | 19131 |
| 1030 | AAAAGCUU G UCUUAAAU | 8561 | ATTTAAGA GGCTAGCTACAACGA AAGCTTTT | 19132 |
| 1037 | UGUCUUAA A UUGUACAG | 8562 | CTGTACAA GGCTAGCTACAACGA TTAAGACA | 19133 |
| 1040 | CUUAAAUU G UACAGCAA | 8563 | TTGCTGTA GGCTAGCTACAACGA AATTTAAG | 19134 |
| 1042 | UAAAUUGU A CAGCAAGA | 1643 | TCTTGCTG GGCTAGCTACAACGA ACAATTTA | 19135 |
| 1045 | AUUGUACA G CAAGAACU | 8564 | AGTTCTTG GGCTAGCTACAACGA TGTACAAT | 19136 |
| 1051 | CAGCAAGA A CUGAACUA | 8565 | TAGTTCAG GGCTAGCTACAACGA TCTTGCTG | 19137 |
| 1056 | AGAACUGA A CUAAAUGU | 8566 | ACATTTAG GGCTAGCTACAACGA TCAGTTCT | 19138 |
| 1061 | UGAACUAA A UGUGGGA | 8567 | TCCCCACA GGCTAGCTACAACGA TTAGTTCA | 19139 |
| 1063 | AACUAAAU G UGGGGAUU | 8568 | AATCCCCA GGCTAGCTACAACGA ATTTAGTT | 19140 |
| 1069 | AUGUGGGG A UUGACUUC | 8569 | GAAGTCAA GGCTAGCTACAACGA CCCCACAT | 19141 |
| 1073 | CGGGAUUG A CUUCAACU | 8570 | AGTTGAAG GGCTAGCTACAACGA CAATCCCC | 19142 |
| 1079 | UGACUUCA A CUGGGAAU | 8571 | ATTCCCAG GGCTAGCTACAACGA TGAAGTCA | 19143 |
| 1086 | AACUGGGA A UACCCUUC | 8572 | GAAGGGTA GGCTAGCTACAACGA TCCCAGTT | 19144 |
| 1088 | CUGGGAAU A CCCUUCUU | 1648 | AAGAAGGG GGCTAGCTACAACGA ATTCCCAG | 19145 |
| 1101 | UCUUCGAA G CAUCAGCA | 8573 | TGCTGATG GGCTAGCTACAACGA TTCGAAGA | 19146 |
| 1103 | UUCGAAGC A UCAGCAUA | 6259 | TATGCTGA GGCTAGCTACAACGA GCTTCGAA | 19147 |
| 1107 | AAGCAUCA G CAUAAGAA | 8574 | TTCTTATG GGCTAGCTACAACGA TGATGCTT | 19148 |
| 1109 | GCAUCAGC A UAAGAAAC | 6261 | GTTTCTTA GGCTAGCTACAACGA GCTGATGC | 19149 |
| 1116 | CAUAAGAA A CUUGUAAA | 8575 | TTTACAAG GGCTAGCTACAACGA TTCTTATG | 19150 |
| 1120 | AGAAACUU G UAAACCGA | 8576 | TCGGTTTA GGCTAGCTACAACGA AAGTTTCT | 19151 |
| 1124 | ACUUGUAA A CCGAGACC | 8577 | GGTCTCGG GGCTAGCTACAACGA TTACAAGT | 19152 |
| 1130 | AAACCGAG A CCUAAAAA | 8578 | TTTTTAGG GGCTAGCTACAACGA CTCGGTTT | 19153 |
| 1138 | ACCUAAAA A CCCAGUCU | 8579 | AGACTGGG GGCTAGCTACAACGA TTTTAGGT | 19154 |
| 1143 | AAACCCA G UCUGGGAG | 8580 | CTCCCAGA GGCTAGCTACAACGA TGGGTTTT | 19155 |
| 1151 | GUCUGGGA G UGAGAUGA | 8581 | TCATCTCA GGCTAGCTACAACGA TCCCAGAC | 19156 |
| 1156 | GGAGUGAG A UGAAGAAA | 8582 | TTTCTTCA GGCTAGCTACAACGA CTCACTCC | 19157 |
| 1164 | AUGAAGAA A UUUUUGAG | 8583 | CTCAAAAA GGCTAGCTACAACGA TTCTTCAT | 19158 |
| 1172 | AUUUUUGA G CACCUUAA | 8584 | TTAAGGTG GGCTAGCTACAACGA TCAAAAAT | 19159 |
| 1174 | UUUUGAGC A CCUUAACU | 6270 | AGTTAAGG GGCTAGCTACAACGA GCTCAAAA | 19160 |
| 1180 | GCACCUUA A CUAUAGAU | 8585 | ATCTATAG GGCTAGCTACAACGA TAAGGTGC | 19161 |
| 1183 | CCUUAACU A UAGAUGGU | 1665 | ACCATCTA GGCTAGCTACAACGA AGTTAAGG | 19162 |

TABLE XXII-continued

Human KDR DNAzyme and Substrate sequence

| Pos | Substrate | Seq ID No | DNAzyme | Seq ID No |
|---|---|---|---|---|
| 1187 | AACUAUAG A UGGUGUAA | 8586 | TTACACCA GGCTAGCTACAACGA CTATAGTT | 19163 |
| 1190 | UAUAGAUG G UGUAACCC | 8587 | GGGTTACA GGCTAGCTACAACGA CATCTATA | 19164 |
| 1192 | UAGAUGGU G UAACCCGG | 8588 | CCGGGTTA GGCTAGCTACAACGA ACCATCTA | 19165 |
| 1195 | AUGGUGUA A CCCGGAGU | 8589 | ACTCCGGG GGCTAGCTACAACGA TACACCAT | 19166 |
| 1202 | AACCCGGA G UGACCAAG | 8590 | CTTGGTCA GGCTAGCTACAACGA TCCGGGTT | 19167 |
| 1205 | CCGGAGUG A CCAAGGAU | 8591 | ATCCTTGG GGCTAGCTACAACGA CACTCCGG | 19168 |
| 1212 | GACCAAGG A UUGUACAC | 8592 | GTGTACAA GGCTAGCTACAACGA CCTTGGTC | 19169 |
| 1215 | CAAGGAUU G UACACCUG | 8593 | CAGGTGTA GGCTAGCTACAACGA AATCCTTG | 19170 |
| 1217 | AGGAUUGU A CACCUGUG | 1669 | CACAGGTG GGCTAGCTACAACGA ACAATCCT | 19171 |
| 1219 | GAUUGUAC A CCUGUGCA | 6278 | TGCACAGG GGCTAGCTACAACGA GTACAATC | 19172 |
| 1223 | GUACACCU G UGCAGCAU | 8594 | ATGCTGCA GGCTAGCTACAACGA AGGTGTAC | 19173 |
| 1225 | ACACCUGU G CAGCAUCC | 8595 | GGATGCTG GGCTAGCTACAACGA ACAGGTGT | 19174 |
| 1228 | CCUGUGCA G CAUCCAGU | 8596 | ACTGGATG GGCTAGCTACAACGA TGCACAGG | 19175 |
| 1230 | UGUGCAGC A UCCAGUGG | 6282 | CCACTGGA GGCTAGCTACAACGA GCTGCACA | 19176 |
| 1235 | AGCAUCCA G UGGGCUGA | 8597 | TCAGCCCA GGCTAGCTACAACGA TGGATGCT | 19177 |
| 1239 | UCCAGUGG G CUGAUGAC | 8598 | GTCATCAG GGCTAGCTACAACGA CCACTGGA | 19178 |
| 1243 | GUGGGCUG A UGACCAAG | 8599 | CTTGGTCA GGCTAGCTACAACGA CAGCCCAC | 19179 |
| 1246 | GGCUGAUG A CCAAGAAG | 8600 | CTTCTTGG GGCTAGCTACAACGA CATCAGCC | 19180 |
| 1256 | CAAGAAGA A CAGCACAU | 8601 | ATGTGCTG GGCTAGCTACAACGA TCTTCTTG | 19181 |
| 1259 | GAAGAACA G CACAUUUG | 8602 | CAAATGTG GGCTAGCTACAACGA TGTTCTTC | 19182 |
| 1261 | AGAACAGC A CAUUUGUC | 6289 | GACAAATG GGCTAGCTACAACGA GCTGTTCT | 19183 |
| 1263 | AACAGCAC A UUUGUCAG | 6290 | CTGACAAA GGCTAGCTACAACGA GTGCTGTT | 19184 |
| 1267 | GCACAUUU G UCAGGGUC | 8603 | GACCCTGA GGCTAGCTACAACGA AAATGTGC | 19185 |
| 1273 | UUGUCAGG G UCCAUGAA | 8604 | TTCATGGA GGCTAGCTACAACGA CCTGACAA | 19186 |
| 1277 | CAGGGUCC A UGAAAAAC | 6293 | GTTTTTCA GGCTAGCTACAACGA GGACCCTG | 19187 |
| 1284 | CAUGAAAA A CCUUUUGU | 8605 | ACAAAAGG GGCTAGCTACAACGA TTTTCATG | 19188 |
| 1291 | AACCUUUU G UUGCUUUU | 8606 | AAAAGCAA GGCTAGCTACAACGA AAAAGGTT | 19189 |
| 1294 | CUUUUGUU G CUUUUGGA | 8607 | TCCAAAAG GGCTAGCTACAACGA AACAAAAG | 19190 |
| 1304 | UUUUGGAA G UGGCAUGG | 8608 | CCATGCCA GGCTAGCTACAACGA TTCCAAAA | 19191 |
| 1307 | UGGAAGUG G CAUGGAAU | 8609 | ATTCCATG GGCTAGCTACAACGA CACTTCCA | 19192 |
| 1309 | GAAGUGGC A UGGAAUCU | 6297 | AGATTCCA GGCTAGCTACAACGA GCCACTTC | 19193 |
| 1314 | GGCAUGGA A UCUCUGGU | 8610 | ACCAGAGA GGCTAGCTACAACGA TCCATGCC | 19194 |
| 1321 | AAUCUCUG G UGGAAGCC | 8611 | GGCTTCCA GCCTAGCTACAACGA CAGAGATT | 19195 |
| 1327 | UGGUGGAA G CCACGGUG | 8612 | CACCGTGG GGCTAGCTACAACGA TTCCACCA | 19196 |
| 1330 | UGGAAGCC A CGGUGGGG | 6301 | CCCCACCG GGCTAGCTACAACGA GGCTTCCA | 19197 |
| 1333 | AAGCCACG G UGGGGGAG | 8613 | CTCCCCCA GGCTAGCTACAACGA CGTGGCTT | 19198 |
| 1341 | GUGGGGGA G CGUGUCAG | 8614 | CTGACACG GGCTAGCTACAACGA TCCCCCAC | 19199 |

TABLE XXII-continued

Human KDR DNAzyme and Substrate sequence

| Pos | Substrate | Seq ID No | DNAzyme | Seq ID No |
|---|---|---|---|---|
| 1343 | GGGGGAGC G UGUCAGAA | 8615 | TTCTGACA GGCTAGCTACAACGA GCTCCCCC | 19200 |
| 1345 | GGGAGCGU G UCAGAAUC | 8616 | GATTCTGA GGCTAGCTACAACGA ACGCTCCC | 19201 |
| 1351 | GUGUCAGA A UCCCUGCG | 8617 | CGCAGGGA GGCTAGCTACAACGA TCTGACAC | 19202 |
| 1357 | GAAUCCCU G CGAAGUAC | 8618 | GTACTTCG GGCTAGCTACAACGA AGGGATTC | 19203 |
| 1362 | CCUGCGAA U ACCUUGG | 8619 | CCAAGGTA GCCTAGCTACAACGA TTCGCAGG | 19204 |
| 1364 | UGCGAAGU A CCUUGGUU | 1686 | AACCAAGG GCCTAGCTACAACGA ACTTCGCA | 19205 |
| 1370 | GUACCUUG G UUACCCAC | 8620 | GTGGGTAA GGCTAGCTACAACGA CAAGGTAC | 19206 |
| 1373 | CCUUGGUU A CCCACCCC | 1689 | GGGGTGGG GGCTAGCTACAACGA AACCAAGG | 19207 |
| 1377 | GGUUACCC A CCCCCAGA | 6310 | TCTGGGGG GGCTAGCTACAACGA GGGTAACC | 19208 |
| 1387 | CCCCAGAA A UAAAAUGG | 8621 | CCATTTTA GGCTAGCTACAACGA TTCTGGGG | 19209 |
| 1392 | GAAAUAAA A UGGUAUAA | 8622 | TTATACCA GGCTAGCTACAACGA TTTATTTC | 19210 |
| 1395 | AUAAAAUG G UAUAAAA | 8623 | TTTTTATA GGCTAGCTACAACGA CATTTTAT | 19211 |
| 1397 | AAAAUGGU A UAAAAUG | 1691 | CATTTTTA GGCTAGCTACAACGA ACCATTTT | 19212 |
| 1403 | GUAUAAAA A UGGAAUAC | 8624 | GTATTCCA GGCTAGCTACAACGA TTTTATAC | 19213 |
| 1408 | AAAAUGGA A UACCCCUU | 8625 | AAGGGGTA GGCTAGCTACAACGA TCCATTTT | 19214 |
| 1410 | AAUGGAAU A CCCCUUGA | 1693 | TCAAGGGG GGCTAGCTACAACGA ATTCCATT | 19215 |
| 1419 | CCCCUUGA G UCCAAUCA | 8626 | TGATTGGA GGCTAGCTACAACGA TCAAGGGG | 19216 |
| 1424 | UGAGUCCA A UCACACAA | 8627 | TTGTGTGA GGCTAGCTACAACGA TGGACTCA | 19217 |
| 1427 | GUCCAAUC A CACAAUUA | 6322 | TAATTGTG GGCTAGCTACAACGA GATTGGAC | 19218 |
| 1429 | CCAAUCAC A CAAUUAAA | 6323 | TTTAATTG GGCTAGCTACAACGA GTCATTGG | 19219 |
| 1432 | AUCACACA A UUAAAGCG | 8628 | CGCTTTAA GGCTAGCTACAACGA TGTGTGAT | 19220 |
| 1438 | CAAUUAAA G CGGGGCAU | 8629 | ATGCCCCG GGCTAGCTACAACGA TTTAATTG | 19221 |
| 1443 | AAAGCGGG G CAUGUACU | 8630 | AGTACATG GGCTAGCTACAACGA CCCGCTTT | 19222 |
| 1445 | AGCGGGGC A UGUACUGA | 6325 | TCAGTACA GGCTAGCTACAACGA GCCCCGCT | 19223 |
| 1447 | CGGGGCAU G UACUGACG | 8631 | CGTCAGTA GGCTAGCTACAACGA ATGCCCCG | 19224 |
| 1449 | GGGCAUGU A CUGACGAU | 1699 | ATCGTCAG GGCTAGCTACAACGA ACATGCCC | 19225 |
| 1453 | AUGUACUG A CGAUUAUG | 8632 | CATAATCG GCCTAGCTACAACGA CAGTACAT | 19226 |
| 1456 | UACUGACG A UUAUGGAA | 8633 | TTCCATAA GGCTAGCTACAACGA CGTCAGTA | 19227 |
| 1459 | UGACGAUU A UGGAAGUG | 1701 | CACTTCCA GGCTAGCTACAACGA AATCGTCA | 19228 |
| 1465 | UUAUGGAA G UGAGUGAA | 8634 | TTCACTCA GGCTAGCTACAACGA TTCCATAA | 19229 |
| 1469 | GGAAGUGA G UGAAAGAG | 8635 | CTCTTTCA GGCTAGCTACAACGA TCACTTCC | 19230 |
| 1478 | UGAAAGAG A CACAGGAA | 8636 | TTCCTGTG GCCTAGCTACAACGA CTCTTTCA | 19231 |
| 1480 | AAAGAGAC A CAGGAAAU | 6327 | ATTTCCTG GGCTAGCTACAACGA GTCTCTTT | 19232 |
| 1487 | CACAGGAA A UUACACUG | 8637 | CAGTGTAA GGCTAGCTACAACGA TTCCTGTG | 19233 |
| 1490 | AGGAAAUU A CACUGUCA | 1703 | TGACAGTG GGCTAGCTACAACGA AATTTCCT | 19234 |
| 1492 | GAAAUUAC A CUGUCAUC | 6329 | GATGACAG GGCTAGCTACAACGA GTAATTTC | 19235 |
| 1495 | AUUACACU G UCAUCCUU | 8638 | AAGGATGA GGCTAGCTACAACGA AGTGTAAT | 19236 |

TABLE XXII-continued

Human KDR DNAzyme and Substrate sequence

| Pos | Substrate | Seq ID No | DNAzyme | Seq ID No |
|---|---|---|---|---|
| 1498 | ACACUGUC A UCCUUACC | 6331 | GGTAAGGA GGCTAGCTACAACGA GACAGTGT | 19237 |
| 1504 | UCAUCCUU A CCAAUCCC | 1707 | GGGATTGG GGCTAGCTACAACGA AAGGATGA | 19238 |
| 1508 | CCUUACCA A UCCCAUUU | 8639 | AAATGGGA GGCTAGCTACAACGA TGGTAAGG | 19239 |
| 1513 | CCAAUCCC A UUUCAAAG | 6338 | CTTTGAAA GGCTAGCTACAACGA GGGATTGG | 19240 |
| 1527 | AAGGAGAA G CAGAGCCA | 8640 | TGGCTCTG GGCTAGCTACAACGA TTCTCCTT | 19241 |
| 1532 | GAAGCAGA G CCAUGUGG | 8641 | CCACATGG GGCTAGCTACAACGA TCTGCTTC | 19242 |
| 1535 | GCAGAGCC A UGUGGUCU | 6342 | AGACCACA GGCTAGCTACAACGA GGCTCTGC | 19243 |
| 1537 | AGAGCCAU G UGGUCUCU | 8642 | AGAGACCA GGCTAGCTACAACGA ATGGCTCT | 19244 |
| 1540 | GCCAUGUG G UCUCUCUG | 8643 | CAGAGAGA GGCTAGCTACAACGA CACATGGC | 19245 |
| 1549 | UCUCUCUG G UUGUGUAU | 8644 | ATACACAA GGCTAGCTACAACGA CAGAGAGA | 19246 |
| 1552 | CUCUGGUU G UGUAUGUC | 8645 | GACATACA GGCTAGCTACAACGA AACCAGAG | 19247 |
| 1554 | CUGGUUGU G UAUGUCCC | 8646 | GGGACATA GGCTAGCTACAACGA ACAACCAG | 19248 |
| 1556 | GGUUGUGU A UGUCCCAC | 1716 | GTGGGACA GGCTAGCTACAACGA ACACAACC | 19249 |
| 1558 | UUGUGUAU G UCCCACCC | 8647 | GGGTGGGA GGCTAGCTACAACGA ATACACAA | 19250 |
| 1563 | UAUGUCCC A CCCCAGAU | 6348 | ATCTGGGG GGCTAGCTACAACGA GGGACATA | 19251 |
| 1570 | CACCCCAG A UUGGUGAG | 8648 | CTCACCAA GGCTAGCTACAACGA CTGGGGTG | 19252 |
| 1574 | CCAGAUUG G UGAGAAAU | 8649 | ATTTCTCA GGCTAGCTACAACGA CAATCTGG | 19253 |
| 1581 | GGUGAGAA A UCUCUAAU | 8650 | ATTAGAGA GGCTAGCTACAACGA TTCTCACC | 19254 |
| 1588 | AAUCUCUA A UCUCUCCU | 8651 | AGGAGAGA GGCTAGCTACAACGA TAGAGATT | 19255 |
| 1597 | UCUCUCCU G UGGAUUCC | 8652 | GGAATCCA GGCTAGCTACAACGA AGGAGAGA | 19256 |
| 1601 | UCCUGUGG A UUCCUACC | 8653 | GGTAGGAA GGCTAGCTACAACGA CCACAGGA | 19257 |
| 1607 | GGAUUCCU A CCAGUACG | 1727 | CGTACTGG GGCTAGCTACAACGA AGGAATCC | 19258 |
| 1611 | UCCUACCA G UACGGCAC | 8654 | GTGCCGTA GGCTAGCTACAACGA TGGTAGGA | 19259 |
| 1613 | CUACCAGU A CGGCACCA | 1728 | TGGTGCCG GGCTAGCTACAACGA ACTGGTAG | 19260 |
| 1616 | CCAGUACG G CACCACUC | 8655 | GAGTGGTG GGCTAGCTACAACGA CGTACTGG | 19261 |
| 1618 | AGUACGGC A CCACUCAA | 6363 | TTGAGTGG GGCTAGCTACAACGA GCCGTACT | 19262 |
| 1621 | ACGGCACC A CUCAAACG | 6365 | CGTTTGAG GGCTAGCTACAACGA GGTGCCGT | 19263 |
| 1627 | CCACUCAA A CGCUGACA | 8656 | TGTCAGCG GGCTAGCTACAACGA TTGAGTGG | 19264 |
| 1629 | ACUCAAAC G CUGACAUG | 8657 | CATGTCAG GGCTAGCTACAACGA GTTTGAGT | 19265 |
| 1633 | AAACGCUG A CAUGUACG | 8658 | CGTACATG GGCTAGCTACAACGA CAGCGTTT | 19266 |
| 1635 | ACGCUGAC A UGUACGGU | 6369 | ACCGTACA GGCTAGCTACAACGA GTCAGCGT | 19267 |
| 1637 | GCUGACAU G UACGGUCU | 8659 | AGACCGTA GGCTAGCTACAACGA ATGTCAGC | 19268 |
| 1639 | UGACAUGU A CGGUCUAU | 1730 | ATAGACCG GGCTAGCTACAACGA ACATGTCA | 19269 |
| 1642 | CAUGUACG G UCUAUGCC | 8660 | GGCATAGA GGCTAGCTACAACGA CGTACATG | 19270 |
| 1646 | UACGGUCU A UGCCAUUC | 1732 | GAATGGCA GGCTAGCTACAACGA AGACCGTA | 19271 |
| 1648 | CGGUCUAU G CCAUUCCU | 8661 | AGGAATGG GGCTAGCTACAACGA ATAGACCG | 19272 |
| 1651 | UCUAUGCC A UUCCUCCC | 6372 | GGGAGGAA GGCTAGCTACAACGA GGCATAGA | 19273 |

TABLE XXII-continued

Human KDR DNAzyme and Substrate sequence

| Pos | Substrate | Seq ID No | DNAzyme | Seq ID No |
|---|---|---|---|---|
| 1662 | CCUCCCCC G CAUCACAU | 8662 | ATGTGATG GGCTAGCTACAACGA GGGGGAGG | 19274 |
| 1664 | UCCCCCGC A UCACAUCC | 6379 | GGATGTGA GGCTAGCTACAACGA GCGGGGGA | 19275 |
| 1667 | CCCGCAUC A CAUCCACU | 6380 | AGTGGATG GGCTAGCTACAACGA GATGCGGG | 19276 |
| 1669 | CGCAUCAC A UCCACUGG | 6381 | CCAGTGGA GGCTAGCTACAACGA GTGATGCG | 19277 |
| 1673 | UCACAUCC A CUGGUAUU | 6383 | AATACCAG GGCTAGCTACAACGA GGATGTGA | 19278 |
| 1677 | AUCCACUG G UAUUGGCA | 8663 | TGCCAATA GGCTAGCTACAACGA CAGTGGAT | 19279 |
| 1679 | CCACUGGU A UUGGCAGU | 1738 | ACTGCCAA GGCTAGCTACAACGA ACCAGTGG | 19280 |
| 1683 | UGGUAUUG G CAGUUGGA | 8664 | TCCAACTG GGCTAGCTACAACGA CAATACCA | 19281 |
| 1686 | UAUUGGCA G UGGAGGA | 8665 | TCCTCCAA GGCTAGCTACAACGA TGCCAATA | 19282 |
| 1698 | GAGGAAGA G UGCGCCAA | 8666 | TTGGCGCA GGCTAGCTACAACGA TCTTCCTC | 19283 |
| 1700 | GGAAGAGU G CGCCAACG | 8667 | CGTTGGCG GGCTAGCTACAACGA ACTCTTCC | 19284 |
| 1702 | AAGAGUGC G CCAACGAG | 8668 | CTCGTTGC GGCTAGCTACAACGA GCACTCTT | 19285 |
| 1706 | GUGCGCCA A CGAGCCCA | 8669 | TGGGCTCG GGCTAGCTACAACGA TGGCGCAC | 19286 |
| 1710 | GCCAACGA G CCCAGCCA | 8670 | TGGCTGGG GGCTAGCTACAACGA TCGTTGGC | 19287 |
| 1715 | CGAGCCCA G CCAAGCUG | 8671 | CAGCTTGG GGCTAGCTACAACGA TGGGCTCG | 19288 |
| 1720 | CCAGCCAA G CUGUCUCA | 8672 | TGAGACAG GGCTAGCTACAACGA TTGGCTGG | 19289 |
| 1723 | GCCAAGCU G UCUCAGUG | 8673 | CACTGAGA GGCTAGCTACAACGA AGCTTGGC | 19290 |
| 1729 | CUGUCUCA G UGACAAAC | 8674 | GTTTGTCA GGCTAGCTACAACGA TGAGACAG | 19291 |
| 1732 | UCUCAGUG A CAAACCCA | 8675 | TGGGTTTG GGCTAGCTACAACGA CACTGAGA | 19292 |
| 1736 | AGUGACAA A CCCAUACC | 8676 | GGTATGGG GGCTAGCTACAACGA TTGTCACT | 19293 |
| 1740 | ACAAACCC A UACCCUUG | 6399 | CAAGGGTA GGCTAGCTACAACGA GGGTTTGT | 19294 |
| 1742 | AAACCCAU A CCCUUGUG | 1743 | CACAAGGG GGCTAGCTACAACGA ATGGGTTT | 19295 |
| 1748 | AUACCCUU G UGAAGAAU | 8677 | ATTCTTCA GGCTAGCTACAACGA AAGGGTAT | 19296 |
| 1755 | UGUGAAGA A UGGAGAAG | 8678 | CTTCTCCA GGCTAGCTACAACGA TCTTCACA | 19297 |
| 1763 | AUGGAGAA G UGUGGAGG | 8679 | CCTCCACA GGCTAGCTACAACGA TTCTCCAT | 19298 |
| 1765 | GGAGAAGU G UGGAGGAC | 8680 | GTCCTCCA GGCTAGCTACAACGA ACTTCTCC | 19299 |
| 1772 | UGUGGAGG A CUUCCAGG | 8681 | CCTGGAAG GGCTAGCTACAACGA CCTCCACA | 19300 |
| 1787 | GGGAGGAA A UAAAAUUG | 8682 | CAATTTTA GGCTAGCTACAACGA TTCCTCCC | 19301 |
| 1792 | GAAAUAAA A UUGAAGUU | 8683 | AACTTCAA GGCTAGCTACAACGA TTTATTTC | 19302 |
| 1798 | AAAUUGAA G UUAAUAAA | 8684 | TTTATTAA GGCTAGCTACAACGA TTCAATTT | 19303 |
| 1802 | UGAAGUUA A UAAAAAUC | 8685 | GATTTTTA GGCTAGCTACAACGA TAACTTCA | 19304 |
| 1808 | UAAUAAAA A UCAAUUUG | 8686 | CAAATTGA GGCTAGCTACAACGA TTTTATTA | 19305 |
| 1812 | AAAAAUCA A UUUGCUCU | 8687 | AGAGCAAA GGCTAGCTACAACGA TGATTTTT | 19306 |
| 1816 | AUCAAUUU G CUCUAAUU | 8688 | AATTAGAG GGCTAGCTACAACGA AAATTGAT | 19307 |
| 1822 | UUGCUCUA A UUGAAGGA | 8689 | TCCTTCAA GGCTAGCTACAACGA TAGAGCAA | 19308 |
| 1835 | AGGAAAAA A CAAAACUG | 8690 | CAGTTTTG GGCTAGCTACAACGA TTTTTCCT | 19309 |
| 1840 | AAAACAAA A CUGUAAGU | 8691 | ACTTACAG GCCTAGCTACAACGA TTTGTTTT | 19310 |

TABLE XXII-continued

Human KDR DNAzyme and Substrate sequence

| Pos | Substrate | Seq ID No | DNAzyme | Seq ID No |
|---|---|---|---|---|
| 1843 | ACAAAACU G UAAGUACC | 8692 | GGTACTTA GGCTAGCTACAACGA AGTTTTGT | 19311 |
| 1847 | AACUGUAA G UACCCUUG | 8693 | CAAGGGTA GGCTAGCTACAACGA TTACAGTT | 19312 |
| 1849 | CUGUAAGU A CCCUUGUU | 1759 | AACAAGGG GGCTAGCTACAACGA ACTTACAG | 19313 |
| 1855 | GUACCCUU G UUAUCCAA | 8694 | TTGGATAA GGCTAGCTACAACGA AAGGGTAC | 19314 |
| 1858 | CCCUUGUU A UCCAAGCG | 1762 | CGCTTGGA GGCTAGCTACAACGA AACAAGGG | 19315 |
| 1864 | UUAUCCAA G CGGCAAAU | 8695 | ATTTGCCG GGCTAGCTACAACGA TTGGATAA | 19316 |
| 1867 | UCCAAGCG G CAAAUGUG | 8696 | CACATTTG GGCTAGCTACAACGA CGCTTGGA | 19317 |
| 1871 | AGCGGCAA A UCUGUCAG | 8697 | CTGACACA GGCTAGCTACAACGA TTGCCGCT | 19318 |
| 1873 | CGGCAAAU G UGUCAGCU | 8698 | AGCTGACA GGCTAGCTACAACGA ATTTGCCG | 19319 |
| 1875 | GCAAAUGU G UCAGCUUU | 8699 | AAAGCTGA GGCTAGCTACAACGA ACATTTGC | 19320 |
| 1879 | AUGUGUCA G CUUUGUAC | 8700 | GTACAAAG GGCTAGCTACAACGA TGACACAT | 19321 |
| 1884 | UCAGCUUU G UACAAAUG | 8701 | CATTTGTA GGCTAGCTACAACGA AAAGCTGA | 19322 |
| 1886 | AGCUUUGU A CAAAUGUG | 1767 | CACATTTG GGCTAGCTACAACGA ACAAAGCT | 19323 |
| 1890 | UUGUACAA A UGUGAAGC | 8702 | GCTTCACA GGCTAGCTACAACGA TTGTACAA | 19324 |
| 1892 | GUACAAAU G UGAAGCGG | 8703 | CCGCTTCA GGCTAGCTACAACGA ATTTGTAC | 19325 |
| 1897 | AAUGUGAA G CGGUCAAC | 8704 | GTTGACCG GGCTAGCTACAACGA TTCACATT | 19326 |
| 1900 | GUGAAGCG G UCAACAAA | 8705 | TTTGTTGA GGCTAGCTACAACGA CGCTTCAC | 19327 |
| 1904 | AGCGGUCA A CAAAGUCG | 8706 | CGACTTTG GCCTAGCTACAACGA TGACCGCT | 19328 |
| 1909 | UCAACAAA G UCGGGAGA | 8707 | TCTCCCGA GGCTACCTACAACGA TTTGTTGA | 19329 |
| 1927 | GAGAGAGG G UGAUCUCC | 8708 | GGAGATCA GGCTAGCTACAACGA CCTCTCTC | 19330 |
| 1930 | AGAGGGUG A UCUCCUUC | 8709 | GAAGGAGA GGCTAGCTACAACGA CACCCTCT | 19331 |
| 1940 | CUCCUUCC A CGUGACCA | 6426 | TGGTCACG GGCTAGCTACAACGA GGAAGGAG | 19332 |
| 1942 | CCUUCCAC G UGACCAGG | 8710 | CCTGGTCA GGCTAGCTACAACGA GTGGAAGG | 19333 |
| 1945 | UCCACGUG A CCAGGGGU | 8711 | ACCCCTGG GGCTAGCTACAACGA CACGTGGA | 19334 |
| 1952 | GACCAGGG G UCCUGAAA | 8712 | TTTCAGGA GGCTAGCTACAACGA CCCTGGTC | 19335 |
| 1960 | GUCCUGAA A UUACUUUG | 8713 | CAAAGTAA GGCTAGCTACAACGA TTCAGGAC | 19336 |
| 1963 | CUGAAAUU A CUUUGCAA | 1776 | TTGCAAAG GGCTAGCTACAACGA AATTTCAG | 19337 |
| 1968 | AUUACUUU G CAACCUGA | 8714 | TCAGGTTG GGCTAGCTACAACGA AAAGTAAT | 19338 |
| 1971 | ACUUUGCA A CCUGACAU | 8715 | ATGTCAGG GGCTAGCTACAACGA TGCAAAGT | 19339 |
| 1976 | GCAACCUG A CAUGCAGC | 8716 | GCTGCATG GGCTAGCTACAACGA CAGGTTGC | 19340 |
| 1978 | AACCUGAC A UGCAGCCC | 6435 | GGGCTGCA GGCTAGCTACAACGA GTCAGGTT | 19341 |
| 1980 | CCUGACAU G CAGCCCAC | 8717 | GTGGGCTG GGCTAGCTACAACGA ATGTCAGG | 19342 |
| 1983 | GACAUGCA G CCCACUGA | 8718 | TCAGTGGG GGCTAGCTACAACGA TGCATGTC | 19343 |
| 1987 | UGCAGCCC A CUGAGCAG | 6439 | CTGCTCAG GGCTAGCTACAACGA GGGCTGCA | 19344 |
| 1992 | CCCACUGA G CAGGAGAG | 8719 | CTCTCCTG GGCTAGCTACAACGA TCAGTGGG | 19345 |
| 2000 | GCAGGAGA G CGUGUCUU | 8720 | AAGACACG GGCTAGCTACAACGA TCTCCTGC | 19346 |
| 2002 | AGGAGAGC G UGUCUUUG | 8721 | CAAAGACA GGCTAGCTACAACGA GCTCTCCT | 19347 |

TABLE XXII-continued

Human KDR DNAzyme and Substrate sequence

| Pos | Substrate | Seq ID No | DNAzyme | Seq ID No |
|---|---|---|---|---|
| 2004 | GAGAGCGU G UCUUUGUG | 8722 | CACAAAGA GGCTAGCTACAACGA ACGCTCTC | 19348 |
| 2010 | GUGUCUUU G UGGUGCAC | 8723 | GTGCACCA GGCTAGCTACAACGA AAAGACAC | 19349 |
| 2013 | UCUUUGUG G UGCACUGC | 8724 | GCAGTGCA GGCTAGCTACAACGA CACAAAGA | 19350 |
| 2015 | UUUGUGGU G CACUGCAG | 8725 | CTGCAGTG GGCTAGCTACAACGA ACCACAAA | 19351 |
| 2017 | UGUGGUGC A CUGCAGAC | 6443 | GTCTGCAG GGCTAGCTACAACGA GCACCACA | 19352 |
| 2020 | GGUGCACU G CAGACAGA | 8726 | TCTGTCTG GGCTAGCTACAACGA AGTGCACC | 19353 |
| 2024 | CACUGCAG A CAGAUCUA | 8727 | TAGATCTG GGCTAGCTACAACGA CTGCAGTG | 19354 |
| 2028 | GCAGACAG A UCUACGUU | 8728 | AACGTAGA GGCTAGCTACAACGA CTGTCTGC | 19355 |
| 2032 | ACAGAUCU A CGUUUGAG | 1783 | CTCAAACG GGCTAGCTACAACGA AGATCTGT | 19356 |
| 2034 | AGAUCUAC G UUUGAGAA | 8729 | TTCTCAAA GGCTAGCTACAACGA GTAGATCT | 19357 |
| 2042 | GUUUGAGA A CCUCACAU | 8730 | ATGTGAGG GGCTAGCTACAACGA TCTCAAAC | 19358 |
| 2047 | AGAACCUC A CAUGGUAC | 6450 | GTACCATG GGCTAGCTACAACGA GAGGTTCT | 19359 |
| 2049 | AACCUCAC A UGGUACAA | 6451 | TTGTACCA GGCTAGCTACAACGA GTGAGGTT | 19360 |
| 2052 | CUCACAUG G UACAAGCU | 8731 | AGCTTGTA GGCTAGCTACAACGA CATGTGAG | 19361 |
| 2054 | CACAUGGU A CAAGCUUG | 1787 | CAAGCTTG GGCTAGCTACAACGA ACCATGTG | 19362 |
| 2058 | UGGUACAA G CUUGGCCC | 8732 | GGGCCAAG GGCTAGCTACAACGA TTGTACCA | 19363 |
| 2063 | CAAGCUUG G CCCACAGC | 8733 | GCTGTGGG GGCTAGCTACAACGA CAAGCTTG | 19364 |
| 2067 | CUUGGCCC A CAGCCUCU | 6456 | AGAGGCTG GGCTAGCTACAACGA GGGCCAAG | 19365 |
| 2070 | GGCCCACA G CCUCUGCC | 8734 | GGCAGAGG GGCTAGCTACAACGA TGTGGGCC | 19366 |
| 2076 | CAGCCUCU G CCAAUCCA | 8735 | TGGATTGG GGCTAGCTACAACGA AGAGGCTG | 19367 |
| 2080 | CUCUGCCA A UCCAUGUG | 8736 | CACATGGA GGCTAGCTACAACGA TGGCAGAG | 19368 |
| 2084 | GCCAAUCC A UGUGGGAG | 6464 | CTCCCACA GGCTAGCTACAACGA GGATTGGC | 19369 |
| 2086 | CAAUCCAU G UGGGAGAG | 8737 | CTCTCCCA GGCTAGCTACAACGA ATGGATTG | 19370 |
| 2094 | GUGGGAGA G UUGCCCAC | 8738 | GTGGGCAA GGCTAGCTACAACGA TCTCCCAC | 19371 |
| 2097 | GGAGAGUU G CCCACACC | 8739 | GGTGTGGG GGCTAGCTACAACGA AACTCTCC | 19372 |
| 2101 | AGUUGCCC A CACCUGUU | 6467 | AACAGGTG GGCTAGCTACAACGA GGGCAACT | 19373 |
| 2103 | UUGCCCAC A CCUGUUUG | 6468 | CAAACAGG GGCTAGCTACAACGA GTGGGCAA | 19374 |
| 2107 | CCACACCU G UUUGCAAG | 8740 | CTTGCAAA GGCTAGCTACAACGA AGGTGTGG | 19375 |
| 2111 | ACCUGUUU G CAAGAACU | 8741 | AGTTCTTG GGCTAGCTACAACGA AAACAGGT | 19376 |
| 2117 | UUGCAAGA A CUUGGAUA | 8742 | TATCCAAG GGCTAGCTACAACGA TCTTGCAA | 19377 |
| 2123 | GAACUUGG A UACUCUUU | 8743 | AAAGAGTA GGCTAGCTACAACGA CCAAGTTC | 19378 |
| 2125 | ACUUGGAU A CUCUUUGG | 1795 | CCAAAGAG GGCTAGCTACAACGA ATCCAAGT | 19379 |
| 2136 | CUUUGGAA A UUGAAUGC | 8744 | GCATTCAA GGCTAGCTACAACGA TTCCAAAG | 19380 |
| 2141 | GAAAUUGA A UGCCACCA | 8745 | TGGTGGCA GGCTAGCTACAACGA TCAATTTC | 19381 |
| 2143 | AAUUGAAU G CCACCAUG | 8746 | CATGGTGG GGCTAGCTACAACGA ATTCAATT | 19382 |
| 2146 | UGAAUGCC A CCAUGUUC | 6476 | GAACATGG GGCTAGCTACAACGA GGCATTCA | 19383 |
| 2149 | AUGCCACC A UGUUCUCU | 6478 | AGAGAACA GGCTAGCTACAACGA GGTGGCAT | 19384 |

TABLE XXII-continued

Human KDR DNAzyme and Substrate sequence

| Pos | Substrate | Seq ID No | DNAzyme | Seq ID No |
|---|---|---|---|---|
| 2151 | GCCACCAU G UUCUCUAA | 8747 | TTAGAGAA GGCTAGCTACAACGA ATGGTGGC | 19385 |
| 2159 | GUUCUCUA A UAGCACAA | 8748 | TTGTGCTA GGCTAGCTACAACGA TAGAGAAC | 19386 |
| 2162 | CUCUAAUA G CACAAAUG | 8749 | CATTTGTG GGCTAGCTACAACGA TATTAGAG | 19387 |
| 2164 | CUAAUAGC A CAAAUGAC | 6481 | GTCATTTG GGCTAGCTACAACGA GCTATTAG | 19388 |
| 2168 | UAGCACAA A UGACAUUU | 8750 | AAATGTCA GGCTAGCTACAACGA TTGTGCTA | 19389 |
| 2171 | CACAAAUG A CAUUUUGA | 8751 | TCAAAATG GGCTAGCTACAACGA CATTTGTG | 19390 |
| 2173 | CAAAUGAC A UUUUGAUC | 6483 | GATCAAAA GGCTAGCTACAACGA GTCATTTG | 19391 |
| 2179 | ACAUUUUG A UCAUGGAG | 8752 | CTCCATGA GGCTAGCTACAACGA CAAAATGT | 19392 |
| 2182 | UUUUGAUC A UGGAGCUU | 6484 | AAGCTCCA GGCTAGCTACAACGA GATCAAAA | 19393 |
| 2187 | AUCAUGGA G CUUAAGAA | 8753 | TTCTTAAG GGCTAGCTACAACGA TCCATGAT | 19394 |
| 2195 | GCUUAAGA A UGCAUCCU | 8754 | AGGATGCA GGCTAGCTACAACGA TCTTAAGC | 19395 |
| 2197 | UUAAGAAU G CAUCCUUG | 8755 | CAAGGATG GGCTAGCTACAACGA ATTCTTAA | 19396 |
| 2199 | AAGAAUGC A UCCUUGCA | 6486 | TGCAAGGA GGCTAGCTACAACGA GCATTCTT | 19397 |
| 2205 | GCAUCCUU G CAGGACCA | 8756 | TGGTCCTG GGCTAGCTACAACGA AAGGATGC | 19398 |
| 2210 | CUUGCAGG A CCAAGGAG | 8757 | CTCCTTGG GGCTAGCTACAACGA CCTGCAAG | 19399 |
| 2219 | CCAAGGAG A CUAUGUCU | 8758 | AGACATAG GGCTAGCTACAACGA CTCCTTGG | 19400 |
| 2222 | AGGAGACU A UGUCUGCC | 1813 | GGCAGACA GGCTAGCTACAACGA AGTCTCCT | 19401 |
| 2224 | GAGACUAU G UCUGCCUU | 8759 | AAGGCAGA GGCTAGCTACAACGA ATAGTCTC | 19402 |
| 2228 | CUAUGUCU G CCUUGCUC | 8760 | GAGCAAGG GGCTAGCTACAACGA AGACATAG | 19403 |
| 2233 | UCUGCCUU G CUCAAGAC | 8761 | GTCTTGAG GGCTAGCTACAACGA AAGGCAGA | 19404 |
| 2240 | UGCUCAAG A CAGGAAGA | 8762 | TCTTCCTG GGCTAGCTACAACGA CTTGAGCA | 19405 |
| 2248 | ACAGGAAG A CCAAGAAA | 8763 | TTTCTTGG GGCTAGCTACAACGA CTTCCTGT | 19406 |
| 2259 | AAGAAAAG A CAUUGCGU | 8764 | ACGCAATG GGCTAGCTACAACGA CTTTTCTT | 19407 |
| 2261 | GAAAAGAC A UUGCGUGG | 6501 | CCACGCAA GGCTAGCTACAACGA GTCTTTTC | 19408 |
| 2264 | AAGACAUU G CGUGGUCA | 8765 | TGACCACG GGCTAGCTACAACGA AATGTCTT | 19409 |
| 2266 | GACAUUGC G UGGUCAGG | 8766 | CCTGACCA GGCTAGCTACAACGA GCAATGTC | 19410 |
| 2269 | AUUGCGUG G UCAGGCAG | 8767 | CTGCCTGA GGCTAGCTACAACGA CACGCAAT | 19411 |
| 2274 | GUGGUCAG G CAGCUCAC | 8768 | GTGAGCTG GGCTAGCTACAACGA CTGACCAC | 19412 |
| 2277 | GUCAGGCA G CUCACAGU | 8769 | ACTGTGAG GGCTAGCTACAACGA TGCCTGAC | 19413 |
| 2281 | GGCAGCUC A CAGUCCUA | 6505 | TAGGACTG GGCTAGCTACAACGA GAGCTGCC | 19414 |
| 2284 | AGCUCACA G UCCUAGAG | 8770 | CTCTAGGA GGCTAGCTACAACGA TGTGAGCT | 19415 |
| 2292 | GUCCUAGA G CGUGUGGC | 8771 | GCCACACG GGCTAGCTACAACGA TCTAGGAC | 19416 |
| 2294 | CCUAGAGC G UGUGGCAC | 8772 | GTGCCACA GGCTAGCTACAACGA GCTCTAGG | 19417 |
| 2296 | UAGAGCGU G UGGCACCC | 8773 | GGGTGCCA GGCTAGCTACAACGA ACGCTCTA | 19418 |
| 2299 | AGCGUGUG G CACCCACG | 8774 | CGTGGGTG GGCTAGCTACAACGA CACACGCT | 19419 |
| 2301 | CGUGUGGC A CCCACGAU | 6509 | ATCGTGGG GGCTAGCTACAACGA GCCACACG | 19420 |
| 2305 | UGGCACCC A CGAUCACA | 6512 | TGTGATCG GGCTAGCTACAACGA GGGTGCCA | 19421 |

TABLE XXII-continued

Human KDR DNAzyme and Substrate sequence

| Pos | Substrate | Seq ID No | DNAzyme | Seq ID No |
|---|---|---|---|---|
| 2308 | CACCCACG A UCACAGGA | 8775 | TCCTGTGA GGCTAGCTACAACGA CGTGGGTG | 19422 |
| 2311 | CCACGAUC A CAGGAAAC | 6513 | GTTTCCTG GGCTAGCTACAACGA GATCGTGG | 19423 |
| 2318 | CACAGGAA A CCUGGAGA | 8776 | TCTCCAGG GGCTAGCTACAACGA TTCCTGTG | 19424 |
| 2327 | CCUGGAGA A UCAGACGA | 8777 | TCGTCTGA GGCTAGCTACAACGA TCTCCAGG | 19425 |
| 2332 | AGAAUCAG A CGACAAGU | 8778 | ACTTGTCG GGCTAGCTACAACGA CTGATTCT | 19426 |
| 2335 | AUCAGACG A CAAGUAUU | 8779 | AATACTTG GGCTAGCTACAACGA CGTCTGAT | 19427 |
| 2339 | GACGACAA G UAUUGGGG | 8780 | CCCCAATA GGCTAGCTACAACGA TTGTCGTC | 19428 |
| 2341 | CGACAAGU A UUGGGGAA | 1824 | TTCCCCAA GGCTAGCTACAACGA ACTTGTCG | 19429 |
| 2351 | UGGGGAAA G CAUCGAAG | 8781 | CTTCGATG GGCTAGCTACAACGA TTTCCCCA | 19430 |
| 2353 | GGGAAAGC A UCGAAGUC | 6519 | GACTTCGA GGCTAGCTACAACGA GCTTTCCC | 19431 |
| 2359 | GCAUCGAA G UCUCAUGC | 8782 | GCATGAGA GGCTAGCTACAACGA TTCGATGC | 19432 |
| 2364 | GAAGUCUC A UGCACGGC | 6521 | GCCGTGCA GGCTAGCTACAACGA GAGACTTC | 19433 |
| 2366 | AGUCUCAU G CACGGCAU | 8783 | ATGCCGTG GGCTAGCTACAACGA ATGAGACT | 19434 |
| 2368 | UCUCAUGC A CGGCAUCU | 6522 | AGATGCCG GGCTAGCTACAACGA GCATGAGA | 19435 |
| 2371 | CAUGCACG G CAUCUGGG | 8784 | CCCAGATG GGCTAGCTACAACGA CGTGCATG | 19436 |
| 2373 | UGCACGGC A UCUGGGAA | 6523 | TTCCCAGA GGCTAGCTACAACGA GCCGTGCA | 19437 |
| 2381 | AUCUGGGA A UCCCCCUC | 8785 | GAGGGGGA GGCTAGCTACAACGA TCCCAGAT | 19438 |
| 2391 | CCCCCUCC A CAGAUCAU | 6531 | ATGATCTG GGCTAGCTACAACGA GGAGGGGG | 19439 |
| 2395 | CUCCACAG A UCAUGUGG | 8786 | CCACATGA GGCTAGCTACAACGA CTGTGGAG | 19440 |
| 2398 | CACAGAUC A UGUGGUUU | 6533 | AAACCACA GGCTAGCTACAACCA GATCTGTG | 19441 |
| 2400 | CAGAUCAU G UGGUUUAA | 8787 | TTAAACCA GGCTAGCTACAACGA ATGATCTG | 19442 |
| 2403 | AUCAUGUG G UGGAAAGA | 8788 | TCTTTAAA GGCTAGCTACAACGA CACATGAT | 19443 |
| 2411 | GUUUAAAG A UAAUGAGA | 8789 | TCTCATTA GGCTAGCTACAACGA CTTTAAAC | 19444 |
| 2414 | UAAAGAUA A UGAGACCC | 8790 | GGGTCTCA GGCTAGCTACAACGA TATCTTTA | 19445 |
| 2419 | AUAAUGAG A CCCUUCUA | 8791 | TACAAGGG GGCTAGCTACAACGA CTCATTAT | 19446 |
| 2425 | AGACCCUU G UAGAAGAC | 8792 | GTCTTCTA GGCTAGCTACAACGA AAGGGTCT | 19447 |
| 2432 | UGUAGAAG A CUCAGGCA | 8793 | TGCCTGAG GGCTAGCTACAACGA CTTCTACA | 19448 |
| 2438 | AGACUCAG G CAUUGUAU | 8794 | ATACAATG GGCTAGCTACAACGA CTGAGTCT | 19449 |
| 2440 | ACUCAGGC A UUGUAUUG | 6539 | CAATACAA GGCTAGCTACAACGA GCCTGACT | 19450 |
| 2443 | CAGGCAUU G UAUUGAAG | 8795 | CTTCAATA GGCTAGCTACAACGA AATGCCTG | 19451 |
| 2445 | GGCAUUGU A UUGAAGGA | 1841 | TCCTTCAA GGCTAGCTACAACGA ACAATGCC | 19452 |
| 2453 | AUUGAAGG A UGGGAACC | 8796 | GGTTCCCA GGCTAGCTACAACGA CCTTCAAT | 19453 |
| 2459 | GGAUGGGA A CCGGAACC | 8797 | GGTTCCGG GGCTAGCTACAACGA TCCCATCC | 19454 |
| 2465 | GAACCGGA A CCUCACUA | 8798 | TAGTGAGG GGCTAGCTACAACGA TCCGGTTC | 19455 |
| 2470 | GGAACCUC A CUAUCCGC | 6543 | GCGGATAG GGCTAGCTACAACGA GAGGTTCC | 19456 |
| 2473 | ACCUCACU A UCCGCAGA | 1844 | TCTGCGGA GGCTAGCTACAACGA AGTGAGGT | 19457 |
| 2477 | CACUAUCC G CAGAGUGA | 8799 | TCACTCTG GGCTAGCTACAACGA GGATAGTG | 19458 |

TABLE XXII-continued

Human KDR DNAzyme and Substrate sequence

| Pos | Substrate | Seq ID No | DNAzyme | Seq ID No |
|---|---|---|---|---|
| 2482 | UCCGCAGA G UGAGGAAG | 8800 | CTTCCTCA GGCTAGCTACAACGA TCTGCGGA | 19459 |
| 2495 | GAAGGAGG A CGAAGGCC | 8801 | GGCCTTCG GGCTAGCTACAACGA CCTCCTTC | 19460 |
| 2501 | GGACGAAG G CCUCUACA | 8802 | TGTAGAGG GGCTAGCTACAACGA CTTCGTCC | 19461 |
| 2507 | AGGCCUCU A CACCUGCC | 1847 | GGCAGGTG GGCTAGCTACAACGA AGAGGCCT | 19462 |
| 2509 | GCCUCUAC A CCUGCCAG | 6550 | CTGGCAGG GGCTAGCTACAACGA GTAGAGGC | 19463 |
| 2513 | CUACACCU G CCAGGCAU | 8803 | ATGCCTGG GGCTAGCTACAACGA AGGTGTAG | 19464 |
| 2518 | CCUGCCAG G CAUGCAGU | 8804 | ACTGCATG GGCTAGCTACAACGA CTGGCAGG | 19465 |
| 2520 | UGCCAGGC A UGCAGUGU | 6555 | ACACTGCA GGCTAGCTACAACGA GCCTGGCA | 19466 |
| 2522 | CCAGGCAU G CAGUGUUC | 8805 | GAACACTG GGCTAGCTACAACGA ATGCCTGG | 19467 |
| 2525 | GGCAUGCA G UGUUCUUG | 8806 | CAAGAACA GGCTAGCTACAACGA TGCATGCC | 19468 |
| 2527 | CAUGCAGU G UUCUUGGC | 8807 | GCCAAGAA GGCTAGCTACAACGA ACTGCATG | 19469 |
| 2534 | UGUUCUUG G CUGUGCAA | 8808 | TTGCACAG GGCTAGCTACAACGA CAAGAACA | 19470 |
| 2537 | UCUUGGCU G UGCAAAAG | 8809 | CTTTTGCA GGCTAGCTACAACGA AGCCAAGA | 19471 |
| 2539 | UUGGCUGU G CAAAAGUG | 8810 | CACTTTTG GGCTAGCTACAACGA ACAGCCAA | 19472 |
| 2545 | GUGCAAAA G UGGAGGCA | 8811 | TGCCTCCA GGCTAGCTACAACGA TTTTGCAC | 19473 |
| 2551 | AAGUGGAG G CAUUUUUC | 8812 | GAAAAATG GGCTAGCTACAACGA CTCCACTT | 19474 |
| 2553 | GUGGAGGC A UUUUUCAU | 6560 | ATGAAAAA GGCTAGCTACAACGA GCCTCCAC | 19475 |
| 2560 | CAUUUUUC A UAAUAGAA | 6561 | TTCTATTA GGCTAGCTACAACGA GAAAAATG | 19476 |
| 2563 | UUUUCAUA A UAGAAGGU | 8813 | ACCTTCTA GGCTAGCTACAACGA TATGAAAA | 19477 |
| 2570 | AAUAGAAG G UGCCCAGG | 8814 | CCTGGGCA GGCTAGCTACAACGA CTTCTATT | 19478 |
| 2572 | UAGAAGGU G CCCAGGAA | 8815 | TTCCTGGG GGCTAGCTACAACGA ACCTTCTA | 19479 |
| 2584 | AGGAAAAG A CGAACUUG | 8818 | CAAGTTCG GGCTAGCTACAACGA CTTTTCCT | 19480 |
| 2588 | AAAGACGA A CUUGGAAA | 8817 | TTTCCAAG GGCTAGCTACAACGA TCGTCTTT | 19481 |
| 2596 | ACUUGGAA A UCAUUAUU | 8818 | AATAATGA GGCTAGCTACAACGA TTCCAAGT | 19482 |
| 2599 | UGGAAAUC A UUAUUCUA | 6568 | TAGAATAA GGCTAGCTACAACGA GATTTCCA | 19483 |
| 2602 | AAAUCAUU A UUCUAGUA | 1861 | TACTAGAA GGCTAGCTACAACGA AATGATTT | 19484 |
| 2608 | UUAUUCUA G UAGGCACG | 8819 | CGTGCCTA GGCTAGCTACAACGA TAGAATAA | 19485 |
| 2612 | UCUAGUAG G CACGGCGG | 8820 | CCGCCGTG GGCTAGCTACAACGA CTACTAGA | 19486 |
| 2614 | UAGUAGGC A CGGCGGUG | 8821 | CACCGCCG GGCTAGCTACAACGA GCCTACTA | 19487 |
| 2617 | UAGGCACG G CGGUGAUU | 8822 | AATCACCG GGCTAGCTACAACGA CGTGCCTA | 19488 |
| 2620 | GCACGGCG G UGAUUGCC | 8823 | GGCAATCA GGCTAGCTACAACGA CGCCGTGC | 19489 |
| 2623 | CGGCGGUG A UUGCCAUG | 8824 | CATGGCAA GGCTAGCTACAACGA CACCGCCG | 19490 |
| 2626 | CGGUGAUU G CCAUGUUC | 8825 | GAACATCG GGCTAGCTACAACGA AATCACCG | 19491 |
| 2629 | UGAUUGCC A UGUUCUUC | 6570 | GAAGAACA GGCTAGCTACAACGA GGCAATCA | 19492 |
| 2631 | AUUGCCAU G UUCUUCUG | 8826 | CAGAAGAA GGCTAGCTACAACGA ATGGCAAT | 19493 |
| 2640 | UUCUUCUG G UACUUCUU | 8827 | ACAAGTAG GGCTAGCTACAACGA CAGAACAA | 19494 |
| 2643 | UUCUGGCU A CUUCUUGU | 1871 | ACAAGAAG GGCTAGCTACAACGA AGCCACAA | 19495 |

TABLE XXII-continued

Human KDR DNAzyme and Substrate sequence

| Pos | Substrate | Seq ID No | DNAzyme | Seq ID No |
|---|---|---|---|---|
| 2650 | UACUUCUU G UCAUCAUC | 8828 | GATGATGA GGCTAGCTACAACGA AAGAACTA | 19496 |
| 2653 | UUCUUGUC A UCAUCCUA | 8576 | TAGGATGA GGCTAGCTACAACGA GACAAGAA | 19497 |
| 2656 | UUGUCAUC A UCCUACGG | 8829 | CCCTAGGA GGCTAGCTACAACGA GATGACAA | 19498 |
| 2661 | AUCAUCCU A CGGACCGU | 8830 | ACGGTCCG GGCTAGCTACAACGA AGGATGAT | 19499 |
| 2665 | UCCUACGG A CCGUUAAG | 8831 | CTTAACGG GGCTAGCTACAACGA CCCTAGGA | 19500 |
| 2668 | UACCCACC G UUAAGCGG | 8832 | CCGCTTAA GGCTAGCTACAACGA CGTCCGTA | 19501 |
| 2673 | ACCCUUAA G CCGGCCAA | 8833 | TTCGCCCG GGCTAGCTACAACGA TTAACGGT | 19502 |
| 2677 | UUAACCCG G CCAAUCGA | 8834 | TCCATTGG GGCTAGCTACAACGA CCGCTTAA | 19503 |
| 2681 | GCGGGCCA A UGGAGGGG | 8835 | CCCCTCCA GGCTAGCTACAACGA TGGCCCGC | 19504 |
| 2691 | GCACGGCA A CUGAACAC | 8836 | GTCTTCAG GGCTAGCTACAACGA TCCCCTCC | 19505 |
| 2698 | AACUGAAG A CAGGCUAC | 8837 | GTAGCCTG GGCTAGCTACAACGA CTTCAGTT | 19506 |
| 2702 | GAAGACAG G CUACUUGU | 8838 | ACAAGTAG GGCTAGCTACAACGA CTCTCTTC | 19507 |
| 2705 | GACAGGCU A CUUGUCCA | 1881 | TGGACAAG GGCTAGCTACAACGA ACCCTGTC | 19508 |
| 2709 | GGCUACUU G UCCAUCGU | 8839 | ACGATGCA GGCTAGCTACAACGA AACTAGCC | 19509 |
| 2713 | ACUUCUCC A UCGUCAUC | 6588 | CATCACCA GGCTAGCTACAACGA GGACAAGT | 19510 |
| 2716 | UCUCCAUC G UCAUGGAU | 8840 | ATCCATCA GGCTAGCTACAACGA GATGGACA | 19511 |
| 2719 | CCAUCGUC A UGGAUCCA | 8589 | TGCATCCA GGCTAGCTACAACGA CACGATGC | 19512 |
| 2723 | CCUCAUCC A UCCACAUG | 8841 | CATCTGCA GGCTAGCTACAACGA CCATCACC | 19513 |
| 2729 | CCAUCCAG A UGAACUCC | 8842 | CGACTTCA GGCTAGCTACAACGA CTGCATCC | 19514 |
| 2733 | CCAGAUGA A CUCCCAUU | 8843 | AATCCCAC GGCTAGCTACAACGA TCATCTGG | 19515 |
| 2739 | GAACUCCC A CUGGAUGA | 8595 | TCATCCAA GGCTAGCTACAACGA CCCAGTTC | 19516 |
| 2744 | CCCAUUGG A UGAACAUU | 8844 | AATCTTCA GGCTAGCTACAACGA CCAATGGC | 19517 |
| 2748 | UUGCAUGA A CACUCUGA | 8845 | TCACAATG GGCTAGCTACAACGA TCATCCAA | 19518 |
| 2750 | GGAUGAAC A UUCUGAAC | 6596 | GTTCACAA GGCTAGCTACAACGA GTTCATCC | 19519 |
| 2753 | UGAACAUU G UGAACCAC | 8848 | GTCCTTCA GGCTAGCTACAACGA AATGTTCA | 19520 |
| 2757 | CAUUGUGA A CCACUGCC | 8847 | CGCACTCC GGCTAGCTACAACGA TCACAATC | 19521 |
| 2760 | UGUCAACG A CUGCCUUA | 8848 | TAAGCCAG GGCTAGCTACAACGA CGTTCACA | 19522 |
| 2763 | CAACGACU G CCUUAUCA | 8849 | TCATAACC GGCTAGCTACAACGA AGTCGTTC | 19523 |
| 2768 | ACUGCCUU A UGAUGCCA | 1891 | TGGCATCA GGCTAGCTACAACGA AAGCCACT | 19524 |
| 2771 | CCCUUAUC A UCCCAGCA | 8850 | TGCTCGCA GGCTAGCTACAACGA CATAACGC | 19525 |
| 2773 | CUUAUGAU G CCAGCAAA | 8851 | TTTCCTGC GGCTAGCTACAACGA ATCATAAG | 19526 |
| 2777 | UGAUGCCA G CAAAUGGG | 8852 | CCCATTTG GGCTAGCTACAACGA TGGCATCA | 19527 |
| 2781 | GCCAGCAA A UGGGAAUU | 8853 | AATTCCCA GGCTAGCTACAACGA TTGCTGGC | 19528 |
| 2787 | AAAUGGGA A UUCCCCAG | 8854 | CTGGGGAA GGCTAGCTACAACGA TCCCATTT | 19529 |
| 2798 | CCCCAGAG A CCGGCUGA | 8855 | TCAGCCGG GGCTAGCTACAACGA CTCTGGGG | 19530 |
| 2802 | AGAGACCG G CUGAAGCU | 8856 | AGCTTCAG GGCTAGCTACAACGA CGGTCTCT | 19531 |
| 2808 | CGGCUGAA G CUAGGUAA | 8857 | TTACCTAG GGCTAGCTACAACGA TTCAGCCG | 19532 |

TABLE XXII-continued

Human KDR DNAzyme and Substrate sequence

| Pos | Substrate | Seq ID No | DNAzyme | Seq ID No |
|---|---|---|---|---|
| 2813 | GAAGCUAG G UAAGCCUC | 8858 | GAGGCTTA GGCTAGCTACAACGA CTAGCTTC | 19533 |
| 2817 | CUAGGUAA G CCUCUUGG | 8859 | CCAAGAGG GGCTAGCTACAACGA TTACCTAG | 19534 |
| 2825 | GCCUCUUG G GCCUGGUG | 8860 | CACCACGG GGCTAGCTACAACGA CAAGAGGC | 19535 |
| 2828 | UCUUGGCC G UGGUGCCU | 8881 | AGGCACCA GGCTAGCTACAACGA GGCCAAGA | 19536 |
| 2831 | UCGCCGUG G UGCCUUUG | 8862 | CAAAGGCA GGCTAGCTACAACGA CACGGCCA | 19537 |
| 2833 | GCCGUGGU G CCUUUGGC | 8863 | GCCAAAGG GGCTAGCTACAACGA ACCACGGC | 19538 |
| 2840 | UGCCUUUG G CCAAGUGA | 8884 | TCACTTGG GGCTAGCTACAACGA CAAAGGCA | 19539 |
| 2845 | UUGGCCAA G UGAUUGAA | 8865 | TTCAATCA GGCTAGCTACAACGA TTGGCCAA | 19540 |
| 2848 | GCCAAGUG A UUGAAGCA | 8866 | TGCTTCAA GGCTAGCTACAACGA CACTTGGC | 19541 |
| 2854 | UGAUUGAA G CAGAUGCC | 8867 | GGCATCTG GGCTAGCTACAACGA TTCAATCA | 19542 |
| 2858 | UGAAGCAG A UGCCUUUG | 8868 | CAAAGGCA GGCTAGCTACAACGA CTCCTTCA | 19543 |
| 2860 | AAGCAGAU G CCUUUGGA | 8869 | TCCAAACG GGCTAGCTACAACGA ATCTCCTT | 19544 |
| 2869 | CCUUUGGA A UUCACAAG | 8870 | CTTCTCAA GGCTAGCTACAACGA TCCAAAGC | 19545 |
| 2873 | UGGAAUUG A CAAGACAG | 8871 | CTGTCTTG GGCTAGCTACAACGA CAATTCCA | 19546 |
| 2878 | UUGACAAG A CAGCAACU | 8872 | AGTTGCTG GGCTAGCTACAACGA CTTGTCAA | 19547 |
| 2881 | ACAAGACA G CAACUUGC | 8873 | GCAAGTTG GGCTAGCTACAACGA TGTCTTGT | 19548 |
| 2884 | ACACACCA A CUUGCAGG | 8874 | CCTCCAAG GGCTAGCTACAACGA TGCTGTCT | 19549 |
| 2888 | ACCAACUU G CAGGACAC | 8875 | CTGTCCTG GGCTAGCTACAACGA AAGTTGCT | 19550 |
| 2893 | CUUGCAGG A CACUAGCA | 8876 | TCCTACTC GGCTAGCTACAACGA CCTCCAAG | 19551 |
| 2896 | GCAGGACA G UAGCAGUC | 8877 | GACTCCTA GGCTAGCTACAACGA TCTCCTGC | 19552 |
| 2899 | GGACAGUA G CAGUCAAA | 8878 | TTTCACTC GGCTAGCTACAACGA TACTGTCC | 19553 |
| 2902 | CACUAGCA G UCAAAAUG | 8879 | CATTTTGA GGCTAGCTACAACGA TGCTACTC | 19554 |
| 2908 | CAGUCAAA A UGUUGAAA | 8880 | TTTCAACA GGCTAGCTACAACGA TTTGACTG | 19555 |
| 2910 | GUCAAAAU G UUGAAAGA | 8881 | TCTTTCAA GGCTAGCTACAACGA ATTTTGAC | 19556 |
| 2923 | AAGAAGGA G CAACACAC | 8882 | CTGTGTTG GGCTAGCTACAACGA TCCTTCTT | 19557 |
| 2926 | AAGGAGCA A CACACAGU | 8883 | ACTGTGTG GGCTAGCTACAACGA TCCTCCTT | 19558 |
| 2928 | GGAGCAAC A CACAGUGA | 6631 | TCACTCTC GGCTAGCTACAACGA GTTGCTCC | 19559 |
| 2930 | AGCAACAC A CAGUGAGC | 6632 | GCTCACTG GGCTAGCTACAACGA GTGTTGCT | 19560 |
| 2933 | AACACACA G UGAGCAUC | 8884 | GATGCTCA GGCTAGCTACAACGA TGTGTGTT | 19561 |
| 2937 | CACAGUGA G CAUCGAGC | 8885 | GCTCGATG GGCTAGCTACAACGA TCACTGTG | 19562 |
| 2939 | CACUGAGC A UCCACCUC | 6634 | GAGCTCGA GGCTAGCTACAACGA GCTCACTG | 19563 |
| 2944 | ACCAUCCA G CUCUCAUG | 8886 | CATGAGAG GGCTAGCTACAACGA TCCATGCT | 19564 |
| 2950 | GACCUCUC A UGUCUGAA | 6637 | TTCAGACA GGCTAGCTACAACGA GACAGCTC | 19565 |
| 2952 | CCUCUCAU G UCUCAACU | 8887 | ACTTCAGA GGCTAGCTACAACGA ATCACAGC | 19566 |
| 2958 | AUGUCUGA A CUCAAGAU | 8888 | ATCTTGAG GGCTAGCTACAACGA TCACACAT | 19567 |
| 2965 | AACUCAAG A UCCUCAUU | 8889 | AATCACGA GGCTAGCTACAACGA CTTCAGTT | 19568 |
| 2971 | ACAUCCUC A UUCAUAUU | 6643 | AATATGAA GGCTAGCTACAACGA GAGGATCT | 19569 |

TABLE XXII-continued

Human KDR DNAzyme and Substrate sequence

| Pos | Substrate | Seq ID No | DNAzyme | Seq ID No |
|---|---|---|---|---|
| 2975 | CCUCAUUC A UAUUCGUC | 6644 | GACCAATA GGCTAGCTACAACGA GAATCACG | 19570 |
| 2977 | UCAUUCAU A UUCCUCAC | 1917 | CTCACCAA GGCTAGCTACAACGA ATGAATGA | 19571 |
| 2981 | UCAUAUUG G UCACCAUC | 8890 | GATCGTGA GGCTAGCTACAACGA CAATATGA | 19572 |
| 2984 | UAUUGGUC A CCAUCUCA | 6645 | TCACATGG GGCTAGCTACAACGA CACCAATA | 19573 |
| 2987 | UCGUCACC A UCUCAAUG | 6647 | CATTCACA GGCTAGCTACAACGA CGTGACCA | 19574 |
| 2993 | CCAUCUCA A UGUGGUCA | 8891 | TGACCACA GGCTAGCTACAACGA TCACATGC | 19575 |
| 2995 | AUCUCAAU G UGGUCAAC | 8892 | GTTGACCA GGCTAGCTACAACGA ATTGAGAT | 19576 |
| 2998 | UCAAUGUG G UCAACCUU | 8893 | AAGGTTGA GGCTAGCTACAACGA CACATTGA | 19577 |
| 3002 | UGUGGUCA A CCUUCUAG | 8894 | CTAGAAGG GGCTAGCTACAACGA TGACCACA | 19578 |
| 3011 | CCUUCUAG G UGCCUGUA | 8895 | TACAGGCA GGCTAGCTACAACGA CTAGAAGG | 19579 |
| 3013 | UUCUAGGU G CCUGUACC | 8896 | GGTACAGG GGCTAGCTACAACGA ACCTAGAA | 19580 |
| 3017 | AGGUGCCU G UACCAAGC | 8897 | GCTTGGTA GGCTAGCTACAACGA AGGCACCT | 19581 |
| 3019 | GUGCCUGU A CCAAGCCA | 1926 | TGGCTTGG GGCTAGCTACAACGA ACAGGCAC | 19582 |
| 3024 | UGUACCAA G CCAGGAGG | 8898 | CCTCCTGG GGCTAGCTACAACGA TTGGTACA | 19583 |
| 3033 | CCAGGAGG G CCACUCAU | 8899 | ATGAGTGG GGCTAGCTACAACGA CCTCCTGG | 19584 |
| 3036 | GGAGGGCC A CUCAUGGU | 6661 | ACCATGAG GGCTAGCTACAACGA GGCCCTCC | 19585 |
| 3040 | GGCCACUC A UGGUGAUU | 6663 | AATCACCA GGCTAGCTACAACGA GAGTGGCC | 19586 |
| 3043 | CACUCAUG G UGAUUGUG | 8900 | CACAATCA GGCTAGCTACAACGA CATGAGTG | 19587 |
| 3046 | UCAUGGUG A UUGUGGAA | 8901 | TTCCACAA GGCTAGCTACAACGA CACCATGA | 19588 |
| 3049 | UGGUGAUU G UGGAAUUC | 8902 | GAATTCCA GGCTAGCTACAACGA AATCACCA | 19589 |
| 3054 | AUUGUGGA A UUCUGCAA | 8903 | TTGCAGAA GGCTAGCTACAACGA TCCACAAT | 19590 |
| 3059 | GGAAUUCU G CAAAUUUG | 8904 | CAAATTTG GGCTAGCTACAACGA AGAATTCC | 19591 |
| 3063 | UUCUGCAA A UUUGGAAA | 8905 | TTTCCAAA GGCTAGCTACAACGA TTGCAGAA | 19592 |
| 3071 | AUUUGGAA A CCUGUCCA | 8906 | TGGACAGG GGCTAGCTACAACGA TTCCAAAT | 19593 |
| 3075 | GGAAACCU G UCCACUUA | 8907 | TAAGTGGA GGCTAGCTACAACGA AGGTTTCC | 19594 |
| 3079 | ACCUGUCC A CUUACCUG | 6669 | CAGGTAAG GGCTAGCTACAACGA GGACAGGT | 19595 |
| 3083 | GUCCACUU A CCUGAGGA | 1935 | TCCTCAGG GGCTAGCTACAACGA AAGTGGAC | 19596 |
| 3092 | CCUGAGGA G CAAGAGAA | 8908 | TTCTCTTG GGCTAGCTACAACGA TCCTCAGG | 19597 |
| 3101 | CAAGAGAA A UGAAUUUG | 8909 | CAAATTCA GGCTAGCTACAACGA TTCTCTTG | 19598 |
| 3105 | AGAAAUGA A UUUGUCCC | 8910 | GGGACAAA GGCTAGCTACAACGA TCATTTCT | 19599 |
| 3109 | AUGAAUUU G UCCCCUAC | 8911 | GTAGGGGA GGCTAGCTACAACGA AAATTCAT | 19600 |
| 3116 | UGUCCCCU A CAAGACCA | 1939 | TGGTCTTG GGCTAGCTACAACGA AGGGGACA | 19601 |
| 3121 | CCUACAAG A CCAAAGGG | 8912 | CCCTTTGG GGCTAGCTACAACGA CTTGTAGG | 19602 |
| 3130 | CCAAAGGG G CACGAUUC | 8913 | GAATCGTG GGCTAGCTACAACGA CCCTTTGG | 19603 |
| 3132 | AAAGGGGC A CGAUUCCG | 6681 | CGGAATCG GGCTAGCTACAACGA GCCCCTTT | 19604 |
| 3135 | GGGGCACG A UUCCGUCA | 8914 | TGACGGAA GGCTAGCTACAACGA CGTGCCCC | 19605 |
| 3140 | ACGAUUCC G UCAAGGGA | 8915 | TCCCTTGA GGCTAGCTACAACGA GGAATCGT | 19606 |

TABLE XXII-continued

Human KDR DNAzyme and Substrate sequence

| Pos | Substrate | Seq ID No | DNAzyme | Seq ID No |
|---|---|---|---|---|
| 3152 | AGGGAAAG A CUACGUUG | 8916 | CAACGTAG GGCTAGCTACAACGA CTTTCCCT | 19607 |
| 3155 | GAAAGACU A CGUUGGAG | 1943 | CTCCAACG GGCTAGCTACAACGA AGTCTTTC | 19608 |
| 3157 | AAGACUAC G UUGGAGCA | 8917 | TGCTCCAA GGCTAGCTACAACGA GTAGTCTT | 19609 |
| 3163 | ACGUUGGA G CAAUCCCU | 8918 | AGGGATTG GGCTAGCTACAACGA TCCAACGT | 19610 |
| 3166 | UUGGAGCA A UCCCUGUG | 8919 | CACAGGGA GGCTAGCTACAACGA TGCTCCAA | 19611 |
| 3172 | CAAUCCCU G UGGAUCUG | 8920 | CAGATCCA GGCTAGCTACAACGA AGGGATTG | 19612 |
| 3176 | CCCUGUGG A UCUGAAAC | 8921 | GTTTCAGA GGCTAGCTACAACGA CCACAGGG | 19613 |
| 3183 | GAUCUGAA A CGGCGCUU | 8922 | AAGCGCCG GGCTAGCTACAACGA TTCAGATC | 19614 |
| 3186 | CUGAAACG G CGCUUGGA | 8923 | TCCAAGCG GGCTAGCTACAACGA CGTTTCAG | 19615 |
| 3188 | GAAACGGC G CUUGGACA | 8924 | TGTCCAAG GGCTAGCTACAACGA GCCGTTTC | 19616 |
| 3194 | GCGCUUGG A CAGCAUCA | 8925 | TGATGCTG GGCTAGCTACAACGA CCAAGCGC | 19617 |
| 3197 | CUUGGACA G CAUCACCA | 8926 | TGGTGATG GGCTAGCTACAACGA TGTCCAAG | 19618 |
| 3199 | UGGACAGC A UCACCAGU | 6692 | ACTGGTGA GGCTAGCTACAACGA GCTGTCCA | 19619 |
| 3202 | ACAGCAUC A CCAGUAGC | 6693 | GCTACTGG GGCTAGCTACAACGA GATGCTGT | 19620 |
| 3206 | CAUCACCA G UAGCCAGA | 8927 | TCTGGCTA GGCTAGCTACAACGA TGGTGATG | 19621 |
| 3209 | CACCAGUA G CCAGAGCU | 8928 | AGCTCTGG GGCTAGCTACAACGA TACTGGTG | 19622 |
| 3215 | UAGCCAGA G CUCAGCCA | 8929 | TGGCTGAG GGCTAGCTACAACGA TCTGGCTA | 19623 |
| 3220 | AGAGCUCA G CCAGCUCU | 8930 | AGAGCTGG GGCTAGCTACAACGA TGAGCTCT | 19624 |
| 3224 | CUCAGCCA G CUCUGGAU | 8931 | ATCCAGAG GGCTAGCTACAACGA TGGCTGAG | 19625 |
| 3231 | AGCUCUGG A UUUGUGGA | 8932 | TCCACAAA GGCTAGCTACAACGA CCAGAGCT | 19626 |
| 3235 | CUGGAUUU G UGGAGGAG | 8933 | CTCCTCCA GGCTAGCTACAACGA AAATCCAG | 19627 |
| 3246 | GAGGAGAA G UCCCUCAG | 8934 | CTGAGGGA GGCTAGCTACAACGA TTCTCCTC | 19628 |
| 3254 | GUCCCUCA G UGAUGUAG | 8935 | CTACATCA GGCTAGCTACAACGA TGAGGGAC | 19629 |
| 3257 | CCUCAGUG A UGUAGAAG | 8936 | CTTCTACA GGCTAGCTACAACGA CACTGAGG | 19630 |
| 3259 | UCAGUGAU G UAGAAGAA | 8937 | TTCTTCTA GGCTAGCTACAACGA ATCACTGA | 19631 |
| 3274 | AAGAGGAA G CUCCUGAA | 8938 | TTCAGGAG GGCTAGCTACAACGA TTCCTCTT | 19632 |
| 3284 | UCCUGAAG A UCUGUAUA | 8939 | TATACAGA GGCTAGCTACAACGA CTTCAGGA | 19633 |
| 3288 | GAAGAUCU G UAUAAGGA | 8940 | TCCTTATA GGCTAGCTACAACGA AGATCTTC | 19634 |
| 3290 | AGAUCUGU A UAAGGACU | 1959 | AGTCCTTA GGCTAGCTACAACGA ACAGATCT | 19635 |
| 3296 | GUAUAAGG A CUUCCUGA | 8941 | TCAGGAAG GGCTAGCTACAACGA CCTTATAC | 19636 |
| 3304 | ACUUCCUG A CCUUGGAG | 8942 | CTCCAAGG GGCTAGCTACAACGA CAGGAAGT | 19637 |
| 3312 | ACCUUGGA G CAUCUCAU | 8943 | ATGAGATG GGCTAGCTACAACGA TCCAAGGT | 19638 |
| 3314 | CUUGGAGC A UCUCAUCU | 6717 | AGATGAGA GGCTAGCTACAACGA GCTCCAAG | 19639 |
| 3319 | AGCAUCUC A UCUGUUAC | 6719 | GTAACAGA GGCTAGCTACAACGA GAGATGCT | 19640 |
| 3323 | UCUCAUCU G UUACAGCU | 8944 | AGCTGTAA GGCTAGCTACAACGA AGATGAGA | 19641 |
| 3326 | CAUCUGUU A CAGCUUCC | 1968 | GGAAGCTG GGCTAGCTACAACGA AACAGATG | 19642 |
| 3329 | CUGUUACA G CUUCCAAG | 8945 | CTTGGAAG GGCTAGCTACAACGA TGTAACAG | 19643 |

TABLE XXII-continued

Human KDR DNAzyme and Substrate sequence

| Pos | Substrate | Seq ID No | DNAzyme | Seq ID No |
|---|---|---|---|---|
| 3337 | GCUUCCAA G UGGCUAAG | 8946 | CTTAGCCA GGCTAGCTACAACGA TTGGAAGC | 19644 |
| 3340 | UCCAAGUG G CUAAGGGC | 8947 | GCCCTTAG GGCTAGCTACAACGA CACTTGGA | 19645 |
| 3347 | GGCUAAGG G CAUGGAGU | 8948 | ACTCCATG GGCTAGCTACAACGA CCTTAGCC | 19646 |
| 3349 | CUAAGGGC A UGGAGUUC | 6726 | GAACTCCA GGCTAGCTACAACGA GCCCTTAG | 19647 |
| 3354 | GGCAUGGA G UUCUUGGC | 8949 | GCCAAGAA GGCTAGCTACAACGA TCCATGCC | 19648 |
| 3361 | AGUUCUUG G CAUCGCGA | 8950 | TCGCGATG GGCTAGCTACAACGA CAAGAACT | 19649 |
| 3363 | UUCUUGGC A UCGCGAAA | 6728 | TTTCGCGA GGCTAGCTACAACGA GCCAAGAA | 19650 |
| 3366 | UUGGCAUC G CGAAAGUG | 8951 | CACTTTCG GGCTAGCTACAACGA GATGCCAA | 19651 |
| 3372 | UCGCGAAA G UGUAUCCA | 8952 | TGGATACA GGCTAGCTACAACGA TTTCGCGA | 19652 |
| 3374 | GCGAAAGU G UAUCCACA | 8953 | TGTGGATA GGCTAGCTACAACGA ACTTTCGC | 19653 |
| 3376 | GAAAGUGU A UCCACAGG | 1976 | CCTGTGGA GGCTAGCTACAACGA ACACTTTC | 19654 |
| 3380 | GUGUAUCC A CAGGGACC | 6730 | GGTCCCTG GGCTAGCTACAACGA GGATACAC | 19655 |
| 3386 | CCACAGGG A CCUGGCGG | 8954 | CCGCCAGG GGCTAGCTACAACGA CCCTGTGG | 19656 |
| 3391 | GGGACCUG G CGGCACGA | 8955 | TCGTGCCG GGCTAGCTACAACGA CAGGTCCC | 19657 |
| 3394 | ACCUGGCG G CACGAAAU | 8956 | ATTTCGTG GGCTAGCTACAACGA CGCCAGGT | 19658 |
| 3396 | CUGGCGGC A CGAAAUAU | 6734 | ATATTTCG GGCTAGCTACAACGA GCCGCCAG | 19659 |
| 3401 | GGCACGAA A UAUCCUCU | 8957 | AGAGGATA GGCTAGCTACAACGA TTCGTGCC | 19660 |
| 3403 | CACGAAAU A UCCUCUUA | 1978 | TAAGAGGA GGCTAGCTACAACGA ATTTCGTG | 19661 |
| 3411 | AUCCUCUU A UCGGAGAA | 1982 | TTCTCCGA GGCTAGCTACAACGA AAGAGGAT | 19662 |
| 3422 | GGAGAAGA A CGUGGUUA | 8958 | TAACCACG GGCTAGCTACAACGA TCTTCTCC | 19663 |
| 3424 | AGAAGAAC G UGGUUAAA | 8959 | TTTAACCA GGCTAGCTACAACGA GTTCTTCT | 19664 |
| 3427 | AGAACGUG G UUAAAAUC | 8960 | GATTTTAA GGCTAGCTACAACGA CACGTTCT | 19665 |
| 3433 | UGGUUAAA A UCUGUGAC | 8961 | GTCACAGA GGCTAGCTACAACGA TTTAACCA | 19666 |
| 3437 | UAAAAUCU G UGACUUUG | 8962 | CAAAGTCA GGCTAGCTACAACGA AGATTTTA | 19667 |
| 3440 | AAUCUGUG A CUUUGGCU | 8963 | AGCCAAAG GGCTAGCTACAACGA CACAGATT | 19668 |
| 3446 | UGACUUUG G CUUGGCCC | 8964 | GGGCCAAG GGCTAGCTACAACGA CAAAGTCA | 19669 |
| 3451 | UUGGCUUG G CCCGGGAU | 8965 | ATCCCGGG GGCTAGCTACAACGA CAAGCCAA | 19670 |
| 3458 | GGCCCGGG A UAUUUAUA | 8966 | TATAAATA GGCTAGCTACAACGA CCCGGGCC | 19671 |
| 3460 | CCCGGGAU A UUUAUAAA | 1990 | TTTATAAA GGCTAGCTACAACGA ATCCCGGG | 19672 |
| 3464 | GGAUAUUU A UAAAGAUC | 1993 | GATCTTTA GGCTAGCTACAACGA AAATATCC | 19673 |
| 3470 | UUAUAAAG A UCCAGAUU | 8967 | AATCTGGA GGCTAGCTACAACGA CTTTATAA | 19674 |
| 3476 | AGAUCCAG A UUAUGUCA | 8968 | TGACATAA GGCTAGCTACAACGA CTGGATCT | 19675 |
| 3479 | UCCAGAUU A UGUCAGAA | 1997 | TTCTGACA GGCTAGCTACAACGA AATCTGGA | 19676 |
| 3481 | CAGAUUAU G UCAGAAAA | 8969 | TTTTCTGA GGCTAGCTACAACGA ATAATCTG | 19677 |
| 3494 | AAAAGGAG A UGCUCGCC | 8970 | GGCGAGCA GGCTAGCTACAACGA CTCCTTTT | 19678 |
| 3496 | AAGGAGAU G CUCGCCUC | 8971 | GAGGCGAG GGCTAGCTACAACGA ATCTCCTT | 19679 |
| 3500 | AGAUGCUC G CCUCCCUU | 8972 | AAGGGAGG GGCTAGCTACAACGA GAGCATCT | 19680 |

TABLE XXII-continued

Human KDR DNAzyme and Substrate sequence

| Pos | Substrate | Seq ID No | DNAzyme | Seq ID No |
|---|---|---|---|---|
| 3513 | CCUUUGAA A UGGAUGGC | 8973 | GCCATCCA GGCTAGCTACAACGA TTCAAAGG | 19681 |
| 3517 | UGAAAUGG A UGGCCCCA | 8974 | TGGGGCCA GGCTAGCTACAACGA CCATTTCA | 19682 |
| 3520 | AAUGGAUG G CCCCAGAA | 8975 | TTCTGGGG GGCTAGCTACAACGA CATCCATT | 19683 |
| 3529 | CCCCAGAA A CAAUUUUU | 8976 | AAAAATTG GGCTAGCTACAACGA TTCTGGGG | 19684 |
| 3532 | CAGAAACA A UUUUUGAC | 8977 | GTCAAAAA GGCTAGCTACAACGA TGTTTCTG | 19685 |
| 3539 | AAUUUUUG A CAGAGUGU | 8978 | ACACTCTG GGCTAGCTACAACGA CAAAAATT | 19686 |
| 3544 | UUGACAGA G UGUACACA | 8979 | TGTGTACA GGCTAGCTACAACGA TCTGTCAA | 19687 |
| 3546 | GACAGAGU G UACACAAU | 8980 | ATTGTGTA GGCTAGCTACAACGA ACTCTGTC | 19688 |
| 3548 | CAGAGUGU A CACAAUCC | 2007 | GGATTGTG GGCTAGCTACAACGA ACACTCTG | 19689 |
| 3550 | GAGUGUAC A CAAUCCAG | 6758 | CTGGATTG GGCTAGCTACAACGA GTACACTC | 19690 |
| 3553 | UGUACACA A UCCAGAGU | 8981 | ACTCTGGA GGCTAGCTACAACGA TGTGTACA | 19691 |
| 3560 | AAUCCAGA G UGACGUCU | 8982 | AGACGTCA GGCTAGCTACAACGA TCTGGATT | 19692 |
| 3563 | CCAGAGUG A CGUCUGGU | 8983 | ACCAGACG GGCTAGCTACAACGA CACTCTGG | 19693 |
| 3565 | AGAGUGAC G UCUGGUCU | 8984 | AGACCAGA GGCTAGCTACAACGA GTCACTCT | 19694 |
| 3570 | GACGUCUG G UCUUUUGG | 8985 | CCAAAAGA GGCTAGCTACAACGA CAGACGTC | 19695 |
| 3578 | GUCUUUUG G UGUUUUGC | 8986 | GCAAAACA GGCTAGCTACAACGA CAAAAGAC | 19696 |
| 3580 | CUUUUGGU G UUUUGCUG | 8987 | CAGCAAAA GGCTAGCTACAACGA ACCAAAAG | 19697 |
| 3585 | GGUGUUUU G CUGUGGGA | 8988 | TCCCACAG GGCTAGCTACAACGA AAAACACC | 19698 |
| 3588 | GUUUUGCU G UGGGAAAU | 8989 | ATTTCCCA GGCTAGCTACAACGA AGCAAAAC | 19699 |
| 3595 | UGUGGGAA A UAUUUUCC | 8990 | GGAAAATA GGCTAGCTACAACGA TTCCCACA | 19700 |
| 3597 | UGGGAAAU A UUUUCCUU | 2017 | AAGGAAAA GGCTAGCTACAACGA ATTTCCCA | 19701 |
| 3608 | UUCCUUAG G UGCUUCUC | 8991 | GAGAAGCA GGCTAGCTACAACGA CTAAGGAA | 19702 |
| 3610 | CCUUAGGU G CUUCUCCA | 8992 | TGGAGAAG GGCTAGCTACAACGA ACCTAAGG | 19703 |
| 3618 | GCUUCUCC A UAUCCUGG | 6770 | CCAGGATA GGCTAGCTACAACGA GGAGAAGC | 19704 |
| 3620 | UUCUCCAU A UCCUGGGG | 2027 | CCCCAGGA GGCTAGCTACAACGA ATGGAGAA | 19705 |
| 3628 | AUCCUGGG G UAAAGAUU | 8993 | AATCTTTA GGCTAGCTACAACGA CCCAGGAT | 19706 |
| 3634 | GGGUAAAG A UUGAUGAA | 8994 | TTCATCAA GGCTAGCTACAACGA CTTTACCC | 19707 |
| 3638 | AAAGAUUG A UGAAGAAU | 8995 | ATTCTTCA GGCTAGCTACAACGA CAATCTTT | 19708 |
| 3645 | GAUGAAGA A UUUUGUAG | 8996 | CTACAAAA GGCTAGCTACAACGA TCTTCATC | 19709 |
| 3650 | AGAAUUUU G UAGGCGAU | 8997 | ATCGCCTA GGCTAGCTACAACGA AAAATTCT | 19710 |
| 3654 | UUUUGUAG G CGAUUGAA | 8998 | TTCAATCG GGCTAGCTACAACGA CTACAAAA | 19711 |
| 3657 | UGUAGGCG A UUGAAAGA | 8999 | TCTTTCAA GGCTAGCTACAACGA CGCCTACA | 19712 |
| 3670 | AAGAAGGA A CUAGAAUG | 9000 | CATTCTAG GGCTAGCTACAACGA TCCTTCTT | 19713 |
| 3676 | GAACUAGA A UGAGGGCC | 9001 | GGCCCTCA GGCTAGCTACAACGA TCTAGTTC | 19714 |
| 3682 | GAAUGAGG G CCCCUGAU | 9002 | ATCAGGGG GGCTAGCTACAACGA CCTCATTC | 19715 |
| 3689 | GGCCCCUG A UUAUACUA | 9003 | TAGTATAA GGCTAGCTACAACGA CAGGGGCC | 19716 |
| 3692 | CCCUGAUU A UACUACAC | 2038 | GTGTAGTA GGCTAGCTACAACGA AATCAGGG | 19717 |

TABLE XXII-continued

Human KDR DNAzyme and Substrate sequence

| Pos | Substrate | Seq ID No | DNAzyme | Seq ID No |
|---|---|---|---|---|
| 3694 | CUGAUUAU A CUACACCA | 2039 | TGGTGTAG GGCTAGCTACAACGA ATAATCAG | 19718 |
| 3697 | AUUAUACU A CACCAGAA | 2040 | TTCTGGTG GGCTAGCTACAACGA AGTATAAT | 19719 |
| 3699 | UAUACUAC A CCAGAAAU | 6779 | ATTTCTGG GGCTAGCTACAACGA GTAGTATA | 19720 |
| 3706 | CACCAGAA A UGUACCAG | 9004 | CTGGTACA GGCTAGCTACAACGA TTCTGGTG | 19721 |
| 3708 | CCAGAAAU G UACCAGAC | 9005 | GTCTGGTA GGCTAGCTACAACGA ATTTCTGG | 19722 |
| 3710 | AGAAAUGU A CCAGACCA | 2041 | TGGTCTGG GGCTAGCTACAACGA ACATTTCT | 19723 |
| 3715 | UGUACCAG A CCAUGCUG | 9006 | CAGCATGG GGCTAGCTACAACGA CTGGTACA | 19724 |
| 3718 | ACCAGACC A UGCUGGAC | 6785 | GTCCAGCA GGCTAGCTACAACGA GGTCTGGT | 19725 |
| 3720 | CAGACCAU G CUGGACUG | 9007 | CAGTCCAG GGCTAGCTACAACGA ATGGTCTG | 19726 |
| 3725 | CAUGCUGG A CUGCUGGC | 7740 | GCCAGCAG GGCTAGCTACAACGA CCAGCATG | 17305 |
| 3728 | GCUGGACU G CUGGCACG | 9008 | CGTGCCAG GGCTAGCTACAACGA AGTCCAGC | 19727 |
| 3732 | GACUGCUG G CACGGGGA | 9009 | TCCCCGTG GGCTAGCTACAACGA CAGCAGTC | 19728 |
| 3734 | CUGCUGGC A CGGGGAGC | 6788 | GCTCCCCG GGCTAGCTACAACGA GCCAGCAG | 19729 |
| 3741 | CACGGGGA G CCCAGUCA | 9010 | TGACTGGG GGCTAGCTACAACGA TCCCCGTG | 19730 |
| 3746 | GGAGCCCA G UCAGAGAC | 9011 | GTCTCTGA GGCTAGCTACAACGA TGGGCTCC | 19731 |
| 3753 | AGUCAGAG A CCCACGUU | 9012 | AACGTGGG GGCTAGCTACAACGA CTCTGACT | 19732 |
| 3757 | AGAGACCC A CGUUUCA | 6795 | TGAAAACG GGCTAGCTACAACGA GGGTCTCT | 19733 |
| 3759 | AGACCCAC G UUUCAGA | 9013 | TCTGAAAA GGCTAGCTACAACGA GTGGGTCT | 19734 |
| 3768 | UUUUCAGA G UUGGUGGA | 9014 | TCCACCAA GGCTAGCTACAACGA TCTGAAAA | 19735 |
| 3772 | CAGAGUUG G UGGAACAU | 9015 | ATGTTCCA GGCTAGCTACAACGA CAACTCTG | 19736 |
| 3777 | UUGGUGGA A CAUUUGGG | 9016 | CCCAAATG GGCTAGCTACAACGA TCCACCAA | 19737 |
| 3779 | GGUGGAAC A UUUGGGAA | 6797 | TTCCCAAA GGCTAGCTACAACGA GTTCCACC | 19738 |
| 3788 | UUUGGGAA A UCUCUUGC | 9017 | GCAAGAGA GGCTAGCTACAACGA TTCCCAAA | 19739 |
| 3795 | AAUCUCUU G CAAGCUAA | 9018 | TTAGCTTG GGCTAGCTACAACGA AAGAGATT | 19740 |
| 3799 | UCUUGCAA G CUAAUGCU | 9019 | AGCATTAG GGCTAGCTACAACGA TTGCAAGA | 19741 |
| 3803 | GCAAGCUA A UGCUCAGC | 9020 | GCTGAGCA GGCTAGCTACAACGA TAGCTTGC | 19742 |
| 3805 | AAGCUAAU G CUCAGCAG | 9021 | CTGCTGAG GGCTAGCTACAACGA ATTAGCTT | 19743 |
| 3810 | AAUGCUCA G CAGGAUGG | 9022 | CCATCCTG GGCTAGCTACAACGA TGAGCATT | 19744 |
| 3815 | UCAGCAGG A UGGCAAAG | 9023 | CTTTGCCA GGCTAGCTACAACGA CCTGCTGA | 19745 |
| 3818 | GCAGGAUG G CAAAGACU | 9024 | AGTCTTTG GGCTAGCTACAACGA CATCCTGC | 19746 |
| 3824 | UGGCAAAG A CUACAUUG | 9025 | CAATGTAG GGCTAGCTACAACGA CTTTGCCA | 19747 |
| 3827 | CAAAGACU A CAUUGUUC | 2055 | GAACAATG GGCTAGCTACAACGA AGTCTTTG | 19748 |
| 3829 | AAGACUAC A UUGUUCUU | 6807 | AAGAACAA GGCTAGCTACAACGA GTAGTCTT | 19749 |
| 3832 | ACUACAUU G UUCUUCCG | 9026 | CGGAAGAA GGCTAGCTACAACGA AATGTAGT | 19750 |
| 3841 | UUCUUCCG A UAUCAGAG | 9027 | CTCTGATA GGCTAGCTACAACGA CGGAAGAA | 19751 |
| 3843 | CUUCCGAU A UCAGAGAC | 2061 | GTCTCTGA GGCTAGCTACAACGA ATCGGAAG | 19752 |
| 3850 | UAUCAGAG A CUUUGAGC | 9028 | GCTCAAAG GGCTAGCTACAACGA CTCTGATA | 19753 |

TABLE XXII-continued

Human KDR DNAzyme and Substrate sequence

| Pos | Substrate | Seq ID No | DNAzyme | Seq ID No |
|---|---|---|---|---|
| 3857 | GACUUUGA G CAUGGAAG | 9029 | CTTCCATG GGCTAGCTACAACGA TCAAAGTC | 19754 |
| 3859 | CUUUGAGC A UGGAAGAG | 6812 | CTCTTCCA GGCTAGCTACAACGA GCTCAAAG | 19755 |
| 3869 | GCAAGAGC A UUCUCGAC | 9030 | GTCCAGAA GGCTAGCTACAACGA CCTCTTCC | 19756 |
| 3876 | GAUUCUGG A CUCUCUCU | 9031 | AGAGAGAG GGCTAGCTACAACGA CCAGAATC | 19757 |
| 3885 | CUCUCUCU G CCUACCUC | 9032 | GAGGTACG GGCTAGCTACAACGA ACAGACAG | 19758 |
| 3889 | CUCUGCCU A CCUCACCU | 2070 | AGGTGAGG GGCTAGCTACAACGA AGGCAGAG | 19759 |
| 3894 | CCUACCUC A CCUGUUUC | 6822 | GAAACAGG GGCTAGCTACAACGA GAGGTAGG | 19760 |
| 3898 | CCUCACCU G UUUCCUGU | 9033 | ACAGCAAA GGCTAGCTACAACGA AGCTCAGC | 19761 |
| 3905 | UGUUUCCU G UAUCGAGG | 9034 | CCTCCATA GGCTAGCTACAACGA ACGAAACA | 19762 |
| 3907 | UUUCCUGU A UGGAGGAG | 2075 | CTCCTCCA GGCTAGCTACAACGA ACAGGAAA | 19763 |
| 3922 | AGGACGAA G UAUGUCAC | 9035 | CTCACATA GGCTAGCTACAACGA TTCCTCCT | 19764 |
| 3924 | GAGCAAGU A UGUGACCC | 2076 | CGCTCACA GGCTAGCTACAACGA ACTTCCTC | 19765 |
| 3926 | GCAAGUAU G UGACCCCA | 9036 | TGCGCTCA GGCTAGCTACAACGA ATACTTCC | 19766 |
| 3929 | AGUAUCUG A CCCCAAAU | 9037 | ATTTGCCG GGCTAGCTACAACGA CACATACT | 19767 |
| 3936 | GACCCCAA A UUCCAUUA | 9038 | TAATGCAA GGCTAGCTACAACGA TTGCCGTC | 19768 |
| 3941 | CAAAUUCC A UUAUGACA | 6832 | TGTCATAA GGCTAGCTACAACGA CGAATTTG | 19769 |
| 3944 | AUUCCAUU A UGACAACA | 2080 | TCTTGTCA GGCTAGCTACAACGA AATCCAAT | 19770 |
| 3947 | CCAUUAUG A CAACACAG | 9039 | CTGTGTTG GGCTAGCTACAACGA CATAATGG | 19771 |
| 3950 | UUAUGACA A CACAGCAG | 9040 | CTGCTGTG GGCTAGCTACAACGA TGTCATAA | 19772 |
| 3952 | AUGACAAC A CAGCAGGA | 6834 | TCCTGCTG GGCTAGCTACAACGA GTTGTCAT | 19773 |
| 3955 | ACAACACA G CAGGAAUC | 9041 | GATTCCTG GGCTAGCTACAACGA TGTGTTGT | 19774 |
| 3961 | CAGCAGGA A UCAGUCAG | 9042 | CTGACTGA GGCTAGCTACAACGA TCCTGCTG | 19775 |
| 3965 | AGGAAUCA G UCAGUAUC | 9043 | GATACTGA GGCTAGCTACAACGA TGATTCCT | 19776 |
| 3969 | AUCAGUCA G UAUCUGCA | 9044 | TGCAGATA GGCTAGCTACAACGA TGACTGAT | 19777 |
| 3971 | CAGUCAGU A UCUGCAGA | 2083 | TCTGCAGA GGCTAGCTACAACGA ACTGACTG | 19778 |
| 3975 | CAGUAUCU G CAGAACAG | 9045 | CTGTTCTG GGCTAGCTACAACGA AGATACTG | 19779 |
| 3980 | UCUGCAGA A CAGUAAGC | 9046 | GCTTACTG GGCTAGCTACAACGA TCTGCAGA | 19780 |
| 3983 | GCAGAACA G UAAGCGAA | 9047 | TTCGCTTA GGCTAGCTACAACGA TGTTCTGC | 19781 |
| 3987 | AACAGUAA G CGAAAGAG | 9048 | CTCTTTCG GGCTAGCTACAACGA TTACTGTT | 19782 |
| 3995 | GCGAAAGA G CCGGCCUG | 9049 | CAGGCCGG GGCTAGCTACAACGA TCTTTCGC | 19783 |
| 3999 | AAGAGCCG G CCUGUGAG | 9050 | CTCACAGG GGCTAGCTACAACGA CGGCTCTT | 19784 |
| 4003 | GCCGGCCU G UGAGUGUA | 9051 | TACACTCA GGCTAGCTACAACGA AGGCCGGC | 19785 |
| 4007 | GCCUGUGA G UGUAAAAA | 9052 | TTTTTACA GGCTAGCTACAACGA TCACAGGC | 19786 |
| 4009 | CUGUGAGU G UAAAACA | 9053 | TGTTTTTA GGCTAGCTACAACGA ACTCACAG | 19787 |
| 4015 | GUGUAAAA A CAUUUGAA | 9054 | TTCAAATG GGCTAGCTACAACGA TTTTACAC | 19788 |
| 4017 | GUAAAAAC A UUUGAAGA | 6845 | TCTTCAAA GGCTAGCTACAACGA GTTTTTAC | 19789 |
| 4025 | AUUUGAAG A UAUCCCGU | 9055 | ACGGGATA GGCTAGCTACAACGA CTTCAAAT | 19790 |

TABLE XXII-continued

Human KDR DNAzyme and Substrate sequence

| Pos | Substrate | Seq ID No | DNAzyme | Seq ID No |
|---|---|---|---|---|
| 4027 | UUGAAGAU A UCCCGUUA | 2089 | TAACGGGA GGCTAGCTACAACGA ATCTTCAA | 19791 |
| 4032 | GAUAUCCC G UUAGAAGA | 9056 | TCTTCTAA GGCTAGCTACAACGA GGGATATC | 19792 |
| 4041 | UUAGAAGA A CCAGAAGU | 9057 | ACTTCTGG GGCTAGCTACAACGA TCTTCTAA | 19793 |
| 4048 | AACCAGAA G UAAAAGUA | 9058 | TACTTTTA GGCTAGCTACAACGA TTCTGGTT | 19794 |
| 4054 | AAGUAAAA G UAAUCCCA | 9059 | TGGGATTA GGCTAGCTACAACGA TTTTACTT | 19795 |
| 4057 | UAAAAGUA A UCCCAGAU | 9060 | ATCTGGGA GGCTAGCTACAACGA TACTTTTA | 19796 |
| 4064 | AAUCCCAG A UGACAACC | 9061 | GGTTGTCA GGCTAGCTACAACGA CTGGGATT | 19797 |
| 4067 | CCCAGAUG A CAACCAGA | 9062 | ACTGGTTG GGCTAGCTACAACGA CATCTGGG | 19798 |
| 4070 | AGAUGACA A CCAGACGG | 9063 | CCGTCTGG GGCTAGCTACAACGA TGTCATCT | 19799 |
| 4075 | ACAACCAG A CGGACAGU | 9064 | ACTGTCCG GGCTAGCTACAACGA CTGGTTGT | 19800 |
| 4079 | CCAGACGG A CAGUGGUA | 9065 | TACCACTG GGCTAGCTACAACGA CCGTCTGG | 19801 |
| 4082 | GACGGACA G UGGUAUGG | 9066 | CCATACCA GGCTAGCTACAACGA TGTCCGTC | 19802 |
| 4085 | GGACAGUG G UAUGGUUC | 9067 | GAACCATA GGCTAGCTACAACGA CACTGTCC | 19803 |
| 4087 | ACAGUGGU A UGGUUCUU | 2096 | AAGAACCA GGCTAGCTACAACGA ACCACTGT | 19804 |
| 4090 | GUGGUAUG G UUCUUGCC | 9068 | GGCAAGAA GGCTAGCTACAACGA CATACCAC | 19805 |
| 4096 | UGGUUCUU G CCUCAGAA | 9069 | TTCTGAGG GGCTAGCTACAACGA AAGAACCA | 19806 |
| 4107 | UCAGAAGA G CUGAAAAC | 9070 | GTTTTCAG GGCTAGCTACAACGA TCTTCTGA | 19807 |
| 4114 | AGCUGAAA A CUUUGGAA | 9071 | TTCCAAAG GGCTAGCTACAACGA TTTCAGCT | 19808 |
| 4124 | UUUGGAAG A CAGAACCA | 9072 | TGGTTCTG GGCTAGCTACAACGA CTTCCAAA | 19809 |
| 4129 | AAGACAGA A CCAAAUUA | 9073 | TAATTTGG GGCTAGCTACAACGA TCTGTCTT | 19810 |
| 4134 | AGAACCAA A UUAUCUCC | 9074 | GGAGATAA GGCTAGCTACAACGA TTGGTTCT | 19811 |
| 4137 | ACCAAAUU A UCUCCAUC | 2104 | GATGGAGA GGCTAGCTACAACGA AATTTGGT | 19812 |
| 4143 | UUAUCUCC A UCUUUUGG | 6868 | CCAAAAGA GGCTAGCTACAACGA GGAGATAA | 19813 |
| 4151 | AUCUUUUG G UGGAAUGG | 9075 | CCATTCCA GGCTAGCTACAACGA CAAAAGAT | 19814 |
| 4156 | UUGGUGGA A UGGUGCCC | 9076 | GGGCACCA GGCTAGCTACAACGA TCCACCAA | 19815 |
| 4159 | GUGGAAUG G UGCCCAGC | 9077 | GCTGGGCA GGCTAGCTACAACGA CATTCCAC | 19816 |
| 4161 | GGAAUGGU G CCCAGCAA | 9078 | TTGCTGGG GGCTAGCTACAACGA ACCATTCC | 19817 |
| 4166 | GGUGCCCA G CAAAAGCA | 9079 | TGCTTTTG GGCTAGCTACAACGA TGGGCACC | 19818 |
| 4172 | CAGCAAAA G CAGGGAGU | 9080 | ACTCCCTG GGCTAGCTACAACGA TTTTGCTG | 19819 |
| 4179 | AGCAGGGA G UCUGUGGC | 9081 | GCCACAGA GGCTAGCTACAACGA TCCCTGCT | 19820 |
| 4183 | GGGAGUCU G UGGCAUCU | 9082 | AGATGCCA GGCTAGCTACAACGA AGACTCCC | 19821 |
| 4186 | AGUCUGUG G CAUCUGAA | 9083 | TTCAGATG GGCTAGCTACAACGA CACAGACT | 19822 |
| 4188 | UCUGUGGC A UCUGAAGG | 6876 | CCTTCAGA GGCTAGCTACAACGA GCCACAGA | 19823 |
| 4196 | AUCUGAAG G CUCAAACC | 9084 | GGTTTGAG GGCTAGCTACAACGA CTTCAGAT | 19824 |
| 4202 | AGGCUCAA A CCAGACAA | 9085 | TTGTCTGG GGCTAGCTACAACGA TTGAGCCT | 19825 |
| 4207 | CAAACCAG A CAAGCGGC | 9086 | GCCGCTTG GGCTAGCTACAACGA CTGGTTTG | 19826 |
| 4211 | CCAGACAA G CGGCUACC | 9087 | GGTAGCCG GGCTAGCTACAACGA TTGTCTGG | 19827 |

TABLE XXII-continued

Human KDR DNAzyme and Substrate sequence

| Pos | Substrate | Seq ID No | DNAzyme | Seq ID No |
|-----|-----------|-----------|---------|-----------|
| 4214 | GACAAGCG G CUACCAGU | 9088 | ACTGGTAG GGCTAGCTACAACGA CGCTTGTC | 19828 |
| 4217 | AAGCGGCU A CCAGUCCG | 2114 | CGGACTGG GGCTAGCTACAACGA AGCCGCTT | 19829 |
| 4221 | GGCUACCA G UCCGGAUA | 9089 | TATCCGGA GGCTAGCTACAACGA TGGTAGCC | 19830 |
| 4227 | CAGUCCGG A UAUCACUC | 9090 | GAGTGATA GGCTAGCTACAACGA CCGGACTG | 19831 |
| 4229 | GUCCGGAU A UCACUCCG | 2116 | CGGAGTGA GGCTAGCTACAACGA ATCCGGAC | 19832 |
| 4232 | CGGAUAUC A CUCCGAUG | 6887 | CATCGGAG GGCTAGCTACAACGA GATATCCG | 19833 |
| 4238 | UCACUCCG A UGACACAG | 9091 | CTGTGTCA GGCTAGCTACAACGA CGGAGTGA | 19834 |
| 4241 | CUCCGAUG A CACAGACA | 9092 | TGTCTGTG GGCTAGCTACAACGA CATCGGAG | 19835 |
| 4243 | CCGAUGAC A CAGACACC | 6890 | GGTGTCTG GGCTAGCTACAACGA GTCATCGG | 19836 |
| 4247 | UGACACAG A CACCACCG | 9093 | CGGTGGTG GGCTAGCTACAACGA CTGTGTCA | 19837 |
| 4249 | ACACAGAC A CCACCGUG | 6892 | CACGGTGG GGCTAGCTACAACGA GTCTGTGT | 19838 |
| 4252 | CAGACACC A CCGUGUAC | 6894 | GTACACGG GGCTAGCTACAACGA GGTGTCTG | 19839 |
| 4255 | ACACCACC G UGUACUCC | 9094 | GGAGTACA GGCTAGCTACAACGA GGTGGTGT | 19840 |
| 4257 | ACCACCGU G UACUCCAG | 9095 | CTGGAGTA GGCTAGCTACAACGA ACGGTGGT | 19841 |
| 4259 | CACCGUGU A CUCCAGUG | 2119 | CACTGGAG GGCTAGCTACAACGA ACACGGTG | 19842 |
| 4265 | GUACUCCA G UGAGGAAG | 9096 | CTTCCTCA GGCTAGCTACAACGA TGGAGTAC | 19843 |
| 4273 | GUGAGGAA G CAGAACUU | 9097 | AAGTTCTG GGCTAGCTACAACGA TTCCTCAC | 19844 |
| 4278 | GAAGCAGA A CUUUUAAA | 9098 | TTTAAAAG GGCTAGCTACAACGA TCTGCTTC | 19845 |
| 4287 | CUUUUAAA G CUGAUAGA | 9099 | TCTATCAG GGCTAGCTACAACGA TTTAAAAG | 19846 |
| 4291 | UAAAGCUG A UAGAGAUU | 9100 | AATCTCTA GGCTAGCTACAACGA CAGCTTTA | 19847 |
| 4297 | UGAUAGAG A UUGGAGUG | 9101 | CACTCCAA GGCTAGCTACAACGA CTCTATCA | 19848 |
| 4303 | AGAUUGGA G UGCAAACC | 9102 | GGTTTGCA GGCTAGCTACAACGA TCCAATCT | 19849 |
| 4305 | AUUGGAGU G CAAACCGG | 9103 | CCGGTTTG GGCTAGCTACAACGA ACTCCAAT | 19850 |
| 4309 | GAGUGCAA A CCGGUAGC | 9104 | GCTACCGG GGCTAGCTACAACGA TTGCACTC | 19851 |
| 4313 | GCAAACCG G UAGCACAG | 9105 | CTGTGCTA GGCTAGCTACAACGA CGGTTTGC | 19852 |
| 4316 | AACCGGUA G CACAGCCC | 9106 | GGGCTGTG GGCTAGCTACAACGA TACCGGTT | 19853 |
| 4318 | CCGGUAGC A CAGCCCAG | 6904 | CTGGGCTG GGCTAGCTACAACGA GCTACCGG | 19854 |
| 4321 | GUAGCACA G CCCAGAUU | 9107 | AATCTGGG GGCTAGCTACAACGA TGTGCTAC | 19855 |
| 4327 | CAGCCCAG A UUCUCCAG | 9108 | CTGGAGAA GGCTAGCTACAACGA CTGGGCTG | 19856 |
| 4335 | AUUCUCCA G CCUGACUC | 9109 | GAGTCAGG GGCTAGCTACAACGA TGGAGAAT | 19857 |
| 4340 | CCAGCCUG A CUCGGGGA | 9110 | TCCCCGAG GGCTAGCTACAACGA CAGCCTGG | 19858 |
| 4348 | ACUCGGGG A CCACACUG | 9111 | CAGTGTGG GGCTAGCTACAACGA CCCCGAGT | 19859 |
| 4351 | CGGGGACC A CACUGAGC | 6916 | GCTCAGTG GGCTAGCTACAACGA GGTCCCCG | 19860 |
| 4353 | GGGACCAC A CUGAGCUC | 6917 | GAGCTCAG GGCTAGCTACAACGA GTGGTCCC | 19861 |
| 4358 | CACACUGA G CUCUCCUC | 9112 | GAGGAGAG GGCTAGCTACAACGA TCAGTGTG | 19862 |
| 4369 | CUCCUCCU G UUUAAAAG | 9113 | CTTTTAAA GGCTAGCTACAACGA AGGAGGAG | 19863 |
| 4381 | AAAAGGAA G CAUCCACA | 9114 | TGTGGATG GGCTAGCTACAACGA TTCCTTTT | 19864 |

TABLE XXII-continued

Human KDR DNAzyme and Substrate sequence

| Pos | Substrate | Seq ID No | DNAzyme | Seq ID No |
|---|---|---|---|---|
| 4383 | AAGGAAGC A UCCACACC | 6925 | GGTGTGGA GGCTAGCTACAACGA GCTTCCTT | 19865 |
| 4387 | AAGCAUCC A CACCCCAA | 6927 | TTGGGGTG GGCTAGCTACAACGA GGATCCTT | 19866 |
| 4389 | GCAUCCAC A CCCCAACU | 6928 | AGTTGGCG GGCTAGCTACAACGA GTGGATGC | 19867 |
| 4395 | ACACCCCA A CUCCCGGA | 9115 | TCCGGGAG GGCTAGCTACAACGA TGGGGTGT | 19868 |
| 4403 | ACUCCCGG A CAUCACAU | 9116 | ATGTGATG GGCTAGCTACAACGA CCGGGAGT | 19869 |
| 4405 | UCCCGGAC A UCACAUGA | 6936 | TCATGTGA GGCTAGCTACAACGA GTCCGGGA | 19870 |
| 4408 | CGGACAUC A CAUGAGAG | 6937 | CTCTCATG GGCTAGCTACAACGA GATGTCCG | 19871 |
| 4410 | GACAUCAC A UGAGAGGU | 6938 | ACCTCTCA GGCTAGCTACAACGA GTGATGTC | 19872 |
| 4417 | CAUGAGAG G UCUGCUCA | 9117 | TGAGCAGA GGCTAGCTACAACGA CTCTCATG | 19873 |
| 4421 | AGAGGUCU G CUCAGAUU | 9118 | AATCTGAG GGCTAGCTACAACGA AGACCTCT | 19874 |
| 4427 | CUGCUCAG A UUUUGAAG | 9119 | CTTCAAAA GGCTAGCTACAACGA CTGAGCAG | 19875 |
| 4435 | AUUUUGAA G UGUUGUUC | 9120 | GAACAACA GGCTAGCTACAACGA TTCAAAAT | 19876 |
| 4437 | UUUGAAGU G UUGUUCUU | 9121 | AAGAACAA GGCTAGCTACAACGA ACTTCAAA | 19877 |
| 4440 | GAAGUGUU G UUCUUUCC | 9122 | GGAAAGAA GGCTAGCTACAACGA AACACTTC | 19878 |
| 4449 | UUCUUUCC A CCAGCAGG | 6944 | CCTGCTGG GGCTAGCTACAACGA GGAAAGAA | 19879 |
| 4453 | UUCCACCA G CAGGAAGU | 9123 | ACTTCCTG GGCTAGCTACAACGA TGGTGGAA | 19880 |
| 4460 | AGCAGGAA G UAGCCGCA | 9124 | TGCGGCTA GGCTAGCTACAACGA TTCCTGCT | 19881 |
| 4463 | AGGAAGUA G CCGCAUUU | 9125 | AAATGCGG GGCTAGCTACAACGA TACTTCCT | 19882 |
| 4466 | AAGUAGCC G CAUUUGAU | 9126 | ATCAAATG GGCTAGCTACAACGA GGCTACTT | 19883 |
| 4468 | GUAGCCGC A UUUGAUUU | 6949 | AAATCAAA GGCTAGCTACAACGA GCGGCTAC | 19884 |
| 4473 | CGCAUUUG A UUUUCAUU | 9127 | AATGAAAA GGCTAGCTACAACGA CAAATGCG | 19885 |
| 4479 | UGAUUUUC A UUUCGACA | 6950 | TGTCGAAA GGCTAGCTACAACGA GAAAATCA | 19886 |
| 4485 | UCAUUUCG A CAACAGAA | 9128 | TTCTGTTG GGCTAGCTACAACGA CGAAATGA | 19887 |
| 4488 | UUUCGACA A CAGAAAAA | 9129 | TTTTTCTG GGCTAGCTACAACGA TGTCGAAA | 19888 |
| 4499 | GAAAAAGG A CCUCGGAC | 9130 | GTCCGAGG GGCTAGCTACAACGA CCTTTTTC | 19889 |
| 4506 | GACCUCGG A CUGCAGGG | 9131 | CCCTGCAG GGCTAGCTACAACGA CCGAGGTC | 19890 |
| 4509 | CUCGGACU G CAGGGAGC | 9132 | GCTCCCTG GGCTAGCTACAACGA AGTCCGAG | 19891 |
| 4516 | UGCAGGGA G CCAGUCUU | 9133 | AAGACTGG GGCTAGCTACAACGA TCCCTGCA | 19892 |
| 4520 | GGGAGCCA G UCUUCUAG | 9134 | CTAGAAGA GGCTAGCTACAACGA TGGCTCCC | 19893 |
| 4529 | UCUUCUAG G CAUAUCCU | 9135 | AGGATATG GGCTAGCTACAACGA CTAGAAGA | 19894 |
| 4531 | UUCUAGGC A UAUCCUGG | 9136 | CCAGGATA GGCTAGCTACAACGA GCCTAGAA | 19895 |
| 4533 | CUAGGCAU A UCCUGGAA | 9137 | TTCCAGGA GGCTAGCTACAACGA ATGCCTAG | 19896 |
| 4545 | UGGAAGAG G CUUGUGAC | 9138 | GTCACAAG GGCTAGCTACAACGA CTCTTCCA | 19897 |
| 4549 | AGAGGCUU G UGACCCAA | 9139 | TTGGGTCA GGCTAGCTACAACGA AAGCCTCT | 19898 |
| 4552 | GGCUUGUG A CCCAAGAA | 9140 | TTCTTGGG GGCTAGCTACAACGA CACAAGCC | 19899 |
| 4560 | ACCCAAGA A UGUGUCUG | 9141 | CAGACACA GGCTAGCTACAACGA TCTTGGGT | 19900 |
| 4562 | CCAAGAAU G UGUCUGUG | 9142 | CACAGACA GGCTAGCTACAACGA ATTCTTGG | 19901 |

TABLE XXII-continued

Human KDR DNAzyme and Substrate sequence

| Pos | Substrate | Seq ID No | DNAzyme | Seq ID No |
|---|---|---|---|---|
| 4564 | AAGAAUGU G UCUGUGUC | 9143 | GACACAGA GGCTAGCTACAACGA ACATTCTT | 19902 |
| 4568 | AUGUGUCU G UGUCUUCU | 9144 | AGAAGACA GGCTAGCTACAACGA AGACACAT | 19903 |
| 4570 | GUGUCUGU G UCUUCUCC | 9145 | GGAGAAGA GGCTAGCTACAACGA ACAGACAC | 19904 |
| 4581 | UUCUCCCA G UGUUGACC | 9146 | GGTCAACA GGCTAGCTACAACGA TGGGAGAA | 19905 |
| 4583 | CUCCCAGU G UUGACCUG | 9147 | CAGGTCAA GGCTAGCTACAACGA ACTGGGAG | 19906 |
| 4587 | CAGUGUUG A CCUGAUCC | 9148 | GGATCAGG GGCTAGCTACAACGA CAACACTG | 19907 |
| 4592 | UUGACCUG A UCCUCUUU | 9149 | AAAGAGGA GGCTAGCTACAACGA CAGGTCAA | 19908 |
| 4605 | CUUUUUUC A UUCAUUUA | 9150 | TAAATGAA GGCTAGCTACAACGA GAAAAAAG | 19909 |
| 4609 | UUUCAUUC A UUUAAAAA | 9151 | TTTTTAAA GGCTAGCTACAACGA GAATGAAA | 19910 |
| 4618 | UUUAAAAA G CAUUAUCA | 9152 | TGATAATG GGCTAGCTACAACGA TTTTTAAA | 19911 |
| 4620 | UAAAAAGC A UUAUCAUG | 9153 | CATGATAA GGCTAGCTACAACGA GCTTTTTA | 19912 |
| 4623 | AAAGCAUU A UCAUGCCC | 9154 | GGGCATGA GGCTAGCTACAACGA AATGCTTT | 19913 |
| 4626 | GCAUUAUC A UGCCCUG | 9155 | CAGGGGCA GGCTAGCTACAACGA GATAATGC | 19914 |
| 4628 | AUUAUCAU G CCCCUGCU | 9156 | AGCAGGGG GGCTAGCTACAACGA ATGATAAT | 19915 |
| 4634 | AUGCCCCU G CUGCGGGU | 9157 | ACCCGCAG GGCTAGCTACAACGA AGGGGCAT | 19916 |
| 4637 | CCCCUGCU G CGGGUCUC | 9158 | GAGACCCG GGCTAGCTACAACGA AGCAGGGG | 19917 |
| 4641 | UGCUGCGG G UCUCACCA | 9159 | TGGTGAGA GGCTAGCTACAACGA CCGCAGCA | 19918 |
| 4646 | CGGGUCUC A CCAUGGGU | 9160 | ACCCATGG GGCTAGCTACAACGA GAGACCCG | 19919 |
| 4649 | GUCUCACC A UGGGUUUA | 9161 | TAAACCCA GGCTAGCTACAACGA GGTGAGAC | 19920 |
| 4653 | CACCAUGG G UUUAGAAC | 9162 | GTTCTAAA GGCTAGCTACAACGA CCATGGTG | 19921 |
| 4660 | GGUUUAGA A CAAAGAGC | 9163 | GCTCTTTG GGCTAGCTACAACGA TCTAAACC | 19922 |
| 4667 | AACAAAGA G CUUCAAGC | 9164 | GCTTGAAG GGCTAGCTACAACGA TCTTTGTT | 19923 |
| 4674 | AGCUUCAA G CAAUGGCC | 9165 | GGCCATTG GGCTAGCTACAACGA TTGAAGCT | 19924 |
| 4677 | UUCAACCA A UGGCCCCA | 9166 | TGGGGCCA GGCTAGCTACAACGA TGCTTGAA | 19925 |
| 4680 | AAGCAAUG G CCCCAUCC | 9167 | GGATGGGG GGCTAGCTACAACGA CATTGCTT | 19926 |
| 4685 | AUGGCCCC A UCCUCAAA | 9168 | TTTGAGGA GGCTAGCTACAACGA GGGGCCAT | 19927 |
| 4697 | UCAAAGAA G UAGCAGUA | 9169 | TACTGCTA GGCTAGCTACAACGA TTCTTTGA | 19928 |
| 4700 | AAGAAGUA G CAGUACCU | 9170 | AGGTACTG GGCTAGCTACAACGA TACTTCTT | 19929 |
| 4703 | AAGUAGCA G UACCUGGG | 9171 | CCCAGGTA GGCTAGCTACAACGA TGCTACTT | 19930 |
| 4705 | GUAGCAGU A CCUGGGA | 9172 | TCCCCAGG GGCTAGCTACAACGA ACTGCTAC | 19931 |
| 4714 | CCUGGGGA G CUGACACU | 9173 | AGTGTCAG GGCTAGCTACAACGA TCCCCAGG | 19932 |
| 4718 | GGGAGCUG A CACUUCUG | 9174 | CAGAAGTG GGCTAGCTACAACGA CAGCTCCC | 19933 |
| 4720 | GAGCUGAC A CUUCUGUA | 9175 | TACAGAAG GGCTAGCTACAACGA GTCACCTC | 19934 |
| 4726 | ACACUUCU G UAAACUA | 9176 | TAGTTTTA GGCTAGCTACAACGA AGAAGTGT | 19935 |
| 4731 | UCUGUAAA A CUAGAAGA | 9177 | TCTTCTAG GGCTAGCTACAACGA TTTACAGA | 19936 |
| 4739 | ACUAGAAG A UAAACCAG | 9178 | CTGGTTTA GGCTAGCTACAACGA CTTCTAGT | 19937 |
| 4743 | GAAGAUAA A CCAGGCAA | 9179 | TTGCCTGG GGCTAGCTACAACGA TTATCTTC | 19938 |

TABLE XXII-continued

Human KDR DNAzyme and Substrate sequence

| Pos | Substrate | Seq ID No | DNAzyme | Seq ID No |
|---|---|---|---|---|
| 4748 | UAAACCAG G CAACGUAA | 9180 | TTACGTTG GGCTAGCTACAACGA CTGGTTTA | 19939 |
| 4751 | ACCAGGCA A CGUAAGUG | 9181 | CACTTACG GGCTAGCTACAACGA TGCCTGGT | 19940 |
| 4753 | CAGGCAAC G UAAGUGUU | 9182 | AACACTTA GGCTAGCTACAACGA GTTGCCTG | 19941 |
| 4757 | CAACGUAA G UGUUCGAG | 9183 | CTCGAACA GGCTAGCTACAACGA TTACGTTG | 19942 |
| 4759 | ACGUAAGU G UUCGAGGU | 9184 | ACCTCGAA GGCTAGCTACAACGA ACTTACGT | 19943 |
| 4766 | UGUUCGAG G UGUUGAAG | 9185 | CTTCAACA GGCTAGCTACAACGA CTCGAACA | 19944 |
| 4768 | UUCGAGGU G UUGAAGAU | 9186 | ATCTTCAA GGCTAGCTACAACGA ACCTCGAA | 19945 |
| 4775 | UGUUGAAG A UGGGAAGG | 9187 | CCTTCCCA GGCTAGCTACAACGA CTTCAACA | 19946 |
| 4784 | UGGGAAGG A UUUGCAGG | 9188 | CCTGCAAA GGCTAGCTACAACGA CCTTCCCA | 19947 |
| 4788 | AAGGAUUU G CAGGGCUC | 9189 | CAGCCCTG GGCTAGCTACAACGA AAATCCTT | 19948 |
| 4793 | UUUGCAGG G CUGAGUCU | 9190 | AGACTCAG GGCTAGCTACAACGA CCTGCAAA | 19949 |
| 4798 | AGGGCUGA G UCUAUCCA | 9191 | TGGATAGA GGCTAGCTACAACGA TCAGCCCT | 19950 |
| 4802 | CUGACUCU A UCCAAGAG | 9192 | CTCTTGGA GGCTAGCTACAACGA AGACTCAG | 19951 |
| 4811 | UCCAAGAG G CUUUGUUU | 9193 | AAACAAAG GGCTAGCTACAACGA CTCTTGGA | 19952 |
| 4816 | GAGGCUUU G UUUAGGAC | 9194 | GTCCTAAA GGCTAGCTACAACGA AAAGCCTC | 19953 |
| 4823 | UGUUUAGG A CGUGGGUC | 9195 | GACCCACG GGCTAGCTACAACGA CCTAAACA | 19954 |
| 4825 | UUUAGGAC G UGGGUCCC | 9196 | GGGACCCA GGCTAGCTACAACGA GTCCTAAA | 19955 |
| 4829 | CGACGUGG G UCCCAAGC | 9197 | GCTTGGGA GGCTAGCTACAACGA CCACGTCC | 19956 |
| 4836 | GGUCCCAA G CCAAGCCU | 9198 | AGGCTTGG GGCTAGCTACAACGA TTGGGACC | 19957 |
| 4841 | CAACCCAA G CCUUAAGU | 9199 | ACTTAAGG GGCTAGCTACAACGA TTGGCTTG | 19958 |
| 4848 | AGCCUUAA G UGUGGAAU | 9200 | ATTCCACA GGCTAGCTACAACGA TTAAGGCT | 19959 |
| 4850 | CCUUAAGU G UGGAAUUC | 9201 | GAATTCCA GGCTAGCTACAACGA ACTTAAGG | 19960 |
| 4855 | AGUGUCCA A UUCGCAUU | 9202 | AATCCGAA GGCTAGCTACAACGA TCCACACT | 19961 |
| 4861 | GAAUUCGG A UUGAUAGA | 9203 | TCTATCAA GCCTAGCTACAACGA CCGAATTC | 19962 |
| 4865 | UCGGAUUG A UAGAAAGC | 9204 | CCTTTCTA GGCTAGCTACAACGA CAATCCGA | 19963 |
| 4877 | AAAGGAAG A CUAACGUU | 9205 | AACGTTAG GGCTAGCTACAACGA CTTCCTTT | 19964 |
| 4881 | GAAGACUA A CGUUACCU | 9206 | AGGTAACG GGCTAGCTACAACGA TAGTCTTC | 19965 |
| 4883 | AGACUAAC G UUACCUUG | 9207 | CAAGGTAA GCCTAGCTACAACGA GTTAGTCT | 19966 |
| 4886 | CUAACGUU A CCUUGCUU | 9208 | AAGCAAGG GGCTAGCTACAACGA AACGTTAG | 19967 |
| 4891 | GUUACCUU G CUUGGAG | 9209 | CTCCAAAG GGCTAGCTACAACGA AAGGTAAC | 19968 |
| 4901 | UUUGGAGA G UACUGGAG | 9210 | CTCCAGTA GGCTAGCTACAACGA TCTCCAAA | 19969 |
| 4903 | UGGAGAGU A CUGGAGCC | 9211 | GGCTCCAG GGCTAGCTACAACGA ACTCTCCA | 19970 |
| 4909 | GUACUGGA G CCUGCAAA | 9212 | TTTGCAGG GGCTAGCTACAACGA TCCAGTAC | 19971 |
| 4913 | UCGAGCCU G CAAAUGCA | 9213 | TGCATTTG GGCTAGCTACAACGA AGGCTCCA | 19972 |
| 4917 | GCCUGCAA A UGCAUUGU | 9214 | ACAATGCA GGCTAGCTACAACGA TTGCAGGC | 19973 |
| 4919 | CUGCAAAU G CAUUGUGU | 9215 | ACACAATG GGCTAGCTACAACGA ATTTGCAG | 19974 |
| 4921 | GCAAAUGC A UUGUGUUU | 9216 | AAACACAA GGCTAGCTACAACGA GCATTTGC | 19975 |

TABLE XXII-continued

Human KDR DNAzyme and Substrate sequence

| Pos | Substrate | Seq ID No | DNAzyme | Seq ID No |
|---|---|---|---|---|
| 4924 | AAUGCAUU G UCUUUGCU | 9217 | AGCAAACA GGCTAGCTACAACGA AATGCATT | 19976 |
| 4926 | UGCAUUGU G UUUGCUCU | 9218 | AGAGCAAA GGCTAGCTACAACGA ACAATGCA | 19977 |
| 4930 | UUGUGUUU G CUCUGGUG | 9219 | CACCAGAG GGCTAGCTACAACGA AAACACAA | 19978 |
| 4936 | UUGCUCUG G UGGAGGUG | 9220 | CACCTCCA GGCTAGCTACAACGA CAGAGCAA | 19979 |
| 4942 | UGGUGGAG G UGGGCAUG | 9221 | CATGCCCA GGCTAGCTACAACGA CTCCACCA | 19980 |
| 4946 | GGAGGUGG G CAUGGGGU | 9222 | ACCCCATG GGCTAGCTACAACGA CCACCTCC | 19981 |
| 4948 | AGGUGGGC A UGGGGUCU | 9223 | AGACCCCA GGCTAGCTACAACGA GCCCACCT | 19982 |
| 4953 | GGCAUGGG G UCUGUUCU | 9224 | AGAACAGA GGCTAGCTACAACGA CCCATGCC | 19983 |
| 4957 | UGGGGUCU G UUCUGAAA | 9225 | TTTCAGAA GGCTAGCTACAACGA AGACCCCA | 19984 |
| 4965 | GUUCUGAA A UGUAAAGG | 9226 | CCTTTACA GGCTAGCTACAACGA TTCAGAAC | 19985 |
| 4967 | UCUGAAAU G UAAAGGGU | 9227 | ACCCTTTA GGCTAGCTACAACGA ATTTCAGA | 19986 |
| 4974 | UGUAAAGG G UUCAGACG | 9228 | CGTCTGAA GGCTAGCTACAACGA CCTTTACA | 19987 |
| 4980 | GCGUUCAG A CGGGGUUU | 9229 | AAACCCCG GGCTAGCTACAACGA CTGAACCC | 19988 |
| 4985 | CAGACGGG G UUUCUGGU | 9230 | ACCAGAAA GGCTAGCTACAACGA CCCGTCTG | 19989 |
| 4992 | GGUUUCUG G UUUUAGAA | 9231 | TTCTAAAA GGCTAGCTACAACGA CAGAAACC | 19990 |
| 5002 | UUUAGAAG G UUGCGUGU | 9232 | ACACGCAA GGCTAGCTACAACGA CTTCTAAA | 19991 |
| 5005 | AGAAGGUU G CGUGUUCU | 9233 | ACAACACG GGCTAGCTACAACGA AACCTTCT | 19992 |
| 5007 | AAGGUUGC G UGUUCUUC | 9234 | GAAGAACA GGCTAGCTACAACGA GCAACCTT | 19993 |
| 5009 | GGUUGCGU G UUCUUCGA | 9235 | TCGAAGAA GGCTAGCTACAACGA ACGCAACC | 19994 |
| 5018 | UUCUUCGA G UUGGGCUA | 9236 | TACCCCAA GCCTAGCTACAACGA TCGAAGAA | 19995 |
| 5023 | CGAGUUGG G CUAAAGUA | 9237 | TACTTTAG GGCTAGCTACAACGA CCAACTCG | 19996 |
| 5029 | GGGCUAAA G UAGAGUUC | 9238 | GAACTCTA GGCTAGCTACAACGA TTTAGCCC | 19997 |
| 5034 | AAAGUACA G UUCGUUGU | 9239 | ACAACGAA GGCTAGCTACAACGA TCTACTTT | 19998 |
| 5038 | UAGAGUUC G UUGUGCUG | 9240 | CAGCACAA GGCTAGCTACAACGA GAACTCTA | 19999 |
| 5041 | AGUUCGUU G UGCUGUUU | 9241 | AAACAGCA GGCTAGCTACAACGA AACGAACT | 20000 |
| 5043 | UUCGUUGU G CUGUUUCU | 9242 | AGAAACAG GGCTAGCTACAACGA ACAACGAA | 20001 |
| 5046 | GUUGUGCU G UUUCUCAC | 9243 | GTCAGAAA GGCTAGCTACAACGA AGCACAAC | 20002 |
| 5053 | UGUUUCUG A CUCCUAAU | 9244 | ATTAGGAG GGCTAGCTACAACGA CAGAAACA | 20003 |
| 5060 | GACUCCUA A UGAGAGUU | 9245 | AACTCTCA GGCTAGCTACAACGA TAGGAGTC | 20004 |
| 5066 | UAAUGAGA G UUCCUUCC | 9246 | GGAAGGAA GGCTAGCTACAACGA TCTCATTA | 20005 |
| 5077 | CCUUCCAG A CCCUUACC | 9247 | GCTAACCG GGCTAGCTACAACGA CTGGAAGG | 20006 |
| 5080 | UCCAGACC G UUACCGUU | 9248 | ACAGCTAA GGCTAGCTACAACGA GCTCTGGA | 20007 |
| 5084 | GACCGUUA G CUGUCUCC | 9249 | GGAGACAG GGCTAGCTACAACGA TAACGGTC | 20008 |
| 5087 | CCUUACCU G UCUCCUUG | 9250 | CAAGGACA GGCTAGCTACAACGA AGCTAACG | 20009 |
| 5095 | GUCUCCUU G CCAAGCCC | 9251 | GCGCTTGG GGCTAGCTACAACGA AAGGAGAC | 20010 |
| 5100 | CUUGCCAA G CCCCACGA | 9252 | TCCTGGCG GGCTAGCTACAACGA TTCGCAAG | 20011 |
| 5114 | GGAAGAAA A UGAUCCAG | 9253 | CTGCATCA GGCTAGCTACAACGA TTTCTTCC | 20012 |

TABLE XXII-continued

Human KDR DNAzyme and Substrate sequence

| Pos | Substrate | Seq ID No | DNAzyme | Seq ID No |
|---|---|---|---|---|
| 5117 | AGAAAAUG A UCCACCUC | 9254 | GACCTGCA GGCTAGCTACAACGA CATTTTCT | 20013 |
| 5119 | AAAAUGAU G CACCUCUG | 9255 | CAGACCTG GGCTAGCTACAACGA ATCATTTT | 20014 |
| 5122 | AUGAUCCA G CUCUGGCU | 9256 | ACCCAGAG GGCTAGCTACAACGA TGCATCAT | 20015 |
| 5128 | CAGCUCUG G CUCCUUGU | 9257 | ACAAGGAG GGCTAGCTACAACGA CAGAGCTG | 20016 |
| 5135 | GGCUCCUU G UCUCCCAG | 9258 | CTGGGAGA GGCTAGCTACAACGA AAGGAGCC | 20017 |
| 5144 | UCUCCCAG G CUGAUCCU | 9259 | AGGATCAG GGCTAGCTACAACGA CTGGGAGA | 20018 |
| 5148 | CCAGGCUG A UCCUUUAU | 9260 | ATAAAGGA GGCTAGCTACAACGA CAGCCTGG | 20019 |
| 5155 | GAUCCUUU A UUCAGAAU | 9261 | ATTCTGAA GGCTAGCTACAACGA AAAGGATC | 20020 |
| 5162 | UAUUCAGA A UACCACAA | 9262 | TTGTGGTA GGCTAGCTACAACGA TCTGAATA | 20021 |
| 5164 | UUCAGAAU A CCACAAAG | 9263 | CTTTGTGG GGCTAGCTACAACGA ATTCTGAA | 20022 |
| 5167 | AGAAUACC A CAAAGAAA | 9264 | TTTCTTTG GGCTAGCTACAACGA GGTATTCT | 20023 |
| 5178 | AAGAAAGG A CAUUCAGC | 9265 | GCTGAATG GGCTAGCTACAACGA CCTTTCTT | 20024 |
| 5180 | GAAAGGAC A UUCAGCUC | 9266 | GAGCTGAA GGCTAGCTACAACGA GTCCTTTC | 20025 |
| 5185 | GACAUUCA G CUCAAGGC | 9267 | GCCTTGAG GGCTAGCTACAACGA TGAATGTC | 20026 |
| 5192 | AGCUCAAG G CUCCCUGC | 9268 | GCAGGGAG GGCTAGCTACAACGA CTTGAGCT | 20027 |
| 5199 | GGCUCCCU G CCGUGUUG | 9269 | CAACACGG GGCTAGCTACAACGA AGGGAGCC | 20028 |
| 5202 | UCCCUGCC G UGUUGAAG | 9270 | CTTCAACA GGCTAGCTACAACGA GGCAGGGA | 20029 |
| 5204 | CCUGCCGU G UUGAAGAG | 9271 | CTCTTCAA GGCTAGCTACAACGA ACGGCAGG | 20030 |
| 5212 | GUUGAAGA G UUCUGACU | 9272 | AGTCAGAA GGCTAGCTACAACGA TCTTCAAC | 20031 |
| 5218 | GAGUUCUG A CUGCACAA | 9273 | TTGTGCAG GGCTAGCTACAACGA CAGAACTC | 20032 |
| 5221 | UUCUGACU G CACAAACC | 9274 | GGTTTGTG GGCTAGCTACAACGA AGTCAGAA | 20033 |
| 5223 | CUGACUGC A CAAACCAG | 9275 | CTGGTTTG GGCTAGCTACAACGA GCAGTCAG | 20034 |
| 5227 | CUGCACAA A CCAGCUUC | 9276 | GAAGCTGG GGCTAGCTACAACGA TTGTGCAG | 20035 |
| 5231 | ACAAACCA G CUUCUGGU | 9277 | ACCAGAAG GGCTAGCTACAACGA TGGTTTGT | 20036 |
| 5238 | AGCUUCUG G UUUCUUCU | 9278 | AGAAGAAA GGCTAGCTACAACGA CAGAAGCT | 20037 |
| 5250 | CUUCUGGA A UGAAUACC | 9279 | GCTATTCA GGCTAGCTACAACGA TCCAGAAG | 20038 |
| 5254 | UGGAAUGA A UACCCUCA | 9280 | TGAGGGTA GGCTAGCTACAACGA TCATTCCA | 20039 |
| 5256 | GAAUGAAU A CCCUCAUA | 9281 | TATGAGGG GGCTAGCTACAACGA ATTCATTC | 20040 |
| 5262 | AUACCCUC A UAUCUGUC | 9282 | GACAGATA GGCTAGCTACAACGA GAGGGTAT | 20041 |
| 5264 | ACCCUCAU A UCUGUCCU | 9283 | AGGACAGA GGCTAGCTACAACGA ATGAGGGT | 20042 |
| 5268 | UCAUAUCU G UCCUGAUG | 9284 | CATCAGGA GGCTAGCTACAACGA AGATATGA | 20043 |
| 5274 | CUGUCCUG A UGUGAUAU | 9285 | ATATCACA GGCTAGCTACAACGA CAGGACAG | 20044 |
| 5276 | GUCCUGAU G UGAUAUGU | 9286 | ACATATCA GGCTAGCTACAACGA ATCAGGAC | 20045 |
| 5279 | CUGAUGUG A UAUGUCUG | 9287 | CAGACATA GGCTAGCTACAACGA CACATCAG | 20046 |
| 5281 | GAUGUGAU A UGUCUGAG | 9288 | CTCAGACA GGCTAGCTACAACGA ATCACATC | 20047 |
| 5283 | UGUGAUAU G UCUGAGAC | 9289 | GTCTCAGA GGCTAGCTACAACGA ATATCACA | 20048 |
| 5290 | UGUCUGAG A CUGAAUGC | 9290 | GCATTCAG GGCTAGCTACAACGA CTCAGACA | 20049 |

TABLE XXII-continued

Human KDR DNAzyme and Substrate sequence

| Pos | Substrate | Seq ID No | DNAzyme | Seq ID No |
|---|---|---|---|---|
| 5295 | GAGACUGA A UGCGGGAG | 9291 | CTCCCGCA GGCTAGCTACAACGA TCAGTCTC | 20050 |
| 5297 | GACUGAAU G CGGGAGGU | 9292 | ACCTCCCG GGCTAGCTACAACGA ATTCAGTC | 20051 |
| 5304 | UGCGGGAG G UUCAAUGU | 9293 | ACATTGAA GGCTAGCTACAACGA CTCCCGCA | 20052 |
| 5309 | GAGGUUCA A UGUGAAGC | 9294 | GCTTCACA GGCTAGCTACAACGA TGAACCTC | 20053 |
| 5311 | GGUUCAAU G UGAAGCUG | 9295 | CAGCTTCA GGCTAGCTACAACGA ATTGAACC | 20054 |
| 5316 | AAUGUGAA G CUGUGUGU | 9296 | ACACACAG GGCTAGCTACAACGA TTCACATT | 20055 |
| 5319 | GUGAAGCU G UGUGGUGU | 9297 | ACCACACA GGCTAGCTACAACGA AGCTTCAC | 20056 |
| 5321 | GAAGCUGU G UGUGGUGU | 9298 | ACACCACA GGCTAGCTACAACGA ACAGCTTC | 20057 |
| 5323 | AGCUGUGU G UGGUGUCA | 9299 | TGACACCA GGCTAGCTACAACGA ACACAGCT | 20058 |
| 5326 | UGUGUGUG G UGUCAAAG | 9300 | CTTTGACA GGCTAGCTACAACGA CACACACA | 20059 |
| 5328 | UGUGUGGU G UCAAAGUU | 9301 | AACTTTGA GGCTAGCTACAACGA ACCACACA | 20060 |
| 5334 | GUGUCAAA G UUUCAGGA | 9302 | TCCTGAAA GGCTAGCTACAACGA TTTGACAC | 20061 |
| 5346 | CAGGAAGG A UUUUACCC | 9303 | GGGTAAAA GGCTAGCTACAACGA CCTTCCTG | 20062 |
| 5351 | AGGAUUUU A CCCUUUUG | 9304 | CAAAAGGG GGCTAGCTACAACGA AAAATCCT | 20063 |
| 5359 | ACCCUUUU G UUCUUCCC | 9305 | GGGAAGAA GGCTAGCTACAACGA AAAAGGGT | 20064 |
| 5371 | UUCCCCCU G UCCCCAAC | 9306 | GTTGGGGA GGCTAGCTACAACGA AGGGGGAA | 20065 |
| 5378 | UGUCCCCA A CCCACUCU | 9307 | AGAGTGGG GGCTAGCTACAACGA TGGGGACA | 20066 |
| 5382 | CCCAACCC A CUCUCACC | 9308 | GGTGAGAG GGCTAGCTACAACGA GGGTTGGG | 20067 |
| 5388 | CCACUCUC A CCCCGCAA | 9309 | TTGCGGGG GGCTAGCTACAACGA GAGAGTGG | 20068 |
| 5393 | CUCACCCC G CAACCCAU | 9310 | ATGGGTTG GGCTAGCTACAACGA GGGGTGAG | 20069 |
| 5396 | ACCCCGCA A CCCAUCAG | 9311 | CTGATGGG GGCTAGCTACAACGA TGCGGGGT | 20070 |
| 5400 | CGCAACCC A UCAGUAUU | 9312 | AATACTGA GGCTAGCTACAACGA GGGTTGCG | 20071 |
| 5404 | ACCCAUCA G UAUUUUAG | 9313 | CTAAAATA GGCTAGCTACAACGA TGATGGGT | 20072 |
| 5406 | CCAUCAGU A UUUUAGUU | 9314 | AACTAAAA GGCTAGCTACAACGA ACTGATGG | 20073 |
| 5412 | GUAUUUUA G UUAUUUGG | 9315 | CCAAATAA GGCTAGCTACAACGA TAAAATAC | 20074 |
| 5415 | UUUUAGUU A UUUGGCCU | 9316 | AGGCCAAA GGCTAGCTACAACGA AACTAAAA | 20075 |
| 5420 | GUUAUUUG G CCUCUACU | 9317 | AGTAGAGG GGCTAGCTACAACGA CAAATAAC | 20076 |
| 5426 | UGGCCUCU A CUCCAGUA | 9318 | TACTGGAG GGCTAGCTACAACGA AGAGGCCA | 20077 |
| 5432 | CUACUCCA G UAAACCUG | 9319 | CAGGTTTA GGCTAGCTACAACGA TGGAGTAG | 20078 |
| 5436 | UCCAGUAA A CCUGAUUG | 9320 | CAATCAGG GGCTAGCTACAACGA TTACTGGA | 20079 |
| 5441 | UAAACCUG A UUGGGUUU | 9321 | AAACCCAA GGCTAGCTACAACGA CAGGTTTA | 20080 |
| 5446 | CUGAUUGG G UUUGUUCA | 9322 | TGAACAAA GGCTAGCTACAACGA CCAATCAG | 20081 |
| 5450 | UUGGGUUU G UUCACUCU | 9323 | AGAGTGAA GGCTAGCTACAACGA AAACCCAA | 20082 |
| 5454 | GUUUGUUC A CUCUCUGA | 9324 | TCAGAGAG GGCTAGCTACAACGA GAACAAAC | 20083 |
| 5463 | CUCUCUGA A UGAUUAUU | 9325 | AATAATCA GGCTAGCTACAACGA TCAGAGAG | 20084 |
| 5466 | UCUGAAUG A UUAUUAGC | 9326 | GCTAATAA GGCTAGCTACAACGA CATTCAGA | 20085 |
| 5469 | GAAUGAUU A UUAGCCAG | 9327 | CTGGCTAA GGCTAGCTACAACGA AATCATTC | 20086 |

TABLE XXII-continued

Human KDR DNAzyme and Substrate sequence

| Pos | Substrate | Seq ID No | DNAzyme | Seq ID No |
|---|---|---|---|---|
| 5473 | GAUUAUUA G CCAGACUU | 9328 | AAGTCTGG GGCTAGCTACAACGA TAATAATC | 20087 |
| 5478 | UUAGCCAG A CUUCAAAA | 9329 | TTTTGAAG GGCTAGCTACAACGA CTGGCTAA | 20088 |
| 5486 | ACUUCAAA A UUAUUUUA | 9330 | TAAAATAA GGCTAGCTACAACGA TTTGAAGT | 20089 |
| 5489 | UCAAAAUU A UUUUAUAG | 9331 | CTATAAAA GGCTAGCTACAACGA AATTTTGA | 20090 |
| 5494 | AUUAUUUU A UAGCCCAA | 9332 | TTGGGCTA GGCTAGCTACAACGA AAAATAAT | 20091 |
| 5497 | AUUUUAUA G CCCAAAUU | 9333 | AATTTGGG GGCTAGCTACAACGA TATAAAAT | 20092 |
| 5503 | UAGCCCAA U UAUAACA | 9334 | TGTTATAA GGCTAGCTACAACGA TTGGGCTA | 20093 |
| 5506 | CCCAAAUU A UAACAUCU | 9335 | AGATGTTA GGCTAGCTACAACGA AATTTGGG | 20094 |
| 5509 | AAAUUAUA A CAUCUAUU | 9336 | AATAGATG GGCTAGCTACAACGA TATAATTT | 20095 |
| 5511 | AUUAUAAC A UCUAUUGU | 9337 | ACAATAGA GGCTAGCTACAACGA GTTATAAT | 20096 |
| 5515 | UAACAUCU A UUGUAUUA | 9338 | TAATACAA GGCTAGCTACAACGA AGATGTTA | 20097 |
| 5518 | CAUCUAUU G UAUUAUUU | 9339 | AAATAATA GGCTAGCTACAACGA AATAGATG | 20098 |
| 5520 | UCUAUUGU A UUAUUUAG | 9340 | CTAAATAA GGCTAGCTACAACGA ACAATAGA | 20099 |
| 5523 | AUUGUAUU A UUUAGACU | 9341 | AGTCTAAA GGCTAGCTACAACGA AATACAAT | 20100 |
| 5529 | UUAUUUAG A CUUUUAAC | 9342 | GTTAAAAG GGCTAGCTACAACGA CTAAATAA | 20101 |
| 5536 | GACUUUUA A CAUAUAGA | 9343 | TCTATATG GGCTAGCTACAACGA TAAAAGTC | 20102 |
| 5538 | CUUUUAAC A UAUAGAGC | 9344 | GCTCTATA GGCTAGCTACAACGA GTTAAAAG | 20103 |
| 5540 | UUUAACAU A UAGAGCUA | 9345 | TAGCTCTA GGCTAGCTACAACGA ATGTTAAA | 20104 |
| 5545 | CAUAUAGA G CUAUUUCU | 9346 | AGAAATAG GGCTAGCTACAACGA TCTATATG | 20105 |
| 5548 | AUAGAGCU A UUUCUACU | 9347 | AGTAGAAA GGCTAGCTACAACGA AGCTCTAT | 20106 |
| 5554 | CUAUUUCU A CUGAUUUU | 9348 | AAAATCAG GGCTAGCTACAACGA AGAAATAG | 20107 |
| 5558 | UUCUACUG A UUUUGCC | 9349 | GGCAAAAA GGCTAGCTACAACGA CAGTAGAA | 20108 |
| 5564 | UGAUUUUU G CCCUUGUU | 9350 | AACAAGGG GGCTAGCTACAACGA AAAAATCA | 20109 |
| 5570 | UUGCCCUU G UUCUGUCC | 9351 | GGACAGAA GGCTAGCTACAACGA AAGGGCAA | 20110 |
| 5575 | CUUGUUCU G UCCUUUUU | 9352 | AAAAAGGA GGCTAGCTACAACGA AGAACAAG | 20111 |
| 5597 | AAAGAAA A UGUGUUUU | 9353 | AAAACACA GGCTAGCTACAACGA TTTCTTTT | 20112 |
| 5599 | AAGAAAAU G UUUUUUU | 9354 | AAAAAACA GGCTAGCTACAACGA ATTTTCTT | 20113 |
| 5601 | GAAAAUGU G UUUUUUGU | 9355 | ACAAAAAA GGCTAGCTACAACGA ACATTTTC | 20114 |
| 5608 | UGUUUUUU G UUUGGUAC | 9356 | GTACCAAA GGCTAGCTACAACGA AAAAAACA | 20115 |
| 5613 | UUUGUUUG A UACCAUAG | 9357 | CTATGGTA GGCTAGCTACAACGA CAAACAAA | 20116 |
| 5615 | UGUUUGGU A CCAUAGUG | 9358 | CACTATGG GGCTAGCTACAACGA ACCAAACA | 20117 |
| 5618 | UUGGUACC A UAGUGUGA | 9359 | TCACACTA GGCTAGCTACAACGA GGTACCAA | 20118 |
| 5621 | GUACCAUA G UGUGAAAU | 9360 | ATTTCACA GGCTAGCTACAACGA TATGGTAC | 20119 |
| 5623 | ACCAUAGU G UGAAAUGC | 9361 | GCATTTCA GGCTAGCTACAACGA ACTATGGT | 20120 |
| 5628 | AGUGUGAA A UGCUGGGA | 9362 | TCCCAGCA GGCTAGCTACAACGA TTCACACT | 20121 |
| 5630 | UGUGAAAU G CUGGGAAC | 9363 | GTTCCCAG GGCTAGCTACAACGA ATTTCACA | 20122 |
| 5637 | UGCUGGGA A CAAUGACU | 9364 | AGTCATTG GGCTAGCTACAACGA TCCCAGCA | 20123 |

TABLE XXII-continued

Human KDR DNAzyme and Substrate sequence

| Pos | Substrate | Seq ID No | DNAzyme | Seq ID No |
|---|---|---|---|---|
| 5640 | UGGGAACA A UGACUAUA | 9365 | TATAGTCA GGCTAGCTACAACGA TGTTCCCA | 20124 |
| 5643 | GAACAAUG A CUAUAAGA | 9366 | TCTTATAG GGCTAGCTACAACGA CATTGTTC | 20125 |
| 5646 | CAAUGACU A UAAGACAU | 9367 | ATGTCTTA GGCTAGCTACAACGA AGTCATTG | 20126 |
| 5651 | ACUAUAAG A CAUGCUAU | 9368 | ATAGCATG GGCTAGCTACAACGA CTTATAGT | 20127 |
| 5653 | UAUAAGAC A UGCUAUGG | 9369 | CCATAGCA GGCTAGCTACAACGA GTCTTATA | 20128 |
| 5655 | UAAGACAU G CUAUGGCA | 9370 | TGCCATAG GGCTAGCTACAACGA ATGTCTTA | 20129 |
| 5658 | GACAUGCU A UGGCACAU | 9371 | ATGTGCCA GGCTAGCTACAACGA AGCATGTC | 20130 |
| 5661 | AUGCUAUG G CACAUAUA | 9372 | TATATGTG GGCTAGCTACAACGA CATAGCAT | 20131 |
| 5663 | GCUAUGGC A CAUAUAUU | 9373 | AATATATG GGCTAGCTACAACGA GCCATAGC | 20132 |
| 5665 | UAUGGCAC A UAUAUUUA | 9374 | TAAATATA GGCTAGCTACAACGA GTGCCATA | 20133 |
| 5667 | UGGCACAU A UAUUUAUA | 9375 | TATAAATA GGCTAGCTACAACGA ATGTGCCA | 20134 |
| 5669 | GCACAUAU A UUUAUAGU | 9376 | ACTATAAA GGCTAGCTACAACGA ATATGTGC | 20135 |
| 5673 | AUAUAUUU A UAGUCUGU | 9377 | ACAGACTA GGCTAGCTACAACGA AAATATAT | 20136 |
| 5676 | UAUUUAUA G UCUGUUUA | 9378 | TAAACAGA GGCTAGCTACAACGA TATAAATA | 20137 |
| 5680 | UAUAGUCU G UUUAUGUA | 9379 | TACATAAA GGCTAGCTACAACGA AGACTATA | 20138 |
| 5684 | GUCUGUUU A UGUAGAAA | 9380 | TTTCTACA GGCTAGCTACAACGA AAACAGAC | 20139 |
| 5686 | CUGUUUAU G UAGAAACA | 9381 | TGTTTCTA GGCTAGCTACAACGA ATAAACAG | 20140 |
| 5692 | AUGUAGAA A CAAAUGUA | 9382 | TACATTTG GGCTAGCTACAACGA TTCTACAT | 20141 |
| 5696 | AGAAACAA A UGUAAUAU | 9383 | ATATTACA GGCTAGCTACAACGA TTGTTTCT | 20142 |
| 5698 | AAACAAAU G UAAUAUAU | 9384 | ATATATTA GGCTAGCTACAACGA ATTTGTTT | 20143 |
| 5701 | CAAAUGUA A UAUAUUAA | 9385 | TTAATATA GGCTAGCTACAACGA TACATTTG | 20144 |
| 5703 | AAUGUAAU A UAUUAAAG | 9386 | CTTTAATA GGCTAGCTACAACGA ATTACATT | 20145 |
| 5705 | UGUAAUAU A UUAAAGCC | 9387 | GGCTTTAA GGCTAGCTACAACGA ATATTACA | 20146 |
| 5711 | AUAUUAAA G CCUUAUAU | 9388 | ATATAAGG GGCTAGCTACAACGA TTTAATAT | 20147 |
| 5716 | AAAGCCUU A UAUAAUAU | 9389 | ATTATATA GGCTAGCTACAACGA AAGGCTTT | 20148 |
| 5718 | AGCCUUAU A UAUAAUGA | 9390 | TCATTATA GGCTAGCTACAACGA ATAAGGCT | 20149 |
| 5720 | CCUUAUAU A UAAUGAAC | 9391 | GTTCATTA GGCTAGCTACAACGA ATATAAGG | 20150 |
| 5723 | UAUAUAUA A UGAACUUU | 9392 | AAAGTTCA GGCTAGCTACAACGA TATATATA | 20151 |
| 5727 | UAUAAUGA A CUUUGUAC | 9393 | GTACAAAG GGCTAGCTACAACGA TCATTATA | 20152 |
| 5732 | UGAACUUU G UACUAUUC | 9394 | GAATAGTA GGCTAGCTACAACGA AAAGTTCA | 20153 |
| 5734 | AACUUUGU A CUAUUCAC | 9395 | GTGAATAG GGCTAGCTACAACGA ACAAAGTT | 20154 |
| 5737 | UUUGUACU A UUCACAUU | 9396 | AATGTGAA GGCTAGCTACAACGA AGTACAAA | 20155 |
| 5741 | UACUAUUC A CAUUUUGU | 9397 | ACAAAATG GGCTAGCTACAACGA GAATAGTA | 20156 |
| 5743 | CUAUUCAC A UUUUGUAU | 9398 | ATACAAAA GGCTAGCTACAACGA GTGAATAG | 20157 |
| 5748 | CACAUUUU G UAUCAGUA | 9399 | TACTGATA GGCTAGCTACAACGA AAAATGTG | 20158 |
| 5750 | CAUUUUGU A UCAGUAUU | 9400 | AATACTGA GGCTAGCTACAACGA ACAAAATG | 20159 |
| 5754 | UUGUAUCA G UAUUAUGU | 9401 | ACATAATA GGCTAGCTACAACGA TGATACAA | 20160 |

TABLE XXII-continued

Human KDR DNAzyme and Substrate sequence

| Pos | Substrate | Seq ID No | DNAzyme | Seq ID No |
|---|---|---|---|---|
| 5756 | GUAUCAGU A UUAUGUAG | 9402 | CTACATAA GGCTAGCTACAACGA ACTGATAC | 20161 |
| 5759 | UCAGUAUU A UGUAGCAU | 9403 | ATGCTACA GGCTAGCTACAACGA AATACTGA | 20162 |
| 5761 | AGUAUUAU G UAGCAUAA | 9404 | TTATGCTA GGCTAGCTACAACGA ATAATACT | 20163 |
| 5764 | AUUAUGUA G CAUAACAA | 9405 | TTGTTATG GGCTAGCTACAACGA TACATAAT | 20164 |
| 5766 | UAUGUAGC A UAACAAAG | 9406 | CTTTGTTA GGCTAGCTACAACGA GCTACATA | 20165 |
| 5769 | GUAGCAUA A CAAAGGUC | 9407 | GACCTTTG GGCTAGCTACAACGA TATGCTAC | 20166 |
| 5775 | UAACAAAG G UCAUAAUG | 9408 | CATTATGA GGCTAGCTACAACGA CTTTGTTA | 20167 |
| 5778 | CAAAGGUC A UAAUGCUU | 9409 | AAGCATTA GGCTAGCTACAACGA GACCTTTG | 20168 |
| 5781 | AGGUCAUA A UGCUUUCA | 9410 | TGAAAGCA GGCTAGCTACAACGA TATGACCT | 20169 |
| 5783 | GUCAUAAU G CUUUCAGC | 9411 | GCTGAAAG GGCTAGCTACAACGA ATTATGAC | 20170 |
| 5790 | UGCUUUCA G CAAUUGAU | 9412 | ATCAATTG GGCTAGCTACAACGA TGAAAGCA | 20171 |
| 5793 | UUUCAGCA A UUGAUGUC | 9413 | GACATCAA GGCTAGCTACAACGA TGCTGAAA | 20172 |
| 5797 | AGCAAUUG A UGUCAUUU | 9414 | AAATGACA GGCTAGCTACAACGA CAATTGCT | 20173 |
| 5799 | CAAUUGAU G UCAUUUUA | 9415 | TAAAATGA GGCTAGCTACAACGA ATCAATTG | 20174 |
| 5802 | UUGAUGUC A UUUUAUUA | 9416 | TAATAAAA GGCTAGCTACAACGA GACATCAA | 20175 |
| 5807 | GUCAUUUU A UUAAAGAA | 9417 | TTCTTTAA GGCTAGCTACAACGA AAAATGAC | 20176 |
| 5815 | AUUAAAGA A CAUUGAAA | 9418 | TTTCAATG GGCTAGCTACAACGA TCTTTAAT | 20177 |
| 5817 | UAAAGAAC A UUGAAAAA | 9419 | TTTTTCAA GGCTAGCTACAACGA GTTCTTTA | 20178 |

Input Sequence = AF035121. Cut Site = R/Y
Arm Length = 8. Core Sequence = GGCTAGCTACAACGA (SEQ ID NO. 20828).
AF035121 (*Homo sapiens* KDR/flk-1 protein mRNA, complete cds.; Acc# AF035121; 5830 bp)

TABLE XXIII

Human KDR Ziuzyme and Substrate Sequence

| Pos | Substrate | Seq ID No | Zinzyme | Seq ID No |
|---|---|---|---|---|
| 25 | CCGGGAGA G CGGUCAGU | 8365 | ACUGACCG GCCGAAAGGCGAGUGAGGUCU UCUCCCGG | 20179 |
| 28 | GGAGAGCG G UCAGUGUG | 8366 | CACACUGA GCCGAAAGGCGAGUGAGGUCU CGCUCUCC | 20180 |
| 32 | AGCGGUCA G UGUGGUG | 8367 | ACCACACA GCCGAAAGGCGAGUGAGGUCU UGACCGCU | 20181 |
| 34 | CGGUCAGU G UGGUCG | 8368 | CGACCACA GCCGAAAGGCGAGUGAGGUCU ACUGACCG | 20182 |
| 36 | GUCAGUGU G UGGUCGCU | 8369 | AGCGACCA GCCGAAAGGCGAGUGAGGUCU ACACUGAC | 20183 |
| 39 | AGUGUGUG G UCGCUGCG | 8370 | CGCAGCGA GCCGAAAGGCGAGUGAGGUCU CACACACU | 20184 |
| 42 | GUGUGGUC G CUGCGUUU | 8371 | AAACGCAG GCCGAAAGGCGAGUGAGGUCU GACCACAC | 20185 |
| 45 | UGGUCGCU G CGUUUCCU | 8372 | AGGAAACG GCCGAAAGGCGAGUGAGGUCU AGCGACCA | 20186 |
| 47 | GUCGCUGC G UUUCCUCU | 8373 | AGAGGAAA GCCGAAAGGCGAGUGAGGUCU GCAGCGAC | 20187 |
| 56 | UUUCCUCU G CCUGCGCC | 8374 | GGCGCAGG GCCGAAAGGCGAGUGAGGUCU AGAGGAAA | 20188 |
| 60 | CUCUGCCU G CGCCGGGC | 8375 | GCCCGGCG GCCGAAAGGCGAGUGAGGUCU AGGCAGAG | 20189 |
| 62 | CUGCCUGC G CCGGGCAU | 8376 | AUGCCCGG GCCGAAAGGCGAGUGAGGUCU GCAGGCAG | 20190 |

TABLE XXIII-continued

Human KDR Ziuzyme and Substrate Sequence

| Pos | Substrate | Seq ID No | Zinzyme | Seq ID No |
|---|---|---|---|---|
| 67  | UGCGCCGG G CAUCACUU | 8377 | AAGUGAUG GCCGAAAGGCGAGUGAGGUCU CCGGCGCA | 20191 |
| 76  | CAUCACUU G CGCGCCGC | 8380 | GCGGCGCG GCCGAAAGGCGAGUGAGGUCU AAGUGAUG | 20192 |
| 78  | UCACUUGC G CGCCGCAG | 8381 | CUGCGGCG GCCGAAAGGCGAGUGAGGUCU GCAAGUGA | 20193 |
| 80  | ACUUGCGC G CCGCAGAA | 8382 | UUCUGCGG GCCGAAAGGCGAGUGAGGUCU GCGCAAGU | 20194 |
| 83  | UGCGCGCC G CAGAAAGU | 8383 | ACUUUCUG GCCGAAAGGCGAGUGAGGUCU GGCGCGCA | 20195 |
| 90  | CGCAGAAA G UCCGUCUG | 8384 | CAGACGGA GCCGAAAGGCGAGUGAGGUCU UUUCUGCG | 20196 |
| 94  | GAAAGUCC G UCUGGCAG | 8385 | CUGCCAGA GCCGAAAGGCGAGUGAGGUCU GGACUUUC | 20197 |
| 99  | UCCGUCUG G CAGCCUGG | 8386 | CCAGGCUG GCCGAAAGGCGAGUGAGGUCU CAGACGGA | 20198 |
| 102 | GUCUGGCA G CCUGGAUA | 8387 | UAUCCAGG GCCGAAAGGCGAGUGAGGUCU UGCCAGAC | 20199 |
| 124 | UCCUACCG G CACCCGCA | 8391 | UGCGGGUG GCCGAAAGGCGAGUGAGGUCU CGGUAGGA | 20200 |
| 130 | CGGCACCC G CAGACGCC | 8393 | GGCGUCUG GCCGAAAGGCGAGUGAGGUCU GGGUGCCG | 20201 |
| 136 | CCGCAGAC G CCCCUGCA | 8395 | UGCAGGGG GCCGAAAGGCGAGUGAGGUCU GUCUGCGG | 20202 |
| 142 | ACGCCCCU G CAGCCGCC | 8396 | GGCGGCUG GCCGAAAGGCGAGUGAGGUCU AGGGGCGU | 20203 |
| 145 | CCCCUGCA G CCGCCGGU | 8397 | ACCGGCGG GCCGAAAGGCGAGUGAGGUCU UGCAGGGG | 20204 |
| 148 | CUGCAGCC G CCGGUCGG | 8398 | CCGACCGG GCCGAAAGGCGAGUGAGGUCU GGCUGCAG | 20205 |
| 152 | AGCCGCCG G UCGGCGCC | 8399 | GGCGCCGA GCCGAAAGGCGAGUGAGGUCU CGGCGGCU | 20206 |
| 156 | GCCGGUCG G CGCCCGGG | 8400 | CCCGGGCG GCCGAAAGGCGAGUGAGGUCU CGACCGGC | 20207 |
| 158 | CGGUCGGC G CCCGGGCU | 8401 | AGCCCGGG GCCGAAAGGCGAGUGAGGUCU GCCGACCG | 20208 |
| 164 | GCGCCCGG G CUCCCUAG | 8402 | CUAGGGAG GCCGAAAGGCGAGUGAGGUCU CCGGGCGC | 20209 |
| 172 | GCUCCCUA G CCCUGUGC | 8403 | GCACAGGG GCCGAAAGGCGAGUGAGGUCU UAGGGAGC | 20210 |
| 177 | CUAGCCCU G UGCGCUCA | 8404 | UGAGCGCA GCCGAAAGGCGAGUGAGGUCU AGGGCUAG | 20211 |
| 179 | AGCCCUGU G CGCUCAAC | 8405 | GUUGAGCG GCCGAAAGGCGAGUGAGGUCU ACAGGGCU | 20212 |
| 181 | CCCUGUGC G CUCAACUG | 8406 | CAGUUGAG GCCGAAAGGCGAGUGAGGUCU GCACAGGG | 20213 |
| 189 | GCUCAACU G UCCGCGC | 8408 | GCGCAGGA GCCGAAAGGCGAGUGAGGUCU AGUUGAGC | 20214 |
| 194 | ACUGUCCU G CGCUGCGG | 8409 | CCGCAGCG GCCGAAAGGCGAGUGAGGUCU AGGACAGU | 20215 |
| 196 | UGUCCUGC G CUGCGGGG | 8410 | CCCCGCAG GCCGAAAGGCGAGUGAGGUCU GCAGGACA | 20216 |
| 199 | CCUGCGCU G CGGGGUGC | 8411 | GCACCCCG GCCGAAAGGCGAGUGAGGUCU AGCGCAGG | 20217 |
| 204 | GCUGCGGG G UGCCGCGA | 8412 | UCGCGGCA GCCGAAAGGCGAGUGAGGUCU CCCGCAGC | 20218 |
| 206 | UGCGGGGU G CCGCGAGU | 8413 | ACUCGCGG GCCGAAAGGCGAGUGAGGUCU ACCCCGCA | 20219 |
| 209 | GGGGUGCC G CGAGUUCC | 8414 | GGAACUCG GCCGAAAGGCGAGUGAGGUCU GGCACCCC | 20220 |
| 213 | UGCCGCGA G UUCCACCU | 8415 | AGGUGGAA GCCGAAAGGCGAGUGAGGUCU UCGCGGCA | 20221 |
| 224 | CCACCUCC G CGCCUCCU | 8417 | AGGAGGCG GCCGAAAGGCGAGUGAGGUCU GGAGGUGG | 20222 |
| 226 | ACCUCCGC G CCUCCUUC | 8418 | GAAGGAGG GCCGAAAGGCGAGUGAGGUCU GCGGAGGU | 20223 |
| 244 | CUAGACAG G CGCUGGGA | 8420 | UCCCAGCG GCCGAAAGGCGAGUGAGGUCU CUGUCUAG | 20224 |
| 246 | AGACAGGC G CUGGGAGA | 8421 | UCUCCCAG GCCGAAAGGCGAGUGAGGUCU GCCUGUCU | 20225 |
| 263 | AAGAACCG G CUCCCGAG | 8423 | CUCGGGAG GCCGAAAGGCGAGUGAGGUCU CGGUUCUU | 20226 |
| 271 | GCUCCCGA G UUCUGGGC | 8424 | GCCCAGAA GCCGAAAGGCGAGUGAGGUCU UCGGGAGC | 20227 |

TABLE XXIII-continued

Human KDR Ziuzyme and Substrate Sequence

| Pos | Substrate | Seq ID No | Zinzyme | Seq ID No |
|---|---|---|---|---|
| 278 | AGUUCUGG G CAUUUCGC | 8425 | GCGAAAUG GCCGAAAGGCGAGUGAGGUCU CCAGAACU | 20228 |
| 285 | GGCAUUUC G CCCGGCUC | 8427 | GAGCCGGG GCCGAAAGGCGAGUGAGGUCU GAUAUGCC | 20229 |
| 290 | UUCGCCCG G CUCGAGGU | 8428 | ACCUCCAG GCCGAAAGGCGAGUGAGGUCU CGGGCGAA | 20230 |
| 297 | GGCUCGAG G UGCAGGAU | 8429 | AUCCUGCA GCCGAAAGGCGAGUGAGGUCU CUCGAGCC | 20231 |
| 299 | CUCGAGGU G CAGGAUGC | 8430 | GCAUCCUG GCCGAAAGGCGAGUGAGGUCU ACCUCGAG | 20232 |
| 306 | UGCAGGAU G CAGAGCAA | 8432 | UUGCUCUG GCCGAAAGGCGAGUGAGGUCU AUCCUGCA | 20233 |
| 311 | GAUGCAGA G CAAGGUGC | 8433 | GCACCUUG GCCGAAAGGCGAGUGAGGUCU UCUGCAUC | 20234 |
| 316 | AGAGCAAG G UGCUGCUG | 8434 | CAGCAGCA GCCGAAAGGCGAGUGAGGUCU CUUGCUCU | 20235 |
| 318 | AGCAAGGU G CUGCUGGC | 8435 | GCCAGCAG GCCGAAAGGCGAGUGAGGUCU ACCUUGCU | 20236 |
| 321 | AAGGUGCU G CUGGCCGU | 8436 | ACGGCCAG GCCGAAAGGCGAGUGAGGUCU AGCACCUU | 20237 |
| 325 | UGCUGCUG G CCGUCGCC | 8437 | GGCGACGG GCCGAAAGGCGAGUGAGGUCU CAGCAGCA | 20238 |
| 328 | UGCUGGCC G UCGCCCUG | 8438 | CAGGGCGA GCCGAAAGGCGAGUGAGGUCU GGCCAGCA | 20239 |
| 331 | UGGCCGUC G CCCUGUGG | 8439 | CCACAGGG GCCGAAAGGCGAGUGAGGUCU GACGGCCA | 20240 |
| 336 | GUCGCCCU G UGGCUCUG | 8440 | CAGAGCCA GCCGAAAGGCGAGUGAGGUCU AGGGCGAC | 20241 |
| 339 | GCCCUGUG G CUCUGCGU | 8441 | ACGCAGAG GCCGAAAGGCGAGUGAGGUCU CACAGGGC | 20242 |
| 344 | GUGGCUCU G CGUGGAGA | 8442 | UCUCCACG GCCGAAAGGCGAGUGAGGUCU AGAGCCAC | 20243 |
| 346 | GGCUCUGC G UGGAGACC | 8443 | GGUCUCCA GCCGAAAGGCGAGUGAGGUCU GCAGAGCC | 20244 |
| 358 | AGACCCGG G CCGCCUCU | 8445 | AGAGGCGG GCCGAAAGGCGAGUGAGGUCU CCGGGUCU | 20245 |
| 361 | CCCGGGCC G CCUCUGUG | 8446 | CACAGAGG GCCGAAAGGCGAGUGAGGUCU GGCCCGGG | 20246 |
| 367 | CCGCCUCU G UGGGUUUG | 8447 | CAAACCCA GCCGAAAGGCGAGUGAGGUCU AGAGGCGG | 20247 |
| 371 | CUCUGUGG G UUUGCCUA | 8448 | UAGGCAAA GCCGAAAGGCGAGUGAGGUCU CCACAGAG | 20248 |
| 375 | GUGGGUUU G CCUAGUGU | 8449 | ACACUAGG GCCGAAAGGCGAGUGAGGUCU AAACCCAC | 20249 |
| 380 | UUUGCCUA G UGUUCUC | 8450 | GAGAAACA GCCGAAAGGCGAGUGAGGUCU UAGGCAAA | 20250 |
| 382 | UGCCUAGU G UUUCUCUU | 8451 | AAGAGAAA GCCGAAAGGCGAGUGAGGUCU ACUAGGCA | 20251 |
| 396 | CUUGAUCU G CCCAGGCU | 8453 | AGCCUGGG GCCGAAAGGCGAGUGAGGUCU AGAUCAAG | 20252 |
| 402 | CUGCCCAG G CUCAGCAU | 8454 | AUGCUGAG GCCGAAAGGCGAGUGAGGUCU CUGGGCAG | 20253 |
| 407 | CAGGCUCA G CAUACAAA | 8455 | UUUGUAUG GCCGAAAGGCGAGUGAGGUCU UGAGCCUG | 20254 |
| 436 | CAAUUAAG G CUAAUACA | 8458 | UGUAUUAG GCCGAAAGGCGAGUGAGGUCU CUUAAUUG | 20255 |
| 461 | AAUUACUU G CAGGGGAC | 8462 | GUCCCCUG GCCGAAAGGCGAGUGAGGUCU AAGUAAUU | 20256 |
| 486 | UUGGACUG G CUUUGGCC | 8466 | GGCCAAAG GCCGAAAGGCGAGUGAGGUCU CAGUCCAA | 20257 |
| 492 | UGGCUUUG G CCCAAUAA | 8467 | UUAUUGGG GCCGAAAGGCGAGUGAGGUCU CAAAGCCA | 20258 |
| 506 | UAAUCAGA G UGGCAGUG | 8470 | CACUGCCA GCCGAAAGGCGAGUGAGGUCU UCUGAUUA | 20259 |
| 509 | UCAGAGUG G CAGUGAGC | 8471 | GCUCACUG GCCGAAAGGCGAGUGAGGUCU CACUCUGA | 20260 |
| 512 | GAGUGGCA G UGAGCAAA | 8472 | UUUGCUCA GCCGAAAGGCGAGUGAGGUCU UGCCACUC | 20261 |
| 516 | GGCAGUGA G CAAAGGGU | 8473 | ACCCUUUG GCCGAAAGGCGAGUGAGGUCU UCACUGCC | 20262 |
| 523 | AGCAAAGG G UGGAGGUG | 8474 | CACCUCCA GCCGAAAGGCGAGUGAGGUCU CCUUUGCU | 20263 |
| 529 | GGGUGGAG G UGACUGAG | 8475 | CUCAGUCA GCCGAAAGGCGAGUGAGGUCU CUCCACCC | 20264 |

TABLE XXIII-continued

Human KDR Ziuzyme and Substrate Sequence

| Pos | Substrate | Seq ID No | Zinzyme | Seq ID No |
|---|---|---|---|---|
| 537 | GUGACUGA G UGCAGCGA | 8477 | UCGCUGCA GCCGAAAGGCGAGUGAGGUCU UCAGUCAC | 20265 |
| 539 | GACUGAGU G CAGCGAUG | 8478 | CAUCGCUG GCCGAAAGGCGAGUGAGGUCU ACUCAGUC | 20266 |
| 542 | UGAGUGCA G CGAUGGCC | 8479 | GGCCAUCG GCCGAAAGGCGAGUGAGGUCU UGCACUCA | 20267 |
| 548 | CAGCGAUG G CCUCUUCU | 8481 | AGAAGAGG GCCGAAAGGCGAGUGAGGUCU CAUCGCUG | 20268 |
| 557 | CCUCUUCU G UAAGACAC | 8482 | GUGUCUUA GCCGAAAGGCGAGUGAGGUCU AGAAGAGG | 20269 |
| 580 | UUCCAAAA G UGAUCGGA | 8485 | UCCGAUCA GCCGAAAGGCGAGUGAGGUCU UUUUGGAA | 20270 |
| 601 | ACACUGGA G CCUACAAG | 8489 | CUUGUAGG GCCGAAAGGCGAGUGAGGUCU UCCAGUGU | 20271 |
| 609 | GCCUACAA G UGCUUCUA | 8490 | UAGAAGCA GCCGAAAGGCGAGUGAGGUCU UUGUAGGC | 20272 |
| 611 | CUACAAGU G CUUCUACC | 8491 | GGUAGAAG GCCGAAAGGCGAGUGAGGUCU ACUUGUAG | 20273 |
| 634 | CUGACUUG G CCUCGGUC | 8494 | GACCGAGG GCCGAAACGCGAGUGAGGUCU CAAGUCAG | 20274 |
| 640 | UGGCCUCG G UCAUUUAU | 8495 | AUAAAUGA GCCGAAAGGCGAGUGAGGUCU CGAGGCCA | 20275 |
| 649 | UCAUUUUU G UCUAUGUU | 8496 | AACAUAGA GCCGAAAGGCGAGUGAGGUCU AUAAAUGA | 20276 |
| 655 | AUGUCUAU G UUCAAGAU | 8497 | AUCUUGAA GCCGAAAGGCGAGUGAGGUCU AUAGACAU | 20277 |
| 682 | CAUUUAUU G CUUCUGUU | 8500 | AACAGAAG GCCGAAAGGCGAGUGAGGUCU AAUAAAUG | 20278 |
| 688 | UUGCUUCU G UUAGUGAC | 8501 | GUCACUAA GCCGAAAGGCGAGUGAGGUCU AGAAGCAA | 20279 |
| 692 | UUCUGUUA G UGACCAAC | 8502 | GUUGGUCA GCCGAAAGGCGAGUGAGGUCU UAACAGAA | 20280 |
| 706 | AACAUGGA G UCGUGUAC | 8505 | GUACACGA GCCGAAAGGCGAGUGAGGUCU UCCAUGUU | 20281 |
| 709 | AUGGAGUC G UGUACAUU | 8506 | AAUGUACA GCCGAAAGGCGAGUGAGGUCU GACUCCAU | 20282 |
| 711 | GGAGUCGU G UACAUUAC | 8507 | GUAAUGUA GCCGAAAGGCGAGUGAGGUCU ACGACUCC | 20283 |
| 739 | ACAAAACU G UGGUGAUU | 8511 | AAUCACCA GCCGAAAGGCGAGUGAGGUCU AGUUUUGU | 20284 |
| 742 | AAACUGUG G UGAUUCCA | 8512 | UGGAAUCA GCCGAAAGGCGAGUGAGGUCU CACAGUUU | 20285 |
| 752 | GAUUCCAU G UCUCGGGU | 8514 | ACCCGAGA GCCGAAAGGCGAQUGAGGUCU AUGGAAUC | 20286 |
| 759 | UGUCUCGG G UCCAUUUC | 8515 | GAAAUGGA GCCGAAAGGCGAGUGAGGUCU CCGAGACA | 20287 |
| 778 | AUCUCAAC G UGUCACUU | 8518 | AAGUGACA GCCGAAAGGCGAGUGAGGUCU GUUGAGAU | 20288 |
| 780 | CUCAACGU G UCACUUUG | 8519 | CAAAGUGA GCCGAAAGGCGAGUGAGGUCU ACGUUGAG | 20289 |
| 788 | GUCACUUU G UGCAAGAU | 8520 | AUCUUGCA GCCGAAAGGCGAGUGAGGUCU AAAGUGAC | 20290 |
| 790 | CACUUUGU G CAAGAUAC | 8521 | GUAUCUUG GCCGAAAGGCGAGUGAGGUCU ACAAAGUG | 20291 |
| 814 | AGAGAUUU G UUCCUGAU | 8524 | AUCAGGAA GCCGAAAGGCGAGUGAGGUCU AAAUCUCU | 20292 |
| 824 | UCCUGAUG G UAACAGAA | 8526 | UUCUGUUA GCCGAAAGGCGAGUGAGGUCU CAUCAGGA | 20293 |
| 845 | CUGGGACA G CAAGAAGG | 8530 | CCUUCUUG GCCGAAAGGCGAGUGAGGUCU UGUCCCAG | 20294 |
| 854 | CAAGAAGG G CUUUACUA | 8531 | UAGUAAAG GCCGAAAGGCGAGUGAGGUCU CCUUCUUG | 20295 |
| 869 | UAUUCCCA G CUACAUGA | 8532 | UCAUGUAG GCCGAAAGGCGAGUGAGGUCU UGGGAAUA | 20296 |
| 881 | CAUGAUCA G CUAUGCUG | 8534 | CAGCAUAG GCCGAAAGGCGAGUGAGGUCU UGAUCAUG | 20297 |
| 886 | UCAGCUAU G CUGGCAUG | 8535 | CAUGCCAG GCCGAAAGGCGAGUGAGGUCU AUAGCUGA | 20298 |
| 890 | CUAUGCUG G CAUGGUCU | 8536 | AGACCAUG GCCGAAAGGCGAGUGAGGUCU CAGCAUAG | 20299 |
| 895 | CUGGCAUG G UCUUCUGU | 8537 | ACAGAAGA GCCGAAAGGCGAGUGAGGUCU CAUGCCAG | 20300 |
| 902 | GGUCUUCU G UGAAGCAA | 8538 | UUGCUUCA GCCGAAAGGCGAGUGAGGUCU AGAAGACC | 20301 |

TABLE XXIII-continued

Human KDR Ziuzyme and Substrate Sequence

| Pos | Substrate | Seq ID No | Zinzyme | Seq ID No |
|---|---|---|---|---|
| 907 | UCUGUGAA G CAAAAAUU | 8539 | AAUUUUUG GCCGAAAGGCGAGUGAGGUCU UUCACAGA | 20302 |
| 926 | UGAUGAAA G UUACCAGU | 8543 | ACUGGUAA GCCGAAAGGCGAGUGAGGUCU UUUCAUCA | 20303 |
| 933 | AGUUACCA G UCUAUUAU | 8544 | AUAAUAGA GCCGAAAGGCGAGUGAGGUCU UGGUAACU | 20304 |
| 942 | UCUAUUAU G UACAUAGU | 8545 | ACUAUGUA GCCGAAAGGCGAGUGAGGUCU AUAAUAGA | 20305 |
| 949 | UGUACAUA G UUGUCGUU | 8546 | AACGACAA GCCGAAAGGCGAGUGAGGUCU UAUGUACA | 20306 |
| 952 | ACAUAGUU G UCGUUGUA | 8547 | UACAACGA GCCGAAAGGCGAGUGAGGUCU AACUAUGU | 20307 |
| 955 | UAGUUGUC G UUGUAGGG | 8548 | CCCUACAA GCCGAAAGGCGAGUGAGGUCU GACAACUA | 20308 |
| 958 | UUGUCGUU G UAGGGUAU | 8549 | AUACCCUA GCCGAAAGGCGAGUGAGGUCU AACGACAA | 20309 |
| 963 | GUUGUAGG G UAUAGGAU | 8550 | AUCCUAUA GCCGAAAGGCGAGUGAGGUCU CCUACAAC | 20310 |
| 979 | UUUAUGAU G UGGUUCUG | 8553 | CAGAACCA GCCGAAAGGCGAGUGAGGUCU AUCAUAAA | 20311 |
| 982 | AUGAUGUG G UUCUGAGU | 8554 | ACUCAGAA GCCGAAAGGCGAGUGAGGUCU CACAUCAU | 20312 |
| 989 | GGUUCUGA G UCCGUCUC | 8555 | GAGACGGA GCCGAAAGGCGAGUGAGGUCU UCAGAACC | 20313 |
| 993 | CUGAGUCC G UCUCAUGG | 8556 | CCAUGAGA GCCGAAAGGCGAGUGAGGUCU GGACUCAG | 20314 |
| 1015 | AACUAUCU G UUGGAGAA | 8559 | UUCUCCAA GCCGAAAGGCGAGUGAGGUCU AGAUAGUU | 20315 |
| 1026 | GGAGAAAA G CUUGUCUU | 8560 | AAGACAAG GCCGAAAGGCGAGUGAGGUCU UUUUCUCC | 20316 |
| 1030 | AAAAGCUU G UCU1AAAU | 8561 | AUUUAAGA GCCGAAAGGCGAGUGAGGUCU AAGCUUUU | 20317 |
| 1040 | CUUAAAUU G UACAGCAA | 8563 | UUGCUGUA GCCGAAAGGCGAGUGAGGUCU AAUUUAAG | 20318 |
| 1045 | AUUGUACA G CAAGAACU | 8564 | AGUUCUUG GCCGAAAGGCGAGUGAGGUCU UGUACAAU | 20319 |
| 1063 | AACUAAAU G UGGGGAUU | 8568 | AAUCCCCA GCCGAAAGGCGAGUGAGGUCU AUUUAGUU | 20320 |
| 1101 | UCUUCGAA G CAUCAGCA | 8573 | UCCUGAUG GCCGAAAGGCGAGUGAGGUCU UUCGAAGA | 20321 |
| 1107 | AAGCAUCA G CAUAAGAA | 8574 | UUCUUAUG GCCGAAAGGCGAGUGAGGUCU UGAUGCUU | 20322 |
| 1120 | AGAAACUU G UAAACCGA | 8576 | UCGGUUUA GCCGAAAGGCGAGUGAGGUCU AAGUUUCU | 20323 |
| 1143 | AAAACCCA G UCUGGGAG | 8580 | CUCCCAGA GCCGAAAGGCGAGUGAGGUCU UGGGUUUU | 20324 |
| 1151 | GUCUGGGA G UGAGAUGA | 8581 | UCAUCUCA GCCGAAAGGCGAGUGAGGUCU UCCCAGAC | 20325 |
| 1172 | AUUUUUGA G CACCUEUA | 8584 | UUAAGGUG GCCGAAAGGCGAGUGAGGUCU UCAAAAAU | 20326 |
| 1190 | UAUAGAUG G UGUAACCC | 8587 | GGGUUACA GCCGAAAGGCGAGUGAGGUCU CAUCUAUA | 20327 |
| 1192 | UAGAUGGU G UAACCCGG | 8588 | CCGGGUUA GCCGAAAGGCGAGUGAGGUCU ACCAUCUA | 20328 |
| 1202 | AACCCGGA G UGACCAAG | 8590 | CUUGGUCA GCCGAAAGGCGAGUGAGGUCU UCCGGGUU | 20329 |
| 1215 | CAAGGAUU G UACACCUG | 8593 | CAGGUGUA GCCGAAAGGCGAGUGAGGUCU AAUCCUUG | 20330 |
| 1223 | GUACACCU G UGCAGCAU | 8594 | AUGCUGCA GCCGAAAGGCGAGUGAGGUCU AGGUGUAC | 20331 |
| 1225 | ACACCUGU G CAGCAUCC | 8595 | GGAUGCUG GCCGAAAGGCGAGUGAGGUCU ACAGGUGU | 20332 |
| 1228 | CCUGUGCA G CAUCCAGU | 8596 | ACUGGAUG GCCGAAAGGCGAGUGAGGUCU UGCACAGG | 20333 |
| 1235 | AGCAUCCA G UGGGCUGA | 8597 | UCAGCCCA GCCGAAAGGCGAGUGAGGUCU UGGAUGCU | 20334 |
| 1239 | UCCAGUGG G CUGAUGAC | 8598 | GUCAUCAG GCCGAAAGGCGAGUGAG3UCU UCACUGGA | 20335 |
| 1259 | GAAGAACA G CACAUUUG | 8602 | CAAAUGUG GCCGAAAGGCGAGUGAGGUCU UGUUCUUC | 20336 |
| 1267 | GCACAUUU G UCAGGGUC | 8603 | GACCCUGA GCCGAAAGGCGAGUGAGGUCU AAAUGUGC | 20337 |
| 1273 | UUGUCAGG G UCCAUGAA | 8604 | UUCAUGGA GCCGAAAGGCGAGUGAGGUCU CCUGACAA | 20338 |

TABLE XXIII-continued

Human KDR Ziuzyme and Substrate Sequence

| Pos | Substrate | Seq ID No | Zinzyme | Seq ID No |
|---|---|---|---|---|
| 1291 | AACCUUUU G UUGCUUUU | 8606 | AAAAGCAA GCCGAAAGGCGAGUGAGGUCU AAAAGGUU | 20339 |
| 1294 | CUUUUGUU G CUUUUGGA | 8607 | UCCAAAAG GCCGAAAGGCGAGUGAGGUCU AACAAAAG | 20340 |
| 1304 | UUUUGGAA G UGGCAUGG | 8608 | CCAUGCCA GCCGAAAGGCGAGUGAGGUCU UUCCAAAA | 20341 |
| 1307 | UGGAAGUG G CAUGGAAU | 8609 | AUUCCAUG GCCGAAAGGCGAGUGAGGUCU CACUUCCA | 20342 |
| 1321 | AAUCUCUG G UGGAAGCC | 8611 | GGCUUCCA GCCGAAAGGCGAGUGAGGUCU CAGAGAUG | 20343 |
| 1327 | UGGUGGAA G CCACGGUG | 8612 | CACCGUGG GCCGAAAGGCGAGUGAGGUCU UUCCACCA | 20344 |
| 1333 | AAGCCACG G UGGGGGAG | 8613 | CUCCCCCA GCCGAAAGGCGAGUGAGGUCU CGUGGCUU | 20345 |
| 1341 | GUGGGGGA G CGUGUCAG | 8614 | CUGACACG GCCGAAAGGCGAGUGAGGUCU UCCCCCAC | 20346 |
| 1343 | GGGGGAGC G UGUCAGAA | 8615 | UUCUGACA GCCGAAAGGCGAGUGAGGUCU GCUCCCCC | 20347 |
| 1345 | GGGAGCGU G UCAGAAUC | 8616 | GACUCUGA GCCGAAAGGCGAGUGAGGUCU ACGCUCCC | 20348 |
| 1357 | GAAUCCCU G CGAAGUAC | 8618 | GUACUUCG GCCGAAAGGCGAGUGAGGUCU AGGGAUUC | 20349 |
| 1362 | CCUGCGAA G UACCUUGG | 8619 | CCAAGGUA GCCGAAAGGCGAGUGAGGUCU UUCGCAGG | 20350 |
| 1370 | GUACCUUG G UUACCCAC | 8620 | GUGGGUAA GCCGAAAGGCGAGUGAGGUCU CAAGGUAC | 20351 |
| 1395 | AUAAAAUG G UAUAAAAA | 8623 | UUUUUAUA GCCGAAAGGCGAGUGAGGUCU CAUUUUAU | 20352 |
| 1419 | CCCCUUGA G UCCAAUCA | 8626 | UGAUUGGA GCCGAAAGGCGAGUGAGGUCU UCAAGGGG | 20353 |
| 1438 | CAAUEUAA G CGGGGCAU | 8629 | AUGCCCCG GCCGAAAGGCGAGUGAGGUCU UUEUAUUG | 20354 |
| 1443 | AAAGCGGG G CAUGUACU | 8630 | AGUACAUG GCCGA1AGGCGAGUGAGGUCU CCCGCUUU | 20355 |
| 1447 | CGGGGCAU G UACUGACG | 8631 | CGUCAGUA GCCGAAAGGCGAGUGAGGUCU AUGCCCCG | 20356 |
| 1465 | UUAUGGAU G UGAGUGAA | 8634 | UUCACUCA GCCGAAAGGCGAGUGAGGUCU UUCCAUAA | 20357 |
| 1469 | GGAAGUGA G UGAAAGAG | 8635 | CUCUUUCA GCCGAAAGGCGAGUGAGGUCU UCACUUCC | 20358 |
| 1495 | AUUACACU G UCAUCCUG | 8638 | AAGGAUGA GCCGAAAGGCGAGUGAGGUCU AGUGUAAU | 20359 |
| 1527 | AAGGAGAA G CAGAGCCA | 8640 | UGGCUCUG GCCGAAAGGCGAGUGAGGUCU UUCUCCUU | 20360 |
| 1532 | GAAGCAGA G CCAUGUGG | 8641 | CCACAUGG GCCGAAAGGCGAGUGAGGUCU UCUGCUUC | 20361 |
| 1537 | AGAGCCAU G UGGUCUCU | 8642 | AGAGACCA GCCGAAAGGCGAGUGAGGUCU AUGGCUCU | 20362 |
| 1540 | GCCAUGUG G UCUCUCUG | 8643 | CAGAGAGA GCCGAAAGGCGAGUGAGGUCU CACAUGGC | 20363 |
| 1549 | UCUCUCUG G UUGUGUAU | 8644 | AUACACAA GCCGAAAGGCGAGUGAGGUCU CAGAGAGA | 20364 |
| 1552 | CUCUGGUU G UGUAUGUC | 8645 | GACAUACA GCCGAAAGGCGAGUGAGGUCU AACCAGAG | 20365 |
| 1554 | CUGGUUGU G UAUGUCCC | 8646 | GGGACAUA GCCGAAAGGCGAGUGAGGUCU ACAACCAG | 20366 |
| 1558 | UUGUGUAU G UCCCACCC | 8647 | GGCUCGCA GCCGAAACGCGAGUGAGGUCU AUACACAA | 20367 |
| 1574 | CCAGAUUG G UGAGAAAU | 8649 | AUUUCUCA GCCGAAAGGCGAGUGAGGUCU CAAUCUGG | 20368 |
| 1597 | UCUCUCCU G UGGAUUCC | 8652 | GGAAUCCA CCCGAAAGGCGAGUGAGGUCU AGGAGAGA | 20369 |
| 1611 | UCCUACCA G UACGGCAC | 8654 | GUGCCGUA GCCGAAACGCGAGUGAGGUCU UGGUAGGA | 20370 |
| 1616 | CCAGUACG G CACCACUC | 8655 | GAGUGGUG GCCGAAAGGCGAGUGAGGUCU CGUACUGG | 20371 |
| 1629 | ACUCAAAC G CUGACAUG | 8657 | CAUGUCAG GCCGAAAGGCGAGUGAGGUCU GUUUGAGU | 20372 |
| 1637 | GCUGACAU G UACGGUCU | 8659 | AGACCGUA GCCGAAAGGCGAGUGAGGUCU AUGUCAGC | 20373 |
| 1642 | CAUGUACG G UCUAUGCC | 8660 | GGCAUAGA GCCGAAAGGCGAGUGAGGUCU CGUACAUG | 20374 |
| 1648 | CGGUCUAU G CCAUUCCU | 8661 | AGGAAUGG GCCGAAAGGCGAGUGAGGUCU AUAGACCG | 20375 |

TABLE XXIII-continued

Human KDR Ziuzyme and Substrate Sequence

| Pos | Substrate | Seq ID No | Zinzyme | Seq ID No |
|---|---|---|---|---|
| 1662 | CCUCCCCC G CAUCACAU | 8662 | AUGUGAUG GCCGAAAGGCGAGUGAGGUCU GGGGGAGG | 20376 |
| 1677 | AUCCACUG G UAUUGGCA | 8663 | UGCCAAUA GCCGAAAGGCGAGUGAGGUCU CAGUGGAU | 20377 |
| 1683 | UGGUAUUG G CAGUUGGA | 8664 | UCCAACUG GCCGAAAGGCGAGUGAGGUCU CAAUACCA | 20378 |
| 1686 | UAUUGGCA G UUGGAGGA | 8665 | UCCUCCAA GCCGAAAGGCGAGUGAGGUCU UGCCAAUA | 20379 |
| 1698 | GAGGAAGA G UGCGCCAA | 8666 | UUGGCGCA GCCGAAAGGCGAGUGAGGUCU UCUUCCUC | 20380 |
| 1700 | GGAAGAGU G CGCCAACG | 8667 | CGUUGGCG GCCGAAAGGCGAGUGAGGUCU ACUCUUCC | 20381 |
| 1702 | AAGAGUGC G CCAACGAG | 8668 | CUCGUUGG GCCGAAAGGCGAGUGAGGUCU GCACUCUU | 20382 |
| 1710 | GCCAACGA G CCCAGCCA | 8670 | UGGCUGGG GCCGAAAGGCGAGUGAGGUCU UCGUUGGC | 20383 |
| 1715 | CGAGCCCA G CCAAGCUG | 8671 | CAGCUUGG GCCGAAAGGCGAGUGAGGUCU UGGGCUCG | 20384 |
| 1720 | CCAGCCAA G CUGUCUCA | 8672 | UGAGACAG GCCGAAAGGCGAGUGAGGUCU UUGGCUGG | 20385 |
| 1723 | GCCAAGCU G UCUCAGUG | 8673 | CACUGAGA GCCGAAAGGCGAGUGAGGUCU AGCUUGGC | 20386 |
| 1729 | CUGUCUCA G UGACAAAC | 8674 | GUUUGUCA GCCGAAAGGCGAGUGAGGUCU UGAGACAG | 20387 |
| 1748 | AUACCCUU G UGAAGAAU | 8677 | AUUCUUCA GCCGAAAGGCGAGUGAGGUCU AAGGGUAU | 20388 |
| 1763 | AUGGAGAA G UGUGGAGG | 8679 | CCUCCACA GCCGAAAGGCGAGUGAGGUCU UUCUCCAU | 20389 |
| 1765 | GGAGAAGU G UGGAGGAC | 8680 | GUCCUCCA GCCGAAAGGCGAGUGAGGUCU ACUUCUCC | 20390 |
| 1798 | AAAUUGAA G UUAAUAAA | 8684 | UUUAUUAA GCCGAAAGGCGAGUGAGGUCU UUCAAUUU | 20391 |
| 1816 | AUCAAUUU G CUCUAAUU | 8688 | AAUUAGAG GCCGAAAGGCGAGUGAGGUCU AAAUUGAU | 20392 |
| 1843 | ACAAAACU G UAAGUACC | 8692 | GGUACUUA GCCGAAAGGCGAGUGAGGUCU AGUUUUGU | 20393 |
| 1847 | AACUGUAA G UACCCUUG | 8693 | CAAGGGUA GCCGAAAGGCGAGUGAGGUCU UUACAGUU | 20394 |
| 1855 | GUACCCUU G UUAUCCAA | 8694 | UUGGAUAA GCCGAAAGGCGAGUGAGGUCU AAGGGUAC | 20395 |
| 1864 | UUAUCCAA G CGGCAAAU | 8695 | AUUUGCCG GCCGAAAGGCGAGUGAGGUCU UUGGAUAA | 20396 |
| 1867 | UCCAAGCG G CAAAUGUG | 8696 | CACAUUUG GCCGAAAGGCGAGUGAGGUCU CGCUUGGA | 20397 |
| 1873 | CGGCAAAU G UGUCAGCU | 8698 | AGCUGACA GCCGAAAGGCGAGUGAGGUCU AUUUGCCG | 20398 |
| 1875 | GCAAAUGU G UCAGCUUU | 8699 | AAAGCUGA GCCGAAAGGCGAGUGAGGUCU ACAUUUGC | 20399 |
| 1879 | AUGUGUCA G CUUUGUAC | 8700 | GUACAAAG GCCGAAAGGCGAGUGAGGUCU UGACACAU | 20400 |
| 1884 | UCAGCUUU G UACAAAUG | 8701 | CAUUUGUA GCCGAAAGGCGAGUGAGGUCU AAAGCUGA | 20401 |
| 1892 | GUACAAAU G UGAAGCGG | 8703 | CCGCUUCA GCCGAAAGGCGAGUGAGGUCU AUUUGUAC | 20402 |
| 1897 | AAUGUGAA G CGGUCAAC | 8704 | GUUGACCG GCCGAAAGGCGAGUGAGGUCU UUCACAUU | 20403 |
| 1900 | GUGAAGCG G UCAACAAA | 8705 | UUUGUUGA GCCGAAAGGCGAGUGAGGUCU CGCUUCAC | 20404 |
| 1909 | UCAACAAA G UCGGGAGA | 8707 | UCUCCCGA GCCGAAAGGCGAGUGAGGUCU UUUGUUGA | 20405 |
| 1927 | GAGAGAGG G UGAUCUCC | 8708 | GGAGAUCA GCCGAAAGGCGAGUGAGGUCU CCUCUCUC | 20406 |
| 1942 | CCUUCCAC G UGACCAGG | 8710 | CCUGGUCA GCCGAAAGGCGAGUGAGGUCU GUGGAAGG | 20407 |
| 1952 | GACCAGGG G UCCUGAAA | 8712 | UUUCAGGA GCCGAAAGGCGAGUGAGGUCU CCCUGGUC | 20408 |
| 1968 | AUUACUUU G CAACCUGA | 8714 | UCAGGUUG GCCGAAAGGCGAGUGAGGUCU AAAGUAAU | 20409 |
| 1980 | CCUGACAU G CAGCCCAC | 8717 | GUGGGCUG GCCGAAAGGCGAGUGAGGUCU AUGUCAGG | 20410 |
| 1983 | GACAUGCA G CCCACUGA | 8718 | UCAGUGGG GCCGAAAGGCGAGUGAGGUCU UGCAUGUC | 20411 |
| 1992 | CCCACUGA G CAGGAGAG | 8719 | CUCUCCUG GCCGAAAGGCGAGUGAGGUCU UCAGUGGG | 20412 |

TABLE XXIII-continued

Human KDR Ziuzyme and Substrate Sequence

| Pos | Substrate | Seq ID No | Zinzyme | Seq ID No |
|---|---|---|---|---|
| 2000 | GCAGGAGA G CGUGUCUU | 8720 | AAGACACG GCCGAAAGGCGAGUGAGGUCU UCUCCUGC | 20413 |
| 2002 | AGGAGAGC G UGUCUUUG | 8721 | CAAAGACA GCCGAAAGGCGAGUGAGGUCU GCUCUCCU | 20414 |
| 2004 | GAGAGCGU G UCUUUGUG | 8722 | CACAAAGA GCCGAAAGGCGAGUGAGGUCU ACGCUCUC | 20415 |
| 2010 | GUGUCUUU G UGGUGCAC | 8723 | GUGCACCA GCCGAAAGGCGAGUGAGGUCU AAAGACAC | 20416 |
| 2013 | UCUUUGUG G UCCACUGC | 8724 | GCAGUGCA GCCGAAAGGCGAGUGAGGUCU CACAAAGA | 20417 |
| 2015 | UUUGUGGU G CACUGCAG | 8725 | CUGCAGUG GCCGAAAGGCGAGUGAGGUCU ACCACAAA | 20418 |
| 2020 | GGUGCACU G CAGACAGA | 8726 | UCUGUCUG GCCGAAAGGCGAGUGAGGUCU AGUGCACC | 20419 |
| 2034 | AGAUCUAC G UUUGAGAA | 8729 | UUCUCAAA GCCGAAAGGCGAGUGAGGUCU GUAGAUCU | 20420 |
| 2052 | CUCACAUG G UACAAGCU | 8731 | AGCUUGUA GCCGAAAGGCGAGUGAGGUCU CAUGUGAG | 20421 |
| 2058 | UGGUACAA G CUUGGCCC | 8732 | GGGCCAAG GCCGAAAGGCGAGUGAGGUCU UUGUACCA | 20422 |
| 2063 | CAAGCUUG G CCCACAGC | 8733 | GCUGUGGG GCCGAAAGGCGAGUGAGGUCU CAAGCUUG | 20423 |
| 2070 | GGCCCACA G CCUCUGCC | 8734 | GGCAGAGG GCCGAAAGGCGAGUGAGGUCU UGUGGGCC | 20424 |
| 2076 | CAGCCUCU G CCAAUCCA | 8735 | UGGAUUGG GCCGAAAGGCGAGUGAGGUCU AGAGGCUG | 20425 |
| 2086 | CAAUCCAU G UGGGAGAG | 8737 | CUCUCCCA GCCGAAAGGCGAGUGAGGUCU AUGGAUUG | 20426 |
| 2094 | GUGGGAGA G UUGCCCAC | 8738 | GUGGGCAA GCCGAAAGGCGAGUGAGGUCU UCUCCCAC | 20427 |
| 2097 | GGAGAGUU G CCCACACC | 8739 | GGUGUGGG GCCGAAAGGCGAGUGAGGUCU AACUCUCC | 20428 |
| 2107 | CCACACCU G UUUGCAAG | 8740 | CUUGCAAA GCCGAAAGGCGAGUGAGGUCU AGGUGUGG | 20429 |
| 2111 | ACCUGUUU G CAAGAACU | 8741 | AGUUCUUG GCCGAAAGGCGAGUGAGGUCU AAACAGGU | 20430 |
| 2143 | AAUUGAAU G CCACCAUG | 8746 | CAUGGUGG GCCGAAAGGCGAGUGAGGUCU AUUCAAUU | 20431 |
| 2151 | GCCACCAU G UUCUCUAA | 8747 | UUAGAGAA GCCGAAAGGCGAGUGAGGUCU AUGGUGGC | 20432 |
| 2162 | CUCUAAUA G CACAAAUG | 8749 | CAUUUGUG GCCGAAAGGCGAGUGAGGUCU UAUEUGAG | 20433 |
| 2187 | AUCAUGGA G CUUAAGAA | 8753 | UUCUUAAG GCCGAAAGGCGAGUGAGGUCU UCCAUGAU | 20434 |
| 2197 | UUAAGAAU G CAUCCUUG | 8755 | CAAGGAUG GCCGAAAGGCGAGUGAGGUCU AUUCUUAA | 20435 |
| 2205 | GCAUCCUU G CAGGACCA | 8756 | UGGUCCUG GCCGAAAGGCGAGUGAGGUCU AAGGAUGC | 20436 |
| 2224 | GAGACUAU G UCUGCCUU | 8759 | AAGGCAGA GCCGAAAGGCGAGUGAGGUCU AUAGUCUC | 20437 |
| 2228 | CUAUGUCU G CCUUGCUC | 8760 | GAGCAAGG GCCGAAAGGCGAGUGAGGUCU AGACAUAG | 20438 |
| 2233 | UCUGCCUU G CUCAAGAC | 8761 | GUCUUGAG GCCGAAAGGCGAGUGAGGUCU AAGGCAGA | 20439 |
| 2264 | AAGACAUU G CGUGGUCA | 8765 | UGACCACG GCCGAAAGGCGAGUGAGGUCU AAUGUCUU | 20440 |
| 2266 | GACAUUGC G UGGUCAGG | 8766 | CCUGACCA GCCGAAAGGCGAGUGAGGUCU GCAAUGUC | 20441 |
| 2269 | AUUGCGUG G UCAGGCAG | 8767 | CUGCCUGA GCCGAAAGGCGAGUGAGGUCU CACGCAAU | 20442 |
| 2274 | GUGGUCAG G CAGCUCAC | 8768 | GUGAGCUG GCCGAAAGGCGAGUGAGGUCU CUGACCAC | 20443 |
| 2277 | GUCAGGCA G CUCACAGU | 8769 | ACUGUGAG GCCGAAAGGCGAGUGAGGUCU UGCCUGAC | 20444 |
| 2284 | AGCUCACA G UCCUAGAG | 8770 | CUCUAGGA GCCGAAAGGCGAGUGAGGUCU UGUGAGCU | 20445 |
| 2292 | GUCCUAGA G CGUGUGGC | 8771 | GCCACACG GCCGAAAGGCGAGUGAGGUCU UCUAGGAC | 20446 |
| 2294 | CCUAGAGC G UGUGGCAC | 8772 | GUGCCACA GCCGAAAGGCGAGUGAGGUCU GCUCUAGG | 20447 |
| 2296 | UAGAGCGU G UGGCACCC | 8773 | GGGUGCCA GCCGAAAGGCGAGUGAGGUCU ACGCUCUA | 20448 |
| 2299 | AGCGUGUG G CACCCACG | 8774 | CGUGGGUG GCCGAAAGGCGAGUGAGGUCU CACACGCU | 20449 |

TABLE XXIII-continued

Human KDR Ziuzyme and Substrate Sequence

| Pos | Substrate | Seq ID No | Zinzyme | Seq ID No |
|---|---|---|---|---|
| 2339 | GACGACAA G UAUUGGGG | 8780 | CCCCAAUA GCCGAAAGGCGAGUGAGGUCU UUGUCGUC | 20450 |
| 2351 | UGGGGAAA G CAUCGAAG | 8781 | CUUCGAUG GCCGAAAGGCGAGUGAGGUCU UUUCCCCA | 20451 |
| 2359 | GCAUCGAA G UCUCAUGC | 8782 | GCAUGAGA GCCGAAAGGCGAGUGAGGUCU UUCGAUGC | 20452 |
| 2366 | AGUCUCAU G CACGGCAU | 8783 | AUGCCGUG GCCGAAAGGCGAGUGAGGUCU AUGAGACU | 20453 |
| 2371 | CAUGCACG G CAUCUGGG | 8784 | CCCAGAUG GCCGAAAGGCGAGUGAGGUCU CGUGCAUG | 20454 |
| 2400 | CAGAUCAU G UGGUUUAA | 8787 | UUAAACCA GCCGAAAGGCGAGUGAGGUCU AUGAUCUG | 20455 |
| 2403 | AUCAUGUG G UUUAAAGA | 8788 | UCUUUAAA GCCGAAAGGCGAGUGAGGUCU CACAUGAU | 20456 |
| 2425 | AGACCCUU G UAGAAGAC | 8792 | GUCUUCUA GCCGAAAGGCGAGUGAGGUCU AAGGGUCU | 20457 |
| 2438 | AGACUCAG G CAUUGUAU | 8794 | AUACAAUG GCCGAAAGGCGAGUGAGGUCU CUGAGUCU | 20458 |
| 2443 | CAGGCAUU G UAUUGAAG | 8795 | CUUCAAUA GCCGAAAGGCGAGUGAGGUCU AAUGCCUG | 20459 |
| 2477 | CACUAUCC G CAGAGUGA | 8799 | UCACUCUG GCCGAAAGGCGAGUGAGGUCU GGAUAGUG | 20460 |
| 2482 | UCCGCAGA G UGAGGAAG | 8800 | CUUCCUCA GCCGAAAGGCGAGUGAGGUCU UCUGCGGA | 20461 |
| 2501 | GGACGAAG G CCUCUACA | 8802 | UGUAGAGG GCCGAAAGGCGAGUGAGGUCU CUUCGUCC | 20462 |
| 2513 | CUACACCU G CCAGGCAU | 8803 | AUGCCUGG GCCGAAAGGCGAGUGAGGUCU AGGUGUAG | 20463 |
| 2518 | CCUGCCAG G CAUGCAGU | 8804 | ACUGCAUG GCCGAAAGGCGAGUGAGGUCU CUGGCAGG | 20464 |
| 2522 | CCAGGCAU G CAGUGUUC | 8805 | GAACACUG GCCGAAAGGCGAGUGAGGUCU AUGCCUGG | 20465 |
| 2525 | GGCAUGCA G UGUUCUUG | 8806 | CAAGAACA GCCGAAAGGCGAGUGAGGUCU UGCAUGCC | 20466 |
| 2527 | CAUGCAGU G UUCUUGGC | 8807 | GCCAAGAA GCCGAAAGGCGAGUGAGGUCU ACUGCAUG | 20467 |
| 2534 | UGUUCUUG G CUGUGCAA | 8808 | UUGCACAG GCCGAAAGGCGAGUGAGGUCU CAAGAACA | 20468 |
| 2537 | UCUUGGCU G UGCAAAAG | 8809 | CUUUUGCA GCCGAAAGGCGAGUGAGGUCU AGCCAAGA | 20469 |
| 2539 | UUGGCUGU G CAAAAGUG | 8810 | CACUUUUG GCCGAAAGGCGAGUGAGGUCU ACAGCCAA | 20470 |
| 2545 | GUGCAAAA G UGGAGGCA | 8811 | UGCCUCCA GCCGAAAGGCGAGUGAGGUCU UUUUGCAC | 20471 |
| 2551 | AAGUGGAG G CAUUUUUC | 8812 | GAAAAAUG GCCGAAAGGCGAGUGAGGUCU CUCCACUU | 20472 |
| 2570 | AAUAGAAG G UGCCCAGG | 8814 | CCUGGGCA GCCGAAAGGCGAGUGAGGUCU CUUCUAUU | 20473 |
| 2572 | UAGAAGGU G CCCAGGAA | 8815 | UUCCUGGG GCCGAAAGGCGAGUGAGGUCU ACCUUCUA | 20474 |
| 2608 | UUAUUCUA G UAGGCACG | 8819 | CGUGCCUA GCCGAAAGGCGAGUGAGGUCU UAGAAUAA | 20475 |
| 2612 | UCUAGUAG G CACGGCGG | 8820 | CCGCCGUG GCCGAAAGGCGAGUGAGGUCU CUACUAGA | 20476 |
| 2617 | UAGGCACG G CGGUGAUU | 8822 | AAUCACCG GCCGAAAGGCGAGUGAGGUCU CGUGCCUA | 20477 |
| 2620 | GCACGGCG G UGAUUGCC | 8823 | GGCAAUCA GCCGAAAGGCGAGUGAGGUCU CGCCGUGC | 20478 |
| 2626 | CGGUGAUU G CCAUGUUC | 8825 | GAACAUGG GCCGAAAGGCGAGUGAGGUCU AAUCACCG | 20479 |
| 2631 | AUUGCCAU G UUCUUCUG | 8826 | CAGAAGAA GCCGAAAGGCGAGUGAGGUCU AUGGCAAU | 20480 |
| 2640 | UUCUUCUG G CUACUUCU | 8827 | AGAAGUAG GCCGAAAGGCGAGUGAGGUCU CAGAAGAA | 20481 |
| 2650 | UACUUCUU G UCAUCAUC | 8828 | GAUGAUGA GCCGAAAGGCGAGUGAGGUCU AAGAAGUA | 20482 |
| 2668 | UACGGACC G UUAAGCGG | 8832 | CCGCUUAA GCCGAAAGGCGAGUGAGGUCU GGUCCGUA | 20483 |
| 2673 | ACCGUUAA G CGGGCCAA | 8833 | UUGGCCCG GCCGAAAGGCGAGUGAGGUCU UUAACGGU | 20484 |
| 2677 | UUAAGCGG G CCAAUGGA | 8834 | UCCAUUGG GCCGAAAGGCGAGUGAGGUCU CCGCUUAA | 20485 |
| 2702 | GAAGACAG G CUACUUGU | 8838 | ACAAGUAG GCCGAAAGGCGAGUGAGGUCU CUGUCUUC | 20486 |

TABLE XXIII-continued

Human KDR Ziuzyme and Substrate Sequence

| Pos | Substrate | Seq ID No | Zinzyme | Seq ID No |
|---|---|---|---|---|
| 2709 | GGCUACUU G UCCAUCGU | 8839 | ACGAUGGA GCCGAAAGGCGAGUGAGGUCU AAGUAGCC | 20487 |
| 2716 | UGUCCAUC G UCAUGGAU | 8840 | AUCCAUGA GCCGAAAGGCGAGUGAGGUCU GAUGGACA | 20488 |
| 2753 | UGAACAUU G UGAACGAC | 8846 | GUCGUUCA GCCGAAAGGCGAGUGAGGUCU AAUGUUCA | 20489 |
| 2763 | GAACGACU G CCUUAUGA | 8849 | UCAUAAGG GCCGAAAGGCGAGUGAGGUCU AGUCGUUC | 20490 |
| 2773 | CUUAUGAU G CCAGCAAA | 8851 | UUUGCUGG GCCGAAAGGCGAGUGAGGUCU AUCAUAAG | 20491 |
| 2777 | UGAUGCCA G CAAAUGGG | 8852 | CCCAUUUG GCCGAAAGGCGAGUGAGGUCU UGGCAUCA | 20492 |
| 2802 | AGAGACCG G CUGAAGCU | 8856 | AGCUUCAG GCCGAAAGGCGAGUGAGGUCU CGGUCUCU | 20493 |
| 2808 | CGGCUGAA G CUAGGUAA | 8857 | UUACCUAG GCCGAAAGGCGAGUGAGGUCU UUCAGCCG | 20494 |
| 2813 | GAAGCUAG G UAAGCCUC | 8858 | GAGGCUUA GCCGAAAGGCGAGUGAGGUCU CUAGCUUC | 20495 |
| 2817 | CUAGGUAA G CCUCUUGG | 8859 | CCAAGAGG GCCGAAAGGCGAGUGAGGUCU UUACCUAG | 20496 |
| 2825 | GCCUCUUG G CCGUGGUG | 8860 | CACCACGG GCCGAAAGGCGAGUGAGGUCU CAAGAGGC | 20497 |
| 2828 | UCUUGGCC G UGGUGCCU | 8861 | AGGCACCA GCCGAAAGGCGAGUGAGGUCU GGCAAGA | 20498 |
| 2831 | UGGCCGUG G UGCCUUUG | 8862 | CAAAGGCA GCCGAAAGGCGAGUGAGGUCU CACGGCCA | 20499 |
| 2833 | GCCGUGGU G CCUUUGGC | 8863 | GCCAAAGG GCCGAAAGGCGAGUGAGGUCU ACCACGGC | 20500 |
| 2840 | UGCCUUUG G CCAAGUGA | 8864 | UCACUUGG GCCGAAAGGCGAGUGAGGUCU CAAAGGCA | 20501 |
| 2845 | UUGGCCAA G UGAUUGAA | 8865 | UUCAAUCA GCCGAAAGGCGAGUGAGGUCU UUGGCCAA | 20502 |
| 2854 | UGAUUGAA G CAGAUGCC | 8867 | GGCAUCUG GCCGAAAGGCGAGUGAGGUCU UUCAAUCA | 20503 |
| 2860 | AAGCAGAU G CCUUUGGA | 8869 | UCCAAAGG GCCGAAAGGCGAGUGAGGUCU AUCUGCUU | 20504 |
| 2881 | ACAAGACA G CAACUUGC | 8873 | GCAAGUUG GCCGAAAGGCGAGUGAGGUCU UGUCUUGU | 20505 |
| 2888 | AGCAACUU G CAGGACAG | 8875 | CUGUCCUG CCCGAAAGGCGAGUGAGGUCU AAGUUGCU | 20506 |
| 2896 | GCAGGACA G UAGCAGUC | 8877 | GACUGCUA GCCGAAAGGCGAGUGAGGUCU UGUCCUGC | 20507 |
| 2899 | CGACAGUA G CAGUCAAA | 8878 | UUUGACUG GCCGAAAGGCGAGUGAGGUCU UACUGUCC | 20508 |
| 2902 | CAGUAGCA G UCAAAAUG | 8879 | CAUUUUGA GCCGAAAGGCGAGUGAGGUCU UCCUACUG | 20509 |
| 2910 | GUCAAAAU G UUGAAAGA | 8881 | UCUUUCAA GCCGAAAGGCGAGUGACGUCU AUUUUGAC | 20510 |
| 2923 | AAGAACGA G CAACACAC | 8882 | GUGUGUUG GCCGAAAGGCGAGUGAGGUCU UCCUUCUU | 20511 |
| 2933 | AACACACA G UGAGCAUC | 8884 | GAUGCUCA GCCGAAAGGCGAGUGAGGUCU UGUGUGUU | 20512 |
| 2937 | CACAGUGA G CAUCGAGC | 8885 | GCUCCAUG GCCGAAAGGCGAGUGAGCUCU UCACUGUC | 20513 |
| 2944 | ACCAUCCA G CUCUCAUC | 8886 | CAUGAGAC GCCCAAACGCGACUGACGUCU UCCAUGCU | 20514 |
| 2952 | GCUCUCAU G UCUGAACU | 8887 | AGUUCAGA GCCGAAAGGCGACUGAGGUCU AUGAGAGC | 20515 |
| 2981 | UCAUAUUG G UCACCAUC | 8890 | GAUCCUGA GCCCAAACCCGACUGAGGUCU CAAUAUGA | 20516 |
| 2995 | AUCUCAAU G UGGUCAAC | 8892 | GUUGACCA GCCGAAAGGCGAGUGAGGUCU AUUGAGAU | 20517 |
| 2998 | UCAUGUG G UCAACCUU | 8893 | AAGGUUGA GCCGAAAGGCGAGUGAGGUCU CACAUUGA | 20518 |
| 3011 | CCUUCUAG G UGCCUGUA | 8895 | UACAGGCA GCCGAAAGGCGAGUGAGGUCU CUAGAAGG | 20519 |
| 3013 | UUCUAGGU G CCUGUACC | 8896 | GGUACAGG GCCGAAAGGCGAGUGAGGUCU ACCUAGAA | 20520 |
| 3017 | AGGUGCCU G UACCAAGC | 8897 | GCUUGGUA GCCGAAAGGCGAGUGAGGUCU AGGCACCU | 20521 |
| 3024 | UGUACCAA G CCAGGAGG | 8898 | CCUCCUGG GCCGAAAGGCGAGUGAGGUCU UUGGUACA | 20522 |
| 3033 | CCAGGAGG G CCACUCAU | 8899 | AUCAGUGG GCCGAAAGGCGAGUCACGUCU CCUCCUGG | 20523 |

TABLE XXIII-continued

Human KDR Ziuzyme and Substrate Sequence

| Pos | Substrate | | | Seq ID No | Zinzyme | Seq ID No |
|---|---|---|---|---|---|---|
| 3043 | CACUCAUG | G | UGAUUGUG | 8900 | CACAAUCA GCCGAAAGGCGAGUGAGGUCU CAUGAGUG | 20524 |
| 3049 | UGGUGAUU | G | UGGAAUUC | 8902 | GAAUUCCA GCCGAAAGGCGAGUGAGGUCU AAUCACCA | 20525 |
| 3059 | CGAAUUCU | G | CAAAUUUG | 8904 | CAAAUUUG GCCGAAAGCCGAGUGAGGUCU AGAAUUCC | 20526 |
| 3075 | GGAAACCU | G | UCCACUUA | 8907 | UAAGUCGA GCCGAAAGCCGACUGAGGUCU AGGUUUCC | 20527 |
| 3092 | CCUGAGGA | G | CAACAGAA | 8908 | UUCUCUUG GCCGAAAGGCGAGUGAGGUCU UCCUCAGG | 20528 |
| 3109 | AUGAAUUU | G | UCCCCUAC | 8911 | GUAGGGGA GCCGAAAGGCGAGUGAGGUCU AAAUUCAU | 20529 |
| 3130 | CCAAAGGG | G | CACGAUUC | 8913 | GAAUCGUG GCCGAAAGGCCAGUGAGGUCU CCCUUUCG | 20530 |
| 3140 | ACGAUUCC | G | UCAAGGGA | 8915 | UCCCUUCA GCCGAAAGGCGAGUGAGGUCU GGAAUCGU | 20531 |
| 3157 | AAGACUAC | G | UUGGAGCA | 8917 | UGCUCCAA GCCGAAAGGCGAGUGAGGUCU GUAGUCUU | 20532 |
| 3163 | ACGUUGGA | G | CAAUCCCU | 8918 | AGGGAUUG GCCGAAAGGCGAGUGAGCUCU UCCAACGU | 20533 |
| 3172 | CAAUCCCU | G | UGGAUCUG | 8920 | CAGAUCCA GCCGAAAGGCGACUGAGGUCU AGGGAUUG | 20534 |
| 3186 | CUGAAACG | G | CGCUUGGA | 8923 | UCCAACCG GCCGAAAGGCGAGUGAGGUCU CGUUUCAG | 20535 |
| 3188 | CAAACGGC | G | CUUCCACA | 8924 | UGUCCAAG GCCGAAAGGCGAGUGAGGUCU GCCGUUUC | 20536 |
| 3197 | CUUGGACA | G | CAUCACCA | 8926 | UCCUGAUG GCCGAAAGGCGAGUGAGGUCU UGUCCAAG | 20537 |
| 3206 | CAUCACCA | G | UAGCCACA | 8927 | UCUGGCUA GCCGAAACGCGAGUGAGGUCU UGCUGAUG | 20538 |
| 3209 | CACCAGUA | G | CCACAGCU | 8928 | AGCUCUGG CCCGAAAGGCGAGUGAGGUCU UACUGGUG | 20539 |
| 3215 | UAGCCAGA | G | CUCAGCCA | 8929 | UGGCUCAG GCCGAAAGGCGACUGAGGUCU UCUGGCUA | 20540 |
| 3220 | AGACCUCA | G | CCACCUCU | 8930 | AGAGCUGG GCCGAAAGGCGAGUGAGGUCU UCAGCUCU | 20541 |
| 3224 | CUCAGCCA | G | CUCUCCAU | 8931 | AUCCAGAG GCCGAAACGCCAGUGAGGUCU UGGCUGAG | 20542 |
| 3235 | CUGGAUUU | G | UGGAGGAG | 8933 | CUCCUCCA GCCGAAAGGCGAGUGAGCUCU AAAUCCAC | 20543 |
| 3246 | GAGGAGAA | G | UCCCUCAG | 8934 | CUGAGGGA CCCGAAAGGCGAGUGAGGUCU UUCUCCUC | 20544 |
| 3254 | GUCCCUCA | G | UGAUGUAG | 8935 | CUACAUCA GCCGAAAGGCGAGUGAGGUCU UGAGGGAC | 20545 |
| 3259 | UCACUGAU | G | UAGAAGAA | 8937 | UUCUUCUA CCCCAAAGGCCACUGAGGUCU AUCACUGA | 20546 |
| 3274 | AAGAGGAA | G | CUCCUGAA | 8938 | UUCAGCAG GCCGAAAGGCGACUGAGGUCU UUCCUCUU | 20547 |
| 3288 | GAAGAUCU | G | UAUAAGGA | 8940 | UCCUUAUA CCCCAAAGGCCAGUGAGCUCU AGAUCUUC | 20548 |
| 3312 | ACCUUGCA | G | CAUCUCAU | 8943 | AUGAGAUG GCCGAAAGGCGAGUCAGGUCU UCCAAGCU | 20549 |
| 3323 | UCUCAUCU | G | UUACAGCU | 8944 | AGCUGUAA GCCGAAAGGCGACUCAGGUCU AGAUCACA | 20550 |
| 3329 | CUGUUACA | G | CUUCCAAC | 8945 | CUUGGAAG GCCCAAACCCAGUGACCUCU UCUAACAG | 20551 |
| 3337 | GCUUCCAA | G | UGGCUAAG | 8946 | CUUAGCCA CCCCAAACGCCACUGACGUCU UUCGAAGC | 20552 |
| 3340 | UCCAAGUC | G | CUAAGCGC | 8947 | CCCCUUAG GCCCAAAGGCGACUGAGGUCU CACUUGCA | 20553 |
| 3347 | CGCUAAGG | G | CAUGGAGU | 8948 | ACUCCAUC GCCCAAACCCACUCACGUCU CCUUACCC | 20554 |
| 3354 | GCCAUCCA | G | UUCUUCGC | 8949 | CCCAACAA CCCCAAACGCGAGUGAGGUCU UCCAUCCC | 20555 |
| 3361 | AGUUCUUC | G | CAUCCCCA | 8950 | UCGCCAUC CCCCAAAGGCGAGUGAGGUCU CAACAACU | 20556 |
| 3366 | UUGGCAUC | G | CGAAAGUC | 8951 | CACUUUCC CCCCAAAGCCGAGUCACCUCU CAUCCCAA | 20557 |
| 3372 | UCCCCAAA | G | UCUAUCCA | 8952 | UCCAUACA CCCCAAACCCACUCACGUCU UUUCCCCA | 20558 |
| 3374 | GCGAAAGU | G | UAUUCCACA | 8953 | UGUCCAUA CCCCAAACGCGAGUCACCUCU ACUUUCGC | 20559 |
| 3391 | CGGACCUC | G | CGCCACCA | 8955 | UCCUCCCC GCCGAAAGCCGAGUCAGCUCU CACGUCCC | 20560 |

TABLE XXIII-continued

Human KDR Ziuzyme and Substrate Sequence

| Pos | Substrate | Seq ID No | Zinzyme | Seq ID No |
|---|---|---|---|---|
| 3394 | ACCUCCCC G CACCAAAU | 8956 | AUUUCCUG CCCCAAACCCGAGUGACCUCU CGCCAGCU | 20561 |
| 3424 | AGAACAAC G UGGUUAAA | 8959 | UUUAACCA GCCGAAAGGCCAGUGACGUCU CUUCUUCU | 20562 |
| 3427 | ACAACCUG G UUAAAAUC | 8960 | CAUUUUAA CCCCAAACGCCAGUGACGUCU CACCUUCU | 20563 |
| 3437 | UAAAAUCU G UGACUUUC | 8962 | CAAAGUCA GCCGAAAGGCGAGUGAGGUCU ACAUUUUA | 20564 |
| 3446 | UCACUCUC G CUUGCCCC | 8964 | CCGCCAAC CCCCAAACCCACUCACCUCU CAAACUCA | 20565 |
| 3451 | UUCGCUUG G CCCCCGAU | 8965 | AUCCCCCC GCCGAAAGGCGACUGAGGUCU CAAGCCAA | 20566 |
| 3481 | CAGAUUAU G UCAGAAAA | 8969 | UUUUCUGA GCCGAAAGGCGAGUGAGGUCU AUAAUCUG | 20567 |
| 3496 | AAGGAGAU G CUCGCCUC | 8971 | GAGGCGAG GCCGAAAGGCGAGUGAGGUCU AUCUCCUU | 20568 |
| 3500 | AGAUGCUC G CCUCCCUU | 8972 | AAGGGAGG GCCGAAAGGCGAGUGAGGUCU GAGCAUCU | 20569 |
| 3520 | AAUGGAUG G CCCCAGAA | 8975 | UUCUGGGG GCCGAAAGGCGAGUGAGGUCU CAUCCAUU | 20570 |
| 3544 | UUGACAGA G UGUACACA | 8979 | UGUGUACA GCCGAAAGGCGAGUGAGGUCU UCUGUCAA | 20571 |
| 3546 | GACAGAGU G UACACAAU | 8980 | AUUGUGUA GCCGAAAGGCGAGUGAGGUCU ACUCUGUC | 20572 |
| 3560 | AAUCCAGA G UGACGUCU | 8982 | AGACGUCA GCCGAAAGGCGAGUGAGGUCU UCUGGAUU | 20573 |
| 3565 | AGAGUGAC G UCUGGUCU | 8984 | AGACCAGA GCCGAAAGGCGAGUGAGGUCU GUCACUCU | 20574 |
| 3570 | GACGUCUG G UCUUUUGG | 8985 | CCAAAAGA GCCGAAAGGCGAGUGAGGUCU CAGACGUC | 20575 |
| 3578 | GUCUUUUG G UGUUUUGC | 8986 | GCAAAACA GCCGAAAGGCGAGUGAGGUCU CAAAAGAC | 20576 |
| 3580 | CUUUUGGU G UUUUGCUG | 8987 | CAGCAAAA GCCGAAAGGCGAGUGAGGUCU ACCAAAAG | 20577 |
| 3585 | GGUGUUUU G CUGUGGGA | 8988 | UCCCACAG GCCGAAAGGCGAGUGAGGUCU AAAACACC | 20578 |
| 3588 | GUUUUGCU G UGGGAAAU | 8989 | AUUUCCCA GCCGAAAGGCGAGUGAGGUCU AGCAAAAC | 20579 |
| 3608 | UUCCUUAG G UGCUUCUC | 8991 | GAGAAGCA GCCGAAAGGCGAGUGAGGUCU CUAAGGAA | 20580 |
| 3610 | CCUUAGGU G CUUCUCCA | 8992 | UGGAGAAG GCCGAAAGGCGAGUGAGGUCU ACCUAAGG | 20581 |
| 3628 | AUCCUGGG G UAAAGAUU | 8993 | AAUCUUUA GCCGAAAGGCGAGUGAGGUCU CCCAGGAU | 20582 |
| 3650 | AGAAUUUU G UAGGCGAU | 8997 | AUCGCCUA GCCGAAAGGCGAGUGAGGUCU AAAAUUCU | 20583 |
| 3654 | UUUUGUAG G CGAUUGAA | 8998 | UUCAAUCG GCCGAAAGGCGAGUGAGGUCU CUACAAAA | 20584 |
| 3682 | GAAUGAGG G CCCCUGAU | 9002 | AUCAGGGG GCCGAAAGGCGAGUGAGGUCU CCUCAUUC | 20585 |
| 3708 | CCAGAAAU G UACCAGAC | 9005 | GUCUGGUA GCCGAAAGGCGAGUGAGGUCU AUUUCUGG | 20586 |
| 3720 | CAGACCAU G CUGGACUG | 9007 | CAGUCCAG GCCGAAAGGCGAGUGAGGUCU AUGGUCUG | 20587 |
| 3728 | GCUGGACU G CUGGCACG | 9008 | CGUGCCAG GCCGAAAGGCGAGUGAGGUCU AGUCCAGC | 20588 |
| 3732 | GACUGCUG G CACGGGGA | 9009 | UCCCCGUG GCCGAAAGGCGAGUGAGGUCU CAGCAGUC | 20589 |
| 3741 | CACGGGGA G CCCAGUCA | 9010 | UGACUGGG GCCGAAAGGCGAGUGAGGUCU UCCCCGUG | 20590 |
| 3746 | GGAGCCCA G UCAGAGAC | 9011 | GUCUCUGA GCCGAAAGGCGAGUGAGGUCU UGGGCUCC | 20591 |
| 3759 | AGACCCAC G UUUUCAGA | 9013 | UCUGAAAA GCCGAAAGGCGAGUGAGGUCU GUGGGUCU | 20592 |
| 3768 | UUUUCAGA G UUGGUGGA | 9014 | UCCACCAA GCCGAAAGGCGAGUGAGGUCU UCUGAAAA | 20593 |
| 3772 | CAGAGUUG G UGGAACAU | 9015 | AUGUUCCA GCCGAAAGGCGAGUGAGGUCU CAACUCUG | 20594 |
| 3795 | AAUCUCUU G CAAGCUAA | 9018 | UUAGCUUG GCCGAAAGGCGAGUGAGGUCU AAGAGAUU | 20595 |
| 3799 | UCUUGCAA G CUAAUGCU | 9019 | AGCAUUAG GCCGAAAGGCGAGUGAGGUCU UUGCAAGA | 20596 |
| 3805 | AAGCUAAU G CUCAGCAG | 9021 | CUGCUGAG GCCGAAAGGCGAGUGAGGUCU AUUAGCUU | 20597 |

TABLE XXIII-continued

Human KDR Ziuzyme and Substrate Sequence

| Pos | Substrate | Seq ID No | Zinzyme | Seq ID No |
|---|---|---|---|---|
| 3810 | AAUGCUCA G CAGGAUGG | 9022 | CCAUCCUG GCCGAAAGGCGAGUGAGGUCU UGAGCAUU | 20598 |
| 3818 | GCAGGAUG G CAAAGACU | 9024 | AGUCUUUG GCCGAAAGGCGAGUGAGGUCU CAUCCUGC | 20599 |
| 3832 | ACUACAUU G UUCUUCCG | 9026 | CGGAAGAA GCCGAAAGGCGAGUGAGGUCU AAUGUAGU | 20600 |
| 3857 | GACUUUGA G CAUGGAAG | 9029 | CUUCCAUG GCCGAAAGGCGAGUGAGGUCU UCAAAGUC | 20601 |
| 3885 | CUCUCUCU G CCUACCUC | 9032 | GAGGUAGG GCCGAAAGGCGAGUGAGGUCU AGAGAGAG | 20602 |
| 3898 | CCUCACCU G UUUCCUGU | 9033 | ACAGGAAA GCCGAAAGGCGAGUGAGGUCU AGGUGAGG | 20603 |
| 3905 | UGUUUCCU G UAUGGAGG | 9034 | CCUCCAUA GCCGAAAGGCGAGUGAGGUCU AGGAAACA | 20604 |
| 3922 | AGGAGGAA G UAUGUGAC | 9035 | GUCACAUA GCCGAAAGGCGAGUGAGGUCU UUCCUCCU | 20605 |
| 3926 | GGAAGUAU G UGACCCCA | 9036 | UGGGGUCA GCCGAAAGGCGAGUGAGGUCU AUACUUCC | 20606 |
| 3955 | ACAACACA G CAGGAAUC | 9041 | GAUUCCUG GCCGAAAGGCGAGUGAGGUCU UGUGUUGU | 20607 |
| 3965 | AGGAAUCA G UCAGUAUC | 9043 | GAUACUGA GCCGAAAGGCGAGUGAGGUCU UGAUUCCU | 20608 |
| 3969 | AUCAGUCA G UAUCUGCA | 9044 | UGCAGAUA GCCGAAAGGCGAGUGAGGUCU UGACUGAU | 20609 |
| 3975 | CAGUAUCU G CAGAACAG | 9045 | CUGUUCUG GCCGAAAGGCGAGUGAGGUCU AGAUACUG | 20610 |
| 3983 | GCAGAACA G UAAGCGAA | 9047 | UUCGCUUA GCCGAAAGGCGAGUGAGGUCU UGUUCUGC | 20611 |
| 3987 | AACAGUAA G CGAAAGAG | 9048 | CUCUUUCG GCCGAAAGGCGAGUGAGGUCU UUACUGUU | 20612 |
| 3995 | GCGAAAGA G CCGGCCUG | 9049 | CAGGCCGG GCCGAAAGGCGAGUGAGGUCU UCUUUCGC | 20613 |
| 3999 | AAGAGCCG G CCUGUGAG | 9050 | CUCACAGG GCCGAAAGGCGAGUGAGGUCU CGGCUCUU | 20614 |
| 4003 | GCCGGCCU G UGAGUGUA | 9051 | UACACUCA GCCGAAAGGCGAGUGAGGUCU AGGCCGGC | 20615 |
| 4007 | GCCUGUGA G UGUAAAAA | 9052 | UUUUUACA GCCGAAAGGCGAGUGAGGUCU UCACAGGC | 20616 |
| 4009 | CUGUGAGU G UAAAACA | 9053 | UGUUUUA GCCGAAAGGCGAGUGAGGUCU ACUCACAG | 20617 |
| 4032 | GAUAUCCC G UUAGAAGA | 9056 | UCUUCUAA GCCGAAAGGCGAGUGAGGUCU GGGAUAUC | 20618 |
| 4048 | AACCAGAA G UAAAAGUA | 9058 | UACUUUUA GCCGAAAGGCGAGUGAGGUCU UUCGGUU | 20619 |
| 4054 | AAGUAAAA G UAAUCCCA | 9059 | UGGGAUUA GCCGAAAGGCGAGUGAGGUCU UUUUACUU | 20620 |
| 4082 | GACGGACA G UGGUAUGG | 9066 | CCAUACCA GCCGAAAGGCGAGUGAGGUCU UGUCCGUC | 20621 |
| 4085 | GGACAGUG G UAUGGUUC | 9067 | GAACCAUA GCCGAAAGGCGAGUGAGGUCU CACUGUCC | 20622 |
| 4090 | GUGGUAUG G UUCUUGCC | 9068 | GGCAAGAA GCCGAAAGGCGAGUGAGGUCU CAUACCAC | 20623 |
| 4096 | UGGUUCUU G CCUCAGAA | 9069 | UUCUGAGG GCCGAAAGGCGAGUGAGGUCU AAGAACCA | 20624 |
| 4107 | UCAGAAGA G CUGAAAAC | 9070 | GUUUUCAG GCCGAAAGGCGAGUGAGGUCU UCUUCUGA | 20625 |
| 4151 | AUCUUUUG G UGGAAUGG | 9075 | CCAUUCCA GCCGAAAGGCGAGUGAGGUCU CAAAAGAU | 20626 |
| 4159 | GUGGAAUG G UGCCCAGC | 9077 | GCUGGGCA GCCGAAAGGCGAGUGAGGUCU CAUUCCAC | 20627 |
| 4161 | GGAAUGGU G CCCAGCAA | 9078 | UUGCUGGG GCCGAAAGGCGAGUGAGGUCU ACCAUUCC | 20628 |
| 4166 | GGUGCCCA G CAAAAGCA | 9079 | UGCUUUUG GCCGAAAGGCGAGUGAGGUCU UGGGCACC | 20629 |
| 4172 | CAGCAAAA G CAGGGAGU | 9080 | ACUCCCUG GCCGAAAGGCGAGUGAGGUCU UUUUGCUG | 20630 |
| 4179 | AGCAGGGA G UCUGUGGC | 9081 | GCCACAGA GCCGAAAGGCGAGUGAGGUCU UCCCUGCU | 20631 |
| 4183 | GGGAGUCU G UGGCAUCU | 9082 | AGAUGCCA GCCGAAAGGCGAGUGAGGUCU AGACUCCC | 20632 |
| 4186 | AGUCUGUG G CAUCUGAA | 9083 | UUCAGAUG GCCGAAAGGCGAGUGAGGUCU CACAGACU | 20633 |
| 4196 | AUCUGAAG G CUCAAACC | 9084 | GGUUUGAG GCCGAAAGGCGAGUGAGGUCU CUUCAGAU | 20634 |

TABLE XXIII-continued

Human KDR Ziuzyme and Substrate Sequence

| Pos | Substrate | Seq ID No | Zinzyme | Seq ID No |
|---|---|---|---|---|
| 4211 | CCAGACAA G CGGCUACC | 9087 | GGUAGCCG GCCGAAAGGCGAGUGAGGUCU UUGUCUGG | 20635 |
| 4214 | GACAAGCG G CUACCAGU | 9088 | ACUGGUAG GCCGAAAGGCGAGUGAGGUCU CGCUUGUC | 20636 |
| 4221 | GGCUACCA G UCCGGAUA | 9089 | UAUCCGGA GCCGAAAGGCGAGUGAGGUCU UGGUAGCC | 20637 |
| 4255 | ACACCACC G UGUACUCC | 9094 | GGAGUACA GCCGAAAGGCGAGUGAGGUCU GGUGGUGU | 20638 |
| 4257 | ACCACCGU G UACUCCAG | 9095 | CUGGAGUA GCCGAAAGGCGAGUGAGGUCU ACGGUGGU | 20639 |
| 4265 | GUACUCCA G UGAGGAAG | 9096 | CUUCCUCA GCCGAAAGGCGAGUGAGGUCU UGGAGUAC | 20640 |
| 4273 | GUGAGGAA G CAGAACUU | 9097 | AAGUUCUG GCCGAAAGGCGAGUGAGGUCU UUCCUCAC | 20641 |
| 4287 | CUUUUAAA G CUGAUAGA | 9099 | UCUAUCAG GCCGAAAGGCGAGUGAGGUCU UUUAAAAG | 20642 |
| 4303 | AGAUUGGA G UGCAAACC | 9102 | GGUUUGCA GCCGAAAGGCGAGUGAGGUCU UCCAAUCU | 20643 |
| 4305 | AUUGGAGU G CAAACCGG | 9103 | CCGGUUUG GCCGAAAGGCGAGUGAGGUCU ACUCCAAU | 20644 |
| 4313 | GCAAACCG G UAGCACAG | 9105 | CUGUGCUA GCCGAAAGGCGAGUGAGGUCU CGGUUUGC | 20645 |
| 4316 | AACCGGUA G CACAGCCC | 9106 | GGGCUGUG GCCGAAAGGCGAGUGAGGUCU UACCGGUU | 20646 |
| 4321 | GUAGCACA G CCCAGAUU | 9107 | AAUCUGGG GCCGAAAGGCGAGUGAGGUCU UGUGCUAC | 20647 |
| 4335 | AUUCUCCA G CCUGACUC | 9109 | GAGUCAGG GCCGAAAGGCGAGUGAGGUCU UGGAGAAU | 20648 |
| 4358 | CACACUGA G CUCUCCUC | 9112 | GAGGAGAG GCCGAAAGGCGAGUGAGGUCU UCAGUGUG | 20649 |
| 4369 | CUCCUCCU G UUUAAAAG | 9113 | CUUUUAAA GCCGAAAGGCGAGUGAGGUCU AGGAGGAG | 20650 |
| 4381 | AAAAGGAA G CAUCCACA | 9114 | UGUGGAUG GCCGAAAGGCGAGUGAGGUCU UUCCUUUU | 20651 |
| 4417 | CAUGAGAG G UCUGCUCA | 9117 | UGAGCAGA GCCGAAAGGCGAGUGAGGUCU CUCUCAUG | 20652 |
| 4421 | AGAGGUCU G CUCAGAUU | 9118 | AAUCUGAG GCCGAAAGGCGAGUGAGGUCU AGACCUCU | 20653 |
| 4435 | AUUUUGAA G UGUUGUUC | 9120 | GAACAACA GCCGAAAGGCGAGUGAGGUCU UUCAAAAU | 20654 |
| 4437 | UUUGAAGU G UUGUUCUU | 9121 | AAGAACAA GCCGAAAGGCGAGUGAGGUCU ACUUCAAA | 20655 |
| 4440 | GAAGUGUU G UUCUUUCC | 9122 | GGAAAGAA GCCGAAAGGCGAGUGAGGUCU AACACUUC | 20656 |
| 4453 | UUCCACCA G CAGGAAGU | 9123 | ACUUCCUG GCCGAAAGGCGAGUGAGGUCU UGGUGGAA | 20657 |
| 4460 | AGCAGGAA G UAGCCGCA | 9124 | UGCGGCUA GCCGAAAGGCGAGUGAGGUCU UUCCUGCU | 20658 |
| 4463 | AGGAAGUA G CCGCAUUU | 9125 | AAAUGCGG GCCGAAAGGCGAGUGAGGUCU UACUUCCU | 20659 |
| 4466 | AAGUAGCC G CAUUUGAU | 9126 | AUCAAAUG GCCGAAAGGCGAGUGAGGUCU GGCUACUU | 20660 |
| 4509 | CUCGGACU G CAGGGAGC | 9132 | GCUCCCUG GCCGAAAGGCGAGUGAGGUCU AGUCCGAG | 20661 |
| 4516 | UGCAGGGA G CCAGUCUU | 9133 | AAGACUGG GCCGAAAGGCGAGUGAGGUCU UCCCUGCA | 20662 |
| 4520 | GGGAGCCA G UCUUCUAG | 9134 | CUAGAAGA GCCGAAAGGCGAGUGAGGUCU UGGCUCCC | 20663 |
| 4529 | UCUUCUAG G CAUAUCCU | 9135 | AGGAUAUG GCCGAAAGGCGAGUGAGGUCU CUAGAAGA | 20664 |
| 4545 | UGGAAGAG G CUUGUGAC | 9138 | GUCACAAG GCCGAAAGGCGAGUGAGGUCU CUCUUCCA | 20665 |
| 4549 | AGAGGCUU G UGACCCAA | 9139 | UUGGGUCA GCCGAAAGGCGAGUGAGGUCU AAGCCUCU | 20666 |
| 4562 | CCAAGAAU G UGUCUGUG | 9142 | CACAGACA GCCGAAAGGCGAGUGAGGUCU AUUCUUGG | 20667 |
| 4564 | AAGAAUGU G UCUGUGUC | 9143 | GACACAGA GCCGAAAGGCGAGUGAGGUCU ACAUUCUU | 20668 |
| 4566 | AUGUCUGU G UGUCUUCU | 9144 | AGAAGACA GCCGAAAGGCGAGUGAGGUCU AGACACAU | 20669 |
| 4570 | GUCUGUGU G UCUUCUCC | 9145 | GGAGAAGA GCCGAAAGGCGAGUGAGGUCU ACAGACAC | 20670 |
| 4581 | UUCUCCCA G UGUUGACC | 9146 | GGUCAACA GCCGAAAGGCGAGUGAGGUCU UGGGAGAA | 20671 |

TABLE XXIII-continued

Human KDR Ziuzyme and Substrate Sequence

| Pos | Substrate | Seq ID No | Zinzyme | Seq ID No |
|---|---|---|---|---|
| 4583 | CUCCCAGU G UUGACCUG | 9147 | CAGGUCAA GCCGAAAGGCGAGUGAGGUCU ACUGGGAG | 20672 |
| 4618 | UUUAAAAA G CAUUAUCA | 9152 | UGAUAAUG GCCGAAAGGCGAGUGAGGUCU UUUUUAAA | 20673 |
| 4628 | AUUAUCAU G CCCCUGCU | 9156 | AGCAGGGG GCCGAAAGGCGAGUGAGGUCU AUGAUAAU | 20674 |
| 4634 | AUGCCCCU G CUGCGGGU | 9157 | ACCCGCAG GCCGAAAGGCGAGUGAGGUCU AGGGGCAU | 20675 |
| 4637 | CCCCUGCU G CGGGUCUC | 9158 | GAGACCCG GCCGAAAGGCGAGUGAGGUCU AGCAGGGG | 20676 |
| 4641 | UGCUGCGG G UCUCACCA | 9159 | UGGUGAGA GCCGAAAGGCGAGUGAGGUCU CCGCAGCA | 20677 |
| 4653 | CACCAUGG G UUUAGAAC | 9162 | GUUCUAAA GCCGAAAGGCGAGUGAGGUCU CCAUGGUG | 20678 |
| 4667 | AACAAAGA G CUUCAAGC | 9164 | GCUUGAAG GCCGAAAGGCGAGUGAGGUCU UCUUUGUU | 20679 |
| 4674 | AGCUUCAA G CAAUGGCC | 9165 | GGCCAUUG GCCGAAAGGCGAGUGAGGUCU UUGAAGCU | 20680 |
| 4680 | AAGCAAUG G CCCCAUCC | 9167 | GGAUGGGG GCCGAAAGGCGAGUGAGGUCU CAUUGCUU | 20681 |
| 4697 | UCAAAGAA G UAGCAGUA | 9169 | UACUGCUA GCCGAAAGGCGAGUGAGGUCU UUCUUUGA | 20682 |
| 4700 | AAGAAGUA G CAGUACCU | 9170 | AGGUACUG GCCGAAAGGCGAGUGAGGUCU UACUUCUU | 20683 |
| 4703 | AAGUAGCA G UACCUGGG | 9171 | CCCAGGUA GCCGAAAGGCGAGUGAGGUCU UGCUACUU | 20684 |
| 4714 | CCUGGGGA G CUGACACU | 9173 | AGUGUCAG GCCGAAAGGCGAGUGAGGUCU UCCCCAGG | 20685 |
| 4726 | ACACUUCU G UAAAACUA | 9176 | UAGUUUUA GCCGAAAGGCGAGUGAGGUCU AGAAGUGU | 20686 |
| 4748 | UAAACCAG G CAACGUAA | 9180 | UUACGUUG GCCGAAAGGCGAGUGAGGUCU CUGGUUUA | 20687 |
| 4753 | CAGGCAAC G UAAGUGUU | 9182 | AACACUUA GCCGAAAGGCGAGUGAGGUCU GUUGCCUG | 20688 |
| 4757 | CAACGUAA G UGUUCGAG | 9183 | CUCGAACA GCCGAAAGGCGAGUGAGGUCU UUACGUUG | 20689 |
| 4759 | ACGUAAGU G UUCGAGGU | 9184 | ACCUCGAA GCCGAAAGGCGAGUGAGGUCU ACUUACGU | 20690 |
| 4766 | UGUUCGAG G UGUUGAAG | 9185 | CUUCAACA GCCGAAAGGCGAGUGAGGUCU CUCGAACA | 20691 |
| 4768 | UUCGAGGU G UUGAAGAU | 9186 | AUCUUCAA GCCGAAAGGCGAGUGAGGUCU ACCUCGAA | 20692 |
| 4788 | AAGGAUUU G CAGGGCUG | 9189 | CAGCCCUG GCCGAAAGGCGAGUGAGGUCU AAAUCCUU | 20693 |
| 4793 | UUUGCAGG G CUGAGUCU | 9190 | AGACUCAG GCCGAAAGGCGAGUGAGGUCU CCUGCAAA | 20694 |
| 4798 | AGGGCUGA G UCUAUCCA | 9191 | UGGAUAGA GCCGAAAGGCGAGUGAGGUCU UCAGCCCU | 20695 |
| 4811 | UCCAAGAG G CUUUGUUU | 9193 | AAACAAAG GCCGAAAGGCGAGUGAGGUCU CUCUUGGA | 20696 |
| 4816 | GAGGCUUU G UUUAGGAC | 9194 | GUCCUAAA GCCGAAAGGCGAGUGAGGUCU AAAGCCUC | 20697 |
| 4825 | UUEUGGAC G UGGGUCCC | 9196 | GGGACCCA GCCGAAAGGCGAGUGAGGUCU GUCCUAAA | 20698 |
| 4829 | GGACGUGG G UCCCAAGC | 9197 | GCUUGGGA GCCGAAAGGCGAGUGAGGUCU CCACGUCC | 20699 |
| 4836 | GGUCCCAA G CCAAGCCU | 9198 | AGGCUUGG GCCGAAAGGCGAGUGAGGUCU UUGGGACC | 20700 |
| 4841 | CAAGCCAA G CCUUAAGU | 9199 | ACUUAAGG GCCGAAAGGCGAGUGAGGUCU UUGGCUUG | 20701 |
| 4848 | AGCCUUAA G UGGAAUU | 9200 | AUUCCACA GCCGAAAGGCGAGUGAGGUCU UUAAGGCU | 20702 |
| 4850 | CCUUAAGU G UGGAAUUC | 9201 | GAAUUCCA GCCGAAAGGCGAGUGAGGUCU ACUUAAGG | 20703 |
| 4883 | AGACUAAC G UUACCUUG | 9207 | CAAGGUAA GCCGAAAGGCGAGUGAGGUCU GUUAGUCU | 20704 |
| 4891 | GUUACCUU G CUUUGGAG | 9209 | CUCCAAAG GCCGAAAGGCGAGUGAGGUCU AAGGUAAC | 20705 |
| 4901 | UUUGGAGA G UACUGGAG | 9210 | CUCCAGUA GCCGAAAGGCGAGUGAGGUCU UCUCCAAA | 20706 |
| 4909 | GUACUGGA G CCUGCAAA | 9212 | UUUGCAGG GCCGAAAGGCGAGUGAGGUCU UCCAGUAC | 20707 |
| 4913 | UGGAGCCU G CAAAUGCA | 9213 | UGCAUUUG GCCGAAAGGCGAGUGAGGUCU AGGCUCCA | 20708 |

TABLE XXIII-continued

Human KDR Ziuzyme and Substrate Sequence

| Pos | Substrate | Seq ID No | Zinzyme | Seq ID No |
|---|---|---|---|---|
| 4919 | CUGCAAAU G CAUUGUGU | 9215 | ACACAAUG GCCGAAAGGCGAGUGAGGUCU AUUUGCAG | 20709 |
| 4924 | AAUGCAUU G UGUUUGCU | 9217 | AGCAAACA GCCGAAAGGCGAGUGAGGUCU AAUGCAUU | 20710 |
| 4926 | UGCAUUGU G UUUGCUCU | 9218 | AGAGCAAA GCCGAAAGGCGAGUGAGGUCU ACAAUGCA | 20711 |
| 4930 | UUGUGUUU G CUCUGGUG | 9219 | CACCAGAG GCCGAAAGGCGAGUGAGGUCU AAACACAA | 20712 |
| 4936 | UUGCUCUG G UGGAGGUG | 9220 | CACCUCCA GCCGAAAGGCGAGUGAGGUCU CAGAGCAA | 20713 |
| 4942 | UGGUGGAG G UGGGCAUG | 9221 | CAUGCCCA GCCGAAAGGCGAGUGAGGUCU CUCCACCA | 20714 |
| 4946 | GGAGGUGG G CAUGGGGU | 9222 | ACCCCAUG GCCGAAAGGCGAGUGAGGUCU CCACCUCC | 20715 |
| 4953 | GGCAUGGG G UCUGUUCU | 9224 | AGAACAGA GCCGAAAGGCGAGUGAGGUCU CCCAUGCC | 20716 |
| 4957 | UGGGGUCU G UUCUGAAA | 9225 | UUUCAGAA GCCGAAAGGCGAGUGAGGUCU AGACCCCA | 20717 |
| 4967 | UCUGAAAU G UAAAGGGU | 9227 | ACCCUUUA GCCGAAAGGCGAGUGAGGUCU AUUUCAGA | 20718 |
| 4974 | UGUAAAGG G UUCAGACG | 9228 | CGUCUGAA GCCGAAAGGCGAGUGAGGUCU CCUUUACA | 20719 |
| 4985 | CAGACGGG G UUUCUGGU | 9230 | ACCAGAAA GCCGAAAGGCGAGUGAGGUCU CCCGUCUG | 20720 |
| 4992 | GGUUUCUG G UUUUAGAA | 9231 | UUCUAAAA GCCGAAAGGCGAGUGAGGUCU CAGAAACC | 20721 |
| 5002 | UUUAGAAG G UUGCGUGU | 9232 | ACACGCAA GCCGAAAGGCGAGUGAGGUCU CUUCUAAA | 20722 |
| 5005 | AGAAGGUU G CGUGUUCU | 9233 | AGAACACG GCCGAAAGGCGAGUGAGGUCU AACCUUCU | 20723 |
| 5007 | AAGGUUGC G UGUUCUUC | 9234 | GAAGAACA GCCGAAAGGCGAGUGAGGUCU GCAACCUU | 20724 |
| 5009 | GGUUGCGU G UUCUUCGA | 9235 | UCGAAGAA GCCGAAAGGCGAGUGAGGUCU ACGCAACC | 20725 |
| 5018 | UUCUUCGA G UUGGGCUA | 9236 | UACCCCAA GCCGAAAGGCGAGUGAGGUCU UCGAAGAA | 20726 |
| 5023 | CGAGUUGG G CUAAAGUA | 9237 | UACUUUAG GCCGAAAGGCGAGUGAGGUCU CCAACUCG | 20727 |
| 5029 | GGGCUAAA G UAGAGUUC | 9238 | GAACUCUA GCCGAAAGGCGAGUGAGGUCU UUUAGCCC | 20728 |
| 5034 | AAAGUAGA G UUCGUUGU | 9239 | ACAACGAA GCCGAAAGGCGAGUGAGGUCU UCUACUUU | 20729 |
| 5038 | UAGAGUUC G UUGUGCUG | 9240 | CAGCACAA GCCGAAAGGCGAGUGAGGUCU GAACUCUA | 20730 |
| 5041 | AGUUCGUU G UGCUGUUU | 9241 | AAACAGCA GCCGAAAGGCGAGUGAGGUCU AACGAACU | 20731 |
| 5043 | UUCGUUGU G CUGUUUCU | 9242 | AGAAACAG GCCGAAAGGCGAGUGAGGUCU ACAACGAA | 20732 |
| 5046 | GUUGUGCU G UUUCUGAC | 9243 | GUCAGAAA GCCGAAAGGCGAGUGAGGUCU AGCACAAC | 20733 |
| 5066 | UAAUGAGA G UUCCUUCC | 9246 | GGAAGGAA GCCGAAAGGCGAGUGAGGUCU UCUCAUUA | 20734 |
| 5080 | UCCAGACC G UUAGCUGU | 9248 | ACAGCUAA GCCGAAAGGCGAGUGAGGUCU GGUCUGGA | 20735 |
| 5084 | GACCGUUA G CUGUCUCC | 9249 | GGAGACAG GCCGAAAGGCGAGUGAGGUCU UAACGGUC | 20736 |
| 5087 | CGUUAGCU G UCUCCUUG | 9250 | CAAGGAGA GCCGAAAGGCGAGUGAGGUCU AGCUAACG | 20737 |
| 5095 | GUCUCCUU G CCAAGCCC | 9251 | GGGCUUGG GCCGAAAGGCGAGUGAGGUCU AAGGAGAC | 20738 |
| 5100 | CUUGCCAA G CCCCAGGA | 9252 | UCCUGGGG GCCGAAAGGCGAGUGAGGUCU UUGGCAAG | 20739 |
| 5119 | AAAAUGAU G CAGCUCUG | 9255 | CAGAGCUG GCCGAAAGGCGAGUGAGGUCU AUCAUUUU | 20740 |
| 5122 | AUGAUGCA G CUCUGGCU | 9256 | AGCCAGAG GCCGAAAGGCGAGUGAGGUCU UGCAUCAU | 20741 |
| 5128 | CAGCUCUG G CUCCUUGU | 9257 | ACAAGGAG GCCGAAAGGCGAGUGAGGUCU CAGAGCUG | 20742 |
| 5135 | GGCUCCUU G UCUCCCAG | 9258 | CUGGGAGA GCCGAAAGGCGAGUGAGGUCU AAGGAGCC | 20743 |
| 5144 | UCUCCCAG G CUGAUCCU | 9259 | AGGAUCAG GCCGAAAGGCGAGUGAGGUCU CUGGGAGA | 20744 |
| 5185 | GACAUUCA G CUCAAGGC | 9267 | GCCUUGAG GCCGAAAGGCGAGUGAGGUCU UGAAUGUC | 20745 |

TABLE XXIII-continued

Human KDR Ziuzyme and Substrate Sequence

| Pos | Substrate | Seq ID No | Zinzyme | Seq ID No |
|---|---|---|---|---|
| 5192 | AGCUCAAG G CUCCCUGC | 9268 | GCAGGGAG GCCGAAAGGCGAGUGAGGUCU CUUGAGCU | 20746 |
| 5199 | GGCUCCCU G CCGUGUUG | 9269 | CAACACGG GCCGAAAGGCGAGUGAGGUCU AGGGAGCC | 20747 |
| 5202 | UCCCUGCC G UGUUGAAG | 9270 | CUUCAACA GCCGAAAGGCGAGUGAGGUCU GGCAGGGA | 20748 |
| 5204 | CCUGCCGU G UUGAAGAG | 9271 | CUCUUCAA GCCGAAAGGCGAGUGAGGUCU ACGGCAGG | 20749 |
| 5212 | GUUGAAGA G UUCUGACU | 9272 | AGUCAGAA GCCGAAAGGCGAGUGAGGUCU UCUUCAAC | 20750 |
| 5221 | UUCUGACU G CACAAACC | 9274 | GGUUUGUG GCCGAAAGGCGAGUGAGGUCU AGUCAGAA | 20751 |
| 5231 | ACAAACCA G CUUCUGGU | 9277 | ACCAGAAG GCCGAAAGGCGAGUGAGGUCU UGGUUUGU | 20752 |
| 5238 | AGCUUCUG G UUUCUUCU | 9278 | AGAAGAAA GCCGAAAGGCGAGUGAGGUCU CAGAAGCU | 20753 |
| 5268 | UCAUAUCU G UCCUGAUG | 9284 | CAUCAGGA GCCGAAAGGCGAGUGAGGUCU AGAUAUGA | 20754 |
| 5276 | GUCCUGAU G UGAUAUGU | 9286 | ACAUAUCA GCCGAAAGGCGAGUGAGGUCU AUCAGGAC | 20755 |
| 5283 | UGUGAUAU G UCUGAGAC | 9289 | GUCUCAGA GCCGAAAGGCGAGUGAGGUCU AUAUCACA | 20756 |
| 5297 | GACUGAAU G CGGGAGGU | 9292 | ACCUCCCG GCCGAAAGGCGAGUGAGGUCU AUUCAGUC | 20757 |
| 5304 | UGCGGGAG G UUCAAUGU | 9293 | ACAUUGAA GCCGAAAGGCGAGUGAGGUCU CUCCCGCA | 20758 |
| 5311 | GGUUCAAU G UGAAGCUG | 9295 | CAGCUUCA GCCGAAAGGCGAGUGAGGUCU AUUGAACC | 20759 |
| 5316 | AAUGUGAA G CUGUGUGU | 9296 | ACACACAG GCCGAAAGGCGAGUGAGGUCU UUCACAUU | 20760 |
| 5319 | GUGAAGCU G UGUGGGU | 9297 | ACCACACA GCCGAAAGGCGAGUGAGGUCU AGCUUCAC | 20761 |
| 5321 | GAAGCUGU G UGGGUGU | 9298 | ACACCACA GCCGAAAGGCGAGUGAGGUCU ACAGCUUC | 20762 |
| 5323 | AGCUGUGU G UGGGUCA | 9299 | UGACACCA GCCGAAAGGCGAGUGAGGUCU ACACAGCU | 20763 |
| 5326 | UGUGUGUG G UGUCAAAG | 9300 | CUUUGACA GCCGAAAGGCGAGUGAGGUCU CACACACA | 20764 |
| 5329 | UGUGUGGU G UCAAAGUU | 9301 | AACUUUGA GCCGAAAGGCGAGUGAGGUCU ACCACACA | 20765 |
| 5334 | GUGUCAAA G UUUCAGGA | 9302 | UCCUGAAA GCCGAAAGGCGAGUGAGGUCU UUUGACAC | 20766 |
| 5359 | ACCCUUUU G UUCUUCCC | 9305 | GGGAAGAA GCCGAAAGGCGAGUGAGGUCU AAAAGGGU | 20767 |
| 5371 | UUCCCCCU G UCCCCAAC | 9306 | GUUGGGGA GCCGAAAGGCGAGUGAGGUCU AGGGGAA | 20768 |
| 5393 | CUCACCCC G CAACCCAU | 9310 | AUGGGUUG GCCGAAAGGCGAGUGAGGUCU GGGGUGAG | 20769 |
| 5404 | ACCCAUCA G UAUUUUAG | 9313 | CUAAAAUA GCCGAAAGGCGAGUGAGGUCU UGAUGGGU | 20770 |
| 5412 | GUAUUUUA G UUAUUUGG | 9315 | CCAAAUAA GCCGAAAGGCGAGUGAGGUCU UAAAAUAC | 20771 |
| 5420 | GUUAUUUG G CCUCUACU | 9317 | AGUAGAGG GCCGAAAGGCGAGUGAGGUCU CAAAUAAC | 20772 |
| 5432 | CUACUCCA G UAAACCUG | 9319 | CAGGUUUA GCCGAAAGGCGAGUGAGGUCU UGGAGUAG | 20773 |
| 5446 | CUGAUUGG G UUUGUUCA | 9322 | UGAACAAA GCCGAAAGGCGAGUGAGGUCU CCAAUCAG | 20774 |
| 5450 | UUGGGUUU G UUCACUCU | 9323 | AGAGUGAA GCCGAAAGGCGAGUGAGGUCU AAACCCAA | 20775 |
| 5473 | GAUUAUUA G CCAGACUU | 9326 | AAGUCUGG GCCGAAAGGCGAGUGAGGUCU UAAUAAUC | 20776 |
| 5497 | AUUUUAUA G CCCAAAUU | 9333 | AAUUUGGG GCCGAAAGGCGAGUGAGGUCU UAUAAAAU | 20777 |
| 5518 | CAUCUAUU G UAUUAUUU | 9339 | AAAUAAUA GCCGAAAGGCGAGUGAGGUCU AAUAGAUG | 20778 |
| 5545 | CAUAUAGA G CUAUUUCU | 9346 | AGAAAUAG GCCGAAAGGCGAGUGAGGUCU UCUAUAUG | 20779 |
| 5564 | UGAUUUUU G CCCUUGUU | 9350 | AACAAGGG GCCGAAAGGCGAGUGAGGUCU AAAAAUCA | 20780 |
| 5570 | UUGCCCUU G UUCUGUCC | 9351 | GGACAGAA GCCGAAAGGCGAGUGAGGUCU AAGGGCAA | 20781 |
| 5575 | CUUGUUCU G UCCUUUUU | 9352 | AAAAAGGA GCCGAAAGGCGAGUGAGGUCU AGAACAAG | 20782 |

TABLE XXIII-continued

Human KDR Ziuzyme and Substrate Sequence

| Pos | Substrate | Seq ID No | Zinzyme | Seq ID No |
|---|---|---|---|---|
| 5599 | AAGAAAAU G UGUUUUUU | 9354 | AAAAAACA GCCGAAAGGCGAGUGAGGUCU AUUUUCUU | 20783 |
| 5601 | GAAAAUGU G UUUUUUGU | 9355 | ACAAAAAA GCCGAAAGGCGAGUGAGGUCU ACAUUUUC | 20784 |
| 5608 | UGUUUUUU G UUUGGUAC | 9356 | GUACCAAA GCCGAAAGGCGAGUGAGGUCU AAAAAACA | 20785 |
| 5613 | UUUGUUUG G UACCAUAG | 9357 | CUAUGGUA GCCGAAAGGCGAGUGAGGUCU CAAACAAA | 20786 |
| 5621 | GUACCAUA G UGUGAAAU | 9360 | AUUUCACA GCCGAAAGGCGAGUGAGGUCU UAUGGUAC | 20787 |
| 5623 | ACCAUAGU G UGAAAUGC | 9361 | GCAUUUCA GCCGAAAGGCGAGUGAGGUCU ACUAUGGU | 20788 |
| 5630 | UGUGAAAU G CUGGGAAC | 9363 | GUUCCCAG GCCGAAAGGCGAGUGAGGUCU AUUUCACA | 20789 |
| 5655 | UAAGACAU G CUAUGGCA | 9370 | UGCCAUAG GCCGAAAGGCGAGUGAGGUCU AUGUCUCA | 20790 |
| 5661 | AUGCUAUG G CACAUAUA | 9372 | UAUAUGUG GCCGAAAGGCGAGUGAGGUCU CAUAGCAU | 20791 |
| 5676 | UAUUUAUA G UCUGUCCA | 9378 | UAAACAGA GCCGAAAGGCGAGUGAGGUCU UAUAAAUA | 20792 |
| 5680 | UAUAGUCU G UUUAUGUA | 9379 | UACAUAAA GCCGAAAGGCGAGUGAGGUCU AGACUAUA | 20793 |
| 5686 | CUGUUUAU G UAGAAACA | 9381 | UGUUUCUA GCCGAAAGGCGAGUGAGGUCU AUAAACAG | 20794 |
| 5698 | AAACAAAU G UAAUAUAU | 9384 | AUAUAUUA GCCGAAAGGCGAGUGAGGUCU AUUUGUUU | 20795 |
| 5711 | AUAUUAAA G CCUUAUAU | 9388 | AUAUAAGG GCCGAAAGGCGAGUGAGGUCU UUUAAUAU | 20796 |
| 5732 | UGAACUUU G UACUAUUC | 9394 | GAAUAGUA GCCGAAAGGCGAGUGAGGUCU AAAGUUCA | 20797 |
| 5748 | CACAUUUU G UAUCAGUA | 9399 | UACUGAUA GCCGAAAGGCGAGUGAGGUCU AAAAUGUG | 20798 |
| 5754 | UUGUAUCA G UAUUAUGU | 9401 | ACAUAAUA GCCGAAAGGCGAGUGAGGUCU UGAUACAA | 20799 |
| 5761 | AGUAUUAU G UAGCAUAA | 9404 | UUAUGCUA GCCGAAAGGCGAGUGAGGUCU AUAAUACU | 20800 |
| 5764 | AUUAUGUA G CAUAACAA | 9405 | UUGUUAUG GCCGAAAGGCGAGUGAGGUCU UACAUAAU | 20801 |
| 5775 | UAACAAAG G UCAUAAUG | 9408 | CAUUAUGA GCCGAAAGGCGAGUGAGGUCU CUUUGUUA | 20802 |
| 5783 | GUCAUAAU G CUUUCAGC | 9411 | GCUGAAAG GCCGAAAGGCGAGUGAGGUCU AUCAUGAC | 20803 |
| 5790 | UGCUUUCA G CAAUUGAU | 9412 | AUCAAUUG GCCGAAAGGCGAGUGAGGUCU UGAAAGCA | 20804 |
| 5799 | CAAUUGAU G UCAUUUUA | 9415 | UAAAAUGA GCCGAAAGGCGAGUGAGGUCU AUCAAUUG | 20805 |

Input Sequence = AF035121.
Cut Site = G/Y
Arm Length = 8.
Core Sequence = GCcgaaagGCGaGuCaaGGuCu (SEQ ID NO. 20829).
AF035121 (*Homo sapiens* KDR/flk-1 protein mRNA, complete cds.; Acc# AF035121; 5830 bp)

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07034009B2). An electronic copy of the "Sequence Listing" will also be available from the USPTO upon request and payment of the fee set forth in 37 CFR 1.19(b)(3).

What is claimed is:

1. A compound having Formula II: (SEQ ID NO: 13488) 5'-u$_s$a$_s$c$_s$ a$_s$au ucU GAu Gag gcg aaa gcc Gaa Aag aca aB-3' wherein each a is 2'-O-methyl adenosine nucleotide, each g is a 2'-O-methyl guanosine nucleotide, each c is a 2'-O-methyl cytidine nucleotide, each u is a 2'-O-methyl uridine nucleotide, each A is adenosine, each G is guanosine, each s individually represents a phosphorothioate internucleotide linkage, U is 2'-deoxy-2'-C-allyl uridine, and B is an inverted deoxyabasic moiety.

2. A composition comprising the compound of claim 1 and a pharmaceutically acceptable carrier or diluent.

3. A method of locally or intraconjunctivally administering to a cell the compound of claim 1 comprising contacting said cell with the compound under conditions suitable for said administration.

4. The method of claim 3, wherein said cell is a mammalian cell.

5. The method of claim 3, wherein said cell is a human cell.

6. The method of claim 3, wherein said administration is in the presence of a delivery reagent.

7. The method of claim 6, wherein said delivery reagent is a lipid.

8. The method of claim 7, wherein said lipid is a cationic lipid.

9. The method of claim 7, wherein said lipid is a phospholipid.

10. The method of claim 6, wherein said delivery reagent is a liposome.

11. A method of inhibiting ocular angiogenesis in a patient comprising the step of locally or intraconjunctivally administering the compound of claim 1 to the patient under conditions suitable for said inhibition.

12. The method of claim 11, wherein said ocular angiogenesis is associated with diabetic retinopathy.

13. The method of claim 11, wherein said ocular angiogenesis is associated with age related diabetic retinopathy.

14. A method of locally or intraconjunctivally administering to a mammal the compound of claim 1 comprising contacting said mammal with the compound under conditions suitable for said administration.

15. The method of claim 14, wherein said mammal is a human.

16. The method of claim 14, wherein said administration is in the presence of a delivery reagent.

17. The method of claim 16, wherein said delivery reagent is a lipid.

18. The method of claim 17, wherein said lipid is a cationic lipid.

19. The method of claim 17, wherein said lipid is a phospholipid.

20. The method of claim 16, wherein said delivery reagent is a liposome.

* * * * *